(12) United States Patent
Robl et al.

(10) Patent No.: US 9,062,028 B2
(45) Date of Patent: Jun. 23, 2015

(54) BICYCLIC NITROGEN CONTAINING HETEROARYL TGR5 RECEPTOR MODULATORS

(75) Inventors: Jeffrey A. Robl, Newtown, PA (US); Jun Li, Princeton, NJ (US); Lawrence J. Kennedy, Titusville, NJ (US); Steven J. Walker, Pennington, NJ (US); Haixia Wang, Columbus, NJ (US); William N. Washburn, Titusville, NJ (US); Saleem Ahmad, Wall, NJ (US); Khehyong Ngu, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/113,593

(22) PCT Filed: Apr. 27, 2012

(86) PCT No.: PCT/US2012/035327
§ 371 (c)(1),
(2), (4) Date: Oct. 24, 2013

(87) PCT Pub. No.: WO2012/149236
PCT Pub. Date: Nov. 1, 2012

(65) Prior Publication Data
US 2014/0080788 A1    Mar. 20, 2014

Related U.S. Application Data

(60) Provisional application No. 61/479,917, filed on Apr. 28, 2011.

(51) Int. Cl.
C07D 401/04    (2006.01)
C07D 401/14    (2006.01)
C07D 403/04    (2006.01)
C07D 413/04    (2006.01)
C07D 413/14    (2006.01)
A61K 31/47     (2006.01)
A61K 31/4709   (2006.01)
A61K 31/473    (2006.01)
C07D 215/08    (2006.01)
C07D 417/04    (2006.01)
A61K 31/4747   (2006.01)
A61K 31/496    (2006.01)
A61K 31/506    (2006.01)
(Continued)

(52) U.S. Cl.
CPC ........... *C07D 401/04* (2013.01); *C07D 215/08* (2013.01); *C07D 401/14* (2013.01); *C07D 403/04* (2013.01); *C07D 413/04* (2013.01); *C07D 413/14* (2013.01); *C07D 417/04* (2013.01); *A61K 31/47* (2013.01); *A61K 31/4709* (2013.01); *A61K 31/473* (2013.01); *A61K 31/4747* (2013.01); *A61K 31/496* (2013.01); *A61K 31/506* (2013.01); *A61K 31/5377* (2013.01); *A61K 31/5415* (2013.01); *A61K 31/55* (2013.01); *A61K 31/553* (2013.01); *A61K 31/554* (2013.01); *A61K 31/675* (2013.01); *A61K 45/06* (2013.01); *C07D 221/16* (2013.01); *C07D 401/12* (2013.01); *C07D405/14* (2013.01); *C07D 409/14* (2013.01); *C07F 9/60* (2013.01)

(58) Field of Classification Search
USPC ........... 546/165, 23, 18, 79; 514/314, 311, 82
See application file for complete search history.

(56) References Cited

U.S. PATENT DOCUMENTS 7,989,461 B2 *  8/2011  De Morin et al. .......... 514/266.2
8,309,734 B2   11/2012  Bissantz et al.

FOREIGN PATENT DOCUMENTS

JP        7-242663     9/1995
WO    WO 2010/107768   9/2010

OTHER PUBLICATIONS

Zhao, S.-H. et al., "3,4-Dihydro-2H-benzo[1,4]oxazine derivatives as 5-HT$_6$ receptor antagonists", Bioorganic & Medicinal Chemistry Letters, vol. 17, pp. 3504-3507 (2007).

*Primary Examiner* — Kahsay Habte
(74) *Attorney, Agent, or Firm* — Terence J. Bogie

(57) ABSTRACT

Novel compounds of Formula I:or an enantiomer, diastereomer, tautomer, prodrug or salt thereof, wherein m, Q, T, U, V, ring A, X, Y, $R_3$, $R_4$, $R_{4a}$, $R_{5a}$, $R_{5b}$, $R_{5c}$, $R_{5d}$, $R_{5e}$, $R_{6a}$, $R_{6b}$, and $R_{6c}$ are defined herein, are provided which are TGR5 G protein-coupled receptor modulators. TGR5 G protein-coupled receptor modulators are useful in treating, preventing, or slowing the progression of diseases requiring TGR5 G protein-coupled receptor modulator therapy. Thus, the disclosure also concerns compositions comprising these novel compounds and methods of treating diseases or conditions related to the activity of the TGR5 G protein-coupled receptor by using any of these novel compounds or a composition comprising any of such novel compounds.

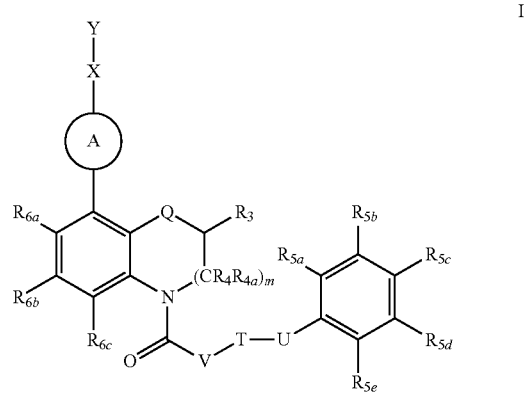

14 Claims, No Drawings

(51) Int. Cl.
*A61K 31/5377* (2006.01)
*A61K 31/5415* (2006.01)
*A61K 31/55* (2006.01)
*A61K 31/553* (2006.01)
*A61K 31/554* (2006.01)
*A61K 31/675* (2006.01)
*A61K 45/06* (2006.01)
*C07D 221/16* (2006.01)
*C07D 401/12* (2006.01)
*C07D 405/14* (2006.01)
*C07D 409/14* (2006.01)
*C07F 9/60* (2006.01)

BICYCLIC NITROGEN CONTAINING HETEROARYL TGR5 RECEPTOR MODULATORS

CROSS REFERENCES TO RELATED APPLICATIONS

This application claims the benefit of International Application No. PCT/US2012/035327, filed Apr. 27, 2012, which claims the benefit of U.S. Provisional Application Ser. No. 61/479,917, filed on Apr. 28, 2011. The entire teachings of the referenced applications are herein incorporated by reference in their entirety.

FIELD OF THE INVENTION

The present invention provides novel bicyclic nitrogen containing heteroaryl compounds, preferably tetrahydroquinolinyl, tetrahydrocyclopropaquinolinyl, dihydrobenzooxazinyl, tetrahydrobenzoazepinyl and tetrahydrobenzooxazepinyl compounds, and analogues thereof, which are agonists of the TGR5 G protein-coupled receptor, compositions containing them, and methods of using them, for example, for the prevention and/or treatment of diseases or disorders associated with the modulation of the TGR5 G protein-coupled receptor, e.g., diabetes and obesity.

BACKGROUND OF THE INVENTION

Diabetes mellitus is an epidemic disease that is the fourth leading cause of death worldwide, the leading cause of kidney disease in developed countries and the leading cause of blindness in industrialized nations. In 2007, $174 billion of cost was attributed to the disease from lost productivity and health-care related expense. The most prevalent form, type 2 diabetes, targets multiple organs and is a progressive disease, requiring additional treatment and expense as it progresses. Therefore, new and differentiated treatment options represent a major unmet medical need. One major recent therapeutic advance targets the incretin axis, and therapies that either directly provide additional glucagon like peptide-1 (GLP-1) through administration of stable GLP-1 analogs or prevent the degradation of naturally produced GLP-1 via the inhibition of degradative, protelytic enzymes such as dipeptidyl peptidase IV (DPP4). In turn, GLP-1 can modulate insulin secretion resulting in enhanced insulin secretion and glucose uptake.

Bile acids play essential roles in the absorption of dietary lipids and in the regulation of bile acid biosynthesis. While bile acids have long been known to be essential in dietary lipid absorption and cholesterol catabolism, in recent years an important role for bile acids as signaling molecules has emerged. Bile acids are ligands for the G-protein-coupled receptor (GPCR) TGR5 and activate nuclear hormone receptors such as farnesoid X receptor a (FXR-a). Through activation of these diverse signaling pathways, bile acids can regulate their own enterohepatic circulation, but also triglyceride, cholesterol, energy, and glucose homeostasis. Thus, bile acid (BA) controlled signaling pathways are promising novel drug targets to treat common metabolic diseases, such as obesity, type II diabetes, hyperlipidemia, and atherosclerosis.

The receptor commonly referred to as TGR5 (also known as GPBAR1, BG37, AXOR109, GPCR19, and GPR131) has been shown to respond to bile acids, and thus is postulated to mediate the recently discovered signaling properties attributed to these molecules. The membrane-bound receptor is highly expressed in the gall bladder, but also throughout the intestinal tract, and has also been reported in myocytes, monocytes/macrophages as well as other tissues and organs. The TGR5 receptor is known to be coupled to the Gs type G protein which activates cAMP biosynthesis, which in turn is thought to mediate some or all of the TGR5-mediated biologic actions.

Glucagon-like peptide-1 (GLP-1) is produced by L-cells in the distal digestive tract and affects multiple metabolic parameters, including enhanced insulin secretion, glucagon suppression, and lowering of blood glucose. Modulation of the TGR5 receptor has been proposed to result in the stimulation of GLP-1 secretion in the gastrointestinal tract, which upon acting on the pancreatic beta cell could then result in additional glucose-stimulated insulin secretion (GSIS). TGR5 receptor signaling has also been suggested to increase oxidative phosphorylation and energy metabolism in muscle and mediate anti-inflammatory actions at other sites of diabetic injury, which together or separately may hold potential benefits for treatment of the disease. Administration of bile acids to mice has also been reported to increase energy expenditure, thereby preventing obesity and insulin resistance. This novel metabolic effect of bile acids is thought to be dependent on induction of type 2 iodothyronine deiodinase (D2) and conversion of T4 to T3, because it is absent in D2-/- mice.

Accordingly, compounds that activate TGR5, alone or in combination with other medicaments, could demonstrate a wide range of utilities in treating inflammatory, allergic, autoimmune, metabolic, cancer and/or cardiovascular diseases, in particular diabetes mellitus. PCT Publication Nos. WO 2010/093845 A1, WO 2011/071565 A1, WO 2010/059859 A1, WO 2010/016846 A1, WO 2009/026241 A1, WO 2008/067222 A1, WO 2008/097976 A1 and WO 2008/067219 A2, disclose compounds that activate TGR5 and methods of treating diseases associated with TGR5. The references also disclose various processes to prepare these compounds.

SUMMARY OF THE INVENTION

In accordance with the present invention, compounds are provided that have the general structure of Formula I:

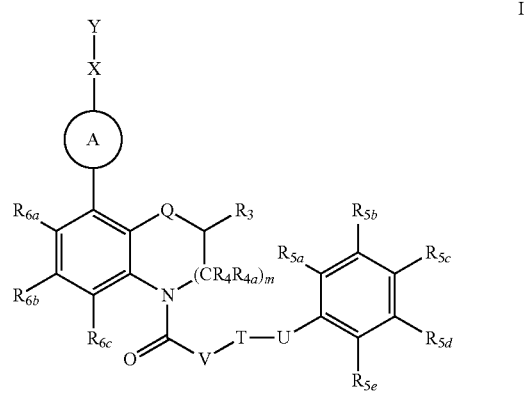

or an enantiomer, diastereomer, tautomer, prodrug or salt thereof, wherein m, Q, T, U, V, ring A, X, Y, $R_3$, $R_4$, $R_{4a}$, $R_{5a}$, $R_{5b}$, $R_{5c}$, $R_{5d}$, $R_{5e}$, $R_{6a}$, $R_{6b}$, and $R_{6c}$ are defined below.

Compounds of the present invention modulate the activity of G protein-coupled receptors. Preferably, compounds of the present invention modulate the activity of the TGR5 G protein-coupled receptor ("TGR5"). Consequently, the compounds of the present invention may be used in the treatment of multiple diseases or disorders associated with TGR5, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the TGR5 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, vascular restenosis, and pancreatitis.

In addition, the present invention relates to a formulated product wherein the selected formulation is made by using a compound of Formula I, Ia, Ib, Ic, Id, Ie, If, Ig, Ih, Ij and the examples, as the only active ingredient or by combining (a) a compound of Formula I, Ia, Ib, Ic, Id, Ie, If, Ig, Ih, Ij and the examples, (using any of the compound embodiments listed herein) and (b) an additional active ingredient, for example, a dipeptidyl peptidase-IV (DPP4) inhibitor (for example, a member selected from saxagliptin, sitagliptin, vildagliptin and alogliptin).

In addition, the present invention relates to a formulated product wherein the selected formulation is made by using a compound of Formula I, Ia, Ib, Ic, Id, Ie, If, Ig, Ih, Ij and the examples, as the only active ingredient or by combining (a) a compound of Formula I, Ia, Ib, Ic, Id, Ie, If, Ig, Ih, Ij and the examples, (using any of the compound embodiments listed herein) and (b) a dipeptidyl peptidase-IV (DPP4) inhibitor, wherein the DPP4 inhibitor is saxagliptin.

In addition, the present invention relates to a formulated product wherein the selected formulation is made by using a compound of Formula I, Ia, Ib, Ic, Id, Ie, If, Ig, Ih, Ij and the examples, as the only active ingredient or by combining (a) a compound of Formula I, Ia, Ib, Ic, Id, Ie, If, Ig, Ih, Ij and the examples, (using any of the compound embodiments listed herein) and (b) an additional active ingredient, for example, an SGLT2 inhibitor (for example, a member selected from 3-(benzo[b]furan-5-yl)-2',6'-dihydroxy-4'-methylpropiophenone-2'-O-(6-O-methoxycarbonyl)-β-d-glucopyranoside, phlorizin, TS-033, dapagliflozin, sergiflozin, AVE 2268 and canagliflozin).

In addition, the present invention relates to a formulated product wherein the selected formulation is made by using a compound of Formula I, Ia, Ib, Ic, Id, Ie, If, Ig, Ih, Ij and the examples, as the only active ingredient or by combining (a) a compound of Formula I, Ia, Ib, Ic, Id, Ie, If, Ig, Ih, Ij and the examples, (using any of the compound embodiments listed herein) and (b) an SGLT2 inhibitor, wherein the SGLT2 inhibitor is dapagliflozin.

Therefore, in another embodiment of the present invention provides for compounds of Formula I, Ia, Ib, Ic, Id, Ie, If, Ig, Ih, Ij and the examples, pharmaceutical compositions containing such compounds, and for methods of using such compounds. In particular, the present invention provides a pharmaceutical composition comprising a therapeutically effective amount of a compound of Formula I, Ia, Ib, Ic, Id, Ie, If, Ig, Ih, Ij and the examples, alone or in combination with a pharmaceutically acceptable carrier.

Further, in another embodiment of the present invention provides a method for preventing, modulating, or treating the progression or onset of diseases or disorders associated with the activity of the TGR5 G protein-coupled receptor, such as defined above and hereinafter, wherein a therapeutically effective amount of a compound of Formula I, Ia, Ib, Ic, Id, Ie, If, Ig, Ih, Ij and the examples, is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I, Ia, Ib, Ic, Id, Ie, If, Ig, Ih, Ij and the examples, and another compound of Formula I, Ia, Ib, Ic, Id, Ie, If, Ig, Ih, Ij and the examples, and/or at least one other type of therapeutic agent, is administered to a mammalian, i.e., human, patient in need of treatment.

DETAILED DESCRIPTION

In one embodiment, the present invention provides a compound of Formula I:

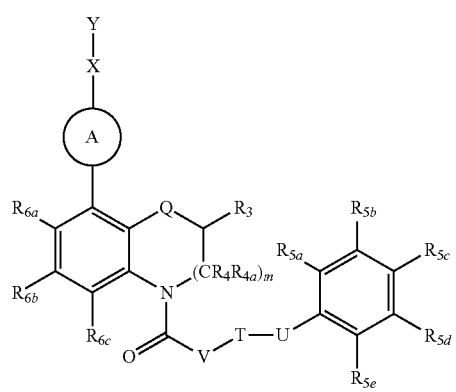

enantiomer, diastereomer, tautomer, prodrug or salt thereof wherein:

m is 1 or 2;

Q is $CR_{2a}R_2$, O, —$CR_{2a}R_2$—O—, S, SO or $SO_2$;

T is $(C_1-C_5)$-alkyl, $(C_2-C_6)$-alkenyl, $(C_{5-10})$-aryl or $(C_{5-10})$-heteroaryl, all of which may be optionally substituted with one or more substituents selected from hydrogen, $^2H$, halogen, $C_1-C_6$ alkyl, $C_1-C_6$ alkoxy, CN, $(C_3-C_{12})$-cycloalkyl or halo($C_1-C_6$)-alkyl and wherein a carbon atom of the alkyl chain may be replaced with a heteroatom selected from N, O, and S;

U is a bond, S, $NR_{7a}$, O or a $(C_3-C_6)$-cycloalkyl;

V is a bond, —$CH_2$—, O or a $(C_3-C_6)$-cycloalkyl;

Ring A is a 5- to 6-membered aryl or heteroaryl, wherein the aryl and heteroaryl may be optionally substituted with one or more substituents selected from hydrogen, halogen, oxo, $C_1-C_6$ alkyl, $C_1-C_6$ alkoxy, CN, $(C_3-C_{12})$-cycloalkyl and halo $(C_1-C_6)$-alkyl and the heteroaryl contains 1-4 heteroatoms selected from N, O, and S;

X is a bond, $(C_1-C_6)$-alkyloxy, $(C_3-C_6)$-cycloalkyl, $(C_3-C_6)$-cycloalkyl-$(C_1-C_6)$-alkyl, $(C_{5-10})$-aryl, $(C_{5-10})$-aryloxy, $(C_{5-10})$-aryl-$(C_1-C_6)$-alkyl, $(C_{5-10})$-aryl-oxy-$(C_1-C_6)$-alkyl, $(C_{5-10})$-aryl-$(C_1-C_6)$-alkyloxy or heteroaryl-$(C_1-C_6)$-alkyl, wherein the heteroaryl contains 4- to 10-members and 1-4 heteroatoms selected from N, O, and S and any alkyl, aryl and heteroaryl may be optionally substituted with one or more substituents selected from hydrogen, halogen, $C_1$-$C_6$ alkyl, $C_1$-$C_6$ alkoxy, CN, —COOH, —$NR_{28}R_{29}$, —OH, ($C_3$-$C_{12}$)-cycloalkyl, ($C_3$-$C_{12}$)-cycloalkyloxy and halo($C_1$-$C_6$)-alkyl;
Y is —$(CR_{22}R_{22a})_n$—W;
W is hydrogen, —OH, cyano, heteroaryl, which may be optionally substituted with one or more $R_{20}$'s, heterocyclo, which may be optionally substituted with one or more $R_{20}$'s, —$N(R_{18})R_{19}$,
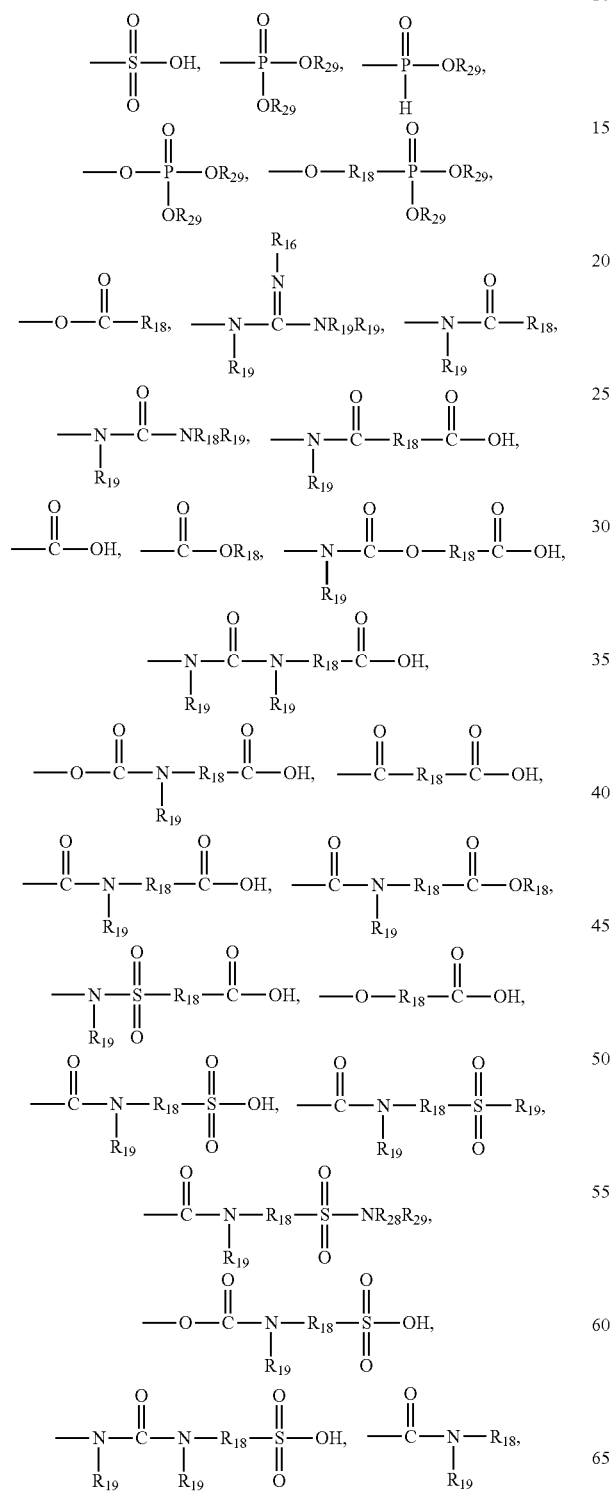
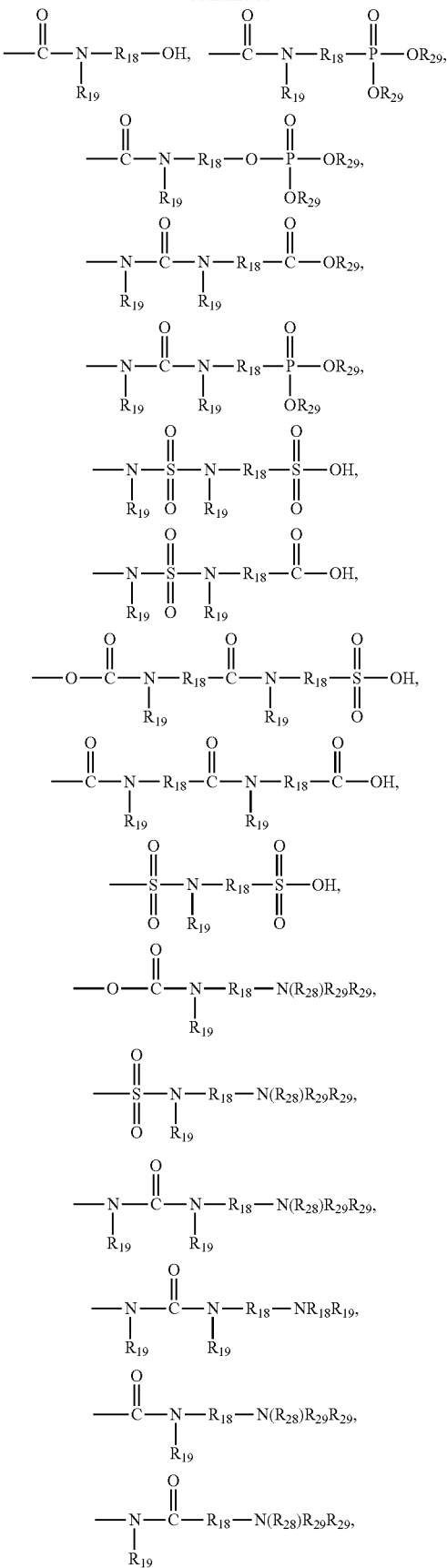

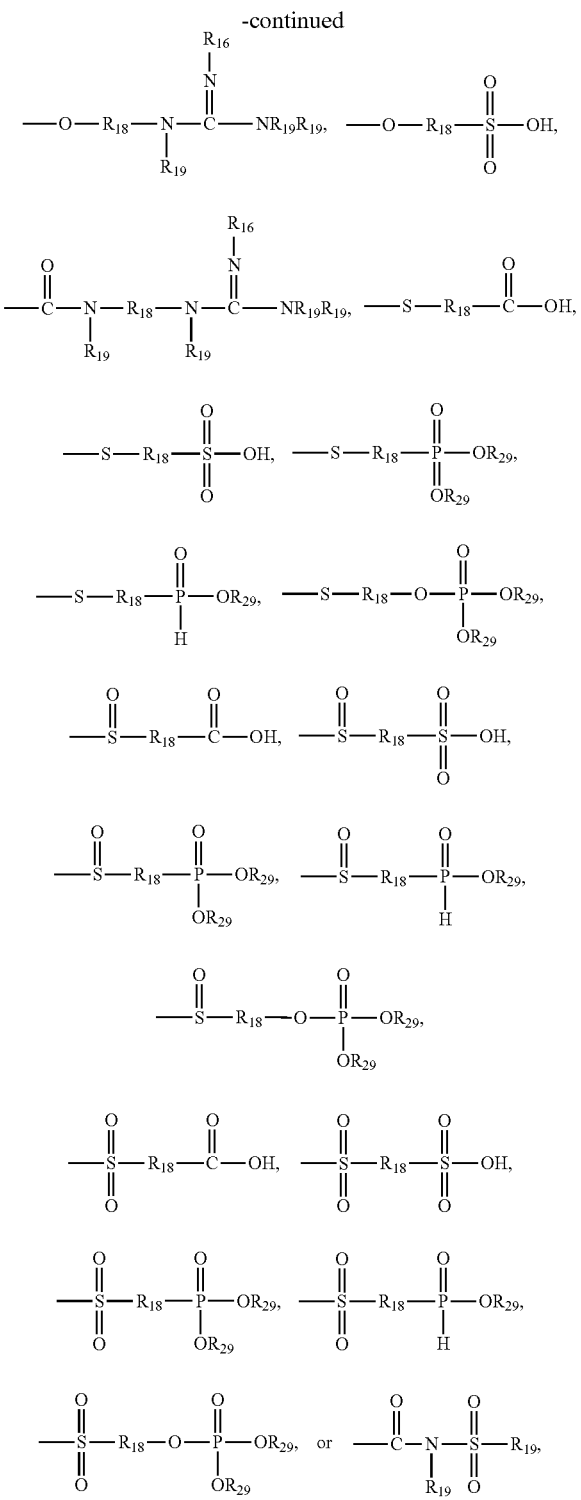

wherein the amino, hydroxy or acidic moiety may attach at any position of $R_{18}$;

$R_2$ is hydrogen, —OH, oxo, $(C_1-C_6)$-alkyl, $(C_3-C_{12})$-cycloalkyl or halo$(C_1-C_6)$-alkyl;

$R_{2a}$ is hydrogen, —OH, oxo, $(C_1-C_6)$-alkyl, $(C_3-C_{12})$-cycloalkyl or halo$(C_1-C_6)$-alkyl;

or $R_2$ and $R_{2a}$ can optionally be linked to form a linking group containing 1-2 carbon atoms;

$R_3$ is hydrogen, $(C_1-C_6)$-alkyl, $(C_3-C_{12})$-cycloalkyl or halo$(C_1-C_6)$-alkyl;

or $R_2$ and $R_3$ can optionally be linked to form a linking group containing 1-5 carbon atoms to form a $(C_3-C_7)$-cycloalkyl ring, a halo$(C_3-C_7)$-cycloalkyl ring or an aryl ring;

$R_4$, at each occurrence, is independently hydrogen, —OH, halogen, halo$(C_1-C_6)$-alkyl or $(C_1-C_8)$alkyl;

$R_{4a}$, at each occurrence, is independently is hydrogen, —OH, halogen, halo$(C_1-C_6)$-alkyl or $(C_1-C_8)$alkyl;

or $R_3$ and $R_4$ can optionally be linked with the carbons to which they are attached to form a linking group containing 1-5 carbon atoms to form a $(C_3-C_7)$-cycloalkyl ring, a halo$(C_3-C_7)$-cycloalkyl ring or an aryl ring;

or $R_4$ and $R_{4a}$ can optionally be linked to form a linking group containing 1-4 carbon atoms;

$R_{5a}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5b}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5c}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5d}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5e}$ is hydrogen, halogen, $C_1-C_6$ alkyl, $C_1-C_6$ alkoxy, CN, $(C_3-C_6)$-cycloalkyl or halo$(C_1-C_6)$-alkyl;

or two of $R_{5a}$, $R_{5b}$, $R_{5c}$, $R_{5d}$ or $R_{5e}$ may be taken together with the atoms to which both are attached form a 3- to 8-membered ring, which may optionally contain 1-4 heteroatoms selected from N, O, and S;

$R_{6a}$ is hydrogen, halogen or $C_1-C_6$ alkyl;

$R_{6b}$ is hydrogen, halogen or $C_1-C_6$ alkyl;

$R_{6c}$ is hydrogen, halogen or $C_1-C_6$ alkyl;

$R_{7a}$ is hydrogen, $C_1-C_6$ alkyl or —$CO_2(C_1-C_6)$-alkyl;

n is 0-6;

$R_{16}$ is H or —CN;

$R_{18}$, at each occurrence, is independently $(C_1-C_8)$alkyl, $(C_3-C_{12})$-cycloalkyl, a fused $(C_3-C_{18})$-cycloalkyl, $(C_1-C_8)$alkyl-$(C_3-C_{12})$-cycloalkyl-$(C_1-C_8)$alkyl, $(C_1-C_8)$alkyl-$(C_3-C_{12})$-cycloalkyl, $(C_{5-10})$-aryl, $(C_5-C_{10})$-aryl$(C_1-C_8)$alkyl, a heteroaryl, a heteroaryl$(C_1-C_8)$alkyl, a heterocyclo$(C_1-C_8)$alkyl or a heterocyclo, all of which may be optionally substituted with one or more $R_{20}$'s and wherein the heteroaryl and heterocyclo contain 4- to 10-members and contain 1-4 heteroatoms selected from N, O, and S;

$R_{19}$, at each occurrence, is independently hydrogen, $(C_1-C_6)$-alkyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is selected from halo, —OH, $(C_1-C_6)$-alkyl, $(C_2-C_6)$-alkenyl, $(C_2-C_6)$-alkynyl, —$(C_3-C_{12})$-cycloalkyl, $(C_1-C_6)$-alkyloxy, cyano, oxo, nitro, —COOH, —$SO_3H$, —$CO(C_1-C_6)$-alkyl, —$CO(C_6-C_{12})$-aryl, —$CO_2(C_1-C_6)$-alkyl, —$CONR_{28}R_{29}$, —$NR_{28}R_{29}$, —$NR_{28}C(=O)NR_{28}R_{29}$, —$NR_{28}C(=NR_{29})NR_{28}R_{29}$, —$SR_{28}$, —$S(=O)(=NR_{28})R_{29}$, —$S(—OH)R_{29}$, —$S(=O)R_{29}$, —$S(=O)_2R_{29}$, —$NR_{29}CO_2(C_1-C_6)$-alkyl, —$NR_{28}SO_2R_{19}$, —$O(C=O)$—$(C_1-C_6)$-alkyl, —$O(C=O)NR_{28}R_{29}$; —$(C_1-C_6)$-alkylCOOH, —$(C_1-C_6)$-alkylOH, —$(C_1-C_6)$-alkyl$(NH_2)COOH$, —$(C_1-C_6)$-alkylCONR$_{28}R_{29}$, —$(C_1-C_6)$-alkyl-$CO_2(C_1-C_6)$-alkyl, —O—$P(=O)(OH)(OR_{29})$, —O—CR$_{28}$R$_{29}$—P(═O)(OH)(OR$_{29}$), —P(═O)(OH)(OR$_{29}$), (C$_{6-10}$)aryl, (C$_{6-10}$)aryl(C$_1$-C$_6$)-alkyl, (C$_{6-10}$)aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —N(R$_{28}$)R$_{29}$R$_{29}$, —O(C═O)—(C$_1$-C$_6$)-alkyl, —O(C═O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(═O)(OH)(OR$_{29}$), —O—CR$_{28}$R$_{29}$—P(═O)(OH)(OR$_{29}$), —P(═O)(OH)(OR$_{29}$), —S(═O)$_2$OH, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_{22}$, at each occurrence, is independently hydrogen, —OH, (C$_1$-C$_6$)-alkyl, (C$_3$-C$_{12}$)-cycloalkyl, (C$_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, —OH, halogen, C$_1$-C$_6$ alkyl, C$_1$-C$_6$ alkoxy, CN, (C$_3$-C$_{12}$)-cycloalkyl and halo(C$_1$-C$_6$)-alkyl;

R$_{22a}$, at each occurrence, is independently hydrogen, —OH, (C$_1$-C$_6$)-alkyl, (C$_3$-C$_{12}$)-cycloalkyl, (C$_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, —OH, halogen, C$_1$-C$_6$ alkyl, C$_1$-C$_6$ alkoxy, CN, (C$_3$-C$_{12}$)-cycloalkyl and halo(C$_1$-C$_6$)-alkyl;

R$_{28}$ and R$_{29}$, at each occurrence, are independently hydrogen, (C$_3$-C$_{12}$)-cycloalkyl, or (C$_1$-C$_8$)alkyl, wherein the cycloalkyl and alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{38}$R$_{39}$, —NR$_{38}$R$_{39}$, —O(C═O)—(C$_1$-C$_6$)-alkyl, —O(C═O)NR$_{38}$R$_{39}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{38}$R$_{39}$, —(C$_1$-C$_6$)-alkyl-CO$_2$(C$_1$-C$_6$)-alkyl, —O—P(═O)(OH)(OR$_{39}$), —O—CR$_{38}$R$_{39}$—P(═O)(OH)(OR$_{39}$), —P(═O)(OH)(OR$_{39}$), —S(═O)$_2$OH, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

or R$_{28}$ and R$_{29}$ are taken together with the nitrogen to which both are attached to form a 3- to 8-membered ring, which may optionally contain 1-4 heteroatoms selected from N, O, and S;

R$_{38}$ and R$_{39}$, at each occurrence, are independently hydrogen or (C$_1$-C$_8$)alkyl;

or R$_{38}$ and R$_{39}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, prodrugs or salts thereof, wherein the compounds are compounds of formula Ia:

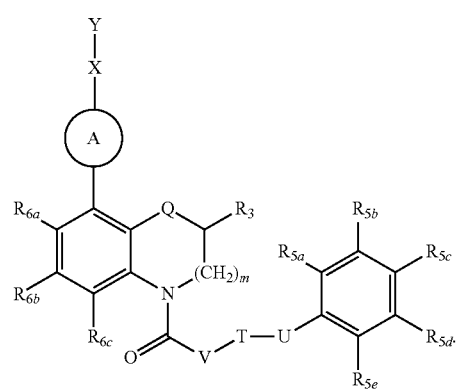

Ia

In yet another embodiment, the present invention provides compounds, enantiomers, diastereomers, tautomers, prodrugs or salts thereof, wherein the compounds are compounds of formula Ib:

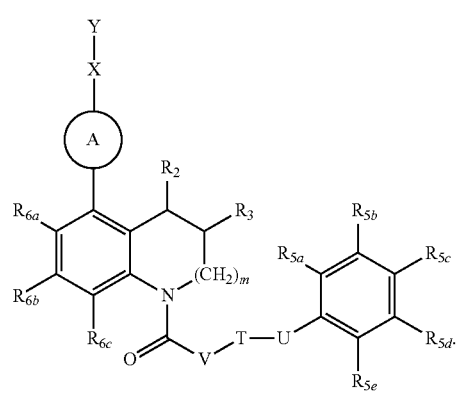

Ib

In yet another embodiment, the present invention provides compounds, enantiomers, diastereomers, tautomers, prodrugs or salts thereof, wherein the compounds are compounds of formula Ic:

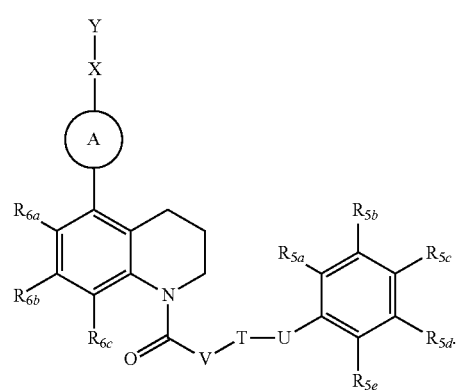

Ic

In still yet another embodiment, the present invention provides compounds, enantiomers, diastereomers, tautomers, prodrugs or salts thereof, wherein the compounds are compounds of formula Id:

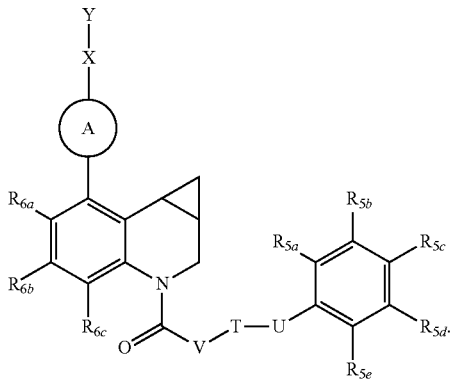

Id

In one embodiment, the present invention provides compounds, enantiomers, diastereomers, tautomers, prodrugs or salts thereof, wherein the compounds are compounds of formula Ie:

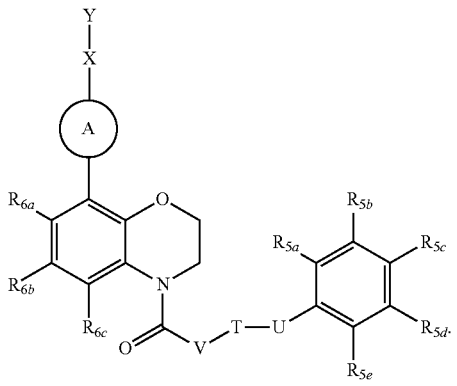

Ie

In another embodiment, the present invention provides compounds, enantiomers, diastereomers, tautomers, prodrugs or salts thereof, wherein the compounds are compounds of formula If:

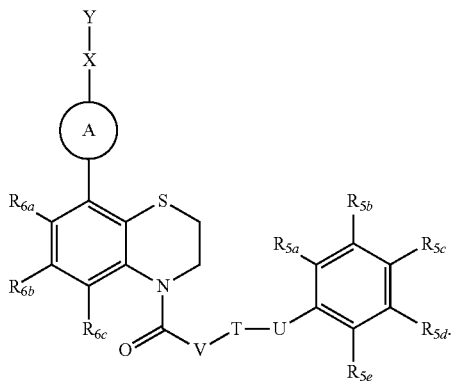

If

In yet another embodiment, the present invention provides compounds, enantiomers, diastereomers, tautomers, prodrugs or salts thereof, wherein the compounds are compounds of formula Ig:

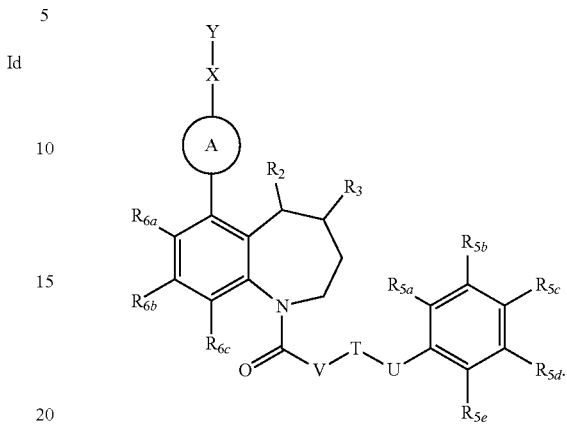

Ig

In yet another embodiment, the present invention provides compounds, enantiomers, diastereomers, tautomers, prodrugs or salts thereof, wherein the compounds are compounds of formula Ih:

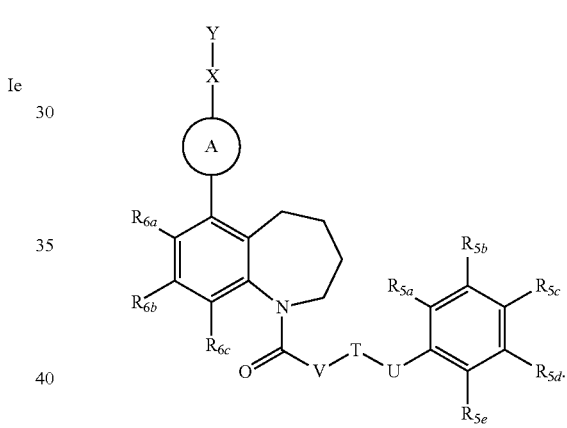

Ih

In yet another embodiment, the present invention provides compounds, enantiomers, diastereomers, tautomers, prodrugs or salts thereof, wherein the compounds are compounds of formula Ij:

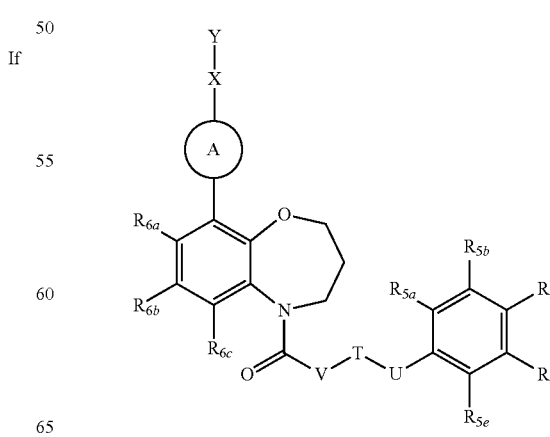

Ij

In another embodiment, the present invention provides compounds, enantiomers, diastereomers, tautomers, prodrugs or salts thereof, $R_{22}$ and $R_{22a}$ are both hydrogen.

In yet another embodiment, the present invention provides compounds, enantiomers, diastereomers, tautomers, prodrugs or salts thereof, wherein $R_{6a}$, $R_{6b}$ and $R_{6c}$ are all hydrogen.

In still yet another embodiment, the present invention provides compounds, enantiomers, diastereomers, tautomers, prodrugs or salts thereof, wherein V is a bond, —CH$_2$—, or O.

In one embodiment, the present invention provides compounds, enantiomers, diastereomers, tautomers, prodrugs or salts thereof, wherein V is a bond or O.

In another embodiment, the present invention provides compounds, enantiomers, diastereomers, tautomers, prodrugs or salts thereof, wherein V is a bond.

In another embodiment, the present invention provides compounds, enantiomers, diastereomers, tautomers, prodrugs or salts thereof, wherein U is O.

In another embodiment, the present invention provides compounds, enantiomers, diastereomers, tautomers, prodrugs or salts thereof, wherein V is a bond, —CH$_2$— or O and U is O.

In one embodiment, the present invention provides compounds, enantiomers, diastereomers, tautomers, prodrugs or salts thereof, wherein V is a bond or O and U is O.

In another embodiment, the present invention provides compounds, enantiomers, diastereomers, tautomers, prodrugs or salts thereof, wherein V is a bond and U is O.

In another embodiment, the present invention provides compounds, enantiomers, diastereomers, tautomers, prodrugs or salts thereof, wherein $R_4$, $R_{4a}$, $R_{6a}$, $R_{6b}$, $R_{6c}$, $R_{22}$ and $R_{22a}$ are all hydrogen, V is a bond and U is O.

In one embodiment, the present invention provides compounds, enantiomers, diastereomers, tautomers, prodrugs or salts thereof, wherein:

W is heteroaryl, which may be optionally substituted with one or more $R_{20}$'s,

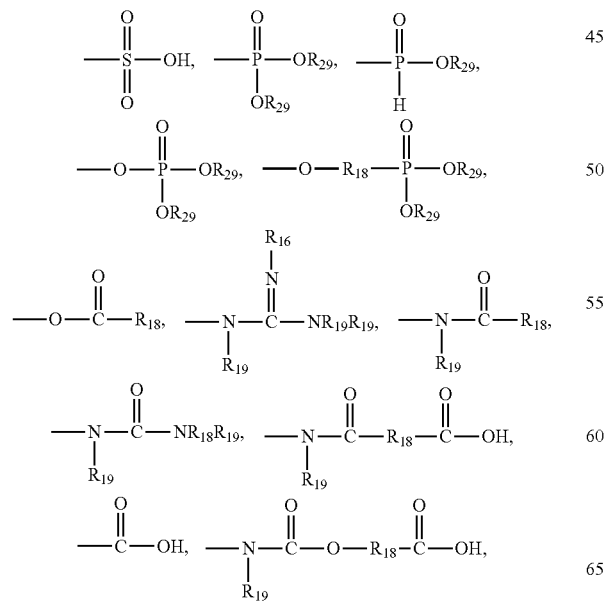
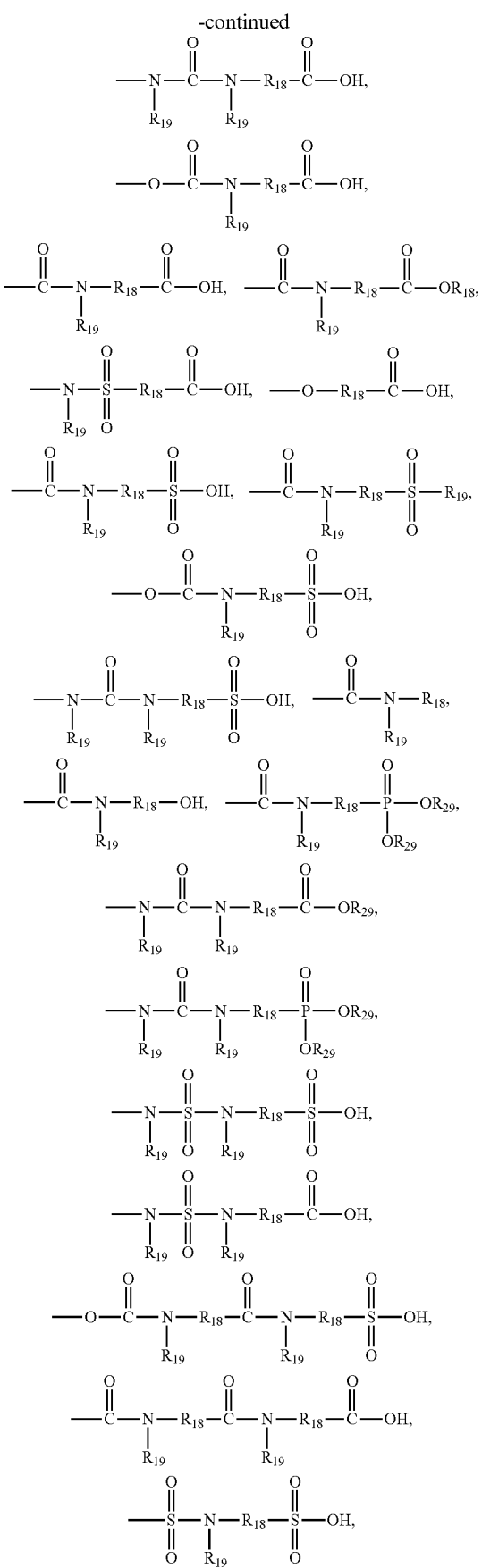

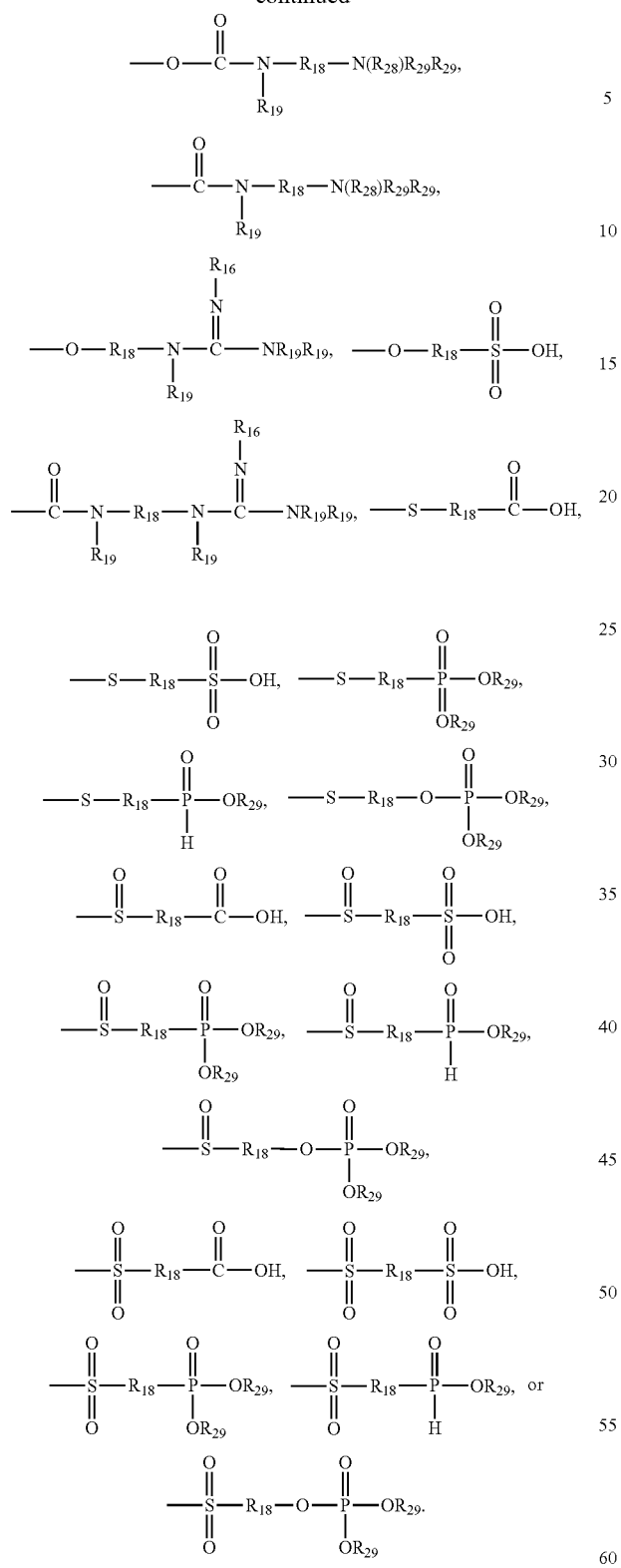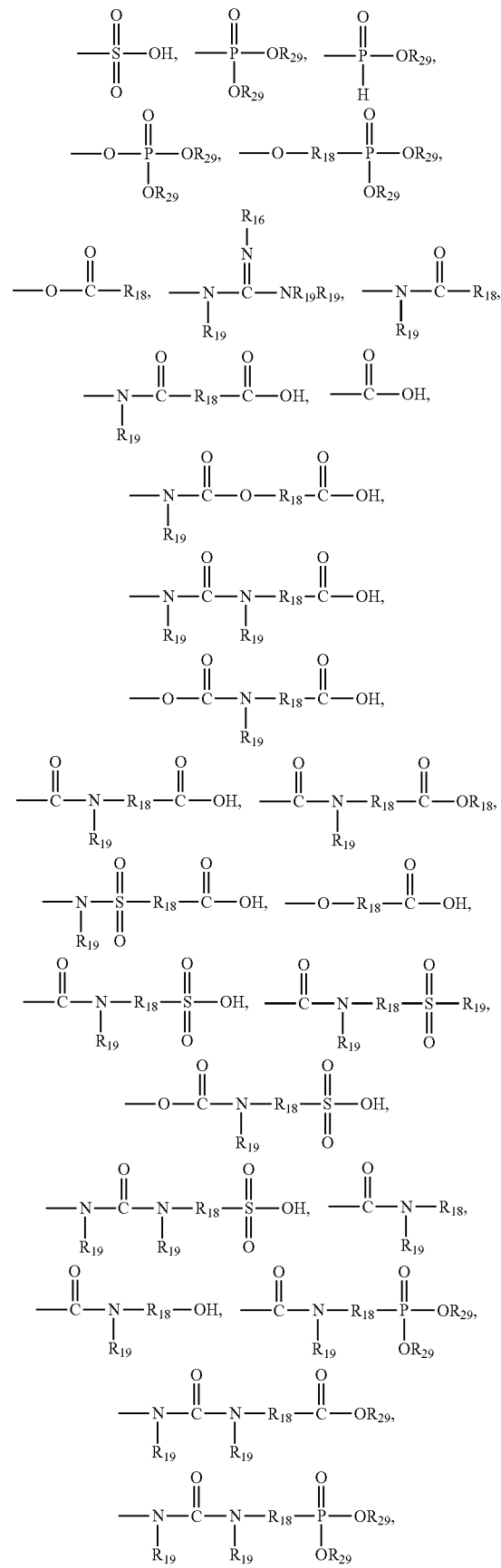
In another embodiment, the present invention provides compounds, enantiomers, diastereomers, tautomers, prodrugs or salts thereof, wherein:
W is heteroaryl, which may be optionally substituted with one or more $R_{20}$'s,

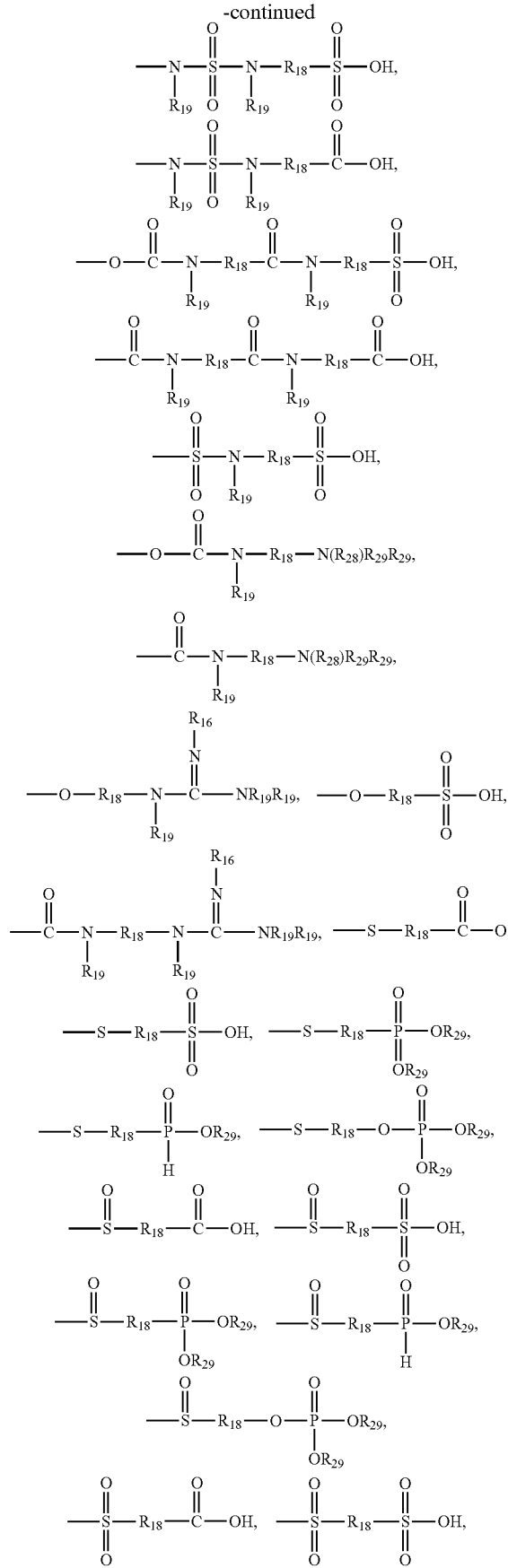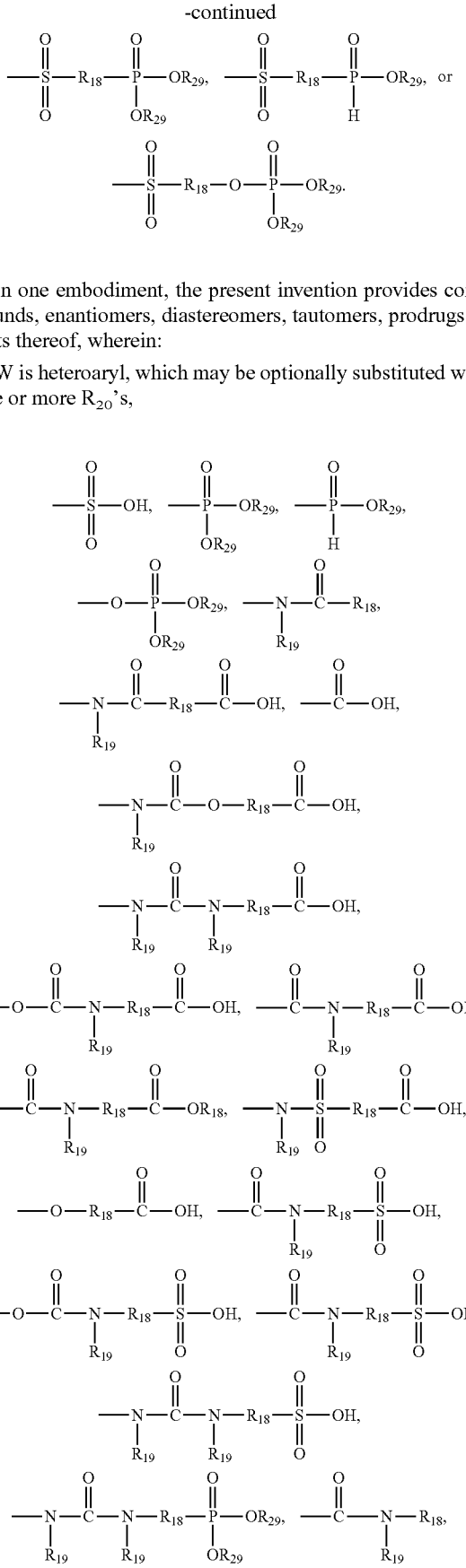
In one embodiment, the present invention provides compounds, enantiomers, diastereomers, tautomers, prodrugs or salts thereof, wherein:
W is heteroaryl, which may be optionally substituted with one or more $R_{20}$'s, -continued

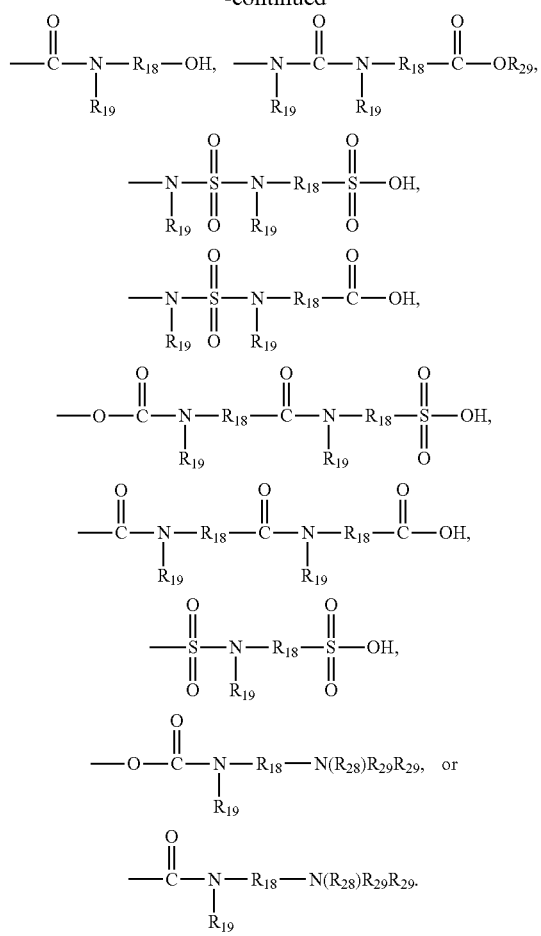

In another embodiment, the present invention provides compounds, enantiomers, diastereomers, tautomers, prodrugs or salts thereof, wherein:

W is heteroaryl, which may be optionally substituted with one or more $R_{20}$'s,

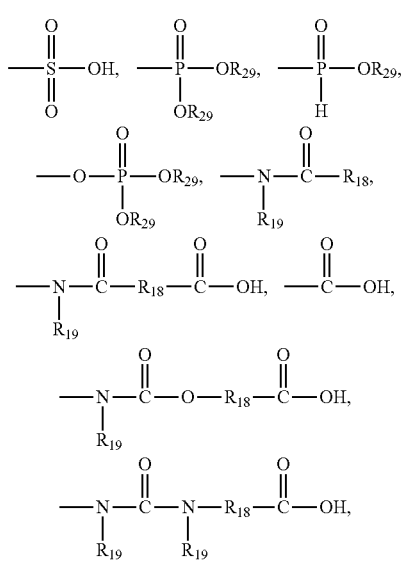

-continued

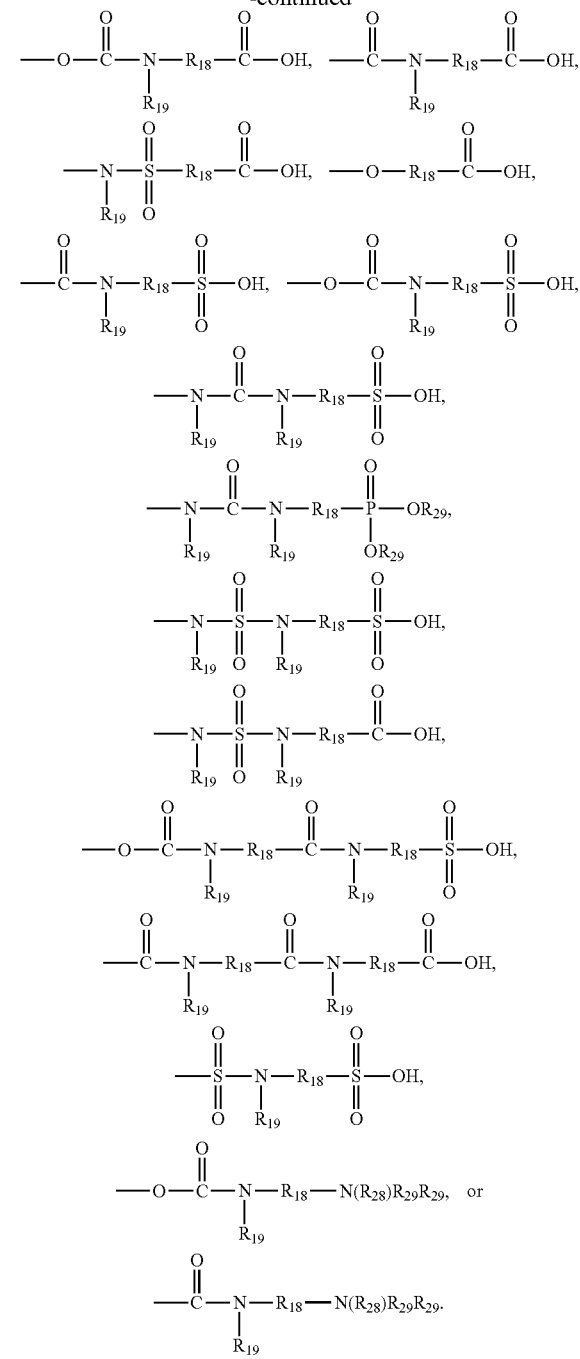

In one embodiment, the present invention provides compounds, enantiomers, diastereomers, tautomers, prodrugs or salts thereof, wherein:

W is

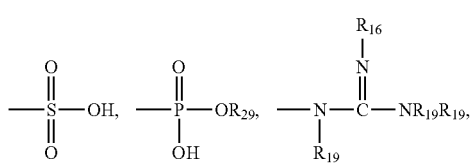

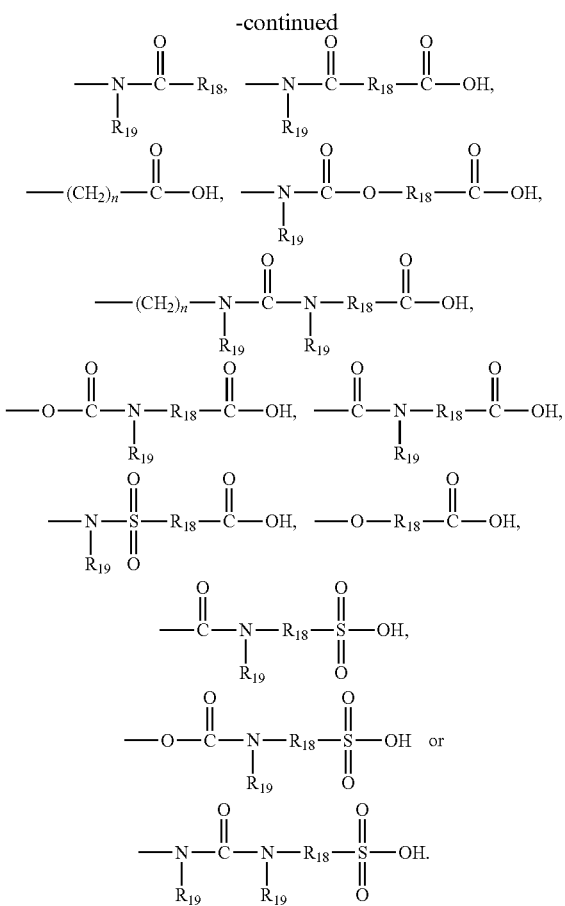

In another embodiment, the present invention provides compounds, enantiomers, diastereomers, tautomers, prodrugs or salts thereof, wherein A is a 5- to 6-membered aryl.

In another embodiment, the present invention provides compounds, enantiomers, diastereomers, tautomers, prodrugs or salts thereof, wherein A is a 6-membered aryl.

In another embodiment, the present invention provides compounds, enantiomers, diastereomers, tautomers, prodrugs or salts thereof, wherein A is phenyl.

In another embodiment, the present invention provides compounds, enantiomers, diastereomers, tautomers, prodrugs or salts thereof, wherein A is a 5- to 6-membered heteroaryl, wherein the heteroaryl contains 1-4 heteroatoms selected from N, O, and S.

In another embodiment, the present invention provides compounds, enantiomers, diastereomers, tautomers, prodrugs or salts thereof, wherein A is pyrazolyl, thiazolyl, tetrazolyl, thiophenyl or pyridinyl.

In another embodiment, the present invention provides compounds, enantiomers, diastereomers, tautomers, prodrugs or salts thereof, wherein A is pyrazolyl, tetrazolyl, thiophenyl or pyridinyl.

In another embodiment, the present invention provides compounds, enantiomers, diastereomers, tautomers, prodrugs or salts thereof, wherein A is pyrazolyl or thiazolyl.

In another embodiment, the present invention provides compounds, enantiomers, diastereomers, tautomers, prodrugs or salts thereof, wherein A is pyrazolyl.

In another embodiment, the present invention provides compounds, enantiomers, diastereomers, tautomers, prodrugs or salts thereof, wherein:

m is 1 or 2;

Q is $CR_{2a}R_2$, O, S, SO or $SO_2$;

T is a $(C_1-C_5)$-alkyl, which may be optionally substituted with one or more substituents selected from hydrogen, halogen, $C_1-C_6$ alkyl, $C_1-C_6$ alkoxy, CN, $(C_3-C_{12})$-cycloalkyl or halo$(C_1-C_6)$-alkyl and wherein a carbon atom of the alkyl chain may be replaced with a heteroatom selected from N, O, and S;

U is a bond or O;

V is a bond, —$CH_2$—, O, or a $(C_3-C_6)$-cycloalkyl;

Ring A is a 5- to 6-membered aryl or heteroaryl, wherein the aryl and heteroaryl may be optionally substituted with one or more substituents selected from hydrogen, halogen, oxo, $C_1-C_6$ alkyl, $C_1-C_6$ alkoxy, CN, $(C_3-C_{12})$-cycloalkyl and halo$(C_1-C_6)$-alkyl and the heteroaryl contains 1-4 heteroatoms selected from N, O, and S;

X is a bond, $(C_1-C_6)$-alkyloxy, $(C_3-C_6)$-cycloalkyl, $(C_3-C_6)$-cycloalkyl-$(C_1-C_6)$-alkyl, $(C_{5-10})$-aryl, $(C_{5-10})$-aryloxy, $(C_{5-10})$-aryl-$(C_1-C_6)$-alkyl, $(C_{5-10})$-aryl-oxy-$(C_1-C_6)$-alkyl, $(C_{5-10})$-aryl-$(C_1-C_6)$-alkyloxy or heteroaryl-$(C_1-C_6)$-alkyl, wherein the heteroaryl contains 4- to 10-members and 1-4 heteroatoms selected from N, O, and S and any alkyl, aryl and heteroaryl may be optionally substituted with one or more substituents selected from hydrogen, halogen, $C_1-C_6$ alkyl, $C_1-C_6$ alkoxy, CN, $(C_3-C_{12})$-cycloalkyl, $(C_3-C_{12})$-cycloalkyloxy and halo$(C_1-C_6)$-alkyl;

Y is —$(CR_{22}R_{22a})_n$—W;

W is heteroaryl, which may be optionally substituted with one or more $R_{20}$'s, heterocyclo, which may be optionally substituted with one or more $R_{20}$'s, —$N(R_{18})R_{19}$,

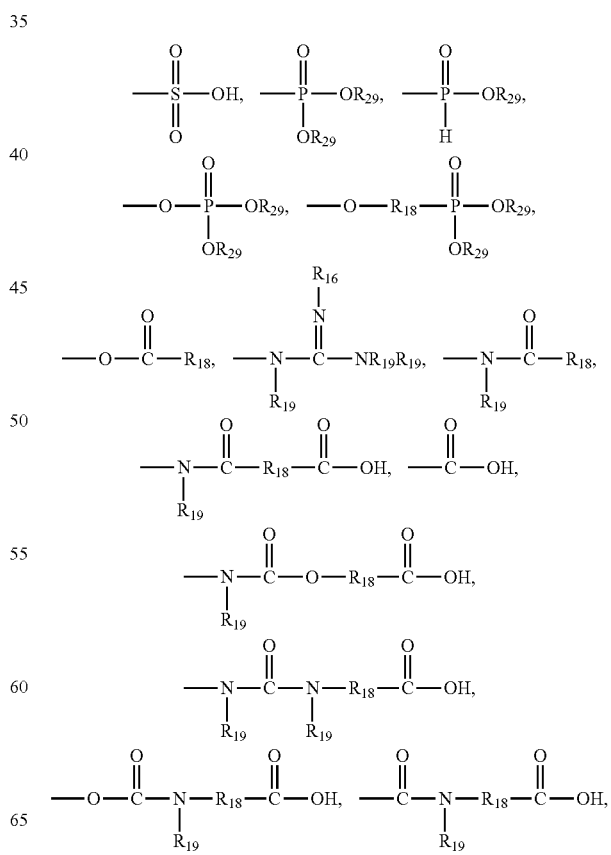

-continued

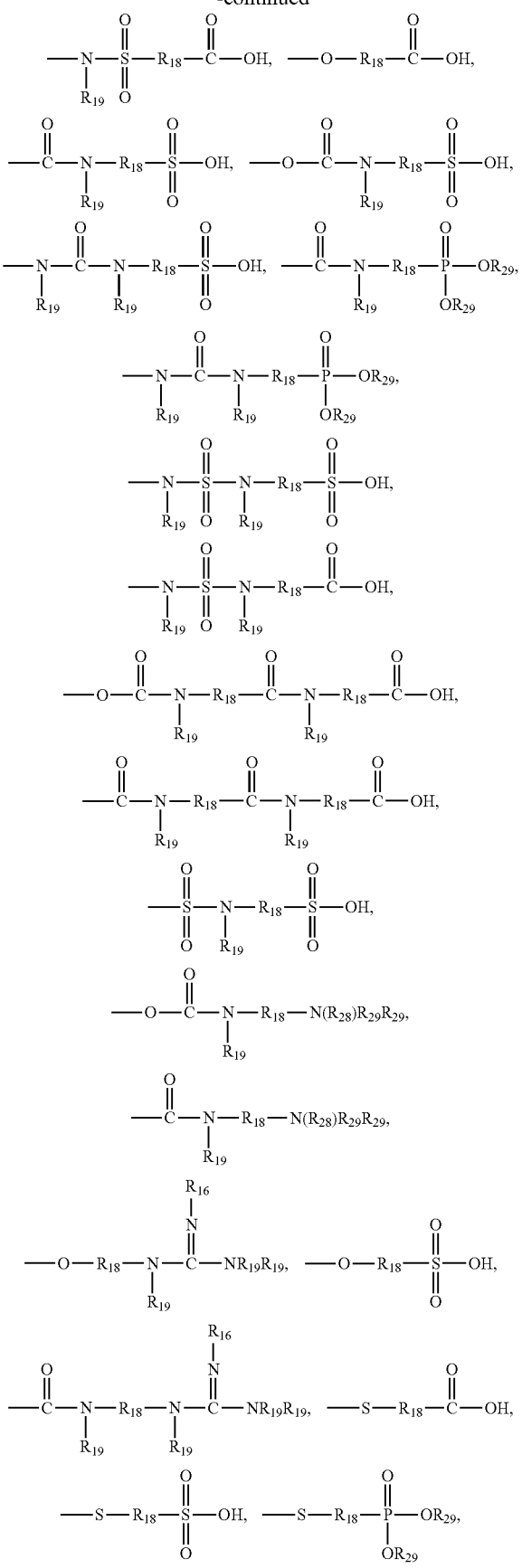

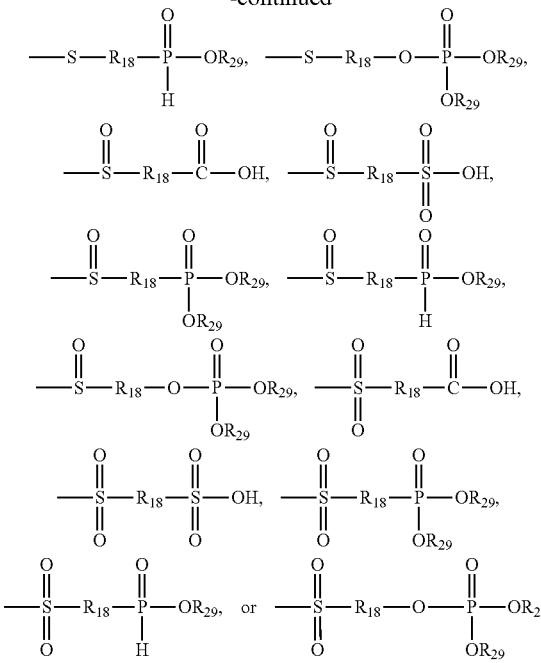

R$_2$ is hydrogen, (C$_1$-C$_6$)-alkyl, (C$_3$-C$_{12}$)-cycloalkyl or halo(C$_1$-C$_6$)-alkyl;

R$_{2a}$ is hydrogen, (C$_1$-C$_6$)-alkyl, (C$_3$-C$_{12}$)-cycloalkyl or halo(C$_1$-C$_6$)-alkyl;

or R$_2$ and R$_{2a}$ can optionally be linked to form a linking group containing 1-2 carbon atoms;

R$_3$ is hydrogen, (C$_1$-C$_6$)-alkyl, (C$_3$-C$_{12}$)-cycloalkyl or halo(C$_1$-C$_6$)-alkyl;

or R$_2$ and R$_3$ can optionally be linked to form a linking group containing 1-2 carbon atoms to form a (C$_3$-C$_4$)-cycloalkyl ring, a halo(C$_3$-C$_4$)-cycloalkyl ring or an aryl ring;

R$_4$, at each occurrence, is independently hydrogen or (C$_1$-C$_8$)alkyl;

R$_{4a}$, at each occurrence, is independently is hydrogen or (C$_1$-C$_8$)alkyl;

or R$_4$ and R$_{4a}$ can optionally be linked to form a linking group containing 1-2 carbon atoms;

R$_{5a}$ is hydrogen, halogen, C$_1$-C$_6$ alkyl, C$_1$-C$_6$ alkoxy, CN, (C$_3$-C$_6$)-cycloalkyl or halo(C$_1$-C$_6$)-alkyl;

R$_{5b}$ is hydrogen, halogen, C$_1$-C$_6$ alkyl, C$_1$-C$_6$ alkoxy, CN, (C$_3$-C$_6$)-cycloalkyl or halo(C$_1$-C$_6$)-alkyl;

R$_{5c}$ is hydrogen, halogen, C$_1$-C$_6$ alkyl, C$_1$-C$_6$ alkoxy, CN, (C$_3$-C$_6$)-cycloalkyl or halo(C$_1$-C$_6$)-alkyl;

R$_{5d}$ is hydrogen, halogen, C$_1$-C$_6$ alkyl, C$_1$-C$_6$ alkoxy, CN, (C$_3$-C$_6$)-cycloalkyl or halo(C$_1$-C$_6$)-alkyl;

R$_{5e}$ is hydrogen, halogen, C$_1$-C$_6$ alkyl, C$_1$-C$_6$ alkoxy, CN, (C$_3$-C$_6$)-cycloalkyl or halo(C$_1$-C$_6$)-alkyl;

or two of R$_{5a}$, R$_{5b}$, R$_{5c}$, R$_{5d}$ or R$_{5e}$ may be taken together with the atoms to which both are attached form a 3- to 8-membered ring, which may optionally contain 1-4 heteroatoms selected from N, O, and S;

R$_{6a}$ is hydrogen, halogen or C$_1$-C$_6$ alkyl;

R$_{6b}$ is hydrogen, halogen or C$_1$-C$_6$ alkyl;

R$_{6c}$ is hydrogen, halogen or C$_1$-C$_6$ alkyl;

n is 0-4;

R$_{16}$ is H or —CN;

R$_{18}$, at each occurrence, is independently (C$_1$-C$_8$)alkyl, (C$_3$-C$_{12}$)-cycloalkyl, (C$_1$-C$_8$)alkyl-(C$_3$-C$_{12}$)-cycloalkyl-(C$_1$-C$_8$)alkyl, (C$_{5-10}$-aryl, (C$_5$-C$_{10}$)-aryl(C$_1$-C$_8$)alkyl, a heteroaryl, a heteroaryl($C_1$-$C_8$)alkyl or a heterocyclo, all of which may be optionally substituted with one or more $R_{20}$'s and wherein the heteroaryl and heterocyclo contain 4- to 10-members and contain 1-4 heteroatoms selected from N, O, and S;

$R_{19}$, at each occurrence, is independently hydrogen, ($C_1$-$C_6$)-alkyl, ($C_3$-$C_{12}$)-cycloalkyl, ($C_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is selected from halo, —OH, ($C_1$-$C_6$)-alkyl, ($C_2$-$C_6$)-alkenyl, ($C_2$-$C_6$)-alkynyl, —($C_3$-$C_{12}$)-cycloalkyl, ($C_1$-$C_6$)-alkyloxy, cyano, oxo, nitro, —COOH, —$SO_3H$, —CO($C_1$-$C_6$)-alkyl, —CO($C_6$-$C_{12}$)-aryl, —$CO_2$($C_1$-$C_6$)-alkyl, —$CONR_{28}R_{29}$, —$NR_{28}R_{29}$, —$NR_{28}C(=O)NR_{28}R_{29}$, —$NR_{28}C(=NR_{29})NR_{28}R_{29}$, —$SR_{28}$, —S(=O)(=$NR_{28}$)$R_{29}$, —S(—OH)$R_{29}$, —S(=O)$R_{29}$, —$NR_{29}CO_2$($C_1$-$C_6$)-alkyl, —O(C=O)—($C_1$-$C_6$)-alkyl, —O(C=O)$NR_{28}R_{29}$, —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{28}R_{29}$, —($C_1$-$C_6$)-alkyl-$CO_2$($C_1$-$C_6$)-alkyl, —O—P(=O)(OH)($OR_{29}$), —O—$CR_{28}R_{29}$—P(=O)(OH)($OR_{29}$), —P(=O)(OH)($OR_{29}$), ($C_{6-10}$)aryl, ($C_{6-10}$)aryl($C_1$-$C_6$)-alkyl, ($C_{6-10}$) aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_{28}R_{29}$, —$NR_{28}R_{29}$, —O(C=O)—($C_1$-$C_6$)-alkyl, —O(C=O)$NR_{28}R_{29}$, —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{28}R_{29}$, —($C_1$-$C_6$)-alkyl-$CO_2$($C_1$-$C_6$)-alkyl, —O—P(=O)(OH)($OR_{29}$), —O—$CR_{28}R_{29}$—P(=O)(OH)($OR_{29}$), —P(=O)(OH)($OR_{29}$), —S(=O)$_2$OH, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

$R_{22}$, at each occurrence, is independently hydrogen, ($C_1$-$C_6$)-alkyl, ($C_3$-$C_{12}$)-cycloalkyl, ($C_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, $C_1$-$C_6$ alkyl, $C_1$-$C_6$ alkoxy, CN, ($C_3$-$C_{12}$)-cycloalkyl and halo($C_1$-$C_6$)-alkyl;

$R_{22a}$, at each occurrence, is independently hydrogen, ($C_1$-$C_6$)-alkyl, ($C_3$-$C_{12}$)-cycloalkyl, ($C_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, $C_1$-$C_6$ alkyl, $C_1$-$C_6$ alkoxy, CN, ($C_3$-$C_{12}$)-cycloalkyl and halo($C_1$-$C_6$)-alkyl;

$R_{28}$ and $R_{29}$, at each occurrence, are independently hydrogen or ($C_1$-$C_8$)alkyl, wherein the alkyl may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_{38}R_{39}$, —$NR_{38}R_{39}$, —O(C=O)—($C_1$-$C_6$)-alkyl, —O(C=O)$NR_{38}R_{39}$, —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{38}R_{39}$, —($C_1$-$C_6$)-alkyl-$CO_2$($C_1$-$C_6$)-alkyl, —O—P(=O)(OH)($OR_{39}$), —O—$CR_{38}R_{39}$—P(=O)(OH)($OR_{39}$), —P(=O)(OH)($OR_{39}$), —S(=O)$_2$OH, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

or $R_{28}$ and $R_{29}$ are taken together with the nitrogen to which both are attached to form a 3- to 8-membered ring, which may optionally contain 1-4 heteroatoms selected from N, O, and S;

$R_{38}$ and $R_{39}$, at each occurrence, are independently hydrogen or ($C_1$-$C_8$)alkyl;

or $R_{38}$ and $R_{39}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, prodrugs or salts thereof, wherein:

m is 1 or 2;

Q is $CR_{2a}R_2$, O, S, SO or $SO_2$;

T is ($C_1$-$C_5$)-alkyl or ($C_2$-$C_6$)-alkenyl, both of which may be optionally substituted with one or more substituents selected from hydrogen, $^2H$, halogen, $C_1$-$C_6$ alkyl, $C_1$-$C_6$ alkoxy, CN, ($C_3$-$C_{12}$)-cycloalkyl or halo($C_1$-$C_6$)-alkyl and wherein a carbon atom of the alkyl chain may be replaced with a heteroatom selected from N, O, and S;

U is a bond, $NR_{7a}$ or O;

V is a bond, —$CH_2$—, or O;

Ring A is a 5- to 6-membered aryl or heteroaryl, wherein the aryl and heteroaryl may be optionally substituted with one or more substituents selected from hydrogen, halogen, oxo, $C_1$-$C_6$ alkyl, $C_1$-$C_6$ alkoxy, CN, ($C_3$-$C_{12}$)-cycloalkyl and halo ($C_1$-$C_6$)-alkyl and the heteroaryl contains 1-4 heteroatoms selected from N, O, and S;

X is a bond, ($C_1$-$C_6$)-alkyloxy, ($C_3$-$C_6$)-cycloalkyl, ($C_3$-$C_6$)-cycloalkyl-($C_1$-$C_6$)-alkyl, ($C_{5-10}$)-aryl, ($C_{5-10}$)-aryloxy, ($C_{5-10}$)-aryl-($C_1$-$C_6$)-alkyl, ($C_{5-10}$)-aryl-oxy-($C_1$-$C_6$)-alkyl, ($C_{5-10}$)-aryl-($C_1$-$C_6$)-alkyloxy or heteroaryl-($C_1$-$C_6$)-alkyl, wherein the heteroaryl contains 4- to 10-members and 1-4 heteroatoms selected from N, O, and S and any alkyl, aryl and heteroaryl may be optionally substituted with one or more substituents selected from hydrogen, halogen, $C_1$-$C_6$ alkyl, $C_1$-$C_6$ alkoxy, CN, —$NR_{28}R_{29}$, ($C_3$-$C_{12}$)-cycloalkyl, ($C_3$-$C_{12}$)-cycloalkyloxy and halo($C_1$-$C_6$)-alkyl;

Y is —($CR_{22}R_{22a}$)$_n$—W;

W is heteroaryl, which may be optionally substituted with one or more $R_{20}$'s,

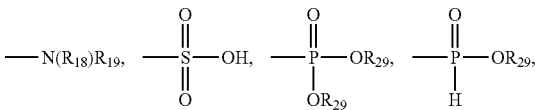

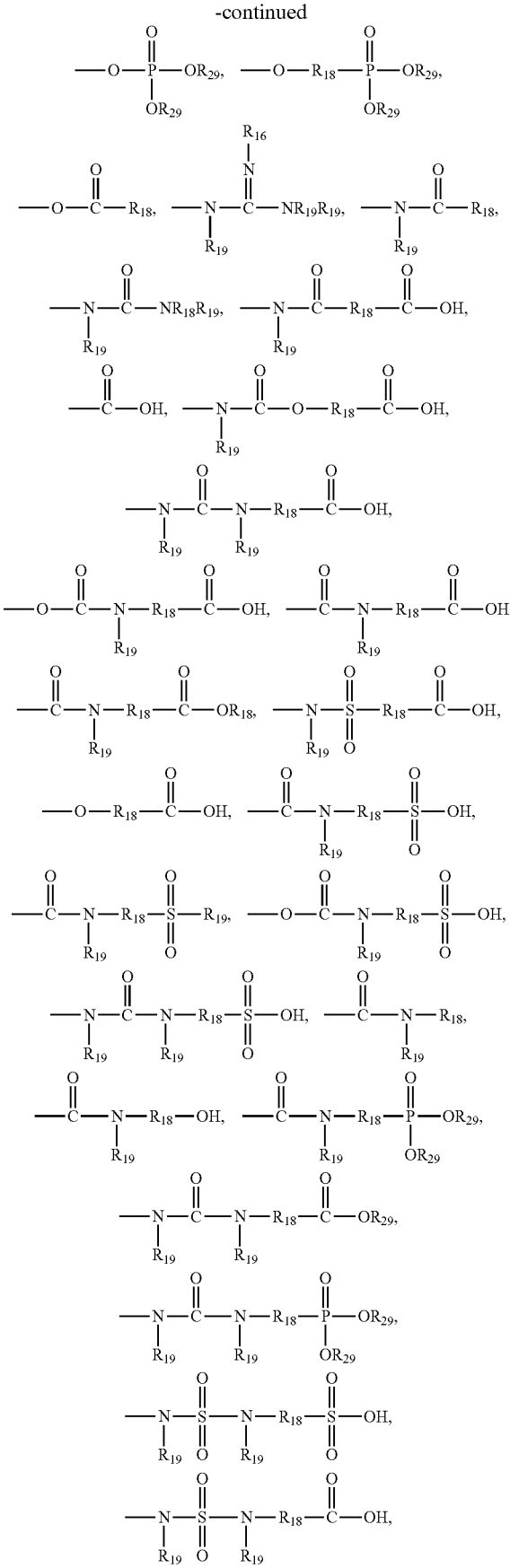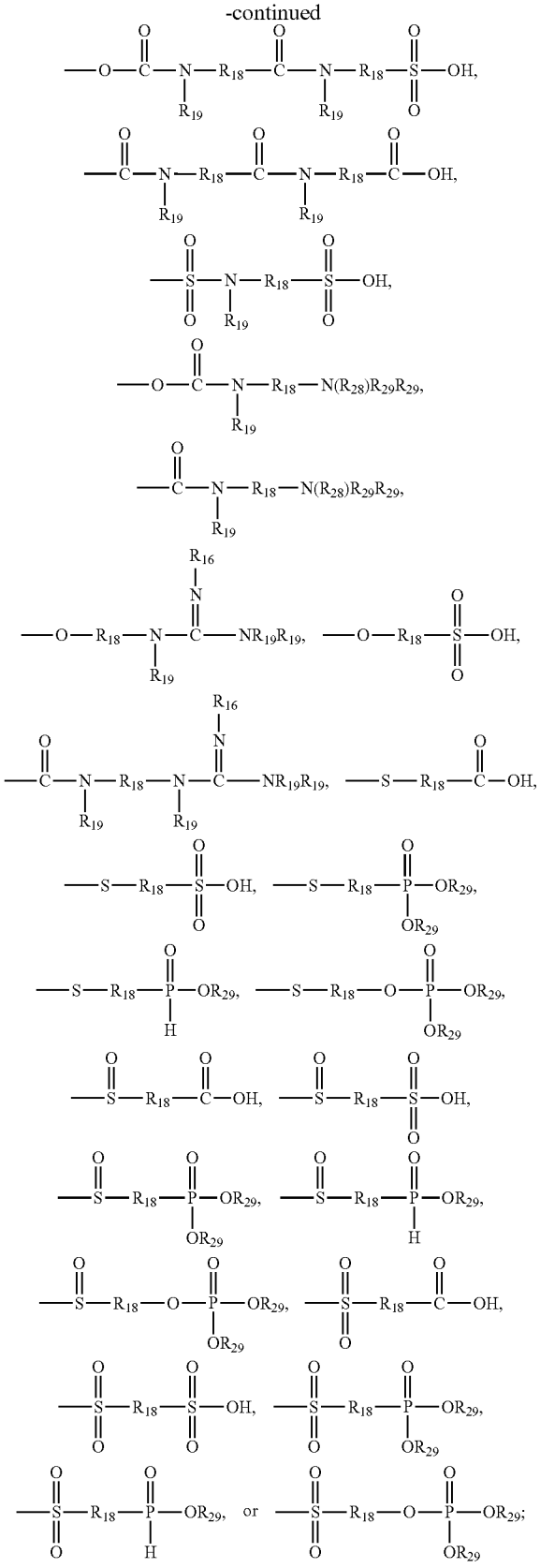
$R_2$ is hydrogen, —OH, oxo, $(C_1$-$C_6)$-alkyl, $(C_3$-$C_{12})$-cycloalkyl or halo$(C_1$-$C_6)$-alkyl;

$R_{2a}$ is hydrogen, —OH, $(C_1\text{-}C_6)$-alkyl, $(C_3\text{-}C_{12})$-cycloalkyl or halo$(C_1\text{-}C_6)$-alkyl;

or $R_2$ and $R_{2a}$ can optionally be linked to form a linking group containing 1-2 carbon atoms;

$R_3$ is hydrogen, $(C_1\text{-}C_6)$-alkyl or halo$(C_1\text{-}C_6)$-alkyl;

or $R_2$ and $R_3$ can optionally be linked to form a linking group containing 1-5 carbon atoms to form a $(C_3\text{-}C_7)$-cycloalkyl ring, a halo$(C_3\text{-}C_7)$-cycloalkyl ring or an aryl ring;

$R_4$, at each occurrence, is independently hydrogen, —OH, halogen or $(C_1\text{-}C_8)$alkyl;

$R_{4a}$, at each occurrence, is independently is hydrogen, —OH, halogen or $(C_1\text{-}C_8)$alkyl;

or $R_4$ and $R_{4a}$ can optionally be linked to form a linking group containing 1-3 carbon atoms;

$R_{5a}$ is hydrogen, halogen, $C_1\text{-}C_6$ alkyl, CN, $(C_3\text{-}C_6)$-cycloalkyl or halo$(C_1\text{-}C_6)$-alkyl;

$R_{5b}$ is hydrogen, halogen, $C_1\text{-}C_6$ alkyl, CN, $(C_3\text{-}C_6)$-cycloalkyl or halo$(C_1\text{-}C_6)$-alkyl;

$R_{5c}$ is hydrogen, halogen, $C_1\text{-}C_6$ alkyl, CN, $(C_3\text{-}C_6)$-cycloalkyl or halo$(C_1\text{-}C_6)$-alkyl;

$R_{5d}$ is hydrogen, halogen, $C_1\text{-}C_6$ alkyl, CN, $(C_3\text{-}C_6)$-cycloalkyl or halo$(C_1\text{-}C_6)$-alkyl;

$R_{5e}$ is hydrogen, halogen, $C_1\text{-}C_6$ alkyl, CN, $(C_3\text{-}C_6)$-cycloalkyl or halo$(C_1\text{-}C_6)$-alkyl;

or two of $R_{5a}$, $R_{5b}$, $R_{5c}$, $R_{5d}$ or $R_{5e}$ may be taken together with the atoms to which both are attached form a 3- to 8-membered ring, which may optionally contain 1-4 heteroatoms selected from N, O, and S;

$R_{6a}$ is hydrogen, halogen or $C_1\text{-}C_6$ alkyl;
$R_{6b}$ is hydrogen, halogen or $C_1\text{-}C_6$ alkyl;
$R_{6c}$ is hydrogen, halogen or $C_1\text{-}C_6$ alkyl;
$R_{7a}$ is hydrogen or $C_1\text{-}C_6$ alkyl;
n is 0-5;
$R_{16}$ is H or —CN;

$R_{18}$, at each occurrence, is independently $(C_1\text{-}C_8)$alkyl, $(C_3\text{-}C_{12})$-cycloalkyl, $(C_1\text{-}C_8)$alkyl-$(C_3\text{-}C_{12})$-cycloalkyl-$(C_1\text{-}C_8)$alkyl, $(C_{5\text{-}10})$-aryl, $(C_{5\text{-}10})$-aryl$(C_1\text{-}C_8)$alkyl, a heteroaryl, a heteroaryl$(C_1\text{-}C_8)$alkyl or a heterocyclo, all of which may be optionally substituted with one or more $R_{20}$'s and wherein the heteroaryl and heterocyclo contain 4- to 10-members and contain 1-4 heteroatoms selected from N, O, and S;

$R_{19}$, at each occurrence, is independently hydrogen, $(C_1\text{-}C_6)$-alkyl, $(C_3\text{-}C_{12})$-cycloalkyl, $(C_{6\text{-}10})$aryl or a 4- to 10-membered heteroaryl, which contains 1-4 heteroatoms selected from N, O, and S, wherein the alkyl, cycloalkyl, aryl, heteroaryl and heterocyclo may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is selected from halo, —OH, $(C_1\text{-}C_6)$-alkyl, $(C_2\text{-}C_6)$-alkenyl, $(C_2\text{-}C_6)$-alkynyl, —$(C_3\text{-}C_{12})$-cycloalkyl, $(C_1\text{-}C_6)$-alkyloxy, cyano, oxo, nitro, —COOH, —SO$_3$H, —CO$(C_1\text{-}C_6)$-alkyl, —CO$(C_6\text{-}C_{12})$-aryl, —CO$_2$$(C_1\text{-}C_6)$-alkyl, —CONR$_{28}$R$_{29}$, —NR$_{28}$R$_{29}$, —NR$_{28}$C(=O)NR$_{28}$R$_{29}$, —NR$_{28}$C(=NR$_{29}$)NR$_{28}$R$_{29}$, —SR$_{28}$, —S(=O)(=NR$_{28}$)R$_{29}$, —S(—OH)R$_{29}$, —S(=O)R$_{29}$, —S(=O)$_2$R$_{29}$, —NR$_{29}$CO$_2$$(C_1\text{-}C_6)$-alkyl, —NR$_{28}$SO$_2$R$_{19}$, —O(C=O)—$(C_1\text{-}C_6)$-alkyl, —O(C=O)NR$_{28}$R$_{29}$; —$(C_1\text{-}C_6)$-alkylCOOH, —$(C_1\text{-}C_6)$-alkylOH, —$(C_1\text{-}C_6)$-alkyl(NH$_2$)COOH, —$(C_1\text{-}C_6)$-alkylCONR$_{28}$R$_{29}$, —$(C_1\text{-}C_6)$-alkyl-CO$_2$$(C_1\text{-}C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), $(C_{6\text{-}10})$aryl, $(C_{6\text{-}10})$aryl$(C_1\text{-}C_6)$-alkyl, $(C_{6\text{-}10})$aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1\text{-}C_6)$-alkyl, $(C_2\text{-}C_6)$-alkenyl, $(C_2\text{-}C_6)$-alkynyl, $(C_1\text{-}C_6)$-alkyloxy, cyano, nitro, —COOH, —CO$(C_1\text{-}C_6)$-alkyl, —CO$_2$$(C_1\text{-}C_6)$-alkyl, —CONR$_{28}$R$_{29}$, —NR$_{28}$R$_{29}$, —N(R$_{28}$)R$_{29}$R$_{29}$, —O(C=O)—$(C_1\text{-}C_6)$-alkyl, —O(C=O)NR$_{28}$R$_{29}$; —$(C_1\text{-}C_6)$-alkylCOOH, —$(C_1\text{-}C_6)$-alkylOH, —$(C_1\text{-}C_6)$-alkyl(NH$_2$)COOH, —$(C_1\text{-}C_6)$-alkylCONR$_{28}$R$_{29}$, —$(C_1\text{-}C_6)$-alkyl-CO$_2$$(C_1\text{-}C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, $(C_{6\text{-}10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1\text{-}C_6)$alkyl, and halo$(C_1\text{-}C_6)$alkyloxy;

$R_{22}$, at each occurrence, is independently hydrogen, —OH, $(C_1\text{-}C_6)$-alkyl, $(C_3\text{-}C_{12})$-cycloalkyl, $(C_{6\text{-}10})$aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, $C_1\text{-}C_6$ alkyl, $C_1\text{-}C_6$ alkoxy, CN, $(C_3\text{-}C_{12})$-cycloalkyl and halo$(C_1\text{-}C_6)$-alkyl;

$R_{22a}$, at each occurrence, is independently hydrogen, —OH, $(C_1\text{-}C_6)$-alkyl, $(C_3\text{-}C_{12})$-cycloalkyl, $(C_{6\text{-}10})$aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, $C_1\text{-}C_6$ alkyl, $C_1\text{-}C_6$ alkoxy, CN, $(C_3\text{-}C_{12})$-cycloalkyl and halo$(C_1\text{-}C_6)$-alkyl;

$R_{28}$ and $R_{29}$, at each occurrence, are independently hydrogen or $(C_1\text{-}C_8)$alkyl, wherein the alkyl may be optionally substituted with one or more substituents selected from the group consisting of: halo, —OH, $(C_1\text{-}C_6)$-alkyl, $(C_2\text{-}C_6)$-alkenyl, $(C_2\text{-}C_6)$-alkynyl, $(C_1\text{-}C_6)$-alkyloxy, cyano, nitro, —COOH, —CO$(C_1\text{-}C_6)$-alkyl, —CO$_2$$(C_1\text{-}C_6)$-alkyl, —CONR$_{38}$R$_{39}$, —NR$_{38}$R$_{39}$, —O(C=O)—$(C_1\text{-}C_6)$-alkyl, —O(C=O)NR$_{38}$R$_{39}$, —$(C_1\text{-}C_6)$-alkylCOOH, —$(C_1\text{-}C_6)$-alkylOH, —$(C_1\text{-}C_6)$-alkyl(NH$_2$)COOH, —$(C_1\text{-}C_6)$-alkylCONR$_{38}$R$_{39}$, —$(C_1\text{-}C_6)$-alkyl-CO$_2$$(C_1\text{-}C_6)$-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, $(C_{6\text{-}10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1\text{-}C_6)$alkyl, and halo$(C_1\text{-}C_6)$alkyloxy;

or $R_{28}$ and $R_{29}$ are taken together with the nitrogen to which both are attached to form a 3- to 8-membered ring, which may optionally contain 1-4 heteroatoms selected from N, O, and S;

$R_{38}$ and $R_{39}$, at each occurrence, are independently hydrogen or $(C_1\text{-}C_8)$alkyl;

or $R_{38}$ and $R_{39}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, prodrugs or salts thereof, wherein:

m is 1 or 2;
Q is CR$_{2a}$R$_2$, O or S;

T is $(C_1$-$C_5)$-alkyl, which may be optionally substituted with one or more substituents selected from hydrogen, $^2$H, halogen, $C_1$-$C_6$ alkyl, $C_1$-$C_6$ alkoxy, CN, $(C_3$-$C_{12})$-cycloalkyl or halo$(C_1$-$C_6)$-alkyl and wherein a carbon atom of the alkyl chain may be replaced with a heteroatom selected from N, O, and S;

U is a bond or O;

V is a bond or O;

Ring A is a 5- to 6-membered aryl or heteroaryl, wherein the aryl and heteroaryl may be optionally substituted with one or more substituents selected from hydrogen, halogen, oxo, $C_1$-$C_6$ alkyl, $C_1$-$C_6$ alkoxy, CN, $(C_3$-$C_{12})$-cycloalkyl and halo $(C_1$-$C_6)$-alkyl and the heteroaryl contains 1-4 heteroatoms selected from N, O, and S;

X is a bond, $(C_1$-$C_6)$-alkyloxy, $(C_3$-$C_6)$-cycloalkyl, $(C_3$-$C_6)$-cycloalkyl-$(C_1$-$C_6)$-alkyl, $(C_{5-10})$-aryl, $(C_{5-10})$-aryloxy, $(C_{5-10})$-aryl-$(C_1$-$C_6)$-alkyl or heteroaryl-$(C_1$-$C_6)$-alkyl, wherein the heteroaryl contains 4- to 10-members and 1-4 heteroatoms selected from N, O, and S and any alkyl, aryl and heteroaryl may be optionally substituted with one or more substituents selected from hydrogen, halogen, $C_1$-$C_6$ alkyl, $C_1$-$C_6$ alkoxy, CN, $(C_3$-$C_{12})$-cycloalkyl, $(C_3$-$C_{12})$-cycloalkyloxy and halo$(C_1$-$C_6)$-alkyl;

Y is —$(CR_{22}R_{22a})_n$—W;

W is heteroaryl, which may be optionally substituted with one or more $R_{20}$'s,

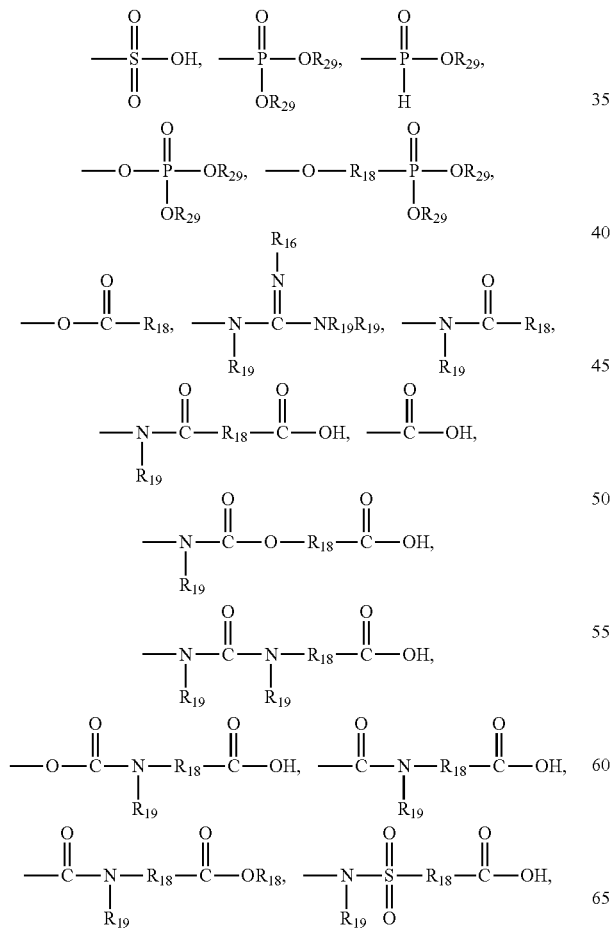
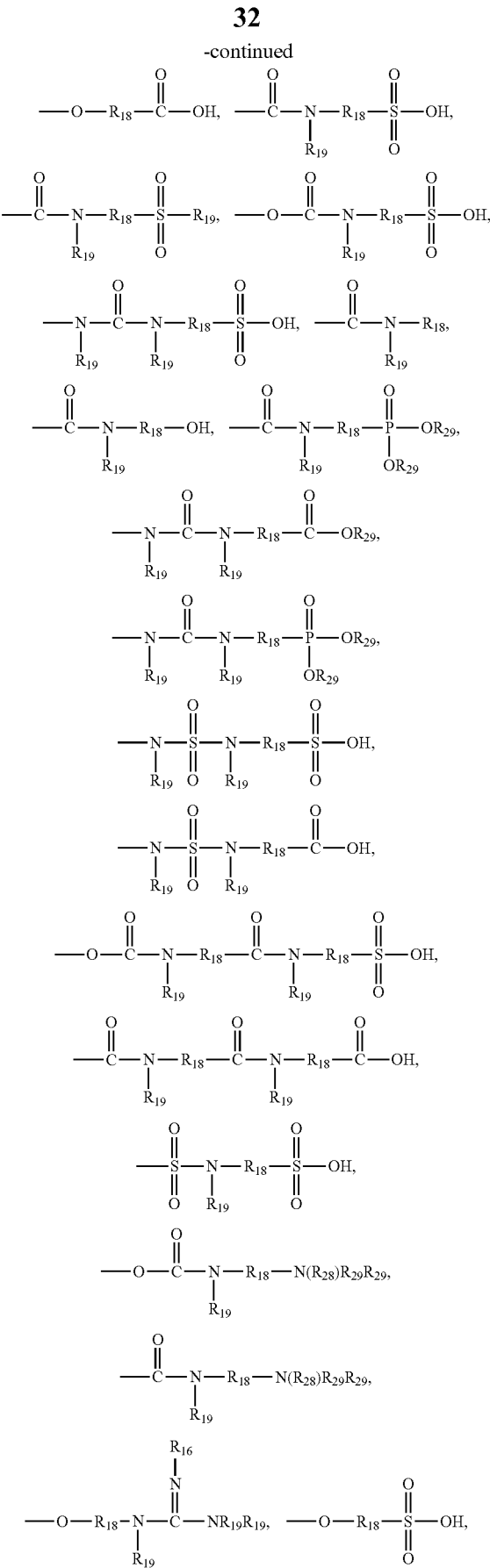

-continued

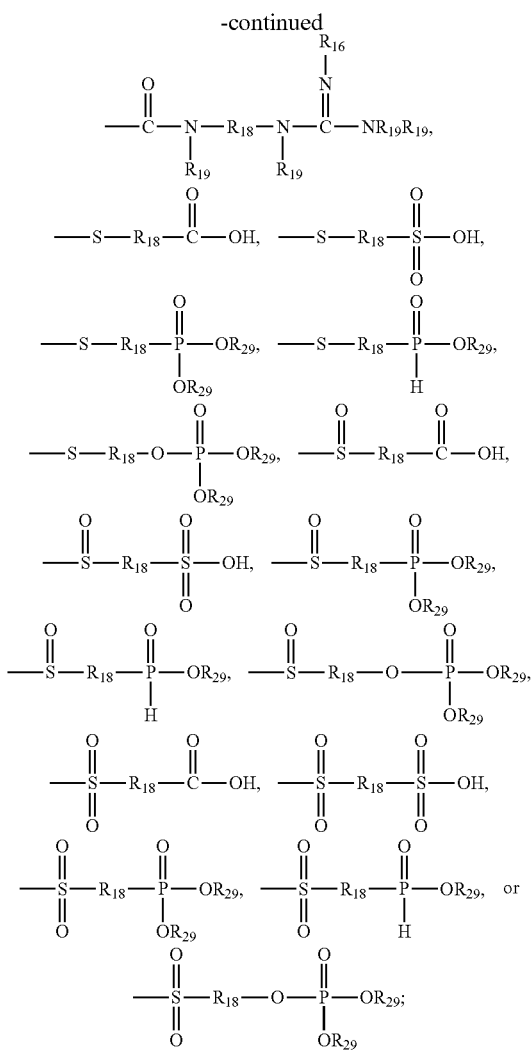

R$_2$ is hydrogen, OH, (C$_1$-C$_6$)-alkyl, (C$_3$-C$_{12}$)-cycloalkyl or halo(C$_1$-C$_6$)-alkyl;

R$_{2a}$ is hydrogen, —OH, (C$_1$-C$_6$)-alkyl, (C$_3$-C$_{12}$)-cycloalkyl or halo(C$_1$-C$_6$)-alkyl;

or R$_2$ and R$_{2a}$ can optionally be linked to form a linking group containing 1-2 carbon atoms;

R$_3$ is hydrogen or (C$_1$-C$_6$)-alkyl;

or R$_2$ and R$_3$ can optionally be linked to form a linking group containing 1-5 carbon atoms to form a (C$_3$-C$_7$)-cycloalkyl ring, a halo(C$_3$-C$_7$)-cycloalkyl ring or an aryl ring;

R$_4$, at each occurrence, is independently hydrogen, —OH, or (C$_1$-C$_8$)alkyl;

R$_{4a}$, at each occurrence, is independently is hydrogen, —OH, or (C$_1$-C$_8$)alkyl;

or R$_4$ and R$_{4a}$ can optionally be linked to form a linking group containing 1-2 carbon atoms;

R$_{5a}$ is hydrogen, halogen, C$_1$-C$_6$ alkyl, (C$_3$-C$_6$)-cycloalkyl or halo(C$_1$-C$_6$)-alkyl;

R$_{5b}$ is hydrogen, halogen, C$_1$-C$_6$ alkyl, (C$_3$-C$_6$)-cycloalkyl or halo(C$_1$-C$_6$)-alkyl;

R$_{5c}$ is hydrogen, halogen, C$_1$-C$_6$ alkyl, (C$_3$-C$_6$)-cycloalkyl or halo(C$_1$-C$_6$)-alkyl;

R$_{5d}$ is hydrogen, halogen, C$_1$-C$_6$ alkyl, (C$_3$-C$_6$)-cycloalkyl or halo(C$_1$-C$_6$)-alkyl;

R$_{5e}$ is hydrogen, halogen, C$_1$-C$_6$ alkyl, (C$_3$-C$_6$)-cycloalkyl or halo(C$_1$-C$_6$)-alkyl;

or two of R$_{5a}$, R$_{5b}$, R$_{5c}$, R$_{5d}$ or R$_{5e}$ may be taken together with the atoms to which both are attached form a 3- to 8-membered ring, which may optionally contain 1-4 heteroatoms selected from N, O, and S;

R$_{6a}$ is hydrogen or C$_1$-C$_6$ alkyl;

R$_{6b}$ is hydrogen or C$_1$-C$_6$ alkyl;

R$_{6c}$ is hydrogen or C$_1$-C$_6$ alkyl;

n is 0-3;

R$_{18}$, at each occurrence, is independently (C$_1$-C$_8$)alkyl, (C$_3$-C$_{12}$)-cycloalkyl, (C$_{5-10}$)-aryl, a heteroaryl, a heteroaryl(C$_1$-C$_8$)alkyl or a heterocyclo, all of which may be optionally substituted with one or more R$_{20}$'s and wherein the heteroaryl and heterocyclo contain 4- to 10-members and contain 1-4 heteroatoms selected from N, O, and S;

R$_{19}$, at each occurrence, is independently hydrogen, (C$_1$-C$_6$)-alkyl, (C$_3$-C$_{12}$)-cycloalkyl, (C$_{6-10}$)aryl or a 4- to 10-membered heteroaryl, which contains 1-4 heteroatoms selected from N, O, and S, wherein the alkyl, cycloalkyl, aryl, heteroaryl and heterocyclo may be optionally substituted with one or more R$_{20}$'s;

or R$_{18}$ and R$_{19}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$, at each occurrence, is selected from halo, —OH, (C$_1$-C$_6$)-alkyl, (C$_2$-C$_6$)-alkenyl, (C$_2$-C$_6$)-alkynyl, —(C$_3$-C$_{12}$)-cycloalkyl, (C$_1$-C$_6$)-alkyloxy, cyano, oxo, nitro, —COOH, —SO$_3$H, —CO(C$_1$-C$_6$)-alkyl, —CO(C$_6$-C$_{12}$)-aryl, —CO$_2$(C$_1$-C$_6$)-alkyl, —CONR$_{28}$R$_{29}$, —NR$_{28}$R$_{29}$, —NR$_{28}$C(=O)NR$_{28}$R$_{29}$, —NR$_{28}$C(=NR$_{29}$)NR$_{28}$R$_{29}$, —SR$_{28}$, —S(=O)(=NR$_{28}$)R$_{29}$, —S(—OH)R$_{29}$, —S(=O)R$_{29}$, —S(=O)$_2$R$_{29}$, —NR$_{29}$CO$_2$(C$_1$-C$_6$)-alkyl, —NR$_{28}$SO$_2$R$_{19}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), (C$_{6-10}$)aryl, (C$_{6-10}$)aryl(C$_1$-C$_6$)-alkyl, (C$_{6-10}$)aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_{22}$, at each occurrence, is independently hydrogen, (C$_1$-C$_6$)-alkyl, (C$_3$-C$_{12}$)-cycloalkyl, (C$_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, C$_1$-C$_6$ alkyl, C$_1$-C$_6$ alkoxy, CN, (C$_3$-C$_{12}$)-cycloalkyl and halo(C$_1$-C$_6$)-alkyl;

$R_{22a}$, at each occurrence, is independently hydrogen, ($C_1$-$C_6$)-alkyl, ($C_3$-$C_{12}$)-cycloalkyl, ($C_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, $C_1$-$C_6$ alkyl, $C_1$-$C_6$ alkoxy, CN, ($C_3$-$C_{12}$)-cycloalkyl and halo($C_1$-$C_6$)-alkyl;

$R_{28}$ and $R_{29}$, at each occurrence, are independently hydrogen or ($C_1$-$C_8$)alkyl, wherein the alkyl may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{38}$R$_{39}$, —NR$_{38}$R$_{39}$, —O(C=O)—($C_1$-$C_6$)-alkyl, —O(C=O)NR$_{38}$R$_{39}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{38}$R$_{39}$, —($C_1$-$C_6$)-alkyl-CO$_2$($C_1$-$C_6$)-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

or $R_{28}$ and $R_{29}$ are taken together with the nitrogen to which both are attached to form a 3- to 8-membered ring, which may optionally contain 1-4 heteroatoms selected from N, O, and S;

$R_{38}$ and $R_{39}$, at each occurrence, are independently hydrogen or ($C_1$-$C_8$)alkyl;

or $R_{38}$ and $R_{39}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, prodrugs or salts thereof, wherein:

m is 1 or 2;

Q is CR$_{2a}$R$_2$ or O;

T is ($C_1$-$C_4$)-alkyl, which may be optionally substituted with one or more substituents selected from hydrogen, $^2$H, halogen, $C_1$-$C_6$ alkyl, $C_1$-$C_6$ alkoxy, CN, ($C_3$-$C_{12}$)-cycloalkyl or halo($C_1$-$C_6$)-alkyl;

U is a bond or O;

V is a bond or O;

Ring A is a 5- to 6-membered aryl or heteroaryl, wherein the aryl and heteroaryl may be optionally substituted with one or more substituents selected from hydrogen, halogen, oxo, $C_1$-$C_6$ alkyl, $C_1$-$C_6$ alkoxy, CN, and halo($C_1$-$C_6$)-alkyl and the heteroaryl contains 1-4 heteroatoms selected from N, O, and S;

X is a bond, ($C_1$-$C_6$)-alkyloxy, ($C_3$-$C_6$)-cycloalkyl, ($C_3$-$C_6$)-cycloalkyl-($C_1$-$C_6$)-alkyl, ($C_{5-10}$)-aryl, ($C_{5-10}$)-aryloxy or ($C_{5-10}$)-aryl-($C_1$-$C_6$)-alkyl, wherein any alkyl and aryl may be optionally substituted with one or more substituents selected from hydrogen, halogen, $C_1$-$C_6$ alkyl, $C_1$-$C_6$ alkoxy, CN, ($C_3$-$C_{12}$)-cycloalkyl, ($C_3$-$C_{12}$)-cycloalkyloxy and halo($C_1$-$C_6$)-alkyl;

Y is —(CR$_{22}$R$_{22a}$)$_n$—W;

W is heteroaryl, which may be optionally substituted with one or more R$_{20}$'s,

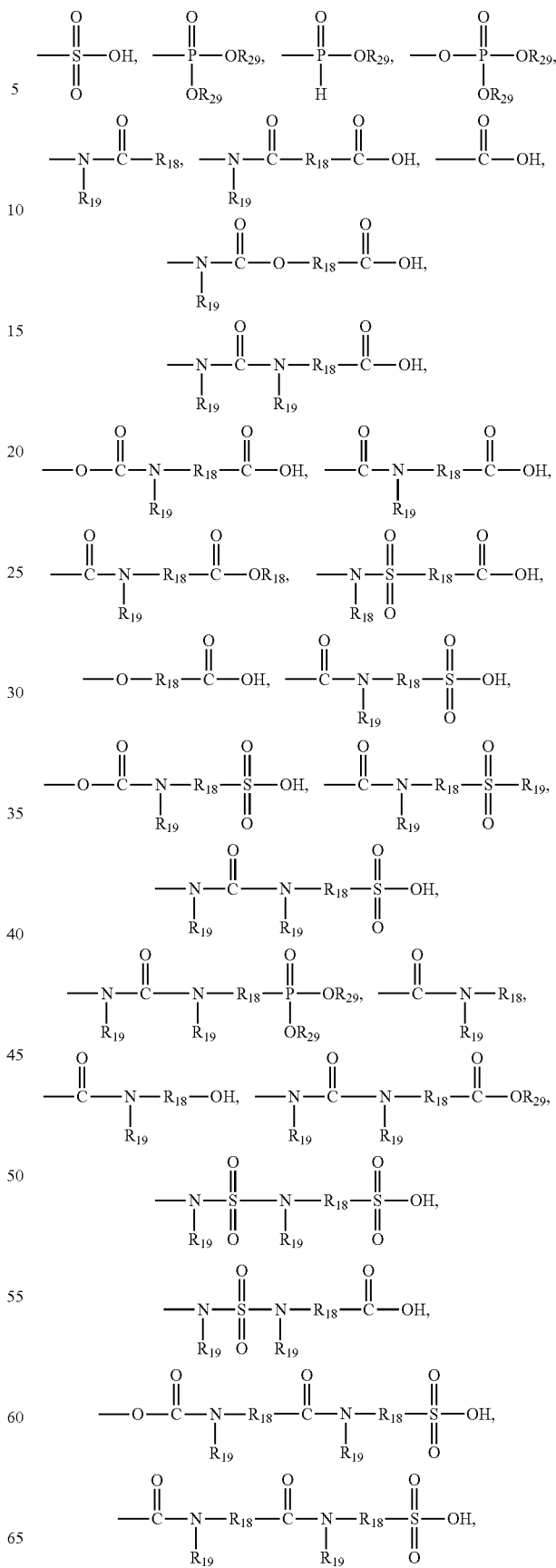

-continued

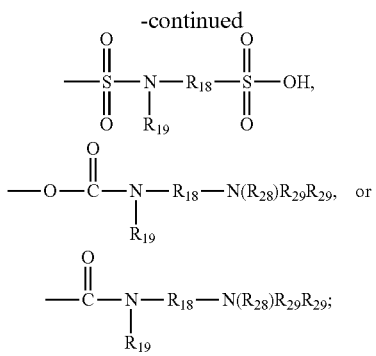

R$_2$ is hydrogen, (C$_1$-C$_6$)-alkyl, (C$_3$-C$_{12}$)-cycloalkyl or halo(C$_1$-C$_6$)-alkyl;

R$_{2a}$ is hydrogen, (C$_1$-C$_6$)-alkyl, (C$_3$-C$_{12}$)-cycloalkyl or halo(C$_1$-C$_6$)-alkyl;

R$_3$ is hydrogen or (C$_1$-C$_6$)-alkyl;

or R$_2$ and R$_3$ can optionally be linked to form a linking group containing 1-5 carbon atoms to form a (C$_3$-C$_7$)-cycloalkyl ring, a halo(C$_3$-C$_7$)-cycloalkyl ring or an aryl ring;

R$_4$, at each occurrence, is independently hydrogen or (C$_1$-C$_8$)alkyl;

R$_{4a}$, at each occurrence, is independently is hydrogen or (C$_1$-C$_8$)alkyl;

or R$_4$ and R$_{4a}$ can optionally be linked to form a linking group containing 1-2 carbon atoms;

R$_{5a}$ is hydrogen, halogen, C$_1$-C$_6$ alkyl or halo(C$_1$-C$_6$)-alkyl;

R$_{5b}$ is hydrogen, halogen, C$_1$-C$_6$ alkyl or halo(C$_1$-C$_6$)-alkyl;

R$_{5c}$ is hydrogen, halogen, C$_1$-C$_6$ alkyl or halo(C$_1$-C$_6$)-alkyl;

R$_{5d}$ is hydrogen, halogen, C$_1$-C$_6$ alkyl or halo(C$_1$-C$_6$)-alkyl;

R$_{5e}$ is hydrogen, halogen, C$_1$-C$_6$ alkyl or halo(C$_1$-C$_6$)-alkyl;

or two of R$_{5a}$, R$_{5b}$, R$_{5c}$, R$_{5d}$ or R$_{5e}$ may be taken together with the atoms to which both are attached form a 3- to 8-membered ring, which may optionally contain 1-4 heteroatoms selected from N, O, and S;

R$_{6a}$ is hydrogen or C$_1$-C$_6$ alkyl;

R$_{6b}$ is hydrogen or C$_1$-C$_6$ alkyl;

R$_{6c}$ is hydrogen or C$_1$-C$_6$ alkyl;

n is 0-2;

R$_{18}$, at each occurrence, is independently (C$_1$-C$_8$)alkyl, (C$_3$-C$_{12}$)-cycloalkyl, (C$_{5-10}$)-aryl, a heteroaryl or a heteroaryl(C$_1$-C$_8$)alkyl, all of which may be optionally substituted with one or more R$_{20}$'s and wherein the heteroaryl contains 4- to 10-members and contains 1-4 heteroatoms selected from N, O, and S;

R$_{19}$, at each occurrence, is independently hydrogen, (C$_1$-C$_6$)-alkyl, (C$_3$-C$_{12}$)-cycloalkyl, (C$_{6-10}$)aryl or a 4- to 10-membered heteroaryl, which contains 1-4 heteroatoms selected from N, O, and S;

or R$_{18}$ and R$_{19}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$, at each occurrence, is selected from halo, —OH, (C$_1$-C$_6$)-alkyl, (C$_2$-C$_6$)-alkenyl, (C$_2$-C$_6$)-alkynyl, —(C$_3$-C$_{12}$)-cycloalkyl, (C$_1$-C$_6$)-alkyloxy, cyano, oxo, nitro, —COOH, —SO$_3$H, —CO(C$_1$-C$_6$)-alkyl, —CO(C$_6$-C$_{12}$)-aryl, —CO$_2$(C$_1$-C$_6$)-alkyl, —CONR$_{28}$R$_{29}$, —NR$_{28}$R$_{29}$, —NR$_{28}$C(=O)NR$_{28}$R$_{29}$, —NR$_{28}$C(=NR$_{29}$)NR$_{28}$R$_{29}$, —SR$_{28}$, —S(=O) (=NR$_{28}$)R$_{29}$, —S(—OH)R$_{29}$, —S(=O)R$_{29}$, —NR$_{29}$CO$_2$(C$_1$-C$_6$)-alkyl, —NR$_{28}$SO$_2$R$_{19}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), (C$_{6-10}$)aryl, (C$_{6-10}$)aryl(C$_1$-C$_6$)-alkyl, (C$_{6-10}$)aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_{22}$, at each occurrence, is independently hydrogen, (C$_1$-C$_6$)-alkyl, (C$_3$-C$_{12}$)-cycloalkyl, (C$_{6-10}$)aryl, or a 4- to 10-membered heteroaryl, which contains 1-4 heteroatoms selected from N, O, and S; wherein the alkyl, cycloalkyl, aryl and heteroaryl may be optionally substituted with one or more substituents selected from hydrogen, halogen, C$_1$-C$_6$ alkyl, C$_1$-C$_6$ alkoxy, CN, (C$_3$-C$_{12}$)-cycloalkyl and halo(C$_1$-C$_6$)-alkyl;

R$_{22a}$, at each occurrence, is independently hydrogen, (C$_1$-C$_6$)-alkyl, (C$_3$-C$_{12}$)-cycloalkyl, (C$_{6-10}$)aryl, or a 4- to 10-membered heteroaryl, which contains 1-4 heteroatoms selected from N, O, and S; wherein the alkyl, cycloalkyl, aryl and heteroaryl may be optionally substituted with one or more substituents selected from hydrogen, halogen, C$_1$-C$_6$ alkyl, C$_1$-C$_6$ alkoxy, CN, (C$_3$-C$_{12}$)-cycloalkyl and halo(C$_1$-C$_6$)-alkyl;

R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{38}$R$_{39}$, —NR$_{38}$R$_{39}$, —O(C=O)—(C$_1$-C$_6$)-alkyl, —O(C=O)NR$_{38}$R$_{39}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{38}$R$_{39}$, —(C$_1$-C$_6$)-alkyl-CO$_2$(C$_1$-C$_6$)-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

or R$_{28}$ and R$_{29}$ are taken together with the nitrogen to which both are attached to form a 3- to 8-membered ring, which may optionally contain 1-4 heteroatoms selected from N, O, and S;

R$_{38}$ and R$_{39}$, at each occurrence, are independently hydrogen or (C$_1$-C$_8$)alkyl;

or R$_{38}$ and R$_{39}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, prodrugs or salts thereof, wherein:

m is 1 or 2;

Q is $CHR_2$ or O;

T is $(C_1-C_4)$-alkyl, which may be optionally substituted with one or more substituents selected from hydrogen, halogen, $C_1-C_6$ alkyl, $C_1-C_6$ alkoxy, $(C_3-C_{12})$-cycloalkyl or halo$(C_1-C_6)$-alkyl;

U is O;

V is a bond;

Ring A is a 5- to 6-membered aryl or heteroaryl, wherein the aryl and heteroaryl may be optionally substituted with one or more substituents selected from hydrogen, halogen, oxo, $C_1-C_6$ alkyl, $C_1-C_6$ alkoxy, CN, and halo$(C_1-C_6)$-alkyl and the heteroaryl contains 1-4 heteroatoms selected from N, O, and S;

X is a bond, $(C_3-C_6)$-cycloalkyl, $(C_{5-10})$-aryl, $(C_{5-10})$-aryloxy or $(C_{5-10})$-aryl-$(C_1-C_6)$-alkyl, wherein any aryl may be optionally substituted with one or more substituents selected from hydrogen, halogen, $C_1-C_6$ alkyl, $C_1-C_6$ alkoxy, CN, $(C_3-C_{12})$-cycloalkyl, $(C_3-C_{12})$-cycloalkyloxy and halo$(C_1-C_6)$-alkyl;

Y is $—(CR_{22}R_{22})_n—W$;

W is heteroaryl, which may be optionally substituted with one or more $R_{20}$'s,

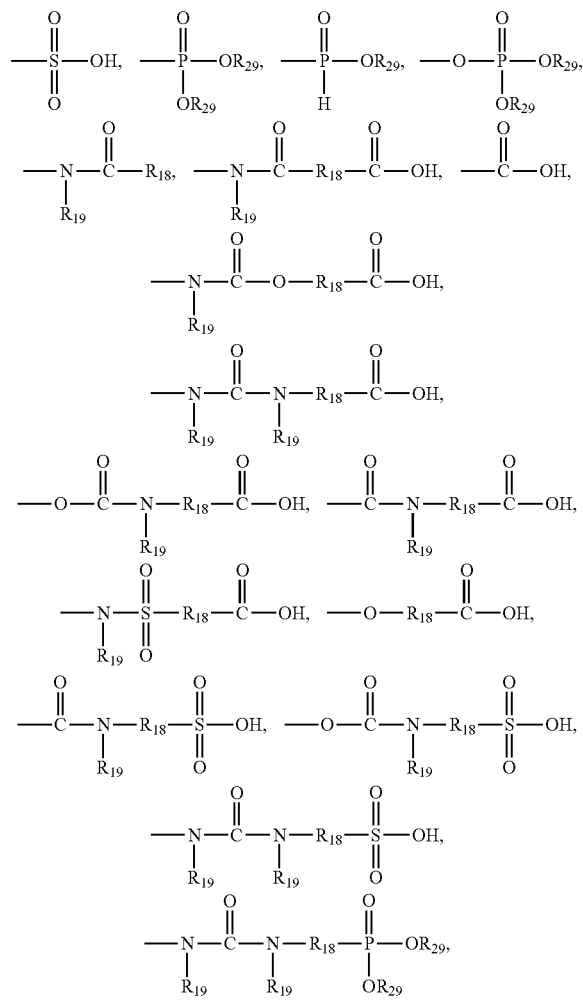

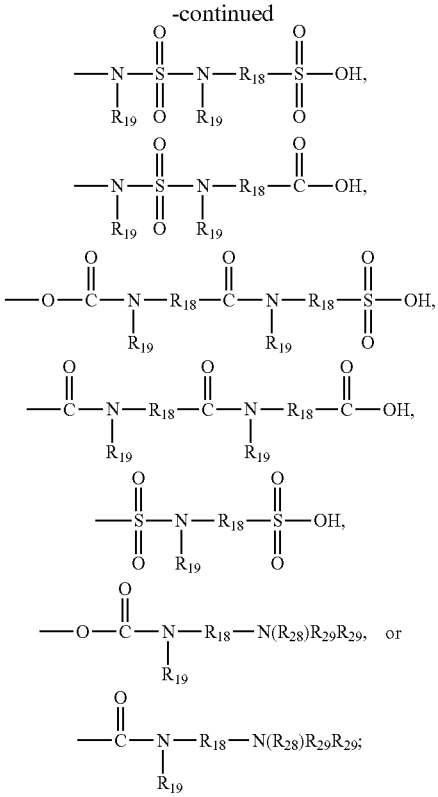

$R_2$ is hydrogen, $(C_1-C_6)$-alkyl or halo$(C_1-C_6)$-alkyl;

$R_3$ is hydrogen or $(C_1-C_6)$-alkyl;

or $R_2$ and $R_3$ can optionally be linked to form a linking group containing 1-3 carbon atoms to form a $(C_3-C_5)$-cycloalkyl ring, a halo$(C_3-C_5)$-cycloalkyl ring or an aryl ring;

$R_4$ and $R_{4a}$ are hydrogen;

$R_{5a}$ is hydrogen, halogen, $C_1-C_6$ alkyl or halo$(C_1-C_6)$-alkyl;

$R_{5b}$ is hydrogen, halogen, $C_1-C_6$ alkyl or halo$(C_1-C_6)$-alkyl;

$R_{5c}$ is hydrogen, halogen, $C_1-C_6$ alkyl or halo$(C_1-C_6)$-alkyl;

$R_{5d}$ is hydrogen, halogen, $C_1-C_6$ alkyl or halo$(C_1-C_6)$-alkyl;

$R_{5e}$ is hydrogen, halogen, $C_1-C_6$ alkyl or halo$(C_1-C_6)$-alkyl;

$R_{6a}$, $R_{6b}$ and $R_{6c}$ are hydrogen;

n is 0-2;

$R_{18}$, at each occurrence, is independently $(C_1-C_8)$alkyl, $(C_3-C_{12})$-cycloalkyl, $(C_{5-10})$-aryl or a heteroaryl, all of which may be optionally substituted with one or more $R_{20}$'s and wherein the heteroaryl contains 4- to 10-members and contains 1-4 heteroatoms selected from N, O, and S;

$R_{19}$, at each occurrence, is independently hydrogen, $(C_1-C_6)$-alkyl, $(C_3-C_{12})$-cycloalkyl or $(C_{6-10})$aryl;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is selected from halo, —OH, $(C_1-C_6)$-alkyl, $(C_2-C_6)$-alkenyl, $(C_2-C_6)$-alkynyl, —$(C_3-C_{12})$-cycloalkyl, $(C_1-C_6)$-alkyloxy, cyano, oxo, nitro, —COOH, —$SO_3H$, —$CO(C_1-C_6)$-alkyl, —$CO(C_6-C_{12})$-aryl, —$CO_2(C_1-C_6)$-alkyl, —$CONR_{28}R_{29}$, —$NR_{28}R_{29}$, —$NR_{28}C(=O)NR_{28}R_{29}$, —$NR_{28}C(=NR_{29})NR_{28}R_{29}$, —$SR_{28}$, —$S(=O)$ (=NR$_{28}$)R$_{29}$, —S(—OH)R$_{29}$, —S(=O)R$_{29}$, —NR$_{29}$CO$_2$(C$_1$-C$_6$)-alkyl, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), (C$_{6-10}$)aryl, (C$_{6-10}$)aryl(C$_1$-C$_6$)-alkyl, (C$_{6-10}$)aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

R$_{22}$, at each occurrence, is independently hydrogen, (C$_1$-C$_6$)-alkyl, (C$_3$-C$_{12}$)-cycloalkyl, (C$_{6-10}$)aryl, or a 4- to 10-membered heteroaryl, which contains 1-4 heteroatoms selected from N, O, and S;

R$_{22a}$, at each occurrence, is independently hydrogen, (C$_1$-C$_6$)-alkyl, (C$_3$-C$_{12}$)-cycloalkyl, (C$_{6-10}$)aryl, or a 4- to 10-membered heteroaryl, which contains 1-4 heteroatoms selected from N, O, and S;

R$_{28}$ and R$_{29}$, at each occurrence, are independently hydrogen or (C$_1$-C$_8$)alkyl, wherein the alkyl may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{38}$R$_{39}$, —NR$_{38}$R$_{39}$, —O(C=O)—(C$_1$-C$_6$)-alkyl, —O(C=O)NR$_{38}$R$_{39}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{38}$R$_{39}$, —(C$_1$-C$_6$)-alkyl-CO$_2$(C$_1$-C$_6$)-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, (C$_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C$_1$-C$_6$)alkyl, and halo(C$_1$-C$_6$)alkyloxy;

or R$_{28}$ and R$_{29}$ are taken together with the nitrogen to which both are attached to form a 3- to 8-membered ring, which may optionally contain 1-4 heteroatoms selected from N, O, and S;

R$_{38}$ and R$_{39}$, at each occurrence, are independently hydrogen or (C$_1$-C$_8$)alkyl;

or R$_{38}$ and R$_{39}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, prodrugs or salts thereof, wherein:

m is 1 or 2;
Q is CHR$_2$;
T is a (C$_1$-C$_4$)-alkyl;
U is O;
V is a bond;

Ring A is a 5- to 6-membered aryl or heteroaryl, wherein the heteroaryl contains 1-4 heteroatoms selected from N, O, and S;

X is a bond, (C$_3$-C$_6$)-cycloalkyl, (C$_{5-10}$)-aryl, or (C$_{5-10}$)-aryl-(C$_1$-C$_6$)-alkyl, wherein any aryl may be optionally substituted with one or more substituents selected from hydrogen, halogen, C$_1$-C$_6$ alkyl, C$_1$-C$_6$ alkoxy, CN, (C$_3$-C$_{12}$)-cycloalkyl, (C$_3$-C$_{12}$)-cycloalkyloxy and halo(C$_1$-C$_6$)-alkyl;

Y is —(CR$_{22}$R$_{22a}$)$_n$—W,

W is

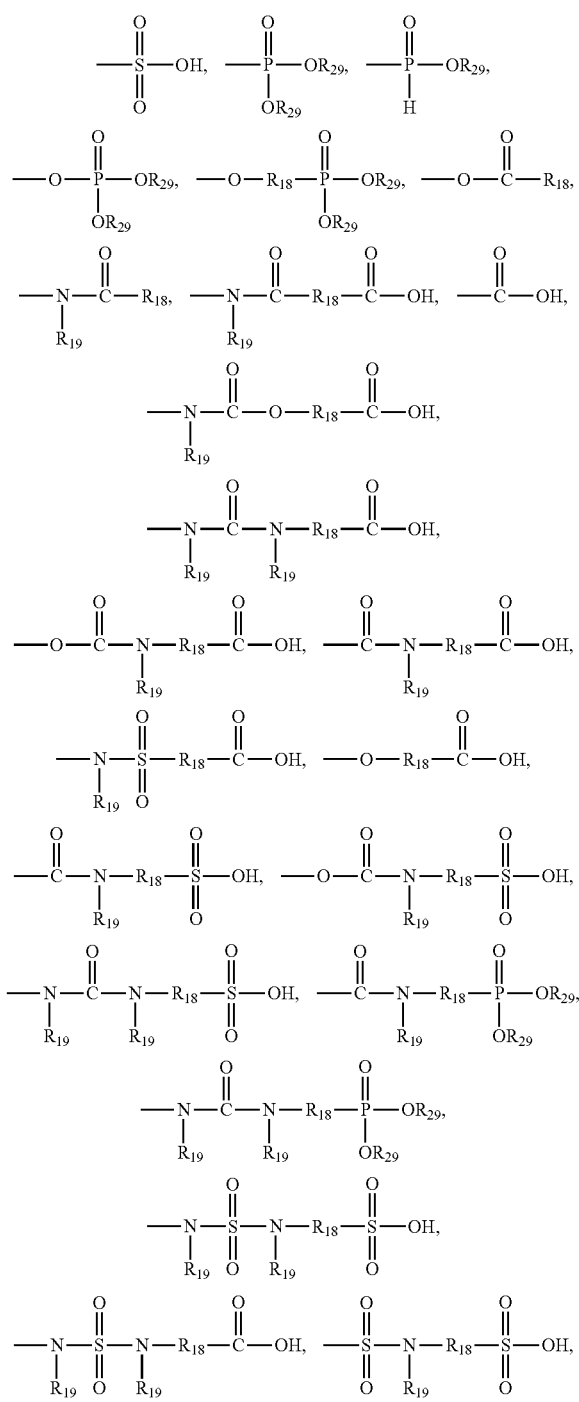

-continued

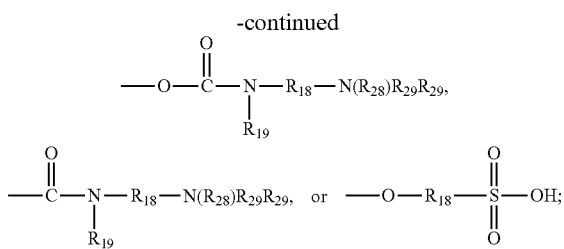

$R_2$ and $R_3$ are hydrogen;

or $R_2$ and $R_3$ can optionally be linked to form a linking group containing 1-3 carbon atoms to form a $(C_3-C_5)$-cycloalkyl ring, a halo$(C_3-C_5)$-cycloalkyl ring or an aryl ring;

$R_4$ and $R_{4a}$ are hydrogen;

$R_{5a}$ is hydrogen, halogen or $C_1-C_6$ alkyl;

$R_{5b}$ is hydrogen, halogen or $C_1-C_6$ alkyl;

$R_{5c}$ is hydrogen, halogen or $C_1-C_6$ alkyl;

$R_{5d}$ is hydrogen, halogen or $C_1-C_6$ alkyl;

$R_{5e}$ is hydrogen, halogen or $C_1-C_6$ alkyl;

$R_{6a}$, $R_{6b}$ and $R_{6c}$ are hydrogen;

n is 0-2;

$R_{18}$, at each occurrence, is independently $(C_1-C_8)$alkyl, $(C_3-C_{12})$-cycloalkyl or $(C_{5-10})$-aryl, all of which may be optionally substituted with one or more $R_{20}$'s;

$R_{19}$, at each occurrence, is independently hydrogen, $(C_1-C_6)$-alkyl or $(C_3-C_{12})$-cycloalkyl;

$R_{20}$, at each occurrence, is selected from halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, oxo, nitro, —COOH, —SO$_3$H, —CO$(C_1-C_6)$-alkyl, —CO$(C_6-C_{12})$-aryl, —CO$_2(C_1-C_6)$-alkyl, —CONR$_{28}$R$_{29}$, —NR$_{28}$R$_{29}$, —NR$_{28}$C(=O)NR$_{28}$R$_{29}$, —NR$_{28}$C(=NR$_{29}$)NR$_{28}$R$_{29}$, —SR$_{28}$, —S(=O)(=NR$_{28}$)R$_{29}$, —S(—OH)R$_{29}$, —S(=O)R$_{29}$, —NR$_{29}$CO$_2(C_1-C_6)$-alkyl, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), $(C_{6-10})$aryl, $(C_{6-10})$aryl$(C_1-C_6)$-alkyl, $(C_{6-10})$aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_{22}$, at each occurrence, is independently hydrogen, $(C_1-C_6)$-alkyl, $(C_3-C_{12})$-cycloalkyl or $(C_{6-10})$aryl;

$R_{22a}$, at each occurrence, is independently hydrogen, $(C_1-C_6)$-alkyl, $(C_3-C_{12})$-cycloalkyl or $(C_{6-10})$aryl;

$R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{38}$R$_{39}$, —NR$_{38}$R$_{39}$, —O(C=O)—$(C_1-C_6)$-alkyl, —O(C=O)NR$_{38}$R$_{39}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{38}$R$_{39}$, —$(C_1-C_6)$-alkyl-CO$_2(C_1-C_6)$-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy; and $R_{38}$ and $R_{39}$, at each occurrence, are independently hydrogen or $(C_1-C_8)$alkyl.

In another embodiment, the present invention provides compounds, enantiomers, diastereomers, tautomers, prodrugs or salts thereof, wherein:

m is 1 or 2;

Q is CHR$_2$;

T is a $(C_1-C_4)$-alkyl;

U is O;

V is a bond;

A is a 5- to 6-membered aryl or heteroaryl, wherein the heteroaryl contains 1-4 heteroatoms selected from N, O, and S;

X is a bond, $(C_{5-10})$-aryl, or $(C_{5-10})$-aryl-$(C_1-C_6)$-alkyl, wherein any aryl may be optionally substituted with one or more substituents selected from hydrogen, halogen, $C_1-C_6$ alkyl, $C_1-C_6$ alkoxy, CN, $(C_3-C_{12})$-cycloalkyl, $(C_3-C_{12})$-cycloalkyloxy and halo$(C_1-C_6)$-alkyl;

Y is —(CR$_{22}$R$_{22a}$)$_n$—W;

W is

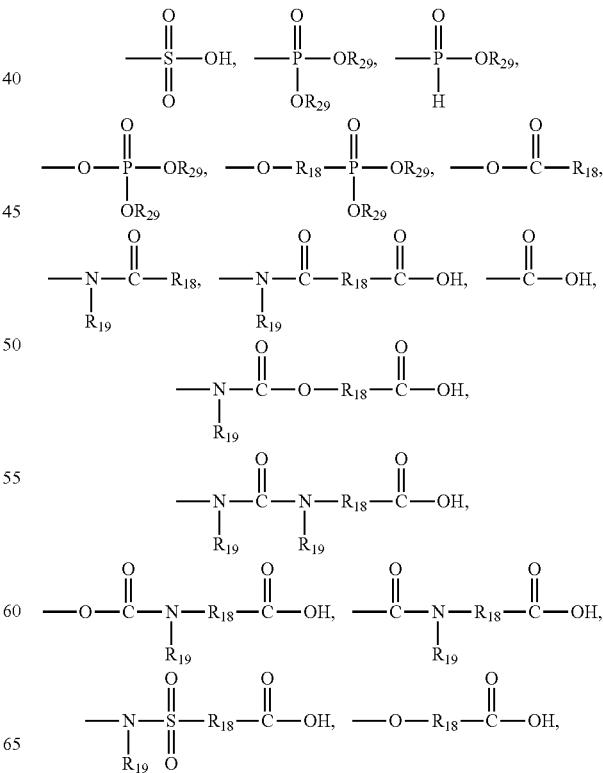

-continued

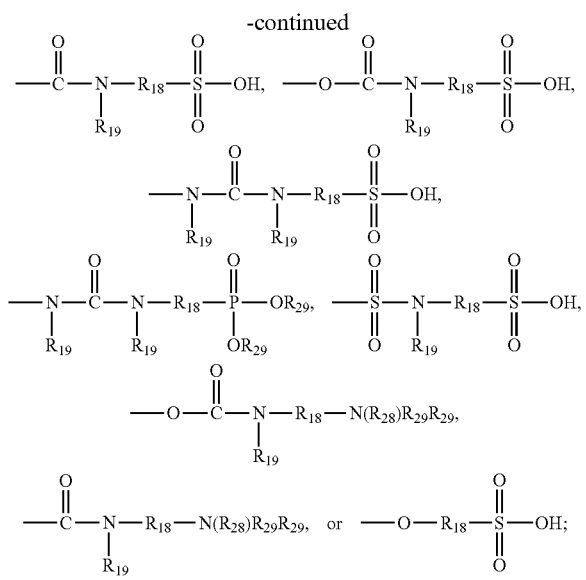

$R_2$ and $R_3$ are hydrogen;

or $R_2$ and $R_3$ can optionally be linked to form a linking group containing 1-3 carbon atoms to form a $(C_3-C_5)$-cycloalkyl ring, a halo$(C_3-C_5)$-cycloalkyl ring or an aryl ring;

$R_4$ and $R_{4a}$ are hydrogen;

$R_{5a}$ is hydrogen, halogen or $C_1-C_6$ alkyl;

$R_{5b}$ is hydrogen, halogen or $C_1-C_6$ alkyl;

$R_{5c}$ is hydrogen, halogen or $C_1-C_6$ alkyl;

$R_{5d}$ is hydrogen, halogen or $C_1-C_6$ alkyl;

$R_{5e}$ is hydrogen, halogen or $C_1-C_6$ alkyl;

$R_{6a}$, $R_{6b}$ and $R_{6c}$ are hydrogen;

n is 0-2;

$R_{18}$, at each occurrence, is independently $(C_1-C_8)$alkyl or $(C_3-C_{12})$-cycloalkyl, both of which may be optionally substituted with one or more $R_{20}$'s;

$R_{19}$, at each occurrence, is independently hydrogen or $(C_1-C_6)$-alkyl;

$R_{20}$, at each occurrence, is selected from halo, —OH, $(C_1-C_6)$-alkyl, $(C_2-C_6)$-alkenyl, $(C_2-C_6)$-alkynyl, —$(C_3-C_{12})$-cycloalkyl, $(C_1-C_6)$-alkyloxy, cyano, oxo, nitro, —COOH, —SO$_3$H, —CO$(C_1-C_6)$-alkyl, —CO$(C_6-C_{12})$-aryl, —CO$_2$$(C_1-C_6)$-alkyl, —CONR$_{28}$R$_{29}$, —NR$_{28}$R$_{29}$, —NR$_{28}$C(=O)NR$_{28}$R$_{29}$, —NR$_{28}$C(=NR$_{29}$)NR$_{28}$R$_{29}$, —SR$_{28}$, —S(=O)(=NR$_{28}$)R$_{29}$, —S(—OH)R$_{29}$, —S(=O)R$_{29}$, —NR$_{29}$CO$_2$$(C_1-C_6)$-alkyl, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), $(C_{6-10})$aryl, $(C_{6-10})$aryl$(C_1-C_6)$-alkyl, $(C_{6-10})$aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2$$(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_{22}$, at each occurrence, is independently hydrogen, $(C_1-C_6)$-alkyl or $(C_{6-10})$aryl;

$R_{22a}$, at each occurrence, is independently hydrogen, $(C_1-C_6)$-alkyl or $(C_{6-10})$aryl;

$R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2$$(C_1-C_6)$-alkyl, —CONR$_{38}$R$_{39}$, —NR$_{38}$R$_{39}$, —O(C=O)—$(C_1-C_6)$-alkyl, —O(C=O)NR$_{38}$R$_{39}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{38}$R$_{39}$, —$(C_1-C_6)$-alkyl-CO$_2$$(C_1-C_6)$-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy; and $R_{38}$ and $R_{39}$, at each occurrence, are independently hydrogen or $(C_1-C_8)$alkyl.

In another embodiment, the present invention provides compounds, enantiomers, diastereomers, tautomers, prodrugs or salts thereof, wherein:

m is 1 or 2;

Q is CHR$_2$;

T is a $(C_1-C_4)$-alkyl;

U is O;

V is a bond;

Ring A is phenyl, pyrazolyl, tetrazolyl, thiophenyl or pyridinyl;

X is a bond or $(C_{5-10})$-aryl-$(C_1-C_6)$-alkyl, wherein the aryl may be optionally substituted with one or more substituents selected from hydrogen, halogen, $C_1-C_6$ alkyl, $C_1-C_6$ alkoxy, CN, $(C_3-C_{12})$-cycloalkyl, $(C_3-C_{12})$-cycloalkyloxy and halo$(C_1-C_6)$-alkyl;

Y is —$(CR_{22}R_{22a})_n$—W;

W is

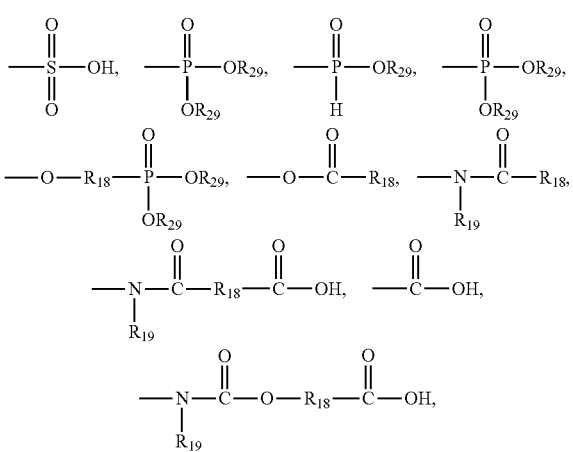

-continued

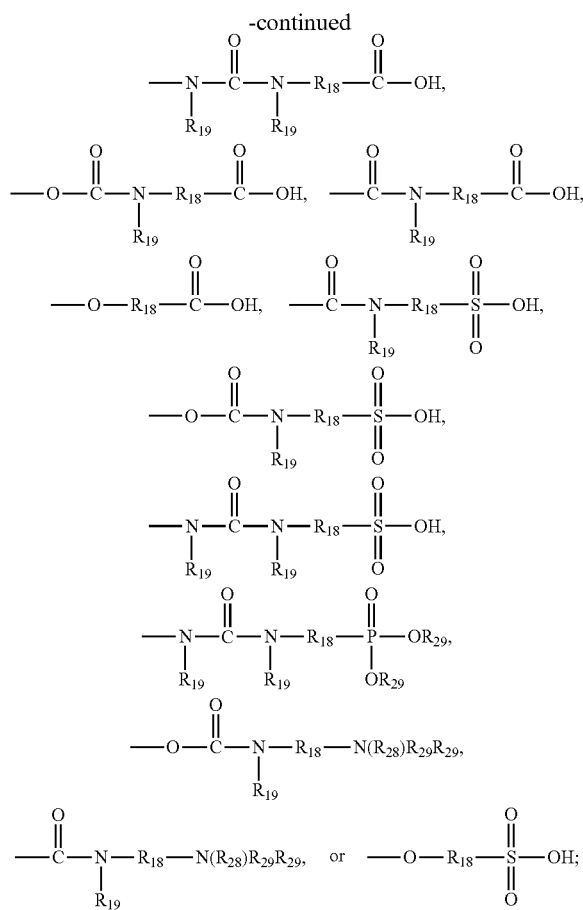

$R_2$, $R_3$, $R_4$ and $R_{4a}$ are hydrogen;
$R_{5a}$ is hydrogen, Cl, F or methyl;
$R_{5b}$ is hydrogen, Cl, F or methyl;
$R_{5c}$ is hydrogen, Cl, F or methyl;
$R_{5d}$ is hydrogen, Cl, F or methyl;
$R_{5e}$ is hydrogen, Cl, F or methyl;
$R_{6a}$, $R_{6b}$ and $R_{6c}$ are hydrogen;
n is 0-2;
$R_{18}$, at each occurrence, is independently $(C_1$-$C_8)$alkyl, which may be optionally substituted with one or more $R_{20}$'s;
$R_{19}$, at each occurrence, is independently hydrogen or $(C_1$-$C_6)$-alkyl;
$R_{20}$, at each occurrence, is selected from halo, —OH, $(C_1$-$C_6)$-alkyl, $(C_2$-$C_6)$-alkenyl, $(C_2$-$C_6)$-alkynyl, —$(C_3$-$C_{12})$-cycloalkyl, $(C_1$-$C_6)$-alkyloxy, cyano, oxo, nitro, —COOH, —$SO_3H$, —CO$(C_1$-$C_6)$-alkyl, —CO$(C_6$-$C_{12})$-aryl, —$CO_2$$(C_1$-$C_6)$-alkyl, —CONR$_{28}$R$_{29}$, —NR$_{28}$R$_{29}$, —NR$_{28}$C(=O)NR$_{28}$R$_{29}$, —NR$_{28}$C(=NR$_{29}$)NR$_{28}$R$_{29}$, —SR$_{28}$, —S(=O)(=NR$_{28}$)R$_{29}$, —S(—OH)R$_{29}$, —S(=O)R$_{29}$, —NR$_{29}$CO$_2$$(C_1$-$C_6)$-alkyl, —O(C=O)—$(C_1$-$C_6)$-alkyl, —O(C=O)NR$_{28}$R$_{29}$; —$(C_1$-$C_6)$-alkylCOOH, —$(C_1$-$C_6)$-alkylOH, —$(C_1$-$C_6)$-alkyl(NH$_2$)COOH, —$(C_1$-$C_6)$-alkylCONR$_{28}$R$_{29}$, —$(C_1$-$C_6)$-alkyl-CO$_2$$(C_1$-$C_6)$-alkyl, —O—P(=O)(OH)(OR$_{29}$), —O—CR$_{28}$R$_{29}$—P(=O)(OH)(OR$_{29}$), —P(O)(OH)(OR$_{29}$), $(C_{6-10})$aryl, $(C_{6-10})$aryl$(C_1$-$C_6)$-alkyl, $(C_{6-10})$aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1$-$C_6)$-alkyl, $(C_2$-$C_6)$-alkenyl, $(C_2$-$C_6)$-alkynyl, $(C_1$-$C_6)$-alkyloxy, cyano, nitro, —COOH, —CO$(C_1$-$C_6)$-alkyl, —CO$_2$$(C_1$-$C_6)$-alkyl, —CONR$_{28}$R$_{29}$, —NR$_{28}$R$_{29}$, —O(C=O)—$(C_1$-$C_6)$-alkyl, —O(C=O)NR$_{28}$R$_{29}$; —$(C_1$-$C_6)$-alkylCOOH, —$(C_1$-$C_6)$-alkylOH, —$(C_1$-$C_6)$-alkyl(NH$_2$)COOH, —$(C_1$-$C_6)$-alkylCONR$_{28}$R$_{29}$, —$(C_1$-$C_6)$-alkyl-CO$_2$$(C_1$-$C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1$-$C_6)$alkyl, and halo$(C_1$-$C_6)$alkyloxy;
$R_{22}$, at each occurrence, is independently hydrogen or $(C_1$-$C_6)$-alkyl;
$R_{22a}$, at each occurrence, is independently hydrogen or $(C_1$-$C_6)$-alkyl;
$R_{28}$ and $R_{29}$, at each occurrence, are independently hydrogen or $(C_1$-$C_8)$alkyl, wherein the alkyl may be optionally substituted with one or more substituents selected from the group consisting of: halo, —OH, $(C_1$-$C_6)$-alkyl, $(C_2$-$C_6)$-alkenyl, $(C_2$-$C_6)$-alkynyl, $(C_1$-$C_6)$-alkyloxy, cyano, nitro, —COOH, —CO$(C_1$-$C_6)$-alkyl, —CO$_2$$(C_1$-$C_6)$-alkyl, —CONR$_{38}$R$_{39}$, —NR$_{38}$R$_{39}$, —O(C=O)—$(C_1$-$C_6)$-alkyl, —O(C=O)NR$_{38}$R$_{39}$; —$(C_1$-$C_6)$-alkylCOOH, —$(C_1$-$C_6)$-alkylOH, —$(C_1$-$C_6)$-alkyl(NH$_2$)COOH, —$(C_1$-$C_6)$-alkylCONR$_{38}$R$_{39}$, —$(C_1$-$C_6)$-alkyl-CO$_2$$(C_1$-$C_6)$-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1$-$C_6)$alkyl, and halo$(C_1$-$C_6)$alkyloxy; and
$R_{38}$ and $R_{39}$, at each occurrence, are independently hydrogen or $(C_1$-$C_8)$alkyl.

In another embodiment, the present invention provides compounds, enantiomers, diastereomers, tautomers, prodrugs or salts thereof, wherein:
m is 1;
Q is CHR$_2$;
T is a $(C_1$-$C_4)$-alkyl;
U is O;
V is a bond;
Ring A is phenyl, pyrazolyl, tetrazolyl, thiophenyl or pyridinyl;
X is a bond or phenyl-$(C_1$-$C_6)$-alkyl, wherein the phenyl may be optionally substituted with one or more substituents selected from hydrogen, halogen, $C_1$-$C_6$ alkyl, $C_1$-$C_6$ alkoxy, CN and halo$(C_1$-$C_6)$-alkyl;
Y is —(CR$_{22}$R$_{22a}$)$_n$—W;
W is

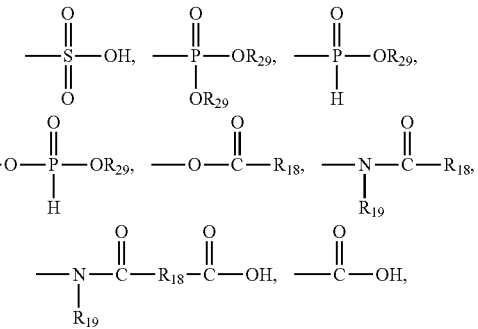

-continued

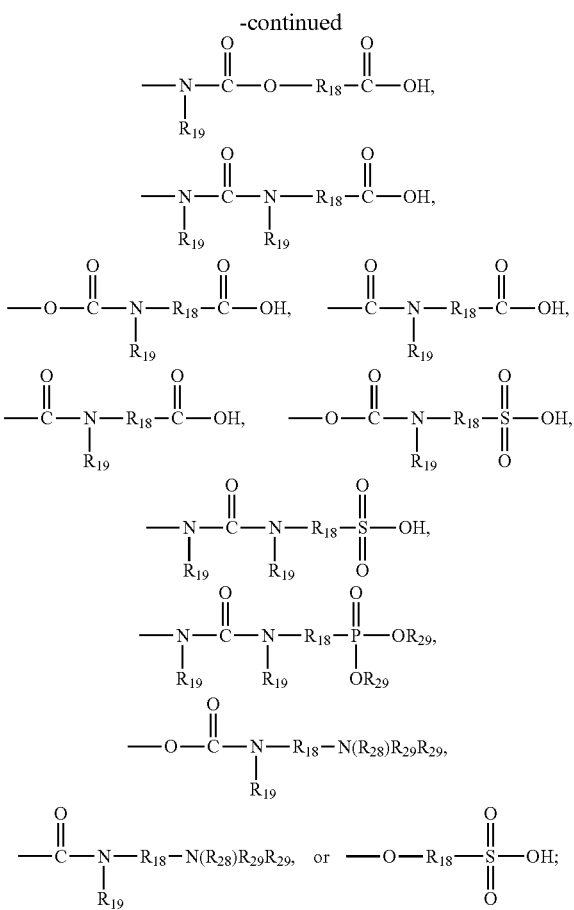

$R_2$, $R_3$, $R_4$ and $R_{4a}$ are hydrogen;
$R_{5a}$ is hydrogen, Cl, F or methyl;
$R_{5b}$ is hydrogen, Cl, F or methyl;
$R_{5c}$ is hydrogen, Cl, F or methyl;
$R_{5d}$ is hydrogen, Cl, F or methyl;
$R_{5e}$ is hydrogen, Cl, F or methyl;
$R_{6a}$, $R_{6b}$ and $R_{6c}$ are hydrogen;
n is 0 or 1;
$R_{18}$, at each occurrence, is independently $(C_1-C_6)$alkyl, which may be optionally substituted with one or more $R_{20}$'s;
$R_{19}$, at each occurrence, is independently hydrogen or $(C_1-C_6)$-alkyl;
$R_{20}$, at each occurrence, is selected from halo, —OH, $(C_1-C_6)$-alkyl, $(C_2-C_6)$-alkenyl, $(C_2-C_6)$-alkynyl, $-(C_3-C_{12})$-cycloalkyl, $(C_1-C_6)$-alkyloxy, cyano, oxo, nitro, —COOH, —SO$_3$H, —CO$(C_1-C_6)$-alkyl, —CO$(C_6-C_{12})$-aryl, —CO$_2$$(C_1-C_6)$-alkyl, —CONR$_{28}$R$_{29}$, —NR$_{28}$R$_{29}$, —NR$_{28}$C(=O)NR$_{28}$R$_{29}$, —NR$_{28}$C(=NR$_{29}$)NR$_{28}$R$_{29}$, —SR$_{28}$, —S(=O)(=NR$_{28}$)R$_{29}$, —S(—OH)R$_{29}$, —S(=O)R$_{29}$, —NR$_{29}$CO$_2$$(C_1-C_6)$-alkyl, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), $(C_{6-10})$aryl, $(C_{6-10})$aryl$(C_1-C_6)$-alkyl, $(C_{6-10})$aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2$$(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;
$R_{22}$ and $R_{22a}$ are hydrogen; and
$R_{28}$ and $R_{29}$, at each occurrence, are independently hydrogen or $(C_1-C_6)$alkyl.

The terms "Formula I", "Formula Ia", "Formula Ib", "Formula Ic", "Formula Id", "Formula Ie", "Formula If", "Formula Ig", "Formula Ih", "Formula Ij" and all embodiments thereof shall include enantiomers, diastereomers, prodrugs, solvates and salts thereof (particularly enantiomers, diastereomers and pharmaceutically acceptable salts thereof).

In another embodiment, the present invention provides a compound of Formula I, or an enantiomer, a diastereomer, or a pharmaceutically acceptable salt thereof, wherein the compound is selected from one of the examples, preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B.

In another embodiment, the present invention provides a pharmaceutical composition comprised of a therapeutically effective amount of a compound of Formula I, Ia, Ib, Ic, Id, Ie, If, Ig, Ih or Ij, or an enantiomer, a diastereomer, or a pharmaceutically acceptable salt thereof, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916. 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, and a pharmaceutically acceptable carrier.

In another embodiment, the present invention provides a pharmaceutical composition comprised of a therapeutically effective amount of a compound of Formula I, Ia, Ib, Ic, Id, Ie, If, Ig, Ih or Ij, or an enantiomer, a diastereomer, or a pharmaceutically acceptable salt thereof, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916. 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, and one or more other therapeutically active agents.

In another embodiment, the present invention relates to a pharmaceutical composition, wherein the selected composition is made by combining (a) a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B (using any of the compound embodiments listed above), and (b) a dipeptidyl peptidase-IV (DPP4) inhibitor (for example, a member selected from saxagliptin, sitagliptin, vildagliptin and alogliptin).

In another embodiment, the present invention relates to a pharmaceutical composition, wherein the selected composition is made by combining (a) a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B (using any of the compound embodiments listed above), and (b) a dipeptidyl peptidase-IV (DPP4) inhibitor, wherein the DPP4 inhibitor is saxagliptin.

In another embodiment, the present invention relates to a pharmaceutical composition, wherein the selected composition is made by combining (a) a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B (using any of the compound embodiments listed above), and (b) an SGLT2 inhibitor (for example, a member selected from 3-(benzo[b]furan-5-yl)-2',6'-dihydroxy-4'-methylpropiophenone-2'-O-(6-O-methoxycarbonyl)-β-d-glucopyranoside, phlorizin, TS-033, dapagliflozin, sergiflozin, AVE 2268, and canagliflozin).

In another embodiment, the present invention relates to a pharmaceutical composition, wherein the selected composition is made by combining (a) a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B (using any of the compound embodiments listed above), and (b) an SGLT2 inhibitor wherein the SGLT2 inhibitor is dapagliflozin.

In one embodiment, the present invention relates to methods of modulating the activity of the TGR5 G protein-coupled receptor comprising administering to a mammalian patient, for example, a human patient, in need thereof a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

In one embodiment, the present invention relates to a method for preventing, modulating, or treating the progression or onset of diseases or disorders associated with the modulation of the TGR5 G protein-coupled receptor comprising administering to a mammalian patient, for example, a human patient, in need of prevention, modulation, or treatment a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

Examples of diseases or disorders associated with the modulation of the TGR5 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis and pancreatitis.

In another embodiment, the present invention relates to a method for preventing, modulating, or treating the progression or onset of diabetes, hyperglycemia, obesity, dyslipidemia, and hypertension comprising administering to a mammalian patient, for example, a human patient, in need of prevention, modulation, or treatment a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

In another embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

In yet another embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

In still yet another embodiment, the present invention relates to a method for preventing, modulating, or treating the progression or onset of obesity comprising administering to a mammalian patient, for example, a human patient, in need of prevention, modulation, or treatment a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

In one embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916. 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

In another embodiment, the present invention relates to a method for preventing, modulating, or treating the progression or onset of hypertension comprising administering to a mammalian patient, for example, a human patient, in need of prevention, modulation, or treatment a therapeutically effective amount of a compound of Formula I, Ia, Ib, Ic, Id, Ie, If, Ig, Ih or Ij, preferably, a compound selected from one of the examples, more preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone, or, optionally, in combination with another compound of the present invention and/or at least one other type of therapeutic agent.

For each of the embodiments described in this application, further and more particular values of the terms used in each of the embodiments may be selected from the following definitions; these values may be used individually in any of the embodiments or in any combination. It is noted that for any occurrences of "=O", these may be used with suitable accommodation in the bond structure at that site as will be appreciated by those skilled in the art.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I, Ia, Ib, Ic, Id, Ie, If, Ig, Ih or Ij may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Young, S. D. et al., *Antimicrobial Agents and Chemotherapy*, 2602-2605 (1995).

To the extent that compounds of Formula I, Ia, Ib, Ic, Id, Ie, If, Ig, Ih, Ij and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_{20}$) occurs more than one time in any constituent or formula for a compound, its definition at each occurrence is independent of its definition at every other occurrence. Thus, for example, if a group is shown to be substituted with one or more $R_{20}$, then said group may optionally be substituted with more than on $R_{20}$ groups and $R_{20}$ at each occurrence is selected independently from the definition of $R_{20}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

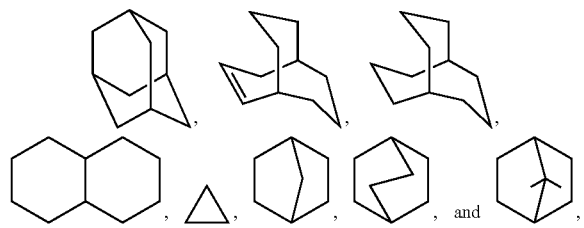

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example,

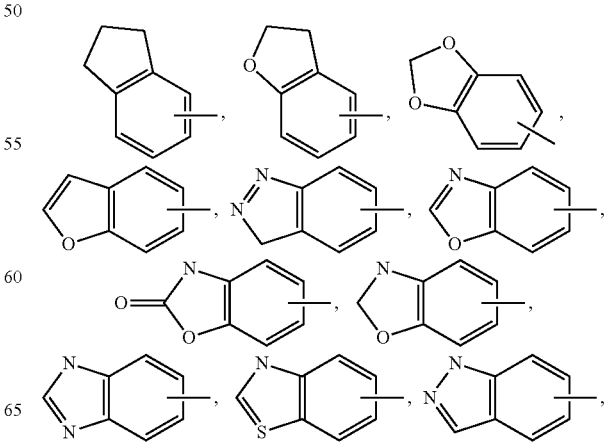

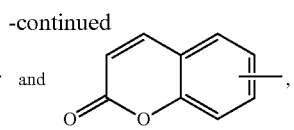

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

Unless otherwise indicated, the term "heterocyclyl" is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, pyrrolidonyl, 4-piperidonyl, chromanyl, decahydroquinolinyl, dihydrofuro[2,3-b]tetrahydrofuran, indolinyl, isochromanyl, isoindolinyloctahydroisoquinolinyl, piperazinyl, piperidinyl, piperidonyl, 4-piperidonyl, tetrahydrofuranyl, tetrahydroisoquinolinyl, tetrahydroquinolinyl, morpholinyl, dihydrofuranyl, tetrahydrothiophenyl, pyranyl, dihydropyranyl, 1,4-dioxanyl and 1,3-dioxanyl. Also included are fused ring and spiro compounds containing, for example, the above heterocycles.

Unless otherwise indicated, the term "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro-[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinolinyl, 4H-quinolizinyl, quinoxalinyl, quinuclidinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazolinyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an —NO$_2$ group.
The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Any compound that can be converted in vivo to provide the bioactive agent (i.e., a compound of Formula I, Ia, Ib, Ic, Id, Ie, If, Ig, Ih or Ij) is a prodrug within the scope and spirit of the invention.

The term "prodrugs" as employed herein includes esters and carbonates formed by reacting one or more hydroxyls of compounds of Formula I, Ia, Ib, Ic, Id, Ie, If Ig, Ih or Ij with alkyl, alkoxy or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) Bundgaard, H., ed., *Design of Prodrugs*, Elsevier (1985);

c) Bundgaard, H., Chapter 5, "Design and Application of Prodrugs," Krosgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

Said references are incorporated herein by reference, particularly as to the description of prodrugs.

In addition, compounds of Formula I, Ia, Ib, Ic, Id, Ie, If, Ig, Ih or Ij are, subsequent to their preparation, preferably isolated and purified to obtain a composition containing an amount by weight equal to or greater than 99% of a compound of Formula I, Ia, Ib, Ic, Id, Ie, If, Ig, Ih or Ij ("substantially pure" compound), which is then used or formulated as described herein. Such "substantially pure" compounds of Formula I, Ia, Ib, Ic, Id, Ie, If, Ig, Ih or Ij are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of Formula I, Ia, Ib, Ic, Id, Ie, If, Ig, Ih or Ij can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increase in vivo half-life or reduced dosage requirements, and hence may be preferred in some circumstances. Substitution with positron emitting isotopes, such as $^{11}$C, $^{18}$F, $^{15}$O, and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate TGR5 or effective to treat or prevent various disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or variations thereof as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Scheme 1 describes a method for preparing compounds of formula III-a. An intermediate II-a can be prepared by methods known in the literature or by other methods known to one skilled in the art. Formation of a compound III-a can be carried out from a II-a and an acid II-b using propane phosphonic acid anhydride (T3P) and Hunig's Base, DIEA, or other commonly used amine/acid coupling methods such as HATU in the presence of an appropriate base, such as DIEA, or directly coupling of II-a with corresponding acid chloride II-c in the presence of an appropriate base, such as sodium carbonate or DIEA.

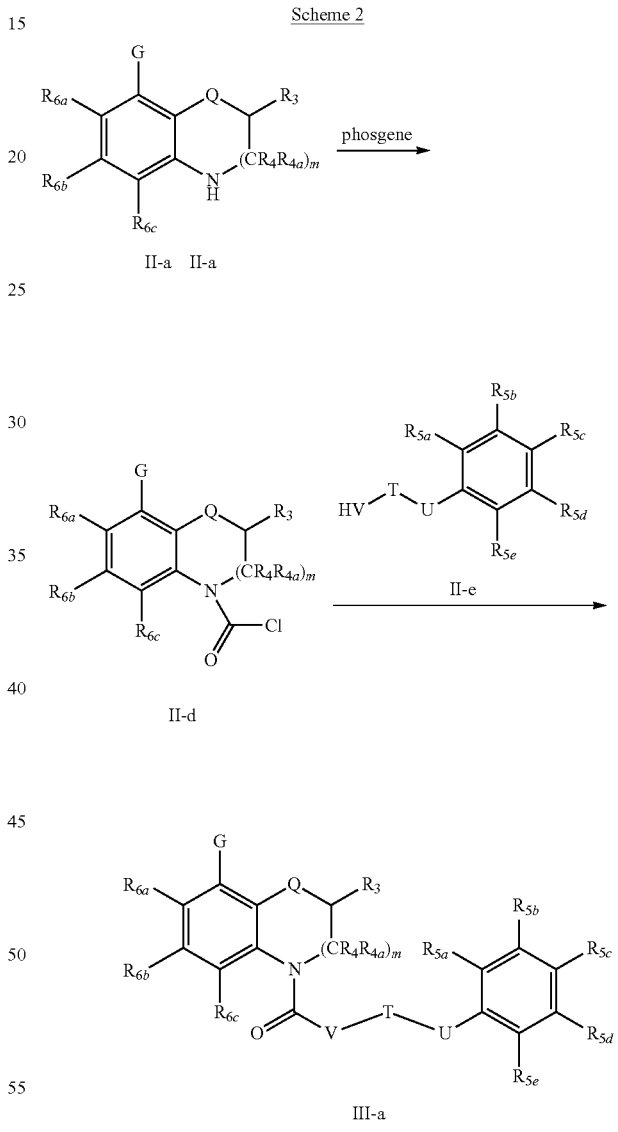

Alternatively, as described in Scheme 2, when V is —O— in II-e, compound III-a can be prepared through a carbonyl chloride intermediate II-d, by treating II-a with phosgene or similar reagents such as diphogene or triphosgene in the presence of base such as DIEA. The resulting intermediate II-d is then treated with II-e in the presence of base such as Hunig's base or aqueous $Na_2CO_3$ to get desired III-a.

Scheme 3

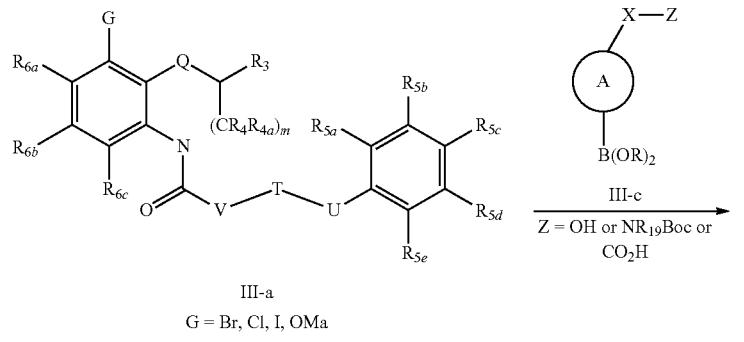

III-a
G = Br, Cl, I, OMa

III-c
Z = OH or NR19Boc or CO2H

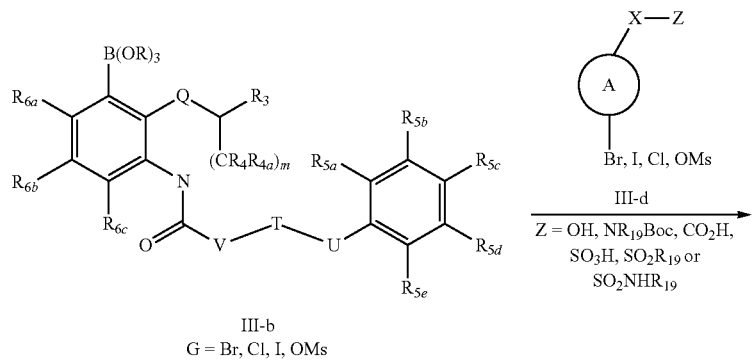

III-b
G = Br, Cl, I, OMs

III-d
Z = OH, NR19Boc, CO2H, SO3H, SO2R19 or SO2NHR19

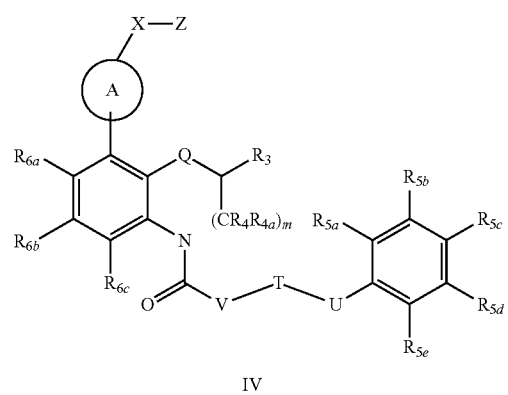

IV

Scheme 3 describes a method for preparing compounds of formula IV. Boronic acid or ester III-c can be obtained commercially, or prepared by methods known in the literature or by other methods known to one skilled in the art. Formation of a compound IV can be obtained via coupling reaction of boronic acid or ester III-c with III-a in the presence of palladium catalyst. The reactions can be carried out at room temperature, or with heating, or done in a microwave reactor. Alternatively, compound with formula IV can be prepared through coupling III-b with III-d in a similar fashion described above, while compound III-b can be prepared via the coupling reaction of bis(pinacola)diboron with III-a in the presence of palladium catalyst such as [1,1'-bis(diphenylphosphino)ferrocene]dichloropalladium(II).

Scheme 4

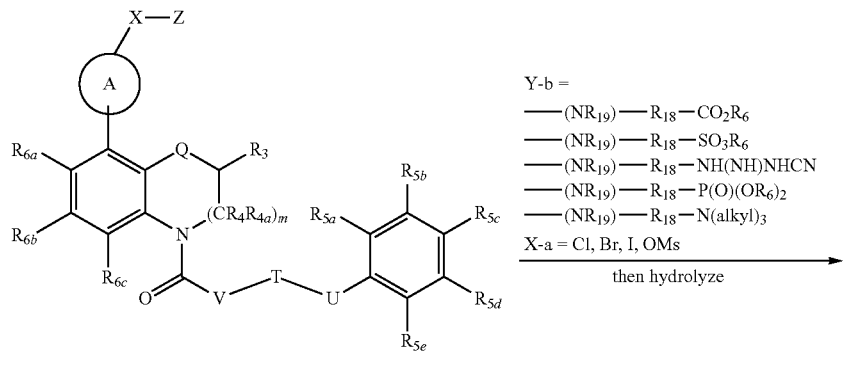

IV
Z = OH, NHR$_{19}$

Y-b =
— (NR$_{19}$) — R$_{18}$ — CO$_2$R$_6$
— (NR$_{19}$) — R$_{18}$ — SO$_3$R$_6$
— (NR$_{19}$) — R$_{18}$ — NH(NH)NHCN
— (NR$_{19}$) — R$_{18}$ — P(O)(OR$_6$)$_2$
— (NR$_{19}$) — R$_{18}$ — N(alkyl)$_3$
X-a = Cl, Br, I, OMs
then hydrolyze

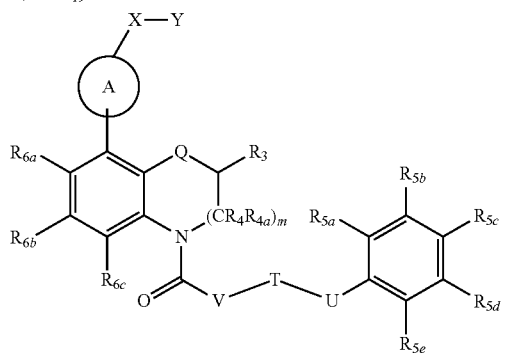

I-b

Y =
— OCO(NR$_{19}$) — R$_{18}$ — CO$_2$H
— OCO(NR$_{19}$) — R$_{18}$ — SO$_3$H
— OCO(NR$_{19}$) — R$_{18}$ — NH(NH)NH$_2$
— OCO(NR$_{19}$) — R$_{18}$ — P(O)(OH)(OR$_6$)
— OCO(NR$_{19}$) — R$_{18}$ — N(alkyl)$_3$ Y =
— NR$_{19}$CO(NR$_{19}$) — R$_{18}$ — CO$_2$H
— NR$_{19}$CO(NR$_{19}$) — R$_{18}$ — SO$_3$H
— NR$_{19}$CO(NR$_{19}$) — R$_{18}$ — NH(NH)NH$_2$
— NR$_{19}$CO(NR$_{19}$) — R$_{18}$ — P(O)(OH)(OR$_6$)
— NR$_{19}$CO(NR$_{19}$) — R$_{18}$ — N(alkyl)$_3$ As described in Scheme 4, when Z is —OH or NHR$_{19}$, compound I-b can be prepared through treatment IV with phosgene or similar reagents such as diphosgene or triphosgene in the presence of base such as DIEA. The resulting intermediate carbonochloridate or carbamic chloride can be then treated with amine Y-b in the presence of base such as Hunig's base or aqueous Na$_2$CO$_3$ to get desired I-b directly or after hydrolysis under basic condition such as aqueous LiOH. The compound I-b can be also obtained through direct treatment with a suitable isocyanate in the presence of a base such as DIEA, LDA, or LiHMDS, and then hydrolyzed under a basic condition such as aqueous LiOH.

Scheme 5

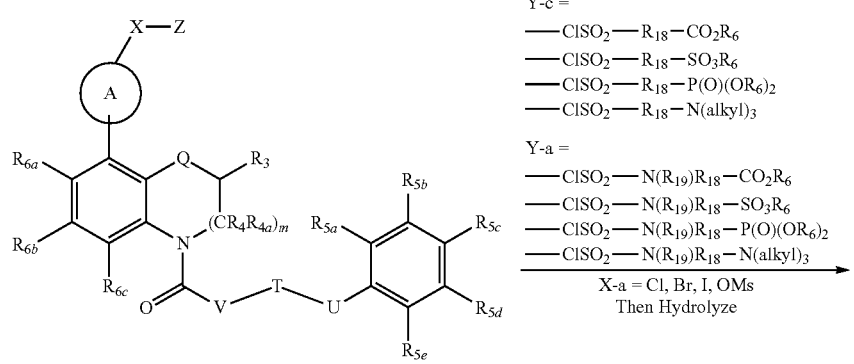

IV
Z = NHR$_{19}$

Y-c =
— ClSO$_2$ — R$_{18}$ — CO$_2$R$_6$
— ClSO$_2$ — R$_{18}$ — SO$_3$R$_6$
— ClSO$_2$ — R$_{18}$ — P(O)(OR$_6$)$_2$
— ClSO$_2$ — R$_{18}$ — N(alkyl)$_3$ Y-a =
— ClSO$_2$ — N(R$_{19}$)R$_{18}$ — CO$_2$R$_6$
— ClSO$_2$ — N(R$_{19}$)R$_{18}$ — SO$_3$R$_6$
— ClSO$_2$ — N(R$_{19}$)R$_{18}$ — P(O)(OR$_6$)$_2$
— ClSO$_2$ — N(R$_{19}$)R$_{18}$ — N(alkyl)$_3$
X-a = Cl, Br, I, OMs
Then Hydrolyze

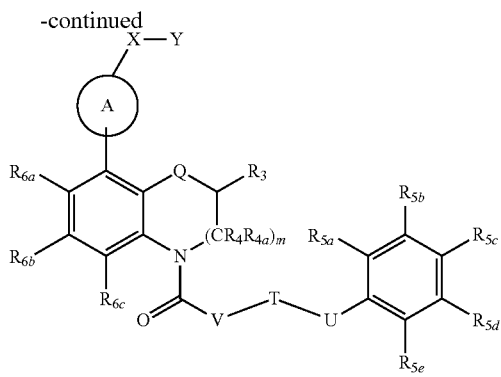

I-c

Y =
—NR$_{19}$SO$_2$—R$_{18}$—CO$_2$H
—NR$_{19}$SO$_2$—R$_{18}$—SO$_3$H
—NR$_{19}$SO$_2$—R$_{18}$—P(O)(OH)(OR$_6$)
—NR$_{19}$SO$_2$—R$_{18}$—N(alkyl)$_3$ —NR$_{19}$SO$_2$—N(R$_{19}$)R$_{18}$—CO$_2$H$_6$
—NR$_{19}$SO$_2$—N(R$_{19}$)R$_{18}$—SO$_3$H
—NR$_{19}$SO$_2$—N(R$_{19}$)R$_{18}$—P(O)(OH)(OR$_6$)
—NR$_{19}$SO$_2$—N(R$_{19}$)R$_{18}$—N(alkyl)$_3$ As described in Scheme 5, when Z is NHR$_{19}$, the compound I-c can also be directly obtained through treatment with a suitable sulfonyl chloride or sulfamoyl chloride in the presence of a base, such as DIEA, at room temperature or elevated temperature, and then, if required, hydrolyzed under a basic condition, such as aqueous LiOH to afford I-c.

Scheme 6

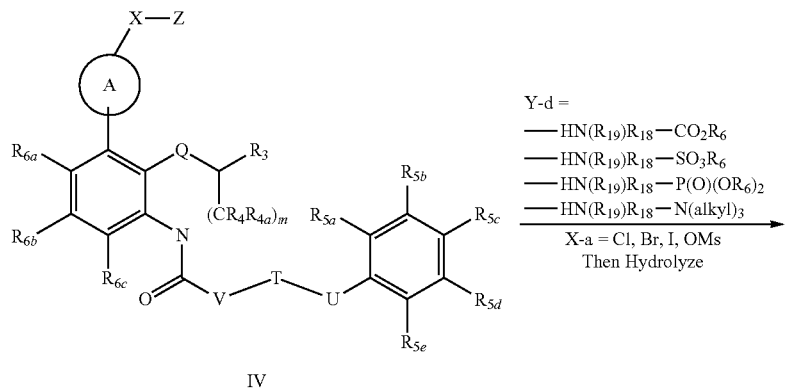

IV

Z = SO$_3$H or CO$_2$H

Y-d =
—HN(R$_{19}$)R$_{18}$—CO$_2$R$_6$
—HN(R$_{19}$)R$_{18}$—SO$_3$R$_6$
—HN(R$_{19}$)R$_{18}$—P(O)(OR$_6$)$_2$
—HN(R$_{19}$)R$_{18}$—N(alkyl)$_3$
X-a = Cl, Br, I, OMs
Then Hydrolyze

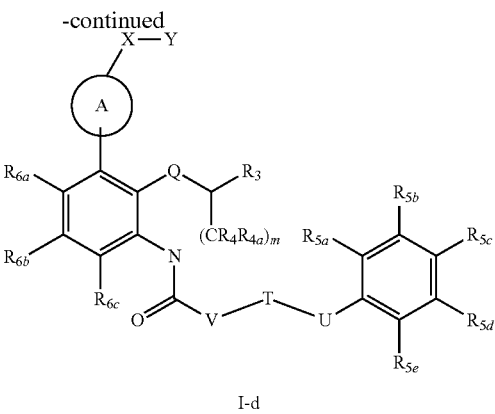

I-d

Y =
— $SO_2$—$N(R_{19})R_{18}$—$CO_2H$
— $SO_2$—$N(R_{19})R_{18}$—$SO_3H$
— $SO_2$—$N(R_{19})R_{18}$—$P(O)(OH)(OR_6)$
— $SO_2$—$N(R_{19})R_{18}$—$N(alkyl)_3$
— $CO$—$N(R_{19})R_{18}$—$CO_2H$
— $CO$—$N(R_{19})R_{18}$—$SO_3H$
— $CO$—$N(R_{19})R_{18}$—$SO_3R_{18}$
— $CO$—$N(R_{19})R_{18}$—$P(O)(OH)(OR_6)$
— $CO_2$—$N(R_{19})R_{18}$—$N(alkyl)_3$ As described in Schemed 6, when Z is $SO_3H$ or $CO_2H$, the sulfonic acid can first be converted to the corresponding sulfonyl chloride under standard condition, such as thionyl chloride. The obtained sulfonyl chloride is then treated with amine Y-e in the presence of a base such as DIEA at room temperature or elevated temperature to give desired I-d after, if required, hydrolysis under a basic condition, such as aqueous LiOH.

Scheme 7

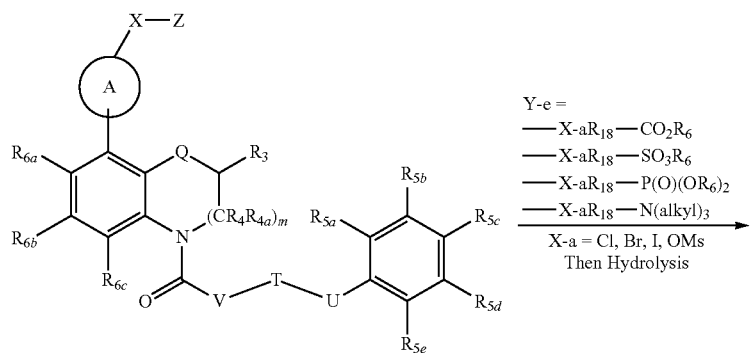

Y-e =
— X-a$R_{18}$—$CO_2R_6$
— X-a$R_{18}$—$SO_3R_6$
— X-a$R_{18}$—$P(O)(OR_6)_2$
— X-a$R_{18}$—$N(alkyl)_3$
X-a = Cl, Br, I, OMs
Then Hydrolysis

IV

Z = $SO_2NHR_{19}$

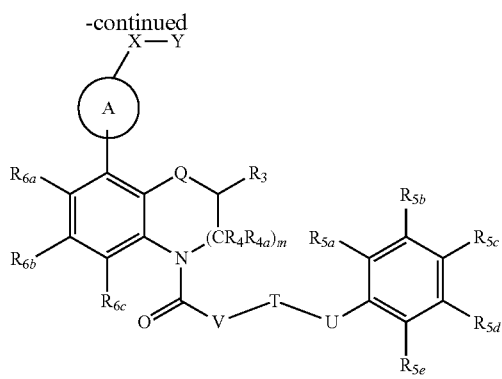

I-e

Y =
—SO$_2$—NR$_{18}$—CO$_2$H
—SO$_2$—NR$_{18}$—SO$_3$H
—SO$_2$—NR$_{18}$—P(O)(OH)(OR$_6$)
—SO$_2$—NR$_{18}$—N(alkyl)$_3$ As described in Scheme 7, when Z is SO$_2$NHR$_{19}$, IV may react with electrophiles Y-e, under suitable basic conditions, such as with K$_2$CO$_3$, LiHMDS, or LDA, to give compound I-e after hydrolysis under a basic condition, such as aqueous LiOH.

Scheme 8

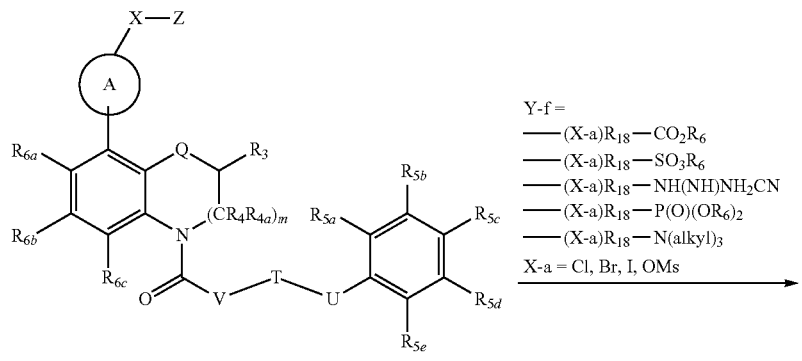

IV

Z = OH, SH, NHR$_{19}$

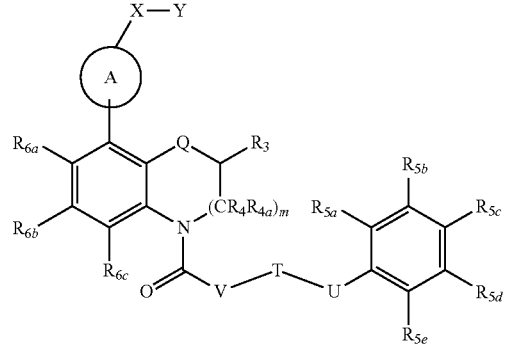

I-f

| Y = | Y = | Y = |
|---|---|---|
| —OR$_{18}$—CO$_2$H | —SR$_{18}$—CO$_2$H | —NR$_{19}$R$_{18}$—CO$_2$H |
| —OR$_{18}$—SO$_3$H | —SR$_{18}$—SO$_3$H | —NR$_{19}$R$_{18}$—SO$_3$H |
| —OR$_{18}$—P(O)(OH)(OR$_6$) | —SR$_{18}$—P(O)(OH)(OR$_6$) | —NR$_{19}$R$_{18}$—P(O)(OH)(OR$_6$) |
| —OR$_{18}$—N(alkyl)$_3$ | —SR$_{18}$—N(alkyl)$_3$ | —NR$_{19}$R$_{18}$—N(alkyl)$_3$ |

As described in Scheme 8, when Z is —OH, SH or NHR$_{19}$, compound I-f can be prepared through treatment IV with bases, such as DIEA, K2CO3, LDA, or LiHMDS, and then reacted with electrophiles Y-f to give desired I-f after hydrolysis under a basic condition, such as aqueous LiOH.

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$H-NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein, throughout the specification. For ease of reference, the abbreviations include, but are not necessarily limited to: Aq=aqueous; AcOH=acetic acid; DIBAL-H=Diisobutylaluminum hydride; t-BuOH=tert butyl alcohol; BOC=tert-butoxycarbonyl; BOP=Benzotriazole-1-yl-oxy-tris(dimethylamino)phosphonium hexafluorophosphate; CAN=cerium (IV) ammonium nitrate; $CH_2Cl_2$ or DCM=methylene chloride; MeCN or $CH_3CN$=acetonitrile; DEAD=diethyl azodicarboxylate; DIAD=diisopropyl azodicarboxylate; DIPEA=diisopropylethylamine; DME=dimethyoxyethane; DMF=N,N-dimethylformamide; DMAP=4-Dimethylaminopyridine; DMSO=dimethyl sulfoxide; EtOAc=ethyl acetate; TEA or $Et_3N$=triethylamine; $Et_2O$=diethyl ether; HATU=O-(7-Azabenzotriazole-1-yl)-1,1,3,3-tetramethyluronium hexafluorophosphate; HPLC or LC=high performance liquid chromatography; $K_2CO_3$=potassium carbonate; LiOH=lithium hydroxide; m-CPBA=m-chloroperoxybenzoic acid; MeOH=methanol; $MgSO_4$=magnesium sulfate; MS or Mass Spec=mass spectrometry; NaH=sodium hydride; $NaHCO_3$=sodium bicarbonate; $NH_4OAc$=ammonium acetate; $Na_2SO_4$=sodium sulfate; $Na_2CO_3$=sodium carbonate; NaHMDS=sodium hexamethyldisilazide; NaOH=sodium hydroxide; $NaClO_2$=Sodium Chlorite; $NaHPO_4$=Sodium phosphate; $Pd_2(dba)_3$=tris(dibenzylideneacetone)dipalladium (0); $Pd(dppf)Cl_2$=[1,1'-bis(diphenylphosphino)ferrocene]dichloropalladium(II); $Pd(dppf)Cl_2$—$CH_2Cl_2$=[1,1'-bis(diphenylphosphino)ferrocene]dichloropalladium(II) methylene chloride; $Ph_3P$=triphenylphosphine; $PCl_5$=phosphine pentachloride; rt=room temperature; RT=retention time; TFA=trifluoroacetic acid; THF=tetrahydrofuran; T3P=Propylphosphonic anhydride; $TMS-N_3$=trimethylsilyl azide; min=minute(s); h or hr=hour(s); L or l.=liter(s); mL or ml=milliliter(s); μL or μl=microliter(s); μm or μM=micromolar(s); g or gm=gram(s); mg=milligram(s); mol=moles; mmol=millimole(s); M=molar; nm=nanometer; [M+H]=parent plus a proton; rt=room temperature; LCMS=liquid chromatographic mass spectrometry and MS=low resolution mass spectrometry.

"α", "β", "R" and "S" are stereochemical designations familiar to those skilled in the art.

General

The term HPLC refers to a Shimadzu high performance liquid chromatography with one of following methods:

HPLC-1: Sunfire C18 (4.6×150 mm) 3.5 micron, gradient 10 to 100% B:A for 12 min, then 3 min hold at 100% B.

Mobile phase A: 0.05% TFA in water:$CH_3CN$ (95:5)

Mobile phase B: 0.05% TFA in $CH_3CN$:water (95:5)

TFA Buffer pH=2.5; Flow rate: 1 mL/min; Wavelength: 254 nm, 220 nm.

HPLC-2: XBridge Phenyl (4.6×150 mm) 3.5 micron, gradient 10 to 100% B:A for 12 min, then 3 min hold at 100% B.

Mobile phase A: 0.05% TFA in water:$CH_3CN$ (95:5)

Mobile phase B: 0.05% TFA in $CH_3CN$:water (95:5)

TFA Buffer pH=2.5; Flow rate: 1 mL/min; Wavelength: 254 nm, 220 nm.

HPLC-3: SUPELCO® Ascentis 4.6×50 mm 2.7 μm C18, gradient 0 to 100% B:A for 4 min.

Mobile phase A: water:$CH_3CN$ (90:10)+10 μM $NH_4OAc$

Mobile phase B: $CH_3CN$:water (90:10)+10 μM $NH_4OAc$

HPLC-4: Waters Xbridge 4.6×100 mm 5 micron C18, gradient 0 to 100% B:A for 4 min.

Mobile phase A: water+10 μM $NH_4OAc$

Mobile phase B: $CH_3CN$+10 μM $NH_4OAc$

HPLC-5: SunFire 4.6×50 mm COMBISCREEN®, gradient 0 to 100% B:A for 4 min, then 1 min hold at 100% B.

Mobile phase A=10% MeOH-90% $H_2O$-0.1% TFA

Mobile phase B=90% MeOH-10% $H_2O$-0.1% TFA

Gradient Time=4 min

Flow Rate=4 ml/min

Wavelength=220

Method A: PHENOMENEX® C18 5 micron 4.6×50 mm column using a 4 minute gradient of 0-100% solvent B [90% MeOH:10% $H_2O$:0.2% $H_3PO_4$] and 100-0% solvent A [10% MeOH:90% $H_2O$:0.2% $H_3PO_4$] with 4 mL/min flow rate and a 1 min. hold, an ultra violet (UV) detector set at 220 nm.

Method B: PHENOMENEX® S5 ODS 4.6×30 mm column, gradient elution 0-100% B/A over 2 min (solvent A=10% MeOH/$H_2O$ containing 0.1% TFA, solvent B=90% MeOH/$H_2O$ containing 0.1% TFA), flow rate 5 mL/min, UV detection at 220 nm.

Method C: YMC S7 ODS 3.0×50 mm column, gradient elution 0-100% B/A over 2 min (solvent A=10% MeOH/$H_2O$ containing 0.1% TFA, solvent B=90% MeOH/$H_2O$ containing 0.1% TFA), flow rate 5 mL/min, UV detection at 220 nm.

Method D: YMC S-5 C18 5 micron 4.6×50 mm column using a 4 minute gradient of 0-100% solvent B [90% $CH_3CN$: 10% $H_2O$:0.1% TFA] and 100-0% solvent A [10% $CH_3CN$: 90% $H_2O$:0.1% TFA] with 4 mL/min flow rate and a 1 min. hold (100% B), an ultra violet (UV) detector set at 220 nm The term prep HPLC refers to an automated Shimadzu HPLC system using a mixture of solvent A (10% MeOH/90% $H_2O$/0.1% TFA) and solvent B (90% MeOH/10% $H_2O$/0.1% TFA) or a mixture of solvent A (10% $CH_3CN$/90% $H_2O$/0.1% TFA) and solvent B (90% $CH_3CN$/10% $H_2O$/0.1% TFA). The preparative columns were packed with YMC or PHENOMENEX® ODS C18 5 micron resin or equivalent.

Example 1

2-(4-(1-(4-(2,3-Dimethylphenoxy)butanoyl)-1,2,3,4-tetrahydroquinolin-5-yl)-1H-pyrazol-1-yl)acetic acid

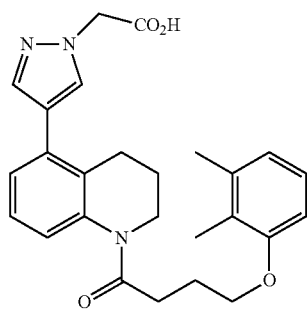 [SMILES: Cc1cccc(OCCCC(=O)N2CCCc3c(-c4cnn(CC(=O)O)c4)cccc32)c1C]

Step A. 4-Bromo-2,3-dihydro-1H-inden-1-one oxime

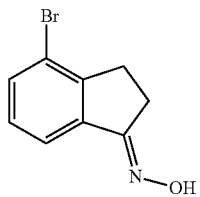 [SMILES: O/N=C1\CCc2c(Br)cccc21]

To a solution of 4-bromo-2,3-dihydro-1H-inden-1-one (3.00 g, 14.21 mmol) in MeOH (40 mL) was added hydroxylamine hydrochloride (3.95 g, 56.9 mmol). The resulting mixture was refluxed for 1 h and concentrated in vacuo. The resulting residue was partitioned between DCM and 50% saturated NaHCO$_3$, and stirred vigorously for 20 min. The organic layer was separated, dried over anhydrous Na$_2$SO$_4$, filtered and concentrated to afford the title compound (3.18 g, 99% yield) as a pale yellow solid. LCMS, [M+H]$^+$=226.0.

Step B. 5-Bromo-1,2,3,4-tetrahydroquinoline, HCl salt

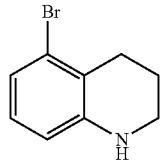 [SMILES: Brc1cccc2c1CCCN2]

To a partial suspension of 4-bromo-2,3-dihydro-1H-inden-1-one oxime (3.16 g, 13.98 mmol) in DCM (70 mL) at 0° C. was added DIBAL-H (84 mL, 84.0 mmol, 1.0 M in toluene) over 30 min. Upon completion of addition, the reaction mixture was allowed to slowly warm to room temperature, where it stirred overnight. After this time, the reaction mixture was cooled to 0° C. under a stream of argon, and sodium fluoride (35.2 g, 839 mmol) was added portion-wise, followed by addition of water (4 mL) at such a rate as to keep the internal temperature below 10° C. After 30 min the resulting mixture was filtered through CELITE®, and the filtrate was concentrated. The resulting residue was re-dissolved in ethyl acetate (40 mL) and filtered. Concentrated HCl (2 mL) was added to the filtrate and the resulting mixture was stirred for 30 min. At the conclusion of this period, the resulting solid was collected by filtration, washed with ethyl acetate, and dried to afford the title compound (2.57 g, 74% yield). LCMS, [M+H]$^+$=212.0. $^1$H NMR (400 MHz, MeOD) δ 7.74 (dd, J=7.6, 1.5 Hz, 1H), 7.38-7.28 (m, 2H), 3.56-3.46 (m, 2H), 2.95-2.87 (m, 2H), 2.26-2.16 (m, 2H).

Step C. Ethyl 4-(2,3-dimethylphenoxy)butanoate

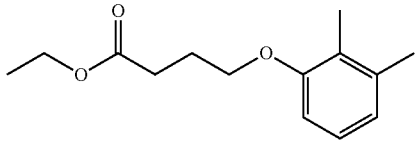 [SMILES: CCOC(=O)CCCOc1cccc(C)c1C]

A mixture of 2,3-dimethylphenol (12.2 g, 100 mmol), tetrabutylammonium iodide (0.738 g, 1.997 mmol), ethyl 4-bromobutanoate (14.29 mL, 100 mmol), and potassium carbonate (27.6 g, 200 mmol) in THF (100 mL) was heated at 60° C. for 20 h. After this time, the reaction mixture was cooled to room temperature. Once at the prescribed temperature, the reaction mixture was quenched with water (50 mL), and extracted with EtOAc (2×50 mL). The combined organic phases were concentrated, and purified by flash chromatography (0 to 30% EtOAc:hexanes) to afford the title compound (22.5 g, 90% yield) as colorless oil. LCMS, [M+Na]$^+$=259.1. $^1$H NMR (400 MHz, CDCl$_3$) δ 7.01 (dd, J=8.2, 7.5 Hz, 1H), 6.75 (d, J=7.5 Hz, 1H), 6.67 (d, J=8.2 Hz, 1H), 4.13 (q, J=7.1 Hz, 2H), 3.97 (t, J=6.0 Hz, 2H), 2.52 (t, J=7.4 Hz, 2H), 2.25 (s, 3H), 2.15-2.07 (m, 2H), 2.12 (s, 3H), 1.24 (t, J=7.1 Hz, 3H).

Step D. 4-(2,3-Dimethylphenoxy)butanoic acid

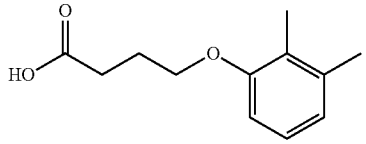

A mixture of ethyl 4-(2,3-dimethylphenoxy)butanoate (22.28 g, 94 mmol), 4 N LiOH (94 mL, 377 mmol) in dioxane (50 mL) was heated at 60° C. for 4 h. After cooling to room temperature, the mixture was adjusted to pH 2-3 with 3 N HCl, and extracted with EtOAc (2×10 mL). The combined organic phases were washed with brine, dried over anhydrous Na$_2$SO$_4$, filtered, and concentrated to afford the title compound (20 g, 100% yield). LCMS, [M−H]$^+$=207.1. $^1$H NMR (400 MHz, CDCl$_3$) δ 7.02 (dd, J=8.2, 7.5 Hz, 1H), 6.76 (d, J=7.5 Hz, 1H), 6.67 (d, J=8.2 Hz, 1H), 3.99 (t, J=6.0 Hz, 2H), 2.60 (t, J=7.3 Hz, 2H), 2.25 (s, 3H), 2.18-2.09 (m, 2H), 2.12 (s, 3H).

Step E. 1-(5-Bromo-3,4-dihydroquinolin-1(2H)-yl)-4-(2,3-dimethylphenoxy)butan-1-one

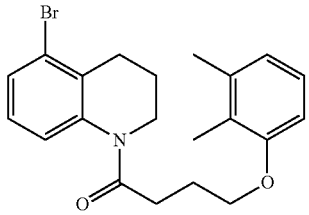

To a solution of 4-(2,3-dimethylphenoxy)butanoic acid (1.35 g, 6.5 mmol), 5-bromo-1,2,3,4-tetrahydroquinoline, HCl salt (1.24 g, 5.0 mmol), and Hunig's base (3.49 mL, 20 mmol) in ethyl acetate (25 mL) at 0° C. was added a solution of T3P in $Et_2O$ (50% w/w, 5.95 mL, 10 mmol) dropwise. The reaction mixture was allowed to slowly warm to room temperature where it stirred overnight. At the conclusion of this period, additional ethyl acetate and water were added, and the resulting mixture was stirred vigorously for 15 min. After this time, the organic layer was separated, washed with saturated $NaHCO_3$ and brine, dried over anhydrous $Na_2SO_4$, filtered, and concentrated. The resulting residue was purified by flash chromatography (0-30% ethyl acetate:hexanes) to afford the title compound as an off-white solid (1.50 g, 74% yield). LCMS, $[M+H]^+$=402.0. $^1$H NMR (400 MHz, $CDCl_3$) δ 7.39 (d, J=8.5 Hz, 1H), 7.02 (dd, J=14.9, 7.7 Hz, 2H), 6.74 (t, J=11.0 Hz, 1H), 6.64 (d, J=8.2 Hz, 1H), 5.30 (s, 1H), 3.95 (t, J=5.6 Hz, 2H), 3.77 (t, J=6.0 Hz, 2H), 2.73 (t, J=7.1 Hz, 2H), 2.68 (t, J=6.6 Hz, 2H), 2.25 (s, 3H), 2.18 (ddd, J=13.1, 6.5, 6.3 Hz, 2H), 2.02-1.84 (m, 5H).

Example 1

Argon was vigorously bubbled through a stirring mixture of 1-(5-bromo-3,4-dihydroquinolin-1(2H)-yl)-4-(2,3-dimethylphenoxy)butan-1-one (40 mg, 0.099 mmol), potassium carbonate (55 mg, 0.398 mmol), and ethyl 2-(4-(4,4,5,5-tetramethyl-1,3,2-dioxaborolan-2-yl)-1H-pyrazol-1-yl)acetate (56 mg, 0.199 mmol) in a 4:1 THF/water solution (1 mL) in a pressure vessel for 5 min. Tetrakis(triphenylphosphine)palladium (11 mg, 9.94 μmol) was added, and the vessel was flushed with argon and capped. The reaction mixture was stirred at 80° C. for 16 h. After this time, water and ethyl acetate were added, and the resulting mixture was stirred vigorously for 15 min. Upon completion of this period, the organic layer was separated. The aqueous phase was adjusted to pH 2-3 with 1 N HCl, and then extracted with ethyl acetate. The organic extracts were combined with the previous organic layer, dried over anhydrous $Na_2SO_4$, filtered, and concentrated. The resulting residue was purified by preparative HPLC (PHENOMENEX® Axia Luna column, 5 μm, C18, 30×75 mm; 10 min gradient from 100% A:0% B to 0% A:100% B and 3 min 100% B (A=90% $H_2O$/10% MeCN+ 0.1% TFA); (B=90% MeCN/10% $H_2O$+0.1% TFA); detection at 220 nm) to afford Example 1 (14.3 mg, 32% yield).

LCMS, $[M+H]^+$=448.2. $^1$H NMR (400 MHz, $CDCl_3$) δ 7.60 (s, 1H), 7.33 (s, 1H), 7.23-7.14 (m, 2H), 7.02 (t, J=7.9 Hz, 1H), 6.74 (d, J=7.5 Hz, 1H), 6.64 (d, J=8.1 Hz, 1H), 5.01 (s, 2H), 3.92 (s, 2H), 3.79 (t, J=6.8 Hz, 2H), 2.76 (t, J=7.1 Hz, 2H), 2.56 (s, 2H), 2.23-2.11 (m, 5H), 1.86 (m, 5H). HPLC-1: Rt=9.3 min, purity=98.6%; HPLC-2: Rt=8.4 min, purity=99.7%.

Example 2

4-(1-(4-(2,3-Dimethylphenoxy)butanoyl)-1,2,3,4-tetrahydroquinolin-5-yl)picolinic acid

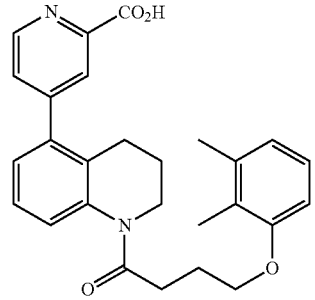 [SMILES: Cc1cccc(OCCCC(=O)N2CCCc3c(-c4ccnc(C(=O)O)c4)cccc32)c1C]

Step A. 4-(2,3-Dimethylphenoxy)-1-(5-(4,4,5,5-tetramethyl-1,3,2-dioxaborolan-2-yl)-3,4-dihydroquinolin-1(2H)-yl)butan-1-one

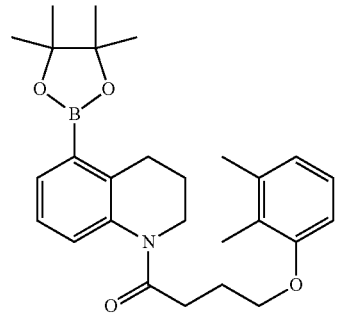 [SMILES: Cc1cccc(OCCCC(=O)N2CCCc3c(B4OC(C)(C)C(C)(C)O4)cccc32)c1C]

Argon was vigorously bubbled through a stirring mixture of 1-(5-bromo-3,4-dihydroquinolin-1(2H)-yl)-4-(2,3-dimethylphenoxy)butan-1-one (0.50 g, 1.24 mmol), potassium acetate (0.49 g, 4.97 mmol), and bis(pinacolato)diboron (0.47 g, 1.86 mmol) in THF (6.2 mL) in a pressure vessel for 5 min. After this time, $Pd(dppf)Cl_2$—$CH_2Cl_2$ (0.10 g, 0.12 mmol) was added. Upon completion of addition, the vessel flushed with argon, capped, and heated to 80° C. for 16 h. At the conclusion of this period, water and ethyl acetate were added, and the resulting mixture was stirred vigorously for 20 min. The organic layer was separated, dried over anhydrous $Na_2SO_4$, filtered, and concentrated. The resulting residue was purified by flash chromatography (0-30% ethyl acetate:hexanes) to afford the title compound (0.54 g, 97% yield) as a colorless viscous oil. LCMS, [M+H]$^+$=450.1.

Step B. Methyl 4-(1-(4-(2,3-dimethylphenoxy)butanoyl)-1,2,3,4-tetrahydroquinolin-5-yl)picolinate

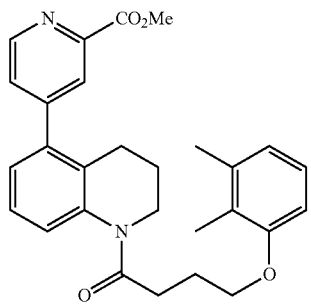 [SMILES: COC(=O)c1cc(-c2cccc3c2CCCN3C(=O)CCCOc2cccc(C)c2C)ccn1]

To a degassed solution of 4-(2,3-dimethylphenoxy)-1-(5-(4,4,5,5-tetramethyl-1,3,2-dioxaborolan-2-yl)-3,4-dihydroquinolin-1(2H)-yl)butan-1-one (0.020 g, 0.045 mmol), methyl 4-bromopicolinate (0.019 g, 0.089 mmol) and potassium carbonate (0.018 g, 0.134 mmol) in dioxane (0.50 mL)/water (0.20 mL) was added tetrakis(triphenylphosphine)palladium (2.57 mg, 2.225 μmol). Upon completion of addition, the vial was purged with argon, sealed, and stirred at 90° C. for 16 h. After cooling to room temperature, the mixture was extracted with EtOAc. The combined organic layer was dried over anhydrous MgSO$_4$, filtered, and concentrated in vacuo. The crude material was purified by flash chromatography (0-100% ethyl acetate:hexanes) to afford the title compound (17.7 mg, 87% yield) as a clear colorless oil. LCMS, [M+H]$^+$=459.1.

Example 2

A mixture of methyl 4-(1-(4-(2,3-dimethylphenoxy)butanoyl)-1,2,3,4-tetrahydroquinolin-5-yl)picolinate (0.050 g, 0.109 mmol) and 4 M LiOH (0.109 mL, 0.436 mmol) in THF (1.0 mL) was stirred at room temperature for 16 h. The mixture was adjusted to pH 6-7 with 1 N aq. HCl, and extracted with EtOAc. The combined organic layer was dried over anhydrous MgSO$_4$, filtered, and concentrated in vacuo to give Example 2 (45 mg, 90% yield) as a white solid. LCMS, [M+H]$^+$=445.1. $^1$H NMR (400 MHz, MeOD) δ 9.17 (s, 1H), 8.67-8.49 (br. s, 1H), 8.41 (s, 1H), 7.43 (br. s, 1H), 7.38 (t, J=7.7 Hz, 1H), 7.24 (d, J=7.9 Hz, 1H), 6.99 (t, J=7.9 Hz, 1H), 6.72 (d, J=7.6 Hz, 1H), 6.69 (d, J=8.2 Hz, 1H), 3.92 (br. s, 2H), 3.78 (t, J=6.9 Hz, 2H), 2.86 (t, J=6.9 Hz, 2H), 2.42 (br. s, 2H), 2.21-2.09 (m, 5H), 1.93-1.74 (m, 5H). HPLC-1: Rt=8.9 min, purity=98.9%; HPLC-2: Rt=8.2 min, purity=98.4%.

The following Examples were prepared in a manner analogous to Example 2.

TABLE 1

| Example | Name | —(A)—X—Y | LCMS, [M + H]$^+$ | $^1$H NMR (400 MHz, CDCl$_3$) δ | HPLC-1: Rt min, purity; HPLC-2: Rt min, purity | Synthesis comment |
|---|---|---|---|---|---|---|
| 3 | 2-(4-(1-(4-(2,3-Dimethylphenoxy)butanoyl)-1,2,3,4-tetrahydroquinolin-5-yl)-1H-pyrazol-1-yl)propanoic acid | | 462.1 | 7.61 (s, 1H), 7.41 (s, 1H), 7.23-7.13 (m, 2H), 7.02 (t, J = 7.9 Hz, 1H), 6.75 (d, J = 7.5 Hz, 1H), 6.64 (d, J = 8.2 Hz, 1H), 5.09 (dd, J = 14.6, 7.3 Hz, 1H), 3.93 (s, 2H), 3.79 (t, J = 6.8 Hz, 2H), 2.76 (t, J = 7.1 Hz, 2H), 2.56 (s, 2H), 2.25-2.12 (m, 5H), 1.86 (dd, J = 13.4, 7.0 Hz, 7H) | 9.5 min, 100% 8.4 min, 100% | Ester hydrolyzed during coupling |
| 4 | 2-(3-(1-(4-(2,3-Dimethylphenoxy)butanoyl)-1,2,3,4-tetrahydroquinolin-5-yl)phenyl)acetic acid | | 458.2 | 7.36 (t, J = 7.6 Hz, 1H), 7.30-7.18 (m, 4H), 7.17-7.07 (m, 2H), 7.00 (t, J = 7.8 Hz, 1H), 6.73 (d, J = 7.5 Hz, 1H), 6.63 (d, J = 8.2 Hz, 1H), 3.98-3.88 (m, 2H), 3.78 (t, J = 7.0 Hz, 2H), 3.69 (s, 2H), 2.77 (t, J = 7.2 Hz, 2H), 2.47 (t, J = 6.1 Hz, 2H), 2.24-2.13 (m, 5H), 1.93 (s, | 11.1 min, 99.5% 9.6 min, 99.5% | Ester hydrolyzed during coupling |

TABLE 1-continued

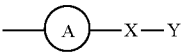

| Example | Name | —A—X—Y | LCMS, [M + H]⁺ | ¹H NMR (400 MHz, CDCl₃) δ | HPLC-1: Rt min, purity; HPLC-2: Rt min, purity | Synthesis comment |
|---|---|---|---|---|---|---|
| | | | | 3H), 1.79 (dt, J = 13.6, 6.8 Hz, 2H) | | |
| 5 | 3-(4-(1-(4-(2,3-Dimethyl-phenoxy)butanoyl)-1,2,3,4-tetrahydro-quinolin-5-yl)phenyl)propanoic acid | 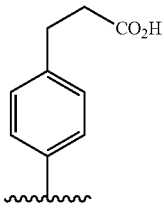 [SMILES: *c1ccc(CCC(=O)O)cc1] | 472.1 | 7.27-7.17 (m, 4H), 7.16-7.06 (m, 3H), 7.00 (t, J = 7.9 Hz, 1H), 6.74 (d, J = 7.5 Hz, 1H), 6.64 (d, J = 8.1 Hz, 1H), 3.94 (t, J = 5.2 Hz, 2H), 3.77 (t, J = 7.0 Hz, 2H), 3.00 (t, J = 7.7 Hz, 2H), 2.80-2.69 (m, 4H), 2.46 (t, J = 6.0 Hz, 2H), 2.25-2.12 (m, 5H), 1.93 (s, 3H), 1.84-1.73 (m, 2H) | 11.6 min, 99.2% 9.8 min, 99.2% | |
| 6 | 2-(4-(1-(4-(2,3-Dimethyl-phenoxy)butanoyl)-1,2,3,4-tetrahydro-quinolin-5-yl)phenyl)acetic acid | 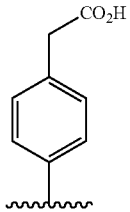 [SMILES: *c1ccc(CC(=O)O)cc1] | 458.1 | 7.32 (s, 1H), 7.30 (s, 1H), 7.26-7.13 (m, 4H), 7.09 (d, J = 6.8 Hz, 1H), 7.00 (t, J = 7.8 Hz, 1H), 6.73 (d, J = 7.5 Hz, 1H), 6.63 (d, J = 8.1 Hz, 1H), 3.93 (s, 2H), 3.76 (t, J = 6.7 Hz, 2H), 3.69 (s, 2H), 2.75 (t, J = 7.0 Hz, 2H), 2.45 (s, 2H), 2.19 (br. s, 5H), 1.93 (s, 3H), 1.83-1.71 (m, 2H) | 11.0 min, 100% 9.4 min, 100% | |
| 7 | 3-(3-(1-(4-(2,3-Dimethyl-phenoxy)butanoyl)-1,2,3,4-tetrahydro-quinolin-5-yl)phenyl)propanoic acid | 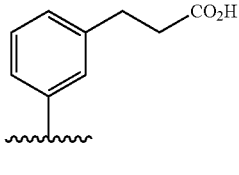 [SMILES: *c1cccc(CCC(=O)O)c1] | 472.1 | 7.24 (s, 1H), 7.15-7.00 (m, 3H), 6.95 (d, J = 7.0 Hz, 1H), 6.92 (s, 1H), 6.88-6.76 (m, 2H), 6.57 (d, J = 7.5 Hz, 1H), 6.48 (d, J = 8.1 Hz, 1H), 3.77 (br. s, 2H), 3.59 (t, J = 7.0 Hz, 2H), 2.84-2.72 (m, 2H), 2.61 (t, J = 7.2 Hz, 2H), 2.44-2.35 (m, 2H), 2.30 (br. s, 2H), 2.11-1.92 (m, 5H), 1.76 (s, 3H), 1.70-1.56 (m, 2H) | 11.8 min, 100% 10.0 min, 100% | |
| 8 | 1-(4-(1-(4-(2,3-Dimethyl-phenoxy)butanoyl)-1,2,3,4-tetrahydro-quinolin-5-yl)phenyl)cyclopropane-carboxylic acid | 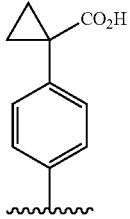 [SMILES: *c1ccc(C2(C(=O)O)CC2)cc1] | 484.2 | 7.37 (d, J = 8.2 Hz, 2H), 7.29-7.13 (m, 4H), 7.11 (d, J =7.8 Hz, 1H), 7.00 (t, J = 7.9 Hz, 1H), 6.74 (d, J = 7.5 Hz, 1H), 6.64 (d, J = 8.2 Hz, 1H), 3.94 (t, J = 5.3 Hz, 2H), 3.77 (t, J = 7.0 Hz, 2H), 2.75 (t, J = 7.2 Hz, 2H), 2.52-2.41 (m, 2H), 2.26-2.12 (m, 5H), 1.93 (s, 3H), 1.78 (dt, J = 13.5, 6.8 Hz, 2H), 1.71 (dd, J = 7.0, 3.9 Hz, 2H), 1.31 (dd, J = 7.0, 4.0 Hz, 2H) | 11.8 min, 100% 10.1 min, 100% | |

Example 9

3-((4-(3-(4-(2,3-Dimethylphenoxy)butanoyl)-1a,2,3,7b-tetrahydro-1H-cyclopropa[c]quinolin-7-yl)-1H-pyrazol-1-yl)methyl)benzoic acid

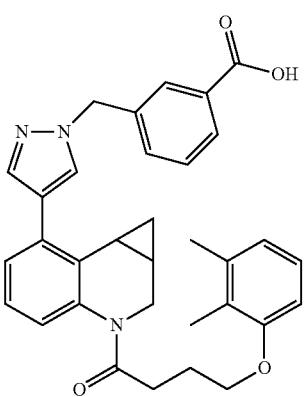

Step A. 5-Bromoquinoline 1-oxide

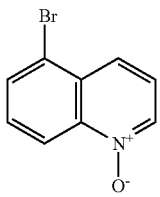 [SMILES: [O-][n+]1cccc2c(Br)cccc21]

To a solution of 5-bromoquinoline (2.5 g, 12.02 mmol) in DCM (50 mL) was added m-CPBA (3.50 g, 15.62 mmol) in three portions at room temperature. Upon completion of addition, the reaction mixture was stirred at room temperature for 3 h. After this time, 1N NaOH (40 ml) was added to the reaction, and the resulting mixture was extracted with DCM (2×50 mL). The combined organic layers were washed with brine, dried over anhydrous MgSO$_4$, filtered, and concentrated to afford the title compound (2.7 g, 99% yield) as light yellow solid. LCMS, [M+H]$^+$=223.9. $^1$H NMR (400 MHz, CDCl$_3$) δ 8.75 (d, J=8.8 Hz, 1H), 8.65 (d, J=6.0 Hz, 1H), 8.18 (d, J=8.8 Hz, 1H), 7.95 (d, J=7.7 Hz, 1H), 7.68-7.56 (m, 1H), 7.44 (dd, J=8.2, 6.0 Hz, 1H).

Step B. 5-Bromoquinolin-2(1H)-one

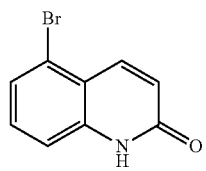 [SMILES: O=c1ccc2c(Br)cccc2[nH]1]

To a solution of 5-bromoquinoline 1-oxide (2.7 g, 12.05 mmol) in DMF (8 mL) was added trifluoroacetic anhydride (8.51 mL, 60.3 mmol) in three portions at 0° C. The reaction was allowed to warm to room temperature where it stirred overnight. At the conclusion of this period, the reaction mixture was poured into a saturated aq. NaHCO$_3$ (100 mL) solution, and extracted with DCM (2×50 mL). The combined organic layers were washed with brine, dried over anhydrous MgSO$_4$, filtered, and concentrated to afford the title compound (2.76 g, 98% yield) as a light yellow solid. LCMS, [M+H]$^+$=223.9. $^1$H NMR (400 MHz, DMSO-d$_6$) δ 11.98 (s, 1H), 8.05 (d, J=9.8 Hz, 1H), 7.50 (dd, J=8.0 Hz, 1H), 7.44 (t, J=8.0 Hz, 1H), 7.36 (d, J=8.0 Hz, 1H), 6.63 (d, J=9.8 Hz, 1H).

Step C. 5-Bromo-1-(4-methoxybenzyl)quinolin-2(1H)-one

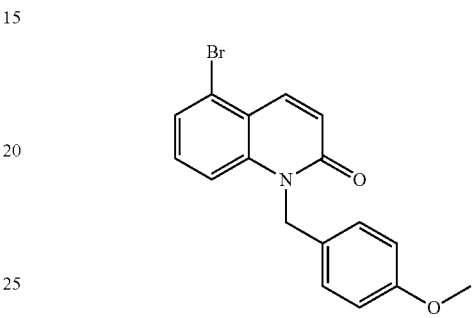

To a solution of 5-bromoquinolin-2(1H)-one (0.84 g, 2.29 mmol) in DMF (20 mL) at room temperature was added sodium hydride (0.57 g, 14.22 mmol) and 4-methoxybenzyl chloride (1.24 mL, 9.10 mmol). Upon completion of addition, the reaction mixture was stirred at room temperature for 2 d, and then heat to 75° C. where it stirred for 2 h. After cooling to room temperature, the reaction mixture was quenched with water, and extracted with EtOAc. The combined organic layer was washed with brine, dried over anhydrous Na$_2$SO$_4$, filtered, and concentrated. The resulting residue was purified by flash chromatography (0 to 30% ethyl acetate:hexanes) to afford the title compound (0.84 g, 40% yield) as a white powder. LCMS, [M+H]$^+$=344.0. $^1$H NMR (400 MHz, CDCl$_3$) δ 8.20 (d, J=9.8 Hz, 1H), 7.44 (dd, J=6.6, 2.2 Hz, 1H), 7.28-7.23 (m, 3H), 7.14 (d, J=8.2 Hz, 1H), 6.89 (d, J=9.8 Hz, 1H), 6.83 (d, J=8.6 Hz, 2H), 5.5 (s, 2H), 3.76 (s, 3H).

Step D. 7-Bromo-3-(4-methoxybenzyl)-3,7b-dihydro-1H-cyclopropa[c]quinolin-2(1aH)-one

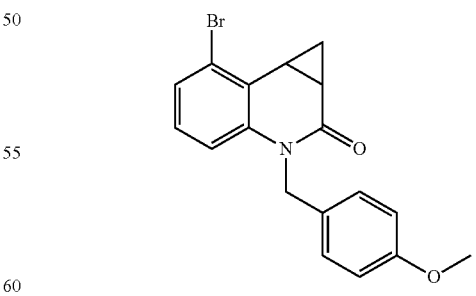

To a suspension of sodium hydride (136 mg, 3.40 mmol) in DMSO (5 mL) at room temperature was added trimethylsulfoxonium iodide (661 mg, 3.00 mmol) slowly under nitrogen. The reaction mixture was stirred at room temperature for 1 h, and then 5-bromo-1-(4-methoxybenzyl)quinolin-2(1H)-one (689 mg, 2.00 mmol) in 1 mL DMSO was added. Upon completion of addition, the reaction mixture was stirred at room temperature for 2 h, and then heated to 90° C. for 2 d. After cooling to room temperature, the reaction mixture was quenched with water and extracted with EtOAc. The combined organic layer was washed with brine, dried over anhydrous Na$_2$SO$_4$, filtered, and concentrated. The resulting residue was purified by flash chromatography (0 to 30% ethyl acetate:hexanes) to afford the title compound (330 mg, 45% yield) as a white powder. LCMS, [M+H]$^+$=358.0. $^1$H NMR (400 MHz, CDCl$_3$) δ 7.21 (d, J=7.7 Hz, 1H), 7.08 (d, J=8.2 Hz, 2H), 6.91 (t, J=8.0 Hz, 1H), 6.85-6.75 (m, 3H), 4.97-5.25 (m, 2H), 3.75 (s, 3H), 2.90 (td, J=8.1, 5.2 Hz, 1H), 2.40 (ddd, J=9.6, 8.0, 4.9 Hz, 1H), 1.74 (td, J=9.1, 4.4 Hz, 1H), 0.69 (q, J=4.8 Hz, 1H).

Step E. 7-Bromo-3,7b-dihydro-1H-cyclopropa[c]quinolin-2(1aH)-one

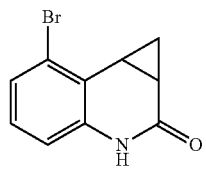 [SMILES: O=C1Nc2cccc(Br)c2C2CC12]

To a suspension of 7-bromo-3-(4-methoxybenzyl)-3,7b-dihydro-1H-cyclopropa[c]quinolin-2(1aH)-one (0.300 g, 0.837 mmol) in 9:1 acetonitrile/water (5.5 mL) was added CAN (0.459 g, 0.837 mmol) at room temperature. After stirring at room temperature overnight, the reaction mixture was quenched with water (10 mL) and adjusted pH to 7-9 by using saturated Na$_2$CO$_3$. The resulting mixture was extracted with EtOAc. The combined organic layer was concentrated and purified by flash chromatography (0 to 50% ethyl acetate: hexanes) to afford the title compound (0.18 g, 95% yield) as a pale yellow solid. LCMS, [M+H]$^+$=237.9. $^1$H NMR (400 MHz, CDCl$_3$) δ 8.15 (s, 1H), 7.24 (d, J=7.7 Hz, 1H), 7.00 (t, J=7.7 Hz, 1H), 6.69 (d, J=7.7 Hz, 1H), 2.84 (td, J=8.1, 5.2 Hz, 1H), 2.22-2.13 (m, 1H), 1.76 (td, J=9.2, 4.7 Hz, 1H), 0.75 (dd, J=10.0, 5.0 Hz, 1H).

Step F. 7-Bromo-1a,2,3,7b-tetrahydro-1H-cyclopropa[c]quinoline

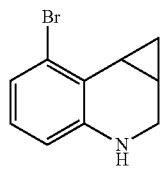

The mixture of 7-bromo-3,7b-dihydro-1H-cyclopropa[c]quinolin-2(1aH)-one (100 mg, 0.420 mmol) and borane tetrahydrofuran complex (5 mL, 5.00 mmol) was heated at 80° C. for 4 h. After this time, MeOH (5 mL) was added slowly to the reaction mixture, followed by 3 mL of conc. HCl. The resulting mixture was heated at 100° C. for 1 h, and then cooled to room temperature. After removing most of the solvent, the mixture was adjusted to a pH of 8-9 by using saturated Na$_2$CO$_3$. The aqueous solution was extracted with EtOAc (2×10 mL). The combined organic layers were concentrated and purified by flash chromatography (0 to 30% ethyl acetate:hexanes) to afford the title compound (78 mg, 83% yield) as an oil. LCMS, [M+H]$^+$=223.9. $^1$H NMR (400 MHz, CDCl$_3$) δ 8.15 (s, 1H), 7.24 (d, J=7.7 Hz, 1H), 7.00 (t, J=7.7 Hz, 1H), 6.69 (d, J=7.7 Hz, 1H), 2.84 (td, J=8.1, 5.2 Hz, 1H), 2.22-2.13 (m, 1H), 1.76 (td, J=9.2, 4.7 Hz, 1H), 0.75 (dd, J=10.0, 5.0 Hz, 1H).

Step F-a. (1aR,7bS)-7-Bromo-1a,2,3,7b-tetrahydro-1H-cyclopropa[c]quinoline

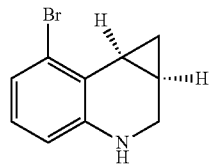 [SMILES: Brc1cccc2c1[C@H]1C[C@H]1CN2]

The separation of 10 g of racemates-bromo-1a,2,3,7b-tetrahydro-1H-cyclopropa[c]quinoline was achieved by SFC (Supercritical Fluid Chromatography) using CHIRALCEL® OJ column (250 mm×4.6 mm, 5 micron) from chiral technology. The resolution was achieved with 85% of CO$_2$ and 15% methanol at a flow of 3 ml/min at 100-bar backpressure. The detector was set a 220 nm. 4.7 g of desired enantiomer (1aR, 7bS)-7-bromo-1a,2,3,7b-tetrahydro-1H-cyclopropa[c] quinoline was obtained (95% recovery).

Step G. 1-(7-Bromo-1a,2-dihydro-1H-cyclopropa[c]quinolin-3(7bH)-yl)-4-(2,3-dimethylphenoxy)butan-1-one

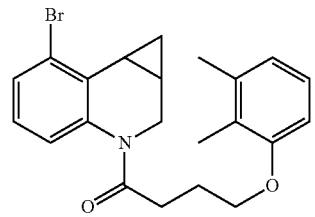 [SMILES: Cc1cccc(OCCCC(=O)N2CC3CC3c3c(Br)cccc32)c1C]

The title compound was prepared using a procedure analogous to Step E, Example 1 except that 5-bromo-1,2,3,4-tetrahydroquinoline, HCl salt was replaced with 7-bromo-1a,2,3,7b-tetrahydro-1H-cyclopropa[c]quinoline. LCMS, [M+H]$^+$=414.1.

Step H. Methyl 3-((4-bromo-1H-pyrazol-1-yl)methyl)benzoate

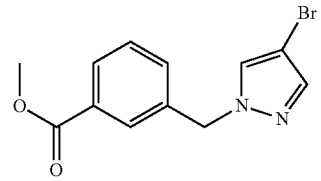 [SMILES: COC(=O)c1cccc(Cn2cc(Br)cn2)c1]

To a solution of 4-bromo-1H-pyrazole (1.00 g, 6.80 mmol) in DMF (11.7 mL) at 0° C. was added 1 M solution of NaHMDS in THF (7.48 mL, 7.48 mmol) slowly over 2 min.

The reaction mixture was stirred for 10 min and then the cooling bath was removed. After 30 min a solution of methyl 3-(bromomethyl)benzoate (1.71 g, 7.48 mmol) in DMF (1.9 mL) was added slowly, and the resulting mixture was stirred at room temperature overnight. At the conclusion of this period, the reaction mixture was quenched with saturated aq ammonium chloride (~1 mL), and partitioned between diethyl ether and water. The resulting mixture was stirred vigorously for 15 min. After this time, the organic layer was separated, dried over anhydrous Na₂SO₄, filtered, and concentrated. The resulting residue was purified by flash chromatography (0-60% ethyl acetate:hexanes) to afford the title compound (1.59 g, 79%). LCMS, [M+H]⁺=295.0. ¹H NMR (400 MHz, CDCl₃) δ 8.00 (d, J=7.1 Hz, 1H), 7.94 (s, 1H), 7.50 (s, 1H), 7.47-7.36 (m, 3H), 5.31 (s, 2H), 3.92 (s, 3H).

Step I. Methyl 3-((4-(4,4,5,5-tetramethyl-1,3,2-dioxaborolan-2-yl)-1H-pyrazol-1-yl)methyl)benzoate

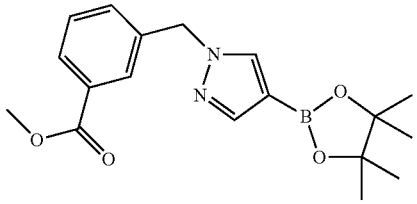

The title compound was prepared using a procedure analogous to Step A, Example 2 except that 1-(5-bromo-3,4-dihydroquinolin-1(2H)-yl)-4-(2,3-dimethylphenoxy)butan-1-one was replaced with methyl 3-((4-bromo-1H-pyrazol-1-yl)methyl)benzoate. LCMS, [M+H]⁺=343.1. ¹H NMR (400 MHz, CDCl₃) δ 8.01-7.92 (m, 2H), 7.82 (s, 1H), 7.68 (s, 1H), 7.43-7.39 (m, 2H), 5.35 (s, 2H), 3.91 (s, 3H), 1.30 (s, 12H).

Example 9

A stirring mixture of 1-(7-bromo-1a,2-dihydro-1H-cyclopropa[c]quinolin-3(7bH)-yl)-4-(2,3-dimethylphenoxy)butan-1-one (0.02 g, 0.048 mmol), potassium carbonate (0.013 g, 0.097 mmol), and methyl 3-((4-(4,4,5,5-tetramethyl-1,3,2-dioxaborolan-2-yl)-1H-pyrazol-1-yl)methyl)benzoate (0.033 g, 0.097 mmol) in a THF/water solution (4:1, 1.4 mL) in a pressure vessel was purged with argon vigorously for 5 min. After this time, tetrakis(triphenylphosphine)palladium (0.011 g, 9.65 μmol) was added, and the vessel was flushed with argon, capped, and heated to 85° C. for 20 h. After cooling to room temperature, 4 M LiOH (0.12 mL, 0.48 mmol) was added and the reaction was heated to 65° C. for 3 h. At the conclusion of this period, the reaction mixture was filtered and the filtrate was purified by preparative HPLC (PHENOMENEX® Axia Luna, 5μ, C18 30×100 mm; 10 min gradient from 90% A:10% B to 0% A:100% B and 5 min 100% B (A=90% H₂O/10% MeCN+0.1% TFA); (B=90% MeCN/10% H₂O+0.1% TFA); detection at 220 nm) to afford Example 9 (20 mg, 75% yield). LCMS, [M+H]⁺=536.5. ¹H NMR (400 MHz, CDCl₃) δ 8.08 (d, J=7.5 Hz, 1H), 8.06 (s, 1H), 7.78 (s, 1H), 7.58 (br. s, 1H), 7.56-7.46 (m, 2H), 7.21-7.08 (m, 2H), 6.99 (t, J=7.8 Hz, 2H), 6.72 (d, J=7.5 Hz, 1H), 6.62 (d, J=8.0 Hz, 1H), 5.48 (m, 2H), 3.96 (br. s, 1H), 3.88 (br. s, 1H), 2.84-2.70 (m, 1H), 2.63 (m, 1H), 2.18 (s, 6H), 2.05 (m, 1H), 1.89 (s, 2H), 1.72 (s, 1H), 0.94 (m, 1H), 0.58 (br. s, 1H). HPLC-1: Rt=10.6 min, purity=97.5%; HPLC-2: Rt=9.4 min, purity=95.7%.

Example 10

3-((4-(4-(4-(2,3-Dimethylphenoxy)butanoyl)-3,4-dihydro-2H-benzo[b][1,4]oxazin-8-yl)-1H-pyrazol-1-yl)methyl)benzoic acid

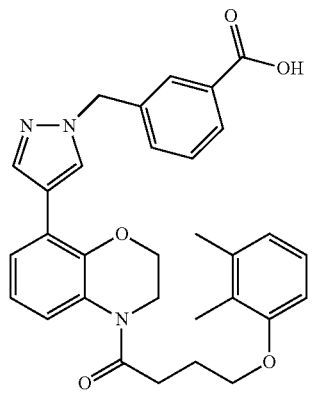

Step A. 8-Bromo-2H-benzo[b][1,4]oxazin-3(4H)-one

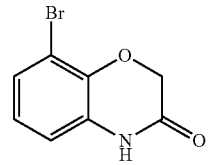 [SMILES: O=C1COc2c(Br)cccc2N1]

To a solution of 2-amino-6-bromophenol (1 g, 5.32 mmol) in acetonitrile (10 mL) and water (10 mL) was added sodium bicarbonate (1.028 g, 12.23 mmol). The mixture was cooled to 0° C. and chloroacetyl chloride (0.554 mL, 6.91 mmol) was added dropwise. The reaction was refluxed overnight. After cooling to room temperature, the mixture was diluted with EtOAc, washed with water, dried over anhydrous MgSO₄, filtered, and concentrated to afford the title compound (1.14 g, 94% yield) as a dark brown solid. ¹H NMR (400 MHz, CDCl₃) δ 8.22 (br. s, 1H), 7.23 (dd, J=8.0, 1.4 Hz, 1H), 6.86 (t, J=8.0 Hz, 1H), 6.76 (dd, J=7.9, 1.3 Hz, 1H), 4.74 (s, 2H).

Step B.
8-Bromo-3,4-dihydro-2H-benzo[b][1,4]oxazine

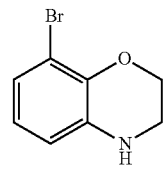 [SMILES: Brc1cccc2c1OCCN2]

The title compound was prepared using a procedure analogous to bromo-1a,2,3,7b-tetrahydro-1H-cyclopropa[c]

quinoline except that 7-bromo-3,7b-dihydro-1H-cyclopropa[c]quinolin-2(1aH)-one was replaced with 8-bromo-2H-benzo[b][1,4]oxazin-3(4H)-one. LCMS, [M+H]⁺=214.0. ¹H NMR (400 MHz, CDCl₃) δ 6.90 (dd, J=7.9, 1.5 Hz, 1H), 6.63 (t, J=7.9 Hz, 1H), 6.53 (dd, J=7.9, 1.5 Hz, 1H), 4.33-4.39 (m, 2H), 3.42-3.48 (m, 2H).

Step C. 1-(8-Bromo-2H-benzo[b][1,4]oxazin-4(3H)-yl)-4-(2,3-dimethylphenoxy)butan-1-one

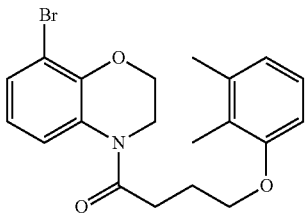

The title compound was prepared using a procedure analogous to 1-(5-bromo-3,4-dihydroquinolin-1(2H)-yl)-4-(2,3-dimethylphenoxy)butan-1-one except that 5-bromo-1,2,3,4-tetrahydroquinoline, HCl salt was replaced by 8-bromo-3,4-dihydro-2H-benzo[b][1,4]oxazine. LCMS, [M+H]⁺=404.1. ¹H NMR (400 MHz, CDCl₃) δ 7.33 (d, J=8.0 Hz, 1H), 7.26-7.21 (m, 1H), 7.00 (t, J=8.0 Hz, 1H), 6.78-6.71 (m, 2H), 6.64 (d, J=8.1 Hz, 1H), 4.36-4.28 (m, 2H), 3.98 (t, J=5.8 Hz, 2H), 3.95-3.90 (m, 2H), 2.80 (t, J=7.2 Hz, 2H), 2.24 (s, 3H), 2.19 (dt, J=13.1, 6.4 Hz, 2H), 2.02 (s, 3H).

Example 10

Example 10 was prepared using a procedure analogous to Example 9 except that 1-(7-bromo-1a,2-dihydro-1H-cyclopropa[c]quinolin-3(7bH)-yl)-4-(2,3-dimethylphenoxy)butan-1-one was replaced with 1-(8-bromo-2H-benzo[b][1,4]oxazin-4(3H)-yl)-4-(2,3-dimethylphenoxy)butan-1-one. LCMS, [M+H]⁺=526.3. ¹H NMR (400 MHz, CDCl₃) δ 8.07-7.98 (m, 2H), 7.94 (s, 1H), 7.86 (s, 1H), 7.53-7.40 (m, 2H), 7.32 (d, J=8.0 Hz, 1H), 7.24 (s, 1H), 6.98 (t, J=7.7 Hz, 1H), 6.87 (t, J=7.9 Hz, 1H), 6.71 (d, J=7.7 Hz, 1H), 6.63 (d, J=8.1 Hz, 1H), 5.40 (s, 2H), 4.37-4.29 (m, 2H), 4.02-3.92 (m, 4H), 2.84 (t, J=6.9 Hz, 2H), 2.25-2.13 (m, 5H), 1.98 (s, 3H). HPLC-1: Rt=10.8 min, purity=99.4%; HPLC-2: Rt=10.0 min, purity=99.3%.

Example 11

3-((4-(4-(4-(2,3-Dimethylphenoxy)butanoyl)-2-methyl-3,4-dihydro-2H-benzo[b][1,4]oxazin-8-yl)-1H-pyrazol-1-yl)methyl)benzoic acid

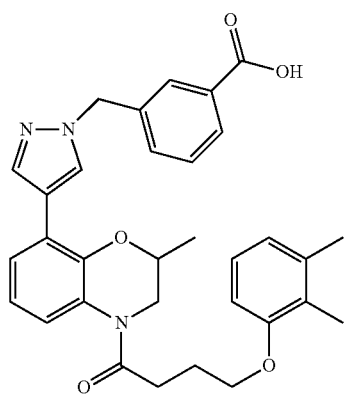 [SMILES: Cc1cccc(OCCCC(=O)N2CC(C)Oc3c(-c4cnn(Cc5cccc(C(=O)O)c5)c4)cccc32)c1C]

Step A.
2-Bromo-N-(3-bromo-2-hydroxyphenyl)propanamide

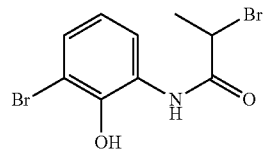

To a mixture of 2-amino-6-bromophenol (3 g, 15.96 mmol) and sodium bicarbonate (3.35 g, 39.9 mmol) in ethyl acetate (30 mL) and water (10 mL) at 0° C. was added 2-bromopropionyl chloride (1.61 ml, 15.96 mmol) dropwise. The reaction mixture was stirred at 0° C. for 3 h and then diluted with water. The resulting mixture was extracted with EtOAc and the organic layer was washed with brine, dried over anhydrous MgSO₄, filtered, and concentrated to afford the title compound (4.7 g, 73% yield). LCMS, [M+H]⁺=323.8.

Step B.
8-Bromo-2-methyl-2H-benzo[b][1,4]oxazin-3(4H)-one

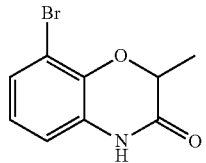

A mixture of 2-bromo-N-(3-bromo-2-hydroxyphenyl)propanamide (4.72 g, 14.61 mmol) and potassium carbonate (2.020 g, 14.61 mmol) in DMF (50 mL) was stirred at room temperature overnight. At the conclusion of this period, the reaction mixture was diluted with water and extracted with ether. The organic layer was dried over anhydrous MgSO₄, filtered, and concentrated. The resulting residue was purified by flash chromatography (100:0:0 to 0:90:10 hexanes:ethyl acetate:methanol) to afford the title compound (3.35 g, 95% yield) as a brown solid. ¹H NMR (400 MHz, CDCl₃) δ 8.17 (br. S, 1H), 7.22 (dd, J=8.0, 1.4 Hz, 1H), 6.85 (t, J=7.9 Hz, 1H), 6.76 (dd, J=7.8, 1.4 Hz, 1H), 4.78 (q, J=6.8 Hz, 1H), 1.64 (d, J=6.8 Hz, 3H).

Example 11

Example 11 was prepared using a procedure analogous to Example 10 except that 8-bromo-2H-benzo[b][1,4]oxazin-3(4H)-one was replaced with 8-bromo-2-methyl-2H-benzo[b][1,4]oxazin-3(4H)-one. LCMS, [M+H]⁺=540.4. ¹H NMR (500 MHz, MeOD) δ 8.03 (s, 1H), 7.95-7.99 (m, 2H), 7.92 (s, 1H), 7.44-7.54 (m, 2H), 7.40 (dd, J=7.8, 1.4 Hz, 1H), 7.26 (br. s, 1H), 6.85-6.95 (m, 2H), 6.65 (d, J=7.8 Hz, 2H), 5.43 (s, 2H), 4.32-4.39 (m, 1H), 4.23-4.31 (m, 1H), 3.92-4.01 (m, 2H), 3.15-3.25 (m, 1H), 2.90-2.98 (m, 1H), 2.80-2.88 (m, 1H), 2.15 (quin, J=6.5 Hz, 2H), 2.09 (s, 3H), 1.91 (s, 3H), 1.30

(d, J=6.4 Hz, 3H). HPLC-1: Rt=11.2 min, purity=99.4%; HPLC-2: Rt=10.2 min, purity=99.4%.

Example 12

3-((4-(1-(4-(2,3-Dimethylphenoxy)butanoyl)-2,3,4,5-tetrahydro-1H-benzo[b]azepin-6-yl)-1H-pyrazol-1-yl)methyl)benzoic acid

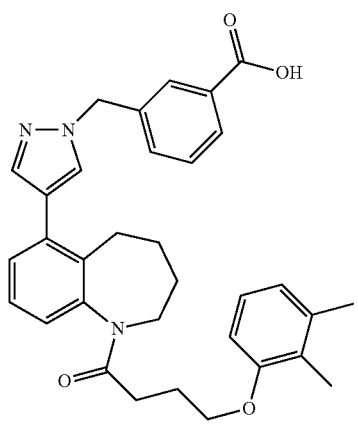 [SMILES: Cc1cccc(OCCCC(=O)N2CCCCc3c(-c4cnn(Cc5cccc(C(=O)O)c5)c4)cccc32)c1C]

Step A.
(E)-5-Bromo-3,4-dihydronaphthalen-1(2H)-one oxime

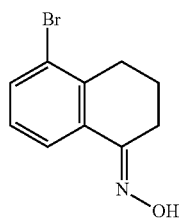 [SMILES: O/N=C1\CCCc2c(Br)cccc21]

To a solution of 5-bromo-3,4-dihydronaphthalen-1(2H)-one (1.0 g, 4.44 mmol) in pyridine (15 mL) was added hydroxylamine hydrochloride (0.617 g, 8.89 mmol). The reaction mixture was stirred at room temperature for 1 h and then concentrated. The resulting residue was treated with water (60 mL) and extracted with ethyl acetate (60 mL). The organic layer was dried over anhydrous Na$_2$SO$_4$, filtered, and concentrated to afford the title compound (1.41 g, 99% yield) as white solid. LCMS, [M+Na]$^+$=240.0.

Step B.
6-Bromo-2,3,4,5-tetrahydro-1H-benzo[b]azepine

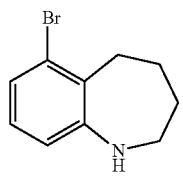

To a solution of (E)-5-bromo-3,4-dihydronaphthalen-1(2H)-one oxime (1.41 g, 5.87 mmol) in DCM (20 mL) at −10° C. under nitrogen was slowly added a solution of 1.0 M DIBAL-H in hexane (35.2 mL, 35.2 mmol). Upon completion of addition, the reaction mixture was stirred at room temperature for 2 h. After this time, the reaction mixture was cooled to 0° C. and then sodium fluoride (7.40 g, 176 mmol) and water (3.0 mL) were slowly added. The resulting mixture was stirred at 0° C. for 30 min and then CELITE® was added. The mixture was filtered and rinsed with DCM (100 mL). The filtrate was dried over anhydrous Na$_2$SO$_4$, filtered, and concentrated to provide the crude product. The crude product was converted to the HCl salt with aqueous 1.0 N HCl (3.0 mL) and then purified by preparative HPLC (PHENOMENEX® Axia Luna 5μ C18 30×100 mm; 10 min gradient from 80% A:20% B to 0% A:100% B and 5 min 100% B (A=90% H$_2$O/10% MeOH+0.1% TFA); (B=90% MeOH/10% H$_2$O+0.1% TFA); detection at 220 nm). The purified product was free based with a solution of saturated sodium bicarbonate (15 mL) and was then extracted with ethyl acetate (20 mL). The organic layer was dried over anhydrous Na$_2$SO$_4$, filtered, and concentrated to afford the title compound (612 mg, 45% yield). LCMS, [M+Na]$^+$=236.0. $^1$H NMR (400 MHz, MeOD) δ 7.12 (dd, J=7.8, 1.4 Hz, 1H), 6.88 (t, J=7.8 Hz, 1H), 6.83 (dd, J=7.8, 1.4 Hz, 1H), 3.08-3.02 (m, 4H), 1.86-1.79 (m, 2H), 1.69-1.62 (m, 2H).

Example 12

Example 12 was prepared using a procedure analogous to Example 9 except that 7-bromo-1a,2,3,7b-tetrahydro-1H-cyclopropa[c]quinoline was replaced with 6-bromo-2,3,4,5-tetrahydro-1H-benzo[b]azepine. LCMS, [M+H]$^+$=538.4. $^1$H NMR (400 MHz, MeOD) δ 8.02 (dt, J=7.3, 1.6 Hz, 1H), 7.97 (s, 1H), 7.77 (s, 1H), 7.60-7.49 (m, 3H), 7.36 (dd, J=7.7, 1.3 Hz, 1H), 7.27 (t, J=7.7 Hz, 1H), 7.16 (dd, J=7.7, 1.3 Hz, 1H), 6.97 (t, J=7.9 Hz, 1H), 6.67 (d, J=7.4 Hz, 1H), 6.66 (d, J=8.2 Hz, 1H), 5.50 (s, 2H), 4.65 (dt, J=12.7, 3.4 Hz, 1H), 3.98-3.85 (m, 2H), 3.39 (s, 2H), 2.92 (dd, J=14.1, 6.2 Hz, 1H), 2.82-2.71 (m, 1H), 2.52-2.37 (m, 2H), 2.10 (s, 5H), 1.99-1.86 (m, 2H), 1.84 (s, 3H), 1.82-1.73 (m, 1H). HPLC-1: Rt=9.5 min, purity=98.6%; HPLC-2: Rt=8.7 min, purity=98.2%.

Example 13

3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzoic acid

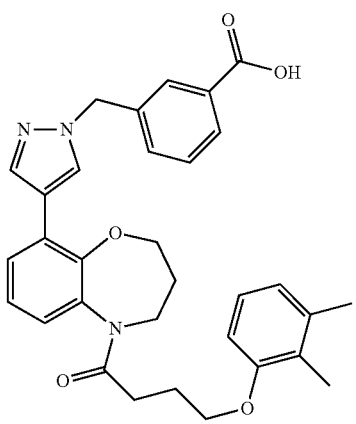 [SMILES: Cc1cccc(OCCCC(=O)N2CCCOc3c(-c4cnn(Cc5cccc(C(=O)O)c5)c4)cccc32)c1C]

Step A.
1-Bromo-2-(3,3-diethoxypropoxy)-3-nitrobenzene

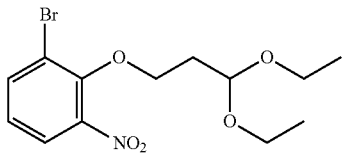 [SMILES: CCOC(CCOc1c(Br)cccc1[N+](=O)[O-])OCC]

To a mixture of triphenylphosphine (1.323 g, 5.05 mmol), 3,3-diethoxypropan-1-ol (0.748 g, 5.05 mmol) and 6-nitrophenol (1.47 g, 4.01 mmol) in anhydrous THF (10 mL) was added DIAD (0.981 mL, 5.05 mmol) dropwise under nitrogen. The reaction mixture was stirred at room temperature for 18 h and then concentrated. The resulting residue was purified by flash chromatography (0-30% ethyl acetate:hexanes) to afford the title compound (1.47 g, 87% yield) as a light yellow oil. LCMS, [M+Na+2]$^+$=372.0. $^1$H NMR (400 MHz, CDCl$_3$) δ 7.77 (dd, J=8.0, 1.6 Hz, 1H), 7.73 (dd, J=8.2, 1.6 Hz, 1H), 7.09 (t, J=8.1 Hz, 1H), 4.79 (t, J=5.7 Hz, 1H), 4.21 (t, J=6.2 Hz, 2H), 3.70 (dq, J=9.3, 7.0 Hz, 2H), 3.56 (dq, J=9.3, 7.1 Hz, 2H), 2.15 (q, J=6.1 Hz, 2H), 1.22 (t, J=7.1 Hz, 6H).

Step B.
9-Bromo-2,3,4,5-tetrahydrobenzo[b][1,4]oxazepine

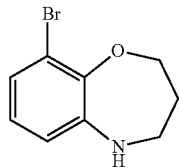 [SMILES: Brc1cccc2c1OCCCN2]

To a solution of 1-bromo-2-(3,3-diethoxypropoxy)-3-nitrobenzene (500 mg, 1.436 mmol) in AcOH (5.0 mL) was added zinc (939 mg, 14.36 mmol) and the mixture was stirred at room temperature for 90 min. After this time, the reaction mixture was filtered and the filtrate was concentrated. The resulting residue was dissolved in DCM (5 mL) and treated with TFA (5 mL) and triethylsilane (1.147 mL, 7.18 mmol). The resulting mixture was stirred at room temperature for 1 h and then concentrated. The resulting residue was purified by preparative HPLC (PHENOMENEX® Axia Luna, 5μ, C18 30×100 mm; 10 min gradient from 80% A:20% B to 0% A:100% B and 5 min 100% B (A=90% H$_2$O/10% MeOH+ 0.1% TFA); (B=90% MeOH/10% H$_2$O+0.1% TFA); detection at 220 nm). The purified product was free based with a solution of saturated sodium bicarbonate (15 ml) and was then extracted with ethyl acetate (20 mL). The organic layer was dried over anhydrous Na$_2$SO$_4$, filtered, and concentrated to afford the title compound (181 mg, 53% yield). LCMS, [M+Na]$^+$=228.0. $^1$H NMR (400 MHz, CDCl$_3$) δ 7.01 (dd, J=7.8, 1.6 Hz, 1H), 6.68 (t, J=7.9 Hz, 1H), 6.62 (dd, J=7.9, 1.6 Hz, 1H), 4.20-4.13 (m, 2H), 3.31-3.22 (m, 2H), 2.08-1.98 (m, 2H).

Example 13

Example 13 was prepared using a procedure analogous to Example 9 except that 7-bromo-1a,2,3,7b-tetrahydro-1H-cyclopropa[c]quinoline was replaced with 9-bromo-2,3,4,5-tetrahydrobenzo[b][1,4]oxazepine. LCMS, [M+H]$^+$=540.3. $^1$H NMR (400 MHz, MeOD) δ 8.05-7.97 (m, 3H), 7.94 (s, 1H), 7.66 (dd, J=6.2, 3.3 Hz, 1H), 7.53 (dt, J=15.1, 7.7 Hz, 2H), 7.20-7.13 (m, 2H), 6.92 (t, J=7.8 Hz, 1H), 6.65 (s, 1H), 6.63 (d, J=2.2 Hz, 1H), 5.47 (s, 2H), 4.79 (ddd, J=13.7, 6.4, 2.9 Hz, 1H), 4.52-4.43 (m, 1H), 3.94-3.79 (m, 2H), 3.59 (td, J=11.6, 1.8 Hz, 1H), 2.92-2.79 (m, 1H), 2.54-2.36 (m, 2H), 2.35-2.20 (m, 1H), 2.10 (s, 3H), 2.08-1.99 (m, 2H), 1.83 (s, 3H), 1.80-1.74 (m, 1H). HPLC-1: Rt=13.7 min, purity=97.8%; HPLC-2: Rt=12.5 min, purity=98.7%.

Example 14

3-((4-(5-(4-(2,3-Dimethylphenoxy)butanoyl)-2-methyl-2,3,4,5-tetrahydrobenzo[b][1,4]oxazepin-9-yl)-1H-pyrazol-1-yl)methyl)benzoic acid

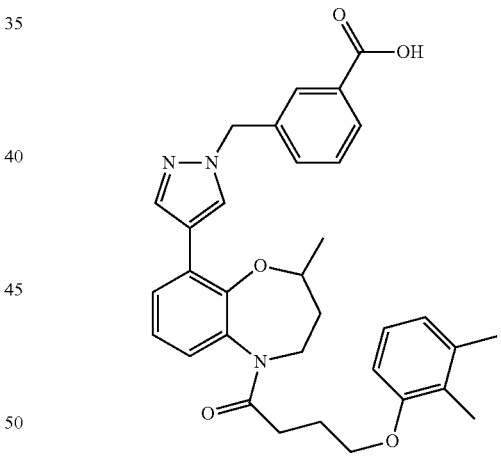

Example 14 was prepared using a procedure analogous to Example 13 except that 3,3-diethoxypropan-1-ol was replaced by 4,4-dimethoxybutan-2-ol. LCMS, [M+H]$^+$= 554.4. $^1$H NMR (400 MHz, MeOD) δ $^1$H NMR (400 MHz, MeOD) δ 8.04-7.99 (m, 1H), 7.97 (s, 1H), 7.87 (s, 1H), 7.77 (s, 1H), 7.60 (dd, J=7.1, 2.4 Hz, 1H), 7.58-7.49 (m, 2H), 7.20-7.10 (m, 2H), 7.00 (d, J=15.7 Hz, 1H), 6.71 (d, J=12.7 Hz, 1H), 6.69 (d, J=13.4 Hz, 1H), 5.44 (d, J=8.5 Hz, 2H), 4.72 (dt, J=13.6, 3.5 Hz, 1H), 3.93-3.82 (m, 3H), 3.67 (ddd, J=10.4, 6.1, 1.5 Hz, 1H), 2.86-2.77 (m, 1H), 2.52 (ddd, J=15.0, 8.3, 6.7 Hz, 1H), 2.36 (dt, J=15.1, 6.3 Hz, 1H), 2.09 (s, 3H), 2.07-1.99 (m, 2H), 1.79 (s, 3H), 1.77-1.71 (m, 1H), 1.19

(d, J=6.2 Hz, 3H). HPLC-1: Rt=9.5 min, purity=99.6%; HPLC-2: Rt=8.8 min, purity=99.5%.

Example 15

3-((4-(1-(2-(2,3-Dimethylphenethoxy)acetyl)-1,2,3,4-tetrahydroquinolin-5-yl)-1H-pyrazol-1-yl)methyl)benzoic acid

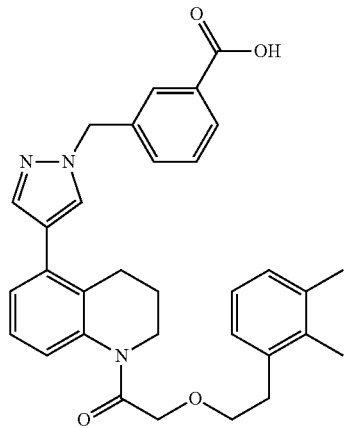 [SMILES: Cc1cccc(CCOCC(=O)N2CCCc3c(-c4cnn(Cc5cccc(C(=O)O)c5)c4)cccc32)c1C]

Step A. 1-(5-Bromo-3,4-dihydroquinolin-1(2H)-yl)-2-chloroethanone

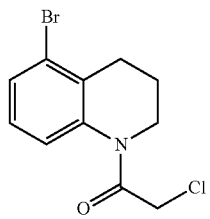 [SMILES: O=C(CCl)N1CCCc2c(Br)cccc21]

To a solution of 5-bromo-1,2,3,4-tetrahydroquinoline, HCl salt (300 mg, 1.42 mmol) and triethylamine (0.591 mL, 4.24 mmol) in EtOAc (5.0 mL) was added 2-chloroacetyl chloride (157 mg, 1.39 mmol) dropwise and the reaction was stirred at room temperature for 30 min. After this time, the reaction mixture was diluted with saturated sodium bicarbonate (30 mL) and then extracted with ethyl acetate (20 mL). The organic layer was dried over anhydrous Na$_2$SO$_4$, filtered, and concentrated to provide the crude product. The crude product was purified by flash chromatography (0-60% ethyl acetate/hexanes) to afford the title compound (446 mg, 100% yield) as a light brown oil. LCMS, [M+H]$^+$=290.0. $^1$H NMR (400 MHz, CDCl$_3$) δ 7.43 (d, J=8.5 Hz, 1H), 7.32 (br. s, 1H), 7.08 (t, J=8.0 Hz, 1H), 4.19 (s, 2H), 3.83-3.77 (m, 2H), 2.82 (t, J=6.9 Hz, 2H), 2.02 (dq, J=13.1, 6.7 Hz, 2H).

Step B. 1-(5-Bromo-3,4-dihydroquinolin-1(2H)-yl)-2-(2,3-dimethylphenethoxy)ethanone

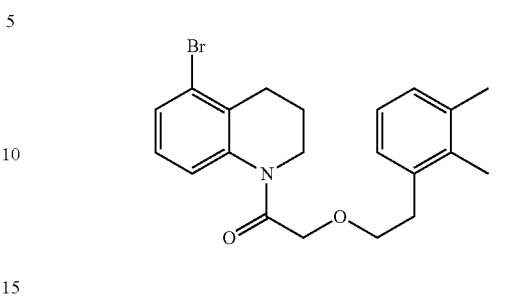

To a suspension of sodium hydride (35.1 mg, 1.46 mmol) in anhydrous THF (3.0 mL) under nitrogen was added 2-(2,3-dimethylphenyl)ethanol (220 mg, 1.46 mmol). The reaction mixture was stirred at room temperature for 15 min and then a solution of 1-(5-bromo-3,4-dihydroquinolin-1(2H)-yl)-2-chloroethanone (352 mg, 1.22 mmol) in anhydrous THF (3.0 mL) was added. The resulting mixture was stirred at room temperature for 18 h. After this time, the reaction mixture was diluted with saturated sodium bicarbonate (55 mL) and then extracted with ethyl acetate (60 mL). The organic layer was dried over anhydrous Na$_2$SO$_4$, filtered, and concentrated. The resulting residue was purified by preparative HPLC (PHENOMENEX® Axia Luna, 5µ, C18, 30×250 mm; 25 min gradient from 80% A:20% B to 0% A:100% B and 5 min 100% B (A=90% H$_2$O/10% MeOH+0.1% TFA); (B=90% MeOH/10% H$_2$O+0.1% TFA); detection at 220 nm) to afford the title compound (55 mg, 11% yield) as white powder. LCMS, [M+H]$^+$=402.1. $^1$H NMR (400 MHz, CDCl$_3$) δ 7.37 (d, J=8.0 Hz, 1H), 7.30 (br. s, 1H), 7.02-6.96 (m, 4H), 4.20 (s, 2H), 3.74-3.69 (m, 2H), 3.66 (t, J=7.4 Hz, 2H), 2.92 (t, J=7.4 Hz, 2H), 2.78 (t, J=6.9 Hz, 2H), 2.24 (s, 3H), 2.18 (s, 3H), 1.99-1.90 (m, 2H).

Example 15

Example 15 was prepared using a procedure analogous to Example 9 except that 1-(7-bromo-1a,2-dihydro-1H-cyclopropa[c]quinolin-3(7bH)-yl)-4-(2,3-dimethylphenoxy)butan-1-one was replaced with 1-(5-bromo-3,4-dihydroquinolin-1(2H)-yl)-2-(2,3-dimethylphenethoxy)ethanone. LCMS, [M+H]$^+$=524.3. $^1$H NMR (400 MHz, MeOD) δ 8.01 (d, J=7.4 Hz, 1H), 7.95 (d, J=5.5 Hz, 1H), 7.94 (s, 1H), 7.69 (s, 1H), 7.58-7.48 (m, 2H), 7.35-7.16 (m, 3H), 7.00 (d, J=10.3 Hz, 3H), 5.50 (s, 2H), 4.27 (s, 2H), 3.74 (t, J=5.6 Hz, 2H), 3.65 (t, J=6.8 Hz, 2H), 2.92 (t, J=7.0 Hz, 2H), 2.79 (t, J=6.5 Hz, 2H), 2.26 (s, 3H), 2.21 (s, 3H), 1.91 (p, J=6.6 Hz, 2H). HPLC-1: Rt=9.1 min, purity=99.0%; HPLC-2: Rt=8.6 min, purity=99.2%.

Example 16

3-((3-(1-((2-(2,3-Dimethylphenoxy)ethoxy)carbonyl)-1,2,3,4-tetrahydroquinolin-5-yl)benzyloxy)carbonylamino)propanoic acid

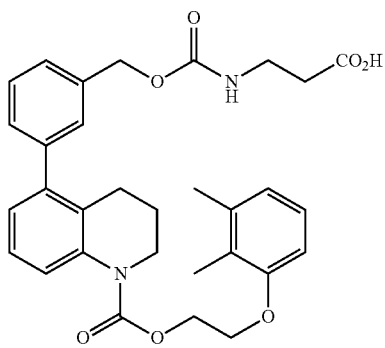 [SMILES: Cc1cccc(OCCOC(=O)N2CCCc3c(-c4cccc(COC(=O)NCCC(=O)O)c4)cccc32)c1C]

Step A.
5-Bromo-3,4-dihydroquinoline-1(2H)-carbonyl chloride

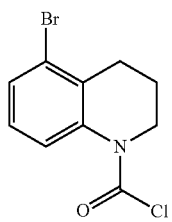 [SMILES: O=C(Cl)N1CCCc2c(Br)cccc21]

To a solution of 5-bromo-1,2,3,4-tetrahydroquinoline, HCl salt (1.00 g, 4.72 mmol), TEA (1.314 mL, 9.43 mmol) and DMAP (0.115 g, 0.943 mmol) in DCM (12 mL) at 0° C. was added diphosgene (0.626 mL, 5.19 mmol) dropwise over a period of 10 min. Upon the conclusion of this period, the reaction mixture was slowly warmed to room temperature where it stirred for 16 h. After this time, the mixture was concentrated in vacuo and the resulting residue was purified by flash chromatography (0-50% ethyl acetate:hexanes) to afford the title compound (0.804 g, 62% yield) as a white solid. LCMS, [M+Na]$^+$=297.1.

Step B. Ethyl 2-(2,3-dimethylphenoxy)acetate

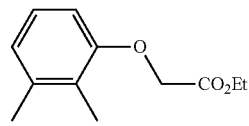

A mixture of 2,3-dimethylphenol (1.0 g, 8.19 mmol), ethyl bromoacetate (1.0 mL, 9.0 mmol) and cesium carbonate (2.67 g, 8.19 mmol) in DMF (10 mL) was stirred at 80° C. for 16 h. After this time, the reaction mixture was partitioned between EtOAc and water. The organic layer was washed with water and brine, dried and concentrated in vacuo to afford the title compound (1.7 g, 100% yield). LCMS, [M+Na]$^+$=231.0.

Step C. 2-(2,3-Dimethylphenoxy)ethanol

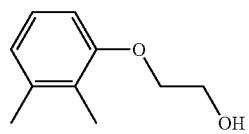

To a solution of ethyl 2-(2,3-dimethylphenoxy)acetate (1.7 g, 8.16 mmol) in THF (50 mL) at 0° C. was added lithium borohydride (2 M in THF, 8.16 mL, 16.33 mmol) dropwise over a period of 10 min. At the conclusion of this period, the reaction mixture was slowly warmed to room temperature where it stirred for 16 h. After this time, the reaction mixture was quenched slowly with saturated NH$_4$Cl, and the organic layer was separated, washed with water and brine, dried over anhydrous MgSO$_4$, filtered, and concentrated in vacuo to afford the title compound (1.06 g, 78% yield). LCMS, [M+H]$^+$=167.0.

Step D. 2-(2,3-Dimethylphenoxy)ethyl 5-bromo-3,4-dihydroquinoline-1(2H)-carboxylate

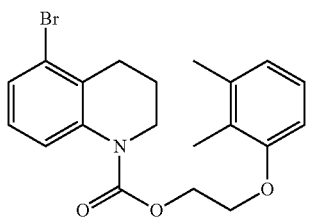

A mixture of 5-bromo-3,4-dihydroquinoline-1(2H)-carbonyl chloride (0.05 g, 0.182 mmol), 2-(2,3-dimethylphenoxy)ethanol (0.038 g, 0.228 mmol) and TEA (0.076 mL, 0.546 mmol) in DCM (1.5 mL) was stirred at room temperature for 16 h. To the mixture was then added potassium tert-butoxide (1 M in THF, 0.364 mL, 0.364 mmol) and the resulting mixture was stirred at room temperature for 24 h before being quenched with water. The organic layer was separated and the aqueous phase was extracted with DCM. The combined organic layers were dried over anhydrous MgSO$_4$ and concentrated in vacuo to provide the crude material. The crude material was purified by flash chromatography (0-50% ethyl acetate/hexanes) to afford the title compound (51 mg, 69.3% yield). LCMS, [M+Na]$^+$=427.9.

Step E. 3-Bromobenzyl 4-nitrophenyl carbonate

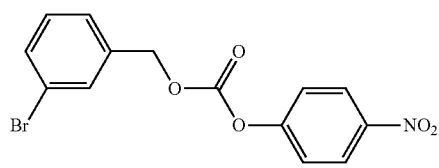 [SMILES: O=C(OCc1cccc(Br)c1)Oc1ccc([N+](=O)[O-])cc1]

To a solution of (3-bromophenyl)methanol (10 g, 53.5 mmol) and pyridine (8.65 mL, 107 mmol) in DCM (80 mL) at 0° C. was added a solution of 4-nitrophenyl carbonochloridate (12.93 g, 64.2 mmol) in DCM (20 mL) dropwise. Upon the completion of addition, the reaction mixture was stirred at 0° C. for 2 h. After this time, the reaction was quenched with water. The organic layer was separated and washed with water, brine, dried over anhydrous MgSO$_4$, filtered, and concentrated to afford the title compound (19.5 g, 100%). $^1$H NMR (400 MHz, CDCl$_3$) δ 8.31-8.29 (m, 1H), 8.28-8.25 (m, 1H), 7.61 (t, J=1.6 Hz, 1H), 7.53 (d, J=8.2 Hz, 1H), 7.42-7.34 (m, 3H), 7.30 (d, J=7.8 Hz, 1H), 5.26 (s, 2H).

Step F. tert-Butyl 3-((3-bromobenzyloxy)carbonylamino)propanoate

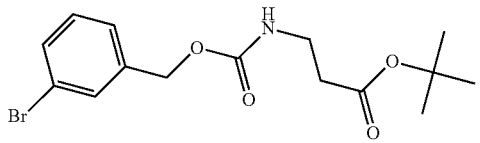 [SMILES: CC(C)(C)OC(=O)CCNC(=O)OCc1cccc(Br)c1]

To a solution of 3-bromobenzyl 4-nitrophenyl carbonate (8 g, 21.58 mmol) in DCM (50 mL) was added N-ethyl-N-isopropylpropan-2-amine (7.47 mL, 43.2 mmol) and tert-butyl 3-aminopropanoate hydrochloride (3.92 g, 21.58 mmol). Upon the completion of addition, the reaction mixture was stirred at room temperature for 1 h and then quenched with water. The resulting mixture was extracted with CH$_2$Cl$_2$ and the combined organic layer was dried over anhydrous Na$_2$SO$_4$, filtered, and concentrated. The resulting residue was purified by flash chromatography (0-50% ethyl acetate:hexanes) to afford the title compound (7.10 g, 89% yield) as a light brown oil. LCMS, [M-tBu+2H]$^+$=302.1. $^1$H NMR (400 MHz, CDCl$_3$) δ 7.50 (s, 1H), 7.44 (d, J=7.7 Hz, 1H), 7.29-7.19 (m, 2H), 5.31 (br. s, 1H), 5.06 (s, 2H), 3.43 (dd, J=12.1, 6.1 Hz, 2H), 2.46 (t, J=6.0 Hz, 2H), 1.45 (s, 9H).

Step G. tert-Butyl 3-((3-(4,4,5,5-tetramethyl-1,3,2-dioxaborolan-2-yl)benzyloxy)carbonylamino)propanoate

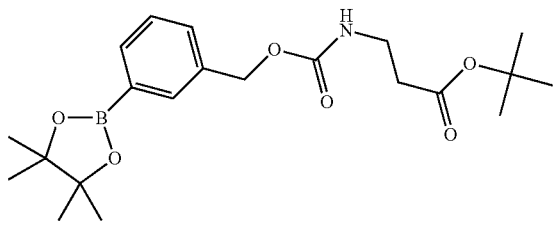 [SMILES: CC(C)(C)OC(=O)CCNC(=O)OCc1cccc(B2OC(C)(C)C(C)(C)O2)c1]

The title compound was prepared using a procedure analogous to 4-(2,3-dimethylphenoxy)-1-(5-(4,4,5,5-tetramethyl-1,3,2-dioxaborolan-2-yl)-3,4-dihydroquinolin-1(2H)-yl)butan-1-one except that 1-(5-bromo-3,4-dihydroquinolin-1(2H)-yl)-4-(2,3-dimethylphenoxy)butan-1-one was replaced with tert-butyl 3-((3-bromobenzyloxy)carbonylamino)propanoate. LCMS, [M+Na]$^+$=428.2.

Step H. 2-(2,3-Dimethylphenoxy)ethyl 5-(3-((3-tert-butoxy-3-oxopropylcarbamoyloxy)methyl)phenyl)-3,4-dihydroquinoline-1(2H)-carboxylate

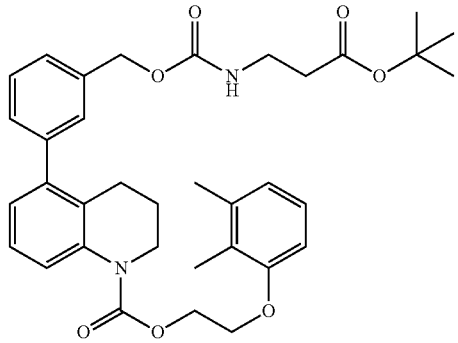 [SMILES: Cc1cccc(OCCOC(=O)N2CCCc3c(-c4cccc(COC(=O)NCCC(=O)OC(C)(C)C)c4)cccc32)c1C]

The title compound was prepared using a procedure analogous to methyl 4-(1-(4-(2,3-dimethylphenoxy)butanoyl)-1,2,3,4-tetrahydroquinolin-5-yl)picolinate except that 4-(2,3-dimethylphenoxy)-1-(5-(4,4,5,5-tetramethyl-1,3,2-dioxaborolan-2-yl)-3,4-dihydroquinolin-1(2H)-yl)butan-1-one was replaced by tert-butyl 3-((3-(4,4,5,5-tetramethyl-1,3,2-dioxaborolan-2-yl)benzyloxy)carbonylamino)propanoate, and methyl 4-bromopicolinate was replaced by 2-(2,3-dimethylphenoxy)ethyl 5-bromo-3,4-dihydroquinoline-1(2H)-carboxylate. LCMS, [M-tBu+2H]$^+$=547.2. $^1$H NMR (400 MHz, CDCl$_3$) δ 7.64 (d, J=8.1 Hz, 1H), 7.46-7.35 (m, 2H), 7.34-7.27 (m, 1H), 7.27-7.20 (m, 1H), 7.16 (t, J=7.9 Hz, 1H), 7.03 (t, J=7.9 Hz, 1H), 6.97 (d, J=7.5 Hz, 1H), 6.79 (d, J=7.7 Hz, 1H), 6.70 (d, J=8.1 Hz, 1H), 5.12 (s, 2H), 4.60-4.52 (m, 2H), 4.24-4.19 (m, 2H), 3.73 (t, J=6.4 Hz, 2H), 3.41 (dd, J=12.0, 6.0 Hz, 2H), 2.57 (t, J=6.3 Hz, 2H), 2.44 (t, J=5.9 Hz, 2H), 2.26 (s, 3H), 2.17 (s, 3H), 1.86-1.75 (m, 2H), 1.42 (s, 9H).

Example 16

A solution of 2-(2,3-dimethylphenoxy)ethyl 5-(3-((3-tert-butoxy-3-oxopropylcarbamoyloxy)methyl)phenyl)-3,4-dihydroquinoline-1(2H)-carboxylate (0.0255 g, 0.042 mmol), 4-chlorophenol (10.88 mg, 0.085 mmol) and TFA (0.5 mL, 6.49 mmol) in DCM (1 mL) was stirred at room temperature for 16 h. At the conclusion of this period, the solvent was removed in vacuo. The resulting residue was purified by preparative HPLC (PHENOMENEX® Axia Luna column, 5μ, C18, 30×75 mm; 10 min gradient from 75% A:25% B to 0% A:100% B (A=90% H$_2$O/10% MeCN+0.1% TFA); (B=90% MeCN/10% H$_2$O+0.1% TFA); detection at 220 nm) to afford the title compound (9.5 mg, 40% yield) as a white solid. LCMS, [M+H]$^+$=547.2. $^1$H NMR (400 MHz, CDCl$_3$) δ 7.61 (d, J=8.3 Hz, 1H), 7.41-7.34 (m, 1H), 7.29 (d, J=7.1 Hz, 1H), 7.21 (d, J=4.2 Hz, 2H), 7.16 (t, J=7.9 Hz, 1H), 7.03 (t, J=7.8 Hz, 1H), 6.97 (d, J=7.1 Hz, 1H), 6.79 (d, J=7.5 Hz, 1H), 6.70 (d, J=8.2 Hz, 1H), 5.13 (s, 2H), 4.59-4.53 (m, 2H), 4.24-4.18 (m, 2H), 3.73 (t, J=6.5 Hz, 2H), 3.45 (dd, J=12.0, 6.1 Hz, 2H), 2.72-2.39 (m, 7H), 2.26 (s, 3H), 2.17 (s, 3H), 1.80 (dt, J=12.8, 6.4 Hz, 2H). HPLC-1: Rt=11.3 min, purity=100%; HPLC-2: Rt=10.0 min, purity=99.3%.

The following Examples were prepared in a manner analogous to Example 16.

TABLE 2

| Example | Name | R | ◁ present | LCMS, [M + H]⁺ | ¹H NMR (400 MHz, CDCl₃) δ | HPLC-1: Rt min, purity; HPLC-2: Rt min, purity |
|---|---|---|---|---|---|---|
| 17 | 3-((3-(1-((2-(3-Chloro-2-methyl-phenoxy)ethoxy)carbonyl)-1,2,3,4-tetrahydroquinolin-5-yl)benzyloxy)carbonylamino)propanoic acid | 3-Cl, 2-Me-phenyl | No | 567.1 | 7.58 (d, J = 7.7 Hz, 1H), 7.38 (t, J = 7.8 Hz, 1H), 7.29 (d, J = 7.9 Hz, 1H), 7.27-7.19 (m, 3H), 7.16 (t, J = 7.9 Hz, 1H), 7.05 (t, J = 8.1 Hz, 1H), 6.98 (d, J = 7.8 Hz, 2H), 6.73 (d, J = 7.9 Hz, 1H), 5.13 (s, 2H), 4.61-4.54 (m, 2H), 4.27-4.19 (m, 2H), 3.72 (t, J = 6.5 Hz, 2H), 3.45 (dd, J = 11.8, 5.9 Hz, 2H), 2.64-2.50 (m, 4H), 2.29 (s, 3H), 1.87-1.75 (m, 2H) | 11.7 min, 100% 10.3 min, 100% |
| 18 | 3-((3-(1-((2-(2,3-Dichlorophenoxy)ethoxy)carbonyl)-1,2,3,4-tetrahydroquinolin-5-yl)benzyloxy)carbonylamino)propanoic acid | 2,3-diCl-phenyl | No | 587.1 | 7.61 (d, J = 8.0 Hz, 1H), 7.38 (t, J = 7.7 Hz, 1H), 7.29 (d, J = 7.9 Hz, 1H), 7.27-7.21 (m, 2H), 7.18 (t, J = 8.0 Hz, 1H), 7.15-7.06 (m, 2H), 6.99 (d, J = 7.3 Hz, 1H), 6.84 (dd, J = 7.8, 1.7 Hz, 1H), 5.13 (s, 2H), 4.62-4.56 (m, 2H), 4.34-4.27 (m, 2H), 3.73 (t, J = 6.5 Hz, 2H), 3.47 (dd, J = 12.0, 6.0 Hz, 2H), 2.61 (d, J = 5.7 Hz, 2H), 2.56 (t, J = 6.4 Hz, 2H), 1.85-1.76 (m, 2H) | 11.2 min, 100% 10.0 min, 100% |
| 19 | 3-((3-(1-((2-(2,5-Dichlorophenoxy)ethoxy)carbonyl)-1,2,3,4-tetrahydroquinolin-5-yl)benzyloxy)carbonylamino)propanoic acid | 2,5-diCl-phenyl | No | 587.2 | 7.62 (d, J = 8.2 Hz, 1H), 7.42-7.34 (m, 1H), 7.28 (d, J = 8.5 Hz, 2H), 7.27-7.20 (m, 2H), 7.17 (t, J = 7.9 Hz, 1H), 6.97 (d, J = 7.0 Hz, 1H), 6.93 (d, J = 2.2 Hz, 1H), 6.90 (dd, J = 8.4, 2.2 Hz, 1H), 5.13 (s, 2H), 4.62-4.54 (m, 2H), 4.33-4.26 (m, 2H), 3.73 (t, J = 6.5 Hz, 2H), 3.45 (dd, J = 11.9, 6.1 Hz, 2H), 2.64-2.50 (m, 4H), 1.80 (dt, J = 12.9, 6.4 Hz, 2H) | 10.9 min, 100% 9.7 min, 100% |
| 20 | 3-((3-(1-((2-(3-Fluoro-2-methyl-phenoxy)ethoxy)carbonyl)-1,2,3,4-tetrahydroquinolin-5-yl)benzyloxy)carbonylamino)propanoic acid | 3-F, 2-Me-phenyl | No | 551.3 | 7.59 (d, J = 8.0 Hz, 1H), 7.38 (t, J = 7.6 Hz, 1H), 7.29 (d, J = 7.7 Hz, 1H), 7.26-7.19 (m, 2H), 7.16 (t, J = 7.9 Hz, 1H), 7.07 (dd, J = 15.1, 8.2 Hz, 1H), 6.97 (d, J = 7.6 Hz, 1H), 6.67 (t, J = 8.6 Hz, 1H), 6.61 (d, J = 8.3 Hz, 1H), 5.13 (s, 2H), 4.59-4.54 (m, 2H), 4.27-4.21 (m, 2H), 3.72 (t, J = 6.5 Hz, 2H), 3.45 (dd, J = 11.9, 6.0 Hz, 2H), 2.65-2.48 (m, 4H), 2.15 (s, 3H), 1.85-1.75 (m, 2H) | 11.0 min, 100% 9.9 min, 100% |
| 21 | 3-((3-(3-((2-(3-Chloro-2-methyl-phenoxy)ethoxy)carbonyl)-1a,2,3,7b-tetrahydro-1H-cyclopropa[c]quinolin-7-yl) | 3-Cl, 2-Me-phenyl | Yes | 579.3 | 7.45-7.36 (m, 2H), 7.37-7.29 (m, 2H), 7.25 (d, J = 7.1 Hz, 1H), 7.08 (t, J = 8.1 Hz, 2H), 7.02 (d, J = 7.4 Hz, 1H), 6.96 (d, J = 8.0 Hz, 1H), 6.85 (d, J = 8.2 Hz, 1H), 5.10 (d, J = 12.6 Hz, 2H), 4.60-4.51 (m, 2H), 4.47 (dt, J = 8.8, 4.1 Hz, | 13.0 min, 99.6% 12.5 min, 99.6% |

TABLE 2-continued

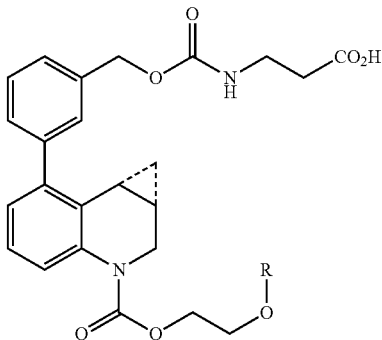

| Example | Name | R | ◁ present | LCMS, [M + H]+ | ¹H NMR (400 MHz, CDCl₃) δ | HPLC-1: Rt min, purity; HPLC-2: Rt min, purity |
|---|---|---|---|---|---|---|
| | benzyloxy) carbonylamino) propanoic acid | | | | 1H), 4.23 (t, J = 4.0 Hz, 2H), 3.40-3.32 (m, 2H), 2.94 (d, J = 12.8 Hz, 1H), 2.49 (t, J = 6.8 Hz, 2H), 2.21 (s, 3H), 1.89 (td, J = 8.6, 4.6 Hz, 1H), 1.75 (dd, J = 13.4, 7.9 Hz, 1H), 0.93 (td, J = 8.3, 5.0 Hz, 1H), 0.68-0.61 (m, 1H)* | |
| 22 | 3-((3-(3-((2-(3-Fluoro-2-methyl-phenoxy)ethoxy)carbonyl)-1a,2,3,7b-tetrahydro-1H-cyclopropa[c]quinolin-7-yl)benzyloxy)carbonylamino)propanoic acid | 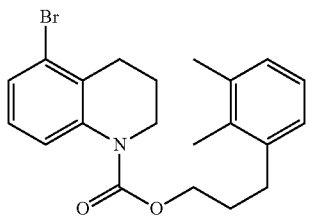 | Yes | 563.3 | 7.47-7.36 (m, 2H), 7.36-7.29 (m, 2H), 7.25 (d, J = 7.4 Hz, 1H), 7.09 (dd, J = 15.4, 8.1 Hz, 2H), 7.02 (d, J = 7.3 Hz, 1H), 6.72 (d, J = 8.3 Hz, 1H), 6.66 (t, J = 8.8 Hz, 1H), 5.11 (s, 2H), 4.61-4.50 (m, 2H), 4.46 (dt, J = 8.8, 4.1 Hz, 1H), 4.23 (t, J = 4.2 Hz, 2H), 3.40-3.32 (m, 2H), 2.94 (d, J = 12.9 Hz, 1H), 2.48 (t, J = 6.8 Hz, 2H), 2.07 (s, 3H), 1.88 (td, J = 8.6, 4.6 Hz, 1H), 1.75 (dt, J = 13.6, 6.9 Hz, 1H), 0.92 (td, J = 8.3, 5.0 Hz, 1H), 0.69-0.60 (m, 1H)* | 14.8 min, 99.7% 14.6 min, 100% |

*¹H NMR (400 MHz, MeOD) δ.

Example 23

3-((4-(1-((3-(2,3-Dimethylphenyl)propoxy)carbonyl)-1,2,3,4-tetrahydroquinolin-5-yl)-1H-pyrazol-1-yl)methyl)benzoic acid

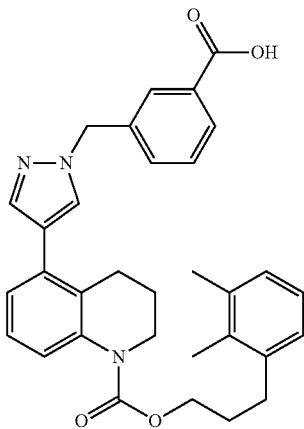 [SMILES: Cc1cccc(CCCOC(=O)N2CCCc3c(-c4cnn(Cc5cccc(C(=O)O)c5)c4)cccc32)c1C]

Step A. 3-(2,3-Dimethylphenyl)propyl 5-bromo-3,4-dihydroquinoline-1(2H)-carboxylate The title compound was prepared using a procedure analogous to 2-(2,3-dimethylphenoxy)ethyl 5-bromo-3,4-dihydroquinoline-1(2H)-carboxylate except that ethyl 2-(2,3-dimethylphenoxy)acetate was replaced by methyl 3-(2,3-dimethylphenyl)propanoate. LCMS, [M+Na]⁺=426.0.

Example 23

Example 23 was prepared using a procedure analogous to Example 9 except that 1-(7-bromo-1a,2-dihydro-1H-cyclopropa[c]quinolin-3(7bH)-yl)-4-(2,3-dimethylphenoxy)butan-1-one was replaced with 3-(2,3-dimethylphenyl)propyl 5-bromo-3,4-dihydroquinoline-1(2H)-carboxylate. LCMS,

[M+H]⁺=524.3. ¹H NMR (400 MHz, MeOD) δ 8.02 (dt, J=7.3, 1.5 Hz, 1H), 7.97 (s, 1H), 7.90 (s, 1H), 7.68 (s, 1H), 7.62-7.46 (m, 3H), 7.21 (t, J=7.9 Hz, 1H), 7.15 (dd, J=7.6, 1.3 Hz, 1H), 7.07-6.94 (m, 3H), 5.50 (s, 2H), 4.23 (t, J=6.2 Hz, 2H), 3.84-3.70 (m, 2H), 2.82 (t, J=6.5 Hz, 2H), 2.79-2.70 (m, 2H), 2.29 (s, 3H), 2.22 (s, 3H), 2.00-1.88 (m, 4H). HPLC-1: Rt=11.9 min, purity=100%; HPLC-2: Rt=10.9 min, purity=100%.

The following Examples were prepared in a manner analogous to Example 23.

TABLE 3

| Example | Name | Formula I | LCMS, [M + H]⁺ | ¹H NMR (400 MHz, CDCl₃) δ | HPLC-1: Rt min, purity; HPLC-2: Rt min, purity |
| --- | --- | --- | --- | --- | --- |
| 24 | 3-((4-(3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzoic acid | | 556.4 | 8.06 (m, 2H), 7.75 (s, 1H), 7.58 (s, 1H), 7.49 (m, 2H), 7.19 (d, J = 7.4 Hz, 1H), 7.12 (t, J = 7.7 Hz, 1H), 7.02 (m, 1H), 6.93 (m, 2H), 6.66 (d, J = 8.0 Hz, 1H), 5.42 (s, 2H), 4.04-3.94 (m, 1H), 3.88 (m, 1H), 2.78-2.68 (m, 1H), 2.63 (m, 1H), 2.21-2.12 (m, 2H), 2.07 (br. s, 1H), 1.99 (s, 3H), 1.69 (m, 1H), 0.84 (m, 1H), 0.46 (m, 1H) | 12.9 min, 97.5% 12.6 min, 99.5% |
| 25 | 3-((4-(1-((2-(3-Chloro-2-methylphenoxy)ethoxy)carbonyl)-1,2,3,4-tetrahydroquinolin-5-yl)-1H-pyrazol-1-yl)methyl)benzoic acid | | 546.2 | 8.08-7.99 (m, 2H), 7.65 (s, 1H), 7.61-7.52 (m, 1H), 7.52-7.39 (m, 3H), 7.11 (t, J = 7.9 Hz, 1H), 7.07-7.00 (m, 2H), 6.97 (d, J = 7.5 Hz, 1H), 6.72 (d, J = 8.0 Hz, 1H), 5.42 (s, 2H), 4.57-4.51 (m, 2H), 4.23-4.17 (m, 2H), 3.76-3.68 (m, 2H), 2.72 (t, J = 6.5 Hz, 2H), 2.34-2.21 (m, 3H), 1.86 (dt, J = 12.7, 6.4 Hz, 2H) | 11.4 min, 97.1% 9.9 min, 92.7% |
| 26 | 3-((4-(3-((2-(3-Chloro-2-methylphenoxy)ethoxy)carbonyl)-1a,2,3,7b-tetrahydro-1H-cyclopropa[c]quinolin-7-yl)-1H-pyrazol-1-yl)methyl)benzoic acid | | 558.2 | 7.95-7.88 (m, 2H), 7.61 (s, 1H), 7.51 (s, 1H), 7.38-7.27 (m, 2H), 7.16 (s, 1H), 7.04-6.94 (m, 3H), 6.91 (d, J = 7.9 Hz, 1H), 6.65 (d, J = 8.0 Hz, 1H), 5.30 (s, 2H), 4.58-4.48 (m, 1H) 4.48-4.33 (m, 2H), 4.12 (dd, J = 10.4, 6.5 Hz, 2H), 3.32 (dt, J = 3.3, 1.6 Hz, 1H), 2.20 (s, 3H), 2.06 (td, J = 8.6, 4.7 Hz, 1H), 1.68 (dt, J = 13.6, 6.8 Hz, 1H), 0.86-0.77 (m, 1H), 0.67 (dd, J = 9.8, 4.8 Hz, 1H) | 10.6 min, 96.6% 10.5 min, 100% |

TABLE 3-continued

| Example | Name | Formula I | LCMS, [M + H]+ | $^1$H NMR (400 MHz, CDCl$_3$) δ | HPLC-1: Rt min, purity; HPLC-2: Rt min, purity |
|---|---|---|---|---|---|
| 27 | 3-((4-(3-((2-(3-Fluoro-2-methyl-phenoxy)ethoxy)carbonyl)-1a,2,3,7b-tetrahydro-1H-cyclopropa[c]quinolin-7-yl)-1H-pyrazol-1-yl)methyl)benzoic acid | | 542.3 | 8.03 (d, J = 7.2 Hz, 1H), 7.98 (s, 2H), 7.75 (s, 1H), 7.64-7.47 (m, 2H), 7.26 (d, J = 7.3 Hz, 1H), 7.23-7.06 (m, 3H), 6.77 (d, J = 8.3 Hz, 1H), 6.71 (t, J = 8.7 Hz, 1H), 5.54 (s, 2H), 4.60 (dd, J = 10.3, 6.4 Hz, 1H), 4.57-4.46 (m, 2H), 4.29 (d, J = 3.9 Hz, 2H), 3.09 (d, J = 12.5 Hz, 1H), 2.20 (br. s, 1H), 2.12 (s, 3H), 1.85 (br. s, 1H), 1.08 (br. s, 1H), 0.69 (br. s, 1H)* | 14.6 min, 99.4% 14.5 min, 100% |
| 28 | 4-((4-(4-((2-(2,3-Dimethylphenoxy)ethoxy)carbonyl)-3,4-dihydro-2H-benzo[b][1,4]oxazin-8-yl)-1H-pyrazol-1-yl)methyl)benzoic acid | 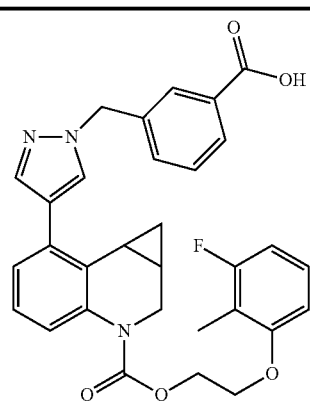 | 528.3 | 8.07 (d, J = 8.4 Hz, 2H), 7.97 (s, 1H), 7.86-7.92 (m, 1H), 7.73 (br. s, 1H), 7.31 (d, J = 8.4 Hz, 2H), 7.25 (d, J = 1.3 Hz, 2H), 7.05 (t, J = 7.8 Hz, 1H), 6.89 (t, J = 7.9 Hz, 1H), 6.81 (d, J = 7.7 Hz, 1H), 6.72 (d, J = 8.1 Hz, 1H), 5.44 (s, 2H), 4.59-4.62 (m, 2H), 4.33-4.38 (m, 2H), 4.22-4.26 (m, 2H), 3.93-3.97 (m, 2H), 2.28 (s, 2H), 2.17 (s, 3H) | 11.0 min, 100% 10.2 min, 99.8% |
| 29 | 3-((4-(4-((2-(2,3-Dimethylphenoxy)ethoxy)carbonyl)-3,4-dihydro-2H-benzo[b][1,4]oxazin-8-yl)-1H-pyrazol-1-yl)methyl)benzoic acid | 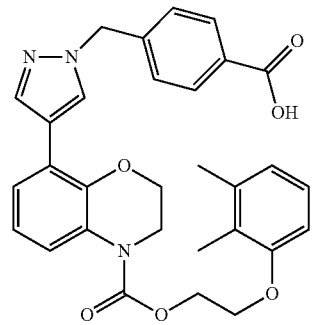 [SMILES: Cc1cccc(OCCOC(=O)N2CCOc3c(-c4cnn(Cc5ccc(C(=O)O)cc5)c4)cccc32)c1C] | 528.2 | 8.09 (s, 1H), 8.05 (dt, J = 7.1, 1.7 Hz, 1H), 7.96 (s, 1H), 7.90 (s, 1H), 7.73 (br. s, 1H), 7.43-7.51 (m, 2H), 7.25 (d, J = 1.3 Hz, 1H), 7.05 (t, J = 7.9 Hz, 1H), 6.88 (t, J = 8.0 Hz, 1H), 6.81 (d, J = 7.5 Hz, 1H), 6.72 (d, J = 8.4 Hz, 1H), 5.41 (s, 2H), 4.58-4.63 (m, 2H), 4.34-4.39 (m, 2H), 4.22-4.27 (m, 2H), 3.93-3.98 (m, 2H), 2.28 (s, 3H), 2.18 (s, 3H) | 11.2 min, 99.0% 10.3 min, 99.1% |
| 30 | 4-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzoic acid | 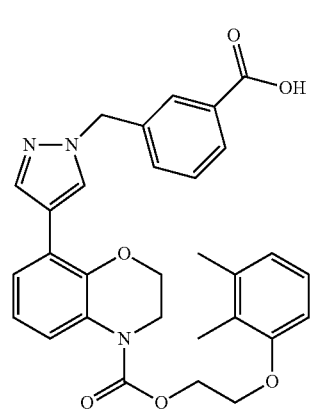 | 540.3 | 8.06 (s, 1H), 8.04 (d, J= 8.4 Hz, 2H), 7.96 (s, 1H), 7.67 (dd, J= 6.1, 3.5 Hz, 1H), 7.37 (d, J = 8.3 Hz, 2H), 7.17 (d, J = 2.6 Hz, 1H), 7.16 (s, 1H), 6.93 (t, J = 7.9 Hz, 1H), 6.66 (d, J = 5.8 Hz, 1H), 6.64 (d, J = 7.6 Hz, 1H), 5.49 (s, 2H), 4.79 (dt, J = 6.1, 3.3 Hz, 1H), 4.49 (dt, J = 12.0, 3.0 Hz, 1H), 3.94-3.80 (m, 2H), 3.60 (td, J = 11.8, 1.8 Hz, 1H), 2.91-2.82 (m, 1H), 2.52-2.37 (m, 2H), 2.36-2.22 (m, 1H), 2.11 (s, 3H), 2.10-2.01 (m, 2H), 1.84 (s, 3H), 1.82-1.76 (m, 1H)* | 13.5 min, 100% 12.4 min, 100% |

TABLE 3-continued

| Example | Name | Formula I | LCMS, [M + H]+ | 1H NMR (400 MHz, CDCl3) δ | HPLC-1: Rt min, purity; HPLC-2: Rt min, purity |
| --- | --- | --- | --- | --- | --- |
| 31 | 4-((4-(1-(4-(2,3-Dimethylphenoxy)butanoyl)-2,3,4,5-tetrahydro-1H-benzo[b]azepin-6-yl)-1H-pyrazol-1-yl)methyl)benzoic acid | | 538.3 | 8.22 (d, J = 8.3 Hz, 2H), 7.78 (s, 1H), 7.72 (s, 1H), 7.49 (d, J = 8.2 Hz, 2H), 7.47 (dd, J = 7.8, 1.3 Hz, 1H), 7.40 (t, J = 7.7 Hz, 1H), 7.27 (dd, J = 7.7, 1.1 Hz, 1H), 7.15 (t, J = 7.9 Hz, 1H), 6.88 (d, J = 7.5 Hz, 1H), 6.81 (d, J = 8.2 Hz, 1H), 5.63 (s, 2H), 4.84-4.78 (m, 1H), 4.14-4.01 (m, 2H), 3.14 (dd, J = 14.1, 6.1 Hz, 1H), 2.97-2.89 (m, 1H), 2.70-2.54 (m, 2H), 2.48 (dt, J = 17.6, 4.7 Hz, 1H), 2.34 (s, 3H), 2.31-2.22 (m, 2H), 2.15-2.08 (m, 2H), 2.06 (s, 3H), 2.00-1.92 (m, 1H), 1.63-1.53 (m, 1H)* | No data |
| 32 | 3-((4-(1-(4-(2-Methyl-3-(trifluoromethyl)phenoxy)butanoyl)-1,2,3,4-tetrahydroquinolin-5-yl)-1H-pyrazol-1-yl)methyl)benzoic acid | | 578.2 | 8.02 (dt, J = 6.9, 1.8 Hz, 1H), 7.97 (s, 1H), 7.76 (s, 1H), 7.60-7.49 (m, 3H), 7.31-7.22 (m, 4H), 7.18 (d, J = 7.7 Hz, 1H), 7.13 (d, J = 8.3 Hz, 1H), 5.49 (s, 2H), 4.03 (br. s, 2H), 3.80 (t, J = 6.8 Hz, 2H), 2.85 (t, J = 7.0 Hz, 2H), 2.66 (br. s, 2H), 2.24-2.15 (m, 2H), 2.07 (br. s, 3H), 1.94-1.84 (m, 2H)* | 9.9 min, 96.5% 9.1 min, 96.3% |
| 32A | 3-((4-(3-((2-(2,6-Difluorophenoxy)ethoxy)carbonyl)-1a,2,3,7b-tetrahydro-1H-cyclopropa[c]quinolin-7-yl)-1H-pyrazol-1-yl)methyl)benzoic acid | | 546.1 | 7.96 (d, J = 7.5 Hz, 1H), 7.92 (d, J = 11.4 Hz, 2H), 7.70 (s, 1H), 7.60-7.42 (m, 2H), 7.21 (d, J = 7.9 Hz, 1H), 7.17-7.05 (m, 2H), 7.05-6.82 (m, 3H), 5.47 (s, 2H), 4.55-4.27 (m, 4H), 3.00 (d, J = 12.7 Hz, 1H), 2.24-2.08 (m, 1H), 1.76 (d, J = 20.6 Hz, 1H), 1.29 (s, 1H), 1.16-0.98 (m, 1H), 0.73-0.59 (m, 1H)* | 9.5 min, 82.7% 9.8 min, 99.0% |

TABLE 3-continued

| Example | Name | Formula I | LCMS, [M + H]+ | ¹H NMR (400 MHz, CDCl₃) δ | HPLC-1: Rt min, purity; HPLC-2: Rt min, purity |
|---|---|---|---|---|---|
| 32B | 3-((4-(3-((2-(4-Chloro-3-methoxyphenoxy)ethoxy)carbonyl)-1a,2,3,7b-tetrahydro-1H-cyclopropa[c]quinolin-7-yl)-1H-pyrazol-1-yl)methyl)benzoic acid | | 576.0 | 8.12-8.04 (m, 1H), 8.01 (s, 1H), 7.82 (s, 1H), 7.61 (s, 1H), 7.57-7.46 (m, 2H), 7.33-7.27 (m, 1H), 7.22 (d, J = 8.7 Hz, 1H), 7.07 (d, J = 3.5 Hz, 2H), 6.52 (d, J = 2.3 Hz, 1H), 6.42 (dd, J = 8.7, 2.4 Hz, 1H), 5.50 (s, 2H), 4.67-4.34 (m, 3H), 4.25-4.11 (m, 2H), 3.85 (s, 3H), 3.08 (d, J = 12.9 Hz, 1H), 2.13-2.03 (m, 1H), 1.77 (dd, J = 13.5, 7.9 Hz, 1H), 1.03 (td, J = 8.3, 5.2 Hz, 1H), 0.77 (dd, J = 9.5, 4.7 Hz, 1H) | 9.8 min, 100.0% 10.2 min, 97.5% |
| 32C | 4-Chloro-3-((4-(3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzoic acid | | 594.0 | 8.04 (dd, J = 8.3, 2.0 Hz, 1H), 8.02-7.98 (m, 1H), 7.86 (s, 1H), 7.71 (s, 1H), 7.55 (d, J = 8.3 Hz, 1H), 7.29 (m, 1H), 7.10 (d, J = 4.2 Hz, 2H), 7.09-7.03 (m, 1H), 7.00 (d, J = 7.1 Hz, 1H), 6.73 (d, J = 7.9 Hz, 1H), 5.60 (s, 2H), 4.68-4.58 (m, 1H), 4.58-4.42 (m, 2H), 4.29-4.13 (m, 2H), 3.10 (d, J = 13.1 Hz, 1H), 2.28 (s, 3H), 2.20-2.04 (m, 1H), 1.78 (dd, J = 13.5, 7.9 Hz, 1H), 1.04 (td, J = 8.3, 5.2 Hz, 1H), 0.78 (dd, J = 9.9, 5.0 Hz, 1H) | 11.0 min, 100% 11.1 min, 100% |
| 32D | 3-((4-((1aR,7bS)-3-(4-(2,4,5-Trichlorophenoxy)butanoyl)-1a,2,3,7b-tetrahydro-1H-cyclopropa[c]quinolin-7-yl)-1H-pyrazol-1-yl)methyl)benzoic acid | | 612.1 | 10.88 (br. s, 1H), 8.14-7.99 (m, 2H), 7.80 (s, 1H), 7.61 (s, 1H), 7.57-7.44 (m, 1H), 7.36 (s, 2H), 7.23-7.09 (m, 2H), 6.95 (s, 2H), 5.48 (s, 2H), 5.21-4.79 (m, 1H), 4.05 (s, 2H), 2.80 (s, 2H), 2.67-2.42 (m, 1H), 2.33-2.04 (m, 3H), 1.92-1.56 (m, 1H), 1.10-0.83 (m, 1H), 0.66-0.43 (m, 1H) | 13.5 min, 92.2% 12.3 min, 99.3% |

TABLE 3-continued

| Example | Name | Formula I | LCMS, [M + H]+ | 1H NMR (400 MHz, CDCl3) δ | HPLC-1: Rt min, purity; HPLC-2: Rt min, purity |
|---|---|---|---|---|---|
| 32E | 3-((4-((1aR,7bS)-3-(2-((2,4,5-Trichloro-phenoxy)methyl)cyclopropane-carbonyl)-1a,2,3,7b-tetrahydro-1H-cyclopropa[c]quinolin-7-yl)-1H-pyrazol-1-yl)methyl)benzoic acid | 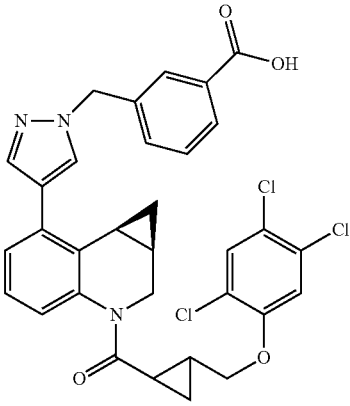 [SMILES: O=C(O)c1cccc(Cn2cc(-c3cccc4c3[C@H]3C[C@H]3CN4C(=O)C3CC3COc3cc(Cl)c(Cl)cc3Cl)cn2)c1] | 624.1 | 8.10 (d, J = 7.3 Hz, 1H), 8.03 (s, 1H), 7.87 (s, 1H), 7.65 (s, 1H), 7.61-7.46 (m, 2H), 7.34 (s, 1H), 7.24-7.08 (m, 3H), 6.83 (s, 1H), 5.52 (s, 2H), 5.17-4.84 (m, 1H), 4.23-3.95 (m, 1H), 3.61 (s, 1H), 2.93-2.62 (m, 1H), 2.25-1.92 (m, 3H), 1.88-1.67 (m, 1H), 1.55-1.34 (m, 1H), 1.19-0.97 (m, 2H), 0.93-0.69 (m, 1H) | 13.3 min, 97.5% 12.2 min, 94.7% |
| 32F | 3-((4-(1-(4-(4-Bromo-2,3-dimethyl-phenoxy)butanoyl)-1,2,3,4-tetrahydro-quinolin-5-yl)-1H-pyrazol-1-yl)methyl)benzoic acid | 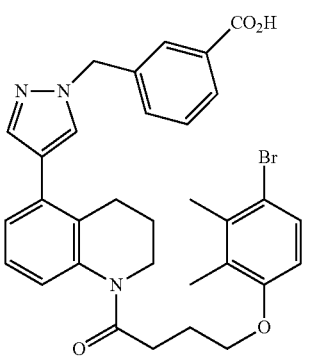 [SMILES: Cc1c(Br)ccc(OCCCC(=O)N2CCCc3c(-c4cnn(Cc5cccc(C(=O)O)c5)c4)cccc32)c1C] | 603.8 | 8.08 (dt, J = 6.7, 1.7 Hz, 1H), 8.02 (s, 1H), 7.65 (s, 1H), 7.57-7.48 (m, 2H), 7.35-7.28 (m, 2H), 7.24-7.15 (m, 2H), 6.57-6.48 (m, 2H), 5.48 (s, 2H), 3.93-3.84 (m, 2H), 3.79 (t, J = 6.9 Hz, 2H), 2.78 (t, J = 7.0 Hz, 2H), 2.59-2.47 (m, 2H), 2.24 (s, 3H), 2.17 (dt, J = 12.7, 6.5 Hz, 2H), 2.00-1.78 (m, 5H) | |
| 32G | 3-((4-(1-(4-(2,3-Dimethylphenoxy)butanoyl)-1,2,3,4-tetrahydro-quinolin-5-yl)-3-methyl-1H-pyrazol-1-yl)methyl)benzoic acid | 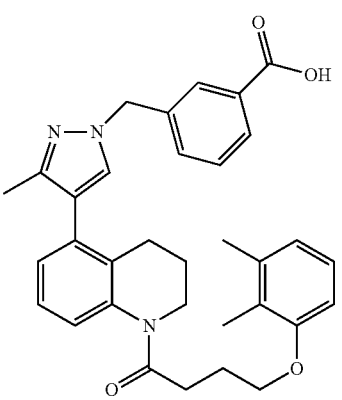 [SMILES: Cc1cccc(OCCCC(=O)N2CCCc3c(-c4cn(Cc5cccc(C(=O)O)c5)nc4C)cccc32)c1C] | 538.3 | 8.02-7.93 (m, 1H), 7.86 (s, 1H), 7.54-7.44 (m, 2H), 7.42-7.29 (m, 1H), 7.23 (m, 2H), 7.17-7.04 (m, 1H), 6.94 (t, J = 7.9 Hz, 1H), 6.71-6.60 (m, 2H), 5.35 (s, 2H), 3.88 (m, 2H), 3.75 (t, J = 6.9 Hz, 2H), 2.80 (t, J = 7.0 Hz, 2H), 2.46-2.32 (m, 2H), 2.18-2.05 (m, 8H), 1.82 (dd, J = 13.4, 6.7 Hz, 5H)* | 9.7 min, 99.4% 9.0 min, 99.2% |
| 32H | 3-((4-(1-(4-(2,3-Dimethylphenoxy)butanoyl)-1,2,3,4-tetrahydro-quinolin-5-yl)-5-methyl-1H-pyrazol-1-yl)methyl)benzoic acid | 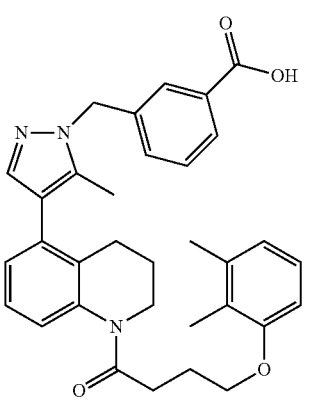 [SMILES: Cc1cccc(OCCCC(=O)N2CCCc3c(-c4cnn(Cc5cccc(C(=O)O)c5)c4C)cccc32)c1C] | 538.3 | 7.96 (d, J = 7.7 Hz, 1H), 7.71 (s, 1H), 7.48 (t, J = 7.7 Hz, 1H), 7.40 (d, J = 7.7 Hz, 1H), 7.32 (s, 1H), 7.29-7.16 (m, 2H), 7.16-7.04 (m, 1H), 6.95 (t, J = 7.9 Hz, 1H), 6.69 (d, J = 7.5 Hz, 1H), 6.65 (d, J = 8.2 Hz, 1H), 5.46 (s, 2H), 3.90 (m, 2H), 3.75 (t, J = 6.9 Hz, 2H), 2.80 (t, J = 7.0 Hz, 2H), 2.46-2.33 (m, 2H), 2.14 (s, 3H), 2.13-2.08 (m, 2H), 2.06 (s, 3H), 1.93-1.74 (m, 5H)* | 9.8 min, 99.6% 9.0 min, 98.8% |

TABLE 3-continued

| Example | Name | Formula I | LCMS, [M + H]+ | 1H NMR (400 MHz, CDCl3) δ | HPLC-1: Rt min, purity; HPLC-2: Rt min, purity |
|---|---|---|---|---|---|
| 32J | 3-((4-(1-(4-(2,3,5-Trimethylphenoxy)butanoyl)-1,2,3,4-tetrahydroquinolin-5-yl)-1H-pyrazol-1-yl)methyl)benzoic acid | | 538.1 | 7.98 (dt, J = 7.2, 1.5 Hz, 1H), 7.91 (s, 1H), 7.66-7.55 (m, 1H), 7.54-7.44 (m, 3H), 7.28-7.18 (m, 2H), 7.18-7.03 (m, 1H), 6.47 (s, 2H), 5.43 (s, 2H), 3.88-3.77 (m, 2H), 3.72 (t, J = 6.8 Hz, 2H), 2.79 (t, J = 6.8 Hz, 2H), 2.55-2.38 (m, 2H), 2.19 (s, 3H), 2.16-2.02 (m, 2H), 1.96 (s, 3H), 1.84-1.72 (m, 2H), 1.64 (s, 3H)* | 12.5 min, 57.5% 13.4 min, 97.7% |
| 32K | 3-((4-(1-(4-(2,3-Dimethylphenoxy)butanoyl)-1,2,3,4-tetrahydroquinolin-5-yl)-1H-pyrazol-1-yl)methyl)-2,4-difluorobenzoic acid | | 560.1 | 8.04 (dd, J = 15.1, 8.6 Hz, 1H), 7.61 (s, 1H), 7.43 (s, 1H), 7.30-7.07 (m, 4H), 6.95 (t, J = 7.8 Hz, 1H), 6.65 (t, J = 8.9 Hz, 2H), 5.49 (s, 2H), 3.93-3.80 (m, 2H), 3.73 (t, J = 6.8 Hz, 2H), 2.80 (t, J = 6.8 Hz, 2H), 2.55-2.37 (m, 2H), 2.11 (dt, J = 12.4, 6.3 Hz, 2H), 2.04 (s, 3H), 1.85-1.64 (m, 5H)* | 9.8 min, 99.5% 10.1 min, 100% |

*1H NMR (400 MHz, MeOD) δ.

Example 33

2-((4-(1-(4-(2,3-Dimethylphenoxy)butanoyl)-1,2,3,4-tetrahydroquinolin-5-yl)thiazol-2-yl)methoxy)benzoic acid

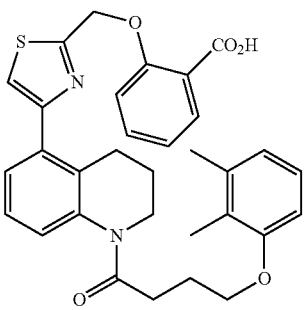 [SMILES: Cc1cccc(OCCCC(=O)N2CCCc3c(-c4csc(COc5ccccc5C(=O)O)n4)cccc32)c1C]

Step A. (5-Bromothiazol-2-yl)methanol

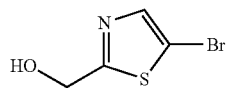

To a solution of sodium borohydride (0.030 g, 0.781 mmol) in MeOH (2.0 mL) was added a solution of 5-bromothiazole-2-carbaldehyde (0.100 g, 0.521 mmol) in MeOH (1.00 mL) dropwise over a period of 5 min at room temperature. Upon the conclusion of this period, the reaction mixture was stirred at room temperature for 1 h. After this time, the solvent was removed in vacuo and the resulting residue was partitioned between EtOAc and water. The organic layer was separated and the aqueous phase was extracted with EtOAc. The combined organic layer was dried over anhydrous MgSO4, filtered, and concentrated in vacuo to afford the title compound (0.067 g, 66% yield) as a dark oil. LCMS, [M+H]+=195.9.

Step B. 4-(2,3-Dimethylphenoxy)-1-(5-(2-(hydroxymethyl)thiazol-4-yl)-3,4-dihydroquinolin-1(2H)-yl)butan-1-one

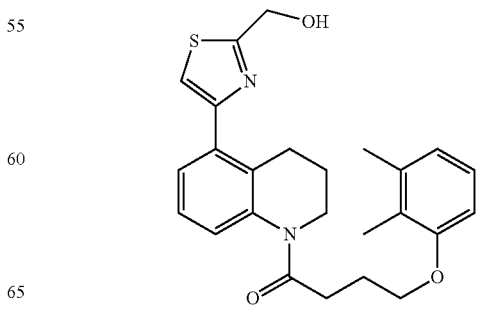

The title compound was prepared using a procedure analogous to methyl 4-(1-(4-(2,3-dimethylphenoxy)butanoyl)-1,2,3,4-tetrahydroquinolin-5-yl)picolinate except that methyl 4-bromopicolinate was replaced with (5-bromothiazol-2-yl)methanol. LCMS, [M+H]⁺=437.1. ¹H NMR (400 MHz, CDCl₃) δ 7.33 (d, J=7.0 Hz, 1H), 7.26-7.19 (m, 2H), 7.06 (s, 1H), 7.03-6.95 (m, 1H), 6.73 (d, J=7.5 Hz, 1H), 6.63 (d, J=8.2 Hz, 1H), 5.01 (s, 2H), 3.92 (t, J=5.2 Hz, 2H), 3.79 (t, J=6.9 Hz, 2H), 2.74 (t, J=7.3 Hz, 2H), 2.62 (t, J=6.2 Hz, 2H), 2.25-2.11 (m, 5H), 1.93 (s, 3H), 1.89-1.80 (m, 2H).

Example 33

To a solution of 4-(2,3-dimethylphenoxy)-1-(5-(2-(hydroxymethyl)thiazol-4-yl)-3,4-dihydroquinolin-1(2H)-yl)butan-1-one (0.010 g, 0.023 mmol), Ph₃P (7.81 mg, 0.030 mmol) and methyl 2-hydroxybenzoate (4.36 mg, 0.029 mmol) in THF (10 mL) was added DEAD (4.71 μL, 0.030 mmol) under sonication. The reaction mixture was sonicated for 20 min and then stirred at room temperature for 16 h. After this time, the reaction mixture was quenched with water and extracted with EtOAc. The combined organic layer was dried over anhydrous MgSO₄, filtered, and concentrated in vacuo. The resulting residue was dissolved in THF (0.20 mL), and 4 M LiOH (0.023 mL, 0.092 mmol) was added. The resulting mixture was stirred at room temperature for 5 h. After this time, the mixture was adjusted to a pH of 6-7 with 1 N HCl and then extracted with EtOAc. The combined organic layer was dried over anhydrous MgSO₄, filtered, and concentrated in vacuo to provide a residue. The residue was purified by preparative HPLC (PHENOMENEX® Axia Luna column, 5μ, C18, 30×75 mm; 10 min gradient from 75% A:25% B to 0% A:100% B (A=90% H₂O/10% MeCN+0.1% TFA); (B=90% MeCN/10% H₂O+0.1% TFA); detection at 220 nm) to afford Example 33 (3 mg, 23% yield) as an off-white solid. LCMS, [M+H]⁺=557.2. ¹H NMR (400 MHz, DMSO-d₆) δ 8.15 (dd, J=7.7, 1.6 Hz, 1H), 7.80-7.61 (m, 2H), 7.58-7.51 (m, 1H), 7.44-7.26 (m, 2H), 7.18 (dd, J=12.6, 5.0 Hz, 2H), 7.02-6.97 (m, 1H), 6.72 (d, J=7.5 Hz, 1H), 6.64 (d, J=8.2 Hz, 1H), 5.63 (s, 2H), 4.01-3.87 (m, 2H), 3.78 (t, J=6.8 Hz, 2H), 2.73 (t, J=7.2 Hz, 2H), 2.68-2.58 (m, 2H), 2.26-2.08 (m, 5H), 1.94 (s, 3H), 1.84 (dt, J=13.2, 6.6 Hz, 2H). HPLC-1: Rt=11.5 min, purity=100%; HPLC-2: Rt=10.3 min, purity=98.0%.

Example 34

3-((5-(1-(4-(2,3-Dimethylphenoxy)butanoyl)-1,2,3,4-tetrahydroquinolin-5-yl)thiazol-2-yl)methyl)benzoic acid

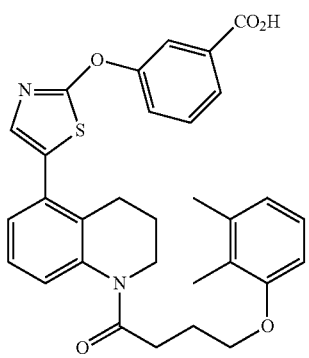 [SMILES: Cc1cccc(OCCCC(=O)N2CCCc3c(-c4cnc(Oc5cccc(C(=O)O)c5)s4)cccc32)c1C]

Step A. Methyl 3-(5-bromothiazol-2-yloxy)benzoate

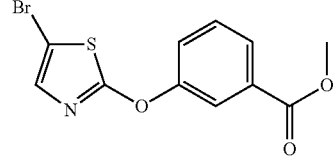

A mixture of 2,5-dibromothiazole (500 mg, 2.06 mmol), methyl 3-hydroxybenzoate (313 mg, 2.06 mmol) and potassium carbonate (341 mg, 2.47 mmol) in DMF (4 mL) was heated at 140° C. in a microwave reactor for 20 min. After cooling to room temperature, the reaction mixture was poured into water and extracted with ethyl acetate. The organic layer was separated, washed with brine, dried over anhydrous MgSO₄, filtered, and concentrated. The resulting residue was purified by flash chromatography (0-100% ethyl acetate:hexanes) to afford the title compound (520 mg, 80% yield). LCMS, [M+H]⁺=315.9.

Example 34

Example 34 was prepared using a procedure analogous to Example 2 except that methyl 4-bromopicolinate was replaced with methyl 3-(5-bromothiazol-2-yloxy)benzoate. LCMS, [M+H]⁺=543.4. ¹H NMR (400 MHz, CD₃CN) δ 7.99-7.89 (m, 2H), 7.65-7.54 (m, 2H), 7.37 (br. s, 1H), 7.29-7.17 (m, 2H), 7.08 (s, 1H), 6.99 (t, J=7.9 Hz, 1H), 6.70 (t, J=7.1 Hz, 2H), 3.92 (t, J=5.8 Hz, 2H), 3.71 (t, J=6.6 Hz, 2H), 2.71 (t, J=7.1 Hz, 2H), 2.64 (t, J=6.3 Hz, 2H), 2.17 (s, 3H), 2.08 (dt, J=13.0, 6.5 Hz, 2H), 1.91 (s, 3H), 1.83 (dt, J=13.1, 6.6 Hz, 2H). HPLC-1: Rt=14.2 min, purity=96.9%; HPLC-2: Rt=13.5 min, purity=95.7%.

Example 35

2-((4-(1-(4-(2,3-Dimethylphenoxy)butanoyl)-1,2,3,4-tetrahydroquinolin-5-yl)benzyloxy)carbonylamino)acetic acid

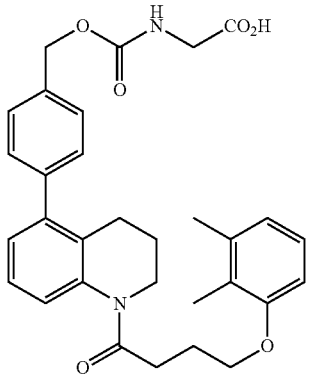 [SMILES: Cc1cccc(OCCCC(=O)N2CCCc3c(-c4ccc(COC(=O)NCC(=O)O)cc4)cccc32)c1C]

Step A. 4-(2,3-Dimethylphenoxy)-1-(5-(4-(hydroxymethyl)phenyl)-3,4-dihydroquinolin-1(2H)-yl)butan-1-one

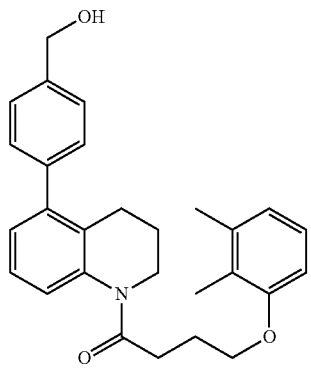 [SMILES: Cc1cccc(OCCCC(=O)N2CCCc3c(-c4ccc(CO)cc4)cccc32)c1C]

To a degassed solution of 1-(5-bromo-3,4-dihydroquinolin-1(2H)-yl)-4-(2,3-dimethylphenoxy)butan-1-one (0.216 g, 0.537 mmol), 4-(hydroxymethyl)phenylboronic acid (0.122 g, 0.805 mmol) and potassium carbonate (0.223 g, 1.611 mmol) in dioxane (3.00 mL)/water (1.20 mL) was added tetrakis(triphenylphosphine)palladium (0.016 g, 0.013 mmol). Upon completion of addition, the vial was purged with argon, sealed and stirred at 90° C. for 16 h. After this time, the reaction mixture was partitioned between water and EtOAc, and the organic layer was separated. The aqueous phase was extracted with EtOAc and the combined organic layer was dried over anhydrous MgSO$_4$, filtered, and concentrated in vacuo to provide the crude material. The crude material was purified by flash chromatography (0-50% ethyl acetate:hexanes) to afford the title compound (0.215 g, 93% yield) as a clear colorless oil. LCMS, [M+H]$^+$=430.2.

Step B. 4-(1-(4-(2,3-Dimethylphenoxy)butanoyl)-1,2,3,4-tetrahydroquinolin-5-yl)benzyl 4-nitrophenyl carbonate

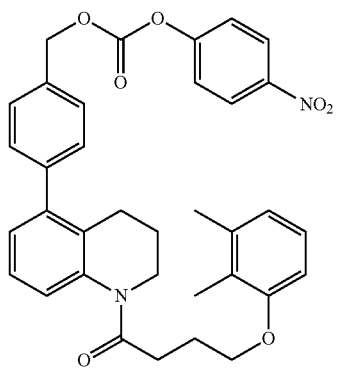 [SMILES: Cc1cccc(OCCCC(=O)N2CCCc3c(-c4ccc(COC(=O)Oc5ccc([N+](=O)[O-])cc5)cc4)cccc32)c1C]

The title compound was prepared using a procedure analogous to 3-bromobenzyl 4-nitrophenyl carbonate except that (3-bromophenyl)methanol was replaced with 4-(2,3-dimethylphenoxy)-1-(5-(4-(hydroxymethyl)phenyl)-3,4-dihydroquinolin-1(2H)-yl)butan-1-one. LCMS, [M+H]$^+$=595.2. $^1$H NMR (400 MHz, CDCl$_3$) δ 8.32-8.16 (m, 2H), 7.44 (d, J=7.8 Hz, 2H), 7.37 (d, J=9.1 Hz, 2H), 7.28-7.13 (m, 4H), 7.09 (s, 1H), 6.98 (t, J=7.8 Hz, 1H), 6.72 (d, J=7.4 Hz, 1H), 6.62 (d, J=8.0 Hz, 1H), 5.31 (s, 2H), 3.92 (br. s, 2H), 3.76 (t, J=6.7 Hz, 2H), 2.74 (t, J=7.1 Hz, 2H), 2.44 (br. s, 2H), 2.29-2.08 (m, 5H), 1.92 (s, 3H), 1.84-1.71 (m, 2H).

Step C. Methyl 2-((4-(1-(4-(2,3-dimethylphenoxy)butanoyl)-1,2,3,4-tetrahydroquinolin-5-yl)benzyloxy)carbonylamino)acetate

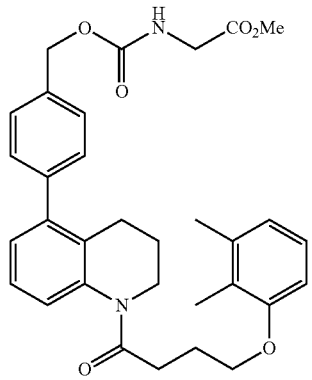

A solution of 4-(1-(4-(2,3-dimethylphenoxy)butanoyl)-1,2,3,4-tetrahydroquinolin-5-yl)benzyl 4-nitrophenyl carbonate (0.020 g, 0.034 mmol), methyl 2-aminoacetate hydrochloride (5.07 mg, 0.040 mmol) and TEA (9.38 μL, 0.067 mmol) in DCM (0.200 mL) was stirred at room temperature for 16 h. After this time, the reaction mixture was quenched with 1 N NaOH. The organic layer was washed with water and brine, dried over anhydrous MgSO$_4$, filtered, and concentrated in vacuo. The resulting residue was purified by preparative HPLC (PHENOMENEX® Axia Luna column, 5μ, C18, 30×100 mm; 10 min gradient from 75% A:25% B to 0% A:100% B (A=90% H$_2$O/10% MeOH+0.1% TFA); (B=90% MeOH/10% H$_2$O+0.1% TFA); detection at 220 nm) to afford the title compound (11.6 mg, 63% yield) as a clear colorless oil. LCMS, [M+H]$^+$=545.2. $^1$H NMR (400 MHz, MeOD) δ 7.37 (d, J=7.9 Hz, 2H), 7.25 (d, J=7.4 Hz, 2H), 7.13 (d, J=7.5 Hz, 1H), 7.09 (d, J=6.8 Hz, 2H), 6.98 (t, J=7.9 Hz, 1H), 6.72 (d, J=7.5 Hz, 1H), 6.66 (d, J=8.1 Hz, 1H), 5.14 (s, 2H), 3.87 (s, 3H), 3.79-3.63 (m, 6H), 2.82 (t, J=6.9 Hz, 2H), 2.35 (s, 2H), 2.20-2.04 (m, 5H), 1.87-1.66 (m, 5H).

Example 35

Example 35 was prepared using a procedure analogous to Example 2 except that methyl 4-(1-(4-(2,3-dimethylphenoxy)butanoyl)-1,2,3,4-tetrahydroquinolin-5-yl)picolinate was replaced with methyl 2-((4-(1-(4-(2,3-dimethylphenoxy)butanoyl)-1,2,3,4-tetrahydroquinolin-5-yl)benzyloxy)carbonylamino)acetate. LCMS, [M+H]$^+$=531.2. $^1$H NMR (400 MHz, CDCl$_3$) δ 7.38 (d, J=7.9 Hz, 2H), 7.24 (s, 2H), 7.20 (t, J=7.6 Hz, 2H), 7.11 (d, J=7.7 Hz, 1H), 7.00 (t, J=7.9 Hz, 1H), 6.74 (d, J=7.5 Hz, 1H), 6.63 (d, J=8.1 Hz, 1H), 5.17 (s, 2H), 4.07 (d, J=5.6 Hz, 2H), 3.93 (br. s, 2H), 3.78 (t, J=7.0 Hz, 2H), 2.78 (t, J=7.2 Hz, 2H), 2.45 (br. s, 2H), 2.25-2.12 (m, 5H), 1.92 (s, 3H), 1.84-1.74 (m, 2H). HPLC-1: Rt=10.4 min, purity=100%; HPLC-2: Rt=9.3 min, purity=100%.

Example 36

3-(Cyclopropyl((3-(1-(4-(2,3-dimethylphenoxy)butanoyl)-1,2,3,4-tetrahydroquinolin-5-yl)benzyloxy)carbonyl)amino)propane-1-sulfonic acid

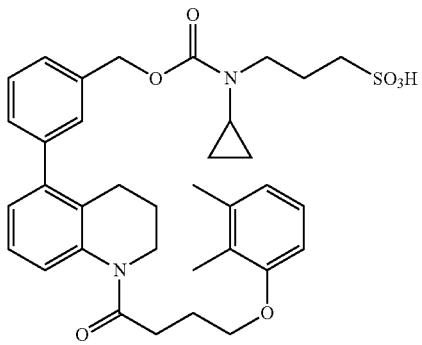 [SMILES: Cc1cccc(OCCCC(=O)N2CCCc3c(-c4cccc(COC(=O)N(CCCS(=O)(=O)O)C5CC5)c4)cccc32)c1C]

Step A. 3-(Cyclopropylamino)propane-1-sulfonic acid

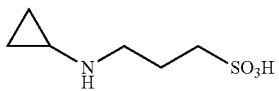

To a solution of 1,3-propane sultone (2.246 g, 18.39 mmol) in THF (20.0 mL) was added cyclopropanamine (1.214 mL, 17.51 mmol) at room temperature. Upon completion of addition, the reaction mixture was stirred at 40° C. for 30 min, at which point the mixture became a thick white paste. At the conclusion of this period, the reaction mixture was vigorously stirred at 65° C. for 2 h. After cooling to room temperature, the resulting solid was collected by filtration to afford the tilted compound (0.522 g, 17% yield) as a white solid. $^1$H NMR (400 MHz, DMSO-d$_6$) δ 8.67 (br. s, 1H), 3.12 (t, J=6.9 Hz, 2H), 2.72-2.63 (m, 1H), 2.60 (t, J=6.8 Hz, 2H), 2.51-2.46 (m, 1H), 1.97-1.85 (m, 2H), 0.79-0.70 (m, 4H).

Step B. 3-(1-(4-(2,3-Dimethylphenoxy)butanoyl)-1,2,3,4-tetrahydroquinolin-5-yl)benzyl 4-nitrophenyl carbonate

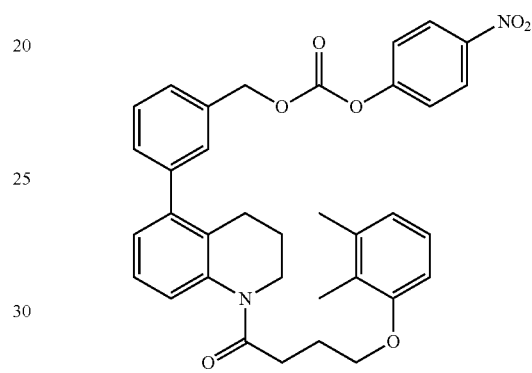

The title compound was prepared using a procedure analogous to 4-(1-(4-(2,3-dimethylphenoxy)butanoyl)-1,2,3,4-tetrahydroquinolin-5-yl)benzyl 4-nitrophenyl carbonate except that 4-(hydroxymethyl)phenylboronic acid was replaced with 3-(hydroxymethyl)phenylboronic acid. LCMS, [M+H]$^+$= 595.3.

Example 36

To a solution of 3-(1-(4-(2,3-dimethylphenoxy)butanoyl)-1,2,3,4-tetrahydroquinolin-5-yl)benzyl 4-nitrophenyl carbonate (0.020 g, 0.034 mmol) and DIPEA (0.018 mL, 0.101 mmol) in DCM (0.5 mL) was added 3-(cyclopropylamino)propane-1-sulfonic acid (7.54 mg, 0.042 mmol). The resulting mixture was stirred at room temperature for 3 days. At the conclusion of this period, the solvent was removed in vacuo, and the resulting residue was purified by preparative HPLC (PHENOMENEX® Axia Luna column, 5µ, C18, 30×75 mm; 10 min gradient from 70% A:30% B to 0% A:100% B (A=90% H$_2$O/10% MeCN+0.1% TFA); (B=90% MeCN/10% H$_2$O+0.1% TFA); detection at 220 nm) to afford Example 36 (4.4 mg, 20% yield). LCMS, [M+H]$^+$=635.3. $^1$H NMR (400 MHz, MeOD) δ 7.42-7.37 (m, 2H), 7.33-7.25 (m, 2H), 7.21-7.14 (m, 2H), 7.08 (br. s, 1H), 6.99 (t, J=7.9 Hz, 1H), 6.73 (d, J=7.5 Hz, 1H), 6.68 (d, J=8.1 Hz, 1H), 5.16 (s, 2H), 3.90 (br. s, 2H), 3.76 (t, J=7.0 Hz, 2H), 3.43 (t, J=7.3 Hz, 2H), 2.85 (t, J=6.9 Hz, 2H), 2.82-2.74 (m, 2H), 2.65 (ddd, J=10.8, 7.2, 3.9 Hz, 1H), 2.39 (br. s, 1H), 2.20-2.10 (m, 5H), 2.10-2.01 (m, 2H), 1.90-1.70 (m, 5H), 0.78 (dd, J=12.4, 6.9 Hz, 2H), 0.71-0.62 (m, 2H). HPLC-2: Rt=8.4 min, purity=100%.

Example 37

3-(4-((3-(1-(4-(2,3-Dimethylphenoxy)butanoyl)-1,2,3,4-tetrahydroquinolin-5-yl)benzyloxy)carbonyl)piperazin-1-yl)propanoic acid

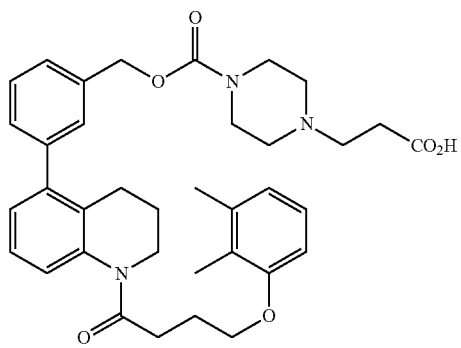 [SMILES: Cc1cccc(OCCCC(=O)N2CCCc3c(-c4cccc(COC(=O)N5CCN(CCC(=O)O)CC5)c4)cccc32)c1C]

Step A. 1-tert-Butyl 4-(3-(1-(4-(2,3-dimethylphenoxy)butanoyl)-1,2,3,4-tetrahydroquinolin-5-yl)benzyl)piperazine-1,4-dicarboxylate

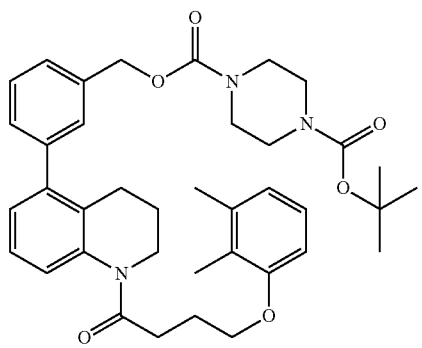 [SMILES: Cc1cccc(OCCCC(=O)N2CCCc3c(-c4cccc(COC(=O)N5CCN(C(=O)OC(C)(C)C)CC5)c4)cccc32)c1C]

The title compound was prepared using a procedure analogous to Example 36 except that 3-(cyclopropylamino)propane-1-sulfonic acid was replaced by tert-butyl piperazine-1-carboxylate. LCMS, [M-Boc+2H]$^+$=542.2.

Step B. 3-(1-(4-(2,3-Dimethylphenoxy)butanoyl)-1,2,3,4-tetrahydroquinolin-5-yl)benzyl piperazine-1-carboxylate

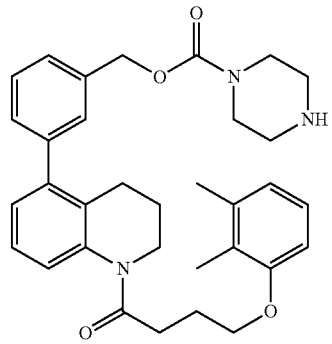 [SMILES: Cc1cccc(OCCCC(=O)N2CCCc3c(-c4cccc(COC(=O)N5CCNCC5)c4)cccc32)c1C]

To a solution of 1-tert-butyl 4-(3-(1-(4-(2,3-dimethylphenoxy)butanoyl)-1,2,3,4-tetrahydroquinolin-5-yl)benzyl)piperazine-1,4-dicarboxylate (0.16 g, 0.25 mmol) in DCM (1.0 mL) was added TFA (1 mL, 12.98 mmol). Upon completion of addition, the reaction mixture was stirred at room temperature for 2 h. After this time, the pH was adjusted to 7-8 with 1 N NaOH and saturated NaHCO$_3$. The organic layer was separated, washed with water and brine, dried over anhydrous MgSO$_4$, filtered, and concentrated to afford the title compound (115 mg, 84% yield). LCMS, [M+H]$^+$=542.2.

Example 37

The mixture of 3-(1-(4-(2,3-dimethylphenoxy)butanoyl)-1,2,3,4-tetrahydroquinolin-5-yl)benzyl piperazine-1-carboxylate (0.050 g, 0.092 mmol), methyl 3-bromopropanoate (0.019 g, 0.115 mmol) and K$_2$CO$_3$ (0.026 g, 0.185 mmol) in acetonitrile (1.0 mL) was stirred at 60° C. for 16 h. After this time, 4 M LiOH (0.2 ml, 0.800 mmol) was added and the resulting mixture was stirred at room temperature for 16 h. The cloudy mixture was adjusted to pH 3-4 with TFA and concentrated. The resulting residue was purified by preparative HPLC (PHENOMENEX® Axia Luna column, 5µ, C18, 30×75 mm; 10 min gradient from 80% A:20% B to 0% A:100% B (A=90% H$_2$O/10% MeCN+0.1% TFA); (B=90% MeCN/10% H$_2$O+0.1% TFA); detection at 220 nm) to afford Example 37 (19.6 mg, 33% yield) as a white solid. LCMS, [M+H]$^+$=614.3. $^1$H NMR (400 MHz, MeOD) δ 7.50-7.41 (m, 2H), 7.38-7.28 (m, 2H), 7.25 (s, 1H), 7.22-7.18 (m, 1H), 7.16 (s, 1H), 7.04 (t, J=7.9 Hz, 1H), 6.78 (d, J=7.5 Hz, 1H), 6.73 (d, J=8.2 Hz, 1H), 5.25 (s, 2H), 3.96 (br. s, 4H), 3.81 (t, J=7.0 Hz, 4H), 3.50 (t, J=7.0 Hz, 4H), 3.39 (br. s, 2H), 2.89 (dd, J=15.4, 7.0 Hz, 4H), 2.44 (s, 2H), 2.27-2.13 (m, 5H), 1.89 (s, 3H), 1.83 (dt, J=13.5, 6.8 Hz, 2H). HPLC-1: Rt=11.0 min, purity=92.1%; HPLC-2: Rt=11.1 min, purity=92.6%.

The following Examples were prepared in a manner analogous to Example 35.

TABLE 4

| Example | Name | —A—X—Y | V | R$_{5b}$ | LCMS, [M + H]$^+$ | $^1$H NMR (400 MHz, CDCl$_3$) δ | HPLC-1: Rt min, purity; HPLC-2: Rt min, purity | Synthesis Comment |
|---|---|---|---|---|---|---|---|---|
| 38 | 1-((4-(1-(4-(2,3-Dimethyl-phenoxy)butanoyl)-1,2,3,4-tetrahydro-quinolin-5-yl)benzyloxy)carbonyl)aze-tidine-3-carboxylic acid | 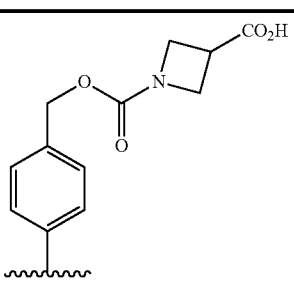 | CH$_2$ | Me | 557.3 | 7.36 (d, J = 8.0 Hz, 2H), 7.26-7.20 (m, 2H), 7.18 (d, J = 8.0 Hz, 2H), 7.12 (d, J = 7.4 Hz, 1H), 7.00 (t, J = 7.9 Hz, 1H), 6.74 (d, J = 7.5 Hz, 1H), 6.63 (d, J = 8.1 Hz, 1H), 5.14 (s, 2H), 4.24 (d, J = 7.6 Hz, 4H), 3.93 (br. s, 2H), 3.79 (t, J = 7.0 Hz, 2H), 3.46 (dt, J = 15.0, 7.5 Hz, 1H), 2.79 (t, J = 7.2 Hz, 2H), 2.46 (br. s, 2H), 2.25-2.13 (m, 5H), 1.91 (s, 3H), 1.80 (dt, J = 13.2, 6.6 Hz, 2H) | 10.7 min, 98.8% 9.5 min, 98.8% | Amino acid used, no hydrolysis step |
| 39 | 2-(((4-(1-(4-(2,3-Dimethyl-phenoxy)butanoyl)-1,2,3,4-tetrahydro-quinolin-5-yl)benzyloxy)carbonyl)(methyl)amino)acetic acid | 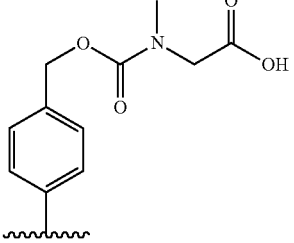 | CH$_2$ | Me | 545.2 | 7.38 (d, J = 7.9 Hz, 1H), 7.33 (d, J = 7.9 Hz, 1H), 7.25-7.14 (m, 4H), 7.12 (d, J = 5.8 Hz, 1H), 7.00 (t, J = 7.9 Hz, 1H), 6.74 (d, J = 7.5 Hz, 1H), 6.63 (d, J = 8.1 Hz, 1H), 5.18 (d, J = 11.2 Hz, 2H), 4.09 (d, J = 9.0 Hz, 2H), 3.93 (s, 2H), 3.77 (d, J = 6.4 Hz, 2H), 3.03 (s, 3H), 2.78 (t, J = 7.1 Hz, 2H), 2.46 (s, 2H), 2.27-2.11 (m, 5H), 1.92 (s, 3H), 1.85-1.73 (m, 2H) | 10.8 min, 100% 9.3 min, 100% | Amino ester used |
| 40 | 1-((4-(1-(4-(2,3-Dimethyl-phenoxy)butanoyl)-1,2,3,4-tetrahydro-quinolin-5-yl)benzyloxy)carbonyl)pyrrolidine-2-carboxylic acid | 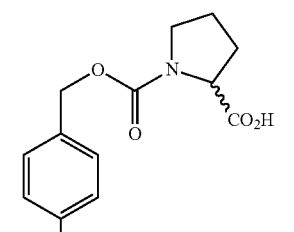 | CH$_2$ | Me | 571.2 | 7.38 (d, J = 7.8 Hz, 1H), 7.33 (d, J = 6.8 Hz, 1H), 7.31-7.14 (m, 4H), 7.10 (d, J = 6.7 Hz, 1H), 7.00 (t, J = 7.8 Hz, 1H), 6.74 (d, J = 7.5 Hz, 1H), 6.64 (d, J = 8.2 Hz, 1H), 5.22 (s, 2H), 4.43 (dd, J = 8.3, 2.9 Hz, 1H), 3.99-3.88 (m, 2H), 3.77 (t, J = 6.8 Hz, 2H), 3.61-3.52 (m, 2H), 3.52-3.41 (m, 2H), 2.76 (t, J = 7.2 Hz, 2H), 2.46 (br. s, 2H), 2.41-2.31 (m, 1H), 2.25-2.13 (m, 5H), 2.13-2.03 (m, 1H), | 11.0 min, 100% 9.6 min, 100% | Amino acid used, no hydrolysis step |

TABLE 4-continued

| Example | Name | —A—X—Y | V | R$_{5b}$ | LCMS, [M + H]$^+$ | $^1$H NMR (400 MHz, CDCl$_3$) δ | HPLC-1: Rt min, purity; HPLC-2: Rt min, purity | Synthesis Comment |
|---|---|---|---|---|---|---|---|---|
| | | | | | | 2.02-1.89 (m, 5H), 1.86-1.72 (m, 2H) | | |
| 41 | 2-((3-(1-(4-(2,3-Dimethyl-phenoxy)butanoyl)-1,2,3,4-tetrahydro-quinolin-5-yl)benzyloxy)carbonyl-amino)propanoic acid | (benzyl with CO$_2$H, NH, carbamate) | CH$_2$ | Me | 545.2 | 7.38 (t, J = 7.6 Hz, 1H), 7.32 (d, J = 7.6 Hz, 1H), 7.29-7.19 (m, 3H), 7.18-7.09 (m, 2H), 7.00 (t, J = 7.9 Hz, 1H), 6.74 (d, J = 7.5 Hz, 1H), 6.63 (d, J = 8.2 Hz, 1H), 5.27 (d, J = 7.2 Hz, 1H), 5.21-5.07 (m, 2H), 4.41 (dt, J = 15.0, 7.6 Hz, 1H), 3.93 (s, 2H), 3.78 (t, J = 7.0 Hz, 2H), 2.78 (t, J = 7.3 Hz, 2H), 2.50-2.43 (m, 2H), 2.24-2.12 (m, 5H), 1.92 (s, 3H), 1.80 (dt, J = 13.2, 6.5 Hz, 2H), 1.46 (d, J = 7.2 Hz, 3H) | 11.0 min, 100% 9.6 min, 100% | Amino acid used, no hydrolysis step |
| 42 | 2-((3-(1-(4-(2,3-Dimethyl-phenoxy)butanoyl)-1,2,3,4-tetrahydro-quinolin-5-yl)benzyloxy)carbonyl-amino)acetic acid | (benzyl with CO$_2$H, NH, carbamate) | CH$_2$ | Me | 531.2 | 7.38 (t, J = 7.6 Hz, 1H), 7.31 (d, J = 7.6 Hz, 1H), 7.29-7.19 (m, 3H), 7.18-7.09 (m, 2H), 7.00 (t, J = 7.9 Hz, 1H), 6.74 (d, J = 7.5 Hz, 1H), 6.63 (d, J = 8.2 Hz, 1H), 5.31-5.24 (m, 1H), 5.16 (s, 2H), 4.02 (d, J = 5.6 Hz, 2H), 3.93 (br. s, 2H), 3.78 (t, J = 7.0 Hz, 2H), 2.78 (t, J = 7.3 Hz, 2H), 2.46 (t, J = 6.0 Hz, 2H), 2.24-2.11 (m, 5H), 1.92 (s, 3H), 1.79 (dt, J = 13.3, 6.7 Hz, 2H) | 10.6 min, 100% 9.2 min, 100% | Amino ester used |
| 43 | 3-((3-(1-(4-(2,3-Dimethyl-phenoxy)butanoyl)-1,2,3,4-tetrahydro-quinolin-5-yl)benzyloxy)carbonyl-amino)propanoic | (benzyl with CO$_2$H, NH, carbamate) | CH$_2$ | Me | 545.2 | 7.38 (t, J = 7.5 Hz, 1H), 7.31 (d, J = 7.0 Hz, 1H), 7.28-7.20 (m, 2H), 7.19-7.05 (m, 3H), 7.00 (t, J = 7.9 Hz, 1H), 6.74 (d, J = 7.5 Hz, 1H), 6.62 (d, J = 8.1 Hz, 1H), 5.13 (s, 2H), 3.92 (br. s, 2H), 3.80 (t, J = 6.9 Hz, 2H), 3.47 (d, J = 5.5 Hz, | 10.7 min, 98.0% 9.3 min, 98.0% | Amino acid used, no hydrolysis step |

TABLE 4-continued

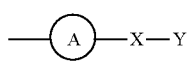

| Example | Name | —A—X—Y | V | R$_{5b}$ | LCMS, [M + H]$^+$ | $^1$H NMR (400 MHz, CDCl$_3$) δ | HPLC-1: Rt min, purity; HPLC-2: Rt min, purity | Synthesis Comment |
|---|---|---|---|---|---|---|---|---|
| | acid | | | | | 2H), 2.84 (t, J = 7.3 Hz, 2H), 2.67-2.54 (m, 2H), 2.46 (br. s, 2H), 2.25-2.10 (m, 5H), 1.88 (s, 3H), 1.85-1.75 (m, 2H) | | |
| 44 | 3-(((3-(1-(4-(2,3-Dimethylphenoxy)butanoyl)-1,2,3,4-tetrahydroquinolin-5-yl)benzyloxy)carbonyl)(methyl)amino)propanoic acid | | CH$_2$ | Me | 559.2 | 7.38 (t, J = 7.6 Hz, 1H), 7.32 (d, J = 7.3 Hz, 1H), 7.27-7.20 (m, 2H), 7.19 (s, 1H), 7.18-7.10 (m, 2H), 7.00 (t, J = 7.9 Hz, 1H), 6.74 (d, J = 7.5 Hz, 1H), 6.63 (d, J = 8.1 Hz, 1H), 5.15 (s, 2H), 3.93 (br. s, 2H), 3.79 (t, J = 7.0 Hz, 2H), 3.58 (t, J = 6.8 Hz, 2H), 2.96 (s, 3H), 2.81 (t, J = 7.3 Hz, 2H), 2.69-2.54 (m, 2H), 2.47 (br. s, 2H), 2.25-2.11 (m, 5H), 1.92 (s, 3H), 1.81 (dd, J = 13.1, 6.6 Hz, 2H) | 11.2 min, 98.1% 9.7 min, 98.2% | Amino acid used, no hydrolysis step |
| 45 | 2-((3-(1-(4-(2,3-Dimethylphenoxy)butanoyl)-1,2,3,4-tetrahydroquinolin-5-yl)benzyloxy)carbonylamino)ethanesulfonic acid | | CH$_2$ | Me | 581.3 | 7.40-7.31 (m, 2H), 7.30-7.19 (m, 2H), 7.18-7.09 (m, 2H), 7.04 (br. s, 1H), 6.98 (t, J = 7.9 Hz, 1H), 6.72 (d, J = 7.5 Hz, 1H), 6.67 (d, J = 8.2 Hz, 1H), 5.09 (s, 2H), 3.88 (br. s, 2H), 3.74 (t, J = 7.0 Hz, 2H), 3.54 (t, J = 7.0 Hz, 2H), 2.97 (t, J = 6.9 Hz, 2H), 2.83 (t, J = 6.9 Hz, 2H), 2.37 (br. s, 2H), 2.18-2.07 (m, 5H), 1.81 (s, 3H), 1.79-1.70 (m, 2H)* | 12.6 min, 97.8% 7.5 min, 94.7% | Amino sulfonic acid used |

TABLE 4-continued

| Example | Name | —A—X—Y | V | R$_{5b}$ | LCMS, [M + H]$^+$ | $^1$H NMR (400 MHz, CDCl$_3$) δ | HPLC-1: Rt min, purity; HPLC-2: Rt min, purity | Synthesis Comment |
|---|---|---|---|---|---|---|---|---|
| 46 | 3-(((4-(1-(4-(2,3-Dimethyl-phenoxy)butanoyl)-1,2,3,4-tetrahydro-quinolin-5-yl)thiazol-2-yl)methoxy)carbonyl-amino)propanoic acid | (thiazol-CH$_2$-O-C(O)-NH-CH$_2$CH$_2$-CO$_2$H) | CH$_2$ | Me | 552.2 | 7.40-7.31 (m, 1H), 7.29-7.18 (m, 2H), 7.08 (s, 1H), 7.00 (t, J = 7.9 Hz, 1H), 6.72 (d, J = 7.5 Hz, 1H), 6.63 (d, J = 8.1 Hz, 1H), 5.50-5.43 (m, 1H), 5.41 (s, 2H), 3.92 (br. s, 2H), 3.79 (t, J = 6.8 Hz, 2H), 3.50 dd, J = 11.8, 5.9 Hz, 2H), 2.76 (t, J = 7.2 Hz, 2H), 2.69-2.55 (m, 4H), 2.24-2.08 (m, 5H), 1.92 (s, 3H), 1.85 (dd, J = 13.3, 6.7 Hz, 2H) | 9.9 min, 99.7% 9.0 min, 99.7% | Amino acid used, no hydrolysis step |
| 47 | 3-((3-(1-((2-(3-Fluoro-2-methyl-phenoxy)ethoxy)carbonyl)-1,2,3,4-tetrahydro-quinolin-5-yl)benzyloxy)carbonyl-amino)butanoic acid | (benzyl-CH$_2$-O-C(O)-NH-CH(CH$_3$)CH$_2$-CO$_2$H) | O | F | 565.3 | 7.58 (d, J = 8.1 Hz, 1H), 7.38 (t, J = 7.5 Hz, 1H), 7.29 (d, J = 7.7 Hz, 1H), 7.26-7.19 (m, 2H), 7.16 (t, J = 7.9 Hz, 1H), 7.07 (dd, J = 15.1, 8.2 Hz, 1H), 7.01-6.94 (m, 1H), 6.67 (t, J = 8.7 Hz, 1H), 6.61 (d, J = 8.3 Hz, 1H), 5.19 (d, J = 7.6 Hz, 1H), 5.12 (s, 2H), 4.60-4.53 (m, 2H), 4.26-4.19 (m, 2H), 4.16-4.04 (m, 1H), 3.72 (t, J = 6.5 Hz, 2H), 2.56 (t, J = 6.3 Hz, 4H), 2.14 (d, J = 1.8 Hz, 3H), 1.86-1.75 (m, 2H), 1.25 (d, J = 6.8 Hz, 3H) | 11.2 min, 100% 9.9 min, 100% | Amino acid used, no hydrolysis step |
| 48 | 3-((3-(1-((2-(3-Chloro-2-methyl-phenoxy)ethoxy)carbonyl)-1,2,3,4-tetrahydro-quinolin-5-yl)benzyloxy)(carbonyl-amino) | (benzyl-CH$_2$-O-C(O)-NH-CH(CH$_3$)CH$_2$-CO$_2$H) | O | Cl | 581.3 | 7.58 (d, J = 8.0 Hz, 1H), 7.37 (d, J = 7.8 Hz, 1H), 7.29 (d, J = 7.8 Hz, 1H), 7.26-7.20 (m, 2H), 7.16 (t, J = 7.9 Hz, 1H), 7.05 (t, J = 8.1 Hz, 1H), 6.98 (d, J = 7.9 Hz, 2H), 6.73 (d, J = 8.0 Hz, 1H), 5.20 (br. s, 1H), 5.13 (s, 2H), 4.59-4.53 (m, 2H), 4.25-4.18 (m, 2H), 4.15-4.04 (m, 1H), 3.72 | 11.9 min, 100% 10.4 min, 100% | Amino acid used, no hydrolysis step |

TABLE 4-continued

| Example | Name | —Ⓐ—X—Y | V | $R_{5b}$ | LCMS, [M + H]⁺ | ¹H NMR (400 MHz, CDCl₃) δ | HPLC-1: Rt min, purity; HPLC-2: Rt min, purity | Synthesis Comment |
|---|---|---|---|---|---|---|---|---|
| | butanoic acid | | | | | (t, J = 6.5 Hz, 2H), 2.59-2.53 (m, 4H), 2.29 (s, 3H), 1.86-1.75 (m, 2H), 1.25 (d, J = 6.8 Hz, 3H) | | |
| 49 | 4-((3-(1-((2-(3-Chloro-2-methyl-phenoxy)ethoxy)carbonyl)-1,2,3,4-tetrahydro-quinolin-5-yl)benzyloxy)carbonyl-amino)-2-hydroxy-butanoic acid | 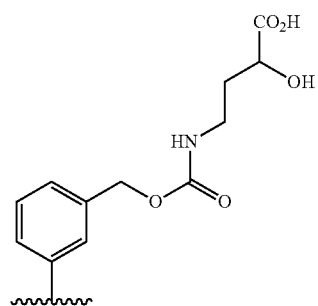 [SMILES: *c1cccc(COC(=O)NCCC(O)C(=O)O)c1] | O | Cl | 597.3 | 7.58 (d, J = 7.9 Hz, 1H), 7.37 (t, J = 7.8 Hz, 1H), 7.28 (d, J = 7.4 Hz, 1H), 7.26-7.19 (m, 2H), 7.15 (t, J = 7.9 Hz, 1H), 7.05 (t, J = 8.1 Hz, 1H), 7.00-6.93 (m, 2H), 6.73 (d, J = 8.0 Hz, 1H), 5.24-5.08 (m, 2H), 4.60-4.51 (m, 2H), 4.27-4.18 (m, 3H), 3.94 (br. s, 2H), 3.71 (t, J = 6.5 Hz, 2H), 3.48-3.22 (m, 2H), 2.54 (t, J = 6.3 Hz, 2H), 2.28 (s, 3H), 1.79 (dt, J = 12.8, 6.4 Hz, 2H) | 11.7 min, 98.4% 10.5 min, 100% | Amino acid used, no hydrolysis step |
| 50 | 4-((3-(1-((2-(3-Fluoro-2-methyl-phenoxy)ethoxy)carbonyl)-1,2,3,4-tetrahydro-quinolin-5-yl)benzyloxy)carbonyl-amino)-2-hydroxy-butanoic acid | 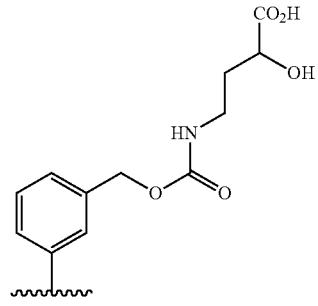 [SMILES: *c1cccc(COC(=O)NCCC(O)C(=O)O)c1] | O | F | 581.3 | 7.58 (d, J = 7.8 Hz, 1H), 7.37 (t, J = 7.7 Hz, 1H), 7.32-7.19 (m, 3H), 7.15 (t, J = 7.9 Hz, 1H), 7.06 (dd, J = 15.1, 8.1 Hz, 1H), 6.95 (d, J = 7.4 Hz, 1H), 6.66 (t, J = 8.6 Hz, 1H), 6.61 (d, J = 8.3 Hz, 1H), 5.28-5.06 (m, 2H), 4.60-4.51 (m, 2H), 4.28-4.16 (m, 3H), 3.71 (t, J = 6.4 Hz, 2H), 3.69-3.18 (m, 4H), 2.54 (t, J = 6.3 Hz, 2H), 2.14 (d, J = 1.7 Hz, 3H), 1.79 (dt, J = 12.7, 6.3 Hz, 2H) | 11.1 min, 98.7% 10.1 min, 100% | Amino acid used, no hydrolysis step |

TABLE 4-continued

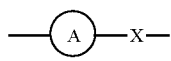

| Example | Name | ⎯⎯A⎯X⎯Y | V | R_{5b} | LCMS, [M + H]+ | ¹H NMR (400 MHz, CDCl₃) δ | HPLC-1: Rt min, purity; HPLC-2: Rt min, purity | Synthesis Comment |
|---|---|---|---|---|---|---|---|---|
| 51 | 3-((3-((4-(1-(4-(2,3-Dimethyl-phenoxy)butanoyl)-1,2,3,4-tetrahydro-quinolin-5-yl)-1H-pyrazol-1-yl)methyl)benzyloxy)carbonyl-amino)propanoic acid | 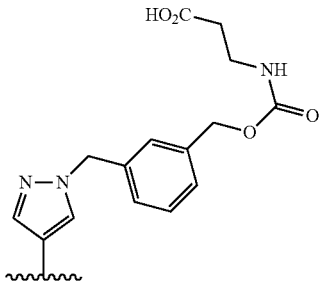 [SMILES: *c1cnn(Cc2cccc(COC(=O)NCCC(=O)O)c2)c1] | CH₂ | Me | 625.4 | 7.64 (br. s, 1H), 7.52 (s, 1H), 7.46-7.31 (m, 3H), 7.32-7.22 (m, 3H), 7.20 (br. s, 1H), 7.00 (t, J = 7.9 Hz, 1H), 6.75-6.63 (m, 2H), 5.41 (s, 2H), 5.11 (s, 2H), 3.90 (br. s, 2H), 3.78 (t, J = 6.8 Hz, 2H), 3.40 (td, J = 6.7, 0.8 Hz, 2H), 2.84 (t, J = 6.8 Hz, 2H), 2.58-2.46 (m, 4H), 2.21-2.11 (m, 2H), 2.07 (s, 3H), 1.89-1.81 (m, 2H), 1.78 (s, 3H)* | 11.5 min, 100% 11.7 min, 100% | Amino acid used, no hydrolysis step |
| 52 | ((3-((4-(1-(4-(2,3-Dimethyl-phenoxy)butanoyl)-1,2,3,4-tetrahydro-quinolin-5-yl)-1H-pyrazol-1-yl)methyl)benzyloxy)carbonyl-amino)methane-sulfonic acid | 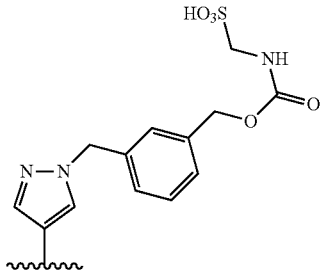 [SMILES: *c1cnn(Cc2cccc(COC(=O)NCS(=O)(=O)O)c2)c1] | CH₂ | Me | 647.4 | 8.03 (br. s, 1H), 7.83 (br. s, 1H), 7.55-7.38 (m, 3H), 7.32 (s, 4H), 7.01 (t, J = 7.8 Hz, 1H), 6.71 (d, J = 7.5 Hz, 2H), 5.55 (s, 2H), 5.21 (s, 2H), 4.28 (s, 2H), 3.93 (br. s, 2H), 3.81 (t, J = 6.7 Hz, 2H), 2.85 (t, J = 6.9 Hz, 2H), 2.58 (br. s, 2H), 2.26-2.13 (m, 2H), 2.10 (s, 3H), 1.93-1.85 (m, 2H), 1.83 (s, 3H)* | 15.0 min, 100% 11.8 min, 99.1% | Amino sulfonic acid used |
| 53 | 2-((3-((4-(1-(4-(2,3-Dimethyl-phenoxy)butanoyl)-1,2,3,4-tetrahydro-quinolin-5-yl)-1H-pyrazol-1-yl)methyl)benzyloxy)carbonyl-amino)ethane-sulfonic acid | 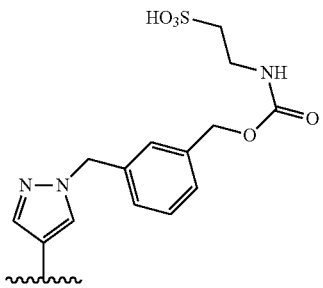 [SMILES: *c1cnn(Cc2cccc(COC(=O)NCCS(=O)(=O)O)c2)c1] | CH₂ | Me | 661.4 | 8.02 (br.s, 1H), 7.84 (br. s, 1H), 7.49-7.36 (m, 3H), 7.36-7.23 (m, 4H), 7.00 (t, J = 7.9 Hz, 1H), 6.69 (d, J = 7.9 Hz, 2H), 5.55 (s, 2H), 5.15 (s, 2H), 3.91 (br. s, 2H), 3.79 (t, J = 6.8 Hz, 2H), 3.58 (t, J = 6.3 Hz, 2H), 3.02 (t, J = 6.6 Hz, 2H), 2.84 (t, J = 6.9 Hz, 2H), 2.56 (br. s, 2H), 2.21-2.11 (m, 2H), 2.08 (s, 3H), 1.92-1.84 (m, 2H), 1.81 (s, 3H)* | 14.6 min, 100% 11.9 min, 100% | Amino sulfonic acid used |

TABLE 4-continued

| Example | Name | —A—X—Y | V | R5b | LCMS, [M + H]+ | 1H NMR (400 MHz, CDCl3) δ | HPLC-1: Rt min, purity; HPLC-2: Rt min, purity | Synthesis Comment |
|---|---|---|---|---|---|---|---|---|
| 54 | 3-((3-((4-(1-(4-(2,3-Dimethyl-phenoxy)butanoyl)-1,2,3,4-tetrahydro-quinolin-5-yl)-1H-pyrazol-1-yl)methyl)benzyloxy)carbonyl-amino)propane-1-sulfonic acid | 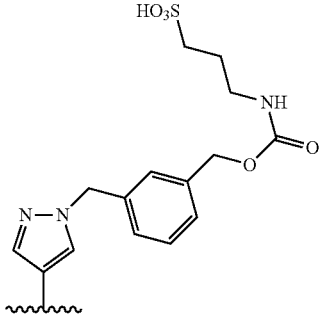 [SMILES: *c1cnn(Cc2cccc(COC(=O)NCCCS(=O)(=O)O)c2)c1] | $CH_2$ | Me | 675.3 | 7.92 (br. s, 1H), 7.75 (br. s, 1H), 7.44-7.29 (m, 3H), 7.31-7.11 (m, 4H), 6.95 (t, J = 7.9 Hz, 1H), 6.64 (d, J = 7.8 Hz, 2H), 5.50 (s, 2H), 5.08 (s, 2H), 3.85 (br. s, 2H), 3.74 (t, J = 6.7 Hz, 2H), 3.21 (t, J = 6.4 Hz, 2H), 2.91-2.67 (m, 4H), 2.50 (br. s, 2H), 2.10 (dt, J = 12.4, 6.1 Hz, 2H), 2.03 (s, 3H), 2.00-1.89 (m, 2H), 1.88-1.77 (m, 2H), 1.74 (s, 3H)* | 10.2 min, 99.0% 10.4 min, 100% | Amino sulfonic acid used |
| 55 | 3-((3-(1-(4-(2,3-Dimethyl-phenoxy)butanoyl)-1,2,3,4-tetrahydro-quinolin-5-yl)benzyloxy)carbonyl-amino)propane-1-sulfonic acid | 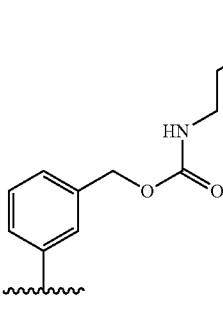 | $CH_2$ | Me | 595.2 | 7.49-7.39 (m, 2H), 7.39-7.28 (m, 2H), 7.27-7.18 (m, 2H), 7.13 (d, J = 6.3 Hz, 1H), 7.06 (t, J = 7.9 Hz, 1H), 6.80 (d, J = 7.5 Hz, 1H), 6.75 (d, J = 8.2 Hz, 1H), 5.17 (s, 2H), 3.98 (br. s, 2H), 3.83 (t, J = 7.0 Hz, 2H), 3.32 (t, J = 6.8 Hz, 2H), 2.96-2.86 (m, 4H), 2.46 (br. s, 2H), 2.30-2.15 (m, 5H), 2.10-1.99 (m, 2H), 1.92 (s, 3H), 1.85 (dt, J = 13.3, 6.7 Hz, 2H)* | 10.6 min, 99.4% 10.6 min, 100% | Amino sulfonic acid used |
| 56 | 2-(((3-(1-(4-(2,3-Dimethyl-phenoxy)butanoyl)-1,2,3,4-tetrahydro-quinolin-5-yl)benzyloxy)carbonyl)(methyl)amino)ethane-sulfonic acid | 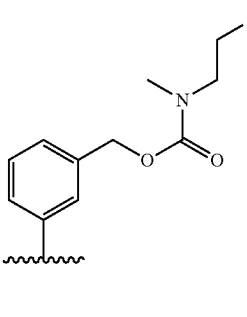 | $CH_2$ | Me | 595.2 | 7.39-7.27 (m, 2H), 7.27-7.15 (m, 2H), 7.11 (d, J = 7.8 Hz, 1H), 7.09 (s, 1H), 7.01 (s, 1H), 6.93 (t, J = 7.9 Hz, 1H), 6.67 (d, J = 7.5 Hz, 1H), 6.62 (d, J = 8.1 Hz, 1H), 5.09 (s, 2H), 3.83 (br. s, 2H), 3.70 (t, J = 7.1 Hz, 2H), 3.67-3.60 (m, 2H), 3.05-2.95 (m, 2H), 2.92 (s, 3H), 2.78 (t, J = 6.9 Hz, 2H), 2.33 (br. s, 2H), 2.16-2.01 (m, 5H), 1.85-1.64 (m, 5H)* | 10.7 min, 100% 10.7 min, 100% | Amino sulfonic acid used |

TABLE 4-continued

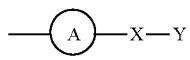

| Example | Name | 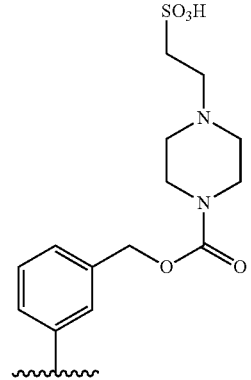 [SMILES: *c1cccc(COC(=O)N2CCN(CCS(=O)(=O)O)CC2)c1] —X—Y | V | R$_{5b}$ | LCMS, [M + H]$^+$ | $^1$H NMR (400 MHz, CDCl$_3$) δ | HPLC-1: Rt min, purity; HPLC-2: Rt min, purity | Synthesis Comment |
|---|---|---|---|---|---|---|---|---|
| 57 | 2-(4-((3-(1-(4-(2,3-Dimethyl-phenoxy)butanoyl)-1,2,3,4-tetrahydro-quinolin-5-yl)benzyloxy)carbonyl)piperazin-1-yl)ethane-sulfonic acid | 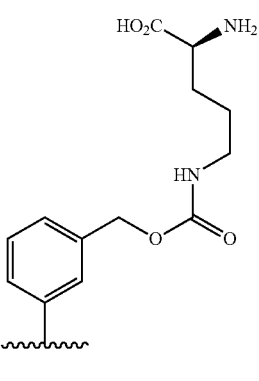 [SMILES: *c1cccc(COC(=O)NCCC[C@H](N)C(=O)O)c1] | CH$_2$ | Me | 650.3 | 7.40-7.35 (m, 2H), 7.30-7.22 (m, 2H), 7.19-7.11 (m, 2H), 7.07 (s, 1H), 6.97 (t, J = 7.9 Hz, 1H), 6.71 (d, J = 7.5 Hz, 1H), 6.66 (d, J = 8.2 Hz, 1H), 5.18 (s, 2H), 4.28 (d, J = 13.6 Hz, 2H), 3.88 (br. s, 2H), 3.74 (t, J = 7.0 Hz, 2H), 3.61 (br. s, 2H), 3.53 (t, J = 7.0 Hz, 2H), 3.35-3.25 (m, 2H), 3.21 (t, J = 7.0 Hz, 2H), 3.17-3.05 (m, 2H), 2.82 (t, J = 6.9 Hz, 2H), 2.36 (br. s, 2H), 2.18-2.06 (m, 5H), 1.85-1.70 (m, 5H)* | 10.8 min, 100% 10.9 min, 100% | Amino sulfonic acid used |
| 58 | (S)-2-Amino-5-((3-(1-(4-(2,3-dimethyl-phenoxy)butanoyl)-1,2,3,4-tetrahydro-quinolin-5-yl)benzyloxy)carbonyl-amino)pentanoic acid |  | CH$_2$ | Me | 588.3 | 7.41-7.30 (m, 2H), 7.29-7.19 (m, 2H), 7.19-7.08 (m, 2H), 7.04 (br. s, 1H), 6.95 (t, J = 7.8 Hz, 1H), 6.69 (d, J = 7.5 Hz, 1H), 6.64 (d, J = 8.1 Hz, 1H), 5.07 (s, 2H), 4.01-3.91 (m, 1H), 3.87 (br. s, 2H), 3.71 (t, J = 7.0 Hz, 2H), 3.34-3.24 (m, 2H), 3.15 (t, J = 6.7 Hz, 2H), 2.79 (t, J = 6.9 Hz, 2H), 2.35 (br. s, 2H), 2.20-2.05 (m, 5H), 2.01-1.54 (m, 7H)* | 10.9 min, 91.9% 11.3 min, 90.7% | (S)-5-Amino-2-(tert-butoxy-carbonyl-amino)pentanoic acid used, Boc depro-tection using TFA |

*$^1$H NMR (400 MHz, MeOD) δ.

Example 59

3-(((5-(1-(4-(2,3-Dimethylphenoxy)butanoyl)-1,2,3,4-tetrahydroquinolin-5-yl)pyridin-2-yl)methoxy)carbonylamino)propanoic acid

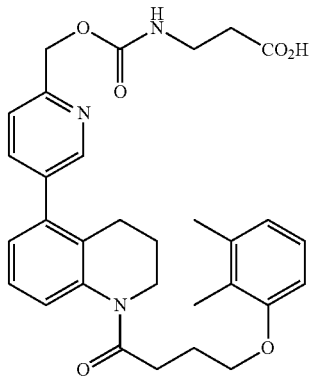 [SMILES: Cc1cccc(OCCCC(=O)N2CCCc3c(-c4ccc(COC(=O)NCCC(=O)O)nc4)cccc32)c1C]

Step A. (5-Bromopyridin-2-yl)methanol

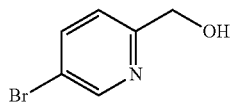

To a solution of NaBH$_4$ (0.822 g, 21.73 mmol) in MeOH (25 mL) was added ethyl 5-bromopicolinate (1.0 g, 4.35 mmol) portion-wise over a period of 10 min at room temperature. The mixture was stirred at room temperature for 10 min and then heated to 70° C. for 30 min. The solvent was removed in vacuo, and the resulting residue was diluted with EtOAc and water. The aqueous phase was adjusted to pH 7 with 1 N aq. HCl, and extracted with EtOAc. The combined organic layer was dried over MgSO$_4$, filtered, and concentrated in vacuo to afford the title compound (0.65 g, 80% yield) as a white solid. LCMS, [M+H]$^+$=187.9.

Step B. (5-Bromopyridin-2-yl)methyl 4-nitrophenyl carbonate

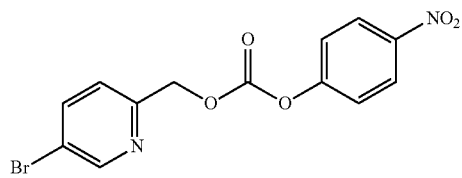 [SMILES: O=C(OCc1ccc(Br)cn1)Oc1ccc([N+](=O)[O-])cc1]

The title compound was prepared using a procedure analogous to 3-bromobenzyl 4-nitrophenyl carbonate except that (3-bromophenyl)methanol was replaced with (5-bromopyridin-2-yl)methanol. LCMS, [M+H]$^+$=352.9.

Step C. Methyl 3-(((5-bromopyridin-2-yl)methoxy)carbonylamino)propanoate

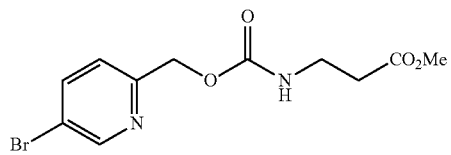 [SMILES: COC(=O)CCNC(=O)OCc1ccc(Br)cn1]

The title compound was prepared using a procedure analogous to methyl 2-((4-(1-(4-(2,3-dimethylphenoxy)butanoyl)-1,2,3,4-tetrahydroquinolin-5-yl)benzyloxy)carbonylamino)acetate except that 4-(1-(4-(2,3-dimethylphenoxy)butanoyl)-1,2,3,4-tetrahydroquinolin-5-yl)benzyl 4-nitrophenyl carbonate was replaced with (5-bromopyridin-2-yl)methyl 4-nitrophenyl carbonate and methyl 2-aminoacetate hydrochloride was replaced with methyl 3-aminopropanoate hydrochloride. LCMS, [M+H]$^+$=317.0.

Example 59

Example 59 was prepared using a procedure analogous to Example 2 except that methyl 4-bromopicolinate was replaced with methyl 3-(((5-bromopyridin-2-yl)methoxy)carbonylamino)propanoate. LCMS, [M+H]$^+$=546.3. $^1$H NMR (400 MHz, MeOD) δ δ 8.74 (s, 1H), 8.47 (br. s, 1H), 8.04 (br. s, 1H), 7.43 (br. s, 1H), 7.37 (t, J=7.8 Hz, 1H), 7.23 (d, J=7.7 Hz, 1H), 7.00 (t, J=7.9 Hz, 1H), 6.72 (d, J=7.5 Hz, 1H), 6.69 (d, J=8.2 Hz, 1H), 5.25 (br. s, 2H), 3.90 (s, 2H), 3.77 (t, J=6.9 Hz, 2H), 3.37 (t, J=6.7 Hz, 2H), 2.84 (t, J=7.0 Hz, 2H), 2.49 (t, J=6.7 Hz, 2H), 2.42 (br. s, 2H), 2.24-2.05 (m, 5H), 1.95-1.73 (m, 5H). HPLC-1: Rt=6.6 min, purity=100%; HPLC-2: Rt=7.1 min, purity=100%.

Example 60

3-(4-(4-(1-(4-(2,3-Dimethylphenoxy)butanoyl)-1,2,3,4-tetrahydroquinolin-5-yl)pyridin-2-yl)piperazin-1-yl)propanoic acid

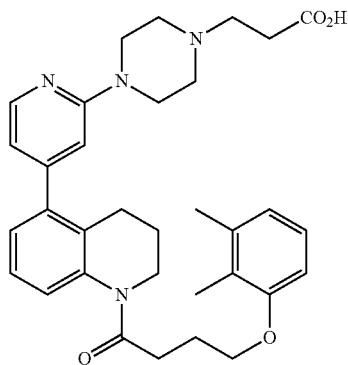 [SMILES: Cc1cccc(OCCCC(=O)N2CCCc3c(-c4ccnc(N5CCN(CCC(=O)O)CC5)c4)cccc32)c1C]

Step A. 4-(2,3-Dimethylphenoxy)-1-(5-(2-(piperazin-1-yl)pyridin-4-yl)-3,4-dihydroquinolin-1(2H)-yl)butan-1-one

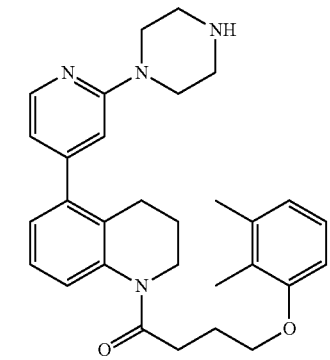 [SMILES: Cc1cccc(OCCCC(=O)N2CCCc3c(-c4ccnc(N5CCNCC5)c4)cccc32)c1C]

The title compound was prepared using a procedure analogous to 4-(2,3-dimethylphenoxy)-1-(5-(4-(hydroxymethyl)phenyl)-3,4-dihydroquinolin-1(2H)-yl)butan-1-one except that 4-(hydroxymethyl)phenylboronic acid was replaced by 1-(4-(4,4,5,5-tetramethyl-1,3,2-dioxaborolan-2-yl)pyridin-2-yl)piperazine. LCMS, [M+H]$^+$=485.3. $^1$H NMR (400 MHz, CDCl$_3$) δ 8.21 (d, J=5.1 Hz, 1H), 7.22-7.28 (m, 2H), 7.07-7.13 (m, 1H), 7.03 (t, J=7.9 Hz, 1H), 6.76 (d, J=7.5 Hz, 1H), 6.67 (d, J=8.1 Hz, 1H), 6.53 (s, 1H), 6.50 (d, J=5.9 Hz, 1H), 3.98 (t, J=5.7 Hz, 2H), 3.80 (t, J=6.9 Hz, 2H), 3.47-3.59 (m, 4H), 2.95-3.04 (m, 4H), 2.77 (t, J=7.3 Hz, 2H), 2.53 (t, J=6.5 Hz, 2H), 2.16-2.27 (m, 5H), 2.00 (br. s, 3H), 1.85 (quin, J=6.7 Hz, 2H).

Example 60

A mixture of 4-(2,3-dimethylphenoxy)-1-(5-(2-(piperazin-1-yl)pyridin-4-yl)-3,4-dihydroquinolin-1(2H)-yl)butan-1-one (9 mg, 0.019 mmol), ethyl 3-bromopropanoate (16.8 mg, 0.093 mmol) and potassium carbonate (12.8 mg, 0.093 mmol) in dioxane (0.5 mL) was heated at 130° C. in a sealed vial for 5 h. After this time, 1 M sodium hydroxide (0.2 mL, 0.200 mmol) and MeOH (0.2 mL) were added and the reaction mixture was stirred at room temperature for 3 h. At the conclusion of this period, the mixture was titrated with 1 N HCl to pH 7 and extracted with EtOAc. The organic layer was dried over anhydrous MgSO$_4$, filtered, and concentrated. The resulting residue was purified by preparative HPLC (Waters XBridge, 5μ, C18, 19×250 mm, 25 min gradient from 85% A:15% B to 0% A:100% B, then 5 min hold at 100% B (A=95% H$_2$O/5% MeCN+0.05% TFA); (B=95% MeCN/5% H$_2$O+0.05% TFA); detection at 220 nm) to afford Example 60 (3 mg, 28% yield). LCMS, [M+H]$^+$=557.2. $^1$H NMR (500 MHz, MeOD) δ 8.37 (d, J=5.1 Hz, 1H), 8.17 (s, 1H), 7.50 (t, J=7.6 Hz, 2H), 7.35 (br. s, 1H), 7.21 (t, J=7.9 Hz, 1H), 6.95 (d, J=7.5 Hz, 1H), 6.91 (s, 1H), 6.87 (d, J=8.1 Hz, 1H), 6.78 (br. s, 1H), 4.15 (br. s, 2H), 4.06 (br. s, 2H), 3.99 (t, J=6.9 Hz, 2H), 3.62 (t, J=6.9 Hz, 2H), 3.59-3.54 (m, 4H), 3.21 (s, 1H), 3.09 (s, 1H), 3.06 (t, J=6.9 Hz, 2H), 3.01 (t, J=7.1 Hz, 2H), 2.68 (br. s, 2H), 2.43-2.34 (m, 5H), 2.12 (s, 3H), 2.07-2.00 (m, 2H).

Example 61

2-(4-((4-(1-(4-(2,3-Dimethylphenoxy)butanoyl)-1,2,3,4-tetrahydroquinolin-5-yl)-1H-pyrazol-1-yl)methyl)pyrimidin-2-ylamino)ethanesulfonic acid, TFA salt

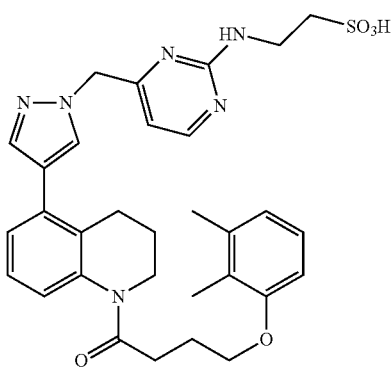 [SMILES: Cc1cccc(OCCCC(=O)N2CCCc3c(-c4cnn(Cc5ccnc(NCCS(=O)(=O)O)n5)c4)cccc32)c1C]

Step A. 2-(Methylthio)-4-((4-(4,4,5,5-tetramethyl-1,3,2-dioxaborolan-2-yl)-1H-pyrazol-1-yl)methyl) pyrimidine

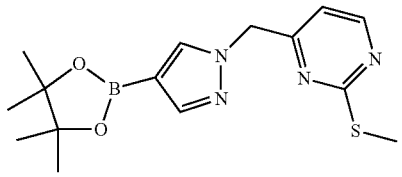

A mixture of 4-(4,4,5,5-tetramethyl-1,3,2-dioxaborolan-2-yl)-1H-pyrazole (0.5 g, 2.58 mmol), potassium carbonate (0.356 g, 2.58 mmol) and 5-(bromomethyl)-2-(methylthio) pyrimidine (30% in THF, 2.070 g, 2.83 mmol) in DMF (5 mL) was stirred at room temperature for 14 h. After this time, the reaction mixture was diluted with EtOAc, washed with saturated sodium bicarbonate, dried over anhydrous MgSO$_4$, filtered, and concentrated. The resulting residue was purified by flash chromatography (0-100% ethyl acetate:hexanes) to afford the title compound (0.6 g, 70% yield) as a light yellow solid. LCMS, [M+H]$^+$=333.2. $^1$H NMR (400 MHz, CDCl$_3$) δ 8.43 (d, J=5.1 Hz, 1H), 7.87 (s, 1H), 7.81 (s, 1H), 6.49 (d, J=5.1 Hz, 1H), 5.36 (s, 2H), 2.56 (s, 3H), 1.33 (s, 12H).

Step B. 4-(2,3-Dimethylphenoxy)-1-(5-(1-((2-(methylthio)pyrimidin-4-yl)methyl)-1H-pyrazol-4-yl)-3,4-dihydroquinolin-1(2H)-yl)butan-1-one

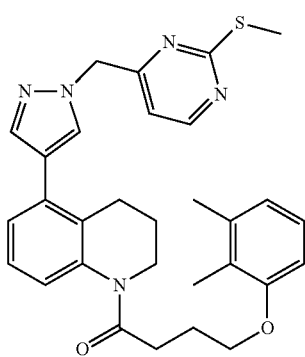

The title compound was prepared using a procedure analogous to 4-(2,3-dimethylphenoxy)-1-(5-(4-(hydroxymethyl) phenyl)-3,4-dihydroquinolin-1(2H)-yl)butan-1-one except that 4-(hydroxymethyl)phenylboronic acid was replaced with 2-(methylthio)-4-((4-(4,4,5,5-tetramethyl-1,3,2-dioxaborolan-2-yl)-1H-pyrazol-1-yl)methyl)pyrimidine. LCMS, [M+H]$^+$=528.4. $^1$H NMR (400 MHz, CDCl$_3$) δ 8.51 (d, J=5.3 Hz, 1H), 7.62 (s, 1H), 7.46 (s, 1H), 7.16-7.25 (m, 3H), 7.02 (t, J=7.8 Hz, 1H), 6.74 (d, J=7.5 Hz, 1H), 6.69 (d, J=5.1 Hz, 1H), 6.65 (d, J=8.4 Hz, 1H), 5.40 (s, 2H), 3.94 (t, J=5.5 Hz, 2H), 3.81 (t, J=6.8 Hz, 2H), 2.79 (t, J=7.2 Hz, 2H), 2.54-2.63 (m, 5H), 2.11-2.26 (m, 5H), 1.82-1.97 (m, 5H).

Step C. 4-(2,3-Dimethylphenoxy)-1-(5-(1-((2-(methylsulfonyl)pyrimidin-4-yl)methyl)-1H-pyrazol-4-yl)-3,4-dihydroquinolin-1(2H)-yl)butan-1-one

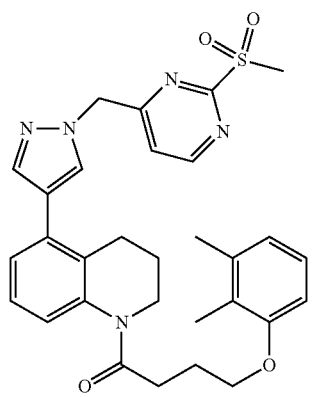 [SMILES: Cc1cccc(OCCCC(=O)N2CCCc3c(-c4cnn(Cc5ccnc(S(C)(=O)=O)n5)c4)cccc32)c1C]

A mixture of 4-(2,3-dimethylphenoxy)-1-(5-(1-((2-(methylthio)pyrimidin-4-yl)methyl)-1H-pyrazol-4-yl)-3,4-dihydroquinolin-1(2H)-yl)butan-1-one (90 mg, 0.17 mmol) and m-CPBA (84 mg, 0.38 mmol) in DCM (3 mL) was stirred at room temperature for 3 h. After this time, the reaction mixture was diluted with DCM, washed with 5% aq. Na$_2$CO$_3$, dried over anhydrous MgSO$_4$, filtered, and concentrated to afford the title compound (93 mg, 97% yield) as a yellow gum. LCMS, [M+H]$^+$=560.3. $^1$H NMR (400 MHz, CDCl$_3$) δ 8.88 (d, J=5.1 Hz, 1H), 7.65 (s, 1H), 7.49 (s, 1H), 7.14-7.25 (m, 4H), 7.02 (t, J=7.8 Hz, 1H), 6.75 (d, J=7.7 Hz, 1H), 6.66 (d, J=8.1 Hz, 1H), 5.60 (s, 2H), 3.95 (t, J=5.3 Hz, 2H), 3.81 (t, J=6.8 Hz, 2H), 3.38 (s, 3H), 2.76 (t, J=7.0 Hz, 2H), 2.61 (t, J=6.2 Hz, 2H), 2.13-2.25 (m, 5H), 1.84-1.99 (m, 5H).

Example 61

A mixture of 4-(2,3-dimethylphenoxy)-1-(5-(1-((2-(methylsulfonyl)pyrimidin-4-yl)methyl)-1H-pyrazol-4-yl)-3,4-dihydroquinolin-1(2H)-yl)butan-1-one (10 mg, 0.018 mmol), 2-aminoethanesulfonic acid (22.36 mg, 0.179 mmol), and TEA (49.8 μl, 0.357 mmol) in DMF (0.3 mL) was heated at 120° C. for 1 h. After this time, the reaction mixture was diluted with CH$_2$Cl$_2$, washed with saturated NaHCO$_3$, dried over anhydrous MgSO$_4$, filtered, and concentrated. The resulting residue was purified by preparative HPLC (PHENOMENEX® Axia Luna column, 5μ, C18, 30×75 mm; 10 min gradient from 100% A: 0% B to 0% A:100% B (A=90% H$_2$O/10% MeOH+0.1% TFA); (B=90% MeOH/10% H$_2$O+

0.1% TFA); detection at 220 nm) to afford Example 61 (3.5 mg, 26% yield). LCMS, [M+H]⁺=605.2. ¹H NMR (400 MHz, CDCl₃) δ 9.02 (br. s, 1H), 8.04 (br. s, 1H), 7.63 (s, 1H), 7.50 (br. s, 1H), 7.12-7.24 (m, 3H), 7.01 (t, J=7.7 Hz, 1H), 6.74 (d, J=7.5 Hz, 1H), 6.64 (d, J=7.9 Hz, 1H), 6.37 (br. s, 1H), 5.43 (br. s, 2H), 3.85-4.06 (m, 4H), 3.79 (t, J=6.5 Hz, 2H), 3.23 (br. s, 2H), 2.77 (t, J=6.9 Hz, 2H), 2.59 (br. s, 2H), 2.11-2.24 (m, 5H), 1.82-2.01 (m, 5H). HPLC-1: Rt=7.6 min, purity=100%; HPLC-2: Rt=7.2 min, purity=100%.

Example 62

3-(4-((4-(1-(4-(2,3-Dimethylphenoxy)butanoyl)-1,2,3,4-tetrahydroquinolin-5-yl)-1H-pyrazol-1-yl)methyl)pyrimidin-2-ylamino)propanoic acid, TFA salt

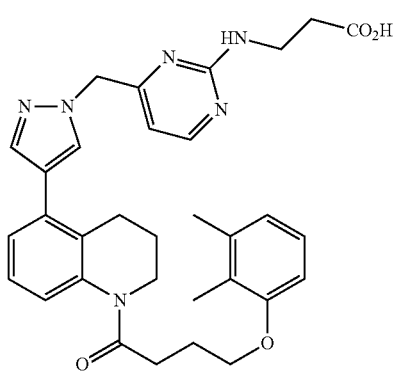 [SMILES: Cc1cccc(OCCCC(=O)N2CCCc3c(-c4cnn(Cc5ccnc(NCCC(=O)O)n5)c4)cccc32)c1C]

A mixture of 4-(2,3-dimethylphenoxy)-1-(5-(1-((2-(methylsulfonyl)pyrimidin-4-yl)methyl)-1H-pyrazol-4-yl)-3,4-dihydroquinolin-1(2H)-yl)butan-1-one (26 mg, 0.047 mmol), tert-butyl 3-aminopropanoate, HCl salt (43.0 mg, 0.237 mmol), and TEA (66.0 nl, 0.474 mmol) in DMF (0.5 mL) was heated at 70° C. for 2 h. The reaction mixture was diluted with EtOAc, washed with saturated NaHCO₃, dried over anhydrous MgSO₄, filtered, and concentrated to provide the crude ester. The crude ester was dissolved in DCM (0.3 mL) and treated with TFA (91 μL, 1.184 mmol). The reaction mixture was stirred at room temperature for 1 h and concentrated. The resulting residue was purified by preparative HPLC (PHENOMENEX® Axia Luna column, 5μ, C18, 30×75 mm; 10 min gradient from 100% A: 0% B to 0% A:100% B (A=90% H₂O/10% MeOH+0.1% TFA); (B=90% MeOH/10% H₂O+ 0.1% TFA); detection at 220 nm) to afford Example 62 (0.7 mg, 2% yield) as a colorless gum. LCMS, [M+H]⁺=569.2. ¹H NMR (400 MHz, CDCl₃) δ 9.74 (br. s, 1H), 8.09 (br. s, 1H), 7.65 (s, 1H), 7.49 (br. s, 1H), 7.13-7.26 (m, 3H), 7.03 (t, J=7.8 Hz, 1H), 6.75 (d, J=7.5 Hz, 1H), 6.66 (d, J=8.1 Hz, 1H), 6.43 (d, J=6.2 Hz, 1H), 5.42 (s, 2H), 3.95 (t, J=5.1 Hz, 2H), 3.81 (t, J=6.7 Hz, 4H), 2.78 (t, J=7.0 Hz, 2H), 2.56-2.72 (m, 4H), 2.15-2.27 (m, 5H), 1.82-2.03 (m, 5H). HPLC-1: Rt=7.9 min, purity=98.8%; HPLC-2: Rt=8.2 min, purity=98.5%.

Example 63

2-(4-(1-(4-(2,3-Dimethylphenoxy)butanoyl)-1,2,3,4-tetrahydroquinolin-5-yl)-1H-pyrazol-1-yl)-2-phenylacetic acid

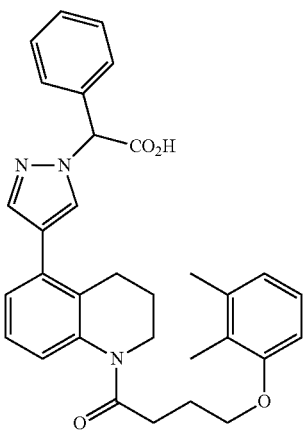 [SMILES: Cc1cccc(OCCCC(=O)N2CCCc3c(-c4cnn(C(C(=O)O)c5ccccc5)c4)cccc32)c1C]

Step A. Ethyl 2-(4-bromo-1H-pyrazol-1-yl)-2-phenylacetate

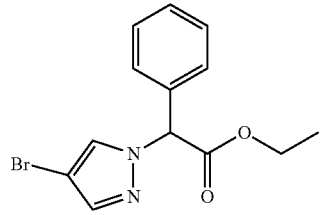 [SMILES: CCOC(=O)C(c1ccccc1)n1cc(Br)cn1]

The title compound was prepared using a procedure analogous to methyl 3-((4-bromo-1H-pyrazol-1-yl)methyl)benzoate except that methyl 3-(bromomethyl)benzoate was replaced with ethyl 2-bromo-2-phenylacetate. LCMS, [M+H]⁺=308.9. ¹H NMR (400 MHz, CDCl₃) δ 7.52 (s, 1H), 7.45-7.36 (m, 6H), 6.14 (s, 1H), 4.34-4.23 (m, 2H), 1.27 (t, J=7.1 Hz, 3H).

Example 63

Example 63 was prepared using a procedure analogous to Example 2 except that methyl 4-bromopicolinate was replaced with ethyl 2-(4-bromo-1H-pyrazol-1-yl)-2-phenylacetate. The ester was hydrolyzed during the Suzuki coupling step. LCMS, [M+H]⁺=524.2. ¹H NMR (400 MHz, CDCl₃) δ 7.65 (s, 1H), 7.41 (s, 5H), 7.33 (d, J=13.2 Hz, 1H), 7.20-7.09 (m, 3H), 7.00 (t, J=7.8 Hz, 1H), 6.70 (d, J=7.5 Hz, 1H), 6.62 (d, J=8.0 Hz, 1H), 6.17 (s, 1H), 5.30 (s, 1H), 3.91 (s, 2H), 3.77 (t, J=6.7 Hz, 2H), 2.74 (t, J=7.1 Hz, 2H), 2.52 (s, 2H), 2.22-2.06 (m, 5H), 1.96-1.74 (m, 5H). HPLC-1: Rt=10.2 min, purity=99%; HPLC-2: Rt=9.2 min, purity=98.6%.

The following Examples were prepared in a manner analogous to Example 63.

TABLE 5

| Example | Name | —X—Y | ◁ present | LCMS, [M + H]⁺ | ¹H NMR (400 MHz, CDCl₃) δ | HPLC-1: Rt min, purity; HPLC-2: Rt min, purity |
|---|---|---|---|---|---|---|
| 64 | 1-(4-(1-(4-(2,3-Dimethylphenoxy)butanoyl)-1,2,3,4-tetrahydroquinolin-5-yl)-1H-pyrazol-1-yl)cyclobutanecarboxylic acid | cyclobutyl-CO₂H | No | 488.2 | 7.60 (s, 1H), 7.50 (s, 1H), 7.21-7.12 (m, 3H), 6.99 (t, J = 7.8 Hz, 1H), 6.72 (d, J = 7.5 Hz, 1H), 6.62 (d, J = 8.2 Hz, 1H), 3.91 (t, J = 5.3 Hz, 2H), 3.77 (t, J = 6.9 Hz, 2H), 3.00 (ddd, J = 13.5, 7.0, 3.7 Hz, 2H), 2.80-2.68 (m, 4H), 2.55 (br. s, 2H), 2.34-2.23 (m, 1H), 2.22-2.02 (m, 6H), 1.94-1.77 (m, 5H) | 9.9 min, 99.5% 8.8 min, 99.6% |
| 65 | 2-(4-(1-(4-(2,3-Dimethylphenoxy)butanoyl)-1,2,3,4-tetrahydroquinolin-5-yl)-1H-pyrazol-1-yl)-2-methylpropanoic acid | C(CH₃)₂-CO₂H | No | 476.2 | 7.60 (s, 1H), 7.52 (s, 1H), 7.22-7.07 (m, 3H), 7.00 (t, J = 7.9 Hz, 1H), 6.73 (d, J = 7.5 Hz, 1H), 6.62 (d, J = 8.2 Hz, 1H), 3.91 (t, J = 5.4 Hz, 2H), 3.77 (t, J = 6.8 Hz, 3H), 2.74 (t, J = 7.1 Hz, 2H), 2.54 (br. s, 2H), 2.24-2.09 (m, 5H), 2.00-1.75 (m, 11H) | 9.7 min, 99.7% 8.7 min, 97.2% |
| 66 | 2-((4-(1-(4-(2,3-Dimethylphenoxy)butanoyl)-1,2,3,4-tetrahydroquinolin-5-yl)-1H-pyrazol-1-yl)methyl)benzoic acid | 2-(CO₂H)benzyl | No | 524.2 | 8.04 (dd, J = 7.8, 1.1 Hz, 1H), 7.55 (s, 1H), 7.51 (td, J = 7.5, 1.3 Hz, 1H), 7.46 (s, 1H), 7.41 (t, J = 7.1 Hz, 1H), 7.24 (s, 1H), 7.21-7.11 (m, 2H), 7.07 (d, J = 7.6 Hz, 1H), 6.99 (t, J = 7.9 Hz, 1H), 6.71 (d, J = 7.5 Hz, 1H), 6.62 (d, J = 8.1 Hz, 1H), 5.69 (s, 2H), 3.91 (br. s, 2H), 3.76 (t, J = 6.8 Hz, 2H), 2.73 (t, J = 7.1 Hz, 2H), 2.57 (br. s, 2H), 2.24-2.07 (m, 5H), 1.95-1.78 (m, 5H) | 11.0 min, 100% 9.5 min, 100% |
| 67 | 1-(4-(1-(4-(2,3-Dimethylphenoxy)butanoyl)-1,2,3,4-tetrahydroquinolin-5-yl)-1H-pyrazol-1-yl)cyclopropanecarboxylic acid | cyclopropyl-CO₂H | No | 474.2 | 7.54 (s, 1H), 7.43 (s, 1H), 7.21-7.08 (m, 3H), 6.99 (t, J = 7.8 Hz, 1H), 6.72 (d, J = 7.5 Hz, 1H), 6.62 (d, J = 8.1 Hz, 1H), 3.91 (br. s, 2H), 3.76 (t, J = 6.8 Hz, 2H), 2.73 (t, J = 7.1 Hz, 2H), 2.55 (br. s, 2H), 2.25-2.08 (m, 5H), 1.97-1.76 (m, 7H), 1.72 (dd, J = 8.1, 4.9 Hz, 2H) | 9.6 min, 99.9% 8.4 min, 99.9% |
| 68 | 3-Chloro-4-((4-(1-(4-(2,3-dimethylphenoxy)butanoyl)-1,2,3,4-tetrahydroquinolin-5-yl)-1H-pyrazol-1-yl)methyl)-5-fluorobenzoic acid | 3-Cl-5-F-4-CH₂-benzoic acid | No | 576.3 | 8.01 (s, 1H), 7.79 (dd, J = 9.1, 1.4 Hz, 1H), 7.58 (s, 1H), 7.43 (s, 1H), 7.13-7.24 (m, 3H), 6.98-7.05 (m, 1H), 6.74 (d, J = 7.7 Hz, 1H), 6.60-6.66 (m, 1H), 5.64 (d, J = 1.32 Hz, 2H), 3.89-3.98 (m, 2H), 3.81 (t, J = 6.8 Hz, 2H), 2.81 (t, J = 7.2 Hz, 2H), 2.55 (br. s, 2H), 2.11-2.23 (m, 5H), 1.82-1.95 (m, 5H) | 11.5 min, 100% 10.4 min, 99.3% |

TABLE 5-continued

| Example | Name | —X—Y | ◁ present | LCMS, [M + H]⁺ | ¹H NMR (400 MHz, CDCl₃) δ | HPLC-1: Rt min, purity; HPLC-2: Rt min, purity |
|---|---|---|---|---|---|---|
| 69 | 3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzoic acid | (Cl, F, CO₂H substituted benzyl) | Yes | 588.3 | 7.99 (s, 1H), 7.78 (dd, J = 9.1, 1.4 Hz, 1H), 7.70 (s, 1H), 7.65 (s, 1H), 7.08-7.21 (m, 2H), 6.90-7.06 (m, 2H), 6.74 (d, J = 7.7 Hz, 1H), 6.64 (d, J = 7.9 Hz, 1H), 5.61 (s, 2H), 5.02 (br. s, 1H), 3.84-4.05 (m, 3H), 2.76 (dd, J = 14.9, 7.6 Hz, 2H), 2.54-2.68 (m, 1H), 2.11-2.31 (m, 5H), 2.07 (d, J = 6.2 Hz, 1H), 1.86-1.97 (m, 3H), 1.71 (d, J = 5.5 Hz, 1H), 0.86-0.99 (m, 1H), 0.60 (br. s, 1H) | 11.9 min, 99.7% 10.7 min, 99.7% |
| 69A | (2S)-2-Amino-5-(3-chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)pentanoic acid | (Cl, F, amide-linked ornithine) | Yes | 702.3 | 7.79 (2 H, s), 7.57-7.64 (2 H, m), 7.18-7.23 (1 H, m), 7.14 (1 H, t, J = 7.8 Hz), 7.03-7.10 (1 H, m), 6.94 (1 H, t, J = 7.8 Hz), 6.66 (2 H, dd, J = 14.6, 7.9 Hz), 5.61 (2 H, d, J = 1.1 Hz), 4.72 (1 H, br. s.), 4.00 (1 H, t, J = 6.4 Hz), 3.92-3.98 (1 H, m), 3.83-3.92 (1 H, m), 3.39-3.52 (2 H, m), 2.96 (1 H, br. s.), 2.65-2.77 (2 H, m), 2.13 (3 H, s), 2.06-2.12 (2 H, m), 1.97-2.06 (2 H, m), 1.90-1.97 (2 H, m), 1.67-1.89 (6 H, m), 0.83-0.91 (1 H, m), 0.50 (1 H, d, J = 3.3 Hz)* | 7.7 min, 96.7% 8.7 min, 98.0% |
| 69B | (3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)methanesulfonic acid | (Cl, F, amide-CH₂-SO₃H) | Yes | 681.2 | 7.92-7.85 (m, 2H), 7.78 (s, 1H), 7.70 (dd, J = 10.0, 1.4 Hz, 1H), 7.61 (s, 1H), 7.21 (d, J = 7.8 Hz, 1H), 7.14 (t, J = 7.8 Hz, 1H), 7.09-7.02 (m, 1H), 6.95 (t, J = 7.9 Hz, 1H), 6.69 (d, J = 7.7 Hz, 2H), 6.65 (d, J = 8.3 Hz, 1H), 5.62 (d, J = 1.2 Hz, 2H), 4.51 (s, 2H), 3.99-3.92 (m, 1H), 3.92-3.83 (m, 1H), 2.76-2.67 (m, 2H), 2.14 (s, 3H), 2.12-2.05 (m, 2H), 2.05-1.96 (m, 1H), 1.92-1.80 (m, 3H), 1.79-1.68 (m, 1H), 0.94-0.84 (m, 1H), 0.54-0.46 (m, 1H)* | N/A 8.4 min, 98.4% |

TABLE 5-continued

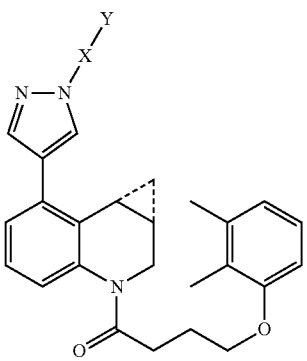

| Example | Name | —X—Y | ◁ present | LCMS, [M + H]+ | 1H NMR (400 MHz, CDCl3) δ | HPLC-1: Rt min, purity; HPLC-2: Rt min, purity |
|---|---|---|---|---|---|---|
| 69C | 2-(3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)ethanesulfonic acid | 3-Cl, 5-F benzamide-NH-CH2CH2-SO3H | Yes | 695.2 | 7.79 (d, J = 9.1 Hz, 2H), 7.65-7.57 (m, 2H), 7.21 (d, J = 7.9 Hz, 1H), 7.14 (t, J = 7.8 Hz, 1H), 7.04 (t, J = 14.9 Hz, 1H), 6.94 (t, J = 7.9 Hz, 1H), 6.67 (d, J = 7.6 Hz, 1H), 6.64 (d, J = 8.2 Hz, 1H), 5.61 (d, J = 1.1 Hz, 2H), 4.87-4.59 (m, 1H), 3.99-3.91 (m, 1H), 3.91-3.82 (m, 1H), 3.80 (t, J = 6.5 Hz, 2H), 3.08 (t, J = 6.5 Hz, 2H), 2.92 (d, J = 63.9 Hz, 1H), 2.71 (m, 2H), 2.13 (s, 3H), 2.12-2.05 (m, 2H), 2.03-1.96 (m, 1H), 1.85 (s, 3H), 1.77-1.69 (m, 1H), 0.88 (m, 1H), 0.54-0.45 (m, 1H)* | N/A 8.3 min, 98.7% |
| 69D | 2-(3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)acetic acid | 3-Cl, 5-F benzamide-NH-CH2-COOH | Yes | 645.2 | 7.83 (s, 1H), 7.78 (s, 1H), 7.65 (dd, J = 9.9, 1.6 Hz, 1H), 7.60 (s, 1H), 7.21 (d, J = 7.9 Hz, 1H), 7.14 (t, J = 7.8 Hz, 1H), 7.11-7.01 (m, 1H), 6.94 (t, J = 7.9 Hz, 1H), 6.68 (d, J = 7.6 Hz, 1H), 6.64 (d, J = 8.3 Hz, 1H), 5.61 (d, J = 1.3 Hz, 2H), 4.10 (s, 2H), 3.99-3.92 (m, 1H), 3.91-3.79 (m, 1H), 3.33 (d, J = 7.0 Hz, 2H), 2.71 (td, J = 7.0, 3.1 Hz, 2H), 2.13 (s, 3H), 2.12-2.04 (m, 2H), 2.04-1.95 (m, 1H), 1.85 (s, 3H), 1.76-1.68 (m, 1H), 0.92-0.82 (m, 1H), 0.54-0.44 (m, 1H)* | 10.7 min, 97.8% 9.9 min, 97.6% |
| 69E | 3-(3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)propanoic acid | 3-Cl, 5-F benzamide-NH-CH2CH2-COOH | Yes | 659.3 | 7.77 (d, J = 5.1 Hz, 2H), 7.63-7.56 (m, 2H), 7.21 (d, J = 8.2 Hz, 1H), 7.14 (t, J = 7.8 Hz, 1H), 7.11-7.01 (m, 1H), 6.94 (t, J = 7.9 Hz, 1H), 6.67 (d, J = 7.7 Hz, 1H), 6.64 (d, J = 8.1 Hz, 1H), 5.60 (d, J = 1.3 Hz, 2H), 4.54-4.49 (m, 1H), 3.94 (s, 1H), 3.91-3.81 (m, 1H), 3.63 (t, J = 6.8 Hz, 2H), 3.33 (dd, J = 4.2, 2.5 Hz, 2H), 2.71 (td, J = 7.0, 3.1 Hz, 2H), 2.63 (t, J = 6.9 Hz, 2H), 2.13 (s, 3H), 2.12-2.05 (m, 2H), 2.05-1.95 (m, 1H), 1.94-1.77 (m, 3H), 1.77-1.67 (m, 1H), 0.93-0.81 (m, 1H), 0.56-0.43 (m, 1H)* | 10.7 min, 97.4% 9.9 min, 96.9% |

TABLE 5-continued

| Example | Name | —X—Y | ◁ present | LCMS, [M + H]+ | 1H NMR (400 MHz, CDCl3) δ | HPLC-1: Rt min, purity; HPLC-2: Rt min, purity |
|---|---|---|---|---|---|---|
| 69F | (2S)-5-(3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)-2-guanidinopentanoic acid | | Yes | 744.3 | 7.79 (2 H, s), 7.58-7.64 (2 H, m), 7.18-7.24 (1 H, m), 7.14 (1 H, t, J = 7.77 Hz), 7.06 (1 H, d, J = 7.21 Hz), 6.94 (1 H, t, J = 7.91 Hz), 6.66 (2 H, dd, J = 14.43, 7.77 Hz), 5.61 (2 H, d, J = 1.11 Hz), 4.73 (1 H, br. s.), 4.31 (1 H, dd, J = 7.35, 5.41 Hz), 3.92-3.99 (1 H, m), 3.81-3.92 (1 H, m), 3.36-3.51 (2 H, m), 2.95 (1 H, br. s.), 2.64-2.78 (2 H, m), 2.13 (3 H, s), 1.95-2.12 (5 H, m), 1.79-1.92 (4 H, m), 1.68-1.80 (3 H, m), 0.84-0.92 (1 H, m), 0.50 (1 H, br. s.) | 7.7 min, 100% 9.0 min, 99% |
| 69G | 1-(7-(1-(3-Aminobenzyl)-1H-pyrazol-4-yl)-1a,2-dihydro-1H-cyclopropa[c]quinolin-3(7bH)-yl)-4-(2,3-dimethylphenoxy)butan-1-one | | Yes | 507.3 | 7.68 (s, 1H), 7.50 (s, 1H), 7.19-7.12 (m, 2H), 7.09 (t, J = 7.8 Hz, 1H), 6.99 (t, J = 7.9 Hz, 1H), 6.97-6.88 (m, 1H), 6.73 (d, J = 7.4 Hz, 1H), 6.69-6.60 (m, 3H), 6.60-6.55 (m, 1H), 5.26 (s, 2H), 4.03-3.94 (m, 1H), 3.94-3.82 (m, 1H), 3.78-3.59 (m, 2H), 2.84-2.65 (m, 2H), 2.65-2.48 (m, 1H), 2.20 (s, 3H), 2.18-2.06 (m, 4H), 1.93 (s, 3H), 1.76-1.62 (m, 1H), 0.99-0.81 (m, 1H), 0.66-0.47 (m, 1H) | 9.6 min, 99.3% 10.3 min, 93.0% |
| 69H | 4-Chloro-3-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)benzoic acid | | Yes | 570.2 | 8.07 (d, J = 1.6 Hz, 1H), 8.04 (dd, J = 8.3, 2.0 Hz, 1H), 7.83 (s, 1H), 7.69 (s, 1H), 7.54 (d, J = 8.3 Hz, 1H), 7.21 (d, J = 7.3 Hz, 1H), 7.15 (t, J = 7.7 Hz, 1H), 7.06-6.92 (m, 2H), 6.73 (d, J = 7.4 Hz, 1H), 6.62 (d, J = 7.9 Hz, 1H), 5.59 (s, 2H), 4.06-3.91 (m, 2H), 3.91-3.78 (m, 1H), 2.88-2.73 (m, 1H), 2.73-2.58 (m, 1H), 2.18 (s, 5H), 2.14-1.97 (m, 2H), 1.88 (s, 3H), 1.81-1.63 (m, 1H), 1.10-0.88 (m, 2H), 0.68-0.47 (m, 1H) | 10.7 min, 99.1% 10.8 min, 100% |

TABLE 5-continued

| Example | Name | —X—Y | ◁ present | LCMS, [M+H]+ | 1H NMR (400 MHz, CDCl3) δ | HPLC-1: Rt min, purity; HPLC-2: Rt min, purity |
|---|---|---|---|---|---|---|
| 69J | 2-(3-((1-((4-(1-(4-(2,3-Dimethylphenoxy)butanoyl)-1,2,3,4-tetrahydroquinolin-5-yl)-1H-pyrazol-1-yl)methyl)cyclopropyl)methyl)ureido)ethanesulfonic acid | | No | 624.4 | 8.17 (s, 1H), 7.97 (s, 1H), 7.42-7.19 (m, 3H), 6.99 (t, J = 7.9 Hz, 1H), 6.71 (d, J = 7.6 Hz, 1H), 6.68 (d, J = 8.2 Hz, 1H), 4.33 (s, 2H), 3.97-3.84 (m, 2H), 3.78 (t, J = 6.7 Hz, 2H), 3.64 (t, J = 6.2 Hz, 2H), 3.08 (s, 2H), 3.00 (t, J = 6.2 Hz, 2H), 2.81 (t, J = 7.0 Hz, 2H), 2.66-2.51 (m, 2H), 2.12 (s, 5H), 1.96-1.71 (m, 5H), 0.80 (t, J = 5.4 Hz, 2H), 0.67 (t, J = 5.4 Hz, 2H)* | N/A 8.8 min, 99.6% |
| 69K | 2-(3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)-N,N,N-trimethylethanaminium, TFA | | Yes | 675.3 | 1H NMR (400 MHz, MeOD) δ 7.90-7.78 (m, 2H), 7.65 (dd, J = 9.8, 1.5 Hz, 1H), 7.58 (s, 1H), 7.28-7.20 (m, 1H), 7.16 (t, J = 7.7 Hz, 1H), 7.12-7.01 (m, 1H), 6.95 (t, J = 8.3 Hz, 1H), 6.73-6.59 (m, 2H), 5.62 (s, 2H), 4.00-3.89 (m, 1H), 3.84 (s, 3H), 3.57 (t, J = 6.7 Hz, 2H), 3.36-3.33 (m, 1H), 3.22 (s, 9H), 2.73 (s, 3H), 2.18-2.02 (m, 6H), 1.73 (s, 4H), 0.90-0.74 (m, 1H), 0.50-0.37 (m, 1H) | 7.7 min, 98.6% 9.1 min, 98.5% |
| 69L | 2-(4-Chloro-3-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)benzamido)ethanesulfonic acid | | Yes | 677.2 | 7.89 (s, 1H), 7.77 (dd, J = 8.3, 2.1 Hz, 1H), 7.72 (s, 1H), 7.66 (s, 1H), 7.56 (d, J = 8.3 Hz, 1H), 7.36-7.24 (m, 1H), 7.17 (t, J = 7.7 Hz, 1H), 7.07 (d, J = 7.3 Hz, 1H), 6.95 (t, J = 8.0 Hz, 1H), 6.78-6.55 (m, 2H), 5.59 (s, 2H), 4.01-3.86 (m, 1H), 3.86-3.70 (m, 3H), 3.06 (t, J = 6.6 Hz, 2H), 2.82-2.66 (m, 3H), 2.10 (s, 6H), 1.77 (s, 3H), 1.38-1.26 (m, 2H), 0.94-0.79 (m, 1H), 0.44 (s, 1H)* | 13.1 min, 95.9% 13.7 min, 98.2% |
| 69M | 2-(3-((4-(1-(4-(2,3-Dimethylphenoxy)butanoyl)-1,2,3,4-tetrahydroquinolin-5-yl)-1H-pyrazol-1-yl)methyl)phenoxy)ethylphosphonic acid | | No | 604.3 | 7.57 (s, 1H), 7.47 (s, 1H), 7.28 (t, J = 7.9 Hz, 1H), 7.26-7.19 (m, 2H), 7.19-7.06 (m, 1H), 6.96 (t, J = 7.9 Hz, 1H), 6.93-6.82 (m, 3H), 6.71-6.57 (m, 2H), 5.33 (s, 2H), 4.23 (dt, J = 10.7, 7.6 Hz, 2H), 3.93-3.78 (m, 2H), 3.73 (t, J = 6.8 Hz, 2H), 2.80 (t, J = 6.8 Hz, 2H), 2.55-2.37 (m, 2H), 2.25 (t, J = 7.5 Hz, 1H), 2.21 (t, J = 7.5 Hz, 1H), 2.17-2.07 (m, 2H), 2.03 (s, 3H), 1.85-1.77 (m, 2H), 1.77-1.61 (m, 3H)* | 9.8 min, 99.1% 9.3 min, 99.2% |

TABLE 5-continued

| Example | Name | —X—Y | ⊲ present | LCMS, [M + H]+ | 1H NMR (400 MHz, CDCl3) δ | HPLC-1: Rt min, purity; HPLC-2: Rt min, purity |
|---|---|---|---|---|---|---|
| 69N | (3-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)methanesulfonic acid | | Yes | 644.1 | 7.79 (s, 1H), 7.63 (s, 1H), 7.37 (s, 1H), 7.32 (d, J = 7.3 Hz, 1H), 7.29-7.20 (m, 2H), 7.15 (t, J = 7.7 Hz, 1H), 7.05 (m, 1H), 6.95 (t, J = 7.7 Hz, 1H), 6.89 (d, J = 7.3 Hz, 1H), 6.76-6.56 (m, 2H), 5.34 (s, 2H), 4.30 (s, 2H), 4.03-3.88 (m, 1H), 3.88-3.74 (m, 1H), 3.00 (q, J = 7.2 Hz, 4H), 2.73 (s, 2H), 2.10 (m, 7H), 1.86-1.67 (m, 4H), 1.29 (d, J = 7.2 Hz, 6H), 0.97-0.79 (m, 4H)* | 10.1 min, 100% 10.4 min, 100% |
| 69P | (3-(3-((4-((1aS,7bR)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)methanesulfonic acid | | Yes | 644.1 | 7.79 (s, 1H), 7.63 (s, 1H), 7.37 (s, 1H), 7.32 (d, J = 7.3 Hz, 1H), 7.29-7.20 (m, 2H), 7.15 (t, J = 7.7 Hz, 1H), 7.05 (m, 1H), 6.95 (t, J = 7.7 Hz, 1H), 6.89 (d, J = 7.3 Hz, 1H), 6.76-6.56 (m, 2H), 5.34 (s, 2H), 4.30 (s, 2H), 4.03-3.88 (m, 1H), 3.88-3.74 (m, 1H), 3.00 (q, J = 7.2 Hz, 4H), 2.73 (s, 2H), 2.10 (m, 7H), 1.86-1.67 (m, 4H), 1.29 (d, J = 7.2 Hz, 6H), 0.97-0.79 (m, 4H)* | 10.1 min, 98.1% 10.4 min, 100% |
| 69Q | 4-(N-(3-((4-(1-(4-(2,3-Dimethylphenoxy)butanoyl)-1,2,3,4-tetrahydroquinolin-5-yl)-1H-pyrazol-1-yl)methyl)phenyl)sulfamoylamino)butanoic acid | | No | 660.3 | 7.60 (s, 1H), 7.49 (s, 1H), 7.30 (t, J = 8.0 Hz, 1H), 7.27-7.18 (m, 2H), 7.15 (d, J = 7.5 Hz, 3H), 6.97 (t, J = 7.9 Hz, 2H), 6.67 (t, J = 8.2 Hz, 2H), 5.35 (s, 2H), 3.94-3.82 (m, 2H), 3.74 (t, J = 6.8 Hz, 2H), 2.97 (t, J = 6.8 Hz, 2H), 2.81 (t, J = 6.8 Hz, 2H), 2.57-2.44 (m, 2H), 2.22 (t, J = 7.3 Hz, 2H), 2.12 (dt, J = 12.6, 6.4 Hz, 2H), 2.05 (s, 3H), 1.87-1.63 (m, 7H)* | 9.0 min, 88.6% 9.0 min, 89.0% |
| 69S | 3-(N-(3-((4-(1-(4-(2,3-Dimethylphenoxy)butanoyl)-1,2,3,4-tetrahydroquinolin-5-yl)-1H-pyrazol-1-yl)methyl)phenyl)sulfamoylamino)propanoic acid | | No | 646.3 | 7.60 (s, 1H), 7.49 (s, 1H), 7.35-7.27 (m, 1H), 7.28-7.19 (m, 2H), 7.19-7.10 (m, 3H), 6.97 (t, J = 7.7 Hz, 2H), 6.67 (t, J = 7.9 Hz, 2H), 5.35 (s, 2H), 3.94-3.80 (m, 2H), 3.74 (t, J = 6.8 Hz, 2H), 3.19 (t, J = 7.0 Hz, 2H), 2.81 (t, J = 6.9 Hz, 2H), 2.55-2.47 (m, 2H), 2.45 (t, J = 7.0 Hz, 2H), 2.18-2.09 (m, 2H), 2.05 (s, 3H), 1.88-1.64 (m, 5H)* | 8.9 min, 93.2% 8.5 min, 92.5% |

TABLE 5-continued

| Example | Name | —X—Y | ◁ present | LCMS, [M + H]+ | 1H NMR (400 MHz, CDCl3) δ | HPLC-1: Rt min, purity; HPLC-2: Rt min, purity |
|---|---|---|---|---|---|---|
| 69T | 2-(3-(3-Chloro-4-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorophenyl)ureido)acetic acid | | No | 660.3 | 9.13 (s, 1H), 7.87 (s, 1H), 7.61 (s, 1H), 7.40 (s, 1H), 7.35 (dd, J = 12.2, 1.9 Hz, 1H), 7.21-7.17 (m, 1H), 7.16-7.07 (m, 2H), 6.97 (t, J = 7.8 Hz, 1H), 6.70 (d, J = 7.8 Hz, 2H), 6.51 (t, J = 5.8 Hz, 1H), 5.41 (s, 2H), 4.65 (br. s., 1H), 4.00-3.91 (m, 1H), 3.87 (br. s., 1H), 3.81 (d, J = 5.8 Hz, 2H), 2.90-2.63 (m, 3H), 2.14 (s, 3H), 2.09-1.91 (m, 4H), 1.88 (s, 3H), 1.80-1.72 (m, 1H), 0.96-0.85 (m, 1H), 0.45 (d, J = 4.4 Hz, 1H)** | 10.9 min, 96.6% 10.0 min, 97.5% |

*1H NMR (400 MHz, CD3OD) δ.
**1H NMR (500 MHz, DMSO-d6) δ.

Example 70

2-(3-(1-(4-(2,3-Dimethylphenoxy)butanoyl)-1,2,3,4-tetrahydroquinolin-5-yl)benzylcarbamoyloxy)acetic acid

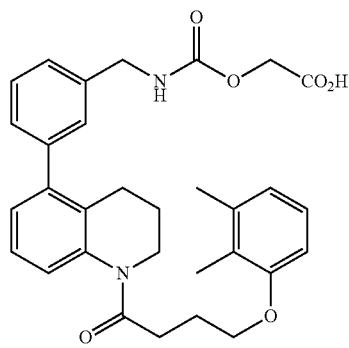

Step A. tert-Butyl 3-(1-(4-(2,3-dimethylphenoxy)butanoyl)-1,2,3,4-tetrahydroquinolin-5-yl)benzylcarbamate

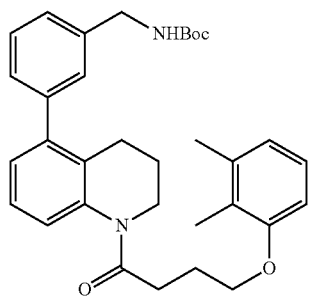 [SMILES: Cc1cccc(OCCCC(=O)N2CCCc3c(-c4cccc(CN)c4)cccc32)c1C]

The title compound was prepared using a procedure analogous to 4-(2,3-dimethylphenoxy)-1-(5-(4-(hydroxymethyl)phenyl)-3,4-dihydroquinolin-1(2H)-yl)butan-1-one except that 4-(hydroxymethyl)phenylboronic acid was replaced with tert-butyl 3-(4,4,5,5-tetramethyl-1,3,2-dioxaborolan-2-yl)benzylcarbamate. LCMS, [M+Na]⁺=551.4.

Step B. 1-(5-(3-(Aminomethyl)phenyl)-3,4-dihydroquinolin-1(2H)-yl)-4-(2,3-dimethylphenoxy)butan-1-one

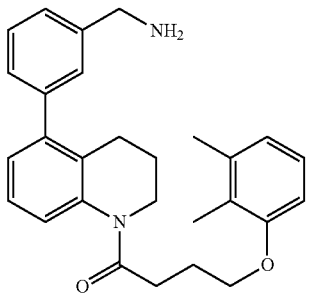

To a solution of tert-butyl 3-(1-(4-(2,3-dimethylphenoxy)butanoyl)-1,2,3,4-tetrahydroquinolin-5-yl)benzylcarbamate (0.12 g, 0.227 mmol) in DCM (2.5 mL) at 0° C. was added TFA (0.35 mL, 4.54 mmol) dropwise. The reaction mixture was slowly warmed to room temperature and stirred for 16 h. After this time, the reaction mixture was quenched with 50% saturated NaHCO₃, and the aqueous phase was extracted with DCM. The combined organic layer was dried over anhydrous MgSO₄, filtered, and concentrated in vacuo to afford the title compound (0.075 g, 77% yield). LCMS, [M+H]⁺=429.2.

Step C. Ethyl 2-((4-nitrophenoxy)carbonyloxy)acetate

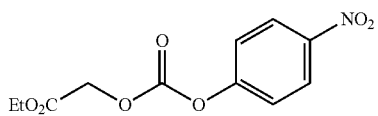

The title compound was prepared using a procedure analogous to 3-bromobenzyl 4-nitrophenyl carbonate except that (3-bromophenyl)methanol was replaced with ethyl 2-hydroxyacetate. LCMS, [M+Na]⁺=292.0. ¹H NMR (400 MHz, CDCl₃) δ 8.24 (d, J=9.2 Hz, 2H), 7.37 (d, J=9.2 Hz, 2H), 4.72 (s, 2H), 4.25 (q, J=7.2 Hz, 2H), 1.28 (t, J=7.1 Hz, 3H).

Example 70

Example 70 was prepared using a procedure analogous to Example 35 except that 4-(1-(4-(2,3-dimethylphenoxy)butanoyl)-1,2,3,4-tetrahydroquinolin-5-yl)benzyl 4-nitrophenyl carbonate was replaced by ethyl 2-((4-nitrophenoxy)carbonyloxy)acetate, and methyl-2-aminoacetate was replaced with 1-(5-(3-(aminomethyl)phenyl)-3,4-dihydroquinolin-1(2H)-yl)-4-(2,3-dimethylphenoxy)butan-1-one. LCMS, [M+H]⁺=531.2. ¹H NMR (400 MHz, CDCl₃) δ 7.36 (t, J=7.6 Hz, 1H), 7.24 (dd, J=24.5, 7.3 Hz, 3H), 7.17 (s, 1H), 7.13 (t, J=6.9 Hz, 2H), 7.00 (t, J=7.9 Hz, 1H), 6.74 (d, J=7.5 Hz, 1H), 6.64 (d, J=8.1 Hz, 1H), 4.65 (s, 2H), 4.43 (d, J=6.1 Hz, 2H), 3.93 (br. s, 2H), 3.79 (t, J=7.0 Hz, 2H), 2.79 (t, J=7.3 Hz, 2H), 2.48 (t, J=6.2 Hz, 2H), 2.23-2.12 (m, 5H), 1.93 (s, 3H), 1.79 (dt, J=13.3, 6.7 Hz, 2H). HPLC-1: Rt=10.5 min, purity=99.6%; HPLC-2: Rt=9.4 min, purity=99.9%.

Example 71

3-((3-(1-(4-(2,3-Dimethylphenoxy)butanoyl)-1,2,3,4-tetrahydroquinolin-5-yl)benzylcarbamoyloxy)methyl)benzoic acid

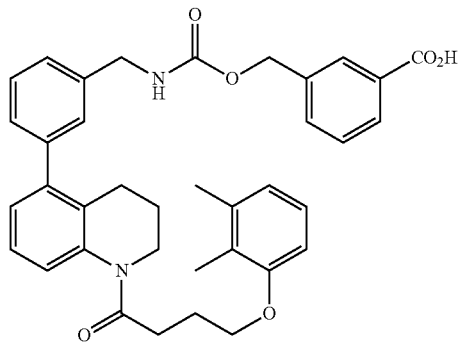 [SMILES: Cc1cccc(OCCCC(=O)N2CCCc3c(-c4cccc(CNC(=O)OCc5cccc(C(=O)O)c5)c4)cccc32)c1C]

Step A. Methyl 3-(hydroxymethyl)benzoate

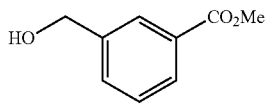 [SMILES: COC(=O)c1cccc(CO)c1]

To a solution of 3-(methoxycarbonyl)benzoic acid (0.200 g, 1.11 mmol) in THF (6.0 mL) at 0° C. was added borane tetrahydrofuran complex (5.55 mL, 5.55 mmol) slowly. The reaction mixture was slowly warmed to room temperature and stirred at for 3 h. After this time, the reaction mixture was diluted with EtOAc and quenched very slowly with water. The organic layer was separated, washed with water and brine, dried over anhydrous MgSO₄, filtered, and concentrated to afford the title compound (0.16 g, 84% yield) as a colorless oil. LCMS, [M+H]⁺=167.0.

Example 71

Example 71 was prepared using a procedure analogous to Example 70 except that ethyl 2-hydroxyacetate was replaced with methyl 3-(hydroxymethyl)benzoate. LCMS, [M+H]$^+$=607.3. $^1$H NMR (400 MHz, MeOD) δ 8.10 (s, 1H), 8.00 (d, J=7.3 Hz, 1H), 7.63 (d, J=7.0 Hz, 1H), 7.47 (t, J=7.6 Hz, 1H), 7.39 (t, J=7.5 Hz, 1H), 7.36-7.25 (d, J=8.1 Hz, 3H), 7.19 (br. s, 2H), 7.10-6.99 (m, 2H), 6.77 (d, J=7.5 Hz, 1H), 6.73 (d, J=8.1 Hz, 1H), 5.21 (s, 2H), 4.40 (s, 2H), 3.96 (br. s, 2H), 3.80 (t, J=6.9 Hz, 2H), 2.44 (br. s, 2H), 2.27-2.12 (m, 5H), 1.91 (s, 3H), 1.86-1.73 (m, 2H). HPLC-1: Rt=5.2 min, purity=100%; HPLC-2: Rt=5.4 min, purity=100%.

Example 72

3-(N-(3-(1-(4-(2,3-Dimethylphenoxy)butanoyl)-1,2,3,4-tetrahydroquinolin-5-yl)benzyl)sulfamoyl)propanoic acid

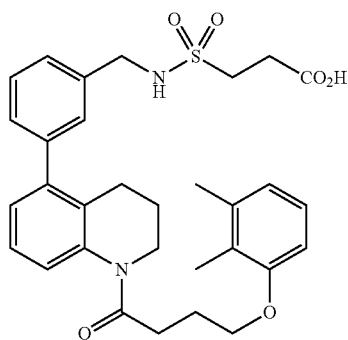 [SMILES: Cc1cccc(OCCCC(=O)N2CCCc3c(-c4cccc(CNS(=O)(=O)CCC(=O)O)c4)cccc32)c1C]

To a solution of 1-(5-(3-(aminomethyl)phenyl)-3,4-dihydroquinolin-1(2H)-yl)-4-(2,3-dimethylphenoxy)butan-1-one (0.025 g, 0.058 mmol) and TEA (0.024 mL, 0.175 mmol) in DCM (0.6 mL) was added methyl 3-(chlorosulfonyl)propanoate (0.016 g, 0.088 mmol). The reaction mixture was stirred at room temperature for 5 h and concentrated in vacuo. The resulting residue was dissolved in 1 mL of THF, added 4 M LiOH (0.102 mL, 0.408 mmol), and stirred at room temperature for 16 h. After this time, the mixture was adjusted to pH 5-6 with 1 N aq. HCl, and then extracted with EtOAc. The combined organic layer was dried over anhydrous MgSO$_4$, filtered, and concentrated in vacuo. The resulting residue was purified by preparative HPLC (PHENOMENEX® Axia Luna column, 5μ, C18, 30×75 mm; 10 min gradient from 75% A:25% B to 0% A:100% B (A=90% H$_2$O/10% MeCN+0.1% TFA); (B=90% MeCN/10% H$_2$O+0.1% TFA); detection at 220 nm) to afford Example 72 (27.5 mg, 79% yield) as a white solid. LCMS, [M+H]$^+$=565.3. $^1$H NMR (400 MHz, CDCl$_3$) δ 7.38 (t, J=7.6 Hz, 1H), 7.30 (d, J=7.7 Hz, 1H), 7.21 (d, J=7.7 Hz, 2H), 7.18 (s, 1H), 7.14 (d, J=7.4 Hz, 1H), 7.10 (d, J=7.0 Hz, 1H), 7.01 (t, J=7.9 Hz, 1H), 6.74 (d, J=7.5 Hz, 1H), 6.64 (d, J=8.1 Hz, 1H), 4.72 (t, J=5.8 Hz, 1H), 4.33 (d, J=5.8 Hz, 2H), 3.94 (br. s, 2H), 3.78 (t, J=7.0 Hz, 2H), 3.28 (t, J=7.3 Hz, 2H), 2.86-2.75 (m, 4H), 2.49-2.40 (m, 2H), 2.24-2.12 (m, 5H), 1.94 (s, 3H), 1.81 (dt, J=13.4, 6.6 Hz, 2H). HPLC-1: Rt=10.4 min, purity=93.2%; HPLC-2: Rt=9.4 min, purity=98.8%.

Example 73

3-(3-(1-(4-(2,3-Dimethylphenoxy)butanoyl)-1,2,3,4-tetrahydroquinolin-5-yl)benzylamino)-3-oxopropanoic acid

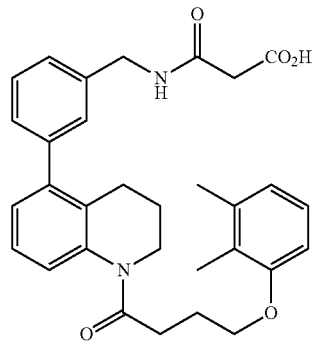 [SMILES: Cc1cccc(OCCCC(=O)N2CCCc3c(-c4cccc(CNC(=O)CC(=O)O)c4)cccc32)c1C]

To a solution of 1-(5-(3-(aminomethyl)phenyl)-3,4-dihydroquinolin-1(2H)-yl)-4-(2,3-dimethylphenoxy)butan-1-one (0.040 g, 0.093 mmol), 3-methoxy-3-oxopropanoic acid (0.017 g, 0.140 mmol) and DIPEA (0.082 mL, 0.467 mmol) in ethyl acetate (1 mL) was added T3P (50% w/w in EtOAc, 0.069 mL, 0.117 mmol). The reaction mixture was stirred at room temperature for 16 h and concentrated in vacuo. The resulting residue was dissolved in THF (1 mL), added 4 N NaOH (0.093 mL, 0.373 mmol), and stirred at 65° C. for 24 h. After this time, the mixture was adjusted to pH 5-6 with 1 N aq. HCl, and extracted with EtOAc. The combined organic layer was dried over anhydrous MgSO$_4$, filtered, and concentrated in vacuo to provide a residue. The residue was purified by preparative HPLC (PHENOMENEX® Axia Luna column, 5μ, C18, 30×75 mm; 10 min gradient from 75% A:25% B to 0% A:100% B (A=90% H$_2$O/10% MeCN+0.1% TFA); (B=90% MeCN/10% H$_2$O+0.1% TFA); detection at 220 nm) to afford Example 73 (0.035 g, 71% yield). LCMS, [M+H]$^+$=515.3. $^1$H NMR (400 MHz, CDCl$_3$) δ 7.37 (t, J=7.8 Hz, 1H), 7.29-7.18 (m, 2H), 7.12 (br. s, 3H), 7.00 (t, J=7.9 Hz, 2H), 6.74 (d, J=7.5 Hz, 1H), 6.63 (d, J=8.2 Hz, 1H), 4.52 (d, J=5.6 Hz, 2H), 3.93 (br. s, 2H), 3.77 (t, J=6.9 Hz, 2H), 3.35 (s, 2H), 2.78 (t, J=7.3 Hz, 2H), 2.45 (br. s, 2H), 2.24-2.11 (m, 5H), 1.92 (s, 3H), 1.85-1.73 (m, 2H). HPLC-1: Rt=10.2 min, purity=99.5%; HPLC-2: Rt=9.1 min, purity=99.7%.

Example 74

2-(3-(3-(1-(4-(2,3-Dimethylphenoxy)butanoyl)-1,2,3,4-tetrahydroquinolin-5-yl)benzyl)ureido)acetic acid

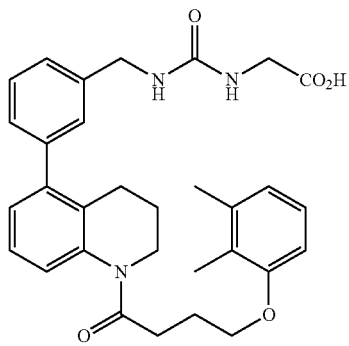 [SMILES: Cc1cccc(OCCCC(=O)N2CCCc3c(-c4cccc(CNC(=O)NCC(=O)O)c4)cccc32)c1C]

Step A. Methyl 2-((4-nitrophenoxy)carbonylamino)acetate

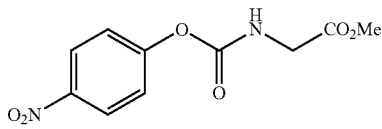 [SMILES: COC(=O)CNC(=O)Oc1ccc([N+](=O)[O-])cc1]

To a solution of methyl 2-aminoacetate hydrochloride (0.137 g, 1.09 mmol) and DIPEA (0.52 mL, 2.98 mmol) in DCM (5 mL) at 0° C. was added a solution of 4-nitrophenyl carbonochloridate (0.20 g, 0.992 mmol) in DCM (2 mL) dropwise. The reaction mixture was slowly warmed to room temperature and stirred for 16 h. After this time, the reaction was quenched with water, and the organic layer was separated. The aqueous phase was extracted with DCM, and the combined organic layers were dried over anhydrous MgSO$_4$, filtered, and concentrated in vacuo to provide the crude material. The crude material was purified by flash chromatography (0-50% ethyl acetate:hexanes) to afford the title compound (0.213 g, 84% yield) as a white solid. LCMS, [M+Na]$^+$= 277.1. $^1$H NMR (400 MHz, CDCl$_3$) δ 8.24 (d, J=9.1 Hz, 2H), 7.32 (d, J=9.1 Hz, 2H), 5.62 (br. s, 1H), 4.07 (d, J=5.5 Hz, 2H), 3.80 (s, 3H).

Example 74

A solution of 1-(5-(3-(aminomethyl)phenyl)-3,4-dihydroquinolin-1(2H)-yl)-4-(2,3-dimethylphenoxy)butan-1-one (0.030 g, 0.070 mmol), methyl 2-((4-nitrophenoxy)carbonylamino)acetate (0.022 g, 0.088 mmol) and DIPEA (0.037 mL, 0.210 mmol) in DCM (1 mL) was stirred at room temperature for 11 d. After this time, the reaction mixture was quenched with water and the organic layer was separated. The aqueous layer was extracted with DMC, and the combined organic layers were dried over anhydrous MgSO$_4$, filtered, and concentrated in vacuo. The resulting residue was dissolved in THF (1 mL)/MeOH (0.05 mL) and then 4 N aq. LiOH (0.3 mL) was added. The resulting mixture was stirred at 65° C. for 16 h. At the conclusion of this period, the mixture was diluted in EtOAc, and adjusted to pH 6-7 with 1 N HCl. The organic layer was separated, washed with water and brine, dried over anhydrous MgSO$_4$, filtered, and concentrated in vacuo. The resulting residue was purified by preparative HPLC (PHENOMENEX® Axia Luna column, 5μ, C18, 30×75 mm; 10 min gradient from 75% A:25% B to 0% A:100% B (A=90% H$_2$O/10% MeCN+0.1% TFA); (B=90% MeCN/10% H$_2$O+0.1% TFA); detection at 220 nm) to afford Example 74 (5.4 mg, 14% yield) as a white solid. LCMS, [M+H]$^+$=530.3. $^1$H NMR (400 MHz, CDCl$_3$) δ 7.34 (t, J=7.5 Hz, 1H), 7.30-7.15 (m, 3H), 7.16-7.05 (m, 3H), 7.04-6.95 (m, 1H), 6.74 (d, J=7.5 Hz, 1H), 6.62 (d, J=8.2 Hz, 1H), 4.37 (s, 2H), 3.95-3.84 (m, 4H), 3.80-3.68 (m, 2H), 2.74 (t, J=7.3 Hz, 2H), 2.45 (br. s, 2H), 2.19 (s, 3H), 2.12 (dt, J=12.9, 6.5 Hz, 2H), 1.94 (s, 3H), 1.83-1.68 (m, 2H). HPLC-1: Rt=9.5 min, purity=98.3%; HPLC-2: Rt=8.6 min, purity=97.6%.

Example 75

2-(3-(3-((4-(1-(4-(2,3-Dimethylphenoxy)butanoyl)-1,2,3,4-tetrahydroquinolin-5-yl)-1H-pyrazol-1-yl)methyl)benzyl)ureido)acetic acid

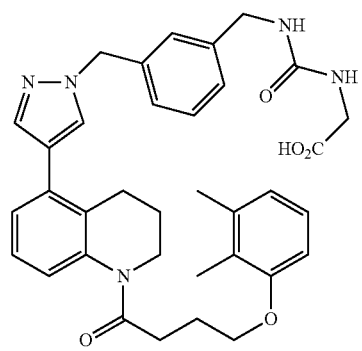 [SMILES: Cc1cccc(OCCCC(=O)N2CCCc3c(-c4cnn(Cc5cccc(CNC(=O)NCC(=O)O)c5)c4)cccc32)c1C]

Step A.
3-((4-Bromo-1H-pyrazol-1-yl)methyl)benzoic acid

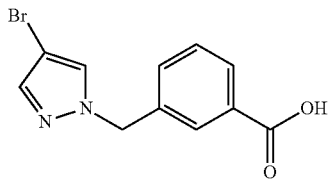 [SMILES: O=C(O)c1cccc(Cn2cc(Br)cn2)c1]

The title compound was prepared using a procedure analogous to Example 2 except that methyl 4-(1-(4-(2,3-dimethylphenoxy)butanoyl)-1,2,3,4-tetrahydroquinolin-5-yl)picolinate was replaced by methyl 3-((4-bromo-1H-pyrazol-1-yl)methyl)benzoate. LCMS, [M+H]$^+$=281.0.

Step B.
3-((4-Bromo-1H-pyrazol-1-yl)methyl)benzamide

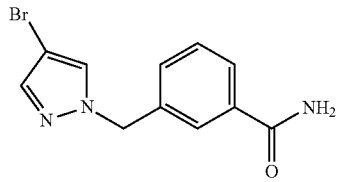 [SMILES: NC(=O)c1cccc(Cn2cc(Br)cn2)c1]

To a solution of 3-((4-bromo-1H-pyrazol-1-yl)methyl) benzoic acid (0.20 g, 0.711 mmol) in THF (3.5 mL) at 0° C. was added N-methylmorpholine (0.086 g, 0.854 mmol), and isobutyl chloroformate (0.107 g, 0.783 mmol) slowly. The reaction was stirred at 0° C. for 1.5 h and ammonium hydroxide (0.249 g, 7.11 mmol) was slowly added. The reaction was allowed to warm to room temperature where it stirred overnight. At the conclusion of this period, the reaction mixture was partitioned between DCM and water. The organic layer was separated, dried over anhydrous Na$_2$SO$_4$, filtered, and concentrated. The resulting residue was purified by flash chromatography (0-100% ethyl acetate:hexanes) to afford the title compound (0.188 g, 94%). LCMS, [M+H]$^+$=280.0.

Step C. (3-((4-Bromo-1H-pyrazol-1-yl)methyl)phenyl)methanamine

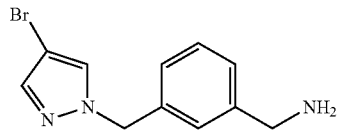 [SMILES: NCc1cccc(Cn2cc(Br)cn2)c1]

The title compound was prepared using a procedure analogous to bromo-1a,2,3,7b-tetrahydro-1H-cyclopropa[c]quinoline except that 7-bromo-3,7b-dihydro-1H-cyclopropa[c]quinolin-2(1aH)-one was replaced with 3-((4-bromo-1H-pyrazol-1-yl)methyl)benzamide. LCMS, [M+H]$^+$=266.1. $^1$H NMR (500 MHz, CDCl$_3$) δ 7.47 (s, 1H), 7.36 (s, 1H), 7.33-7.25 (m, 2H), 7.18 (s, 1H), 7.09 (d, J=7.4 Hz, 1H), 5.24 (s, 2H), 3.85 (s, 2H), 1.78 (s, 2H).

Step D. tert-Butyl 3-((4-bromo-1H-pyrazol-1-yl)methyl)benzylcarbamate

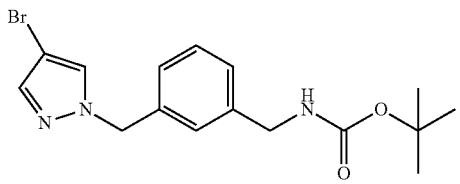 [SMILES: CC(C)(C)OC(=O)NCc1cccc(Cn2cc(Br)cn2)c1]

To a solution of (3-((4-bromo-1H-pyrazol-1-yl)methyl)phenyl)methanamine (84 mg, 0.317 mmol) in THF (1.6 mL) was added saturated NaHCO$_3$ (0.75 mL), followed by slow addition of di-tert-butyl dicarbonate (0.38 mL, 0.38 mmol, 1.0 M in THF). The reaction was stirred at room temperature overnight and then partitioned between DCM and water. The organic layer was separated, dried over anhydrous Na$_2$SO$_4$, filtered, and concentrated. The resulting residue was purified by flash chromatography (0-100% ethyl acetate:hexanes) to afford the title compound (93 mg, 81% yield). LCMS, [M+H]$^+$=366.1.

Step E. tert-Butyl 3-((4-(1-(4-(2,3-dimethylphenoxy)butanoyl)-1,2,3,4-tetrahydroquinolin-5-yl)-1H-pyrazol-1-yl)methyl)benzylcarbamate

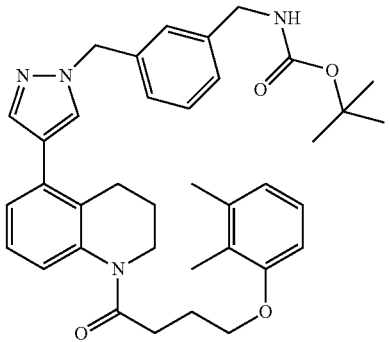 [SMILES: Cc1cccc(OCCCC(=O)N2CCCc3c(-c4cnn(Cc5cccc(CNC(=O)OC(C)(C)C)c5)c4)cccc32)c1C]

The title compound was prepared using a procedure analogous to 4-(2,3-dimethylphenoxy)-1-(5-(4-(hydroxymethyl)phenyl)-3,4-dihydroquinolin-1(2H)-yl)butan-1-one except that 4-(hydroxymethyl)phenylboronic acid was replaced with tert-butyl 3-((4-bromo-1H-pyrazol-1-yl)methyl)benzylcarbamate. LCMS, [M+H]$^+$=609.4.

Step F. 1-(5-(1-(3-(Aminomethyl)benzyl)-1H-pyrazol-4-yl)-3,4-dihydroquinolin-1(2H)-yl)-4-(2,3-dimethylphenoxy)butan-1-one

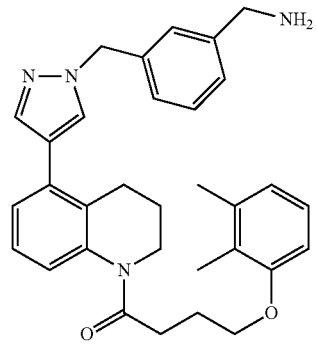 [SMILES: Cc1cccc(OCCCC(=O)N2CCCc3c(-c4cnn(Cc5cccc(CN)c5)c4)cccc32)c1C]

The title compound was prepared using a procedure analogous to 14543-(aminomethyl)phenyl)-3,4-dihydroquinolin-1(2H)-yl)-4-(2,3-dimethylphenoxy)butan-1-one except that tert-butyl 3-(1-(4-(2,3-dimethylphenoxy)butanoyl)-1,2,3,4-tetrahydroquinolin-5-yl)benzylcarbamate was replaced with tert-butyl 3-((4-(1-(4-(2,3-dimethylphenoxy)butanoyl)-1,2,3,4-tetrahydroquinolin-5-yl)-1H-pyrazol-1-yl)methyl)benzylcarbamate. LCMS, [M+H]$^+$=509.4.

Example 75

To a solution of 1-(5-(1-(3-(aminomethyl)benzyl)-1H-pyrazol-4-yl)-3,4-dihydroquinolin-1(2H)-yl)-4-(2,3-dimethylphenoxy)butan-1-one (15 mg, 0.029 mmol) and Hunig's base (5.7 mg, 0.044 mmol) in THF (0.3 mL) at 0° C. was added ethyl 2-isocyanatoacetate (4.2 mg, 0.032 mmol, 10% in THF) dropwise. Upon completion of addition, the reaction was allowed to warm to room temperature where it stirred overnight. The reaction mixture was partitioned between DCM and saturated NaHCO$_3$ and stirred for 15 min. The organic layer was separated, dried over anhydrous Na$_2$SO$_4$, filtered, and concentrated to provide the crude ester. The crude ester was re-dissolved in THF/MeOH (9:1, 0.3 mL) and added 4 N LiOH (73 µL, 0.29 mmol). The reaction mixture was stirred at reflux overnight. At the conclusion of this period, the organic solvents were removed and the mixture was adjusted to pH~5 with conc. HCl. The resulting mixture was partitioned between 5% citric acid and DCM and stirred for 15 min. After this time, the organic layer was separated, dried over anhydrous Na$_2$SO$_4$, filtered, and concentrated. The resulting residue was purified by preparative HPLC (PHENOMENEX® Axia Luna column, 5µ, C18, 30×75 mm; 10 min gradient from 100% A:0% B to 0% A:100% B and 3 min 100% B (A=90% H$_2$O/10% MeCN+0.1% TFA); (B=90% MeCN/10% H$_2$O+0.1% TFA); detection at 220 nm) to afford Example 75 (13 mg, 73% yield). LCMS, [M+H]$^+$=610.4. $^1$H NMR (400 MHz, CDCl$_3$) δ 7.53 (d, J=5.1 Hz, 1H), 7.37 (s, 1H), 7.23-7.10 (m, 3H), 7.02 (t, J=7.9 Hz, 1H), 6.74 (d, J=7.5 Hz, 1H), 6.64 (d, J=8.1 Hz, 1H), 4.46 (t, J=6.3 Hz, 2H), 3.93 (s, 2H), 3.78 (t, J=6.8 Hz, 2H), 3.02 (t, J=6.3 Hz, 2H), 2.75 (t, J=7.1 Hz, 2H), 2.57 (s, 2H), 2.25-2.10 (m, 5H), 1.97-1.78 (m, 5H). HPLC-1: Rt=12.7 min, purity=99.2%; HPLC-2: Rt=13.0 min, purity=100%.

Example 76

3-(3-((4-(1-(4-(2,3-Dimethylphenoxy)butanoyl)-1,2, 3,4-tetrahydroquinolin-5-yl)-1H-pyrazol-1-yl)methyl)benzylamino)-3-oxopropanoic acid

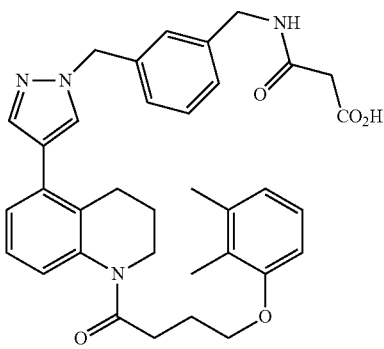 [SMILES: Cc1cccc(OCCCC(=O)N2CCCc3c(-c4cnn(Cc5cccc(CNC(=O)CC(=O)O)c5)c4)cccc32)c1C]

Example 76 was prepared using a procedure analogous to Example 73 except that 1-(5-(3-(aminomethyl)phenyl)-3,4-dihydroquinolin-1(2H)-yl)-4-(2,3-dimethylphenoxy)butan-1-one was replaced with 1-(5-(1-(3-(aminomethyl)benzyl)-1H-pyrazol-4-yl)-3,4-dihydroquinolin-1(2H)-yl)-4-(2,3-dimethylphenoxy)butan-1-one. LCMS, [M+H]⁺=595.2. ¹H NMR (400 MHz, MeOD) δ 7.59 (s, 1H), 7.45 (s, 1H), 7.37-7.27 (m, 3H), 7.27-7.07 (m, 4H), 6.96 (t, J=7.9 Hz, 1H), 6.70-6.60 (m, 2H), 5.35 (s, 2H), 4.41 (s, 2H), 3.85 (br. s, 2H), 3.78-3.68 (m, 2H), 3.37-3.28 (m, 2H), 2.80 (t, J=6.8 Hz, 2H), 2.46 (br. s, 2H), 2.11 (dt, J=12.5, 6.3 Hz, 2H), 2.03 (s, 3H), 1.84-1.74 (m, 2H), 1.71 (s, 3H). HPLC-1: Rt=10.7 min, purity=97.7%; HPLC-2: Rt=10.9 min, purity=99.4%.

Example 77

1-(3-((4-(1-(4-(2,3-Dimethylphenoxy)butanoyl)-1,2, 3,4-tetrahydroquinolin-5-yl)-1H-pyrazol-1-yl)methyl)benzylcarbamoyl)cyclopropanecarboxylic acid

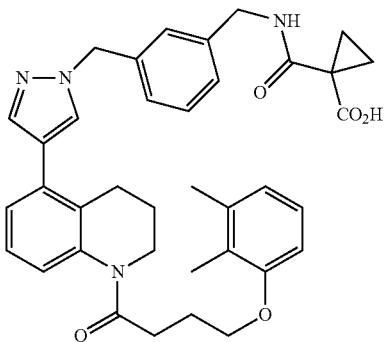 [SMILES: Cc1cccc(OCCCC(=O)N2CCCc3c(-c4cnn(Cc5cccc(CNC(=O)C6(C(=O)O)CC6)c5)c4)cccc32)c1C]

Example 77 was prepared using a procedure analogous to Example 76 except that 3-methoxy-3-oxopropanoic acid was replaced with 1-(methoxycarbonyl)cyclopropanecarboxylic acid. LCMS, [M+H]⁺=621.3. ¹H NMR (400 MHz, MeOD) δ 7.57 (br. s, 1H), 7.46 (br. s, 1H), 7.34 (t, J=7.6 Hz, 1H), 7.30-7.07 (m, 6H), 6.95 (t, J=7.9 Hz, 1H), 6.70-6.59 (m, 2H), 5.36 (s, 2H), 4.45 (s, 2H), 3.85 (br. s, 2H), 3.73 (t, J=6.8 Hz, 2H), 2.80 (t, J=6.8 Hz, 2H), 2.45 (br. s, 2H), 2.11 (dt, J=12.5, 6.3 Hz, 2H), 2.01 (s, 3H), 1.82-1.74 (m, 2H), 1.70 (s, 3H), 1.58-1.46 (m, 4H). HPLC-1: Rt=11.7 min, purity=97.2%; HPLC-2: Rt=11.6 min, purity=97.0%.

Example 78

(1-(3-((4-(1-(4-(2,3-Dimethylphenoxy)butanoyl)-1,2, 3,4-tetrahydroquinolin-5-yl)-1H-pyrazol-1-yl)methyl)benzylcarbamoyl)cyclopropanecarboxamido) methanesulfonic acid

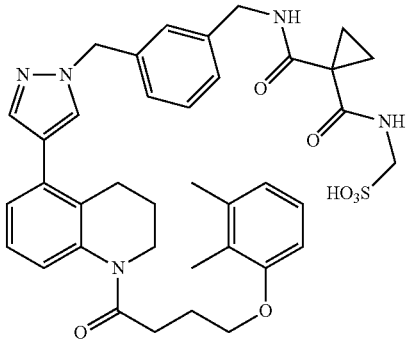 [SMILES: Cc1cccc(OCCCC(=O)N2CCCc3c(-c4cnn(Cc5cccc(CNC(=O)C6(C(=O)NCS(=O)(=O)O)CC6)c5)c4)cccc32)c1C]

To a solution of Example 77 (20.0 mg, 0.032 mmol), aminomethanesulfonic acid (10.7 mg, 0.097 mmol) and DIPEA (0.028 mL, 0.161 mmol) in THF (1 mL) was added T3P (50% w/w in EtOAc, 0.038 mL, 0.064 mmol). The reaction mixture was stirred at 50° C. for 16 h and concentrated in vacuo. The resulting residue was purified by preparative HPLC (PHENOMENEX® Axia Luna column, 5μ, C18, 30×75 mm; 15 min gradient from 100% A:0% B to 0% A:100% B (A=90% H₂O/10% MeCN+0.1% TFA); (B=90% MeCN/10% H₂O+0.1% TFA); detection at 220 nm) to afford Example 78 (14 mg, 60% yield). LCMS, [M+H]⁺=714.3. ¹H NMR (400 MHz, MeOD) δ 7.99 (br. s, 1H), 7.76 (br. s, 1H), 7.39 (s, 1H), 7.37-7.11 (m, 6H), 6.96 (t, J=7.9 Hz, 1H), 6.65 (d, J=7.4 Hz, 2H), 5.50 (s, 2H), 4.41 (s, 2H), 4.36 (s, 2H), 3.86 (br. s, 2H), 3.75 (t, J=6.8 Hz, 2H), 3.34 (s, 2H), 2.80 (t, J=6.9 Hz, 2H), 2.51 (br. s, 2H), 2.11 (dt, J=12.6, 6.4 Hz, 2H), 2.04 (s, 3H), 1.87-1.78 (m, 2H), 1.75 (s, 3H), 1.39-1.23 (m, 4H). HPLC-1: Rt=11.9 min, purity=92.0%; HPLC-2: Rt=9.9 min, purity=97.7%.

Example 79

2-(1-(3-((4-(1-(4-(2,3-Dimethylphenoxy)butanoyl)-1,2,3,4-tetrahydroquinolin-5-yl)-1H-pyrazol-1-yl)methyl)benzylcarbamoyl)cyclopropanecarboxamido)ethanesulfonic acid

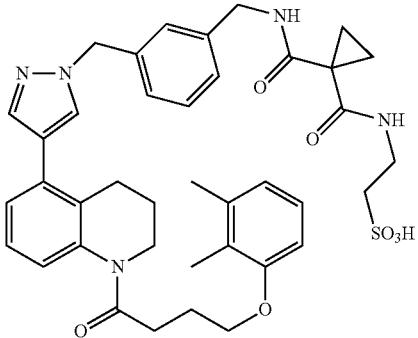 [SMILES: Cc1cccc(OCCCC(=O)N2CCCc3c(-c4cnn(Cc5cccc(CNC(=O)C6(C(=O)NCCS(=O)(=O)O)CC6)c5)c4)cccc32)c1C]

Example 79 was prepared using a procedure analogous to Example 78 except that aminomethanesulfonic acid was replaced by 2-aminoethanesulfonic acid. LCMS, [M+H]$^+$=728.3. $^1$H NMR (400 MHz, MeOD) δ 7.97 (br. s, 1H), 7.76 (br. s, 1H), 7.41-7.10 (m, 7H), 6.95 (t, J=7.9 Hz, 1H), 6.65 (d, J=7.8 Hz, 2H), 5.50 (s, 2H), 4.40 (s, 2H), 3.86 (br. s, 2H), 3.74 (t, J=6.8 Hz, 2H), 3.64-3.56 (m, 2H), 3.33 (s, 2H), 3.02-2.91 (m, 2H), 2.80 (t, J=6.9 Hz, 2H), 2.50 (br. s, 2H), 2.11 (dt, J=12.6, 6.4 Hz, 2H), 2.03 (s, 3H), 1.90-1.77 (m, 2H), 1.75 (s, 3H), 1.38-1.19 (m, 4H). HPLC-1: Rt=10.2 min, purity=98.8%; HPLC-2: Rt=7.3 min, purity=99.0%.

Example 80

3-(3-(3-((4-(1-(4-(2,3-Dimethylphenoxy)butanoyl)-1,2,3,4-tetrahydroquinolin-5-yl)-1H-pyrazol-1-yl)methyl)phenyl)ureido)propanoic acid

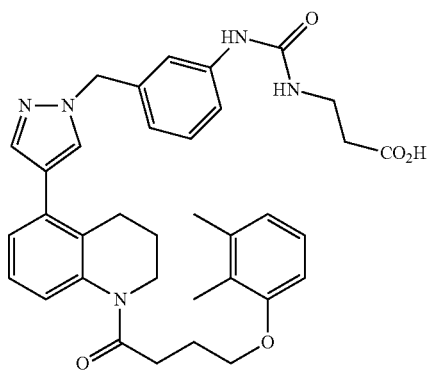 [SMILES: Cc1cccc(OCCCC(=O)N2CCCc3c(-c4cnn(Cc5cccc(NC(=O)NCCC(=O)O)c5)c4)cccc32)c1C]

Step A. tert-Butyl 3-((4-(4,4,5,5-tetramethyl-1,3,2-dioxaborolan-2-yl)-1H-pyrazol-1-yl)methyl)phenylcarbamate

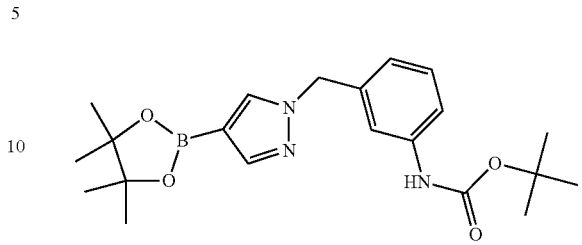

To a solution of 4-(4,4,5,5-tetramethyl-1,3,2-dioxaborolan-2-yl)-1H-pyrazole (0.88 g, 4.54 mmol) in acetonitrile (20 mL) was added cesium carbonate (4.43 g, 13.61 mmol) and tert-butyl 3-(bromomethyl)phenylcarbamate (1.298 g, 4.54 mmol). The reaction was stirred at room temperature for 3 h. After this time, the reaction mixture was diluted with ethyl acetate and washed with water and brine. The aqueous phase was extracted with CHCl$_3$. The combined organic layer was dried over anhydrous MgSO$_4$, filtered, and concentrated. The resulting residue was purified by (0-100% ethyl acetate:hexanes) to afford the title compound (1.06 g, 2.65 mmol, 59% yield) as a colorless oil. LCMS, [M+H]$^+$=400.3.

Step B. 1-(5-(1-(3-Aminobenzyl)-1H-pyrazol-4-yl)-3,4-dihydroquinolin-1(2H)-yl)-4-(2,3-dimethylphenoxy)butan-1-one

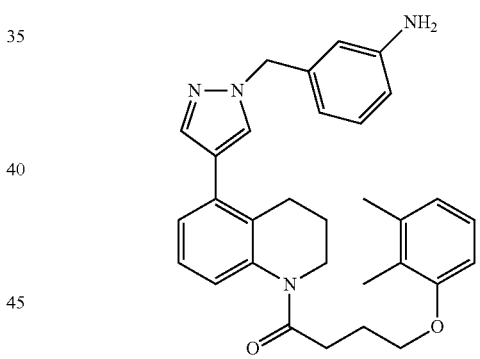

The title compound was prepared using a procedure analogous to 1-(5-(1-(3-(aminomethyl)benzyl)-1H-pyrazol-4-yl)-3,4-dihydroquinolin-1(2H)-yl)-4-(2,3-dimethylphenoxy)butan-1-one except that tert-butyl 3-((4-bromo-1H-pyrazol-1-yl)methyl)benzylcarbamate was replaced by 1-(5-bromo-3,4-dihydroquinolin-1(2H)-yl)-4-(2,3-dimethylphenoxy)butan-1-one and 4-(2,3-dimethylphenoxy)-1-(5-(4,4,5,5-tetramethyl-1,3,2-dioxaborolan-2-yl)-3,4-dihydroquinolin-1(2H)-yl)butan-1-one was replaced by tert-butyl 3-((4-(4,4,5,5-tetramethyl-1,3,2-dioxaborolan-2-yl)-1H-pyrazol-1-yl)methyl)phenylcarbamate. LCMS, [M+H]$^+$=495.4.

Example 80

To a solution of 1-(5-(1-(3-aminobenzyl)-1H-pyrazol-4-yl)-3,4-dihydroquinolin-1(2H)-yl)-4-(2,3-dimethylphenoxy)butan-1-one (20 mg, 0.040 mmol) in CH$_2$Cl$_2$ (1 mL) was added triethylamine (40.9 mg, 0.404 mmol) and phosgene (20% wt in toluene, 200 mg, 0.404 mmol). The reaction was stirred at room temperature for 5 min and concentrated. The resulting residue was re-dissolved in $CH_2Cl_2$ (1 mL) and added 3-aminopropanoic acid (18 mg, 0.202 mmol) in DMF (0.5 mL). The resulting mixture was stirred at room temperature for 30 min and then heated at 50° C. for 30 min. The reaction mixture was concentrated and purified by preparative HPLC (PHENOMENEX® Axia Luna column, 5μ, C18, 30×75 mm; 18 min gradient from 90% A:10% B to 0% A:100% B (A=90% $H_2O$/10% MeCN+0.1% TFA); (B=90% MeCN/10% $H_2O$+0.1% TFA); detection at 220 nm) to Example 80 (9.8 mg, 38% yield) as a white powder. LCMS, $[M+H]^+$=610.5. $^1H$ NMR (500 MHz, $CD_2Cl_2$) δ 7.84 (s, 1H), 7.54 (s, 1H), 7.45 (s, 1H), 7.32 (s, 1H), 7.23-7.07 (m, 5H), 6.96 (t, J=7.8 Hz, 1H), 6.83 (d, J=6.9 Hz, 1H), 6.70 (d, J=7.5 Hz, 1H), 6.62 (d, J=8.1 Hz, 1H), 5.96 (br. s, 1H), 5.22 (s, 2H), 3.91 (br. s, 2H), 3.71 (t, J=6.6 Hz, 2H), 3.39 (br. s, 2H), 2.71 (t, J=7.1 Hz, 2H), 2.58 (br. s, 2H), 2.46 (t, J=5.7 Hz, 2H), 2.23-2.06 (m, 5H), 1.94 (s, 3H), 1.86-1.74 (m, 2H). HPLC-1: Rt=9.3 min, purity=95.0%; HPLC-2: Rt=8.5 min, purity=94.7%.

Example 81

(3-(3-(1-(4-(1-(4-(2,3-Dimethylphenoxy)butanoyl)-1,2,3,4-tetrahydroquinolin-5-yl)-1H-pyrazol-1-yl)ethyl)phenyl)ureido)methanesulfonic acid

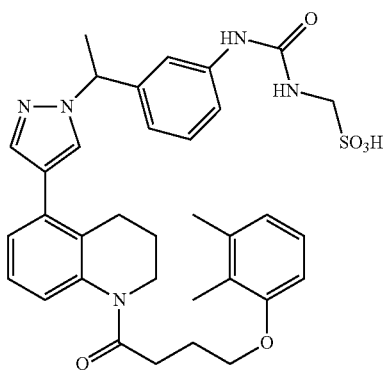 [SMILES: Cc1cccc(OCCCC(=O)N2CCCc3c(-c4cnn(C(C)c5cccc(NC(=O)NCS(=O)(=O)O)c5)c4)cccc32)c1C]

Step A. tert-Butyl 3-(1-hydroxyethyl)phenylcarbamate

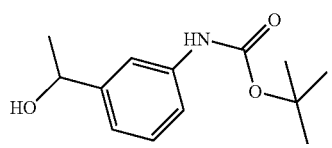 [SMILES: CC(O)c1cccc(NC(=O)OC(C)(C)C)c1]

To a solution of 1-(3-aminophenyl)ethanol (5 g, 36.4 mmol) in THF (120 mL) at 0° C. was added triethylamine (5.33 mL, 38.3 mmol) and di-tert-butyldicarbonate (9.21 mL, 40.1 mmol). The reaction was allowed to slowly warm to room temperature where it stirred overnight. At the conclusion of this period, the solvent was removed in vacuo. The resulting residue was re-dissolved in ethyl acetate, washed with 0.1N HCl, saturated $NaHCO_3$, and brine, dried over anhydrous $MgSO_4$, filtered, and concentrated to afford the title compound (10.01 g, 100% yield) as a yellow oil. $^1H$ NMR (400 MHz, $CDCl_3$) δ 7.40 (s, 1H), 7.27-7.21 (m, 2H), 7.03 (dt, J=7.2, 1.4 Hz, 1H), 6.47 (s, 1H), 4.85 (qd, J=6.4, 3.7 Hz, 1H), 1.82 (d, J=3.7 Hz, 1H), 1.50 (s, 9H), 1.46 (d, J=6.4 Hz, 3H).

Step B. tert-Butyl 3-(1-bromoethyl)phenylcarbamate

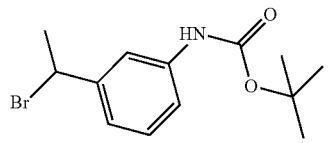 [SMILES: CC(Br)c1cccc(NC(=O)OC(C)(C)C)c1]

To a solution of tert-butyl 3-(1-hydroxyethyl)phenylcarbamate (5.8 g, 24.44 mmol) in $CH_2Cl_2$ (30 mL) and THF (20 mL) at 0° C. was added tribromophosphine (1 M solution in $CH_2Cl_2$, 24.44 mL, 24.44 mmol). The reaction was stirred at 0-10° C. for 1.5 h and then quenched with water. The mixture was extracted with $CH_2Cl_2$. The organic layer was washed with saturated $NaHCO_3$ and brine, dried over anhydrous $MgSO_4$, filtered and concentrated to afford the title compound (5.7 g, 78% yield) as a colorless oil. LCMS, $[M+Na]^+$= 322.1.

Step C. 1-(5-(1-(1-(3-Aminophenyl)ethyl)-1H-pyrazol-4-yl)-3,4-dihydroquinolin-1(2H)-yl)-4-(2,3-dimethylphenoxy)butan-1-one

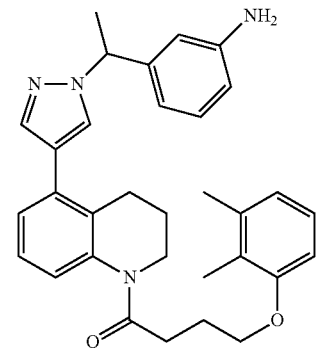 [SMILES: Cc1cccc(OCCCC(=O)N2CCCc3c(-c4cnn(C(C)c5cccc(N)c5)c4)cccc32)c1C]

The title compound was prepared using a procedure analogous to 1-(5-(1-(3-aminobenzyl)-1H-pyrazol-4-yl)-3,4-dihydroquinolin-1(2H)-yl)-4-(2,3-dimethylphenoxy)butan-1-one except that tert-butyl 3-(bromomethyl)phenylcarbamate was replaced with tert-butyl 3-(1-bromoethyl)phenylcarbamate. LCMS, $[M+H]^+$=509.5.

Example 81

Example 81 was prepared using a procedure analogous to Example 80 except that 1-(5-(1-(3-aminobenzyl)-1H-pyrazol-4-yl)-3,4-dihydroquinolin-1(2H)-yl)-4-(2,3-dimethylphenoxy)butan-1-one was replaced with 1-(5-(1-(1-(3-aminophenyl)ethyl)-1H-pyrazol-4-yl)-3,4-dihydroquinolin-1 (2H)-yl)-4-(2,3-dimethylphenoxy)butan-1-one and 3-aminopropanoic acid was replaced with aminomethanesulfonic acid. LCMS, $[M+H]^+$=646.5. $^1H$ NMR (400 MHz, $CD_3CN$) δ 7.69 (br. s, 1H), 7.53 (s, 1H), 7.41 (s, 1H), 7.30-7.07 (m, 5H), 6.95 (t, J=7.9 Hz, 1H), 6.84 (d, J=7.4 Hz, 1H), 6.65 (t, J=8.7 Hz, 2H), 5.53 (dd, J=14.0, 7.0 Hz, 1H), 4.20 (s, 2H), 3.83 (br. s, 2H), 3.74-3.62 (m, 2H), 2.69 (t, J=7.0 Hz, 2H), 2.48 (br. s, 2H), 2.11-1.97 (m, 5H), 1.83 (d, J=7.0 Hz, 3H), 1.79-1.67 (m, 5H). HPLC-1: Rt=13.9 min, purity=99.8%; HPLC-2: Rt=12.4 min, purity=100%.

Example 82

2-(3-(3-(1-(4-(1-(4-(2,3-Dimethylphenoxy)butanoyl)-1,2,3,4-tetrahydroquinolin-5-yl)-1H-pyrazol-1-yl)ethyl)phenyl)ureido)ethanesulfonic acid

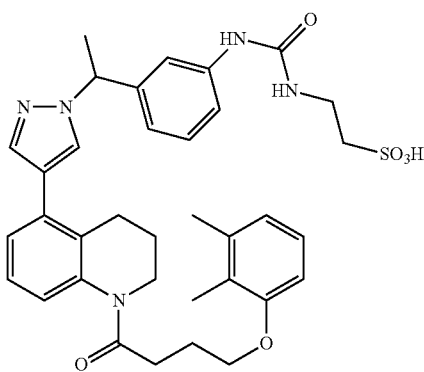 [SMILES: Cc1cccc(OCCCC(=O)N2CCCc3c(-c4cnn(C(C)c5cccc(NC(=O)NCCS(=O)(=O)O)c5)c4)cccc32)c1C]

Example 82 was prepared using a procedure analogous to Example 81 except that aminomethanesulfonic acid was replaced with 2-aminoethanesulfonic acid. LCMS, [M+H]⁺= 660.5. ¹H NMR (400 MHz, CD₃CN) δ 7.69 (br. s, 1H), 7.53 (s, 1H), 7.39 (s, 1H), 7.28-7.10 (m, 5H), 6.95 (t, J=7.9 Hz, 1H), 6.84 (d, J=7.2 Hz, 1H), 6.65 (t, J=8.3 Hz, 2H), 5.52 (q, J=7.1 Hz, 1H), 3.83 (br. s, 2H), 3.71-3.55 (m, 2H), 3.48 (t, J=6.5 Hz, 2H), 2.90 (t, J=6.5 Hz, 2H), 2.69 (t, J=7.0 Hz, 2H), 2.49 (br. s, 2H), 2.09-1.97 (m, 5H), 1.83 (d, J=7.1 Hz, 3H), 1.80-1.66 (m, 5H). HPLC-1: Rt=11.8 min, purity=99.1%; HPLC-2: Rt=9.1 min, purity=99.7%.

Example 83

2-(3-(3-((4-(1-(4-(2,3-Dimethylphenoxy)butanoyl)-1,2,3,4-tetrahydroquinolin-5-yl)-1H-pyrazol-1-yl)methyl)phenyl)ureido)acetic acid

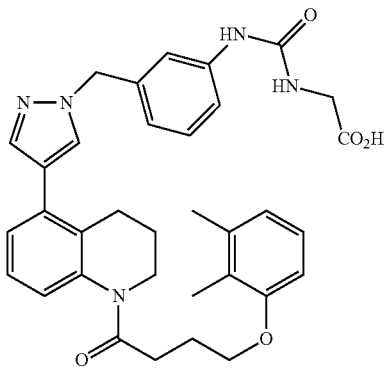 [SMILES: Cc1cccc(OCCCC(=O)N2CCCc3c(-c4cnn(Cc5cccc(NC(=O)NCC(=O)O)c5)c4)cccc32)c1C]

Step A. Ethyl 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)acetate

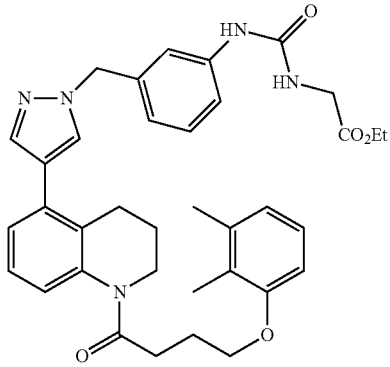 [SMILES: CCOC(=O)CNC(=O)Nc1cccc(Cn2cc(-c3cccc4c3CCCN4C(=O)CCCOc3cccc(C)c3C)cn2)c1]

The title compound was prepared using a procedure analogous to Example 80 except that 3-aminopropanoic acid was replaced with ethyl 2-aminoacetate. LCMS, [M+H]⁺=624.5.

Example 83

Example 83 was prepared using a procedure analogous to Example 2 except that methyl 4-(1-(4-(2,3-dimethylphenoxy)butanoyl)-1,2,3,4-tetrahydroquinolin-5-yl)picolinate was replaced with ethyl 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)acetate. LCMS, [M+H]⁺= 596.3. ¹H NMR (500 MHz, CD₂Cl₂) δ 8.06 (s, 1H), 7.53 (s, 1H), 7.45 (s, 1H), 7.29 (s, 1H), 7.20 (d, J=7.7 Hz, 2H), 7.16-7.05 (m, 4H), 6.95 (t, J=7.8 Hz, 1H), 6.79 (d, J=7.5 Hz, 1H), 6.69 (d, J=7.5 Hz, 1H), 6.62 (d, J=8.1 Hz, 1H), 6.11 (br. s, 1H), 5.19 (s, 2H), 3.90 (br. s, 3H), 3.80 (s, 2H), 3.69 (t, J=6.6 Hz, 2H), 2.70 (t, J=7.1 Hz, 2H), 2.56 (br. s, 2H), 2.22-2.07 (m, 5H), 1.93 (s, 3H), 1.78 (d, J=6.2 Hz, 2H). HPLC-1: Rt=9.1 min, purity=100%; HPLC-2: Rt=8.2 min, purity=100%.

Example 84

2-(3-((4-(1-(4-(2,3-Dimethylphenoxy)butanoyl)-1,2,3,4-tetrahydroquinolin-5-yl)-1H-pyrazol-1-yl)methyl)benzylcarbamoyloxy)acetic acid

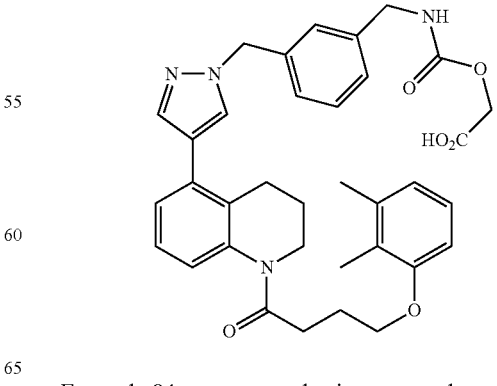

Example 84 was prepared using a procedure analogous to Example 83 except that 1-(5-(1-(3-aminobenzyl)-1H-pyrazol-4-yl)-3,4-dihydroquinolin-1(2H)-yl)-4-(2,3-dimethylphenoxy)butan-1-one was replaced with 1-(5-(1-(3-(aminomethyl)benzyl)-1H-pyrazol-4-yl)-3,4-dihydroquinolin-1(2H)-yl)-4-(2,3-dimethylphenoxy)butan-1-one and ethyl 2-aminoacetate was replaced with methyl 2-hydroxyacetate. LCMS, [M+H]$^+$=611.2. $^1$H NMR (400 MHz, MeOD) δ 7.60 (br. s, 1H), 7.45 (br. s, 1H), 7.36-7.07 (m, 7H), 6.95 (t, J=7.9 Hz, 1H), 6.71-6.57 (m, 2H), 5.35 (s, 2H), 4.54 (s, 2H), 4.31 (s, 2H), 3.85 (br. s, 2H), 3.73 (t, J=6.8 Hz, 2H), 2.80 (t, J=6.8 Hz, 2H), 2.46 (br. s, 2H), 2.11 (dt, J=12.4, 6.3 Hz, 2H), 2.02 (s, 3H), 1.85-1.73 (m, 2H), 1.71 (s, 3H). HPLC-1: Rt=11.6 min, purity=98.8%; HPLC-2: Rt=11.1 min, purity=100%.

The following Examples were prepared in a manner analogous to Example 80.

TABLE 6

| Example | Name | Y | LCMS, [M + H]$^+$ | $^1$H NMR (400 MHz, CDCl$_3$) δ | HPLC-1: Rt min, purity; HPLC-2: Rt min, purity |
|---|---|---|---|---|---|
| 85 | 2-(3-(3-((4-(1-(4-(2,3-Dimethylphenoxy)butanoyl)-1,2,3,4-tetrahydroquinolin-5-yl)-1H-pyrazol-1-yl)methyl)phenyl)ureido)ethanesulfonic acid | HN-C(O)-NH-CH$_2$CH$_2$-SO$_3$H | 646.5 | 7.84 (br. s, 1H), 7.70 (s, 1H), 7.44 (s, 1H), 7.34-7.17 (m, 6H), 7.02-6.90 (m, 2H), 6.68 (d, J = 7.2 Hz, 2H), 5.43 (s, 2H), 3.88 (br. s, 2H), 3.77 (t, J = 6.7 Hz, 2H), 3.64 (t, J = 6.1 Hz, 2H), 3.01 (t, J = 6.1 Hz, 2H), 2.82 (t, J = 6.8 Hz, 2H), 2.52 (br. s, 2H), 2.17-2.11 (m, 2H), 2.06 (s, 3H), 1.89-1.81 (m, 2H), 1.77 (s, 3H)* | 10.4 min, 99.3% 7.2 min, 98.4% |
| 86 | (3-(3-((4-(1-(4-(2,3-Dimethylphenoxy)butanoyl)-1,2,3,4-tetrahydroquinolin-5-yl)-1H-pyrazol-1-yl)methyl)phenyl)ureido)methanesulfonic acid | HN-C(O)-NH-CH$_2$-SO$_3$H | 632.4 | 7.75 (br. s, 1H), 7.64 (br. s, 1H), 7.38 (br. s, 1H), 7.29 (d, J = 8.7 Hz, 1H), 7.25-7.12 (m, 4H), 6.96 (t, J = 7.8 Hz, 1H), 6.83 (d, J = 7.4 Hz, 1H), 6.72-6.62 (m, 2H), 5.28 (s, 2H), 4.20 (s, 2H), 3.87 (br. s, 2H), 3.68 (t, J = 6.7 Hz, 2H), 2.70 (t, J = 7.0 Hz, 2H), 2.60-2.49 (m, 2H), 2.14-2.01 (m, 5H), 1.84 (s, 3H), 1.81-1.74 (m, 2H)** | 10.5 min, 99.6% 6.9 min, 100% |
| 87 | (3-(3-((4-(1-(4-(2,3-Dimethylphenoxy)butanoyl)-1,2,3,4-tetrahydroquinolin-5-yl)-1H-pyrazol-1-yl)methyl)benzyl)ureido)methanesulfonic acid | CH$_2$-NH-C(O)-NH-CH$_2$-SO$_3$H | 646.3 | 7.60-7.37 (m, 2H), 7.32-7.08 (m, 5H), 7.08-6.83 (m, 3H), 6.70 (d, J = 7.2 Hz, 1H), 6.60 (d, J = 7.7 Hz, 1H), 5.32 (s, 2H), 4.41 (br. s, 2H), 4.29 (br. s, 2H), 3.97-3.82 (m, 2H), 3.78-3.61 (m, 2H), 2.72 (br. s, 2H), 2.45 (br. s, 2H), 2.24-2.02 (m, 5H), 1.97-1.68 (m, 5H) | 13.5 min, 98.8% 11.5 min, 99.3% |
| 88 | 2-(3-(3-((4-(1-(4-(2,3-Dimethylphenoxy)butanoyl)-1,2,3,4-tetrahydroquinolin-5-yl)-1H-pyrazol-1-yl)methyl)benzyl)ureido)ethanesulfonic acid | CH$_2$-NH-C(O)-NH-CH$_2$CH$_2$-SO$_3$H | 660.4 | 7.88 (s, 1H), 7.63-7.42 (m, 2H), 7.35-7.13 (m, 5H), 7.12-6.95 (m, 2H), 6.72 (d, J = 7.5 Hz, 1H), 6.62 (d, J = 8.0 Hz, 1H), 5.37 (s, 2H), 4.33 (s, 2H), 3.89 (br. s, 2H), 3.74 (t, J = 6.5 Hz, 2H), 3.59 (br. s, 2H), 3.04 (s, 2H), 2.72 (t, J = 7.0 Hz, 2H), 2.48 (br. s, 2H), 2.24-2.07 (m, 5H), 1.93-1.72 (m, 5H) | 11.5 min, 100% 8.7 min, 98.7% |

*$^1$H NMR (400 MHz, MeOD).

**$^1$H NMR (400 MHz, CD$_3$CN).

Example 89

3-(N-(3-((4-(1-(4-(2,3-Dimethylphenoxy)butanoyl)-1,2,3,4-tetrahydroquinolin-5-yl)-1H-pyrazol-1-yl)methyl)phenyl)sulfamoyl)propanoic acid

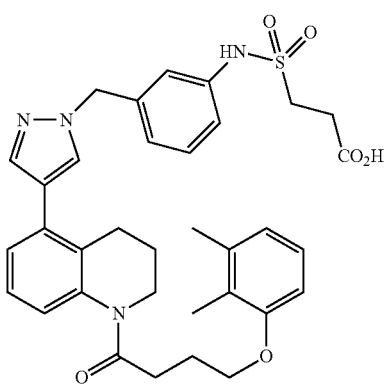 [SMILES: Cc1cccc(OCCCC(=O)N2CCCc3c(-c4cnn(Cc5cccc(NS(=O)(=O)CCC(=O)O)c5)c4)cccc32)c1C]

Example 89 was prepared using a procedure analogous to Example 72 except that 1-(5-(3-(aminomethyl)phenyl)-3,4-dihydroquinolin-1(2H)-yl)-4-(2,3-dimethylphenoxy)butan-1-one was replaced with 1-(5-(1-(3-aminobenzyl)-1H-pyrazol-4-yl)-3,4-dihydroquinolin-1(2H)-yl)-4-(2,3-dimethylphenoxy)butan-1-one. LCMS, [M+H]$^+$=631.5. $^1$H NMR (500 MHz, CD$_2$Cl$_2$) δ 7.62 (s, 1H), 7.46 (s, 1H), 7.37 (t, J=7.9 Hz, 1H), 7.30 (d, J=8.3 Hz, 1H), 7.25-7.16 (m, 3H), 7.11-7.05 (m, 2H), 7.02-6.95 (m, 2H), 6.72 (d, J=7.5 Hz, 1H), 6.64 (d, J=8.4 Hz, 1H), 5.37 (s, 2H), 3.91 (br. s, 2H), 3.78 (t, J=6.8 Hz, 2H), 3.43 (t, J=6.5 Hz, 2H), 2.83-2.74 (m, 4H), 2.58 (s, 2H), 2.22-2.11 (m, 5H), 1.96-1.81 (m, 5H). HPLC-1: Rt=10.4 min, purity=100%; HPLC-2: Rt=9.6 min, purity=100%.

Example 90

1-(3-((4-(1-(4-(2,3-Dimethylphenoxy)butanoyl)-1,2,3,4-tetrahydroquinolin-5-yl)-1H-pyrazol-1-yl)methyl)phenyl)guanidine

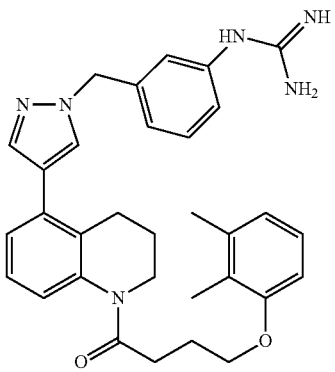 [SMILES: Cc1cccc(OCCCC(=O)N2CCCc3c(-c4cnn(Cc5cccc(NC(=N)N)c5)c4)cccc32)c1C]

A mixture of 1-(5-(1-(3-aminobenzyl)-1H-pyrazol-4-yl)-3,4-dihydroquinolin-1(2H)-yl)-4-(2,3-dimethylphenoxy)butan-1-one (20 mg, 0.040 mmol), cyanamide (34 mg, 0.809 mmol), and 12 N HCl (0.05 mL) in EtOAc (7 mL) was heated to reflux for 5 h. The reaction was concentrated and purified by preparative HPLC (PHENOMENEX® Axia Luna column, 5μ, C18, 30×100 mm; 18 min gradient from 100% A:0% B to 0% A:100% B (A=90% H$_2$O/10% MeOH+0.1% TFA); (B=90% MeOH/10% H$_2$O+0.1% TFA); detection at 220 nm) to afford Example 90 (12.9 mg, 58% yield) as a white powder. LCMS, [M+H]$^+$=537.5. $^1$H NMR (500 MHz, MeOD) δ 7.75 (s, 1H), 7.52 (t, J=7.8 Hz, 2H), 7.34-7.18 (m, 6H), 7.01 (t, J=7.9 Hz, 1H), 6.72 (d, J=7.7 Hz, 1H), 6.70 (d, J=8.2 Hz, 1H), 5.45 (s, 2H), 3.91 (br. s, 2H), 3.78 (t, J=6.8 Hz, 2H), 2.85 (t, J=6.8 Hz, 2H), 2.54 (br. s, 2H), 2.21-2.13 (m, 2H), 2.11 (s, 3H), 1.89-1.81 (m, 2H), 1.79 (s, 3H). HPLC-1: Rt=7.3 min, purity=100%; HPLC-2: Rt=8.3 min, purity=100%.

Example 91

1-(3-((4-(1-(4-(2,3-Dimethylphenoxy)butanoyl)-1,2,3,4-tetrahydroquinolin-5-yl)-1H-pyrazol-1-yl)methyl)benzyl)guanidine

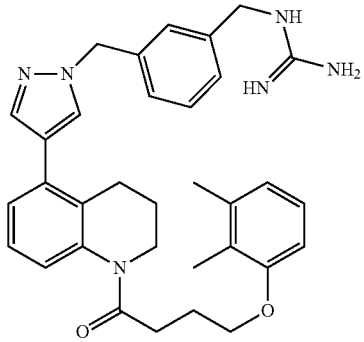 [SMILES: Cc1cccc(OCCCC(=O)N2CCCc3c(-c4cnn(Cc5cccc(CNC(=N)N)c5)c4)cccc32)c1C]

Example 91 was prepared using a procedure analogous to Example 90 except that 1-(5-(1-(3-aminobenzyl)-1H-pyrazol-4-yl)-3,4-dihydroquinolin-1(2H)-yl)-4-(2,3-dimethylphenoxy)butan-1-one was replaced with 1-(5-(1-(3-(aminomethyl)benzyl)-1H-pyrazol-4-yl)-3,4-dihydroquinolin-1(2H)-yl)-4-(2,3-dimethylphenoxy)butan-1-one. LCMS, [M+H]$^+$=551.3. $^1$H NMR (500 MHz, MeOD) δ 7.89-7.76 (m, 1H), 7.69-7.57 (m, 1H), 7.47 (s, 1H), 7.41 (t, J=7.5 Hz, 1H), 7.35-7.10 (m, 5H), 6.97 (t, J=7.9 Hz, 1H), 6.75-6.58 (m, 2H), 5.39 (s, 2H), 4.41 (t, J=2.8 Hz, 2H), 3.86 (br. s, 2H), 3.74 (t, J=6.8 Hz, 2H), 2.81 (t, J=6.8 Hz, 2H), 2.48 (br. s, 2H), 2.12 (dt, J=12.4, 6.3 Hz, 2H), 2.04 (s, 3H), 1.88-1.76 (m, 2H), 1.73 (s, 3H). HPLC-1: Rt=8.4 min, purity=97.3%; HPLC-2: Rt=10.4 min, purity=98.2%.

Example 92

2-Cyano-1-(3-((4-(1-(4-(2,3-dimethylphenoxy)butanoyl)-1,2,3,4-tetrahydroquinolin-5-yl)-1H-pyrazol-1-yl)methyl)phenyl)guanidine

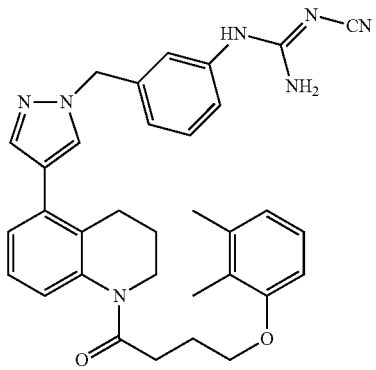 [SMILES: Cc1cccc(OCCCC(=O)N2CCCc3c(-c4cnn(Cc5cccc(N/C(N)=N/C#N)c5)c4)cccc32)c1C]

A mixture of 1-(5-(1-(3-aminobenzyl)-1H-pyrazol-4-yl)-3,4-dihydroquinolin-1(2H)-yl)-4-(2,3-dimethylphenoxy)butan-1-one (16 mg, 0.032 mmol), sodium dicyanamide (5.76 mg, 0.065 mmol), and 6 N HCl (10.78 µL, 0.065 mmol) in dioxane (0.5 mL) was heated at 60° C. overnight. The reaction was concentrated and purified by preparative HPLC (PHENOMENEX® Axia Luna column, 5µ, C18, 30×100 mm; 18 min gradient from 100% A:0% B to 0% A:100% B (A=90% H₂O/10% MeOH+0.1% TFA); (B=90% MeOH/10% H₂O+0.1% TFA); detection at 220 nm) to afford Example 92 (15.1 mg, 83% yield) as a white powder. LCMS, [M+H]⁺=562.5. ¹H NMR (400 MHz, MeOD) δ 7.66 (s, 1H), 7.54 (s, 1H), 7.46-7.37 (m, 2H), 7.37-7.19 (m, 4H), 7.14 (d, J=7.5 Hz, 1H), 7.03 (t, J=7.9 Hz, 1H), 6.78-6.68 (m, 2H), 5.43 (s, 2H), 3.92 (br. s, 2H), 3.80 (t, J=6.8 Hz, 2H), 2.87 (t, J=6.8 Hz, 2H), 2.55 (br. s, 2H), 2.18 (dt, J=12.9, 6.5 Hz, 2H), 2.11 (s, 3H), 1.87 (dt, J=13.5, 6.7 Hz, 2H), 1.80 (s, 3H). HPLC-1: Rt=9.6 min, purity=98.7%; HPLC-2: Rt=8.7 min, purity=99.1%.

Example 93

(S)-5-((3-(1-(4-(2,3-Dimethylphenoxy)butanoyl)-1,2,3,4-tetrahydroquinolin-5-yl)benzyloxy)carbonylamino)-2-guanidinopentanoic acid

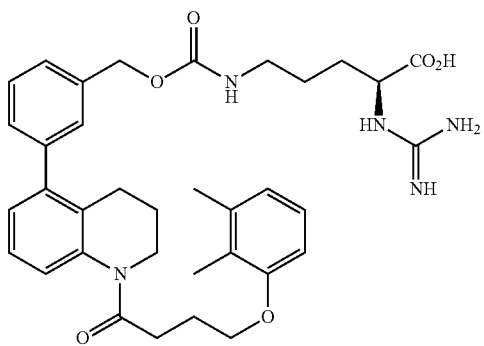 [SMILES: Cc1cccc(OCCCC(=O)N2CCCc3c(-c4cccc(COC(=O)NCCC[C@H](NC(=N)N)C(=O)O)c4)cccc32)c1C]

A mixture of Example 58 (0.068 g, 0.116 mmol), tert-butyl (1H-pyrazol-1-yl)methylenedicarbamate (0.045 g, 0.145 mmol) and DIPEA (0.061 mL, 0.347 mmol) in MeOH (1.0 mL) was stirred at room temperature for 16 h. The solvent was removed in vacuo. The resulting residue was dissolved in DCM (1.0 mL) and treated with TFA (0.5 mL, 6.49 mmol). The mixture was stirred at room temperature for 16 h and concentrated to provide a residue. The residue was purified by preparative HPLC (PHENOMENEX® Axia Luna column, 5µ, C18, 30×100 mm; 18 min gradient from 75% A:25% B to 0% A:100% B (A=90% H₂O/10% MeOH+0.1% TFA); (B=90% MeOH/10% H₂O+0.1% TFA); detection at 220 nm) to afford Example 93 as a white solid. LCMS, [M+H]⁺=630.3. ¹H NMR (400 MHz, MeOD) δ 7.40-7.29 (m, 2H), 7.29-7.19 (m, 2H), 7.12 (br. s, 2H), 7.04 (d, J=4.5 Hz, 1H), 6.96 (t, J=7.9 Hz, 1H), 6.70 (d, J=7.5 Hz, 1H), 6.65 (d, J=8.2 Hz, 1H), 5.08 (s, 2H), 4.24 (dd, J=7.6, 4.8 Hz, 1H), 3.87 (br. s, 2H), 3.72 (t, J=7.0 Hz, 2H), 3.19-3.09 (m, 2H), 2.81 (t, J=6.9 Hz, 2H), 2.35 (br. s, 2H), 2.18-2.06 (m, 5H), 2.02-1.88 (m, 1H), 1.86-1.68 (m, 6H), 1.64-1.52 (m, 2H). HPLC-1: Rt=11.3 min, purity=96.8%; HPLC-2: Rt=11.8 min, purity=97.3%.

Example 94

2-((2-(4-(1-(4-(2,3-Dimethylphenoxy)butanoyl)-1,2,3,4-tetrahydroquinolin-5-yl)-1H-pyrazol-1-yl)-2-methylpropoxy)carbonylamino)ethanesulfonic acid

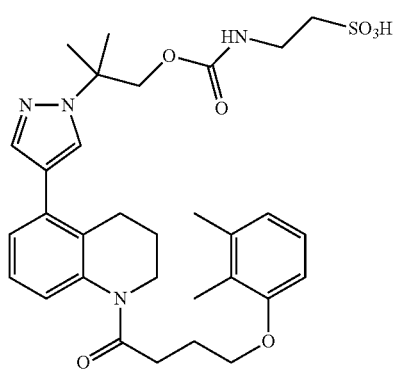 [SMILES: Cc1cccc(OCCCC(=O)N2CCCc3c(-c4cnn(C(C)(C)COC(=O)NCCS(=O)(=O)O)c4)cccc32)c1C]

Step A. Ethyl 2-(4-bromo-1H-pyrazol-1-yl)-2-methylpropanoate

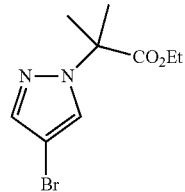

The title compound was prepared using a procedure analogous to methyl 3-((4-bromo-1H-pyrazol-1-yl)methyl)benzoate except that methyl 3-(bromomethyl)benzoate was replaced with ethyl 2-bromo-2-methylpropanoate. LCMS, [M+H]⁺=261.0.

Step B. 2-(4-Bromo-1H-pyrazol-1-yl)-2-methylpropan-1-ol

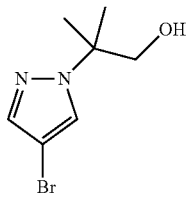

To a solution of ethyl 2-(4-bromo-1H-pyrazol-1-yl)-2-methylpropanoate (0.8 g, 3.06 mmol) in MeOH (10 mL) was added sodium borohydride (0.348 g, 9.19 mmol). The reaction was stirred at room temperature for 3 h and quenched with saturated NH₄Cl solution. The mixture was extracted with ethyl acetate. The organic layer was washed with brine, Step C. 4-(2,3-Dimethylphenoxy)-1-(5-(1-(1-hydroxy-2-methylpropan-2-yl)-1H-pyrazol-4-yl)-3,4-dihydroquinolin-1(2H)-yl)butan-1-one

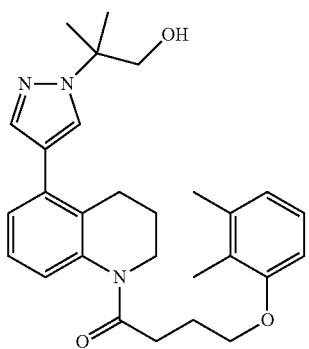 [SMILES: Cc1cccc(OCCCC(=O)N2CCCc3c(-c4cnn(C(C)(C)CO)c4)cccc32)c1C]

The title compound was prepared using a procedure analogous to Example 2 except that methyl 4-bromopicolinate was replaced with 2-(4-bromo-1H-pyrazol-1-yl)-2-methylpropan-1-ol. LCMS, [M+H]$^+$=462.4.

Step D. 2-(4-(1-(4-(2,3-Dimethylphenoxy)butanoyl)-1,2,3,4-tetrahydroquinolin-5-yl)-1H-pyrazol-1-yl)-2-methylpropyl 4-nitrophenyl carbonate

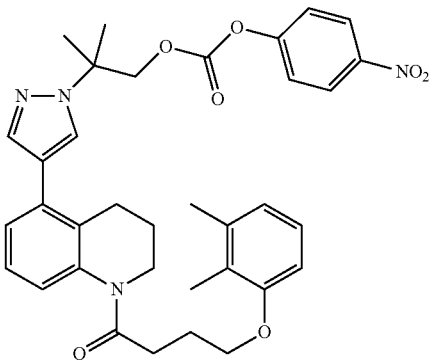 [SMILES: Cc1cccc(OCCCC(=O)N2CCCc3c(-c4cnn(C(C)(C)COC(=O)Oc5ccc([N+](=O)[O-])cc5)c4)cccc32)c1C]

The title compound was prepared using a procedure analogous to 3-bromobenzyl 4-nitrophenyl carbonate except that (3-bromophenyl)methanol was replaced with 4-(2,3-dimethylphenoxy)-1-(5-(1-(1-hydroxy-2-methylpropan-2-yl)-1H-pyrazol-4-yl)-3,4-dihydroquinolin-1(2H)-yl)butan-1-one. LCMS, [M+H]$^+$=627.5.

Example 94

A mixture of 2-aminoethanesulfonic acid (21.6 mg, 0.172 mmol), potassium phosphate (36.6 mg, 0.172 mmol), and 2-(4-(1-(4-(2,3-dimethylphenoxy)butanoyl)-1,2,3,4-tetrahydroquinolin-5-yl)-1H-pyrazol-1-yl)-2-methylpropyl 4-nitrophenyl carbonate (36 mg, 0.057 mmol) in DMSO was heated at 100° C. in a microwave reactor for 10 min. The reaction was concentrated and purified by preparative HPLC (PHENOM-ENEX® Axia Luna column, 5µ, C18, 30×100 mm; 18 min gradient from 95% A:5% B to 0% A:100% B (A=90% H$_2$O/10% MeOH+0.1% TFA); (B=90% MeOH/10% H$_2$O+0.1% TFA); detection at 220 nm) to afford Example 94 (32 mg, 0.052 mmol, 91% yield) as a white powder. LCMS, [M+H]$^+$= 613.3. $^1$H NMR (400 MHz, MeOD) δ 8.07 (s, 1H), 7.80 (s, 1H), 7.28 (br. s, 3H), 7.00 (t, J=7.8 Hz, 1H), 6.73 (d, J=7.5 Hz, 1H), 6.69 (d, J=8.1 Hz, 1H), 4.36 (s, 2H), 3.91 (br. s, 2H), 3.77 (t, J=6.7 Hz, 2H), 3.47 (t, J=6.7 Hz, 2H), 2.92 (t, J=6.6 Hz, 2H), 2.82 (t, J=6.9 Hz, 2H), 2.57 (s, 2H), 2.22-2.08 (m, 5H), 1.94-1.82 (m, 6H), 1.74 (s, 6H). HPLC-1: Rt=10.9 min, purity=99.1%; HPLC-2: Rt=6.9 min, purity=100%.

Example 95

3-((4-(1-(4-(2,3-Dimethylphenoxy)butanoyl)-1,2,3,4-tetrahydroquinolin-5-yl)-1H-pyrazol-1-yl)methyl)benzoic acid

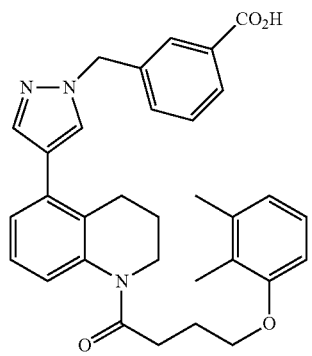 [SMILES: Cc1cccc(OCCCC(=O)N2CCCc3c(-c4cnn(Cc5cccc(C(=O)O)c5)c4)cccc32)c1C]

Step A. 1-(5-(1H-Pyrazol-4-yl)-3,4-dihydroquinolin-1(2H)-yl)-4-(2,3-dimethylphenoxy)butan-1-one

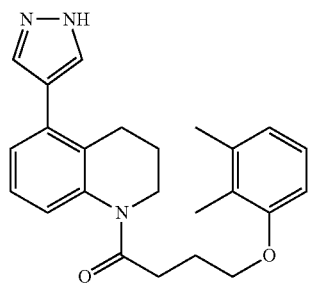 [SMILES: Cc1cccc(OCCCC(=O)N2CCCc3c(-c4cn[nH]c4)cccc32)c1C]

The title compound was prepared using a procedure analogous to Example 1 except that ethyl 2-(4-(4,4,5,5-tetramethyl-1,3,2-dioxaborolan-2-yl)-1H-pyrazol-1-yl)acetate was replaced with tert-butyl 4-(4,4,5,5-tetramethyl-1,3,2-dioxaborolan-2-yl)-1H-pyrazole-1-carboxylate. LCMS, [M+H]$^+$= 390.2.

Example 95

To a solution of 1-(5-(1H-pyrazol-4-yl)-3,4-dihydroquinolin-1(2H)-yl)-4-(2,3-dimethylphenoxy)butan-1-one (19 mg, 0.05 mmol) in DMF (0.43 mL) at 0° C. was added sodium bis(trimethylsilyl)amide (1.0 M in THF, 55 µL, 0.055 mmol) slowly over 2 min. After 30 min a solution of methyl 3-(bromomethyl)benzoate (13 mg, 0.055 mmol) in DMF (0.07 mL) was added quickly. The resulting mixture was allowed to warm to room temperature and stirred overnight. The reaction was quenched with saturated aq. ammonium chloride (~20 µL), and partitioned between diethyl ether and water. The resulting mixture was stirred vigorously for 15 min. The organic layer was separated, dried over anhydrous $Na_2SO_4$, filtered, and concentrated. The resulting residue was re-dissolved in THF/$H_2O$ (9:1, 0.5 mL) and treated with 4 M LiOH (125 µL, 0.5 mmol). The reaction was heated at 65° C. for 45 min and cooled to room temperature. The reaction mixture was adjusted to pH~5 with conc. HCl, and partitioned between 5% citric acid and DCM. The mixture was stirred for 15 min. The organic layer was separated, dried over anhydrous $Na_2SO_4$, filtered, and concentrated to provide a residue. The residue was purified by preparative HPLC (PHENOMENEX® Axia Luna column, 5µ, C18, 30×75 mm; 15 min gradient from 100% A:0% B to 0% A:100% B and 3 min 100% B (A=90% $H_2O$/10% MeCN+0.1% TFA); (B=90% MeCN/10% $H_2O$+0.1% TFA); detection at 220 nm) to afford Example 95 (14 mg, 53% yield). LCMS, [M+H]$^+$=524.2. $^1$H NMR (400 MHz, CDCl$_3$) δ 8.11-8.03 (m, 2H), 7.60 (s, 1H), 7.54-7.44 (m, 2H), 7.37 (s, 1H), 7.26 (s, 1H), 7.23-7.10 (m, 2H), 7.00 (t, J=7.8 Hz, 1H), 6.72 (d, J=7.5 Hz, 1H), 6.63 (d, J=8.1 Hz, 1H), 5.41 (s, 2H), 3.92 (t, J=5.3 Hz, 2H), 3.78 (t, J=6.8 Hz, 2H), 2.75 (t, J=7.1 Hz, 2H), 2.58 (s, 2H), 2.25-2.09 (m, 5H), 1.96-1.76 (m, 5H). HPLC-1: Rt=10.6 min, purity=100%; HPLC-2: Rt=9.5 min, purity=100%.

The following Examples were prepared in a manner analogous to Example 95.

TABLE 7

| Example | Name | —X—Y | LCMS, [M+H]$^+$ | $^1$H NMR (400 MHz, CDCl$_3$) δ | HPLC-1: Rt min, purity; HPLC-2: Rt min, purity |
|---|---|---|---|---|---|
| 96 | 4-((4-(1-(4-(2,3-Dimethylphenoxy)butanoyl)-1,2,3,4-tetrahydroquinolin-5-yl)-1H-pyrazol-1-yl)methyl)benzoic acid | 4-CH$_2$-C$_6$H$_4$-CO$_2$H | 524.3 | 8.08 (d, J = 8.2 Hz, 2H), 7.56 (s, 1H), 7.32 (d, J = 8.1 Hz, 2H), 7.31 (s, 1H), 7.24 (s, 1H), 7.20-7.12 (m, 2H), 6.98 (t, J = 7.9 Hz, 1H), 6.70 (d, J = 7.5 Hz, 1H), 6.61 (d, J = 8.2 Hz, 1H), 5.41 (s, 2H), 3.91 (t, J = 5.4 Hz, 2H), 3.76 (t, J = 6.8 Hz, 2H), 2.73 (t, J = 7.1 Hz, 2H), 2.55 (br. s, 2H), 2.22-2.10 (m, 5H), 1.87 (s, 3H), 1.86-1.79 (m, 2H) | 10.5 min, 99.8% 9.4 min, 99.8% |
| 97 | 2-((4-(1-(4-(2,3-Dimethylphenoxy)butanoyl)-1,2,3,4-tetrahydroquinolin-5-yl)-1H-pyrazol-1-yl)methyl)-5-fluorobenzoic acid | 2-CO$_2$H, 5-F-C$_6$H$_3$-CH$_2$- | 542.2 | 7.70 (d, J = 7.9 Hz, 1H), 7.55 (s, 1H), 7.46 (s, 1H), 7.27-7.05 (m, 5H), 6.99 (t, J = 7.8 Hz, 1H), 6.71 (d, J = 7.5 Hz, 1H), 6.62 (d, J = 8.1 Hz, 1H), 5.66 (s, 2H), 3.91 (br. s, 2H), 3.76 (t, J = 6.7 Hz, 2H), 2.73 (t, J = 7.1 Hz, 2H), 2.56 (br. s, 2H), 2.24-2.08 (m, 5H), 1.89 (s, 3H), 1.87-1.76 (m, 2H) | 11.0 min, 99.1% 9.7 min, 98.8% |
| 98 | 3-Chloro-2-((4-(1-(4-(2,3-dimethylphenoxy)butanoyl)-1,2,3,4-tetrahydroquinolin-5-yl)-1H-pyrazol-1-yl)methyl)benzoic acid | 2-CO$_2$H, 3-Cl-C$_6$H$_3$-CH$_2$- | 558.2 | 7.77 (d, J = 7.7 Hz, 1H), 7.59 (s, 1H), 7.53 (d, J = 7.0 Hz, 1H), 7.48 (s, 1H), 7.41 (t, J = 7.9 Hz, 1H), 7.24 (s, 1H), 7.19 (t, J = 7.6 Hz, 1H), 7.10 (d, J = 8.4 Hz, 1H), 7.00 (t, J = 7.9 Hz, 1H), 6.73 (d, J = 7.5 Hz, 1H), 6.63 (d, J = 8.1 Hz, 1H), 5.57 (s, 2H), 3.91 (t, J = 5.2 Hz, 2H), 3.77 (t, J = 6.8 Hz, 2H), 2.73 (t, J = 7.1 Hz, 2H), 2.53 (br. s, 2H), 2.23-2.10 (m, 5H), 1.88 (s, 3H), 1.88-1.78 (m, 2H) | 11.4 min, 98.7% 10.0 min, 98.6% |

TABLE 7-continued

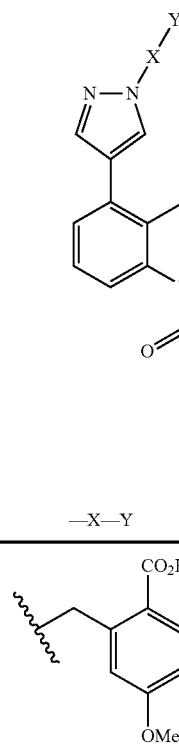

| Example | Name | —X—Y | LCMS, [M + H]+ | ¹H NMR (400 MHz, CDCl₃) δ | HPLC-1: Rt min, purity; HPLC-2: Rt min, purity |
|---|---|---|---|---|---|
| 99 | 2-((4-(1-(4-(2,3-Dimethylphenoxy)butanoyl)-1,2,3,4-tetrahydroquinolin-5-yl)-1H-pyrazol-1-yl)methyl)-4-methoxybenzoic acid | 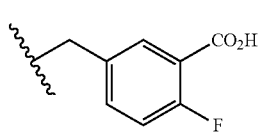 [SMILES: *Cc1ccc(F)c(C(=O)O)c1] | 554.3 | 8.09 (d, J = 8.8 Hz, 1H), 7.58 (s, 1H), 7.47 (s, 1H), 7.24 (s, 1H), 7.16 (d, J = 4.0 Hz, 2H), 6.98 (t, J = 7.9 Hz, 1H), 6.87 (dd, J = 8.8, 2.5 Hz, 1H), 6.71 (d, J = 7.5 Hz, 1H), 6.62 (d, J = 8.1 Hz, 1H), 6.43 (d, J = 2.5 Hz, 1H), 5.77 (s, 2H), 3.91 (t, J = 5.2 Hz, 2H), 3.82-3.69 (m, 5H), 2.73 (t, J = 7.1 Hz, 2H), 2.59 (s, 2H), 2.24-2.09 (m, 5H), 1.89 (s, 3H), 1.83 (dt, J = 13.2, 6.7 Hz, 2H) | 10.8 min, 99.3% 9.5 min, 99.4% |
| 100 | 5-((4-(1-(4-(2,3-Dimethylphenoxy)butanoyl)-1,2,3,4-tetrahydroquinolin-5-yl)-1H-pyrazol-1-yl)methyl)-2-fluorobenzoic acid | 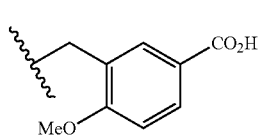 [SMILES: *Cc1cc(C(=O)O)ccc1OC] | 542.2 | 8.05 (dd, J = 6.8, 2.3 Hz, 1H), 7.62 (s, 1H), 7.45 (ddd, J = 8.2, 4.3, 2.5 Hz, 1H), 7.37 (s, 1H), 7.24 (s, 1H), 7.19-7.08 (m, 3H), 6.99 (t, J = 7.9 Hz, 1H), 6.71 (d, J = 7.5 Hz, 1H), 6.62 (d, J = 8.2 Hz, 1H), 5.35 (s, 2H), 3.91 (t, J = 5.4 Hz, 2H), 3.77 (t, J = 6.8 Hz, 2H), 2.73 (t, J = 7.1 Hz, 2H), 2.56 (br. s, 2H), 2.22-2.08 (m, 5H), 1.88 (s, 3H), 1.88-1.78 (m, 2H) | 10.5 min, 97.4% 9.5 min, 99.9% |
| 101 | 3-((4-(1-(4-(2,3-Dimethylphenoxy)butanoyl)-1,2,3,4-tetrahydroquinolin-5-yl)-1H-pyrazol-1-yl)methyl)-4-methoxybenzoic acid | 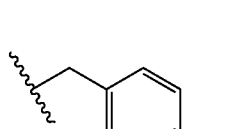 | 554.3 | 8.17 (d, J = 1.8 Hz, 1H), 8.09 (dd, J = 8.6, 2.0 Hz, 1H), 7.63 (s, 1H), 7.46 (s, 1H), 7.24 (s, 1H), 7.19-7.11 (m, 2H), 6.99 (t, J = 7.8 Hz, 1H), 6.94 (d, J = 8.7 Hz, 1H), 6.72 (d, J = 7.5 Hz, 1H), 6.63 (d, J = 8.1 Hz, 1H), 5.38 (s, 2H), 3.91 (s, 5H), 3.76 (t, J = 6.8 Hz, 2H), 2.73 (t, J = 7.2 Hz, 2H), 2.59 (br. s, 2H), 2.24-2.10 (m, 5H), 1.90 (s, 3H), 1.83 (dt, J = 13.3, 6.7 Hz, 2H) | 10.7 min, 100% 9.6 min, 99.3% |
| 102 | 4-((4-(1-(4-(2,3-Dimethylphenoxy)butanoyl)-1,2,3,4-tetrahydroquinolin-5-yl)-1H-pyrazol-1-yl)methyl)-3-methoxybenzoic acid | 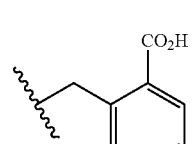 | 554.2 | 8.18 (d, J = 1.9 Hz, 1H), 8.09 (dd, J = 8.5, 2.1 Hz, 1H), 7.64 (s, 1H), 7.47 (s, 1H), 7.24 (s, 1H), 7.19-7.10 (m, 2H), 6.99 (t, J = 7.8 Hz, 1H), 6.94 (d, J = 8.7 Hz, 1H), 6.72 (d, J = 7.5 Hz, 1H), 6.63 (d, J = 8.2 Hz, 1H), 5.38 (s, 2H), 3.98-3.86 (m, 5H), 3.76 (t, J = 6.8 Hz, 2H), 2.73 (t, J = 7.1 Hz, 2H), 2.59 (br. s, 2H), 2.24-2.10 (m, 5H), 1.90 (s, 3H), 1.83 (dt, J = 13.2, 6.7 Hz, 2H) | 10.3 min, 100% 9.1 min, 97.6% |
| 103 | 2-((4-(1-(4-(2,3-Dimethylphenoxy)butanoyl)-1,2,3,4-tetrahydroquinolin-5-yl)-1H-pyrazol-1-yl)methyl)-3-fluorobenzoic acid | | 542.2 | 7.70 (d, J = 7.8 Hz, 1H), 7.53 (s, 1H), 7.51-7.41 (m, 2H), 7.30-7.19 (m, 2H), 7.16 (d, J = 7.6 Hz, 1H), 7.10 (d, J = 8.4 Hz, 1H), 7.00 (t, J = 7.9 Hz, 1H), 6.73 (d, J = 7.5 Hz, 1H), 6.62 (d, J = 8.1 Hz, 1H), 5.53 (d, J = 1.8 Hz, 2H), 3.91 (br. s, 2H), 3.76 (t, J = 6.8 Hz, 2H), 2.72 (t, J = 7.1 Hz, 2H), 2.53 (br. s, 2H), 2.23-2.08 (m, 5H), 1.88 (s, 3H), 1.87-1.77 (m, 2H) | 10.7 min, 99.0% 9.4 min, 99.5% |

TABLE 7-continued

| Example | Name | —X—Y | LCMS, [M + H]+ | 1H NMR (400 MHz, CDCl3) δ | HPLC-1: Rt min, purity; HPLC-2: Rt min, purity |
|---|---|---|---|---|---|
| 104 | 2-((4-(1-(4-(2,3-Dimethylphenoxy)butanoyl)-1,2,3,4-tetrahydroquinolin-5-yl)-1H-pyrazol-1-yl)methyl)oxazole-4-carboxylic acid | | 515.2 | 8.29 (s, 1H), 7.56 (s, 1H), 7.46 (s, 1H), 7.26 (s, 1H), 7.19-7.08 (m, 3H), 6.99 (t, J = 7.9 Hz, 1H), 6.72 (d, J = 7.5 Hz, 1H), 6.62 (d, J = 8.2 Hz, 1H), 5.53 (s, 2H), 3.91 (br. s, 2H), 3.77 (t, J = 6.8 Hz, 2H), 2.73 (t, J = 7.1 Hz, 2H), 2.55 (br. s, 2H), 2.26-2.05 (m, 5H), 1.88 (s, 3H), 1.87-1.76 (m, 2H) | 9.0 min, 99.6%; 8.2 min, 100% |
| 105 | 5-((4-(1-(4-(2,3-Dimethylphenoxy)butanoyl)-1,2,3,4-tetrahydroquinolin-5-yl)-1H-pyrazol-1-yl)methyl)furan-2-carboxylic acid | | 547.3 | 7.65 (s, 1H), 7.52 (s, 1H), 7.18-7.10 (m, 2H), 6.99 (t, J = 7.9 Hz, 1H), 6.72 (d, J = 7.4 Hz, 1H), 6.69 (d, J = 5.9 Hz, 1H), 6.62 (d, J = 8.1 Hz, 1H), 3.91 (d, J = 5.4 Hz, 2H), 3.75 (t, J = 6.8 Hz, 2H), 3.43 (dd, J = 12.0, 6.0 Hz, 2H), 2.73 (t, J = 7.1 Hz, 2H), 2.55 (br. s, 2H), 2.50 (t, J = 6.0 Hz, 2H), 2.22-2.10 (m, 5H), 1.90 (s, 3H), 1.86 (s, 6H), 1.85-1.79 (m, 2H) | 9.3 min, 100%; 8.3 min, 100% |
| 106 | 2-((4-(1-(4-(2,3-Dimethylphenoxy)butanoyl)-1,2,3,4-tetrahydroquinolin-5-yl)-1H-pyrazol-1-yl)methyl)furan-3-carboxylic acid | | 514.2 | 7.60 (s, 1H), 7.50 (s, 1H), 7.39 (d, J = 2.0 Hz, 1H), 7.20-7.10 (m, 2H), 6.99 (t, J = 7.8 Hz, 1H), 6.78 (d, J = 1.9 Hz, 1H), 6.72 (d, J = 7.5 Hz, 1H), 6.62 (d, J = 8.1 Hz, 1H), 5.70 (s, 2H), 3.91 (br. s, 2H), 3.76 (t, J = 6.8 Hz, 2H), 2.73 (t, J = 7.1 Hz, 2H), 2.56 (br. s, 2H), 2.23-2.09 (m, 5H), 1.89 (s, 3H), 1.83 (dt, J = 13.1, 6.7 Hz, 2H) | 10.0 min, 100%; 8.9 min, 100% |
| 107 | 3-((4-(1-(4-(2,3-Dimethylphenoxy)butanoyl)-1,2,3,4-tetrahydroquinolin-5-yl)-1H-pyrazol-1-yl)methyl)thiophene-2-carboxylic acid | | 530.1 | 7.56 (s, 1H), 7.50 (d, J = 5.0 Hz, 1H), 7.45 (s, 1H), 7.24 (s, 1H), 7.19-7.10 (m, 2H), 6.99 (dd, J = 10.3, 5.3 Hz, 1H), 6.88 (d, J = 5.2 Hz, 1H), 6.71 (d, J = 7.5 Hz, 1H), 6.62 (d, J = 8.1 Hz, 1H), 5.68 (s, 2H), 3.91 (br. s, 2H), 3.76 (t, J = 6.8 Hz, 2H), 2.73 (t, J = 7.1 Hz, 2H), 2.56 (br. s, 2H), 2.23-2.10 (m, 5H), 1.88 (s, 3H), 1.87-1.79 (m, 2H) | 10.5 min, 98.4%; 9.3 min, 98.2% |
| 108 | 4-Cyano-3-((4-(1-(4-(2,3-dimethylphenoxy)butanoyl)-1,2,3,4-tetrahydroquinolin-5-yl)-1H-pyrazol-1-yl)methyl)benzoic acid | | 549.3 | 8.55 (s, 1H), 8.19 (dd, J = 8.0, 1.3 Hz, 1H), 7.80 (d, J = 8.0 Hz, 1H), 7.77 (s, 2H), 7.24 (s, 1H), 7.21-7.09 (m, 2H), 7.00 (t, J = 7.9 Hz, 1H), 6.72 (d, J = 7.5 Hz, 1H), 6.64 (d, J = 8.2 Hz, 1H), 5.60 (s, 2H), 3.93 (t, J = 5.4 Hz, 2H), 3.78 (t, J = 6.8 Hz, 2H), 2.73 (t, J = 7.2 Hz, 2H), 2.62 (br. s, 2H), 2.26-2.07 (m, 5H), 1.92 (s, 3H), 1.85 (dt, J = 13.2, 6.6 Hz, 2H) | 10.3 min, 100%; 9.2 min, 100% |

TABLE 7-continued

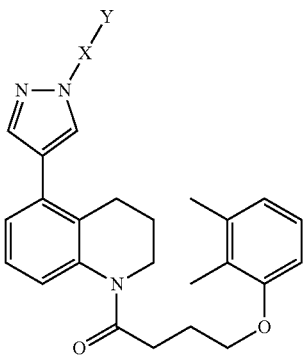

| Example | Name | —X—Y | LCMS, [M + H]⁺ | ¹H NMR (400 MHz, CDCl₃) δ | HPLC-1: Rt min, purity; HPLC-2: Rt min, purity |
|---|---|---|---|---|---|
| 109 | 5-((4-(1-(4-(2,3-Dimethylphenoxy)butanoyl)-1,2,3,4-tetrahydroquinolin-5-yl)-1H-pyrazol-1-yl)methyl)thiophene-2-carboxylic acid | thiophene-CO₂H | 530.3 | 7.73 (d, J = 3.8 Hz, 1H), 7.55 (s, 1H), 7.34 (s, 1H), 7.19-7.10 (m, 3H), 7.05 (d, J = 3.7 Hz, 1H), 6.99 (t, J = 7.9 Hz, 1H), 6.71 (d, J = 7.5 Hz, 1H), 6.62 (d, J = 8.1 Hz, 1H), 5.51 (s, 2H), 3.90 (br. s, 2H), 3.76 (t, J = 6.8 Hz, 2H), 2.73 (t, J = 7.1 Hz, 2H), 2.54 (br. s, 2H), 2.24-2.08 (m, 5H), 1.87 (s, 3H), 1.86-1.76 (m, 2H) | 9.8 min, 100% 8.6 min, 100% |
| 110 | 2-(3-((4-(1-(4-(2,3-Dimethylphenoxy)(butanoyl)-1,2,3,4-tetrahydroquinolin-5-yl)-1H-pyrazol-1-yl)methyl)phenyl)acetic acid | phenyl-CH₂CO₂H | 538.3 | 7.53 (s, 1H), 7.35-7.28 (m, 2H), 7.28-7.22 (m, 2H), 7.21 (s, 1H), 7.18-7.09 (m, 3H), 6.98 (t, J = 7.8 Hz, 1H), 6.70 (d, J = 7.5 Hz, 1H), 6.61 (d, J = 8.1 Hz, 1H), 5.32 (s, 2H), 3.90 (t, J = 5.2 Hz, 2H), 3.75 (t, J = 6.8 Hz, 2H), 3.63 (s, 2H), 2.72 (t, J = 7.1 Hz, 2H), 2.54 (br. s, 2H), 2.22-2.07 (m, 5H), 1.88 (s, 3H), 1.81 (dt, J = 13.3, 6.7 Hz, 2H) | 10.5 min, 99.0% 9.4 min, 100% |
| 110A | 1-(5-(1-((2-(Dimethylamino)pyrimidin-4-yl)methyl)-1H-pyrazol-4-yl)-3,4-dihydroquinolin-1(2H)-yl)-4-(2,3-dimethylphenoxy)butan-1-one | pyrimidin-N(CH₃)₂ | 525.3 | 8.45 (1 H, d, J = 5.94 Hz), 7.63 (1 H, s), 7.45 (1 H, s), 7.14-7.26 (3 H, m), 7.02 (1 H, t, J = 7.81 Hz), 6.75 (1 H, d, J = 7.48 Hz), 6.65 (1 H, d, J = 8.14 Hz), 6.39 (1 H, d, J = 5.94 Hz), 5.40 (2 H, s), 3.94 (2 H, t, J = 5.28 Hz), 3.82 (2 H, t, J = 6.82 Hz), 3.31 (6 H, s), 2.79 (2 H, t, J = 7.15 Hz), 2.59 (2 H, t, J = 5.83 Hz), 2.13-2.27 (5 H, m), 1.83-2.00 (5 H, m) | 9.0 min, 94.4% 9.0 min, 93.2% |
| 110B | 2-(4-((4-(1-(4-(2,3-Dimethylphenoxy)butanoyl)-1,2,3,4-tetrahydroquinolin-5-yl)-1H-pyrazol-1-yl)methyl)pyrimidin-2-ylamino)acetic acid | pyrimidin-NH-CH₂CO₂H | 555.3 | 8.15 (1 H, br. s.), 7.60 (1 H, s), 7.45 (1 H, s), 7.12-7.25 (3 H, m), 7.01 (1 H, t, J = 7.81 Hz), 6.74 (1 H, d, J = 7.48 Hz), 6.65 (1 H, d, J = 8.14 Hz), 6.25 (1 H, d, J = 5.06 Hz), 5.28 (2 H, s), 4.23 (2 H, d, J = 3.52 Hz), 3.94 (2 H, t, J = 5.61 Hz), 3.79 (2 H, t, J = 6.82 Hz), 2.76 (2 H, t, J = 7.15 Hz), 2.62 (2 H, t, J = 6.16 Hz), 2.13-2.26 (5 H, m), 1.82-1.96 (5 H, m) | 8.6 min, 95.2% 8.6 min, 98.3% |
| 110C | 2-(4-((4-(1-(4-(2,3-Dimethylphenoxy)butanoyl)-1,2,3,4-tetrahydroquinolin-5-yl)-1H-pyrazol-1-yl)methyl)benzamido)ethanesulfonic acid | phenyl-C(O)NH-CH₂CH₂SO₃H | 631.1 | 7.84 (d, J = 8.2 Hz, 2H), 7.79-7.68 (m, 1H), 7.66-7.51 (m, 1H), 7.36 (d, J = 8.3 Hz, 2H), 7.31-7.08 (m, 3H), 6.96 (t, J = 7.9 Hz, 1H), 6.72-6.59 (m, 2H), 5.48 (s, 2H), 3.86 (s, 2H), 3.80 (t, J = 6.6 Hz, 2H), 3.74 (t, J = 6.8 Hz, 2H), 3.08 (t, J = 6.7 Hz, 2H), 2.81 (t, J = 6.8 Hz, 2H), 2.49 (s, 2H), 2.18-2.07 (m, 2H), 2.02 (s, 3H), 1.91-1.60 (m, 5H)* | 9.3 min, 99.9% 7.0 min, 99.3% |

TABLE 7-continued

| Example | Name | —X—Y | LCMS, [M + H]+ | 1H NMR (400 MHz, CDCl3) δ | HPLC-1: Rt min, purity; HPLC-2: Rt min, purity |
|---|---|---|---|---|---|
| 110D | (3-(3-(2-(4-(1-(4-(2,3-Dimethylphenoxy)butanoyl)-1,2,3,4-tetrahydroquinolin-5-yl)-1H-pyrazol-1-yl)ethyl)phenyl)ureido)methanesulfonic acid | | 646.5 | 7.44 (s, 1H), 7.20 (dd, J = 12.1, 8.4 Hz, 3H), 7.14 (d, J = 7.5 Hz, 1H), 7.09 (t, J = 7.8 Hz, 2H), 7.01 (t, J = 7.9 Hz, 1H), 6.98-6.82 (m, 1H), 6.73 (d, J = 7.5 Hz, 1H), 6.64 (d, J = 7.6 Hz, 2H), 4.41 (t, J = 6.6 Hz, 2H), 4.32 (s, 2H), 3.89-3.75 (m, 2H), 3.70 (t, J = 6.8 Hz, 2H), 3.09 (t, J = 6.5 Hz, 2H), 2.79 (t, J = 6.7 Hz, 2H), 2.15-2.06 (m, 4H), 2.04 (s, 3H), 1.78-1.66 (m, 2H), 1.66-1.49 (m, 3H)* | N/A 9.3 min, 99.5% |
| 110E | 1-(5-(1-(3-Aminophenethyl)-1H-pyrazol-4-yl)-3,4-dihydroquinolin-1(2H)-yl)-4-(2,3-dimethylphenoxy)butan-1-one | | 509.3 | 7.53 (s, 1H), 7.23-6.93 (m, 6H), 6.74 (d, J = 7.1 Hz, 1H), 6.64 (d, J = 7.4 Hz, 1H), 6.52 (dd, J = 15.1, 7.9 Hz, 2H), 6.41 (s, 1H), 4.43-4.26 (m, 2H), 4.02-3.87 (m, 2H), 3.87-3.70 (m, 2H), 3.70-3.49 (m, 2H), 3.17-3.01 (m, 2H), 2.82-2.66 (m, 2H), 2.59-2.39 (m, 2H), 2.19 (s, 5H), 1.92 (s, 3H), 1.87-1.72 (m, 2H) | |
| 110F | 2-(3-(2-(4-(1-(4-(2,3-Dimethylphenoxy)butanoyl)-1,2,3,4-tetrahydroquinolin-5-yl)-1H-pyrazol-1-yl)ethyl)ureido)ethanesulfonic acid | | 584.1 | 7.88-7.64 (m, 2H), 7.35-7.13 (m, 3H), 7.00 (t, J = 7.9 Hz, 1H), 6.72 (d, J = 7.5 Hz, 1H), 6.68 (d, J = 8.2 Hz, 1H), 4.35 (t, J = 5.6 Hz, 2H), 3.94-3.84 (m, 2H), 3.76 (t, J = 6.8 Hz, 2H), 3.62-3.55 (m, 2H), 3.51 (t, J = 6.3 Hz, 2H), 2.96-2.87 (m, 2H), 2.80 (t, J = 6.9 Hz, 2H), 2.64-2.46 (m, 2H), 2.12 (s, 5H), 1.85 (s, 5H)* | 10.6 min, 99.7% 7.1 min, 99.5% |
| 110G | 2-(3-(2-(4-(1-(4-(2,3-Dimethylphenoxy)butanoyl)-1,2,3,4-tetrahydroquinolin-5-yl)-1H-pyrazol-1-yl)ethyl)ureido)acetic acid | | 534.1 | 7.55 (s, 1H), 7.47 (s, 1H), 7.32-7.18 (m, 2H), 7.18-7.05 (m, 1H), 6.99 (t, J = 1.9 Hz, 1H), 6.72 (d, J = 7.6 Hz, 1H), 6.66 (d, J = 8.1 Hz, 1H), 5.49 (s, 1H), 4.26 (t, J = 5.9 Hz, 2H), 3.92-3.83 (m, 3H), 3.74 (t, J = 6.8 Hz, 2H), 3.55 (t, J = 5.9 Hz, 2H), 3.39-3.32 (m, 2H), 2.80 (t, J = 6.9 Hz, 2H), 2.61-2.42 (m, 2H), 2.11 (d, J = 7.9 Hz, 4H), 1.89-1.65 (m, 4H)* | 8.9 min, 99.5% 8.7 min, 99.0% |
| 110H | 1-(2-(4-(1-(4-(2,3-Dimethylphenoxy)butanoyl)-1,2,3,4-tetrahydroquinolin-5-yl)-1H-pyrazol-1-yl)ethylcarbamoyl)cyclopropanecarboxylic acid | | 545.1 | 7.54-7.36 (m, 2H), 7.33-7.06 (m, 3H), 6.99 (t, J = 7.9 Hz, 1H), 6.72 (d, J = 7.5 Hz, 1H), 6.66 (d, J = 8.1 Hz, 1H), 4.31 (t, J = 5.8 Hz, 2H), 3.86 (s, 2H), 3.80-3.64 (m, 4H), 2.81 (t, J = 6.8 Hz, 2H), 2.58-2.35 (m, 2H), 2.21-2.00 (m, 5H), 1.91-1.60 (m, 5H), 1.58-1.42 (m, 4H)* | 10.3 min, 99.6% 9.6 min, 99.3% |

TABLE 7-continued

| Example | Name | —X—Y | LCMS, [M + H]+ | ¹H NMR (400 MHz, CDCl₃) δ | HPLC-1: Rt min, purity; HPLC-2: Rt min, purity |
|---|---|---|---|---|---|
| 110J | 3-(2-(4-(1-(4-(2,3-Dimethylphenoxy)butanoyl)-1,2,3,4-tetrahydroquinolin-5-yl)-1H-pyrazol-1-yl)ethylamino)-3-oxopropanoic acid | | 519.1 | 7.55 (s, 1H), 7.47 (s, 1H), 7.36-7.07 (m, 3H), 6.99 (t, J = 7.8 Hz, 1H), 6.72 (d, J = 7.5 Hz, 1H), 6.67 (d, J = 8.1 Hz, 1H), 4.31 (t, J = 5.7 Hz, 2H), 3.94-3.81 (m, 2H), 3.74 (t, J = 6.7 Hz, 2H), 3.64 (t, J = 5.7 Hz, 2H), 3.24 (s, 2H), 2.80 (tp, J = 6.8 Hz, 2H), 2.60-2.44 (m, 2H), 2.21-2.04 (m, 5H), 1.89-1.66 (m, 5H)* | 9.3 min, 99.2% 8.9 min, 99.6% |
| 110K | 2-(1-(2-(4-(1-(4-(2,3-Dimethylphenoxy)butanoyl)-1,2,3,4-tetrahydroquinolin-5-yl)-1H-pyrazol-1-yl)ethylcarbamoyl)cyclopropanecarboxamido)ethanesulfonic acid | | 652.1 | 7.87 (s, 1H), 7.74 (s, 1H), 7.35-7.13 (m, 3H), 6.99 (t, J = 7.9 Hz, 1H), 6.72 (d, J = 7.5 Hz, 1H), 6.68 (d, J = 8.2 Hz, 1H), 4.50-4.39 (m, 2H), 3.97-3.82 (m, 2H), 3.76 (t, J = 6.8 Hz, 2H), 3.72-3.65 (m, 2H), 3.65-3.57 (m, 2H), 3.06-2.96 (m, 2H), 2.81 (t, J = 6.9 Hz, 2H), 2.65-2.46 (m, 2H), 2.21-2.05 (m, 5H), 1.83 (dd, J = 13.6, 6.8 Hz, 5H), 1.37 (dd, J = 6.7, 3.4 Hz, 1H), 1.29-1.17 (m, 3H)* | 8.7 min, 100% 6.7 min, 100% |
| 110L | (N-(3-((4-(1-(4-(2,3-Dimethylphenoxy)butanoyl)-1,2,3,4-tetrahydroquinolin-5-yl)-1H-pyrazol-1-yl)methyl)phenyl)sulfamoylamino)methanesulfonic acid | | 668.3 | 7.69 (s, 1H), 7.52 (s, 1H), 7.37-7.27 (m, 3H), 7.27-7.19 (m, 3H), 7.00 (d, J = 7.7 Hz, 1H), 6.96 (d, J = 7.9 Hz, 1H), 6.66 (t, J = 8.9 Hz, 2H), 5.37 (s, 2H), 4.07 (s, 2H), 3.92-3.81 (m, 2H), 3.74 (t, J = 6.9 Hz, 2H), 2.80 (t, J = 6.8 Hz, 2H), 2.59-2.43 (m, 2H), 2.11 (dt, J = 13.0, 6.6 Hz, 2H), 2.05 (s, 3H), 1.88-1.79 (m, 2H), 1.79-1.67 (m, 3H)* | N/A 7.4 min, 93.7% |
| 110M | 3-((4-(1-(4-(2,3-Dimethylphenoxy)butanoyl)-1,2,3,4-tetrahydroquinolin-5-yl)-1H-pyrazol-1-yl)methyl)benzenesulfonic acid | | 560.2 | 7.86 (s, 1H), 7.84-7.80 (m, 1H), 7.78 (s, 1H), 7.69 (s, 1H), 7.47 (t, J = 7.7 Hz, 1H), 7.40 (d, J = 7.8 Hz, 1H), 7.32-7.13 (m, 3H), 6.97 (t, J = 7.9 Hz, 1H), 6.67 (t, J = 8.2 Hz, 2H), 5.52 (s, 2H), 3.86 (m, 2H), 3.75 (t, J = 6.8 Hz, 2H), 2.81 (t, J = 6.9 Hz, 2H), 2.60-2.42 (m, 2H), 2.12 (dt, J = 12.5, 6.4 Hz, 2H), 2.05 (s, 3H), 1.90-1.64 (m, 5H)* | |
| 110N | 3-(4-(1-(4-(2,3-Dimethylphenoxy)butanoyl)-1,2,3,4-tetrahydroquinolin-5-yl)-1H-pyrazol-1-yl)benzoic acid | | 510.0 | 8.39 (s, 1H), 8.13-8.02 (m, 2H), 7.78 (s, 2H), 7.64 (t, J = 7.9 Hz, 1H), 7.27 (d, J = 3.8 Hz, 2H), 7.23-7.10 (m, 1H), 7.05 (t, J = 7.9 Hz, 1H), 6.74 (d, J = 7.5 Hz, 1H), 6.65 (d, J = 8.1 Hz, 1H), 3.92 (s, 2H), 3.83 (t, J = 6.8 Hz, 2H), 2.84 (t, J = 7.0 Hz, 2H), 2.60 (s, 2H), 2.29-2.16 (m, 2H), 2.11 (s, 3H), 2.01-1.70 (m, 5H) | N/A 13.3 min, 100% |

TABLE 7-continued

| Example | Name | —X—Y | LCMS, [M + H]+ | 1H NMR (400 MHz, CDCl3) δ | HPLC-1: Rt min, purity; HPLC-2: Rt min, purity |
|---|---|---|---|---|---|
| 110P | 2-(3-(4-(1-(4-(2,3-Dimethylphenoxy)butanoyl)-1,2,3,4-tetrahydroquinolin-5-yl)-1H-pyrazol-1-yl)phenyl)acetic acid | | 524.1 | 1H NMR (400 MHz, CHLOROFORM-D) δ 7.77 (s, 1H), 7.73 (s, 1H), 7.72-7.68 (m, 1H), 7.64-7.57 (m, 1H), 7.45 (t, J = 7.9 Hz, 1H), 7.30-7.24 (m, 1H), 7.24-7.20 (m, 2H), 7.20-7.06 (m, 1H), 7.02 (t, J = 7.9 Hz, 1H), 6.72 (d, J = 7.5 Hz, 1H), 6.65 (d, J = 8.1 Hz, 1H), 3.93 (s, 2H), 3.80 (t, J = 6.8 Hz, 2H), 3.76 (s, 2H), 2.78 (t, J = 7.1 Hz, 2H), 2.61 (m, 2H), 2.20 (dt, J = 12.9, 6.6 Hz, 2H), 2.14 (s, 3H), 1.97-1.76 (m, 5H) | N/A 13.1 min, 99.7% |
| 110Q | 4-((4-(1-(4-(2,3-Dimethylphenoxy)butanoyl)-1,2,3,4-tetrahydroquinolin-5-yl)-1H-pyrazol-1-yl)methyl)-2,3,5,6-tetrafluorobenzoic acid | | 596.0 | 7.69 (s, 1H), 7.46 (s, 1H), 7.33-7.09 (m, 3H), 6.97 (t, J = 7.8 Hz, 1H), 6.68 (d, J = 7.6 Hz, 1H), 6.65 (d, J = 8.0 Hz, 1H), 5.56 (s, 2H), 3.87 (s, 2H), 3.74 (t, J = 6.8 Hz, 2H), 2.80 (t, J = 6.8 Hz, 2H), 2.60-2.40 (m, 2H), 2.19-2.04 (m, 5H), 1.90-1.64 (m, 5H)* | 12.0 min, 95.8% 13.1 min, 97.9% |
| 110R | Diethyl 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)ethylphosphonate | | 702.3 | 7.54 (s, 1H), 7.46 (s, 1H), 7.36 (s, 1H), 7.32-7.21 (m, 3H), 7.15 (s, 2H), 7.00 (t, J = 7.8 Hz, 1H), 6.92-6.85 (m, 1H), 6.72 (d, J = 7.5 Hz, 1H), 6.64 (d, J = 8.2 Hz, 1H), 6.00-5.89 (m, 1H), 5.29 (s, 2H), 4.15-4.02 (m, 4H), 3.93 (t, J = 5.3 Hz, 2H), 3.77 (t, J = 6.8 Hz, 2H), 3.59 (dd, J = 11.8, 5.8 Hz, 1H), 3.55 (dd, J = 11.6, 5.7 Hz, 1H), 2.73 (t, J = 7.2 Hz, 2H), 2.59 (t, J = 5.7 Hz, 2H), 2.22-2.13 (m, 5H), 2.09-2.00 (m, 2H), 1.92 (s, 3H), 1.88-1.80 (m, 2H), 1.31 (t, J = 7.1 Hz, 6H) | 10.1 min, 95.7% 9.2 min, 96.4% |
| 110S | (3-((4-(1-(4-(2,3-Dimethylphenoxy)butanoyl)-1,2,3,4-tetrahydroquinolin-5-yl)-1H-pyrazol-1-yl)methyl)phenylsulfonamido)methanesulfonic acid | | 653.2 | 7.86 (d, J = 7.7 Hz, 1H), 7.81 (s, 1H), 7.67 (s, 1H), 7.56 (t, J = 7.7 Hz, 1H), 7.51 (s, 1H), 7.49 (s, 1H), 7.26 (d, J = 8.2 Hz, 1H), 7.22 (t, J = 7.6 Hz, 1H), 7.20-7.05 (m, 1H), 6.96 (t, J = 7.9 Hz, 1H), 6.71-6.60 (m, 1H), 5.47 (s, 2H), 3.97 (s, 2H), 3.93-3.80 (m, 2H), 3.74 (t, J = 6.8 Hz, 2H), 2.80 (t, J = 6.8 Hz, 2H), 2.60-2.39 (m, 2H), 2.11 (dt, J = 12.4, 6.1 Hz, 2H), 2.05 (s, 3H), 1.91-1.63 (m, 5H)* | 10.6 min, 72.2% 8.8 min, 100% |

TABLE 7-continued

| Example | Name | —X—Y | LCMS, [M + H]+ | 1H NMR (400 MHz, CDCl3) δ | HPLC-1: Rt min, purity; HPLC-2: Rt min, purity |
|---|---|---|---|---|---|
| 110T | 2-(3-((4-(1-(4-(2,3-Dimethylphenoxy)butanoyl)-1,2,3,4-tetrahydroquinolin-5-yl)-1H-pyrazol-1-yl)methyl)phenylsulfonamido)ethanesulfonic acid | | 667.2 | 7.83 (d, J = 7.9 Hz, 1H), 7.78 (s, 1H), 7.69 (s, 1H), 7.59 (t, J = 7.7 Hz, 1H), 7.53 (d, J = 8.2 Hz, 2H), 7.27 (d, J = 7.9 Hz, 1H), 7.23 (t, J = 7.6 Hz, 1H), 7.21-7.06 (m, 1H), 6.97 (t, J = 7.9 Hz, 1H), 6.73-6.60 (m, 2H), 5.49 (s, 2H), 3.94-3.80 (m, 2H), 3.75 (t, J = 6.8 Hz, 2H), 3.30-3.24 (m, 2H), 2.95-2.86 (m, 2H), 2.81 (t, J = 6.9 Hz, 2H), 2.61-2.43 (m, 2H), 2.12 (dt, J = 12.5, 6.3 Hz, 2H), 2.06 (s, 3H), 1.89-1.63 (m, 5H)* | 11.1 min, 98.1% 7.7 min, 96.4% |
| 110U | 2-(3-(3-((4-(1-(4-(2,3-Dimethylphenoxy)butanoyl)-1,2,3,4-tetrahydroquinolin-5-yl)-1H-pyrazol-1-yl)methyl)phenyl)ureido)ethylphosphonic acid | | 646.2 | 7.57 (s, 1H), 7.48 (s, 1H), 7.33 (s, 1H), 7.33-7.29 (m, 1H), 7.29-7.20 (m, 3H), 7.20-7.08 (m, 1H), 6.96 (t, J = 7.9 Hz, 1H), 6.91 (d, J = 7.5 Hz, 1H), 6.65 (t, J = 7.4 Hz, 2H), 5.33 (s, 2H), 3.93-3.79 (m, 2H), 3.74 (t, J = 6.8 Hz, 2H), 3.53-3.41 (m, 2H), 2.81 (t, J = 6.8 Hz, 2H), 2.59-2.39 (m, 2H), 2.18-2.08 (m, 2H), 2.04 (s, 3H), 2.02-1.98 (m, 1H), 1.98-1.92 (m, 1H), 1.79 (d, J = 6.4 Hz, 2H), 1.72 (s, 3H)* | 8.4 min, 98.9% 8.0 min, 99.0% |
| 110V | Ethyl hydrogen 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)ethylphosphonate | | 674.3 | 7.57 (s, 1H), 7.47 (s, 1H), 7.33 (s, 1H), 7.32-7.28 (m, 3H), 7.28-7.17 (m, 3H), 7.18-7.06 (m, 1H), 6.96 (t, J = 7.9 Hz, 1H), 6.90 (d, J = 7.3 Hz, 1H), 6.71-6.59 (m, 2H), 5.33 (s, 2H), 4.06 (dt, J = 14.7, 7.2 Hz, 2H), 3.91-3.78 (m, 2H), 3.73 (t, J = 6.8 Hz, 2H), 3.52-3.40 (m, 2H), 2.81 (t, J = 6.8 Hz, 2H), 2.55-2.39 (m, 2H), 2.11 (dt, J = 12.5, 6.3 Hz, 2H), 2.07-1.94 (m, 5H), 1.84-1.76 (m, 2H), 1.76-1.58 (m, 3H), 1.30 (t, J = 7.1 Hz, 3H)* | 9.3 min, 96.6% 8.4 min, 95.0% |
| 110W | (3-(3-((4-(1-(4-(2,3-Dimethylphenoxy)butanoyl)-1,2,3,4-tetrahydroquinolin-5-yl)-1H-pyrazol-1-yl)methyl)phenyl)ureido)methylphosphonic acid | | 632.2 | 7.56 (s, 1H), 7.47 (s, 1H), 7.35 (s, 1H), 7.31 (d, J = 8.3 Hz, 1H), 7.28-7.17 (m, 3H), 7.17-7.03 (m, 1H), 6.95 (t, J = 7.9 Hz, 1H), 6.89 (d, J = 7.3 Hz, 1H), 6.64 (t, J = 7.6 Hz, 2H), 5.31 (s, 2H), 3.90-3.78 (m, 2H), 3.78-3.67 (m, 3H), 3.57 (d, J = 11.7 Hz, 1H), 2.79 (t, J = 6.8 Hz, 2H), 2.52-2.38 (m, 2H), 2.10 (dt, J = 12.5, 6.2 Hz, 2H), 2.01 (s, 3H), 1.83-1.73 (m, 2H), 1.73-1.58 (m, 3H)* | 8.7 min, 83.7% 7.8 min, 95.9% |

TABLE 7-continued

| Example | Name | —X—Y | LCMS, [M + H]+ | 1H NMR (400 MHz, CDCl3) δ | HPLC-1: Rt min, purity; HPLC-2: Rt min, purity |
|---|---|---|---|---|---|
| 110X | 2-(3-(4-(1-(4-(2,3-Dimethylphenoxy)butanoyl)-1,2,3,4-tetrahydroquinolin-5-yl)-1H-pyrazol-1-yl)benzamido)ethanesulfonic acid | *3-benzamido group with —NHCH2CH2SO3H* | 617.2 | 8.24 (m, 1H), 8.18-8.03 (m, 1H), 7.98 (dd, J = 8.1, 1.7 Hz, 1H), 7.80 (d, J = 7.8 Hz, 1H), 7.71 (s, 1H), 7.62 (t, J = 7.9 Hz, 1H), 7.36 (d, J = 7.7 Hz, 1H), 7.27 (t, J = 7.7 Hz, 1H), 7.24-7.10 (m, 1H), 7.00 (t, J = 7.9 Hz, 1H), 6.67 (t, J = 8.3 Hz, 2H), 3.93-3.81 (m, 4H), 3.77 (t, J = 6.8 Hz, 2H), 3.14 (t, J = 6.7 Hz, 2H), 2.83 (t, J = 6.8 Hz, 2H), 2.66-2.45 (m, 2H), 2.13 (dt, J = 12.4, 6.3 Hz, 2H), 2.02 (s, 3H), 1.92-1.79 (m, 2H), 1.72 (s, 3H)* | 8.9 min, 82.5% 8.9 min, 98.4% |
| 110Y | 2-(5-((4-(1-(4-(2,3-Dimethylphenoxy)butanoyl)-1,2,3,4-tetrahydroquinolin-5-yl)-1H-pyrazol-1-yl)methyl)-2-fluorobenzamido)ethanesulfonic acid | *2-fluoro-5-methylene benzamido with —NHCH2CH2SO3H* | 649.1 | 7.79 (dd, J = 6.9, 2.3 Hz, 1H), 7.74 (s, 1H), 7.55 (s, 1H), 7.47 (ddd, J = 8.2, 4.6, 2.4 Hz, 1H), 7.31-7.20 (m, 3H), 7.20-7.10 (m, 1H), 6.97 (t, J = 7.9 Hz, 1H), 6.66 (t, J = 7.9 Hz, 2H), 5.43 (s, 2H), 3.93-3.84 (m, 2H), 3.82 (t, J = 6.6 Hz, 2H), 3.74 (t, J = 6.8 Hz, 2H), 3.07 (t, J = 6.6 Hz, 2H), 2.81 (t, J = 6.8 Hz, 2H), 2.57-2.39 (m, 2H), 2.12 (dt, J = 12.4, 6.3 Hz, 2H), 2.04 (s, 3H), 1.88-1.76 (m, 2H), 1.73 (s, 3H) | 9.4 min, 98.0% 8.6 min, 99.4% |
| 110Z | 2-(3-((4-(1-(4-(2,3-Dimethylphenoxy)butanoyl)-1,2,3,4-tetrahydroquinolin-5-yl)-1H-pyrazol-1-yl)methyl)-2,4-difluorobenzamido)ethanesulfonic acid | *2,4-difluoro-3-methylene benzamido with —NHCH2CH2SO3H* | 667.0 | 7.90 (dd, J = 15.1, 8.5 Hz, 1H), 7.72 (s, 1H), 7.48 (s, 1H), 7.31-7.09 (m, 4H), 6.96 (t, J = 7.9 Hz, 1H), 6.73-6.60 (m, 2H), 5.52 (s, 2H), 3.93-3.85 (m, 2H), 3.82 (t, J = 6.5 Hz, 2H), 3.74 (t, J = 6.8 Hz, 2H), 3.09 (d, J = 6.5 Hz, 2H), 2.79 (t, J = 6.8 Hz, 2H), 2.57-2.42 (m, 2H), 2.18-2.09 (m, 2H), 2.06 (s, 3H), 1.90-1.65 (m, 5H)* | 9.7 min, 93.7% 10.1 min, 94.8% |

*1H NMR (400 MHz, CD3OD) δ.

Example 111

3-((5-(1-(4-(2,3-Dimethylphenoxy)butanoyl)-1,2,3,4-tetrahydroquinolin-5-yl)-1H-tetrazol-1-yl)methyl)benzoic acid

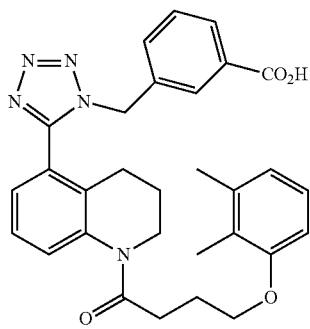 [SMILES: Cc1cccc(OCCCC(=O)N2CCCc3c(-c4nnnn4Cc4cccc(C(=O)O)c4)cccc32)c1C]

Step A. 1-(4-(2,3-Dimethylphenoxy)butanoyl)-1,2,3,4-tetrahydroquinoline-5-carbonitrile

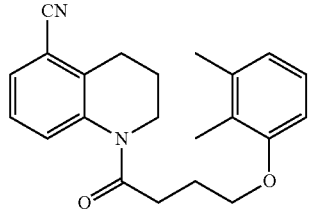 [SMILES: Cc1cccc(OCCCC(=O)N2CCCc3c(C#N)cccc32)c1C]

To a degassed solution of 1-(5-bromo-3,4-dihydroquinolin-1(2H)-yl)-4-(2,3-dimethylphenoxy)butan-1-one (0.330 g, 0.820 mmol) and dicyanozinc (0.116 g, 0.984 mmol) in DMF (1.50 mL) was added 1,1'-bis(diphenylphosphino)ferrocene (0.023 g, 0.041 mmol) and Pd$_2$(dba)$_3$ (0.038 g, 0.041 mmol). The vial was purged with argon, sealed, and heated at 120° C. for 16 h. The mixture was partitioned between EtOAc and water. The organic layer was washed with water and brine, dried over anhydrous MgSO$_4$, filtered, and concentrated in vacuo to provide the crude material. The crude material was purified by flash chromatography (0-50% ethyl acetate:hexanes) to afford the title compound (0.246 g, 82% yield) as an off-white solid. LCMS, [M+H]$^+$=349.1. $^1$H NMR (400 MHz, CDCl$_3$) δ 7.41 (d, J=7.7 Hz, 1H), 7.28-7.17 (m, 2H), 7.01 (t, J=7.9 Hz, 1H), 6.75 (d, J=7.5 Hz, 1H), 6.64 (d, J=8.2 Hz, 1H), 3.96 (t, J=5.6 Hz, 2H), 3.82-3.71 (m, 2H), 2.85 (s, 2H), 2.73 (t, J=7.1 Hz, 2H), 2.24 (s, 3H), 2.18 (dt, J=12.9, 6.4 Hz, 2H), 2.05-1.88 (m, 5H).

Step B. 1-(5-(1H-Tetrazol-5-yl)-3,4-dihydroquinolin-1(2H)-yl)-4-(2,3-dimethylphenoxy)butan-1-one

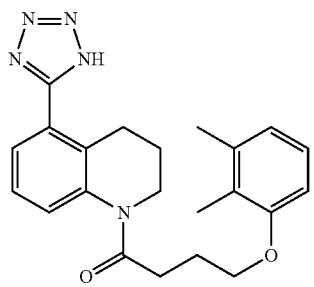 [SMILES: Cc1cccc(OCCCC(=O)N2CCCc3c(-c4nnn[nH]4)cccc32)c1C]

A solution of 1-(4-(2,3-dimethylphenoxy)butanoyl)-1,2,3,4-tetrahydroquinoline-5-carbonitrile (0.020 g, 0.057 mmol), dibutylstannanone (2.86 mg, 0.011 mmol) and TMS-N$_3$ (0.030 mL, 0.230 mmol) in DME (0.3 mL) was stirred at 100° C. for 3 days, and then concentrated in vacuo. The resulting residue was purified by preparative HPLC (PHENOMENEX® Axia Luna column, 5μ, C18, 30×75 mm; 10 min gradient from 75% A:25% B to 0% A:100% B (A=90% H$_2$O/10% MeCN+0.1% TFA); (B=90% MeCN/10% H$_2$O+0.1% TFA); detection at 220 nm) to afford the title compound (18.7 mg, 82% yield) as an off-white solid. LCMS, [M+H]$^+$=392.1.

Example 111

A solution of 1-(5-(1H-tetrazol-5-yl)-3,4-dihydroquinolin-1(2H)-yl)-4-(2,3-dimethylphenoxy)butan-1-one (0.010 g, 0.026 mmol), methyl 3-(bromomethyl)benzoate (5.85 mg, 0.026 mmol) and potassium carbonate (7.06 mg, 0.051 mmol) in DMF (0.20 mL) was stirred at 80° C. for 16 h. 4 M LiOH (0.064 mL, 0.255 mmol) was added and the mixture was stirred at 80° C. for 5 h. The mixture was diluted with EtOAc, and adjusted to pH 6-7 with 1 N HCl. The organic layer was separated, washed with water and brine, dried over MgSO$_4$, filtered, and concentrated in vacuo. The resulting residue was purified by preparative HPLC (PHENOMENEX® Axia Luna column, 5μ, C18, 30×75 mm; 10 min gradient from 75% A:25% B to 0% A:100% B (A=90% H$_2$O/10% MeCN+0.1% TFA); (B=90% MeCN/10% H$_2$O+0.1% TFA); detection at 220 nm) to afford Example 111 (1.9 mg, 11% yield). LCMS, [M+H]$^+$=526.2. $^1$H NMR (400 MHz, CDCl$_3$) δ 7.94 (d, J=6.7 Hz, 1H), 7.51 (s, 1H), 7.38-7.26 (m, 3H), 7.26-7.15 (m, 1H), 7.01-6.92 (m, 2H), 6.71 (d, J=7.5 Hz, 1H), 6.64 (d, J=8.2 Hz, 1H), 5.42 (s, 2H), 3.97 (t, J=5.6 Hz, 2H), 3.70-3.60 (m, 2H), 2.76-2.65 (m, 2H), 2.25-2.12 (m, 5H), 2.12-1.98 (m, 5H), 1.65 (dt, J=13.0, 6.5 Hz, 2H).

Example 112

3-((5-(1-(4-(2,3-Dimethylphenoxy)butanoyl)-1,2,3,4-tetrahydroquinolin-5-yl)-2H-tetrazol-2-yl)methyl)benzoic acid

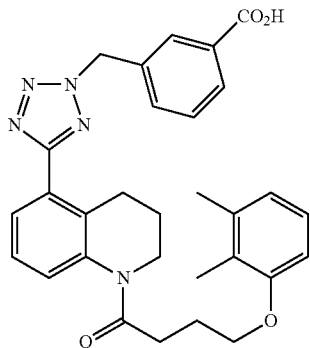 [SMILES: Cc1cccc(OCCCC(=O)N2CCCc3c(-c4nnn(Cc5cccc(C(=O)O)c5)n4)cccc32)c1C]

Example 112 (6.3 mg, 37.5% yield) was obtained as an additional product while synthesizing Example 111 from 1-(5-(1H-tetrazol-5-yl)-3,4-dihydroquinolin-1(2H)-yl)-4-(2,3-dimethylphenoxy)butan-1-one. LCMS, [M+H]$^+$=526.2. $^1$H NMR (400 MHz, CDCl$_3$) δ 8.19 (s, 1H), 8.10 (d, J=7.8 Hz, 1H), 7.82 (d, J=8.6 Hz, 1H), 7.66 (d, J=7.7 Hz, 1H), 7.51 (t, J=7.7 Hz, 1H), 7.31-7.18 (m, 2H), 6.96 (t, J=7.5 Hz, 1H), 6.67 (d, J=7.5 Hz, 1H), 6.61 (d, J=8.1 Hz, 1H), 5.88 (s, 2H), 3.93 (br. s, 2H), 3.80 (t, J=6.6 Hz, 2H), 2.98 (t, J=6.2 Hz, 2H), 2.73 (t, J=7.3 Hz, 2H), 2.24-2.07 (m, 5H), 2.01-1.84 (m, 5H). HPLC-1: Rt=10.8 min, purity=100%; HPLC-2: Rt=9.5 min, purity=100%.

Example 113

2-(5-(3-(1-(4-(2,3-Dimethylphenoxy)butanoyl)-1,2,3,4-tetrahydroquinolin-5-yl)benzyl)-1H-tetrazol-1-yl)acetic acid

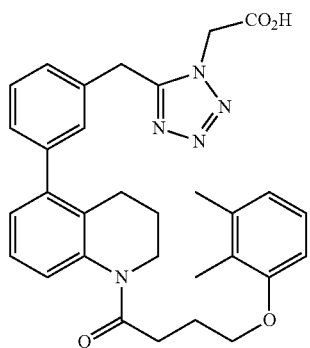 [SMILES: Cc1cccc(OCCCC(=O)N2CCCc3c(-c4cccc(Cc5nnnn5CC(=O)O)c4)cccc32)c1C]

Step A. 2-(3-(1-(4-(2,3-Dimethylphenoxy)butanoyl)-1,2,3,4-tetrahydroquinolin-5-yl)phenyl)acetonitrile

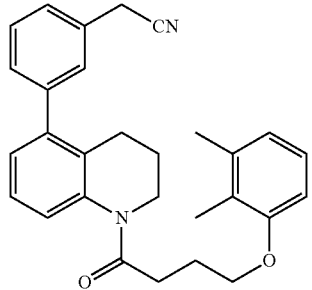

The title compound was prepared using a procedure analogous to methyl 4-(1-(4-(2,3-dimethylphenoxy)butanoyl)-1,2,3,4-tetrahydroquinolin-5-yl)picolinate except that methyl 4-bromopicolinate was replace with 2-(3-bromophenyl)acetonitrile. LCMS, [M+H]$^+$=439.3.

Example 113

Example 113 was prepared using a procedure analogous to Example 111 except that 1-(4-(2,3-dimethylphenoxy)butanoyl)-1,2,3,4-tetrahydroquinoline-5-carbonitrile was replaced with 2-(3-(1-(4-(2,3-dimethylphenoxy)butanoyl)-1,2,3,4-tetrahydroquinolin-5-yl)phenyl)acetonitrile. LCMS, [M+H]$^+$=540.2. $^1$H NMR (400 MHz, CDCl$_3$) δ 7.35 (t, J=7.6 Hz, 2H), 7.22-7.10 (m, 3H), 7.10-7.03 (m, 2H), 6.99 (t, J=7.8 Hz, 1H), 6.73 (d, J=7.6 Hz, 1H), 6.63 (d, J=8.1 Hz, 1H), 4.89 (s, 2H), 4.32 (s, 2H), 3.92 (br. s, 2H), 3.74 (t, J=7.0 Hz, 2H), 2.76 (t, J=7.3 Hz, 2H), 2.42 (t, J=6.4 Hz, 2H), 2.19 (s, 3H), 2.18-2.11 (m, 2H), 1.95 (s, 3H), 1.84-1.73 (m, 2H). HPLC-1: Rt=10.3 min, purity=97.4%; HPLC-2: Rt=10.2 min, purity=100%.

Example 114

2-(5-(3-(1-(4-(2,3-Dimethylphenoxy)butanoyl)-1,2,3,4-tetrahydroquinolin-5-yl)benzyl)-2H-tetrazol-2-yl)acetic acid

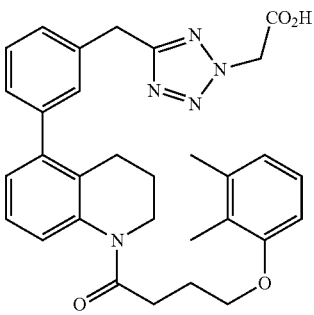 [SMILES: Cc1cccc(OCCCC(=O)N2CCCc3c(-c4cccc(Cc5nnn(CC(=O)O)n5)c4)cccc32)c1C]

Example 114 was obtained as an additional product while synthesizing Example 113 from 2-(3-(1-(4-(2,3-dimethylphenoxy)butanoyl)-1,2,3,4-tetrahydroquinolin-5-yl)phenyl)acetonitrile. LCMS, [M+H]$^+$=540.2. $^1$H NMR (400 MHz, CDCl$_3$) δ 7.39-7.28 (m, 3H), 7.18 (d, J=7.6 Hz, 1H), 7.16-7.08 (m, 2H), 7.05 (s, 1H), 6.99 (t, J=7.9 Hz, 1H), 6.73

(d, J=7.5 Hz, 1H), 6.63 (d, J=8.1 Hz, 1H), 5.36 (s, 2H), 4.32 (s, 2H), 3.93 (t, J=5.7 Hz, 2H), 3.75 (t, J=7.0 Hz, 2H), 2.74 (t, J=7.3 Hz, 2H), 2.41 (t, J=6.4 Hz, 2H), 2.19 (s, 3H), 2.17-2.10 (m, 2H), 1.94 (s, 3H), 1.76 (dt, J=13.6, 6.7 Hz, 2H). HPLC-1: Rt=10.7 min, purity=97.7%; HPLC-2: Rt=10.6 min, purity=98.7%.

Example 115

2-(3-(3-((5-(1-(4-(2,3-Dimethylphenoxy)butanoyl)-1,2,3,4-tetrahydroquinolin-5-yl)-2H-tetrazol-2-yl)methyl)phenyl)ureido)ethanesulfonic acid

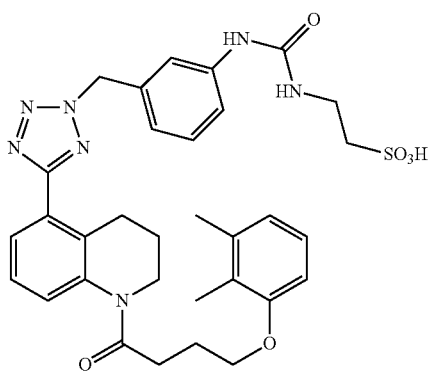 [SMILES: Cc1cccc(OCCCC(=O)N2CCCc3c(-c4nnn(Cc5cccc(NC(=O)NCCS(=O)(=O)O)c5)n4)cccc32)c1C]

Step A. tert-Butyl 3-((5-(1-(4-(2,3-dimethylphenoxy)butanoyl)-1,2,3,4-tetrahydroquinolin-5-yl)-2H-tetrazol-2-yl)methyl)phenylcarbamate

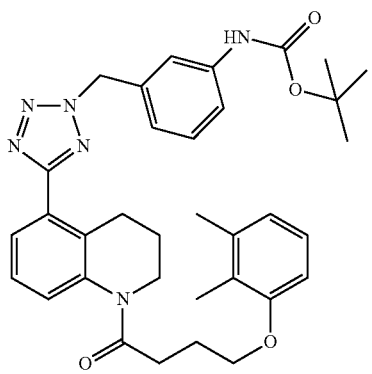 [SMILES: Cc1cccc(OCCCC(=O)N2CCCc3c(-c4nnn(Cc5cccc(NC(=O)OC(C)(C)C)c5)n4)cccc32)c1C]

A mixture of 1-(5-(1H-tetrazol-5-yl)-3,4-dihydroquinolin-1(2H)-yl)-4-(2,3-dimethylphenoxy)butan-1-one (0.16 g, 0.409 mmol), tert-butyl 3-(bromomethyl)phenylcarbamate (0.152 g, 0.531 mmol) and $K_2CO_3$ (0.113 g, 0.817 mmol) in DMF (1 mL) was stirred at 80° C. for 16 h. The mixture was partitioned between EtOAc and water. The organic layer was separated, washed with water and brine, dried over anhydrous $MgSO_4$, filtered, and concentrated in vacuo to provide the crude material. The crude material was purified by flash chromatography (0-50% ethyl acetate:hexanes) to afford the title compound (96 mg, 40% yield). LCMS, $[M+H]^+$=597.4.

Step B. 1-(5-(2-(3-Aminobenzyl)-2H-tetrazol-5-yl)-3,4-dihydroquinolin-1(2H)-yl)-4-(2,3-dimethylphenoxy)butan-1-one

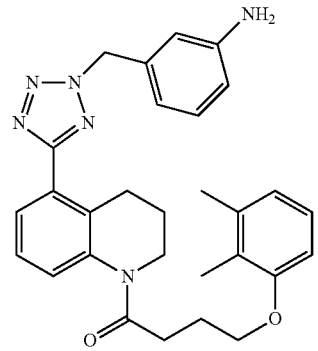 [SMILES: Cc1cccc(OCCCC(=O)N2CCCc3c(-c4nnn(Cc5cccc(N)c5)n4)cccc32)c1C]

The title compound was prepared using a procedure analogous to 1-(5-(3-(aminomethyl)phenyl)-3,4-dihydroquinolin-1(2H)-yl)-4-(2,3-dimethylphenoxy)butan-1-one except that tert-butyl 3-(1-(4-(2,3-dimethylphenoxy)butanoyl)-1,2,3,4-tetrahydroquinolin-5-yl)benzylcarbamate was replaced with tert-butyl 3-((5-(1-(4-(2,3-dimethylphenoxy)butanoyl)-1,2,3,4-tetrahydroquinolin-5-yl)-2H-tetrazol-2-yl)methyl)phenylcarbamate. LCMS, $[M+H]^+$=497.3.

Example 115

To a solution of 1-(5-(2-(3-aminobenzyl)-2H-tetrazol-5-yl)-3,4-dihydroquinolin-1(2H)-yl)-4-(2,3-dimethylphenoxy)butan-1-one (0.03 g, 0.060 mmol), DIPEA (0.042 mL, 0.242 mmol) and DMAP (1.476 mg, 0.012 mmol) in DCM (1 mL) was added diphosgene (8.02 µL, 0.066 mmol) dropwise at room temperature. The reaction was stirred at room temperature for 30 min and concentrated in vacuo. The resulting residue was dissolved in DMF (1 mL) and treated with DIPEA (0.042 mL, 0.242 mmol) and taurine (0.015 g, 0.121 mmol). The resulting mixture was stirred at 80° C. for 16 h. After cooling to room temperature, the mixture was partitioned between EtOAc and water. The organic layer was washed with water and brine, dried over anhydrous $MgSO_4$, filtered, and concentrated in vacuo to provide a residue. The residue was purified by preparative HPLC (PHENOMENEX® Axia Luna column, 5µ, C18, 30×75 mm; 10 min gradient from 75% A:25% B to 0% A:100% B and 3 min 100% B (A=90% $H_2O$/10% MeOH+0.1% TFA); (B=90% MeOH/10% $H_2O$+0.1% TFA); detection at 220 nm) to afford Example 115 (3.1 mg, 7.5% yield). LCMS, $[M+H]^+$=648.4. $^1$H NMR (400 MHz, MeOD) δ 7.83 (d, J=7.7 Hz, 1H), 7.55 (s, 1H), 7.44-7.25 (m, 4H), 7.04 (d, J=7.6 Hz, 1H), 6.95-6.84 (m, 1H), 6.62 (d, J=7.9 Hz, 1H), 6.56 (d, J=6.7 Hz, 1H), 5.87 (s, 2H), 3.89 (br. s, 2H), 3.77 (t, J=6.6 Hz, 2H), 3.68-3.58 (m, 2H), 3.37-3.26 (m, 2H), 3.04-2.95 (m, 2H), 2.91-2.74 (m, 5H), 2.11 (dd, J=12.4, 6.3 Hz, 2H), 1.98 (s, 3H), 1.91-1.80 (m, 2H), 1.76 (s, 2H). HPLC-1: Rt=10.3 min, purity=100%; HPLC-2: Rt=10.2 min, purity=99.8%.

Example 116

(3-(3-((4-(3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)methanesulfonic acid

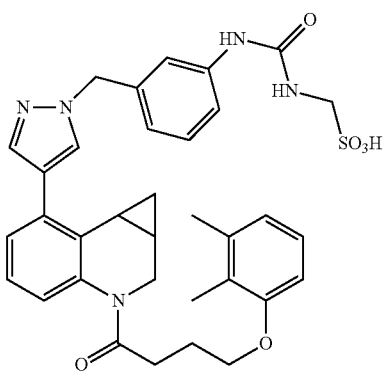

Step A. 1-(7-(1-(3-Aminobenzyl)-1H-pyrazol-4-yl)-1a,2-dihydro-1H-cyclopropa[c]quinolin-3(7bH)-yl)-4-(2,3-dimethylphenoxy)butan-1-one

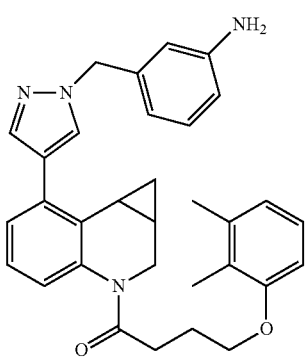 [SMILES: Cc1cccc(OCCCC(=O)N2CC3CC3c3c(-c4cnn(Cc5cccc(N)c5)c4)cccc32)c1C]

The title compound was prepared using a procedure analogous to 1-(5-(1-(3-(aminomethyl)benzyl)-1H-pyrazol-4-yl)-3,4-dihydroquinolin-1(2H)-yl)-4-(2,3-dimethylphenoxy)butan-1-one except that Example 3 was replaced by 1-(7-bromo-1a,2-dihydro-1H-cyclopropa[c]quinolin-3(7bH)-yl)-4-(2,3-dimethylphenoxy)butan-1-one. LCMS, [M+H]$^+$= 507.4.

Example 116

Example 116 was prepared using a procedure analogous to Example 115 except that 1-(5-(2-(3-aminobenzyl)-2H-tetrazol-5-yl)-3,4-dihydroquinolin-1(2H)-yl)-4-(2,3-dimethylphenoxy)butan-1-one was replaced with 1-(7-(1-(3-aminobenzyl)-1H-pyrazol-4-yl)-1a,2-dihydro-1H-cyclopropa[c]quinolin-3(7bH)-yl)-4-(2,3-dimethylphenoxy)butan-1-one and taurine was replaced with aminomethanesulfonic acid. LCMS, [M+H]$^+$=644.4. $^1$H NMR (400 MHz, MeOD) δ 7.97 (br. s, 1H), 7.80 (br. s, 1H), 7.47 (s, 1H), 7.43-7.27 (m, 3H), 7.27-7.19 (m, 1H), 7.18-7.07 (m, 1H), 7.06-6.92 (m, 2H), 6.80-6.64 (m, 2H), 5.45 (s, 2H), 4.35 (s, 2H), 4.07-3.94 (m, 1H), 3.94-3.80 (m, 1H), 2.94-2.66 (m, 4H), 2.15 (s, 6H), 1.82 (s, 4H), 1.01-0.88 (m, 1H), 0.59-0.42 (m, 1H). HPLC-1: Rt=10.3 min, purity=97.7%; HPLC-2: Rt=10.3 min, purity=97.8%.

Example 117

2-(3-(3-((4-(3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)ethanesulfonic acid

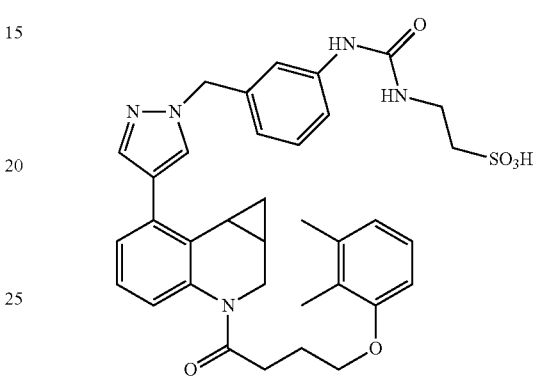

Example 117 was prepared using a procedure analogous to Example 115 except that 1-(5-(2-(3-aminobenzyl)-2H-tetrazol-5-yl)-3,4-dihydroquinolin-1(2H)-yl)-4-(2,3-dimethylphenoxy)butan-1-one was replaced with 1-(7-(1-(3-aminobenzyl)-1H-pyrazol-4-yl)-1a,2-dihydro-1H-cyclopropa[c]quinolin-3(7bH)-yl)-4-(2,3-dimethylphenoxy)butan-1-one. LCMS, [M+H]$^+$=658.5. $^1$H NMR (500 MHz, CD$_3$CN) δ 7.85-7.78 (m, 1H), 7.65 (s, 1H), 7.40 (s, 1H), 7.30-7.18 (m, 3H), 7.12 (t, J=7.8 Hz, 1H), 7.02 (br. s, 1H), 6.96 (t, J=7.6 Hz, 1H), 6.86 (d, J=7.2 Hz, 1H), 6.68 (d, J=7.6 Hz, 1H), 6.64 (d, J=8.1 Hz, 1H), 5.28 (s, 2H), 4.84 (br. s, 1H), 3.91 (br. s, 2H), 3.78 (br. s, 1H), 3.48 (t, J=6.4 Hz, 2H), 2.88 (t, J=6.5 Hz, 2H), 2.71-2.62 (m, 2H), 2.57 (br. s, 1H), 2.15-2.05 (m, 5H), 1.76 (s, 3H), 1.73-1.66 (m, 1H), 0.94-0.82 (m, 1H), 0.46-0.35 (m, 1H). HPLC-1: Rt=14.3 min, purity=100%; HPLC-2: Rt=11.5 min, purity=95.1%.

Example 118

2-(4-(3-(1-(4-(2,3-Dimethylphenoxy)butanoyl)-1,2,3,4-tetrahydroquinolin-5-yl)benzylcarbamoyl)piperazin-1-yl)ethanesulfonic acid

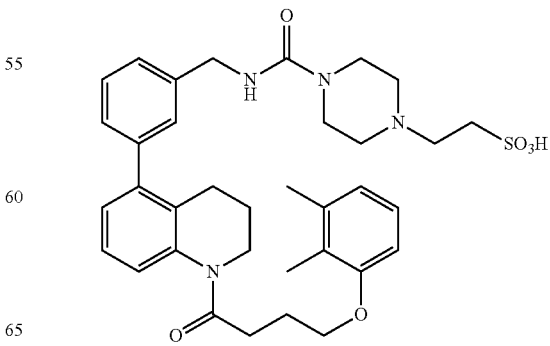

Example 118 was prepared using a procedure analogous to Example 115 except that 1-(5-(2-(3-aminobenzyl)-2H-tetrazol-5-yl)-3,4-dihydroquinolin-1(2H)-yl)-4-(2,3-dimethylphenoxy)butan-1-one was replaced with 1-(5-(3-(aminomethyl)phenyl)-3,4-dihydroquinolin-1(2H)-yl)-4-(2,3-dimethylphenoxy)butan-1-one and taurine was replaced with 2-(piperazin-1-yl)ethanesulfonic acid. LCMS, [M+H]$^+$= 649.3. $^1$H NMR (400 MHz, MeOD) δ 7.48-7.30 (m, 4H), 7.28-7.17 (m, 2H), 7.13-7.00 (m, 2H), 6.79 (d, J=7.5 Hz, 1H), 6.75 (d, J=8.2 Hz, 1H), 4.48 (s, 2H), 4.28 (br. s, 2H), 3.99 (t, J=5.2 Hz, 2H), 3.83 (t, J=7.0 Hz, 2H), 3.72 (br. s, 2H), 3.62 (t, J=6.9 Hz, 2H), 3.43-3.38 (m, 2H), 3.29 (t, J=6.9 Hz, 2H), 3.20 (br. s, 2H), 2.89 (t, J=7.0 Hz, 2H), 2.49 (t, J=6.1 Hz, 2H), 2.31-2.15 (m, 5H), 1.94 (s, 3H), 1.90-1.80 (m, 2H). HPLC-1: Rt=10.5 min, purity=99.3%; HPLC-2: Rt=10.4 min, purity=100%.

Example 119

2-(3-(3-((4-(3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)acetic acid

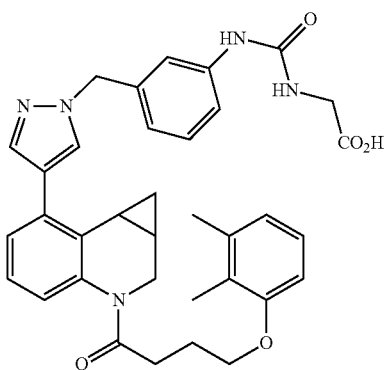 [SMILES: Cc1cccc(OCCCC(=O)N2CC3CC3c3c(-c4cnn(Cc5cccc(NC(=O)NCC(=O)O)c5)c4)cccc32)c1C]

Step A. Ethyl 2-(3-(3-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)phenyl)ureido)acetate

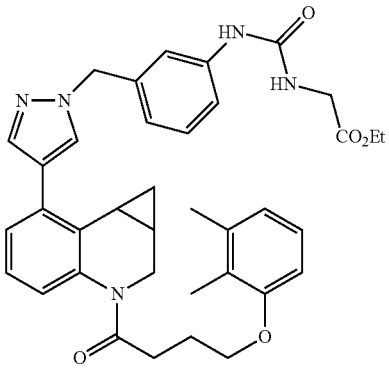 [SMILES: CCOC(=O)CNC(=O)Nc1cccc(Cn2cc(-c3cccc4c3C3CC3CN4C(=O)CCCOc3cccc(C)c3C)cn2)c1]

The title compound was prepared using a procedure analogous to Example 116 except that aminomethanesulfonic acid was replaced with ethyl 2-aminoacetate. LCMS, [M+H]$^+$= 636.4.

Example 119

Example 119 was prepared using a procedure analogous to Example 2 except that methyl 4-(1-(4-(2,3-dimethylphenoxy)butanoyl)-1,2,3,4-tetrahydroquinolin-5-yl)picolinate was replaced with ethyl 2-(3-(3-((4-(3-(4-(2,3-dimethylphenoxy)butanoyl)-1a,2,3,7b-tetrahydro-1H-cyclopropa[c]quinolin-7-yl)-1H-pyrazol-1-yl)methyl)phenyl)ureido)acetate. LCMS, [M+H]$^+$=608.4. $^1$H NMR (500 MHz, CD$_3$CN) δ 7.79 (s, 1H), 7.66 (s, 1H), 7.47-7.40 (m, 2H), 7.28-7.18 (m, 3H), 7.13 (t, J=7.8 Hz, 1H), 7.04 (br. s, 1H), 6.98 (t, J=7.9 Hz, 1H), 6.91 (d, J=6.7 Hz, 1H), 6.71 (d, J=7.5 Hz, 1H), 6.67 (d, J=7.3 Hz, 1H), 5.52 (br. s, 1H), 5.31 (s, 2H), 3.99-3.91 (m, 1H), 3.86 (s, 2H), 2.74-2.65 (m, 2H), 2.54 (br. s, 1H), 2.15 (s, 3H), 2.09-1.99 (m, 2H), 1.96-1.90 (m, 2H), 1.85 (s, 3H), 1.72 (br. s, 1H), 0.95-0.86 (m, 1H), 0.51-0.41 (m, 1H). HPLC-1: Rt=13.0 min, purity=99.1%; HPLC-2: Rt=13.1 min, purity=99.0%.

Example 120

3-(3-(3-((4-(3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)propanoic acid

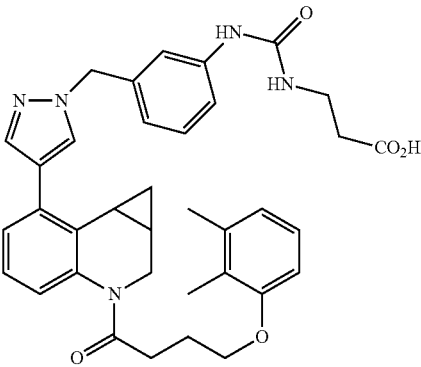 [SMILES: Cc1cccc(OCCCC(=O)N2CC3CC3c3c(-c4cnn(Cc5cccc(NC(=O)NCCC(=O)O)c5)c4)cccc32)c1C]

Example 120 was prepared using a procedure analogous to Example 119 except that ethyl 2-aminoacetate was replaced with methyl 3-aminopropanoate. LCMS, [M+H]$^+$=622.5. $^1$H NMR (500 MHz, CD$_3$CN) δ $^1$H NMR (500 MHz, CD$_3$CN) δ 7.76 (s, 1H), 7.63 (s, 1H), 7.40 (s, 1H), 7.26-7.17 (m, 4H), 7.12 (t, J=7.8 Hz, 1H), 7.03 (s, 1H), 6.97 (t, J=7.8 Hz, 1H), 6.88 (d, J=6.7 Hz, 1H), 6.70 (d, J=7.5 Hz, 1H), 6.66 (d, J=7.9 Hz, 1H), 5.45-5.39 (m, 1H), 5.29 (s, 2H), 4.89 (br. s, 1H), 3.99-3.90 (m, 1H), 3.89-3.78 (m, 1H), 3.38 (t, J=6.3 Hz, 2H), 2.74-2.64 (m, 2H), 2.58-2.51 (m, 1H), 2.48 (t, J=6.3 Hz, 2H), 2.14 (s, 3H), 2.07-1.99 (m, 2H), 1.85 (s, 3H), 1.75-1.66 (m, 1H), 0.94-0.84 (m, 1H), 0.51-0.41 (m, 1H). HPLC-1: Rt=13.1 min, purity=100%; HPLC-2: Rt=13.2 min, purity=100%.

Example 121

2-(3-(3-((4-(3-((2-(3-Chloro-2-methylphenoxy)ethoxy)carbonyl)-1a,2,3,7b-tetrahydro-1H-cyclopropa[c]quinolin-7-yl)-1H-pyrazol-1-yl)methyl)phenyl)ureido)ethanesulfonic acid

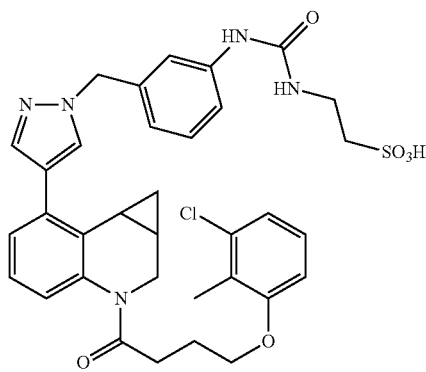

Step A. 2-(3-Chloro-2-methylphenoxy)ethyl 7-bromo-1a,2-dihydro-1H-cyclopropa[c]quinoline-3(7bH)-carboxylate

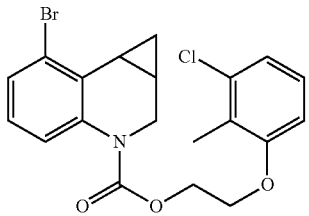 [SMILES: Cc1c(Cl)cccc1OCCOC(=O)N1CC2CC2c2c(Br)cccc21]

The title compound was prepared using a procedure analogous to 2-(2,3-dimethylphenoxy)ethyl 5-bromo-3,4-dihydroquinoline-1(2H)-carboxylate except that 5-bromo-1,2,3,4-tetrahydroquinoline, HCl salt was replaced with bromo-1a,2,3,7b-tetrahydro-1H-cyclopropa[c]quinoline, and 2,3-dimethylphenol was replaced with 3-chloro-2-methylphenol. LCMS, [M+Na]⁺=460.0.

Example 121 was prepared using a procedure analogous to Example 117 except that 1-(5-(2-(3-aminobenzyl)-2H-tetrazol-5-yl)-3,4-dihydroquinolin-1(2H)-yl)-4-(2,3-dimethylphenoxy)butan-1-one was replaced with 2-(3-chloro-2-methylphenoxy)ethyl 7-bromo-1a,2-dihydro-1H-cyclopropa[c]quinoline-3(7bH)-carboxylate. LCMS, [M+H]⁺=666.3. ¹H NMR (400 MHz, MeOD) δ 7.95 (s, 1H), 7.76 (s, 1H), 7.44 (s, 1H), 7.42-7.36 (m, 1H), 7.36-7.28 (m, 1H), 7.29-7.23 (m, 1H), 7.23-7.17 (m, 1H), 7.17-7.09 (m, 2H), 7.04 (s, 1H), 7.02-6.96 (m, 1H), 6.95-6.89 (m, 1H), 5.43 (s, 2H), 4.67-4.59 (m, 1H), 4.58-4.50 (m, 2H), 4.38 (s, 2H), 4.30 (br. s, 2H), 3.11 (d, J=12.3 Hz, 1H), 2.95-2.71 (m, 2H), 2.28 (s, 3H), 2.27-2.19 (m, 1H), 1.94-1.84 (m, 1H), 1.16-1.07 (m, 1H), 0.74-0.63 (m, 1H). HPLC-1: Rt=11.9 min, purity=98.6%; HPLC-2: Rt=11.9 min, purity=100%.

Example 122

(3-(3-((4-(3-((2-(3-Fluoro-2-methylphenoxy)ethoxy)carbonyl)-1a,2,3,7b-tetrahydro-1H-cyclopropa[c]quinolin-7-yl)-1H-pyrazol-1-yl)methyl)phenyl)ureido)methanesulfonic acid

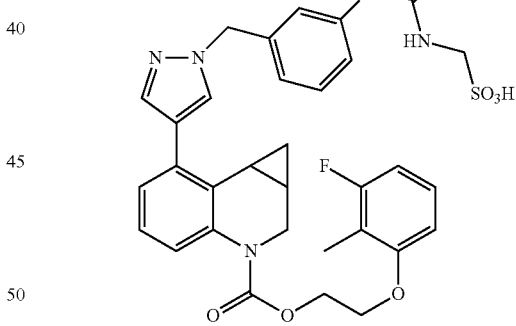

Example 122 was prepared using a procedure analogous to Example 121 except that 3-chloro-2-methylphenol was replaced with 3-fluoro-2-methylphenol and taurine was replaced with aminomethanesulfonic acid. LCMS, [M+H]⁺=650.3. ¹H NMR (400 MHz, MeOD) δ 8.19 (s, 1H), 8.03 (s, 1H), 7.52 (br. s, 1H), 7.40-7.26 (m, 3H), 7.26-7.09 (m, 3H), 6.99 (d, J=6.4 Hz, 1H), 6.78 (d, J=8.4 Hz, 1H), 6.72 (t, J=8.7 Hz, 1H), 5.51 (s, 2H), 4.65-4.50 (m, 2H), 4.37 (s, 2H), 4.30 (d, J=3.6 Hz, 2H), 3.16-3.04 (m, 1H), 2.28-2.08 (m, 5H), 1.98-1.83 (m, 1H), 1.21-1.05 (m, 1H), 0.79-0.63 (m, 1H). HPLC-1: Rt=14.8 min, purity=100%; HPLC-2: Rt=12.1 min, purity=100%.

Example 123

3-((6-(1-(4-(2,3-Dimethylphenoxy)butanoyl)-1,2,3,4-tetrahydroquinolin-5-yl)pyridin-3-yloxy)methyl)benzoic acid

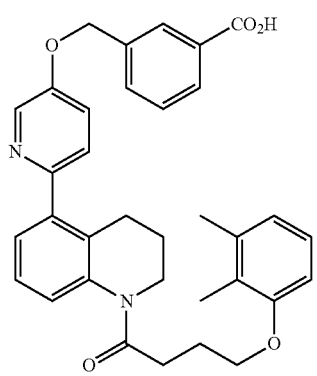 [SMILES: Cc1cccc(OCCCC(=O)N2CCCc3c(-c4ccc(OCc5cccc(C(=O)O)c5)cn4)cccc32)c1C]

Step A. Methyl 3-((6-bromopyridin-3-yloxy)methyl)benzoate

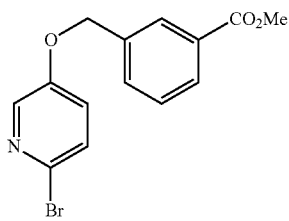 [SMILES: COC(=O)c1cccc(COc2ccc(Br)nc2)c1]

To a solution of 6-bromopyridin-3-ol (0.500 g, 2.87 mmol) in DMF (3.0 mL) at 0° C. was added NaH (60% in mineral oil, 0.149 g, 3.74 mmol) portion-wise over a period of 10 min. The mixture was warmed to room temperature, stirred for 30 min, and methyl 3-(bromomethyl)benzoate (0.790 g, 3.45 mmol) was added in one portion. The reaction was stirred at room temperature for 16 h. The mixture was partitioned between EtOAc and water. The organic layer was separated, washed with water and brine, dried over anhydrous $MgSO_4$, filtered, and concentrated in vacuo to provide the crude material. The crude material was purified by flash chromatography (0-50% ethyl acetate:hexanes) to afford the title compound (0.726 g, 78% yield) as an off-white solid. LCMS, $[M+H]^+$=322.0.

Example 123

Example 123 was prepared using a procedure analogous to Example 2 except that methyl 4-bromopicolinate was replaced with methyl 3-((6-bromopyridin-3-yloxy)methyl)benzoate. LCMS, $[M+H]^+$=551.2. $^1$H NMR (400 MHz, $CDCl_3$) δ 8.96 (s, 1H), 8.20 (s, 1H), 8.11 (d, J=7.7 Hz, 1H), 7.78 (d, J=7.8 Hz, 1H), 7.71 (d, J=7.5 Hz, 1H), 7.53 (t, J=7.7 Hz, 1H), 7.41-7.25 (m, 3H), 7.01 (t, J=7.8 Hz, 1H), 6.73 (d, J=7.5 Hz, 2H), 6.65 (d, J=8.1 Hz, 1H), 5.36 (s, 2H), 3.93 (br. s, 2H), 3.80 (t, J=6.6 Hz, 2H), 2.76 (t, J=7.0 Hz, 2H), 2.49 (br. s, 2H), 2.30-2.08 (m, 5H), 2.05-1.79 (m, 5H). HPLC-1: Rt=9.3 min, purity=100%; HPLC-2: Rt=9.1 min, purity=100%.

Example 124

2-(5-(1-(4-(2,3-Dimethylphenoxy)butanoyl)-1,2,3,4-tetrahydroquinolin-5-yl)pyrimidin-2-yloxy)acetic acid, TFA salt

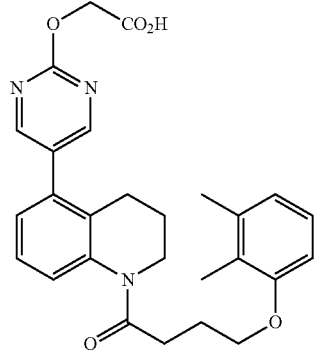 [SMILES: Cc1cccc(OCCCC(=O)N2CCCc3c(-c4cnc(OCC(=O)O)nc4)cccc32)c1C]

Step A. Ethyl 2-(5-bromopyrimidin-2-yloxy)acetate

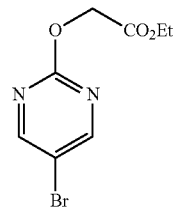 [SMILES: CCOC(=O)COc1ncc(Br)cn1]

To a solution of ethyl 2-hydroxyacetate (0.081 g, 0.775 mmol) in toluene (1.0 mL) was added NaH (60% in mineral oil, 0.037 g, 0.931 mmol) at room temperature. The mixture was stirred for 30 min and a solution of 5-bromo-2-chloropyrimidine (0.100 g, 0.517 mmol) in toluene (0.5 mL) was added. The reaction mixture was stirred at 60° C. for 16 h. The mixture was diluted with EtOAc and slowly quenched with water. The organic layer was separated, washed with water and brine, dried over anhydrous MgSO$_4$, filtered, and concentrated in vacuo to provide the crude material. The crude material was purified by flash chromatography (0-50% ethyl acetate:hexanes) to afford the title compound (82 mg, 61% yield) as a clear colorless oil. LCMS, [M+H]$^+$=260.9.

Example 124

Example 124 was prepared using a procedure analogous to Example 2 except that methyl 4-bromopicolinate was replaced with ethyl 2-(5-bromopyrimidin-2-yloxy)acetate. LCMS, [M+H]$^+$=476.1. $^1$H NMR (400 MHz, CDCl$_3$) δ 8.38 (s, 2H), 7.35-7.17 (m, 2H), 7.07 (d, J=8.2 Hz, 1H), 7.01 (t, J=7.9 Hz, 1H), 6.75 (d, J=7.5 Hz, 1H), 6.63 (d, J=8.2 Hz, 1H), 5.07 (d, J=14.1 Hz, 2H), 3.99-3.86 (m, 2H), 3.79 (t, J=6.9 Hz, 2H), 2.78 (t, J=7.2 Hz, 2H), 2.50-2.35 (m, 2H), 2.28-2.09 (m, 5H), 1.98-1.76 (m, 5H). HPLC-1: Rt=8.2 min, purity=95.5%; HPLC-2: Rt=7.3 min, purity=98.5%.

Example 125

3-((5-(1-(4-(2,3-Dimethylphenoxy)butanoyl)-1,2,3,4-tetrahydroquinolin-5-yl)-2-oxopyridin-1(2H)-yl)methyl)benzoic acid

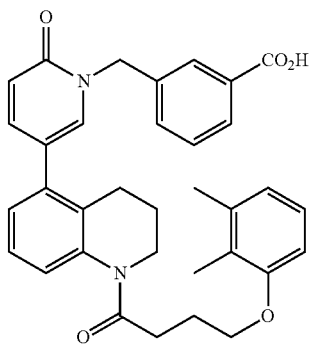 [SMILES: Cc1cccc(OCCCC(=O)N2CCCc3c(-c4ccc(=O)n(Cc5cccc(C(=O)O)c5)c4)cccc32)c1C]

Step A. Methyl 3-((5-bromo-2-oxopyridin-1(2H)-yl)methyl)benzoate

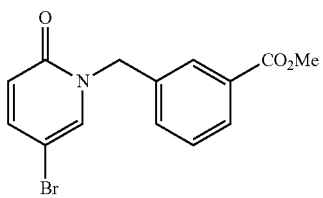 [SMILES: COC(=O)c1cccc(Cn2cc(Br)ccc2=O)c1]

To a solution of 5-bromopyridin-2-ol (0.250 g, 1.437 mmol) in DMF (1.50 mL) at 0° C., was added NaH (60% in mineral oil, 0.075 g, 1.868 mmol) portion-wise over a period of 10 min. The mixture was warmed to room temperature and stirred for 30 min. To the mixture was added methyl 3-(bromomethyl)benzoate (0.395 g, 1.724 mmol) in one portion. The reaction was stirred at room temperature for 16 h and partitioned between EtOAc and water. The organic layer was washed with water and brine, dried over anhydrous MgSO$_4$, filtered, and concentrated in vacuo to provide the crude material. The crude material was purified by flash chromatography (0-50% ethyl acetate:hexanes) to afford the title compound (0.274 g, 59% yield) as clear pale-yellow oil. LCMS, [M+H]$^+$= 322.0. $^1$H NMR (400 MHz, CDCl$_3$) δ 7.98 (d, J=7.7 Hz, 1H), 7.95 (s, 1H), 7.51 (d, J=7.7 Hz, 1H), 7.43 (t, J=7.7 Hz, 1H), 7.37 (d, J=2.7 Hz, 1H), 7.33 (dd, J=9.7, 2.7 Hz, 1H), 6.52 (d, J=9.7 Hz, 1H), 5.11 (s, 2H), 3.90 (s, 3H).

Example 125

Example 125 was prepared using a procedure analogous to Example 2 except that methyl 4-bromopicolinate was replaced with methyl 3-((5-bromo-2-oxopyridin-1(2H)-yl)methyl)benzoate. LCMS, [M+H]$^+$=551.2. $^1$H NMR (400 MHz, CDCl$_3$) δ 8.38 (s, 2H), 7.35-7.17 (m, 2H), 7.07 (d, J=8.2 Hz, 1H), 7.01 (t, J=7.9 Hz, 1H), 6.75 (d, J=7.5 Hz, 1H), 6.63 (d, J=8.2 Hz, 1H), 5.07 (d, J=14.1 Hz, 2H), 3.99-3.86 (m, 2H), 3.79 (t, J=6.9 Hz, 2H), 2.78 (t, J=7.2 Hz, 2H), 2.50-2.35 (m, 2H), 2.28-2.09 (m, 5H), 1.98-1.76 (m, 5H). HPLC-1: Rt=9.6 min, purity=97.2%; HPLC-2: Rt=8.6 min, purity=99.3%.

Example 126

2-(2-(4-(1-(4-(2,3-Dmethylphenoxy)butanoyl)-1,2,3,4-tetrahydroquinolin-5-yl)-1H-pyrazol-1-yl)acetamido)acetic acid

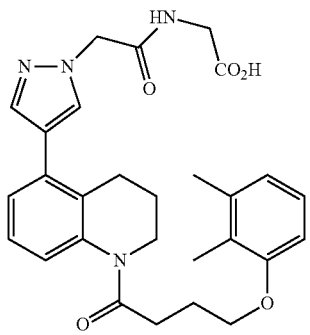 [SMILES: Cc1cccc(OCCCC(=O)N2CCCc3c(-c4cnn(CC(=O)NCC(=O)O)c4)cccc32)c1C]

To a solution of Example 1 (15 mg, 0.034 mmol), methyl 2-aminoacetate hydrochloride (6.3 mg, 0.05 mmol), and Hunig's base (20 µL, 0.117 mmol) in ethyl acetate (0.3 mL) was added a 50% w/w solution of T3P (30 µL, 0.05 mmol) in Et$_2$O dropwise. The reaction was stirred at room temperature for 16 h and partitioned between DCM and water. The resulting mixture was stirred vigorously for 15 min. The organic layer was separated, washed with saturated NaHCO$_3$, water, 5% aq. citric acid, and brine. The solution was dried over anhydrous Na₂SO₄, filtered, and concentrated. The resulting residue was re-dissolved in THF/H₂O (9:1, 0.5 mL) and added 4 M LiOH (85 µL, 0.34 mmol) and stirred at room temperature overnight. The reaction mixture was adjusted to pH~5 with conc. HCl, partitioned between 5% citric acid and DCM, and stirred for 15 min. The organic layer was separated, dried over anhydrous Na₂SO₄, filtered, and concentrated to provide a residue. The residue was purified by preparative HPLC (PHENOMENEX® Axia Luna column, 5µ, C18, 30×75 mm; 15 min gradient from 80% A:20% B to 40% A:60% B and 3 min 100% B (A=90% H₂O/10% MeCN+0.1% TFA); (B=90% MeCN/10% H₂O+0.1% TFA); detection at 220 nm) to afford Example 126 (4 mg, 24% yield). LCMS, [M+H]⁺=505.2. ¹H NMR (400 MHz, CDCl₃) δ 7.64 (s, 1H), 7.37 (s, 1H), 7.23-7.12 (m, 2H), 7.04-6.98 (m, 1H), 6.95 (s, 1H), 6.75 (d, J=7.5 Hz, 1H), 6.64 (d, J=8.2 Hz, 1H), 4.92 (s, 2H), 4.11 (d, J=5.2 Hz, 2H), 3.93 (s, 2H), 3.79 (t, J=6.9 Hz, 2H), 2.75 (t, J=7.1 Hz, 2H), 2.56 (s, 2H), 2.24-2.11 (m, 5H), 1.97-1.81 (m, 5H). HPLC-1: Rt=8.6 min, purity=100%; HPLC-2: Rt=8.0 min, purity=100%.

Example 127

Ethyl hydrogen 2-(3-((4-(1-(4-(2,3-dimethylphenoxy)butanoyl)-1,2,3,4-tetrahydroquinolin-5-yl)-1H-pyrazol-1-yl)methyl)benzamido)ethylphosphonate

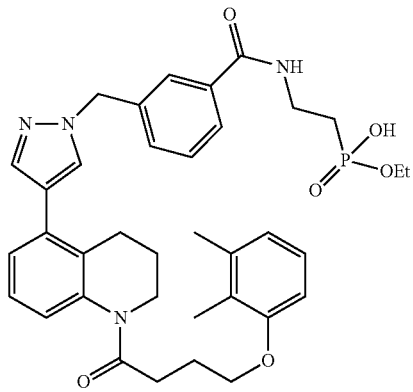 [SMILES: CCOP(=O)(O)CCNC(=O)c1cccc(Cn2cc(-c3cccc4c3CCCN4C(=O)CCCOc3cccc(C)c3C)cn2)c1]

Example 127 was prepared using a procedure analogous to Example 126 except that Example 1 was replaced with Example 95 and methyl 2-aminoacetate hydrochloride was replaced with diethyl 2-aminoethylphosphonate. LCMS, [M+H]⁺=659.3. ¹H NMR (400 MHz, MeOD) δ 7.83-7.73 (m, 2H), 7.65 (s, 1H), 7.55-7.41 (m, 3H), 7.29-7.19 (m, 2H), 7.16 (s, 1H), 6.96 (t, J=7.9 Hz, 1H), 6.66 (d, J=7.3 Hz, 1H), 6.65 (d, J=7.9 Hz, 1H), 5.43 (s, 2H), 4.13-4.02 (m, 2H), 3.86 (br. s, 2H), 3.74 (t, J=6.8 Hz, 2H), 3.69-3.58 (m, 2H), 2.81 (t, J=6.8 Hz, 2H), 2.48 (br. s, 2H), 2.19-2.06 (m, 4H), 2.03 (s, 3H), 1.84-1.76 (m, 2H), 1.72 (s, 3H), 1.30 (t, J=7.0 Hz, 3H). HPLC-1: Rt=9.9 min, purity=97.7%; HPLC-2: Rt=10.0 min, purity=98.0%.

Example 128

3-(4-((3-(1-(4-(2,3-Dimethylphenoxy)butanoyl)-1,2,3,4-tetrahydroquinolin-5-yl)benzyloxy)carbonyl)piperazin-1-yl)-3-oxopropanoic acid

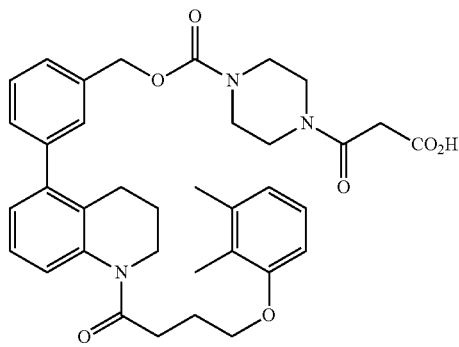 [SMILES: Cc1cccc(OCCCC(=O)N2CCCc3c(-c4cccc(COC(=O)N5CCN(C(=O)CC(=O)O)CC5)c4)cccc32)c1C]

Example 128 was prepared using a procedure analogous to Example 126 except that Example 1 was replaced with 3-methoxy-3-oxopropanoic acid and methyl 2-aminoacetate hydrochloride was replaced with 3-(1-(4-(2,3-dimethylphenoxy)butanoyl)-1,2,3,4-tetrahydroquinolin-5-yl)benzyl piperazine-1-carboxylate. LCMS, [M+H]⁺=628.3. ¹H NMR (400 MHz, MeOD) δ 7.54-7.42 (m, 2H), 7.41-7.31 (m, 2H), 7.30-7.14 (m, 3H), 7.06 (t, J=7.9 Hz, 1H), 6.79 (d, J=7.5 Hz, 1H), 6.75 (d, J=8.1 Hz, 1H), 5.25 (s, 2H), 3.97 (br, s, 2H), 3.83 (t, J=7.0 Hz, 2H), 3.74-3.55 (m, 8H), 2.90 (t, J=6.9 Hz, 2H), 2.46 (br. s, 2H), 2.31-2.16 (m, 5H), 1.91 (s, 3H), 1.85 (dt, J=13.3, 6.8 Hz, 2H), 1.37 (s, 2H). HPLC-1: Rt=10.8 min, purity=95.0%; HPLC-2: Rt=10.9 min, purity=93.1%.

The following Examples were prepared in a manner analogous to Example 126.

TABLE 8

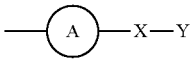

| Example | Name | —⟨A⟩—X—Y | ◁ present | $R_{5b}$ | LCMS, [M + H]+ | 1H NMR (400 MHz, CDCl3) δ | HPLC-1: Rt min, purity; HPLC-2: Rt min, purity |
|---|---|---|---|---|---|---|---|
| 129 | 2-(2-(4-(1-(4-(2,3-Dimethylphenoxy)butanoyl)-1,2,3,4-tetrahydroquinolin-5-yl)-1H-pyrazol-1-yl)-2-methylpropanamido)acetic acid |  | No | Me | 533.2 | 7.66 (s, 1H), 7.58 (s, 1H), 7.23-7.15 (m, 2H), 7.01 (t, J = 7.9 Hz, 1H), 6.82 (t, J = 5.2 Hz, 1H), 6.74 (d, J = 7.5 Hz, 1H), 6.64 (d, J = 8.2 Hz, 1H), 4.02 (d, J = 5.3 Hz, 2H), 3.93 (t, J = 5.2 Hz, 2H), 3.78 (t, J = 6.8 Hz, 2H), 2.76 (t, J = 7.1 Hz, 2H), 2.58 (s, 2H), 2.25-2.12 (m, 5H), 1.96-1.80 (m, 11H) | 9.1 min, 99.7% 8.1 min, 99.7% |
| 130 | 2-(2-(4-(1-(4-(2,3-Dimethylphenoxy)butanoyl)-1,2,3,4-tetrahydroquinolin-5-yl)-1H-pyrazol-1-yl)-N-methylacetamido)acetic acid | 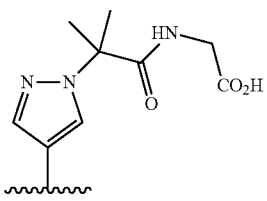 [SMILES: *c1cnn(C(C)(C)C(=O)NCC(=O)O)c1] | No | Me | 519.2 | 7.54 (d, J = 9.1 Hz, 1H), 7.47 (d, J = 9.6 Hz, 1H), 7.24 (s, 1H), 7.21-7.10 (m, 2H), 7.00 (t, J = 7.8 Hz, 1H), 6.72 (d, J = 7.5 Hz, 1H), 6.63 (d, J = 8.1 Hz, 1H), 5.26, 5.19 (2 s, 2H), 4.18, 4.10 (2 s, 2H), 3.92 (t, J = 5.3 Hz, 2H), 3.76 (t, J = 6.7 Hz, 2H), 3.16, 3.04 (2 s, 3H), 2.73 (t, J = 7.1 Hz, 2H), 2.59 (br. s, 2H), 2.24-2.10 (m, 5H), 1.91 (s, 3H), 1.89-1.79 (m, 2H) | 8.5 min, 100% 7.8 min, 100% |
| 131 | 2-(2-(4-(1-(4-(2,3-Dimethylphenoxy)butanoyl)-1,2,3,4-tetrahydroquinolin-5-yl)-1H-pyrazol-1-yl)acetamido)propanoic acid | 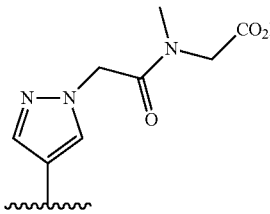 | No | Me | 519.2 | 7.59 (s, 1H), 7.39 (s, 1H), 7.21-7.10 (m, 2H), 7.04-6.94 (m, 2H), 6.73 (d, J = 7.5 Hz, 1H), 6.62 (d, J = 8.2 Hz, 1H), 4.98 (d, J = 16.2 Hz, 1H), 4.83 (d, J = 16.2 Hz, 1H), 4.63-4.52 (m, 1H), 3.90 (br. s, 2H), 3.83-3.69 (m, 2H), 2.73 (t, J = 7.1 Hz, 2H), 2.54 (br. s, 2H), 2.22-2.09 (m, 5H), 1.93-1.77 (m, 5H), 1.44 (d, J = 7.1 Hz, 3H) | 8.6 min, 100% 7.8 min, 100% |
| 132 | 2-(2-(4-(1-(4-(2,3-Dimethylphenoxy)butanoyl)-1,2,3,4-tetrahydroquinolin-5-yl)-1H-pyrazol-1-yl)-N,2-dimethylpropanamido)acetic acid | 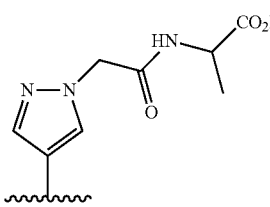 | No | Me | 547.3 | 7.58 (s, 2H), 7.24 (s, 1H), 7.21-7.10 (m, 2H), 6.99 (t, J = 7.8 Hz, 1H), 6.72 (d, J = 7.5 Hz, 1H), 6.62 (d, J = 8.1 Hz, 1H), 4.14 (br. s, 2H), 3.92 (t, J = 5.2 Hz, 2H), 3.77 (t, J = 6.7 Hz, 2H), 2.73 (t, J = 7.2 Hz, 2H), 2.65-2.49 (m, 4H), 2.24-2.09 (m, 5H), 1.98-1.77 (m, 9H) | 9.4 min, 100% 8.3 min, 100% |

TABLE 8-continued

| Example | Name | A—X—Y | cyclopropyl present | $R_{5b}$ | LCMS, $[M+H]^+$ | $^1$H NMR (400 MHz, CDCl$_3$) δ | HPLC-1: Rt min, purity; HPLC-2: Rt min, purity |
|---|---|---|---|---|---|---|---|
| 133 | 2-(2-(4-(1-(4-(2,3-Dimethylphenoxy)butanoyl)-1,2,3,4-tetrahydroquinolin-5-yl)-1H-pyrazol-1-yl)-2-methylpropanamido)propanoic acid |  | No | Me | 547.3 | 7.64 (s, 1H), 7.55 (s, 1H), 7.22-7.07 (m, 2H), 6.99 (t, J = 7.8 Hz, 1H), 6.82 (d, J = 6.9 Hz, 1H), 6.72 (d, J = 7.5 Hz, 1H), 6.62 (d, J = 8.1 Hz, 1H), 4.52-4.39 (m, 1H), 3.91 (br. s, 2H), 3.84-3.69 (m, 2H), 2.74 (t, J = 7.1 Hz, 2H), 2.55 (br. s, 2H), 2.25-2.09 (m, 5H), 2.02-1.75 (m, 11H), 1.37 (d, J = 7.2 Hz, 3H) | 9.6 min, 100% 8.5 min, 100% |
| 134 | 3-(2-(4-(1-(4-(2,3-Dimethylphenoxy)butanoyl)-1,2,3,4-tetrahydroquinolin-5-yl)-1H-pyrazol-1-yl)-2-methylpropanamido)propanoic acid | 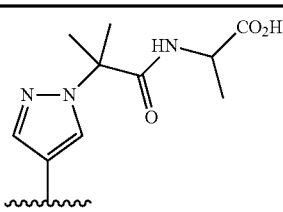 | No | Me | 547.3 | 7.65 (s, 1H), 7.52 (s, 1H), 7.24 (s, 1H), 7.18-7.08 (m, 3H), 6.99 (t, J = 7.9 Hz, 1H), 6.72 (d, J = 7.4 Hz, 1H), 6.69 (d, J = 5.9 Hz, 1H), 6.62 (d, J = 8.1 Hz, 1H), 3.91 (t, J = 5.3 Hz, 2H), 3.75 (t, J = 6.8 Hz, 2H), 3.43 (dd, J = 12.0, 6.0 Hz, 2H), 2.73 (t, J = 7.1 Hz, 2H), 2.55 (br. s, 2H), 2.50 (t, J = 6.0 Hz, 2H), 2.23-2.08 (m, 5H), 1.90 (s, 3H), 1.86 (s, 6H), 1.87-1.77 (m, 2H) | 9.3 min, 100% 8.3 min, 100% |
| 135 | 2-(3-((4-(1-(4-(2,3-Dimethylphenoxy)butanoyl)-1,2,3,4-tetrahydroquinolin-5-yl)-1H-pyrazol-1-yl)methyl)benzamido)acetic acid | 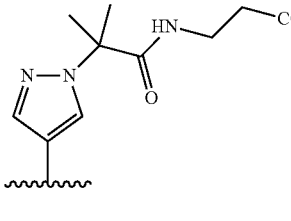 | No | Me | 581.4 | 7.88 (d, J = 7.7 Hz, 1H), 7.83 (s, 1H), 7.54 (s, 1H), 7.44 (t, J = 7.6 Hz, 1H), 7.38 (d, J = 7.9 Hz, 1H), 7.37 (s, 1H), 7.22-7.07 (m, 3H), 6.99 (t, J = 7.9 Hz, 1H), 6.70 (d, J = 7.5 Hz, 1H), 6.61 (d, J = 8.2 Hz, 1H), 5.39 (s, 2H), 4.23 (d, J = 5.1 Hz, 2H), 3.90 (t, J = 5.1 Hz, 2H), 3.76 (t, J = 6.8 Hz, 2H), 2.73 (t, J = 7.1 Hz, 2H), 2.52 (br. s, 2H), 2.21-2.06 (m, 5H), 1.93-1.76 (m, 5H) | 9.2 min, 100% 8.5 min, 100% |

TABLE 8-continued

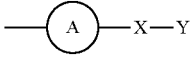

| Example | Name | A—X—Y | present | R5b | LCMS, [M + H]+ | 1H NMR (400 MHz, CDCl3) δ | HPLC-1: Rt min, purity; HPLC-2: Rt min, purity |
|---|---|---|---|---|---|---|---|
| 136 | 2-(3-((4-(1-(4-(2,3-Dimethylphenoxy)butanoyl)-1,2,3,4-tetrahydroquinolin-5-yl)-1H-pyrazol-1-yl)methyl)benzamido)propanoic acid |  | No | Me | 595.3 | 7.85 (d, J = 7.6 Hz, 1H), 7.78 (s, 1H), 7.55 (s, 1H), 7.44 (t, J = 7.6 Hz, 1H), 7.38 (d, J = 6.3 Hz, 1H), 7.37 (s, 1H), 7.23-7.08 (m, 3H), 6.99 (t, J = 7.9 Hz, 1H), 6.70 (d, J = 7.5 Hz, 1H), 6.61 (d, J = 8.2 Hz, 1H), 5.44 (d, J = 15.2 Hz, 1H), 5.34 (d, J = 15.2 Hz, 1H), 4.86-4.74 (m, 1H), 3.90 (br. s, 2H), 3.76 (t, J = 6.8 Hz, 2H), 2.73 (t, J = 7.1 Hz, 2H), 2.53 (br. s, 2H), 2.22-2.07 (m, 5H), 1.92-1.77 (m, 5H), 1.45 (d, J = 7.2 Hz, 3H) | 9.8 min, 98.9% 8.9 min, 100% |
| 137 | 2-(3-((4-(1-(4-(2,3-Dimethylphenoxy)butanoyl)-1,2,3,4-tetrahydroquinolin-5-yl)-1H-pyrazol-1-yl)methyl)-N-methylbenzamido)acetic acid | 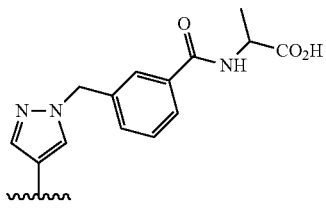 [SMILES: *c1cnn(Cc2cccc(C(=O)NC(C)C(=O)O)c2)c1] | No | Me | 595.4 | 7.55 (s, 1H), 7.46-7.27 (m, 4H), 7.24 (s, 2H), 7.20-7.08 (m, 2H), 6.98 (t, J = 7.9 Hz, 1H), 6.71 (d, J = 7.5 Hz, 1H), 6.62 (d, J = 8.1 Hz, 1H), 5.36 (s, 2H), 4.28 (s, 1H), 3.92 (br. s, 3H), 3.75 (t, J = 6.8 Hz, 2H), 3.10 (s, 1H), 3.03 (br. s, 2H), 2.72 (t, J = 7.1 Hz, 2H), 2.55 (br. s, 2H), 2.22-2.05 (m, 5H), 1.96-1.75 (m, 5H) | 9.6 min, 99.9% 8.8 min, 99.8% |
| 138 | 2-(3-(1-(4-(2,3-Dimethylphenoxy)butanoyl)-1,2,3,4-tetrahydroquinolin-5-yl)benzamido)acetic acid | 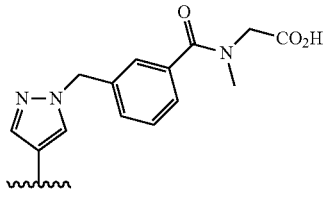 [SMILES: *c1cnn(Cc2cccc(C(=O)N(C)CC(=O)O)c2)c1] | No | Me | 501.3 | 7.78 (d, J = 7.7 Hz, 1H), 7.70 (s, 1H), 7.47 (t, J = 7.7 Hz, 1H), 7.33 (d, J = 7.6 Hz, 1H), 7.29-7.19 (m, 1H), 7.11 (d, J = 8.0 Hz, 1H), 7.00 (t, J = 7.9 Hz, 1H), 6.73 (d, J = 7.5 Hz, 1H), 6.69 (br. s, 1H), 6.64 (d, J = 8.2 Hz, 1H), 4.29 (d, J = 4.9 Hz, 2H), 4.00-3.89 (m, 2H), 3.78 (t, J = 6.9 Hz, 2H), 2.77 (t, J = 7.3 Hz, 2H), 2.50-2.40 (m, 2H), 2.23-2.16 (m, 5H), 1.96 (s, 3H), 1.86-1.76 (m, 2H) | 9.9 min, 100% 8.9 min, 100% |

TABLE 8-continued

| Example | Name |  A—X—Y | present 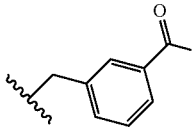 | R$_{5b}$ | LCMS, [M + H]$^+$ | $^1$H NMR (400 MHz, CDCl$_3$) δ | HPLC-1: Rt min, purity; HPLC-2: Rt min, purity |
|---|---|---|---|---|---|---|---|
| 138A | 2-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)ethanesulfonic acid | 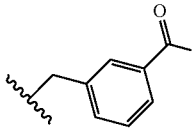 | Yes | Cl | 663.4 | 7.86 (s, 1H), 7.82-7.71 (m, 2H), 7.68 (s, 1H), 7.50-7.40 (m, 2H), 7.29 (d, J = 7.4 Hz, 1H), 7.18 (t, J = 7.8 Hz, 1H), 7.05 (t, J = 6.7 Hz, 2H), 6.90 (d, J = 8.0 Hz, 1H), 6.76 (d, J = 8.2 Hz, 1H), 5.46 (s, 2H), 4.05-3.92 (m, 2H), 3.90-3.82 (m, 2H), 3.80 (t, J = 6.7 Hz, 2H), 3.08 (t, J = 6.5 Hz, 2H), 3.06-2.99 (m, 2H), 2.82-2.65 (m, 2H), 2.17-1.98 (m, 4H), 1.90-1.83 (m, 3H), 1.81-1.65 (m, 2H), 1.29 (s, 6H), 0.87-0.69 (m, 1H), 0.42-0.27 (m, 1H)* | N/A 9.6 min, 97.7% |
| 138B | 2-(3-((4-((1aS,7bR)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)ethanesulfonic acid | 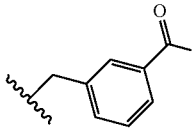 | Yes | Cl | 663.4 | 7.86 (s, 1H), 7.82-7.71 (m, 2H), 7.68 (s, 1H), 7.50-7.40 (m, 2H), 7.29 (d, J = 7.4 Hz, 1H), 7.18 (t, J = 7.8 Hz, 1H), 7.05 (t, J = 6.7 Hz, 2H), 6.90 (d, J = 8.0 Hz, 1H), 6.76 (d, J = 8.2 Hz, 1H), 5.46 (s, 2H), 4.05-3.92 (m, 2H), 3.90-3.82 (m, 2H), 3.80 (t, J = 6.7 Hz, 2H), 3.08 (t, J = 6.5 Hz, 2H), 3.06-2.99 (m, 2H), 2.82-2.65 (m, 2H), 2.17-1.98 (m, 4H), 1.90-1.83 (m, 3H), 1.81-1.65 (m, 2H), 1.29 (s, 6H), 0.87-0.69 (m, 1H), 0.42-0.27 (m, 1H)* | N/A 9.6 min, 99.8% |
| 138C | 3-((4-(1-(4-(3-Cyclopropyl-2-methylphenoxy)butanoyl)-1,2,3,4-tetrahydroquinolin-5-yl)-1H-pyrazol-1-yl)methyl)benzoic acid | 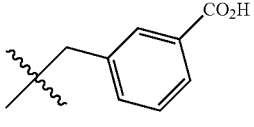 [SMILES: *Cc1cccc(C(=O)O)c1] | No | Cyclopropyl | 550.1 | 8.14-8.00 (m, 2H), 7.60 (s, 1H), 7.56-7.43 (m, 2H), 7.37 (s, 1H), 7.23-7.08 (m, 3H), 7.01 (t, J = 7.9 Hz, 1H), 6.64 (d, J = 8.2 Hz, 1H), 6.60 (d, J = 7.7 Hz, 1H), 5.42 (s, 2H), 3.93 (t, J = 5.5 Hz, 2H), 3.79 (t, J = 6.8 Hz, 2H), 2.77 (t, J = 7.1 Hz, 2H), 2.60 (t, J = 6.4 Hz, 2H), 2.18 (dt, J = 12.9, 6.5 Hz, 2H), 2.08 (s, 3H), 1.86 (dt, J = 13.6, 6.8 Hz, 2H), 1.78 (ddd, J = 13.6, 8.5, 5.5 Hz, 1H), 0.90-0.79 (m, 2H), 0.60-0.49 (m, 2H) | 10.3 min, 95% 10.6 min, 96.8% |

*$^1$H NMR (400 MHz, MeOD) δ.

Example 139

3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)propanoic acid

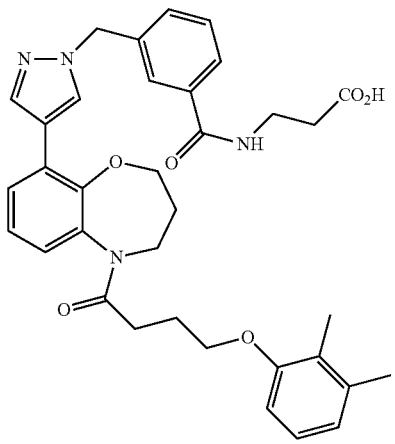 [SMILES: Cc1cccc(OCCCC(=O)N2CCCOc3c(-c4cnn(Cc5cccc(C(=O)NCCC(=O)O)c5)c4)cccc32)c1C]

A mixture of Example 13 (20 mg, 0.037 mmol), tert-butyl 3-aminopropanoate hydrochloride (13.47 mg, 0.074 mmol), DIPEA (0.019 mL, 0.111 mmol) and BOP (18.03 mg, 0.041 mmol) in DMF (1.0 mL) was stirred at room temperature for 60 min. The crude product was purified by preparative HPLC (PHENOMENEX® Axia Luna column, 5μ, C18, 30×100 mm; 25 min gradient from 80% A:20% B to 0% A:100% B (A=90% $H_2O$/10% MeOH+0.1% TFA); (B=90% MeOH/10% $H_2O$+0.1% TFA); detection at 220 nm) to give the ester. The ester was dissolved in DCM (3.0 mL) and treated with TFA (0.857 mL, 11.12 mmol). The mixture was stirred at room temperature for 30 min and concentrated. The resulting residue was purified by prep-HPLC preparative HPLC (PHENOMENEX® Axia Luna column, 5μ, C18, 30×100 mm; 25 min gradient from 80% A:20% B to 0% A:100% B (A=90% $H_2O$/10% MeOH+0.1% TFA); (B=90% MeOH/10% $H_2O$+0.1% TFA); detection at 220 nm) to afford Example 139 (12.2 mg, 51% yield) as a white powder. LCMS, $[M+H]^+$=611.2. $^1$H NMR (400 MHz, MeOD) δ 8.03 (s, 1H), 7.94 (s, 1H), 7.81 (s, 1H), 7.80-7.76 (m, 1H), 7.66 (dd, J=6.1, 3.4 Hz, 1H), 7.52-7.45 (m, 2H), 7.16 (d, J=2.7 Hz, 1H), 7.15 (s, 1H), 6.93 (t, J=7.8 Hz, 1H), 6.65 (d, J=4.1 Hz, 1H), 6.63 (d, J=5.0 Hz, 1H), 5.45 (s, 2H), 4.79 (dt, J=13.2, 3.4 Hz, 1H), 4.48 (dt, J=6.1, 3.3 Hz, 1H), 3.93-3.80 (m, 2H), 3.65 (t, J=6.9 Hz, 2H), 3.59 (td, J=11.7, 1.5 Hz, 1H), 2.91-2.81 (m, 1H), 2.66 (t, J=6.9 Hz, 2H), 2.50-2.37 (m, 2H), 2.34-2.23 (m, 1H), 2.11 (s, 3H), 2.09-2.01 (m, 2H), 1.83 (s, 3H), 1.82-1.75 (m, 1H). HPLC-1: Rt=8.2 min, purity=94.1%; HPLC-2: Rt=7.9 min, purity=93.9%.

The following Examples were prepared in a manner analogous to Example 139.

TABLE 9

| Example | Name | Formula I | LCMS, $[M+H]^+$ | $^1$H NMR (500 MHz, MeOD) δ | HPLC-1: Rt min, purity; HPLC-2: Rt min, purity |
|---|---|---|---|---|---|
| 140 | 2-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)acetic acid | | 597.2 | 8.03 (s, 1H), 7.94 (s, 1H), 7.89-7.82 (m, 2H), 7.66 (dd, J = 6.1, 3.4 Hz, 1H), 7.55-7.47 (m, 2H), 7.20-7.12 (m, 2H), 6.93 (t, J = 7.9 Hz, 1H), 6.66 (d, J = 6.3 Hz, 1H), 6.64 (d, J = 7.5 Hz, 1H), 5.46 (s, 2H), 4.83-4.74 (m, 1H), 4.51-4.43 (m, 1H), 4.12 (s, 2H), 3.94-3.79 (m, 2H), 3.64-3.54 (m, 1H), 2.91-2.80 (m, 1H), 2.51-2.36 (m, 2H), 2.35-2.19 (m, 1H), 2.11 (s, 3H), 2.09-2.01 (m, 2H), 1.83 (s, 3H), 1.82-1.75 (m, 1H) | 8.2 min, 98.8% 7.9 min, 98.6% |

TABLE 9-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 141 | 2-(4-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)acetic acid | | 597.3 | 8.08 (s, 1H), 8.06 (s, 1H), 8.04 (d, J = 8.3 Hz, 2H), 7.73 (dd, J = 7.7, 1.7 Hz, 1H), 7.50 (d, J = 8.3 Hz, 2H), 7.30 (t, J = 7.7 Hz, 1H), 7.25 (dd, J = 7.7, 1.7 Hz, 1H), 7.12 (t, J = 7.9 Hz, 1H), 6.85 (d, J = 7.5 Hz, 1H), 6.78 (d, J = 8.2 Hz, 1H), 5.61 (d, J = 15.6 Hz, 1H), 5.57 (d, J = 15.6 Hz, 1H), 4.98-4.93 (m, 1H), 4.66-4.60 (m, 1H), 4.23 (s, 2H), 4.07 (dt, J = 11.1, 5.6 Hz, 1H), 4.03-3.97 (m, 1H), 3.77 (td, J = 11.7, 1.5 Hz, 1H), 3.04-2.96 (m, 1H), 2.65-2.42 (m, 3H), 2.32 (s, 3H), 2.27-2.18 (m, 2H), 2.05 (s, 3H), 1.96 (d, J = 14.8 Hz, 1H) | |
| 142 | 3-(4-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)propanoic acid | | 611.3 | 8.09 (s, 1H), 8.07 (s, 1H), 7.99 (d, J = 8.3 Hz, 2H), 7.74 (dd, J = 7.7, 1.7 Hz, 1H), 7.50 (d, J = 8.3 Hz, 2H), 7.31 (t, J = 7.7 Hz, 1H), 7.27 (dd, J = 7.8, 1.7 Hz, 1H), 7.13 (t, J = 7.9 Hz, 1H), 6.86 (d, J = 7.5 Hz, 1H), 6.79 (d, J = 8.2 Hz, 1H), 5.61 (d, J = 15.6 Hz, 1H), 5.57 (d, J = 15.5 Hz, 1H), 5.00-4.94 (m, 1H), 4.66-4.61 (m, 1H), 4.08 (dt, J = 11.1, 5.6 Hz, 1H), 4.04-3.98 (m, 1H), 3.83 (t, J = 6.6 Hz, 2H), 3.78 (t, J = 11.0 Hz, 1H), 3.05-2.97 (m, 1H), 2.81 (t, J = 6.6 Hz, 2H), 2.67-2.43 (m, 3H), 2.33 (s, 3H), 2.28-2.18 (m, 2H), 2.06 (s, 3H), 1.98 (d, J = 14.9 Hz, 1H) | |
| 143 | 2-(4-((4-(1-(4-(2,3-Dimethylphenoxy)butanoyl)-2,3,4,5-tetrahydro-1H-benzo[b]azepin-6-yl)-1H-pyrazol-1-yl)methyl)benzamido)acetic acid | | 595.4 | 8.06 (d, J = 8.3 Hz, 2H), 7.73 (s, 1H), 7.72 (s, 1H), 7.52 (d, J = 8.3 Hz, 2H), 7.47 (dd, J = 7.7, 1.2 Hz, 1H), 7.40 (t, J = 7.7 Hz, 1H), 7.27 (dd, J = 7.7, 1.2 Hz, 1H), 7.16 (t, J = 7.9 Hz, 1H), 6.89 (d, J = 7.6 Hz, 1H), 6.81 (d, J = 8.2 Hz, 1H), 5.63 (s, 2H), 4.83-4.79 (m, 1H), 4.28 (s, 2H), 4.15-4.03 (m, 2H), 3.14 (dd, J = 14.1, 6.1 Hz, 1H), 2.99-2.90 (m, 1H), 2.67 (ddd, J = 15.6, 7.6, 6.6 Hz, 1H), 2.59 (t, J = 12.8 Hz, 1H), 2.52-2.45 (m, 1H), 2.35 (s, 3H), 2.27 (td, J = 13.3, 6.4 Hz, 2H), 2.17-2.09 (m, 2H), 2.07 (s, 3H), 2.00-1.93 (m, 1H), 1.61-1.53 (m, 1H) | |

TABLE 9-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 144 | 3-(4-((4-(1-(4-(2,3-Dimethylphenoxy)butanoyl)-2,3,4,5-tetrahydro-1H-benzo[b]azepin-6-yl)-1H-pyrazol-1-yl)methyl)benzamido)propanoic acid | | 609.4 | 8.00 (d, J = 8.3 Hz, 2H), 7.72 (s, 1H), 7.71 (s, 1H), 7.51 (d, J = 8.3 Hz, 2H), 7.46 (dd, J = 7.7, 1.2 Hz, 1H), 7.40 (t, J = 7.7 Hz, 1H), 7.27 (dd, J = 7.6, 1.1 Hz, 1H), 7.16 (t, J = 7.9 Hz, 1H), 6.89 (d, J = 7.5 Hz, 1H), 6.81 (d, J = 8.2 Hz, 1H), 5.62 (s, 2H), 4.84-4.78 (m, 1H), 4.14-4.02 (m, 2H), 3.83 (t, J = 6.6 Hz, 2H), 3.14 (dd, J = 14.1, 6.1 Hz, 1H), 2.98-2.90 (m, 1H), 2.82 (t, J = 6.6 Hz, 2H), 2.71-2.55 (m, 2H), 2.53-2.45 (m, 1H), 2.34 (s, 3H), 2.32-2.21 (m, 2H), 2.17-2.08 (m, 2H), 2.07 (s, 3H), 2.01-1.92 (m, 1H), 1.64-1.51 (m, 1H) | |
| 145 | 2-(3-((4-(5-(4-(2,3-Dimethylphenoxy)butanoyl)-2-methyl-2,3,4,5-tetrahydrobenzo[b][1,4]oxazepin-9-yl)-1H-pyrazol-1-yl)methyl)benzamido)acetic acid | | 611.3 | 8.04 (s, 1H), 8.03 (s, 1H), 8.01 (d, J = 7.7 Hz, 1H), 7.94 (s, 1H), 7.68 (dd, J = 7.7, 1.6 Hz, 1H), 7.64 (t, J = 7.7 Hz, 1H), 7.58 (d, J = 7.9 Hz, 1H), 7.29 (t, J = 7.7 Hz, 1H), 7.24 (dd, J = 7.7, 1.6 Hz, 1H), 7.16 (t, J = 8.0 Hz, 1H), 6.89 (d, J = 7.5 Hz, 1H), 6.82 (d, J = 8.2 Hz, 1H), 5.59 (d, J = 15.1 Hz, 1H), 5.54 (d, J = 15.1 Hz, 1H), 4.93-4.89 (m, 1H), 4.22 (s, 2H), 4.11-3.98 (m, 2H), 3.92-3.83 (m, 1H), 2.96 (t, J = 12.1 Hz, 1H), 2.63-2.51 (m, 2H), 2.31 (s, 3H), 2.28-2.21 (m, 2H), 2.03 (s, 3H), 1.90 (d, J = 13.3 Hz, 1H), 1.41 (d, J = 6.2 Hz, 3H), 1.14 (d, J = 6.4 Hz, 1H) | |
| 146 | 3-(3-((4-(5-(4-(2,3-Dimethylphenoxy)butanoyl)-2-methyl-2,3,4,5-tetrahydrobenzo[b][1,4]oxazepin-9-yl)-1H-pyrazol-1-yl)methyl)benzamido)propanoic acid | | 625.3 | 8.02 (s, 1H), 7.97 (s, 1H), 7.94 (d, J = 7.8 Hz, 1H), 7.93 (s, 1H), 7.68 (dd, J = 7.7, 1.6 Hz, 1H), 7.62 (t, J = 7.7 Hz, 1H), 7.57 (d, J = 7.8 Hz, 1H), 7.29 (t, J = 7.8 Hz, 1H), 7.24 (dd, J = 7.7, 1.7 Hz, 1H), 7.16 (t, J = 7.9 Hz, 1H), 6.88 (d, J = 7.5 Hz, 1H), 6.81 (d, J = 8.2 Hz, 1H), 5.58 (d, J = 15.0 Hz, 1H), 5.52 (d, J = 15.0 Hz, 1H), 4.93-4.89 (m, 1H), 4.13-3.96 (m, 2H), 3.91-3.85 (m, 1H), 3.83 (t, J = 6.6 Hz, 2H), 3.03-2.93 (m, 1H), 2.79 (t, J = 6.6 Hz, 2H), 2.62-2.51 (m, 2H), 2.31 (s, 3H), 2.26-2.21 (m, 2H), 2.03 (s, 3H), 1.90 (d, J = 14.4 Hz, 1H), 1.40 (d, J = 6.2 Hz, 3H), 1.13 (d, J = 6.4 Hz, 1H) | |

TABLE 9-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 146A | 3-((4-(5-(4-(2,3-Dimethylphenoxy)butanoyl)-4,5-dihydro-2H-spiro[benzo[b][1,4]oxazepine-3,1'-cyclopropane]-9-yl)-1H-pyrazol-1-yl)methyl)benzoic acid | | 566.3 | 7.98 (d, J = 6.0 Hz, 2H), 7.91 (d, J = 13.8 Hz, 2H), 7.65 (d, J = 7.5 Hz, 1H), 7.49 (dt, J = 15.2, 7.6 Hz, 2H), 7.21-7.04 (m, 2H), 6.90 (t, J = 7.9 Hz, 1H), 6.62 (dd, J = 7.8, 4.3 Hz, 2H), 5.43 (s, 2H), 4.35 (d, J = 13.5 Hz, 1H), 3.93-3.81 (m, 2H), 3.72 (s, 2H), 3.04 (d, J = 13.7 Hz, 1H), 2.52 (dt, J = 15.1, 7.5 Hz, 1H), 2.44-2.31 (m, 1H), 2.06 (s, 3H), 2.05-1.97 (m, 2H), 1.79 (s, 3H), 1.04-0.91 (m, 1H), 0.71-0.61 (m, 1H), 0.54-0.44 (m, 1H), 0.42-0.31 (m, 1H)* | 9.8 min, 98.6% 9.0 min, 92.8% |
| 146B | 2-(3-((4-(5-(4-(2,3-Dimethylphenoxy)butanoyl)-4,5-dihydro-2H-spiro[benzo[b][1,4]oxazepine-3,1'-cyclopropane]-9-yl)-1H-pyrazol-1-yl)methyl)benzamido)ethanesulfonic acid | | 673.3 | 8.07 (s, 1H), 7.95 (s, 1H), 7.81-7.72 (m, 2H), 7.64 (dd, J = 7.5, 1.9 Hz, 1H), 7.45 (d, J = 7.7 Hz, 2H), 7.20-7.05 (m, 2H), 6.89 (t, J = 7.9 Hz, 1H), 6.61 (t, J = 6.9 Hz, 2H), 5.44 (s, 2H), 4.93-4.86 (m, 1H), 4.34 (d, J = 13.6 Hz, 1H), 3.92-3.82 (m, 2H), 3.78 (s, 4H), 3.05 (dd, J = 16.4, 9.9 Hz, 3H), 2.57-2.45 (m, 1H), 2.41-2.31 (m, 1H), 2.05 (s, 3H), 2.04-1.97 (m, 2H), 1.77 (s, 3H), 0.96 (s, 1H), 0.67 (s, 1H), 0.47 (d, J = 8.9 Hz, 1H), 0.40 (s, 1H)* | 10.4 min, 99.0% 7.1 min, 92.4% |
| 146C | 3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)propane-1-sulfonic acid | | 661.4 | 8.19 (s, 1H), 8.06 (d, J = 0.6 Hz, 1H), 7.85-7.76 (m, 2H), 7.64 (dd, J = 6.4, 3.1 Hz, 1H), 7.53-7.43 (m, 2H), 7.15 (m, 2H), 6.88 (t, J = 7.9 Hz, 1H), 6.60 (d, J = 2.3 Hz, 1H), 6.58 (s, 1H), 5.50 (s, 2H), 4.75 (dt, J = 13.3, 2.9 Hz, 1H), 4.46 (dt, J = 10.7, 3.0 Hz, 1H), 3.89-3.75 (m, 2H), 3.57 (td, J = 11.7, 1.8 Hz, 1H), 3.50 (t, J = 6.7 Hz, 2H), 2.90 (dd, J = 8.3, 6.7 Hz, 2H), 2.86-2.76 (m, 1H), 2.45 (dt, J = 15.0, 7.5 Hz, 1H), 2.40-2.32 (m, 1H), 2.32-2.18 (m, 1H), 2.14-1.94 (m, 7H), 1.83-1.78 (m, 1H), 1.77 (s, 3H) | 9.1 min, 98.1% 6.8 min, 95.3% |

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 146D | 4-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)butanoic acid | | 625.3 | 8.01 (s, 1H), 7.91 (s, 1H), 7.79-7.77 (m, 1H), 7.76-7.73 (m, 1H), 7.62 (dd, J = 6.1, 3.4 Hz, 1H), 7.51-7.40 (m, 2H), 7.13 (d, J = 2.8 Hz, 1H), 7.12 (s, 1H), 6.88 (d, J = 7.9 Hz, 1H), 6.62 (d, J = 4.3 Hz, 1H), 6.60 (d, J = 5.1 Hz, 1H), 5.42 (s, 2H), 4.75 (dt, J = 13.3, 3.3 Hz, 1H), 4.44 (dt, J = 5.9, 3.2 Hz, 1H), 3.90-3.76 (m, 2H), 3.55 (td, J = 11.7, 1.5 Hz, 1H), 3.41 (t, J = 7.0 Hz, 2H), 2.89-2.77 (m, 1H), 2.48-2.33 (m, 4H), 2.32-2.18 (m, 1H), 2.07 (s, 3H), 2.06-1.96 (m, 2H), 1.96-1.86 (m, 2H), 1.80 (s, 3H), 1.79-1.71 (m, 1H) | 8.3 min, 99.2% 8.0 min, 97.2% |
| 146E | 3-(3-((4-(5-(4-(2,3-Dimethylphenoxy)butanoyl)-4,5-dihydro-2H-spiro[benzo[b][1,4]oxazepine-3,1'-cyclopropane]-9-yl)-1H-pyrazol-1-yl)methyl)benzamido)propanoic acid | | 637.3 | 7.97 (s, 1H), 7.89 (s, 1H), 7.80-7.70 (m, 2H), 7.64 (dd, J = 7.7, 1.8 Hz, 1H), 7.49-7.38 (m, 2H), 7.14 (t, J = 7.7 Hz, 1H), 7.09 (dd, J = 7.8, 1.8 Hz, 1H), 6.90 (t, J = 7.8 Hz, 1H), 6.66-6.58 (m, 2H), 5.40 (s, 2H), 4.35 (d, J = 13.4 Hz, 1H), 3.96-3.80 (m, 2H), 3.73 (s, 2H), 3.61 (t, J = 6.9 Hz, 2H), 3.04 (d, J = 13.6 Hz, 1H), 2.62 (t, J = 6.9 Hz, 2H), 2.50 (dt, J = 15.0, 7.5 Hz, 1H), 2.44-2.30 (m, 1H), 2.06 (s, 3H), 2.05-1.97 (m, 2H), 1.80 (s, 3H), 0.97 (dt, J = 10.5, 5.4 Hz, 1H), 0.66 (dt, J = 9.6, 4.9 Hz, 1H), 0.48 (dt, J = 9.1, 5.4 Hz, 1H), 0.38 (dt, J = 10.8, 5.6 Hz, 1H) | 8.3 min, 96.1% 8.8 min, 99.2% |
| 146F | (3-((4-(5-(4-(2,3-Dimethylphenoxy)butanoyl)-4,5-dihydro-2H-spiro[benzo[b][1,4]oxazepine-3,1'-cyclopropane]-9-yl)-1H-pyrazol-1-yl)methyl)benzamido)methanesulfonic acid | | 659.3 | 8.14 (s, 1H), 8.01 (s, 1H), 7.92-7.82 (m, 2H), 7.66 (dd, J = 7.2, 2.2 Hz, 1H), 7.55-7.40 (m, 2H), 7.21-7.09 (m, 2H), 6.91 (t, J = 7.9 Hz, 1H), 6.63 (d, J = 5.1 Hz, 1H), 6.61 (d, J = 4.4 Hz, 1H), 5.48 (s, 2H), 4.52 (s, 2H), 4.36 (d, J = 13.7 Hz, 1H), 3.87 (m, 2H), 3.82-3.70 (m, 2H), 3.04 (d, J = 13.5 Hz, 1H), 2.52 (dt, J = 14.9, 7.4 Hz, 1H), 2.43-2.32 (m, 1H), 2.07 (s, 3H), 2.06-1.94 (m, 2H), 1.79 (s, 3H), 1.04-0.92 (m, 1H), 0.74-0.63 (m, 1H), 0.49 (dt, J = 9.1, 5.4 Hz, 1H), 0.40 (dt, J = 9.1, 5.3 Hz, 1H) | 10.5 min, 98.5% 7.1 min, 95.4% |

TABLE 9-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 146G | 2-(3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)phenyl)ureido)ethanesulfonic acid | | 662.2 | 8.02 (s, 1H), 7.94 (s, 1H), 7.62 (dd, J = 5.5, 4.0 Hz, 1H), 7.37-7.28 (m, 2H), 7.24 (t, J = 7.8 Hz, 1H), 7.13 (d, J = 1.5 Hz, 1H), 7.12 (s, 1H), 6.93-6.85 (m, 2H), 6.61 (d, J = 2.9 Hz, 1H), 6.59 (d, J = 4.1 Hz, 1H), 5.34 (s, 2H), 4.80-4.69 (m, 1H), 4.44 (d, J = 12.4 Hz, 1H), 3.92-3.75 (m, 2H), 3.61 (m, 2H), 3.59-3.50 (m, 1H) 3.02-2.92 (m, 2H), 2.88-2.76 (m, 1H), 2.39 (qd, J = 15.0, 6.9 Hz, 2H), 2.32-2.17 (m, 1H), 2.07 (s, 3H), 2.05-1.97 (m, 2H), 1.79 (s, 3H), 1.78-1.68 (m, 1H) | 9.5 min, 99.6% 6.9 min, 92.7% |
| 146H | 2-(2-(3-((4-(5-(4-(2,3-Dimethylphenoxy)butanoyl)-4,5-dihydro-2H-spiro[benzo[b][1,4]oxazepine-3,1'-cyclopropane]-9-yl)-1H-pyrazol-1-yl)methyl)benzamido)acetamido)acetic acid | | 680.4 | 7.97 (s, 1H), 7.88 (d, J = 0.5 Hz, 1H), 7.85-7.77 (m, 2H), 7.63 (dd, J = 7.7, 1.8 Hz, 1H), 7.51-7.41 (m, 2H), 7.13 (t, J = 7.7 Hz, 1H), 7.08 (dd, J = 7.8, 1.8 Hz, 1H), 6.90 (t, J = 7.9 Hz, 1H), 6.62 (d, J = 7.9 Hz, 2H), 5.41 (s, 2H), 4.33 (d, J = 13.6 Hz, 1H), 4.08 (s, 2H), 3.94 (s, 2H), 3.92-3.79 (m, 2H), 3.78-3.64 (m, 2H), 3.03 (d, J = 13.8 Hz, 1H), 2.49 (dt, J = 15.0, 7.6 Hz, 1H), 2.43-2.32 (m, 1H), 2.06 (s, 3H), 2.05-1.97 (m, 2H), 1.79 (s, 3H), 1.02-0.90 (m, 1H), 0.69-0.60 (m, 1H), 0.47 (dt, J = 8.7, 5.4 Hz, 1H), 0.37 (dt, J = 9.4, 5.7 Hz, 1H) | 8.2 min, 97.7% 7.9 min, 93.7% |
| 146J | 2-(3-((4-(5-(4-(2,3-Dimethylphenoxy)butanoyl)-4,5-dihydro-2H-spiro[benzo[b][1,4]oxazepine-3,1'-cyclopropane]-9-yl)-1H-pyrazol-1-yl)methyl)benzamido)acetic acid | | 623.3 | 7.97 (s, 1H), 7.89 (s, 1H), 7.85-7.75 (m, 2H), 7.64 (dd, J = 7.6, 1.8 Hz, 1H), 7.47 (dd, J = 9.3, 5.2 Hz, 2H), 7.14 (t, J = 7.7 Hz, 1H), 7.09 (dd, J = 7.8, 1.8 Hz, 1H), 6.89 (d, J = 7.9 Hz, 1H), 6.62 (d, J = 8.0 Hz, 2H), 5.41 (s, 2H), 4.34 (d, J = 13.5 Hz, 1H), 4.07 (s, 2H), 3.94-3.80 (m, 2H), 3.78-3.66 (m, 2H), 3.03 (d, J = 13.5 Hz, 1H), 2.49 (dt, J = 15.1, 7.6 Hz, 1H), 2.43-2.31 (m, 1H), 2.06 (s, 3H), 2.05-1.96 (m, 2H), 1.79 (s, 3H), 1.01-0.91 (m, 1H), 0.66 (dt, J = 9.8, 5.0 Hz, 1H), 0.47 (dt, J = 9.3, 5.8 Hz, 1H), 0.37 (dt, J = 9.4, 5.3 Hz, 1H) | 8.8 min, 98.8% 8.3 min, 94.8% |

TABLE 9-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 146M | 3-(3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)phenyl)ureido)propanoic acid | | 626.2 | 7.95 (s, 1H), 7.88 (s, 1H), 7.61 (dd, J = 6.4, 3.1 Hz, 1H), 7.30 (m, 2H), 7.23 (dd, J = 8.6, 7.5 Hz, 1H), 7.17-7.06 (m, 2H), 6.94-6.84 (m, 2H), 6.61 (t, J = 7.2 Hz, 2H), 5.31 (s, 2H), 4.75 (dt, J = 7.5, 3.4 Hz, 1H), 4.43 (dt, J = 5.9, 3.2 Hz, 1H), 3.91-3.75 (m, 2H), 3.55 (td, J = 11.9, 1.9 Hz, 1H), 3.42 (t, J = 6.4 Hz, 2H), 2.89-2.75 (m, 1H), 2.57-2.33 (m, 4H), 2.32-2.18 (m, 1H), 2.07 (s, 3H), 2.06-1.96 (m, 2H), 1.80 (s, 3H), 1.79-1.69 (m, 1H) | 8.4 min, 97.8% 8.1 min, 96.0% |
| 146N | 2-(3-((4-(5-(4-(2,3-Dimethylphenoxy)butanoyl)-4,5-dihydro-2H-spiro[benzo[b][1,4]oxazepine-3,1'-cyclopropane]-9-yl)-1H-pyrazol-1-yl)methyl)benzamido)-N,N,N-trimethylethanaminium, TFA | | 651.4 | 8.01 (s, 1H), 7.90 (s, 1H), 7.83-7.72 (m, 2H), 7.64 (dd, J = 7.6, 1.9 Hz, 1H), 7.48 (d, J = 5.2 Hz, 2H), 7.14 (t, J = 7.7 Hz, 1H), 7.10 (dd, J = 7.8, 1.9 Hz, 1H), 6.89 (t, J = 7.9 Hz, 1H), 6.63 (d, J = 4.6 Hz, 1H), 6.61 (d, J = 4.0 Hz, 1H), 5.42 (s, 2H), 4.35 (d, J = 13.7 Hz, 1H), 3.93-3.80 (m, 4H), 3.73 (t, J = 8.7 Hz, 2H), 3.55 (t, J = 6.7 Hz, 2H), 3.18 (d, J = 21.8 Hz, 9H), 3.04 (d, J = 13.6 Hz, 1H), 2.48 (dt, J = 15.1, 7.5 Hz, 1H), 2.43-2.33 (m, 1H), 2.06 (s, 3H), 2.05-1.96 (m, 2H), 1.80 (s, 3H), 0.97 (dt, J = 9.8, 5.0 Hz, 1H), 0.71-0.59 (m, 1H), 0.49 (dt, J = 9.0, 5.5 Hz, 1H), 0.37 (dt, J = 9.2, 5.5 Hz, 1H) | 6.6 min, 99.8% 7.8 min, 97.9% |
| 146P | 2-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)-N,N,N-trimethylethanaminium, TFA | | 625.4 | 8.03 (s, 1H), 7.91 (s, 1H), 7.85-7.73 (m, 2H), 7.62 (dd, J = 5.3, 4.2 Hz, 1H), 7.49 (d, J = 5.1 Hz, 2H), 7.18-7.09 (m, 2H), 6.89 (t, J = 7.9 Hz, 1H), 6.61 (dd, J = 7.8, 2.9 Hz, 2H), 5.43 (s, 2H), 4.81-4.69 (m, 1H), 4.51-4.39 (m, 1H), 3.94-3.74 (m, 4H), 3.64-3.49 (m, 3H), 3.21 (s, 9H), 2.90-2.77 (m, 1H), 2.40 (td, J = 7.1, 2.4 Hz, 2H), 2.32-2.18 (m, 1H), 2.07 (s, 3H), 2.05-1.96 (m, 2H), 1.80 (s, 3H), 1.79-1.72 (m, 1H) | 6.2 min, 99.4% 7.3 min, 98.4% |

TABLE 9-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 146Q | 3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzoic acid | | 561.2 | 8.01 (d, J = 0.4 Hz, 1H), 7.99-7.93 (m, 2H), 7.89 (d, J = 0.6 Hz, 1H), 7.61 (dd, J = 6.6, 2.9 Hz, 1H), 7.55-7.49 (m, 1H), 7.47 (t, J = 7.8 Hz, 1H), 7.18-7.07 (m, 2H), 6.94 (t, J = 8.2 Hz, 1H), 6.78 (d, J = 7.5 Hz, 1H), 6.70 (d, J = 8.2 Hz, 1H), 5.43 (s, 2H), 4.74 (dt, J = 6.8, 3.2 Hz, 1H), 4.44 (dt, J = 11.5, 2.9 Hz, 1H), 3.95-3.79 (m, 2H), 3.54 (td, J = 11.8, 1.9 Hz, 1H), 2.87-2.75 (m, 1H), 2.46 (dt, J = 15.1, 7.5 Hz, 1H), 2.35 (dt, J = 15.1, 6.5 Hz, 1H), 2.30-2.16 (m, 1H), 2.09-1.96 (m, 2H), 1.90 (s, 3H), 1.81-1.69 (m, 1H) | 9.6 min, 98.3% 8.9 min, 97.2% |
| 146R | (3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)methanesulfonic acid | | 655.1 | 8.20 (s, 1H), 8.06 (s, 1H), 7.92-7.82 (m, 2H), 7.65 (dd, J = 6.0, 3.5 Hz, 1H), 7.54-7.44 (m, 2H), 7.22-7.11 (m, 2H), 6.97 (s, 1H), 6.79 (d, J = 8.1 Hz, 1H), 6.72 (d, J = 8.1 Hz, 1H), 5.51 (s, 2H), 4.80-4.70 (m, 1H), 4.52 (s, 2H), 4.50-4.41 (m, 1H), 3.96-3.79 (m, 2H), 3.57 (td, J = 11.4, 1.4 Hz, 1H), 2.89-2.76 (m, 1H), 2.48 (dt, J = 15.1, 7.6 Hz, 1H), 2.40-2.30 (m, 1H), 2.30-2.17 (m, 1H), 2.13-1.94 (m, 2H), 1.89 (s, 3H), 1.83-1.73 (m, 1H) | 10.0 min, 97.6% 7.0 min, 94.9% |
| 146S | 2-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)ethanesulfonic acid | | 669.3 | 8.22 (s, 1H), 8.08 (s, 1H), 7.85-7.77 (m, 2H), 7.65 (dd, J = 6.1, 3.4 Hz, 1H), 7.55-7.44 (m, 2H), 7.22-7.12 (m, 2H), 6.96 (t, J = 8.2 Hz, 1H), 6.78 (d, J = 7.7 Hz, 1H), 6.71 (d, J = 8.2 Hz, 1H), 5.52 (s, 2H), 4.81-4.70 (m, 1H), 4.52-4.41 (m, 1H), 3.94-3.83 (m, 2H), 3.79 (t, J = 6.6 Hz, 2H), 3.58 (td, J = 11.6, 1.4 Hz, 1H), 3.07 (t, J = 6.6 Hz, 2H), 2.87-2.76 (m, 1H), 2.55-2.42 (m, 1H), 2.34 (dt, J = 15.0, 6.3 Hz, 1H), 2.30-2.17 (m, 1H), 2.13-1.95 (m, 2H), 1.88 (s, 3H), 1.83-1.72 (m, 1H) | 9.9 min, 99.2% 7.0 min, 97.6% |

TABLE 9-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 146T | 3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)propane-1-sulfonic acid | | 683.0 | 8.19 (s, 1H), 8.04 (d, J = 0.6 Hz, 1H), 7.87-7.75 (m, 2H), 7.65 (dd, J = 5.6, 4.0 Hz, 1H), 7.53-7.42 (m, 2H), 7.21-7.09 (m, 2H), 6.96 (t, J = 8.1 Hz, 1H), 6.78 (d, J = 7.6 Hz, 1H), 6.71 (d, J = 8.3 Hz, 1H), 5.50 (s, 2H), 4.75 (dt, J = 13.5, 3.4 Hz, 1H), 4.46 (dt, J = 12.1, 3.1 Hz, 1H), 3.95-3.79 (m, 2H), 3.57 (td, J = 11.7, 1.7 Hz, 1H), 3.51 (t, J = 6.7 Hz, 2H), 2.90 (dd, J = 8.2, 6.8 Hz, 2H), 2.87-2.76 (m, 1H), 2.54-2.42 (m, 1H), 2.40-2.30 (m, 1H), 2.30-2.15 (m, 1H), 2.16-1.95 (m, 4H), 1.88 (s, 3H), 1.83-1.72 (m, 1H) | 9.5 min, 98.8% 6.9 min, 96.6% |
| 146U | 3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)propanoic acid | | 632.2 | 8.00 (s, 1H), 7.89 (d, J = 0.5 Hz, 1H), 7.77 (s, 1H), 7.76-7.71 (m, 1H), 7.61 (dd, J = 6.5, 3.0 Hz, 1H), 7.50-7.40 (m, 2H), 7.18-7.08 (m, 2H), 6.94 (t, J = 8.1 Hz, 1H), 6.79 (d, J = 7.5 Hz, 1H), 6.70 (d, J = 8.3 Hz, 1H), 5.41 (d, J = 1.3 Hz, 2H), 4.79-4.69 (m, 1H), 4.50-4.38 (m, 1H), 3.94-3.79 (m, 2H), 3.61 (t, J = 6.9 Hz, 2H), 3.55 (td, J = 11.7, 1.8 Hz, 1H), 2.88-2.75 (m, 1H), 2.62 (t, J = 6.9 Hz, 2H), 2.45 (dt, J = 15.1, 7.6 Hz, 1H), 2.35 (dt, J = 15.1, 6.5 Hz, 1H), 2.30-2.16 (m, 1H), 2.10-1.95 (m, 2H), 1.91 (s, 3H), 1.83-1.70 (m, 1H) | 8.5 min, 97.7% 8.2 min, 95.4% |
| 146W | 4-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)butanoic acid | | 646.3 | 8.01 (s, 1H), 7.89 (s, 1H), 7.78 (s, 1H), 7.75 (dt, J = 6.7, 2.0 Hz, 1H), 7.61 (dd, J = 6.8, 2.7 Hz, 1H), 7.45 (d, J = 6.7 Hz, 2H), 7.17-7.08 (m, 2H), 6.94 (t, J = 8.1 Hz, 1H), 6.79 (d, J = 7.8 Hz, 1H), 6.70 (d, J = 8.3 Hz, 1H), 5.42 (d, J = 2.4 Hz, 2H), 4.75 (dt, J = 13.6, 3.3 Hz, 1H), 4.44 (dt, J = 6.4, 2.8 Hz, 1H), 3.96-3.81 (m, 2H), 3.55 (td, J = 11.7, 1.7 Hz, 1H), 3.41 (t, J = 7.0 Hz, 2H), 2.86-2.75 (m, 1H), 2.45 (dt, J = 15.1, 7.5 Hz, 1H), 2.41-2.31 (m, 3H), 2.31-2.17 (m, 1H), 2.08-1.96 (m, 2H), 1.96-1.86 (m, 5H), 1.82-1.70 (m, 1H) | 8.6 min, 97.9% 8.2 min, 95.4% |

TABLE 9-continued

| Example | Name | Formula I | LCMS, [M+H]+ | 1H NMR (500 MHz, MeOD) δ | HPLC-1: Rt min, purity; HPLC-2: Rt min, purity |
|---|---|---|---|---|---|
| 146X | 2-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)-N,N,N-trimethylethanaminium, TFA | | 646.3 | 8.04 (s, 1H), 7.90 (d, J = 0.4 Hz, 1H), 7.81 (s, 1H), 7.80-7.75 (m, 1H), 7.62 (dd, J = 6.2, 3.2 Hz, 1H), 7.53-7.47 (m, 2H), 7.18-7.10 (m, 2H), 6.94 (t, J = 8.2 Hz, 1H), 6.78 (d, J = 7.7 Hz, 1H), 6.70 (d, J = 8.2 Hz, 1H), 5.44 (d, J = 2.5 Hz, 2H), 4.75 (dt, J = 6.0, 3.3 Hz, 1H), 4.45 (dt, J = 11.9, 2.8 Hz, 1H), 3.95-3.79 (m, 4H), 3.61-3.51 (m, 3H), 3.22 (s, 9H), 2.87-2.76 (m, 1H), 2.44 (dt, J = 15.1, 7.5 Hz, 1H), 2.40-2.31 (m, 1H), 2.31-2.18 (m, 1H), 2.09-1.96 (m, 2H), 1.91 (s, 3H), 1.84-1.72 (m, 1H) | 6.3 min, 93.1% 7.5 min, 93.4% |

*1H NMR (400 MHz, MeOD) δ.

Example 146Y 2-(2-(4-(1-(4-(2,3-Dimethylphenoxy)butanoyl)-1,2,3,4-tetrahydroquinolin-5-yl)-1H-pyrazol-1-yl)-2-methylpropanamido)ethanesulfonic acid

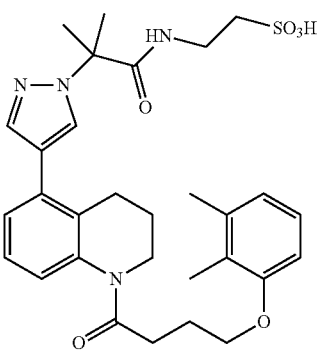 [SMILES: Cc1cccc(OCCCC(=O)N2CCCc3c(-c4cnn(C(C)(C)C(=O)NCCS(=O)(=O)O)c4)cccc32)c1C]

A solution of ethyl 1,2-dihydro-2-ethoxy-1-quinolinecarboxylate (52.0 mg, 0.210 mmol) in 95% ethanol (0.4 mL) and a solution of taurine (15.79 mg, 0.126 mmol) in 1 N NaOH (0.1 mL) were added to a stirring solution of Example 65 (10 mg, 0.021 mmol) in 95% ethanol (0.4 mL). The reaction mixture was heat at 140° C. in a microwave reactor for 40 min. The reaction was concentrated and purified by preparative HPLC (PHENOMENEX® Axia Luna column, 5μ, C18, 30×100 mm; 18 min gradient from 80% A:20% B to 40% A:60% B and 3 min 100% B (A=90% H$_2$O/10% MeOH+0.1% TFA); (B=90% MeOH/10% H$_2$O+0.1% TFA); detection at 220 nm) to afford Example 146 (8.2 mg, 66% yield) as a white powder. LCMS, [M+H]$^+$=583.5. $^1$H NMR (500 MHz, MeOD) δ 7.93 (s, 1H), 7.68 (s, 1H), 7.32 (d, J=7.9 Hz, 1H), 7.25 (t, J=7.6 Hz, 1H), 7.21 (br. s, 1H), 6.99 (t, J=7.9 Hz, 1H), 6.72 (d, J=7.5 Hz, 1H), 6.68 (d, J=8.1 Hz, 1H), 3.89 (br. s, 2H), 3.76 (t, J=6.8 Hz, 2H), 3.62 (t, J=6.3 Hz, 2H), 2.96 (t, J=6.3 Hz, 2H), 2.82 (t, J=6.9 Hz, 2H), 2.58 (br. s, 2H), 2.19-2.08 (m, 5H), 1.89 (s, 6H), 1.88-1.74 (m, 5H). HPLC-1: Rt=9.9 min, purity=100%; HPLC-2: Rt=6.7 min, purity=100%.

Example 147

1-(5-(1-((1H-Tetrazol-5-yl)methyl)-1H-pyrazol-4-yl)-3,4-dihydroquinolin-1(2H)-yl)-4-(2,3-dimethylphenoxy)butan-1-one

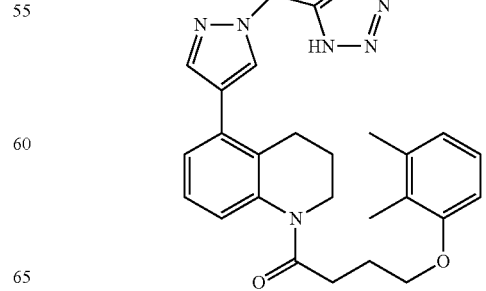

Step A. N-(2-Cyanoethyl)-2-(4-(1-(4-(2,3-dimethylphenoxy)butanoyl)-1,2,3,4-tetrahydroquinolin-5-yl)-1H-pyrazol-1-yl)acetamide

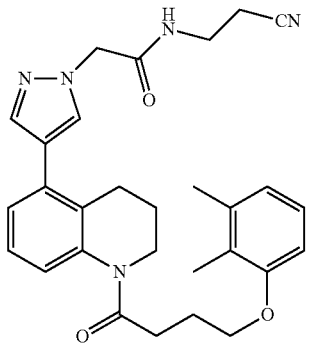 [SMILES: Cc1cccc(OCCCC(=O)N2CCCc3c(-c4cnn(CC(=O)NCCC#N)c4)cccc32)c1C]

To a partial suspension of Example 1 (100 mg, 0.223 mmol), 3-aminopropanenitrile (23 mg, 0.335 mmol), and Hunig's base (0.117 mL, 0.67 mmol) in ethyl acetate (2.2 mL) was added a solution of T3P (107 mg, 0.335 mmol) in THF dropwise. The reaction was stirred at room temperature for 16 h and water was added. The resulting mixture was stirred vigorously for 15 min. The organic layer was separated, washed with saturated NaHCO$_3$, followed by water, 5% citric acid and brine. The solution was dried over anhydrous Na$_2$SO$_4$, filtered, and concentrated. The resulting residue was purified by flash chromatography (0-100% ethyl acetate:hexanes) to afford the title compound (108 mg, 96% yield) as white foam. LCMS, [M+H]$^+$=500.2. $^1$H NMR (400 MHz, CDCl$_3$) δ 7.65 (s, 1H), 7.32 (s, 1H), 7.19 (dt, J=15.9, 7.9 Hz, 2H), 7.02 (dd, J=13.7, 6.0 Hz, 2H), 6.75 (d, J=7.5 Hz, 1H), 6.65 (d, J=8.1 Hz, 1H), 4.85 (s, 2H), 3.93 (s, 2H), 3.79 (t, J=6.8 Hz, 2H), 3.55 (dd, J=12.7, 6.4 Hz, 2H), 2.75 (t, J=7.1 Hz, 2H), 2.64 (t, J=6.5 Hz, 2H), 2.56 (s, 2H), 2.25-2.11 (m, 5H), 1.95-1.79 (m, 5H).

Step B. 3-(5-((4-(1-(4-(2,3-Dimethylphenoxy)butanoyl)-1,2,3,4-tetrahydroquinolin-5-yl)-1H-pyrazol-1-yl)methyl)-1H-tetrazol-1-yl)propanenitrile

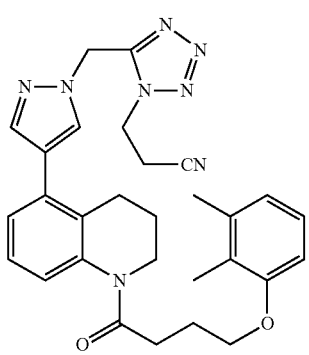 [SMILES: Cc1cccc(OCCCC(=O)N2CCCc3c(-c4cnn(Cc5nnnn5CCC#N)c4)cccc32)c1C]

To a solution of N-(2-cyanoethyl)-2-(4-(1-(4-(2,3-dimethylphenoxy)butanoyl)-1,2,3,4-tetrahydroquinolin-5-yl)-1H-pyrazol-1-yl)acetamide (20 mg, 0.04 mmol) and pyridine (19 μL, 0.24 mmol) in DCM (0.4 mL) under argon was added PCl$_5$ (13 mg, 0.06 mmol) in one portion, and the resulting mixture was heated to reflux for 3 h. The reaction was cooled to room temperature and trimethylsilyl azide (18 mg, 0.16 mmol) was added. The resulting mixture was stirred at room temperature overnight and carefully quenched with saturated aqueous NaHCO$_3$. The resulting mixture was stirred vigorously for 15 min. The organic phase was separated, dried over anhydrous Na$_2$SO$_4$, filtered, and concentrated. The resulting residue was purified by flash chromatography (0-100% ethyl acetate:hexanes) to afford the title compound (17 mg, 81% yield) as white foam. LCMS, [M+H]$^+$=525.2. $^1$H NMR (400 MHz, CDCl$_3$) δ 7.54 (s, 1H), 7.47 (s, 1H), 7.30-7.16 (m, 2H), 7.10 (d, J=8.7 Hz, 1H), 7.03 (t, J=7.9 Hz, 1H), 6.76 (d, J=7.5 Hz, 1H), 6.64 (d, J=8.2 Hz, 1H), 5.74 (s, 2H), 4.95 (t, J=6.9 Hz, 2H), 3.93 (s, 2H), 3.78 (t, J=6.8 Hz, 2H), 3.06 (t, J=6.9 Hz, 2H), 2.74 (t, J=7.1 Hz, 2H), 2.52 (s, 2H), 2.24-2.11 (m, 5H), 1.96-1.78 (m, 5H).

Example 147

To a solution of the 3-(5-((4-(1-(4-(2,3-dimethylphenoxy)butanoyl)-1,2,3,4-tetrahydroquinolin-5-yl)-1H-pyrazol-1-yl)methyl)-1H-tetrazol-1-yl)propanenitrile (14.4 mg, 0.027 mmol) in THF (0.3 mL) under argon was added 1 N NaOH (82 μL, 0.082 mmol). The resulting mixture stirred vigorously at room temperature for 1 h. The reaction mixture was adjusted to pH 3 with 5% aq. citric acid, and extracted with DCM (3 times). The combined organic layer was dried over anhydrous Na$_2$SO$_4$, filtered, and concentrated to afford Example 147 (11.8 mg, 90% yield). LCMS, [M+H]$^+$=472.1. $^1$H NMR (400 MHz, CDCl$_3$) δ 7.63 (s, 1H), 7.44 (s, 1H), 7.22-7.06 (m, 3H), 7.01 (t, J=7.9 Hz, 1H), 6.75 (d, J=7.5 Hz, 1H), 6.64 (d, J=8.1 Hz, 1H), 5.72 (s, 2H), 3.92 (s, 2H), 3.78 (t, J=7.0 Hz, 2H), 2.77 (t, J=7.1 Hz, 2H), 2.53 (s, 2H), 2.26-2.07 (m, 5H), 1.95-1.75 (m, 5H), 1.25 (s, 1H). HPLC-1: Rt=8.9 min, purity=99.7%; HPLC-2: Rt=7.9 min, purity=100%.

The following Examples were prepared in a manner analogous to N-(2-cyanoethyl)-2-(4-(1-(4-(2,3-dimethylphenoxy)butanoyl)-1,2,3,4-tetrahydroquinolin-5-yl)-1H-pyrazol-1-yl)acetamide.

TABLE 10

| Example | Name | Formula I | LCMS, [M + H]+ | 1H NMR (400 MHz, CDCl3) δ | HPLC-1: Rt min, purity; HPLC-2: Rt min, purity; |
|---|---|---|---|---|---|
| 148 | 2-(3-(1-(4-(2,3-Dimethylphenoxy)butanoyl)-1,2,3,4-tetrahydroquinolin-5-yl)benzamido)ethanesulfonic acid | | 551.3 | 7.82 (d, J = 7.8 Hz, 1H), 7.74 (s, 1H), 7.48 (t, J = 7.7 Hz, 1H), 7.35-7.15 (m, 4H), 7.00 (t, J = 7.9 Hz, 1H), 6.73 (d, J = 7.6 Hz, 1H), 6.69 (d, J = 8.2 Hz, 1H), 3.92 (br. s, 2H), 3.83 (t, J = 6.5 Hz, 2H), 3.77 (t, J = 7.0 Hz, 2H), 3.10 (t, J = 6.5 Hz, 2H), 2.84 (t, J = 7.0 Hz, 2H), 2.43 (br. s, 2H), 2.22-2.08 (m, 5H), 1.93-1.75 (m, 5H)* | 10.9 min, 99.9% 7.2 min, 99.95 |
| 149 | (3-((4-(1-(4-(2,3-Dimethylphenoxy)butanoyl)-1,2,3,4-tetrahydroquinolin-5-yl)1H-pyrazol-1-yl)methyl)benzamido)methanesulfonic acid | | 617.3 | 9.05 (br. s, 1H), 8.08 (s, 1H), 7.98 (s, 1H), 7.85 (br. s, 1H), 7.51 (d, J = 6.2 Hz, 1H), 7.27-7.20 (m, 2H), 7.17 (t, J = 7.7 Hz, 1H), 7.12 (t, J = 6.5 Hz, 1H), 7.06 (d, J = 6.5 Hz, 1H), 6.98 (t, J = 7.9 Hz, 1H), 6.71 (d, J = 7.5 Hz, 1H), 6.61 (d, J = 8.1 Hz, 1H), 5.58 (s, 2H), 4.69 (br. s, 2H), 3.90 (s, 2H), 3.72 (t, J = 6.1 Hz, 2H), 2.71 (t, J = 7.0 Hz, 2H), 2.49 (br. s, 2H), 2.23-2.05 (m, 5H), 1.91 (s, 3H), 1.87-1.78 (m, 2H) | 14.0 min, 100% 11.4 min, 100% |
| 150 | (3-((4-(3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)methanesulfonic acid | | 629.4 | 7.94-7.79 (m, 3H), 7.63 (s, 1H), 7.53-7.40 (m, 2H), 7.27 (d, J = 7.4 Hz, 1H), 7.16 (t, J = 7.7 Hz, 1H), 7.05 (d, J = 7.7 Hz, 1H), 6.95 (t, J = 7.8 Hz, 1H), 6.67 (d, J = 7.3 Hz, 1H), 6.63 (d, J = 8.0 Hz, 1H), 5.46 (s, 2H), 4.52 (s, 2H), 4.00-3.87 (m, 1H), 3.85-3.74 (m, 1H), 3.07-2.95 (m, 2H, 2.73 (br. s, 2H), 2.09 (br. s, 5H), 1.75 (s, 3H), 1.35-1.21 (m, 2H), 0.84 (br. s, 1H), 0.42 (br. s, 1H)* | 14.4 min, 96.4% 11.8 min, 98.4% |
| 151 | 2-(3-((4-(3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)ethanesulfonic acid | | 643.4 | 8.25 (br. s, 1H), 8.08-7.83 (m, 2H), 7.72 (s, 1H), 7.33-7.25 (m, 2H), 7.09 (br. s, 2H), 7.05-6.86 (m, 2H), 6.69 (d, J = 7.3 Hz, 1H), 6.59 (d, J = 7.1 Hz, 1H), 5.57 (s, 2H), 3.96 (br. s, 4H), 3.80 (s, 2H), 3.18 (s, 2H), 2.82-2.63 (m, 2H), 2.51 (br. s, 1H), 2.25-2.01 (m, 5H), 1.88 (s, 3H), 1.71 (br. s, 1H), 1.04-0.89 (m, 1H), 0.57 (br. s, 1H) | 14.2 min, 98.3% 11.8 min, 99.5% |

TABLE 10-continued

| Example | Name | Formula I | LCMS, [M + H]+ | $^1$H NMR (400 MHz, CDCl$_3$) δ | HPLC-1: Rt min, purity; HPLC-2: Rt min, purity; |
|---|---|---|---|---|---|
| 152 | 2-(3-((4-(3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)ethanesulfonic acid | | 66.34 | 8.05 (s, 1H), 7.94-7.79 (m, 3H), 7.57-7.47 (m, 2H), 7.35 (d, J = 1.2 Hz, 1H), 7.25 (t, J = 7.8 Hz, 1H), 7.15 (s, 1H), 7.14-7.06 (m, 1H), 6.95 (d, J = 7.9 Hz, 1H), 6.82 (d, J = 8.3 Hz, 1H), 5.58 (s, 2H), 4.12-3.99 (m, 1H), 3.97-3.89 (m, 1H), 3.86 (t, J = 6.4 Hz, 2H), 3.14 (t, J = 6.4 Hz, 2H), 2.79 (t, J = 6.0 Hz, 2H), 2.17 (br. s, 2H), 2.13-2.04 (m, 1H), 1.94 (s, 3H), 1.87-1.74 (m, 1H), 1.55-1.43 (m, 1H), 1.42-1.28 (m, 1H), 0.99-0.81 (m, 1H), 0.51-0.35 (m, 1H)* | 12.0 min, 98.3% 10.1 min, 99.4% |
| 153 | 2-(3-((4-(1-(4-(2,3-Dimethylphenoxy)butanoyl)-1,2,3,4-tetrahydroquinolin-5-1H-pyrazol-1-yl)methyl)benzamido)ethanesulfonic acid | | 631.3 | 8.28 (s, 1H), 7.98 (s, 1H), 7.82 (s, 1H), 7.74 (s, 2H), 7.37-7.23 (m, 2H), 7.20-7.12 (m, 1H), 7.08 (s, 1H), 6.99 (t, J = 7.8 Hz, 1H), 6.71 (d, J = 7.6 Hz, 1H), 6.62 (d, J = 8.2 Hz, 1H), 5.55 (s, 2H), 3.90 (s, 2H), 3.77-3.68 (m, 2H), 3.50 (s, 2H), 3.21 (s, 2H), 2.73 (t, J = 7.0 Hz, 2H), 2.49 (s, 2H), 2.24-2.04 (m, 5H), 1.90 (s, 3H), 1.86-1.74 (m, 2H) | 9.9 min, 100% 6.8 min, 99.8% |
| 154 | (3-((3-(3-((2-(3-Fluoro-2-methylphenoxy)ethoxy)carbonyl)-1a,2,3,7b-tetrahydro-1H-cyclopropa[c]quinolin-7-yl)benzyloxy)carbonylamino)propanamido)methanesulfonic | | 656.3 | 7.52-7.35 (m, 4H), 7.31 (d, J = 7.2 Hz, 1H), 7.22-7.05 (m, 3H), 6.78 (d, J = 8.2 Hz, 1H), 6.72 (t, J = 8.7 Hz, 1H), 5.18 (s, 2H), 4.69-4.57 (m, 2H), 4.52 (dt, J = 11.9, 4.1 Hz, 1H), 4.35 (s, 2H), 4.30 (t, J = 4.3 Hz, 2H), 3.47 (t, J = 6.6 Hz, 2H), 3.01 (d, J = 12.7 Hz, 1H), 2.52 (t, J = 6.5 Hz, 2H), 2.13 (s, 3H), 1.95 (td, J = 8.6, 4.6 Hz, 1H), 1.88-1.77 (m, 1H), 0.99 (td, J = 8.3, 5.0 Hz, 1H), 0.71 (dd, J = 9.4, 4.6 Hz, 1H)* | 14.9 min, 100% 12.4 min, 99.2% |
| 155 | (3-((4-(3-((2-(3-Fluoro-2-methylphenoxy)ethoxy)carbonyl)-1a,2,3,7b-tetrahydro-1H-cyclopropa[c]quinolin-7-yl)-1H-pyrazol-1-yl)methyl)benzamido)methanesulfonic acid | | 635.3 | 7.99 (s, 1H), 7.97-7.86 (m, 2H), 7.77 (s, 1H), 7.54 (d, J = 5.6 Hz, 2H), 7.31-7.23 (m, 1H), 7.22-7.08 (m, 3H), 6.79 (d, J = 9.0 Hz, 1H), 6.73 (t, J = 8.7 Hz, 1H), 5.53 (s, 2H), 4.65-4.49 (m, 5H), 4.30 (t, J = 4.1 Hz, 2H), 3.10 (d, J = 12.2 Hz, 1H), 2.22 (td, J = 8.6, 4.6 Hz, 1H), 2.14 (s, 3H), 1.94-1.83 (m, 1H), 1.10 (td, J = 7.7, 4.5 Hz, 1H), 0.70 (dd, J = 9.5, 4.6 Hz, 1H)* | 14.4 min, 100% 12.0 min, 100% |

TABLE 10-continued

| Example | Name | Formula I | LCMS, [M + H]+ | 1H NMR (400 MHz, CDCl3) δ | HPLC-1: Rt min, purity; HPLC-2: Rt min, purity; |
|---|---|---|---|---|---|
| 156 | 2-(3-(4-((3-(1-(4-(2,3-Dimethylphenoxy)butanoyl)-1,2,3,4-tetrahydroquinolin-5-yl)benzyloxy)carbonyl)piperazin-1-yl)propanamido)ethanesulfonic acid | | 721.3 | 7.54-7.44 (m, 2H), 7.43-7.33 (m, 2H), 7.31-7.21 (m, 2H), 7.19 (br. s, 1H), 7.07 (t, J = 7.9 Hz, 1H), 6.81 (d, J = 7.5 Hz, 1H), 6.76 (d, J = 8.1 Hz, 1H), 5.27 (s, 2H), 4.34 (br. s, 2H), 3.99 (br. s, 2H), 3.84 (t, J = 7.0 Hz, 2H), 3.74-3.67 (m, 2H), 3.57-3.50 (m, 2H), 3.46-3.39 (m, 4H), 3.10 (dd, J = 6.7, 5.6 Hz, 4H), 2.91 (t, J = 6.9 Hz, 2H), 2.77 (t, J = 6.3 Hz, 2H), 2.47 (br. s, 2H), 2.32-2.18 (m, 5H), 1.93 (s, 3H), 1.86 (dt, J = 13.2, 6.5 Hz, 2H)* | 10.9 min, 95.0% 11.0 min, 95.0% |
| 157 | (3-(5-(1-(4-(2,3-Dimethylphenoxy)butanoyl)-1,2,3,4-tetrahydroquinolin-5-yl)thiazol-2-yloxy)benzamido)methanesulfonic acid | | 636.4 | 7.81-7.76 (m, 2H), 7.56 (t, J = 8.2 Hz, 1H), 7.50-7.45 (m, 1H), 7.27 (br. s, 1H), 7.22-7.18 (m, 2H), 7.01 (s, 1H), 6.94 (t, J = 7.9 Hz, 1H), 6.71-6.61 (m, 2H), 4.40 (s, 2H), 3.84 (t, J = 5.4 Hz, 2H), 3.65 (t, J = 6.7 Hz, 2H), 2.68 (t, J = 7.1 Hz, 2H), 2.55 (t, J = 6.0 Hz, 2H), 2.10 (s, 3H), 2.01 (dt, J = 13.1, 6.6 Hz, 2H), 1.89-1.72 (m, 5H)** | 9.7 min, 98.4% (HPLC-2) |
| 158 | (3-((4-(1-(4-(2,3-Dimethylphenoxy)butanoyl)-2,3,4,5-tetrahydro-1H-benzo[b]azepin-6-yl)-1H-pyrazol-1-yl)methyl)benzamido)methanesulfonic acid | | 631.3 | 7.93 (s, 1H), 7.90 (dt, J = 7.4, 1.7 Hz, 1H), 7.87 (s, 1H), 7.65 (s, 1H), 7.56-7.47 (m, 2H), 7.36 (dd, J = 7.7, 1.3 Hz, 1H), 7.28 (t, J = 7.7 Hz, 1H), 7.16 (dd, J = 7.7, 1.2 Hz, 1H), 6.97 (t, J = 7.9 Hz, 1H), 6.69 (d, J = 8.1 Hz, 1H), 6.67 (d, J = 8.5 Hz, 1H), 5.52 (s, 2H), 4.65 (dt, J = 12.7, 3.7 Hz, 1H), 4.57 (s, 2H), 3.98-3.84 (m, 2H), 2.91 (t, J = 14.4, 6.4 Hz, 1H), 2.81-2.72 (m, 1H), 2.53-2.33 (m, 3H), 2.13 (s, 3H), 2.12-2.05 (m, 2H), 1.98-1.88 (m, 2H), 1.86 (s, 3H), 1.82-1.73 (m, 1H), 1.48-1.32 (m, 1H)* | 10.0 min, 99.2% 6.9 min, 99.0% |
| 159 | 2-(3-((4-(1-(4-(2,3-Dimethylphenoxy)butanoyl)-2,3,4,5-tetrahydro-1H-benzo[b]azepin-6-yl)-1H-pyrazol-1-yl)methyl)benzamido)ethanesulfonic acid | | 645.3 | 7.88 (s, 1H), 7.86-7.80 (m, 2H), 7.67 (s, 1H), 7.55-7.46 (m, 2H), 7.37 (dd, J = 7.7, 1.2 Hz, 1H), 7.28 (t, J = 7.7 Hz, 1H), 7.17 (dd, J = 7.1, 1.1 Hz, 1H), 6.97 (t, J = 7.8 Hz, 1H), 6.67 (d, J = 8.1 Hz, 2H), 5.53 (s, 2H), 4.65 (dt, J = 7.1, 3.2 Hz, 1H), 3.98-3.86 (m, 2H), 3.84 (t, J = 6.6 Hz, 2H), 3.12 (t, J = 6.6 Hz, 2H), 2.90 (dd, J = 13.6, 6.0 Hz, 1H), 2.81-2.71 (m, 1H), 2.52-2.33 (m, 3H), 2.11 (s, 3H), 2.08 (dd, J = 13.1, 6.2 Hz, 2H), 1.98-1.87 (m, 2H), 1.85 (s, 3H), 1.82-1.73 (m, 1H), 1.49-1.31 (m, 1H)* | 9.8 min, 100% 6.8 min, 100% |

TABLE 10-continued

| Example | Name | Formula I | LCMS, [M + H]+ | $^1$H NMR (400 MHz, CDCl$_3$) δ | HPLC-1: Rt min, purity; HPLC-2: Rt min, purity; |
|---|---|---|---|---|---|
| 160 | (3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)methanesulfonic acid | | 633.2 | 8.04 (s, 1H), 7.96-7.85 (m, 3H), 7.66 (dd, J = 6.5, 3.0 Hz, 1H), 7.53-7.45 (m, 2H), 7.20-7.11 (m, 2H), 6.94 (t, J = 7.9 Hz, 1H), 6.66 (t, J = 8.0 Hz, 2H), 5.46 (s, 2H), 4.83-4.74 (m, 1H), 4.56 (s, 2H), 4.53-4.43 (m, 1H), 3.95-3.80 (m, 2H), 3.65-3.55 (m, 1H), 2.92-2.80 (m, 1H), 2.52-2.38 (m, 2H), 2.35-2.19 (m, 1H), 2.12 (s, 3H), 2.10-2.01 (m, 2H), 1.84 (s, 3H), 1.84-1.76 (m, 1H)* | 8.5 min, 89.8% 6.7 min, 88.0% |
| 161 | 2-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)ethanesulfonic acid | | 647.2 | 8.18 (s, 1H), 8.05 (d, J = 0.4 Hz, 1H), 7.86-7.79 (m, 2H), 7.67 (dd, J = 5.8, 3.7 Hz, 1H), 7.55-7.47 (m, 2H), 7.22-7.13 (m, 2H), 6.92 (t, J = 7.9 Hz, 1H), 6.63 (d, J = 7.9 Hz, 2H), 5.52 (s, 2H), 4.79 (dt, J = 13.2, 3.5 Hz, 1H), 4.49 (dt, J = 11.8, 3.0 Hz, 1H), 3.93-3.84 (m, 2H), 3.82 (t, J = 6.7 Hz, 2H), 3.61 (td, J = 11.7, 1.8 Hz, 1H), 3.10 (t, J = 6.6 Hz, 2H), 2.92-2.80 (m, 1H), 2.54-2.35 (m, 2H), 2.35-2.21 (m, 1H), 2.09 (s, 3H), 2.07-1.99 (m, 2H), 1.87-1.77 (m, 4H)* | 8.7 min, 100% 6.6 min, 100% |
| 162 | 2-(4-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)ethanesulfonic acid | | 647.1 | 8.08 (s, 1H), 8.05 (s, 1H), 8.00 (d, J = 8.3 Hz, 2H), 7.73 (dd, J = 7.7, 1.6 Hz, 1H), 7.48 (d, J = 8.3 Hz, 2H), 7.29 (t, J = 7.7 Hz, 1H), 7.25 (dd, J = 7.7, 1.6 Hz, 1H), 7.12 (t, J = 7.9 Hz, 1H), 6.85 (d, J = 7.5 Hz, 1H), 6.79 (d, J = 8.2 Hz, 1H), 5.60 (d, J = 15.5 Hz, 1H), 5.56 (d, J = 15.6 Hz, 1H), 4.98-4.93 (m, 1H), 4.65-4.59 (m, 1H), 4.07 (dt, J = 11.0, 5.6 Hz, 1H), 4.02-3.99 (m, 2H), 3.77 (t, J = 11.0 Hz, 1H), 3.29-3.23 (m, 2H), 3.04-2.96 (m, 1H), 2.67-2.42 (m, 3H), 2.32 (s, 3H), 2.28-2.18 (m, 2H), 2.05 (s, 3H), 1.97 (d, J = 14.8 Hz, 1H), 1.50 (d, J = 8.1 Hz, 1H)* | |

TABLE 10-continued

| Example | Name | Formula I | LCMS, [M + H]+ | 1H NMR (400 MHz, CDCl3) δ | HPLC-1: Rt min, purity; HPLC-2: Rt min, purity; |
|---|---|---|---|---|---|
| 163 | (3-((4-(5-(4-(2,3-Dimethylphenoxy)butanoyl)-2-methyl-2,3,4,5-tetrahydrobenzo[b][1,4]oxazepin-9-yl)-1H-pyrazol-1-yl)methyl)benzamido)methanesulfonic acid | | 647.5 | 7.96 (s, 1H), 7.95 (s, 1H), 7.93-7.86 (m, 2H), 7.61 (dd, J = 5.3, 4.2 Hz, 1H), 7.56-7.47 (m, 2H), 7.18 (d, J = 1.2 Hz, 1H), 7.17 (s, 1H), 6.99 (t, J = 7.9 Hz, 1H), 6.69 (t, J = 8.3 Hz, 2H), 5.52 (d, J = 15.1 Hz, 1H), 5.47 (d, J = 15.2 Hz, 1H), 4.72 (dt, J = 13.6, 3.6 Hz, 1H), 4.56 (s, 2H), 3.87 (dq, J = 9.4, 5.1 Hz, 2H), 3.76-3.65 (m, 1H), 2.83 (dd, J = 19.7, 7.9 Hz, 1H), 2.56-2.44 (m, 1H), 2.43-2.31 (m, 1H), 2.09 (s, 3H), 2.06-1.96 (m, 2H), 1.79 (s, 3H), 1.78-1.72 (m, 1H), 1.22 (d, J = 6.2 Hz, 3H), 0.91 (d, J = 6.3 Hz, 1H)* | 9.9 min, 99.3% 6.9 min, 98.3% |
| 164 | 2-(3-((4-(5-(4-(2,3-Dimethylphenoxy)butanoyl)-2-methyl-2,3,4,5-tetrahydrobenzo[b][1,4]oxazepin-9-yl)-1H-pyrazol-1-yl)methyl)benzamido)ethanesulfonic acid | | 661.4 | 7.96 (s, 1H), 7.95 (s, 1H), 7.87-7.80 (m, 2H), 7.61 (dd, J = 5.3, 4.2 Hz, 1H), 7.56-7.48 (m, 2H), 7.19 (d, J = 1.2 Hz, 1H), 7.18 (s, 1H), 6.99 (t, J = 7.9 Hz, 1H), 6.69 (d, J = 6.5 Hz, 1H), 6.68 (d, J = 7.3 Hz, 1H), 5.52 (d, J = 15.1 Hz, 1H), 5.48 (d, J = 15.1 Hz, 1H), 4.72 (dt, J = 7.4, 3.3 Hz, 1H), 3.91-3.80 (m, 4H), 3.74-3.67 (m, 1H), 3.11 (t, J = 6.6 Hz, 2H), 2.87-2.77 (m, 1H), 2.56-2.46 (m, 1H), 2.40-2.31 (m, 1H), 2.07 (s, 3H), 2.06-1.99 (m, 2H), 1.78 (s, 3H), 1.76-1.72 (m, 1H), 1.21 (d, J = 6.2 Hz, 3H), 0.90 (d, J = 6.5 Hz, 1H)* | 9.8 min, 100% 6.8 min, 99.6% |
| 165 | (4-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)methanesulfonic acid | | 633.1 | 8.09 (s, 1H), 8.07 (d, J = 7.7 Hz, 2H), 8.07 (s, 1H), 7.74 (dd, J = 7.7, 1.7 Hz, 1H), 7.50 (d, J = 8.3 Hz, 2H), 7.30 (t, J = 7.7 Hz, 1H), 7.26 (dd, J = 7.7, 1.7 Hz, 1H), 7.13 (t, J = 7.9 Hz, 1H), 6.86 (d, J = 7.5 Hz, 1H), 6.79 (d, J = 8.2 Hz, 1H), 5.62 (d, J = 15.6 Hz, 1H), 5.58 (d, J = 15.6 Hz, 1H), 4.96 (dt, J = 13.1, 3.1 Hz, 1H), 4.73 (s, 2H), 4.66-4.61 (m, 1H), 4.11-4.05 (m, 1H), 4.04-3.98 (m, 1H), 3.81-3.75 (m, 1H), 3.05-2.97 (m, 1H), 2.67-2.44 (m, 3H), 2.33 (s, 3H), 2.28-2.18 (m, 2H), 2.06 (s, 3H), 1.98 (d, J = 14.8 Hz, 1H)* | |

TABLE 10-continued

| Example | Name | Formula I | LCMS, [M + H]⁺ | ¹H NMR (400 MHz, CDCl₃) δ | HPLC-1: Rt min, purity; HPLC-2: Rt min, purity; |
|---|---|---|---|---|---|
| 166 | (4-((4-(1-(4-(2,3-Dimethylphenoxy)butanoyl)-2,3,4,5-tetrahydro-1H-benzo[b]azepin-6-yl)-1H-pyrazol-1-yl)methyl)benzamido)methanesulfonic acid | | 631.2 | 8.10 (s, 1H), 8.08 (s, 1H), 7.72 (d, J = 7.7 Hz, 2H), 7.52 (d, J = 8.3 Hz, 2H), 7.46 (dd, J = 7.8, 1.2 Hz, 1H), 7.40 (t, J = 7.7 Hz, 1H), 7.27 (dd, J = 7.7, 1.0 Hz, 1H), 7.16 (t, J = 7.9 Hz, 1H), 6.89 (d, J = 7.5 Hz, 1H), 6.81 (d, J = 8.2 Hz, 1H), 5.63 (s, 2H), 4.84-4.78 (m, 1H), 4.74 (s, 1H), 4.48 (s, 2H), 4.15-4.03 (m, 2H), 3.15 (dd, J = 14.0, 6.1 Hz, 1H), 2.98-2.90 (m, 1H), 2.72-2.45 (m, 3H), 2.35 (s, 3H), 2.27 (td, J = 13.4, 7.2 Hz, 2H), 2.16-2.09 (m, 2H), 2.08 (s, 3H), 1.99-1.93 (m, 1H), 1.62-1.54 (m, 1H)* | |
| 167 | 2-(4-((4-(1-(4-(2,3-Dimethylphenoxy)butanoyl)-2,3,4,5-tetrahydro-1H-benzo[b]azepin-6-yl)-1H-pyrazol-1-yl)methyl)benzamido)ethanesulfonic acid | | 645.2 | 8.02 (d, J = 8.3 Hz, 2H), 7.71 (s, 2H), 7.50 (d, J = 8.3 Hz, 2H), 7.46 (dd, J = 7.7, 1.2 Hz, 1H), 7.40 (t, J = 7.7 Hz, 1H), 7.26 (dd, J = 7.7, 1.1 Hz, 1H), 7.16 (t, J = 7.9 Hz, 1H), 6.89 (d, J = 7.5 Hz, 1H), 6.81 (d, J = 8.2 Hz, 1H), 5.61 (s, 2H), 4.81 (dt, J = 6.5, 3.5 Hz, 1H), 4.48 (s, 2H), 4.14-3.99 (m, 3H), 3.31-3.25 (m, 2H), 3.14 (dd, J = 14.0, 6.2 Hz, 1H), 2.99-2.90 (m, 1H), 2.72-2.55 (m, 2H), 2.53-2.44 (m, 1H), 2.35 (s, 3H), 2.31-2.21 (m, 2H), 2.17-2.09 (m, 1H), 2.07 (s, 3H), 2.00-1.92 (m, 1H), 1.62-1.51 (m, 1H)* | |
| 168 | 2-(3-((4-(1-(4-(2-Methyl-3-(trifluoromethyl)(phenoxy)butanoyl)-1,2,3,4-tetrahydroquinolin-5-yl)-1H-pyrazol-1-yl)methyl)benzamido)ethanesulfonic acid | | 685.3 | 7.89 (s, 1H), 7.86-7.79 (m, 2H), 7.67 (s, 1H), 7.55-7.45 (m, 2H), 7.34-7.21 (m, 4H), 7.17 (d, J = 7.6 Hz, 1H), 7.13 (d, J = 8.3 Hz, 1H), 5.51 (s, 2H), 4.02 (br. s, 2H), 3.87-3.75 (m, 4H), 3.11 (t, J = 6.6 Hz, 2H), 2.84 (t, J = 7.0 Hz, 2H), 2.65 (br. s, 2H), 2.23-2.14 (m, 2H), 2.07 (br. s, 3H), 1.94-1.83 (m, 2H)* | 11.3 min, 97.9%<br>7.2 min, 98.1% |
| 168A | 4-(4-(1-(4-(2,3-Dimethylphenoxy)butanoyl)-1,2,3,4-tetrahydroquinolin-5-yl)pyridin-2-ylamino)benzoic acid | | 536.3 | 8.06-8.12 (2 H, m), 8.02 (1 H, d, J = 6.38 Hz), 7.40 (2 H, d, J = 8.80 Hz), 7.26-7.33 (2 H, m), 7.10 (1 H, s), 7.06 (1 H, d, J = 8.14 Hz), 7.00 (1H, t, J = 7.92 Hz), 6.73 (1 H, d, J = 7.70 Hz), 6.71 (1 H, br. s.), 6.64 (1 H, d, J = 8.14 Hz), 3.95 (2 H, t, J = 5.39 Hz), 3.79 (2 H, t, J = 6.93 Hz), 2.63-2.90 (11 H, m), 2.49 (2 H, t, J = 6.05 Hz), 2.12-2.28 (5 H, m), 1.79-2.03 (5 H, m) | 8.2 min, 93.3%<br>8.6 min, 93.2% |

TABLE 10-continued

| Example | Name | Formula I | LCMS, [M + H]+ | 1H NMR (400 MHz, CDCl3) δ | HPLC-1: Rt min, purity; HPLC-2: Rt min, purity; |
|---|---|---|---|---|---|
| 168B | (S)-2-Amino-3-((3-(1-(4-(2,3-dimethylphenoxy)butanoyl)-1,2,3,4-tetrahydroquinolin-5-yl)benzyloxy)carbonylamino)propanoic acid | | 560.2 | 7.23 (d, J = 7.2 Hz, 1H), 7.21-7.04 (m, 5H), 7.03-6.99 (m, 1H), 6.97 (t, J = 7.9 Hz, 1H), 6.71 (d, J = 7.5 Hz, 1H), 6.61 (d, J = 8.1 Hz, 1H), 5.11-4.89 (m, 4H), 4.13-4.00 (m, 1H), 3.96-3.83 (m, 2H), 3.77-3.61 (m, 3H), 3.61-3.39 (m, 2H), 2.72 (t, J = 7.1 Hz, 2H), 2.40 (s, 2H), 2.17 (s, 3H), 2.16-2.06 (m, 2H), 1.96 (s, 3H), 1.77-1.62 (m, 2H) | 10.7 min, 97% 10.8 min, 98% |
| 168C | 2-(4-((4-(1-(4-(2,3-Dimethylphenoxy)butanoyl)-1,2,3,4-tetrahydroquinolin-5-yl)benzyloxy)carbonyl)piperazin-1-yl)ethanesulfonic acid | | 650.2 | 7.43 (d, J = 8.0 Hz, 2H), 7.35-7.24 (m, 2H), 7.14 (d, J = 5.6 Hz, 3H), 7.00 (t, J = 7.9 Hz, 1H), 6.74 (d, J = 7.5 Hz, 1H), 6.69 (d, J = 8.1 Hz, 1H), 5.22 (s, 2H), 4.41-4.25 (m, 2H), 3.96-3.86 (m, 2H), 3.82-3.71 (m, 2H), 3.71-3.61 (m, 2H), 3.58 (s, 2H), 3.40-3.35 (m, 1H), 3.25 (t, J = 7.0 Hz, 3H), 3.22-3.08 (m, 2H), 2.84 (t, J = 6.9 Hz, 2H), 2.45-2.30 (m, 2H), 2.23-2.08 (m, 5H), 1.91-1.69 (m, 5H)* | 10.7 min, 100% 10.9 min, 99.1% |
| 168D | 2-((4-(1-(4-(2,3-Dimethylphenoxy)butanoyl)-1,2,3,4-tetrahydroquinolin-5-yl)benzyloxy)carbonylamino)ethanesulfonic acid | | 581.1 | 7.38 (d, J = 7.8 Hz, 2H), 7.33-7.20 (m, 2H), 7.16 (d, J = 7.4 Hz, 1H), 7.11 (d, J = 7.0 Hz, 2H), 7.00 (t, J = 7.9 Hz, 1H), 6.74 (d, J = 7.5 Hz, 1H), 6.68 (d, J = 8.2 Hz, 1H), 5.13 (s, 2H), 3.96-3.81 (m, 2H), 3.75 (t, J = 7.0 Hz, 2H), 3.57 (t, J = 7.0 Hz, 2H), 3.01 (t, J = 6.9 Hz, 2H), 2.84 (t, J = 6.9 Hz, 2H), 2.45-2.30 (m, 2H), 2.15 (s, 5H), 1.93-1.66 (m, 5H)* | 10.5 min, 97.3% 10.5 min, 97.5% |
| 168E | (2S,4S)-1-((3-(1-(4-(2,3-Dimethylphenoxy)butanoyl)-1,2,3,4-tetrahydroquinolin-5-yl)benzyloxy)carbonyl)-4-hydroxypyrrolidine-2-carboxylic acid | | 587.1 | 7.36 (s, 2H), 7.21 (d, J = 36.8 Hz, 5H), 7.02 (t, J = 7.7 Hz, 1H), 6.76 (d, J = 7.4 Hz, 1H), 6.65 (d, J = 8.0 Hz, 1H), 5.31-5.10 (m, 2H), 4.59-4.43 (m, 2H), 4.03-3.89 (m, 2H), 3.81 (t, J = 6.6 Hz, 2H), 3.73-3.51 (m, 2H), 2.89-2.75 (m, 2H), 2.55-2.45 (m, 3H), 2.39-2.27 (m, 2H), 2.27-2.11 (m, 5H), 1.95 (s, 3H), 1.89-1.72 (m, 2H) | 10.4 min, 99.3% 10.6 min, 100% |

TABLE 10-continued

| Example | Name | Formula I | LCMS, [M + H]+ | 1H NMR (400 MHz, CDCl3) δ | HPLC-1: Rt min, purity; HPLC-2: Rt min, purity; |
|---|---|---|---|---|---|
| 168F | (S)-3-((3-(1-(4-(2,3-Dimethylphenoxy)butanoyl)-1,2,3,4-tetrahydroquinolin-5-yl)benzyloxy)carbonylamino)-2-guanidinopropanoic acid | | 602.1 | 7.36-6.92 (m, 8H), 6.72 (d, J = 7.4 Hz, 1H), 6.62 (d, J = 8.0 Hz, 1H), 5.05 (s, 2H), 4.32-4.17 (m, 1H), 4.00-3.86 (m, 2H), 3.71 (m, 2H), 3.54-3.31 (m, 2H), 2.75 (t, J = 7.0 Hz, 2H), 2.43 (s, 2H), 2.24-2.08 (m, 5H), 1.97 (m, 3H), 1.83-1.64 (m, 2H) | |
| 168G | (S)-3-(1-(4-(2,3-Dimethylphenoxy)butanoyl)-1,2,3,4-tetrahydroquinolin-5-yl)benzyl-3-hydroxypyrrolidine-1-carboxylate | | 543.1 | 7.46-7.34 (m, 2H), 7.31-7.21 (m, 3H), 7.21-7.11 (m, 2H), 7.02 (t, J = 7.9 Hz, 1H), 6.76 (d, J = 7.5 Hz, 1H), 6.65 (d, J = 8.2 Hz, 1H), 5.20 (s, 2H), 4.03-3.90 (m, 3H), 3.82 (t, J = 7.0 Hz, 2H), 3.77-3.64 (m, 1H), 3.64-3.41 (m, 3H), 2.82 (t, J = 7.3 Hz, 2H), 2.56-2.41 (m, 2H), 2.32-2.13 (m, 6H), 2.08-1.89 (m, 4H), 1.89-1.76 (m, 2H) | 14.7 min, 97% N/A |
| 168H | 2-(3-((4-(1-(4-(2,3-Dimethylphenoxy)butanoyl)-1,2,3,4-tetrahydroquinolin-5-yl)-3-methyl-1H-pyrazol-1-yl)methyl)benzamido)ethanesulfonic acid | | 645.3 | 7.83 (dt, J = 7.1, 1.8 Hz, 1H), 7.81-7.77 (m, 1H), 7.76 (s, 1H), 7.52 (d, J = 6.9 Hz, 2H), 7.41-7.30 (m, 1H), 7.28 (t, J = 7.7 Hz, 1H), 7.16 (d, J = 8.2 Hz, 1H), 6.95 (d, J = 7.9 Hz, 1H), 6.68 (s, 1H), 6.66 (s, 1H), 5.51 (s, 2H), 3.91 (t, J = 4.7 Hz, 2H), 3.80 (t, J = 5.3 Hz, 2H), 3.77 (t, J = 5.6 Hz, 2H), 3.07 (t, J = 6.5 Hz, 2H), 2.80 (t, J = 7.1 Hz, 2H), 2.43 (t, J = 5.9 Hz, 2H), 2.20 (s, 3H), 2.14 (s, 3H), 2.13-2.07 (m, 2H), 1.96-1.79 (m, 5H)* | 10.6 min, 97.5% 7.1 min, 96.9% |
| 168J | 2-(3-((4-(1-(4-(2,3-Dimethylphenoxy)butanoyl)-1,2,3,4-tetrahydroquinolin-5-yl)-5-methyl-1H-pyrazol-1-yl)methyl)benzamido)ethanesulfonic acid | | 645.3 | 7.82 (d, J = 7.8 Hz, 1H), 7.70 (s, 1H), 7.67-7.57 (m, 1H), 7.53 (t, J = 7.8 Hz, 1H), 7.38 (d, J = 8.2 Hz, 1H), 7.37-7.33 (m, 1H), 7.31 (t, J = 7.6 Hz, 1H), 7.17 (d, J = 8.6 Hz, 1H), 7.00 (t, J = 7.9 Hz, 1H), 6.73 (d, J = 7.7 Hz, 1H), 6.70 (d, J = 8.3 Hz, 1H), 5.58 (s, 2H), 4.01-3.89 m, 2H), 3.88-3.76 (m, 4H), 3.11 (t, J = 6.5 Hz, 2H), 2.84 (t, J = 7.0 Hz, 2H), 2.44 (t, J = 5.8 Hz, 2H), 2.21 (s, 3H), 2.19 (s, 3H), 2.18-2.10 (m, 2H), 1.88 (dd, J = 16.7, 10.0 Hz, 5H)* | 10.8 min, 99.6% 7.1 min, 96.1% |

TABLE 10-continued

| Example | Name | Formula I | LCMS, [M + H]+ | 1H NMR (400 MHz, CDCl3) δ | HPLC-1: Rt min, purity; HPLC-2: Rt min, purity; |
|---|---|---|---|---|---|
| 168K | (S)-4-Carboxy-4-((3-(1-(4-(2,3-dimethylphenoxy)butanoyl)-1,2,3,4-tetrahydroquinolin-5-yl)benzyloxy)carbonylamino)-N,N,N-trimethylbutan-1-aminium, TFA | | 631.3 | 7.39 (m, 2H), 7.33-7.23 (m, 2H), 7.20 (s, 1H), 7.18-7.12 (m, 1H), 7.12-7.04 (m, 1H), 6.99 (t, J = 7.9 Hz, 1H), 6.73 (d, J = 7.5 Hz, 1H), 6.68 (d, J = 8.2 Hz, 1H), 5.15 (s, 2H), 4.26 (dd, J = 9.0, 3.8 Hz, 1H), 3.92 (t, J = 5.2 Hz, 2H), 3.76 (t, J = 7.0 Hz, 2H), 3.43-3.33 (m, 2H), 3.09 (s, 9H), 2.83 (t, J = 6.9 Hz, 2H), 2.40 (t, J = 5.6 Hz, 2H), 2.16 (s, 3H), 2.15-2.09 (m, 2H), 2.00-1.83 (m, 6H), 1.83-1.67 (m, 3H)* | 13.1 min, 98.3% N/A |
| 168L | 1-(5-(3-(3-Aminophenoxy)phenyl)-3,4-dihydroquinolin-1(2H)-yl)-4-(2,3-dimethylphenoxy)butan-1-one | | 507.2 | 7.34 (t, J = 7.9 Hz, 1H), 7.21 (t, J = 7.6 Hz, 2H), 7.11 (t, J = 8.0 Hz, 2H), 7.01 (t, J = 7.7 Hz, 2H), 6.97-6.89 (m, 2H), 6.74 (d, J = 7.5 Hz, 1H), 6.66 (d, J = 8.2 Hz, 1H), 6.48-6.41 (m, 2H), 6.38 (t, J = 2.1 Hz, 1H), 3.96 (t, J = 5.2 Hz, 2H), 3.78 (t, J = 6.9 Hz, 2H), 3.70 (s, 2H), 2.76 (t, J = 12 Hz, 2H), 2.50 (t, J = 6.1 Hz, 2H), 2.22 (s, 3H), 2.20-2.13 (m, 2H), 1.98 (s, 3H), 1.89-1.75 (m, 2H) | |
| 168M | 3-((3-(1-(4-(2,3-Dimethylphenoxy)butanoyl)-1,2,3,4-tetrahydroquinolin-5-yl)-1H-pyrrol-1-yl)methyl)benzoic acid | | 523.1 | 7.95 (d, J = 7.4 Hz, 1H), 7.85 (s, 2H), 7.46 (t, J = 7.5 Hz, 1H), 7.42 (d, J = 7.7 Hz, 1H), 7.38-7.22 (m, 1H), 7.16 (d, J = 7.6 Hz, 1H), 6.98 (d, J = 7.9 Hz, 1H), 6.94 (d, J = 8.3 Hz, 1H), 6.73 (t, J = 2.3 Hz, 1H), 6.66 (d, J = 7.6 Hz, 1H), 6.60-6.46 (m, 1H), 6.41-6.18 (m, 1H), 6.00 (s, 1H), 5.15 (s, 2H), 4.02-3.90 (m, 1H), 3.90-3.79 (m, 2H), 3.20-2.98 (m, 1H), 2.88 (dd, J = 13.2, 6.2 Hz, 1H), 2.24 (,, 2H), 2.04 (s, 3H), 2.00-1.89 (m, 2H), 1.84-1.59 (m, 3H), 1.58-1.43 (m, 2H)* | 12.7 min, 98.9% 11.7 min, 98.9% |
| 168N | 2-(3-((3-(1-(4-(2,3-Dimethylphenoxy)butanoyl)-1,2,3,4-tetrahydroquinolin-5-1H-pyrrol-1-yl)methyl)benzamido)ethanesulfonic acid | | | 7.78-7.71 (m, 1H), 7.68 (d, J = 7.5 Hz, 1H), 7.59 (s, 1H), 7.45 (t, J = 7.6 Hz, 1H), 7.40-7.21 (m, 3H), 7.19 (d, J = 7.7 Hz, 1H), 7.04-6.92 (m, 2H), 6.67 (d, J = 7.6 Hz, 2H), 6.60-6.43 (m, 1H), 5.15 (s, 2H), 4.03-3.78 (m, 5H), 3.75 (t, J = 6.7 Hz, 2H), 3.10 (t, J = 6.8 Hz, 2H), 3.04 (t, J = 6.7 Hz, 2H), 2.89 (dd, J = 13.2, 6.1 Hz, 1H), 2.36-2.13 (m, 2H), 2.05 (s, 3H), 1.84-1.58 (m, 4H), 1.58-1.44 (m, 1H)* | N/A 7.7 min, 97.2% |

TABLE 10-continued

| Example | Name | Formula I | LCMS, [M + H]+ | 1H NMR (400 MHz, CDCl3) δ | HPLC-1: Rt min, purity; HPLC-2: Rt min, purity; |
|---|---|---|---|---|---|
| 168P | 3-((4-(1-(4-(2,3-Dimethylphenoxy)butanoyl)-1,2,3,4-tetrahydroquinolin-5-1H-imidazol-1-yl)methyl)benzoic acid | | 524.1 | 9.19 (d, J = 0.9 Hz, 1H), 8.15-8.05 (m, 2H), 7.72 (d, J = 7.7 Hz, 1H), 7.61 (t, J = 8.0 Hz, 1H), 7.57-7.41 (m, 2H), 7.41-7.28 (m, 2H), 6.93 (t, J = 7.9 Hz, 1H), 6.66 (d, J = 8.1 Hz, 1H), 6.61 (d, J = 7.4 Hz, 1H), 5.56 (s, 2H), 3.98-3.84 (m, 2H), 3.77 (t, J = 6.7 Hz, 2H), 2.80 (t, J = 7.0 Hz, 2H), 2.62-2.44 (m, 2H), 2.13 (dt, J = 12.9, 6.5 Hz, 2H), 2.06 (s, 3H), 1.97-1.63 (m, 5H)* | 7.3 min, 96.7% 9.3 min, 99.0% |

*1H NMR (400 MHz, CD3OD) δ.
**1H NMR (400 MHz, CD3CN) δ.

Example 169

3-(3-((4-(4-((2-(2,3-Dimethylphenoxy)ethoxy)carbonyl)-3,4-dihydro-2H-benzo[b][1,4]oxazin-8-yl)-1H-pyrazol-1-yl)methyl)benzamido)propanoic acid

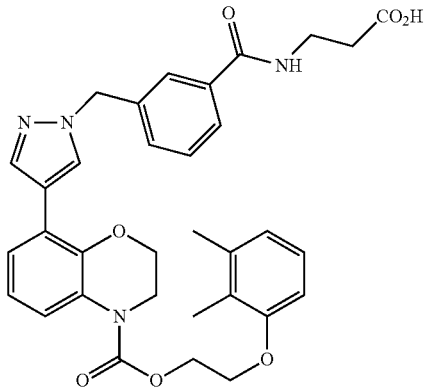 [SMILES: Cc1cccc(OCCOC(=O)N2CCOc3c(-c4cnn(Cc5cccc(C(=O)NCCC(=O)O)c5)c4)cccc32)c1C]

To a mixture of Example 29 (13 mg, 0.025 mmol), tert-butyl 3-aminopropanoate hydrochloride (4.92 mg, 0.027 mmol), and HATU (10.31 mg, 0.027 mmol) in DMF (0.5 mL) was added DIPEA (8.61 µL, 0.049 mmol). The reaction was stirred at room temperature for 1 h and diluted with DCM. The solution was washed with water and saturated NaHCO3, dried over anhydrous MgSO4, filtered, and concentrated. The resulting residue was dissolved in DCM and treated with TFA (0.5 mL). The reaction was stirred at room temperature for 1.5 h and concentrated to provide a residue. The residue was purified by preparative HPLC (PHENOMENEX® Axia Luna column, 5µ, C18, 30×100 mm; 10 min gradient from 100% A:0% B to 40% A:60% B and 3 min 100% B (A=90% H2O/10% MeOH+0.1% TFA); (B=90% MeOH/10% H2O+0.1% TFA); detection at 220 nm) to afford Example 169 (13 mg, 85% yield) as a light yellow solid. LCMS, [M+H]+=599.2. 1H NMR (500 MHz, MeOD) δ 8.16 (s, 1H), 7.94 (s, 1H), 7.71-7.77 (m, 2H), 7.66 (d, J=7.3 Hz, 1H), 7.38-7.48 (m, 2H), 7.32 (dd, J=7.7, 1.5 Hz, 1H), 7.00 (t, J=7.8 Hz, 1H), 6.83 (t, J=8.0 Hz, 1H), 6.76 (t, J=7.2 Hz, 2H), 5.42 (s, 2H), 4.57 (dd, J=5.4, 3.9 Hz, 2H), 4.30-4.36 (m, 2H), 4.25 (dd, J=5.4, 3.6 Hz, 2H), 3.89-3.94 (m, 2H), 3.62 (t, J=6.9 Hz, 2H), 2.63 (t, J=6.8 Hz, 2H), 2.23 (s, 3H), 2.12 (s, 3H). HPLC-1: Rt=10.1 min, purity=96.2%; HPLC-2: Rt=9.5 min, purity=96.3%.

Example 170

(S)-2-Amino-5-(3-chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)pentanoic acid, TFA salt

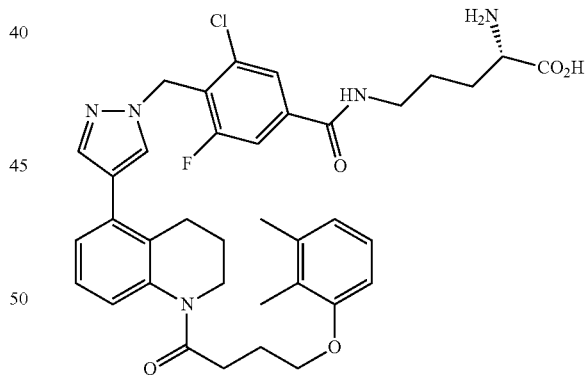

Example 170 was prepared using a procedure analogous to Example 169 except that Example 29 was replaced with Example 68 and tert-butyl 3-aminopropanoate hydrochloride was replaced with (S)-tert-butyl 5-amino-2-(tert-butoxycarbonylamino)pentanoate hydrochloride. LCMS, [M+H]+= 690.3. 1H NMR (400 MHz, MeOD) δ 7.81 (d, J=1.3 Hz, 1H), 7.64 (dd, J=9.9, 1.5 Hz, 2H), 7.43 (s, 1H), 7.22 (d, J=4.4 Hz, 2H), 7.17 (br. s, 1H), 6.96 (t, J=7.9 Hz, 1H), 6.66 (t, J=7.2 Hz, 2H), 5.59 (s, 2H), 4.02 (t, J=6.4 Hz, 1H), 3.83-3.90 (m, 2H), 3.74 (t, J=6.7 Hz, 2H), 3.38-3.52 (m, 3H), 2.81 (t, J=6.8 Hz, 2H), 2.46 (br. s, 2H), 2.08-2.17 (m, 2H), 2.05 (s, 3H), 1.87-2.03 (m, 2H), 1.69-1.87 (m, 6H). HPLC-1: Rt=7.4 min, purity=98.4%; HPLC-2: Rt=8.4 min, purity=98.3%.

Example 171

(S)-5-(3-Chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)-2-guanidinopentanoic acid, TFA salt

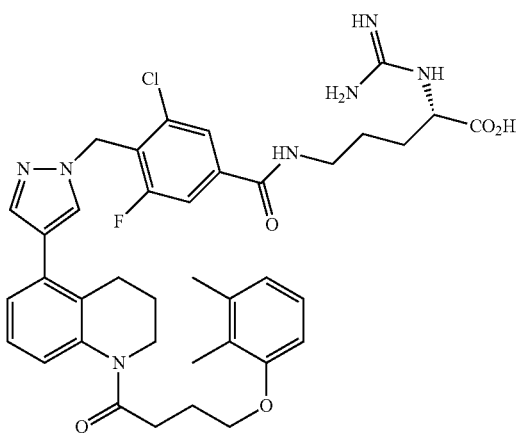 [SMILES: Cc1cccc(OCCCC(=O)N2CCCc3c(-c4cnn(Cc5c(F)cc(C(=O)NCCC[C@H](NC(=N)N)C(=O)O)cc5Cl)c4)cccc32)c1C]

Example 171 was prepared using a procedure analogous to Example 93 except that Example 170 was replaced with Example 58. LCMS, [M+H]$^+$=732.4. $^1$H NMR (500 MHz, MeOD) δ 7.86 (s, 1H), 7.68 (dd, J=9.9, 1.6 Hz, 1H), 7.66 (s, 1H), 7.48 (s, 1H), 7.26 (d, J=4.6 Hz, 2H), 7.21 (s, 1H), 7.01 (t, J=7.9 Hz, 1H), 6.70 (t, J=7.9 Hz, 2H), 5.63 (s, 2H), 4.35 (dd, J=7.5, 5.0 Hz, 1H), 3.91 (br. s, 2H), 3.78 (t, J=6.8 Hz, 2H), 3.54-3.42 (m, 2H), 2.85 (t, J=6.8 Hz, 2H), 2.50 (br. s, 2H), 2.21-2.13 (m, 2H), 2.13-2.01 (m, 5H), 1.94-1.66 (m, 7H). HPLC-1: Rt=7.5 min, purity=98.7%; HPLC-2: Rt=8.7 min, purity=98.2%.

The following Examples were prepared in a manner analogous to Example 169.

TABLE 11

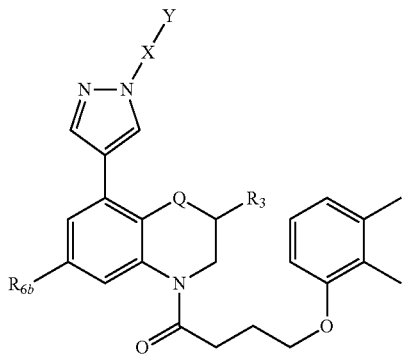

| Example | Name | —X—Y | Q | R$_3$ | R$_{6b}$ | LCMS, [M+H]$^+$ | $^1$H NMR (500 MHz, MeOD) δ | HPLC-1: Rt min, purity; HPLC-2: Rt min, purity |
|---|---|---|---|---|---|---|---|---|
| 172 | 2-(3-((4-(4-(4-(2,3-Dimethylphenoxy)butanoyl)-3,4-dihydro-2H-benzo[b][1,4]oxazin-8-yl)-1H-pyrazol-1-yl)methyl)benzamido)acetic acid | (structure with —NH—CH$_2$—CO$_2$H benzamide) | O | H | H | 583.3 | 7.98 (s, 1H), 7.94 (s, 1H), 7.88 (d, J = 7.5 Hz, 1H), 7.79 (s, 1H), 7.44 (ddd, J = 15.7, 7.8, 7.7 Hz, 2H), 7.34 (d, J = 7.9 Hz, 1H), 7.22-7.25 (m, 1H), 6.98-7.04 (m, 1H), 6.91 (t, J = 7.9 Hz, 1H), 6.74 (d, J = 7.5 Hz, 1H), 6.66 (d, J = 8.1 Hz, 1H), 5.44 (s, 2H), 4.36 (t, J = 4.8 Hz, 2H), 4.23 (d, J = 5.1 Hz, 2H), 3.97-4.02 (m, 4H), 2.87 (t, J = 7.0 Hz, 2H), 2.18-2.26 (m, 5H), 2.03 (s, 3H)* | 9.7 min, 99.1% 9.2 min, 99.2% |

TABLE 11-continued

| Example | Name | —X—Y | Q | $R_3$ | $R_{6b}$ | LCMS, [M + H]$^+$ | $^1$H NMR (500 MHz, MeOD) δ | HPLC-1: Rt min, purity; HPLC-2: Rt min, purity |
|---|---|---|---|---|---|---|---|---|
| 173 | 3-(3-((4-(4-(4-(2,3-Dimethylphenoxy)butanoyl)-3,4-dihydro-2H-benzo[b][1,4]oxazin-8-yl)-1H-pyrazol-1-yl)methyl)benzamido)propanoic acid | benzamide-CH2CH2-CO2H | O | H | H | 597.3 | 7.95 (s, 1H), 7.89 (s, 1H), 7.69-7.74 (m, 2H), 7.39-7.45 (m, 2H), 7.34 (d, J = 13.2 Hz, 1H), 6.98-7.05 (m, 1H), 6.87-6.96 (m, 2H), 6.74 (d, J = 7.7 Hz, 1H), 6.66 (d, J = 8.8 Hz, 1H), 5.40 (s, 2H), 4.33-4.38 (m, 2H), 3.96-4.03 (m, 4H), 3.69-3.77 (m, 2H), 2.83-2.90 (m, 2H), 2.71 (t, J = 5.7 Hz, 2H), 2.19-2.26 (m, 5H), 2.02 (br. s, 3H)* | 9.7 min, 95.5% 9.2 min, 95.6% |
| 174 | 3-(3-((4-(4-(4-(2,3-Dimethylphenoxy)butanoyl)-2-methyl-3,4-dihydro-2H-benzo[b][1,4]oxazin-8-yl)-1H-pyrazol-1-yl)methyl)benzamido)propanoic acid | benzamide-CH2CH2-CO2H | O | Me | H | 611.4 | 8.02 (s, 1H), 7.91 (s, 1H), 7.77 (s, 1H), 7.74 (ddd, J = 6.5, 2.1, 1.9 Hz, 1H), 7.40-7.47 (m, 2H), 7.38 (dd, J = 7.8, 1.4 Hz, 1H), 7.26 (br. s, 1H), 6.85-6.95 (m, 2H), 6.65 (d, J = 8.1 Hz, 2H), 5.40 (s, 2H), 4.24-4.38 (m, 2H), 3.91-4.02 (m, 2H), 3.60-3.66 (m, 2H), 3.17-3.26 (m, 1H), 2.88-2.98 (m, 1H), 2.79-2.88 (m, 1H), 2.62 (t, J = 6.9 Hz, 2H), 2.14 (dt, J = 13.0, 6.5 Hz, 2H), 2.10 (s, 3H), 1.91 (s, 3H), 1.30 (d, J = 6.1 Hz, 3H) | 10.1 min, 98.0% 9.5 min, 97.8% |
| 175 | 2-(3-((4-(4-(4-(2,3-Dimethylphenoxy)butanoyl)-2-methyl-3,4-dihydro-2H-benzo[b][1,4]oxazin-8-yl)-1H-pyrazol-1-yl)methyl)benzamido)acetic acid | benzamide-CH2-CO2H | O | Me | H | 597.3 | 8.03 (s, 1H), 7.92 (s, 1H), 7.78-7.86 (m, 2H), 7.43-7.50 (m, 2H), 7.39 (dd, J = 7.8, 1.4 Hz, 1H), 7.27 (br. s, 1H), 6.86-6.96 (m, 2H), 6.66 (d, J = 8.05 Hz, 2H), 5.42 (s, 2H), 4.26-4.38 (m, 2H), 4.09 (s, 2H), 3.92-4.02 (m, 2H), 3.18-3.26 (m, 1H), 2.89-2.98 m, 1H), 2.81-2.88 (m, 1H), 2.15 (dq, J = 6.7, 6.5 Hz, 2H), 2.11 (s, 3H), 1.92 (s, 3H), 1.31 (d, J = 6.1 Hz, 3H) | 10.1 min, 96.2% 9.5 min, 96.2% |

TABLE 11-continued

| Example | Name | —X—Y | Q | R₃ | R₆ᵦ | LCMS, [M + H]⁺ | ¹H NMR (500 MHz, MeOD) δ | HPLC-1: Rt min, purity; HPLC-2: Rt min, purity |
|---|---|---|---|---|---|---|---|---|
| 176 | 3-(3-Chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)propanoic acid | 3-chloro-5-fluoro-4-(CH₂-)benzamido-CH₂CH₂CO₂H | $CH_2$ | H | H | 647.3 | 8.76 (s, 1H), 7.84 (s, 1H), 7.66 (dd, J = 9.9, 1.8 Hz, 1H), 7.63 (br. s, 1H), 7.46 (s, 1H), 7.25 (d, J = 5.1 Hz, 2H), 7.19 (br. s, 1H), 6.99 (t, J = 7.8 Hz, 1H), 6.69 (t, J = 7.5 Hz, 2H), 5.61 (d, J = 1.1 Hz, 2H), 3.89 (br. s, 2H), 3.76 (t, J = 6.8 Hz, 2H), 3.62-3.68 (m, 2H), 2.84 (t, J = 6.8 Hz, 2H), 2.67 (t, J = 6.9 Hz, 2H), 2.44-2.54 (m, 2H), 2.11-2.20 (m, 2H), 2.05-2.10 (m, 3H), 1.69-1.87 (m, 5H) | 10.3 min, 98.9% 9.6 min, 98.9% |
| 177 | 2-(3-Chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)acetic acid | 3-chloro-5-fluoro-4-(CH₂-)benzamido-CH₂CO₂H | $CH_2$ | H | H | 633.2 | 7.86 (d, J = 1.5 Hz, 1H), 7.68 (dd, J = 9.9, 1.5 Hz, 1H), 7.60 (br. s, 1H), 7.43 (s, 1H), 7.23 (m, 2H), 7.16 (br. s, 1H), 6.96 t, J = 7.9 Hz, 1H), 6.61-6.70 (m, 2H), 5.60 (d, J = 1.1 Hz, 2H), 4.06-4.12 (m, 2H), 3.86 (br. s, 2H), 3.70-3.77 (m, 2H), 2.81 (t, J = 6.8 Hz, 2H), 2.45 (br. s, 2H), 2.08-2.17 (m, 2H), 2.05 (br. s, 3H), 1.65-1.85 (m, 5H) | 10.3 min, 98.9% 9.6 min, 99.0% |
| 177A | 3-(3-(3-((4-(4-(2,3-Dimethylphenoxy)butanoyl)-3,4-dihydro-2H-benzo[b][1,4]oxazin-8-yl)-1H-pyrazol-1-yl)methyl)phenyl)ureido)propanoic acid | 3-(CH₂-)phenyl-NH-C(O)-NH-CH₂CH₂CO₂H | O | H | H | 612.3 | 8.00 (1 H, s), 7.89 (1 H, s), 7.39 (1 H, dd, J = 7.91, 1.53 Hz), 7.32 (1 H, d, J = 8.05 Hz), 7.28 (1 H, s), 7.23 (2 H, t, J = 7.91 Hz), 6.87-6.96 (3 H, m), 6.66 (2 H, dd, J = 7.91, 3.19 Hz), 5.31 (2 H, s), 4.26-4.31 (2 H, m), 3.92-3.99 (4 H, m), 3.43-3.47 (2 H, m), 2.89 (2 H, t, J = 7.07 Hz), 2.52 (2 H, t, J = 6.52 Hz), 2.12-2.19 (2 H, m), 2.10 (3 H, s), 1.93 (3 H, s) | 9.8 min, 98.2% 9.3 min, 96.2% |

TABLE 11-continued

| Example | Name | —X—Y | Q | R$_3$ | R$_{6b}$ | LCMS, [M + H]$^+$ | $^1$H NMR (500 MHz, MeOD) δ | HPLC-1: Rt min, purity; HPLC-2: Rt min, purity |
|---|---|---|---|---|---|---|---|---|
| 177B | 2-(3-(3-((4-(4-(2,3-Dimethylphenoxy)butanoyl)-3,4-dihydro-2H-benzo[b][1,4]oxazin-8-yl)-1H-pyrazol-1-yl)methyl)phenyl)ureido)acetic acid | | O | H | H | 598.2 | 8.01 (1 H, s), 7.88 (1 H, s), 7.39 (1 H, dd, J = 7.77, 1.39 Hz), 7.34 (1 H, d, J = 9.16 Hz), 7.30 (1 H, s), 7.22-7.28 (2 H, m), 6.86-6.96 (3 H, m), 6.66 (2 H, dd, J = 7.91, 2.91 Hz), 5.31 (2 H, s), 4.28 (2 H, t, J = 4.99 Hz), 3.93-3.99 (4 H, m), 3.92 (2 H, s), 2.88 (2 H, t, J = 7.07 Hz), 2.15 (2 H, dq, J = 6.66, 6.47 Hz), 2.10 (3 H, s), 1.92 (3 H, s) | 9.8 min, 98.3% 9.3 min, 98.4% |
| 177C | 3-((4-(4-(4-(2,3-Dimethylphenoxy)butanoyl)-6-methyl-3,4-dihydro-2H-benzo[b][1,4]oxazin-8-yl)-1H-pyrazol-1-yl)methyl)benzoic acid | | O | H | Me | 540.3 | 8.04 (1 H, s), 7.94-7.99 (2 H, m), 7.89 (1 H, s), 7.43-7.52 (2 H, m), 7.22 (1 H, d, J = 1.39 Hz), 7.09 (1 H, br. s.), 6.92 (1 H, t, J = 7.91 Hz), 6.65 (2 H, t, J = 8.60 Hz), 5.42 (2 H, s), 4.24 (2 H, t, J = 4.99 Hz), 3.96 (2 H, t, J = 5.83 Hz), 3.89-3.94 (2 H, m), 2.89 (2 H, t, J = 7.07 Hz), 2.27 (3 H, s), 2.12-2.19 (2 H, m), 2.09 (3 H, s), 1.92 (3 H, s) | 11.3 min, 98.9% 10.3 min, 97.2% |
| 177D | (3-((4-(4-(4-(2,3-Dimethylphenoxy)butanoyl)-6-methyl-3,4-dihydro-2H-benzo[b][1,4]oxazin-8-yl)-1H-pyrazol-1-yl)methyl)benzamido)methanesulfonic acid | | O | H | Me | 633.2 | 8.06 (1 H, s), 7.91 (1 H, s), 7.87 (1 H, s), 7.83 (1 H, d, J =7.21 Hz), 7.40-7.48 (2 H, m), 7.22 (1 H, d, J = 1.39 Hz), 7.11 (1 H, br. s.), 6.93 (1 H, t, J = 7.77 Hz), 6.66 (2 H, t, J = 6.80 Hz), 5.42 (2 H, s), 4.52 (2 H, s), 4.26 (2 H, t, J = 4.86 Hz), 3.97 (2 H, t, J = 5.83 Hz), 3.90-3.95 (2 H, m), 2.84-2.91 (2 H, m), 2.27 (3 H, s), 2.13-2.19 (2 H, m), 2.10-2.13 (3 H, m), 1.94 (3 H, s) | 12.1 min, 97.8% 8.1 min, 97.0% |

TABLE 11-continued

| Example | Name | —X—Y | Q | R₃ | R₆ᵦ | LCMS, [M + H]⁺ | ¹H NMR (500 MHz, MeOD) δ | HPLC-1: Rt min, purity; HPLC-2: Rt min, purity |
|---|---|---|---|---|---|---|---|---|
| 177E | 2-(3-((4-(4-(2,3-Dimethylphenoxy)butanoyl)-6-methyl-3,4-dihydro-2H-benzo[b][1,4]oxazin-8-yl)-1H-pyrazol-1-yl)methyl)benzamido)ethanesulfonic acid | | O | H | Me | 647.5 | 8.20 (s, 1H), 8.05 (s, 1H), 7.84-7.74 (m, 2H), 7.52-7.40 (m, 2H), 7.24 (s, 1H), 7.21-7.04 (m, 1H), 6.93 (t, J = 7.8 Hz, 1H), 6.69-6.62 (m, 2H), 5.48 (s, 2H), 4.33-4.23 (m, 2H), 3.97 (t, J = 5.9 Hz, 2H), 3.95-3.90 (m, 2H), 3.81 (t, J = 6.3 Hz, 2H), 3.13-3.03 (m, 2H), 2.88 (t, J = 7.0 Hz, 2H), 2.28 (s, 3H), 2.19-2.12 (m, 2H), 2.11 (s, 3H), 1.94 (s, 3H) | 11.9 min, 98.3% 8.1 min, 98.9% |
| 177F | 3-(3-((4-(4-(2,3-Dimethylphenoxy)butanoyl)-6-methyl-3,4-dihydro-2H-benzo[b][1,4]oxazin-8-yl)-1H-pyrazol-1-yl)methyl)benzamido)propanoic acid | | O | H | Me | 611.5 | 7.89 (1 H, s), 7.72-7.77 (2 H, m), 7.40-7.47 (2 H, m), 7.22 (1 H, d, J = 1.39 Hz), 7.10 (1 H, br. s.), 6.93 (1 H, t, J = 7.91 Hz), 6.66 (2 H, t, J = 8.05 Hz), 5.40 (2 H, s), 4.25 (2 H, t, J = 4.86 Hz), 3.97 (2 H, t, J = 5.96 Hz), 3.90-3.95 (2 H, m), 3.63 (2 H, t, J = 6.94 Hz), 2.89 (2 H, t, J = 7.07 Hz), 2.63 (2 H, t, J = 6.80 Hz), 2.28 (3 H, s), 2.12-2.19 (2 H, m), 2.10 (3 H, s), 1.93 (3 H, s) | 10.2 min, 94.9% 9.5 min, 94.5% |
| 177G | 2-(3-((4-(4-(2,3-Dimethylphenoxy)butanoyl)-6-methyl-3,4-dihydro-2H-benzo[b][1,4]oxazin-8-yl)-1H-pyrazol-1-yl)methyl)benzamido)acetic acid | | O | H | Me | 597.4 | 8.04 (1 H, s), 7.89 (1 H, s), 7.78-7.83 (2 H, m), 7.42-7.49 (2 H, m), 7.22 (1 H, d, J = 1.39 Hz), 7.11 (1 H, br. s.), 6.93 (1 H, t, J = 7.77 Hz), 6.66 (2 H, t, J = 7.35 Hz), 5.42 (2 H, s), 4.25 (2 H, t, J = 4.86 Hz), 4.10 (2 H, s), 3.97 (2 H, t, J = 5.96 Hz), 3.90-3.94 (2 H, m), 2.89 (2 H, t, J = 6.94 Hz), 2.28 (3 H, s), 2.12-2.19 (2 H, m, J = 6.66, 6.45, 6.35, 6.35 Hz), 2.11 (3 H, s), 1.93 (3 H, s) | 10.2 min, 97.2% 9.5 min, 96.3% |

TABLE 11-continued

| Example | Name | —X—Y | Q | R₃ | R₆ᵦ | LCMS, [M + H]⁺ | ¹H NMR (500 MHz, MeOD) δ | HPLC-1: Rt min, purity; HPLC-2: Rt min, purity |
|---|---|---|---|---|---|---|---|---|
| 177H | 3-Chloro-4-((4-(4-(4-(2,3-dimethylphenoxy) butanoyl)-3,4-dihydro-2H-benzo[b][1,4] oxazin-8-yl)-1H-pyrazol-1-yl)methyl)-5-fluorobenzoic acid | 3-Cl, 5-F benzoic acid-CH₂- | O | H | H | 580.1 | 8.00 (1 H, s), 7.93 (1 H, s), 7.83 (1 H, s), 7.74 (1 H, dd, J = 9.71, 1.39 Hz), 7.37 (1 H, dd, J = 7.77, 1.39 Hz), 7.26 (1 H, br. s.), 6.86-6.95 (2 H, m), 6.65 (2 H, t, J = 7.91 Hz), 5.58 (2 H, d, J = 1.39 Hz), 4.27 (2 H, t, J = 4.99 Hz), 3.95 (4 H, dt, J = 8.95, 5.38 Hz), 2.89 (2 H, t, J = 6.94 Hz), 2.12-2.18 (2 H, m), 2.09 (3 H, s), 1.91 (3 H, s) | 11.6 min, 99.1% 10.6 min, 98.6% |
| 177J | (3-Chloro-4-((4-(4-(4-(2,3-dimethylphenoxy) butanoyl)-3,4-dihydro-2H-benzo[b][1,4] oxazin-8-yl)-1H-pyrazol-1-yl)methyl)-5-fluorobenzamido) methanesulfonic acid | 3-Cl, 5-F benzamido-CH₂-SO₃H | O | H | H | 671.2 | 7.99 (1 H, s), 7.88 (1 H, s), 7.86 (1 H, s), 7.69 (1 H, dd, J = 9.85, 1.53 Hz), 7.36 (1 H, dd, J = 7.77, 1.39 Hz), 7.27 (1 H, br. s.), 6.86-6.95 (2 H, m), 6.65 (2 H, dd, J = 7.63, 3.19 Hz), 5.58 (2 H, d, J = 1.39 Hz), 4.50 (2 H, s), 4.27 (2 H, t, J = 4.86 Hz), 3.95 (4 H, dt, J = 10.61, 5.38 Hz), 2.84-2.91 (2 H, m), 2.15 (2 H, dq, J = 6.66, 6.47 Hz), 2.10 (3 H, s), 1.91 (3 H, s) | 12.4 min, 99.2% 8.3 min, 97.6% |
| 177K | 2-(3-Chloro-4-((4-(4-(4-(2,3-dimethylphenoxy) butanoyl)-3,4-dihydro-2H-benzo[b][1,4] oxazin-8-yl)-JH-pyrazol-1-yl)methyl)-5-fluorobenzamido) ethanesulfonic acid | 3-Cl, 5-F benzamido-CH₂CH₂-SO₃H | O | H | H | 686.2 | 7.96 (s, 1H), 7.83 (s, 1H), 7.80 (s, 1H), 7.62 (dd, J = 10.5, 1.1 Hz, 1H), 7.36 (dd, J = 7.7, 1.2 Hz, 1H), 7.33-7.20 (m, 1H), 6.92 (t, J = 8.2 Hz, 1H), 6.88 (t, J = 7.9 Hz, 1H), 6.70-6.62 (m, 2H), 5.56 (d, J = 1.5 Hz, 2H), 4.26 (t, J = 4.5 Hz, 2H), 4.00-3.90 (m, 4H), 3.80 (t, J = 6.5 Hz, 2H), 3.07 (t, J = 6.6 Hz, 2H), 2.88 (t, J = 7.0 Hz, 2H), 2.19-2.12 (m, 2H), 2.10 (s, 3H), 1.91 (s, 3H) | 12.4 min, 98.2% 8.3 min, 98.3% |

TABLE 11-continued

| Example | Name | —X—Y | Q | R₃ | R₆ᵦ | LCMS, [M + H]⁺ | ¹H NMR (500 MHz, MeOD) δ | HPLC-1: Rt min, purity; HPLC-2: Rt min, purity |
|---|---|---|---|---|---|---|---|---|
| 177L | 3-(3-Chloro-4-((4-(4-(4-(2,3-dimethylphenoxy)butanoyl)-3,4-dihydro-2H-benzo[b][1,4]oxazin-8-yl)-1H-pyrazol-1-yl)methyl)-5-fluorobenzamido)propanoic acid | Cl, F-substituted benzyl with NH-CH₂CH₂-COOH amide | O | H | H | 650.1 | 7.99 (1 H, s), 7.83 (1 H, s), 7.78 (1 H, s), 7.60 (1 H, dd, J = 9.85, 1.53 Hz), 7.36 (1 H, dd, J = 7.77, 1.66 Hz), 7.26 (1 H, br. s.), 6.86-6.96 (2 H, m), 6.65 (2 H, t, J = 7.07 Hz), 5.57 (2 H, d, J = 1.66 Hz), 4.26 (2 H, t, J = 4.86 Hz), 3.95 (4 H, ddd, J = 9.99, 5.41, 5.13 Hz), 3.63 (2 H, t, J = 6.80 Hz), 2.89 (2 H, t, J = 7.07 Hz), 2.60-2.67 (2 H, m), 2.12-2.19 (2 H, m), 2.10 (3 H, s), 1.91 (3 H, s) | 10.5 min, 97.5% 9.8 min, 96.5% |
| 177M | 2-(3-Chloro-4-((4-(4-(4-(2,3-dimethylphenoxy)butanoyl)-3,4-dihydro-2H-benzo[b][1,4]oxazin-8-yl)-1H-pyrazol-1-yl)methyl)-5-fluorobenzamido)ethanesulfonic acid | Cl, F-substituted benzyl with NH-CH₂-COOH amide | O | H | H | 636.3 | 8.00 (1 H, s), 7.84 (2 H, s), 7.65 (1 H, dd, J = 9.85, 1.53 Hz), 7.37 (1 H, dd, J = 7.77, 1.39 Hz), 7.27 (1 H, br. s.), 6.85-6.95 (2 H, m), 6.62-6.68 (2 H, m), 5.58 (2 H, d, J = 1.39 Hz), 4.27 (2 H, t, J = 4.86 Hz), 4.10 (2 H, s), 3.91-3.99 (4 H, m), 2.89 (2 H, t, J = 7.07 Hz), 2.12-2.18 (2 H, m), 2.09 (3 H, s), 1.91 (3 H, s) | 10.5 min, 98.3% 9.8 min, 97.4% |
| 177N | 2-(3-(3-((4-(4-(4-(2,3-Dimethylphenoxy)butanoyl)-3,4-dihydro-2H-benzo[b][1,4]oxazin-8-yl)-1H-pyrazol-1-yl)methyl)phenyl)ureido)ethanesulfonic acid | phenyl with NH-C(=O)-NH-CH₂CH₂-SO₃H | O | H | H | 648.2 | 8.17 (1 H, s), 8.04 (1 H, s), 7.41 (1 H, dd, J = 7.77, 1.39 Hz), 7.36 (1 H, s), 7.27-7.34 (2 H, m), 7.24 (1 H, t, J = 7.77 Hz), 6.88-6.95 (3 H, m), 6.66 (2 H, dd, J = 7.77, 4.99 Hz), 5.38 (2 H, s), 4.28-4.32 (2 H, m), 3.93-3.98 (5 H, m), 3.61-3.65 (2 H, m), 2.98 (2 H, t, J = 6.10 Hz), 2.85-2.90 (2 H, m), 2.15 (2 H, quin, J = 6.59 Hz), 2.11 (3 H, s), 1.93 (3 H, s) | 11.2 min, 92.9% 8.0 min, 93.3% |

TABLE 11-continued

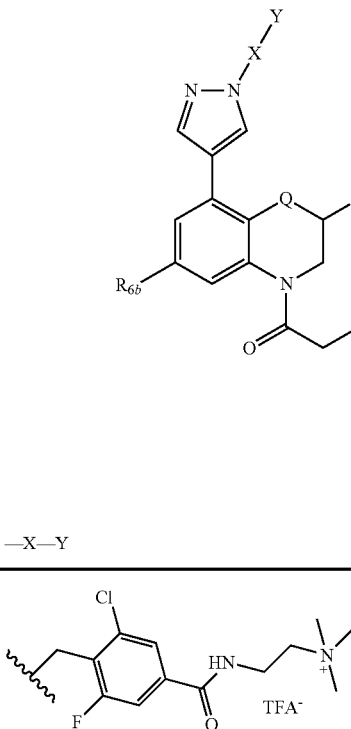

| Example | Name | —X—Y | Q | R₃ | R₆ᵦ | LCMS, [M + H]⁺ | ¹H NMR (500 MHz, MeOD) δ | HPLC-1: Rt min, purity; HPLC-2: Rt min, purity |
|---|---|---|---|---|---|---|---|---|
| 177P | 2-(3-Chloro-4-((4-(4-(4-(2,3-dimethylphenoxy) butanoyl)-3,4-dihydro-2H-benzo[b][1,4] oxazin-8-yl)-1H-pyrazol-1-yl)methyl)-5-fluorobenzamido)-N,N,N-trimethylethanaminium, TFA | 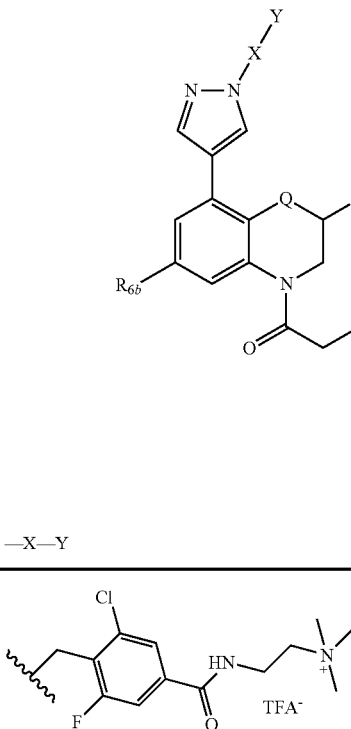 | O | H | H | 664.3 | 8.11 (1 H, s), 7.88 (1 H, s), 7.86 (1 H, s), 7.68 (1 H, dd, J = 9.79, 1.65 Hz), 7.43 (1 H, d, J = 7.48 Hz), 7.21 (1 H, br. s.), 6.90-7.00 (2 H, m), 6.62-6.73 (2 H, m), 5.62 (2 H, d, J = 1.32 Hz), 4.27 (2 H, br. s.), 3.93-4.02 (4 H, m), 3.88 (2 H, t, J = 6.60 Hz), 3.60 (2 H, t, J = 6.71 Hz), 3.26 (9 H, s), 2.94 (2 H, t, J = 6.71 Hz), 2.14-2.24 (2 H, m, J = 6.60, 6.38, 6.27, 6.27 Hz), 2.00-2.14 (3 H, m), 1.86 (3 H, br. s.) | 7.7 min, 99.3% 9.0 min, 98.6% |
| 177Q | 2-(3-((4-(4-(4-(2,3-Dimethylphenoxy) butanoyl)-3,4-dihydro-2H-benzo[b][1,4] oxazin-8-yl)-1H-pyrazol-1-yl)methyl) benzamido)-N,N,N-trimethylethanaminium, TFA | 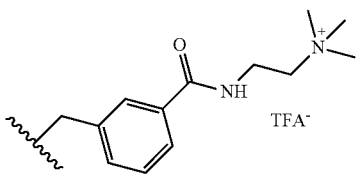 | O | H | H | 611.4 | 8.15 (1 H, s), 7.97 (1 H, s), 7.78-7.83 (2 H, m), 7.51-7.55 (2 H, m), 7.47 (1 H, d, J = 7.70 Hz), 7.24 (1 H, br. s.), 6.91-7.00 (2 H, m), 6.64-6.73 (2 H, m), 5.47 (2 H, s), 4.29 (2 H, br. s.), 3.99 (4 H, t, J = 4.84 Hz), 3.87 (2 H, t, J = 6.05 Hz), 3.59 (2 H, t, J = 6.71 Hz), 3.25 (9 H, s), 2.95 (2 H, t, J = 6.60 Hz), 2.19 (2 H, quin, J = 6.27 Hz), 2.09 (3 H, br. s.), 1.89 (3 H, br. s.) | 7.3 min, 99.6% 8.6 min, 98.1% |
| 177R | (3-(3-((4-(4-(4-(2,3-Dimethylphenoxy) butanoyl)-3,4-dihydro-2H-benzo[b][1,4] oxazin-8-yl)-1H-pyrazol-1-yl)methyl) phenyl)ureido) methanesulfonic acid | 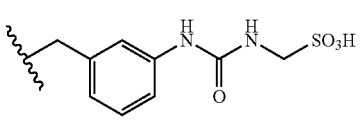 [SMILES: *Cc1cccc(NC(=O)NCS(=O)(=O)O)c1] | O | H | H | 634.0 | 7.90 (s, 1H), 7.85 (s, 1H), 7.39-7.31 (m, 2H), 7.29 (d, J = 8.2 Hz, 1H), 7.19 (t, J = 7.9 Hz, 1H), 7.06-6.96 (m, 1H), 6.94 (t, J = 7.8 Hz, 1H), 6.87 (t, J = 7.9 Hz, 1H), 6.81 (d, J = 7.6 Hz, 1H), 6.66 (d, J = 7.1 Hz, 1H), 6.62 (d, J = 7.2 Hz, 1H), 5.26 (s, 2H), 4.29 (s, 4H), 4.00-3.86 (m, 4H), 2.83 (d, J = 19.4 Hz, 2H), 2.23-2.02 (m, 5H), 1.93-1.79 (m, 3H) | |

TABLE 11-continued

| Example | Name | —X—Y | Q | R₃ | R₆ᵦ | LCMS, [M + H]⁺ | ¹H NMR (500 MHz, MeOD) δ | HPLC-1: Rt min, purity; HPLC-2: Rt min, purity |
|---|---|---|---|---|---|---|---|---|
| 177S | 4-((4-(4-(4-(2,3-Dimethylphenoxy) butanoyl)-3,4-dihydro-2H-benzo[b][1,4] oxazin-8-yl)-1H-pyrazol-1-yl)methyl) benzoic acid | (4-carboxybenzyl group) | O | H | H | 526.3 | 8.11 (s, 1H), 8.01 (d, J = 8.4 Hz, 2H), 7.94 (s, 1H), 7.44 (d, J = 7.4 Hz, 1H), 7.32 (d, J = 8.4 Hz, 2H), 7.27-7.06 (m, 1H), 6.99-6.86 (m, 2H), 6.64 (t, J = 8.2 Hz, 2H), 5.45 (s, 2H), 4.34-4.19 (m, 2H), 4.03-3.87 (m, 4H), 2.92 (t, J = 5.8 Hz, 2H), 2.22-2.12 (m, 2H), 2.12-1.97 (m, 3H), 1.97-1.69 (m, 3H) | 10.7 min, 99.0% 10.0 min, 98.8% |
| 177T | 2-(3-(3-Chloro-4-((4-(4-(4-(2,3-dimethylphenoxy) butanoyl)-3,4-dihydro-2H-benzo[b][1,4] oxazin-8-yl)-1H-pyrazol-1-yl)methyl)-5-fluorophenyl)ureido) acetic acid | (3-chloro-5-fluoro-4-substituted phenyl ureido acetic acid group) | O | H | H | 650.3 | 9.13 (s, 1H), 8.04 (s, 1H), 7.83 (d, J = 0.6 Hz, 1H), 7.40 (d, J = 1.9 Hz, 2H), 7.38-7.30 (m, 2H), 6.98 (t, J = 7.9 Hz, 1H), 6.86 (t, J = 7.9 Hz, 1H), 6.72 (dd, J = 14.3, 7.6 Hz, 2H), 6.50 (t, J = 5.5 Hz, 1H), 5.38 (s, 2H), 4.31 (t, J = 4.7 Hz, 2H), 3.97 (t, J = 6.2 Hz, 2H), 3.92-3.87 (m, 2H), 3.81 (d, J = 5.8 Hz, 2H), 2.78 (t, J = 7.1 Hz, 2H), 2.15 (s, 3H), 2.05 (quin, J = 6.7 Hz, 2H), 1.98 (s, 3H)** | 10.6 min, 91.2% 9.8 min, 97.0% |
| 177U | 3-(3-(4-((4-(4-(4-(2,3-Dimethylphenoxy) butanoyl)-3,4-dihydro-2H-benzo[b][1,4] oxazin-8-yl)-1H-pyrazol-1-yl)methyl)-3,5-difluorophenyl) ureido)propanoic acid | (3,5-difluoro-4-substituted phenyl ureido propanoic acid group) | O | H | H | 648.3 | 8.92 (s, 1H), 8.04 (s, 1H), 7.83 (d, J = 0.6 Hz, 1H), 7.43 (br. s., 1H), 7.35 (dd, J = 7.8, 1.4 Hz, 1H), 7.20-7.11 (m, 2H), 6.98 (t, J = 7.8 Hz, 1H), 6.86 (t, J = 7.9 Hz, 1H), 6.72 (dd, J = 14.0, 7.9 Hz, 2H), 6.32 (br. s., 1H), 5.29 (s, 2H), 4.32 (t, J = 4.9 Hz, 2H), 3.97 (t, J = 6.2 Hz, 2H), 3.92-3.87 (m, 2H), 3.37-3.28 (m, 2H), 2.78 (t, J = 7.1 Hz, 2H), 2.46-2.38 (m, 2H), 2.15 (s, 3H), 2.05 (quin, J = 6.7 Hz, 2H), 1.98 (s, 3H)** | 10.5 min, 97.7% 9.8 min, 98.0% |

TABLE 11-continued

| Example | Name | —X—Y | Q | R₃ | R₆ᵦ | LCMS, [M + H]⁺ | ¹H NMR (500 MHz, MeOD) δ | HPLC-1: Rt min, purity; HPLC-2: Rt min, purity |
|---|---|---|---|---|---|---|---|---|
| 177V | 3,5-Dichloro-4-((4-(4-(4-(2,3-dimethylphenoxy)butanoyl)-3,4-dihydro-2H-benzo[b][1,4]oxazin-8-yl)-1H-pyrazol-1-yl)methyl)benzoic acid | 3,5-dichloro-4-methylbenzoic acid fragment | O | H | H | 594.3 | 8.04 (s, 2H), 7.94 (s, 1H), 7.87-7.81 (m, 1H), 7.36 (d, J = 7.8 Hz, 1H), 7.26 (br. s., 1H), 6.96-6.85 (m, 2H), 6.69-6.60 (m, 2H), 5.71 (s, 2H), 4.25 (t, J = 4.9 Hz, 2H), 3.94 (s, 4H), 2.91-2.86 (m, 2H), 2.19-2.11 (m, 2H), 2.09 (s, 3H), 1.94-1.87 (m, 3H) | 12.0 min, 95.9% 10.9 min, 91.6% |
| 177W | 3-(4-((4-(4-(4-(2,3-Dimethylphenoxy)butanoyl)-3,4-dihydro-2H-benzo[b][1,4]oxazin-8-yl)-1H-pyrazol-1-yl)methyl)-3,5-difluorobenzamido)propanoic acid | 3,5-difluoro-4-methylbenzamido propanoic acid fragment | O | H | H | 633.3 | 8.01 (s, 1H), 7.83 (s, 1H), 7.48 (d, J = 8.0 Hz, 2H), 7.37 (d, J = 7.8 Hz, 1H), 7.27 (br. s., 1H), 6.91 (dt, J = 19.1, 7.9 Hz, 2H), 6.69-6.63 (m, 2H), 5.48 (s, 2H), 4.28 (t, J = 4.9 Hz, 2H), 4.00-3.93 (m, 4H), 3.63 (t, J = 6.8 Hz, 2H), 2.92-2.85 (m, 2H), 2.63 (t, J = 6.8 Hz, 2H), 2.15 (quin, J = 6.5 Hz, 2H), 2.09 (s, 3H), 1.91 (s, 3H) | 10.2 min, 96.5% 9.6 min, 95.5% |
| 177X | 2-(4-((4-(4-(4-(2,3-Dimethylphenoxy)butanoyl)-3,4-dihydro-2H-benzo[b][1,4]oxazin-8-yl)-1H-pyrazol-1-yl)methyl)-3,5-difluorobenzamido)ethanesulfonic acid | 3,5-difluoro-4-methylbenzamido ethanesulfonic acid fragment | O | H | H | 669.3 | 8.00 (s, 1H), 7.84 (s, 1H), 7.50 (d, J = 8.0 Hz, 2H), 7.37 (d, J = 6.7 Hz, 1H), 7.27 (br. s., 1H), 6.97-6.85 (m, 2H), 6.71-6.63 (m, 2H), 5.48 (s, 2H), 4.28 (t, J = 4.9 Hz, 2H), 4.00-3.91 (m, 4H), 3.80 (t, J = 6.5 Hz, 2H), 3.07 (t, J = 6.5 Hz, 2H), 2.94-2.83 (m, 2H), 2.15 (quin, J = 6.5 Hz, 2H), 2.10 (s, 3H), 1.98-1.87 (m, 3H) | 12.5 min, 97.7% 8.3 min, 96.0% |
| 177Y | 4-((4-(4-(4-(2,3-Dimethylphenoxy)butanoyl)-3,4-dihydro-2H-benzo[b][1,4]oxazin-8-yl)-1H-pyrazol-1-yl)methyl)-3,5-difluorobenzoic acid | 3,5-difluoro-4-methylbenzoic acid fragment | O | H | H | 562.2 | 8.02 (s, 1H), 7.83 (d, J = 0.6 Hz, 1H), 7.66-7.59 (m, 2H), 7.37 (dd, J = 7.8, 1.7 Hz, 1H), 7.26 (br. s., 1H), 6.96-6.87 (m, 2H), 6.65 (t, J = 7.4 Hz, 2H), 5.49 (s, 2H), 4.28 (t, J = 4.9 Hz, 2H), 3.99-3.93 (m, 4H), 2.89 (t, J = 7.1 Hz, 2H), 2.15 (quin, J = 6.5 Hz, 2H), 2.09 (s, 3H), 1.91 (s, 3H) | 11.2 min, 99.3% 10.3 min, 96.2% |

TABLE 11-continued

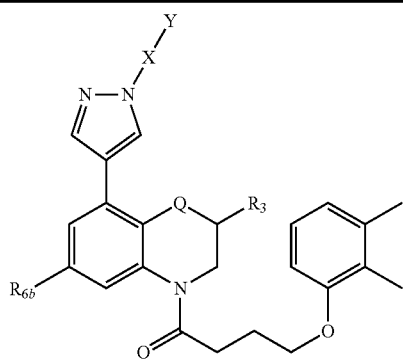

| Example | Name | —X—Y | Q | $R_3$ | $R_{6b}$ | LCMS, $[M+H]^+$ | $^1$H NMR (500 MHz, MeOD) δ | HPLC-1: Rt min, purity; HPLC-2: Rt min, purity |
|---|---|---|---|---|---|---|---|---|
| 177Z | 2-(3,5-Dichloro-4-((4-(4-(4-(2,3-dimethylphenoxy)butanoyl)-3,4-dihydro-2H-benzo[b][1,4]oxazin-8-yl)-1H-pyrazol-1-yl)methyl)benzamido)ethanesulfonic acid | (Cl, Cl-substituted benzamide with —SO₃H ethyl group) | O | H | H | 703.2 | 7.92 (s, 2H), 7.89 (s, 1H), 7.83 (s, 1H), 7.35 (dd, J = 7.8, 1.3 Hz, 1H), 7.32-7.18 (m, 1H), 6.91 (t, J = 7.7 Hz, 1H), 6.87 (t, J = 8.0 Hz, 1H), 6.64 (t, J = 7.9 Hz, 2H), 5.68 (s, 2H), 4.24 (t, J = 5.0 Hz, 2H), 3.98-3.90 (m, 4H), 3.80 (t, J = 6.5 Hz, 2H), 3.07 (t, J = 6.5 Hz, 2H), 2.87 (t, J = 7.1 Hz, 2H), 2.16-2.12 (m, 2H), 2.09 (s, 3H), 1.90 (s, 3H) | 16.9 min, 85.3% 8.6 min, 97.8% |
| 177AA | 3-(3,5-Dichloro-4-((4-(4-(4-(2,3-dimethylphenoxy)butanoyl)-3,4-dihydro-2H-benzo[b][1,4]oxazin-8-yl)-1H-pyrazol-1-yl)methyl)benzamido)propanoic acid | (Cl, Cl-substituted benzamide with —OH propanoic group) | O | H | H | 667.2 | 7.95-7.88 (m, 3H), 7.83 (s, 1H), 7.36 (d, J = 7.5 Hz, 1H), 7.26 (br. s., 1H), 6.96-6.84 (m, 2H), 6.64 (t, J = 8.6 Hz, 2H), 5.69 (s, 2H), 4.25 (t, J = 4.7 Hz, 2H), 4.00-3.90 (m, 4H), 3.63 (t, J = 6.8 Hz, 2H), 2.88 (t, J = 6.9 Hz, 2H), 2.68-2.59 (m, 2H), 2.15 (quin, J = 6.5 Hz, 2H), 2.09 (s, 3H), 1.90 (s, 3H) | 10.9 min, 98.6% 10.1 min, 97.8% |

*$^1$H NMR (400 MHz, CDCl₃) δ.
**$^1$H NMR (500 MHz, DMSO-d₆) δ.

Example 178

2-(3-((4-(4-(4-(2,3-Dimethylphenoxy)butanoyl)-3,4-dihydro-2H-benzo[b][1,4]oxazin-8-yl)-1H-pyrazol-1-yl)methyl)benzamido)ethanesulfonic acid

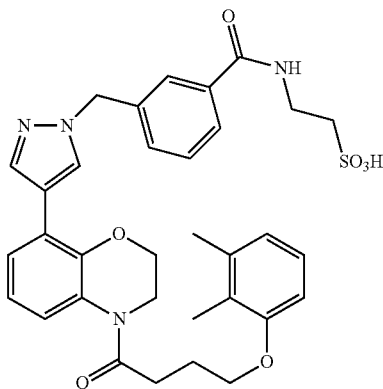 [SMILES: Cc1cccc(OCCCC(=O)N2CCOc3c(-c4cnn(Cc5cccc(C(=O)NCCS(=O)(=O)O)c5)c4)cccc32)c1C]

To a mixture of Example 10 (15 mg, 0.029 mmol), 2-aminoethanesulfonic acid (3.9 mg, 0.031 mmol), and HATU (11.9 mg, 0.031 mmol) in DMF (285 μL) was added DIPEA (9.97 μL, 0.057 mmol). The resulting mixture was stirred at room temperature for 2 h. After this time, the reaction mixture was quenched with sat. NaHCO₃ and extracted with DCM. The organic layer was dried over anhydrous MgSO₄, filtered, and concentrated. The resulting residue was purified by preparative HPLC (PHENOMENEX® Axia Luna column, 5μ, C18, 30×100 mm; 10 min gradient from 100% A:0% B to 40% A:60% B and 3 min 100% B (A=90% H₂O/10% MeOH+ 0.1% TFA); (B=90% MeOH/10% H₂O+0.1% TFA); detection at 220 nm) to afford Example 178 (7 mg, 39% yield). LCMS, [M+H]⁺=633.3. $^1$H NMR (400 MHz, MeOD) δ 8.15 (s, 1H), 7.99 (s, 1H), 7.75-7.84 (m, 2H), 7.39-7.50 (m, 3H), 7.25-7.35 (m, 1H), 6.88-6.96 (m, 2H), 6.66 (t, J=7.5 Hz, 2H), 5.45 (s, 2H), 4.30 (t, J=5.0 Hz, 2H), 3.92-4.01 (m, 4H), 3.81 (t, J=6.4 Hz, 2H), 3.07 (t, J=6.4 Hz, 2H), 2.89 (t, J=7.1 Hz, 2H), 2.12-2.19 (m, 2H), 2.10 (s, 3H), 1.93 (s, 3H). HPLC-1: Rt=11.0 min, purity=99.6%; HPLC-2: Rt=7.8 min, purity=99.6%.

Example 179

(3-Chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)methanesulfonic acid

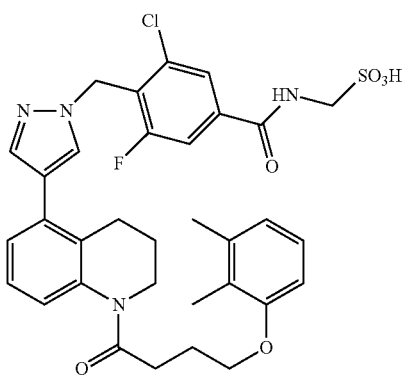

Example 179 was prepared using a procedure analogous to Example 178 except that Example 10 was replaced with Example 68 and 2-aminoethanesulfonic acid was replaced with aminomethanesulfonic acid. LCMS, [M+H]$^+$=669.1. $^1$H NMR (500 MHz, MeOD) δ 7.88 (s, 1H), 7.70 (dd, J=10.0, 1.4 Hz, 1H), 7.59 (s, 1H), 7.45 (s, 1H), 7.13-7.22 (m, 3H), 6.95 (t, J=7.9 Hz, 1H), 6.66 (dd, J=17.2, 7.8 Hz, 2H), 5.59 (d, J=1.4 Hz, 2H), 4.50 (s, 2H), 3.89 (t, J=5.7 Hz, 2H), 3.73 (t, J=6.8 Hz, 2H), 2.77 (t, J=7.1 Hz, 2H), 2.52 (t, J=6.8 Hz, 2H), 2.06-2.15 (m, 5H), 1.77-1.85 (m, 5H). HPLC-1: Rt=12.4 min, purity=99.8%; HPLC-2: Rt=8.0 min, purity=99.5%.

The following Examples were prepared in a manner analogous to Example 178.

TABLE 12

| Example | Name | —X—Y | V | R$_3$ | LCMS, [M + H]$^+$ | 1H NMR (500 MHz, MeOD) δ | HPLC-1: Rt min, purity; HPLC-2: Rt min, purity |
|---|---|---|---|---|---|---|---|
| 180 | (3-((4-(4-(4-(2,3-Dimethylphenoxy)butanoyl)-3,4-dihydro-2H-benzo[b][1,4]oxazin-8-yl)-1H-pyrazol-1-yl)methyl)benzamido)methanesulfonic acid | | CH$_2$ | H | 619.2 | 8.16 (s, 1H), 8.00 (s, 1H), 7.88 (s, 1H), 7.85 (d, J = 7.2 Hz, 1h), 7.43-7.49 (m, 2H), 7.40 (dd, J = 7.8, 1.7 Hz, 1H), 7.31 (br. s, 1H), 6.88-6.96 (m, 2H), 6.66 (dd, J = 7.6, 3.8 Hz, 2H), 5.46 (s, 2H), 4.53 (br. s, 2H), 4.30 (t, J = 4.96 Hz, 2H), 3.93-3.99 (m, 4H), 2.88 (t, J = 7.1 Hz, 2H), 2.12-2.18 (m, 2H), 2.11 (s, 3H), 1.94 (s, 3H) | 11.1 min, 99.9% 7.8 min, 99.9% |
| 181 | (3-((4-(4-((2-(2,3-Dimethylphenoxy)ethoxy)carbonyl)-3,4-dihydro-2H-benzo[b][1,4]oxazin-8-yl)-1H-pyrazol-1-yl)methyl)benzamido)methanesulfonic acid | | O | H | 621.2 | 8.21 (s, 1H), 8.04 (s, 1H), 7.82-7.88 (m, 2H), 7.68 (s, 1H), 7.42-7.49 (m, 2H), 7.30 (dd, J = 7.8, 1.4 Hz, 1H), 6.99 (t, J = 7.9 Hz, 1H), 6.84 (t, J = 8.1 Hz, 1H), 6.76 (t, J = 7.5 Hz, 2H), 5.47 (s, 2H), 4.54-4.59 (m, 2H), 4.52 (br. s, 2H), 4.31-4.34 (m, 2H), 4.24-4.28 (m, 2H), 3.88-3.92 (m, 2H), 2.22 (s, 3H), 2.13 (s, 3H) | 11.6 min, 99.8% 8.1 min, 99.8% |

TABLE 12-continued

| Example | Name | —X—Y | V | R₃ | LCMS, [M + H]⁺ | 1H NMR (500 MHz, MeOD) δ | HPLC-1: Rt min, purity; HPLC-2: Rt min, purity |
|---|---|---|---|---|---|---|---|
| 182 | 2-(3-((4-(4-((2-(2,3-Dimethylphenoxy)ethoxy)carbonyl)-3,4-dihydro-2H-benzo[b][1,4]oxazin-8-yl)-1H-pyrazol-1-yl)methyl)benzamido)ethanesulfonic acid | | O | H | 635.1 | 8.22 (s, 1H), 8.05 (s, 1H), 7.76-7.81 (m, 2H), 7.68 (s, 1H), 7.40-7.47 (m, 2H), 7.30 (dd, J = 7.8, 1.49 Hz, 1H), 6.99 (t, J = 7.9 Hz, 1H), 6.84 (t, J = 8.1 Hz, 1H), 6.76 (t, J = 7.8 Hz, 2H), 5.47 (s, 2H), 4.54-4.58 (m, 2H), 4.31-4.35 (m, 2H), 4.23-4.27 (m, 2H), 3.88-3.92 (m, 2H), 3.80 (t, J = 6.4 Hz, 2H), 3.07 (t, J = 6.48 Hz, 2H), 2.22 (s, 3H), 2.12 (s, 3H) | 11.5 min, 100% 8.1 min, 99.6% |
| 183 | 6-(3-((4-(4-((2-(2,3-Dimethylphenoxy)ethoxy)carbonyl)-3,4-dihydro-2H-benzo[b][1,4]oxazin-8-yl)-1H-pyrazol-1-yl)methyl)benzamido)naphthalene-2-sulfonic acid | | O | H | 733.2 | 10.33 (s, 1H), 8.35 (s, 1H), 8.24 (s, 1H), 8.09 (s, 1H), 7.97-7.88 (m, 4H), 7.82 (dd, J = 8.8, 2.0 Hz, 1H), 7.75 (d, J = 8.5 Hz, 1H), 7.70 (dd, J = 8.5, 1.5 Hz, 1H), 7.64 (dd, J = 8.3, 1.0 Hz, 1H), 7.51 (t, J = 7.9 Hz, 1H), 7.46 (d, J = 7.6 Hz, 1H), 7.31 (dd, J = 7.7, 1.5 Hz, 1H), 7.01 (t, J = 7.9 Hz, 1H), 6.82 (dd, J = 15.2, 7.3 Hz, 2H), 6.76 (d, J = 7.5 Hz, 1H), 5.46 (s, 2H), 4.49 (dd, J = 5.4, 3.8 Hz, 2H), 4.35-4.29 (m, 2H), 4.23 dd, J = 5.4, 3.9 Hz, 2H), 3.89-3.83 m, 2H), 2.20 (s, 3H), 2.08 (s, 3H) | 9.1 min, 98.6% (HPLC-2) |
| 184 | 4-(3-((4-(4-((2-(2,3-Dimethylphenoxy)ethoxy)carbonyl)-3,4-dihydro-2H-benzo[b][1,4]oxazin-8-yl)-1H-pyrazol-1-yl)methyl)benzamido)benzenesulfonic acid | | O | H | 683.2 | 8.25 (s, 1H), 8.02 (s, 1H), 7.96-7.89 (m, 2H), 7.89-7.78 (m, 4H), 7.74-7.65 (m, 1H), 7.58-7.47 (m, 2H), 7.36 (dd, J = 7.8, 1.5 Hz, 1H), 7.03 (t, J = 7.9 Hz, 1H), 6.87 (t, J = 8.0 Hz, 1H), 6.80 (d, J = 14.9 Hz, 2H), 5.51 (s, 2H), 4.60 (dd, J = 5.4, 3.7 Hz, 2H), 4.40-4.34 (m, 2H), 4.29 (dd, J = 5.4, 3.8 Hz, 2H), 3.98-3.91 (m, 2H), 2.26 (s, 3H), 2.16 (s, 3H) | 12.9 min, 100% 8.7 min, 99.8% |
| 185 | 3-(3-((4-(4-(4-(2,3-Dimethylphenoxy)butanoyl)-3,4-dihydro-2H-benzo[b][1,4]oxazin-8-yl)-1H-pyrazol-1-yl)methyl)benzamido)benzenesulfonic acid | | CH₂ | H | 681.3 | 8.49 (s, 1H), 8.39 (t, J = 1.8 Hz, 1H), 8.36 (ddd, J = 8.1, 2.0, 0.9 Hz, 1H), 8.33 (s, 1H), 8.32-8.27 (m, 2H), 8.04-8.00 (m, 1H), 7.92-7.85 (m, 2H), 7.82-7.77 (m, 2H), 7.35-7.27 (m, 2H), 7.05 (dd, J = 7.6, 5.7 Hz, 2H), 5.85 (s, 2H), 4.71-4.67 (m, 2H), 4.39-4.32 (m, 4H), 3.28 (t, J = 7.0 Hz, 2H), 2.58-2.52 (m, 2H), 2.50 (s, 3H), 2.32 (s, 3H) | 12.8 min, 95.4% 8.4 min, 99.8% |

TABLE 12-continued

| Example | Name | —X—Y | V | R₃ | LCMS, [M + H]⁺ | 1H NMR (500 MHz, MeOD) δ | HPLC-1: Rt min, purity; HPLC-2: Rt min, purity |
|---|---|---|---|---|---|---|---|
| 186 | 6-(3-((4-(4-(2,3-Dimethylphenoxy)butanoyl)-3,4-dihydro-2H-benzo[b][1,4]oxazin-8-yl)-1H-pyrazol-1-yl)methyl)benzamido)naphthalene-2-sulfonic acid | (naphthalene-2-sulfonic acid benzamide linker) | CH₂ | H | 731.3 | 8.32 (d, J = 1.9 Hz, 2H), 8.11 (s, 1H), 7.92-7.96 (m, 4H), 7.88-7.91 (m, 1H), 7.83-7.86 (m, 1H), 7.80 (dd, J = 8.7, 2.4 Hz, 1H), 7.47-7.55 (m, 2H), 7.41 (dd, J = 7.8, 1.4 Hz, 1H), 7.24-7.33 (m, 1H), 6.86-6.95 (m, 2H), 6.66 (d, J = 4.4 Hz, 2H), 5.47 (s, 2H), 4.26-4.32 (m, 2H), 3.93-4.00 (m, 4H), 2.84-2.92 (m, 2H), 2.15 (t, J = 6.0 Hz, 2H), 2.10 (s, 3H), 1.92 (s, 3H) | 13.9 min, 99.2% 8.9 min, 98.7% |
| 187 | 4-(3-((4-(4-(2,3-Dimethylphenoxy)butanoyl)-3,4-dihydro-2H-benzo[b][1,4]oxazin-8-yl)-1H-pyrazol-1-yl)methyl)benzamido)benzenesulfonic acid | (4-sulfophenyl benzamide linker) | CH₂ | H | 681.3 | 8.51 (s, 1H), 8.34 (s, 1H), 8.31-8.27 (m, 2H), 8.25-8.20 (m, 2H), 8.17-8.12 (m, 2H), 7.93-7.85 (m, 2H), 7.80 (dd, J = 7.7, 1.4 Hz, 1H), 7.72-7.65 (m, 1H), 7.31 (dt, J = 11.7, 8.0 Hz, 2H), 7.08-7.03 (m, 2H), 5.86 (s, 2H), 4.71-4.66 (m, 2H), 4.39-4.32 (m, 4H), 3.28 (t, J = 7.0 Hz, 2H), 2.58-2.52 (m, 2H), 2.50 (s, 3H), 2.32 (s, 3H) | 12.1 min, 100% 8.4 min, 99.1% |
| 188 | 3-((4-(4-(2,3-Dimethylphenoxy)butanoyl)-2-methyl-3,4-dihydro-2H-benzo[b][1,4]oxazin-8-yl)-1H-pyrazol-1-yl)methyl)benzamido)methanesulfonic acid | (methanesulfonic acid benzamide linker) | CH₂ | Me | 633.3 | 8.12 (s, 1H), 8.01 (s, 1H), 7.89 (s, 1H), 7.85 (d, J = 7.5 Hz, 1H), 7.43-7.50 (m, 2H), 7.40 (dd, J = 7.8, 1.4 Hz, 1H), 7.31 (br. s, 1H), 6.86-6.97 (m, 2H), 6.66 (d, J = 8.1 Hz, 2H), 5.46 (s, 2H), 4.51-4.56 (m, 2H), 4.28-4.37 (m, 2H), 3.94-4.03 (m, 2H), 3.19-3.28 (m, 1H), 2.80-3.00 (m, 2H), 2.13-2.19 (m, 2H), 2.12 (s, 3H), 1.93 (s, 3H), 1.32 (d, J = 6.1 Hz, 3H) | 11.7 min, 99.9% 8.0 min, 99.6% |
| 189 | 2-(3-((4-(4-(2,3-Dimethylphenoxy)butanoyl)-2-methyl-3,4-dihydro-2H-benzo[b][1,4]oxazin-8-yl)-1H-pyrazol-1-yl)methyl)benzamido)ethanesulfonic acid | (ethanesulfonic acid benzamide linker) | CH₂ | Me | 647.3 | 8.08 (s, 1H), 7.97 (s, 1H), 7.82 (s, 1H), 7.78 (d, J = 7.21 Hz, 1H), 7.38-7.48 (m, 3H), 7.29 (br. s, 1H), 6.86-6.96 (m, 2H), 6.66 (d, J = 7.8 Hz, 2H), 5.44 (s, 2H), 4.26-4.39 (m, 2H), 3.92-4.02 (m, 2H), 3.81 (t, J = 6.4 Hz, 2H), 3.20-3.27 (m, 1H), 3.07 (t, J = 6.4 Hz, 2h), 2.89-2.98 (m, 1H), 2.80-2.89 (m, 1H), 2.15 (ddd, J = 12.8, 6.8, 6.5 Hz, 2H), 2.11 (s, 3H), 1.93 (s, 3H), 1.31 (d, J = 6.1 Hz, 3H) | 11.8 min, 99.9% 8.0 min, 99.9% |

Example 190

2-(3-Chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)ethanesulfonic acid

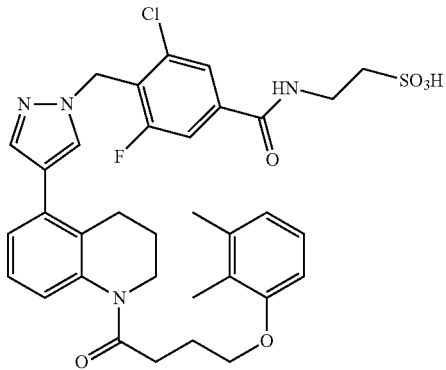 [SMILES: Cc1cccc(OCCCC(=O)N2CCCc3c(-c4cnn(Cc5c(F)cc(C(=O)NCCS(=O)(=O)O)cc5Cl)c4)cccc32)c1C]

Example 190 was prepared using a procedure analogous to Example 178 except that Example 10 was replaced by Example 173. LCMS, [M+H]⁺=683.2. ¹H NMR (500 MHz, MeOD) δ 7.81 (s, 1H), 7.64 (dd, J=9.9, 1.5 Hz, 1H), 7.59 (br. s, 1H), 7.43 (s, 1H), 7.21 (d, J=5.1 Hz, 2H), 7.18 (br. s, 1H), 6.96 (t, J=7.9 Hz, 1H), 6.65 (t, J=8.0 Hz, 2H), 5.58 (d, J=1.3 Hz, 2H), 3.82-3.90 (m, 2H), 3.79 (t, J=6.7 Hz, 2H), 3.73 (t, J=6.8 Hz, 2H), 3.08 (t, J=6.7 Hz, 2H), 2.80 (t, J=6.8 Hz, 2H), 2.45 (br. s, 2H), 2.11 (quin, J=6.2 Hz, 2H), 2.05 (s, 3H), 1.66-1.83 (m, 5H). HPLC-1: Rt=12.1 min, purity=100%; HPLC-2: Rt=8.1 min, purity=99.5%.

Example 191

3-((4-(1-(4-(2,3-Dimethylphenoxy)butanoyl)-1,2,3,4-tetrahydroquinolin-5-yl)-1H-pyrazol-1-yl)methyl)-N-(2-guanidinoethyl)benzamide

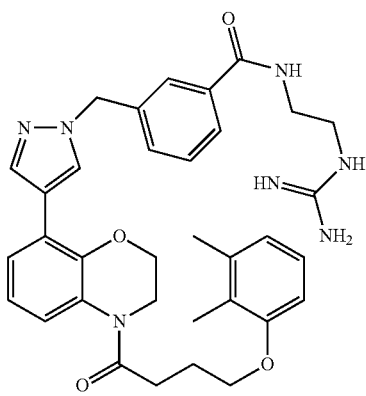 [SMILES: Cc1cccc(OCCCC(=O)N2CCOc3c(-c4cnn(Cc5cccc(C(=O)NCCNC(=N)N)c5)c4)cccc32)c1C]

Step A. tert-Butyl 2-(3-((4-(1-(4-(2,3-dimethylphenoxy)butanoyl)-1,2,3,4-tetrahydroquinolin-5-yl)-1H-pyrazol-1-yl)methyl)benzamido)ethylcarbamate

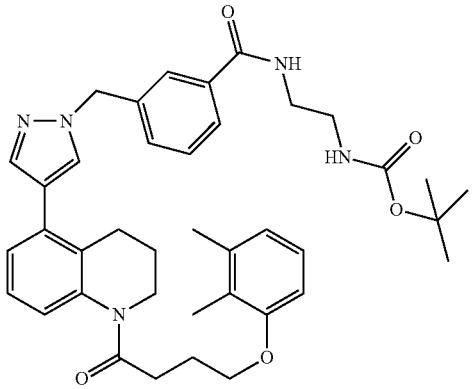 [SMILES: Cc1cccc(OCCCC(=O)N2CCCc3c(-c4cnn(Cc5cccc(C(=O)NCCNC(=O)OC(C)(C)C)c5)c4)cccc32)c1C]

The title compound was prepared using a procedure analogous to N-(2-cyanoethyl)-2-(4-(1-(4-(2,3-dimethylphenoxy)butanoyl)-1,2,3,4-tetrahydroquinolin-5-yl)-1H-pyrazol-1-yl)acetamide except that Example 1 was replaced with Example 95 and 3-aminopropanenitrile was replaced with tert-butyl 2-aminoethylcarbamate. LCMS, [M+H]⁺=666.4.

Step B. N-(2-Aminoethyl)-3-((4-(1-(4-(2,3-dimethylphenoxy)butanoyl)-1,2,3,4-tetrahydroquinolin-5-yl)-1H-pyrazol-1-yl)methyl)benzamide

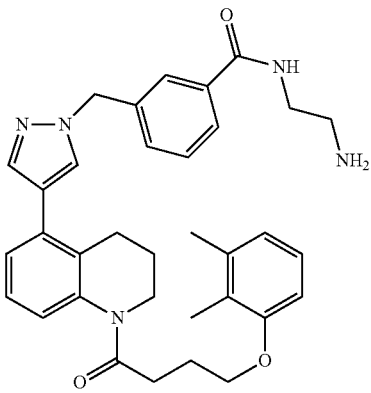 [SMILES: Cc1cccc(OCCCC(=O)N2CCCc3c(-c4cnn(Cc5cccc(C(=O)NCCN)c5)c4)cccc32)c1C]

The title compound was prepared using a procedure analogous to 1-(5-(3-(aminomethyl)phenyl)-3,4-dihydroquinolin-1(2H)-yl)-4-(2,3-dimethylphenoxy)butan-1-one except that tert-butyl 3-(1-(4-(2,3-dimethylphenoxy)butanoyl)-1,2,3,4-tetrahydroquinolin-5-yl)benzylcarbamate was replaced with tert-butyl 2-(3-((4-(1-(4-(2,3-dimethylphenoxy)butanoyl)-1,2,3,4-tetrahydroquinolin-5-yl)-1H-pyrazol-1-yl)methyl)benzamido)ethylcarbamate. LCMS, [M+H]⁺=566.3. ¹H NMR (400 MHz, MeOD) δ 7.89-7.73 (m, 2H), 7.65 (s, 1H), 7.56-7.40 (m, 3H), 7.32-7.19 (m, 2H), 7.17 (br. s, 1H), 6.96 (t, J=7.9 Hz, 1H), 6.71-6.59 (m, 2H), 5.43 (s, 2H), 3.86 (br. s, 2H), 3.74 (t, J=6.8 Hz, 2H), 3.50 (t, J=6.3 Hz, 2H), 2.90 (t, J=6.3 Hz, 2H), 2.81 (t, J=6.8 Hz, 2H), 2.48 (br. s, 2H), 2.12 (dt, J=12.4, 6.3 Hz, 2H), 2.03 (s, 3H), 1.85-1.75 (m, 2H), 1.74 (s, 3H).

Example 191

Example 191 was prepared using a procedure analogous to Example 90 except that 1-(5-(1-(3-aminobenzyl)-1H-pyrazol-4-yl)-3,4-dihydroquinolin-1(2H)-yl)-4-(2,3-dimethylphenoxy)butan-1-one was replaced by with N-(2-aminoethyl)-3-((4-(1-(4-(2,3-dimethylphenoxy)butanoyl)-1,2,3,4-tetrahydroquinolin-5-yl)-1H-pyrazol-1-yl)methyl)benzamide. LCMS, [M+H]$^+$=608.3. $^1$H NMR (500 MHz, MeOD) δ 7.82 (s, 1H), 7.81-7.75 (m, 1H), 7.65 (br. s, 1H), 7.56-7.42 (m, 3H), 7.29-7.08 (m, 3H), 6.96 (t, J=7.9 Hz, 1H), 6.71-6.60 (m, 2H), 5.43 (s, 2H), 3.85 (br. s, 2H), 3.73 (t, J=6.8 Hz, 2H), 3.55 (t, J=6.2 Hz, 2H), 3.45-3.37 (m, 2H), 2.80 (t, J=6.8 Hz, 2H), 2.47 (br. s, 2H), 2.18-2.06 (m, 2H), 2.02 (s, 3H), 1.85-1.75 (m, 2H), 1.71 (s, 3H). HPLC-1: Rt=8.2 min, purity=95.0%; HPLC-2: Rt=10.0 min, purity=96.0%.

Example 193

1-(5-(1-(3-(1H-Tetrazol-5-yl)benzyl)-1H-pyrazol-4-yl)-3,4-dihydroquinolin-1(2H)-yl)-4-(2,3-dimethylphenoxy)butan-1-one

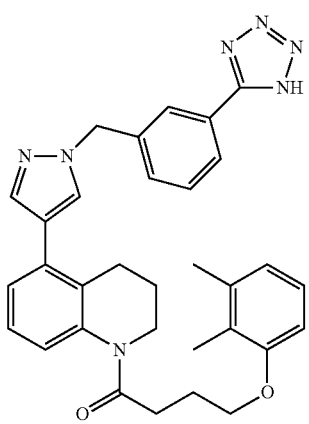 [SMILES: Cc1cccc(OCCCC(=O)N2CCCc3c(-c4cnn(Cc5cccc(-c6nnn[nH]6)c5)c4)cccc32)c1C]

Example 193 was prepared using a procedure analogous Example 147 to except that Example 1 was replaced with Example 95. LCMS, [M+H]$^+$=548.3. $^1$H NMR (400 MHz, CDCl$_3$) δ 7.93 (s, 1H), 7.86 (d, J=7.1 Hz, 1H), 7.59 (s, 1H), 7.46 (s, 1H), 7.40-7.27 (m, 3H), 7.13 (s, 2H), 6.98 (t, J=7.9 Hz, 1H), 6.70 (d, J=7.4 Hz, 1H), 6.62 (d, J=8.0 Hz, 1H), 5.38 (s, 2H), 3.93 (s, 2H), 3.77 (t, J=6.8 Hz, 2H), 2.76 (t, J=7.1 Hz, 2H), 2.59 (s, 2H), 2.29-2.08 (m, 5H), 2.03-1.79 (m, 5H). HPLC-1: Rt=9.7 min, purity=94.9%; HPLC-2: Rt=8.8 min, purity=96.8%.

Example 194

3-((4-(1-(4-(2,3-Dimethylphenoxy)butanoyl)-1,2,3,4-tetrahydroquinolin-5-yl)-1H-pyrazol-1-yl)methyl)phenylphosphonic acid

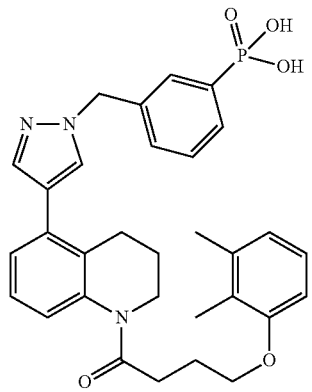 [SMILES: Cc1cccc(OCCCC(=O)N2CCCc3c(-c4cnn(Cc5cccc(P(=O)(O)O)c5)c4)cccc32)c1C]

Step A. 1-(5-(1-(3-Bromobenzyl)-1H-pyrazol-4-yl)-3,4-dihydroquinolin-1(2H)-yl)-4-(2,3-dimethylphenoxy)butan-1-one

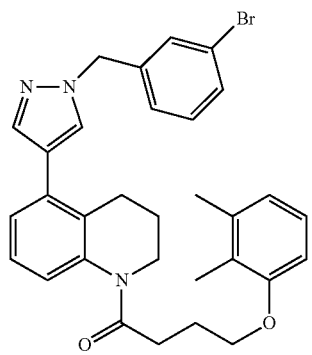

The title compound was prepared using a procedure analogous to methyl 3-((4-bromo-1H-pyrazol-1-yl)methyl)benzoate except that 4-bromo-1H-pyrazole was replaced with 1-(5-(1H-pyrazol-4-yl)-3,4-dihydroquinolin-1(2H)-yl)-4-(2,3-dimethylphenoxy)butan-1-one and methyl 3-(bromomethyl)benzoate was replaced with 1-bromo-3-(bromomethyl)benzene. LCMS, [M+H]$^+$=560.2.

Example 194

Argon was bubbled through a stirring mixture of 1-(5-(1-(3-bromobenzyl)-1H-pyrazol-4-yl)-3,4-dihydroquinolin-1(2H)-yl)-4-(2,3-dimethylphenoxy)butan-1-one (0.05 g, 0.09 mmol), dibenzyl phosphate (0.059 g, 0.224 mmol), Hunig's base (0.035 g, 0.269 mmol), and Pd(dppf)Cl$_2$—CH$_2$Cl$_2$ (7.31 mg, 8.95 µmol) in toluene (0.5 mL) for 5 min. The vessel was then capped and heated at 100° C. overnight. The reaction was cooled to room temperature and concentrated to provide the crude ester. The crude ester was re-dissolved in TFA (1.8 mL) and stirred at room temperature overnight. The reaction was concentrated and purified by preparative HPLC (PHENOMENEX® Axia Luna column, 5µ, C18, 30×75 mm; 15 min gradient from 100% A:0% B to 0% A:100% B and 3 min 100% B (A=90% H$_2$O/10% MeCN+0.1% TFA); (B=90% MeCN/10% H$_2$O+0.1% TFA); detection at 220 nm) to afford Example 194 (24 mg, 47% yield). LCMS, [M+H]$^+$=560.3. $^1$H NMR (400 MHz, DMSO-d$_6$) δ 8.01 (s, 1H), 7.68-7.52 (m, 3H), 7.45-7.36 (m, 2H), 7.29-7.13 (m, 3H), 7.00-6.93 (m, 1H), 6.73-6.65 (m, 2H), 5.39 (s, 2H), 3.92-3.82 (m, 2H), 3.65 (t, J=6.5 Hz, 2H), 2.66 (t, J=7.0 Hz, 2H), 2.63-2.56 (m, 2H), 2.09 (s, 3H), 2.03-1.94 (m, 2H), 1.85 (s, 3H), 1.80-1.70 (m, 2H). HPLC-1: Rt=8.3 min, purity=100%; HPLC-2: Rt=7.5 min, purity=100%.

Example 195

3-(4-(1-(4-(2,3-Dimethylphenoxy)butanoyl)-1,2,3,4-tetrahydroquinolin-5-yl)-1H-pyrazol-1-yl)propanoic acid

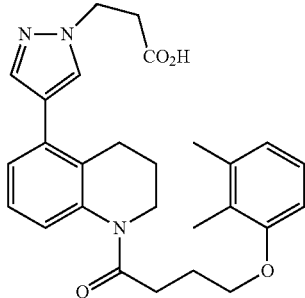 [SMILES: Cc1cccc(OCCCC(=O)N2CCCc3c(-c4cnn(CCC(=O)O)c4)cccc32)c1C]

Step A. 1-(5-(1-(3,3-Dimethoxypropyl)-1H-pyrazol-4-yl)-3,4-dihydroquinolin-1(2H)-yl)-4-(2,3-dimethylphenoxy)butan-1-one

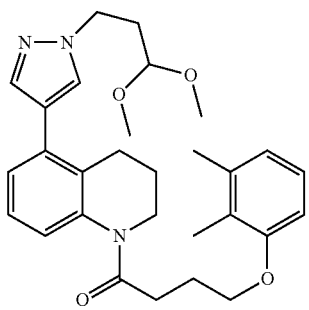 [SMILES: COC(CCn1cc(-c2cccc3c2CCCN3C(=O)CCCOc2cccc(C)c2C)cn1)OC]

The title compound was prepared using a procedure analogous to Example 63 except that ethyl 2-bromo-2-phenylacetate was replaced with 3-bromo-1,1-dimethoxypropane. LCMS, [M+H]$^+$=492.2. $^1$H NMR (400 MHz, CDCl$_3$) δ 7.52 (s, 1H), 7.32 (s, 1H), 7.22-7.13 (m, 3H), 7.02 (t, J=7.9 Hz, 1H), 6.75 (d, J=7.5 Hz, 1H), 6.65 (d, J=8.2 Hz, 1H), 4.37 (t, J=5.7 Hz, 1H), 4.23 (t, J=7.1 Hz, 2H), 3.94 (t, J=5.3 Hz, 2H), 3.79 (t, J=6.8 Hz, 2H), 3.35 (s, 6H), 2.75 (t, J=7.1 Hz, 2H), 2.59 (s, 2H), 2.26-2.13 (m, 7H), 1.97-1.79 (m, 5H).

Step B. 3-(4-(1-(4-(2,3-Dimethylphenoxy)butanoyl)-1,2,3,4-tetrahydroquinolin-5-yl)-1H-pyrazol-1-yl)propanal

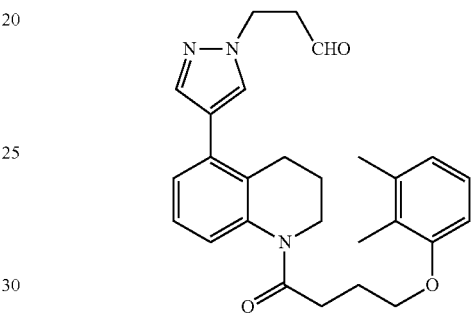

To a solution of 1-(5-(1-(3,3-dimethoxypropyl)-1H-pyrazol-4-yl)-3,4-dihydroquinolin-1(2H)-yl)-4-(2,3-dimethylphenoxy)butan-1-one (40 mg, 0.081 mmol) in acetone (0.8 mL) was added 9 M H$_2$SO$_4$. The reaction mixture was stirred at room temperature for 2 h. After this time, the reaction mixture was partitioned between DCM and saturated NaHCO$_3$, and stirred for 15 min. The organic layer was separated, dried over anhydrous Na$_2$SO$_4$, filtered, and concentrated to afford the title compound (36 mg, 100% yield). $^1$H NMR (400 MHz, CDCl$_3$) δ 9.86 (s, 1H), 7.50 (s, 1H), 7.38 (s, 1H), 7.21-7.12 (m, 2H), 7.02 (t, J=7.9 Hz, 1H), 6.75 (d, J=7.5 Hz, 1H), 6.65 (d, J=8.1 Hz, 1H), 6.09 (s, 1H), 4.48 (t, J=6.3 Hz, 2H), 3.94 (s, 2H), 3.81-3.75 (m, 2H), 3.14 (t, J=6.3 Hz, 2H), 2.74 (t, J=7.1 Hz, 2H), 2.63 (s, 2H), 2.59 (d, J=4.3 Hz, 2H), 2.14 (s, 3H), 1.95-1.81 (m, 5H).

Example 195

To a solution of 3-(4-(1-(4-(2,3-dimethylphenoxy)butanoyl)-1,2,3,4-tetrahydroquinolin-5-yl)-1H-pyrazol-1-yl)propanal (36 mg, 0.081 mmol) in THF/t-BuOH/2-methyl-2-butene (1:3:1, 0.5 mL) was added an aqueous solution of NaClO$_2$ (18 mg, 0.162 mmol) and NaHPO$_4$ (29 mg, 0.243 mmol). The resulting mixture was stirred vigorously at room temperature for 30 min. The organic solvents were removed in vacuo, and the resulting solid was partitioned between DCM and water. The reaction mixture was adjusted to pH~5 with conc. HCl, and then excess 5% citric acid was added. The resulting mixture was stirred for 15 min. The organic layer was separated, dried over anhydrous Na$_2$SO$_4$, filtered, and concentrated. The resulting residue was purified by preparative HPLC (PHENOMENEX® Axia Luna column, 5µ, C18, 30×75 mm; 10 min gradient from 100% A:0% B to 0% A:100% B and 3 min 100% B (A=90% H₂O/10% MeCN+ 0.1% TFA); (B=90% MeCN/10% H₂O+0.1% TFA); detection at 220 nm) to afford Example 195 (18 mg, 47% yield). LCMS, [M+H]$^+$=462.1. $^1$H NMR (400 MHz, CDCl₃) δ 7.53 (d, J=5.1 Hz, 1H), 7.37 (s, 1H), 7.23-7.10 (m, 3H), 7.02 (t, J=7.9 Hz, 1H), 6.74 (d, J=7.5 Hz, 1H), 6.64 (d, J=8.1 Hz, 1H), 4.46 (t, J=6.3 Hz, 2H), 3.93 (s, 2H), 3.78 (t, J=6.8 Hz, 2H), 3.02 (t, J=6.3 Hz, 2H), 2.75 (t, J=7.1 Hz, 2H), 2.57 (s, 2H), 2.25-2.10 (m, 5H), 1.97-1.78 (m, 5H). HPLC-1: Rt=9.3 min, purity=99.4%; HPLC-2: Rt=8.2 min, purity=99.6%.

Example 196

2-(4-(1-(4-(2,4,5-Trichlorophenoxy)butanoyl)-1,2,3,4-tetrahydroquinolin-5-yl)-1H-pyrazol-1-yl)acetic acid

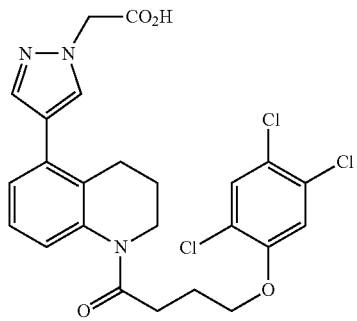 [SMILES: O=C(O)Cn1cc(-c2cccc3c2CCCN3C(=O)CCCOc2cc(Cl)c(Cl)cc2Cl)cn1]

Step A. Methyl 4-(5-bromo-3,4-dihydroquinolin-1(2H)-yl)-4-oxobutanoate

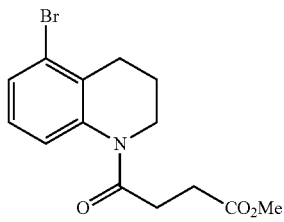 [SMILES: COC(=O)CCC(=O)N1CCCc2c(Br)cccc21]

The title compound was prepared using a procedure analogous to 1-(5-bromo-3,4-dihydroquinolin-1(2H)-yl)-4-(2,3-dimethylphenoxy)butan-1-one except that 4-(2,3-dimethylphenoxy)butanoic acid was replaced by 4-methoxy-4-oxobutanoic acid. LCMS, [M+Na]$^+$=349.9. $^1$H NMR (400 MHz, CDCl₃) δ 7.38 (d, J=8.0 Hz, 1H), 7.25 (br. s, 1H), 7.03 (t, J=8.1 Hz, 1H), 3.80-3.73 (m, 2H), 3.68 (d, J=11.0 Hz, 2H), 3.66 (s, 3H), 2.81 (t, J=6.9 Hz, 2H), 2.78-2.72 (m, 2H), 2.71-2.63 (m, 2H), 1.99 (dd, J=12.5, 6.6 Hz, 2H).

Step B. 1-(5-Bromo-3,4-dihydroquinolin-1(2H)-yl)-4-hydroxybutan-1-one

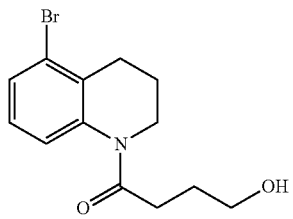 [SMILES: O=C(CCCO)N1CCCc2c(Br)cccc21]

To a solution of methyl 4-(5-bromo-3,4-dihydroquinolin-1(2H)-yl)-4-oxobutanoate (0.9 g, 2.76 mmol) in MeOH (30 mL) was added sodium borohydride (2.088 g, 55.2 mmol), and the resulting mixture was stirred at room temperature for 30 min. After this time, additional sodium borohydride (1.566 g, 41.4 mmol) was added slowly and the reaction was stirred for another 30 min. The reaction mixture was quenched with HCl and extracted with ethyl acetate. The combined organic layer was dried over anhydrous MgSO₄, filtered, and concentrated. The resulting residue was purified by flash chromatography (0-100% ethyl acetate:hexanes then 10% CH₃OH:ethyl acetate) to afford the title compound (0.6 g, 73% yield) as a colorless oil. LCMS, [M+H]$^+$=298.0. $^1$H NMR (400 MHz, MeOD) δ 7.49 (d, J=8.1 Hz, 1H), 7.44 (br. s, 1H), 7.17 (t, J=8.1 Hz, 1H), 3.86-3.80 (m, 2H), 3.61 (t, J=6.2 Hz, 2H), 2.89 (t, J=6.9 Hz, 2H), 2.68 (t, J=7.4 Hz, 2H), 2.10-2.01 (m, 2H), 1.95-1.85 (m, 2H).

Step C. Ethyl 2-(4-(1-(4-hydroxybutanoyl)-1,2,3,4-tetrahydroquinolin-5-yl)-1H-pyrazol-1-yl)acetate

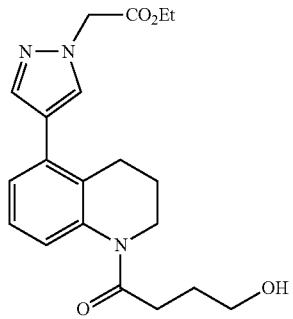 [SMILES: CCOC(=O)Cn1cc(-c2cccc3c2CCCN3C(=O)CCCO)cn1]

To a degassed solution of 1-(5-bromo-3,4-dihydroquinolin-1(2H)-yl)-4-hydroxybutan-1-one (68 mg, 0.228 mmol), ethyl 2-(4-(4,4,5,5-tetramethyl-1,3,2-dioxaborolan-2-yl)-1H-pyrazol-1-yl)acetate (80 mg, 0.285 mmol) and potassium phosphate (145 mg, 0.684 mmol) in THF (1 mL) was added PdCl$_2$(dppf) (15 mg, 0.021 mmol). The vial was purged with argon, sealed, and stirred 80° C. overnight. After this time, the reaction mixture was partitioned between EtOAc and saturated NH$_4$Cl solution, and the organic layer was separated. The aqueous phase was extracted with EtOAc. The combined organic layers were dried over anhydrous MgSO$_4$, filtered, and concentrated in vacuo to provide the crude material. The crude material was purified by flash chromatography (0-100% ethyl acetate:hexanes then 10% ethyl acetate: MeOH) to afford the title compound (80 mg, 85% yield) as a yellow oil. LCMS, [M+H]$^+$=372.1. $^1$H NMR (400 MHz, CDCl$_3$) δ 7.61 (s, 1H), 7.53 (s, 1H), 7.23-7.12 (m, 3H), 4.94 (s, 2H), 4.25 (q, J=7.1 Hz, 2H), 3.78 (t, J=6.9 Hz, 2H), 3.68 (dd, J=11.1, 5.5 Hz, 2H), 2.73 (t, J=6.5 Hz, 2H), 2.64 (t, J=6.7 Hz, 2H), 1.97-1.83 (m, 4H), 1.29 (t, J=7.1 Hz, 3H).

Step D. Ethyl 2-(4-(1-(4-(2,4,5-trichlorophenoxy) butanoyl)-1,2,3,4-tetrahydroquinolin-5-yl)-1H-pyrazol-1-yl)acetate

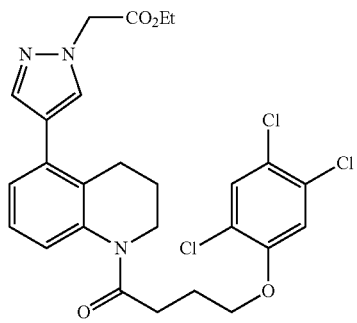

In an oven dried 1-dram vial was a mixture of ethyl 2-(4-(1-(4-hydroxybutanoyl)-1,2,3,4-tetrahydroquinolin-5-yl)-1H-pyrazol-1-yl)acetate (40 mg, 0.108 mmol), 2,4,5-trichlorophenol (34.0 mg, 0.172 mmol), triphenylphosphine (45.2 mg, 0.172 mmol) in CH$_2$Cl$_2$ (35.9 mL). DIAD (29.2 μL, 0.172 mmol) was added, and the reaction mixture was stirred at room temperature overnight. At the conclusion of this period, the reaction mixture was concentrated and purified by preparative HPLC (PHENOMENEX® Axia Luna column, 5μ, C18, 21.2×250 mm; 25 min gradient from 40% A:60% B to 0% A:100% B and 3 min 100% B (A=90% H$_2$O/10% MeOH+0.1% TFA); (B=90% MeOH/10% H$_2$O+0.1% TFA); detection at 220 nm) to afford the title compound (18.9 mg, 32% yield) as a colorless oil. LCMS, [M+H]$^+$=550.1. $^1$H NMR (400 MHz, MeOD) δ 7.76 (s, 1H), 7.61 (s, 1H), 7.48 (s, 1H), 7.28-7.16 (m, 4H), 5.06 (s, 2H), 4.25 (q, J=7.1 Hz, 2H), 4.04 (br. s, 2H), 3.77 (t, J=6.8 Hz, 2H), 2.79 (t, J=7.0 Hz, 2H), 2.66 (br. s, 2H), 2.13 (dt, J=12.7, 6.4 Hz, 2H), 1.92-1.80 (m, 2H), 1.29 (t, J=7.1 Hz, 3H).

Example 196

Example 196 was prepared using a procedure analogous to Example 2 except that methyl 4-(1-(4-(2,3-dimethylphenoxy)butanoyl)-1,2,3,4-tetrahydroquinolin-5-yl)picolinate was replaced with ethyl 2-(4-(1-(4-(2,4,5-trichlorophenoxy)butanoyl)-1,2,3,4-tetrahydroquinolin-5-yl)-1H-pyrazol-1-yl)acetate. LCMS, [M+H]$^+$=522.1. $^1$H NMR (400 MHz, MeOD) δ δ 7.95 (s, 1H), 7.76 (s, 1H), 7.44 (s, 1H), 7.42-7.36 (m, 1H), 7.36-7.28 (m, 1H), 7.29-7.23 (m, 1H), 7.23-7.17 (m, 1H), 7.17-7.09 (m, 2H), 7.04 (s, 1H), 7.02-6.96 (m, 1H), 6.95-6.89 (m, 1H), 5.43 (s, 2H), 4.67-4.59 (m, 1H), 4.58-4.50 (m, 2H), 4.38 (s, 2H), 4.30 (br. s, 2H), 3.11 (d, J=12.3 Hz, 1H), 2.95-2.71 (m, 2H), 2.28 (s, 3H), 2.27-2.19 (m, 1H), 1.94-1.84 (m, 1H), 1.16-1.07 (m, 1H), 0.74-0.63 (m, 1H). HPLC-1: Rt=10.7 min, purity=100%; HPLC-2: Rt=9.5 min, purity=100%.

Example 197

2-(4-(1-(4-(3-Chloro-2-methylphenoxy)butanoyl)-1,2,3,4-tetrahydroquinolin-5-yl)-1H-pyrazol-1-yl)acetic acid

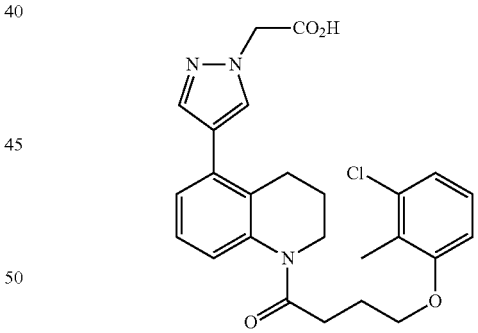

Example 197 was prepared using a procedure analogous to Example 196 except that 2,4,5-trichlorophenol was replaced with 3-chloro-2-methylphenol. LCMS, [M+H]$^+$=468.2. $^1$H NMR (400 MHz, CD$_2$Cl$_2$) δ 7.68-7.60 (m, 1H), 7.50-7.42 (m, 1H), 7.30 7.12 (m, 3H), 7.10-7.02 (m, 1H), 6.94 (d, J=8.0 Hz, 1H), 6.72 (d, J=8.1 Hz, 1H), 5.01 (s, 2H), 3.95 (br. s, 2H), 3.79-3.70 (m, 2H), 2.73 (t, J=6.8 Hz, 2H), 2.57 (br. s, 2H), 2.15 (dt, J=11.9, 6.0 Hz, 2H), 2.03 (s, 3H), 1.84 (br. s, 2H). HPLC-1: Rt=9.6 min, purity=99.4%; HPLC-2: Rt=8.6 min, purity=99.4%.

Example 198

3-((3-(1-(4-(o-Tolyloxy)butanoyl)-1,2,3,4-tetrahydroquinolin-5-yl)benzyloxy)carbonylamino)propanoic acid

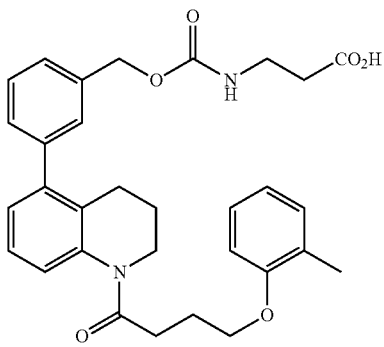 [SMILES: Cc1ccccc1OCCCC(=O)N1CCCc2c(-c3cccc(COC(=O)NCCC(=O)O)c3)cccc21]

Step A. tert-Butyl 3-((3-(1-(4-hydroxybutanoyl)-1,2,3,4-tetrahydroquinolin-5-yl)benzyloxy)carbonylamino)propanoate

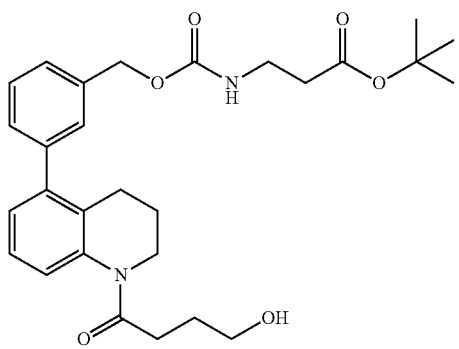 [SMILES: CC(C)(C)OC(=O)CCNC(=O)OCc1cccc(-c2cccc3c2CCCN3C(=O)CCCO)c1]

To a degassed mixture of 1-(5-bromo-3,4-dihydroquinolin-1(2H)-yl)-4-hydroxybutan-1-one (0.208 g, 0.698 mmol), 4,4,4',4',5,5,5',5'-octamethyl-2,2'-bi(1,3,2-dioxaborolane) (0.532 g, 2.094 mmol), and potassium acetate (0.411 g, 4.19 mmol) in DMF (10 mL) was added $PdCl_2(dppf)$-$CH_2Cl_2$ (0.057 g, 0.070 mmol). The vial was purged with argon, sealed, and stirred at 90° C. for 2 d. tert-Butyl 3-((3-bromobenzyloxy)carbonylamino)propanoate (0.5 g, 1.396 mmol), $PdCl_2(dppf)$-$CH_2Cl_2$ (0.057 g, 0.070 mmol), and 2 M $Na_2CO_3$ (2 mL, 1.396 mmol) were added. The reaction mixture was purged with argon and stirred at 95° C. overnight. At the conclusion of this period, the reaction mixture was quenched with water and extracted with ethyl acetate. The organic extract was dried, concentrated, and purified by flash chromatography (0-100% ethyl acetate:hexanes then 10% $CH_3OH$:ethyl acetate) to afford the title compound (0.24 g, 69% yield) as a dark brown oil. LCMS, $[M+H]^+$=497.4.

Step B. tert-Butyl 3-((3-(1-(4-(o-tolyloxy)butanoyl)-1,2,3,4-tetrahydroquinolin-5-yl)benzyloxy)carbonylamino)propanoate

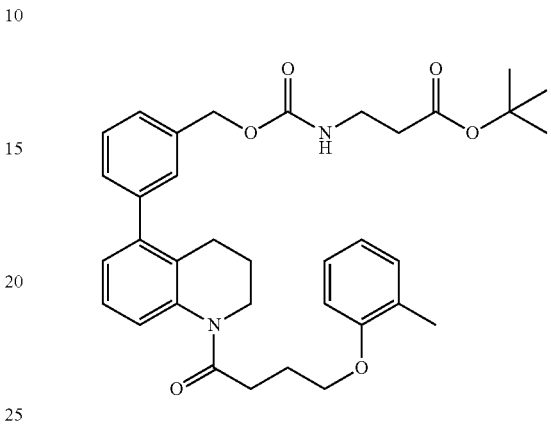

The title compound was prepared using a procedure analogous to ethyl 2-(4-(1-(4-(2,4,5-trichlorophenoxy)butanoyl)-1,2,3,4-tetrahydroquinolin-5-yl)-1H-pyrazol-1-yl)acetate except that ethyl 2-(4-(1-(4-hydroxybutanoyl)-1,2,3,4-tetrahydroquinolin-5-yl)-1H-pyrazol-1-yl)acetate was replaced with tert-butyl 3-((3-(1-(4-hydroxybutanoyl)-1,2,3,4-tetrahydroquinolin-5-yl)benzyloxy)carbonylamino)propanoate and 2,4,5-trichlorophenol was replaced with o-cresol. LCMS, $[M+H]^+$=587.3.

Example 198

To a solution of tert-butyl 3-((3-(1-(4-(o-tolyloxy)butanoyl)-1,2,3,4-tetrahydroquinolin-5-yl)benzyloxy)carbonylamino)propanoate (6 mg, 7.16 μmol) in $CH_2Cl_2$ (200 μL) was added m-cresol (7.74 mg, 0.072 mmol) and TFA (55.2 μL, 0.716 mmol). The reaction mixture was stirred at room temperature for 2 h and then concentrated to provide the crude material. The crude material was purified by preparative HPLC (PHENOMENEX® Axia Luna column, 5μ, C18, 30×75 mm; 10 min gradient from 100% A:0% B to 0% A:100% B and 3 min 100% B (A=90% $H_2O$/10% MeCN+ 0.1% TFA); (B=90% MeCN/10% $H_2O$+0.1% TFA); detection at 220 nm) to afford Example 198 (3.2 mg, 83% yield) as a white powder. LCMS, $[M+H]^+$=531.3. $^1$H NMR (400 MHz, MeCN-$d_3$) δ 7.42 (t, J=7.6 Hz, 1H), 7.35 (d, J=7.2 Hz, 1H), 7.26 (d, J=8.1 Hz, 2H), 7.20 (d, J=7.5 Hz, 1H), 7.46-7.39 (m, 2H), 6.85 (d, J=7.4 Hz, 1H), 6.81 (d, J=7.5 Hz, 1H), 5.82-5.69 (br. s, 1H), 5.10 (s, 2H), 3.96 (t, J=5.6 Hz, 2H), 3.71 (t, J=6.9 Hz, 2H), 3.33 (dd, J=12.8, 6.4 Hz, 2H), 2.73 (t, J=7.1 Hz, 2H), 2.47 (t, J=6.6 Hz, 2H), 2.44-2.36 (m, 2H), 2.10 (dt, J=12.9, 6.3 Hz, 2H), 2.00 (s, 3H), 1.82-1.72 (m, 2H). HPLC-1: Rt=10.2 min, purity=99.7%; HPLC-2: Rt=9.2 min, purity=97.7%.

The following Examples were prepared in a manner analogous to Example 198.

TABLE 13

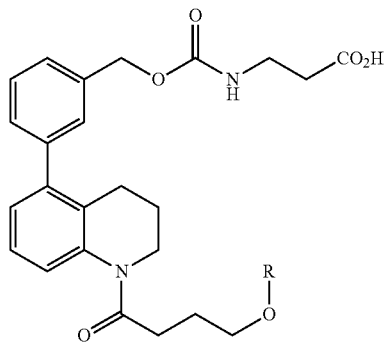

| Example | Name | R | LCMS, [M + H]+ | 1H NMR (400 MHz, CD3CN) δ | HPLC-1: Rt min, purity; HPLC-2: Rt min, purity |
|---|---|---|---|---|---|
| 199 | 3-((3-(1-(4-(3-Chlorophenoxy)butanoyl)-1,2,3,4-tetrahydroquinolin-5-yl)benzyloxy)carbonylamino)propanoic acid | 3-Cl-C6H4 | 551.2 | 7.43 (t, J = 7.6 Hz, 1H), 7.35 (d, J = 7.5 Hz, 1H), 7.30-7.20 (m, 5H), 7.10 (d, J = 7.7 Hz, 1H), 6.94 (d, J = 7.6 Hz, 1H), 6.91 (s, 1H), 6.81 (d, J = 8.4 Hz, 1H), 5.10 (s, 2H), 3.99 (t, J = 6.1 Hz, 2H), 3.71 (t, J = 6.9 Hz, 2H), 3.33 (dd, J = 12.8, 6.4 Hz, 2H), 2.67 (t, J = 7.1 Hz, 2H), 2.54-2.44 (m, 4H), 2.11-2.01 (m, 2H), 1.85-1.74 (m, 2H) | 10.4 min, 100% 9.4 min, 100% |
| 200 | 3-((3-(1-(4-(2-Cyclopropylphenoxy)butanoyl)-1,2,3,4-tetrahydroquinolin-5-yl)benzyloxy)carbonylamino)propanoic acid | 2-cyclopropyl-C6H4 | 557.3 | 7.42 (t, J = 7.6 Hz, 1H), 7.35 (d, J = 7.7 Hz, 1H), 7.28-7.18 (m, 4H), 7.13-7.04 (m, 2H), 6.88-6.78 (m, 3H), 5.09 (s, 2H), 4.00 (t, J = 5.8 Hz, 2H), 3.71 (t, J = 6.9 Hz, 2H), 3.33 (dd, J = 12.8, 6.5 Hz, 2H), 2.75 (t, J = 7.2 Hz, 2H), 2.53-2.41 (m, 4H), 2.16-2.06 (m, 2H), 2.02-1.96 (m, 1H), 1.83-1.73 (m, 2H), 0.75 (d, J = 7.4 Hz, 2H), 0.51 (d, J = 4.3 Hz, 2H) | 10.6 min, 100% 9.5 min, 100% |
| 201 | 3-((3-(1-(4-(2-Chlorophenoxy)butanoyl)-1,2,3,4-tetrahydroquinolin-5-yl)benzyloxy)carbonylamino)propanoic acid, TFA salt | 2-Cl-C6H4 | 551.2 | 7.43 (t, J = 7.6 Hz, 1H), 7.35 (d, J = 7.7 Hz, 2H), 7.30-7.20 (m, 5H), 7.09 (d, J = 7.3 Hz, 1H), 7.03 (d, J = 8.2 Hz, 1H), 6.91 (t, J = 7.7 Hz, 1H), 5.10 (s, 2H), 4.06 (br. s, 2H), 3.71 (t, J = 6.9 Hz, 2H), 3.33 (q, J = 6.4 Hz, 2H), 2.73 (t, J = 7.1 Hz, 2H), 2.52-2.41 (m, 4H), 2.11 (p, J = 6.6 Hz, 2H), 1.78 (p, J = 6.5 Hz, 2H) | 10.0 min, 99.9% 9.1 min, 99.8% |
| 202 | 3-((3-(1-(4-(3-Cyclopropylphenoxy)butanoyl)-1,2,3,4-tetrahydroquinolin-5-yl)benzyloxy)carbonylamino)propanoic acid | 3-cyclopropyl-C6H4 | 557.3 | 7.43 (t, J = 7.6 Hz, 1H), 7.35 (d, J = 7.5 Hz, 2H), 7.30-7.19 (m, 3H), 7.16-7.04 (m, 2H), 6.64 (t, J = 8.3 Hz, 2H), 6.56 (s, 1H), 5.10 (s, 2H), 3.96 (t, J = 6.1 Hz, 2H), 3.71 (t, J = 6.8 Hz, 2H), 3.33 (dd, J = 12.8, 6.5 Hz, 2H), 2.66 (t, J = 7.1 Hz, 2H), 2.55-2.42 (m, 4H), 2.10-2.00 (m, 2H), 1.90-1.73 (m, 3H), 0.95-0.87 (m, 2H), 0.68-0.59 (m, 2H) | 10.6 min, 99.8% 9.5 min, 96.7% |
| 203 | 3-((3-(1-(4-(2,3-Difluorophenoxy)butanoyl)-1,2,3,4-tetrahydroquinolin-5-yl)benzyloxy)carbonylamino)propanoic acid, TFA salt | 2,3-diF-C6H3 | 553.2 | 7.43 (t, J = 7.6 Hz, 1H), 7.39-7.20 (m, 5H), 7.13-7.02 (m, 2H), 6.93-6.78 (m, 2H), 5.10 (s, 2H), 4.09 (t, J = 5.8 Hz, 2H), 3.72 (t, J = 6.8 Hz, 2H), 3.33 (q, J = 6.4 Hz, 2H), 2.69 (t, J = 7.1 Hz, 2H), 2.54-2.44 (m, 4H), 2.11 (p, J = 6.7 Hz, 2H), 1.80 (p, J = 6.6 Hz, 2H) | 9.8 min, 99.9% 8.9 min, 99.8% |

TABLE 13-continued

| Example | Name | R | LCMS, [M + H]+ | ¹H NMR (400 MHz, CD₃CN) δ | HPLC-1: Rt min, purity; HPLC-2: Rt min, purity |
|---|---|---|---|---|---|
| 204 | 3-((3-(1-(4-(3-(Trifluoromethyl) phenoxy)butanoyl)-1,2,3,4-tetrahydroquinolin-5-yl) benzyloxy)carbonylamino) propanoic acid, TFA salt | 3-CF₃-phenyl | 585.3 | 7.48-7.40 (m, 2H), 7.39-7.20 (m, 6H), 7.16 (s, 1H), 7.12 (d, J = 8.7 Hz, 1H), 7.09 (d, J = 7.5 Hz, 1H), 5.10 (s, 2H), 4.06 (t, J = 6.0 Hz, 2H), 3.72 (t, J = 6.8 Hz, 2H), 3.33 (q, J = 6.5 Hz, 2H), 2.68 (t, J = 7.1 Hz, 2H), 2.55-2.42 (m, 4H), 2.09 (p, J = 6.7 Hz, 2H), 1.80 (p, J = 6.7 Hz, 2H) | 10.6 min, 100% 9.5 min, 100% |
| 205 | 3-((3-(1-(4-(m-Tolyloxy) butanoyl)-1,2,3,4-tetrahydroquinolin-5-yl) benzyloxy)carbonylamino) propanoic acid, TFA salt | 3-methylphenyl | 531.4 | 7.41 (t, J = 7.5 Hz, 1H), 7.32 (d, J = 7.4 Hz, 1H), 7.30-7.18 (m, 4H), 7.18-7.08 (m, 2H), 6.74 (d, J = 7.4 Hz, 1H), 6.67 (s, 1H), 6.64 (d, J = 8.5 Hz, 1H), 5.13 (s, 2H), 4.01-3.93 (m, 2H), 3.76 (t, J = 6.9 Hz, 2H), 3.43 (dd, J = 12.0, 6.0 Hz, 2H), 2.73 (t, J = 7.3 Hz, 2H), 2.63-2.45 (m, 4H), 2.28 (s, 3H), 2.13 (dt, J = 13.1, 6.5 Hz, 2H), 1.87-1.75 (m, 2H)* | 10.3 min, 99.0% 9.4 min, 98.9% |
| 206 | 3-((3-(1-(4-(3-Fluoro-2-methylphenoxy)butanoyl)-1,2,3,4-tetrahydroquinolin-5-yl) benzyloxy)carbonylamino) propanoic acid, TFA salt | 3-F-2-methylphenyl | 549.3 | 7.40 (t, J = 7.4 Hz, 1H), 7.33 (d, J = 7.5 Hz, 1H), 7.30-7.12 (m, 5H), 7.07 (dd, J = 15.4, 8.1 Hz, 1H), 6.65 (d, J = 8.8 Hz, 1H), 6.61 (d, J = 7.5 Hz, 1H), 5.13 (s, 2H), 3.98 (br. s, 2H), 3.77 (t, J = 7.0 Hz, 2H), 3.44 (dd, J = 12.0, 6.0 Hz, 2H), 2.63-2.52 (m, 2H), 2.47 (br. s, 2H), 2.17 (dt, J = 12.6, 6.2 Hz, 2H), 1.93 (s, 3H), 1.81 (dd, J = 13.2, 6.6 Hz, 2H)* | 10.3 min, 100% 9.2 min, 100% |
| 207 | 3-((3-(1-(4-(2,3-Dihydro-1H-inden-4-yloxy)butanoyl)-1,2,3,4-tetrahydroquinolin-5-yl) benzyloxy)carbonylamino) propanoic acid, TFA salt | 2,3-dihydro-1H-inden-4-yl | 557.4 | 7.40 (t, J = 7.5 Hz, 1H), 7.33 (d, J = 7.5 Hz, 1H), 7.28-7.11 (m, 5H), 7.06 (t, J = 7.8 Hz, 1H), 6.81 (d, J = 7.4 Hz, 1H), 6.60 (d, J = 8.0 Hz, 1H), 5.13 (s, 2H), 3.98 (br. s, 2H), 3.78 (t, J = 7.0 Hz, 2H), 3.44 (dd, J = 12.1, 6.1 Hz, 2H), 2.84 (t, J = 7.4 Hz, 2H), 2.78 (t, J = 7.3 Hz, 2H), 2.65 (br. s, 2H), 2.61-2.53 (m, 2H), 2.49 (t, J = 5.9 Hz, 2H), 2.14 (dt, J = 13.0, 6.4 Hz, 2H), 2.02-1.89 (m, 2H), 1.87-1.74 (m, 2H)* | 11.0 min, 100% 9.9 min, 100% |
| 208 | 3-((3-(1-(4-(2-Fluoro-3-methylphenoxy)butanoyl)-1,2,3,4-tetrahydroquinolin-5-yl) benzyloxy)carbonylamino) propanoic acid, TFA salt | 2-F-3-methylphenyl | 549.3 | 7.41 (t, J = 7.5 Hz, 1H), 7.38-7.19 (m, 5H), 7.15 (br. s, 1H), 6.92 (t, J = 7.4 Hz, 1H), 6.83-6.71 (m, 2H), 5.13 (s, 2H), 4.05 (t, J = 5.6 Hz, 2H), 3.77 (t, J = 6.9 Hz, 2H), 3.44 (dd, J = 12.1, 6.1 Hz, 2H), 2.76 (t, J = 7.2 Hz, 2H), 2.62-2.48 (m, 4H), 2.23 (d, J = 2.1 Hz, 3H), 2.16 (dd, J = 13.2, 6.6 Hz, 2H), 1.87-1.76 (m, 2H)* | 10.2 min, 100% 9.3 min, 100% |

TABLE 13-continued

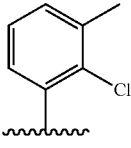 [SMILES: *c1cccc(C)c1Cl]

| Example | Name | R | LCMS, [M + H]+ | ¹H NMR (400 MHz, CD₃CN) δ | HPLC-1: Rt min, purity; HPLC-2: Rt min, purity |
|---|---|---|---|---|---|
| 209 | 3-((3-(1-(4-(2-Chloro-3-methylphenoxy)butanoyl)-1,2,3,4-tetrahydroquinolin-5-yl)benzyloxy)carbonylamino)propanoic acid | 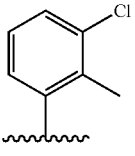 | 565.4 | 7.42 (t, J = 7.6 Hz, 1H), 7.34 (d, J = 7.6 Hz, 1H), 7.29-7.19 (m, 4H), 7.12 (t, J = 7.9 Hz, 1H), 7.08 (d, J = 7.5 Hz, 1H), 6.87 (d, J = 7.6 Hz, 1H), 6.86 (d, J = 8.2 Hz, 1H), 5.09 (s, 2H), 4.03 (t, J = 5.9 Hz, 2H), 3.71 (t, J = 6.9 Hz, 2H), 3.32 (dd, J = 12.7, 6.5 Hz, 2H), 2.73 (t, J = 7.1 Hz, 2H), 2.46 (t, J = 6.6 Hz, 4H), 2.31 (s, 3H), 2.09 (p, J = 6.6 Hz, 2H), 1.78 (p, J = 6.7 Hz, 2H) | 11.0 min, 100% 9.9 min, 100% |
| 210 | 3-((3-(1-(4-(3-Chloro-2-methylphenoxy)butanoyl)-1,2,3,4-tetrahydroquinolin-5-yl)benzyloxy)carbonylamino)propanoic acid | 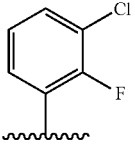 [SMILES: *c1cccc(Cl)c1F] | 565.4 | 7.41 (t, J = 7.5 Hz, 1H), 7.32 (d, J = 7.0 Hz, 1H), 7.29-7.18 (m, 4H), 7.16-7.10 (m, 1H), 7.06 (t, J = 8.1 Hz, 1H), 6.94 (d, J = 7.9 Hz, 1H), 6.74 (d, J = 8.2 Hz, 1H), 5.14 (s, 2H), 3.99 (br. s, 2H), 3.75 (t, J = 6.9 Hz, 2H), 2.75 (t, J = 7.2 Hz, 2H), 2.56 (br. s, 2H), 2.48 (br. s, 2H), 2.22-2.14 (m, 2H), 2.12 (s, 3H), 1.85-1.76 (m, 2H), 1.84-1.76 (m, 2H)* | 11.4 min, 97.8% 10.1 min, 98.4% |
| 211 | 3-((3-(1-(4-(3-Chloro-2-fluorophenoxy)butanoyl)-1,2,3,4-tetrahydroquinolin-5-yl)benzyloxy)carbonylamino)propanoic acid | 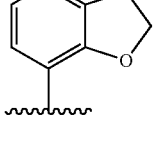 | 569.4 | 7.42 (t, J = 7.6 Hz, 1H), 7.34 (d, J = 7.5 Hz, 1H), 7.29-7.20 (m, 3H), 7.11-6.97 (m, 5H), 5.09 (s, 2H), 4.07 (t, J = 6.1 Hz, 2H), 3.70 (t, J = 6.9 Hz, 2H), 3.32 (q, J = 6.5 Hz, 2H), 2.67 (t, J = 7.1 Hz, 2H), 2.51-2.44 (m, 4H), 2.09 (dt, J = 13.4, 6.7 Hz, 2H), 1.78 (p, J = 6.7 Hz, 2H) | 10.7 min, 98.2% 9.7 min, 98.2% |
| 212 | 3-((3-(1-(4-(Benzo[d][1,3]dioxol-4-yloxy)butanoyl)-1,2,3,4-tetrahydroquinolin-5-yl)benzyloxy)carbonylamino)propanoic acid | 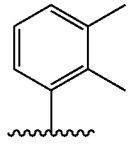 [SMILES: *c1cccc(C)c1C] | 561.4 | 7.42 (t, J = 7.6 Hz, 1H), 7.34 (d, J = 7.6 Hz, 1H), 7.25 (m, 4H), 7.09 (d, J = 7.6 Hz, 1H), 6.79-6.72 (m, 1H), 6.54 (d, J = 8.5 Hz, 1H), 6.51 (d, J = 7.8 Hz, 1H), 5.87 (s, 2H), 5.09 (s, 2H), 4.07 (t, J = 6.1 Hz, 2H), 3.70 (t, J = 6.9 Hz, 2H), 3.32 (q, J = 6.5 Hz, 2H), 2.65 (t, J = 7.2 Hz, 2H), 2.54-2.42 (m, 4H), 2.09-2.01 (m, 2H), 1.79 (p, J = 6.7 Hz, 2H) | 9.7 min, 97.4% 9.1 min, 95.0% |
| 213 | 3-((3-(1-(5-(2,3-Dimethylphenoxy)pentanoyl)-1,2,3,4-tetrahydroquinolin-5-yl)benzyloxy)carbonylamino)propanoic acid |  | 559.4 | 7.42 (t, J = 7.6 Hz, 1H), 7.38-7.15 (m, 5H), 7.06 (d, J = 7.6 Hz, 1H), 6.98 (t, J = 7.9 Hz, 1H), 6.72 (d, J = 7.5 Hz, 1H), 6.68 (d, J = 8.2 Hz, 1H), 5.08 (s, 2H), 3.89 (br. s, 2H), 3.69 (t, J = 6.8 Hz, 2H), 3.31 (dd, J = 12.8, 6.4 Hz, 2H), 2.56 (t, J = 6.9 Hz, 2H), 2.52 (t, J = 6.4 Hz, 2H), 2.45 (t, J = 6.6 Hz, 2H), 2.21 (s, 3H), 2.07 (s, 3H), 1.85-1.72 (m, 6H) | 10.8 min, 100% 9.5 min, 100% |

TABLE 13-continued

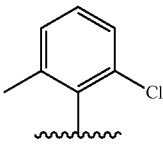 [SMILES: *c1c(C)cccc1Cl]

| Example | Name | R | LCMS, [M + H]⁺ | ¹H NMR (400 MHz, CD₃CN) δ | HPLC-1: Rt min, purity; HPLC-2: Rt min, purity |
|---|---|---|---|---|---|
| 214 | 3-((3-(1-(4-(2-Chloro-6-methylphenoxy)butanoyl)-1,2,3,4-tetrahydroquinolin-5-yl)benzyloxy)carbonylamino)propanoic acid | | 565.3 | 7.43 (t, J = 7.6 Hz, 1H), 7.39-7.18 (m, 6H), 7.12 (d, J = 7.5 Hz, 1H), 7.11-7.05 (m, 1H), 6.97 (t, J = 7.8 Hz, 1H), 5.10 (s, 2H), 3.90 (t, J = 5.9 Hz, 2H), 3.73 (t, J = 6.8 Hz, 2H), 3.32 (q, J = 6.5 Hz, 2H), 2.77 (t, J = 7.2 Hz, 2H), 2.54 (t, J = 6.4 Hz, 2H), 2.46 (t, J = 6.6 Hz, 2H), 2.23 (s, 3H), 2.15-2.06 (m, 2H), 1.81 (p, J = 6.7 Hz, 2H) | 10.7 min, 100% 9.6 min, 100% |

*¹H NMR (400 MHz, CD₂Cl₂) δ.

Example 215

2-(3-((4-(1-(4-(2,3-Dimethylphenoxy)butanoyl)-1,2,3,4-tetrahydroquinolin-5-yl)-1H-pyrazol-1-yl)methyl)phenoxy)ethanesulfonic acid

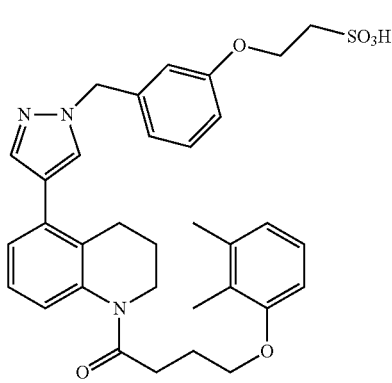 [SMILES: Cc1cccc(OCCCC(=O)N2CCCc3c(-c4cnn(Cc5cccc(OCCS(=O)(=O)O)c5)c4)cccc32)c1C]

Step A. 4-Bromo-1-(3-methoxybenzyl)-1H-pyrazole

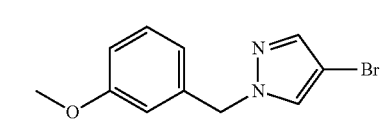

The title compound was prepared using a procedure analogous to methyl 3-((4-bromo-1H-pyrazol-1-yl)methyl)benzoate except that methyl 3-(bromomethyl)benzoate was replaced with 1-(bromomethyl)-3-methoxybenzene. LCMS, [M+H]⁺=267.1.

Step B. 3-((4-Bromo-1H-pyrazol-1-yl)methyl)phenol

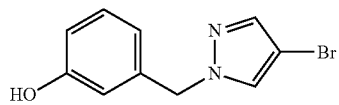 [SMILES: Oc1cccc(Cn2cc(Br)cn2)c1]

To a solution of 4-bromo-1-(3-methoxybenzyl)-1H-pyrazole (3.8 g, 14.23 mmol) was dissolved in CH₂Cl₂ (30 mL) at 0° C. was added boron tribromide (2.69 mL, 28.5 mmol). The reaction mixture was stirred at 0° C. for 30 min and concentrated. The resulting residue was purified by flash chromatography (0-100% ethyl acetate:hexanes) to afford the title compound (2.55 g, 71% yield) as a yellow oil. LCMS, [M+H]⁺= 253.0. ¹H NMR (400 MHz, CDCl₃) δ 7.47 (s, 1H), 7.38 (s, 1H), 7.19 (t, J=8.0 Hz, 1H), 6.76 (d, J=8.0 Hz, 2H), 6.59 (s, 1H), 5.20 (s, 2H).

Step C. 2-(3-((4-Bromo-1H-pyrazol-1-yl)methyl)phenoxy)ethyl acetate

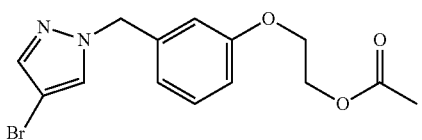 [SMILES: CC(=O)OCCOc1cccc(Cn2cc(Br)cn2)c1]

A mixture of 3-((4-bromo-1H-pyrazol-1-yl)methyl)phenol (0.6 g, 2.37 mmol), 2-bromoethyl acetate (0.792 g, 4.74 mmol) and potassium carbonate (0.655 g, 4.74 mmol) in DMF (5 mL) was heated at 200° C. in a microwave reactor for 1 h. After this time, the reaction mixture was quenched with water and extracted with ethyl acetate. The organic layer was dried and concentrated. The resulting residue was purified by flash chromatography (0-100% ethyl acetate:hexanes) to afford the title compound (0.27 g, 34% yield) as a colorless oil. LCMS, [M+H]$^+$=339.0. $^1$H NMR (400 MHz, CDCl$_3$) δ 7.46 (s, 1H), 7.34 (s, 1H), 7.24 (dd, J=8.3, 7.6 Hz, 2H), 6.83 (dd, J=8.3, 2.4 Hz, 1H), 6.80 (d, J=7.6 Hz, 1H), 6.74 (d, J=2.4 Hz, 1H), 5.20 (s, 2H), 4.41-4.32 (m, 2H), 4.14-4.08 (m, 2H), 2.06 (s, 3H).

Step D. 4-(2,3-Dimethylphenoxy)-1-(5-(1-(3-(2-hydroxyethoxy)benzyl)-1H-pyrazol-4-yl)-3,4-dihydroquinolin-1(2H)-yl)butan-1-one

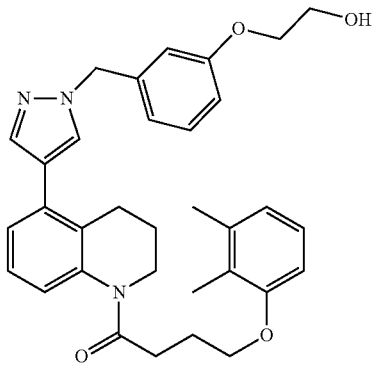 [SMILES: Cc1cccc(OCCCC(=O)N2CCCc3c(-c4cnn(Cc5cccc(OCCO)c5)c4)cccc32)c1C]

The title compound was prepared using a procedure analogous to methyl 4-(1-(4-(2,3-dimethylphenoxy)butanoyl)-1,2,3,4-tetrahydroquinolin-5-yl)picolinate except that methyl 4-bromopicolinate was replaced with 2-(3-((4-bromo-1H-pyrazol-1-yl)methyl)phenoxy)ethyl acetate. LCMS, [M+H]$^+$= 540.4.

Step E. 2-(3-((4-(1-(4-(2,3-Dimethylphenoxy)butanoyl)-1,2,3,4-tetrahydroquinolin-5-yl)-1H-pyrazol-1-yl)methyl)phenoxy)ethyl methanesulfonate

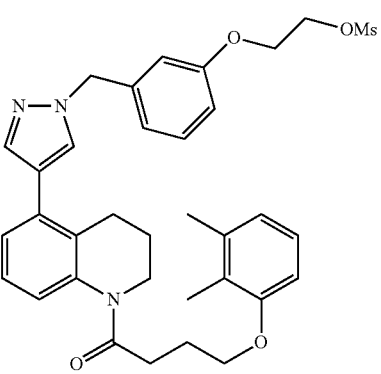 [SMILES: Cc1cccc(OCCCC(=O)N2CCCc3c(-c4cnn(Cc5cccc(OCCOS(C)(=O)=O)c5)c4)cccc32)c1C]

To a solution of 4-(2,3-dimethylphenoxy)-1-(5-(1-(3-(2-hydroxyethoxy)benzyl)-1H-pyrazol-4-yl)-3,4-dihydroquinolin-1(2H)-yl)butan-1-one (0.07 g, 0.13 mmol) in CH$_2$Cl$_2$ (2 mL) at 0° C. was added methanesulfonyl chloride (0.019 g, 0.17 mmol) and triethylamine (0.029 mL, 0.21 mmol) dropwise. The reaction mixture was stirred at 0° C. for 2 h and then quenched with saturated NaHCO$_3$. The resulting mixture was extracted with ethyl acetate. The organic layer was washed with 1 N HCl, saturated NaHCO$_3$, and brine, dried and concentrated to afford the title compound (80 mg, 100%). LCMS, [M+H]$^+$=618.4.

Example 215

A mixture of 2-(3-((4-(1-(4-(2,3-dimethylphenoxy)butanoyl)-1,2,3,4-tetrahydroquinolin-5-yl)-1H-pyrazol-1-yl)methyl)phenoxy)ethyl methanesulfonate (0.08 g, 0.130 mmol) and sodium sulfite (250 mg, 1.983 mmol) in ethanol (2 mL) and water (4 mL) was heated at 150° C. in a microwave reactor for 20 min. The reaction mixture was concentrated and the resulting residue was purified by preparative HPLC (PHENOMENEX® Axia Luna column, 5μ, C18, 30×100 mm; 10 min gradient from 100% A:0% B to 0% A:100% B (A=90% H$_2$O/10% MeOH+0.1% TFA); (B=90% MeOH/10% H$_2$O+0.1% TFA); detection at 220 nm) to afford Example 215 (9 mg, 11% yield) as a white powder. LCMS, [M+H]$^+$=604.4. $^1$H NMR (400 MHz, CD$_3$CN) δ 7.61 (s, 1H), 7.52 (s, 1H), 7.27 (t, J=7.9 Hz, 1H), 7.23-7.09 (m, 3H), 7.02-6.88 (m, 3H), 6.84 (d, J=7.4 Hz, 1H), 6.67 (d, J=7.9 Hz, 1H), 6.65 (d, J=8.9 Hz, 1H), 5.28 (s, 2H), 4.31 (t, J=7.1 Hz, 2H), 3.85 (br. s, 2H), 3.72-3.64 (m, 2H), 3.25-3.17 (m, 2H), 2.70 (t, J=7.1 Hz, 2H), 2.49 (br. s, 2H), 2.10-1.99 (m, 5H), 1.85-1.68 (m, 5H). HPLC-1: Rt=11.9 min, purity=98.2%; HPLC-2: Rt=9.9 min, purity=100%.

Example 216

1-(3-(3-((4-(1-(4-(2,3-Dimethylphenoxy)butanoyl)-1,2,3,4-tetrahydroquinolin-5-yl)-1H-pyrazol-1-yl)methyl)phenoxy)propyl)guanidine, TFA salt

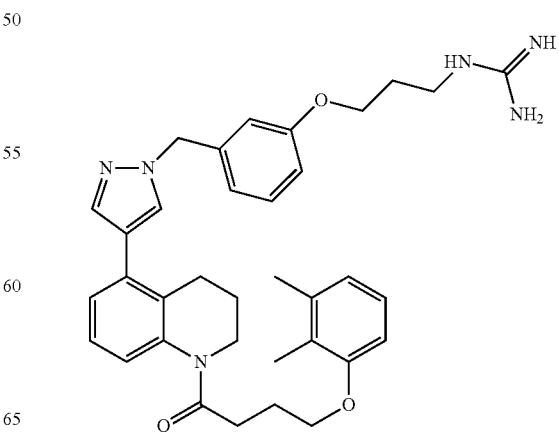

325

Step A. tert-Butyl 3-(3-((4-bromo-1H-pyrazol-1-yl)methyl)phenoxy)propyl carbamate

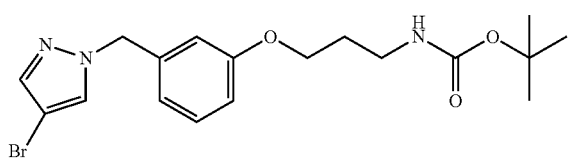 [SMILES: CC(C)(C)OC(=O)NCCCOc1cccc(Cn2cc(Br)cn2)c1]

The title compound was prepared using a procedure analogous to 2-(3-((4-bromo-1H-pyrazol-1-yl)methyl)phenoxy)ethyl acetate except that 2-bromoethyl acetate was replaced with tert-butyl 3-bromopropylcarbamate. LCMS, [M+H]$^+$= 410.0.

Step B. tert-Butyl 3-(3-((4-(1-(4-(2,3-dimethylphenoxy)butanoyl)-1,2,3,4-tetrahydroquinolin-5-yl)-1H-pyrazol-1-yl)methyl)phenoxy)propylcarbamate

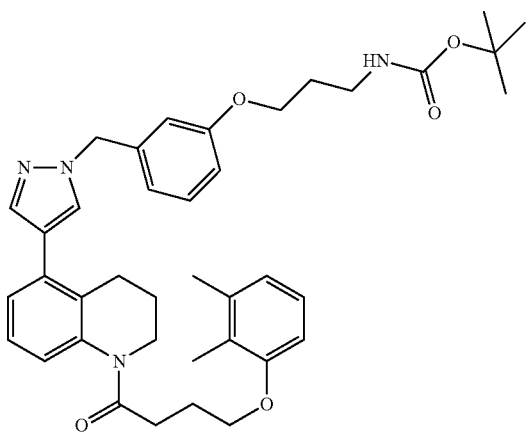 [SMILES: Cc1cccc(OCCCC(=O)N2CCCc3c(-c4cnn(Cc5cccc(OCCCNC(=O)OC(C)(C)C)c5)c4)cccc32)c1C]

The title compound was prepared using a procedure analogous to methyl 4-(1-(4-(2,3-dimethylphenoxy)butanoyl)-1,2,3,4-tetrahydroquinolin-5-yl)picolinate except that methyl 4-bromopicolinate was replaced with tert-butyl 3-(3-((4-bromo-1H-pyrazol-1-yl)methyl)phenoxy)propyl carbamate. LCMS, [M+H]$^+$=653.3.

326

Step C. 1-(5-(1-(3-(3-Aminopropoxy)benzyl)-1H-pyrazol-4-yl)-3,4-dihydroquinolin-1(2H)-yl)-4-(2,3-dimethylphenoxy)butan-1-one

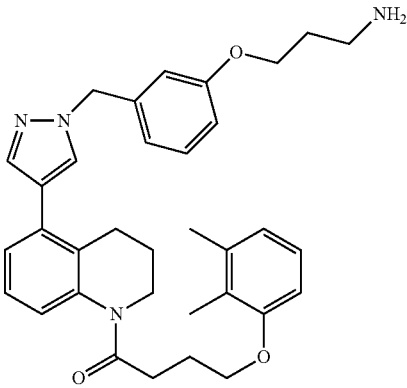 [SMILES: Cc1cccc(OCCCC(=O)N2CCCc3c(-c4cnn(Cc5cccc(OCCCN)c5)c4)cccc32)c1C]

The title compound was prepared using a procedure analogous to 1-(5-(3-(aminomethyl)phenyl)-3,4-dihydroquinolin-1(2H)-yl)-4-(2,3-dimethylphenoxy)butan-1-one except that tert-butyl 3-(1-(4-(2,3-dimethylphenoxy)butanoyl)-1,2,3,4-tetrahydroquinolin-5-yl)benzylcarbamate was replaced with tert-butyl 3-(3-((4-(1-(4-(2,3-dimethylphenoxy)butanoyl)-1,2,3,4-tetrahydroquinolin-5-yl)-1H-pyrazol-1-yl)methyl)phenoxy)propylcarbamate. LCMS, [M+H]$^+$=553.3.

Example 216

To a solution of 1H-pyrazole-1-carboximidamide hydrochloride (2.67 mg, 0.018 mmol) in DMF (0.5 mL) at room temperature was added 1-(5-(1-(3-(3-Aminopropoxy)benzyl)-1H-pyrazol-4-yl)-3,4-dihydroquinolin-1(2H)-yl)-4-(2,3-dimethylphenoxy)butan-1-one (6.7 mg, 0.012 mmol) and N-ethyl-N-isopropylpropan-2-amine (4.35 µL, 0.024 mmol). The reaction mixture was heated to 120° C. in a microwave reactor for 20 min. After cooling to room temperature, the reaction mixture was filtered and the filtrate was purified by preparative HPLC (PHENOMENEX® Axia Luna column, 5µ, C18, 30×100 mm; 10 min gradient from 95% A:5% B to 0% A:100% B (A=90% H$_2$O/10% MeOH+0.1% TFA); (B=90% MeOH/10% H$_2$O+0.1% TFA); detection at 220 nm) to afford Example 216 (8 mg, 89% yield) as a white powder. LCMS, [M+H]$^+$=595.5. $^1$H NMR (400 MHz, MeOD) δ 7.68 (s, 1H), 7.56 (s, 1H), 7.45-7.19 (m, 4H), 7.11-6.91 (m, 4H), 6.81-6.65 (m, 2H), 5.41 (s, 2H), 4.14 (t, J=5.8 Hz, 2H), 3.95 (br. s, 2H), 3.82 (t, J=6.7 Hz, 2H), 3.53-3.44 (m, 2H), 2.88 (t, J=6.7 Hz, 2H), 2.57 (br. s, 2H), 2.28-2.06 (m, 7H), 1.97-1.76 (m, 5H). HPLC-1: Rt=8.7 min, purity=96.9%; HPLC-2: Rt=11.0 min, purity=96.9%.

Example 217

((3-((4-(1-(4-(2,3-Dimethylphenoxy)butanoyl)-1,2,3,4-tetrahydroquinolin-5-yl)-1H-pyrazol-1-yl)methyl)phenoxy)carbonylamino)methanesulfonic acid

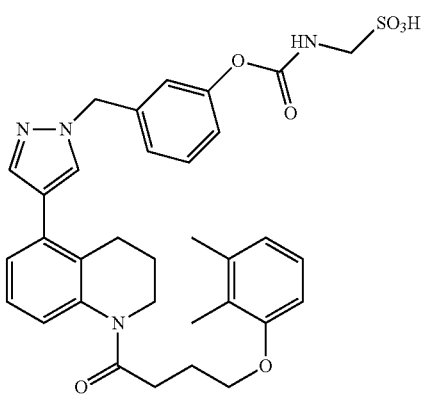 [SMILES: Cc1cccc(OCCCC(=O)N2CCCc3c(-c4cnn(Cc5cccc(OC(=O)NCS(=O)(=O)O)c5)c4)cccc32)c1C]

Step A. 4-(2,3-Dimethylphenoxy)-1-(5-(1-(3-methoxybenzyl)-1H-pyrazol-4-yl)-3,4-dihydroquinolin-1(2H)-yl)butan-1-one

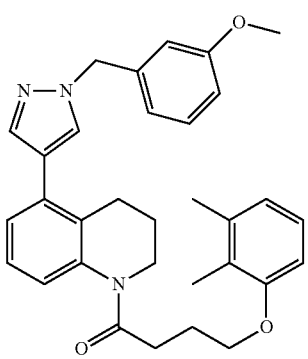 [SMILES: COc1cccc(Cn2cc(-c3cccc4c3CCCN4C(=O)CCCOc3cccc(C)c3C)cn2)c1]

The title compound was prepared using a procedure analogous to methyl 4-(1-(4-(2,3-dimethylphenoxy)butanoyl)-1,2,3,4-tetrahydroquinolin-5-yl)picolinate except that methyl 4-bromopicolinate was replaced with 4-bromo-1-(3-methoxybenzyl)-1H-pyrazole. LCMS, [M+H]$^+$=510.4.

Step B. 4-(2,3-Dimethylphenoxy)-1-(5-(1-(3-hydroxybenzyl)-1H-pyrazol-4-yl)-3,4-dihydroquinolin-1(2H)-yl)butan-1-one

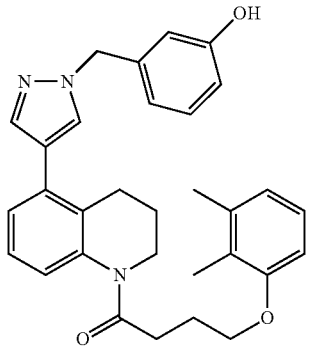

The title compound was prepared using a procedure analogous to 3-((4-bromo-1H-pyrazol-1-yl)methyl)phenol except that 4-bromo-1-(3-methoxybenzyl)-1H-pyrazole was replaced with 4-(2,3-dimethylphenoxy)-1-(5-(1-(3-methoxybenzyl)-1H-pyrazol-4-yl)-3,4-dihydroquinolin-1(2H)-yl)butan-1-one. LCMS, [M+H]$^+$=496.4.

Example 217

To a solution of 4-(2,3-dimethylphenoxy)-1-(5-(1-(3-hydroxybenzyl)-1H-pyrazol-4-yl)-3,4-dihydroquinolin-1(2H)-yl)butan-1-one (45 mg, 0.09 mmol) in THF 0.2 mL) was added triethyl amine (0.038 mL, 0.27 mmol) and a catalytic amount of DMAP (1 mg, 8.19 mmol). The reaction mixture was cooled to 0° C. and 4-nitrophenyl carbonochloridate (36.6 mg, 0.18 mmol) in THF (0.2 mL) was added dropwise. The resulting mixture was stirred at 0° C. to room temperature for 30 min and then treated with aminomethanesulfonic acid (202 mg, 1.82 mmol) in DMF (1 mL). The resulting mixture was heated at 80° C. for 20 min and concentrated. The resulting residue was purified by preparative HPLC (PHENOMENEX® Axia Luna column, 5µ, C18, 30×100 mm; 10 min gradient from 95% A:5% B to 0% A:100% B (A=90% H$_2$O/10% MeOH+0.1% TFA); (B=90% MeOH/10% H$_2$O+0.1% TFA); detection at 220 nm) to afford Example 217 (10 mg, 17% yield) as a white powder. LCMS, [M+H]$^+$=633.4. $^1$H NMR (400 MHz, MeOD) δ 7.66 (s, 1H), 7.54 (s, 1H), 7.49 (t, J=7.9 Hz, 1H), 7.41-7.29 (m, 2H), 7.30-7.16 (m, 4H), 7.07 (t, J=7.8 Hz, 1H), 6.83-6.70 (m, 2H), 5.48 (s, 2H), 4.37 (s, 2H), 3.94 (br. s, 2H), 3.82 (t, J=6.8 Hz, 2H), 2.91 (t, J=6.6 Hz, 2H), 2.51 (br. s, 2H), 2.28-2.16 (m, 2H), 2.10 (s, 3H), 1.96-1.82 (m, 2H), 1.76 (s, 3H). HPLC-1: Rt=11.9 min, purity=99.0%; HPLC-2: Rt=9.9 min, purity=99.1%.

Example 218

1-(2-(3-((4-(1-(4-(2,3-Dimethylphenoxy)butanoyl)-1,2,3,4-tetrahydroquinolin-5-yl)-1H-pyrazol-1-yl)methyl)phenoxy)ethyl)guanidine, TFA salt

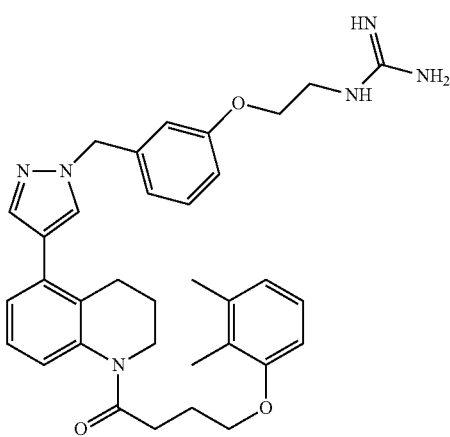 [SMILES: Cc1cccc(OCCCC(=O)N2CCCc3c(-c4cnn(Cc5cccc(OCCNC(=N)N)c5)c4)cccc32)c1C]

Step A. tert-Butyl (tert-butoxycarbonylamino)(2-(3-((4-(1-(4-(2,3-dimethylphenoxy)butanoyl)-1,2,3,4-tetrahydroquinolin-5-yl)-1H-pyrazol-1-yl)methyl)phenoxy)ethylamino)methylenecarbamate

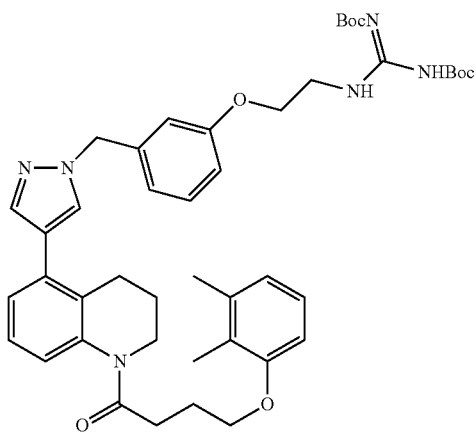

To a solution of 4-(2,3-dimethylphenoxy)-1-(5-(1-(3-(2-hydroxyethoxy)benzyl)-1H-pyrazol-4-yl)-3,4-dihydroquinolin-1(2H)-yl)butan-1-one (0.02 g, 0.037 mmol), 1,3-bis(tert-butoxycarbonyl)-guanidine (0.024 g, 0.093 mmol), triphenylphosphine (0.024 g, 0.093 mmol) in DCM (0.1 mL) was added DEAD (0.040 g, 0.093 mmol, 40% wt in toluene). The reaction mixture was stirred at room temperature for 1 h and then concentrated. The resulting residue was purified by flash chromatography (0-100% ethyl acetate:hexanes) to afford the title compound (0.026 g, 90% yield) as a white powder. LCMS, [M+H]$^+$=781.3.

Example 218

Example 218 was prepared using a procedure analogous to 1-(5-(3-(aminomethyl)phenyl)-3,4-dihydroquinolin-1(2H)-yl)-4-(2,3-dimethylphenoxy)butan-1-one except that tert-butyl 3-(1-(4-(2,3-dimethylphenoxy)butanoyl)-1,2,3,4-tetrahydroquinolin-5-yl)benzylcarbamate was replaced with tert-butyl (tert-butoxycarbonylamino)(2-(3-(4-(1-(4-(2,3-dimethylphenoxy)butanoyl)-1,2,3,4-tetrahydroquinolin-5-yl)-1H-pyrazol-1-yl)methyl)phenoxy)ethylamino)methylenecarbamate. LCMS, [M+H]$^+$=581.5. $^1$H NMR (400 MHz, MeOD) δ 7.60 (br. s, 1H), 7.47 (s, 1H), 7.30 (t, J=7.8 Hz, 1H), 7.27-7.19 (m, 2H), 7.16 (s, 1H), 7.00-6.84 (m, 4H), 6.65 (d, J=7.3 Hz, 2H), 5.34 (s, 2H), 4.11 (t, J=5.1 Hz, 2H), 3.85 (br. s, 2H), 3.73 (t, J=6.8 Hz, 2H), 3.59 (t, J=5.0 Hz, 2H), 2.80 (t, J=6.8 Hz, 2H), 2.46 (br. s, 2H), 2.11 (dt, J=12.5, 6.3 Hz, 2H), 2.02 (s, 3H), 1.83-1.74 (m, 2H), 1.71 (s, 3H). HPLC-1: Rt=8.6 min, purity=95.0%; HPLC-2: Rt=10.3 min, purity=98.8%.

Example 219

3-(3-((4-(1-(4-(2,3-Dimethylphenoxy)butanoyl)-1,2,3,4-tetrahydroquinolin-5-yl)-1H-pyrazol-1-yl)methyl)phenoxy)propane-1-sulfonic acid

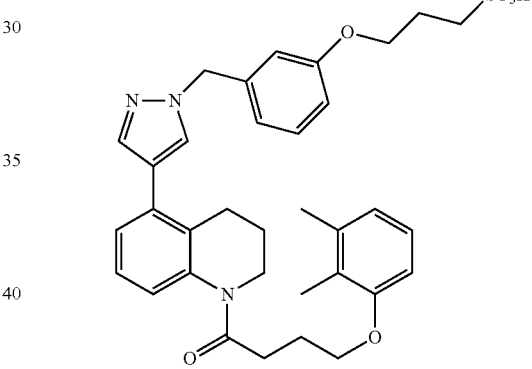

Step A. 1-(5-(1-(3-(3-Bromopropoxy)benzyl)-1H-pyrazol-4-yl)-3,4-dihydroquinolin-1(2H)-yl)-4-(2,3-dimethylphenoxy)butan-1-one

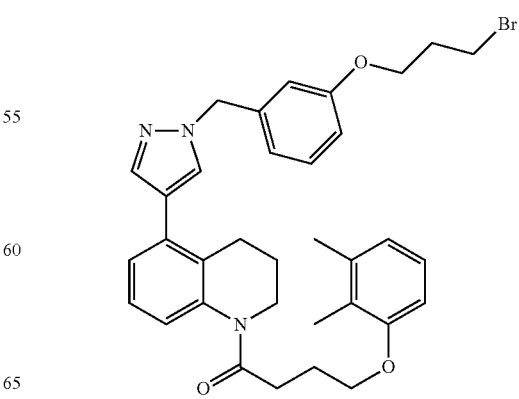

The title compound was prepared using a procedure analogous to tert-butyl (tert-butoxycarbonylamino)(2-(3-((4-(1-(4-(2,3-dimethylphenoxy)butanoyl)-1,2,3,4-tetrahydroquinolin-5-yl)-1H-pyrazol-1-yl)methyl)phenoxy)ethylamino)-methylenecarbamate except that 1,3-bis(tert-butoxycarbonyl)-guanidine was replaced with 3-bromopropan-1-ol. LCMS, [M+H]⁺=616.3.

Example 219

Example 219 was prepared using a procedure analogous to Example 215 except that 2-(3-((4-(1-(4-(2,3-Dimethylphenoxy)butanoyl)-1,2,3,4-tetrahydroquinolin-5-yl)-1H-pyrazol-1-yl)methyl)phenoxy)ethyl methanesulfonate was replaced with 1-(5-(1-(3-(3-bromopropoxy)benzyl)-1H-pyrazol-4-yl)-3,4-dihydroquinolin-1(2H)-yl)-4-(2,3-dimethylphenoxy)butan-1-one. LCMS, [M+H]⁺=618.4. ¹H NMR (400 MHz, MeOD) δ 7.89 (br. s, 1H), 7.75 (s, 1H), 7.44-7.18 (m, 4H), 7.09-6.87 (m, 4H), 6.71 (d, J=7.7 Hz, 2H), 5.48 (s, 2H), 4.18 (t, J=6.3 Hz, 2H), 3.93 (br. s, 2H), 3.81 (t, J=6.8 Hz, 2H), 3.11-2.98 (m, 2H), 2.87 (t, J=6.8 Hz, 2H), 2.56 (br. s, 2H), 2.37-2.24 (m, 2H), 2.18 (dt, J=12.5, 6.3 Hz, 2H), 2.11 (s, 3H), 1.95-1.85 (m, 2H), 1.82 (s, 3H). HPLC-2: Rt=9.1 min, purity=99.9%.

Example 220

3-((3-(1-(1-((3-Chloro-2-methylphenoxy)methyl)cyclopropanecarbonyl)-1,2,3,4-tetrahydroquinolin-5-yl)benzyloxy)carbonylamino)propanoic acid

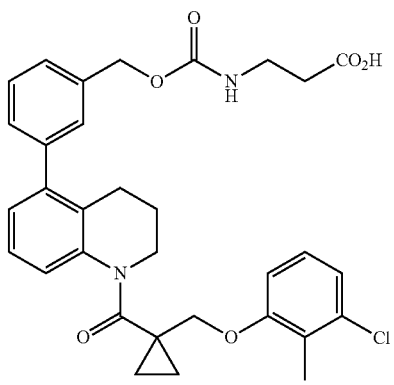 [SMILES: Cc1c(Cl)cccc1OCC1(C(=O)N2CCCc3c(-c4cccc(COC(=O)NCCC(=O)O)c4)cccc32)CC1]

Step A. Methyl 1-(5-bromo-1,2,3,4-tetrahydroquinoline-1-carbonyl)cyclopropanecarboxylate

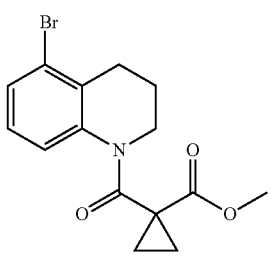 [SMILES: COC(=O)C1(C(=O)N2CCCc3c(Br)cccc32)CC1]

The title compound was prepared using a procedure analogous to 1-(5-bromo-3,4-dihydroquinolin-1(2H)-yl)-4-(2,3-dimethylphenoxy)butan-1-one except that 4-(2,3-dimethylphenoxy)butanoic acid was replaced with 1-(methoxycarbonyl)cyclopropanecarboxylic acid. LCMS, [M+H]⁺=338.0.

Step B. 1-(5-Bromo-1,2,3,4-tetrahydroquinoline-1-carbonyl)cyclopropanecarboxylic acid

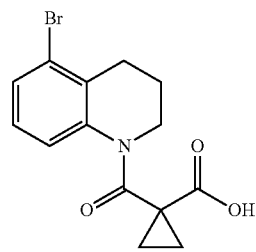 [SMILES: O=C(O)C1(C(=O)N2CCCc3c(Br)cccc32)CC1]

A mixture of methyl 1-(5-bromo-1,2,3,4-tetrahydroquinoline-1-carbonyl)cyclopropanecarboxylate (500 mg, 1.478 mmol) and LiOH (1.478 mL, 5.91 mmol) in 1,4-dioxane (5 mL) was stirred at room temperature for 2 d, and then adjusted to pH 1-3 with 3 N HCl. The resulting mixture was extracted with ethyl acetate (3×15 ml). The combined organic layer was washed with brine, dried over anhydrous Na₂SO₄, filtered, and concentrated to afford the title compound (0.37 g, 37%).

Step C. (5-Bromo-3,4-dihydroquinolin-1(2H)-yl)(1-(hydroxymethyl)cyclopropyl)methanone

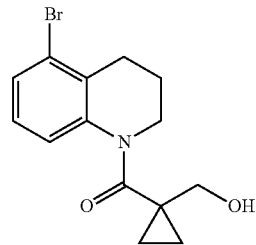 [SMILES: O=C(N1CCCc2c(Br)cccc21)C1(CO)CC1]

To a solution of 1-(5-bromo-1,2,3,4-tetrahydroquinoline-1-carbonyl)cyclopropanecarboxylic acid (0.58 g, 1.789 mmol) in CH₂Cl₂ (17 mL) at 0° C. was added N,N-dimethylformamide (2.78 μL, 0.036 mmol) and oxalyl chloride (0.187 mL, 2.147 mmol) slowly. The reaction mixture was stirred at 0° C. for 60 min, and then at room temperature for 16 h. The solvent was removed under reduced pressure and the crude acyl chloride (0.610 g, 1.78 mmol) was re-dissolved in THF (17.8 mL) and cooled to 0° C. Lithium tri-tert-butoxyaluminum hydride (7.12 mL, 7.12 mmol) was added, and the reaction mixture was stirred at 0° C. for 2 h. The reaction mixture was quenched with saturated NH₄Cl (10 mL) and then stirred at room temperature for 30 min. After this time, the mixture was extracted with EtOAc (2×40 mL). The com- Step D. (5-Bromo-3,4-dihydroquinolin-1(2H)-yl)(1-((3-chloro-2-methylphenoxy)methyl)cyclopropyl)methanone

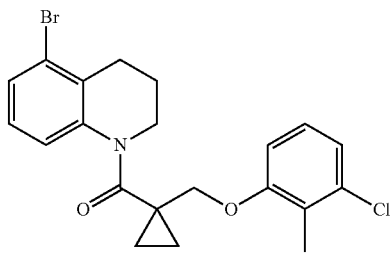 [SMILES: Cc1c(Cl)cccc1OCC1(C(=O)N2CCCc3c(Br)cccc32)CC1]

The title compound was prepared using a procedure analogous to ethyl 2-(4-(1-(4-(2,4,5-trichlorophenoxy)butanoyl)-1,2,3,4-tetrahydroquinolin-5-yl)-1H-pyrazol-1-yl)acetate except that ethyl 2-(4-(1-(4-hydroxybutanoyl)-1,2,3,4-tetrahydroquinolin-5-yl)-1H-pyrazol-1-yl)acetate was replaced with (5-bromo-3,4-dihydroquinolin-1(2H)-yl)(1-(hydroxymethyl)cyclopropyl)methanone and 2,4,5-trichlorophenol was replaced with 3-chloro-2-methylphenol. LCMS, [M+H]⁺=436.1. ¹H NMR (400 MHz, CDCl₃) δ 7.54 (d, J=8.2 Hz, 1H), 7.33 (d, J=7.9 Hz, 1H), 7.04-6.90 (m, 3H), 6.49 (d, J=7.8 Hz, 1H), 3.92-3.82 (m, 4H), 2.65 (t, J=6.9 Hz, 2H), 2.26 (s, 3H), 1.96-1.87 (m, 2H), 1.21 (dd, J=6.9, 4.9 Hz, 2H), 0.94 (q, J=5.0 Hz, 2H).

Example 220

Example 220 was prepared using a procedure analogous to Example 198 except that 1-(5-bromo-3,4-dihydroquinolin-1(2H)-yl)-4-hydroxybutan-1-one was replaced with (5-bromo-3,4-dihydroquinolin-1(2H)-yl)(1-((3-chloro-2-methylphenoxy)methyl)cyclopropyl)methanone. LCMS, [M+H]⁺=577.4. ¹H NMR (500 MHz, CD₂Cl₂) δ 7.47 (d, J=7.9 Hz, 1H), 7.38-7.28 (m, 2H), 7.25 (t, J=7.8 Hz, 1H), 7.10 (d, J=7.4 Hz, 1H), 7.03-6.91 (m, 4H), 6.37 (dd, J=6.1, 2.8 Hz, 1H), 5.07 (s, 2H), 3.80 (t, J=6.8 Hz, 2H), 3.61 (s, 2H), 3.44 (dd, J=11.7, 5.8 Hz, 2H), 2.63-2.49 (m, 2H), 2.37-2.25 (m, 5H), 1.82-1.72 (m, 2H), 1.44-1.34 (m, 2H), 0.91 (q, J=4.7 Hz, 2H). HPLC-1: Rt=10.2 min, purity=100%; HPLC-2: Rt=9.1 min, purity=99.8%.

Example 221

2-(3-((4-(3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)acetic acid

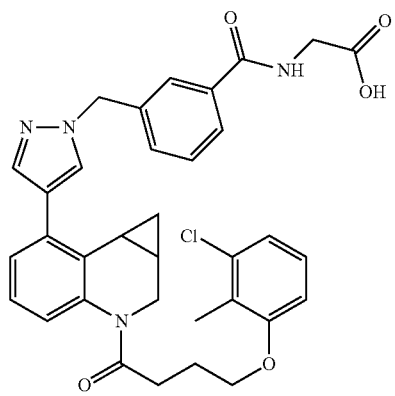 [SMILES: Cc1c(Cl)cccc1OCCCC(=O)N1CC2CC2c2c(-c3cnn(Cc4cccc(C(=O)NCC(=O)O)c4)c3)cccc21]

To a suspension of Example 24 (25 mg, 0.045 mmol), methyl 2-aminoacetate (24.84 mg, 0.198 mmol), and Hunig's base (158 μL, 0.90 mmol) in ethyl acetate (300 μL) was added a 50% w/w solution of T3P in Et₂O (160 μL, 0.27 mmol) dropwise. The reaction mixture was stirred at room temperature for 24 h and concentrated in vacuo. The resulting residue was re-dissolved in THF with one drop of MeOH and LiOH (90 μL, 0.360 mmol) was added. The reaction mixture was stirred at room temperature for 1d, and adjusted to pH 1-3. The resulting mixture was extracted with EtOAc, and the organic layer was concentrated and purified by preparative HPLC (PHENOMENEX® Axia Luna column, 5μ, C18, 30×100 mm; 15 min gradient from 100% A:0% B to 0% A:100% B and 5 min 100% B (A=90% H₂O/10% MeCN+0.1% TFA); (B=90% MeCN/10% H₂O+0.1% TFA); detection at 220 nm) to afford Example 221 (13 mg, 46% yield). LCMS, [M+H]⁺=613.5. ¹H NMR (400 MHz, CDCl₃) δ. HPLC-1: Rt=13.6 min, purity=100%; HPLC-2: Rt=13.6 min, purity=100%.

Example 222

(3-((4-(3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)methanesulfonic acid

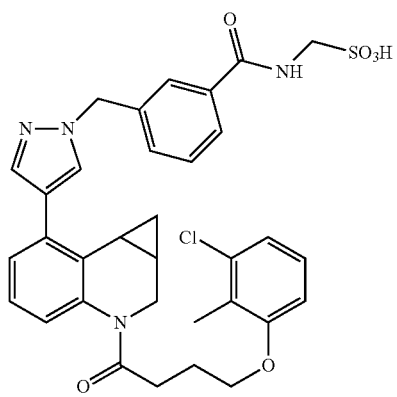 [SMILES: Cc1c(Cl)cccc1OCCCC(=O)N1CC2CC2c2c(-c3cnn(Cc4cccc(C(=O)NCS(=O)(=O)O)c4)c3)cccc21]

To a mixture of Example 24 (20 mg, 0.036 mmol), aminomethanesulfonic acid (7.99 mg, 0.072 mmol), and Hunig's base (31.4 μL, 0.180 mmol) in ethyl acetate (300 μL) and DMF (300 μL) was added T3P (86 μL, 0.144 mmol, 50% w/w in Et$_2$O). The reaction mixture was stirred at room temperature for 1 d. At the conclusion of this period, the reaction mixture was concentrated and purified by preparative HPLC (PHENOMENEX® Axia Luna column, 5μ, C18, 30×75 mm; 10 min gradient from 100% A:0% B to 0% A:100% B and 3 min 100% B (A=90% H$_2$O/10% MeCN+0.1% TFA); (B=90% MeCN/10% H$_2$O+0.1% TFA); detection at 220 nm) to afford Example 222 (13 mg, 55% yield). LCMS, [M+H]$^+$=649.3. $^1$H NMR (400 MHz, MeOD) δ 8.00 (s, 1H), 7.88 (s, 1H), 7.86 (d, J=4.3 Hz, 1H), 7.81 (s, 1H), 7.49 (d, J=5.1 Hz, 2H), 7.30 (d, J=7.4 Hz, 1H), 7.19 (t, J=7.8 Hz, 1H), 7.13-7.00 (m, 2H), 6.90 (d, J=8.0 Hz, 1H), 6.77 (d, J=7.9 Hz, 1H), 5.52 (s, 2H), 4.53 (s, 2H), 4.04-3.93 (m, 2H), 3.85 (s, 2H), 2.74 (t, J=6.3 Hz, 2H), 2.11 (s, 4H), 1.88 (s, 2H), 1.75 (s, 1H), 0.83 (s, 1H), 0.37 (s, 1H). HPLC-2: Rt=12.0 min, purity=99.1%.

Example 223

3-((3-(3-(4-(2,3-Dimethylphenoxy)butanoyl)-1a,2,3,7b-tetrahydro-1H-cyclopropa[c]quinolin-7-yl)benzyloxy)carbonylamino)propanoic acid

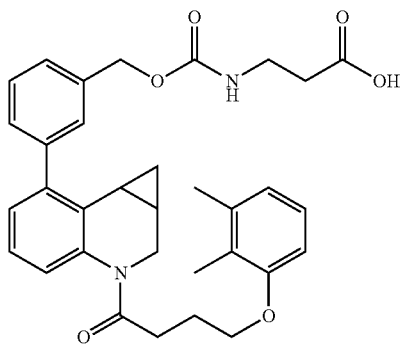

Example 223 was prepared using a procedure analogous to Example 16 except that 2-(2,3-dimethylphenoxy)ethyl 5-bromo-3,4-dihydroquinoline-1(2H)-carboxylate was replaced with Example 24. LCMS, [M−H]$^+$=555.5. $^1$H NMR (400 MHz, CDCl$_3$) δ. HPLC-1: Rt=10.8 min, purity=98.8%; HPLC-2: Rt=9.6 min, purity=98.9%.

Example 224

2-((3-(3-(4-(2,3-Dimethylphenoxy)butanoyl)-1a,2,3,7b-tetrahydro-1H-cyclopropa[c]quinolin-7-yl)benzyloxy)carbonylamino)ethanesulfonic acid

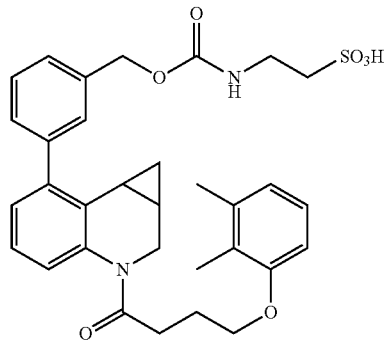 [SMILES: Cc1cccc(OCCCC(=O)N2CC3CC3c3c(-c4cccc(COC(=O)NCCS(=O)(=O)O)c4)cccc32)c1C]

Example 224 was prepared using a procedure analogous to Example 36 except that 1-(5-bromo-3,4-dihydroquinolin-1(2H)-yl)-4-(2,3-dimethylphenoxy)butan-1-one was replaced with 1-(7-bromo-1a,2-dihydro-1H-cyclopropa[c]quinolin-3(7bH)-yl)-4-(2,3-dimethylphenoxy)butan-1-one, and 3-(cyclopropylamino)propane-1-sulfonic acid was replaced with 2-aminoethanesulfonic acid. LCMS, [M+H]$^+$=593.3. $^1$H NMR (400 MHz, MeOD) δ 7.41-7.29 (m, 3H), 7.25 (d, J=7.0 Hz, 1H), 7.21-7.13 (m, 2H), 7.09 (d, J=6.7 Hz, 1H), 6.94 (t, J=7.9 Hz, 1H), 6.68 (d, J=7.5 Hz, 1H), 6.62 (d, J=8.1 Hz, 1H), 5.08 (s, 2H), 3.96-3.87 (m, 1H), 3.85-3.72 (m, 1H), 3.52 (dd, J=14.0, 7.3 Hz, 2H), 2.94 (t, J=7.0 Hz, 2H), 2.85-2.61 (m, 4H), 2.24-1.99 (m, 5H), 1.85-1.71 (m, 4H), 1.70-1.60 (m, 1H), 0.47-0.36 (m, 1H), 0.42 (d, J=4.1 Hz, 1H). HPLC-2: Rt=9.7 min, purity=100%.

Example 225

2-(4-((3-(3-(4-(2,3-Dimethylphenoxy)butanoyl)-1a,2,3,7b-tetrahydro-1H-cyclopropa[c]quinolin-7-yl)benzyloxy)carbonyl)piperazin-1-yl)ethanesulfonic acid

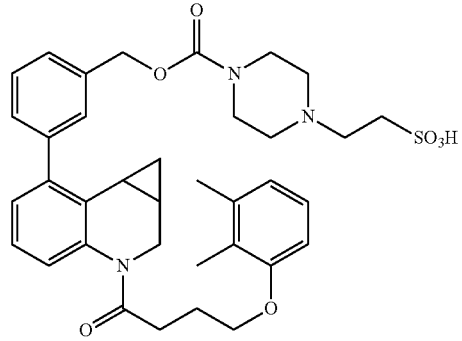 [SMILES: Cc1cccc(OCCCC(=O)N2CC3CC3c3c(-c4cccc(COC(=O)N5CCN(CCS(=O)(=O)O)CC5)c4)cccc32)c1C]

Example 225 was prepared using a procedure analogous to Example 224 except that 2-aminoethanesulfonic acid was replaced with 2-(piperazin-1-yl)ethanesulfonic acid. LCMS, [M+H]$^+$=662.2. $^1$H NMR (400 MHz, MeOD) δ 7.58-7.46 (m, 3H), 7.41 (d, J=6.7 Hz, 1H), 7.37-7.18 (m, 3H), 7.06 (t, J=7.8 Hz, 1H), 6.80 (d, J=7.6 Hz, 1H), 6.75 (d, J=7.1 Hz, 1H), 5.29 (s, 2H), 5.15-5.01 (m, 1H), 4.87 (br. S, 1H), 4.38 (br. S, −2H), 4.06 (br. S, 1H), 3.99-3.86 (m, 1H), 3.72 (br. S, 2H), 3.62 (t, J=6.9 Hz, 2H), 3.29 (t, J=6.9 Hz, 2H), 3.21 (br. S, 2H), 2.95-2.74 (m, 4H), 2.34-2.14 (m, 6H), 1.89 (s, 3H), 1.79 (s, 1H), 0.93-0.76 (m, 1H), 0.58 (s, 1H). HPLC-1: Rt=11.0 min, purity=98.3%; HPLC-2: Rt=11.1 min, purity=98.5%.

Example 226

2-((3-((1aS,7bR)-3-(4-(2,3-Dimethylphenoxy)butanoyl)-1a,2,3,7b-tetrahydro-1H-cyclopropa[c]quinolin-7-yl)benzyloxy)carbonylamino)ethanesulfonic acid

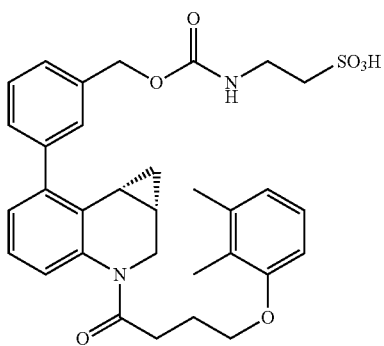 [SMILES: Cc1cccc(OCCCC(=O)N2C[C@H]3C[C@H]3c3c(-c4cccc(COC(=O)NCCS(=O)(=O)O)c4)cccc32)c1C]

Example 224 was purified by chiral HPLC (CHIRALPAK® AD-H, 250×21 cm ID, 5 μm; mobile phase: 78%/22% CO$_2$/acetonitrile-methanol-0.1 v/v % DEA; detection at 220 nm) to afford Example 226 as the faster moving isomer on preparative HPLC. LCMS, [M+H]$^+$=593.5. HPLC (CHIRALPAK® AD-H, 250×4.6 mm ID, 5 μm; mobile phase: 80%/20% CO$_2$/acetonitrile-methanol-0.1 v/v % DEA; flow rate: 3 mL/min; 100 bar BP; 35° C.; wavelength: 235 nm): Rt=20.6 min, purity=99.0%.

Example 227

2-((3-((1aR,7bS)-3-(4-(2,3-Dimethylphenoxy)butanoyl)-1a,2,3,7b-tetrahydro-1H-cyclopropa[c]quinolin-7-yl)benzyloxy)carbonylamino)ethanesulfonic acid

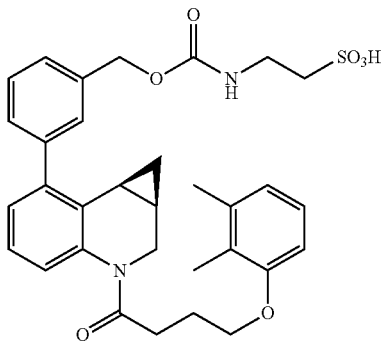 [SMILES: Cc1cccc(OCCCC(=O)N2C[C@@H]3C[C@@H]3c3c(-c4cccc(COC(=O)NCCS(=O)(=O)O)c4)cccc32)c1C]

Example 224 was purified by chiral HPLC (CHIRALPAK® AD-H, 250×21 cm ID, 5 μm; mobile phase: 78%/22% CO$_2$/acetonitrile-methanol-0.1 v/v % DEA; detection at 220 nm) to afford Example 227 as the slower-moving isomer on preparative HPLC. LCMS, [M+H]$^+$=593.5. HPLC (CHIRALPAK® AD-H, 250×4.6 mm ID, 5 μm; mobile phase: 80%/20% CO$_2$/acetonitrile-methanol-0.1 v/v % DEA; flow rate: 3 mL/min; 100 bar BP; 35° C.; wavelength: 235 nm): Rt=22.1 min, purity=91.2%.

Example 228

3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzoic acid

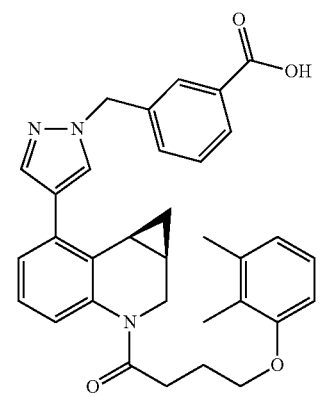 [SMILES: Cc1cccc(OCCCC(=O)N2C[C@@H]3C[C@@H]3c3c(-c4cnn(Cc5cccc(C(=O)O)c5)c4)cccc32)c1C]

Example 9 was purified by chiral HPLC (CHIRALPAK® AD-H, 250×21 cm ID, 5 μm; mobile phase: 70%/30% CO$_2$/methanol; detection at 220 nm) to afford Example 228 as the slower-moving isomer on preparative HPLC. LCMS, [M+H]$^+$=536.5. HPLC (CHIRALPAK® AD-H, 250×4.6 mm ID, 5 μm; mobile phase: 70%/30% CO$_2$/methanol; flow rate: 3 mL/min; 100 bar BP; 35° C.; wavelength: 235 nm): Rt=10.9 min, purity=96.3%.

Example 229

3-((4-((1aS,7bR)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzoic acid

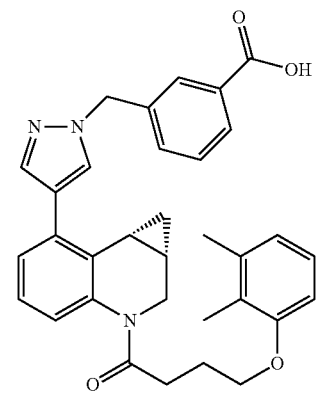

Step A. (1aS,7bR)-7-Bromo-1a,2,3,7b-tetrahydro-1H-cyclopropa[c]quinoline

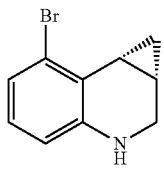 [SMILES: Brc1cccc2c1[C@@H]1C[C@@H]1CN2]

Bromo-1a,2,3,7b-tetrahydro-1H-cyclopropa[c]quinoline was purified by chiral HPLC (CHIRALCEL® OJ-H, 250×30 cm ID, 5 μm; mobile phase: 85%/15% CO$_2$/methanol; detection at 220 nm) to afford the title compound as the faster-moving isomer on preparative HPLC. LCMS, [M+H]$^+$=223.9. HPLC (CHIRALCEL® OJ-H, 250×4.6 mm ID, 5 μm; mobile phase: 85%/15% CO$_2$/methanol; flow rate: 3 mL/min; 100 bar BP; 35° C.; wavelength: 220 nm): Rt=6.5 min, purity=99.8%.

Example 229

Example 229 was prepared using a procedure analogous to Example 9 except that bromo-1a,2,3,7b-tetrahydro-1H-cyclopropa[c]quinoline was replaced with (1aS,7bR)-7-bromo-1a,2,3,7b-tetrahydro-1H-cyclopropa[c]quinoline. LCMS, [M+H]$^+$=536.5. HPLC (CHIRALPAK® AD-H, 250×4.6 mm ID, 5 μm; mobile phase: 70%/30% CO$_2$/methanol; flow rate: 3 mL/min; 100 bar BP; 35° C.; wavelength: 235 nm): Rt=8.1 min, purity=99.5%.

Example 230

3-((4-((1aS,7bR)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzoic acid

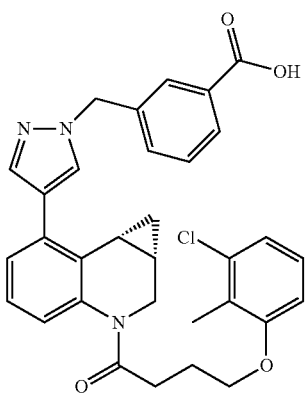

Example 24 was purified by chiral HPLC (CHIRALPAK® AD-H, 250×30 cm ID, 5 μm; mobile phase: 80%/20% CO$_2$/isopropanol; detection at 220 nm) to afford Example 230 as the faster moving isomer on preparative HPLC. LCMS, [M+H]$^+$=556.4. HPLC (CHIRALPAK® AD-H, 250×4.6 mm ID, 5 μm; mobile phase: 80%/20% CO$_2$/isopropanol; flow rate: 3 mL/min; 100 bar BP; 35° C.; wavelength: 220 nm): Rt=11.7 min, purity=99.5%.

Example 231

3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzoic acid

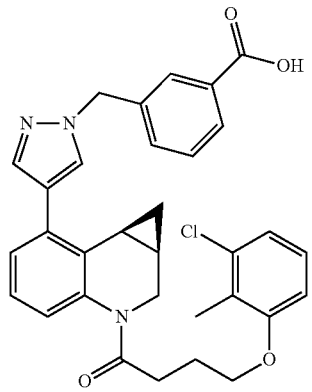 [SMILES: Cc1c(Cl)cccc1OCCCC(=O)N1C[C@@H]2C[C@@H]2c2c(-c3cnn(Cc4cccc(C(=O)O)c4)c3)cccc21]

Example 24 was purified by chiral HPLC (CHIRALPAK® AD-H, 250×30 cm ID, 5 μm; mobile phase: 80%/20% CO$_2$/isopropanol; detection at 220 nm) to afford Example 231 as the slower-moving isomer on preparative HPLC. LCMS, [M+H]$^+$=556.4. HPLC (CHIRALPAK® AD-H, 250×4.6 mm ID, 5 μm; mobile phase: 80%/20% CO$_2$/isopropanol; flow rate: 3 mL/min; 100 bar BP; 35° C.; wavelength: 220 nm): Rt=17.1 min, purity=95.8%.

Example 232

3-((4-((1aS,7bR)-3-((2-(2,3-Dimethylphenoxy)ethoxy)carbonyl)-1a,2,3,7b-tetrahydro-1H-cyclopropa[c]quinolin-7-yl)-1H-pyrazol-1-yl)methyl)benzoic acid

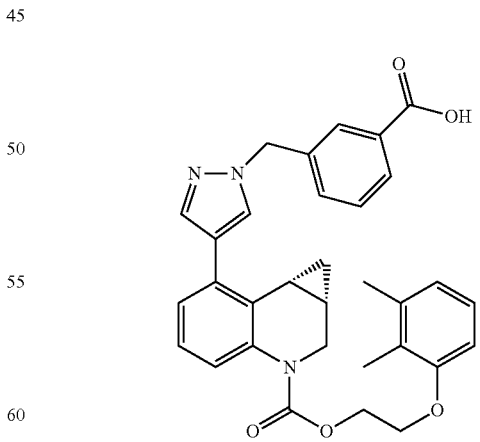

Example 26 was purified by chiral HPLC (CHIRALPAK® AD-H, 250×30 cm ID, 5 μm; mobile phase: 75%/25% CO$_2$/methanol:isopropanol (2:1); detection at 220 nm) to afford Example 232 as the faster moving isomer on preparative HPLC. LCMS, [M+H]$^+$=558.2. HPLC (CHIRALPAK®

AD-H, 250×4.6 mm ID, 5 μm; mobile phase: 75%/25% CO₂/methanol:isopropanol (2:1); flow rate: 3 mL/min; 100 bar BP; 35° C.; wavelength: 220 nm): Rt=6.5 min, purity=98.0%.

Example 233

3-((4-((1aR,7bS)-3-((2-(2,3-Dimethylphenoxy)ethoxy)carbonyl)-1a,2,3,7b-tetrahydro-1H-cyclopropa[c]quinolin-7-yl)-1H-pyrazol-1-yl)methyl)benzoic acid

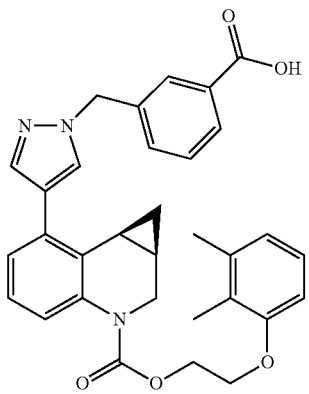 [SMILES: Cc1cccc(OCCOC(=O)N2C[C@@H]3C[C@@H]3c3c(-c4cnn(Cc5cccc(C(=O)O)c5)c4)cccc32)c1C]

Example 26 was purified by chiral HPLC (CHIRALPAK® AD-H, 250×30 cm ID, 5 μm; mobile phase: 75%/25% CO₂/methanol:isopropanol (2:1); detection at 220 nm) to afford Example 233 as the slower-moving isomer on preparative HPLC. LCMS, [M+H]⁺=558.2. HPLC (CHIRALPAK® AD-H, 250×4.6 mm ID, 5 μm; mobile phase: 75%/25% CO₂/methanol:isopropanol (2:1); flow rate: 3 mL/min; 100 bar BP; 35° C.; wavelength: 220 nm): Rt=8.4 min, purity=98.0%.

Example 234

3-((3-((1aR,7bS)-3-((2-(3-Chloro-2-methylphenoxy)ethoxy)carbonyl)-1a,2,3,7b-tetrahydro-1H-cyclopropa[c]quinolin-7-yl)benzyloxy)carbonylamino)propanoic acid

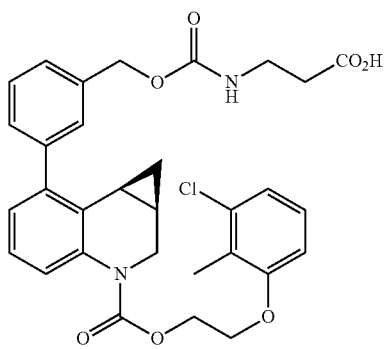 [SMILES: Cc1c(Cl)cccc1OCCOC(=O)N1C[C@@H]2C[C@@H]2c2c(-c3cccc(COC(=O)NCCC(=O)O)c3)cccc21]

Example 21 was purified by chiral HPLC (CHIRALPAK® AD-H, 250×30 cm ID, 5 μm; mobile phase: 75%/25% CO₂/isopropanol; detection at 220 nm) to afford Example 234 as the faster moving isomer on preparative HPLC. LCMS, [M+H]⁺=579.3. HPLC (CHIRALPAK® AD-H, 250×4.6 mm ID, 5 μm; mobile phase: 75%/25% CO₂/isopropanol; flow rate: 3 mL/min; 100 bar BP; 35° C.; wavelength: 220 nm): Rt=8.4 min, purity=95.6%.

Example 235

3-((3-((1aS,7bR)-3-((2-(3-Chloro-2-methylphenoxy)ethoxy)carbonyl)-1a,2,3,7b-tetrahydro-1H-cyclopropa[c]quinolin-7-yl)benzyloxy)carbonylamino)propanoic acid

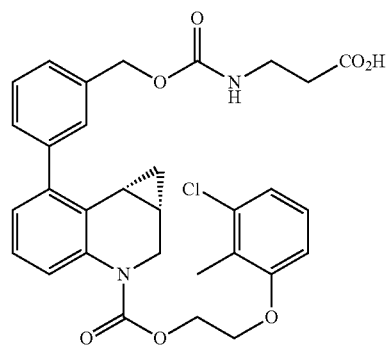 [SMILES: Cc1c(Cl)cccc1OCCOC(=O)N1C[C@H]2C[C@H]2c2c(-c3cccc(COC(=O)NCCC(=O)O)c3)cccc21]

Example 21 was purified by chiral HPLC (CHIRALPAK® AD-H, 250×30 cm ID, 5 μm; mobile phase: 75%/25% CO₂/isopropanol; detection at 220 nm) to afford Example 235 as the slower-moving isomer on preparative HPLC. LCMS, [M+H]⁺=579.3. HPLC (CHIRALPAK® AD-H, 250×4.6 mm ID, 5 μm; mobile phase: 75%/25% CO₂/isopropanol; flow rate: 3 mL/min; 100 bar BP; 35° C.; wavelength: 220 nm): Rt=9.9 min, purity=95.8%.

Example 236

3-((3-((1aS,7bR)-3-(4-(2,3-Dimethylphenoxy)butanoyl)-1a,2,3,7b-tetrahydro-1H-cyclopropa[c]quinolin-7-yl)benzyloxy)carbonylamino)propanoic acid

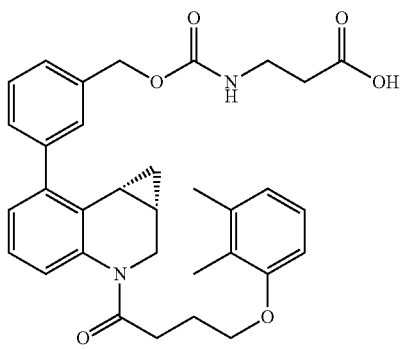 [SMILES: Cc1cccc(OCCCC(=O)N2C[C@H]3C[C@H]3c3c(-c4cccc(COC(=O)NCCC(=O)O)c4)cccc32)c1C]

Example 223 was purified by chiral HPLC (CHIRALPAK® AD-H, 250×30 cm ID, 5 μm); mobile phase: 80%/20% CO₂/methanol; detection at 220 nm) to afford Example 236 as the faster-moving isomer on preparative HPLC. LCMS, [M+H]⁺=557.5. HPLC (CHIRALPAK® AD-H, 250×4.6 mm ID, 5 μm; mobile phase: 80%/20% CO$_2$/methanol; flow rate: 3 mL/min; 100 bar BP; 35° C.; wavelength: 220 nm): Rt=8.4 min, purity=99.5%.

Example 237

3-((3-(((1aR,7bS)-3-(4-(2,3-Dimethylphenoxy)butanoyl)-1a,2,3,7b-tetrahydro-1H-cyclopropa[c]quinolin-7-yl)benzyloxy)carbonylamino)propanoic acid

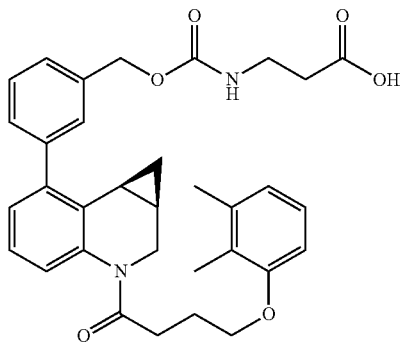 [SMILES: Cc1cccc(OCCCC(=O)N2C[C@@H]3C[C@@H]3c3c(-c4cccc(COC(=O)NCCC(=O)O)c4)cccc32)c1C]

Example 223 was purified by chiral HPLC (CHIRALPAK® AD-H, 250×30 cm ID, 5 μm; mobile phase: 80%/20% CO$_2$/methanol; detection at 220 nm) to afford Example 237 as the slower-moving isomer on preparative HPLC. LCMS, [M+H]$^+$=557.5. HPLC (CHIRALPAK® AD-H, 250×4.6 mm ID, 5 μm; mobile phase: 80%/20% CO$_2$/methanol; flow rate: 3 mL/min; 100 bar BP; 35° C.; wavelength: 220 nm): Rt=10.5 min, purity=95.8%.

Example 238

(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)methanesulfonic acid

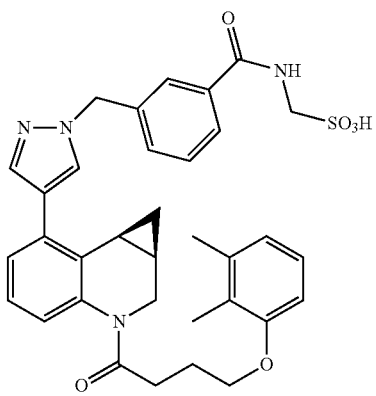 [SMILES: Cc1cccc(OCCCC(=O)N2C[C@@H]3C[C@@H]3c3c(-c4cnn(Cc5cccc(C(=O)NCS(=O)(=O)O)c5)c4)cccc32)c1C]

Example 150 was purified by chiral HPLC (KROMASIL® Cellucoat-5, 250×21 cm ID, 5 μm; mobile phase: 45% methanol-0.1% DEA/55% CO$_2$; detection at 220 nm) to afford Example 238 as the faster-moving isomer on preparative HPLC. LCMS, [M+H]$^+$=629.2. HPLC (KROMASIL® Cellucoat-5, 250×4.6 mm ID, 5 μm; mobile phase: 45% methanol-0.1% DEA/55% CO$_2$; flow rate: 2 mL/min; 100 bar BP; 35° C.; wavelength: 220 nm): Rt=2.5 min, purity=99.5%.

Example 239

(3-((4-((1aS,7bR)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)methanesulfonic acid

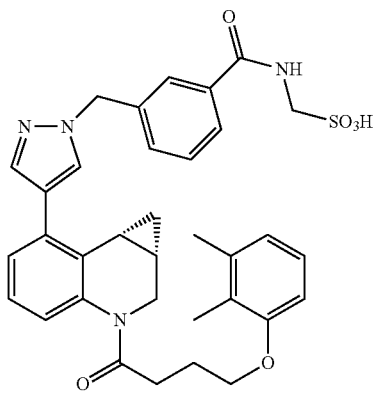 [SMILES: Cc1cccc(OCCCC(=O)N2C[C@H]3C[C@H]3c3c(-c4cnn(Cc5cccc(C(=O)NCS(=O)(=O)O)c5)c4)cccc32)c1C]

Example 150 was purified by chiral HPLC (KROMASIL® Cellucoat-5, 250×21 cm ID, 5 μm; mobile phase: 45% methanol-0.1% DEA/55% CO$_2$; detection at 220 nm) to afford Example 239 as the slower-moving isomer on preparative HPLC. LCMS, [M+H]$^+$=629.2. HPLC (KROMASIL® Cellucoat-5, 250×4.6 mm ID, 5 μm; mobile phase: 45% methanol-0.1% DEA/55% CO$_2$; flow rate: 2 mL/min; 100 bar BP; 35° C.; wavelength: 220 nm): Rt=3.0 min, purity=98.9%.

Example 240

2-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)ethanesulfonic acid

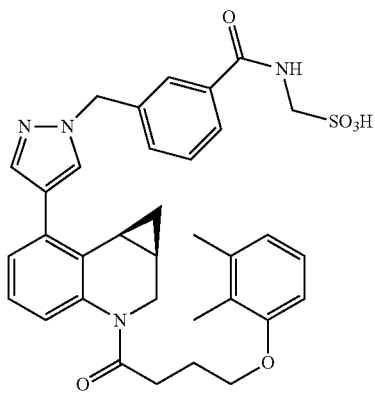 [SMILES: Cc1cccc(OCCCC(=O)N2C[C@@H]3C[C@@H]3c3c(-c4cnn(Cc5cccc(C(=O)NCS(=O)(=O)O)c5)c4)cccc32)c1C]

Example 151 was purified by chiral HPLC (KROMASIL® Cellucoat-5, 250×21 cm ID, 5 μm; mobile phase: 45% methanol-0.1% DEA/55% CO$_2$; detection at 220 nm) to afford Example 240 as the faster-moving isomer on preparative HPLC. LCMS, [M+H]$^+$=643.2. HPLC (KROMASIL® Cel-

Example 241

2-(3-((4-((1aS,7bR)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)ethanesulfonic acid

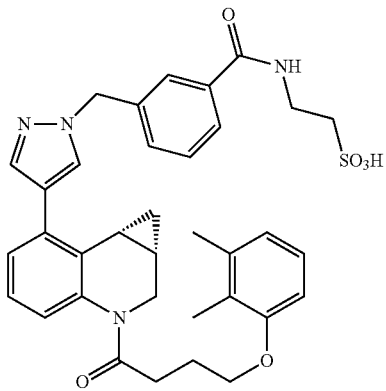 [SMILES: Cc1cccc(OCCCC(=O)N2C[C@H]3C[C@H]3c3c(-c4cnn(Cc5cccc(C(=O)NCCS(=O)(=O)O)c5)c4)cccc32)c1C]

Example 151 was purified by chiral HPLC (KROMASIL® Cellucoat-5, 250×21 cm ID, 5 μm; mobile phase: 45% methanol-0.1% DEA/55% $CO_2$; detection at 220 nm) to afford Example 241 as the slower-moving isomer on preparative HPLC. LCMS, $[M+H]^+$=643.2. HPLC (KROMASIL® Cellucoat-5, 250×4.6 mm ID, 3 nm; mobile phase: 45% methanol-0.1% DEA/55% $CO_2$; flow rate: 2 mL/min; 100 bar BP; 35° C.; wavelength: 220 nm): Rt=2.5 min, purity=98.9%.

Example 242

(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)methanesulfonic acid

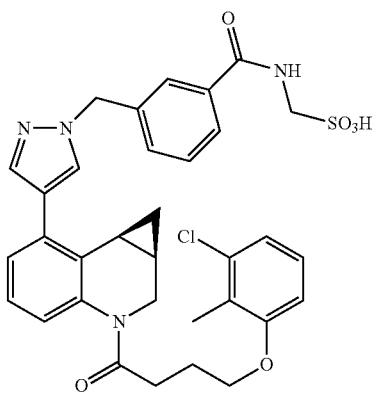 [SMILES: Cc1c(Cl)cccc1OCCCC(=O)N1C[C@@H]2C[C@@H]2c2c(-c3cnn(Cc4cccc(C(=O)NCS(=O)(=O)O)c4)c3)cccc21]

Example 222 was purified by chiral HPLC (KROMASIL® Cellucoat-5, 250×21 cm ID, 5 μm; mobile phase: 45% (1:1) methanol-ethanol-0.1% DEA/55% $CO_2$; detection at 220 nm) to afford Example 242 as the faster-moving isomer on preparative HPLC. LCMS, $[M+H]^+$=649.3. HPLC (KROMASIL® Cellucoat-5, 250×4.6 mm ID, 5 μm; mobile phase: 45% (1:1) methanol-ethanol-0.1% DEA/55% $CO_2$; flow rate: 2 mL/min; 100 bar BP; 35° C.; wavelength: 220 nm): Rt=4.1 min, purity=99.0%.

Example 243

(3-((4-((1aS,7bR)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)methanesulfonic acid

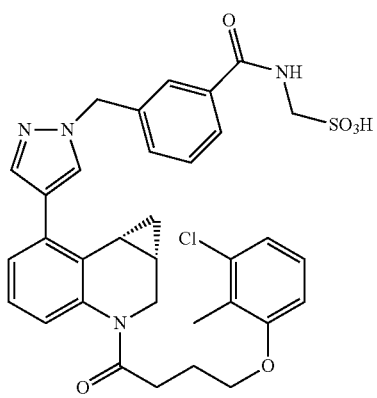

Example 222 was purified by chiral HPLC (KROMASIL® Cellucoat-5, 250×21 cm ID, 5 μm; mobile phase: 45% (1:1) methanol-ethanol-0.1% DEA/55% $CO_2$; detection at 220 nm) to afford Example 243 as the slower-moving isomer on preparative HPLC. LCMS, $[M+H]^+$=649.3. HPLC (KROMASIL® Cellucoat-5, 250×4.6 mm ID, 5 μm; mobile phase: 45% (1:1) methanol-ethanol-0.1% DEA/55% $CO_2$; flow rate: 2 mL/min; 100 bar BP; 35° C.; wavelength: 220 nm): Rt=5.7 min, purity=99.0%.

Example 244

2-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)acetic acid

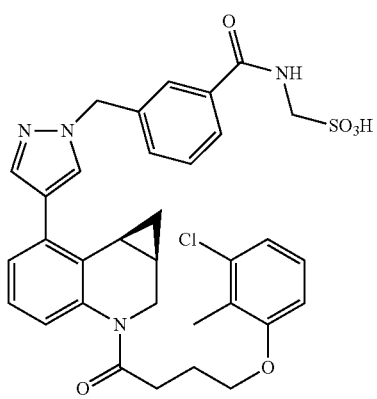 [SMILES: Cc1c(Cl)cccc1OCCCC(=O)N1C[C@@H]2C[C@@H]2c2c(-c3cnn(Cc4cccc(C(=O)NCS(=O)(=O)O)c4)c3)cccc21]

Example 221 was purified by chiral HPLC (CHIRALPAK® AD-H, 250×30 cm ID, 5 μm; mobile phase: 60%/40% CO$_2$/isopropanol; detection at 220 nm) to afford Example 244 as the faster-moving isomer on preparative HPLC. LCMS, [M+H]$^+$=613.4. HPLC (CHIRALPAK® AD-H, 250×4.6 mm ID, 5 μm; mobile phase: 65%/35% CO$_2$/isopropanol; flow rate: 3 mL/min; 100 bar BP; 35° C.; wavelength: 220 nm): Rt=9.0 min, purity=99.5%.

Example 245

2-(3-((4-(((1aS,7bR)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)acetic acid

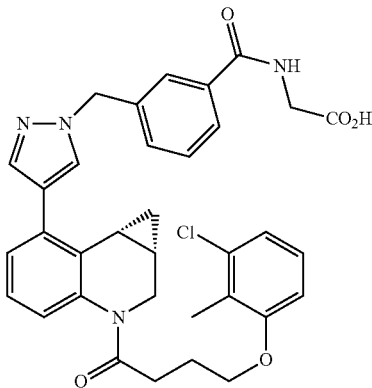 [SMILES: Cc1c(Cl)cccc1OCCCC(=O)N1C[C@H]2C[C@H]2c2c(-c3cnn(Cc4cccc(C(=O)NCC(=O)O)c4)c3)cccc21]

Example 221 was purified by chiral HPLC (CHIRALPAK® AD-H, 250×30 cm ID, 5 μm; mobile phase: 60%/40% CO$_2$/isopropanol; detection at 220 nm) to afford Example 245 as the slower-moving isomer on preparative HPLC. LCMS, [M+H]$^+$=613.4. HPLC (CHIRALPAK® AD-H, 250×4.6 mm ID, 5 μm; mobile phase: 65%/35% CO$_2$/isopropanol; flow rate: 3 mL/min; 100 bar BP; 35° C.; wavelength: 220 nm): Rt=12.3 min, purity=99.5%.

Example 246

2-(3-(3-((4-(((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)ethanesulfonic acid

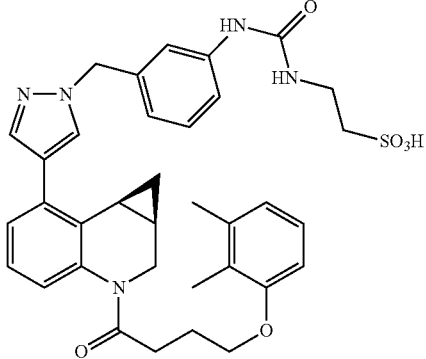 [SMILES: Cc1cccc(OCCCC(=O)N2C[C@@H]3C[C@@H]3c3c(-c4cnn(Cc5cccc(NC(=O)NCCS(=O)(=O)O)c5)c4)cccc32)c1C]

Example 117 was purified by chiral HPLC (KROMASIL® Cellucoat-5, 250×21 cm ID, 5 μm; mobile phase: 30% Methanol-0.1% DEA/70% CO$_2$; detection at 220 nm) to afford Example 246 as the faster-moving isomer on preparative HPLC. LCMS, [M+H]$^+$=658.5. HPLC (KROMASIL® Cellucoat-5, 250×4.6 mm ID, 5 μm; mobile phase: 40% Methanol-0.1% DEA/60% CO$_2$; flow rate: 2 mL/min; 100 bar BP; 35° C.; wavelength: 240 nm): Rt=2.8 min, purity=95.4%.

Example 247

2-(3-(3-((4-(((1aS,7bR)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)ethanesulfonic acid

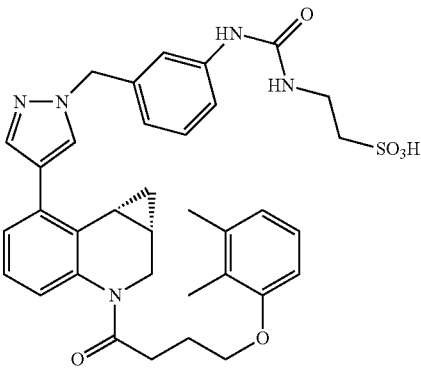 [SMILES: Cc1cccc(OCCCC(=O)N2C[C@H]3C[C@H]3c3c(-c4cnn(Cc5cccc(NC(=O)NCCS(=O)(=O)O)c5)c4)cccc32)c1C]

Example 117 was purified by chiral HPLC (KROMASIL® Cellucoat-5, 250×21 cm ID, 5 μm; mobile phase: 30% Methanol-0.1% DEA/70% CO$_2$; detection at 220 nm) to afford Example 247 as the slower-moving isomer on preparative HPLC. LCMS, [M+H]$^+$=658.5. HPLC (KROMASIL® Cellucoat-5, 250×4.6 mm ID, 5 μm; mobile phase: 40% Methanol-0.1% DEA/60% CO$_2$; flow rate: 2 mL/min; 100 bar BP; 35° C.; wavelength: 240 nm): Rt=3.1 min, purity=96.9%.

Example 248

3-(3-(3-((4-(((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)propanoic acid

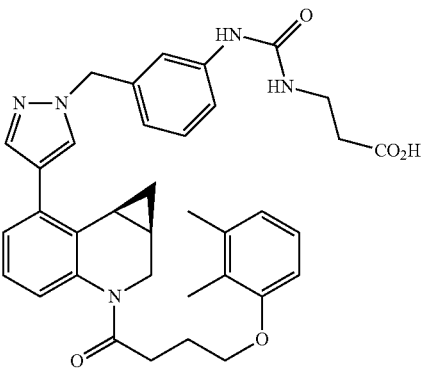

Example 120 was purified by chiral HPLC (KROMASIL® Cellucoat-5, 250×21 cm ID, 5 μm; mobile phase: 30% Methanol/70% CO$_2$; detection at 220 nm) to afford Example 248 as the faster-moving isomer on preparative HPLC. LCMS, [M+H]$^+$=622.5. HPLC (KROMASIL® Cellucoat-5, 250×4.6 mm ID, 5 μm; mobile phase: 30% Methanol/70% CO$_2$; flow rate: 3 mL/min; 100 bar BP; wavelength: 220 nm): Rt=12.5 min, purity=99.5%.

Example 249

3-(3-(3-((4-((1aS,7bR)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)propanoic acid

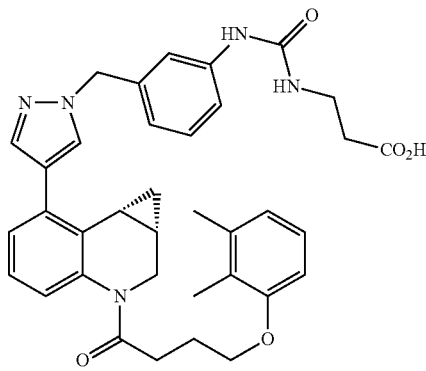 [SMILES: Cc1cccc(OCCCC(=O)N2C[C@H]3C[C@H]3c3c(-c4cnn(Cc5cccc(NC(=O)NCCC(=O)O)c5)c4)cccc32)c1C]

Example 120 was purified by chiral HPLC (KROMASIL® Cellucoat-5, 250×21 cm ID, 5 μm; mobile phase: 30% Methanol/70% CO$_2$; detection at 220 nm) to afford Example 249 as the slower-moving isomer on preparative HPLC. LCMS, [M+H]$^+$=622.5. HPLC (KROMASIL® Cellucoat-5, 250×4.6 mm ID, 5 μm; mobile phase: 30% Methanol/70% CO$_2$; flow rate: 3 mL/min; 100 bar BP; wavelength: 220 nm): Rt=14.4 min, purity=99.5% for Example 249.

Example 250

2-(3-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)acetic acid

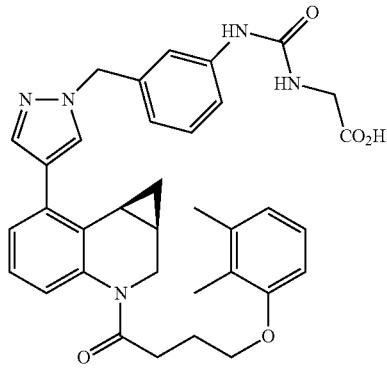 [SMILES: Cc1cccc(OCCCC(=O)N2C[C@@H]3C[C@@H]3c3c(-c4cnn(Cc5cccc(NC(=O)NCC(=O)O)c5)c4)cccc32)c1C]

Example 119 was purified by chiral HPLC (KROMASIL® Cellucoat-5, 250×21 cm ID, 5 μm; mobile phase: 30% Methanol/70% CO$_2$; detection at 220 nm) to afford Example 250 as the faster-moving isomer on preparative HPLC. LCMS, [M+H]$^+$=608.4. HPLC (KROMASIL® Cellucoat-5, 250×4.6 mm ID, 5 μm; mobile phase: 30% Methanol/70% CO$_2$; flow rate: 3 mL/min; 100 bar BP; wavelength: 220 nm): Rt=11.9 min, purity=96.3%.

Example 251

2-(3-(3-((4-((1aS,7bR)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)acetic acid

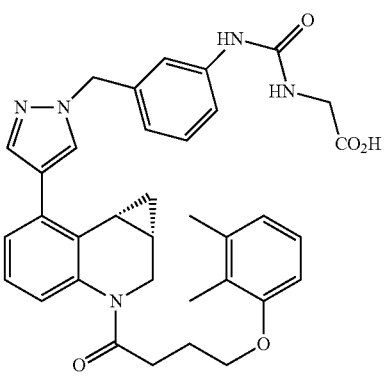

Example 119 was purified by chiral HPLC (KROMASIL® Cellucoat-5, 250×21 cm ID, 5 μm; mobile phase: 30% Methanol/70% CO$_2$; detection at 220 nm) to afford Example 251 as the slower-moving isomer on preparative HPLC. LCMS, [M+H]$^+$=608.4. HPLC (KROMASIL® Cellucoat-5, 250×4.6 mm ID, 5 μm; mobile phase: 30% Methanol/70% CO$_2$; flow rate: 3 mL/min; 100 bar BP; wavelength: 220 nm): Rt=13.8 min, purity=97.4%.

Compounds described in Table 14 were prepared using parallel assay synthesis following the general protocol set forth below.

Benzyl alcohol was treated with phosgene or similar reagents, such as diphosgene or triphosgene, in the presence of a base, such as DIEA, at 0° C. for 30 min. The solvent was then removed via vacuum and the resulting intermediate carbonochloridate was dissolved in an organic solvent, such as DCM or EtOAc, and then treated with amine in the presence of base, such as Hunig's base or aqueous Na$_2$CO$_3$, to provide the desired carbamate. If required, hydrolysis under a basic condition, such as aqueous LiOH, was used to convert the carbamate to the final product. Alternatively, the benzyl alcohol was treated with 4-nitrophenyl carbonochloridate in the presence of base, such as pyridine, at 0° C. The reaction mixture was slowly warmed to room temperature where it was stirred overnight. After this time, the reaction was quenched with water. The organic layer washed with water and brine, dried over MgSO$_4$ and concentrated in vacuum to provide the crude material. The crude material was purified by silica gel flash chromatography to afford the corresponding benzyl 4-nitrophenyl carbonate. The resulting benzyl 4-nitrophenyl carbonate was then treated with amine in the presence of a base, such as Hunig's base or aqueous Na$_2$CO$_3$, to get the desired carbamate. If required, hydrolysis under a basic condition, such as aqueous LiOH, was used to convert the carbamate to the final product.

TABLE 14

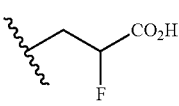

| Example | Name | —R$_{18}$—CO$_2$H or —SO$_3$H | LCMS, [M + H]$^+$ | HPLC-3: Rt (min) | Purity (%) |
|---|---|---|---|---|---|
| 252 | 3-((3-(1-(4-(2,3-Dimethylphenoxy) butanoyl)-1,2,3,4-tetrahydroquinolin-5-yl) benzyloxy)carbonylamino)-2-fluoropropanoic acid | 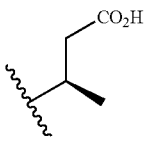 [SMILES: *[C@H](C)CC(=O)O] | 561.4 | 4.62* | 100 |
| 253 | (R)-3-((3-(1-(4-(2,3-Dimethylphenoxy)butanoyl)-1,2,3,4-tetrahydroquinolin-5-yl) benzyloxy)carbonylamino) butanoic acid | 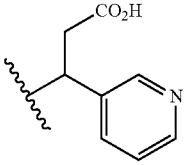 [SMILES: *C(CC(=O)O)c1cccnc1] | 557.5 | 4.77* | 100 |
| 254 | 3-((3-(1-(4-(2,3-Dimethylphenoxy) butanoyl)-1,2,3,4-tetrahydroquinolin-5-yl) benzyloxy)carbonylamino)-3-(pyridin-3-yl)propanoic acid | 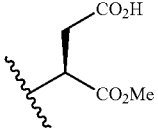 [SMILES: *[C@@H](CC(=O)O)C(=O)OC] | 620.5 | 4.54* | 100 |
| 255 | (S)-3-((3-(1-(4-(2,3-Dimethylphenoxy)butanoyl)-1,2,3,4-tetrahydroquinolin-5-yl) benzyloxy)carbonylamino)-4-methoxy-4-oxobutanoic acid | 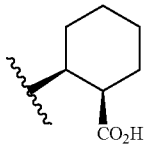 [SMILES: *[C@H]1CCCC[C@H]1C(=O)O] | 601.5 | 4.67* | 99.3 |
| 256 | (1R,2S)-2-((3-(1-(4-(2,3-Dimethylphenoxy)butanoyl)-1,2,3,4-tetrahydroquinolin-5-yl)benzyloxy)carbonylamino) cyclohexanecarboxylic acid |  | 597.5 | 5.45* | 100 |
| 257 | 3-((3-(1-(4-(2,3-Dimethylphenoxy) butanoyl)-1,2,3,4-tetrahydroquinolin-5-yl) benzyloxy)carbonylamino)-2,2-dimethylpropanoic acid | 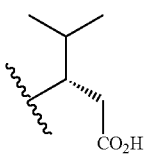 | 571.5 | 5.12* | 100 |
| 258 | (S)-3-((3-(1-(4-(2,3-Dimethylphenoxy)butanoyl)-1,2,3,4-tetrahydroquinolin-5-yl) benzyloxy)carbonylamino)-4-methylpentanoic acid | | 585.5 | 5.15* | 100 |

TABLE 14-continued

| Example | Name | —R₁₈—CO₂H or —SO₃H | LCMS, [M + H]⁺ | HPLC-3: Rt (min) | Purity (%) |
|---|---|---|---|---|---|
| 259 | 4-(((3-(1-(4-(2,3-Dimethylphenoxy)butanoyl)-1,2,3,4-tetrahydroquinolin-5-yl)benzyloxy)carbonylamino)methyl)-2,5-dimethylfuran-3-carboxylic acid | | 623.5 | 5.77* | 100 |
| 260 | 3-Cyclopropyl-3-((3-(1-(4-(2,3-dimethylphenoxy)butanoyl)-1,2,3,4-tetrahydroquinolin-5-yl)benzyloxy)carbonylamino)propanoic acid | | 583.5 | 4.99* | 100 |
| 261 | (R)-4-Amino-2-((3-(1-(4-(2,3-dimethylphenoxy)butanoyl)-1,2,3,4-tetrahydroquinolin-5-yl)benzyloxy)carbonylamino)-4-oxobutanoic acid | | 586.4 | 4.34* | 100 |
| 262 | 4-((3-(1-(4-(2,3-Dimethylphenoxy)butanoyl)-1,2,3,4-tetrahydroquinolin-5-yl)benzyloxy)carbonylamino)-2-hydroxybutanoic acid | | 573.5 | 4.56* | 100 |
| 263 | (1R,2S)-2-((3-(1-(4-(2,3-Dimethylphenoxy)butanoyl)-1,2,3,4-tetrahydroquinolin-5-yl)benzyloxy)carbonylamino)cycloheptanecarboxylic acid | | 611.6 | 5.75* | 100 |
| 264 | (S)-4-((3-(1-(4-(2,3-Dimethylphenoxy)butanoyl)-1,2,3,4-tetrahydroquinolin-5-yl)benzyloxy)carbonylamino)-3-hydroxybutanoic acid | | 573.4 | 4.54* | 100 |
| 265 | 3-((3-(1-(4-(2,3-Dimethylphenoxy)butanoyl)-1,2,3,4-tetrahydroquinolin-5-yl)benzyloxy)carbonylamino)cyclopentanecarboxylic acid | | 583.5 | 5.05* | 100 |

TABLE 14-continued

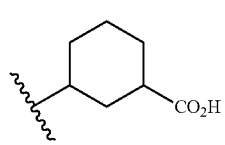 [SMILES: *C1CCCC(C(=O)O)C1]

| Example | Name | —R$_{18}$—CO$_2$H or —SO$_3$H | LCMS, [M + H]$^+$ | HPLC-3: Rt (min) | Purity (%) |
|---|---|---|---|---|---|
| 266 | 3-((3-(1-(4-(2,3-Dimethylphenoxy) butanoyl)-1,2,3,4- tetrahydroquinolin-5-yl) benzyloxy)carbonylamino) cyclohexanecarboxylic acid | 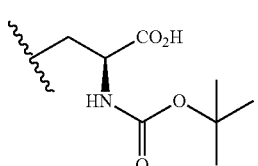 | 597.5 | 5.15* | 96.4 |
| 267 | (S)-2-(tert-Butoxycarbonylamino)- 3-((3-(1-(4-(2,3-dimethylphenoxy) butanoyl)-1,2,3,4- tetrahydroquinolin-5-yl) benzyloxy)carbonylamino) propanoic acid | 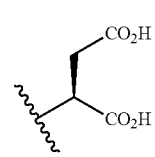 | 658.6 | 5.04* | 97.5 |
| 268 | (S)-2-((3-(1-(4-(2,3- Dimethylphenoxy)butanoyl)- 1,2,3,4-tetrahydroquinolin-5-yl) benzyloxy)carbonylamino)succinic acid | 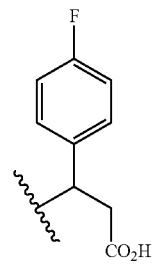 [SMILES: *C(CC(=O)O)c1ccc(F)cc1] | 587.4 | 3.98* | 100 |
| 269 | 3-((3-(1-(4-(2,3-Dimethylphenoxy) butanoyl)-1,2,3,4- tetrahydroquinolin-5-yl) benzyloxy)carbonylamino)-3-(4- fluorophenyl)propanoic acid | 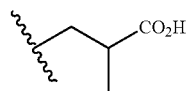 | 637.6 | 5.09* | 100 |
| 270 | 3-((3-(1-(4-(2,3-Dimethylphenoxy) butanoyl)-1,2,3,4- tetrahydroquinolin-5-yl) benzyloxy)carbonylamino)-2- methylpropanoic acid | | 557.4 | 4.80* | 100 |
| 271 | 2-(1-(((3-(1-(4-(2,3- Dimethylphenoxy)butanoyl)- 1,2,3,4-tetrahydroquinolin-5-yl) benzyloxy)carbonylamino)methyl) cyclohexyl)acetic acid | 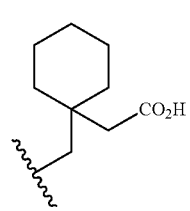 | 625.6 | 5.98* | 100 |

TABLE 14-continued

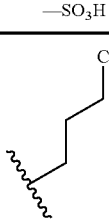

| Example | Name | —R₁₈—CO₂H or —SO₃H | LCMS, [M + H]⁺ | HPLC-3: Rt (min) | Purity (%) |
|---|---|---|---|---|---|
| 272 | 4-((3-(1-(4-(2,3-Dimethylphenoxy)butanoyl)-1,2,3,4-tetrahydroquinolin-5-yl)benzyloxy)carbonylamino)butanoic acid | 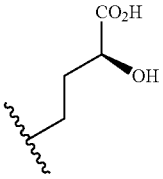 [SMILES: *CC[C@H](O)C(=O)O] | 557.4 | 4.83* | 100 |
| 273 | (S)-4-((3-(1-(4-(2,3-Dimethylphenoxy)butanoyl)-1,2,3,4-tetrahydroquinolin-5-yl)benzyloxy)carbonylamino)-2-hydroxybutanoic acid | | 573.4 | 4.57* | 100 |
| 274 | (S)-4-Amino-2-((3-(1-(4-(2,3-dimethylphenoxy)butanoyl)-1,2,3,4-tetrahydroquinolin-5-yl)benzyloxy)carbonylamino)-4-oxobutanoic acid | 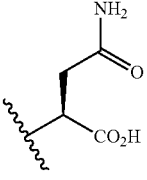 [SMILES: *[C@@H](CC(N)=O)C(=O)O] | 586.5 | 4.34* | 100 |
| 275 | 3-((3-(1-(4-(2,3-Dimethylphenoxy)butanoyl)-1,2,3,4-tetrahydroquinolin-5-yl)benzyloxy)carbonylamino)butanoic acid | 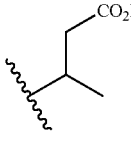 | 557.4 | 4.77* | 99.4 |
| 276 | (R)-2-(tert-Butoxycarbonylamino)-3-((3-(1-(4-(2,3-dimethylphenoxy)butanoyl)-1,2,3,4-tetrahydroquinolin-5-yl)benzyloxy)carbonylamino)propanoic acid | 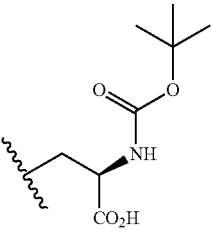 [SMILES: *C[C@@H](NC(=O)OC(C)(C)C)C(=O)O] | 658.6 | 5.00* | 100 |
| 277 | 4-((3-(1-(4-(2,3-Dimethylphenoxy)butanoyl)-1,2,3,4-tetrahydroquinolin-5-yl)benzyloxy)carbonylamino)-3-hydroxybutanoic acid | 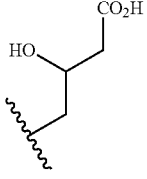 [SMILES: *CC(O)CC(=O)O] | 573.4 | 4.54* | 100 |

TABLE 14-continued

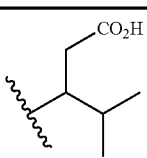

| Example | Name | —R$_{18}$—CO$_2$H or —SO$_3$H | LCMS, [M + H]$^+$ | HPLC-3: Rt (min) | Purity (%) |
|---|---|---|---|---|---|
| 278 | 3-((3-(1-(4-(2,3-Dimethylphenoxy) butanoyl)-1,2,3,4-tetrahydroquinolin-5-yl) benzyloxy)carbonylamino)-4-methylpentanoic acid | 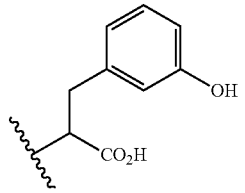 [SMILES: *C(Cc1cccc(O)c1)C(=O)O] | 585.6 | 5.14* | 100 |
| 279 | 2-((3-(1-(4-(2,3-Dimethylphenoxy) butanoyl)-1,2,3,4-tetrahydroquinolin-5-yl) benzyloxy)carbonylamino)-3-(3-hydroxyphenyl)propanoic acid | 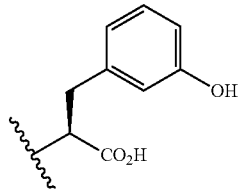 [SMILES: *[C@@H](Cc1cccc(O)c1)C(=O)O] | 637.2 | 4.36 | 100 |
| 280 | (S)-2-((3-(1-(4-(2,3-Dimethylphenoxy)butanoyl)-1,2,3,4-tetrahydroquinolin-5-yl) benzyloxy)carbonylamino)-3-(3-hydroxyphenyl)propanoic acid | 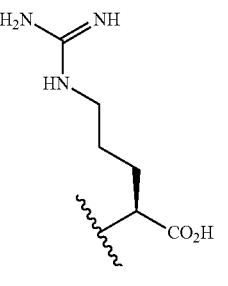 [SMILES: *[C@@H](CCCNC(=N)N)C(=O)O] | 637.2 | 4.28 | 100 |
| 281 | (S)-2-((3-(1-(4-(2,3-Dimethylphenoxy)butanoyl)-1,2,3,4-tetrahydroquinolin-5-yl) benzyloxy)carbonylamino)-5-guanidinopentanoic acid | 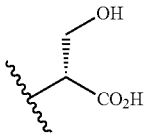 | 630.2 | 4.24 | 100 |
| 282 | (R)-2-((3-(1-(4-(2,3-Dimethylphenoxy)butanoyl)-1,2,3,4-tetrahydroquinolin-5-yl) benzyloxy)carbonylamino)-3-hydroxypropanoic acid | 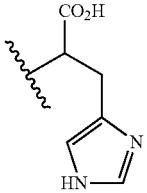 [SMILES: *C(Cc1c[nH]cn1)C(=O)O] | 561.2 | 4.01 | 100 |
| 283 | 2-((3-(1-(4-(2,3-Dimethylphenoxy) butanoyl)-1,2,3,4-tetrahydroquinolin-5-yl) benzyloxy)carbonylamino)-3-(1H-imidazol-4-yl)propanoic acid | | 611.2 | 4.1 | 97.3 |

TABLE 14-continued

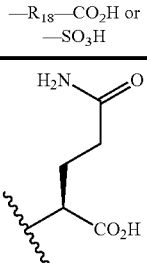

| Example | Name | —R₁₈—CO₂H or —SO₃H | LCMS, [M + H]⁺ | HPLC-3: Rt (min) | Purity (%) |
|---|---|---|---|---|---|
| 284 | (S)-5-Amino-2-((3-(1-(4-(2,3-dimethylphenoxy)butanoyl)-1,2,3,4-tetrahydroquinolin-5-yl)benzyloxy)carbonylamino)-5-oxopentanoic acid | 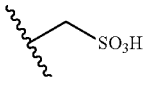 | 602.2 | 3.95 | 100 |
| 285 | ((3-(1-(4-(2,3-Dimethylphenoxy)butanoyl)-1,2,3,4-tetrahydroquinolin-5-yl)benzyloxy)carbonylamino)methanesulfonic acid | 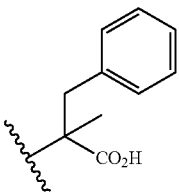 [SMILES: *C(C)(Cc1ccccc1)C(=O)O] | 567.1 | 4.24 | 98.4 |
| 286 | 2-((3-(1-(4-(2,3-Dimethylphenoxy)butanoyl)-1,2,3,4-tetrahydroquinolin-5-yl)benzyloxy)carbonylamino)-2-methyl-3-phenylpropanoic acid | 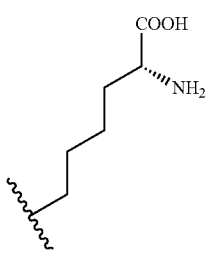 [SMILES: *CCCC[C@@H](N)C(=O)O] | 635.2 | 4.94 | 100 |
| 287 | (R)-2-Amino-6-((3-(1-(4-(2,3-dimethylphenoxy)butanoyl)-1,2,3,4-tetrahydroquinolin-5-yl)benzyloxy)carbonylamino)hexanoic acid | 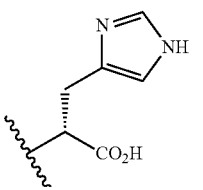 [SMILES: *[C@H](Cc1c[nH]cn1)C(=O)O] | 602.2 | 4.47 | 100 |
| 288 | (R)-2-((3-(1-(4-(2,3-Dimethylphenoxy)butanoyl)-1,2,3,4-tetrahydroquinolin-5-yl)benzyloxy)carbonylamino)-3-(1H-imidazol-4-yl)propanoic acid | 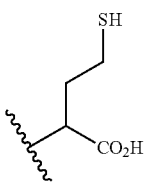 [SMILES: *C(CCS)C(=O)O] | 611.2 | 4.1 | 100 |
| 289 | 2-((3-(1-(4-(2,3-Dimethylphenoxy)butanoyl)-1,2,3,4-tetrahydroquinolin-5-yl)benzyloxy)carbonylamino)-4-mercaptobutanoic acid | | 591.4 | 2.35 | 93.8 |

TABLE 14-continued

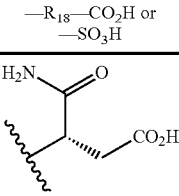

| Example | Name | —R$_{18}$—CO$_2$H or —SO$_3$H | LCMS, [M + H]$^+$ | HPLC-3: Rt (min) | Purity (%) |
|---|---|---|---|---|---|
| 290 | (S)-4-Amino-3-((3-(1-(4-(2,3-dimethylphenoxy)butanoyl)-1,2,3,4-tetrahydroquinolin-5-yl)benzyloxy)carbonylamino)-4-oxobutanoic acid | 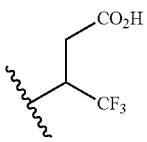 | 588.2 | 4.20 | 100 |
| 291 | 3-((3-(1-(4-(2,3-Dimethylphenoxy)butanoyl)-1,2,3,4-tetrahydroquinolin-5-yl)benzyloxy)carbonylamino)-4,4,4-trifluorobutanoic acid | 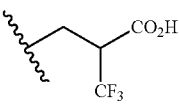 | 613.2 | 4.83 | 100 |
| 292 | 2-(((3-(1-(4-(2,3-Dimethylphenoxy)butanoyl)-1,2,3,4-tetrahydroquinolin-5-yl)benzyloxy)carbonylamino)methyl)-3,3,3-trifluoropropanoic acid | 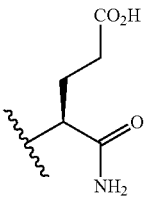 [SMILES: *[C@@H](CCC(=O)O)C(N)=O] | 613.2 | 4.86 | 100 |
| 293 | (S)-5-Amino-4-((3-(1-(4-(2,3-dimethylphenoxy)butanoyl)-1,2,3,4-tetrahydroquinolin-5-yl)benzyloxy)carbonylamino)-5-oxopentanoic acid | 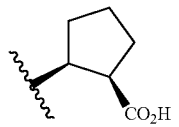 [SMILES: *[C@H]1CCC[C@H]1C(=O)O] | 602.22 | 4.22 | 100 |
| 294 | (1R,2S)-2-((3-(1-(4-(2,3-Dimethylphenoxy)butanoyl)-1,2,3,4-tetrahydroquinolin-5-yl)benzyloxy)carbonylamino)cyclopentanecarboxylic acid | 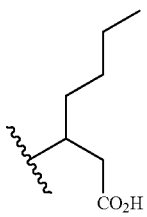 [SMILES: *C(CCCC)CC(=O)O] | 585.2 | 5.09 | 100 |
| 295 | 3-((3-(1-(4-(2,3-Dimethylphenoxy)butanoyl)-1,2,3,4-tetrahydroquinolin-5-yl)benzyloxy)carbonylamino)heptanoic acid | | 601.3 | 5.22 | 91.2 |
| 296 | (S)-3-((3-(1-(4-(2,3-Dimethylphenoxy)butanoyl)-1,2,3,4-tetrahydroquinolin-5-yl)benzyloxy)carbonylamino)-5-methylhexanoic acid | 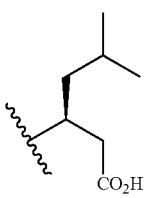 [SMILES: *[C@H](CC(=O)O)CC(C)C] | 601.3 | 5.18 | 93.8 |

TABLE 14-continued

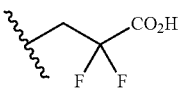

| Example | Name | —R₁₈—CO₂H or —SO₃H | LCMS, [M + H]⁺ | HPLC-3: Rt (min) | Purity (%) |
|---|---|---|---|---|---|
| 297 | 3-((3-(1-(4-(2,3-Dimethylphenoxy)butanoyl)-1,2,3,4-tetrahydroquinolin-5-yl)benzyloxy)carbonylamino)-2,2-difluoropropanoic acid | 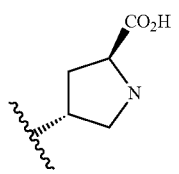 [SMILES: *[C@H]1CN[C@H](C(=O)O)C1] | 581.2 | 4.33 | 100 |
| 298 | (2S,4R)-4-((3-(1-(4-(2,3-Dimethylphenoxy)butanoyl)-1,2,3,4-tetrahydroquinolin-5-yl)benzyloxy)carbonylamino)pyrrolidine-2-carboxylic acid | 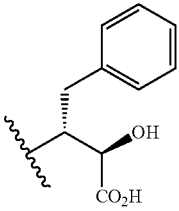 [SMILES: *[C@H](Cc1ccccc1)[C@@H](O)C(=O)O] | 586.3 | 3.98 | 96.9 |
| 299 | (2R,3R)-3-((3-(1-(4-(2,3-Dimethylphenoxy)butanoyl)-1,2,3,4-tetrahydroquinolin-5-yl)benzyloxy)carbonylamino)-2-hydroxy-4-phenylbutanoic acid | 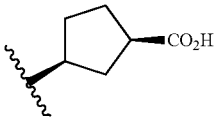 [SMILES: *[C@H]1CC[C@@H](C(=O)O)C1] | 651.2 | 4.69 | 100 |
| 300 | (1R,3S)-3-((3-(1-(4-(2,3-Dimethylphenoxy)butanoyl)-1,2,3,4-tetrahydroquinolin-5-yl)benzyloxy)carbonylamino)cyclopentanecarboxylic acid | 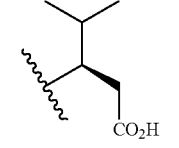 [SMILES: *[C@H](CC(=O)O)C(C)C] | 585.2 | 4.81 | 93.1 |
| 301 | (R)-3-((3-(1-(4-(2,3-Dimethylphenoxy)butanoyl)-1,2,3,4-tetrahydroquinolin-5-yl)benzyloxy)carbonylamino)-4-methylpentanoic acid | 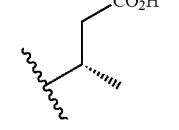 | 587.3 | 4.91 | 98.5 |
| 302 | (S)-3-((3-(1-(4-(2,3-Dimethylphenoxy)butanoyl)-1,2,3,4-tetrahydroquinolin-5-yl)benzyloxy)carbonylamino)butanoic acid | 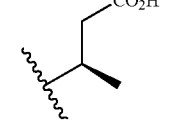 | 559.2 | 4.48 | 96.9 |
| 303 | (R)-3-((3-(1-(4-(2,3-Dimethylphenoxy)butanoyl)-1,2,3,4-tetrahydroquinolin-5-yl)benzyloxy)carbonylamino)butanoic acid | 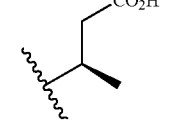 | 559.3 | 4.50 | 98.4 |

TABLE 14-continued

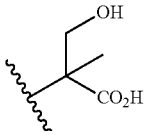

| Example | Name | —R$_{18}$—CO$_2$H or —SO$_3$H | LCMS, [M + H]$^+$ | HPLC-3: Rt (min) | Purity (%) |
|---|---|---|---|---|---|
| 304 | 2-((3-(1-(4-(2,3-Dimethylphenoxy) butanoyl)-1,2,3,4-tetrahydroquinolin-5-yl) benzyloxy)carbonylamino)-3-hydroxy-2-methylpropanoic acid | 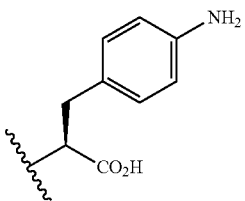 [SMILES: *[C@@H](Cc1ccc(N)cc1)C(=O)O] | 575.2 | 4.01 | 100 |
| 305 | (S)-3-(4-Aminophenyl)-2-((3-(1-(4-(2,3-dimethylphenoxy) butanoyl)-1,2,3,4-tetrahydroquinolin-5-yl) benzyloxy)carbonylamino) propanoic acid | 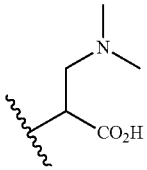 [SMILES: *C(CN(C)C)C(=O)O] | 636.3 | 4.11 | 96.6 |
| 306 | 3-(Dimethylamino)-2-((3-(1-(4-(2,3-dimethylphenoxy)butanoyl)-1,2,3,4-tetrahydroquinolin-5-yl) benzyloxy)carbonylamino) propanoic acid | 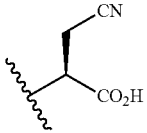 [SMILES: *[C@@H](CC#N)C(=O)O] | 588.2 | 4.29 | 98.3 |
| 307 | (S)-3-Cyano-2-((3-(1-(4-(2,3-dimethylphenoxy)butanoyl)-1,2,3,4-tetrahydroquinolin-5-yl) benzyloxy)carbonylamino) propanoic acid | | 570.2 | 4.15 | 100 |
| 308 | 2-((3-(1-(4-(2,3-Dimethylphenoxy) butanoyl)-1,2,3,4-tetrahydroquinolin-5-yl) benzyloxy)carbonylamino)-3-mercaptopropanoic acid | 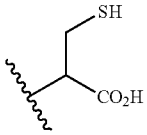 [SMILES: *C(CS)C(=O)O] | 577.2 | 4.22 | 92.8 |
| 309 | (2S)-2-((3-(1-(4-(2,3-Dimethylphenoxy)butanoyl)-1,2,3,4-tetrahydroquinolin-5-yl) benzyloxy)carbonylamino)-4-(S-methylsulfonimidoyl)butanoic acid | 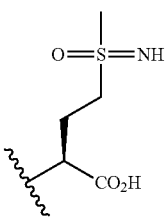 [SMILES: *[C@@H](CCS(C)(=N)=O)C(=O)O] | 636.2 | 3.83 | 100 |

TABLE 14-continued

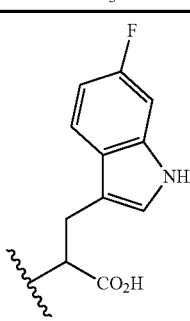

| Example | Name | —R$_{18}$—CO$_2$H or —SO$_3$H | LCMS, [M + H]$^+$ | HPLC-3: Rt (min) | Purity (%) |
|---|---|---|---|---|---|
| 310 | 2-((3-(1-(4-(2,3-Dimethylphenoxy)butanoyl)-1,2,3,4-tetrahydroquinolin-5-yl)benzyloxy)carbonylamino)-3-(6-fluoro-1H-indol-3-yl)propanoic acid | 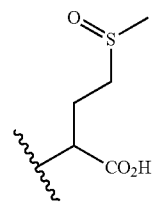 [SMILES: *C(CCS(C)=O)C(=O)O] | 678.2 | 4.56 | 100 |
| 311 | 2-((3-(1-(4-(2,3-Dimethylphenoxy)butanoyl)-1,2,3,4-tetrahydroquinolin-5-yl)benzyloxy)carbonylamino)-4-(methylsulfinyl)butanoic acid | 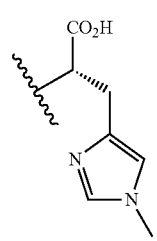 [SMILES: *[C@@H](Cc1cn(C)cn1)C(=O)O] | 621.2 | 3.85 | 97.3 |
| 312 | (S)-2-((3-(1-(4-(2,3-Dimethylphenoxy)butanoyl)-1,2,3,4-tetrahydroquinolin-5-yl)benzyloxy)carbonylamino)-3-(1-methyl-1H-imidazol-4-yl)propanoic acid | 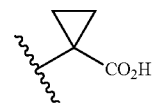 [SMILES: *C1(C(=O)O)CC1] | 625.22 | 4.04 | 100 |
| 313 | 1-((3-(1-(4-(2,3-Dimethylphenoxy)butanoyl)-1,2,3,4-tetrahydroquinolin-5-yl)benzyloxy)carbonylamino)cyclopropanecarboxylic acid | 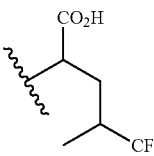 | 557.2 | 4.12 | 100 |
| 314 | 2-((3-(1-(4-(2,3-Dimethylphenoxy)butanoyl)-1,2,3,4-tetrahydroquinolin-5-yl)benzyloxy)carbonylamino)-5,5,5-trifluoro-4-methylpentanoic acid | 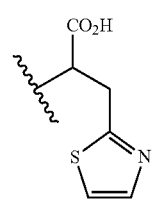 | 641.2 | 4.63 | 100 |
| 315 | 2-((3-(1-(4-(2,3-Dimethylphenoxy)butanoyl)-1,2,3,4-tetrahydroquinolin-5-yl)benzyloxy)carbonylamino)-3-(thiazol-2-yl)propanoic acid | | 628.2 | 4.11 | 100 |

TABLE 14-continued

| Example | Name | —R$_{18}$—CO$_2$H or —SO$_3$H | LCMS, [M + H]$^+$ | HPLC-3: Rt (min) | Purity (%) |
|---|---|---|---|---|---|
| 316 | (S)-2-((3-(1-(4-(2,3-Dimethylphenoxy)butanoyl)-1,2,3,4-tetrahydroquinolin-5-yl)benzyloxy)carbonylamino)-3-(1-methyl-1H-imidazol-5-yl)propanoic acid | | 625.2 | 4.04 | 100 |
| 317 | (S)-2-((3-(1-(4-(2,3-Dimethylphenoxy)butanoyl)-1,2,3,4-tetrahydroquinolin-5-yl)benzyloxy)carbonylamino)-3-ureidopropanoic acid | | 603.3 | 3.81 | 100 |
| 318 | (2S,3R)-2-((3-(1-(4-(2,3-Dimethylphenoxy)butanoyl)-1,2,3,4-tetrahydroquinolin-5-yl)benzyloxy)carbonylamino)-3-(phosphonooxy)butanoic acid | | 655.2 | 3.32 | 100 |
| 319 | 2-((3-(1-(4-(2,3-Dimethylphenoxy)butanoyl)-1,2,3,4-tetrahydroquinolin-5-yl)benzyloxy)carbonylamino)-3-phosphonopropanoic acid | | 625.2 | 3.24 | 100 |
| 320 | (2R,3R)-2-((3-(1-(4-(2,3-Dimethylphenoxy)butanoyl)-1,2,3,4-tetrahydroquinolin-5-yl)benzyloxy)carbonylamino)-3-hydroxybutanoic acid | | 575.2 | 3.96 | 100 |
| 321 | (S)-2-((3-(1-(4-(2,3-Dimethylphenoxy)butanoyl)-1,2,3,4-tetrahydroquinolin-5-yl)benzyloxy)carbonylamino)-3-(phosphonooxy)propanoic acid | | 641.2 | 3.28 | 100 |

TABLE 14-continued

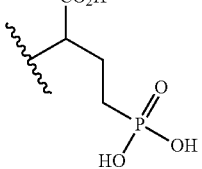

| Example | Name | —R$_{18}$—CO$_2$H or —SO$_3$H | LCMS, [M + H]$^+$ | HPLC-3: Rt (min) | Purity (%) |
|---|---|---|---|---|---|
| 322 | 2-((3-(1-(4-(2,3-Ddimethylphenoxy)butanoyl)-1,2,3,4-tetrahydroquinolin-5-yl)benzyloxy)carbonylamino)-4-phosphonobutanoic acid | 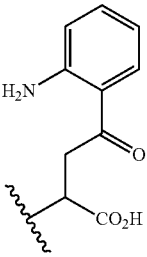 | 639.2 | 3.26 | 100 |
| 323 | 4-(2-Aminophenyl)-2-((3-(1-(4-(2,3-dimethylphenoxy)butanoyl)-1,2,3,4-tetrahydroquinolin-5-yl)benzyloxy)carbonylamino)-4-oxobutanoic acid | 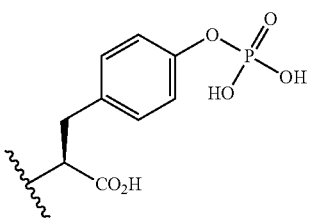 [SMILES: *[C@@H](Cc1ccc(OP(=O)(O)O)cc1)C(=O)O] | 664.2 | 4.44 | 100 |
| 324 | (S)-2-((3-(1-(4-(2,3-Dimethylphenoxy)butanoyl)-1,2,3,4-tetrahydroquinolin-5-yl)benzyloxy)carbonylamino)-3-(4-(phosphonooxy)phenyl)propanoic acid | 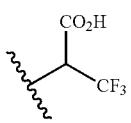 | 717.2 | 3.36 | 98.2 |
| 325 | 2-((3-(1-(4-(2,3-Dimethylphenoxy)butanoyl)-1,2,3,4-tetrahydroquinolin-5-yl)benzyloxy)carbonylamino)-3,3,3-trifluoropropanoic acid | | 599.2 | 4.43 | 100 |

* HPLC-4: Rt (min).

Example 326

2-(3-((4-((1aR,7bS)-3-(4-(2,4,5-Trichlorophenoxy)butanoyl)-1a,2,3,7b-tetrahydro-1H-cyclopropa[c]quinolin-7-yl)-1H-pyrazol-1-yl)methyl)benzamido)ethanesulfonic acid

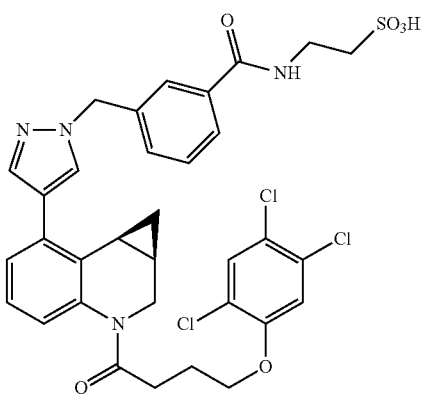 [SMILES: O=C(NCCS(=O)(=O)O)c1cccc(Cn2cc(-c3cccc4c3[C@H]3C[C@H]3CN4C(=O)CCCOc3cc(Cl)c(Cl)cc3Cl)cn2)c1]

Example 326 was prepared using a procedure analogous to Example 222 except that aminomethanesulfonic acid was replaced with 2-aminoethanesulfonic acid and Example 24 was replaced with Example 32D. LCMS, [M+H]$^+$=719.2. $^1$H NMR (400 MHz, CDCl$_3$) δ 8.45-8.25 (m, 2H), 8.18-8.00 (m, 2H), 7.97 (s, 1H), 7.83-7.69 (m, 1H), 7.45-7.28 (m, 2H), 7.21-7.01 (m, 2H), 6.94 (s, 1H), 5.62 (s, 2H), 4.17-3.75 (m, 4H), 3.39-3.13 (m, 2H), 2.93-2.67 (m, 2H), 2.64-2.42 (m, 2H), 2.32-2.02 (m, 2H), 1.99-1.82 (m, 1H), 1.83-1.64 (m, 1H), 1.13-0.87 (m, 1H), 0.68-0.42 (m, 1H). HPLC-1: N/A; HPLC-2: Rt=9.8 min, purity=99.5%.

Example 327

2-(3-((4-((1aR,7bS)-3-(2-((2,4,5-Trichlorophenoxy)methyl)cyclopropanecarbonyl)-1a,2,3,7b-tetrahydro-1H-cyclopropa[c]quinolin-7-yl)-1H-pyrazol-1-yl)methyl)benzamido)ethanesulfonic acid

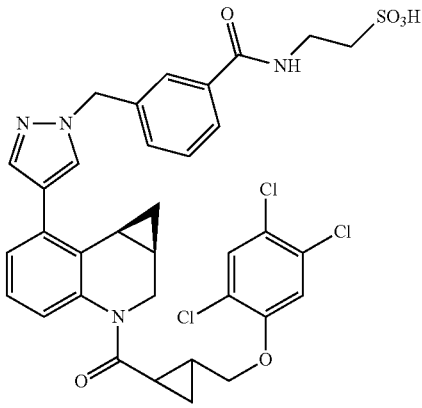 [SMILES: O=C(NCCS(=O)(=O)O)c1cccc(Cn2cc(-c3cccc4c3[C@H]3C[C@H]3CN4C(=O)C3CC3COc3cc(Cl)c(Cl)cc3Cl)cn2)c1]

Example 327 was prepared using a procedure analogous to Example 222 except that aminomethanesulfonic acid was replaced with 2-aminoethanesulfonic acid and Example 24 was replaced with 3-((4-((1aR,7b5)-3-((2-((2,4,5-trichlorophenoxy)methyl)cyclopropyl)carbonyl)-1a,2,3,7b-tetrahydro-1H-cyclopropa[c]quinolin-7-yl)-1H-pyrazol-1-yl)methyl)benzoic acid. LCMS, [M+H]$^+$=731.2 $^1$H NMR (400 MHz, CDCl$_3$) δ 8.42-8.26 (m, 1H), 8.21-8.10 (m, 1H), 8.06 (s, 1H), 8.00 (s, 1H), 7.86-7.72 (m, 2H), 7.35 (d, J=8.2 Hz, 2H), 7.18 (t, J=7.5 Hz, 1H), 7.12 (d, J=7.4 Hz, 1H), 6.83 (s, 1H), 5.76-5.54 (m, 2H), 4.20-4.03 (m, 2H), 3.98-3.80 (m, 2H), 3.71-3.52 (m, 2H), 3.39-3.17 (m, 2H), 2.17-2.04 (m, 1H), 2.04-1.96 (m, 1H), 1.96-1.87 (m, 1H), 1.87-1.75 (m, 1H), 1.49-1.33 (m, 1H), 1.19-0.99 (m, 2H), 0.90-0.73 (m, 1H). HPLC-1: Rt=9.9 min, purity=99.4%; HPLC-2: Rt=9.8 min, purity=99.7%.

Example 328

3-((4-(1-(5-(4-Chlorophenyl)-5,5-difluoropentanoyl)-1,2,3,4-tetrahydroquinolin-5-yl)-1H-pyrazol-1-yl)methyl)benzoic acid

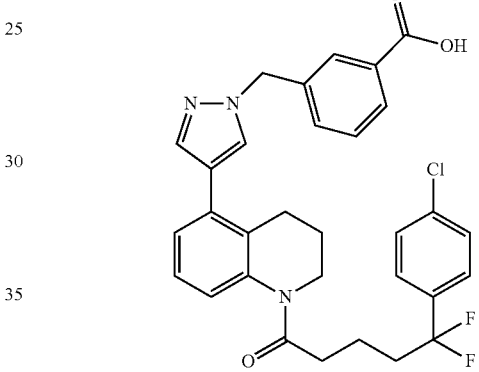

Step A. 1-(5-Bromo-3,4-dihydroquinolin-1(2H)-yl)-5-(4-chlorophenyl)pentane-1,5-dione

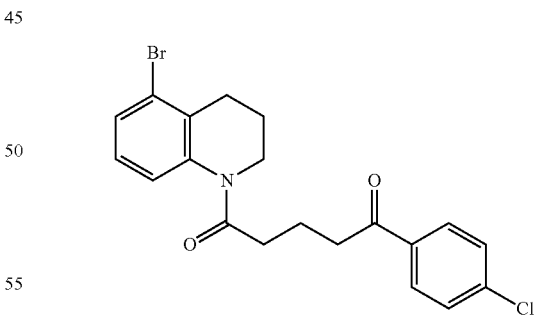

The title compound was prepared using a procedure analogous to Example 1, Step E, except that 4-(2,3-dimethylphenoxy)butanoic acid was replaced by 1-(5-bromo-3,4-dihydroquinolin-1(2H)-yl)-5-(4-chlorophenyl)pentane-1,5-dione. LCMS, [M+H]$^+$=420.0 $^1$H NMR (400 MHz, CDCl$_3$) δ 7.89 (d, J=8.6 Hz, 2H), 7.43 (d, J=8.6 Hz, 2H), 7.40-7.34 (m, 1H), 7.35-7.21 (m, 1H), 7.05 (s, 1H), 3.83-3.70 (m, 2H), 3.04 (t, J=6.8 Hz, 2H), 2.79 (t, J=6.9 Hz, 2H), 2.60 (t, J=7.0 Hz, 2H), 2.10 (p, J=7.0 Hz, 2H), 2.03-1.92 (m, 2H).

Step B. 1-(5-Bromo-3,4-dihydroquinolin-1(2H)-yl)-5-(4-chlorophenyl)-5,5-difluoropentan-1-one

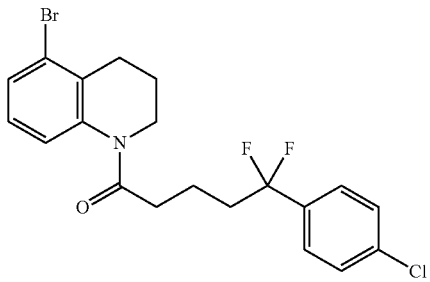 [SMILES: O=C(CCCC(F)(F)c1ccc(Cl)cc1)N1CCCc2c(Br)cccc21]

To 1-(5-bromo-3,4-dihydroquinolin-1(2H)-yl)-5-(4-chlorophenyl)pentane-1,5-dione (100 mg, 0.238 mmol) was added bis-(2-methoxyethyl)aminosulfur trifluoride (657 μl, 3.57 mmol). The orange colored solution was capped under argon and allowed to stir at 90° C. for 3 h. Water (2 mL) was added to the reaction mixture, which was extracted with DCM (2×5 ml). The combined organic layers were concentrated and purified by flash chromatography (0-50% ethyl acetate:hexanes) to afford the title compound (50 mg, 46% yield) as a yellow foam. LCMS, [M+H]$^+$=442.0 $^1$H NMR (400 MHz, CDCl$_3$) δ 7.44-7.34 (m, 6H), 7.04 (t, J=8.0 Hz, 1H), 3.74 (t, J=6.0 Hz, 2H), 2.79 (t, J=6.9 Hz, 2H), 2.50 (t, J=7.2 Hz, 2H), 2.14 (ddd, J=24.1, 15.8, 8.0 Hz, 2H), 2.02-1.89 (m, 2H), 1.78 (dt, J=14.9, 7.4 Hz, 2H).

Example 328

Example 328 was prepared using a procedure analogous to Example 1 except that ethyl 2-(4-(4,4,5,5-tetramethyl-1,3,2-dioxaborolan-2-yl)-1H-pyrazol-1-yl)acetate was replaced by methyl 3-((4-(4,4,5,5-tetramethyl-1,3,2-dioxaborolan-2-yl)-1H-pyrazol-1-yl)methyl)benzoate. LCMS, [M+H]$^+$=564.2 $^1$H NMR (400 MHz, CDCl$_3$) δ 10.79-10.52 (m, 1H), 8.08 (br. s, 2H), 7.70 (s, 1H), 7.56-7.46 (m, 3H), 7.35 (s, 4H), 7.24-7.14 (m, 2H), 7.14-6.95 (m, 1H), 5.46 (s, 2H), 3.76 (t, J=6.6 Hz, 2H), 2.69 (t, J=6.5 Hz, 2H), 2.52 (t, J=7.3 Hz, 2H), 2.21-2.02 (m, 2H), 1.93-1.83 (m, 2H), 1.78 (dt, J=14.6, 7.2 Hz, 2H). HPLC-1: Rt=14.2 min, purity=97.7%; HPLC-2: Rt=13.6 min, purity=100%.

Example 329

(3-((4-(1-(5-(4-Chlorophenyl)-5,5-difluoropentanoyl)-1,2,3,4-tetrahydroquinolin-5-yl)-1H-pyrazol-1-yl)methyl)benzamido)methanesulfonic acid, TFA

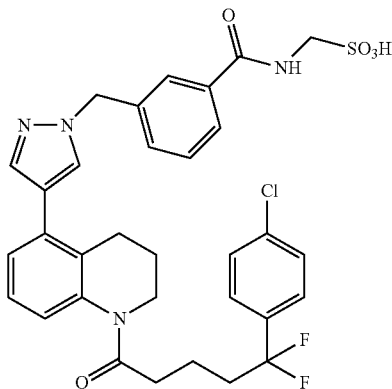 [SMILES: O=C(NCS(=O)(=O)O)c1cccc(Cn2cc(-c3cccc4c3CCCN4C(=O)CCCC(F)(F)c3ccc(Cl)cc3)cn2)c1]

Example 329 was prepared using a procedure analogous to Example 222 except that Example 24 was replaced with Example 328. LCMS, [M+H]$^+$=657.0. $^1$H NMR (400 MHz, CD$_3$OD) δ 7.95 (s, 1H), 7.88 (s, 1H), 7.86-7.80 (m, 1H), 7.69 (s, 1H), 7.46 (d, J=4.9 Hz, 2H), 7.42 (s, 4H), 7.27-7.14 (m, 3H), 5.46 (s, 2H), 4.52 (s, 2H), 3.71 (t, J=6.7 Hz, 2H), 2.72 (t, J=6.5 Hz, 2H), 2.54 (t, J=7.1 Hz, 2H), 2.24-2.06 (m, 2H), 1.92-1.80 (m, 2H), 1.75-1.62 (m, 2H). HPLC-1: Rt=N/A; HPLC-2: Rt=9.2 min, purity=93.4%.

Example 330

2-(3-((4-(1-(5-(4-Chlorophenyl)-5,5-difluoropentanoyl)-1,2,3,4-tetrahydroquinolin-5-yl)-1H-pyrazol-1-yl)methyl)benzamido)ethanesulfonic acid

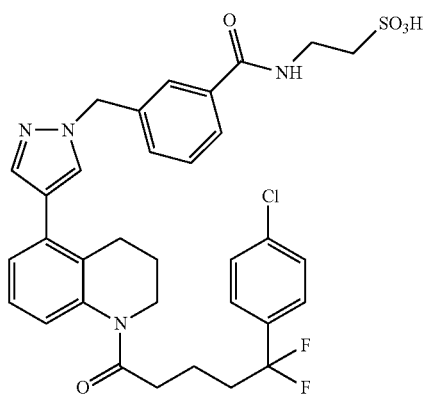 [SMILES: O=C(NCCS(=O)(=O)O)c1cccc(Cn2cc(-c3cccc4c3CCCN4C(=O)CCCC(F)(F)c3ccc(Cl)cc3)cn2)c1]

Example 330 was prepared using a procedure analogous to Example 222 except that Example 24 was replaced with Example 328 and aminomethanesulfonic acid was replaced with 2-aminoethanesulfonic acid. LCMS, [M+H]$^+$=671.0. $^1$H NMR (400 MHz, CD$_3$OD) δ 8.05 (s, 1H), 7.84-7.74 (m, 3H), 7.47 (d, J=5.1 Hz, 2H), 7.42 (s, 4H), 7.30-7.15 (m, 3H), 5.50 (s, 2H), 3.79 (t, J=6.6 Hz, 2H), 3.72 (t, J=6.8 Hz, 2H), 3.08 (t, J=6.6 Hz, 2H), 2.72 (t, J=6.5 Hz, 2H), 2.54 (t, J=7.2 Hz, 2H), 2.22-2.06 (m, 2H), 1.94-1.81 (m, 2H), 1.75-1.63 (m, 2H). HPLC-1: Rt=10.2 min, purity=99.0%; HPLC-2: Rt=9.2 min, purity=99.0%. LCMS, [M+H]$^+$=657.0. $^1$H NMR (400 MHz, CD$_3$OD) δ 7.95 (s, 1H), 7.88 (s, 1H), 7.86-7.80 (m, 1H), 7.69 (s, 1H), 7.46 (d, J=4.9 Hz, 2H), 7.42 (s, 4H), 7.27-7.14 (m, 3H), 5.46 (s, 2H), 4.52 (s, 2H), 3.71 (t, J=6.7 Hz, 2H), 2.72 (t, J=6.5 Hz, 2H), 2.54 (t, J=7.1 Hz, 2H), 2.24-2.06 (m, 2H), 1.92-1.80 (m, 2H), 1.75-1.62 (m, 2H). HPLC-1: Rt=N/A; HPLC-2: Rt=9.2 min, purity=93.4%.

Example 331

3-((4-(4-(4-(2,3-Dimethylphenoxy)butanoyl)-3,4-dihydro-2H-benzo[b][1,4]thiazin-8-yl)-1H-pyrazol-1-yl)methyl)benzoic acid

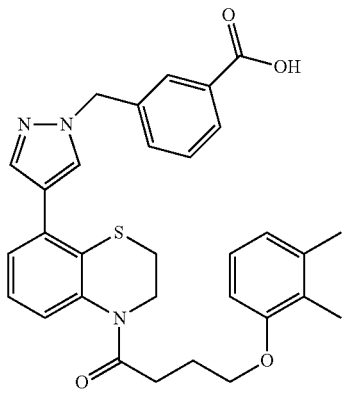 [SMILES: Cc1cccc(OCCCC(=O)N2CCSc3c(-c4cnn(Cc5cccc(C(=O)O)c5)c4)cccc32)c1C]

Step A. Ethyl 2-((2-bromo-6-nitrophenyl)thio)acetate

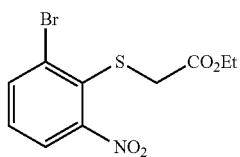

Triethylamine (4.75 mL, 34.1 mmol) was added dropwise to a solution of 1-bromo-2-fluoro-3-nitrobenzene (2.5 g, 11.36 mmol) in DCM (35 mL) and stirred at RT for 1 h. The reaction was diluted with DCM, washed with water, 1N HCl, dried over MgSO$_4$, and concentrated. The crude product was azeotroped from toluene and then acetic acid to afford the title compound (3.64 g, 100% yield). LCMS, [M−H$_2$O+H]$^+$=303.9.

Step B.
8-Bromo-2H-benzo[b][1,4]thiazin-3(4H)-one

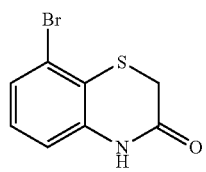 [SMILES: O=C1CSc2c(Br)cccc2N1]

A mixture of ethyl 2-((2-bromo-6-nitrophenyl)thio)acetate (3.64 g, 11.37 mmol) and iron (6.35 g, 114 mmol) in acetic acid (56.8 ml) was stirred at 90° C. for 1.5 h and at room temperature overnight. The mixture was filtered through CELITE®, washed with methanol, followed by hot CHCl$_3$:MeOH:AcOH (1:1:1) till most of the compound came off the CELITE®. The filtrated was concentrated and re-dissolved in EtOAc. The organic solution was washed with water, dried over MgSO$_4$, filtered, and concentrated to afford the title compound (2.59 g, 90% yield). LCMS, [M+H]$^+$=246.0. $^1$H NMR (400 MHz, DMSO-d$_6$) δ 7.27 (dd, J=8.0, 1.0 Hz, 1H), 7.10 (t, J=8.0 Hz, 1H), 6.97 (dd, J=8.0, 1.0 Hz, 1H), 3.53 (s, 2H).

Step C.
8-Bromo-3,4-dihydro-2H-benzo[b][1,4]thiazine

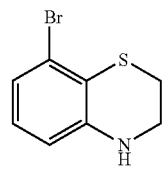 [SMILES: Brc1cccc2c1SCCN2]

The title compound was prepared using a procedure analogous to bromo-1a,2,3,7b-tetrahydro-1H-cyclopropa[c]quinoline except that 7-bromo-3,7b-dihydro-1H-cyclopropa[c]quinolin-2(1aH)-one was replaced with 8-bromo-2H-benzo[b][1,4]thiazin-3(4H)-one. LCMS, [M+H]$^+$=231.9. $^1$H NMR (400 MHz, MeOD) δ 6.86-6.80 (m, 1H), 6.73 (t, J=7.9 Hz, 1H), 6.52 (dd, J=8.1, 1.3 Hz, 1H), 3.56-3.49 (m, 2H), 3.09-3.01 (m, 2H).

Example 331

Example 331 was prepared using a procedure analogous to Example 9 except that 7-bromo-1a,2,3,7b-tetrahydro-1H-cyclopropa[c]quinoline was replaced with 8-bromo-3,4-dihydro-2H-benzo[b][1,4]thiazine. LCMS, [M+H]$^+$=542.2. $^1$H NMR (500 MHz, MeOD) δ 8.00-7.93 (m, 2H), 7.74 (s, 1H), 7.64 (s, 1H), 7.52-7.44 (m, 2H), 7.29-7.25 (m, 1H), 7.19-7.14 (m, 2H), 6.92 (t, J=7.8 Hz, 1H), 6.67-6.62 (m, 2H), 5.43 (s, 2H), 4.14-3.82 (m, 4H), 3.13 (t, J=6.2 Hz, 2H), 2.69 (t, J=7.1 Hz, 2H), 2.10 (s, 3H), 2.09-2.04 (m, 2H), 1.86 (s, 3H). HPLC-1: Rt=10.8 min, purity=99.6%; HPLC-2: Rt=10.0 min, purity=99.6%.

Example 332

3-((4-(4-(4-(2,3-Dimethylphenoxy)butanoyl)-1-oxido-3,4-dihydro-2H-benzo[b][1,4]thiazin-8-yl)-1H-pyrazol-1-yl)methyl)benzoic acid

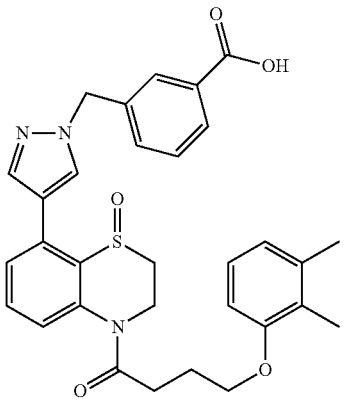 [SMILES: Cc1cccc(OCCCC(=O)N2CCS(=O)c3c(-c4cnn(Cc5cccc(C(=O)O)c5)c4)cccc32)c1C]

To a solution of 3-((4-(4-(4-(2,3-dimethylphenoxy)butanoyl)-3,4-dihydro-2H-benzo[b][1,4]thiazin-8-yl)-1H- pyrazol-1-yl)methyl)benzoic acid (20 mg, 0.037 mmol) in DCM (0.5 mL) was added mCPBA (9.93 mg, 0.044 mmol). The reaction was stirred at room temperature for 20 min and diluted with DCM. The solution was washed with 5% sodium thiosulfate, dried over MgSO$_4$, filtered, and concentrated. The crude product was purified by preparative HPLC (PHENOMENEX® Axia Luna, 5μ, C18 30×100 mm; 10 min gradient from 90% A:10% B to 0% A:100% B and 5 min 100% B (A=90% H$_2$O/10% MeCN+0.1% TFA); (B=90% MeCN/10% H$_2$O+0.1% TFA); detection at 220 nm) to afford Example 332 (18 mg, 85% yield) as a white solid. LCMS, [M+H]$^+$=558.2. $^1$H NMR (500 MHz, MeOD) δ 7.99-7.96 (m, 3H), 7.76 (d, J=0.6 Hz, 1H), 7.60-7.56 (m, 1H), 7.55-7.52 (m, 1H), 7.50-7.42 (m, 3H), 6.94 (t, J=7.8 Hz, 1H), 6.67 (d, J=8.6 Hz, 2H), 5.48 (s, 2H), 4.45-4.42 (m, 1H), 4.07-4.01 (m, 1H), 3.95 (t, J=6.1 Hz, 2H), 3.49-3.43 (m, 1H), 2.96 (ddd, J=14.4, 10.0, 6.1 Hz, 1H), 2.84-2.77 (m, 1H), 2.74-2.67 (m, 1H), 2.18-2.08 (m, 5H), 1.97 (s, 3H). HPLC-1: Rt=9.1 min, purity=99.8%; HPLC-2: Rt=8.8 min, purity=99.1%.

Example 333

3-((4-(4-(4-(2,3-Dimethylphenoxy)butanoyl)-1,1-dioxido-3,4-dihydro-2H-benzo[b][1,4]thiazin-8-yl)-1H-pyrazol-1-yl)methyl)benzoic acid

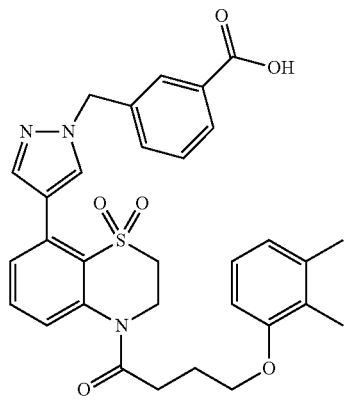 [SMILES: Cc1cccc(OCCCC(=O)N2CCS(=O)(=O)c3c(-c4cnn(Cc5cccc(C(=O)O)c5)c4)cccc32)c1C]

To a solution of 3-((4-(4-(4-(2,3-dimethylphenoxy)butanoyl)-1-oxido-3,4-dihydro-2H-benzo[b][1,4]thiazin-8-yl)-1H-pyrazol-1-yl)methyl)benzoic acid (10.2 mg, 0.018 mmol) in DCM (0.5 mL) was added mCPBA (4.73 mg, 0.027 mmol). The reaction was stirred at room temperature for 20 min and diluted with DCM. The solution was washed with 5% sodium thiosulfate, dried over MgSO$_4$, filtered, and concentrated. The crude product was purified by preparative HPLC (PHENOMENEX® Axia Luna, 5μ, C18 30×100 mm; 10 min gradient from 90% A:10% B to 0% A:100% B and 5 min 100% B (A=90% H$_2$O/10% MeCN+0.1% TFA); (B=90% MeCN/10% H$_2$O+0.1% TFA); detection at 220 nm) to afford Example 333 (6 mg, 55% yield) as a white solid. LCMS, [M+H]$^+$=574.2. $^1$H NMR (500 MHz, MeOD) δ 8.01-7.94 (m, 2H), 7.86 (s, 1H), 7.67 (s, 1H), 7.59-7.52 (m, 1H), 7.49-7.36 (m, 4H), 6.94 (t, J=7.9 Hz, 1H), 6.67 (d, J=7.8 Hz, 2H), 5.44 (s, 2H), 4.38-4.32 (m, 2H), 3.95 (t, J=6.0 Hz, 2H), 3.60-3.54 (m, 2H), 2.72 (t, J=7.1 Hz, 2H), 2.15 (s, 3H), 2.15-2.09 (m, 2H), 1.95 (s, 3H).

Example 334

3-Chloro-4-((4-(5-((2-(3-chloro-2-methylphenoxy)ethoxy)carbonyl)-3-hydroxy-2,3,4,5-tetrahydrobenzo[b][1,4]oxazepin-9-yl)-1H-pyrazol-1-yl)methyl)-5-fluorobenzoic acid

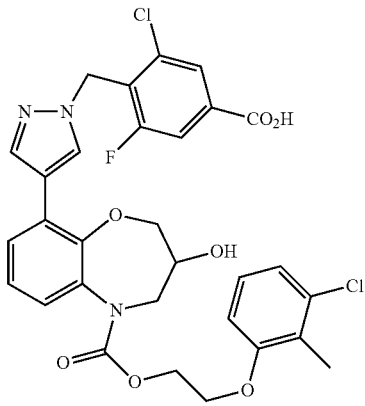 [SMILES: Cc1c(Cl)cccc1OCCOC(=O)N1CC(O)COc2c(-c3cnn(Cc4c(F)cc(C(=O)O)cc4Cl)c3)cccc21]

Step A. 9-Bromo-2,3,4,5-tetrahydrobenzo[b][1,4]oxazepin-3-ol

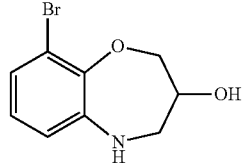 [SMILES: OC1CNc2cccc(Br)c2OC1]

9-Bromo-2,3,4,5-tetrahydrobenzo[b][1,4]oxazepin-3-ol was prepared using a procedure analogous to 9-bromo-2,3,4,5-tetrahydrobenzo[b][1,4]oxazepine except that 3,3-diethoxypropan-1-ol was replaced by 3,3-diethoxypropane-1,2-diol. LCMS, [M+H]$^+$=246.1. $^1$H NMR (400 MHz, CDCl$_3$) δ 7.11 (dd, J=7.7, 1.8 Hz, 1H), 6.81-6.69 (m, 2H), 4.37 (ddd, J=12.3, 3.7, 1.3 Hz, 1H), 3.99 (br. s., 1H), 3.93 (dd, J=12.3, 2.2 Hz, 1H), 3.57 (br. s., 1H), 3.40 (dd, J=13.0, 4.0 Hz, 1H), 3.22 (dd, J=13.0, 2.4 Hz, 1H), 3.01 (br. s., 1H).

Step B. 9-Bromo-3-(tert-butyldimethylsilyloxy)-2,3,4,5-tetrahydrobenzo-[b][1,4]oxazepine

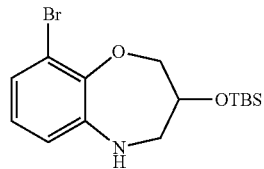 [SMILES: CC(C)(C)[Si](C)(C)OC1CNc2cccc(Br)c2OC1]

To a solution of 9-bromo-2,3,4,5-tetrahydrobenzo[b][1,4]oxazepin-3-ol (0.456 g, 1.868 mmol) and imidazole (0.280 g, 4.11 mmol) in DMF (5.0 mL) was added TBSCl (0.619 g, 4.11 mmol). The reaction was stirred at room temperature for 18 h. The mixture was diluted with a solution of saturated sodium bicarbonate (15 ml) and extracted with ethyl acetate (20 mL). The organic layer was dried over sodium sulfate and concentrated. The crude product was purified by flash chromatography (0-50% ethyl acetate:hexanes) to afford the title compound (648 mg, 1.718 mmol, 92% yield) as clear oil. LCMS, $[M+H]^+$=360.1. $^1$H NMR (400 MHz, CDCl$_3$) δ 6.99 (dd, J=7.8, 1.4 Hz, 1H), 6.69 (t, J=7.9 Hz, 1H), 6.57 (dd, J=7.9, 1.5 Hz, 1H), 4.39 (dd, J=11.9, 4.8 Hz, 1H), 4.19 (tt, J=6.5, 4.7 Hz, 1H), 3.94 (dd, J=11.9, 6.8 Hz, 1H), 3.67 (br. s., 1H), 3.54 (dt, J=13.2, 4.1 Hz, 1H), 3.17 (dd, J=12.3, 5.5 Hz, 1H), 0.93-0.90 (m, 9H), 0.11 (s, 6H).

Step C. 2-(3-Chloro-2-methylphenoxy)ethyl 9-(1-(4-(tert-butoxycarbonyl)-2-chloro-6-fluorobenzyl)-1H-pyrazol-4-yl)-3-(tert-butyldimethylsilyloxy)-3,4-dihydrobenzo[b][1,4]oxazepine-5(2H)-carboxylate

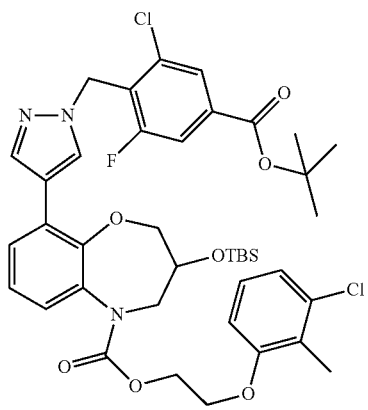 [SMILES: Cc1c(Cl)cccc1OCCOC(=O)N1CC(O[Si](C)(C)C(C)(C)C)COc2c(-c3cnn(Cc4c(F)cc(C(=O)OC(C)(C)C)cc4Cl)c3)cccc21]

The title compound was prepared in a manner analogous to Example 13. LCMS, $[M+H]^+$=800.3.

Example 334

To a solution of 2-(3-chloro-2-methylphenoxy)ethyl 9-(1-(4-(tert-butoxycarbonyl)-2-chloro-6-fluorobenzyl)-1H-pyrazol-4-yl)-3-((tert-butyldimethylsilyl)oxy)-3,4-dihydrobenzo[b][1,4]oxazepine-5(2H)-carboxylate (144 mg, 0.180 mmol) in THF was added 1.0 M TBAF in THF (270 μL, 0.270 mmol). The mixture was stirred at room temperature for 60 min and then concentrated. The residue was suspended in a solution of saturated sodium bicarbonate (15 mL) and extracted with ethyl acetate (20 mL). The organic layer was dried over sodium sulfate and concentrated. The residue was dissolved in DCM (1.0 mL) and TFA (1.0 mL) and stirred at room temperature for 30 min. The mixture was concentrated and the crude product was purified by preparative HPLC (PHENOMENEX® Axia Luna, 5μ, C18 30×100 mm; 10 min gradient from 80% A:20% B to 0% A:100% B and 5 min 100% B (A=90% H$_2$O/10% MeCN+0.1% TFA); (B=90% MeCN/10% H$_2$O+0.1% TFA); detection at 220 nm) to afford Example 334 (7 mg, 70% yield) as a white powder. LCMS, $[M+H]^+$=630.2. $^1$H NMR (400 MHz, MeOD) δ 8.17 (s, 1H), 8.00-7.86 (m, 2H), 7.78 (dd, J=9.7, 1.5 Hz, 1H), 7.51 (d, J=7.5 Hz, 1H), 7.28-6.89 (m, 4H), 6.79 (br. s., 1H), 5.64 (d, J=1.5 Hz, 2H), 4.33 (br. s., 3H), 4.15 (br. s., 5H), 2.42-2.06 (m, 4H). HPLC-1: Rt=9.4 min, purity=99.9%; HPLC-2: Rt=8.9 min, purity=99.8%.

Example 335

3-Chloro-4-((4-(5-((2-(3-chloro-2-methylphenoxy)ethoxy)carbonyl)-3-fluoro-2,3,4,5-tetrahydrobenzo[b][1,4]oxazepin-9-yl)-1H-pyrazol-1-yl)methyl)-5-fluorobenzoic acid

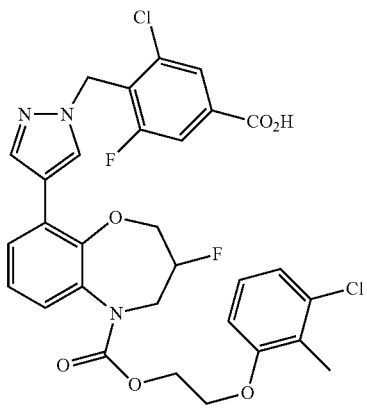 [SMILES: Cc1c(Cl)cccc1OCCOC(=O)N1CC(F)COc2c(-c3cnn(Cc4c(F)cc(C(=O)O)cc4Cl)c3)cccc21]

To a solution of 2-(3-chloro-2-methylphenoxy)ethyl 9-(1-(4-(tert-butoxycarbonyl)-2-chloro-6-fluorobenzyl)-1H-pyrazol-4-yl)-3-hydroxy-3,4-dihydrobenzo[b][1,4]oxazepine-5(2H)-carboxylate (20 mg, 0.029 mmol) in DCM (5 mL) was added bis(e-methoxyethyl)aminosulfur trifluoride (5.37 μl, 0.029 mmol). The reaction was stirred at room temperature for 18 h. The mixture was diluted with a solution of saturated sodium bicarbonate (15 mL) and extracted with DCM (20 mL). The organic layer was dried over sodium sulfate and concentrated. The tert-butyl ester was re-dissolved in DCM (1.0 mL) and TFA (1.0 mL) and stirred at room temperature for 30 min. The mixture was concentrated and was purified by preparative HPLC (PHENOMENEX® Axia Luna, 5μ, C18 30×100 mm; 10 min gradient from 80% A:20% B to 0% A:100% B and 5 min 100% B (A=90% H$_2$O/10% MeCN+0.1% TFA); (B=90% MeCN/10% H$_2$O+0.1% TFA); detection at 220 nm) to afford Example 335 (5 mg, 24% yield) as white powder. LCMS, $[M+H]^+$=632.2. $^1$H NMR (400 MHz, MeOD) δ 8.19 (s, 1H), 7.99-7.88 (m, 2H), 7.78 (dd, J=9.6, 1.4 Hz, 1H), 7.53 (d, J=6.4 Hz, 1H), 7.30-6.74 (m, 5H), 5.65 (d, J=1.5 Hz, 2H), 4.63-4.07 (m, 6H), 3.93 (s, 1H), 2.40-2.07 (m, 5H). HPLC-1: Rt=10.1 min, purity=97.1%; HPLC-2: Rt=9.5 min, purity=97.5%.

Example 336

3-Chloro-4-((4-(5-((2-(3-chloro-2-methylphenoxy)ethoxy)carbonyl)-3,3-difluoro-2,3,4,5-tetrahydrobenzo[b][1,4]oxazepin-9-yl)-1H-pyrazol-1-yl)methyl)-5-fluorobenzoic acid

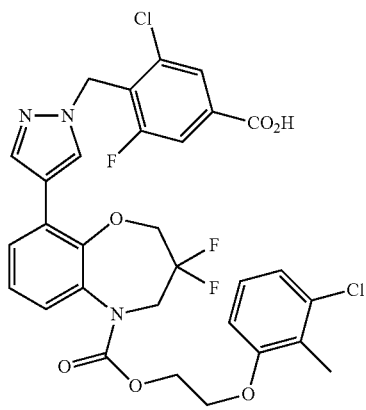 [SMILES: Cc1c(Cl)cccc1OCCOC(=O)N1CC(F)(F)COc2c(-c3cnn(Cc4c(F)cc(C(=O)O)cc4Cl)c3)cccc21]

Step A. 2-(3-Chloro-2-methylphenoxy)ethyl 9-(1-(4-(tert-butoxycarbonyl)-2-chloro-6-fluorobenzyl)-1H-pyrazol-4-yl)-3-oxo-3,4-dihydrobenzo[b][1,4]oxazepine-5(2H)-carboxylate

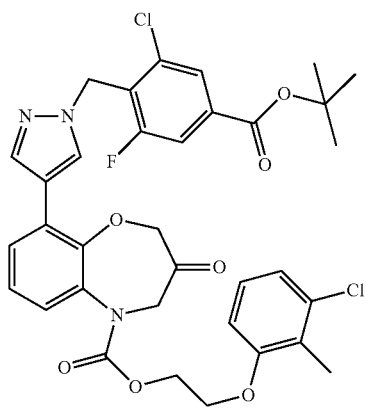 [SMILES: Cc1c(Cl)cccc1OCCOC(=O)N1CC(=O)COc2c(-c3cnn(Cc4c(F)cc(C(=O)OC(C)(C)C)cc4Cl)c3)cccc21]

To a solution of 2-(3-chloro-2-methylphenoxy)ethyl 9-(1-(4-(tert-butoxycarbonyl)-2-chloro-6-fluorobenzyl)-1H-pyrazol-4-yl)-3-hydroxy-3,4-dihydrobenzo[b][1,4]oxazepine-5(2H)-carboxylate (59 mg, 0.086 mmol) in DCM (5.0 mL) was added Dess-Martin periodinane (109 mg, 0.258 mmol). The reaction was stirred at room temperature for 2 d. The mixture was diluted with a solution of saturated sodium bicarbonate (15 mL) and extracted with DCM (20 mL). The organic layer was dried over sodium sulfate and concentrated. The crude product was purified by flash chromatography (0-100% ethyl acetate:hexanes) to afford the title compound (58 mg, 92% yield) as white form. LCMS, [M+H]$^+$=684.3. $^1$H NMR (400 MHz, CDCl$_3$) δ 7.89-7.86 (m, 1H), 7.83 (d, J=6.8 Hz, 2H), 7.66 (dd, J=9.5, 1.5 Hz, 1H), 7.42 (dd, J=7.7, 1.5 Hz, 1H), 7.18 (br. s., 1H), 7.10-6.95 (m, 3H), 6.68 (d, J=7.3 Hz, 1H), 5.54 (d, J=1.5 Hz, 2H), 4.54 (s, 4H), 4.49 (s, 2H), 4.16 (br. s., 2H), 2.21 (br. s., 3H), 1.59 (s, 9H).

Example 336

Example 336 was prepared using a procedure analogous to 3-chloro-4-((4-(5-((2-(3-chloro-2-methylphenoxy)ethoxy)carbonyl)-3-fluoro-2,3,4,5-tetrahydrobenzo[b][1,4]oxazepin-9-yl)-1H-pyrazol-1-yl)methyl)-5-fluorobenzoic acid except that 2-(3-chloro-2-methylphenoxy)ethyl 9-(1-(4-(tert-butoxycarbonyl)-2-chloro-6-fluorobenzyl)-1H-pyrazol-4-yl)-3-hydroxy-3,4-dihydrobenzo[b][1,4]oxazepine-5(2H)-carboxylate was replaced by 2-(3-chloro-2-methylphenoxy)ethyl 9-(1-(4-(tert-butoxycarbonyl)-2-chloro-6-fluorobenzyl)-1H-pyrazol-4-yl)-3-oxo-3,4-dihydrobenzo[b][1,4]oxazepine-5(2H)-carboxylate. LCMS, [M+H]$^+$=650.2. $^1$H NMR (400 MHz, MeOD) δ 8.21 (s, 1H), 8.00-7.87 (m, 2H), 7.78 (dd, J=9.6, 1.4 Hz, 1H), 7.58 (d, J=7.5 Hz, 1H), 7.33-6.72 (m, 5H), 5.65 (d, J=1.3 Hz, 2H), 4.50 (br. s., 2H), 4.15 (br. s., 6H), 2.06 (s, 3H). HPLC-1: Rt=10.4 min, purity=99.4%; HPLC-2: Rt=9.8 min, purity=99.6%.

Example 337

3-Chloro-4-((4-(1-(4-(3-chloro-2-methylphenoxy)butanoyl)-1,2,3,5-tetrahydrobenzo[e][1,4]oxazepin-6-yl)-1H-pyrazol-1-yl)methyl)-5-fluorobenzoic acid

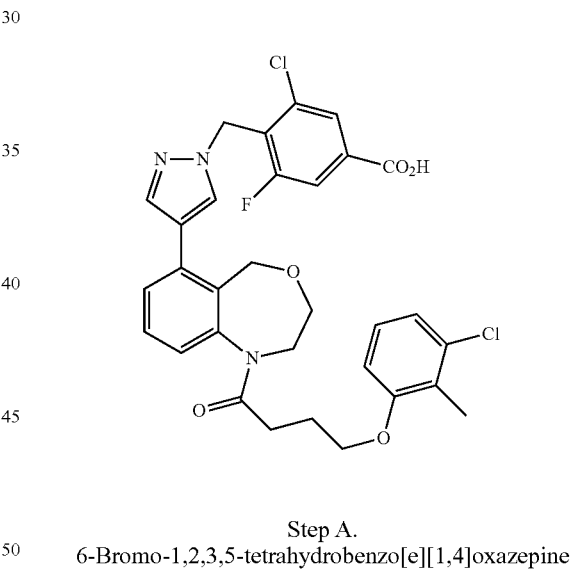

Step A.
6-Bromo-1,2,3,5-tetrahydrobenzo[e][1,4]oxazepine

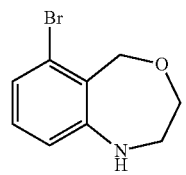 [SMILES: Brc1cccc2c1COCCN2]

To a solution of 2-chloroacetyl chloride (380 mg, 3.37 mmol) in DCM (10 mL) was added (2-amino-6-bromophenyl)methanol (630 mg, 3.12 mmol) followed by DIPEA (1.253 mL, 7.17 mmol). The reaction was stirred at room temperature for 3 d. The mixture was diluted with a solution of saturated sodium bicarbonate (15 mL) and extracted with ethyl acetate (20 mL). The organic layer was dried over sodium sulfate and concentrated to give N-(3-bromo-2-(hydroxymethyl)phenyl)-2-chloroacetamide. The above product was dissolved in IPA (10 mL), and added 50% w/w aqueous NaOH (374 mg, 4.68 mmol). The mixture was stirred at room temperature for 3 h and concentrated. The residue was diluted with a solution of saturated sodium bicarbonate (15 mL) and extracted with DCM (80 mL). The organic layer was dried over sodium sulfate and concentrated to give 6-bromo-3,5-dihydrobenzo[e][1,4]oxazepin-2(1H)-one. The above intermediate was dissolved in THF (60 mL) and added 2.0 M borane dimethyl sulfide methyl sulfide complex in THF (6.24 mL, 12.47 mmol). The reaction was refluxed for 60 min, cooled to room temperature, and added MeOH (5.0 mL) dropwise. The mixture was refluxed for 30 min concentrated. The residue was diluted with a solution of saturated sodium bicarbonate (60 mL) and extracted with ethyl acetate (60 mL). The organic layer was dried over sodium sulfate and concentrated. The crude product was purified by flash chromatography (0-100% ethyl acetate:hexanes) to afford the title compound (237 mg, 32% yield) as clear gum. LCMS, [M+H]$^+$=229.9. $^1$H NMR (400 MHz, CDCl$_3$) δ 7.13 (dd, J=7.9, 1.1 Hz, 1H), 6.94 (t, J=7.9 Hz, 1H), 6.74 (dd, J=7.9, 0.9 Hz, 1H), 4.92 (s, 2H), 4.06 (br. s., 1H), 3.89-3.81 (m, 2H), 3.24-3.17 (m, 2H).

Example 337

Example 337 was prepared in a manner analogous to Example 13. LCMS, [M+H]$^+$=612.1. $^1$H NMR (400 MHz, MeOD) δ 7.97 (s, 1H), 7.84-7.73 (m, 2H), 7.55 (s, 1H), 7.44-7.33 (m, 2H), 7.28 (dd, J=7.2, 1.9 Hz, 1H), 7.12-7.02 (m, 1H), 6.89 (d, J=7.9 Hz, 1H), 6.80 (d, J=8.1 Hz, 1H), 5.65 (d, J=1.3 Hz, 2H), 4.71 (dd, J=13.8, 3.2 Hz, 2H), 4.14 (d, J=13.4 Hz, 1H), 4.07-3.90 (m, 3H), 3.86-3.73 (m, 1H), 3.05-2.91 (m, 1H), 2.58 (t, J=6.9 Hz, 2H), 2.19-2.08 (m, 2H), 1.92 (s, 3H). HPLC-1: Rt=11.5 min, purity=9.69%; HPLC-2: Rt=10.7 min, purity=99.0%.

The compounds exemplified in Table 15 were prepared in a manner analogous to Example 23.

TABLE 15

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 338 | 3-((2-(1-(4-(2,3-Dimethylphenoxy)butanoyl)-1,2,3,4-tetrahydroquinolin-5-yl)thiazol-4-yl)methyl)benzoic acid | | 541.2 | 8.06 (s, 1H), 8.00 (d, J = 8.0 Hz, 1H), 7.58 (d, J = 7.4 Hz, 1H), 7.49-7.41 (m, 2H), 7.30-7.22 (m, 2H), 7.03-6.95 (m, 2H), 6.74 (d, J = 7.7 Hz, 1H), 6.65 (d, J = 8.0 Hz, 1H), 4.29 (s, 2H), 3.96 (t, J = 5.1 Hz, 2H), 3.82 (t, J = 6.7 Hz, 2H), 2.84 (t, J = 6.5 Hz, 2H), 2.76 (t, J = 7.4 Hz, 2H), 2.21 (s, 3H), 2.21-2.12 (m, 3H), 2.00 (br. s., 3H), 1.90 (t, J = 6.6 Hz, 2H) | 10.7 min, 99.8%<br>9.5 min, 100% |
| 339 | 3-((4-(3-(4-(2,3-Dimethylphenoxy)-N-methylbutanamido)phenyl)-1H-pyrazol-1-yl)methyl)benzoic acid | | 498.3 | 8.11-8.02 (m, 1H), 7.81 (s, 1H), 7.52 (s, 1H), 7.50-7.46 (m, 2H), 7.45-7.40 (m, 1H), 7.38-7.33 (m, 1H), 7.24-7.19 (m, 1H), 7.03-6.94 (m, 2H), 6.72 (d, J = 7.7 Hz, 1H), 6.61 (d, J = 8.3 Hz, 1H), 5.38 (s, 2H), 3.88 (t, J = 5.5 Hz, 2H), 3.28 (s, 3H), 2.35 (t, J = 6.9 Hz, 2H), 2.17 (s, 3H), 2.14-2.05 (m, 4H), 1.95-1.87 (m, 3H) | 10.9 min, 98.3%<br>10.1 min, 99.4% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 341 | 2-(3-((4-((1aR,7bS)-3-(4-2,3-Dimethylphenoxy)butanoyl)-1a,2,3,7b-tetrahydro-1H-cyclopropa[c]quinolin-7-yl)-1H-pyrazol-1-yl)methyl)phenoxy)acetic acid | 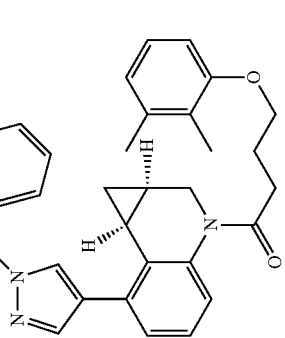 | 566.3 | 7.72 (s, 1H), 7.53 (s, 1H), 7.32-7.26 (m, 1H), 7.19-7.13 (m, 1H), 7.13-7.07 (m, 1H), 7.02-6.97 (m, 1H), 6.95 (br. s., 1H), 6.92-6.84 (m, 3H), 6.72 (d, J = 7.4 Hz, 1H), 6.63 (d, J = 7.7 Hz, 1H), 5.34 (s, 2H), 4.63 (s, 2H), 3.96 (br. s., 1H), 3.88 (br. s., 1H), 2.82-2.67 (m, 2H), 2.59 (br. s., 1H), 2.28-2.01 (m, 7H), 1.91 (br. s., 3H), 1.69 (d, J = 5.8 Hz, 1H), 0.98-0.85 (m, 1H), 0.62-0.49 (m, 1H) | 12.4 min, 99.1% 11.0 min, 99.7% |
| 342 | 3-((4-(4-(2,3-Dihydro-1H-inden-4-yloxy)butanoyl)-1,2,3,4-tetrahydroquinolin-5-yl)-1H-pyrazol-1-yl)methyl)benzoic acid | 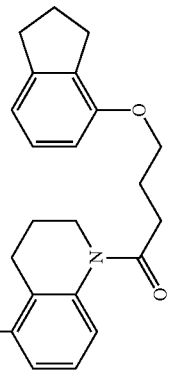 | 536.2 | 8.09-8.05 (m, 2H), 7.59 (s, 1H), 7.54-7.46 (m, 2H), 7.37-7.33 (m, 1H), 7.20-7.10 (m, 3H), 7.08-7.03 (m, 1H), 6.79 (d, J = 7.4 Hz, 1H), 6.58 (d, J = 8.0 Hz, 1H), 5.41 (s, 2H), 3.96 (t, J = 5.1 Hz, 2H), 3.78 (t, J = 6.9 Hz, 2H), 2.79 (t, J = 7.3 Hz, 2H), 2.72 (t, J = 7.0 Hz, 2H), 2.59 (br. s., 4H), 2.16 (quin, J = 6.4 Hz, 2H), 1.97-1.89 (m, 2H), 1.85 (quin, J = 6.7 Hz, 2H) | 12.6 min, 99.4% 10.6 min, 99.1% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 343 | (Z)-3-((4-(1-(4-(2,3-Dimethylphenoxy)but-3-enoyl)-1,2,3,4-tetrahydroquinolin-5-yl)-1H-pyrazol-1-yl)methyl) benzoic acid | | 522.2 | 8.06 (dt, J = 3,6, 1.9 Hz, 2H), 7.63 (d, J = 0.6 Hz, 1H), 7.53-7.46 (m, 3H), 7.44 (s, 1H), 7.14-7.06 (m, 2H), 7.02 (t, J = 7.7 Hz, 1H), 6.86 (d, J = 7.4 Hz, 1H), 6.75 (d, J = 8.3 Hz, 1H), 6.42 (d, J = 6.1 Hz, 1H), 5.42 (s, 2H), 5.14-5.07 (m, 1H), 3.81 (t, J = 6.7 Hz, 2H), 3.49 (dd, J = 7.0, 1.2 Hz, 2H), 2.69 (t, J = 6.6 Hz, 2H), 2.23 (s, 3H), 2.05 (br. s., 3H), 1.94-1.86 (m, 3H) | 11.1 min, 98.2% 9.4 min, 99.2% |
| 344 | (E)-3-((4-(1-(4-(2,3-Dimethylphenoxy)but-2-enoyl)-1,2,3,4-tetrahydroquinolin-5-yl)-1H-pyrazol-1-yl)methyl) benzoic acid | | 522.2 | 8.09-8.03 (m, 1H), 7.68 (d, J = 0.6 Hz, 1H), 7.55-7.45 (m, 4H), 7.17-7.10 (m, 3H), 7.08-7.04 (m, 2H), 6.78 (d, J = 7.4 Hz, 1H), 6.64 (d, J = 8.3 Hz, 1H), 6.61 (dt, J = 15.1, 1.9 Hz, 1H), 5.43 (s, 2H), 4.68 (dd, J = 3.9, 2.2 Hz, 2H), 3.86 (t, J = 6.7 Hz, 2H), 2.74 (t, J = 6.3 Hz, 2H), 2.26-2.21 (m, 3H), 2.02 (s, 3H), 1.95-1.86 (m, 2H) | 11.1 min, 94.8% 9.5 min, 94.2% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 345 | 4-(2,3-Dimethylphenoxy)-1-((1aR,7bS)-7-(1-(3-hydroxybenzyl)-1H-pyrazol-4-yl)-1a,2-dihydro-1H-cyclopropa[c]quinolin-3(7bH)-yl)butan-1-one | | 508.2 | 7.69 (s, 1H), 7.52 (s, 1H), 7.24-7.20 (m, 1H), 7.16 (d, J = 7.7 Hz, 1H), 7.09 (t, J = 7.7 Hz, 1H), 6.99 (t, J = 7.8 Hz, 1H), 6.95 (br. s., 1H), 6.82 (d, J = 7.4 Hz, 1H), 6.80-6.76 (m, 1H), 6.75-6.69 (m, 2H), 6.63 (d, J = 7.7 Hz, 1H), 5.30 (s, 2H), 3.97 (d, J = 4.1 Hz, 1H), 3.88 (br. s., 1H), 2.80-2.70 (m, 2H), 2.58 (br. s., 1H), 2.25-2.06 (m, 7H), 1.91 (brs., 3H), 1.68 (d, J = 5.5 Hz, 1H), 0.96-0.84 (m, 1H), 0.56 (br. s., 1H) | 8.3 min, 94.8% 7.7 min, 99.6% |
| 346 | 2-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenoxy)-2-methylpropanoic acid | | 594.3 | 7.70 (s, 1H), 7.49 (s, 1H), 7.28-7.24 (m, 1H), 7.18-7.13 (m, 1H), 7.13-7.07 (m, 1H), 7.03-6.96 (m, 1H), 6.93 (d, J = 7.7 Hz, 2H), 6.88 (dd, J = 8.3, 1.7 Hz, 1H), 6.81 (s, 1H), 6.73 (d, J = 7.4 Hz, 1H), 6.63 (d, J = 7.7 Hz, 1H), 5.31 (s, 2H), 3.97 (br. s., 1H), 3.88 (br. s., 1H), 2.81-2.68 (m, 3H), 2.58 (br. s., 2H), 2.25-2.03 (m, 7H), 1.91 (br. s., 3H), 1.62-1.51 (m, 6H), 0.94-0.84 (m, 1H), 0.57 (br. s., 1H) | 13.5 min, 99.7% 11.7 min, 99.2% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---------|------|-----------|----------------|--------------------------|-----------------------------------------------|
| 347 | Methyl 3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)benzoate | | 570.2 | 8.04-7.99 (m, 1H), 7.98 (s, 1H), 7.72 (s, 1H), 7.55 (s, 1H), 7.50-7.43 (m, 2H), 7.22-7.17 (m, 1H), 7.16-7.09 (m, 1H), 7.06-6.99 (m, 1H), 6.97-6.91 (m, 2H), 6.67 (d, J = 8.2 Hz, 1H), 5.42 (s, 2H), 4.05-3.97 (m, 1H), 3.92 (s, 3H), 3.90-3.84 (m, 1H), 2.78-2.69 (m, 1H), 2.67-2.57 (m, 1H), 2.21-2.12 (m, 2H), 2.00 (br. s., 3H), 1.73-1.64 (m, 2H), 1.30-1.26 (m, 1H), 1.25 (s, 3H), 0.83 (d, J = 4.9 Hz, 1H), 0.45 (d, J = 3.8 Hz, 1H) | N/A |
| 348 | 2-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)-2,4-dioxotetrahydropyrimidin-1(2H)-yl)acetic acid | | 682.4 | 7.94 (br. s., 1H), 7.76 (s, 1H), 7.69-7.56 (m, 1H), 7.41-7.28 (m, 2H), 7.24-7.10 (m, 3H), 7.08-6.83 (m, 4H), 6.67 (d, J = 7.7 Hz, 1H), 5.47-5.23 (s, 2H), 4.12-3.76 (m, 3H), 3.53 (t, J = 5.5 Hz, 2H), 3.20-2.46 (m, 8H), 2.16 (br. s., 2H), 2.06-1.84 (m, 3H), 1.69 (br. s., 1H), 0.84 (br. s., 1H), 0.44 (br.s, 1H) | 10.2 min, 99.5% 9.2 min, 97.7% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 349 | Ethyl 2-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)phenyl)-2,4-dioxotetrahydropyrimidin-1(2H)-yl)acetate | | 710.5 | 7.77 (s, 1H), 7.60-7.51 (m, 1H), 7.50-7.39 (m, 1H), 7.35-7.27 (m, 1H), 7.23-7.08 (m, 4H), 7.08-6.86 (m, 3H), 6.66 (d, J = 8.2 Hz, 1H), 5.50-5.31 (m, 2H), 4.31-4.13 (m, 4H), 4.07-3.78 (m, 2H), 3.64 (t, J = 6.9 Hz, 2H), 3.15-2.83 (m, 3H), 2.82-2.51 (m, 3H), 2.28-1.85 (m, 6H), 1.78-1.61 (m, 1H), 1.29 (t, J = 7.1 Hz, 3H), 0.88 (d, J = 5.5 Hz, 1H), 0.45 (d, J = 4.4 Hz, 1H) | 11.4 min, 98.7% 10.4 min, 98.5% |
| 350 | 2-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)-2,4-dioxoimidazolidin-1-yl)acetic acid | | 668.4 | 7.72 (s, 1H), 7.59 (s, 1H), 7.56-7.37 (m, 2H), 7.32-7.26 (m, 1H), 7.25-7.08 (m, 3H), 7.07-6.79 (m, 3H), 6.66 (d, J = 7.7 Hz, 1H), 5.44 (s, 2H), 4.27 (s, 1H), 4.19 (s, 1H), 4.06-3.80 (m, 2H), 2.87-2.48 (m, 3H), 2.31-1.52 (m, 9H), 1.36-1.19 (m, 1H), 0.86 (s, 1H), 0.45 (br. s., 1H) | 10.4 min, 91.2% 9.5 min, 93.1% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 351 | Ethyl 2-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)phenyl)-2,4-dioxoimidazolidin-1-yl)acetate | 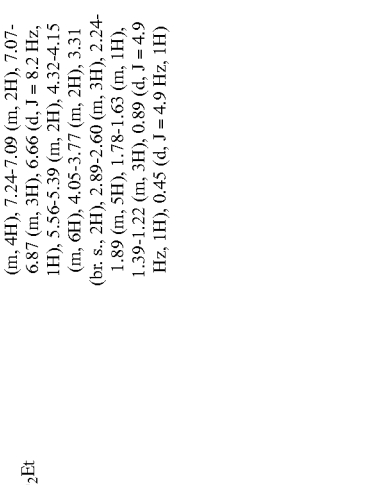 | 696.4 | 7.79 (s, 1H), 7.56 (s, 1H), 7.53-7.28 (m, 4H), 7.24-7.09 (m, 2H), 7.07-6.87 (m, 3H), 6.66 (d, J = 8.2 Hz, 1H), 5.56-5.39 (m, 2H), 4.32-4.15 (m, 6H), 4.05-3.77 (m, 2H), 3.31 (br. s., 2H), 2.89-2.60 (m, 3H), 2.24-1.89 (m, 5H), 1.78-1.63 (m, 1H), 1.39-1.22 (m, 3H), 0.89 (d, J = 4.9 Hz, 1H), 0.45 (d, J = 4.9 Hz, 1H) | 11.7 min, 92.8% 10.7 min, 92.3% |
| 352 | 3-((S)-1-(3-(4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)-2,5-dioxoimidazolidin-4-yl)-N,N,N-trimethylpropan-1-aminium, TFA salt | 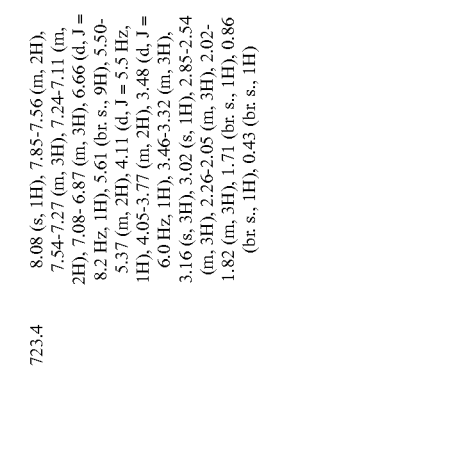 | 723.4 | 8.08 (s, 1H), 7.85-7.56 (m, 2H), 7.54-7.27 (m, 3H), 7.24-7.11 (m, 2H), 7.08-6.87 (m, 3H), 6.66 (d, J = 8.2 Hz, 1H), 5.61 (br. s., 9H), 5.50-5.37 (m, 2H), 4.11 (d, J = 5.5 Hz, 1H), 4.05-3.77 (m, 2H), 3.48 (d, J = 6.0 Hz, 1H), 3.46-3.32 (m, 3H), 3.16 (s, 3H), 3.02 (s, 1H), 2.85-2.54 (m, 3H), 2.26-2.05 (m, 3H), 2.02-1.82 (m, 3H), 1.71 (br. s., 1H), 0.86 (br. s., 1H), 0.43 (br. s., 1H) | 8.3 min, 93.2% 10.3 min, 91.8% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 353 | 4-((1-(4-(2,3-Dimethylphenoxy)butanoyl)-1,2,3,4-tetrahydroquinolin-5-yl)-1H-pyrazol-1-yl)methyl)-3,5-difluorobenzoic acid | | 560.2 | 7.67-7.59 (m, 3H), 7.45 (s, 1H), 7.21-7.13 (m, 3H), 6.98-6.91 (m, 1H), 6.65 (dd, J = 14.7, 7.8 Hz, 2H), 5.50 (s, 2H), 3.89 (t, J = 5.8 Hz, 2H), 3.73 (t, J = 6.8 Hz, 2H), 2.77 (t, J = 6.9 Hz, 2H), 2.52 (t, J = 6.5 Hz, 2H), 2.16-2.05 (m, 5H), 1.86-1.76 (m, 5H) | 11.2 min. 99.9%, 10.2 min. 99.9% |
| 354 | 3-((4-(4-(3-Chloro-2-methylphenoxy)butanoyl)-3,4-dihydro-2H-benzo[b][1,4]thiazin-8-yl)-1H-pyrazol-1-yl)methyl)benzoic acid | | 562.1 | 8.02-7.94 (m, 2H), 7.78 (s, 1H), 7.66 (s, 1H), 7.54-7.42 (m, 2H), 7.32-7.25 (m, 1H), 7.20-7.13 (m, 2H), 7.04-6.96 (m, 1H), 6.85 (d, J = 8.0 Hz, 1H), 6.74 (d, J = 8.0 Hz, 1H), 5.43 (s, 2H), 4.07-3.83 (m, 4H), 3.12 (t, J = 6.2 Hz, 2H), 2.69 (t, J = 6.9 Hz, 2H), 2.08 (quin, J = 6.4 Hz, 2H), 1.98 (s, 3H) | 11.0 min. 99.8%, 11.3 min. 99.7% |

TABLE 15-continued

| Example | Name | Formula I | LCMS, [M + H]⁺ | ¹H NMR (400 MHz, MeOD) δ | HPLC-1: Rt min, purity; HPLC-2: Rt min, purity |
|---|---|---|---|---|---|
| 355 | 4-((4-(4-(2,3-Dimethylphenoxy)butanoyl)-3,4-dihydro-2H-benzo[b][1,4]thiazin-8-yl)-1H-pyrazol-1-yl)methyl)-3,5-difluorobenzoic acid | | 578.2 | 7.77 (s, 1H), 7.68-7.56 (m, 3H), 7.31-7.20 (m, 1H), 7.20-7.11 (m, 2H), 6.92 (t, J = 7.9 Hz, 1H), 6.64 (dd, J = 12.1, 7.9 Hz, 2H), 5.50 (s, 2H), 4.10-3.81 (m, 4H), 3.12 (t, J = 6.2 Hz, 2H), 2.68 (t, J = 7.1 Hz, 2H), 2.11 (s, 3H), 2.10-2.03 (m, 2H), 1.87 (s, 3H) | 11.2 min, 98.4% 10.4 min, 98.1% |
| 356 | 3-((4-(4-(3-Chloro-2-methylphenoxy)butanoyl)-3,4-dihydro-2H-benzo[b][1,4]oxazin-8-yl)-1H-pyrazol-1-yl)methyl)benzoic acid | | 546.1 | 8.06 (s, 1H), 7.99-7.94 (m, 2H), 7.91 (s, 1H), 7.52-7.43 (m, 2H), 7.40 (d, J = 7.2 Hz, 1H), 7.28 (br. s., 1H), 7.03-6.98 (m, 1H), 6.90 (t, J = 7.9 Hz, 1H), 6.85 (d, J = 8.0 Hz, 1H), 6.77 (d, J = 8.3 Hz, 1H), 5.43 (s, 2H), 4.31 (t, J = 4.9 Hz, 2H), 4.01 (t, J = 5.8 Hz, 2H), 3.95 (t, J = 4.9 Hz, 2H), 2.88 (t, J = 6.9 Hz, 2H), 2.16 (quin, J = 6.5 Hz, 2H), 2.06 (s, 3H) | 11.2 min, 99.1% 10.4 min, 98.9% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 357 | 3-Chloro-4-((4-(4-(4-(3-chloro-2-methylphenoxy)butanoyl)-3,4-dihydro-2H-benzo[b][1,4]oxazin-8-yl)-1H-pyrazol-1-yl)methyl)-5-fluorobenzoic acid | | 598.1 | 8.01 (s, 1H), 7.94-7.92 (m, 1H), 7.83 (d, J = 0.6 Hz, 1H), 7.73 (dd, J = 9.7, 1.4 Hz, 1H), 7.37 (dd, J = 7.8, 1.4 Hz, 1H), 7.27 (br. s., 1H), 7.04-6.98 (m, 1H), 6.92-6.83 (m, 2H), 6.77 (d, J = 8.0 Hz, 1H), 5.58 (d, J = 1.4 Hz, 2H), 4.30 (t, J = 5.0 Hz, 2H), 4.00 (t, J = 6.0 Hz, 2H), 3.98-3.93 (m, 2H), 2.88 (t, J = 7.1 Hz, 2H), 2.16 (s, 2H), 2.05 (s, 3H) | 12.0 min, 100% 10.9 min, 100% |
| 358 | 3-Chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzoic acid | | 614.1 | 7.93 (s, 1H), 7.78 (s, 1H), 7.74 (dd, J = 9.7, 1.4 Hz, 1H), 7.61 (s, 1H), 7.29-7.22 (m, 1H), 7.19-7.13 (m, 2H), 7.04-6.97 (m, 1H), 6.86 (d, J = 7.8 Hz, 1H), 6.74 (d, J = 8.3 Hz, 1H), 5.59 (d, J = 1.4 Hz, 2H), 3.93 (t, J = 5.8 Hz, 4H), 3.12 (t, J = 6.2 Hz, 2H), 2.68 (t, J = 6.9 Hz, 2H), 2.08 (quin, J = 6.5 Hz, 2H), 1.98 (s, 3H) | 12.0 min, 99.3% 10.9 min, 99.6% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 359 | 5-((4-(1-(4-(2,3-Dimethylphenoxy)butanoyl)-1,2,3,4-tetrahydroquinolin-5-yl)-1H-pyrazol-1-yl)methyl)nicotinic acid, TFA salt | | 525.3 | 9.12 (d, J = 2.0 Hz, 1H), 8.68 (d, J = 2.0 Hz, 1H), 8.28 (t, J = 2.0 Hz, 1H), 7.57-7.49 (m, 2H), 7.22 (d, J = 4.5 Hz, 2H), 7.10 (br.s., 1H), 6.99 (t, J = 7.7 Hz, 1H), 6.70 (d, J = 7.4 Hz, 1H), 6.64 (d, J = 7.9 Hz, 1H), 5.48 (s, 2H), 3.89 (br. s., 2H), 3.79-3.75 (m, 2H), 2.79 (t, J = 6.9 Hz, 2H), 2.53 (t, J = 7.2 Hz, 2H), 2.20-2.06 (m, 5H), 1.92-1.70 (m, 5H) | 100%* |
| 360 | 4-((4-(4-(4-(3-Chloro-2-methylphenoxy)butanoyl)-3,4-dihydro-2H-benzo[b][1,4]thiazin-8-yl)-1H-pyrazol-1-yl)methyl)-3-fluorobenzoic acid | | 580.1 | 7.85-7.79 (m, 2H), 7.74 (dd, J = 10.5, 1.7 Hz, 1H), 7.67 (d, J = 0.6 Hz, 1H), 7.31-7.22 (m, 2H), 7.21-7.14 (m, 2H), 7.03-6.98 (m, 1H), 6.85 (d, J = 8.0 Hz, 1H), 6.75 (d, J = 8.0 Hz, 1H), 5.49 (s, 2H), 4.10-3.83 (m, 4H), 3.13 (t, J = 6.1 Hz, 2H), 2.69 (t, J = 6.9 Hz, 2H), 2.08 (quin, J = 6.5 Hz, 2H), 1.98 (s, 3H) | 11.4 min, 93.9% 10.5 min, 94.5% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 361 | 3-Chloro-4-((4-(4-(4-(2,3-dimethylphenoxy)butanoyl)-3,4-dihydro-2H-benzo[b][1,4]thiazin-8-yl)-1H-pyrazol-1-yl)methyl)-5-fluorobenzoic acid | 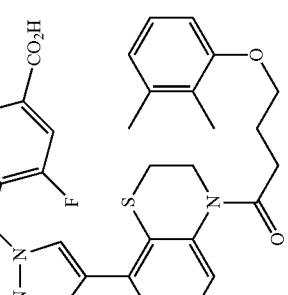 | 594.2 | 7.93 (s, 1H), 7.78-7.71 (m, 2H), 7.60 (s, 1H), 7.27-7.23 (m, 1H), 7.20-7.12 (m, 2H), 6.92 (t, J = 8.0 Hz, 1H), 6.64 (t, J = 8.9 Hz, 2H), 5.59 (d, J = 1.4 Hz, 2H), 4.09-3.84 (m, 4H), 3.12 (t, J = 6.2 Hz, 2H), 2.68 (t, J = 6.9 Hz, 2H), 2.12 (s, 3 H), 2.10-2.03 (m, 2H), 1.87 (s, 3H) | 11.7 min, 97.8% 10.7 min, 97.9% |
| 362 | 4-((4-(4-(2,3-Dimethylphenoxy)butanoyl)-3,4-dihydro-2H-benzo[b][1,4]thiazin-8-yl)-1H-pyrazol-1-yl)methyl)-3-fluorobenzoic acid | 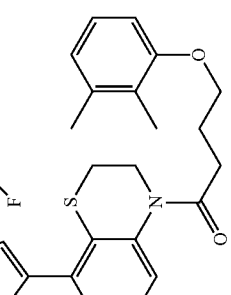 | 560.4 | 7.81 (dd, J = 7.9, 1.5 Hz, 1H), 7.77 (s, 1H), 7.74 (dd, J = 10.7, 1.5 Hz, 1H), 7.65 (s, 1H), 7.31-7.23 (m, 2H), 7.20-7.15 (m, 2H), 6.95-6.90 (m, 1H), 6.65 (t, J = 7.6 Hz, 2H), 5.49 (s, 2H), 4.05-3.86 (m, 4H), 3.14 (t, J = 6.1 Hz, 2H), 2.69 (t, J = 6.9 Hz, 2H), 2.11 (s, 3H), 2.07 (quin, J = 6.4 Hz, 2H), 1.87 (s, 3H) | 11.1 min, 99.3% 10.2 min, 98.4% |

TABLE 15-continued

| Example | Name | Formula I | LCMS, [M+H]+ | 1H NMR (400 MHz, MeOD) δ | HPLC-1: Rt min, purity; HPLC-2: Rt min, purity |
|---|---|---|---|---|---|
| 363 | 3-((4-(4-((2-(2,3-Dimethylphenoxy)ethoxy)carbonyl)-3,4-dihydro-2H-benzo[b][1,4]thiazin-8-yl)-1H-pyrazol-1-yl)methyl)benzoic acid | | 544.3 | 8.03-7.94 (m, 3H), 7.71 (s, 1H), 7.56-7.45 (m, 2H), 7.30 (d, J = 7.9 Hz, 1H), 7.13 (dd, J = 7.7, 1.3 Hz, 1H), 7.01 (dt, J = 12.8, 7.9 Hz, 2H), 6.75 (dd, J = 7.8, 3.6 Hz, 2H), 5.46 (s, 2H), 4.57-4.50 (m, 2H), 4.26-4.17 (m, 2H), 3.94-3.84 (m, 2H), 3.13 (t, J = 5.6 Hz, 2H), 2.23 (s, 3H), 2.16-2.08 (m, 3H) | 11.3 min, 99.3% 10.5 min, 99.4% |
| 364 | 3-Chloro-4-((4-(4-((2-(2,3-dimethylphenoxy)ethoxy)carbonyl)-3,4-dihydro-2H-benzo[b][1,4]thiazin-8-yl)-1H-pyrazol-1-yl)methyl)-5-fluorobenzoic acid | | 596.3 | 7.95-7.90 (m, 1H), 7.86 (s, 1H), 7.73 (dd, J = 9.7, 1.4 Hz, 1H), 7.62 (s, 1H), 7.28 (dd, J = 8.0, 1.4 Hz, 1H), 7.11-7.06 (m, 1H), 7.05-6.92 (m, 2H), 6.74 (t, J = 8.0 Hz, 2H), 5.60 (d, J = 1.7 Hz, 2H), 4.53-4.51 (m, 2H), 4.20 (dd, J = 5.4, 4.0 Hz, 2H), 3.90-3.86 (m, 2H), 3.13-3.09 (m, 2H), 2.22 (s, 3H), 2.10 (s, 3H) | 12.0 min, 98.6% 11.1 min, 98.6% |

TABLE 15-continued

| Example | Name | Formula I | LCMS, [M + H]⁺ | ¹H NMR (400 MHz, MeOD) δ | HPLC-1: Rt min, purity; HPLC-2: Rt min, purity |
|---|---|---|---|---|---|
| 365 | 3-((4-(4-((2-(3-Chloro-2-methylphenoxy)ethoxy)carbonyl)-3,4-dihydro-2H-benzo[b][1,4]thiazin-8-yl)-1H-pyrazol-1-yl)methyl)benzoic acid | | 564.3 | 8.10 (s, 1H), 7.92-7.85 (m, 2H), 7.69 (d, J = 0.8 Hz, 1H), 7.56-7.46 (m, 2H), 7.27 (dd, J = 8.0, 1.4 Hz, 1H), 7.19-7.10 (m, 2H), 7.06-7.00 (m, 2H), 6.96 (d, J = 8.3 Hz, 1H), 5.45 (s, 2H), 4.47 (dd, J = 5.4, 3.7 Hz, 2H), 4.29-4.23 (m, 2H), 3.88-3.80 (m, 2H), 3.13 (d, J = 1.1 Hz, 2H), 2.20 (s, 3H) | 11.6 min, 99.0% 10.8 min, 99.1% |
| 366 | 3-Chloro-4-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)-5-fluorobenzoic acid | | 616.4 | 8.09 (s, 1H), 7.83 (s, 1H), 7.72 (dd, J = 9.5, 1.3 Hz, 1H), 7.63 (d, J = 0.7 Hz, 1H), 7.25 (dd, J = 7.9, 1.3 Hz, 1H), 7.19-7.12 (m, 1H), 7.11-7.06 (m, 1H), 7.05-6.99 (m, 2H), 6.96 (d, J = 8.4 Hz, 1H), 5.34 (s, 2H), 4.49-4.43 (m, 2H), 4.27-4.20 (m, 2H), 3.85-3.78 (m, 2H), 3.16-3.08 (m, 2H), 2.18 (s, 3H) | 12.2 min, 99.1% 11.3 min, 99.8% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 367 | 2-(3-Chloro-2-methylphenoxy)ethyl 8-(1-(2-chloro-5-(methoxycarbonyl)benzyl)-1H-pyrazol-4-yl)-2H-benzo[b][1,4]thiazine-4(3H)-carboxylate | | 612.1 | 7.96 (dd, J = 8.4, 2.2 Hz, 1H), 7.84 (d, J = 2.0 Hz, 1H), 7.79-7.71 (m, 2H), 7.55-7.47 (m, 1H), 7.38-7.30 (m, 1H), 7.13-6.98 (m, 4H), 6.73 (d, J = 7.7 Hz, 1H), 5.52 (s, 2H), 4.59-4.53 (m, 2H), 4.25-4.19 (m, 2H), 3.94 (dd, J = 6.3, 5.0 Hz, 2H), 3.89 (s, 3H), 3.19-3.12 (m, 2H), 2.31-2.26 (m, 3H) | 13.8 min, 94.1% 12.5 min, 94.0% |
| 368 | 4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzoic acid | | 598.0 | 8.16 (s, 1H), 7.89 (dd, J = 8.3, 2.1 Hz, 1H), 7.73 (s, 1H), 7.69 (d, J = 2.0 Hz, 1H), 7.64 (d, J = 8.1 Hz, 1H), 7.27 (d, J = 7.0 Hz, 1H), 7.20-7.10 (m, 2H), 7.08-7.00 (m, 2H), 6.97 (d, J = 8.1 Hz, 1H), 5.55 (s, 2H), 4.50-4.45 (m, 2H), 4.30-4.22 (m, 2H), 3.88-3.80 (m, 2H), 3.16-3.10 (m, 2H), 2.23-2.18 (m, 3H) | 12.4 min, 96.4% 11.4 min, 96.6% |

TABLE 15-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 369 | Methyl 2-chloro-3-((4-(4-(4-(2,3-dimethylphenoxy)butanoyl)-3,4-dihydro-2H-benzo[b][1,4]thiazin-8-yl)-1H-pyrazol-1-yl)methyl)benzoate | | 590.2 | 7.77-7.73 (m, 2H), 7.65 (s, 1H), 7.32 (t, J = 7.8 Hz, 1H), 7.23 (d, J = 8.6 Hz, 1H), 7.18-7.06 (m, 3H), 7.00 (t, J = 7.9 Hz, 1H), 6.73 (d, J = 7.5 Hz, 1H), 6.65 (d, J = 8.1 Hz, 1H), 5.54 (s, 2H), 3.99-3.90 (m, 7H), 3.17 (t, J = 5.8 Hz, 2H), 2.68 (t, J = 7.2 Hz, 2H), 2.19 (s, 3H), 2.17-2.10 (m, 2H), 1.96 (s, 3H) | 12.9 min, 99.9% 11.6 min, 99.9% |
| 370 | 2-Chloro-3-((4-(4-(4-(2,3-dimethylphenoxy)butanoyl)-3,4-dihydro-2H-benzo[b][1,4]thiazin-8-yl)-1H-pyrazol-1-yl)methyl)benzoic acid | | 576.2 | 7.80-7.71 (m, 2H), 7.66 (d, J = 0.6 Hz, 1H), 7.36 (t, J = 7.8 Hz, 1H), 7.28 (dd, J = 6.4, 2.8 Hz, 1H), 7.22-7.13 (m, 3H), 6.92 (t, J = 7.9 Hz, 1H), 6.64 (t, J = 7.5 Hz, 2H), 5.55 (s, 2H), 4.15-3.82 (m, 4H), 3.18-3.09 (m, 2H), 2.69 (t, J = 6.9 Hz, 2H), 2.15-2.02 (m, 5H), 1.86 (s, 3H) | 11.1 min, 98.7% 10.3 min, 97.4% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 371 | Methyl 2-chloro-3-((4-(4-(4-(2,3-dimethylphenoxy)butanoyl)-3,4-dihydro-2H-benzo[b][1,4]oxazin-8-yl)-1H-pyrazol-1-yl)methyl)benzoate | | 574.2 | 7.99 (s, 1H), 7.94 (s, 1H), 7.74 (dd, J = 7.8, 1.7 Hz, 1H), 7.36 (d, J = 7.9 Hz, 1H), 7.32-7.28 (m, 2H), 7.12 (dd, J = 7.7, 1.5 Hz, 1H), 7.05-6.98 (m, 1H), 6.92 (t, J = 7.8 Hz, 1H), 6.74 (d, J = 7.7 Hz, 1H), 6.66 (d, J = 8.1 Hz, 1H), 5.56 (s, 2H), 4.35 (t, J = 4.8 Hz, 2H), 4.00 (d, J = 5.7 Hz, 4H), 3.96 (s, 3H), 2.88 (t, J = 7.0 Hz, 2H), 2.27-2.19 (m, 5H), 2.02 (br. s., 3H) | 12.8 min, 99.9% 11.6 min, 99.8% |
| 372 | 2-Chloro-3-((4-(4-(4-(2,3-dimethylphenoxy)butanoyl)-3,4-dihydro-2H-benzo[b][1,4]oxazin-8-yl)-1H-pyrazol-1-yl)methyl)benzoic acid | | 560.2 | 8.07 (s, 1H), 7.93 (d, J = 0.6 Hz, 1H), 7.73 (dd, J = 7.8, 1.7 Hz, 1H), 7.41 (dd, J = 7.8, 1.4 Hz, 1H), 7.35 (t, J = 7.8 Hz, 1H), 7.27 (br. s., 1H), 7.13 (dd, J = 7.8, 1.7 Hz, 1H), 6.97-6.88 (m, 2H), 6.70-6.63 (m, 2H), 5.56 (s, 2H), 4.28 (t, J = 4.9 Hz, 2H), 3.99-3.92 (m, 4H), 2.90 (t, J = 6.9 Hz, 2H), 2.20-2.12 (m, 2H), 2.11 (s, 3H), 1.92 (s, 3H) | 11.2 min, 100% 10.4 min, 100% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 373 | 2-Chloro-3-((4-(4-(2-(3-chloro-2-methylphenoxy)ethoxy)carbonyl)-3,4-dihydro-2H-benzo[b][1,4]thiazin-8-yl)-1H-pyrazol-1-yl)methyl)benzoic acid | | 598.2 | 8.01 (d, J = 0.7 Hz, 1H), 7.81-7.75 (m, 2H), 7.40 (t, J = 7.7 Hz, 1H), 7.32 (d, J = 7.9 Hz, 1H), 7.22-7.03 (m, 4H), 7.00 (d, J = 7.5 Hz, 1H), 6.90 (d, J = 8.1 Hz, 1H), 5.61 (s, 2H), 4.60-4.54 (m, 2H), 4.31-4.26 (m, 2H), 3.98-3.90 (m, 2H), 3.19-3.15 (m, 3H), 2.25 (s, 3H) | 11.8 min, 100% 11.0 min, 99.9% |
| 374 | (R)-4-((3R,5R,7R,8R,9S,10S,13R,14S,17R)-3-(3-((4-(4-(3-Chloro-2-methylphenoxy)butanoyl)-3,4-dihydro-2H-benzo[b][1,4]thiazin-8-yl)-1H-pyrazol-1-yl)methyl)benzoyloxy)-7-hydroxy-10,13-dimethylhexadecahydro-1H-cyclopenta[a]phenanthren-17-yl)pentanoic acid | | 936.6 | 8.05-7.99 (m, 2H), 7.77-7.72 (m, 1H), 7.60 (s, 1H), 7.48-7.41 (m, 2H), 7.23 (dd, J = 7.5, 1.4 Hz, 1H), 7.17-7.10 (m, 1H), 7.06 (d, J = 6.7 Hz, 1H), 7.04-6.97 (m, 1H), 6.92 (d, J = 7.5 Hz, 1H), 6.68 (d, J = 8.3 Hz, 1H), 5.43-5.38 (m, 2H), 4.93-4.81 (m, 1H), 4.10-3.93 (m, 4H), 3.89 (d, J = 2.5 Hz, 1H), 3.16 (t, J = 6.1 Hz, 2H), 2.66 (t, J = 7.1 Hz, 3H), 2.50-2.38 (m, 2H), 2.29 (ddd, J = 15.9, 9.4, 6.7 Hz, 1H), 2.14 (quin, J = 6.5 Hz, 2H), 2.08 (s, 3H), 2.05-1.80 (m, 6H), 1.71-1.09 (m, 16H), 0.97 (t, J = 3.2 Hz, 6H), 0.70 (s, 3H) | 17.1 min, 99.1% 10.8 min, 95.3% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 375 | 2-(3-(4-((4-(((2-(3-Chloro-2-methylphenoxy)ethoxy)carbonyl)-3,4-dihydro-2H-benzo[b][1,4]thiazin-8-yl)-1H-pyrazol-1-yl)methyl)phenoxy)acetic acid | | 594.3 | 7.77 (s, 1H), 7.69 (s, 1H), 7.34-7.24 (m, 2H), 7.13-7.00 (m, 3H), 6.97 (d, J = 7.9 Hz, 1H), 6.91-6.84 (m, 2H), 6.82 (d, J = 2.0 Hz, 1H), 6.79 (d, J = 8.4 Hz, 1H), 5.33 (s, 2H), 4.57-4.53 (m, 4H), 4.26-4.20 (m, 2H), 3.94-3.90 (m, 2H), 3.17-3.13 (m, 2H), 2.25 (s, 3H) | 100%* |
| 376 | 2-(3-Chloro-2-methylphenoxy)ethyl 8-(1-(2-chloro-5-hydroxybenzyl)-1H-pyrazol-4-yl)-2H-benzo[b][1,4]thiazine-4(3H)-carboxylate | | 570.2 | 7.92 (d, J = 0.4 Hz, 1H), 7.73 (d, J = 0.7 Hz, 1H), 7.28 (d, J = 7.5 Hz, 1H), 7.22 (d, J = 8.8 Hz, 1H), 7.16-7.00 (m, 3H), 6.96 (d, J = 7.9 Hz, 1H), 6.86 (d, J = 8.1 Hz, 1H), 6.72 (dd, J = 8.7, 3.0 Hz, 1H), 6.46 (d, J = 2.9 Hz, 1H), 5.42 (s, 2H), 4.54 (dd, J = 5.3, 3.7 Hz, 2H), 4.27-4.21 (m, 2H), 3.93-3.86 (m, 2H), 3.16-3.11 (m, 2H), 2.22 (s, 3H) | 12.6 min, 95.0% 12.6 min, 95.0% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 377 | 2-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)phenoxy)acetic acid | | 628.2 | 8.12 (s, 1H), 7.73 (s, 1H), 7.42 (d, J = 8.8 Hz, 1H), 7.29 (d, J = 9.2 Hz, 1H), 7.23-7.12 (m, 2H), 7.10-7.01 (m, 2H), 6.99 (d, J = 8.1 Hz, 1H), 6.92 (dd, J = 8.8, 3.1 Hz, 1H), 6.59 (d, J = 3.1 Hz, 1H), 5.45 (s, 2H), 4.64 (s, 2H), 4.52-4.46 (m, 2H), 4.27 (d, J = 4.8 Hz, 2H), 3.88-3.82 (m, 2H), 3.20-3.12 (m, 2H), 2.21 (s, 3H) | 12.2 min, 97.2% N/A |
| 378 | 4-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)phenoxy)butanoic acid | | 656.2 | 8.12 (s, 1H), 7.72 (s, 1H), 7.40 (d, J = 8.8 Hz, 1H), 7.29 (d, J = 6.8 Hz, 1H), 7.23-7.11 (m, 2H), 7.06 (t, J = 8.6 Hz, 2H), 7.02-6.91 (m, 2H), 6.60 (d, J = 3.1 Hz, 1H), 5.44 (s, 2H), 4.52-4.46 (m, 2H), 4.29-4.22 (m, 2H), 3.93 (t, J = 6.5 Hz, 2H), 3.88-3.81 (m, 2H), 3.19-3.11 (m, 2H), 2.35 (t, J = 7.3 Hz, 2H), 2.21 (s, 3H), 1.98-1.85 (m, 2H) | 12.8 min, 94.4% 11.8 min, 92.4% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 379 | 4-Chloro-3-((4-(4-((2-(3-chloro-2-methylphenoxy)ethoxy)carbonyl)-6-fluoro-3,4-dihydro-2H-benzo[b][1,4]oxazin-8-yl)-1H-pyrazol-1-yl)methyl)benzoic acid | | 600.0 | 8.41 (s, 1H), 8.09 (s, 1H), 7.89 (dd, J = 8.4, 2.2 Hz, 1H), 7.65 (d, J = 8.4 Hz, 1H), 7.59 (d, J = 2.0 Hz, 2H), 7.30 (dd, J = 9.6, 3.0 Hz, 1H), 7.24-7.16 (m, 1H), 7.03 (dd, J = 10.6, 8.1 Hz, 2H), 5.55 (s, 2H), 4.58-4.52 (m, 2H), 4.34 (dt, J = 8.1, 4.2 Hz, 4H), 3.93-3.86 (m, 2H), 2.23 (s, 3H) | 12.6 min, 100% 11.4 min, 100% |
| 380 | 3-((4-(4-(3-Chloro-2-methylphenoxy)butanoyl)-6-fluoro-3,4-dihydro-2H-benzo[b][1,4]oxazin-8-yl)-1H-pyrazol-1-yl)methyl)benzoic acid | | 564.2 | 8.21 (s, 1H), 8.06-7.95 (m, 3H), 7.69-7.39 (m, 3H), 7.23 (dd, J = 9.2, 2.4 Hz, 1H), 7.06 (t, J = 8.0 Hz, 1H), 6.86 (dd, J = 18.9, 7.7 Hz, 2H), 5.47 (s, 2H), 4.34 (br. s., 2H), 4.13-4.03 (m, 2H), 3.99 (t, J = 4.7 Hz, 2H), 2.99-2.87 (m, 2H), 2.28-2.19 (m, 2H), 2.16-2.01 (m, 3H) | 11.7 min, 99.7% 10.8 min, 99.4% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 381 | 3-((4-(4-(4-(3-Chloro-4-fluoro-2-methylphenoxy)butanoyl)-3,4-dihydro-2H-benzo[b][1,4]thiazin-8-yl)-1H-pyrazol-1-yl)methyl)benzoic acid | | 580.1 | 8.01 (d, J = 0.8 Hz, 1H), 7.83-7.77 (m, 2H), 7.63 (d, J = 0.8 Hz, 1H), 7.47-7.38 (m, 2H), 7.21-7.14 (m, 2H), 7.10-7.00 (m, 2H), 6.80 (dd, J = 9.2, 4.4 Hz, 1H), 5.37 (s, 2H), 3.87 (t, J = 6.1 Hz, 2H), 3.79 (br. s., 2H), 3.04 (t, J = 6.1 Hz, 2H), 2.50 (t, J = 7.2 Hz, 2H), 1.99 (s, 3H), 1.90 (quin, J = 6.7 Hz, 2H) | 11.2 min, 98.3% 10.4 min, 98.0% |
| 382 | 4-Chloro-3-((4-(4-(4-(3-chloro-4-fluoro-2-methylphenoxy)butanoyl)-3,4-dihydro-2H-benzo[b][1,4]thiazin-8-yl)-1H-pyrazol-1-yl)methyl)benzoic acid | | 614.0 | 7.96 (dd, J = 8.2, 1.7 Hz, 1H), 7.83 (d, J = 1.5 Hz, 1H), 7.73-7.68 (m, 2H), 7.52 (d, J = 8.4 Hz, 1H), 7.29 (d, J = 7.4 Hz, 1H), 7.17 (t, J = 7.7 Hz, 1H), 7.13-7.07 (m, 1H), 6.89 (t, J = 8.7 Hz, 1H), 6.66 (dd, J = 8.9, 4.0 Hz, 1H), 5.52 (s, 2H), 4.72 (br. s., 2H), 3.90 (br. s., 2H), 3.15 (br. s., 2H), 2.74-2.66 (m, 2H), 2.15-2.07 (m, 2H), 2.00 (br. s., 3H) | 99%* |

TABLE 15-continued

| Example | Name | Formula I | LCMS, [M + H]⁺ | ¹H NMR (400 MHz, MeOD) δ | HPLC-1: Rt min, purity; HPLC-2: Rt min, purity |
|---|---|---|---|---|---|
| 383 | 4-Chloro-3-((4-(4-((2-(3-chloro-4-fluoro-2-methylphenoxy)ethoxy)carbonyl)-3,4-dihydro-2H-benzo[b][1,4]thiazin-8-yl)-1H-pyrazol-1-yl)methyl)benzoic acid | | 616.0 | 8.16 (s, 1H), 7.88 (dd, J = 8.3, 2.1 Hz, 1H), 7.73 (d, J = 0.7 Hz, 1H), 7.69 (d, J = 2.0 Hz, 1H), 7.63 (d, J = 8.4 Hz, 1H), 7.26 (dd, J = 8.1, 1.3 Hz, 1H), 7.20 (t, J = 9.0 Hz, 1H), 7.15-7.11 (m, 1H), 7.08-6.97 (m, 2H), 5.55 (s, 2H), 4.50-4.43 (m, 2H), 4.27-4.21 (m, 2H), 3.87-3.81 (m, 2H), 3.16-3.11 (m, 2H), 2.21 (s, 3H) | 12.3 min, 100% 11.3 min, 100% |
| 384 | 4-Chloro-3-((4-(4-((2-(2-chloro-3-fluorophenoxy)ethoxy)carbonyl)-3,4-dihydro-2H-benzo[b][1,4]thiazin-8-yl)-1H-pyrazol-1-yl)methyl)benzoic acid | | 602.0 | 8.18 (s, 1H), 7.90 (dd, J = 8.3, 2.1 Hz, 1H), 7.74 (s, 1H), 7.70 (d, J = 2.0 Hz, 1H), 7.65 (d, J = 8.4 Hz, 1H), 7.40-7.30 (m, 2H), 7.14 (dd, J = 7.7, 1.3 Hz, 1H), 7.10-7.00 (m, 3H), 5.56 (s, 2H), 4.54-4.46 (m, 2H), 4.39 (d, J = 4.8 Hz, 2H), 3.90-3.81 (m, 2H), 3.18-3.13 (m, 2H) | 13.0 min, 100% 12.4 min, 99.6% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 385 | 4-Chloro-3-((4-(4-((2-(3-chloro-2-(trifluoromethyl)phenoxy)ethoxy)carbonyl)-3,4-dihydro-2H-benzo[b][1,4]thiazin-8-yl)-1H-pyrazol-1-yl)methyl)benzoic acid | 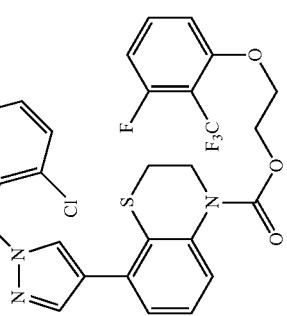 | 652.0 | 8.18 (d, J = 0.7 Hz, 1H), 7.90 (dd, J = 8.3, 2.1 Hz, 1H), 7.74 (d, J = 0.7 Hz, 1H), 7.70 (d, J = 2.0 Hz, 1H), 7.65 (d, J = 8.4 Hz, 1H), 7.60 (t, J = 8.3 Hz, 1H), 7.34-7.23 (m, 3H), 7.17-7.12 (m, 1H), 7.07-7.00 (m, 1H), 5.57 (s, 2H), 4.51-4.44 (m, 2H), 4.40 (d, J = 2.6 Hz, 2H), 3.87-3.81 (m, 2H), 3.17-3.11 (m, 2H) | 13.7 min, 98.0% 12.8 min, 97.4% |
| 386 | 3-((4-(1-(4-(2,3-Dimethylphenoxy)butanoyl)-4-hydroxy-1,2,3,4-tetrahydroquinolin-5-yl)-1H-pyrazol-1-yl)methyl)benzoic acid | 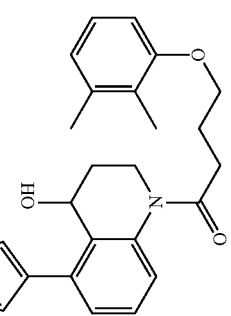 | 540.3 | 8.10-7.90 (m, 3H), 7.82 (s, 1H), 7.65-7.45 (m, 2H), 7.33 (d, J = 3.5 Hz, 3H), 6.98 (t, J = 7.7 Hz, 1H), 6.71 (d, J = 7.9 Hz, 2H), 5.51 (s, 2H), 4.09 (td, J = 11.7, 6.1 Hz, 1H), 3.98 (t, J = 5.7 Hz, 2H), 3.87-3.70 (m, 1H), 3.02-2.64 (m, 2H), 2.32-2.07 (m, 6H), 2.07-1.92 (m, 3H), 1.86-1.65 (m, 1H) | 8.7 min, 95.0% 8.3 min, 95.0% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 387 | 3-((4-(1-(4-(2,3-Dimethylphenoxy)butanoyl)-4-oxo-1,2,3,4-tetrahydroquinolin-5-yl)-1H-pyrazol-1-yl)methyl)benzoic acid | | 538.3 | 8.09-7.96 (m, 1H), 7.90 (s, 1H), 7.63 (s, 1H), 7.60-7.39 (m, 4H), 7.33 (dd, J = 7.7, 0.9 Hz, 1H), 6.98 (t, J = 7.9 Hz, 1H), 6.70 (t, J = 8.6 Hz, 2H), 5.46 (s, 2H), 4.22 (t, J = 6.3 Hz, 2H), 3.98 (t, J = 5.8 Hz, 2H), 2.89 (t, J = 7.2 Hz, 2H), 2.75 (t, J = 6.4 Hz, 2H), 2.28-2.11 (m, 5H), 1.95 (s, 3H) | 9.0 min, 94.8% 8.6 min, 95.0% |
| 388 | 3-((4-(1-(4-(2,3-Dimethylphenoxy)butanoyl)-4-methylene-1,2,3,4-tetrahydroquinolin-5-yl)-1H-pyrazol-1-yl)methyl)benzoic acid | | 536.1 | 8.04-7.93 (m, 1H), 7.89 (s, 1H), 7.65-7.50 (m, 4H), 7.50-7.33 (m, 2H), 7.31-7.17 (m, 2H), 7.10 (br. s., 1H), 6.93 (t, J = 7.9 Hz, 1H), 6.67 (d, J = 7.4 Hz, 1H), 6.56 (d, J = 7.4 Hz, 1H), 5.38 (s, 2H), 5.00 (s, 1H), 3.99-3.77 (m, 4H), 2.83 (t, J = 7.2 Hz, 2H), 2.75-2.59 (m, 3H), 2.18 (s, 3H), 2.07 (br. s., 2H), 1.91 (br. s., 3H) | 100%* |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 389 | 3-((4-(1'-(4-(2,3-Dimethylphenoxy)butanoyl)-2',3'-dihydro-1'H-spiro[cyclopropane-1,4'-quinoline]-5'-yl)-1H-pyrazol-1-yl)methyl)benzoic acid | | 550.3 | 8.07-7.93 (m, 2H), 7.85 (s, 1H), 7.74-7.42 (m, 3H), 7.37-7.14 (m, 3H), 6.97 (t, J = 7.8 Hz, 1H), 6.79-6.51 (m, 2H), 5.64-5.34 (m, 3H), 3.96 (br. s., 3H), 2.69 (br. s., 2H), 2.32-2.06 (m, 6H), 2.05-1.74 (m, 5H), 0.61 (br. s., 2H), 0.31 (br. s., 2H) | 9.9 min, 93.6% 9.1 min, 94.8% |
| 390 | 3-((4-(1-(4-(2,3-Dimethylphenoxy)butanoyl)-4-methyl-1,2,3,4-tetrahydroquinolin-5-yl)-1H-pyrazol-1-yl)methyl)benzoic acid | | 538.3 | 8.01 (d, J = 7.5 Hz, 1H), 7.94 (s, 1H), 7.81 (s, 1H), 7.65-7.44 (m, 3H), 7.34-7.12 (m, 3H), 7.03-6.89 (m, 1H), 6.77-6.58 (m, 2H), 5.51 (s, 2H), 4.24 (br. s., 1H), 3.99 (d, J = 4.4 Hz, 1H), 3.89-3.37 (m, 4H), 3.18 (br. s., 1H), 3.06-2.70 (m, 2H), 2.46 (br. s., 1H), 2.27-2.09 (m, 7H), 2.02-1.87 (m, 4H), 1.80 (br. s., 7H), 1.46-1.18 (m, 2H), 1.07-0.79 (m, 5H) | 9.9 min, 99.8% 9.1 min, 98.6% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 391 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzoic acid | | 612.1 | 8.01 (s, 1H), 7.96 (t, J = 1.3 Hz, 1H), 7.86 (d, J = 0.4 Hz, 1H), 7.78 (dd, J = 9.7, 1.5 Hz, 1H), 7.63 (dd, J = 6.4, 3.1 Hz, 1H), 7.20-7.10 (m, 2H), 7.04-6.93 (m, 1H), 6.83 (d, J = 7.3 Hz, 1H), 6.74 (d, J = 8.4 Hz, 1H), 5.70-5.52 (m, 2H), 4.78 (d, J = 13.9 Hz, 1H), 4.45 (d, J = 11.9 Hz, 1H), 4.00-3.82 (m, 2H), 3.65-3.48 (m, 1H), 2.92-2.75 (m, 1H), 2.58-2.19 (m, 3H), 2.17-1.99 (m, 2H), 1.92 (s, 3H), 1.79 (d, J = 14.7 Hz, 1H) | 10.3 min, 100% 10.3 min, 100% |
| 392 | 3-Chloro-4-((4-(5-(4-(2,3-dimethylphenoxy)butanoyl)-2,3,4,5-tetrahydrobenzo[b][1,4]oxazepin-9-yl)-1H-pyrazol-1-yl)methyl)-5-fluorobenzoic acid | | 592.2 | 7.97 (s, 1H), 7.93 (s, 1H), 7.84 (s, 1H), 7.76 (dd, J = 9.7, 1.3 Hz, 1H), 7.60 (dd, J = 6.1, 3.4 Hz, 1H), 7.16-7.07 (m, 2H), 6.94-6.82 (m, 1H), 6.61 (t, J = 6.9 Hz, 2H), 5.68-5.48 (m, 2H), 4.75 (d, J = 13.9 Hz, 1H), 4.42 (d, J = 11.4 Hz, 1H), 3.97-3.71 (m, 2H), 3.63-3.42 (m, 1H), 2.81 (t, J = 11.6 Hz, 1H), 2.53-2.14 (m, 3H), 2.11-1.96 (m, 5H), 1.86-1.66 (m, 4H) | 10.0 min, 98.8% 9.2 min, 99.1% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 393 | 4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-fluorobenzoic acid | | 753.7 | 7.92 (s, 1H), 7.89-7.76 (m, 3H), 7.51 (dd, J = 7.6, 1.7 Hz, 1H), 7.29 (br. s., 1H), 7.14-6.95 (m, 3H), 6.93-6.85 (m, 1H), 6.65 (d, J = 8.4 Hz, 1H), 5.47 (s, 2H), 4.86 (d, J = 13.2 Hz, 1H), 4.45 (m, 2H), 3.60 (t, J = 10.9 Hz, 1H), 2.78 (t, J = 12.4 Hz, 1H), 2.52-2.20 (m, 3H), 2.16-1.99 (m, 5H), 1.77 (d, J = 14.5 Hz, 1H) | 9.8 min, 99.5% 9.0 min, 99.7% |
| 394 | 4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3,5-difluorobenzoic acid | | 596.2 | 7.88 (d, J = 8.4 Hz, 2H), 7.74-7.62 (m, 2H), 7.49 (dd, J = 1.7, 1.8 Hz, 1H), 7.13-6.94 (m, 3H), 6.92-6.84 (m, 1H), 6.64 (d, J = 8.1 Hz, 1H), 5.48 (d, J = 3.5 Hz, 2H), 4.86 (d, J = 13.6 Hz, 1H), 4.45 (d, J = 11.7 Hz, 1H), 4.00-3.81 (m, 2H), 3.66-3.51 (m, 1H), 2.77 (t, J = 11.3 Hz, 1H), 2.52-2.20 (m, 3H), 2.16-1.98 (m, 5H), 1.77 (d, J = 14.7 Hz, 1H) | 10.0 min, 100% 9.2 min, 100% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 395 | 3-((4-(1-(4-(3-Chloro-2-methylphenoxy)butanoyl)-2,3,4,5-tetrahydro-1H-benzo[b]azepin-6-yl)-1H-pyrazol-1-yl)methyl)benzoic acid | | 558.3 | 8.14-8.01 (m, 2H), 7.59 (s, 1H), 7.56-7.47 (m, 2H), 7.43 (s, 1H), 7.26-7.14 (m, 2H), 7.10-6.96 (m, 2H), 6.91 (d, J = 7.7 Hz, 1H), 6.66 (d, J = 8.1 Hz, 1H), 5.45 (s, 2H), 4.71 (d, J = 13.2 Hz, 1H), 4.04-3.85 (m, 2H), 2.97 (dd, J = 13.3, 6.3 Hz, 1H), 2.79-2.64 (m, 1H), 2.56-2.33 (m, 2H), 2.31-2.07 (m, 3H), 2.00-1.86 (m, 2H), 1.76 (d, J = 14.7 Hz, 1H), 1.36 (d, J = 12.1 Hz, 1H) | 10.1 min, 100%; 9.2 min, 100% |
| 396 | 4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-methoxybenzoic acid | | 590.3 | 7.98 (s, 1H), 7.89 (s, 1H), 7.69-7.55 (m, 3H), 7.19-7.10 (m, 2H), 7.06 (d, J = 7.7 Hz, 1H), 7.01-6.91 (m, 1H), 6.81 (d, J = 7.7 Hz, 1H), 6.72 (d, J = 8.4 Hz, 1H), 5.42 (s, 2H), 4.76 (d, J = 13.6 Hz, 1H), 4.44 (d, J = 11.9 Hz, 1H), 3.95 (s, 3H), 3.92-3.80 (m, 2H), 3.63-3.52 (m, 1H), 2.82 (t, J = 11.7 Hz, 1H), 2.52-2.17 (m, 3H), 2.12-1.97 (m, 2H), 1.92 (s, 3H), 1.77 (d, J = 15.4 Hz, 1H) | 9.9 min, 100%; 9.1 min, 100% |

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 397 | 1-(9-(1-(3-Aminobenzyl)-1H-pyrazol-4-yl)-3,4-dihydrobenzo[b][1,4]oxazepin-5(2H)-yl)-4-(3-chloro-2-methylphenoxy)butan-1-one | | 531.4 | 8.06 (s, 1H), 7.92 (s, 1H), 7.63 (dd, J = 5.7, 3.7 Hz, 1H), 7.52-7.42 (m, 1H), 7.32-7.20 (m, 2H), 7.19-7.10 (m, 3H), 7.04-6.91 (m, 1H), 6.82 (d, J = 7.7 Hz, 1H), 6.72 (d, J = 8.1 Hz, 1H), 5.43 (d, J = 1.5 Hz, 2H), 4.76 (d, J = 13.4 Hz, 1H), 4.47 (d, J = 12.3 Hz, 1H), 3.96-3.81 (m, 2H), 3.63-3.51 (m, 1H), 2.88-2.73 (m, 1H), 2.50-2.16 (m, 3H), 2.10-1.97 (m, 2H), 1.96-1.89 (m, 3H), 1.77 (d, J = 14.5 Hz, 1H) | 7.0 min, 98.8% 7.7 min, 99.2% |
| 398 | 1-(9-(1H-Pyrazol-4-yl)-3,4-dihydrobenzo[b][1,4]oxazepin-5(2H)-yl)-4-(3-chloro-2-methylphenoxy)butan-1-one | | 426.3 | 7.94 (s, 2H), 7.65 (dd, J = 7.0, 2.4 Hz, 1H), 7.19-7.08 (m, 2H), 7.03-6.94 (m, 1H), 6.84 (d, J = 7.7 Hz, 1H), 6.73 (d, J = 8.1 Hz, 1H), 4.76 (d, J = 13.6 Hz, 1H), 4.48 (d, J = 12.1 Hz, 1H), 3.97-3.82 (m, 2H), 3.58 (td, J = 11.8, 1.8 Hz, 1H), 2.90-2.77 (m, 1H), 2.50-2.19 (m, 3H), 2.10-1.98 (m, 2H), 1.95 (s, 3H), 1.78 (d, J = 14.5 Hz, 1H) | 8.9 min, 97.3% 8.3 min, 97.3% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 399 | 3-((4-(5-(4-(3-Chloro-2-methylphenoxy)butanoyl)-2,3,4,5-tetrahydrobenzo[b][1,4]thiazepin-9-yl)-1H-pyrazol-1-yl)methyl)benzoic acid | | 576.2 | 8.03-7.95 (m, 2H), 7.73 (d, J = 3.5 Hz, 2H), 7.50-7.42 (m, 3H), 7.33 (t, J = 7.7 Hz, 1H), 7.16 (dd, J = 7.7, 1.2 Hz, 1H), 7.06-6.97 (m, 1H), 6.88 (d, J = 7.9 Hz, 1H), 6.70 (d, J = 7.9 Hz, 1H), 5.42 (s, 2H), 3.98-3.87 (m, 2H), 2.88-2.71 (m, 2H), 2.67-2.56 (m, 1H), 2.35-1.92 (m, 10H) | 100%* |
| 400 | 4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-methylbenzoic acid | | 574.4 | 7.93 (d, J = 5.1 Hz, 2H), 7.89 (s, 1H), 7.83 (d, J = 8.1 Hz, 1H), 7.63 (dd, J = 6.5, 3.0 Hz, 1H), 7.18-7.10 (m, 2H), 7.08-6.92 (m, 2H), 6.83 (d, J = 7.9 Hz, 1H), 6.72 (d, J = 8.1 Hz, 1H), 5.47 (s, 2H), 4.75 (d, J = 13.9 Hz, 1H), 4.41 (d, J = 11.4 Hz, 1H), 3.97-3.82 (m, 2H), 3.56 (t, J = 10.8 Hz, 1H), 2.82 (t, J = 11.4 Hz, 1H), 2.53-2.14 (m, 6H), 2.13-1.97 (m, 2H), 1.92 (s, 3H), 1.76 (d, J = 15.2 Hz, 1H) | 9.9 min, 100% 9.1 min, 99.9% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 401 | 4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzoic acid | | 560.4 | 8.13-7.99 (m, 3H), 7.94 (s, 1H), 7.66 (dd, J = 6.4, 3.1 Hz, 1H), 7.37 (d, J = 8.4 Hz, 2H), 7.22-7.11 (m, 2H), 7.03-6.94 (m, 1H), 6.83 (d, J = 7.9 Hz, 1H), 6.74 (d, J = 7.9 Hz, 1H), 5.49 (d, J = 1.5 Hz, 2H), 4.78 (d, J = 12.8 Hz, 1H), 4.48 (d, J = 11.7 Hz, 1H), 3.99-3.82 (m, 2H), 3.65-3.54 (m, 1H), 2.85 (t, J = 11.6 Hz, 1H), 2.55-2.19 (m, 3H), 2.14-1.99 (m, 2H), 1.94 (s, 3H), 1.80 (d, J = 14.3 Hz, 1H) | 9.5 min, 100% 8.9 min, 100% |
| 402 | 3-Bromo-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzoic acid | | 640.1 | 8.24 (d, J = 1.0 Hz, 1H), 7.95-7.86 (m, 3H), 7.57 (dd, J = 7.4, 1.5 Hz, 1H), 7.18-7.04 (m, 2H), 7.04-6.93 (m, 2H), 6.84 (d, J = 7.9 Hz, 1H), 6.66 (d, J = 8.4 Hz, 1H), 5.48 (s, 2H), 4.81-4.75 (m, 1H), 4.43 (d, J = 12.4 Hz, 1H), 3.95-3.81 (m, 2H), 3.58 (t, J = 11.1 Hz, 1H), 2.86-2.77 (m, 1H), 2.40 (t, J = 7.2 Hz, 2H), 2.35-2.20 (m, 1H), 2.10-2.02 (m, 2H), 1.96 (s, 3H), 1.78 (d, J = 14.9 Hz, 1H) | 98%* |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 403 | 3,5-Dichloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzoic acid | | 627.8 | 8.05 (s, 2H), 7.83 (d, J = 10.9 Hz, 2H), 7.51 (dd, J = 7.7, 1.7 Hz, 1H), 7.14-7.01 (m, 2H), 6.97-6.90 (m, 1H), 6.83 (d, J = 7.9 Hz, 1H), 6.64 (d, J = 8.4 Hz, 1H), 5.69 (d, J = 5.0 Hz, 2H), 4.76 (d, J = 13.4 Hz, 1H), 4.40 (d, J = 11.9 Hz, 1H), 3.95-3.79 (m, 2H), 3.61-3.50 (m, 1H), 2.84-2.73 (m, 1H), 2.46-2.20 (m, 3H), 2.11-1.98 (m, 2H), 1.96 (s, 3H), 1.77 (d, J = 14.9 Hz, 1H) | 100%* |
| 404 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzoic acid | | 594.2 | 8.06 (d, J = 1.5 Hz, 1H), 7.98-7.90 (m, 2H), 7.70 (s, 2H), 7.59 (dd, J = 7.6, 1.9 Hz, 1H), 7.17-7.02 (m, 3H), 7.00-6.91 (m, 1H), 6.82 (d, J = 7.9 Hz, 1H), 6.68 (s, 1H), 5.53 (s, 2H), 4.43 (d, J = 12.1 Hz, 1H), 3.95-3.81 (m, 2H), 3.58 (t, J = 10.9 Hz, 1H), 2.82 (t, J = 11.4 Hz, 1H), 2.50-2.19 (m, 3H), 2.12-1.98 (m, 2H), 1.93 (s, 3H), 1.77 (d, J = 14.5 Hz, 1H) | 10.3 min, 99.2% 9.4 min, 99.3% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 405 | 2-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzoic acid | | 594.2 | 8.02 (s, 1H), 7.90 (s, 1H), 7.78 (d, J = 2.2 Hz, 1H), 7.62 (dd, J = 6.4, 3.3 Hz, 1H), 7.53-7.45 (m, 1H), 7.39 (dd, J = 8.4, 2.2 Hz, 1H), 7.19-7.08 (m, 2H), 7.00-6.91 (m, 1H), 6.80 (d, J = 7.7 Hz, 1H), 6.71 (d, J = 8.1 Hz, 1H), 5.40 (s, 2H), 4.79-4.71 (m, 1H), 4.46 (d, J = 11.9 Hz, 1H), 3.97-3.81 (m, 2H), 3.55 (t, J = 10.9 Hz, 1H), 2.89-2.76 (m, 1H), 2.54-2.16 (m, 3H), 2.12-1.95 (m, 2H), 1.91 (s, 3H), 1.77 (d, J = 14.1 Hz, 1H) | 9.9 min, 97.4% 9.2 min, 99.0% |
| 406 | 3-Chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzoic acid | | 614.1 | 8.01-7.93 (m, 1H), 7.91 (s, 1H), 7.84 (s, 1H), 7.74-7.66 (m, 1H), 7.41 (d, J = 7.4 Hz, 1H), 7.20-6.79 (m, 4H), 6.67 (d, J = 7.9 Hz, 1H), 5.55 (s, 2H), 4.55 (br. s., 1H), 4.42 (br. s., 2H), 4.33-4.24 (m, 1H), 4.14-3.97 (m, 3H), 2.31 (s, 1H), 2.18-1.98 (m, 5H) | 10.5 min, 99.5% 9.7 min, 98.7% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 407 | 4-Chloro-3-(4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)benzoic acid | | 596.2 | 8.13 (br. s., 1H), 7.98 (d, J = 6.2 Hz, 2H), 7.87-7.78 (m, 2H), 7.73 (s, 1H), 7.60-7.48 (m, 3H), 7.23-6.87 (m, 2H), 6.74 (s, 1H), 5.58 (s, 2H), 4.58 (br. s., 1H), 4.44 (br. s., 2H), 4.33 (br. s., 1H), 4.12 (br. s., 3H), 2.33 (br. s., 1H), 2.20-1.99 (m, 5H) | 10.6 min, 96.6% purity; 9.8 min, 98.2% |
| 408 | 3-Chloro-4-((4-(5-(4-(3-chloro-2-methylphenoxy)butanoyl)-4,5-dihydro-2H-spiro[benzo[b][1,4]oxazepine-3,1'-cyclopropane]-9-yl)-1H-pyrazol-1-yl)methyl)-5-fluorobenzoic acid | | 638.2 | 7.91 (s, 1H), 7.86-7.78 (m, 2H), 7.71 (dd, J = 9.9, 1.0 Hz, 1H), 7.54 (dd, J = 7.9, 1.5 Hz, 1H), 7.11 (t, J = 7.7 Hz, 1H), 7.02 (dd, J = 7.9, 1.5 Hz, 1H), 6.99-6.92 (m, 1H), 6.84 (d, J = 7.9 Hz, 1H), 6.67 (d, J = 8.4 Hz, 1H), 5.60-5.47 (m, 2H), 4.34 (d, J = 13.4 Hz, 2H), 3.96-3.84 (m, 2H), 3.78-3.63 (m, 2H), 3.05-2.98 (m, 1H), 2.51-2.33 (m, 2H), 2.12-2.03 (m, 2H), 1.95 (s, 3H), 0.98 (br. s., 1H), 0.71-0.62 (m, 1H), 0.53-0.44 (m, 1H), 0.41-0.32 (m, 1H) | 99%* |

TABLE 15-continued

| Example | Name | Formula I | LCMS, [M + H]+ | HPLC-1: Rt min, purity; HPLC-2: Rt min, purity |
|---|---|---|---|---|
| 410 | 3-Chloro-4-((4-(5-(4-(3-chloro-2-methylphenoxy)butanoyl)-4,5-dihydro-2H-spiro[benzo[b][1,4]oxazepine-3,1'-cyclobutane]-9-yl)-1H-pyrazol-1-yl)methyl)-5-fluorobenzoic acid | | 652.2 | 91%* |
| | | 1H NMR (400 MHz, MeOD) δ 7.94 (s, 1H), 7.89 (s, 1H), 7.82 (s, 1H), 7.74 (dd, J = 9.7, 1.2 Hz, 1H), 7.50 (dd, J = 7.7, 1.7 Hz, 1H), 7.13-7.05 (m, 1H), 7.03-6.92 (m, 2H), 6.82 (d, J = 7.9 Hz, 1H), 6.65 (d, J = 8.4 Hz, 1H), 5.64-5.51 (m, 2H), 5.08 (d, J = 13.4 Hz, 1H), 4.33-4.24 (m, 1H), 3.95-3.79 (m, 2H), 3.40-3.36 (m, 1H), 2.63 (d, J = 13.4 Hz, 1H), 2.56-2.46 (m, 1H), 2.44-2.34 (m, 1H), 2.29 (d, J = 6.9 Hz, 1H), 2.13-1.95 (m, 5H), 1.91 (s, 3H), 1.82-1.69 (m, 1H), 1.65-1.53 (m, 1H) | | |
| 411 | 4-Chloro-3-((4-(5-(2-(3-chloro-2-methylphenoxy)ethoxycarbonyl)-7-fluoro-2,3,4,5-tetrahydrobenzo[b][1,4]oxazepin-9-yl)-1H-pyrazol-1-yl)methyl)benzoic acid | | 614.3 | 10.7 min, 100% 9.9 min, 99.9% |
| | | 1H NMR: 8.18 (d, J = 2.0 Hz, 2H), 8.12-7.94 (m, 3H), 7.52 (d, J = 8.1 Hz, 1H), 7.13 (dd, J = 9.0, 3.1 Hz, 1H), 7.07-6.91 (m, 2H), 6.80 (br. s., 1H), 6.67 (br. s., 1H), 5.53 (s, 2H), 4.65-4.42 (m, 2H), 4.33-3.98 (m, 4H), 3.75 (br. s., 2H), 2.41-1.97 (m, 5H) | | | |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 412 | 3-Chloro-4-((4-(5-(4-(3-chloro-2-(difluoromethyl)phenoxy)butanoyl)-2,3,4,5-tetrahydrobenzo[b][1,4]oxazepin-9-yl)-1H-pyrazol-1-yl)methyl)-5-fluorobenzoic acid | | 648.1 | 8.05-7.88 (m, 3H), 7.79 (dd, J = 9.2, 1.5 Hz, 1H), 7.51 (dd, J = 7.7, 1.8 Hz, 1H), 7.24 (s, 1H), 7.17-7.05 (m, 2H), 6.99 (d, J = 10.3 Hz, 3H), 5.61 (s, 2H), 4.88 (d, J = 13.9 Hz, 1H), 4.49 (d, J = 11.9 Hz, 1H), 4.12-3.93 (m, 2H), 3.62 (t, J = 10.9 Hz, 1H), 2.80 (t, J = 11.6 Hz, 1H), 2.60-2.31 (m, 2H), 2.29-2.00 (m, 3H), 1.80 (d, J = 14.1 Hz, 1H) | 9.6 min, 99.0% 9.1 min, 98.1% |
| 413 | 3-Chloro-4-((4-(5-(4-(3-chloro-2-fluorophenoxy)butanoyl)-2,3,4,5-tetrahydrobenzo[b][1,4]oxazepin-9-yl)-1H-pyrazol-1-yl)methyl)-5-fluorobenzoic acid | | 616.1 | 8.24 (s, 1H), 7.92-7.80 (m, 2H), 7.77-7.68 (m, 1H), 7.61 (dd, J = 7.8, 1.7 Hz, 1H), 7.25-6.94 (m, 5H), 5.54 (s, 2H), 4.62 (d, J = 12.5 Hz, 1H), 4.48 (d, J = 11.9 Hz, 1H), 3.97 (q, J = 6.3 Hz, 2H), 3.62-3.52 (m, 1H), 2.72 (t, J = 11.8 Hz, 1H), 2.45-2.27 (m, 1H), 2.19-1.65 (m, 5H) | 9.6 min, 99.8% 9.0 min, 99.8% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 414 | 3-Chloro-4-((4-(5-((2-(3-chloro-2-methylphenoxy)-2-methylpropoxy)carbonyl)-2,3,4,5-tetrahydrobenzo[b][1,4]oxazepin-9-yl)-1H-pyrazol-1-yl)methyl)-5-fluorobenzoic acid | | 642.1 | 8.27 (s, 1H), 7.93-7.79 (m, 2H), 7.72 (dd, J = 9.5, 1.3 Hz, 1H), 7.53 (d, J = 8.4 Hz, 1H), 7.24-6.89 (m, 4H), 6.80 (d, J = 7.3 Hz, 1H), 5.55 (s, 3H), 4.30-3.54 (m, 4H), 2.06-1.83 (m, 2H), 1.38 (br. s., 1H), 1.30-1.19 (m, 2H), 1.11 (br. s., 6H), 0.93-0.77 (m, 2H) | 11.0 min, 99.1% 9.9 min, 99.7% |
| 415 | 3-Chloro-4-((4-(5-(4-(3-chloro-2,6-difluorophenoxy)butanoyl)-2,3,4,5-tetrahydrobenzo[b][1,4]oxazepin-9-yl)-1H-pyrazol-1-yl)methyl)-5-fluorobenzoic acid | | 634.1 | 8.04-7.97 (m, 2H), 7.93 (d, J = 0.4 Hz, 1H), 7.79 (dd, J = 9.1, 1.4 Hz, 1H), 7.52 (dd, J = 7.3, 2.2 Hz, 1H), 7.18-7.08 (m, 2H), 7.05-6.95 (m, 1H), 6.80 (ddd, J = 10.1, 9.2, 2.2 Hz, 1H), 5.62 (d, J = 1.3 Hz, 2H), 4.88 (d, J = 13.6 Hz, 1H), 4.49 (d, J = 11.4 Hz, 1H), 4.23-4.07 (m, 2H), 3.63 (t, J = 10.9 Hz, 1H), 2.80 (t, J = 11.1 Hz, 1H), 2.64-2.51 (m, 1H), 2.46-1.93 (m, 4H), 1.80 (d, J = 15.0 Hz, 1H) | 9.7 min, 99.4% 9.1 min, 99.4% |

TABLE 15-continued

| Example | Name | Formula I | LCMS, [M + H]⁺ | ¹H NMR (400 MHz, MeOD) δ | HPLC-1: Rt min, purity; HPLC-2: Rt min, purity |
|---|---|---|---|---|---|
| 416 | 3-Chloro-4-((4-(5-(4-(2-chloro-6-fluoro-3-methylphenoxy)butanoyl)-2,3,4,5-tetrahydrobenzo[b][1,4]oxazepin-9-yl)-1H-pyrazol-1-yl)methyl)-5-fluorobenzoic acid | | 630.1 | 8.01 (d, J = 2.2 Hz, 2H), 7.94 (s, 1H), 7.79 (dd, J = 9.2, 1.5 Hz, 1H), 7.52 (dd, J = 5.6, 3.9 Hz, 1H), 7.17-7.10 (m, 2H), 6.86 (d, J = 8.4 Hz, 2H), 5.62 (d, J = 1.1 Hz, 2H), 4.89 (d, J = 13.6 Hz, 1H), 4.49 (d, J = 11.7 Hz, 1H), 4.07 (dt, J = 17.8, 6.0 Hz, 2H), 3.64 (t, J = 10.9 Hz, 1H), 2.87-2.77 (m, 1H), 2.70-2.59 (m, 1H), 2.44-2.33 (m, 1H), 2.28-2.21 (m, 1H), 2.19-1.98 (m, 2H), 1.81 (d, J = 15.0 Hz, 1H) | 10.0 min, 96.5% 9.2 min, 98.5% |
| 417 | 3-Chloro-4-((4-(5-((2-(3-chloro-2-methylphenoxy)propoxy)carbonyl)-2,3,4,5-tetrahydrobenzo[b][1,4]oxazepin-9-yl)-1H-pyrazol-1-yl)methyl)-5-fluorobenzoic acid | | 628.2 | 8.02-7.86 (m, 3H), 7.76 (dd, J = 9.2, 1.3 Hz, 1H), 7.41-7.34 (m, 1H), 7.13-6.81 (m, 4H), 6.65 (d, J = 7.5 Hz, 1H), 5.60 (s, 2H), 4.78-3.54 (m, 5H), 2.40-1.92 (m, 5H), 1.50-1.15 (m, 4H), 0.97-0.79 (m, 1H) | 10.9 min, 99.8% 9.9 min, 99.7% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 418 | 3-Chloro-4-((4-(5-((2-(3-chloro-2-methylphenoxy)-2,2-dideuteroethoxy)carbonyl)-2,3,4,5-tetrahydrobenzo[b][1,4]oxazepin-9-yl)-1H-pyrazol-1-yl)methyl)-5-fluorobenzoic acid | 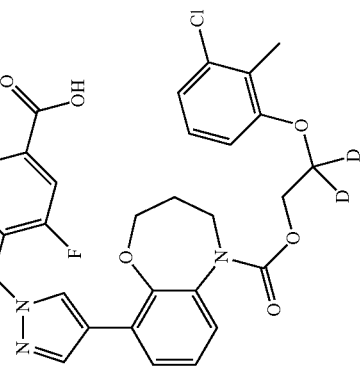 | 616.1 | 8.01-7.88 (m, 3H), 7.76 (dd, J = 9.2, 1.3 Hz, 1H), 7.38 (dd, J = 7.7, 1.8 Hz, 1H), 7.22 (br. s., 4H), 6.85-6.59 (m, 1H), 5.60 (s, 2H), 4.66-4.37 (m, 2H), 4.33-3.59 (m, 4H), 2.41-1.98 (m, 5H) | 10.5 min, 97.9% N/A |
| 419 | 3-Chloro-4-((4-(5-(4-(2-chloro-3-(trifluoromethyl)phenoxy)butanoyl)-2,3,4,5-tetrahydrobenzo[b][1,4]oxazepin-9-yl)-1H-pyrazol-1-yl)methyl)-5-fluorobenzoic acid | 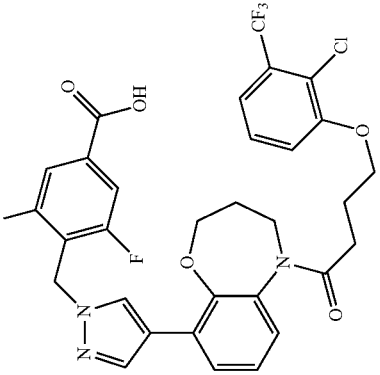 | 666.1 | 7.99 (s, 1H), 7.90 (d, J = 7.5 Hz, 2H), 7.78 (dd, J = 9.1, 1.4 Hz, 1H), 7.47 (dd, J = 7.4, 2.1 Hz, 1H), 7.24-7.17 (m, 2H), 7.15-6.98 (m, 3H), 5.60 (s, 2H), 4.85 (d, J = 13.2 Hz, 1H), 4.45 (d, J = 11.7 Hz, 1H), 4.12-3.93 (m, 2H), 3.59 (t, J = 10.8 Hz, 1H), 2.79 (t, J = 11.4 Hz, 1H), 2.64-2.50 (m, 1H), 2.43-2.26 (m, 2H), 2.22-2.02 (m, 2H), 1.78 (d, J = 14.7 Hz, 1H) | 9.9 min, 98.6% N/A |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 420 | 3-Chloro-4-((4-(5-(3-(3-chloro-2-methylphenoxy)benzoyl)-2,3,4,5-tetrahydrobenzo[b][1,4]oxazepin-9-yl)-1H-pyrazol-1-yl)methyl)-5-fluorobenzoic acid | | 646.0 | 8.16 (s, 1H), 8.02-7.97 (m, 1H), 7.93 (d, J = 0.4 Hz, 1H), 7.82 (dd, J = 9.6, 1.4 Hz, 1H), 7.56-7.45 (m, 1H), 7.37-7.28 (m, 1H), 7.19 (d, J = 7.7 Hz, 1H), 7.01-6.93 (m, 1H), 6.90-6.79 (m, 3H), 6.62 (d, J = 7.7 Hz, 1H), 6.48-6.36 (m, 2H), 5.68 (d, J = 1.3 Hz, 2H), 4.97 (d, J = 11.2 Hz, 1H), 4.56 (d, J = 9.9 Hz, 1H), 3.74-3.60 (m, 1H), 3.04-2.89 (m, 1H), 2.31 (s, 1H), 2.02 (s, 3H), 1.98-1.86 (m, 1H) | 11.9 min, 98.5% 11.1 min, 98.4% |
| 421 | 3-Chloro-4-(4-(4-(2-(3-chloro-2-methylphenoxy)-1,1,2,2-tetradeuteroethoxy)carbonyl)-3-(fluoromethyl)-3,4-dihydro-2H-benzo[b][1,4]oxazin-8-yl)-1H-pyrazol-1-yl)methyl)-5-fluorobenzoic acid | | 636.0 | 8.11 (s, 1H), 7.96-7.83 (m, 2H), 7.82-7.69 (m, 2H), 7.29 (dd, J = 7.7, 1.3 Hz, 1H), 7.15-7.04 (m, 1H), 6.96 (d, J = 7.7 Hz, 1H), 6.92-6.80 (m, 2H), 5.58 (d, J = 1.3 Hz, 2H), 4.98-4.89 (m, 1H), 4.63-4.26 (m, 3H), 4.19 (dt, J = 11.6, 3.6 Hz, 1H), 2.25 (s, 3H) | 12.1 min, 95.6% 11.4 min, 96.7% |

TABLE 15-continued

| Example | Name | Formula I | LCMS, [M + H]+ | ¹H NMR (400 MHz, MeOD) δ | HPLC-1: Rt min, purity; HPLC-2: Rt min, purity |
|---------|------|-----------|----------------|--------------------------|------------------------------------------------|
| 422 | 3-Chloro-4-((4-(5-((2-(3-chloro-2-methylphenoxy)-1,1,2,2-tetradeuteroethoxy)carbonyl)-3-hydroxy-2,3,4,5-tetrahydrobenzo[b][1,4]oxazepin-9-yl)-1H-pyrazol-1-yl)methyl)-5-fluorobenzoic acid | | 634.0 | 7.98 (s, 1H), 7.94-7.82 (m, 2H), 7.71 (dd, J = 9.7, 1.2 Hz, 1H), 7.41 (d, J = 7.4 Hz, 1H), 7.26-6.90 (m, 4H), 6.88-6.63 (m, 1H), 5.56 (s, 2H), 4.31-3.99 (m, 3H), 3.75 (s, 1H), 2.39-2.07 (m, 4H) | N/A |
| 423 | 3-((4-(1-(4-(2,3,6-Trimethylphenoxy)butanoyl)-1,2,3,4-tetrahydroquinolin-5-yl)-1H-pyrazol-1-yl)methyl)benzoic acid | | 538.1 | 8.05-7.85 (m, 3H), 7.65 (s, 1H), 7.61-7.44 (m, 2H), 7.26 (br. s., 3H), 6.96-6.69 (m, 2H), 5.48 (s, 2H), 3.89-3.59 (m, 4H), 2.98-2.66 (m, 4H), 2.29-1.77 (m, 13H) | 10.1 min, 100% 10.1 min, 97.8% |

| Example | Name | Formula I | LCMS, [M+H]+ | 1H NMR (400 MHz, MeOD) δ | HPLC-1: Rt min, purity; HPLC-2: Rt min, purity |
|---|---|---|---|---|---|
| 424 | 3-((4-(1-(4-(2-Ethylphenoxy)butanoyl)-1,2,3,4-tetrahydroquinolin-5-yl)-1H-pyrazol-1-yl)methyl)benzoic acid | | 524.1 | 8.00 (d, J = 7.1 Hz, 1H), 7.93 (br. s., 1H), 7.66 (br. s., 1H), 7.61-7.46 (m, 3H), 7.32-7.16 (m, 3H), 7.16-7.02 (m, 1H), 6.95 (d, J = 6.6 Hz, 1H), 6.90-6.67 (m, 2H), 5.46 (s, 2H), 4.03-3.87 (m, 2H), 3.84-3.68 (m, 2H), 2.90-2.71 (m, 2H), 2.54 (br. s., 2H), 2.28 (br. s., 2H), 2.24-2.09 (m, 2H), 1.93-1.74 (m, 2H), 0.94 (br. s., 3H) | 9.7 min, 100% 9.9 min, 100% |
| 425 | 3-((4-(1-(4-(3-Ethyl-2-methylphenoxy)butanoyl)-1,2,3,4-tetrahydroquinolin-5-yl)-1H-pyrazol-1-yl)methyl)benzoic acid | | 538.1 | 8.04-7.98 (m, 1H), 7.94 (s, 1H), 7.65 (br. s., 1H), 7.56-7.43 (m, 3H), 7.29-7.20 (m, 2H), 7.01 (t, J = 7.8 Hz, 1H), 6.74-6.59 (m, 2H), 5.45 (s, 2H), 3.88 (br. s., 2H), 3.76 (t, J = 6.8 Hz, 3H), 2.82 (t, J = 6.8 Hz, 2H), 2.54 (br. s., 2H), 2.44 (d, J = 7.1 Hz, 2H), 2.13 (t, J = 5.9 Hz, 2H), 1.88-1.74 (m, 4H), 1.02 (t, J = 7.5 Hz, 3H) | N/A |

| Example | Name | Formula I | LCMS, [M + H]⁺ | ¹H NMR (400 MHz, MeOD) δ | HPLC-1: Rt min, purity; HPLC-2: Rt min, purity |
|---|---|---|---|---|---|
| 426 | 3-((4-(1-(4-(o-Tolyloxy)butanoyl)-1,2,3,4-tetrahydroquinolin-5-yl)-1H-pyrazol-1-yl)methyl)benzoic acid | | 510.1 | 8.01 (dd, J = 7.2, 1.6 Hz, 1H), 7.94 (br. s., 1H), 7.67 (br. s., 1H), 7.64-7.47 (m, 3H), 7.37-7.18 (m, 3H), 7.14-7.03 (m, 1H), 6.93 (d, J = 6.8 Hz, 1H), 6.89-6.66 (m, 2H), 5.47 (s, 2H), 4.03-3.87 (m, 2H), 3.83-3.70 (m, 2H), 2.89-2.75 (m, 2H), 2.50 (br. s., 2H), 2.14 (dd, J = 12.3, 5.9 Hz, 2H), 1.97-1.74 (m, 5H) | 9.3 min, 100% 9.5 min, 100% |
| 427 | 3-((4-(1-(2-((2,3-Dimethylphenoxy)methyl)cyclopropanecarbonyl)-1,2,3,4-tetrahydroquinolin-5-yl)-1H-pyrazol-1-yl)methyl)benzoic acid | | 536.3 | 8.09 (dt, J = 7.1, 1.6 Hz, 1H), 8.05 (s, 1H), 7.73 (s, 1H), 7.55-7.49 (m, 3H), 7.47 (dt, J = 6.2, 3.2 Hz, 1H), 7.14-7.10 (m, 2H), 7.01 (t, J = 8.0 Hz, 1H), 6.77 (d, J = 7.7 Hz, 1H), 6.62 (d, J = 8.2 Hz, 2H), 5.48 (s, 2H), 4.13 (dd, J = 10.4, 4.4 Hz, 1H), 4.01-3.87 (m, 1H), 3.78-3.60 (m, 2H), 2.85-2.64 (m, 2H), 2.25 (s, 3H), 2.13-2.07 (m, 4H), 2.07-2.02 (m, 1H), 2.00-1.93 (m, 1H), 1.87 (dd, J = 13.7, 6.6 Hz, 1H), 1.50 (dt, J = 8.8, 4.4 Hz, 1H), 0.93 (ddd, J = 8.0, 6.3, 4.4 Hz, 1H) | 10.1 min, 100% 10.2 min, 100% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 428 | 3-((4-(1-(4-(2,3-Dimethylphenoxy)butanoyl)-1,2,3,4-tetrahydroquinolin-5-yl)-1H-pyrazol-1-yl)methyl)benzonitrile | | 505.3 | 7.62 (td, J = 4.5, 1.6 Hz, 1H), 7.58 (s, 1H), 7.52 (s, 1H), 7.51-7.48 (m, 2H), 7.35 (s, 1H), 7.20-7.15 (m, 2H), 7.00 (t, J = 7.8 Hz, 1H), 6.72 (d, J = 7.6 Hz, 1H), 6.64 (d, J = 8.1 Hz, 1H), 5.37 (s, 2H), 3.93 (t, J = 5.6 Hz, 2H), 3.79 (s, 2H), 2.74 (t, J = 7.1 Hz, 2H), 2.58 (t, J = 6.4 Hz, 2H), 2.24-2.12 (m, 5H), 1.96-1.81 (m, 5H) | 11.0 min, 96.2% 12.0 min, 96.3% |
| 429 | 4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzoic acid | | 591.9 | 8.06 (d, J = 1.8 Hz, 1H), 8.02 (dd, J = 8.3, 2.0 Hz, 1H), 7.84 (s, 1H), 7.72 (s, 1H), 7.53 (d, J = 8.3 Hz, 1H), 7.11-7.06 (m, 2H), 7.04 (d, J = 8.1 Hz, 1H), 7.01-6.96 (m, 1H), 6.71 (d, J = 7.8 Hz, 1H), 5.57 (s, 2H), 4.66-4.58 (m, 1H), 4.56-4.43 (m, 3H), 4.24-4.14 (m, 3H), 3.08 (d, J = 12.1 Hz, 1H), 2.27 (s, 3H), 2.10 (td, J = 8.6, 4.8 Hz, 1H), 1.84-1.68 (m, 1H), 1.02 (td, J = 8.2, 5.3 Hz, 1H), 0.77 (q, J = 4.5 Hz, 1H) | 10.5 min, 100% 10.7 min, 100% |

TABLE 15-continued

| Example | Name | Formula I | LCMS, [M + H]⁺ | ¹H NMR (400 MHz, MeOD) δ | HPLC-1: Rt min, purity; HPLC-2: Rt min, purity |
|---|---|---|---|---|---|
| 430 | 2-(5-(3-((4-(1-(4-(2,3-Dimethylphenoxy)butanoyl)-1,2,3,4-tetrahydroquinolin-5-yl)-1H-pyrazol-1-yl)methyl)phenyl)-2H-tetrazol-2-yl)acetic acid | | 607.1 | 8.07 (d, J = 7.7 Hz, 1H), 8.01 (s, 1H), 7.69 (s, 1H), 7.59-7.52 (m, 2H), 7.49-7.43 (m, 1H), 7.19 (s, 3H), 6.97 (t, J = 8.0 Hz, 1H), 5.53 (s, 2H), 5.44 (s, 2H), 3.89 (t, J = 5.5 Hz, 2H), 3.69 (t, J = 6.6 Hz, 2H), 2.70 (t, J = 6.9 Hz, 2H), 2.58 (br. s., 2H), 2.14-2.03 (m, 5H), 1.86 (br. s., 2H), 1.81-1.76 (m, 2H) | 9.8 min, 96.9% 10.1 min, 97.9% |
| 431 | 2-Amino-5-((4-(1-(4-(2,3-dimethylphenoxy)butanoyl)-1,2,3,4-tetrahydroquinolin-5-yl)-1H-pyrazol-1-yl)methyl)benzoic acid | | 539.1 | 7.74 (d, J = 2.2 Hz, 1H), 7.55 (s, 1H), 7.49 (s, 1H), 7.23 (dd, J = 8.8, 2.2 Hz, 1H), 7.13 (s, 2H), 6.96-6.90 (m, 1H), 6.70 (d, J = 8.2 Hz, 1H), 6.67-6.61 (m, 2H), 5.14 (s, 2H), 3.85 (t, J = 5.8 Hz, 2H), 3.65 (t, J = 6.6 Hz, 2H), 2.65 (t, J = 7.1 Hz, 2H), 2.51 (br. s., 2H), 2.08-1.99 (m, 5H), 1.81 (br. s., 2H), 1.77-1.71 (m, 2H) | 9.4 min, 92.8% 9.6 min, 92.1% |

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 432 | 2-(3-(3-((4-(1-(4-(2,3-Dimethylphenoxy)butanoyl)-1,2,3,4-tetrahydroquinolin-5-yl)-1H-pyrazol-1-yl)methyl)phenyl)-1,2,4-oxadiazol-5-yl)acetic acid | | 606.2 | 8.07 (d, J = 7.8 Hz, 1H), 7.99 (s, 1H), 7.59 (s, 1H), 7.51 (t, J = 7.7 Hz, 1H), 7.44 (s, 1H), 7.33 (s, 1H), 7.17 (s, 2H), 6.99 (s, 1H), 6.71 (d, J = 7.8 Hz, 1H), 6.63 (s, 1H), 5.45 (s, 2H), 4.09 (s, 2H), 3.91 (br. s., 2H), 3.78 (t, J = 6.9 Hz, 2H), 2.76 (t, J = 7.1 Hz, 2H), 2.54 (br. s., 2H), 2.19-2.12 (m, 5H), 1.91-1.79 (m, 5H) | 9.9 min, 95.0% 10.1 min, 90.4% |
| 433 | 3-((5-(1-(4-(2,3-Dimethylphenoxy)butanoyl)-1,2,3,4-tetrahydroquinolin-5-yl)-1,2,4-oxadiazol-3-yl)methyl)benzoic acid | | 526.1 | 8.16 (s, 1H), 8.02 (d, J = 7.7 Hz, 1H), 7.88 (d, J = 8.8 Hz, 1H), 7.65 (d, J = 7.7 Hz, 1H), 7.47 (t, J = 7.7 Hz, 1H), 7.31 (t, J = 8.0 Hz, 1H), 6.98 (t, J = 8.0 Hz, 1H), 6.69 (d, J = 7.7 Hz, 1H), 6.62 (d, J = 8.2 Hz, 1H), 4.23 (s, 2H), 3.94 (br. s., 2H), 3.81 (t, J = 6.6 Hz, 2H), 3.08 (br. s., 2H), 2.73 (t, J = 7.1 Hz, 2H), 2.24-2.13 (m, 5H), 1.94 (t, J = 6.3 Hz, 5H) | 9.9 min, 99.2% 10.0 min, 99.5% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 434 | (1aR,7bS)-2-(3-Chloro-2-methyl)phenoxy)ethyl 7-(1-(3-(2-hydroxypropan-2-yl)benzyl)-1H-pyrazol-4-yl)-1a,2-dihydro-1H-cyclopropa[c]quinoline-3(7bH)-carboxylate | | 572.3 | 7.69 (s, 1H), 7.51 (s, 1H), 7.45-7.40 (m, 2H), 7.32 (t, J = 7.8 Hz, 1H), 7.12 (d, J = 7.3 Hz, 1H), 7.09-6.95 (m, 4H), 6.70 (d, J = 8.1 Hz, 1H), 5.35 (s, 2H), 4.64-4.55 (m, 1H), 4.55-4.38 (m, 2H), 4.23-4.15 (m, 2H), 3.05 (d, J = 12.6 Hz, 1H), 2.27 (s, 3H), 2.19-2.10 (m, 1H), 1.72 (d, J = 6.3 Hz, 2H), 1.56 (s, 6H), 1.26 (d, J = 6.3 Hz, 1H), 1.02-0.93 (m, 1H), 0.74 (q, J = 4.5 Hz, 1H) | 11.8 min, 95.0% 12.7 min, 93.1% |
| 435 | (1aR,7bS)-2-(3-Chloro-2-methyl)phenoxy)ethyl 7-(1-(5-amino-2-chlorobenzyl)-1H-pyrazol-4-yl)-1a,2-dihydro-1H-cyclopropa[c]quinoline-3(7bH)-carboxylate | | 563.2 | 7.78 (s, 1H), 7.65 (s, 1H), 7.17 (d, J = 8.3 Hz, 1H), 7.12-7.02 (m, 3H), 7.01-6.96 (m, 1H), 6.71 (d, J = 7.8 Hz, 1H), 6.61 (dd, J = 8.5, 2.7 Hz, 1H), 6.57 (s, 1H), 5.41 (s, 2H), 4.66-4.57 (m, 1H), 4.56-4.39 (m, 2H), 4.19 (d, J = 5.1 Hz, 2H), 3.08 (d, J = 11.6 Hz, 1H), 2.27 (s, 3H), 2.15-2.02 (m, 1H), 1.76 (d, J = 5.3 Hz, 1H), 1.02 (d, J = 5.1 Hz, 1H), 0.76 (d, J = 5.3 Hz, 1H) | 11.0 min, 98.0% 10.3 min, 95.4% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 436 | 3-Chloro-4-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzoic acid | 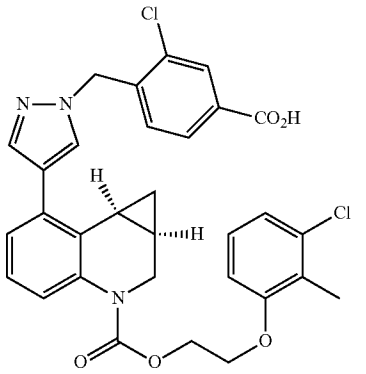 [SMILES: Cc1c(Cl)cccc1OCCOC(=O)N1C[C@@H]2C[C@@H]2c2c(-c3cnn(Cc4ccc(C(=O)O)cc4Cl)c3)cccc21] | 592.2 | 8.16 (d, J = 1.5 Hz, 1H), 7.99 (d, J = 6.6 Hz, 1H), 7.84 (s, 1H), 7.70 (s, 1H), 7.24 (d, J = 7.8 Hz, 1H), 7.13-7.08 (m, 2H), 7.06 (d, J = 8.1 Hz, 1H), 7.03-6.99 (m, 1H), 6.74 (d, J = 8.1 Hz, 1H), 5.63 (s, 2H), 4.67-4.60 (m, 1H), 4.58-4.45 (m, 2H), 4.27-4.16 (m, 2H), 3.11 (d, J = 12.1 Hz, 1H), 2.29 (s, 3H), 2.16-2.06 (m, 1H), 1.85-1.74 (m, 1H), 1.10-1.00 (m, 1H), 0.80 (d, J = 4.5 Hz, 1H) | 10.9 min, 98.8% 11.1 min, 100% |
| 437 | 3((4-((1aR,7bS)-3-(4-(3-Methoxy-2-methylphenoxy)butanoyl)-1a,2,3,7b-tetrahydro-1H-cyclopropa[c]quinolin-7-yl)-1H-pyrazol-1-yl)methyl)benzoic acid | 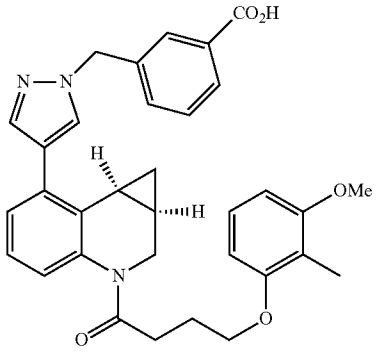 [SMILES: COc1cccc(OCCCC(=O)N2C[C@@H]3C[C@@H]3c3c(-c4cnn(Cc5cccc(C(=O)O)c5)c4)cccc32)c1C] | 552.3 | 8.10 (d, J = 7.3 Hz, 1H), 8.04 (s, 1H), 7.81 (s, 1H), 7.63 (s, 1H), 7.60-7.49 (m, 2H), 7.24-7.11 (m, 2H), 7.07 (t, J = 8.3 Hz, 1H), 7.02 (br. s., 1H), 6.59-6.41 (m, 2H), 5.52 (br. s., 2H), 4.08-3.97 (m, 1H), 3.96-3.86 (m, 1H), 3.80 (s, 3H), 2.86-2.71 (m, 2H), 2.71-2.59 (m, 1H), 2.28-2.09 (m, 2H), 2.09-2.00 (m, 1H), 1.86 (br. s., 3H), 1.81-1.68 (m, 1H), 1.01-0.85 (m, 1H), 0.64-0.50 (m, 1H) | N/A |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 438 | 3-((4-((1aR,7bS)-3-((2-(3-Methoxy-2-methylphenoxy)ethoxy)carbonyl)-1a,2,3,7b-tetrahydro-1H-cyclopropa[c]quinolin-7-yl)-1H-pyrazol-1-yl)methyl)benzoic acid | | 554.3 | 8.10 (d, J = 7.3 Hz, 1H), 8.04 (s, 1H), 7.84 (s, 1H), 7.62 (s, 1H), 7.58-7.50 (m, 2H), 7.32 (br. s., 1H), 7.14-7.06 (m, 3H), 6.57 (d, J = 8.3 Hz, 1H), 6.52 (d, J = 8.3 Hz, 1H), 5.52 (br. s., 2H), 4.67-4.51 (m, 3H), 4.25-4.17 (m, 2H), 3.84 (s, 3H), 3.10 (d, J = 13.1 Hz, 1H), 2.17-2.06 (m, 4H), 1.83-1.73 (m, 1H), 1.04 (d, J = 4.8 Hz, 1H), 0.87-0.75 (m, 1H) | 10.0 min, 99.8% 10.4 min, 99.9% |
| 439 | 3-Chloro-4-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)-5-fluorobenzoic acid | | 610.2 | 7.92 (s, 1H), 7.70 (d, J = 9.3 Hz, 1H), 7.58 (s, 1H), 6.98 (t, J = 8.0 Hz, 2H), 6.94-6.88 (m, 1H), 6.64 (d, J = 7.7 Hz, 1H), 5.57 (br. s., 2H), 4.48-4.32 (m, 2H), 4.12 (br. s., 2H), 3.00 (d, J = 12.6 Hz, 1H), 2.19 (s, 3H), 2.02 (d, J = 17.0 Hz, 1H), 1.69 (br. s., 1H), 0.94 (br. s., 1H), 0.69 (br. s., 1H) | 10.0 min, 99.3% 11.1 min, 100% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 440 | (1aR,7bS)-2-(3-Chloro-2-methylphenoxy)ethyl 7-(1-(2-chloro-5-(ethoxycarbonyl)benzyl)-1H-pyrazol-4-yl)-1a,2-dihydro-1H-cyclopropa[c]quinoline-3(7bH)-carboxylate | 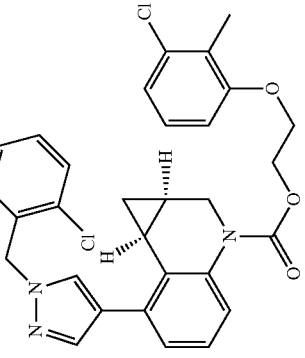 | 620.3 | 7.95 (dd, J = 8.2, 2.2 Hz, 1H), 7.83 (d, J = 2.2 Hz, 1H), 7.77 (s, 1H), 7.61 (s, 1H), 7.48 (d, J = 8.2 Hz, 1H), 7.09-7.00 (m, 3H), 7.00-6.94 (m, 1H), 6.69 (d, J = 8.2 Hz, 1H), 5.54 (s, 2H), 4.66-4.56 (m, 1H), 4.55-4.39 (m, 2H), 4.33 (q, J = 7.1 Hz, 2H), 4.24-4.11 (m, 3H), 3.05 (d, J = 12.6 Hz, 1H), 2.25 (s, 3H), 2.08 (td, J = 8.5, 4.9 Hz, 1H), 1.81-1.69 (m, 1H), 1.41-1.28 (m, 3H), 0.99 (td, J = 8.2, 4.9 Hz, 1H), 0.75 (q, J = 4.9 Hz, 1H) | 13.3 min, 98.3% N/A |
| 441 | (1aR,7bS)-2-(3-Chloro-2-methylphenoxy)ethyl 7-(1-(2-chloro-5-(methoxycarbonyl)benzyl)-1H-pyrazol-4-yl)-1a,2-dihydro-1H-cyclopropa[c]quinoline-3(7bH)-carboxylate | 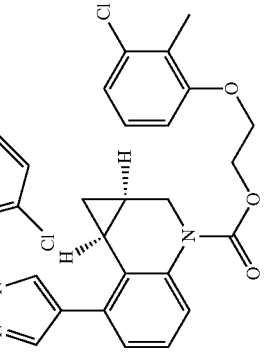 | 606.2 | 8.00 (dd, J = 8.3, 2.3 Hz, 1H), 7.91 (d, J = 2.0 Hz, 1H), 7.84 (d, J = 0.5 Hz, 1H), 7.68-7.66 (m, 1H), 7.53 (d, J = 8.3 Hz, 1H), 7.10 (d, J = 3.8 Hz, 2H), 7.06 (d, J = 8.1 Hz, 1H), 7.03-6.99 (m, 1H), 6.74 (d, J = 8.1 Hz, 1H), 5.60 (s, 2H), 4.63 (ddd, J = 11.9, 5.7, 3.5 Hz, 2H), 4.57-4.44 (m, 3H), 4.22 (dd, J = 5.3, 3.8 Hz, 2H), 3.96-3.88 (m, 3H), 3.11 (d, J = 12.4 Hz, 1H), 2.29 (s, 3H), 2.10 (td, J = 8.5, 4.5 Hz, 1H), 1.80 (dd, J = 5.3, 2.8 Hz, 1H), 1.04 (dd, J = 8.2, 3.2 Hz, 1H), 0.79 (d, J = 5.1 Hz, 1H) | N/A |

TABLE 15-continued

| Example | Name | Formula I | LCMS, [M + H]$^+$ | $^1$H NMR (400 MHz, MeOD) δ | HPLC-1: Rt min, purity; HPLC-2: Rt min, purity |
|---|---|---|---|---|---|
| 442 | 3-((4-((1aR,7bS)-3-((2-(3-Chloro-2-methylphenoxy)ethoxy)carbonyl)-1a,2,3,7b-tetrahydro-1H-cyclopropa[c]quinolin-7-yl)-1H-pyrazol-1-yl)methyl)-4-methoxybenzoic acid | | 588.2 | 8.14 (d, J = 8.6 Hz, 1H), 8.03 (s, 1H), 7.85 (br. s., 1H), 7.65 (br. s., 1H), 7.13-7.04 (m, 3H), 7.03-6.97 (m, 2H), 6.74 (d, J = 8.1 Hz, 2H), 5.51 (br. s, 2H), 4.67-4.59 (m, 1H), 4.57-4.44 (m, 2H), 4.29-4.13 (m, 2H), 4.02-3.90 (m, 3H), 3.10 (d, J = 12.6 Hz, 1H), 2.29 (s, 3H), 2.11 (d, J = 8.6 Hz, 1H), 1.79 (br. s., 1H), 1.04 (br. s., 1H), 0.79 (br. s., 1H) | 10.7 min, 96.3% 10.8 min, 98.5% |
| 443 | 4-((4-((1aR,7bS)-3-((2-(3-Chloro-2-methylphenoxy)ethoxy)carbonyl)-1a,2,3,7b-tetrahydro-1H-cyclopropa[c]quinolin-7-yl)-1H-pyrazol-1-yl)methyl)-3,5-dimethoxybenzoic acid | | 618.3 | 7.71 (s, 1H), 7.59 (s, 1H), 7.36 (s, 2H), 7.11-7.03 (m, 3H), 7.03-6.97 (m, 1H), 6.73 (d, J = 8.1 Hz, 1H), 5.54 (s, 2H), 4.68-4.58 (m, 1H), 4.58-4.42 (m, 2H), 4.29-4.14 (m, 2H), 4.02-3.88 (m, 6H), 3.08 (d, J = 13.4 Hz, 1H), 2.29 (s, 3H), 2.20-2.10 (m, 1H), 1.75 (d, J = 5.6 Hz, 1H), 0.99 (d, J = 4.8 Hz, 1H), 0.78 (d, J = 4.8 Hz, 1H) | N/A |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 444 | 2-(5-(4-Chloro-3-(((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)phenyl)-2H-tetrazol-2-yl)acetic acid | | 674.3 | 8.07 (dd, J = 8.1, 2.0 Hz, 1H), 7.96 (s, 1H), 7.73 (s, 2H), 7.63 (d, J = 8.3 Hz, 1H), 7.20 (d, J = 6.6 Hz, 1H), 7.17-7.13 (m, 1H), 7.06 (d, J = 8.1 Hz, 2H), 6.95 (d, J = 8.1 Hz, 1H), 6.84 (d, J = 8.3 Hz, 1H), 5.62 (s, 2H), 5.58 (s, 2H), 4.58-4.43 (m, 3H), 4.23 (br. s., 2H), 3.04 (d, J = 13.1 Hz, 1H), 2.25-2.11 (m, 4H), 1.88-1.73 (m, 1H), 1.02 (td, J = 8.2, 5.1 Hz, 1H), 0.61 (d, J = 4.5 Hz, 1H) | 11.2 min, 99.6% 11.4 min, 100% |
| 445 | 2-(4-Chloro-3-(((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)phenoxy)acetic acid | | 622.3 | 7.88 (s, 1H), 7.71 (s, 1H), 7.35 (d, J = 8.8 Hz, 1H), 7.19 (d, J = 7.1 Hz, 1H), 7.16-7.11 (m, 1H), 7.10-7.02 (m, 1H), 6.97-6.89 (m, 1H), 6.89 (d, J = 3.3 Hz, 1H), 6.84 (d, J = 7.7 Hz, 1H), 6.56 (d, J = 2.7 Hz, 1H), 5.50-5.46 (m, 2H), 4.59 (s, 2H), 4.57-4.43 (m, 3H), 4.22 (br. s., 1H), 3.02 (d, J = 13.2 Hz, 1H), 2.25-2.07 (m, 4H), 1.84-1.75 (m, 1H), 1.02 (td, J = 8.5, 4.9 Hz, 1H), 0.61 (d, J = 4.9 Hz, 1H) | 11.1 min, 99.0% 11.2 min, 100% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 446 | (1aR,7bS)-2-(3-Chloro-2-methylphenoxy)ethyl 7-(1-(2-chloro-5-(2-hydroxyethoxy)benzyl)-1H-pyrazol-4-yl)-1a,2-dihydro-1H-cyclopropa[c]quinoline-3(7bH)-carboxylate | | 608.3 | 7.73 (d, J = 0.5 Hz, 1H), 7.63 (s, 1H), 7.31 (d, J = 8.6 Hz, 1H), 7.12-7.09 (m, 2H), 7.08-7.03 (m, 2H), 7.01-6.97 (m, 1H), 6.83 (dd, J = 8.7, 2.9 Hz, 1H), 6.72 (d, J = 7.8 Hz, 1H), 6.69 (d, J = 3.0 Hz, 1H), 5.43 (s, 2H), 4.65-4.58 (m, 1H), 4.56-4.42 (m, 2H), 4.24-4.18 (m, 2H), 4.03-3.97 (m, 2H), 3.95-3.89 (m, 2H), 3.09 (d, J = 12.4 Hz, 1H), 2.28 (s, 3H), 2.17 (td, J = 8.6, 4.5 Hz, 1H), 1.87-1.68 (m, 1H), 1.01 (td, J = 8.3, 5.1 Hz, 1H), 0.77 (q, J = 4.9 Hz, 1H) | 12.3 min, 92.5% 13.8 min, 95.1% |
| 447 | (1aR,7bS)-2-(3-Chloro-2-methylphenoxy)ethyl 7-(1-(2-hydroxy-5-(methoxycarbonyl)benzyl)-1H-pyrazol-4-yl)-1a,2-dihydro-1H-cyclopropa[c]quinoline-3(7bH)-carboxylate | | 588.2 | 8.04-7.90 (m, 2H), 7.74 (s, 1H), 7.66 (s, 1H), 7.13-6.98 (m, 5H), 6.74 (d, J = 7.8 Hz, 1H), 5.35 (s, 2H), 4.70-4.60 (m, 1H), 4.57-4.40 (m, 2H), 4.30-4.15 (m, 2H), 3.92 (s, 3H), 3.08 (d, J = 13.4 Hz, 1H), 2.29 (s, 3H), 2.08 (td, J = 8.6, 4.8 Hz, 1H), 1.77 (d, J = 5.8 Hz, 1H), 1.05 (td, J = 8.3, 5.2 Hz, 1H), 0.79 (q, J = 4.9 Hz, 1H) | 10.3 min, 97.6% 11.9 min, 98.3% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 448 | 2-(2-(4-Chloro-3-((4-((1aR,7bS)-3-(2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)phenoxy)ethoxy)acetic acid | | 666.3 | 7.81 (d, J = 0.5 Hz, 1H), 7.71 (s, 1H), 7.33 (d, J = 8.8 Hz, 1H), 7.10 (d, J = 4.0 Hz, 2H), 7.07 (s, 1H), 7.05-6.97 (m, 1H), 6.93-6.84 (m, 3H), 6.74 (d, J = 8.1 Hz, 1H), 5.47 (s, 2H), 4.69-4.59 (m, 1H), 4.57-4.41 (m, 2H), 4.22 (s, 4H), 4.17 (dd, J = 5.3, 3.8 Hz, 2H), 3.94-3.82 (m, 1H), 3.11 (d, J = 13.4 Hz, 1H), 2.29 (s, 3H), 2.12 (td, J = 8.5, 4.8 Hz, 1H), 1.90-1.69 (m, 1H), 1.05 (td, J = 8.3, 5.3 Hz, 1H), 0.79 (q, J = 5.1 Hz, 1H) | 11.4 min, 94.8% 11.6 min, 98.7% |
| 449 | 4-Chloro-3-((4-((1aR,7bS)-3-(2-(3-chloro-2-methylphenoxy)propoxy)carbonyl)-1a,2,3,7b-tetrahydro-1H-cyclopropa[c]quinolin-7-yl)-1H-pyrazol-1-yl)methyl)benzoic acid | | 606.1 | 8.20 (s, 1H), 8.01 (dd, J = 8.2, 2.2 Hz, 1H), 7.83 (s, 1H), 7.75 (d, J = 2.7 Hz, 1H), 7.50 (d, J = 8.2 Hz, 1H), 7.12-6.89 (m, 4H), 6.80-6.64 (m, 1H), 5.53 (s, 2H), 4.59 (dd, J = 9.9, 6.0 Hz, 1H), 4.39-4.30 (m, 1H), 4.26-4.14 (m, 1H), 3.00 (d, J = 12.6 Hz, 1H), 2.22 (br. s., 3H), 2.16 (br. s., 1H), 2.11-2.02 (m, 1H), 2.10-2.02 (m, 1H), 1.71 (br. s., 1H), 1.32 (d, J = 5.5 Hz, 3H), 1.01-0.93 (m, 1H), 0.73-0.59 (m, 1H) | 11.2 min, 94.2% 11.2 min, 100% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 450 | 4-Chloro-3-((4-((1aR,7bS)-3-((2-(3-chloro-2-fluorophenoxy)ethoxy)carbonyl)-1a,2,3,7b-tetrahydro-1H-cyclopropa[c]quinolin-7-yl)-1H-pyrazol-1-yl)methyl)benzoic acid | 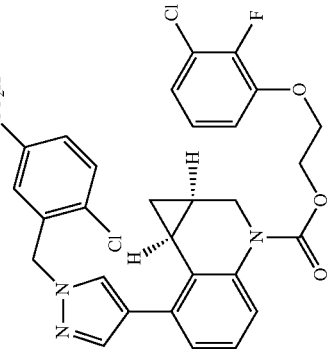 | 596.1 | 8.11 (d, J = 1.9 Hz, 1H), 8.05 (dd, J = 8.3, 2.2 Hz, 1H), 7.88 (s, 1H), 7.76 (s, 1H), 7.56 (d, J = 8.3 Hz, 1H), 7.33 (d, J = 4.4 Hz, 1H), 7.18-7.10 (m, 3H), 7.05-6.94 (m, 3H), 6.93-6.83 (m, 1H), 5.62-5.58 (m, 2H), 5.60 (s, 2H), 4.67-4.59 (m, 1H), 4.58-4.43 (m, 2H), 4.32 (dd, J = 5.6, 3.4 Hz, 2H), 3.11 (d, J = 12.7 Hz, 1H), 2.23-2.03 (m, 1H), 1.80 (td, J = 7.9, 5.9 Hz, 1H), 1.06 (td, J = 8.3, 5.2 Hz, 1H), 0.82 (q, J = 5.0 Hz, 1H) | 10.3 min, 92.0% 10.3 min, 95.7% |
| 451 | 3-((4-(1-(4-(3-Chloro-2-methylphenylthio)butanoyl)-1,2,3,4-tetrahydroquinolin-5-yl)-1H-pyrazol-1-yl)methyl)benzoic acid | 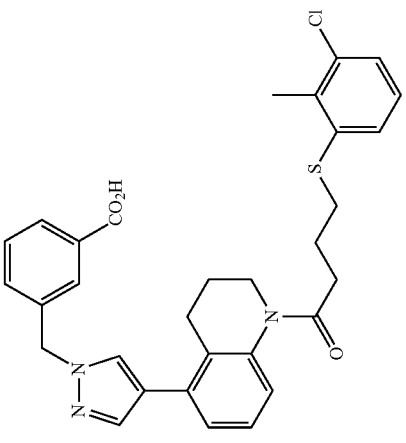 | 560.1 | 8.16-7.94 (m, 2H), 7.67 (s, 1H), 7.57-7.37 (m, 3H), 7.21-7.06 (m, 4H), 7.04-6.90 (m, 2H), 5.43 (s, 2H), 3.75 (t, J = 6.6 Hz, 2H), 2.90 (t, J = 6.3 Hz, 2H), 2.77-2.55 (m, 4H), 2.33 (s, 3H), 2.10-1.79 (m, 4H) | 13.8 min, 99.9% 12.5 min, 99.8% |

TABLE 15-continued

| Example | Name | Formula I | LCMS, [M+H]+ | 1H NMR (400 MHz, MeOD) δ | HPLC-1: Rt min, purity; HPLC-2: Rt min, purity |
|---|---|---|---|---|---|
| 452 | (3-((4-(1-(4-(2,3-Dimethylphenoxy)butanoyl)-1,2,3,4-tetrahydroquinolin-5-yl)-1H-pyrazol-1-yl)methyl)phenyl)methanesulfonic acid | | 574.3 | 7.57 (br. s., 1H), 7.46-7.40 (m, 3H), 7.39-7.31 (m, 2H), 7.29-7.16 (m, 3H), 6.99 (t, J = 8.0 Hz, 1H), 6.77-6.62 (m, 2H), 5.38 (s, 2H), 4.08 (s, 2H), 3.84 (br. s., 2H), 3.73 (t, J = 6.9 Hz, 2H), 2.83 (t, J = 6.6 Hz, 2H), 2.40 (br. s., 3H), 2.17-2.07 (m, 2H), 2.00 (br. s., 2H), 1.77 (br. s., 3H), 1.62 (br. s., 2H) | N/A 8.5 min, 94.3% |
| 453 | (S)-3-(1-(3-((4-(1-(4-(2,3-Dimethylphenoxy)butanoyl)-1,2,3,4-tetrahydroquinolin-5-yl)-1H-pyrazol-1-yl)methyl)phenyl)-2,5-dioxoimidazolidin-4-yl)-N,N,N-trimethylpropan-1-aminium | | 677.5 | 8.58 (s, 1H), 7.96 (s, 1H), 7.56 (s, 1H), 7.41 (t, J = 7.7 Hz, 1H), 7.31-7.05 (m, 5H), 6.91 (t, J = 7.7 Hz, 1H), 6.64 (t, J = 6.9 Hz, 2H), 5.35 (s, 2H), 4.21 (d, J = 4.9 Hz, 1H), 3.92-3.74 (m, 2H), 3.60 (t, J = 6.6 Hz, 2H), 3.27 (t, J = 7.7 Hz, 2H), 2.98 (s, 9H), 2.61 (t, J = 6.9 Hz, 2H), 2.53 (br. s., 3H), 2.03 (s, 3H), 1.98-1.88 (m, 2H), 1.87-1.50 (m, 7H) | 7.1 min, 96.8% 9.3 min, 99.8% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 454 | 4-(2,3-Dimethylphenoxy)-1-(5-(2-methylthiazol-5-yl)-3,4-dihydroquinolin-1(2H)-yl)butan-1-one | | 421.2 | 7.44-7.40 (m, 1H), 7.25-7.15 (m, 3H), 7.02 (t, J = 7.7 Hz, 1H), 6.76 (d, J = 1.1 Hz, 1H), 6.65 (d, J = 8.2 Hz, 1H), 3.96 (t, J = 5.5 Hz, 2H), 3.79 (t, J = 6.9 Hz, 2H), 2.83-2.69 (m, 5H), 2.64 (t, J = 6.3 Hz, 2H), 2.29-2.14 (m, 5H), 1.97 (br. s., 3H), 1.92-1.83 (m, 2H) | 13.3 min, 100% 11.8 min, 100% |
| 455 | 4-(3-((4-(1-(4-(2,3-Dimethylphenoxy)butanoyl)-1,2,3,4-tetrahydroquinolin-5-yl)-1H-pyrazol-1-yl)methyl)phenoxy)butanoic acid | | 582.3 | 7.61 (s, 1H), 7.52 (s, 1H), 7.25 (t, J = 7.7 Hz, 1H), 7.17 (s, 2H), 6.97 (t, J = 8.0 Hz, 1H), 6.89-6.78 (m, 4H), 6.74-6.62 (m, 2H), 5.27 (s, 2H), 3.97 (t, J = 6.3 Hz, 2H), 3.89 (t, J = 5.8 Hz, 2H), 3.68 (t, J = 6.9 Hz, 2H), 2.68 (t, J = 6.9 Hz, 2H), 2.55 (d, J = 6.0 Hz, 2H), 2.42 (t, J = 7.4 Hz, 2H), 2.10 (s, 3H), 2.09-2.02 (m, 2H), 1.98 (t, J = 6.9 Hz, 2H), 1.85 (br. s., 3H), 1.78 (quin, J = 6.6 Hz, 2H) | 12.2 min, 99.0% 11.1 min, 99.9% |

TABLE 15-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 456 | 2-(3-(((4-(1-(4-(2,3-Dimethylphenoxy)butanoyl)-1,2,3,4-tetrahydroquinolin-5-yl)-1H-pyrazol-1-yl)methyl)phenoxy)acetic acid | | 554.2 | 7.54 (s, 1H), 7.45 (s, 1H), 7.19 (t, J = 8.0 Hz, 1H), 7.09 (s, 3H), 6.89 (t, J = 8.0 Hz, 1H), 6.81 (d, J = 7.7 Hz, 1H), 6.79-6.71 (m, 2H), 6.66-6.56 (m, 2H), 5.20 (s, 2H), 4.54 (s, 2H), 3.80 (t, J = 5.5 Hz, 2H), 3.60 (t, J = 6.9 Hz, 2H), 2.60 (t, J = 7.1 Hz, 2H), 2.49 (t, J = 6.0 Hz, 2H), 2.02 (s, 3H), 1.97 (quin, J = 7.1 Hz, 2H), 1.78 (br. s., 3H), 1.75-1.64 (m, 2H) | 11.6 min, 100% 10.7 min, 99.8% |

* Injection 1 conditions: Column: Waters Acquity UPLC BEH C18, 2.1 x 50 mm, 1.7-um particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.
Injection 2 conditions: Column: Waters Acquity UPLC BEH C18, 2.1 x 50 mm, 1.7-um particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

The compounds exemplified in Table 16 were prepared in a manner analogous to Example 35.

TABLE 16

| Example | Name | Formula I | LCMS, [M + H]+ | ¹H NMR (400 MHz, CDCl₃) δ | HPLC-1: Rt min, purity; HPLC-2: Rt min, purity |
|---|---|---|---|---|---|
| 457 | 3-((5-((1aR,7bS)-3-((2-(3-Chloro-2-methylphenoxy)ethoxy)carbonyl)-1a,2,3,7b-tetrahydro-1H-cyclopropa[c]quinolin-7-yl)-2-fluorobenzyloxy)carbonylamino)propanoic acid | | 597.2 | 7.39 (d, J = 7.6 Hz, 2H), 7.34-7.31 (m, 1H), 7.30 (d, J = 1.5 Hz, 1H), 7.18-7.10 (m, 2H), 7.10-7.05 (m, 2H), 7.05-6.99 (m, 1H), 6.76 (d, J = 8.1 Hz, 1H), 5.34 (br. s., 2H), 5.24-5.14 (m, 1H), 4.71-4.56 (m, 2H), 4.56-4.46 (m, 1H), 4.30-4.19 (m, 2H), 3.56-3.39 (m, 3H), 3.04 (d, J = 12.1 Hz, 1H), 2.58 (br. s., 2H), 2.37-2.21 (m, 3H), 1.94-1.82 (m, 1H), 1.73 (d, J = 5.3 Hz, 1H), 1.04-0.94 (m, 1H), 0.88 (br. s., 1H) | 12.9 min, 99.8% 14.8 min, 100% |
| 458 | 3-((2-Chloro-5-((1aR,7bS)-3-((2-(3-chloro-2-methylphenoxy)ethoxy)carbonyl)-1a,2,3,7b-tetrahydro-1H-cyclopropa[c]quinolin-7-yl)benzyloxy)carbonylamino)propanoic acid | | 613.2 | 7.82 (s, 1H), 7.71 (s, 1H), 7.30 (d, J = 8.8 Hz, 2H), 7.08 (d, J = 4.3 Hz, 2H), 7.05 (d, J = 8.1 Hz, 1H), 7.02-6.98 (m, 1H), 6.95 (br. s., 1H), 6.85 (dd, J = 8.7, 2.7 Hz, 1H), 6.72 (d, J = 7.8 Hz, 1H), 5.43 (s, 2H), 4.68-4.56 (m, 1H), 4.55-4.40 (m, 4H), 3.97 (d, J = 4.8 Hz, 2H), 3.95-3.86 (m, 2H), 3.09 (d, J = 13.1 Hz, 1H), 2.28 (s, 3H), 2.15-2.05 (m, 1H), 1.81-1.70 (m, 1H), 1.03 (td, J = 8.3, 5.2 Hz, 1H), 0.77 (q, J = 4.8 Hz, 1H) | 11.4 min, 99.7% 11.6 min, 100% |
| 459 | 2-((4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzyloxy)carbonylamino)acetic acid | | 679.3 | 7.88 (s, 1H), 7.72 (s, 1H), 7.46 (d, J = 8.3 Hz, 1H), 7.36 (d, J = 8.1 Hz, 1H), 7.21 (d, J = 7.1 Hz, 1H), 7.17-7.14 (m, 2H), 7.12-7.04 (m, 3H), 6.97 (d, J = 8.1 Hz, 1H), 6.86 (d, J = 8.1 Hz, 1H), 5.54 (s, 2H), 5.07 (s, 2H), 4.61-4.44 (m, 3H), 4.24 (br. s., 2H), 3.80 (s, 2H), 3.06 (d, J = 12.9 Hz, 1H), 2.29-2.09 (m, 4H), 1.82 (d, J = 6.1 Hz, 1H), 1.09-0.96 (m, 1H), 0.63 (d, J = 4.8 Hz, 1H) | N/A |
| 460 | 2-((2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)phenoxy)ethoxy)carbonylamino)acetic acid | | 709.3 | 7.82 (s, 1H), 7.71 (s, 1H), 7.30 (d, J = 8.8 Hz, 2H), 7.08 (d, J = 4.3 Hz, 2H), 7.05 (d, J = 8.1 Hz, 1H), 7.02-6.98 (m, 1H), 6.95 (br. s., 1H), 6.85 (dd, J = 8.7, 2.7 Hz, 1H), 6.72 (d, J = 7.8 Hz, 1H), 5.43 (s, 2H), 4.68-4.56 (m, 1H), 4.55-4.40 (m, 4H), 3.97 (d, J = 4.8 Hz, 2H), 3.95-3.86 (m, 2H), 3.09 (d, J = 13.1 Hz, 1H), 2.28 (s, 3H), 2.15-2.05 (m, 1H), 1.81-1.70 (m, 1H), 1.03 (td, J = 8.3, 5.2 Hz, 1H), 0.77 (q, J = 4.8 Hz, 1H) | 11.2 min, 94.8% 11.7 min, 100% |

The compounds exemplified in Table 17 were prepared in a manner analogous to Example 63.

TABLE 17

| Example | Name | —X—Y | LCMS, [M + H]+ | 1H NMR (500 MHz, CDCl3) δ | HPLC-1: Rt min, purity; HPLC-2: Rt min, purity |
|---|---|---|---|---|---|
| 461 | 2-Chloro-3-((4-(1-(4-(2,3-dimethylphenoxy)butanoyl)-1,2,3,4-tetrahydroquinolin-5-yl)-1H-pyrazol-1-yl)methyl)benzoic acid | 2-Cl, 3-CO2H benzyl | 558.0 | 7.97-7.85 (m, 1H), 7.65-7.55 (m, 1H), 7.46-7.40 (m, 1H), 7.38-7.31 (m, 1H), 7.25-7.22 (m, 1H), 7.21-7.14 (m, 2H), 7.04-6.97 (m, 1H), 6.73 (d, J = 7.4 Hz, 1H), 6.64 (d, J = 8.3 Hz, 1H), 5.58-5.51 (m, 2H), 4.00-3.88 (m, 2H), 3.79 (t, J = 6.7 Hz, 2H), 2.79-2.71 (m, 2H), 2.59 (br. s., 2H), 2.26-2.12 (m, 5H), 1.99-1.88 (m, 3H), 1.88-1.82 (m, 2H) | 12.5 min, 96.7% 11.5 min, 99.7% |
| 462 | 2-(2-Chloro-3-((4-(1-(4-(2,3-dimethylphenoxy)butanoyl)-1,2,3,4-tetrahydroquinolin-5-yl)-1H-pyrazol-1-yl)methyl)benzamido)ethanesulfonic acid | 2-Cl, 3-C(O)NH-CH2CH2-SO3H benzyl | 665.0 | 7.69 (br. s., 1H), 7.55 (br. s., 1H), 7.52-7.46 (m, 1H), 7.38 (t, J = 7.7 Hz, 1H), 7.28-7.20 (m, 2H), 7.17 (dd, J = 7.8, 1.5 Hz, 2H), 6.97 (t, J = 7.8 Hz, 1H), 6.69 (d, J = 7.4 Hz, 1H), 6.67 (s, 1H), 5.59-5.52 (m, 2H), 5.61-5.50 (m, 2H), 3.87 (br. s., 2H), 3.79 (t, J = 6.9 Hz, 2H), 3.74 (t, J = 6.7 Hz, 2H), 3.10 (t, J = 6.9 Hz, 2H), 2.80 (t, J = 6.7 Hz, 2H), 2.50 (br. s., 2H), 2.17-2.04 (m, 5H), 1.86-1.78 (m, 2H), 1.75 (br. s., 2H), 1.91-1.58 (m, 5H) | 13.6 min, 99.3% 8.7 min, 100% |
| 463 | 5-((4-(1-(4-(2,3-Dimethylphenoxy)butanoyl)-1,2,3,4-tetrahydroquinolin-5-yl)-1H-pyrazol-1-yl)methyl)isophthalic acid | 3,5-di-CO2H benzyl | 568.1 | 8.59 (t, J = 1.5 Hz, 1H), 8.12 (d, J = 1.7 Hz, 2H), 7.65 (br. s., 1H), 7.50 (s, 1H), 7.29-7.20 (m, 2H), 7.16 (br. s., 1H), 6.95 (t, J = 7.8 Hz, 1H), 6.64 (d, J = 7.4 Hz, 2H), 5.51 (s, 2H), 3.85 (br. s., 2H), 3.74 (t, J = 6.7 Hz, 2H), 2.84-2.78 (m, 2H), 2.48 (br. s., 2H), 2.16-2.08 (m, 2H), 2.01 (s, 5H), 1.84-1.76 (m, 2H), 1.71 (br. s., 3H) | 10.6 min, 94.8% 10.2 min, 95.4% |
| 464 | 2-(3-((4-(1-(4-(2,3-Dimethylphenoxy)butanoyl)-1,2,3,4-tetrahydroquinolin-5-yl)-1H-pyrazol-1-yl)methyl)benzamido)-N,N,N-trimethylethanaminium, TFA salt | 3-C(O)NH-CH2CH2-N+(CH3)3 benzyl | 608.3 | 7.84-7.81 (m, 1H), 7.80-7.76 (m, 1H), 7.71-7.61 (m, 1H), 7.53-7.45 (m, 3H), 7.28-7.17 (m, 2H), 7.19-7.09 (m, 1H), 7.03-6.90 (m, 1H), 6.71-6.58 (m, 2H), 5.46-5.40 (m, 2H), 3.92-3.79 (m, 4H), 3.74 (t, J = 6.7 Hz, 2H), 3.57 (t, J = 6.7 Hz, 2H), 3.28-3.19 (m, 9H), 2.80 (t, J = 6.9 Hz, 2H), 2.49 (br. s., 2H), 2.18-2.07 (m, 2H), 2.03 (br. s., 3H), 1.90-1.60 (m, 6H) | 8.0 min, 96.0% 9.6 min, 96.6% |
| 465 | 4-(2,3-Dimethylphenoxy)-1-(5-(1-(pyridin-3-ylmethyl)-1H-pyrazol-4-yl)-3,4-dihydroquinolin-1(2H)-yl)butan-1-one | pyridin-3-ylmethyl | 481.1 | 8.66-8.49 (m, 1H), 7.66-7.59 (m, 1H), 7.56 (s, 1H), 7.34 (s, 2H), 7.23-7.11 (m, 3H), 7.07-6.94 (m, 1H), 6.81-6.69 (m, 1H), 6.68-6.56 (m, 1H), 5.36 (s, 2H), 3.93 (t, J = 5.4 Hz, 2H), 3.78 (t, J = 6.9 Hz, 2H), 2.84-2.68 (m, 2H), 2.64-2.42 (m, 2H), 2.25-2.05 (m, 5H), 1.90 (br. s., 2H), 1.88-1.79 (m, 2H), 1.67-1.46 (m, 2H) | 7.7 min, 95.0% 9.1 min, 97.6% |

TABLE 17-continued

| Example | Name | —X—Y | LCMS, [M + H]+ | 1H NMR (500 MHz, CDCl3) δ | HPLC-1: Rt min, purity; HPLC-2: Rt min, purity |
|---|---|---|---|---|---|
| 466 | 1-(Carboxymethyl)-3-((4-(1-(4-(2,3-dimethylphenoxy)butanoyl)-1,2,3,4-tetrahydroquinolin-5-yl)-1H-pyrazol-1-yl)methyl)pyridinium, TFA salt | pyridinium-CH2CO2H | 539.1 | 9.04-8.84 (m, 2H), 8.54 (d, J = 8.0 Hz, 1H), 8.16 (dd, J = 8.1, 6.2 Hz, 1H), 7.82 (br. s., 1H), 7.56 (s, 1H), 7.35-7.13 (m, 3H), 6.97 (t, J = 8.0 Hz, 1H), 6.75-6.58 (m, 2H), 5.66 (s, 2H), 5.53 (s, 2H), 3.88 (br. s., 2H), 3.75 (t, J = 6.7 Hz, 2H), 2.80 (t, J = 6.9 Hz, 2H), 2.54 (br. s., 2H), 2.19-1.99 (m, 5H), 1.87-1.71 (m, 5H) | 7.2 min, 98.1% 8.5 min, 98.5% |
| 467 | 3-((4-(1-(4-(2,3-Dimethylphenoxy)butanoyl)-1,2,3,4-tetrahydroquinolin-5-yl)-1H-pyrazol-1-yl)methyl)-1-methylpyridinium | 1-methylpyridinium | 495.1 | 9.21 (br. s., 1H), 8.69-8.58 (m, 1H), 8.37 (d, J = 8.0 Hz, 1H), 7.96 (t, J = 6.9 Hz, 1H), 7.71 (s, 1H), 7.59 (s, 1H), 7.22-7.09 (m, 3H), 7.08-6.97 (m, 1H), 6.74 (d, J = 7.4 Hz, 1H), 6.65 (d, J = 8.0 Hz, 1H), 5.64 (s, 2H), 4.50 (s, 3H), 3.95 (br. s., 2H), 3.79 (t, J = 6.7 Hz, 2H), 2.74 (t, J = 7.2 Hz, 2H), 2.61 (br. s., 2H), 2.28-2.13 (m, 5H), 1.95 (br. s., 3H), 1.90-1.83 (m, 2H) | 8.3 min, 93.1% 9.7 min, 98.5% |
| 468 | 2-(2-(3-((4-(1-(4-(2,3-Dimethylphenoxy)butanoyl)-1,2,3,4-tetrahydroquinolin-5-yl)-1H-pyrazol-1-yl)methyl)phenylamino)acetamido)ethanesulfonic acid | phenyl-NH-CH2-C(O)NH-CH2CH2SO3H | 660.1 | 7.75 (br. s., 1H), 7.56 (br. s., 1H), 7.49-7.38 (m, 1H), 7.31-7.10 (m, 6H), 6.97 (t, J = 7.8 Hz, 1H), 6.74-6.60 (m, 2H), 5.48-5.36 (m, 2H), 4.03 (s, 2H), 3.87 (br. s., 2H), 3.75 (t, J = 6.7 Hz, 2H), 3.67-3.57 (m, 2H), 2.95 (t, J = 6.5 Hz, 2H), 2.80 (t, J = 6.9 Hz, 2H), 2.52 (br. s., 2H), 2.16-2.10 (m, 2H), 2.06 (br. s., 3H), 1.89-1.63 (m, 5H)* | 13.2 min, 99.7% 8.5 min, 99.7% |
| 469 | 2-(3-((4-(1-(4-(2,3-Dimethylphenoxy)butanoyl)-1,2,3,4-tetrahydroquinolin-5-yl)-1H-pyrazol-1-yl)methyl)phenylamino)acetic acid | phenyl-NH-CH2CO2H | 553.1 | 7.56 (br. s., 1H), 7.47 (s, 1H), 7.29-7.05 (m, 4H), 6.96 (t, J = 8.0 Hz, 1H), 6.77-6.70 (m, 2H), 6.70-6.58 (m, 3H), 5.33-5.26 (m, 2H), 3.97-3.91 (m, 2H), 3.90-3.78 (m, 2H), 3.73 (t, J = 6.7 Hz, 2H), 2.80 (t, J = 6.7 Hz, 2H), 2.47 (br. s., 2H), 2.11 (quin, J = 6.2 Hz, 2H), 2.00 (m, 3H), 1.85-1.59 (m, 5H)* | 11.7 min, 97.0% 10.9 min, 99.5% |
| 470 | 1-(2-(Dimethylamino)ethyl)-3-(3-((4-(1-(4-(2,3-dimethylphenoxy)butanoyl)-1,2,3,4-tetrahydroquinolin-5-yl)-1H-pyrazol-1-yl)methyl)phenyl)urea | phenyl-NH-C(O)-NH-CH2CH2N(CH3)2 | 609.3 | 7.58-7.51 (m, 1H), 7.37 (s, 1H), 7.34 (s, 1H), 7.26-7.21 (m, 2H), 7.19-7.11 (m, 2H), 7.00 (t, J = 7.8 Hz, 1H), 6.93-6.86 (m, 1H), 6.72 (d, J = 7.4 Hz, 1H), 6.64 (d, J = 8.0 Hz, 1H), 5.30 (s, 2H), 5.26-5.15 (m, 1H), 3.93 (t, J = 5.4 Hz, 2H), 3.77 (t, J = 6.7 Hz, 2H), 3.29 (q, J = 5.4 Hz, 2H), 2.73 (t, J = 7.2 Hz, 2H), 2.59 (br. s., 2H), 2.53-2.47 (m, 2H), 2.29 (s, 6H), 2.23-2.10 (m, 5H), 1.92 (br. s., 3H), 1.84 (quin, J = 6.7 Hz, 2H), 1.68 (br. s., 2H) | 7.1 min, 99.0% 9.4 min, 100% |

TABLE 17-continued

| Example | Name | —X—Y | LCMS, [M + H]+ | $^1$H NMR (500 MHz, CDCl$_3$) δ | HPLC-1: Rt min, purity; HPLC-2: Rt min, purity |
|---|---|---|---|---|---|
| 471 | 2-(3-(3-((4-(1-(4-(2,3-Dimethylphenoxy)butanoyl)-1,2,3,4-tetrahydroquinolin-5-yl)-1H-pyrazol-1-yl)methyl)phenyl)-3-methylureido)-N,N,N-trimethylethanaminium, TFA salt | | 637.3 | 7.59 (s, 1H), 7.40 (t, J = 7.8 Hz, 1H), 7.19 (d, J = 3.3 Hz, 3H), 7.13 (t, J = 7.4 Hz, 3H), 7.01 (t, J = 7.8 Hz, 1H), 6.74 (d, J = 7.7 Hz, 1H), 6.65 (d, J = 8.0 Hz, 1H), 5.96 (br. s., 1H), 5.39 (s, 2H), 3.95 (br. s., 2H), 3.78 (t, J = 6.7 Hz, 2H), 3.65 (br. s., 2H), 3.56 (br. s., 2H), 3.23 (s, 3H), 3.14 (br. s., 9H), 2.75 (t, J = 7.2 Hz, 2H), 2.64 (br. s., 2H), 2.24-2.11 (m, 5H), 1.96 (br. s., 3H), 1.91-1.81 (m, 2H) | 7.7 min, 95.0% 9.6 min, 94.9% |
| 472 | 2-(3-(3-((4-(1-(4-(2,3-Dimethylphenoxy)butanoyl)-1,2,3,4-tetrahydroquinolin-5-yl)-1H-pyrazol-1-yl)methyl)phenyl)-1,3-dimethylureido)-N,N,N-trimethylethanaminium, TFA salt | | 651.3 | 7.59 (s, 1H), 7.46 (d, J = 6.6 Hz, 1H), 7.37 (t, J = 7.8 Hz, 1H), 7.21-7.13 (m, 3H), 7.06 (d, J = 7.7 Hz, 1H), 7.04-6.97 (m, 3H), 6.73 (d, J = 7.4 Hz, 1H), 6.65 (d, J = 8.0 Hz, 1H), 5.34 (s, 2H), 3.95 (br. s., 2H), 3.78 (t, J = 6.7 Hz, 2H), 3.68 (br. s., 2H), 3.61 (br. s., 2H), 3.27-3.19 (m, 9H), 3.17 (s, 3H), 2.74 (t, J = 7.2 Hz, 2H), 2.62 (br. s., 2H), 2.44 (s, 3H), 2.23-2.14 (m, 5H), 1.95 (br. s., 3H), 1.90-1.83 (m, 2H) | 8.0 min, 96.2% 10.2 min, 96.3% |
| 473 | 4-(2,3-Dimethylphenoxy)-1-(5-(1-(3-(hydroxymethyl)benzyl)-1H-pyrazol-4-yl)-3,4-dihydroquinolin-1(2H)-yl)butan-1-one | | 510.3 | 7.59-7.52 (m, 1H), 7.40-7.32 (m, 3H), 7.32-7.28 (m, 1H), 7.23-7.19 (m, 1H), 7.19-7.12 (m, 2H), 7.00 (t, J = 7.8 Hz, 1H), 6.72 (d, J = 7.4 Hz, 1H), 6.64 (d, J = 8.0 Hz, 1H), 5.34 (s, 2H), 4.71 (d, J = 6.1 Hz, 2H), 3.93 (t, J = 5.4 Hz, 2H), 3.77 (t, J = 6.9 Hz, 2H), 2.74 (t, J = 7.2 Hz, 2H), 2.58 (br. s., 2H), 2.23-2.12 (m, 5H), 1.91 (br. s., 3H), 1.84 (quin, J = 6.7 Hz, 2H), 1.71 (t, J = 5.9 Hz, 1H) | 12.4 min, 99.8% 11.6 min, 100% |
| 474 | 4-(2,3-Dimethylphenoxy)-1-(5-(1-(3-(2-hydroxypropan-2-yl)benzyl)-1H-pyrazol-4-yl)-3,4-dihydroquinolin-1(2H)-yl)butan-1-one | | 538.3 | 7.55 (s, 1H), 7.46-7.41 (m, 2H), 7.37-7.31 (m, 2H), 7.20-7.10 (m, 4H), 7.00 (t, J = 8.0 Hz, 1H), 6.72 (d, J = 7.4 Hz, 1H), 6.63 (d, J = 8.3 Hz, 1H), 5.35 (s, 2H), 3.93 (t, J = 5.2 Hz, 2H), 3.77 (t, J = 6.9 Hz, 2H), 2.74 (t, J = 7.2 Hz, 2H), 2.58 (br. s., 2H), 2.22-2.12 (m, 5H), 1.91 (br. s., 3H), 1.84 (quin, J = 6.7 Hz, 2H), 1.73 (s, 1H), 1.57 (s, 6H) | 13.3 min, 99.9% 12.1 min, 100% |
| 475 | 2,2'-(3-((4-(1-(4-(2,3-Dimethylphenoxy)butanoyl)-1,2,3,4-tetrahydroquinolin-5-yl)-1H-pyrazol-1-yl)methyl)benzoylazanediyl)diacetic acid | | 639.3 | 7.61 (s, 1H), 7.44-7.38 (m, 3H), 7.38-7.33 (m, 1H), 7.32-7.26 (m, 1H), 7.21-7.11 (m, 3H), 7.00 (t, J = 7.8 Hz, 1H), 6.72 (d, J = 7.7 Hz, 1H), 6.63 (d, J = 8.0 Hz, 1H), 5.39 (s, 2H), 4.28 (br. s., 2H), 4.08 (br. s., 2H), 3.91 (br. s., 2H), 3.77 (t, J = 6.7 Hz, 2H), 2.77 (t, J = 7.2 Hz, 2H), 2.55 (br. s., 2H), 2.21-2.08 (m, 5H), 1.97-1.76 (m, 5H) | 10.4 min, 99.8% 10.1 min, 100% |

TABLE 17-continued

| Example | Name | —X—Y | LCMS, [M + H]+ | 1H NMR (500 MHz, CDCl3) δ | HPLC-1: Rt min, purity; HPLC-2: Rt min, purity |
|---|---|---|---|---|---|
| 476 | (R)-2-(3-((4-(1-(4-(2,3-Dimethylphenoxy)butanoyl)-1,2,3,4-tetrahydroquinolin-5-yl)-1H-pyrazol-1-yl)methyl)benzamido)succinic acid | 3-benzamido substituted with CH(CO2H)CH2CO2H | 639.3 | 7.84-7.78 (m, 3H), 7.60-7.53 (m, 1H), 7.46-7.34 (m, 2H), 7.31 (d, J = 7.7 Hz, 1H), 7.24-7.12 (m, 2H), 6.99 (t, J = 7.8 Hz, 1H), 6.71 (d, J = 7.4 Hz, 1H), 6.62 (d, J = 8.0 Hz, 1H), 5.52-5.38 (m, 2H), 5.12-5.01 (m, 1H), 3.89 (br. s., 2H), 3.78 (t, J = 6.7 Hz, 2H), 3.19-2.91 (m, 2H), 2.79 (t, J = 7.2 Hz, 2H), 2.52 (br. s., 2H), 2.22-2.07 (m, 5H), 1.89-1.77 (m, 5H) | 10.3 min, 99.3% 10.1 min, 99.0% |
| 477 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)succinic acid | 3-benzamido substituted with CH(CO2H)CH2CO2H | 639.3 | 7.84-7.77 (m, 3H), 7.59-7.52 (m, 1H), 7.45-7.34 (m, 2H), 7.30 (d, J = 7.7 Hz, 1H), 7.24-7.11 (m, 2H), 6.99 (t, J = 7.8 Hz, 1H), 6.71 (d, J = 7.7 Hz, 1H), 6.62 (d, J = 8.0 Hz, 1H), 5.51-5.38 (m, 2H), 5.10-4.99 (m, 1H), 3.89 (br. s., 2H), 3.78 (t, J = 6.7 Hz, 2H), 3.17-3.06 (m, 1H), 3.05-2.93 (m, 1H), 2.78 (t, J = 7.2 Hz, 2H), 2.52 (br. s., 2H), 2.21-2.06 (m, 5H), 1.88-1.76 (m, 5H) | 10.3 min, 99.1% 10.0 min, 99.1% |
| 478 | (R)-Dimethyl 2-(3-((4-(1-(4-(2,3-dimethylphenoxy)butanoyl)-1,2,3,4-tetrahydroquinolin-5-yl)-1H-pyrazol-1-yl)methyl)benzamido)succinate | 3-benzamido substituted with CH(CO2Me)CH2CO2Me | 667.4 | 7.79 (s, 1H), 7.74 (dd, J = 7.4, 1.4 Hz, 1H), 7.56 (s, 1H), 7.49-7.39 (m, 2H), 7.35 (s, 1H), 7.25-7.20 (m, 1H), 7.18-7.13 (m, 2H), 7.00 (t, J = 7.8 Hz, 1H), 6.72 (d, J = 7.4 Hz, 1H), 6.64 (d, J = 8.3 Hz, 1H), 5.39 (s, 2H), 5.08-5.01 (m, 1H), 3.93 (t, J = 5.4 Hz, 2H), 3.80 (s, 3H), 3.79-3.74 (m, 2H), 3.70 (s, 3H), 3.14 (dd, J = 17.3, 4.4 Hz, 1H), 2.98 (dd, J = 17.3, 4.4 Hz, 1H), 2.74 (t, J = 7.2 Hz, 2H), 2.59 (br. s., 2H), 2.22-2.12 (m, 5H), 1.91 (br. s., 3H), 1.85 (quin, J = 6.7 Hz, 2H) | 10.1 min, 97.6% 11.4 min, 98.3% |
| 479 | (S)-3-(3-((4-(1-(4-(2,3-Dimethylphenoxy)butanoyl)-1,2,3,4-tetrahydroquinolin-5-yl)-1H-pyrazol-1-yl)methyl)benzamido)-4-methoxy-4-oxobutanoic acid | 3-benzamido substituted with CH(CO2Me)CH2CO2H | 653.4 | 7.80-7.73 (m, 2H), 7.59 (s, 1H), 7.48-7.40 (m, 2H), 7.40-7.31 (m, 2H), 7.22-7.12 (m, 3H), 7.00 (t, J = 7.8 Hz, 1H), 6.72 (d, J = 7.4 Hz, 1H), 6.63 (d, J = 8.3 Hz, 1H), 5.41 (s, 2H), 5.09-5.02 (m, 1H), 3.91 (br. s., 2H), 3.83-3.74 (m, 5H), 3.22-3.10 (m, 1H), 3.02 (dd, J = 17.6, 4.4 Hz, 1H), 2.78 (t, J = 7.2 Hz, 2H), 2.54 (br. s., 2H), 2.23-2.11 (m, 5H), 1.93-1.79 (m, 5H) | 7.5 min, 98.1% 7.5 min, 99.7% |
| 480 | (S)-3-(3-((4-(1-(4-(2,3-Dimethylphenoxy)butanoyl)-1,2,3,4-tetrahydroquinolin-5-yl)-1H-pyrazol-1-yl)methyl)-N-methylbenzamido)-4-methoxy-4-oxobutanoic acid | 3-(N-methylbenzamido) substituted with CH(CO2Me)CH2CO2H | 667.4 | 7.61 (br. s., 1H), 7.47-7.39 (m, 2H), 7.37-7.31 (m, 2H), 7.24-7.13 (m, 3H), 7.06-6.97 (m, 1H), 6.73 (d, J = 7.4 Hz, 1H), 6.63 (d, J = 8.0 Hz, 1H), 5.46-5.32 (m, 2H), 5.03 (br. s., 0.5H), 4.82 (br. s., 0.5H), 3.92 (br. s., 2H), 3.84-3.77 (m, 5H), 3.37-3.19 (m, 0.5H), 3.09-2.89 (m, 4H), 2.79 (t, J = 7.3 Hz, 2H), 2.67 (br. s., 0.5H), 2.55 (br. s., 2H), 2.24-2.06 (m, 5H), 2.02-1.67 (m, 5H) | 7.5 min, 98.4% 7.6 min, 99.8% |

TABLE 17-continued

| Example | Name | —X—Y | LCMS, [M + H]⁺ | ¹H NMR (500 MHz, CDCl₃) δ | HPLC-1: Rt min, purity; HPLC-2: Rt min, purity |
|---|---|---|---|---|---|
| 481 | (S)-2-(3-((4-(1-(4-(2,3-Dimethylphenoxy)butanoyl)-1,2,3,4-tetrahydroquinolin-5-yl)-1H-pyrazol-1-yl)methyl)-N-methylbenzamido)succinic acid | | 653.4 | 7.60 (br. s., 1H), 7.39 (br. s., 4H), 7.28 (d, J = 3.3 Hz, 1H), 7.22-7.10 (m, 3H), 7.00 (t, J = 7.8 Hz, 1H), 6.72 (d, J = 7.4 Hz, 1H), 6.63 (d, J = 8.0 Hz, 1H), 5.40 (s, 2H), 4.82 (br. s., 0.5H), 3.91 (br. s., 2H), 3.77 (t, J = 6.7 Hz, 2H), 3.20 (d, J = 11.3 Hz, 0.5H), 3.09-2.85 (m, 5H), 2.82-2.71 (m, 2H), 2.65-2.60 (m, 0.5H), 2.54 (br. s., 2H), 2.23-2.11 (m, 5H), 1.98-1.75 (m, 5H) | 7.3 min, 95.2% 7.5 min, 94.0% |
| 482 | Methyl 3-(3-((4-(1-(4-(2,3-dimethylphenoxy)butanoyl)-1,2,3,4-tetrahydroquinolin-5-yl)-1H-pyrazol-1-yl)methyl)benzamido)propanoate | | 609.4 | 7.75 (s, 1H), 7.68 (dt, J = 7.5, 1.5 Hz, 1H), 7.56 (d, J = 0.6 Hz, 1H), 7.46-7.38 (m, 2H), 7.35 (s, 1H), 7.19-7.12 (m, 2H), 7.00 (t, J = 7.8 Hz, 1H), 6.84 (br. s., 1H), 6.72 (d, J = 7.7 Hz, 1H), 6.64 (d, J = 8.3 Hz, 1H), 5.38 (s, 2H), 3.93 (t, J = 5.4 Hz, 2H), 3.78 (t, J = 6.9 Hz, 2H), 3.75-3.70 (m, 5H), 2.74 (t, J = 7.2 Hz, 2H), 2.66 (t, J = 5.8 Hz, 2H), 2.58 (br. s., 2H), 2.22-2.12 (m, 5H), 1.91 (br. s., 3H), 1.85 (quin, J = 6.7 Hz, 3H) | 12.0 min, 99.1% 11.1 min, 99.8% |
| 483 | (2R,3S)-2-(3-((4-(1-(4-(2,3-Dimethylphenoxy)butanoyl)-1,2,3,4-tetrahydroquinolin-5-yl)-1H-pyrazol-1-yl)methyl)benzamido)-3-hydroxybutanoic acid | | 625.4 | 7.95 (s, 1H), 7.87 (d, J = 7.7 Hz, 1H), 7.55 (s, 1H), 7.50-7.44 (m, 1H), 7.44-7.36 (m, 3H), 7.21-7.13 (m, 2H), 7.01 (t, J = 8.0 Hz, 1H), 6.73 (d, J = 7.7 Hz, 1H), 6.63 (d, J = 8.0 Hz, 1H), 5.53-5.34 (m, 2H), 4.84 (dd, J = 8.3, 2.2 Hz, 1H), 4.61-4.51 (m, 1H), 3.92 (br. s., 2H), 3.78 (t, J = 6.7 Hz, 2H), 2.76 (t, J = 7.2 Hz, 2H), 2.55 (br. s., 2H), 2.21-2.12 (m, 5H), 1.96-1.77 (m, 5H), 1.30 (d, J = 6.3 Hz, 3H) | 10.4 min, 89.6% 9.9 min, 93.4% |
| 484 | 2-(3-((4-(1-(4-(2,3-Dimethylphenoxy)butanoyl)-1,2,3,4-tetrahydroquinolin-5-yl)-1H-pyrazol-1-yl)methyl)benzamido)-3-sulfopropanoic acid | | 675.3 | 7.93-7.80 (m, 3H), 7.66 (br. s., 1H), 7.57-7.47 (m, 2H), 7.33-7.15 (m, 3H), 6.99 (t, J = 8.0 Hz, 1H), 6.72-6.62 (m, 2H), 5.53 (s, 2H), 4.91 (dd, J = 8.0, 4.1 Hz, 1H), 3.89 (br. s., 2H), 3.77 (t, J = 6.9 Hz, 2H), 3.52-3.44 (m, 1H), 3.43-3.36 (m, 1H), 2.83 (t, J = 6.9 Hz, 2H), 2.54 (br. s., 2H), 2.14 (quin, J = 6.2 Hz, 3H), 2.07 (br. s., 3H), 1.90-1.66 (m, 5H)* | N/A 8.5 min, 91.5% |

TABLE 17-continued

| Example | Name | —X—Y | LCMS, [M + H]+ | 1H NMR (500 MHz, CDCl3) δ | HPLC-1: Rt min, purity; HPLC-2: Rt min, purity |
|---|---|---|---|---|---|
| 485 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)-3-hydroxypropanoic acid | | 611.4 | 7.97 (s, 1H), 7.85 (s, 1H), 7.61 (d, J = 7.2 Hz, 1H), 7.54 (s, 1H), 7.45-7.40 (m, 2H), 7.38-7.34 (m, 1H), 7.21-7.10 (m, 2H), 7.00 (t, J = 7.8 Hz, 1H), 6.73 (d, J = 7.4 Hz, 1H), 6.63 (d, J = 8.0 Hz, 1H), 5.53-5.32 (m, 3H), 4.90-4.83 (m, 1H), 4.13 (d, J = 8.8 Hz, 1H), 4.00 (d, J = 9.1 Hz, 1H), 3.91 (br. s., 2H), 3.77 (t, J = 6.7 Hz, 2H), 2.76 (t, J = 7.2 Hz, 2H), 2.54 (br. s., 2H), 2.21-2.09 (m, 5H), 1.96-1.76 (m, 5H) | 7.8 min, 99.3% 7.4 min, 99.5% |
| 486 | (3R,5S)-6-(3-((4-(1-(4-(2,3-Dimethylphenoxy)butanoyl)-1,2,3,4-tetrahydroquinolin-5-yl)-1H-pyrazol-1-yl)methyl)benzamido)-3,5-dihydroxyhexanoic acid, Na salt | | 669.5 | 8.03 (s, 1H), 7.99 (d, J = 5.0 Hz, 1H), 7.69 (s, 1H), 7.64 (d, J = 7.4 Hz, 1H), 7.60 (s, 1H), 7.42-7.32 (m, 2H), 7.15 (br. s., 1H), 7.11-7.00 (m, 2H), 6.90 (t, J = 7.8 Hz, 1H), 6.62 (d, J = 7.4 Hz, 2H), 5.38 (s, 2H), 3.85 (br. s., 2H), 3.73 (br. s., 1H), 3.51-3.36 (m, 2H), 2.65 (d, J = 14.3 Hz, 2H), 2.09-1.96 (m, 5H), 1.95-1.83 (m, 3H), 1.82-1.59 (m, 7H), 0.91-0.77 (m, 1H), 0.32 (br. s., 1H)** | 7.5 min, 95.0% 7.1 min, 95.0% |
| 487 | 1-(3-((4-(1-(4-(2,3-Dimethylphenoxy)butanoyl)-1,2,3,4-tetrahydroquinolin-5-yl)-1H-pyrazol-1-yl)methyl)benzoyl)-4-hydroxypiperidine-4-carboxylic acid | | 651.4 | 7.61 (br. s., 1H), 7.46-7.36 (m, 3H), 7.32 (d, J = 7.2 Hz, 1H), 7.21-7.13 (m, 3H), 7.01 (t, J = 7.8 Hz, 1H), 6.74 (d, J = 7.4 Hz, 1H), 6.65 (d, J = 7.7 Hz, 1H), 5.40 (s, 2H), 4.53 (br. s., 1H), 4.03-3.87 (m, 2H), 3.78 (br. s., 2H), 3.55 (br. s., 2H), 3.39 (br. s., 1H), 3.22 (br. s., 1H), 2.76 (t, J = 7.2 Hz, 2H), 2.61 (d, J = 7.4 Hz, 2H), 2.25-2.12 (m, 5H), 2.10-1.78 (m, 8H) | 10.2 min, 99.3% 9.7 min, 99.5% |
| 488 | 4-(4-(1-(4-(2,3-Dimethylphenoxy)butanoyl)-1,2,3,4-tetrahydroquinolin-5-yl)-1H-pyrazol-1-yl)butanoic acid | | 476.2 | 7.53 (s, 1H), 7.32 (s, 1H), 7.22-7.06 (m, 3H), 7.01 (t, J = 7.8 Hz, 1H), 6.74 (d, J = 7.4 Hz, 1H), 6.64 (d, J = 8.3 Hz, 1H), 4.29 (t, J = 6.6 Hz, 2H), 3.93 (t, J = 5.2 Hz, 2H), 3.79 (t, J = 6.9 Hz, 2H), 2.75 (t, J = 7.0 Hz, 2H), 2.58 (br. s., 2H), 2.46-2.37 (m, 2H), 2.23 (quin, J = 6.7 Hz, 2H), 2.20-2.14 (m, 5H), 1.91 (br. s., 3H), 1.89-1.82 (m, 2H) | 11.0 min, 99.5% 9.5 min, 99.5% |
| 489 | 5-(4-(1-(4-(2,3-Dimethylphenoxy)butanoyl)-1,2,3,4-tetrahydroquinolin-5-yl)-1H-pyrazol-1-yl)pentanoic acid | | 490.3 | 7.51 (s, 1H), 7.31 (s, 1H), 7.21-7.06 (m, 3H), 7.01 (t, J = 7.8 Hz, 1H), 6.74 (d, J = 7.4 Hz, 1H), 6.64 (d, J = 8.3 Hz, 1H), 4.18 (t, J = 7.0 Hz, 2H), 3.97-3.88 (m, 2H), 3.78 (t, J = 6.7 Hz, 2H), 2.75 (t, J = 7.2 Hz, 2H), 2.59 (br. s., 2H), 2.41 (t, J = 7.3 Hz, 2H), 2.22-2.15 (m, 5H), 2.03-1.95 (m, 2H), 1.91 (br. s., 2H), 1.85 (quin, J = 6.7 Hz, 2H), 1.75-1.65 (m, 2H) | 11.2 min, 96.5% 10.0 min, 97.8% |

TABLE 17-continued

| Example | Name | —X—Y | LCMS, [M + H]+ | ¹H NMR (500 MHz, CDCl₃) δ | HPLC-1: Rt min, purity; HPLC-2: Rt min, purity |
|---|---|---|---|---|---|
| 490 | (3R,5S)-6-(3-(3-((4-(1-(4-(2,3-Dimethylphenoxy)butanoyl)-1,2,3,4-tetrahydroquinolin-5-yl)-1H-pyrazol-1-yl)methyl)phenyl)ureido)-3,5-dihydroxyhexanoic acid, Na salt | | 684.5 | 8.59 (s, 1H), 7.88 (s, 1H), 7.54 (d, J = 0.6 Hz, 1H), 7.28-7.22 (m, 2H), 7.14-7.07 (m, 2H), 6.91 (t, J = 7.8 Hz, 1H), 6.72 (d, J = 7.4 Hz, 1H), 6.63 (t, J = 8.5 Hz, 2H), 6.10 (t, J = 5.6 Hz, 1H), 5.22 (s, 2H), 3.89-3.79 (m, 3H), 3.59 (t, J = 6.5 Hz, 3H), 3.15-3.07 (m, 1H), 2.93-2.85 (m, 1H), 2.60 (t, J = 7.0 Hz, 2H), 2.58-2.50 (m, 2H), 2.14 (dd, J = 14.9, 4.1 Hz, 1H), 2.07-1.97 (m, 4H), 1.97-1.88 (m, 3H), 1.85-1.75 (m, 3H), 1.74-1.67 (m, 2H), 1.46-1.30 (m, 2H)** | 8.8 min, 95.2% 8.2 min, 94.0% |
| 491 | (3R,5S)-6-(4-(1-(4-(2,3-Dimethylphenoxy)butanoyl)-1,2,3,4-tetrahydroquinolin-5-yl)-1H-pyrazol-1-yl)-3,5-dihydroxyhexanoic acid, Na salt | | 536.3 | 7.72 (s, 1H), 7.48 (s, 1H), 7.17 (br. s., 1H), 7.14-7.08 (m, 2H), 6.92 (t, J = 7.8 Hz, 1H), 6.65 (d, J = 7.2 Hz, 2H), 4.11-4.03 (m, 1H), 4.02-3.91 (m, 2H), 3.86 (dd, J = 7.8, 3.7 Hz, 1H), 3.83 (t, J = 5.5 Hz, 2H), 3.60 (t, J = 6.6 Hz, 2H), 2.60 (t, J = 7.2 Hz, 2H), 2.57-2.50 (m, 2H), 2.12 (dd, J = 14.9, 4.1 Hz, 1H), 2.06 (s, 3H), 1.97-1.89 (m, 3H), 1.86-1.76 (m, 3H), 1.75-1.64 (m, 2H), 1.49-1.29 (m, 2H)** | 8.5 min, 99.5% 7.9 min, 91.6% |
| 492 | 2-Amino-3-(3-((4-(1-(4-(2,3-dimethylphenoxy)butanoyl)-1,2,3,4-tetrahydroquinolin-5-yl)-1H-pyrazol-1-yl)methyl)benzamido)propanoic acid, 2 TFA salt | | 610.4 | | 7.7 min, 97.9% 8.7 min, 98.3% |
| 493 | 5-(4-(1-(4-(2,3-Dimethylphenoxy)butanoyl)-1,2,3,4-tetrahydroquinolin-5-yl)-1H-pyrazol-1-yl)-3,3-dimethyl-4-oxopentanoic acid | | 532.3 | 7.57 (s, 1H), 7.40 (s, 1H), 7.22-7.12 (m, 3H), 7.02 (t, J = 8.0 Hz, 1H), 6.74 (d, J = 7.7 Hz, 1H), 6.65 (d, J = 8.3 Hz, 1H), 4.38 (br. s., 2H), 3.98-3.89 (m, 2H), 3.79 (t, J = 6.9 Hz, 2H), 2.84 (br. s., 1H), 2.75 (t, J = 7.0 Hz, 2H), 2.58 (br. s., 2H), 2.23-2.14 (m, 5H), 1.92 (br. s., 3H), 1.90-1.80 (m, 3H), 1.57 (br. s., 6H) | 11.9 min, 100% 10.5 min, 100% |
| 494 | 1-(5-(1-(Benzo[d]thiazol-6-ylmethyl)-1H-pyrazol-4-yl)-3,4-dihydroquinolin-1(2H)-yl)-4-(2,3-dimethylphenoxy)butan-1-one | | 537.3 | 9.08 (s, 1H), 8.16 (d, J = 8.2 Hz, 1H), 7.89 (d, J = 1.1 Hz, 1H), 7.60 (s, 1H), 7.47 (dd, J = 8.2, 1.6 Hz, 1H), 7.37 (s, 1H), 7.22-7.13 (m, 3H), 7.00 (t, J = 8.0 Hz, 1H), 6.71 (d, J = 7.1 Hz, 1H), 6.63 (d, J = 8.2 Hz, 1H), 5.52 (s, 2H), 3.92 (d, J = 4.9 Hz, 2H), 3.78 (t, J = 6.9 Hz, 2H), 2.76 (t, J = 7.1 Hz, 2H), 2.56 (br. s., 2H), 2.24-2.11 (m, 5H), 1.96-1.79 (m, 5H) | 13.5 min, 95.0% 12.3 min, 95.7% |

TABLE 17-continued

| Example | Name | —X—Y | LCMS, [M + H]⁺ | ¹H NMR (500 MHz, CDCl₃) δ | HPLC-1: Rt min, purity; HPLC-2: Rt min, purity |
|---|---|---|---|---|---|
| 495 | Diethyl 2,2'-(4-(1-(4-(2,3-dimethylphenoxy)butanoyl)-1,2,3,4-tetrahydroquinolin-5-yl)-1H-pyrazole-1-carbonylazanediyl)diacetate | [structure: C(=O)N(CH₂CO₂Et)₂] | 605.3 | 9.08 (s, 1H), 8.16 (d, J = 8.2 Hz, 1H), 7.89 (d, J = 1.1 Hz, 1H), 7.60 (s, 1H), 7.47 (dd, J = 8.2, 1.6 Hz, 1H), 7.37 (s, 1H), 7.22-7.13 (m, 3H), 7.00 (t, J = 8.0 Hz, 1H), 6.71 (d, J = 7.1 Hz, 1H), 6.63 (d, J = 8.2 Hz, 1H), 5.52 (s, 2H), 3.92 (d, J = 4.9 Hz, 2H), 3.78 (t, J = 6.9 Hz, 2H), 2.76 (t, J = 7.1 Hz, 2H), 2.56 (br. s., 2H), 2.24-2.11 (m, 5H), 1.96-1.79 (m, 5H) | 12.4 min, 91.7% 11.1 min, 94.5% |
| 496 | N-(3-((4-(1-(4-(2,3-Dimethylphenoxy)butanoyl)-1,2,3,4-tetrahydroquinolin-5-yl)-1H-pyrazol-1-yl)methyl)phenyl)-4,4,4-trifluoro-2,3-dihydroxy-3-(trifluoromethyl)butanamide | [structure: CH₂-phenyl-NHC(=O)C(OH)(CF₃)C(OH)CF₃] | Not shown | 8.04 (br. s., 1H), 7.66-7.47 (m, 3H), 7.46-7.31 (m, 2H), 7.24-7.05 (m, 4H), 7.05-6.93 (m, 1H), 6.79-6.54 (m, 2H), 5.47-5.22 (m, 2H), 3.92 (br. s., 2H), 3.78 (t, J = 6.9 Hz, 2H), 2.76 (t, J = 7.1 Hz, 2H), 2.58 (br. s., 2H), 2.33-1.71 (m, 12H) | 10.4 min, 98.9% 9.1 min, 98.5% |
| 497 | 2-(3-((4-(1-(4-(2,3-Dimethylphenoxy)butanoyl)-1,2,3,4-tetrahydroquinolin-5-yl)-1H-pyrazol-1-yl)methyl)phenylamino)-2-oxoacetic acid | [structure: CH₂-phenyl-NHC(=O)CO₂H] | 567.3 | 9.14 (s, 1H), 7.70 (s, 1H), 7.63 (s, 1H), 7.60-7.51 (m, 1H), 7.41 (t, J = 8.0 Hz, 1H), 7.38-7.29 (m, 1H), 7.25-7.06 (m, 4H), 7.06-6.91 (m, 1H), 6.81-6.56 (m, 2H), 5.55-5.24 (m, 2H), 3.99-3.86 (m, 2H), 3.80 (t, J = 6.9 Hz, 2H), 2.92-2.72 (m, 2H), 2.62-2.47 (m, 2H), 2.26-2.04 (m, 5H), 1.99-1.59 (m, 5H) | 9.0 min, 100% 10.6 min, 100% |
| 498 | N-(3-((4-(1-(4-(2,3-Dimethylphenoxy)butanoyl)-1,2,3,4-tetrahydroquinolin-5-yl)-1H-pyrazol-1-yl)methyl)phenyl)-2,2,2-trifluoroacetamide | [structure: CH₂-phenyl-NHC(=O)CF₃] | 591.3 | 8.22 (br. s., 1H), 7.59 (d, J = 6.6 Hz, 2H), 7.53 (d, J = 8.2 Hz, 1H), 7.41 (t, J = 8.0 Hz, 1H), 7.36 (br. s., 1H), 7.23-7.08 (m, 4H), 7.01 (t, J = 7.7 Hz, 1H), 6.72 (d, J = 7.1 Hz, 1H), 6.63 (d, J = 8.2 Hz, 1H), 5.39 (s, 2H), 3.91 (br. s., 2H), 3.79 (t, J = 6.9 Hz, 2H), 2.78 (t, J = 7.1 Hz, 2H), 2.56 (br. s., 2H), 2.25-2.07 (m, 5H), 1.97-1.75 (m, 5H) | N/A |
| 499 | N-(3-((4-(1-(4-(2,3-Dimethylphenoxy)butanoyl)-1,2,3,4-tetrahydroquinolin-5-yl)-1H-pyrazol-1-yl)methyl)phenyl)-3,3-bis(trifluoromethyl)oxirane-2-carboxamide | [structure: CH₂-phenyl-NHC(=O)-oxirane(CF₃)₂] | 701.4 | 7.82 (s, 1H), 7.58 (s, 1H), 7.50 (s, 1H), 7.46 (d, J = 8.2 Hz, 1H), 7.39 (d, J = 7.7 Hz, 1H), 7.35 (d, J = 2.2 Hz, 1H), 7.22-7.14 (m, 2H), 7.09 (d, J = 7.7 Hz, 1H), 7.00 (t, J = 8.0 Hz, 1H), 6.72 (d, J = 7.7 Hz, 1H), 6.63 (d, J = 8.2 Hz, 1H), 5.36 (s, 2H), 4.14 (s, 1H), 3.92 (t, J = 4.9 Hz, 2H), 3.78 (t, J = 6.9 Hz, 2H), 2.76 (t, J = 7.1 Hz, 2H), 2.57 (br. s., 2H), 2.24-2.09 (m, 5H), 1.98-1.78 (m, 5H) | N/A |

TABLE 17-continued

| Example | Name | —X—Y | LCMS, [M + H]+ | 1H NMR (500 MHz, CDCl3) δ | HPLC-1: Rt min, purity; HPLC-2: Rt min, purity |
|---|---|---|---|---|---|
| 500 | 2-Amino-N-(3-((4-(1-(4-(2,3-dimethylphenoxy)butanoyl)-1,2,3,4-tetrahydroquinolin-5-yl)-1H-pyrazol-1-yl)methyl)phenyl)-4,4,4-trifluoro-3-hydroxy-3-(trifluoromethyl)butanamide | [CH2-phenyl-NH-C(O)-C(NH2)-C(OH)(CF3)(CF3)] | 718.4 | 7.61-7.53 (m, 2H), 7.52-7.44 (m, 2H), 7.34 (t, J = 8.0 Hz, 1H), 7.28-7.17 (m, 2H), 7.14 (br. s., 1H), 7.06 (d, J = 7.7 Hz, 1H), 6.95 (t, J = 7.7 Hz, 1H), 6.64 (dd, J = 7.4, 4.7 Hz, 2H), 5.36 (s, 2H), 3.99 (s, 1H), 3.84 (br. s., 2H), 3.73 (t, J = 6.9 Hz, 2H), 2.80 (t, J = 6.6 Hz, 2H), 2.46 (br. s., 2H), 2.16-2.07 (m, 2H), 2.01 (br. s., 3H), 1.88-1.73 (m, 3H), 1.69 (br. s., 3H) | N/A |
| 501 | 4-(3-((4-(1-(4-(2,3-Dimethylphenoxy)butanoyl)-1,2,3,4-tetrahydroquinolin-5-yl)-1H-pyrazol-1-yl)methyl)phenyl)-1H-1,2,4-triazol-5(4H)-one | [CH2-phenyl-triazolone] | 563.4 | 7.60 (s, 1H), 7.56-7.46 (m, 3H), 7.40 (s, 1H), 7.33-7.27 (m, 1H), 7.24-7.13 (m, 2H), 7.01 (t, J = 8.0 Hz, 1H), 6.73 (d, J = 7.1 Hz, 1H), 6.63 (d, J = 8.2 Hz, 1H), 5.44 (s, 2H), 3.92 (br. s., 2H), 3.79 (t, J = 6.9 Hz, 2H), 2.77 (t, J = 7.1 Hz, 2H), 2.56 (br. s., 2H), 2.23-2.09 (m, 5H), 2.01 (s, 3H), 1.92-1.75 (m, 5H) | 9.8 min, 99.0%; 8.8 min, 95.7% |
| 502 | 2-(4-(3-((4-(1-(4-(2,3-Dimethylphenoxy)butanoyl)-1,2,3,4-tetrahydroquinolin-5-yl)-1H-pyrazol-1-yl)methyl)phenyl)-5-oxo-4,5-dihydro-1H-1,2,4-triazol-1-yl)acetic acid | [CH2-phenyl-triazolone-CH2-CO2H] | 621.3 | 7.81 (s, 1H), 7.63-7.44 (m, 3H), 7.39 (br. s., 1H), 7.25-7.11 (m, 2H), 7.06-6.94 (m, 1H), 6.80-6.57 (m, 2H), 5.43 (s, 2H), 4.66 (s, 2H), 3.91 (br. s., 2H), 3.78 (t, J = 6.9 Hz, 2H), 2.76 (t, J = 7.1 Hz, 2H), 2.55 (br. s., 2H), 2.27-2.09 (m, 5H), 2.01 (s, 1H), 1.86 (dd, J = 13.7, 6.6 Hz, 5H) | 11.0 min, 100%; 10.0 min, 100% |
| 503 | 4-(2,3-Dimethylphenoxy)-1-(5-(1-(pyridin-2-ylmethyl)-1H-pyrazol-4-yl)-3,4-dihydroquinolin-1(2H)-yl)butan-1-one, TFA salt | [CH2-pyridin-3-yl] | 481.3 | 8.75 (d, J = 4.8 Hz, 1H), 8.28 (t, J = 7.6 Hz, 1H), 7.92-7.71 (m, 2H), 7.66-7.48 (m, 3H), 7.37-7.11 (m, 3H), 6.98 (t, J = 7.7 Hz, 1H), 6.79-6.58 (m, 2H), 5.70 (s, 2H), 3.88 (br. s., 2H), 3.76 (t, J = 6.6 Hz, 2H), 2.80 (t, J = 6.7 Hz, 2H), 2.56 (br. s., 3H), 2.27-1.96 (m, 4H), 1.92-1.70 (m, 5H)* | 9.9 min, 99.6%; 10.0 min, 99.9% |
| 504 | 3-(3-((4-(1-(4-(2,3-Dimethylphenoxy)butanoyl)-1,2,3,4-tetrahydroquinolin-5-yl)-1H-pyrazol-1-yl)methyl)phenyl)imidazolidine-2,4-dione | [CH2-phenyl-hydantoin] | 578.3 | 7.66 (br. s., 1H), 7.54 (br. s., 1H), 7.46 (t, J = 7.4 Hz, 1H), 7.39-7.10 (m, 5H), 6.98 (t, J = 7.4 Hz, 1H), 6.69 (t, J = 8.8 Hz, 2H), 6.23 (s, 1H), 5.36 (br. s., 2H), 3.96 (br. s., 2H), 3.93-3.84 (m, 2H), 3.68 (t, J = 6.3 Hz, 2H), 2.68 (t, J = 6.6 Hz, 2H), 2.58 (br. s., 2H), 2.16 (br. s., 3H), 2.09-2.01 (m, 2H), 1.87 (br. s., 3H), 1.79 (d, J = 6.6 Hz, 2H) | 10.7 min, 99.2%; 10.2 min, 98.7% |

*1H NMR (500 MHz, MeOD) δ.
**1H NMR (500 MHz, DMSO-d6) δ.

The compounds exemplified in Table 18 were prepared in a manner analogous to Example 72.

TABLE 18

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 505 | (S)-4-Carboxy-4-(3-((4-(4-(4-(2,3-dimethylphenoxy)butanoyl)-3,4-dihydro-2H-benzo[b][1,4]oxazin-8-yl)-1H-pyrazol-1-yl)methyl)phenyl-sulfonamido)-N,N,N-trimethylbutan-1-aminium, TFA salt | | 718.4 | 8.09 (s, 1H), 7.93 (d, J = 0.6 Hz, 1H), 7.82 (dd, J = 7.6, 1.2 Hz, 1H), 7.78 (s, 1H), 7.57-7.52 (m, 1H), 7.51-7.47 (m, 1H), 7.41 (dd, J = 7.8, 1.4 Hz, 1H), 7.31 (br. s., 1H), 6.97-6.88 (m, 2H), 6.67 (d, J = 8.0 Hz, 2H), 5.45 (s, 2H), 4.31 (t, J = 4.9 Hz, 2H), 4.01-3.91 (m, 5H), 3.38-3.33 (m, 2H), 3.10 (s, 9H), 2.89 (t, J = 7.1 Hz, 2H), 2.19-2.14 (m, 2H), 2.13 (s, 3H), 1.99-1.83 (m, 6H), 1.77-1.65 (m, 1H) | 7.5 min, 99.2% 8.9 min, 99.5% |
| 506 | 3-(N-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenyl)sulfamoyl)benzoic acid | | 715.4 | 8.37 (t, J = 1.7 Hz, 1H), 8.09 (dt, J = 7.9, 1.3 Hz, 1H), 7.97-7.88 (m, 2H), 7.87-7.79 (m, 1H), 7.65 (dd, J = 7.0, 2.6 Hz, 1H), 7.47 (t, J = 7.8 Hz, 1H), 7.30-7.12 (m, 3H), 7.11-6.89 (m, 4H), 6.80 (d, J = 7.5 Hz, 1H), 6.71 (d, J = 8.1 Hz, 1H), 5.31 (s, 2H), 4.82-4.73 (m, 1H), 4.46 (d, J = 11.9 Hz, 1H), 3.97-3.82 (m, 2H), 3.57 (td, J = 11.8, 2.0 Hz, 1H), 2.93-2.79 (m, 1H), 2.55-2.17 (m, 3H), 2.12-1.99 (m, 2H), 1.94 (s, 3H), 1.79 (d, J = 14.7 Hz, 1H) | 9.7 min, 100% 9.2 min, 100% |
| 507 | (S)-4-Carboxy-4-(3-((4-(1-(4-(2,3-dimethylphenoxy)butanoyl)-1,2,3,4-tetrahydroquinolin-5-yl)-1H-pyrazol-1-yl)methyl)phenyl-sulfonamido)-N,N,N-trimethylbutan-1-aminium | | 716.5 | 7.83 (d, J = 7.7 Hz, 1H), 7.75 (s, 1H), 7.70-7.45 (m, 4H), 7.33-7.16 (m, 3H), 6.97 (t, J = 7.7 Hz, 1H), 6.66 (d, J = 7.7 Hz, 2H), 5.46 (s, 2H), 3.93 (dd, J = 9.3, 3.8 Hz, 1H), 3.86 (br. s., 2H), 3.74 (t, J = 6.9 Hz, 2H), 3.28-3.50 (m, 2H), 3.12 (s, 9H), 2.81 (t, J = 6.6 Hz, 2H), 2.50 (br. s., 3H), 2.19-2.09 (m, 3H), 2.04 (br. s., 3H), 1.96-1.62 (m, 7H) | 7.1 min, 98.9% 9.3 min, 100% |

The compounds exemplified in Table 19 were prepared in a manner analogous to Example 80.

TABLE 19

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 508 | 3-(3-(3-((4-(4-(4-(2,3-Dimethylphenoxy)butanoyl)-3,4-dihydro-2H-benzo[b][1,4]thiazin-8-yl)-1H-pyrazol-1-yl)methyl)phenyl)uriedo)propanoic acid | | 628.2 | 7.61 (s, 1H), 7.56-7.55 (m, 1H), 7.31 (d, J = 11.9 Hz, 2H), 7.25-7.18 (m, 2H), 7.15-7.04 (m, 2H), 6.94 (t, J = 7.9 Hz, 1H), 6.82 (d, J = 7.9 Hz, 1H), 6.66 (d, J = 7.4 Hz, 1H), 6.61 (d, J = 8.4 Hz, 1H), 5.27 (s, 2H), 3.87 (br. s., 4H), 3.43 (t, J = 6.2 Hz, 2H), 3.12 (br. s., 2H), 2.71-2.62 (m, 2H), 2.49 (t, J = 6.2 Hz, 2H), 2.16-2.04 (m, 5H), 1.84 (br. s., 3H) | 99%* |
| 509 | 2-(3-(3-((4-(4-(4-(2,3-dimethylphenoxy)butanoyl)-3,4-dihydro-2H-benzo[b][1,4]thiazin-8-yl)-1H-pyrazol-1-yl)methyl)phenyl)ureido)ethanesulfonic acid | | 664.3 | 7.72 (s, 1H), 7.63 (s, 1H), 7.37-7.30 (m, 2H), 7.30-7.21 (m, 2H), 7.19-7.14 (m, 2H), 6.96-6.86 (m, 2H), 6.65 (t, J = 8.7 Hz, 2H), 5.33-5.30 (m, 2H), 4.12-3.82 (m, 4H), 3.66-3.61 (m, 2H), 3.13 (t, J = 6.2 Hz, 2H), 3.01-2.95 (m, 2H), 2.68 (t, J = 7.1 Hz, 2H), 2.11 (s, 3H), 2.07 (quin, J = 6.5 Hz, 2H), 1.87 (s, 3H) | 11.2 min, 99.2% 8.1 min, 99.1% |
| 510 | 2-(3-(3-((4-(4-(4-(2,3-Dimethylphenoxy)butanoyl)-3,4-dihydro-2H-benzo[b][1,4]thiazin-8-yl)-1H-pyrazol-1-yl)methyl)phenyl)ureido)acetic acid | | 614.3 | 8.84 (s, 1H), 8.03 (s, 1H), 7.69 (d, J = 1.0 Hz, 1H), 7.40-7.33 (m, 2H), 7.31-7.19 (m, 3H), 7.18-7.11 (m, 1H), 6.97 (t, J = 7.9 Hz, 1H), 6.82 (d, J = 7.9 Hz, 1H), 6.70 (d, J = 7.4 Hz, 2H), 6.36 (t, J = 5.7 Hz, 1H), 5.31 (s, 2H), 3.98-3.82 (m, 4H), 3.78 (d, J = 5.4 Hz, 2H), 3.17-3.08 (m, 2H), 2.66-2.56 (m, 2H), 2.17-2.07 (m, 3H), 2.02-1.94 (m, 2H), 1.87 (br. s., 3H)** | 100%* |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 511 | (3-(3-((4-(4-(4-(2,3-Dimethylphenoxy)butanoyl)-3,4-dihydro-2H-benzo[b][1,4]thiazin-8-yl)-1H-pyrazol-1-yl)methyl)phenyl)ureido) methanesulfonic acid | | 650.5 | 7.83 (s, 1H), 7.73 (s, 1H), 7.39 (s, 1H), 7.34 (d, J = 8.0 Hz, 1H), 7.30-7.23 (m, 2H), 7.21-7.15 (m, 2H), 6.92 (q, J = 7.8 Hz, 2H), 6.65 (t, J = 8.2 Hz, 2H), 5.36 (s, 2H), 4.31 (s, 2H), 3.89 (t, J = 5.8 Hz, 4H), 3.14 (t, J = 6.2 Hz, 2H), 2.68 (t, J = 7.1 Hz, 2H), 2.12 (s, 3H), 2.10-2.03 (m, 2H), 1.88 (s, 3H) | 11.4 min, 99.0% 8.2 min, 99.6% |
| 512 | (3-(3-((4-(4-(4-(3-Chloro-2-methylphenoxy)butanoyl)-3,4-dihydro-2H-benzo[b][1,4]thiazin-8-yl)-1H-pyrazol-1-yl)methyl)phenyl)ureido) methanesulfonic acid | | 670.4 | 8.67 (br. s., 1H), 7.91 (d, J = 0.6 Hz, 1H), 7.61 (d, J = 0.8 Hz, 1H), 7.29-7.23 (m, 2H), 7.19 (dd, J = 7.6, 1.2 Hz, 1H), 7.17-7.00 (m, 4H), 6.87 (d, J = 7.5 Hz, 1H), 6.79 (d, J = 8.3 Hz, 1H), 6.72 (d, J = 7.8 Hz, 1H), 5.22 (s, 2H), 3.88 (t, J = 6.1 Hz, 2H), 3.78 (s, 4H), 3.05 (t, J = 6.1 Hz, 2H), 2.51 (t, J = 7.1 Hz, 2H), 1.98 (s, 3H), 1.91 (quin, J = 6.7 Hz, 2H)* | 11.9 min, 95.3% 8.4 min, 98.0% |
| 513 | 2-(3-(3-((4-(4-(4-(3-Chloro-2-methylphenoxy)butanoyl)-3,4-dihydro-2H-benzo[b][1,4]thiazin-8-yl)-1H-pyrazol-1-yl)methyl)phenyl)ureido)ethanesulfonic acid | | 684.3 | 8.67 (br. s., 1H), 7.90 (s, 1H), 7.60 (s, 1H), 7.32-7.27 (m, 2H), 7.22-7.17 (m, 1H), 7.15 (dd, J = 7.8, 1.4 Hz, 1H), 7.11-7.00 (m, 3H), 6.87 (d, J = 8.0 Hz, 1H), 6.79 (d, J = 8.0 Hz, 1H), 6.70 (d, J = 7.8 Hz, 1H), 5.20 (s, 2H), 3.89 (t, J = 6.2 Hz, 2H), 3.79 (br. s., 2H), 3.31-3.27 (m, 2H), 3.05 (t, J = 6.1 Hz, 2H), 2.53-2.46 (m, 4H), 1.98 (s, 3H), 1.91 (quin, J = 6.7 Hz, 2H)* | 11.6 min, 97.7% 8.2 min, 98.2% |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 514 | 2-(3-(3-((4-(4-(4-(3-Chloro-2-methylphenoxy) butanoyl)-3,4-dihydro-2H-benzo[b][1,4]thiazin-8-yl)-1H-pyrazol-1-yl)methyl)phenyl)ureido) acetic acid | | 634.3 | 8.59 (s, 1H), 7.91 (s, 1H), 7.61 (s, 1H), 7.32-7.25 (m, 2H), 7.19 (d, J = 7.5 Hz, 1H), 7.16-7.10 (m, 2H), 7.09-7.00 (m, 2H), 6.87 (d, J = 8.0 Hz, 1H), 6.77 (dd, J = 17.5, 8.0 Hz, 2H), 6.20 (br. s., 1H), 5.22 (s, 2H), 3.88 (t, J = 6.2 Hz, 2H), 3.80 (br. s., 2H), 3.72 (d, J = 5.20 Hz, 2H), 3.05 (t, J = 6.1 Hz, 2H), 2.51 (t, J = 7.1 Hz, 2H), 1.97 (s, 3H), 1.91 (quin, J = 6.7 Hz, 2H)* | 10.1 min, 96.6% 9.6 min, 96.8% |
| 515 | 3-(3-(3-((4-(4-(4-(3-Chloro-2-methylphenoxy) butanoyl)-3,4-dihydro-2H-benzo[b][1,4] thiazin-8-yl)-1H-pyrazol-1-yl) methyl)phenyl)ureido) propanoic acid | | 648.3 | 8.39 (s, 1H), 7.91 (d, J = 0.6 Hz, 1H), 7.61 (s, 1H), 7.29-7.23 (m, 2H), 7.21-6.97 (m, 5H), 6.86 (d, J = 7.8 Hz, 1H), 6.79 (d, J = 8.3 Hz, 1H), 6.73 (d, J = 7.8 Hz, 1H), 6.05 (br. s., 1H), 5.21 (s, 2H), 3.88 (t, J = 6.1 Hz, 2H), 3.79 (br. s., 2H), 3.22 (t, J = 6.4 Hz, 2H), 3.08-3.02 (m, 2H), 2.51 (t, J = 7.1 Hz, 2H), 2.33 (t, J = 6.5 Hz, 2H), 1.97 (s, 3H), 1.91 (quin, J = 6.7 Hz, 2H)* | 10.1 min, 97.7% 9.7 min, 97.6% |
| 516 | (S)-2-Amino-5-(3-(3-((4-(4-(4-(2,3-dimethylphenoxy) butanoyl)-3,4-dihydro-2H-benzo[b][1,4] thiazin-8-yl)-1H-pyrazol-1-yl)methyl)phenyl) ureido)pentanoic acid | | 671.4 | 8.32 (s, 1H), 8.12-8.02 (m, 3H), 7.92 (d, J = 0.6 Hz, 1H), 7.61 (d, J = 0.6 Hz, 1H), 7.30-7.24 (m, 2H), 7.21-7.04 (m, 4H), 6.88 (t, J = 7.8 Hz, 1H), 6.74 (d, J = 7.8 Hz, 1H), 6.62 (d, J = 7.8 Hz, 2H), 6.07 (br. s., 1H), 5.21 (s, 2H), 3.82 (t, J = 6.1 Hz, 4H), 3.07-3.01 (m, 4H), 2.50 (t, J = 7.1 Hz, 2H), 2.07 (s, 3H), 1.93-1.86 (m, 2H), 1.85 (s, 3H), 1.80-1.65 (m, 2H), 1.57-1.39 (m, 2H) | 7.4 min, 100% 8.5 min, 100% |
| 517 | 2-(3-(3-Chloro-4-((4-(4-(4-(3-chloro-2-methylphenoxy) butanoyl)-3,4-dihydro-2H-benzo[b][1,4] thiazin-8-yl)-1H-pyrazol-1-yl)methyl)-5-fluorophenyl)ureido) acetic acid | | 686.3 | 7.68 (s, 1H), 7.61 (s, 1H), 7.40-7.32 (m, 2H), 7.27-7.22 (m, 1H), 7.15 (d, J = 5.0 Hz, 2H), 7.02-6.96 (m, 1H), 6.85 (d, J = 8.0 Hz, 1H), 6.73 (d, J = 8.3 Hz, 1H), 5.45 (s, 2H), 4.03-3.83 (m, 6H), 3.12 (t, J = 6.1 Hz, 2H), 2.68 (t, J = 6.9 Hz, 2H), 2.07 (quin, J = 6.3 Hz, 2H), 1.98 (s, 3H) | 10.9 min, 99.6% 10.1 min, 99.6% |

TABLE 19-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 518 | (3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)phenyl)ureido)methanesulfonic acid | | 648.3 | 8.23 (s, 1H), 8.11 (s, 1H), 7.64 (dd, J = 7.2, 2.3 Hz, 1H), 7.46 (s, 1H), 7.36-7.09 (m, 4H), 6.97-6.82 (m, 2H), 6.59 (d, J = 8.6 Hz, 2H), 5.41 (s, 2H), 4.76 (d, J = 13.4 Hz, 1H), 4.47 (d, J = 12.3 Hz, 1H), 4.32 (s, 2H), 3.91-3.72 (m, 2H), 3.58 (t, J = 10.9 Hz, 1H), 2.82 (t, J = 11.6 Hz, 1H), 2.57-2.16 (m, 3H), 2.11-1.93 (m, 5H), 1.87-1.68 (m, 4H) | 5.8 min, 98.5% 6.9 min, 98.5% |
| 519 | 2-(3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)phenyl)ureido)acetic acid | | 612.3 | 7.98 (s, 1H), 7.92 (s, 1H), 7.64 (dd, J = 6.4, 3.1 Hz, 1H), 7.40-7.32 (m, 2H), 7.30-7.23 (m, 1H), 7.18-7.10 (m, 2H), 6.98-6.87 (m, 2H), 6.64 (t, J = 7.7 Hz, 2H), 5.34 (s, 2H), 4.82-4.71 (m, 1H), 4.46 (d, J = 12.1 Hz, 1H), 3.99-3.76 (m, 4H), 3.57 (td, J = 11.7, 1.8 Hz, 1H), 2.94-2.76 (m, 1H), 2.51-2.35 (m, 2H), 2.27 (dd, J = 11.1, 3.6 Hz, 1H), 2.14-1.98 (m, 5H), 1.91-1.69 (m, 4H) | 8.4 min, 98.5% 8.1 min, 98.0% |
| 520 | 2-(3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenyl)ureido)-N,N,N-trimethylethanaminium, TFA salt | | 659.3 | 7.98 (s, 1H), 7.89 (s, 1H), 7.61 (dd, J = 6.2, 3.3 Hz, 1H), 7.41-7.33 (m, 2H), 7.31-7.23 (m, 1H), 7.19-7.08 (m, 2H), 7.00-6.89 (m, 2H), 6.80 (d, J = 7.9 Hz, 1H), 6.71 (d, J = 8.1 Hz, 1H), 5.33 (d, J = 1.5 Hz, 2H), 4.80-4.70 (m, 1H), 4.45 (d, J = 12.1 Hz, 1H), 3.95-3.79 (m, 2H), 3.71-3.62 (m, 2H), 3.56 (td, J = 11.7, 1.9 Hz, 1H), 3.50-3.43 (m, 2H), 3.25-3.14 (m, 9H), 2.90-2.73 (m, 1H), 2.52-2.16 (m, 3H), 2.12-1.97 (m, 2H), 1.95-1.89 (m, 3H), 1.76 (d, J = 14.7 Hz, 1H) | 6.6 min, 94.0% 7.8 min, 94.8% |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 521 | 2-(3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenyl)ureido)acetic acid | | 632.3 | 7.99 (d, J = 0.7 Hz, 1H), 7.91 (d, J = 0.7 Hz, 1H), 7.64 (dd, J = 6.8, 2.9 Hz, 1H), 7.41-7.31 (m, 2H), 7.31-7.24 (m, 1H), 7.20-7.11 (m, 2H), 7.04-6.90 (m, 2H), 6.83 (d, J = 7.5 Hz, 1H), 6.74 (d, J = 8.1 Hz, 1H), 5.35 (d, J = 1.1 Hz, 2H), 4.81-4.72 (m, 1H), 4.54-4.41 (m, 1H), 4.01-3.82 (m, 4H), 3.63-3.48 (m, 1H), 2.93-2.77 (m, 1H), 2.56-2.18 (m, 3H), 2.05 (dq, J = 12.0, 6.0 Hz, 2H), 1.96 (s, 3H), 1.79 (d, J = 14.5 Hz, 1H) | 8.7 min, 98.9% 8.4 min, 100% |
| 522 | (3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenyl)ureido)methanesulfonic acid | | 668.3 | 8.20 (d, J = 0.4 Hz, 1H), 8.10 (d, J = 0.7 Hz, 1H), 7.72-7.64 (m, 1H), 7.49 (s, 1H), 7.37-7.23 (m, 2H), 7.24-7.14 (m, 2H), 7.05-6.92 (m, 2H), 6.82 (d, J = 7.5 Hz, 1H), 6.74 (d, J = 8.1 Hz, 1H), 5.43 (s, 2H), 4.83-4.73 (m, 1H), 4.56-4.43 (m, 1H), 4.33 (s, 2H), 4.00-3.81 (m, 2H), 3.68-3.54 (m, 1H), 2.93-2.78 (m, 1H), 2.60-2.20 (m, 3H), 2.15-2.00 (m, 2H), 1.91 (s, 3H), 1.82 (d, J = 14.7 Hz, 1H) | 10.5 min, 99.6% 7.3 min, 99.1% |
| 523 | 2-(3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenyl)ureido)ethanesulfonic acid | | 682.2 | 8.03 (s, 1H), 7.95 (s, 1H), 7.65 (dd, J = 6.5, 3.0 Hz, 1H), 7.41-7.32 (m, 2H), 7.31-7.23 (m, 1H), 7.21-7.11 (m, 2H), 7.02-6.89 (m, 2H), 6.83 (d, J = 7.7 Hz, 1H), 6.74 (d, J = 8.1 Hz, 1H), 5.37 (s, 2H), 4.78 (d, J = 13.6 Hz, 1H), 4.48 (d, J = 12.1 Hz, 1H), 3.99-3.83 (m, 2H), 3.69-3.59 (m, 2H), 3.05-2.96 (m, 3H), 2.93-2.79 (m, 1H), 2.57-2.20 (m, 3H), 2.12-2.01 (m, 2H), 1.95 (s, 3H), 1.80 (d, J = 15.0 Hz, 1H) | 10.4 min, 99.6% 7.3 min, 99.4% |

TABLE 19-continued

| Example | Name | Formula I | LCMS, [M + H]⁺ | ¹H NMR (500 MHz, MeOD) δ | HPLC-1: Rt min, purity; HPLC-2: Rt min, purity |
|---|---|---|---|---|---|
| 524 | 3-(3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenyl)ureido)propanoic acid | | 646.4 | 7.99 (d, J = 0.4 Hz, 1H), 7.91 (d, J = 0.7 Hz, 1H), 7.64 (dd, J = 6.6, 2.9 Hz, 1H), 7.40-7.22 (m, 3H), 7.20-7.08 (m, 2H), 7.02-6.89 (m, 2H), 6.83 (dd, J = 7.9, 0.7 Hz, 1H), 6.73 (d, J = 8.1 Hz, 1H), 5.35 (d, J = 1.5 Hz, 2H), 4.82-4.71 (m, 1H), 4.53-4.42 (m, 1H), 4.00-3.82 (m, 2H), 3.58 (td, J = 11.8, 1.9 Hz, 1H), 3.46 (t, J = 6.4 Hz, 2H), 2.93-2.77 (m, 1H), 2.61-2.19 (m, 5H), 2.14-2.00 (m, 2H), 1.95 (s, 3H), 1.79 (d, J = 14.7 Hz, 1H) | 8.9 min, 99.2% 8.5 min, 99.1% |
| 525 | (S)-2-(3-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenyl)ureido)succinic acid | | 690.4 | 7.98 (s, 1H), 7.91 (d, J = 0.4 Hz, 1H), 7.64 (dd, J = 6.7, 2.8 Hz, 1H), 7.40 (s, 1H), 7.36-7.23 (m, 2H), 7.20-7.08 (m, 2H), 7.03-6.90 (m, 2H), 6.83 (d, J = 7.7 Hz, 1H), 6.73 (d, J = 8.4 Hz, 1H), 5.35 (s, 2H), 4.81-4.73 (m, 1H), 4.69 (t, J = 5.1 Hz, 1H), 4.53-4.41 (m, 1H), 3.98-3.82 (m, 2H), 3.64-3.47 (m, 1H), 3.06-2.77 (m, 2H), 2.55-2.19 (m, 2H), 2.15-1.99 (m, 1H), 1.95 (s, 3H), 1.79 (d, J = 14.7 Hz, 1H) | 8.5 min, 96.7% 8.2 min, 96.3% |
| 526 | (3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)phenyl)-3-methylureido)methanesulfonic acid | | 646.1 | 7.78 (br. s., 1H), 7.50 (br. s., 1H), 7.44 (d, J = 7.7 Hz, 1H), 7.39-7.31 (m, 2H), 7.28-7.16 (m, 3H), 6.96 (t, J = 7.7 Hz, 2H), 6.71-6.59 (m, 2H), 5.42 (s, 2H), 4.25 (s, 2H), 3.86 (br. s., 2H), 3.73 (t, J = 6.6 Hz, 2H), 3.25 (s, 3H), 2.80 (t, J = 6.9 Hz, 2H), 2.49 (br. s., 2H), 2.16-2.00 (m, 5H), 1.84-1.65 (m, 5H) | N/A |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 527 | (3-(3-((4-((1aR,7bS)-3-((2-(3-Chloro-2-methyl-phenoxy)ethoxy)carbonyl)-1a,2,3,7b-tetrahydro-1H-cyclopropa[c]quinolin-7-yl)-1H-pyrazol-1-yl)methyl)phenyl)ureido)methanesulfonic acid | | 666.1 | 8.17 (s, 1H), 8.01 (s, 1H), 7.48 (s, 1H), 7.30-7.22 (m, 3H), 7.18-7.14 (m, 1H), 7.10 (t, J = 7.8 Hz, 2H), 6.99-6.92 (m, 2H), 6.86 (d, J = 8.3 Hz, 1H), 5.47 (s, 2H), 4.62-4.46 (m, 3H), 4.33 (s, 2H), 4.25 (d, J = 4.3 Hz, 2H), 3.05 (d, J = 12.1 Hz, 1H), 2.22 (s, 3H), 2.12 (td, J = 8.7, 4.7 Hz, 1H), 1.90-1.80 (m, 1H), 1.08 (td, J = 8.3, 4.9 Hz, 1H), 0.65 (q, J = 4.8 Hz, 1H) | N/A 9.8 min, 98.9% |
| 528 | (3-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)phenyl)ureido)methanesulfonic acid | | 700.1 | 8.06 (br. s., 1H), 7.93 (br. s., 1H), 7.41-7.34 (m, 1H), 7.34-7.21 (m, 3H), 7.21-7.14 (m, 1H), 7.10 (br. s., 2H), 6.98 (d, J = 5.6 Hz, 1H), 6.87 (d, J = 6.3 Hz, 1H), 5.55 (br. s., 2H), 4.63-4.43 (m, 2H), 4.31 (br. s., 2H), 4.25 (br. s., 2H), 3.05 (d, J = 12.1 Hz, 1H), 2.30-2.11 (m, 4H), 1.94-1.77 (m, 1H), 1.40-1.27 (m, 1H), 1.12-1.01 (m, 1H), 0.70-0.58 (m, 1H) | 10.9 min, 97.8% 10.1 min, 97.8% |
| 529 | 2-(3-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)phenyl)ureido)acetic acid | | 664.0 | 8.08 (br. s., 1H), 7.79-7.74 (m, 1H), 7.73-7.68 (m, 1H), 7.14-7.03 (m, 5H), 7.02-6.97 (m, 1H), 6.73 (d, J = 8.3 Hz, 1H), 5.36-5.31 (m, 2H), 4.70-4.43 (m, 3H), 4.21 (d, J = 5.2 Hz, 2H), 3.84 (br. s., 2H), 3.08 (d, J = 12.9 Hz, 1H), 2.29 (s, 3H), 2.16-2.05 (m, 1H), 1.74 (d, J = 5.5 Hz, 1H), 1.01 (d, J = 5.2 Hz, 1H), 0.77 (d, J = 4.7 Hz, 1H) | 11.4 min, 98.5% 10.0 min, 98.9% |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 530 | (3-(3-((4-(1-(4-(2,3-Dimethylphenxoy)butanoyl)-1,2,3,4-tetrahydroquinolin-5-yl)-1H-pyrazol-1-yl)methyl)-4-fluorophenyl)ureido)methanesulfonic acid | | 650.3 | 7.57-7.33 (m, 4H), 7.31-7.21 (m, 2H), 7.16-7.04 (m, 2H), 6.99 (t, J = 8.0 Hz, 1H), 6.66 (d, J = 6.6 Hz, 2H), 5.38 (s, 2H), 4.34 (s, 2H), 3.82 (br. s., 2H), 3.72 (t, J = 6.3 Hz, 2H), 2.83 (t, J = 6.6 Hz, 2H), 2.36 (br. s., 3H), 2.12 (d, J = 4.9 Hz, 2H), 2.02-1.89 (m, 2H), 1.76 (br. s., 3H), 1.50-1.62 (m, 2H), | N/A 9.1 min, 98.8% |
| 531 | (3-(4-Chloro-3-((4-(1-(4-(2,3-dimethylphenoxy)butanoyl)-1,2,3,4-tetrahydroquinolin-5-yl)-1H-pyrazol-1-yl)methyl)phenyl)ureido)methanesulfonic acid | | 666.2 | 7.53-7.21 (m, 7H), 7.12 (br. s., 1H), 6.97 (m, 1H), 6.65 (br. s., 2H), 5.42 (s, 2H), 4.34 (s, 2H), 3.77-3.89 (m, 2H), 3.65-3.75 (m, 2H), 2.75-2.93 (m, 2H), 2.32 (br. s., 3H), 2.05-2.20 (m, 2H), 1.85-2.00 (br. s., 2H), 1.78 (br. s., 3H), 1.46-1.63 (br. s., 2H) | N/A 9.4 min, 99.2% |
| 532 | (S)-4-Carboxy-4-(3-(3-((4-(1-(4-(2,3-dimethyl-phenoxy)butanoyl)-1,2,3,4-tetrahydroquinolin-5-yl)-1H-pyrazol-1-yl)methyl)phenyl)ureido)-N,N,N-trimethylbutan-1-aminium | | 695.4 | 7.55 (br. s., 1H), 7.47 (br. s., 1H), 7.39-7.30 (m, 2H), 7.29-7.16 (m, 4H), 6.95 (t, J = 8.0 Hz, 1H), 6.88 (d, J = 7.7 Hz, 1H), 6.71-6.58 (m, 2H), 5.31 (s, 2H), 4.22 (t, J = 5.5 Hz, 1H), 3.84 (br. s., 2H), 3.72 (t, J = 6.6 Hz, 2H), 3.45-3.32 (m, 2H), 3.06 (s, 9H), 2.80 (t, J = 6.9 Hz, 2H), 2.46 (br. s., 3H), 2.18-2.07 (m, 2H), 2.01 (br. s., 3H), 1.95-1.60 (m, 8H) | 7.3 min, 95.6% 9.2 min, 97.9% |
| 533 | (3-(3-((4-(1-(4-(3-Chloro-2-methylphenoxy)butanoyl)-1,2,3,4-tetrahydroquinolin-5-yl)-1H-pyrazol-1-yl)methyl)phenyl)ureido)methanesulfonic acid | | 652.3 | 7.51 (br. s., 1H), 7.41 (s, 1H), 7.30-7.22 (m, 2H), 7.17-7.06 (m, 4H), 6.95 (t, J = 8.2 Hz, 1H), 6.77 (t, J = 7.7 Hz, 2H), 6.67 (d, J = 8.2 Hz, 1H), 5.20 (s, 2H), 4.22 (s, 2H), 3.80 (br. s., 2H), 3.63 (t, J = 6.9 Hz, 2H), 2.70 (t, J = 6.9 Hz, 2H), 2.40 (br. s., 3H), 2.11-1.95 (m, 2H), 1.87-1.59 (m, 4H) | N/A 8.5 min, 100% |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 534 | (R)-2-(3-(3-((4-(1-(4-(3-Chloro-2-methylphenoxy)butanoyl)-1,2,3,4-tetrahydroquinolin-5-yl)-1H-pyrazol-1-yl)methyl)phenyl)ureido)pentanedioic acid | | 688.4 | 7.60 (br. s., 1H), 7.51 (s, 1H), 7.34 (s, 1H), 7.31-7.17 (m, 5H), 7.03 (t, J = 8.2 Hz, 1H), 6.87 (dd, J = 12.9, 8.0 Hz, 2H), 6.74 (d, J = 8.2 Hz, 1H), 5.32 (s, 2H), 4.38 (dd, J = 8.5, 5.2 Hz, 1H), 3.88 (br. s., 2H), 3.71 (t, J = 6.6 Hz, 2H), 2.78 (t, J = 6.9 Hz, 2H), 2.60-2.28 (m, 5H), 2.27-2.05 (m, 4H), 2.04-1.67 (m, 4H) | 10.9 min, 98.1% 10.5 min, 97.6% |
| 535 | (R)-Dimethyl 2-(3-(3-((4-(1-(4-(3-chloro-2-methylphenoxy)butanoyl)-1,2,3,4-tetrahydroquinolin-5-yl)-1H-pyrazol-1-yl)methyl)phenyl)ureido)pentanedioate | | 716.4 | 7.62 (br. s., 1H), 7.52 (s, 1H), 7.33 (s, 1H), 7.31-7.16 (m, 5H), 7.03 (t, J =7.7 Hz, 1H), 6.88 (dd, J = 17.6, 7.7 Hz, 2H), 6.75 (d, J = 8.2 Hz, 1H), 5.32 (s, 2H), 4.40 (dd, J = 8.2, 5.5 Hz, 1H), 3.89 (br. s., 3H), 3.77-3.68 (m, 4H), 3.63 (s, 3H), 2.78 (t, J = 6.9 Hz, 2H), 2.60-2.34 (m, 5H), 2.26-1.66 (m, 8H) | 12.2 min, 99.5% 11.3 min, 99.6% |
| 536 | Ethyl 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)acetate | | 624.5 | 7.58 (s, 1H), 7.39 (s, 1H), 7.34 (br. s., 1H), 7.28-7.14 (m, 4H), 7.10 (s, 1H), 7.02 (t, J = 7.8 Hz, 1H), 6.93 (d, J = 7.4 Hz, 1H), 6.75 (d, J = 7.7 Hz, 1H), 6.66 (d, J = 8.0 Hz, 1H), 5.60 (t, J = 5.1 Hz, 1H), 5.29 (s, 2H), 4.22 (q, J = 7.2 Hz, 2H), 4.05 (d, J = 5.0 Hz, 2H), 3.96 (br. s., 2H), 3.80 (t, J = 6.7 Hz, 2H), 2.77 (t, J = 7.2 Hz, 2H), 2.62 (br. s., 2H), 2.19 (s, 5H), 1.95 (br. s., 3H), 1.91-1.82 (m, 2H), 1.30 (t, J = 7.2 Hz, 3H) | 12.3 min, 99.6% 11.5 min, 98.9% |

TABLE 19-continued

| Example | Name | Formula I | LCMS, [M+H]+ | ¹H NMR (500 MHz, MeOD) δ | HPLC-1: Rt min, purity; HPLC-2: Rt min, purity |
|---|---|---|---|---|---|
| 537 | Methyl 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)acetate | | 610.5 | 7.64 (s, 1H), 7.61-7.51 (m, 2H), 7.43 (s, 1H), 7.36-7.15 (m, 4H), 7.00 (t, J = 7.8 Hz, 1H), 6.92 (d, J = 7.3 Hz, 1H), 6.79-6.65 (m, 2H), 5.62 (br. s., 1H), 5.30 (s, 2H), 4.05-3.85 (m, 4H), 3.80-3.64 (m, 5H), 2.72 (t, J = 6.9 Hz, 2H), 2.61 (t, J = 6.2 Hz, 2H), 2.52 (br. s., 3H), 2.13-2.04 (m, 2H), 1.91 (br. s., 3H), 1.87-1.71 (m, 2H) | 11.7 min, 99.8% 11.1 min, 99.8% |
| 538 | (S)-2-(3-(3-((4-(1-(4-(3-Chloro-2-methylphenoxy)butanoyl)-1,2,3,4-tetrahydroquinolin-5-yl)-1H-pyrazol-1-yl)methyl)phenyl)ureido)pentanedioic acid | | 688.5 | 7.52 (br. s., 1H), 7.43 (s, 1H), 7.26 (s, 1H), 7.23-7.08 (m, 5H), 6.99-6.91 (m, 1H), 6.79 (dd, J = 12.9, 7.4 Hz, 2H), 6.67 (d, J = 8.2 Hz, 1H), 5.24 (s, 2H), 4.30 (dd, J = 8.5, 5.2 Hz, 1H), 3.81 (br. s., 2H), 3.64 (t, J = 6.6 Hz, 2H), 2.70 (t, J = 6.9 Hz, 2H), 2.51-2.24 (m, 5H), 2.19-1.96 (m, 4H), 1.95-1.81 (m, 2H) | 10.8 min, 98.4% 10.4 min, 100% |
| 539 | Diethyl 2-(3-(3-((4-(1-(4-(3-chloro-2-methyl-phenoxy)butanoyl)-1,2,3,4-tetrahydroquinolin-5-yl)-1H-pyrazol-1-yl)methyl)phenyl)ureido)malonate | | 507.3 | 7.60 (s, 1H), 7.38 (s, 1H), 7.33 (s, 1H), 7.31-7.15 (m, 5H), 7.06-6.95 (m, 3H), 6.91 (d, J = 7.7 Hz, 1H), 6.66 (d, J = 8.2 Hz, 1H), 5.32 (s, 2H), 5.14 (s, 1H), 4.35-4.19 (m, 4H), 3.97-3.90 (m, 2H), 3.77 (t, J = 6.9 Hz, 2H), 3.50 (s, 1H), 2.75 (t, J = 7.1 Hz, 2H), 2.55 (br. s., 3H), 2.18 (quin, J = 6.0 Hz, 2H), 2.01 (br. s., 3H), 1.90-1.76 (m, 2H), 1.29 (t, J = 7.1 Hz, 6H) | 12.8 min, 98.8% 11.7 min, 96.2% |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 540 | Isopropyl 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)acetate | | 638.6 | 7.60 (s, 1H), 7.53 (s, 1H), 7.44 (s, 1H), 7.39 (s, 1H), 7.30-7.11 (m, 4H), 7.00-6.93 (m, 1H), 6.88 (d, J = 7.1 Hz, 1H), 6.73-6.62 (m, 2H), 5.51 (br. s., 1H), 5.26 (s, 2H), 4.96 (dt, J = 12.5, 6.1 Hz, 1H), 3.87 (t, J = 5.8 Hz, 2H), 3.81 (s, 2H), 3.67 (t, J = 6.9 Hz, 2H), 2.68 (t, J = 6.9 Hz, 2H), 2.56 (br. s., 3H), 2.09 (br. s, 2H), 2.04 (quin, J = 6.3 Hz, 2H), 1.85 (br. s., 3H), 1.82-1.71 (m, 2H), 1.19 (d, J = 6.6 Hz, 6H) | 11.2 min, 99.2% 10.2 min, 99.3% |
| 541 | 1-(3-((4-(1-(4-(3-Chloro-2-methyl-phenoxy)butanoyl)-1,2,3,4-tetrahydro-quinolin-5-yl)-1H-pyrazol-1-yl)methyl)phenyl)-3-(2,3-dihydroxypropyl)urea | | 632.4 | 7.68-7.60 (m, 1H), 7.54 (s, 1H), 7.36 (s, 1H), 7.34-7.17 (m, 5H), 7.04 (t, J = 8.1 Hz, 1H), 6.89 (t, J = 8.0 Hz, 2H), 6.76 (d, J = 8.1 Hz, 1H), 5.33 (s, 2H), 3.91 (br. s., 2H), 3.79-3.68 (m, 2H), 3.54 (d, J = 5.3 Hz, 2H), 3.46-3.35 (m, 2H), 3.21 (dd, J = 13.9, 6.6 Hz, 1H), 2.79 (t, J = 6.8 Hz, 2H), 2.52 (br. s., 3H), 2.21-2.06 (m, 2H), 1.91 (br. s., 2H), 1.85-1.74 (m, 2H) | 10.6 min, 96.6% 10.3 min, 94.0% |
| 542 | 2-(3-Chloro-2-methyl-phenoxy)ethyl 5-(1-(2-chloro-5-(3-(2-ethoxy-2-oxoethyl)ureido)benzyl)-1H-pyrazol-4-yl)-3,4-dihydroquinoline-1(2H)-carboxylate | | 680.2 | 7.65 (s, 1H), 7.52 (d, J = 0.5 Hz, 1H), 7.47-7.35 (m, 2H), 7.29-7.18 (m, 2H), 7.10 (d, J = 2.3 Hz, 1H), 7.07-6.96 (m, 3H), 6.91 (d, J = 7.3 Hz, 1H), 6.80 (d, J = 8.3 Hz, 1H), 5.42 (br. s., 1H), 5.31 (s, 2H), 4.41 (dd, J = 5.3, 3.8 Hz, 2H), 4.20-4.12 (m, 2H), 4.04 (q, J = 7.1 Hz, 2H), 3.76 (d, J = 4.8 Hz, 2H), 3.67-3.53 (m, 2H), 2.68 (t, J = 6.4 Hz, 2H), 2.43 (br. s., 3H), 1.74 (quin, J = 6.4 Hz, 2H), 1.12 (t, J = 7.1 Hz, 3H) | 14.3 min, 98.8% 12.8 min, 99.1% |

TABLE 19-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 543 | 2-(3-(4-Chloro-3-((4-(1-((2-(3-chloro-2-methyl-phenoxy)ethoxy)carbonyl)-1,2,3,4-tetrahydroquinolin-5-yl)-1H-pyrazol-1-yl)methyl)phenyl)ureido)acetic acid | | 652.1 | 7.99 (br. s., 1H), 7.66 (br. s., 1H), 7.51-7.25 (m, 3H), 7.22-6.89 (m, 6H), 5.38 (br. s., 2H), 4.46 (br. s., 2H), 4.24 (br. s., 2H), 3.71-3.60 (m, 2H), 3.16-3.08 (m, 2H), 2.80-2.71 (m, 2H), 2.20 (br. s., 3H), 1.84-1.71 (m, 2H) | 13.0 min, 96.4% 11.9 min, 99.5% |
| 544 | 3-(Dimethylamino)propyl 2-(3-(3-((4-(1-(4-(2,3-dimethylphenoxy)butanoyl)-1,2,3,4-tetrahydroquinolin-5-yl)-1H-pyrazol-1-yl)methyl)phenyl)ureido)acetate | | 681.3 | 7.86 (s, 1H), 7.60 (s, 1H), 7.52 (s, 1H), 7.44 (s, 1H), 7.34-7.10 (m, 4H), 6.97 (t, J = 8.0 Hz, 1H), 6.87 (d, J = 7.7 Hz, 1H), 6.68 (t, J = 8.0 Hz, 2H), 5.95 (t, J = 5.5 Hz, 1H), 5.26 (s, 2H), 4.11 (t, J = 6.6 Hz, 2H), 3.95-3.80 (m, 4H), 3.68 (t, J = 6.6 Hz, 2H), 2.68 (t, J = 7.1 Hz, 2H), 2.57 (t, J = 6.0 Hz, 2H), 2.32 (t, J = 7.1 Hz, 2H), 2.22 (br. s., 3H), 2.15 (s, 6H), 2.13-2.00 (m, 4H), 1.86 (br. s., 3H), 1.81-1.70 (m, 2H) | 7.9 min, 96.1% 9.7 min, 93.2% |

*Injection 1 conditions: Column: Waters Acquity UPLC BEH C18, 2.1 × 50 mm, 1.7-μm particles; Mobile Phase A: 5.95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Injection 2 conditions: Column: Waters Acquity UPLC BEH C18, 2.1 × 50 mm, 1.7-μm particles; Mobile Phase A: 5.95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

**1H NMR (500 MHz, DMSO-d6) δ.

The compounds exemplified in Table 20 were prepared in a manner analogous to Example 126.

TABLE 20

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 545 | (S)-4-Carboxy-4-(3-((4-(4-(4-(3-chloro-2-methylphenoxy)butanoyl)-3,4-dihydro-2H-benzo[b][1,4]thiazin-8-yl)-1H-pyrazol-1-yl)methyl)benzamido)-N,N,N-trimethylbutan-1-aminium, TFA salt | | 718.5 | | 7.3 min, 100% 8.6 min, 100% |
| 546 | 2-(3-((4-(1-(4-(2,3-Dimethylphenoxy)butanoyl)-1,2,3,4-tetrahydroquinolin-5-yl)-1H-imidazol-1-yl)methyl)benzamido)ethanesulfonic acid | | 631.1 | 9.19 (d, J = 1.1 Hz, 1H), 7.95-7.82 (m, 2H), 7.67 (d, J = 7.7 Hz, 1H), 7.62-7.41 (m, 3H), 7.40-7.27 (m, 2H), 6.94 (t, J = 7.8 Hz, 1H), 6.65 (dd, J = 16.5, 7.7 Hz, 2H), 5.54 (s, 2H), 3.91 (br. s., 2H), 3.79 (dt, J = 10.2, 6.5 Hz, 4H), 3.12-3.01 (m, 2H), 2.79 (t, J = 7.2 Hz, 2H), 2.58 (br. s., 2H), 2.21-2.02 (m, 5H), 1.96-1.76 (m, 5H) | 7.7 min, 97.9% 8.0 min, 100% |
| 547 | 2-(3-((4-(1-(4-((2,3-Dimethylphenyl)(methyl)amino)butanoyl)-1,2,3,4-tetrahydroquinolin-5-yl)-1H-pyrazol-1-yl)methyl)benzamido)ethanesulfonic acid, TFA salt | | 644.2 | 7.90 (s, 1H), 7.76 (dt, J = 7.6, 1.4 Hz, 1H), 7.73 (s, 1H), 7.64 (s, 1H), 7.54-7.43 (m, 4H), 7.38-7.32 (m, 2H), 7.26 (br. s., 1H), 7.24-7.16 (m, 2H), 5.45 (s, 2H), 3.82-3.74 (m, 4H), 3.09-3.01 (m, 2H), 2.75 (t, J = 6.3 Hz, 3H), 2.70-2.57 (m, 2H), 2.39 (s, 3H), 2.36 (s, 3H), 1.90 (s, 3H), 1.83 (br. s., 2H) | 6.3 min, 99.8% 6.9 min, 100% |

TABLE 20-continued

| Example | Name | LCMS, [M + H]+ | ¹H NMR (500 MHz, MeOD) δ | HPLC-1: Rt min, purity; HPLC-2: Rt min, purity |
|---|---|---|---|---|
| 548 | 2-(3-((4-(1-(4-(2,3-Dimethylphenylamino)butanoyl)-1,2,3,4-tetrahydroquinolin-5-yl)-1H-pyrazol-1-yl)methyl)benzamido)ethanesulfonic acid, TFA salt | 630.2 | 7.90 (s, 1H), 7.78-7.74 (m, 1H), 7.72 (s, 1H), 7.64 (s, 1H), 7.53-7.44 (m, 2H), 7.34-7.29 (m, 1H), 7.28-7.18 (m, 5H), 5.45 (s, 2H), 3.81-3.74 (m, 5H), 3.43-3.35 (m, 3H), 3.05 (t, J = 6.6 Hz, 2H), 2.83-2.64 (m, 5H), 2.35 (s, 3H), 2.32 (s, 3H), 2.04 (d, J = 7.7 Hz, 2H), 1.96-1.84 (m, 2H) | 6.7 min, 99.7% 7.0 min, 100% |
| 549 | 2-(3-((4-(1-(4-((2,3-Dimethylphenyl)(methyl)amino)butanoyl)-1,2,3,4-tetrahydroquinolin-5-yl)-1H-pyrazol-1-yl)methyl)benzamido)acetic acid, TFA salt | 594.2 | 7.82 (d, J = 7.2 Hz, 1H), 7.68 (s, 1H), 7.64 (s, 1H), 7.57 (s, 1H), 7.49-7.41 (m, 2H), 7.33-7.27 (m, 3H), 7.23-7.15 (m, 2H), 7.11 (br. s., 1H), 5.42 (s, 2H), 4.22-4.13 (m, 2H), 3.87-3.55 (m, 6H), 3.19 (s, 3H), 2.68 (t, J = 6.2 Hz, 2H), 2.58 (br. s., 2H), 2.47-2.38 (m, 3H), 2.34 (s, 3H), 1.96-1.78 (m, 4H) | 6.1 min, 99.1% 7.9 min, 99.2% |
| 550 | 2-(3-((4-(1-(4-(2,3-Dimethylphenylamino)butanoyl)-1,2,3,4-tetrahydroquinolin-5-yl)-1H-pyrazol-1-yl)methyl)benzamido)acetic acid, TFA salt | 580.2 | 7.82 (d, J = 12 Hz, 1H), 7.65 (d, J = 3.0 Hz, 2H), 7.59 (s, 1H), 7.52-7.42 (m, 2H), 7.32 (d, J = 7.7 Hz, 1H), 7.24-7.13 (m, 4H), 7.08 (br. s., 1H), 7.05 (s, 1H), 5.42 (s, 2H), 4.18 (d, J = 5.0 Hz, 2H), 3.82 (br. s., 3H), 3.43 (br. s., 4H), 2.81 (br. s., 2H), 2.72 (t, J = 6.5 Hz, 2H), 2.34 (s, 3H), 2.32 (s, 3H), 2.10 (br. s., 1H), 1.97-1.83 (m, 2H) | 6.5 min, 99.8% 7.9 min, 100% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 551 | 2-(3-((4-(3-(4-(2,3-Dimethylphenoxy)-N-methylbutanamido)phenyl)-1H-pyrazol-1-yl)methyl)benzamido)acetic acid | | 555.3 | 7.85 (d, J = 1.1 Hz, 1H), 7.79 (s, 1H), 7.74 (br. s., 1H), 7.56 (s, 1H), 7.48-7.34 (m, 5H), 7.09 (br. s., 1H), 7.06-7.01 (m, 1H), 6.98 (t, J = 7.8 Hz, 1H), 6.72 (d, J = 7.4 Hz, 1H), 6.60 (d, J = 8.0 Hz, 1H), 5.38 (s, 2H), 4.21 (d, J = 5.2 Hz, 2H), 3.87 (t, J = 5.5 Hz, 2H), 3.29 (s, 3H), 2.37 (t, J = 7.0 Hz, 2H), 2.17 (s, 3H), 2.13-2.04 (m, 2H), 1.89 (s, 3H) | 9.6 min, 99.3% 9.2 min, 99.4% |
| 552 | 3-(3-((4-(3-(4-(2,3-Dimethylphenoxy)-N-methylbutanamido)phenyl)-1H-pyrazol-1-yl)methyl)benzamido)propanoic acid | | 569.3 | 7.82-7.75 (m, 2H), 7.69 (s, 1H), 7.51 (s, 1H), 7.45 (d, J = 5.0 Hz, 3H), 7.41-7.36 (m, 1H), 7.24-7.20 (m, 1H), 7.15 (br. s., 1H), 7.06-7.01 (m, 1H), 6.98 (t, J = 7.8 Hz, 1H), 6.72 (d, J = 7.4 Hz, 1H), 6.60 (d, J = 8.0 Hz, 1H), 5.35 (s, 2H), 3.86 (t, J = 5.5 Hz, 2H), 3.75-3.68 (m, 2H), 3.28 (s, 3H), 2.68 (t, J = 5.4 Hz, 2H), 2.38 (t, J = 7.0 Hz, 2H), 2.17 (s, 3H), 2.08 (quin, J = 6.3 Hz, 2H), 1.87 (s, 3H) | 9.6 min, 98.1% 9.2 min, 98.3% |
| 555 | (3-((4-((1aR,7bS)-3-(2-((2,3-Dimethylphenoxy)methyl)cyclopropanecarbonyl)-1a,2,3,7b-tetrahydro-1H-cyclopropa[c]quinolin-7-yl)-1H-pyrazol-1-yl)methyl)benzamido)methanesulfonic acid | | 641.0 | 8.14 (br. s., 1H), 7.94 (br. s., 1H), 7.91-7.83 (m, 2H), 7.52-7.45 (m, 2H), 7.31-7.16 (m, 3H), 6.88 (t, J = 7.4 Hz, 1H), 6.66 (d, J = 7.7 Hz, 1H), 6.57 (d, J = 8.2 Hz, 1H), 5.54 (s, 2H), 4.53 (s, 2H), 4.10 (dd, J = 10.4, 4.9 Hz, 1H), 3.55-3.47 (m, 1H), 2.23-2.12 (m, 4H), 2.06 (dd, J = 8.2, 4.4 Hz, 1H), 1.94 (br. s., 3H), 1.84 (d, J = 5.5 Hz, 1H), 1.29 (dt, J = 8.2, 4.1 Hz, 1H), 1.12-1.03 (m, 2H), 0.68 (d, J = 4.4 Hz, 1H) | N/A 8.9 min, 99.1% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 556 | 2-(3-((4-((1aR,7bS)-3-(2-((2,3-Dimethylphenoxy)methyl)cyclopropanecarbonyl)-1a,2,3,7b-tetrahydro-1H-cyclopropa[c]quinolin-7-yl)-1H-pyrazol-1-yl)methyl)benzamido)ethanesulfonic acid | | 655.1 | 8.18 (br. s., 1H), 7.98 (s, 1H), 7.80 (br. s.,2H), 7.49 (d, J = 3.3 Hz, 2H), 7.37-7.17 (m, 3H), 6.87 (d, J = 7.1 Hz, 1H), 6.72-6.51 (m, 2H), 5.56 (s, 2H), 4.10 (dd, J = 10.4, 4.4 Hz, 1H), 3.79 (br. s., 2H), 3.50 (br. s., 1H), 3.08 (br. s., 2H), 2.28-1.78 (m, 9H), 1.29 (br. s., 1H), 1.08 (br. s.,2H), 0.69 (br. s., 1H) | 10.4 min, 95.7% 8.9 min, 98.7% |
| 557 | (3-((4-((1aR,7bS)-3-(2-((3-Chloro-2-methylphenoxy)methyl)cyclopropanecarbonyl)-1a,2,3,7b-tetrahydro-1H-cyclopropa[c]quinolin-7-yl)-1H-pyrazol-1-yl)methyl)benzamido)methanesulfonic acid | | 661.0 | 8.06 (s, 1H), 7.91-7.80 (m, 3H), 7.54-7.44 (m, 2H), 7.31-7.15(m, 3H), 7.02-6.94 (m, 1H), 6.86 (d, J = 1.1 Hz, 1H), 6.70 (d, J = 1.1 Hz, 1H), 5.58-5.46 (m, 2H), 4.58-4.47 (m, 2H), 4.21-4.12 (m, 1H), 3.60-3.47 (m, 1H), 2.20 (br. s., 1H), 2.12-1.89 (m, 4H), 1.81 (d, J = 5.5 Hz, 1H), 1.36-1.23 (m, 1H), 1.13-0.98 (m, 2H), 0.59 (d, J = 4.4Hz, 1H) | 9.9 min, 90.8% 9.1 min, 86.4% |
| 558 | 2-(3-((4-((1aR,7bS)-3-(2-((3-Chloro-2-methylphenoxy)methyl)cyclopropanecarbonyl)-1a,2,3,7b-tetrahydro-1H-cyclopropa[c]quinolin-7-yl)-1H-pyrazol-1-yl)methyl)benzamido)ethanesulfonic acid | | 675.0 | 8.19 (s, 1H), 8.00 (s, 1H), 7.80 (br. s., 2H), 7.54-7.46 (m, 2H), 7.35-7.17 (m, 3H), 7.03-6.93 (m, 1H), 6.86 (d, J = 8.2 Hz, 1H), 6.70 (d, J = 8.2 Hz, 1H), 5.64-5.50 (m, 2H), 4.18 (dd, J = 10.7, 5.2 Hz, 1H), 3.80 (br. s., 2H), 3.54 (br. s., 1H), 3.18-2.99 (m, 2H), 2.74 (br. s., 1H), 2.19 (br. s., 1H), 2.13-1.90 (m, 4H), 1.84 (d, J = 6.0 Hz, 1H), 1.30 (dd, J = 8.8, 4.4 Hz, 1H), 1.14-1.01 (m, 2H), 0.61 (d, J = 4.4 Hz, 1H) | 11.6 min, 98.5% 9.0 min, 100% |

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 559 | 2-(3-((4-(4-(2,3-Dimethylphenoxy)butanoyl)-3,4-dihydro-2H-benzo[b][1,4]thiazin-8-yl)-1H-pyrazol-1-yl)methyl)benzamido)ethanesulfonic acid | | 649.3 | 7.83-7.74 (m, 3H), 7.67 (s, 1H), 7.49-7.39 (m, 2H), 7.31-7.27 (m, 1H), 7.21-7.14 (m, 2H), 6.92 (t, J = 7.9 Hz, 1H), 6.64 (t, J = 7.4 Hz, 2H), 5.43 (s, 2H), 3.89 (t, J = 5.8 Hz, 4H), 3.82 (t, J = 6.5 Hz, 2H), 3.14 (t, J = 6.2 Hz, 2H), 3.08 (t, J = 6.4 Hz, 2H), 2.68 (t, J = 7.1 Hz, 2H), 2.11 (s, 3H), 2.07 (t, J = 6.1 Hz, 2H), 1.87 (s, 3H) | 10.9 min, 98.7% 7.8 min, 98.8% |
| 560 | 2-(4-((4-(1-(4-(2,3-Dimethylphenoxy)butanoyl)-1,2,3,4-tetrahydroquinolin-5-yl)-1H-pyrazol-1-yl)methyl)-3,5-difluorobenzamido)ethanesulfonic acid | | 667.3 | 8.57 (s, 1H), 7.90 (s, 1H), 7.55 (s, 1H), 7.50 (d, J = 8.0 Hz, 2H), 7.25 (br. s., 1H), 7.20-7.14 (m, 2H), 6.97 (t, J = 7.9 Hz, 1H), 6.71 (dd, J = 7.8, 3.9 Hz, 2H), 5.46 (s, 2H), 3.92 (t, J = 6.0 Hz, 2H), 3.67 (t, J = 6.5 Hz, 2H), 3.57-3.50 (m, 2H), 2.69-2.59 (m, 7H), 2.13 (s, 3H), 2.01 (quin, J = 6.7 Hz, 2H), 1.91 (s, 3H), 1.84-1.75 (m, 2H) | 10.8 min, 98.4% 8.0 min, 98.1% |
| 561 | 3-(4-((4-(1-(4-(2,3-Dimethylphenoxy)butanoyl)-1,2,3,4-tetrahydroquinolin-5-yl)-1H-pyrazol-1-yl)methyl)-3,5-difluorobenzamido)propanoic acid | | 631.3 | 7.62 (s, 1H), 7.52-7.47 (m, 2H), 7.45 (s, 1H), 7.23-7.15 (m, 3H), 6.95 (t, J = 7.8 Hz, 1H), 6.66 (dd, J = 16.5, 7.9 Hz, 2H), 5.49 (s, 2H), 3.90 (t, J = 5.8 Hz, 2H), 3.74 (t, J = 6.9 Hz, 2H), 3.63 (t, J = 6.8 Hz, 2H), 2.77 (t, J = 6.9 Hz, 2H), 2.63 (t, J = 6.8 Hz, 2H), 2.52 (t, J = 6.7 Hz, 2H), 2.14-2.07 (m, 5H), 1.86-1.78 (m, 5H) | 10.1 min, 98.0% 9.5 min, 98.1% |
| 562 | 3-(3-((4-(4-(2,3-Dimethylphenoxy)butanoyl)-3,4-dihydro-2H-benzo[b][1,4]thiazin-8-yl)-1H-pyrazol-1-yl)methyl)benzamido)propanoic acid | | 613.2 | 7.77-7.71 (m, 2H), 7.66-7.60 (m, 2H), 7.43 (t, J = 7.7 Hz, 1H), 7.38-7.34 (m, 1H), 7.24 (d, J = 7.4 Hz, 1H), 7.18-7.06 (m, 2H), 6.94 (t, J = 7.9 Hz, 1H), 6.66 (d, J = 7.9 Hz, 1H), 6.61 (d, J = 7.9 Hz, 1H), 5.37 (s, 2H), 4.30 (br. s., 2H), 3.87 (br. s., 2H), 3.65-3.58 (m, 2H), 3.19-3.08 (m, 2H), 2.68 (t, J = 6.9 Hz, 2H), 2.65-2.58 (m, 2H), 2.17-2.03 (m, 5H), 1.84 (br. s., 3H) | 100%* |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 563 | (3-((4-(4-(4-(2,3-Dimethylphenoxy)butanoyl)-3,4-dihydro-2H-benzo[b][1,4]thiazin-8-yl)-1H-pyrazol-1-yl)methyl)benzamido)methanesulfonic acid | | 635.2 | 8.17 (br. s., 1H), 8.06 (d, J = 0.6 Hz, 1H), 7.88 (s, 1H), 7.82 (d, J = 1.5 Hz, 1H), 7.69 (d, J = 0.6 Hz, 1H), 7.46- 7.37 (m, 2H), 7.30-7.26 (m, 1H), 7.24-7.21 (m, 1H), 7.17-7.11 (m, 1H), 6.97 (t, J = 7.8 Hz, 1H), 6.70 (d, J = 7.8 Hz, 2H), 5.42 (s, 2H), 4.11 (d, J = 6.1 Hz, 2H), 3.90 (t, J = 6.2 Hz, 4H), 3.13 (t, J = 6.0 Hz, 2H), 2.58 (t, J =12 Hz, 3H), 2.15 (s, 3H), 1.97 (quin, J = 6.7 Hz, 2H), 1.93 (s, 3H) | 11.0 min, 99.6% 7.8 min, 99.6% |
| 564 | 2-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)ethanesulfonic acid | | 669.1 | 7.83-7.72 (m, 3H), 7.65 (s, 1H), 7.48-7.36 (m, 2H), 7.30-7.23 (m, 1H), 7.15 (d, J = 5.0 Hz, 2H), 7.03-6.95 (m, 1H), 6.83 (d, J = 7.8 Hz, 1H), 6.73 (d, J = 8.3 Hz, 1H), 5.41 (s, 2H), 3.91 (t, J = 6.0 Hz, 4H), 3.80 (t, J = 6.5 Hz, 2H), 3.12 (t, J = 6.1 Hz, 2H), 3.06 (t, J = 6.4 Hz, 2H), 2.67 (t, J = 6.9 Hz, 2H), 2.06 (quin, J = 6.4 Hz, 2H), 1.97 (s, 3H) | 11.4 min, 99.7% 8.0 min, 99.6% |
| 565 | (3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)methanesulfonic acid | | 655.2 | 7.97-7.82 (m, 3H), 7.76 (s, 1H), 7.53-7.41 (m, 2H), 7.30 (d, J = 4.8 Hz, 1H), 7.24-7.15 (m, 2H), 7.06-6.98 (m, 1H), 6.84 (d, J =1.9 Hz, 1H), 6.75 (d, J = 7.9 Hz, 1H), 5.48 (s, 2H), 4.53 (s, 2H), 3.90 (br. s., 4H), 3.13 (br. s., 2H), 2.79-2.64 (m, 2H), 2.15-2.05 (m, 2H), 1.92 (br. s., 3H) | 11.5 min, 98.3% 8.0 min, 98.2% |
| 566 | 2-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)acetic acid | | 619.2 | 7.84-7.77 (m, 3H), 7.66 (d, J = 0.6 Hz, 1H), 7.50-7.43 (m, 2H), 7.31-7.26 (m, 1H), 7.20-7.15(m, 2H), 7.00 (t, J = 8.0 Hz, 1H), 6.85 (d, J = 8.0 Hz, 1H), 6.74 (d, J = 8.0 Hz, 1H), 5.43 (s, 2H), 4.12-4.08 (m, 2H), 3.93 (t, J = 5.8 Hz, 4H), 3.12 (t, J = 6.2 Hz, 2H), 2.69 (t, J = 7.1 Hz, 2H), 2.13-2.04 (m, 2H), 1.99 (s, 3H) | 9.9 min, 97.7% 9.5 min, 97.7% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 567 | 2-(3-((4-(4-(2,3-Dimethylphenoxy)butanoyl)-3,4-dihydro-2H-benzo[b][1,4]thiazin-8-yl)-1H-pyrazol-1-yl)methyl)benzamido)acetic acid | | 599.2 | 7.84-7.78 (m, 2H), 7.75 (s, 1H), 7.64 (s, 1H), 7.50-7.42 (m, 2H), 7.30-7.26 (m, 1H), 7.20-7.14 (m, 2H), 6.92 (t, J = 7.9 Hz, 1H), 6.65 (t, J = 8.0 Hz, 2H), 5.42 (s, 2H), 4.10 (s, 2H), 4.04-3.85 (m, 4H), 3.13 (t, J = 6.2 Hz, 2H), 2.68 (t, J = 7.1 Hz, 2H), 2.11 (s, 3H), 2.07 (quin, J = 6.5 Hz, 2H), 1.87 (s, 3H) | 9.7 min, 95.9% 9.3 min, 95.9% |
| 568 | 3-(3-((4-(4-(3-Chloro-2-methylphenoxy)butanoyl)-3,4-dihydro-2H-benzo[b][1,4]thiazin-8-yl)-1H-pyrazol-1-yl)methyl)benzamido)propanoic acid | | 633.1 | 7.82-7.72 (m,3H), 7.66 (d, J = 0.8 Hz, 1H), 7.49-7.39 (m, 2H), 7.31-7.26 (m, 1H), 7.21-7.14 (m, 2H), 7.05-6.97 (m, 1H), 6.85 (d, J = 7.8 Hz, 1H), 6.75 (d, J = 8.0 Hz, 1H), 5.42 (s, 2H), 3.93 (t, J = 5.8 Hz, 4H), 3.64 (t, J = 6.8 Hz, 2H), 3.13 (t, J = 6.2 Hz, 2H), 2.69 (t, J = 6.9 Hz, 2H), 2.63 (t, J = 6.9 Hz, 2H), 2.08 (quin, J = 6.4 Hz, 2H), 1.98 (s, 3H) | 99%* |
| 569 | (3-((4-(4-(4-(2,3-Dimethylphenoxy)butanoyl)-1,1-dioxido-3,4-dihydro-2H-benzo[b][1,4]thiazin-8-yl)-1H-pyrazol-1-yl)methyl)benzamido)methanesulfonic acid | | 667.2 | 8.46 (t, J = 6.1 Hz, 1H), 8.11 (s, 1H), 7.86-7.81 (m, 2H), 7.68 (s, 1H), 7.61-7.55 (m, 1H), 7.55-7.51 (m, 1H), 7.45-7.41 (m, 1H), 7.40-7.34 (m, 2H), 7.00 (t, J = 7.9 Hz, 1H), 6.76-6.70 (m, 2H), 5.45 (s, 2H), 4.28 (br. s., 2H), 4.11 (d, J = 6.4 Hz, 2H), 3.94 (t, J = 6.2 Hz, 2H), 3.73 (t, J = 6.1 Hz, 2H), 2.68 (t, J = 7.2 Hz, 2H), 2.17 (s, 3H), 2.07-1.99 (m, 2H), 1.97 (s, 3H) | 10.1 min, 100% 7.6 min, 100% |
| 570 | 2-(3-((4-(4-(3-Chloro-2-methylphenoxy)butanoyl)-3,4-dihydro-2H-benzo[b][1,4]oxazin-8-yl)-1H-pyrazol-1-yl)methyl)benzamido)ethanesulfonic acid | | 653.2 | 8.34 (br. s., 1H), 8.12 (s, 1H), 7.83 (d, J = 0.6 Hz, 1H), 7.68 (s, 1H), 7.60 (d, J =7.8 Hz, 1H), 7.41-7.27 (m, 4H), 7.08-7.02 (m, 1H), 6.88 (d, J = 8.0 Hz, 1H), 6.85-6.76 (m, 2H), 5.32 (s, 2H), 4.27 (t, J = 4.7 Hz, 2H), 3.97-3.94 (m, 2H), 3.86-3.80 (m, 2H), 3.50-3.43 (m, 2H), 2.70 (t, J = 7.2 Hz, 2H), 2.59 (t, J = 6.9 Hz, 2H), 2.06 (s, 3H), 1.98 (quin, J = 6.7 Hz, 2H) | 12.0 min, 99.7% 8.2 min, 98.9% |

TABLE 20-continued

| Example | Name | Formula I | LCMS, [M + H]⁺ | ¹H NMR (500 MHz, MeOD) δ | HPLC-1: Rt min, purity; HPLC-2: Rt min, purity |
|---|---|---|---|---|---|
| 571 | (3-((4-(4-(4-(3-Chloro-2-methylphenoxy)butanoyl)-3,4-dihydro-2H-benzo[b][1,4]oxazin-8-yl)-1H-pyrazol-1-yl)methyl)benzamido)methanesulfonic acid | | 639.2 | 8.15-8.08 (m, 2H), 7.83 (s, 1H), 7.77 (s, 1H), 7.72 (d, J = 7.5 Hz, 1H), 7.41-7.28 (m, 4H), 7.08-7.02 (m, 1H), 6.88 (d, J = 7.5 Hz, 1H), 6.86-6.76 (m, 2H), 5.32 (s, 2H), 4.27 (t, J = 4.7 Hz, 2H), 4.03 (d, J = 6.4 Hz, 2H), 3.96 (t, J = 6.4 Hz, 2H), 3.85-3.81 (m, 2H), 2.70 (t, J = 7.2 Hz, 2H), 2.06 (s, 3H), 2.02-1.95 (m, 2H) | 12.1 min, 99.7% 8.2 min, 100% |
| 572 | 3-(3-((4-(4-(4-(3-Chloro-2-methylphenoxy)butanoyl)-3,4-dihydro-2H-benzo[b][1,4]oxazin-8-yl)-1H-pyrazol-1-yl)methyl)benzamido)propanoic acid | | 617.2 | 8.28 (br. s., 1H), 8.12 (s, 1H), 7.83 (s, 1H), 7.72-7.64 (m, 2H), 7.41-7.27 (m, 4H), 7.08-7.02 (m, 1H), 6.88 (d, J = 1.5 Hz, 1H), 6.85-6.76 (m, 2H), 5.32 (s, 2H), 4.26 (d, J = 4.9 Hz, 2H), 3.96 (t, J = 6.2 Hz, 2H), 3.85-3.81 (m, 2H), 3.65 (br. s., 2H), 3.41-3.36 (m, 2H), 2.71 (t, J = 7.1 Hz, 2H), 2.05 (s, 3H), 1.98 (quin, J = 6.7 Hz, 2H) | 10.2 min, 98.7% 9.6 min, 98.7% |
| 573 | 2-(3-Chloro-4-((4-(4-(4-(3-chloro-2-methylphenoxy)butanoyl)-3,4-dihydro-2H-benzo[b][1,4]oxazin-8-yl)-1H-pyrazol-1-yl)methyl)-5-fluorobenzamido)ethanesulfonic acid | | 705.2 | 8.53 (t, J = 4.0 Hz, 1H), 8.06 (s, 1H), 7.76 (s, 1H), 7.67 (s, 1H), 7.53 (dd, J = 10.0, 1.4 Hz, 1H), 7.36 (br. s., 1H), 7.28 (d, J = 7.8 Hz, 1H), 7.08-7.02 (m, 1H), 6.88 (d, J = 7.8 Hz, 1H), 6.83 (d, J = 8.0 Hz, 1H), 6.78 (t, J = 8.0 Hz, 1H), 5.43 (s,2H), 4.26 (t, J = 4.9 Hz, 2H), 3.96 (t, J = 6.2 Hz, 2H), 3.83 (t, J = 4.9 Hz, 2H), 3.49-3.42 (m, 2H), 2.70 (t, J = 7.2 Hz, 2H), 2.60 (t, J = 6.9 Hz, 2H), 2.05 (s, 3H), 1.98 (quin, J = 6.8 Hz, 2H) | N/A 8.7 min, 99.7% |
| 574 | 2-(3-Chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido)ethanesulfonic acid | | 721.1 | 8.53 (t, J = 5.1 Hz, 1H), 7.91 (s, 1H), 7.68 (s, 1H), 7.59-7.52 (m, 2H), 7.20-7.12 (m, 2H), 7.10-6.98 (m, 2H), 6.87 (d, J = 7.8 Hz, 1H), 6.79 (d, J = 8.3 Hz, 1H), 5.45 (s, 2H), 3.88 (t, J = 6.1 Hz, 2H), 3.78 (br. s., 2H), 3.49-3.41 (m, 2H), 3.05 (t, J = 6.1 Hz, 2H), 2.60 (t, J = 6.9 Hz, 2H), 2.50 (t, J = 12 Hz, 2H), 1.96 (s, 3H), 1.91 (quin, J = 6.6 Hz, 2H) | 15.1 min, 99.6% 8.6 min, 99.5% |

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 575 | 3-(3-Chloro-4-((4-(4-(4-(2,3-dimethylphenoxy)butanoyl)-3,4-dihydro-2H-benzo[b][1,4]thiazin-8-yl)-1H-pyrazol-1-yl)methyl)-5-fluorobenzamido) propanoic acid | | 665.3 | 7.78 (s, 1H), 7.75 (s, 1H), 7.62-7.57 (m, 2H), 7.25 (dd, J = 6.2, 2.6 Hz, 1H), 7.19-7.13 (m, 2H), 6.92 (t, J = 7.9 Hz, 1H), 6.64 (dd, J = 11.7, 7.8 Hz, 2H), 5.57 (d, J = 1.4 Hz, 2H), 4.06-3.86 (m, 4H), 3.63 (t, J = 6.8 Hz, 2H), 3.12 (t, J = 6.2 Hz, 2H), 2.73-2.60 (m, 4H), 2.12 (s, 3H), 2.06 (quin, J = 6.5 Hz, 2H), 1.87 (s, 3H) | 10.6 min, 94.0% 10.0 min, 94.1% |
| 576 | 2-(3-Chloro-4-((4-(4-(4-(2,3-dimethylphenoxy)butanoyl)-3,4-dihydro-2H-benzo[b][1,4]thiazin-8-yl)-1H-pyrazol-1-yl)methyl)-5-fluorobenzamido) acetic acid | | 651.2 | 7.83 (s, 1H), 7.75 (s, 1H), 7.65 (dd, J = 9.7, 1.7 Hz, 1H), 7.59 (d, J = 0.6 Hz, 1H), 7.28-7.23 (m, 1H), 7.19-7.14 (m, 2H), 6.92 (t, J = 7.8 Hz, 1H), 6.65 (dd, J = 12.2, 8.0 Hz, 2H), 5.58 (d, J = 1.4 Hz, 2H), 4.13-4.08 (m, 2H), 4.02-3.86 (m, 4H), 3.12 (t, J = 6.2 Hz, 2H), 2.68 (t, J = 7.1 Hz, 2H), 2.12 (s, 3H), 2.06 (quin, J = 6.5 Hz, 2H), 1.87 (s, 3H) | 10.5 min, 97.8% 9.9 min, 97.9% |
| 577 | 3-(3-Chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido)propanoic acid | | 685.2 | 7.77 (d, J = 6.7 Hz, 2H), 7.63-7.58 (m, 2H), 7.28-7.23 (m, 1H), 7.19-7.14 (m, 2H), 7.03-6.97 (m, 1H), 6.86 (d, J = 1.5 Hz, 1H), 6.74 (d, J = 8.0 Hz, 1H), 5.58 (d, J = 1.4 Hz, 2H), 3.93 (t, J = 5.8 Hz, 4H), 3.63 (t, J = 6.9 Hz, 2H), 3.12 (t, J = 6.2 Hz, 2H), 2.68 (t, J = 6.9 Hz, 2H), 2.66-2.61 (m, 2H), 2.08 (quin, J = 6.5 Hz, 2H), 1.98 (s, 3H) | 100%* |
| 578 | (3-Chloro-4-((4-(4-(4-(2,3-dimethylphenoxy)butanoyl)-3,4-dihydro-2H-benzo[b][1,4]thiazin-8-yl)-1H-pyrazol-1-yl)methyl)-5-fluorobenzamido) methanesulfonic acid | | 687.1 | 7.87 (s, 1H), 7.68 (dd, J = 9.4, 1.5 Hz, 1H),7.63 (s, 1H), 7.59 (s, 1H), 7.21 (d, J = 7.4 Hz, 1H), 7.15-7.05 (m, 2H), 6.95 (t, J = 7.9 Hz, 1H), 6.67 (d, J = 7.4 Hz, 1H), 6.61 (d, J = 7.9 Hz, 1H), 5.54 (s, 2H),4.50 (s, 2H), 4.28 (br. s., 2H), 3.87 (br. s., 2H), 3.19-3.08 (m, 2H), 2.67 (t, J = 6.9 Hz, 2H), 2.16-2.04 (m, 5H), 1.85 (br. s., 3H) | 100%* |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 579 | 2-(3-Chloro-4-((4-(4-(4-(2,3-dimethylphenoxy)butanoyl)-3,4-dihydro-2H-benzo[b][1,4]thiazin-8-yl)-1H-pyrazol-1-yl)methyl)-5-fluorobenzamido)ethanesulfonic acid | | 701.3 | 8.53 (br. s., 1H), 7.92 (s, 1H), 7.68 (s, 1H), 7.59-7.52 (m, 2H), 7.19-7.13 (m, 2H), 7.09-7.03 (m, 1H), 6.88 (t, J = 7.8 Hz, 1H), 6.62 (d, J = 7.8 Hz, 2H), 5.45 (s, 2H), 3.82 (t, J = 6.1 Hz, 4H), 3.49-3.43 (m, 2H), 3.05 (t, J = 6.1 Hz, 2H), 2.60 (t, J = 7.1 Hz, 2H), 2.50 (t, J = 7.1 Hz, 2H), 2.06 (s, 3H), 1.89 (quin, J = 6.7 Hz, 2H), 1.84 (s, 3H) | 12.4 in, 97.1% 8.4 min, 96.2% |
| 580 | 2-(3-Chloro-4-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)-5-fluorobenzamido)-N,N,N-trimethylethanaminium, TFA salt | | 672.3 | 7.80 (s, 2H), 7.63 (dd, J = 9.7, 1.7 Hz, 1H), 7.59 (s, 1H), 7.24-7.19 (m, 1H), 7.14 (t, J = 7.8 Hz, 1H), 7.07 (d, J = 6.7 Hz, 1H), 6.94 (t, J = 7.8 Hz, 1H), 6.66 (dd, J = 13.3, 7.8 Hz, 2H), 5.61 (d, J = 1.4 Hz, 2H), 4.72 (br. s., 1H), 3.99-3.92 (m, 1H), 3.92-3.79 (m, 4H), 3.58 (t, J = 6.8 Hz, 2H), 3.23 (s, 9H), 2.77-2.66 (m, 2H), 2.19-2.05 (m, 5H), 2.01 (br. s., 1H), 1.85 (br. s., 3H), 1.76-1.67 (m, 1H), 0.91-0.83 (m, 1H), 0.49 (br. s., 1H) | 8.0 min, 99.3% 9.4 min, 98.8% |
| 581 | 2-(3-Chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido)acetic acid | | 671.2 | 7.83 (s, 1H), 7.77 (s, 1H), 7.65 (dd, J = 9.8, 1.5 Hz, 1H), 7.61 (s, 1H), 7.28-7.23 (m, 1H), 7.19-7.15 (m, 2H), 7.01 (t, J = 8.0 Hz, 1H), 6.89-6.84 (m, 1H), 6.74 (d, J = 8.3 Hz, 1H), 5.59 (d, J = 1.4 Hz, 2H), 4.10 (s, 2H), 3.93 (t, J = 5.8 Hz, 4H), 3.12 (t, J = 6.2 Hz, 2H), 2.68 (t, J = 6.9 Hz, 2H), 2.13-2.04 (m, 2H), 1.98 (s, 3H) | 10.8 min, 97.8% 10.1 min, 97.6% |
| 582 | 2-(3-Chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido)-N,N,N-trimethylethanaminium, TFA salt | | 698.3 | 7.81 (s, 2H), 7.65-7.59 (m, 2H), 7.26 (dd, J = 6.0, 3.2 Hz, 1H), 7.20-7.14 (m, 2H), 7.04-6.98 (m, 1H), 6.86 (d, J = 1.5 Hz, 1H), 6.75 (d, J = 8.0 Hz, 1H), 5.59 (d, J = 1.4 Hz, 2H), 3.93 (t, J = 5.8 Hz, 3H), 3.85 (t, J = 6.8 Hz, 2H), 3.58 (t, J = 6.7 Hz, 2H), 3.23 (s, 9H), 3.12 (t, J = 6.2 Hz, 2H), 2.68 (t, J = 6.9 Hz, 2H), 2.12-2.04 (m, 2H), 1.97 (s, 3H) | 7.9 min, 98.1% 9.4 min, 98.2% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 583 | (S)-2-Amino-5-(3-chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido)pentanoic acid | | 728.4 | 8.78 (br. s., 1H), 8.01 (s, 1H), 7.85 (s, 1H), 7.71 (dd, J = 10.0, 1.4 Hz, 1H), 7.65 (d, J = 0.8 Hz, 1H), 7.26-7.22 (m, 2H), 7.19-7.08 (m, 2H), 6.95 (d, J = 7.8 Hz, 1H), 6.87 (d, J = 8.6 Hz, 1H), 5.54 (s, 2H), 3.97 (t, J = 6.2 Hz, 2H), 3.87 (br. s., 2H), 3.59 (br. s., 1H), 3.35-3.28 (m, 2H), 3.13-3.10 (m, 2H), 2.59 (t, J = 7.1 Hz, 2H), 2.04 (s,3H), 1.99 (quin, J = 6.1 Hz, 2H), 1.87-1.59 (m, 4H) | 7.9 min, 99.9% 9.0 min, 99.7% |
| 584 | (3-Chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido)methanesulfonic acid | | 707.3 | 7.87 (s, 1H), 7.71-7.65 (m, 2H), 7.60 (s, 1H), 7.22 (d, J = 7.4 Hz, 1H), 7.13 (t, J = 7.9 Hz, 1H), 7.10-7.04 (m, 1H), 7.02-6.95 (m, 1H), 6.86 (d, J = 7.9 Hz, 1H), 6.67 (d, J = 8.4 Hz, 1H), 5.54 (s, 2H), 4.50 (s, 2H), 4.29 (s, 2H), 3.89 (br. s., 2H), 3.11 (br. s.,2H), 2.71-2.62 (m, 2H), 2.14-2.05 (m, 2H), 1.99-1.91 (m, 3H) | 99%* |
| 585 | 2-(4-((4-(4-(4-(2,3-Dimethylphenoxy)butanoyl)-3,4-dihydro-2H-benzo[b][1,4]thiazin-8-yl)-1H-pyrazol-1-yl)methyl)-3,5-difluorobenzamido)ethanesulfonic acid | | 685.3 | 8.62-8.55 (m, 1H), 8.00 (s, 1H), 7.65 (d, J = 0.8 Hz, 1H), 7.55-7.48 (m, 2H), 7.29-7.20 (m, 2H), 7.18-7.10 (m, 1H), 6.96 (t, J = 7.8 Hz, 1H), 6.70 (d, J = 7.8 Hz, 2H), 5.47 (s, 2H), 3.97-3.82 (m, 4H), 3.56 (br. s., 2H), 3.13 (t, J = 6.1 Hz, 2H), 2.68 (t, J = 7.1 Hz, 2H), 2.58 (t, J = 7.1 Hz, 2H), 2.14 (s, 3H), 2.03-1.95 (m, 2H), 1.92 (s, 3H) | 11.9 min, 99.9% 8.3 min, 99.8% |
| 586 | 2-(4-((4-(4-(4-(2,3-Dimethylphenoxy)butanoyl)-3,4-dihydro-2H-benzo[b][1,4]thiazin-8-yl)-1H-pyrazol-1-yl)methyl)-3-fluorobenzamido)ethanesulfonic acid | | 667.3 | 8.41 (br. s., 1H), 7.96 (s, 1H), 7.61 (s, 1H), 7.54-7.48 (m, 2H), 7.27-7.14 (m, 3H), 7.10-7.04 (m, 1H), 6.88 (t, J = 7.9 Hz, 1H), 6.62 (d, J = 8.0 Hz, 2H), 5.40 (s, 2H), 3.82 (t, J = 6.2 Hz, 4H), 3.49-3.43 (m, 2H), 3.05 (t, J = 6.0 Hz, 2H), 2.59 (t, J = 6.9 Hz, 2H), 2.50 (t, J = 1.1 Hz, 2H), 2.07 (s, 3H), 1.89 (quin, J = 6.7 Hz, 2H), 1.84 (s, 3H) | 11.3 min, 98.1% 8.1 min, 98.1% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 587 | (S)-2-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)succinic acid | | 677.4 | 7.79 (d, J = 7.5 Hz, 3H), 7.66 (s, 1H), 7.50-7.42 (m, 2H), 7.31-7.26 (m, 1H), 7.19-7.15 (m, 2H), 7.00 (t, J = 8.0 Hz, 1H), 6.85 (d, J = 7.8 Hz, 1H), 6.75 (d, J = 8.0 Hz, 1H), 5.43 (s, 2H), 4.97 (t, J = 6.1 Hz, 1H), 4.08-3.83 (m, 4H), 3.13 (t, J = 6.2 Hz, 2H), 3.03-2.89 (m, 2H), 2.69 (t, J = 6.9 Hz, 2H), 2.08 (quin, J = 6.5 Hz, 2H), 1.99 (s, 3H) | 9.6 min, 96.6% 9.3 min, 97.1% |
| 588 | (S)-1-Carboxy-4-(3-chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)-N,N,N-trimethylbutan-1-aminium, TFA salt | | 732.4 | 8.63 (t, J = 5.5 Hz, 1H), 7.94 (s, 1H), 7.84 (s, 1H), 7.71 (dd, J = 10.0, 1.4 Hz, 1H), 7.56 (d, J = 0.6 Hz, 1H), 7.28 (d, J = 6.9 Hz, 1H), 7.21-7.14 (m, 2H), 6.99 (t, J = 7.9 Hz, 1H), 6.75-6.70 (m, 2H), 5.55 (s, 2H), 4.12 (dd, J = 11.2, 3.5 Hz, 1H), 3.93 (t, J = 6.2 Hz, 2H), 3.69 (t, J = 6.5 Hz, 2H), 3.42-3.33 (m, 2H), 3.20 (s, 9H), 2.68 (t, J = 7.2 Hz, 2H), 2.65-2.59 (m, 2H), 2.19-2.07 (m, 4H), 2.02 (quin, J = 6.6 Hz, 2H), 1.96-1.86 (m, 4H), 1.81 (quin, J = 6.7 Hz, 2H), 1.67-1.58 (m, 2H) | 8.0 min, 99.4% 8.8 min, 99.9% |
| 589 | (S)-2-(3-((4-(4-(4-(2,3-Dimethylphenoxy)butanoyl)-3,4-dihydro-2H-benzo[b][1,4]thiazin-8-yl)-1H-pyrazol-1-yl)methyl)benzamido)pentanedioic acid | | 671.4 | 7.85-7.77 (m, 2H), 7.76 (s, 1H), 7.64 (s, 1H), 7.52-7.41 (m, 2H), 7.32-7.25 (m, 1H), 7.19-7.13 (m, 2H), 6.92 (t, J = 7.9 Hz, 1H), 6.65 (t, J = 7.8 Hz, 2H), 5.42 (s, 2H), 4.66 (dd, J = 8.9, 5.3 Hz, 1H), 4.10-3.83 (m, 4H), 3.13 (t, J = 6.1 Hz, 2H), 2.68 (t, J = 6.9 Hz, 2H), 2.55-2.41 (m, 2H), 2.37-2.26 (m, 1H), 2.18-2.02 (m, 6H), 1.87 (s, 3H) | 9.3 min, 95.6% 9.1 min, 95.6% |
| 590 | 2-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)-N,N,N-trimethylethanaminium, TFA salt | | 646.4 | 7.81 (s, 2H), 7.80-7.75 (m, 1H), 7.67 (s, 1H), 7.51-7.47 (m, 2H), 7.31-7.26 (m, 1H), 7.20-7.15 (m, 2H), 7.00 (t, J = 8.2 Hz, 1H), 6.85 (d, J = 8.0 Hz, 1H), 6.75 (d, J = 8.3 Hz, 1H), 5.43 (s, 2H), 4.09-3.89 (m, 4H), 3.86 (t, J = 6.7 Hz, 2H), 3.58 (t, J = 6.7 Hz, 2H), 3.23 (s, 9H), 3.13 (t, J = 6.2 Hz, 2H), 2.69 (t, J = 6.9 Hz, 2H), 2.08 (quin, J = 6.4 Hz, 2H), 1.98 (s, 3H) | 7.4 min, 98.3% 8.8 min, 98.4% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 591 | 2-(3-((4-(4-(4-(3-Chloro-2-methylphenoxy)butanoyl)-3,4-dihydro-2H-benzo[b][1,4]oxazin-8-yl)-1H-pyrazol-1-yl)methyl)benzamido)-N,N,N-trimethylethanaminium, TFA salt | | 630.4 | 8.07 (s, 1H), 7.91 (s, 1H), 7.80-7.74 (m, 2H), 7.51-7.46 (m, 2H), 7.40 (dd, J = 7.8, 1.4 Hz, 1H), 7.28 (br. s., 1H), 7.05-6.99 (m, 1H), 6.91 (t, J = 7.9 Hz, 1H), 6.86 (d, J = 7.8 Hz, 1H), 6.78 (d, J = 8.3 Hz, 1H), 5.43 (s, 2H), 4.31 (t, J = 5.0 Hz, 2H), 4.01 (t, J = 6.0 Hz, 2H), 3.98-3.92 (m, 2H), 3.85 (ddd, J = 6.5, 5.2, 1.4 Hz, 2H), 3.57 (t, J = 6.7 Hz, 2H), 3.25-3.20 (m, 9H), 2.89 (t, J = 7.1 Hz, 2H), 2.22-2.13 (m, 2H), 2.06 (s, 3H) | 7.6 min, 100% 9.0 min, 100% |
| 592 | 3-((4-(4-(4-(3-Chloro-2-methylphenoxy)butanoyl)-3,4-dihydro-2H-benzo[b][1,4]thiazin-8-yl)-1H-pyrazol-1-yl)methyl)-N-(2-hydroxyethyl)benzamide | | 605.4 | 7.81-7.76 (m, 3H), 7.66 (d, J = 0.6 Hz, 1H), 7.49-7.40 (m, 2H), 7.31-7.26 (m, 1H), 7.20-7.15 (m, 2H), 7.00 (t, J = 7.9 Hz, 1H), 6.85 (d, J = 7.8 Hz, 1H), 6.75 (d, J = 8.0 Hz, 1H), 5.42 (s, 2H), 3.93 (t, J = 5.8 Hz, 4H), 3.71 (t, J = 5.7 Hz, 2H), 3.55-3.49 (m, 2H), 3.13 (t, J = 6.2 Hz, 2H), 2.69 (t, J = 6.9 Hz, 2H), 2.12-2.04 (m, 2H), 1.99 (s, 3H) | 9.8 min, 99.4% 9.3 min, 99.5% |
| 593 | 3-((4-(4-(4-(3-Chloro-2-methylphenoxy)butanoyl)-3,4-dihydro-2H-benzo[b][1,4]thiazin-8-yl)-1H-pyrazol-1-yl)methyl)-N-(2-hydroxy-2-methylpropyl)benzamide | | 633.5 | 7.82-7.76 (m, 3H), 7.66 (d, J = 0.8 Hz, 1H), 7.50-7.41 (m, 2H), 7.31-7.25 (m, 1H), 7.20-7.14 (m, 2H), 7.04-6.96 (m, 1H), 6.85 (d, J = 8.0 Hz, 1H), 6.75 (d, J = 8.0 Hz, 1H), 5.43 (s, 2H), 3.93 (t, J = 5.8 Hz, 4H), 3.41 (s, 2H), 3.12 (t, J = 6.2 Hz, 2H), 2.69 (t, J = 6.9 Hz, 2H), 2.08 (quin, J = 6.4 Hz, 2H), 1.98 (s, 3H), 1.24 (s, 6H) | 10.4 min, 99.9% 9.7 min, 99.9% |
| 594 | (S)-5-(Carboxymethylamino)-4-(3-((4-(4-(4-(2,3-dimethylphenoxy)butanoyl)-3,4-dihydro-2H-benzo[b][1,4]thiazin-8-yl)-1H-pyrazol-1-yl)methyl)benzamido)-5-oxopentanoic acid | | 728.5 | 7.87-7.80 (m, 2H), 7.76 (s, 1H), 7.64 (s, 1H), 7.52-7.42 (m, 2H), 7.31-7.25 (m, 1H), 7.21-7.13 (m, 2H), 6.92 (t, J = 7.9 Hz, 1H), 6.65 (t, J = 8.3 Hz, 2H), 5.43 (s, 2H), 4.62 (dd, J = 9.0, 4.9 Hz, 1H), 4.06-3.83 (m, 6H), 3.13 (t, J = 6.1 Hz, 2H), 2.68 (t, J = 7.1 Hz, 2H), 2.51-2.40 (m, 2H), 2.38-2.27 (m, 1H), 2.22-2.02 (m, 6H), 1.87 (s, 3H) | 8.8 min, 99.6% 8.6 min, 99.5% |

TABLE 20-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 595 | (S)-5-Carboxy-5-(3-((4-(4-(4-(3-chloro-2-methylphenoxy)butanoyl)-3,4-dihydro-2H-benzo[b][1,4]thiazin-8-yl)-1H-pyrazol-1-yl)methyl)benzamido)-N,N,N-trimethylpentan-1-aminium | | 732.5 | 8.64 (d, J = 7.9 Hz, 1H), 8.09 (s, 1H), 7.90-7.80 (m, 2H), 7.69 (s, 1H), 7.51-7.40 (m, 2H), 7.25 (d, J = 8.1 Hz, 2H), 7.19-7.08 (m, 2H), 6.94 (d, J = 7.9 Hz, 1H), 6.86 (d, J = 8.1 Hz, 1H), 5.43 (s, 2H), 4.46-4.39 (m, 1H), 3.93 (br. s., 4H), 3.26 (ddd, J = 10.1, 6.5, 3.4 Hz, 2H), 3.10 (br. s., 2H), 3.01 (s, 9H), 2.59 (br. s., 2H), 2.07-1.78 (m, 7H), 1.76-1.59 (m, 2H), 1.47-1.28 (m, 2H) | 7.3 min, 97.8% 8.6 min, 97.2% |
| 596 | (3-((4-(4-((2-(2,3-Dimethylphenoxy)ethoxy)carbonyl)-3,4-dihydro-2H-benzo[b][1,4]thiazin-8-yl)-1H-pyrazol-1-yl)methyl)benzamido)methanesulfonic acid | | 637.3 | 8.09 (br. s., 1H), 7.99 (s, 1H), 7.79 (s, 1H), 7.73 (d, J = 7.5 Hz, 1H), 7.59 (d, J = 0.6 Hz, 1H), 7.38-7.29 (m, 2H), 7.19 (dd, J = 8.0, 1.4 Hz, 1H), 7.04 (dd, J = 7.5, 1.4 Hz, 1H), 6.94 (q, J = 7.8 Hz, 2H), 6.70 (dd, J = 11.2, 7.9 Hz, 2H), 5.33 (s, 2H), 4.37 (dd, J = 5.4, 3.7 Hz, 2H), 4.14-4.07 (m, 2H), 4.03 (d, J = 6.1 Hz, 2H), 3.79-3.73 (m, 2H), 3.09-3.02 (m, 2H), 2.13 (s, 3H), 2.00 (s, 3H) | 11.6 min, 98.7% 8.4 min, 98.7% |
| 597 | 2-(3-((4-(4-((2-(2,3-Dimethylphenoxy)ethoxy)carbonyl)-3,4-dihydro-2H-benzo[b][1,4]thiazin-8-yl)-1H-pyrazol-1-yl)methyl)benzamido)ethanesulfonic acid | | 651.4 | 8.41 (br. s., 1H), 8.07 (d, J = 0.6 Hz, 1H), 7.78 (s, 1H), 7.71-7.66 (m, 2H), 7.48-7.37 (m, 2H), 7.27 (dd, J = 8.0, 1.4 Hz, 1H), 7.13 (dd, J = 7.5, 1.4 Hz, 1H), 7.07-6.96 (m, 2H), 6.78 (dd, J = 11.4, 7.8 Hz, 2H), 5.42 (s, 2H), 4.50-4.42 (m, 2H), 4.22-4.16 (m, 2H), 3.87-3.82 (m, 2H), 3.57-3.52 (m, 2H), 3.18-3.10 (m, 2H), 2.67 (t, J = 6.8 Hz, 2H), 2.21 (s, 3H), 2.08 (s, 3H) | 11.5 min, 96.6% 8.4 min, 96.9% |
| 598 | 2-(3-Chloro-4-((4-(4-((2-(2,3-dimethylphenoxy)ethoxy)carbonyl)-3,4-dihydro-2H-benzo[b][1,4]thiazin-8-yl)-1H-pyrazol-1-yl)methyl)-5-fluorobenzamido)ethanesulfonic acid | | 703.5 | 8.56-8.50 (m, 1H), 7.93 (s, 1H), 7.67 (s, 1H), 7.56-7.52 (m, 2H), 7.19 (dd, J = 8.0, 1.4 Hz, 1H), 7.06-7.00 (m, 1H), 6.98-6.88 (m, 2H), 6.73-6.67 (m, 2H), 5.45 (d, J = 1.1 Hz, 2H), 4.37 (dd, J = 5.5, 3.9 Hz, 2H), 4.14-4.08 (m, 2H), 3.78-3.73 (m, 2H), 3.48-3.44 (m, 2H), 3.08-3.01 (m, 2H), 2.60 (t, J = 7.1 Hz, 2H), 2.13 (s, 3H), 2.03-1.97 (m, 3H) | 13.5 min, 99.3% 8.8 min, 99.3% |

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 599 | (3-Chloro-4-((4-(4-((2-(2,3-dimethylphenoxy)ethoxy)carbonyl)-3,4-dihydro-2H-benzo[b][1,4]thiazin-8-yl)-1H-pyrazol-1-yl)methyl)-5-fluorobenzamido)methanesulfonic acid | | 689.3 | 8.78 (t, J = 6.0 Hz, 1H), 8.02 (s, 1H), 7.90 (s, 1H), 7.76 (dd, J = 10.1, 1.5 Hz, 1H), 7.64 (d, J = 0.8 Hz, 1H), 7.28 (dd, J = 8.0, 1.4 Hz, 1H), 7.15-7.09 (m, 1H), 7.07-6.98 (m, 2H), 6.83-6.74 (m, 2H), 5.54 (s, 2H), 4.47 (dd, J = 5.3, 3.9 Hz, 2H), 4.24-4.17 (m, 2H), 4.12 (d, J = 6.1 Hz, 2H), 3.88-3.81 (m, 2H), 3.17-3.11 (m, 2H), 2.22 (s, 3H), 2.09 (s, 3H) | 13.4 min, 99.2% 8.8 min, 99.2% |
| 600 | 3-((4-(4-(4-(2,3-Dimethylphenoxy)butanoyl)-3,4-dihydro-2H-benzo[b][1,4]thiazin-8-yl)-1H-pyrazol-1-yl)methyl)-N-(2-hydroxyethyl)benzamide | | 585.3 | 7.82-7.76 (m, 2H), 7.68-7.59 (m, 2H), 7.49-7.42 (m, 1H), 7.41-7.35 (m, 1H), 7.26 (d, J = 6.4 Hz, 1H), 7.18-7.11 (m, 2H), 6.93 (t, J = 7.9 Hz, 1H), 6.63 (dd, J = 13.6, 7.7 Hz, 2H), 5.39 (s, 2H), 4.49 (br. s., 2H), 3.86 (br. s., 2H), 3.71 (t, J = 5.7 Hz, 2H), 3.50 (t, J = 5.9 Hz, 2H), 3.18-3.09 (m, 2H), 2.69 (t, J = 5.9 Hz, 2H), 2.08 (br. s., 5H), 1.81 (br. s., 3H) | 100%* |
| 601 | (S)-2-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)pentanedioic acid | | 691.4 | 7.84-7.77 (m, 3H), 7.66 (s, 1H), 7.52-7.41 (m, 2H), 7.30-7.25 (m, 1H), 7.20-7.14 (m, 2H), 7.05-6.97 (m, 1H), 6.85 (d, J = 8.0 Hz, 1H), 6.75 (d, J = 8.3 Hz, 1H), 5.43 (s, 2H), 4.66 (dd, J = 9.0, 5.1 Hz, 1H), 3.93 (t, J = 5.8 Hz, 4H), 3.13 (t, J = 6.2 Hz, 2H), 2.69 (t, J = 6.9 Hz, 2H), 2.48 (td, J = 7.4, 3.1 Hz, 2H), 2.31 (td, J = 13.5, 7.8 Hz, 1H), 2.19-2.03 (m, 3H), 1.99 (s, 3H) | 9.6 min, 96.8% 9.2 min, 97.0% |
| 602 | 2-(3-((4-(4-((2-(3-Chloro-2-methylphenoxy)ethoxy)carbonyl)-3,4-dihydro-2H-benzo[b][1,4]thiazin-8-yl)-1H-pyrazol-1-yl)methyl)benzamido)ethanesulfonic acid | | 671.3 | 8.51 (t, J = 5.1 Hz, 1H), 8.13 (s, 1H), 7.78 (s, 1H), 7.71-7.67 (m, 2H), 7.48-7.35 (m, 2H), 7.25 (d, J = 7.0 Hz, 1H), 7.20-7.10 (m, 2H), 7.07-7.00 (m, 2H), 6.97 (d, J = 8.1 Hz, 1H), 5.42 (s, 2H), 4.53-4.42 (m, 2H), 4.27-4.22 (m, 2H), 3.88-3.79 (m, 2H), 3.55-3.47 (m, 2H), 3.20-3.10 (m, 2H), 2.71-2.62 (m, 2H), 2.19 (s, 3H) | 12.6 min, 98.5% 8.6 min, 98.3% |

TABLE 20-continued

| Example | Name | Formula I | LCMS, [M + H]⁺ | ¹H NMR (500 MHz, MeOD) δ | HPLC-1: Rt min, purity; HPLC-2: Rt min, purity |
|---|---|---|---|---|---|
| 603 | (3-((4-(4-((2-(3-Chloro-2-methylphenoxy)ethoxy)carbonyl)-3,4-dihydro-2H-benzo[b][1,4]thiazin-8-yl)-1H-pyrazol-1-yl)methyl)benzamido)methanesulfonic acid | | 657.3 | 8.54 (t, J = 6.3 Hz, 1H), 8.13 (d, J = 0.7 Hz, 1H), 7.89 (s, 1H), 7.83 (d, J = 7.5 Hz, 1H), 7.68 (d, J = 0.7 Hz, 1H), 7.46-7.36 (m, 2H), 7.25 (dd, J = 8.0, 1.2 Hz, 1H), 7.20-7.09 (m, 2H), 7.06-6.99 (m, 2H), 6.97 (d, J = 8.1 Hz, 1H), 5.41 (s, 2H), 4.49-4.45 (m, 2H), 4.25 (d, J = 4.6 Hz, 2H), 4.10 (s, 2H), 3.85-3.79 (m, 2H), 3.16-3.10 (m, 2H), 2.19 (s, 3H) | 12.7 min, 99.7% 8.6 min, 99.6% |
| 604 | (S)-2-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)ethyl 2-amino-3-methylbutanoate, HCl salt | | 704.5 | 7.84-7.75 (m, 3H), 7.67 (s, 1H), 7.52-7.43 (m, 2H), 7.32-7.26 (m, 1H), 7.22-7.15 (m, 2H), 7.05-6.97 (m, 1H), 6.85 (d, J = 8.0 Hz, 1H), 6.75 (d, J = 8.0 Hz, 1H), 5.43 (s, 2H), 4.47-4.42 (m, 2H), 4.13-3.81 (m, 5H), 3.78 (dt, J = 14.6, 5.8 Hz, 1H), 3.72-3.64 (m, 1H), 3.13 (t, J = 6.1 Hz, 2H), 2.69 (t, J = 6.9 Hz, 2H), 2.28 (qd, J = 7.0, 2.1 Hz, 1H), 2.09 (quin, J = 6.4 Hz, 2H), 2.00-1.92 (m, 3H), 1.03 (dd, J = 7.1, 1.0 Hz, 6H) | 7.6 min, 98.3% 8.8 min, 97.9% |
| 605 | 1-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)-2-methylpropan-2-yl 2-aminoacetate, HCl salt | | 690.5 | 7.85 (s, 1H), 7.83-7.77 (m, 2H), 7.70 (s, 1H), 7.52-7.45 (m, 2H), 7.29 (dd, J = 6.2, 2.9 Hz, 1H), 7.22-7.16 (m, 2H), 7.00 (t, J = 8.0 Hz, 1H), 6.84 (d, J = 7.8 Hz, 1H), 6.75 (d, J = 8.3 Hz, 1H), 5.45 (s, 2H), 4.12-3.87 (m, 4H), 3.77 (s, 2H), 3.73 (s, 2H), 3.13 (t, J = 6.2 Hz, 2H), 2.69 (t, J = 6.9 Hz, 2H), 2.09 (quin, J = 6.4 Hz, 2H), 1.97 (s, 3H), 1.58 (s, 6H) | 7.5 min, 99.0% 8.8 min, 99.5% |
| 606 | 2-(3-Chloro-2-methylphenoxy)ethyl 8-(1-(3-(2-hydroxy-2-methylpropylcarbamoyl)benzyl)-1H-pyrazol-4-yl)-2H-benzo[b][1,4]thiazine-4(3H)-carboxylate | | 635.3 | 7.98 (s, 1H), 7.82-7.77 (m, 2H), 7.71 (s, 1H), 7.51-7.40 (m, 2H), 7.29 (d, J = 7.9 Hz, 1H), 7.15-7.06 (m, 2H), 7.06-7.00 (m, 1H), 6.97 (d, J = 8.1 Hz, 1H), 6.87 (d, J = 8.4 Hz, 1H), 5.45 (s, 2H), 4.57-4.52 (m, 2H), 4.28-4.22 (m, 2H), 3.93-3.87 (m, 2H), 3.40 (s, 2H), 3.16-3.12 (m, 2H), 2.23 (s, 3H), 1.24 (s, 6H) | 11.0 min, 99.0% 10.3 min, 99.5% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 607 | 3-Chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluoro-N-(2-hydroxy-2-methylpropyl)benzamide | | 685.4 | 8.53-8.47 (m, 1H), 7.85 (s, 1H), 7.77 (s, 1H), 7.68 (dd, J = 9.9, 1.5 Hz, 1H), 7.60 (s, 1H), 7.28 (d, J = 5.1 Hz, 1H), 7.22-7.16 (m, 2H), 7.07-6.99 (m, 1H), 6.86 (d, J = 7.9 Hz, 1H), 6.76 (d, J = 8.4 Hz, 1H), 5.59 (s, 2H), 3.92 (br. s., 2H), 3.40 (d, J = 6.2 Hz, 2H), 3.16-3.08 (m, 2H), 2.72 (t, J = 6.3 Hz, 2H), 2.13-2.06 (m, 2H), 1.93 (d, J = 12.1 Hz, 3H), 1.23 (s, 6H) | 11.4 min, 98.2% 10.4 min, 98.2% |
| 608 | 3-(3-((4-(4-((2-(3-Chloro-2-methylphenoxy)ethoxy)carbonyl)-3,4-dihydro-2H-benzo[b][1,4]thiazin-8-yl)-1H-pyrazol-1-yl)methyl)benzamido)propanoic acid | | 635.3 | 7.79 (s, 1H), 7.76-7.71 (m, 2H), 7.68 (s, 1H), 7.45-7.40 (m, 1H), 7.37-7.34 (m, 1H), 7.27 (d, J = 6.4 Hz, 1H), 7.10-6.98 (m, 3H), 6.95 (d, J = 7.4 Hz, 1H), 6.76 (d, J = 7.9 Hz, 1H), 5.38 (s, 2H), 4.54-4.50 (m, 2H), 4.23-4.17 (m, 2H), 3.92-3.88 (m, 2H), 3.62 (t, J = 6.7 Hz, 2H), 3.15-3.09 (m, 2H), 2.58 (t, J = 6.7 Hz, 2H), 2.23 (s, 3H) | 100%* |
| 609 | 2-(3-((4-(4-((2-(3-Chloro-2-methylphenoxy)ethoxy)carbonyl)-3,4-dihydro-2H-benzo[b][1,4]thiazin-8-yl)-1H-pyrazol-1-yl)methyl)benzamido)acetic acid | | 621.3 | 7.81-7.77 (m, 3H), 7.68 (s, 1H), 7.47-7.42 (m, 1H), 7.40-7.36 (m, 1H), 7.27 (d, J = 1.4 Hz, 1H), 7.10-6.98 (m, 3H), 6.95 (d, J = 7.9 Hz, 1H), 6.76 (d, J = 7.9 Hz, 1H), 5.39 (s, 2H), 4.55-4.51 (m, 2H), 4.23-4.19 (m, 2H), 4.08 (s, 2H), 3.91-3.87 (m, 2H), 3.15-3.10 (m, 2H), 2.23 (s, 3H) | 100%* |
| 610 | 2-(3-Chloro-2-methylphenoxy)ethyl 8-(1-(2-chloro-6-fluoro-4-(2-hydroxy-2-methylpropylcarbamoyl)benzyl)-1H-pyrazol-4-yl)-2H-benzo[b][1,4]thiazine-4(3H)-carboxylate | | 687.3 | 8.48 (t, J = 5.5 Hz, 1H), 7.92 (s, 1H), 7.84 (s, 1H), 7.70-7.62 (m, 2H), 7.27 (d, J = 7.5 Hz, 1H), 7.13-7.06 (m, 2H), 7.06-6.94 (m, 2H), 6.86 (d, J = 8.4 Hz, 1H), 5.60 (d, J = 1.1 Hz, 2H), 4.57-4.52 (m, 2H), 4.29-4.22 (m, 2H), 3.93-3.85 (m, 2H), 3.44-3.38 (m, 2H), 3.16-3.09 (m, 2H), 2.21 (s, 3H), 1.23 (s, 6H) | 11.8 min, 94.5% 10.8 min, 93.9% |

TABLE 20-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 611 | (S)-4-(3-Chloro-4-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)-5-fluorobenzamido)-5-methoxy-N,N,N-trimethyl-5-oxopentan-1-aminium, TFA salt | | 786.5 | 7.98 (s, 1H), 7.89 (d, J = 1.3 Hz, 1H), 7.71 (dd, J = 9.8, 1.7 Hz, 1H), 7.67 (d, J = 0.7 Hz, 1H), 7.30 (d, J = 7.9 Hz, 1H), 7.15-7.09 (m, 2H), 7.08-7.02 (m, 1H), 6.99 (d, J = 7.5 Hz, 1H), 6.89 (d, J = 8.4 Hz, 1H), 5.64 (d, J = 1.1 Hz, 2H), 4.79-4.71 (m, 1H), 4.57 (dd, J = 5.3, 3.7 Hz, 2H), 4.30-4.25 (m, 2H), 3.95-3.89 (m, 2H), 3.80 (s, 3H), 3.53-3.38 (m, 2H), 3.19-3.13 (m, 11H), 2.24 (s, 3H), 2.13-2.02 (m, 1H), 2.00-1.85 (m, 3H) | 8.5 min, 98.8% 10.1 min, 99.3% |
| 612 | (S)-4-Carboxy-4-(3-chloro-4-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)-5-fluorobenzamido)-N,N,N-trimethylbutan-1-aminium | | 772.5 | 7.95 (s, 1H), 7.86 (s, 1H), 7.69 (dd, J = 9.7, 1.5 Hz, 1H), 7.64 (s, 1H), 7.28 (d, J = 7.5 Hz, 1H), 7.13-7.06 (m, 2H), 7.05-6.94 (m, 2H), 6.86 (d, J = 8.1 Hz, 1H), 5.61 (s, 2H), 4.56-4.51 (m, 2H), 4.27-4.21 (m, 2H), 3.92-3.85 (m, 2H), 3.50-3.39 (m, 2H), 3.17-3.09 (m, 12H), 2.21 (s, 3H), 2.13-2.02 (m, 1H), 2.00-1.84 (m, 3H) | 8.1 min, 99.7% 9.5 min, 99.8% |
| 613 | 2-(3-Chloro-4-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)-5-fluorobenzamido)ethanesulfonic acid | | 723.3 | 7.77 (s, 2H), 7.63 (s, 1H), 7.59 (dd, J = 9.7, 1.2 Hz, 1H), 7.26 (d, J = 6.9 Hz, 1H), 7.08-7.03 (m, 2H), 7.01-6.97 (m, 1H), 6.95 (d, J = 7.9 Hz, 1H), 6.77 (d, J = 7.9 Hz, 1H), 5.54 (s, 2H), 4.55-4.50 (m, 2H), 4.23-4.19 (m, 2H), 3.91-3.87 (m, 2H), 3.79 (t, J = 6.2 Hz, 2H), 3.14-3.10 (m, 2H), 3.07 (t, J = 6.2 Hz, 2H), 2.22 (s, 3H) | 100%* |
| 614 | (S)-4-Amino-2-(3-((4-(4-(4-(3-chloro-2-methylphenoxy)butanoyl)-3,4-dihydro-2H-benzo[b][1,4]thiazin-8-yl)-1H-pyrazol-1-yl)methyl)benzamido)-4-oxobutanoic acid | | 676.5 | 7.83-7.76 (m, 3H), 7.66 (d, J = 0.6 Hz, 1H), 7.51-7.41 (m, 2H), 7.32-7.26 (m, 1H), 7.20-7.14 (m, 2H), 7.03-6.96 (m, 1H), 6.85 (d, J = 7.8 Hz, 1H), 6.75 (d, J = 8.0 Hz, 1H), 5.43 (s, 2H), 4.93 (t, J = 6.0 Hz, 1H), 3.93 (t, J = 5.8 Hz, 4H), 3.13 (t, J = 6.2 Hz, 2H), 2.89 (dd, J = 6.0, 1.8 Hz, 2H), 2.69 (t, J = 7.1 Hz, 2H), 2.13-2.05 (m, 2H), 1.99 (s, 3H) | 9.1 min, 99.7% 8.9 min, 99.1% |

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 615 | 3-((4-(4-(4-(3-Chloro-2-methylphenoxy)butanoyl)-3,4-dihydro-2H-benzo[b][1,4]thiazin-8-yl)-1H-pyrazol-1-yl)methyl)-N-(2-(dimethylamino)ethyl)benzamide, TFA salt | 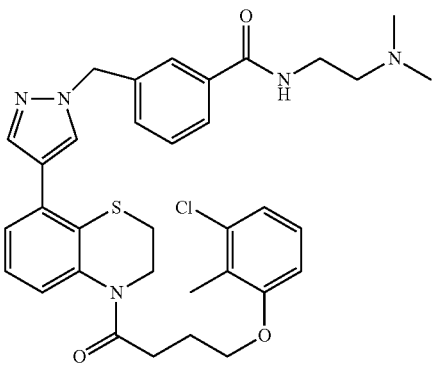 [SMILES: Cc1c(Cl)cccc1OCCCC(=O)N1CCSc2c(-c3cnn(Cc4cccc(C(=O)NCCN(C)C)c4)c3)cccc21] | 632.4 | 7.85 (s, 1H), 7.83-7.79 (m, 2H), 7.67 (d, J = 0.6 Hz, 1H), 7.51-7.47 (m, 2H), 7.31-7.26 (m, 1H), 7.21-7.16 (m, 2H), 7.03-6.98 (m, 1H), 6.86 (s, 1H), 6.75 (d, J = 8.0 Hz, 1H), 5.43 (s, 2H), 3.93 (t, J = 5.8 Hz, 4H), 3.76 (t, J = 5.8 Hz, 2H), 3.39 (t, J = 5.8 Hz, 2H), 3.13 (t, J = 6.2 Hz, 2H), 3.03-2.96 (m, 6H), 2.69 (t, J = 6.9 Hz, 2H), 2.13-2.04 (m, 2H), 1.98 (s, 3H) | 7.4 min, 98.9% 8.7 min, 99.0% |
| 616 | N-(2-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)ethyl)-N,N-dimethylbutan-1-aminium, TFA salt | 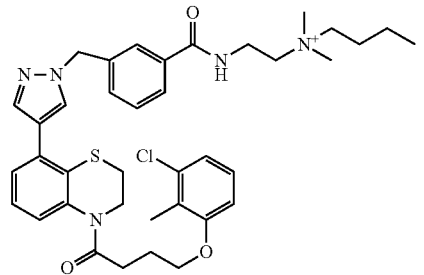 [SMILES: CCCC[N+](C)(C)CCNC(=O)c1cccc(Cn2cc(-c3cccc4c3SCCN4C(=O)CCCOc3cccc(Cl)c3C)cn2)c1] | 688.4 | 7.84-7.75 (m, 3H), 7.67 (d, J = 0.6 Hz, 1H), 7.52-7.46 (m, 2H), 7.31-7.27 (m, 1H), 7.23-7.14 (m, 2H), 7.04-6.96 (m, 1H), 6.85 (d, J = 8.0 Hz, 1H), 6.75 (d, J = 8.0 Hz, 1H), 5.43 (s, 2H), 3.93 (t, J = 5.8 Hz, 4H), 3.83 (t, J = 6.8 Hz, 2H), 3.54 (t, J = 6.8 Hz, 2H), 3.43-3.37 (m, 2H), 3.17 (s, 6H), 3.13 (t, J = 6.2 Hz, 2H), 2.69 (t, J = 7.1 Hz, 2H), 2.08 (quin, J = 6.4 Hz, 2H), 1.98 (s, 3H), 1.85-1.74 (m, 2H), 1.41 (sxt, J = 7.4 Hz, 2H), 1.00 (t, J = 7.4 Hz, 3H) | 7.9 min, 99.1% 9.5 min, 98.4% |
| 617 | (S)-3-Carboxy-3-(3-((4-(4-(4-(3-chloro-2-methylphenoxy)butanoyl)-3,4-dihydro-2H-benzo[b][1,4]thiazin-8-yl)-1H-pyrazol-1-yl)methyl)benzamido)-N,N,N-trimethylpropan-1-aminium, TFA salt | 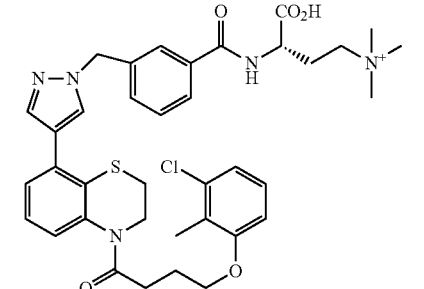 | 704.4 | 7.87-7.80 (m, 3H), 7.67 (d, J = 0.6 Hz, 1H), 7.53-7.47 (m, 2H), 7.31-7.27 (m, 1H), 7.20-7.16 (m, 2H), 7.01 (t, J = 8.2 Hz, 1H), 6.85 (d, J = 7.8 Hz, 1H), 6.75 (d, J = 8.6 Hz, 1H), 5.44 (s, 2H), 4.72 (dd, J = 8.3, 5.5 Hz, 1H), 3.93 (t, J = 5.8 Hz, 4H), 3.59 (td, J = 12.4, 4.9 Hz, 1H), 3.50-3.42 (m, 1H), 3.18-3.15 (m, 9H), 3.13 (t, J = 6.1 Hz, 2H), 2.69 (t, J = 6.9 Hz, 2H), 2.60-2.49 (m, 1H), 2.38-2.27 (m, 1H), 2.09 (quin, J = 6.4 Hz, 2H), 1.97 (s, 3H) | 7.5 min, 99.3% 8.6 min, 99.3% |
| 618 | 3-((4-(4-(4-(3-Chloro-2-methylphenoxy)butanoyl)-3,4-dihydro-2H-benzo[b][1,4]thiazin-8-yl)-1H-pyrazol-1-yl)methyl)-N-(2,3-dihydroxypropyl)benzamide | 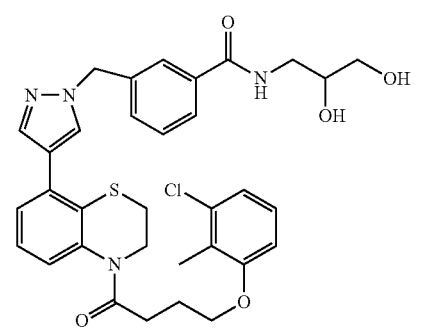 [SMILES: Cc1c(Cl)cccc1OCCCC(=O)N1CCSc2c(-c3cnn(Cc4cccc(C(=O)NCC(O)CO)c4)c3)cccc21] | 635.2 | 7.84-7.75 (m, 3H), 7.64 (s, 1H), 7.52-7.40 (m, 2H), 7.34-7.27 (m, 1H), 7.22-7.16 (m, 2H), 7.07-6.98 (m, 1H), 6.84 (d, J = 1.9 Hz, 1H), 6.75 (d, J = 8.4 Hz, 1H), 5.43 (s, 2H), 3.91 (br. s., 2H), 3.86-3.76 (m, 2H), 3.59-3.53 (m, 3H), 3.46-3.35 (m, 2H), 3.13 (dd, J = 3.3, 1.5 Hz, 2H), 2.76-2.67 (m, 2H), 2.17-2.05 (m, 2H), 1.96-1.87 (m, 3H) | 9.2 min, 99.3% 8.9 min, 98.3% |

TABLE 20-continued

| Example | Name | Formula I | LCMS, [M + H]⁺ | ¹H NMR (500 MHz, MeOD) δ | HPLC-1: Rt min, purity; HPLC-2: Rt min, purity |
|---|---|---|---|---|---|
| 619 | 3-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)propanoic acid | | 669.3 | 7.97 (s, 1H), 7.77-7.71 (m, 2H), 7.62 (d, J = 2.2 Hz, 1H), 7.56 (d, J = 8.4 Hz, 1H), 7.29 (d, J = 8.1 Hz, 1H), 7.17-7.00 (m, 3H), 6.97 (d, J = 7.7 Hz, 1H), 6.87 (d, J = 8.1 Hz, 1H), 5.55 (s, 2H), 4.57-4.52 (m, 2H), 4.27-4.22 (m, 2H), 3.93-3.88 (m, 2H), 3.64-3.57 (m, 2H), 3.17-3.11 (m, 2H), 2.62 (t, J = 6.9 Hz, 2H), 2.23 (s, 3H) | 11.2 min, 96.3% 10.6 min, 96.5% |
| 620 | (S)-2-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)succinic acid | | 713.2 | 7.97 (s, 1H), 7.78 (dd, J = 8.3, 2.1 Hz, 1H), 7.71 (s, 1H), 7.65 (d, J = 2.0 Hz, 1H), 7.57 (d, J = 8.4 Hz, 1H), 7.28 (d, J = 8.4 Hz, 1H), 7.17-6.94 (m, 4H), 6.86 (d, J = 7.9 Hz, 1H), 5.55 (s, 2H), 4.92 (dd, J = 7.0, 5.3 Hz, 1H), 4.58-4.51 (m, 2H), 4.29-4.21 (m, 2H), 3.94-3.86 (m, 2H), 3.17-3.10 (m, 3H), 3.02-2.83 (m, 2H), 2.22 (s, 3H) | 10.7 min, 99.4% 10.2 min, 99.3% |
| 621 | 3-(2-Chloro-3-((4-(4-(4-(2,3-Dimethylphenoxy)butanoyl)-3,4-dihydro-2H-benzo[b][1,4]thiazin-8-yl)-1H-pyrazol-1-yl)methyl)benzamido)propanoic acid | | 647.3 | 7.75 (s, 1H), 7.65 (d, J = 0.6 Hz, 1H), 7.42-7.38 (m, 1H), 7.37-7.32 (m, 1H), 7.29-7.25 (m, 1H), 7.21-7.12 (m, 3H), 6.93 (t, J = 7.8 Hz, 1H), 6.66 (dd, J = 13.5, 7.9 Hz, 2H), 5.52 (s, 2H), 4.05-3.85 (m, 4H), 3.63 (t, J = 6.8 Hz, 2H), 3.13 (t, J = 6.1 Hz, 2H), 2.72-2.62 (m, 4H), 2.13 (s, 3H), 2.10-2.04 (m, 2H), 1.87 (s, 3H) | 9.9 min, 99.9% 9.5 min, 99.9% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 622 | (S)-2-(2-Chloro-3-((4-(4-(4-(2,3-dimethylphenoxy)butanoyl)-3,4-dihydro-2H-benzo[b][1,4]thiazin-8-yl)-1H-pyrazol-1-yl)methyl)benzamido)succinic acid | | 691.3 | 7.74 (s, 1H), 7.65 (d, J = 0.6 Hz, 1H), 7.47 (dd, J = 7.6, 1.5 Hz, 1H), 7.36 (t, J = 7.6 Hz, 1H), 7.28 (dd, J = 6.7, 2.5 Hz, 1H), 7.21-7.13 (m, 3H), 6.93 (t, J = 1.9 Hz, 1H), 6.66 (dd, J = 12.8, 7.8 Hz, 2H), 5.53 (s, 2H), 4.96 (dd, J = 6.9, 5.3 Hz, 1H), 4.08-3.80 (m, 4H), 3.14 (t, J = 6.1 Hz, 2H), 3.03-2.87 (m, 2H), 2.69 (t, J = 6.9 Hz, 2H), 2.13 (s, 3H), 2.07 (quin, J = 6.5 Hz, 2H), 1.87 (s, 3H) | 9.4 min, 100% 9.1 min, 99.7% |
| 623 | 2-(2-Chloro-3-((4-(4-(4-(2,3-dimethylphenoxy)butanoyl)-3,4-dihydro-2H-benzo[b][1,4]thiazin-8-yl)-1H-pyrazol-1-yl)methyl)benzamido)ethanesulfonic acid | | 683.2 | 7.75 (s, 1H), 7.65 (d, J = 0.6 Hz, 1H), 7.48 (dd, J = 7.6, 1.5 Hz, 1H), 7.35 (t, J = 7.6 Hz, 1H), 7.31-7.25 (m, 1H), 7.21-7.11 (m, 3H), 6.97-6.92 (m, 1H), 6.66 (dd, J = 13.3, 7.8 Hz, 2H), 5.53 (s,2H), 3.89 (t, J = 5.8 Hz, 4H), 3.81 (t, J = 6.8 Hz, 2H), 3.12 (dt, J = 20.0, 6.4 Hz, 4H), 2.69 (t, J = 6.9 Hz, 2H), 2.13 (s, 3H), 2.11-2.03 (m, 2H), 1.87 (s, 3H) | 11.0 min, 97.3% 8.0 min, 100% |
| 624 | (S)-2-(2-Chloro-3-((4-(4-(4-(2,3-dimethylphenoxy)butanoyl)-3,4-dihydro-2H-benzo[b][1,4]oxazin-8-yl)-1H-pyrazol-1-yl)methyl)benzamido)succinic acid | | 675.3 | 8.07 (s, 1H), 7.92 (s, 1H), 7.46 (dd, J =7.5, 1.7 Hz, 1H), 7.42-7.39 (m, 1H), 7.35 (t, J = 7.8 Hz, 1H), 7.31-7.24 (m, 1H), 7.14 (d, J = 7.5 Hz, 1H), 6.92 (dt, J = 19.1, 7.9 Hz, 2H), 6.67 (d, J = 7.8 Hz, 2H), 5.53 (s, 2H), 4.96 (dd, J = 6.9, 5.5 Hz, 1H), 4.29 (t, J = 4.9 Hz, 2H), 4.01-3.93 (m, 4H), 3.03-2.86 (m, 4H), 2.20-2.09 (m, 5H), 1.93 (d, J = 2.5 Hz, 3H) | 9.6 min, 97.8% 9.3 min, 98.7% |
| 625 | 2-(2-Chloro-3-((4-(4-(4-(2,3-dimethylphenoxy)butanoyl)-3,4-dihydro-2H-benzo[b][1,4]oxazin-8-yl)-1H-pyrazol-1-yl)methyl)benzamido)ethanesulfonic acid | | 667.3 | 7.99 (s, 1H), 7.91 (s, 1H), 7.45 (dd, J = 7.9, 1.5 Hz, 1H), 7.37 (d, J = 6.9 Hz, 1H),7.27 (t, J = 7.7 Hz, 1H), 7.07-6.93 (m, 3H), 6.89 (t, J = 7.9 Hz, 1H), 6.69 (d, J = 7.4 Hz, 1H), 6.64 (d, J = 7.4 Hz, 1H), 5.49 (s, 2H), 4.32 (br. s., 2H), 4.01-3.92 (m, 4H), 3.82 (t, J = 6.4 Hz, 2H), 3.09 (t, J = 6.4 Hz, 2H), 2.88 (br. s., 2H), 2.21-2.09 (m, 5H), 1.92 (br. s., 3H) | 99%* |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 626 | 2-(2-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)metehyl)benzamido)ethanesulfonic acid | | 705.2 | 7.99 (d, J = 0.4 Hz, 1H), 7.75 (d, J = 0.7 Hz, 1H), 7.51 (dd, J = 7.7, 1.5 Hz, 1H), 7.39 (t, J = 7.1 Hz, 1H), 7.31 (d, J = 7.9 Hz, 1H), 7.18-7.02 (m, 4H), 7.00 (d, J = 7.5 Hz, 1H), 6.90 (d, J = 8.1 Hz, 1H), 5.59 (s, 2H), 4.61-4.54 (m, 2H), 4.32-4.25 (m, 2H), 3.97-3.90 (m, 2H), 3.82 (t, J = 6.9 Hz, 2H), 3.21-3.09 (m, 4H), 2.25 (s, 3H) | 12.8 min, 99.0% 8.7 min, 99.0% |
| 627 | (S)-2-(2-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)succinic acid | | 713.2 | 7.96 (d, J = 0.7 Hz, 1H), 7.72 (d, J = 0.7 Hz, 1H), 7.48-7.43 (m, 1H), 7.37 (t, J = 7.6 Hz, 1H), 7.29 (d, J = 7.5 Hz, 1H), 7.17-6.99 (m, 4H), 6.97 (d, J = 7.5 Hz, 1H), 6.86 (d, J = 8.4 Hz, 1H), 5.55 (s, 2H), 4.95 (dd, J = 7.3, 5.3 Hz, 1H), 4.57-4.52 (m, 2H), 4.27-4.22 (m, 2H), 3.92-3.87 (m, 2H), 3.17-3.11 (m, 2H), 3.03-2.95 (m, 1H), 2.92-2.85 (m, 1H), 2.22 (s, 3H) | 10.2 min, 100% 9.8 min, 99.4% |
| 628 | 3-(2-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)propanoic acid | | 669.2 | 7.96 (s, 1H), 7.72 (s, 1H), 7.44-7.33 (m, 2H), 7.29 (d, J = 7.9 Hz, 1H), 7.18-7.00 (m, 4H), 6.97 (d, J = 7.7 Hz, 1H), 6.87 (d, J = 8.1 Hz, 1H), 5.55 (s, 2H), 4.57-4.52 (m, 2H), 4.29-4.22 (m, 2H), 3.94-3.87 (m, 2H), 3.62 (t, J = 6.8 Hz, 2H), 3.17-3.11 (m, 2H), 2.65 (t, J = 6.8 Hz, 2H), 2.23 (s, 3H) | 10.7 min, 97.8% 10.1 min, 98.0% |
| 629 | 2-(3-Chloro-2-methylphenoxy)ethyl 8-(1-(2-chloro-3-(2-hydroxyethylcarbamoyl)benzyl)-1H-pyrazol-4-yl)-2H-benzo[b][1,4]thiazine-4(3H)-carboxylate | | 641.2 | 7.96 (s, 1H), 7.72 (d, J = 0.7 Hz, 1H), 7.47-7.42 (m, 1H), 7.40-7.33 (m, 1H), 7.29 (d, J = 7.5 Hz, 1H), 7.16-7.00 (m, 4H), 6.97 (d, J = 7.5 Hz, 1H), 6.87 (d, J = 8.1 Hz, 1H), 5.56 (s, 2H), 4.57-4.51 (m, 2H), 4.27-4.22 (m, 2H), 3.93-3.87 (m, 2H), 3.71 (t, J = 5.8 Hz, 2H), 3.52-3.46 (m, 2H), 3.16-3.11 (m, 2H), 2.22 (s, 3H) | 10.5 min, 100% 10.0 min, 100% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 630 | 2-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)ethanesulfonic acid | | 705.2 | 8.03 (s, 1H), 7.85-7.77 (m, 2H), 7.67 (d, J = 2.2 Hz, 1H), 7.59 (d, J = 8.4 Hz, 1H), 7.32 (d, J = 8.4 Hz, 1H), 7.21-7.02 (m, 3H), 6.99 (d, J = 7.5 Hz, 1H), 6.89 (d, J = 7.9 Hz, 1H), 5.61 (s, 2H), 4.61-4.54 (m, 2H), 4.31-4.24 (m, 2H), 3.97-3.89 (m, 2H), 3.80 (t, J = 6.7 Hz, 2H), 3.22-3.14 (m, 2H), 3.09 (t, J = 6.7 Hz, 2H), 2.25 (s, 3H) | 99%* |
| 631 | 3-((4-(4-(4-(3-Chloro-2-methylphenoxy)butanoyl)-3,4-dihydro-2H-benzo[b][1,4]thiazin-8-yl)-1H-pyrazol-1-yl)methyl)-N-((5-oxotetrahydrofuran-2-yl)methyl)benzamide | | 659.3 | 7.81-7.75 (m, 3H), 7.66 (s, 1H), 7.50-7.42 (m, 2H), 7.32-7.26 (m, 1H), 7.21-7.16 (m, 2H), 7.03-6.96 (m, 1H), 6.84 (d, J = 8.0 Hz, 1H), 6.75 (d, J = 8.3 Hz, 1H), 5.43 (s, 2H), 4.76 (qd, J = 7.1, 4.3 Hz, 1H), 3.93 (t, J = 5.8 Hz, 4H), 3.73-3.66 (m, 1H), 3.63-3.57 (m, 1H), 3.13 (t, J = 6.2 Hz, 2H), 2.69 (t, J = 6.9 Hz, 2H), 2.62-2.49 (m, 2H), 2.36 (dddd, J = 12.9, 9.3, 7.2, 5.5 Hz, 1H), 2.13-2.01 (m, 3H), 1.97 (s, 3H) | 10.6 min, 97.1% 10.0 min, 97.2% |
| 632 | 5-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)-4-hydroxypentanoic acid, Na salt | | 677.3 | 7.83-7.77 (m, 3H), 7.65 (d, J = 0.6 Hz, 1H), 7.48-7.39 (m, 2H), 7.30-7.26 (m, 1H), 7.17 (d, J = 4.7 Hz, 2H), 7.03-6.97 (m, 1H), 6.85 (d, J = 8.0 Hz, 1H), 6.75 (d, J = 8.3 Hz, 1H), 5.43 (s, 2H), 3.93 (t, J = 6.0 Hz, 4H), 3.85-3.75 (m, 1H), 3.52-3.46 (m, 1H), 3.38 (dd, J = 13.6, 6.9 Hz, 1H), 3.13 (t, J = 6.2 Hz, 2H), 2.69 (t, J = 6.9 Hz, 2H), 2.35 (td, J = 7.1, 2.8 Hz, 2H), 2.08 (quin, J = 6.4 Hz, 2H), 1.98 (s, 3H), 1.88-1.82 (m, 1H), 1.76 (dt, J = 14.8, 7.2 Hz, 1H) | 9.5 min, 98.5% 9.1 min, 98.4% |
| 633 | (S)-Ethyl 2-amino-5-(3-chloro-4-((4-(4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido)pentanoate, TFA salt | | 756.3 | 7.80 (s, 2H), 7.65-7.58 (m, 2H), 7.30-7.22 (m, 1H), 7.21-7.13 (m, 2H), 7.04-6.97 (m, 1H), 6.86 (d, J = 8.0 Hz, 1H), 6.75 (d, J = 8.3 Hz, 1H), 5.59 (d, J = 1.1 Hz, 2H), 4.36-4.27 (m, 2H), 4.07 (t, J = 6.4 Hz, 1H), 4.04-3.76 (m, 4H), 3.50-3.41 (m, 2H), 3.12 (t, J = 6.2 Hz, 2H), 2.69 (t, J = 6.9 Hz, 2H), 2.08 (quin, J = 6.5 Hz, 2H), 2.04-1.87 (m, 5H), 1.85-1.68 (m, 2H), 1.31 (t, J = 7.1 Hz, 3H) | 8.2 min, 95.8% 9.6 min, 96.4% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 634 | (S)-2-Amino-5-(3-((4-(4-(4-(3-chloro-2-methylphenoxy)butanoyl)-3,4-dihydro-2H-benzo[b][1,4]thiazin-8-yl)-1H-pyrazol-1-yl)methyl)benzamido)pentanoic acid, TFA salt | | 676.4 | 7.82 (s, 2H), 7.78 (d, J = 7.2 Hz, 1H), 7.68 (s, 1H), 7.52-7.44 (m, 2H), 7.34-7.27 (m, 1H), 7.22-7.18 (m, 2H), 7.05-6.99 (m, 1H), 6.87 (d, J = 8.0 Hz, 1H), 6.77 (d, J = 8.0 Hz, 1H), 5.44 (s, 2H), 4.03 (t, J = 6.4 Hz, 1H), 3.95 (t, J = 5.7 Hz, 4H), 3.55-3.41 (m, 2H), 3.14 (t, J = 6.2 Hz, 2H), 2.71 (t, J = 6.9 Hz, 2H), 2.14-2.02 (m, 3H), 2.01-1.93 (m, 4H), 1.90-1.75 (m, 2H) | 7.4 min, 99.1% 8.4 min, 95.9% |
| 635 | (S)-Isopropyl 2-amino-5-(3-((4-(4-(4-(3-chloro-2-methylphenoxy)butanoyl)-3,4-dihydro-2H-benzo[b][1,4]thiazin-8-yl)-1H-pyrazol-1-yl)methyl)benzamido)pentanoate, TFA salt | | 718.5 | 7.82-7.79 (m, 2H), 7.76 (d, J = 7.2 Hz, 1H), 7.66 (s, 1H), 7.50-7.43 (m, 2H), 7.31-7.26 (m, 1H), 7.20-7.16 (m, 2H), 7.00 (t, J = 8.0 Hz, 1H), 6.85 (d, J = 8.0 Hz, 1H), 6.75 (d, J = 8.0 Hz, 1H), 5.42 (s, 2H), 5.12 (quin, J = 6.2 Hz, 1H), 4.03 (t, J = 6.4 Hz, 1H), 3.99-3.79 (m, 4H), 3.51-3.39 (m, 2H), 3.13 (t, J = 6.2 Hz, 2H), 2.69 (t, J = 6.9 Hz, 2H), 2.09 (quin, J = 6.3 Hz, 2H), 2.04-1.88 (m, 6H), 1.85-1.66 (m, 2H), 1.29 (t, J = 6.2 Hz, 6H) | 7.8 min, 98.2% 9.2 min, 97.8% |
| 636 | 2-(3-Chloro-2-methylphenoxy)ethyl 8-(1-(5-(((1H-tetrazol-5-yl)methylcarbamoyl)-2-chlorobenzyl)-1H-pyrazol-4-yl)-2H-benzo[b][1,4]thiazine-4(3H)-carboxylate | | 681.3 | 7.96 (d, J = 0.7 Hz, 1H), 7.85 (dd, J = 8.4, 2.0 Hz, 1H), 7.77 (d, J = 2.0 Hz, 1H), 7.71 (d, J = 0.7 Hz, 1H), 7.57 (d, J = 8.4 Hz, 1H), 7.29 (d, J = 7.9 Hz, 1H), 7.15-7.07 (m, 2H), 7.07-6.96 (m, 2H), 6.87 (d, J = 8.4 Hz, 1H), 5.55 (s, 2H), 4.82 (s, 2H), 4.55 (dd, J = 5.3, 3.7 Hz, 2H), 4.28-4.23 (m, 2H), 3.92-3.86 (m, 2H), 3.15-3.09 (m, 2H), 2.24 (s, 3H) | 11.2 min, 99.1% 10.6 min, 98.8% |
| 637 | (S)-Isopropyl 2-amino-5-(3-chloro-4-((4-(1-(4-(2,3-dimethylphenoxy)butanoyl)-1,2,3,4-tetrahydroquinolin-5-yl)-1H-pyrazol-1-yl)methyl)-5-fluorobenzamido)pentanoate, TFA salt | | 732.6 | 7.80 (d, J = 1.4 Hz, 1H), 7.66-7.58 (m, 2H), 7.45 (s, 1H), 7.24-7.13 (m, 3H), 6.95 (t, J = 7.8 Hz, 1H), 6.66 (dd, J = 11.5, 7.9 Hz, 2H), 5.59 (d, J = 1.4 Hz, 2H), 5.13 (quin, J = 6.2 Hz, 1H), 4.03 (t, J = 6.4 Hz, 1H), 3.89 (t, J = 5.8 Hz, 2H), 3.74 (t, J = 6.9 Hz, 2H), 3.54-3.37 (m, 2H), 2.78 (t, J = 6.9 Hz, 2H), 2.51 (t, J = 6.7 Hz, 2H), 2.15-2.07 (m, 5H), 2.05-1.87 (m, 2H), 1.85-1.68 (m, 7H), 1.30 (dd, J = 6.1, 4.7 Hz, 6H) | 8.2 min, 99.1% 9.4 min, 99.7% |

TABLE 20-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 638 | 2-(3-Chloro-2-methylphenoxy) ethyl 8-(1-(2-chloro-5-(3-(2-morpholinoethoxy)-3-oxopropylcarbamoyl)benzyl)-1H-pyrazol-4-yl)-2H-benzo[b][1,4]thiazine-4(3H)-carboxylate | | 782.5 | 8.05 (d, J = 0.4 Hz, 1H), 7.80-7.74 (m, 2H), 7.60 (d, J = 8.4 Hz, 1H), 7.57 (d, J = 2.2 Hz, 1H), 7.33 (d, J = 7.5 Hz, 1H), 7.21-7.05 (m, 3H), 7.00 (d, J = 7.5 Hz, 1H), 6.90 (d, J = 8.4 Hz, 1H), 5.59 (s, 2H), 4.58 (dd, J = 5.3, 3.7 Hz, 2H), 4.49-4.43 (m, 2H), 4.31-4.26 (m, 2H), 4.01 (br. s., 2H), 3.95-3.89 (m, 2H), 3.79 (br. s., 2H), 3.72 (t, J = 6.4 Hz, 2H), 3.57 (br. s., 2H), 3.53-3.47 (m, 2H), 3.27-3.15 (m, 4H), 2.71 (t, J = 6.3 Hz, 2H), 2.25 (s, 3H) | 8.4 min, 100% 10.0 min, 100% |
| 639 | (S)-Isopropyl 2-amino-5-(3-chloro-4-((4-(4-(3-chloro-2-methylphenoxy)butanoyl)-3,4-dihydro-2H-benzo[b][1,4]thiazin-8-yl)-1H-pyrazol-1-yl)methyl)-5-fluorobenzamido) pentanoate, HCl salt | | 770.5 | 7.79 (s, 2H), 7.65-7.60 (m, 2H), 7.30-7.23 (m, 1H), 7.20-7.13 (m, 2H), 7.05-6.97 (m, 1H), 6.85 (d, J = 8.0 Hz, 1H), 6.75 (d, J = 8.0 Hz, 1H), 5.59 (d, J = 1.1 Hz, 2H), 5.12 (dt, J = 12.6, 6.3 Hz, 1H), 4.02 (t, J = 6.4 Hz, 1H), 3.93 (t, J = 5.7 Hz, 3H), 3.50-3.36 (m, 3H), 3.12 (t, J = 6.1 Hz, 2H), 2.69 (t, J = 6.9 Hz, 2H), 2.08 (quin, J = 6.4 Hz, 2H), 2.03-1.87 (m, 5H), 1.84-1.67 (m, 2H), 1.29 (dd, J = 6.1, 5.0 Hz, 6H) | 8.3 min, 99.4% 9.7 min, 100% |
| 640 | 2-(3-Chloro-2-methylphenoxy) ethyl 8-(1-(2-chloro-5-(3-(2,3-dihydroxypropoxy)-3-oxopropylcarbamoyl)benzyl)-1H-pyrazol-4-yl)-2H-benzo[b][1,4]thiazine-4(3H)-carboxylate | | 743.4 | 8.00 (d, J = 0.7 Hz, 1H), 7.82-7.73 (m, 2H), 7.65 (d, J = 2.0 Hz, 1H), 7.58 (d, J = 8.4 Hz, 1H), 7.32 (d, J = 7.7 Hz, 1H), 7.20-7.02 (m, 3H), 6.99 (d, J = 8.1 Hz, 1H), 6.90 (d, J = 8.4 Hz, 1H), 5.58 (s, 2H), 4.61-4.55 (m, 3H), 4.31-4.25 (m, 2H), 4.25-4.18 (m, 1H), 4.14-4.08 (m, 1H), 3.97-3.90 (m, 2H), 3.85 (dd, J = 6.1, 4.1 Hz, 1H), 3.66 (t, J = 6.6 Hz, 2H), 3.56 (d, J = 5.5 Hz, 2H), 3.21-3.14 (m, 2H), 2.70 (t, J = 6.7 Hz, 2H), 2.25 (s, 3H) | 10.6 min, 97.7% 10.1 min, 97.4% |
| 641 | 2-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)acetic acid | | 655.3 | 7.85-7.79 (m, 2H), 7.77 (d, J = 2.0 Hz, 1H), 7.70 (s, 1H), 7.52 (d, J = 8.4 Hz, 1H), 7.29 (d, J = 6.9 Hz, 1H), 7.14-7.00 (m, 3H), 6.97 (d, J = 7.9 Hz, 1H), 6.78 (d, J = 7.9 Hz, 1H), 5.51 (s, 2H), 4.57-4.52 (m, 2H), 4.25-4.20 (m, 2H), 4.02 (s, 2H), 3.94-3.89 (m, 2H), 3.18-3.11 (m, 2H), 2.25 (s, 3H) | 99%* |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 642 | (S)-2-Amino-5-(4-chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)pentanoic acid, TFA salt | | 712.3 | 8.00 (s, 1H), 7.79-7.75 (m, 1H), 7.73 (s, 1H), 7.67 (d, J = 2.0 Hz, 1H), 7.57 (d, J = 8.4 Hz, 1H), 7.30 (d, J = 8.1 Hz, 1H), 7.19-7.02 (m, 3H), 6.97 (d, J = 7.7 Hz, 1H), 6.87 (d, J = 8.1 Hz, 1H), 5.56 (s, 2H), 4.58-4.52 (m, 2H), 4.29-4.23 (m, 2H), 4.01 (t, J = 6.3 Hz, 1H), 3.95-3.87 (m, 2H), 3.47-3.41 (m, 2H), 3.17-3.12 (m, 3H), 2.22 (s, 3H), 2.11-1.89 (m, 2H), 1.87-1.64 (m, 2H) | 8.2 min, 97.19% 9.4 min, 98.1% |
| 643 | (S)-4-(3-((4-(4-(4-(3-Chloro-2-methylphenoxy)butanoyl)-3,4-dihydro-2H-benzo[b][1,4]thiazin-8-yl)-1H-pyrazol-1-yl)methyl)benzamido)-5-ethoxy-N,N,N-trimethyl-5-oxopentan-1-aminium, TFA salt | | 746.4 | 7.88-7.79 (m, 3H), 7.67 (d, J = 0.6 Hz, 1H), 7.53-7.45 (m, 2H), 7.33-7.25 (m, 1H), 7.21-7.13 (m, 2H), 7.04-6.97 (m, 1H), 6.84 (d, J = 7.8 Hz, 1H), 6.75 (d, J = 8.3 Hz, 1H), 5.44 (s, 2H), 4.76-4.67 (m, 1H), 4.23 (q, J = 7.1 Hz, 2H), 3.93 (t, J = 5.8 Hz, 4H), 3.51-3.34 (m, 2H), 3.15-3.11 (m, 11H), 2.69 (t, J = 6.9 Hz, 2H), 2.16-2.03 (m, 3H), 2.00-1.84 (m, 6H), 1.28 (t, J = 7.1 Hz, 3H) | 7.9 min, 96.9% 9.3 min, 98.0% |
| 644 | (S)-4-Carboxy-4-(4-chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)-N,N,N-trimethylbutan-1-aminium, TFA salt | | 754.2 | 8.02 (s, 1H), 7.82 (dd, J = 8.4, 2.2 Hz, 1H), 7.73 (s, 1H), 7.68 (d, J = 1.8 Hz, 1H), 7.60 (d, J = 8.4 Hz, 1H), 7.30 (d, J = 8.4 Hz, 1H), 7.18-7.01 (m, 3H), 6.97 (d, J = 7.9 Hz, 1H), 6.87 (d, J = 8.6 Hz, 1H), 5.57 (s, 2H), 4.68 (d, J = 8.8 Hz, 1H), 4.58-4.52 (m, 2H), 4.29-4.23 (m, 2H), 3.95-3.88 (m, 2H), 3.49-3.41 (m, 2H), 3.19-3.12 (m, 2H), 3.10 (s, 9H), 2.23 (s, 3H), 2.07 (br. s., 1H), 1.98-1.81 (m, 3H) | 8.2 min, 99.7% 9.6 min, 99.9% |
| 645 | 3-(4-Chloro-3-((4-(4-((2-(3-chloro-2-methylphenoxy)ethoxy)carbonyl)-6-fluoro-3,4-dihydro-2H-benzo[b][1,4]oxazin-8-yl)-1H-pyrazol-1-yl)methyl)benzamido)propanoic acid | | 671.1 | 8.24 (s, 1H), 8.01 (s, 1H), 7.77 (dd, J = 8.4, 2.2 Hz, 1H), 7.70-7.52 (m, 3H), 7.21-7.09 (m, 2H), 7.00 (d, J = 7.5 Hz, 1H), 6.94 (d, J = 8.1 Hz, 1H), 5.56 (s, 2H), 4.67-4.61 (m, 2H), 4.38-4.31 (m, 4H), 4.00-3.92 (m, 2H), 3.66-3.59 (m, 2H), 2.63 (t, J = 6.8 Hz, 2H), 2.29 (s, 3H) | 11.6 min, 99.5% 10.7 min, 98.0% |

TABLE 20-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 646 | 3-(3-((4-(4-(4-(3-Chloro-4-fluoro-2-methylphenoxy)butanoyl)-3,4-dihydro-2H-benzo[b][1,4]thiazin-8-yl)-1H-pyrazol-1-yl)methyl)benzamido)propanoic acid | | 651.2 | 7.80-7.74 (m, 2H), 7.72-7.67 (m, 2H), 7.47-7.43 (m, 1H), 7.41-7.36(m, 1H), 7.28 (d, J = 7.4 Hz, 1H), 7.17 (t, J = 7.7 Hz, 1H), 7.13-7.09 (m, 1H), 6.88 (t, J = 8.7 Hz, 1H), 6.66 (dd, J = 8.9, 4.0 Hz, 1H), 5.40 (s, 2H), 4.73 (br. s., 2H), 3.89 (br. s., 2H), 3.65 (t, J = 6.7 Hz, 2H), 3.14 (br. s., 2H), 2.74-2.60 (m, 4H), 2.15-2.07 (m, 2H), 2.01-1.95 (m, 3H) | 100%* |
| 647 | (S)-2-(3-Chloro-2-methylphenoxy)ethyl 8-(1-(2-chloro-5-(3-hydroxy-4-methoxy-4-oxobutylcarbamoyl)benzyl)-1H-pyrazol-4-yl)-2H-benzo[b][1,4]thiazine-4(3H)-carboxylate | | 713.1 | 8.16 (s, 1H), 7.88 (dd, J = 8.3, 2.1 Hz, 1H),7.73 (d, J = 0.7 Hz, 1H), 7.69 (d, J = 2.0 Hz, 1H), 7.63 (d, J = 8.4 Hz, 1H), 7.26 (dd, J = 8.1, 1.3 Hz, 1H), 7.20 (t, J = 9.0 Hz, 1H), 7.15-7.11 (m, 1H), 7.08-6.97 (m, 2H), 5.55 (s, 2H), 4.50-4.43 (m, 2H), 4.27-4.21 (m, 2H), 3.87-3.81 (m, 2H), 3.16-3.11 (m, 2H), 2.21 (s, 3H) | 11.5 min, 99.7% 10.8 min, 99.7% |
| 648 | (S)-4-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)-2-hydroxybutanoic acid | | 699.1 | 7.97 (d, J = 0.7 Hz, 1H), 7.75 (dd, J = 8.4, 2.2 Hz, 1H), 7.72 (d, J = 0.7 Hz, 1H),7.62 (d, J = 2.0 Hz, 1H), 7.55 (d, J = 8.4 Hz, 1H), 7.28 (d, J = 7.7 Hz, 1H), 7.17-7.00 (m, 3H), 6.96 (d, J = 7.5 Hz, 1H), 6.86 (d, J = 8.1 Hz, 1H), 5.55 (s, 2H), 4.54 (dd, J = 5.4, 3.6 Hz, 2H), 4.29-4.18 (m, 3H), 3.93-3.87 (m, 2H), 3.57-3.48 (m, 2H), 3.17-3.11 (m, 2H), 2.22 (s, 3H), 2.16-2.05 (m, 1H), 1.97-1.87 (m, 1H) | 10.7 min, 98.4% 10.2 min, 98.1% |
| 649 | 4-(4-Chloro-3-((4-(4-((2-(3-chloro-2-methylphenoxy)ethoxy)carbonyl)-3,4-dihydro-2H-benzo[b][1,4]thiazin-8-yl)-1H-pyrazol-1-yl)methyl)benzamido)-3-hydroxybutanoic acid | | 699.2 | 8.00 (d, J = 0.7 Hz, 1H), 7.81 (dd, J = 8.4, 2.2 Hz, 1H), 7.75 (d, J = 0.7 Hz, 1H),7.69 (d, J = 2.2 Hz, 1H), 7.59 (d, J = 8.4 Hz, 1H), 7.31 (d, J = 7.7 Hz, 1H), 7.19-7.03 (m, 3H), 7.00 (d, J = 7.5 Hz, 1H), 6.89 (d, J = 8.1 Hz, 1H), 5.58 (s, 2H), 4.60-4.54 (m, 2H), 4.31-4.21 (m, 3H), 3.95-3.90 (m, 2H), 3.54-3.41 (m, 2H), 3.20-3.14 (m, 2H), 2.61-2.54 (m, 1H), 2.49-2.40 (m, 1H), 2.25 (s, 3H) | 12.2 min, 98.9% 11.7 min, 99.6% |

TABLE 20-continued

| Example | Name | Formula I | LCMS, [M + H]⁺ | ¹H NMR (500 MHz, MeOD) δ | HPLC-1: Rt min, purity; HPLC-2: Rt min, purity |
|---|---|---|---|---|---|
| 650 | 3-(4-Chloro-3-((4-(4-((2-(2-chloro-3-fluorophenoxy)ethoxy)carbonyl)-3,4-dihydro-2H-benzo[b][1,4]thiazin-8-yl)-1H-pyrazol-1-yl)methyl)benzamido)propanoic acid | | 673.0 | 7.86 (s, 1H), 7.75 (dd, J = 8.2, 2.2 Hz, 1H), 7.71 (s, 1H), 7.67 (d, J = 2.0 Hz, 1H), 7.52 (d, J = 8.4 Hz, 1H), 7.37 (d, J = 7.9 Hz, 1H), 7.20 (td, J = 8.3, 6.2 Hz, 1H), 7.13-7.08 (m, 1H), 7.07-6.99 (m, 1H), 6.86-6.79 (m, 2H), 5.51 (s, 2H), 4.59-4.54 (m, 2H), 4.35-4.30 (m, 2H), 3.95-3.91 (m, 2H), 3.62 (t, J = 6.7 Hz, 2H), 3.19-3.15 (m, 2H), 2.61 (t, J = 6.7 Hz, 2H) | 97%* |
| 651 | 3-(4-Chloro-3-((4-(4-((2-(3-chloro-2-(trifluoromethyl)phenoxy)ethoxy)carbonyl)-3,4-dihydro-2H-benzo[b][1,4]thiazin-8-yl)-1H-pyrazol-1-yl)methyl)benzamido)propanoic acid | | 723.1 | 7.84 (s, 1H), 7.74 (dd, J = 8.4, 2.0 Hz, 1H), 7.70 (s, 1H), 7.67 (d, J = 2.0 Hz, 1H), 7.51 (d, J = 8.4 Hz, 1H), 7.39 (t, J = 8.4 Hz, 1H), 7.32 (d, J = 5.9 Hz, 1H), 7.13-7.08 (m, 2H), 7.07-6.96 (m, 2H), 5.50 (s, 2H), 4.56-4.51 (m, 2H), 4.35-4.28 (m, 2H), 3.95-3.89 (m, 2H), 3.62 (t, J = 6.7 Hz, 2H), 3.18-3.13 (m, 2H), 2.61 (t, J = 6.7 Hz, 2H) | 97%* |
| 652 | 2-(3-Chloro-2-methylphenoxy)ethyl 8-(1-(2-chloro-5-(methylsulfonylcarbamoyl)benzyl)-1H-pyrazol-4-yl)-2H-benzo[b][1,4]thiazine-4(3H)-carboxylate | | 675.0 | 7.99 (d, J = 0.4 Hz, 1H), 7.83 (dd, J = 8.4, 2.2 Hz, 1H), 7.72 (d, J = 0.7 Hz, 1H), 7.65 (d, J = 2.2 Hz, 1H), 7.62 (d, J = 8.4 Hz, 1H), 7.29 (d, J = 7.7 Hz, 1H), 7.15-7.00 (m, 3H), 6.97 (d, J = 7.5 Hz, 1H), 6.86 (d, J = 8.1 Hz, 1H), 5.57 (s, 2H), 4.56-4.52 (m, 2H), 4.27-4.23 (m, 2H), 3.92-3.88 (m, 2H), 3.34 (s, 3H), 3.17-3.13 (m, 2H), 2.22 (s, 3H) | 13.7 min, 97.7% 13.1 min, 98.4% |

TABLE 20-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 653 | 3-(3-((4-(1-(4-(2,3-Dimethylphenoxy)butanoyl)-4-oxo-1,2,3,4-tetrahydroquinolin-5-yl)-1H-pyrazol-1-yl)methyl)benzamido)propanoic acid | 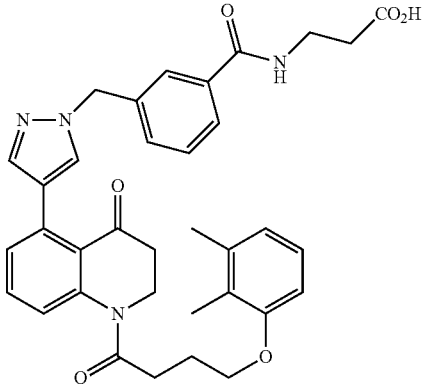 [SMILES: Cc1cccc(OCCCC(=O)N2CCC(=O)c3c(-c4cnn(Cc5cccc(C(=O)NCCC(=O)O)c5)c4)cccc32)c1C] | 609.3 | 7.88 (s, 1H), 7.85-7.76 (m, 1H), 7.68 (s, 1H), 7.65-7.40 (m, 5H), 7.32 (d, J = 7.7 Hz, 1H), 6.97 (t, J = 7.8 Hz, 1H), 6.70 (dd, J = 7.7, 4.4 Hz, 2H), 5.46 (s, 2H), 4.23 (t, J = 6.2 Hz, 2H), 3.98 (t, J = 5.1 Hz, 2H), 3.63 (t, J = 6.8 Hz, 2H), 2.89 (t, J = 7.0 Hz, 2H), 2.77 (t, J = 6.3 Hz, 2H), 2.64 (t, J = 6.9 Hz, 2H), 2.24-2.08 (m, 5H), 1.95 (s, 3H) | 8.2 min, 97.2% 8.0 min, 96.3% |
| 654 | 2-(3-((4-(1-(4-(2,3-Dimethylphenoxy)butanoyl)-4-oxo-1,2,3,4-tetrahydroquinolin-5-yl)-1H-pyrazol-1-yl)methyl)benzamido)ethanesulfonic acid | 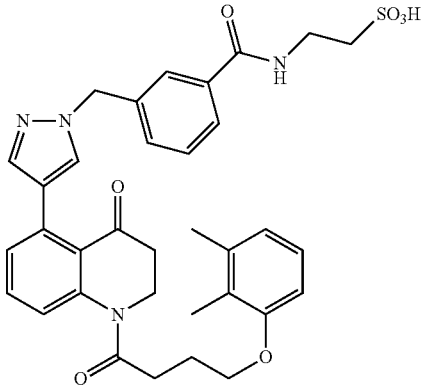 | 645.3 | 8.00 (s, 1H), 7.89-7.71 (m, 3H), 7.64-7.44 (m, 4H), 7.34 (d, J = 7.7 Hz, 1H), 7.03-6.93 (m, 1H), 6.70 (d, J = 7.3 Hz, 2H), 5.51 (s, 2H), 4.24 (t, J = 6.2 Hz, 2H), 3.99 (t, J = 5.1 Hz, 2H), 3.83 (br. s., 2H), 3.13 (br. s., 2H), 2.90 (t, J = 7.0 Hz, 2H), 2.78 (t, J = 6.3 Hz, 2H), 2.29-2.10 (m, 5H), 2.02-1.90 (m, 3H) | 9.2 min, 96.8% 6.8 min, 95.2% |
| 655 | 3-(3-((4-(1-(4-(2,3-Dimethylphenoxy)butanoyl)-4-hydroxy-1,2,3,4-tetrahydroquinolin-5-yl)-1H-pyrazol-1-yl)methyl)benzamido)propanoic acid | 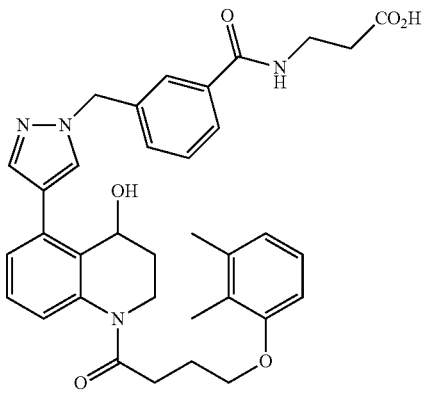 [SMILES: Cc1cccc(OCCCC(=O)N2CCC(O)c3c(-c4cnn(Cc5cccc(C(=O)NCCC(=O)O)c5)c4)cccc32)c1C] | 593.3 | 8.02 (s, 1H), 7.87-7.70 (m, 3H), 7.59-7.43 (m, 2H), 7.42-7.23 (m, 3H), 6.98 (t, J = 7.9 Hz, 1H), 6.71 (d, J = 7.9 Hz, 2H), 5.48 (s, 2H), 4.19-3.90 (m, 3H), 3.81 (d, J = 6.2 Hz, 1H), 3.65 (t, J = 6.8 Hz, 2H), 2.98-2.84 (m, 1H), 2.84-2.58 (m, 3H), 2.28-2.08 (m, 6H), 2.04-1.93 (m, 3H), 1.76 (dt, J = 7.0, 3.5 Hz, 1H) | 7.9 min, 95.0% 7.7 min, 95.4% |

TABLE 20-continued

| Example | Name | LCMS, [M + H]+ | 1H NMR (500 MHz, MeOD) δ | HPLC-1: Rt min, purity; HPLC-2: Rt min, purity |
|---|---|---|---|---|
| 656 | 2-(3-((4-(1-(4-(2,3-Dimethylphenoxy)butanoyl)-4-hydroxy-1,2,3,4-tetrahydroquinolin-5-yl)-1H-pyrazol-1-yl)methyl)benzamido)ethanesulfonic acid | 629.2 | 8.13 (s, 1H), 7.92 (s, 1H), 7.88-7.77 (m, 2H), 7.60-7.45 (m, 2H), 7.45-7.27 (m, 3H), 6.99 (t, J = 7.9 Hz, 1H), 6.71 (d, J = 7.3 Hz, 2H), 5.54 (s, 2H), 4.13-3.91 (m, 3H), 3.83 (t, J = 6.5 Hz, 3H), 3.11 (t, J = 6.5 Hz, 2H), 2.98-2.66 (m, 2H), 2.31-2.08 (m, 6H), 2.01 (s, 3H), 1.88-1.69 (m, 1H) | 9.0 min, 95.7% 6.7 min, 95.2% |
| 657 | 2-(3-((4-(1-(4-(2,3-Dimethylphenoxy)butanoyl)-4-methyl-1,2,3,4-tetrahydroquinolin-5-yl)-1H-pyrazol-1-yl)methyl)benzamido)ethanesulfonic acid | 645.3 | 7.90-7.72 (m, 3H), 7.58 (s, 1H), 7.54-7.41 (m, 2H), 7.35-7.11 (m, 3H), 6.97 (t, J = 7.8 Hz, 1H), 6.81-6.56 (m, 2H), 5.49 (s, 2H), 4.24 (br. s., 1H), 4.00 (d, J = 9.0 Hz, 1H), 3.83 (t, J = 6.6 Hz, 3H), 3.25-3.04 (m, 3H), 3.00-2.64 (m, 2H), 2.31-2.04 (m, 5H), 2.02-1.88 (m, 2H), 1.81 (br. s., 4H), 0.93 (br. s., 4H) | 10.3 min, 99.1% 7.1 min, 99.1% |
| 658 | 3-(3-((4-(1-(4-(2,3-Dimethylphenoxy)butanoyl)-4-methyl-1,2,3,4-tetrahydroquinolin-5-yl)-1H-pyrazol-1-yl)methyl)benzamido)propanoic acid | 609.3 | 7.89-7.70 (m, 3H), 7.59 (s, 1H), 7.55-7.41 (m, 2H), 7.26 (d, J = 4.2 Hz, 3H), 6.97 (t, J = 1.1 Hz, 1H), 6.80-6.55 (m, 2H), 5.48 (s, 2H), 4.24 (br. s., 1H), 3.99 (d, J = 4.6 Hz, 1H), 3.84 (br. s., 1H), 3.66 (t, J = 6.7 Hz, 2H), 3.17 (br. s., 1H), 2.99-2.71 (m, 2H), 2.67 (t, J = 6.9 Hz, 2H), 2.28-2.08 (m, 5H), 2.04-1.88 (m, 2H), 1.81 (br. s., 4H), 0.93 (br. s., 3H) | 8.8 min, 99.5% 8.4 min, 99.3% |
| 659 | 4-(3-((4-(1-(4-(2,3-Dimethylphenoxy)butanoyl)-1,2,3,4-tetrahydroquinolin-5-yl)-1H-pyrazol-1-yl)methyl)benzamido)-N,N,N-trimethylbutan-1-aminium, TFA salt | 636.3 | 7.81 (br. s., 2H), 7.67 (br. s., 1H), 7.57-7.44 (m, 3H), 7.25 (br. s., 1H), 7.02-6.93 (m, 1H), 6.67 (d, J = 7.3 Hz, 2H), 5.45 (s, 2H), 3.89 (br. s., 2H), 3.80-3.69 (m, 2H), 3.48 (t, J = 6.9 Hz, 2H), 3.13 (s, 9H), 2.92-2.79 (m, 2H), 2.52 (br. s., 2H), 2.22-2.02 (m, 7H), 1.98-1.58 (m, 10H) | 10.6 min, 100% 14.9 min, 100% |

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 660 | 2-(4-(3-((4-(1-(4-(2,3-Dimethylphenoxy)butanoyl)-1,2,3,4-tetrahydroquinolin-5-yl)-1H-pyrazol-1-yl)methyl)benzoyl)piperazin-1-yl)ethanesulfonic acid | | 700.2 | 7.70 (s, 1H), 7.54-7.48 (m, 2H), 7.48-7.40 (m, 4H), 7.27-7.20 (m, 2H), 7.01-6.92 (m, 1H), 6.74-6.61 (m, 2H), 5.44 (s, 2H), 3.87 (br. s., 3H), 3.74 (t, J = 6.7 Hz, 3H), 3.58 (t, J = 6.9 Hz, 3H), 3.24 (t, J = 6.8 Hz, 4H), 2.80 (t, J = 6.8 Hz, 3H), 2.51 (br. s., 2H), 2.17-2.03 (m, 5H), 1.81-1.77 (m, 5H), 1.37 (dd, J = 6.1, 3.4 Hz, 2H) | 9.4 min, 99.5% 9.8 min, 99.7% |
| 661 | (3-((5-(1-(4-(2,3-Dimethylphenoxy)butanoyl)-1,2,3,4-tetrahydroquinolin-5-yl)-1,2,4-oxadiazol-3-yl)methyl)benzamido)methanesulfonic acid | | 619.1 | 7.96 (s, 1H), 7.90 (d, J = 7.8 Hz, 1H), 7.84 (d, J = 7.8 Hz, 1H), 7.64-7.52 (m, 2H), 7.52-7.45 (m, 1H), 7.44-7.34 (m, 1H), 6.90 (t, J = 7.8 Hz, 1H), 6.58 (d, J = 7.1 Hz, 1H), 6.63 (d, J = 8.1 Hz, 1H), 4.56 (br. s., 2H), 4.25 (s, 2H), 3.90 (br. s., 2H), 3.79 (t, J = 6.4 Hz, 2H), 2.95 (br. s., 2H), 2.81 (t, J = 6.7 Hz, 2H), 2.19-2.09 (m, 2H), 2.05 (br. s, 3H), 1.89-1.79 (m, 5H) | 8.7 min, 96.4% 8.9 min, 96.6% |
| 662 | (4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)methanesulfonic acid | | 685.2 | 8.05 (s, 1H), 7.91-7.84 (m, 2H), 7.78 (s, 1H), 7.60 (d, J = 8.3 Hz, 1H), 7.24 (d, J = 7.3 Hz, 1H), 7.18-7.13 (m, 1H), 7.13-7.05 (m, 2H), 6.98 (d, J = 7.8 Hz, 1H), 6.87 (d, J = 8.3 Hz, 1H), 5.65 (s, 2H), 4.61-4.44 (m, 5H), 4.25 (br. s., 2H), 3.05 (d, J = 12.9 Hz, 1H), 2.23 (s, 3H), 2.19-2.09 (m, 1H), 1.85 (d, J = 5.6 Hz, 1H), 1.06 (td, J = 8.3, 5.2 Hz, 1H), 0.64 (d, J = 4.8 Hz, 1H) | 10.8 min, 95.0% 11.0 min, 92.1% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 663 | (R)-Dimethyl 2-(4-chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)pentanedioate | | 749.3 | 7.81-7.72 (m, 3H), 7.66 (s, 1H), 7.51 (d, J = 8.3 Hz, 1H), 7.28 (br. s., 1H), 7.11-6.94 (m, 4H), 6.71 (d, J = 8.1 Hz, 1H), 5.54 (s, 2H), 4.75 (dd, J = 7.6, 2.8 Hz, 1H), 4.68-4.58 (m, 1H), 4.58-4.40 (m, 2H), 4.25-4.13 (m, 2H), 3.77 (s, 3H), 3.64 (s, 3H), 3.07 (d, J = 12.6 Hz, 1H), 2.55-2.42 (m, 2H), 2.32-2.25 (m, 5H), 2.20-2.05 (m, 2H), 1.83-1.71 (m, 1H), 1.02 (td, J = 8.2, 5.1 Hz, 1H), 0.76 (q, J = 4.8 Hz, 1H) | 11.9 min, 95.0% 13.4 min, 95.0% |
| 664 | 2,2'-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzoylazanediyl)diacetic acid | | 707.2 | 7.78 (s, 1H), 7.74 (s, 1H), 7.45-7.40 (m, 1H), 7.40-7.32 (m, 2H), 7.08-7.01 (m, 3H), 7.00-6.95 (m, 1H), 6.70 (d, J = 1.1 Hz, 1H), 5.50 (br. s., 2H), 4.59 (d, J = 11.5 Hz, 1H), 4.46 (br. s., 2H), 4.25 (br. s., 2H), 4.18 (br. s., 2H), 4.07 (br. s., 2H), 3.05 (d, J = 12.1 Hz, 1H), 2.26 (s, 3H), 2.07-2.01 (m, 2H), 1.74 (d, J = 6.0 Hz, 1H), 1.08-0.95 (m, 1H), 0.74 (d, J = 4.4 Hz, 1H) | 12.5 min, 95.0% 12.8 min, 91.2% |
| 665 | (R)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)pentanedioic acid | | 721.2 | 7.92 (br. s., 1H), 7.80-7.70 (m, 4H), 7.38 (d, J = 8.2 Hz, 1H), 7.07-7.00 (m, 3H), 6.97 (d, J = 1.1 Hz, 1H), 6.70 (d, J = 7.7 Hz, 1H), 5.57-5.38 (m, 2H), 4.70 (br. s., 1H), 4.58 (d, J = 12.6 Hz, 1H), 4.56-4.39 (m, 2H), 4.18 (m, 2H), 3.04 (d, J = 12.6 Hz, 1H), 2.48 (m, 2H), 2.25 (m, 4H), 2.09-2.00 (m, 1H), 1.72 (d, J = 5.5 Hz, 1H), 1.00 (d, J = 5.5 Hz, 1H), 0.74 (d, J = 4.9 Hz, 1H) | 10.7 min, 99.8% 10.0 min, 99.6% |

TABLE 20-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 666 | (S)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)succinic acid | | 707.2 | 7.92 (d, J = 7.1 Hz, 1H), 7.86 (br. s., 1H), 7.79-7.69 (m, 3H), 7.41 (s, 1H), 7.07-6.99 (m, 3H), 6.99-6.94 (m, 1H), 6.69 (d, J = 1.1 Hz, 1H), 5.50 (br. s., 2H), 5.02 (br. s., 1H), 4.65-4.54 (m, 1H), 4.52-4.36 (m, 2H), 4.18 (br. s., 2H), 3.14-2.86 (m, 3H), 2.25 (s, 3H), 2.05-1.93 (m, 1H), 1.72 (d, J = 6.0 Hz, 1H), 1.07-0.91 (m, 1H), 0.73 (d, J = 4.4 Hz, 1H) | 10.1 min, 98.4% 10.1 min, 99.1% |
| 667 | (R)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)succinic acid | | 707.2 | 7.92 (d, J = 7.1 Hz, 1H), 7.86 (br. s., 1H), 7.79-7.69 (m, 3H), 7.41 (s, 1H), 7.07-6.99 (m, 3H), 6.99-6.94 (m, 1H), 6.69 (d, J = 1.1 Hz, 1H), 5.50 (br. s., 2H), 5.02 (br. s., 1H), 4.65-4.54 (m, 1H), 4.52-4.36 (m, 2H), 4.18 (br. s., 2H), 3.14-2.86 (m, 3H), 2.25 (s, 3H), 2.05-1.93 (m, 1H), 1.72 (d, J = 6.0 Hz, 1H), 1.07-0.91 (m, 1H), 0.73 (d, J = 4.4 Hz, 1H) | 10.0 min, 98.5% 10.1 min, 98.7% |
| 668 | (S)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)pentanedioic acid | | 721.5 | 7.92 (br. s., 1H), 7.80-7.70 (m, 4H), 7.38 (d, J = 8.2 Hz, 1H), 7.07-7.00 (m, 3H), 6.97 (d, J = 1.1 Hz, 1H), 6.70 (d, J = 1.1 Hz, 1H), 5.57-5.38 (m, 2H), 4.70 (br. s., 1H), 4.58 (d, J = 12.6 Hz, 1H), 4.56-4.39 (m, 2H), 4.18 (m, 2H), 3.04 (d, J = 12.6 Hz, 1H), 2.48 (m, 2H), 2.25 (m, 4H), 2.09-2.00 (m, 1H), 1.72 (d, J = 5.5 Hz, 1H), 1.00 (d, J = 5.5 Hz, 1H), 0.74 (d, J = 4.9 Hz, 1H) | 10.1 min, 98.8% 10.0 min, 98.4% |

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 669 | (R)-5-tert-Butyl 1-methyl 2-(4-chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)pentanedioate | | 735.3 | 7.82 (s, 2H), 7.68 (s, 1H), 7.53 (d, J = 8.1 Hz, 1H), 7.46 (d, J = 7.1 Hz, 1H), 7.13-7.06 (m, 3H), 7.06-6.98 (m, 1H), 6.73 (d, J = 8.1 Hz, 1H), 5.58 (s, 2H), 4.73 (td, J = 7.6, 4.9 Hz, 1H), 4.63 (ddd, J = 11.9, 5.7, 3.7 Hz, 1H), 4.59-4.44 (m, 2H), 4.27-4.18 (m, 2H), 3.79 (s, 3H), 3.10 (d, J = 12.1 Hz, 1H), 2.51-2.34 (m, 2H), 2.33-2.20 (m, 4H), 2.18-2.04 (m, 2H), 1.79 (d, J = 5.6 Hz, 1H), 1.44 (s, 9H), 1.11-0.98 (m, 1H), 0.83-0.73 (m, 1H) | 12.8 min, 99.0% 14.7 min, 100% |
| 670 | 2,2'-(3-Chloro-4-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)-5-fluorobenzoylazanediyl)diacetic acid | | | 7.77 (d, J = 3.5 Hz, 3H), 7.42 (s, 1H), 7.24 (d, J = 8.6 Hz, 1H), 7.12-7.02 (m, 4H), 7.02-6.96 (m, 1H), 6.73 (d, J = 8.1 Hz, 1H), 5.63 (br. s., 2H), 4.67-4.57 (m, 1H), 4.55-4.44 (m, 2H), 4.32 (br. s., 2H), 4.26-4.17 (m, 2H), 4.13 (br. s., 2H), 3.08 (d, J = 12.1 Hz, 1H), 2.28 (s, 3H), 2.12-2.00 (m, 1H), 1.77 (d, J = 5.8 Hz, 1H), 1.03 (d, J = 5.1 Hz, 1H), 0.78 (d, J = 4.8 Hz, 1H) | |
| 671 | 2,2'-(3-Chloro-4-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzoylazanediyl)diacetic acid | | 725.3 | 7.84 (br. s., 1H), 7.74 (br. s., 1H), 7.53 (br. s., 1H), 7.09 (br. s., 2H), 7.04 (d, J = 8.1 Hz, 1H), 7.01-6.95 (m, 1H), 6.72 (d, J = 8.1 Hz, 1H), 5.55 (br. s., 2H), 4.68-4.57 (m, 1H), 4.55-4.43 (m, 1H), 4.26 (br. s., 2H), 4.21 (br. s., 2H), 4.08 (br. s., 1H), 3.09 (d, J = 11.9 Hz, 1H), 2.28 (s, 3H), 2.14-2.05 (m, 1H), 1.82-1.74 (m, 1H), 1.13-0.97 (m, 1H), 0.78 (br. s., 1H) | 9.8 min, 97.4% 9.7 min, 98.1% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 672 | (R)-4-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-5-methoxy-5-oxopentanoic acid | 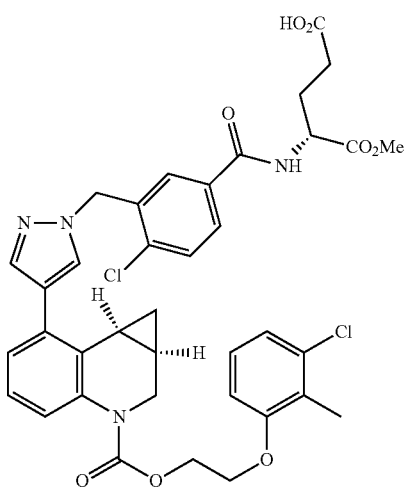 [SMILES: COC(=O)[C@@H](CCC(=O)O)NC(=O)c1ccc(Cl)c(Cn2cc(-c3cccc4c3[C@H]3C[C@H]3CN4C(=O)OCCOc3cccc(Cl)c3C)cn2)c1] | 735.3 | 7.87-7.81 (m, 1H), 7.79 (s, 1H), 7.75 (s, 1H), 7.52-7.47 (m, 1H), 7.35 (d, J = 7.1 Hz, 1H), 7.08-7.00 (m, 2H), 7.00-6.93 (m, 1H), 6.69 (d, J = 1.1 Hz, 1H), 5.65-5.50 (m, 2H), 4.72 (td, J = 8.2, 4.4 Hz, 1H), 4.64-4.56 (m, 1H), 4.56-4.38 (m, 2H), 4.24-4.13 (m, 2H), 3.76 (s, 3H), 3.05 (d, J = 13.2 Hz, 1H), 2.62-2.41 (m, 2H), 2.36-2.16 (m, 5H), 2.09-1.99 (m, 1H), 1.76 (d, J = 5.5 Hz, 1H), 1.01 (dd, J = 13.5, 8.0 Hz, 1H), 0.76 (d, J = 4.4 Hz, 1H) | N/A |
| 673 | (S)-2-(3-((4-((1aR,7bS)-3-((2-(3-Chloro-2-methylphenoxy)ethoxy)carbonyl)-1a,2,3,7b-tetrahydro-1H-cyclopropa[c]quinolin-7-yl)-1H-pyrazol-1-yl)methyl)-4-methoxybenzamido)pentanedioic acid | 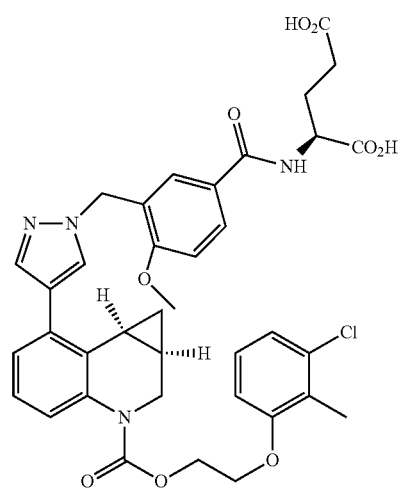 [SMILES: COc1ccc(C(=O)N[C@@H](CCC(=O)O)C(=O)O)cc1Cn1cc(-c2cccc3c2[C@H]2C[C@H]2CN3C(=O)OCCOc2cccc(Cl)c2C)cn1] | 717.4 | 7.93 (d, J = 8.1 Hz, 1H), 7.88 (br. s, 1H), 7.79 (s, 1H), 7.76-7.68 (m, 2H), 7.07 (t, J = 8.2 Hz, 3H), 7.02-6.98 (m, 1H), 6.95 (d, J = 8.3 Hz, 1H), 6.73 (d, J = 7.8 Hz, 1H), 5.45 (br. s., 2H), 4.82-4.72 (m, 1H), 4.67-4.58 (m, 1H), 4.58-4.41 (m, 2H), 4.29-4.14 (m, 2H), 3.91 (s, 3H), 3.08 (d, J = 12.6 Hz, 1H), 2.54 (d, J = 7.6 Hz, 2H), 2.33-2.23 (m, 4H), 2.12-2.03 (m, 1H), 1.76 (d, J = 5.3 Hz, 1H), 1.03 (d, J = 5.3 Hz, 1H), 0.79 (d, J = 4.0 Hz, 1H) | N/A |
| 674 | (S)-4-(3-((4-((1aR,7bS)-3-((2-(3-Chloro-2-methylphenoxy)ethoxy)carbonyl)-1a,2,3,7b-tetrahydro-1H-cyclopropa[c]quinolin-7-yl)-1H-pyrazol-1-yl)methyl)-4-methoxybenzamido)-5-methoxy-5-oxopentanoic acid | 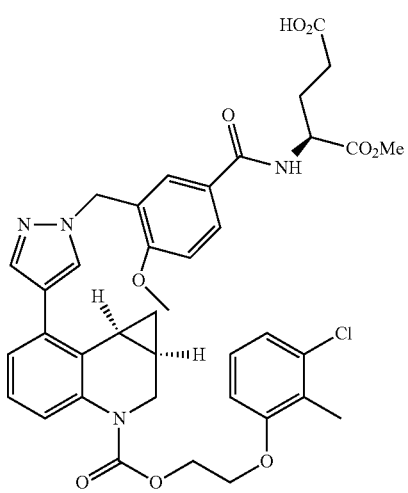 [SMILES: COC(=O)[C@H](CCC(=O)O)NC(=O)c1ccc(OC)c(Cn2cc(-c3cccc4c3[C@H]3C[C@H]3CN4C(=O)OCCOc3cccc(Cl)c3C)cn2)c1] | 731.4 | 7.97 (d, J = 8.3 Hz, 1H), 7.84 (br.s., 2H), 7.74 (br. s., 1H), 7.43 (d, J = 6.3 Hz, 1H), 7.15-7.05 (m, 3H), 7.05-6.95 (m, 2H), 6.74 (d, J = 7.8 Hz, 1H), 5.52 (br. s., 2H), 4.77 (br. s., 1H), 4.68-4.56 (m, 2H), 4.52 (d, J = 9.3 Hz, 2H), 3.95 (s, 3H), 3.80 (s, 3H), 3.09 (d, J = 12.6 Hz, 1H), 2.68-2.45 (m, 2H), 2.40-2.18 (m, 5H), 2.06 (br. s., 1H), 1.80 (br. s., 1H), 1.12-1.00 (m, 1H), 0.87-0.75 (m, 1H) | N/A |

TABLE 20-continued

| Example | Name | Formula I | LCMS, [M + H]+ | 1H NMR (500 MHz, MeOD) δ | HPLC-1: Rt min, purity; HPLC-2: Rt min, purity |
|---|---|---|---|---|---|
| 675 | 1-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzoyl)-4-hydroxypiperidine-4-carboxylic acid | | 719.3 | 7.97 (s, 1H), 7.75 (s, 1H), 7.59 (d, J = 8.1 Hz, 1H), 7.42 (dd, J = 8.1, 1.8 Hz, 1H), 7.22 (d, J = 7.3 Hz, 1H), 7.16 (d, J = 7.6 Hz, 1H), 7.13-7.04 (m, 2H), 7.03-6.95 (m, 2H), 6.87 (d, J = 8.1 Hz, 1H), 5.60 (s, 2H), 4.63-4.44 (m, 3H), 4.35 (br. s., 1H), 4.25 (br. s., 2H), 3.59-3.46 (m, 1H), 3.42 (br. s., 1H), 3.06 (d, J = 12.6 Hz, 1H), 2.28-2.11 (m, 4H), 2.01 (br. s., 1H), 1.96 (br. s., 1H), 1.90-1.77 (m, 2H), 1.63 (br. s., 1H), 1.12-0.98 (m, 1H), 0.63 (d, J = 4.8 Hz, 1H) | 9.8 min, 91.5% N/A |
| 676 | (1aR,7bS)-2-(3-Chloro-2-methylphenoxy)ethyl 7-(1-(2-chloro-5-(2-oxotetrahydrofuran-3-ylcarbamoyl)benzyl)-1H-pyrazol-4-yl)-1a,2-dihydro-1H-cyclopropa[c]quinoline-3(7bH)-carboxylate | | 675.3 | 7.81-7.77 (m, 1H), 7.76-7.70 (m, 1H), 7.50 (d, J = 8.2 Hz, 1H), 7.13 (d, J = 6.6 Hz, 1H), 7.09-7.02 (m, 2H), 7.00-6.95 (m, 1H), 6.69 (d, J = 8.2 Hz, 1H), 5.52 (s, 2H), 4.74 (ddd, J = 11.5, 8.8, 6.6 Hz, 1H), 4.64-4.55 (m, 1H), 4.54-4.39 (m, 3H), 4.36-4.26 (m, 1H), 4.23-4.09 (m, 2H), 3.05 (d, J = 13.2 Hz, 1H), 2.34-2.22 (m, 4H), 2.05 (td, J = 8.5, 4.9 Hz, 1H), 1.81-1.70 (m, 1H), 1.03 (td, J = 8.1, 5.2 Hz, 1H), 0.80-0.70 (m, 1H) | 11.9 min, 97.0% 10.8 min, 96.2% |
| 677 | 2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-4-hydroxybutanoic acid, Na salt | | 693.3 | 7.95-7.90 (m, 1H), 7.82 (dd, J = 8.3, 1.8 Hz, 1H), 7.70 (s, 2H), 7.56 (d, J = 8.3 Hz, 1H), 7.22-7.11 (m, 2H), 7.10-7.02 (m, 2H), 6.99-6.92 (m, 1H), 6.85 (d, J = 8.1 Hz, 1H), 5.57 (s, 2H), 4.58-4.44 (m, 4H), 4.23 (br. s., 2H), 3.66 (t, J = 6.6 Hz, 2H), 3.03 (d, J = 12.9 Hz, 1H), 2.25-2.11 (m, 5H), 1.98-1.75 (m, 2H), 1.07-0.96 (m, 1H), 0.61 (d, J = 4.5 Hz, 1H) | 10.9 min, 95.2% 11.1 min, 96.7% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 678 | (S)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-3-hydroxypropanoic acid | | 679.2 | 8.11 (br. s., 1H), 7.86 (d, J = 8.2 Hz, 1H), 7.82-7.73 (m, 2H), 7.69 (s, 1H), 7.44 (d, J = 8.8 Hz, 1H), 7.03 (t, J = 8.0 Hz, 2H), 6.98-6.90 (m, 1H), 6.69 (d, J = 7.7 Hz, 1H), 5.62-5.43 (m, 1H), 4.88 (d, J = 7.1 Hz, 1H), 4.63-4.54 (m, 1H), 4.54-4.36 (m, 2H), 4.16 (d, J = 9.9 Hz, 2H), 4.00 (d, J = 9.9 Hz, 1H), 3.03 (d, J = 12.6 Hz, 1H), 2.24 (s, 2H), 2.05-1.92 (m, 1H), 1.73 (d, J = 6.0 Hz, 1H), 1.07-0.94 (m, 1H), 0.74 (d, J = 4.9 Hz, 1H) | 10.9 min, 95.0% 11.2 min, 97.2% |
| 679 | 2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)acetic acid | | 649.2 | 7.91-7.82 (m, 1H), 7.77 (s, 1H), 7.50 (d, J = 8.2 Hz, 1H), 7.45-7.40 (m, 1H), 7.07 (d, J = 3.3 Hz, 1H), 7.03 (d, J = 8.2 Hz, 1H), 6.99-6.95 (m, 1H), 6.70 (d, J = 8.2 Hz, 1H), 5.54 (s, 2H), 4.66-4.57 (m, 1H), 4.55-4.35 (m, 2H), 4.24-4.12 (m, 3H), 3.06 (d, J = 12.1 Hz, 2H), 2.26 (s, 3H), 2.09-1.95 (m, 1H), 1.76 (d, J = 5.5 Hz, 1H), 1.12-0.95 (m, 1H), 0.83-0.70 (m, 1H) | 11.0 min, 98.7% 11.3 min, 100% |
| 680 | (R)-2-(3-((4-((1aR,7bS)-3-((2-(3-Chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-3-hydroxypropanoic acid | | 645.3 | 8.10 (br. s., 1H), 7.87 (d, J = 7.3 Hz, 1H), 7.81 (s, 1H), 7.78-7.69 (m, 2H), 7.46 (d, J = 8.3 Hz, 1H), 7.15 (d, J = 7.3 Hz, 2H), 7.10-7.03 (m, 3H), 6.92-6.85 (m, 1H), 6.80 (d, J = 8.3 Hz, 1H), 5.55 (br. s., 2H), 4.89 (br.s., 1H), 4.62 (d, J = 12.4 Hz, 1H), 4.59-4.34 (m, 2H), 4.30-4.15 (m, 3H), 4.09-3.98 (m, 1H), 3.07 (d, J = 12.4 Hz, 1H), 2.23 (s, 3H), 2.10-1.97 (m, 1H), 1.76 (d, J = 5.3 Hz, 1H), 1.12-0.96 (m, 1H), 0.80 (d, J = 4.8 Hz, 1H) | N/A |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 681 | (1aR,7bS)-2-(3-Chloro-2-methylphenoxy)ethyl 7-(1-(2-chloro-5-(1-methoxy-4-(methylthio)-1-oxobutan-2-ylcarbamoyl)benzyl)-1H-pyrazol-4-yl)-1a,2-dihydro-1H-cyclopropa[c]quinoline-3(7bH)-carboxylate | | 723.1 | 7.85 (dd, J = 8.5, 1.9 Hz, 1H), 7.80-7.71 (m, 2H), 7.69-7.61 (m, 1H), 7.49 (dd, J = 8.2, 5.5 Hz, 1H), 7.09-7.00 (m, 2H), 6.99-6.93 (m, 1H), 6.69 (d, J = 7.7 Hz, 1H), 5.65-5.39 (m, 2H), 4.97-4.81 (m, 1H), 4.65-4.54 (m, 1H), 4.53-4.37 (m, 2H), 4.18 (br. s., 2H), 3.04 (br. s., 1H), 2.63-2.40 (m, 2H), 2.25 (s, 2H), 2.11-1.98 (m, 5H), 2.12-1.91 (m, 2H), 1.82-1.65 (m, 1H), 1.13-0.92 (m, 1H), 0.82-0.71 (m, 1H) | 11.2 min, 91.2% 11.5 min, 87.4% |
| 682 | (3R,5R)-7-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-3,5-dihydroxyheptanoic acid | | 751.3 | 7.82 (s, 1H), 7.66 (dd, J = 8.8, 2.2 Hz, 1H), 7.61 (s, 1H), 7.52 (d, J = 1.6 Hz, 1H), 7.45 (d, J = 8.2 Hz, 1H), 7.08 (br. s., 1H), 7.06-7.00 (m, 1H), 6.97 (d, J = 8.2 Hz, 2H), 6.86 (d, J = 8.2 Hz, 1H), 6.75 (d, J = 1.1 Hz, 1H), 5.47 (s, 2H), 5.39 (s, 4H), 4.50-4.35 (m, 3H), 4.13 (br. s., 2H), 4.05-3.96 (m, 1H), 3.83-3.72 (m, 1H), 3.45-3.32 (m, 3H), 2.93 (d, J = 12.1 Hz, 1H), 2.33-2.15 (m, 2H), 2.12-2.01 (m, 4H), 1.77-1.64 (m, 2H), 1.63-1.47 (m, 3H), 1.19 (s, 1H), 0.92 (td, J = 8.2, 4.9 Hz, 1H), 0.51 (d, J = 4.9 Hz, 1H) | 11.0 min, 97.9% 11.2 min, 99.4% |
| 683 | 2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-4-(methylsulfonyl)butanoic acid | | 755.2 | 7.93 (s, 1H), 7.82 (dd, J = 8.2, 2.2 Hz, 1H), 7.71 (s, 1H), 7.65 (s, 1H), 7.57 (d, J = 8.2 Hz, 1H), 7.18 (br. s., 1H), 7.15-7.11 (m, 1H), 7.10-7.01 (m, 2H), 6.95 (d, J = 8.2 Hz, 1H), 6.84 (d, J = 8.2 Hz, 1H), 5.57 (s, 2H), 4.69 (dd, J = 8.8, 4.9 Hz, 1H), 4.60-4.41 (m, 2H), 4.22 (br. s., 2H), 3.27-3.14 (m, 1H), 3.02 (d, J = 12.6 Hz, 1H), 2.95 (s, 2H), 2.55-2.40 (m, 1H), 2.33-2.23 (m, 1H), 2.23-2.08 (m, 4H), 1.83-1.70 (m, 1H), 1.02 (td, J = 8.1, 5.2 Hz, 1H), 0.61 (d, J = 4.9 Hz, 1H) | 10.9 min, 97.5% 11.2 min, 98.8% |

TABLE 20-continued

| Example | Name | Formula I | LCMS, [M + H]⁺ | ¹H NMR (500 MHz, MeOD) δ | HPLC-1: Rt min, purity; HPLC-2: Rt min, purity |
|---|---|---|---|---|---|
| 684 | (1aR,7bS)-2-(3-Chloro-2-methylphenoxy)ethyl 7-(1-(2-chloro-5-(1-methoxy-3-(methylsulfonamido)-1-oxopropan-2-ylcarbamoyl)benzyl)-1H-pyrazol-4-yl)-1a,2-dihydro-1H-cyclopropa[c]quinoline-3(7bH)-carboxylate | | 770.3 | 7.83-7.77 (m, 3H), 7.70 (s, 1H), 7.52 (d, J = 8.1 Hz, 1H), 7.39 (d, J = 7.1 Hz, 1H), 7.15-7.03 (m, 3H), 7.03-6.98 (m, 1H), 6.74 (d, J = 8.1 Hz, 1H), 5.55 (s, 2H), 5.17 (br. s., 1H), 4.97-4.79 (m, 1H), 4.69-4.38 (m, 3H), 4.21 (d, J = 3.8 Hz, 2H), 3.82 (s, 3H), 3.68 (br. s., 2H), 3.13-3.05 (m, 1H), 3.10 (d, J = 12.6 Hz, 1H), 2.96 (s, 3H), 2.29 (s, 3H), 2.22-2.05 (m, 1H), 1.79 (d, J = 5.6 Hz, 1H), 1.15-0.98 (m, 1H), 0.78 (d, J = 5.1 Hz, 1H) | 11.9 min, 95.0% 13.4 min, 95.0% |
| 685 | 2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-3-(methylsulfonamido)propanoic acid | | 756.1 | 8.27 (s, 1H), 8.06 (d, J = 7.1 Hz, 1H), 7.87 (dd, J = 8.5, 1.9 Hz, 1H), 7.75 (d, J = 4.9 Hz, 2H), 7.46 (d, J = 8.8 Hz, 1H), 7.11-7.02 (m, 3H), 6.98 (s, 1H), 6.71 (d, J = 7.7 Hz, 1H), 6.32-6.15 (m, 1H), 5.75-5.40 (m, 2H), 5.05 (d, J = 7.1 Hz, 1H), 4.65-4.59 (m, 1H), 4.55-4.37 (m, 2H), 4.20 (d, J = 5.5 Hz, 2H), 3.83 (dd, J = 13.7, 3.8 Hz, 1H), 3.67-3.57 (m, 1H), 3.10-3.04 (m, 2H), 2.90 (s, 3H), 2.27 (s, 3H), 2.15-2.07 (m, 1H), 1.75 (d, J = 6.0 Hz, 1H), 1.06-0.95 (m, 1H), 0.76-0.68 (m, 1H) | 10.9 min, 97.9% 11.0 min, 100% |
| 686 | (1aR,7bS)-2-(3-Chloro-2-methylphenoxy)ethyl 7-(1-(2-chloro-5-((S)-2-oxotetrahydrofuran-3-ylcarbamoyl)benzyl)-1H-pyrazol-4-yl)-1a,2-dihydro-1H-cyclopropa[c]quinoline-3(7bH)-carboxylate | | 675.3 | 7.81-7.77 (m, 1H), 7.76-7.70 (m, 1H), 7.50 (d, J = 8.2 Hz, 1H), 7.13 (d, J = 6.6 Hz, 1H), 7.09-7.02 (m, 2H), 7.00-6.95 (m, 1H), 6.69 (d, J = 8.2 Hz, 1H), 5.52 (s, 2H), 4.74 (ddd, J = 11.5, 8.8, 6.6 Hz, 1H), 4.64-4.55 (m, 1H), 4.54-4.39 (m, 3H), 4.36-4.26 (m, 1H), 4.23-4.09 (m, 2H), 3.05 (d, J = 13.2 Hz, 1H), 2.34-2.22 (m, 4H), 2.05 (td, J = 8.5, 4.9 Hz, 1H), 1.81-1.70 (m, 1H), 1.03 (td, J = 8.1, 5.2 Hz, 1H), 0.80-0.70 (m, 1H) | 11.9 min, 94.8% 13.3 min, 98.4% |

TABLE 20-continued

| Example | Name | Formula I | LCMS, [M + H]⁺ | ¹H NMR (500 MHz, MeOD) δ | HPLC-1: Rt min, purity; HPLC-2: Rt min, purity |
|---|---|---|---|---|---|
| 687 | 2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)-N-(2-methoxy-2-oxoethyl)benzamido)acetic acid | | N/A | 7.92 (s, 1H), 7.74 (s, 1H), 7.59 (d, J = 8.1 Hz, 1H), 7.40 (d, J = 7.6 Hz, 1H), 7.22 (d, J = 7.3 Hz, 1H), 7.18 (d, J = 7.6 Hz, 1H), 7.12-7.02 (m, 3H), 6.97 (s, 1H), 6.87 (d, J = 8.3 Hz, 1H), 5.59 (s, 2H), 4.62-4.46 (m, 3H), 4.25 (dd, J = 9.9, 6.1 Hz, 4H), 4.10 (d, J = 13.9 Hz, 2H), 3.72-3.60 (m, 1H), 3.65 (s, 1H), 3.75 (s, 2H), 3.05 (d, J = 12.9 Hz, 1H), 2.28-2.13 (m, 4H), 1.83 (br. s., 1H), 1.06 (d, J = 5.1 Hz, 1H), 0.64 (d, J = 4.3 Hz, 1H) | N/A |
| 688 | (S)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-4-hydroxybutanoic acid | | 693.2 | 7.95-7.90 (m, 1H), 7.82 (dd, J = 8.3, 1.8 Hz, 1H), 7.70 (s, 2H), 7.56 (d, J = 8.3 Hz, 1H), 7.22-7.11 (m, 2H), 7.10-7.02 (m, 2H), 6.99-6.92 (m, 1H), 6.85 (d, J = 8.1 Hz, 1H), 5.57 (s, 2H), 4.58-4.44 (m, 4H), 4.23 (br. s., 2H), 3.66 (t, J = 6.6 Hz, 2H), 3.03 (d, J = 12.9 Hz, 1H), 2.25-2.11 (m, 5H), 1.98-1.75 (m, 2H), 1.07-0.96 (m, 1H), 0.61 (d, J = 4.5 Hz, 1H) | N/A |
| 689 | (S)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-3-methoxypropanoic acid | | 693.2 | 7.94 (d, J = 1.6 Hz, 1H), 7.84 (dd, J = 8.2, 2.2 Hz, 1H), 7.76 (d, J = 5.5 Hz, 2H), 7.57-7.43 (m, 2H), 7.12-7.02 (m, 3H), 7.00-6.94 (m, 1H), 6.72 (d, J = 8.2 Hz, 1H), 5.69-5.44 (m, 2H), 5.07-4.93 (m, 1H), 4.67-4.59 (m, 1H), 4.56-4.39 (m, 2H), 4.28-4.14 (m, 2H), 3.95 (dd, J = 9.6, 4.1 Hz, 1H), 3.76 (dd, J = 9.9, 3.8 Hz, 1H), 3.37 (s, 3H), 3.07 (d, J = 12.6 Hz, 1H), 2.28 (s, 3H), 2.11-2.04 (m, 1H), 1.77 (d, J = 5.5 Hz, 1H), 1.04 (td, J = 8.1, 5.2 Hz, 1H), 0.84-0.71 (m, 1H) | 11.0 min, 93.3% 11.1 min, 100% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 690 | (S)-4-Carboxy-4-(4-chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-N,N,N-trimethylbutan-1-aminium, TFA salt | | 748.1 | 8.72 (d, J = 8.2 Hz, 1H), 7.97 (s, 1H), 7.83 (dd, J = 8.2, 2.2 Hz, 1H), 7.72 (s, 1H), 7.65 (d, J = 1.6 Hz, 1H), 7.58 (s, 1H), 7.21 (d, J = 7.1 Hz, 1H), 7.19-7.11 (m, 1H), 7.12-7.04 (m, 2H), 6.97 (d, J = 7.7 Hz, 1H), 6.86 (d, J = 8.2 Hz, 1H), 5.59 (s, 2H), 4.72-4.64 (m, 1H), 4.59-4.43 (m, 3H), 4.24 (br. s., 2H), 3.50-3.35 (m, 2H), 3.10 (s, 6H), 3.04 (d, J = 12.6 Hz, 1H), 2.24-2.13 (m, 4H), 2.11-2.01 (m, 1H), 1.99-1.74 (m, 4H), 1.03 (td, J = 8.2, 4.9 Hz, 1H), 0.63 (d, J = 4.9 Hz, 1H) | 11.4 min, 97.2% 12.8 min, 99.1% |
| 691 | (S)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-3-(methylsulfonamido)propanoic acid | | 756.2 | 8.21 (s, 1H), 8.10 (d, J = 7.3 Hz, 1H), 7.88 (dd, J = 8.3, 2.0 Hz, 1H), 7.77 (d, J = 7.1 Hz, 2H), 7.49 (d, J = 8.3 Hz, 1H), 7.16-6.96 (m, 4H), 6.73 (d, J = 8.1 Hz, 1H), 6.23 (br. s., 1H), 5.71-5.46 (m, 2H), 5.09-4.99 (m, 1H), 4.68-4.58 (m, 1H), 4.54-4.50 (m 3H), 4.28-4.15 (m, 2H), 3.82 (d, J = 13.4 Hz, 1H), 3.66 (d, J = 14.4 Hz, 1H), 3.09 (d, J = 12.4 Hz, 1H), 2.84 (s, 3H), 2.29 (s, 3H), 2.08 (td, J = 8.6, 4.8 Hz, 1H), 1.87-1.65 (m, 1H), 1.04 (td, J = 8.3, 5.2 Hz, 1H), 0.77 (q, J = 4.7 Hz, 1H) | 11.8 min, 97.2% 11.0 min, 98.8% |
| 692 | (S)-2-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)-3-(cyclopropanesulfonamido)propanoic acid | | 782.2 | 8.25 (d, J = 8.2 Hz, 1H), 8.03 (d, J = 1.6 Hz, 1H), 7.85-7.73 (m, 6H), 7.69 (s, 1H), 7.46 (d, J = 8.2 Hz, 1H), 6.98 (s, 1H), 7.14-6.93 (m, 4H), 6.71 (d, J = 1.1 Hz, 1H), 6.23 (br. s., 1H), 5.73-5.38 (m, 2H), 5.04-4.93 (m, 1H), 4.67-4.58 (m, 1H), 4.53-4.39 (m, 2H), 4.28-4.03 (m, 2H), 3.80 (d, J = 13.7 Hz, 1H), 3.57 (d, J = 13.7 Hz, 1H), 3.06 (d, J = 12.6 Hz, 1H), 2.27 (s, 4H), 2.09-2.02 (m, 1H), 1.84-1.65 (m, 1H), 1.15-1.00 (m, 1H), 0.99-0.89 (m, 1H), 0.84-0.70 (m, 4H) | 10.9 min, 91.3% 11.2 min, 95.2% |
| 693 | (2S,4S)-1-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzoyl)-4-hydroxypyrrolidine-2-carboxylic acid | | 705.2 | 7.78 (s, 1H), 7.73 (s, 1H), 7.45-7.44 (m, 1H), 7.41 (s, 1H), 7.10-6.96 (m, 5H), 6.72 (d, J = 8.3 Hz, 1H), 5.54 (s, 2H), 4.76 (d, J = 7.8 Hz, 1H), 4.66-4.58 (m, 1H), 4.55-4.32 (m, 4H), 4.26-4.15 (m, 2H), 3.72 (br. s., 1H), 3.62 (br. s., 1H), 3.08 (d, J = 12.4 Hz, 1H), 2.41-2.32 (m, 1H), 2.28 (s, 3H), 2.12-2.02 (m, 2H), 1.77 (d, J = 5.6 Hz, 1H), 1.09-0.97 (m, 1H), 0.77 (d, J = 4.8 Hz, 1H) | 10.7 min, 95.9% 10.9 min, 100% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---------|------|-----------|----------------|--------------------------|-------------------------------------------------|
| 694 | (1aR,7bS)-2-(3-Chloro-2-methylphenoxy)ethyl 7-(1-(2-chloro-5-((2S,4S)-4-hydroxy-2-(methoxycarbonyl)pyrrolidine-1-carbonyl)benzyl)-1H-pyrazol-4-yl)-1a,2-dihydro-1H-cyclopropa[c]quinoline-3(7bH)-carboxylate | | 719.3 | 7.81 (s, 1H), 7.68 (s, 1H), 7.51 (s, 2H), 7.30 (br. s., 1H), 7.14-6.94 (m, 5H), 6.71 (d, J = 8.1 Hz, 1H), 5.55 (s, 2H), 4.69-4.56 (m, 2H), 4.54-4.43 (m, 2H), 4.38 (br. s., 1H), 4.25-4.13 (m, 3H), 3.83 (s, 4H), 3.64 (br. s., 3H), 3.08 (d, J = 12.6 Hz, 1H), 2.52-2.34 (m, 1H), 2.27 (s, 3H), 2.17-1.97 (m, 2H), 1.77 (d, J = 6.1 Hz, 1H), 1.12-0.97 (m, 1H), 0.76 (d, J = 4.8 Hz, 1H) | N/A |
| 695 | (1aR,7bS)-2-(3-Chloro-2-methylphenoxy)ethyl 7-(1-(5-(4-(aminomethyl)-4-hydroxypiperidine-1-carbonyl)-2-chlorobenzyl)-1H-pyrazol-4-yl)-1a,2-dihydro-1H-cyclopropa[c]quinoline-3(7bH)-carboxylate, TFA salt | | 704.1 | NMR bad, intermediate compound | 5.3 min, 95.0% 8.8 min, 95.0% |
| 696 | (R)-2-Amino-3-(4-chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)propanoic acid, TFA salt | | 678.1 | 8.49 (br. s., 4H), 7.87 (br. s., 1H), 7.71 (d, J = 12.9 Hz, 2H), 7.55 (br. s., 1H), 7.25-7.09 (m, 2H), 7.09-6.89 (m, 5H), 6.70 (d, J = 8.0 Hz, 1H), 5.35 (br. s., 1H), 4.56 (br. s., 1H), 4.45 (br. s., 1H), 4.29 (br. s., 1H), 4.18 (br. s., 3H), 4.03-3.78 (m, 2H), 3.03 (d, J = 11.8 Hz, 1H), 2.26 (s, 3H), 2.00 (d, J = 4.7 Hz, 1H), 1.69 (d, J = 5.5 Hz, 1H), 0.97 (br. s., 1H), 0.71 (br. s., 1H) | 7.5 min, 99.3% 9.2 min, 98.3% |
| 697 | (1aR,7bS)-2-(3-Chloro-2-methylphenoxy)ethyl 7-(1-(2-chloro-5-(4-hydroxy-4-(methylsulfonamidomethyl)piperidine-1-carbonyl)benzyl)-1H-pyrazol-4-yl)-1a,2-dihydro-1H-cyclopropa[c]quinoline-3(7bH)-carboxylate | | 782.1 | 7.61 (s, 1H), 7.51 (s, 1H), 7.29 (d, J = 8.3 Hz, 1H), 7.16 (dd, J = 8.2, 1.9 Hz, 1H), 6.94-6.77 (m, 5H), 6.53 (d, J = 7.8 Hz, 1H), 5.35 (s, 2H), 4.49 (br. s., 1H), 4.41 (d, J = 6.6 Hz, 1H), 4.38-4.24 (m, 3H), 4.07-3.92 (m, 3H), 3.24-3.01 (m, 2H), 2.91 (d, J = 15.2 Hz, 3H), 2.79 (s, 4H), 2.09 (s, 3H), 1.97-1.89 (m, 1H), 1.57 (d, J = 7.6 Hz, 5H), 0.94-0.77 (m, 1H), 0.59 (d, J = 3.8 Hz, 1H) | 10.9 min, 90.2% 9.8 min, 89.0% |

TABLE 20-continued

| Example | Name | Formula I | LCMS, [M + H]+ | ¹H NMR (500 MHz, MeOD) δ | HPLC-1: Rt min, purity; HPLC-2: Rt min, purity |
|---|---|---|---|---|---|
| 698 | 2-(3-(4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)oxetan-3-yl)acetic acid | | 705.1 | 7.82-7.71 (m, 3H), 7.64 (d, J = 8.3 Hz, 1H), 7.41 (d, J = 8.3 Hz, 1H), 7.26 (br. s., 1H), 7.13-7.05 (m, 3H), 7.00 (s, 1H), 6.74 (d, J = 7.7 Hz, 1H), 5.49 (s, 2H), 4.68-4.62 (m, 2H), 4.58-4.42 (m, 3H), 4.29-4.16 (m, 2H), 3.99-3.88 (m, 2H), 3.18-3.04 (m, 2H), 2.77 (dd, J = 17.9, 1.9 Hz, 1H), 2.29 (s, 3H), 2.11 (td, J = 8.5, 4.8 Hz, 1H), 1.86-1.72 (m, 1H), 1.05 (d, J = 5.8 Hz, 1H), 0.79 (d, J = 4.7 Hz, 1H) | 11.7 min, 97.8% 12.9 min, 100% |
| 699 | 1-((4-Chloro-3-((4-((1aR,7bS)-3-((2-(3-chloro-2-methylphenoxy)ethoxy)carbonyl)-1a,2,3,7b-tetrahydro-1H-cyclopropa[c]quinolin-7-yl)-1H-pyrazol-1-yl)methyl)benzamido)methyl)cyclopropanecarboxylic acid | | 688.9 | 7.80 (s, 1H), 7.77 (dd, J = 8.3, 2.3 Hz, 1H), 7.72 (s, 1H), 7.65 (br. s., 1H), 7.52 (d, J = 8.3 Hz, 1H), 7.14-7.04 (m, 3H), 7.02-6.98 (m, 1H), 6.74 (d, J = 8.1 Hz, 1H), 5.55 (s, 2H), 4.67-4.58 (m, 1H), 4.53 (d, J = 14.4 Hz, 2H), 4.25-4.18 (m, 2H), 3.61 (d, J = 6.1 Hz, 2H), 2.29 (s, 3H), 2.14-2.08 (m, 1H), 1.78 (d, J = 5.6 Hz, 1H), 1.39 (d, J = 3.5 Hz, 2H), 1.15 (q, J = 3.5 Hz, 2H), 1.04 (td, J = 8.3, 4.9 Hz, 1H), 0.83-0.71 (m, 1H) | N/A |

The compounds exemplified in Table 21 were prepared in a manner analogous to Example 139.

TABLE 21

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 700 | 3-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)propanoic acid | | 683.2 | 7.99 (s, 1H), 7.84 (d, J = 14.1 Hz, 2H), 7.73-7.55 (m, 2H), 7.27-7.06 (m, 2H), 7.04-6.92 (m, 1H), 6.83 (d, J = 7.7 Hz, 1H), 6.73 (d, J = 8.4 Hz, 1H), 5.69-5.52 (m, 2H), 4.78 (d, J = 13.4 Hz, 1H), 4.44 (d, J = 11.9 Hz, 1H), 4.00-3.79 (m, 2H), 3.72-3.45 (m, 3H), 2.94-2.77 (m, 1H), 2.66 (t, J = 6.9 Hz, 2H), 2.57-2.18 (m, 3H), 2.05 (dq, J = 13.0, 6.5 Hz, 2H), 1.92 (s, 3H), 1.79 (d, J = 15.0 Hz, 1H) | 9.3 min, 98.3% 8.7 min, 98.4% |

TABLE 21-continued

| Example | Name | Formula I | LCMS, [M + H]+ | $^1$H NMR (400 MHz, MeOD) δ | HPLC-1: Rt min, purity; HPLC-2: Rt min, purity |
|---|---|---|---|---|---|
| 701 | 4-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)butanoic acid | | 697.3 | 8.00 (s, 1H), 7.85 (d, J = 10.8 Hz, 2H), 7.74-7.55 (m, 2H), 7.24-7.08 (m, 2H), 7.06-6.92 (m, 1H), 6.83 (d, J = 7.9 Hz, 1H), 6.73 (d, J = 8.1 Hz, 1H), 5.61 (d, J = 3.1 Hz, 2H), 4.81 (d, J = 8.6 Hz, 1H), 4.44 (d, J = 12.1 Hz, 1H), 3.99-3.78 (m, 2H), 3.63-3.38 (m, 3H), 2.84 (t, J = 11.6 Hz, 1H), 2.59-2.17 (m, 5H), 2.14-1.72 (m, 8H) | 9.4 min, 98.4% 8.8 min, 98.7% |
| 702 | (3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)methanesulfonic acid | | 705.2 | 8.00 (s, 1H), 7.93 (s, 1H), 7.89 (s, 1H), 7.75 (dd, J 9.9, 1.5 Hz, 1H), 7.63 (dd, J = 6.4, 3.1 Hz, 1H), 7.23-7.09 (m, 2H), 7.04-6.95 (m, 1H), 6.84 (d, J = 7.5 Hz, 1H), 6.74 (d, J = 8.1 Hz, 1H), 5.62 (d, J = 2.4 Hz, 2H), 4.82-4.73 (m, 1H), 4.53 (s, 2H), 4.44 (d, J = 11.9 Hz, 1H), 4.00-3.81 (m, 2H), 3.64-3.48 (m, 1H), 2.92-2.77 (m, 1H), 2.58-2.17 (m, 3H), 2.15-1.98 (m, 3H), 1.92 (s, 3H), 1.79 (d, J = 14.5 Hz, 1H) | N/A 7.4 min, 100% |
| 703 | 2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)ethanesulfonic acid | | 719.2 | .99 (s, 1H), 7.88 (s, 1H), 7.84 (s, 1H), 7.72-7.59 (m, 2H), 7.17-7.12 (m, 2H), 7.04-6.95 (m, 1H), 6.84 (d, J = 7.7 Hz, 1H), 6.74 (d, J = 8.1 Hz, 1H), 4.78 (d, J = 13.0 Hz, 1H), 4.44 (d, J = 11.9 Hz, 1H), 4.03-3.72 (m, 4H), 3.56 (t, J = 10.9 Hz, 1H), 3.11 (t, J = 6.7 Hz, 2H), 2.84 (t, J = 11.7 Hz, 1H), 2.58-2.17 (m, 3H), 2.15-1.97 (m, 2H), 1.92 (s, 3H), 1.79 (d, J = 15.0 Hz, 1H) | 8.3 min, 100% 7.5 min, 98.2% |
| 704 | (3-Chloro-4-((4-(5-(4-(2,3-dimethylphenoxy)butanoyl)-2,3,4,5-tetrahydrobenzo[b][1,4]oxazepin-9-yl)-1H-pyrazol-1-yl)methyl)-5-fluorobenzamido)methanesulfonic acid | | 685.2 | 8.00 (s, 1H), 7.93 (d, J = 1.1 Hz, 1H), 7.89 (d, J = 0.7 Hz, 1H), 7.75 (dd, J = 10.1, 1.5 Hz, 1H), 7.63 (dd, J = 5.9, 3.7 Hz, 1H), 7.19-7.09 (m, 2H), 6.92 (t, J = 7.9 Hz, 1H), 6.64 (t, J = 8.0 Hz, 2H), 5.61 (dd, J = 3.6, 1.4 Hz, 2H), 4.83-4.72 (m, 1H), 4.53 (s, 2H), 4.44 (d, J = 12.1 Hz, 1H), 3.97-3.76 (m, 2H), 3.64-3.48 (m, 1H), 2.93-2.73 (m, 1H), 2.56-2.18 (m, 3H), 2.15-1.96 (m, 8H), 1.89-1.71 (m, 4H) | 10.9 min, 99.7% 7.3 min, 100% |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 705 | 2-(3-Chloro-4-((4-(5-(4-(2,3-dimethylphenoxy)butanoyl)-2,3,4,5-tetrahydrobenzo[b][1,4]oxazepin-9-yl)-1H-pyrazol-1-yl)methyl)-5-fluorobenzamido)ethanesulfonic acid | | 699.2 | 7.98 (s, 1H), 7.88 (s, 1H), 7.84 (d, J = 1.3 Hz, 1H), 7.73-7.55 (m, 2H), 7.18-7.08 (m, 2H), 6.92 (t, J = 7.9 Hz, 1H), 6.64 (t, J = 7.6 Hz, 2H), 5.60 (dd, J = 4.0, 1.3 Hz, 2H), 4.82-4.72 (m, 1H), 4.44 (d, J = 11.9 Hz, 1H), 3.94-3.77 (m, 4H), 3.55 (td, J = 11.7, 1.8 Hz, 1H), 3.11 (t, J = 6.8 Hz, 2H), 2.92-2.77 (m, 1H), 2.56-2.17 (m, 3H), 2.15-1.94 (m, 6H), 1.86-1.72 (m, 4H) | 10.8 min, 99.4% 7.7 min, 99.4% |
| 706 | 3-(3-Chloro-4-((4-(5-(4-(2,3-dimethylphenoxy)butanoyl)-2,3,4,5-tetrahydrobenzo[b][1,4]oxazepin-9-yl)-1H-pyrazol-1-yl)methyl)-5-fluorobenzamido)propanoic acid | | 663.3 | 7.96 (s, 1H), 7.84 (s, 1H), 7.80 (s, 1H), 7.69-7.54 (m, 2H), 7.16-7.07 (m, 2H), 6.89 (t, J = 7.8 Hz, 1H), 6.61 (t, J = 7.4 Hz, 2H), 5.64-5.50 (m, 2H), 4.79-4.70 (m, 1H), 4.41 (d, J = 11.7 Hz, 1H), 3.92-3.74 (m, 2H), 3.68-3.58 (m, 2H), 3.58-3.46 (m, 1H), 2.92-2.75 (m, 1H), 2.63 (t, J = 6.9 Hz, 2H), 2.51-2.15 (m, 3H), 2.12-1.96 (m, 5H), 1.85-1.67 (m, 4H) | 9.0 min, 99.6% 8.5 min, 99.5% |
| 707 | 4-(3-Chloro-4-((4-(5-(4-(2,3-dimethylphenoxy)butanoyl)-2,3,4,5-tetrahydrobenzo[b][1,4]oxazepin-9-yl)-1H-pyrazol-1-yl)methyl)-5-fluorobenzamido)butanoic acid | | 677.3 | 7.96 (s, 1H), 7.84 (s, 1H), 7.81 (d, J = 1.3 Hz, 1H), 7.70-7.54 (m, 2H), 7.17-7.05 (m, 2H), 6.89 (t, J = 7.8 Hz, 1H), 6.61 (t, J = 7.7 Hz, 2H), 5.61-5.52 (m, 2H), 4.75 (d, J = 13.2 Hz, 1H), 4.41 (d, J = 11.9 Hz, 1H), 3.91-3.74 (m, 2H), 3.59-3.46 (m, 1H), 3.42 (t, J = 6.9 Hz, 2H), 2.91-2.73 (m, 1H), 2.52-2.15 (m, 4H), 2.12-1.97 (m, 4H), 1.96-1.85 (m, 2H), 1.82-1.71 (m, 3H) | 9.1 min, 99.0% 8.6 min, 99.1% |
| 708 | 2-(3-Chloro-4-((4-(5-(4-(2,3-dimethylphenoxy)butanoyl)-2,3,4,5-tetrahydrobenzo[b][1,4]oxazepin-9-yl)-1H-pyrazol-1-yl)methyl)-5-fluorobenzamido)-N,N,N-trimethylethanaminium, TFA salt | | 676.3 | 8.01 (s, 1H), 7.91-7.81 (m, 2H), 7.74-7.56 (m, 2H), 7.21-7.07 (m, 2H), 6.91 (t, J = 7.8 Hz, 1H), 6.69-6.56 (m, 2H), 5.67-5.55 (m, 2H), 4.82-4.72 (m, 1H), 4.44 (d, J = 12.1 Hz, 1H), 3.95-3.78 (m, 4H), 3.67-3.49 (m, 3H), 3.25 (s, 9H), 2.92-2.77 (m, 1H), 2.53-2.17 (m, 3H), 2.14-1.99 (m, 4H), 1.90-1.71 (m, 3H) | 6.6 min, 99.9% 7.8 min, 100% |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---------|------|-----------|----------------|--------------------------|------------------------------------------------|
| 709 | N-(2-Dimethylamino)ethyl)-3-((4-(5-(4-(2,3-dimethylphenoxy)butanoyl)-2,3,4,5-tetrahydrobenzo[b][1,4]oxazepin-9-yl)methyl)benzamide | | 610.4 | 8.04 (s, 1H), 7.93 (s, 1H), 7.82 (s, 2H), 7.65 (dd, J = 5.8, 3.6 Hz, 1H), 7.55-7.42 (m, 2H), 7.22-7.08 (m, 2H), 6.92 (t, J = 7.8 Hz, 1H), 6.70-6.56 (m, 2H), 5.45 (s, 2H), 4.78 (d, J = 13.4 Hz, 1H), 4.47 (d, J = 11.9 Hz, 1H), 3.95-3.78 (m, 2H), 3.65-3.47 (m, 3H), 2.85 (t, J = 11.6 Hz, 1H), 2.62 (t, J = 6.7 Hz, 2H), 2.53-2.18 (m, 9H), 2.14-1.96 (m, 5H), 1.89-1.74 (m, 4H) | 6.3 min, 99.6% 7.5 min, 99.4% |
| 710 | 2-(3-((4-(5-(4-(3-Chloro-2-methylphenoxy)butanoyl)-2,3,4,5-tetrahydrobenzo[b][1,4]oxazepin-9-yl)-1H-phenylamino)-N,N,N-trimethyl-2-oxoethanaminium, TFA salt | | 630.5 | 8.01 (s, 1H), 7.90 (s, 1H), 7.62 (dd, J = 6.1, 3.4 Hz, 1H), 7.59-7.50 (m, 2H), 7.36 (t, J = 7.8 Hz, 1H), 7.19-7.06 (m, 3H), 7.00-6.90 (m, 1H), 6.80 (d, J = 7.9 Hz, 1H), 6.71 (d, J = 8.4 Hz, 1H), 5.38 (s, 2H), 4.80-4.71 (m, 1H), 4.46 (d, J = 12.1 Hz, 1H), 4.24 (s, 2H), 3.97-3.80 (m, 2H), 3.64-3.50 (m, 1H), 3.37 (s, 9H), 2.92-2.73 (m, 1H), 2.51-2.17 (m, 3H), 2.11-1.97 (m, 2H), 1.92 (s, 3H), 1.76 (d, J = 14.7 Hz, 1H) | 6.8 min, 99.8% 8.1 min, 99.7% |
| 711 | 4-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)phenylamino)-N,N,N-trimethyl-4-oxobutan-1-aminium, TFA salt | | 658.5 | 7.99 (s, 1H), 7.90 (s, 1H), 7.62 (dd, J = 6.1, 3.4 Hz, 1H), 7.53 (dd, J = 3.5, 1.8 Hz, 2H), 7.37-7.26 (m, 1H), 7.19-7.08 (m, 2H), 7.04 (d, J = 7.7 Hz, 1H), 6.99-6.90 (m, 1H), 6.80 (d, J = 7.7 Hz, 1H), 6.71 (d, J = 8.4 Hz, 1H), 5.35 (d, J = 1.8 Hz, 2H), 4.79-4.70 (m, 1H), 4.45 (d, J = 12.3 Hz, 1H), 3.96-3.80 (m, 2H), 3.63-3.46 (m, 1H), 3.46-3.33 (m, 2H), 3.14 (s, 9H), 2.88-2.74 (m, 1H), 2.57-1.96 (m, 9H), 1.92 (s, 3H), 1.77 (d, J = 14.7 Hz, 1H) | 6.7 min, 100% 7.9 min, 100% |
| 712 | 2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)-N,N,N-trimethylethanaminium, TFA salt | | 696.4 | 8.03 (s, 1H), 7.89-7.82 (m, 2H), 7.73-7.58 (m, 2H), 7.20-7.10 (m, 2H), 7.04-6.93 (m, 1H), 6.83 (d, J = 7.5 Hz, 1H), 6.74 (d, J = 8.1 Hz, 1H), 5.62 (dd, J = 4.8, 1.3 Hz, 2H), 4.82-4.74 (m, 1H), 4.44 (br. s., 1H), 3.98-3.82 (m, 2H), 3.66-3.55 (m, 3H), 3.28-3.22 (m, 9H), 2.84 (s, 1H), 2.56-2.21 (m, 3H), 2.16-1.99 (m, 2H), 1.91 (s, 3H), 1.85-1.74 (m, 1H) | 6.8 min, 99.9% 8.1 min, 100% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 713 | N-(3-(Dimethylamino) propyl)-3-((4-(5-(4-(2,3-dimethylphenoxy)butanoyl)-2,3,4,5-tetrahydrobenzo[b][1,4]oxazepin-9-yl)-1H-pyrazol-1-yl)methyl) benzamide | | 624.5 | 8.02 (s, 1H), 7.91 (s, 1H), 7.81-7.71 (m, 2H), 7.62 (dd, J = 5.9, 3.5 Hz, 1H), 7.51-7.40 (m, 2H), 7.18-7.07 (m, 2H), 6.89 (t, J = 7.8 Hz, 1H), 6.61 (dd, J = 7.7, 3.7 Hz, 2H), 5.42 (s, 2H), 4.75 (d, J = 14.1 Hz, 1H), 4.45 (d, J = 11.7 Hz, 1H), 3.92-3.74 (m, 2H), 3.56 (t, J = 10.9 Hz, 1H), 3.45-3.36 (m, 2H), 2.90-2.75 (m, 1H), 2.48-2.35 (m, 4H), 2.30-2.18 (m, 7H), 2.12-1.95 (m, 5H), 1.87-1.70 (m, 6H) | 6.4 min, 99.9% 7.6 min, 100% |
| 714 | 3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl) benzamido)-N,N,N-trimethylpropan-1-aminium | | 638.5 | 8.04 (s, 1H), 7.92 (s, 1H), 7.85-7.73 (m, 2H), 7.63 (dd, J = 5.2, 4.3 Hz, 1H), 7.48 (d, J = 5.1 Hz, 2H), 7.17-7.09 (m, 2H), 6.89 (t, J = 7.8 Hz, 1H), 6.61 (dd, J = 7.9, 4.2 Hz, 2H), 5.43 (d, J = 1.3 Hz, 2H), 4.76 (d, J = 13.9 Hz, 1H), 4.46 (d, J = 12.1 Hz, 1H), 3.92-3.75 (m, 2H), 3.62-3.36 (m, 7H), 3.12 (s, 9H), 2.83 (t, J = 11.7 Hz, 1H), 2.45-2.35 (m, 2H), 2.33-2.16 (m, 1H), 2.15-1.95 (m, 5H), 1.85-1.70 (m, 4H) | 6.4 min, 99.9% 7.5 min, 100% |
| 715 | N-(2-tert-Butoxy-2-oxoethyl)-3-(3-((4-(5-(4-(2,3-dimethylphenoxy)butanoyl)-2,3,4,5-tetrahydrobenzo[b][1,4]oxazepin-9-yl)-1H-pyrazol-1-yl)methyl) benzamido)-N,N-dimethylpropan-1-aminium, TFA salt | | 738.6 | 8.04-7.81 (m, 4H), 7.57-7.36 (m, 3H), 7.14-6.94 (m, 3H), 6.73 (d, J = 7.5 Hz, 1H), 6.64 (d, J = 8.1 Hz, 1H), 5.41 (s, 2H), 4.87 (d, J = 13.4 Hz, 1H), 4.48 (d, J = 11.7 Hz, 1H), 4.08 (s, 2H), 4.00-3.80 (m, 4H), 3.71-3.58 (m, 3H), 3.33 (s, 6H), 2.80 (t, J = 11.4 Hz, 1H), 2.58-2.01 (m, 10H), 1.96 (s, 3H), 1.79 (d, J = 14.7 Hz, 1H), 1.58-1.45 (m, 9H) | 7.0 min, 98.1% 8.4 min, 98.5% |
| 716 | N-(Carboxymethyl)-3-(3-((4-(5-(4-(2,3-dimethylphenoxy)butanoyl)-2,3,4,5-tetrahydrobenzo[b][1,4]oxazepin-9-yl)-1H-pyrazol-1-yl)methyl)benzamido)-N,N-dimethylpropan-1-aminium, TFA salt | | 682.6 | 8.04 (s, 1H), 7.92 (s, 1H), 7.83-7.73 (m, 2H), 7.67-7.59 (m, 1H), 7.48 (d, J = 5.1 Hz, 2H), 7.18-7.09 (m, 2H), 6.95-6.84 (m, 1H), 6.61 (dd, J = 7.8, 1.4 Hz, 2H), 5.43 (s, 2H), 4.76 (d, J = 13.6 Hz, 1H), 4.46 (d, J = 12.5 Hz, 1H), 4.25 (s, 2H), 3.92-3.77 (m, 2H), 3.73-3.43 (m, 5H), 3.29-3.22 (m, 6H), 2.90-2.76 (m, 1H), 2.48-2.37 (m, 2H), 2.34-2.15 (m, 1H), 2.13-1.96 (m, 7H), 1.85-1.69 (m, 4H) | 6.6 min, 98.3% 7.4 min, 98.7% |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 717 | 3-(3-((4-(5-(4-(2,3-Dimethylphenoxy)butanoyl)-2,3,4,5-tetrahydrobenzo[b][1,4]oxazepin-9-yl)-1H-pyrazol-1-yl)methyl)benzamido)-N-(2-hydroxyethyl)-N,N-dimethylpropan-1-aminium, TFA salt | | 668.5 | 8.06 (s, 1H), 7.94 (d, J = 0.7 Hz, 1H), 7.87-7.76 (m, 2H), 7.65 (dd, J = 5.3, 4.2 Hz, 1H), 7.50 (d, J = 5.1 Hz, 2H), 7.21-7.10 (m, 2H), 6.97-6.86 (m, 1H), 6.64 (dd, J = 7.8, 4.1 Hz, 2H), 5.45 (d, J = 1.3 Hz, 2H), 4.83-4.73 (m, 1H), 4.53-4.43 (m, 1H), 4.04-3.96 (m, 2H), 3.94-3.78 (m, 2H), 3.67-3.43 (m, 7H), 3.21-3.11 (m, 6H), 2.92-2.78 (m, 1H), 2.43 (td, J = 7.2, 3.5 Hz, 2H), 2.28 (dt, J = 7.5, 3.7 Hz, 1H), 2.18-1.99 (m, 7H), 1.88-1.73 (m, 4H) | 6.3 min, 99.5% 7.3 min, 99.7% |
| 718 | 2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-fluorobenzamido)-N,N,N-trimethylethanaminium, TFA salt | | 662.4 | 8.04 (s, 1H), 7.90 (s, 1H), 7.70-7.59 (m, 3H), 7.31 (t, J = 7.8 Hz, 1H), 7.19-7.10 (m, 2H), 7.01-6.91 (m, 1H), 6.80 (d, J = 7.7 Hz, 1H), 6.72 (d, J = 8.1 Hz, 1H), 5.50 (s, 2H), 4.80-4.71 (m, 1H), 4.45 (d, J = 11.9 Hz, 1H), 3.96-3.79 (m, 4H), 3.62-3.51 (m, 3H), 3.23 (s, 9H), 2.92-2.74 (m, 1H), 2.54-2.17 (m, 3H), 2.11-1.97 (m, 2H), 1.90 (s, 3H), 1.77 (d, J = 14.5 Hz, 1H) | 6.6 min, 100% 7.7 min, 100% |
| 719 | (4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-fluorobenzamido)methanesulfonic acid | | 671.3 | 8.09 (s, 1H), 7.97 (s, 1H), 7.78-7.70 (m, 2H), 7.66 (dd, J = 5.9, 3.7 Hz, 1H), 7.32 (t, J = 7.8 Hz, 1H), 7.21-7.13 (m, 2H), 7.05-6.97 (m, 1H), 6.84 (d, J = 7.7 Hz, 1H), 6.75 (d, J = 8.4 Hz, 1H), 5.54 (s, 2H), 4.83-4.73 (m, 1H), 4.54 (s, 2H), 4.48 (d, J = 12.1 Hz, 1H), 4.00-3.84 (m, 2H), 3.67-3.50 (m, 1H), 2.85 (t, J = 11.4 Hz, 1H), 2.58-2.18 (m, 3H), 2.13-2.01 (m, 2H), 1.94 (s, 3H), 1.80 (d, J = 14.5 Hz, 1H) | 10.6 min, 100% 7.2 min, 100% |
| 720 | 2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-fluorobenzamido)ethanesulfonic acid | | 685.3 | 8.07 (s, 1H), 7.96 (d, J = 0.4 Hz, 1H), 7.71-7.61 (m, 3H), 7.31 (t, J = 7.8 Hz, 1H), 7.21-7.11 (m, 2H), 7.05-6.95 (m, 1H), 6.84 (d, J = 7.5 Hz, 1H), 6.75 (d, J = 8.1 Hz, 1H), 5.53 (s, 2H), 4.83-4.72 (m, 1H), 4.48 (d, J = 12.1 Hz, 1H), 3.98-3.77 (m, 4H), 3.65-3.49 (m, 1H), 3.10 (t, J = 6.7 Hz, 2H), 2.85 (t, J = 11.6 Hz, 1H), 2.57-2.20 (m, 3H), 2.13-2.00 (m, 2H), 1.94 (s, 3H), 1.80 (d, J = 15.4 Hz, 1H) | 10.5 min, 99.2% 7.3 min, 98.8% |

TABLE 21-continued

| Example | Name | Formula I | LCMS, [M + H]⁺ | ¹H NMR (400 MHz, MeOD) δ | HPLC-1: Rt min, purity; HPLC-2: Rt min, purity |
|---|---|---|---|---|---|
| 721 | 3-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-fluorobenzamido)propanoic acid | | 649.3 | 8.04 (s, 1H), 7.92 (d, J = 0.7 Hz, 1H), 7.70-7.56 (m, 3H), 7.29 (t, J = 7.7 Hz, 1H), 7.22-7.12 (m, 2H), 7.05-6.94 (m, 1H), 6.84 (d, J = 7.5 Hz, 1H), 6.74 (d, J = 8.6 Hz, 1H), 5.51 (s, 2H), 4.78 (d, J = 12.5 Hz, 1H), 4.47 (d, J = 12.3 Hz, 1H), 4.01-3.83 (m, 2H), 3.72-3.53 (m, 3H), 2.91-2.79 (m, 1H), 2.65 (t, J = 6.9 Hz, 2H), 2.57-2.18 (m, 3H), 2.15-1.99 (m, 2H), 1.94 (s, 3H), 1.79 (d, J = 14.7 Hz, 1H) | 8.9 min, 99.6% 8.4 min, 99.5% |
| 722 | 4-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-fluorobenzamido)butanoic acid | | 663.3 | 8.02 (s, 1H), 7.90 (s, 1H), 7.69-7.56 (m, 2H), 7.27 (t, J = 7.7 Hz, 1H), 7.19-7.10 (m, 2H), 7.01-6.92 (m, 1H), 6.81 (d, J = 7.9 Hz, 1H), 6.72 (d, J = 8.1 Hz, 1H), 5.49 (s, 2H), 4.80-4.70 (m, 114H), 4.45 (d, J = 11.4 Hz, 94H), 3.97-3.81 (m, 2H), 3.56 (t, J = 11.8 Hz, 1H), 3.42 (t, J = 6.9 Hz, 2H), 2.82 (t, J = 11.7 Hz, 1H), 2.55-2.17 (m, 5H), 2.10-1.97 (m, 2H), 1.96-1.85 (m, 5H), 1.77 (d, J = 15.0 Hz, 1H) | 8.9 min, 99.5% 8.5 min, 99.3% |
| 723 | N-(Carboxymethyl)-2-(3-((4-(5-(4-(2,3-dimethylphenoxy)butanoyl)-2,3,4,5-tetrahydrobenzo[b][1,4]oxazepin-9-yl)-1H-pyrazol-1-yl)methyl)benzamido)-N,N-dimethylethanaminium, TFA salt | | 668.5 | 8.04 (s, 1H), 7.92 (s, 1H), 7.84-7.74 (m, 2H), 7.67-7.60 (m, 1H), 7.49 (d, J = 5.1 Hz, 2H), 7.19-7.07 (m, 2H), 6.89 (t, J = 7.8 Hz, 1H), 6.62 (dd, J = 7.9, 3.5 Hz, 2H), 5.43 (s, 2H), 4.79-4.71 (m, 1H), 4.46 (d, J = 11.9 Hz, 1H), 4.32 (s, 2H), 3.93-3.76 (m, 6H), 3.63-3.52 (m, 1H), 3.36 (s, 6H), 2.83 (t, J = 11.6 Hz, 1H), 2.46-2.17 (m, 3H), 2.08 (s, 3H), 2.02 (quin, J = 6.5 Hz, 2H), 1.83-1.74 (m, 4H) | 6.6 min, 98.2% 7.4 min, 97.8% |
| 724 | 2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3,5-difluorobenzamido)-N,N,N-trimethylethanaminium, TFA salt | | 680.4 | 8.03 (s, 1H), 7.86 (d, J = 0.7 Hz, 1H), 7.67-7.51 (m, 3H), 7.20-7.10 (m, 2H), 7.03-6.94 (m, 1H), 6.82 (d, J = 7.5 Hz, 1H), 6.74 (d, J = 7.9 Hz, 1H), 5.53 (d, J = 2.9 Hz, 2H), 4.83-4.73 (m, 1H), 4.47 (d, J = 12.1 Hz, 1H), 3.98-3.82 (m, 4H), 3.59 (t, J = 6.8 Hz, 3H), 3.25 (s, 9H), 2.84 (t, J = 11.6 Hz, 1H), 2.55-2.20 (m, 3H), 2.14-2.00 (m, 2H), 1.92 (s, 3H), 1.80 (d, J = 14.7 Hz, 1H) | 6.7 min, 99.9% 7.9 min, 99.9% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 725 | 4-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3,5-difluorobenzamido)methanesulfonic acid | | 689.3 | 8.00 (s, 1H), 7.87 (s, 1H), 7.68-7.59 (m, 3H), 7.20-7.09 (m, 2H), 7.04-6.95 (m, 1H), 6.84 (d, J = 7.5 Hz, 1H), 6.74 (d, J = 8.1 Hz, 1H), 5.53 (d, J = 2.2 Hz, 2H), 4.78 (d, J = 12.1 Hz, 1H), 4.53 (s, 2H), 4.46 (d, J = 11.7 Hz, 1H), 3.99-3.82 (m, 2H), 3.62-3.52 (m, 1H), 2.84 (t, J = 11.4 Hz, 1H), 2.57-2.19 (m, 3H), 2.13-2.00 (m, 2H), 1.93 (s, 3H), 1.79 (d, J = 15.0 Hz, 1H) | 11.3 min, 100% 7.3 min, 100% |
| 726 | 2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3,5-difluorobenzamido)ethanesulfonic acid | | 703.3 | 7.97 (s, 1H), 7.84 (s, 1H), 7.60 (dd, J = 6.4, 1.3 Hz, 1H), 7.53 (d, J = 7.9 Hz, 2H), 7.18-7.08 (m, 2H), 7.02-6.91 (m, 1H), 6.81 (d, J = 7.9 Hz, 1H), 6.71 (d, J = 8.4 Hz, 1H), 5.50 (s, 2H), 4.80-4.70 (m, 1H), 4.43 (d, J = 12.3 Hz, 1H), 3.96-3.72 (m, 4H), 3.60-3.50 (m, 1H), 3.08 (t, J = 6.7 Hz, 2H), 2.81 (t, J = 11.8 Hz, 1H), 2.54-2.16 (m, 3H), 2.13-1.98 (m, 2H), 1.90 (s, 3H), 1.77 (d, J = 15.0 Hz, 1H) | 11.0 min, 98.6% 7.3 min, 97.8% |
| 727 | 3-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3,5-difluorobenzamido)propanoic acid | | 667.3 | 7.98 (s, 1H), 7.83 (s, 1H), 7.60 (dd, J = 6.4, 3.1 Hz, 1H), 7.55-7.47 (m, 2H), 7.17-7.08 (m, 2H), 7.01-6.91 (m, 1H), 6.80 (d, J = 7.7 Hz, 1H), 6.71 (d, J = 8.1 Hz, 1H), 5.49 (d, J = 2.2 Hz, 2H), 4.80-4.70 (m, 1H), 4.43 (d, J = 12.1 Hz, 1H), 3.96-3.80 (m, 2H), 3.68-3.50 (m, 3H), 2.81 (t, J = 11.7 Hz, 1H), 2.63 (t, J = 6.8 Hz, 2H), 2.54-2.17 (m, 3H), 2.03 (dd, J = 13.3, 6.3 Hz, 2H), 1.90 (s, 3H), 1.77 (d, J = 14.3 Hz, 1H) | 9.0 min, 99.9% 8.5 min, 99.7% |
| 728 | 4-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3,5-difluorobenzamido)butanoic acid | | 681.3 | 7.98 (s, 1H), 7.83 (s, 1H), 7.60 (dd, J = 6.4, 3.1 Hz, 1H), 7.56-7.47 (m, 2H), 7.16-7.09 (m, 2H), 7.01-6.91 (m, 1H), 6.80 (d, J = 7.7 Hz, 1H), 6.71 (d, J = 8.1 Hz, 1H), 5.50 (d, J = 2.6 Hz, 2H), 4.76 (d, J = 13.9 Hz, 1H), 4.44 (d, J = 11.9 Hz, 1H), 3.96-3.80 (m, 2H), 3.60-3.50 (m, 1H), 3.42 (t, J = 6.9 Hz, 2H), 2.82 (t, J = 11.6 Hz, 1H), 2.54-2.17 (m, 5H), 2.03 (dd, J = 13.1, 6.5 Hz, 2H), 1.96-1.85 (m, 5H), 1.77 (d, J = 14.7 Hz, 1H) | 9.1 min, 99.9% 8.6 min, 99.8% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 729 | 4-(3-((4-(1-(4-(3-Chloro-2-methylphenoxy)butanoyl)-2,3,4,5-tetrahydro-1H-benzo[b]azepin-6-yl)-1H-pyrazol-1-yl)methyl)benzamido)butanoic acid | | 643.4 | 7.84-7.74 (m, 3H), 7.56 (d, J = 0.7 Hz, 1H), 7.53-7.43 (m, 2H), 7.38-7.32 (m, 1H), 7.27 (d, J = 7.7 Hz, 1H), 7.15 (dd, J = 7.7, 1.3 Hz, 1H), 7.10-7.01 (m, 1H), 6.89 (d, J = 7.5 Hz, 1H), 6.79 (d, J = 8.4 Hz, 1H), 5.48 (s, 2H), 4.64 (d, J = 13.0 Hz, 1H), 4.05-3.87 (m, 2H), 3.45 (t, J = 7.0 Hz, 2H), 2.98-2.86 (m, 1H), 2.83-2.70 (m, 1H), 2.54-2.29 (m, 5H), 2.17-2.04 (m, 2H), 2.01-1.85 (m, 7H), 1.77 (d, J = 13.9 Hz, 1H), 1.50-1.31 (m, 1H) | 9.1 min, 98.3% 8.6 min, 98.3% |
| 730 | 3-(3-((4-(1-(4-(3-Chloro-2-methylphenoxy)butanoyl)-2,3,4,5-tetrahydro-1H-benzo[b]azepin-6-yl)-1H-pyrazol-1-yl)methyl)benzamido)propanoic acid | | 629.4 | 7.82-7.68 (m, 3H), 7.53 (s, 1H), 7.51-7.39 (m, 2H), 7.36-7.30 (m, 1H), 7.24 (t, J = 7.7 Hz, 1H), 7.12 (dd, J = 7.7, 1.1 Hz, 1H), 7.07-7.00 (m, 1H), 6.86 (d, J = 7.9 Hz, 1H), 6.76 (d, J = 8.4 Hz, 1H), 5.45 (s, 2H), 4.62 (d, J = 13.4 Hz, 1H), 4.03-3.84 (m, 2H), 3.63 (t, J = 6.9 Hz, 2H), 2.96-2.85 (m, 1H), 2.81-2.69 (m, 1H), 2.64 (t, J = 6.9 Hz, 2H), 2.51-2.26 (m, 3H), 2.14-2.02 (m, 2H), 1.98-1.82 (m, 5H), 1.75 (d, J = 14.1 Hz, 1H), 1.50-1.29 (m, 1H) | 9.0 min, 98.5% 8.9 min, 98.5% |
| 731 | 2-(3-((4-(1-(4-(3-Chloro-2-methylphenoxy)butanoyl)-2,3,4,5-tetrahydro-1H-benzo[b]azepin-6-yl)-1H-pyrazol-1-yl)methyl)benzamido)ethanesulfonic acid | | 665.4 | 7.89-7.74 (m, 3H), 7.63 (s, 1H), 7.54-7.41 (m, 2H), 7.38-7.31 (m, 1H), 7.26 (t, J = 7.7 Hz, 1H), 7.14 (dd, J = 7.7, 1.1 Hz, 1H), 7.08-6.99 (m, 1H), 6.87 (d, J = 7.5 Hz, 1H), 6.77 (d, J = 8.1 Hz, 1H), 5.50 (s, 2H), 4.62 (d, J = 13.4 Hz, 1H), 4.03-3.86 (m, 2H), 3.81 (t, J = 6.7 Hz, 2H), 3.09 (t, J = 6.7 Hz, 2H), 2.94-2.83 (m, 1H), 2.74 (t, J = 11.4 Hz, 1H), 2.51-2.27 (m, 3H), 2.14-2.03 (m, 2H), 1.98-1.84 (m, 5H), 1.75 (d, J = 13.9 Hz, 1H), 1.48-1.34 (m, 1H) | 11.0 min, 99.7% 7.3 min, 99.3% |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 732 | (3-((4-(1-(4-(3-Chloro-2-methylphenoxy)butanoyl)-2,3,4,5-tetrahydro-1H-benzo[b]azepin-6-yl)-1H-pyrazol-1-yl)methyl)benzamido)methanesulfonic acid | | 651.4 | 7.97-7.82 (m, 3H), 7.63 (s, 1H), 7.56-7.44 (m, 2H), 7.39-7.33 (m, 1H), 7.28 (t, J = 7.8 Hz, 1H), 7.16 (dd, J = 7.7, 1.1 Hz, 1H), 7.11-7.03 (m, 1H), 6.90 (d, J = 7.7 Hz, 1H), 6.79 (d, J = 7.9 Hz, 1H), 5.52 (s, 1H), 4.64 (d, J = 13.4 Hz, 1H), 4.56 (s, 2H), 4.05-3.87 (m, 2H), 2.98-2.86 (m, 1H), 2.83-2.70 (m, 1H), 2.55-2.29 (m, 3H), 2.16-2.05 (m, 2H), 2.03-1.86 (m, 5H), 1.78 (d, J = 13.6 Hz, 1H), 1.50-1.36 (m, 1H) | 11.3 min, 100% 7.3 min, 100% |
| 733 | 2-(3-((4-(1-(4-(3-Chloro-2-methylphenoxy)butanoyl)-2,3,4,5-tetrahydro-1H-benzo[b]azepin-6-yl)-1H-pyrazol-1-yl)methyl)benzamido)-N,N,N-trimethylethanaminium, TFA salt | | 642.5 | 7.91-7.76 (m, 3H), 7.60-7.37 (m, 3H), 7.38-7.32 (m, 1H), 7.31-7.23 (m, 1H), 7.16 (dd, J = 7.7, 1.3 Hz, 1H), 7.11-7.02 (m, 1H), 6.89 (d, J = 7.7 Hz, 1H), 6.80 (s, 1H), 5.49 (s, 2H), 4.70-4.59 (m, 1H), 4.05-3.83 (m, 4H), 3.64-3.56 (m, 2H), 3.26 (s, 9H), 2.97-2.88 (m, 1H), 2.82-2.71 (m, 1H), 2.53-2.29 (m, 3H), 2.15-2.05 (m, 2H), 2.00-1.86 (m, 5H), 1.78 (d, J = 13.6 Hz, 1H), 1.51-1.32 (m, 1H) | 6.8 min, 99.8% 7.9 min, 100% |
| 734 | 2-(3-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-methoxybenzamido)-N,N,N-trimethylethanaminium, TFA salt | | 674.5 | 8.01 (d, J = 0.4 Hz, 1H), 7.91 (d, J = 0.7 Hz, 1H), 7.64 (dd, J = 6.4, 3.1 Hz, 1H), 7.43 (dd, J = 7.9, 1.5 Hz, 1H), 7.21-7.10 (m, 3H), 7.02-6.93 (m, 1H), 6.82 (d, J = 7.7 Hz, 1H), 6.74 (d, J = 8.4 Hz, 1H), 5.44 (s, 2H), 4.83-4.74 (m, 1H), 4.46 (d, J = 12.1 Hz, 1H), 3.99 (s, 3H), 3.96-3.84 (m, 4H), 3.60 (t, J = 6.6 Hz, 3H), 3.26 (s, 9H), 2.90-2.79 (m, 1H), 2.54-2.18 (m, 3H), 2.15-1.98 (m, 2H), 1.93 (s, 3H), 1.79 (d, J = 14.7 Hz, 1H) | 6.6 min, 99.0% 7.8 min, 98.6% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 735 | 2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-methoxybenzamido)ethanesulfonic acid | | 697.3 | 8.06 (s, 1H), 7.99 (s, 1H), 7.70-7.60 (m, 1H), 7.52 (d, J = 1.3 Hz, 1H), 7.43 (dd, J = 7.7, 1.5 Hz, 1H), 7.22-7.11 (m, 3H), 7.03-6.95 (m, 1H), 6.83 (d, J = 7.7 Hz, 1H), 6.75 (d, J = 8.1 Hz, 1H), 5.47 (s, 2H), 4.78 (d, J = 12.5 Hz, 1H), 4.46 (d, J = 12.5 Hz, 1H), 3.98 (s, 3H), 3.96-3.78 (m, 4H), 3.65-3.54 (m, 1H), 3.11 (t, J = 6.5 Hz, 2H), 2.85 (t, J = 11.6 Hz, 1H), 2.56-2.20 (m, 3H), 2.15-2.00 (m, 2H), 1.92 (s, 3H), 1.80 (d, J = 15.0 Hz, 1H) | 10.7 min, 99.9% 7.3 min, 99.9% |
| 736 | 3-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-methoxybenzamido)propanoic acid | | 661.4 | 7.96 (s, 1H), 7.88 (s, 1H), 7.62 (dd, J = 6.7, 2.8 Hz, 1H), 7.47 (d, J = 1.5 Hz, 1H), 7.37 (dd, J = 7.8, 1.7 Hz, 1H), 7.18-7.04 (m, 3H), 7.01-6.91 (m, 1H), 6.81 (d, J = 7.7 Hz, 1H), 6.71 (d, J = 8.4 Hz, 1H), 5.40 (s, 2H), 4.77 (d, J = 1.0 Hz, 1H), 4.43 (d, J = 11.9 Hz, 1H), 3.96 (s, 3H), 3.93-3.81 (m, 2H), 3.68-3.51 (m, 3H), 2.82 (t, J = 11.4 Hz, 1H), 2.64 (t, J = 6.9 Hz, 2H), 2.53-2.16 (m, 3H), 2.10-1.96 (m, 2H), 1.92 (s, 3H), 1.77 (d, J = 14.7 Hz, 1H) | 8.9 min, 99.6% 8.5 min, 99.5% |
| 737 | 3-((4-(5-(4-(2,3-Dimethylphenoxy)butanoyl)-2,3,4,5-tetrahydrobenzo[b][1,4]oxazepin-9-yl)-1H-pyrazol-1-yl)methyl)-N-(2-hydroxyethyl)benzamide | | 583.4 | 8.01 (s, 1H), 7.91 (s, 1H), 7.84-7.75 (m, 2H), 7.62 (dd, J = 5.9, 3.5 Hz, 1H), 7.50-7.39 (m, 2H), 7.16-7.07 (m, 2H), 6.93-6.85 (m, 1H), 6.66-6.57 (m, 2H), 5.42 (s, 2H), 4.75 (d, J = 13.2 Hz, 1H), 4.44 (d, J = 12.3 Hz, 1H), 3.92-3.76 (m, 2H), 3.74-3.66 (m, 2H), 3.61-3.46 (m, 3H), 2.82 (t, J = 11.4 Hz, 1H), 2.49-2.16 (m, 3H), 2.08 (s, 3H), 2.06-1.96 (m, 2H), 1.85-1.68 (m, 4H) | 8.4 min, 97.1% 8.1 min, 96.9% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 738 | 3-((4-(5-(4-(2,3-Dimethylphenoxy)butanoyl)-2,3,4,5-tetrahydrobenzo[b][1,4]oxazepin-9-yl)-1H-pyrazol-1-yl)methyl)-N-(3-hydroxypropyl)benzamide | | 597.5 | 8.01 (s, 1H), 7.91 (s, 1H), 7.82-7.72 (m, 2H), 7.62 (dd, J = 6.1, 3.4 Hz, 1H), 7.51-7.39 (m, 2H), 7.17-7.07 (m, 2H), 6.89 (t, J = 7.9 Hz, 1H), 6.61 (dd, J = 7.8, 4.3 Hz, 2H), 5.42 (s, 2H), 4.75 (d, J = 13.2 Hz, 1H), 4.44 (d, J = 11.9 Hz, 1H), 3.91-3.75 (m, 2H), 3.64 (t, J = 6.3 Hz, 2H), 3.56 (t, J = 10.9 Hz, 1H), 3.46 (t, J = 6.9 Hz, 2H), 2.92-2.73 (m, 1H), 2.50-2.15 (m, 3H), 2.11-1.95 (m, 5H), 1.91-1.70 (m, 6H) | 8.2 min, 98.5% 7.9 min, 98.6% |
| 739 | 3-Chloro-4-((4-(5-(4-(3-chloro-2-methylphenoxy)butanoyl)-2,3,4,5-tetrahydrobenzio[b][1,4]oxazepin-9-yl)-1H-pyrazol-1-yl)methyl)-5-fluoro-N-(3-hydroxypropyl)benzamide | | 669.4 | 8.00 (s, 1H), 7.91-7.79 (m, 2H), 7.70-7.56 (m, 2H), 7.20-7.11 (m, 2H), 7.02-6.94 (m, 1H), 6.83 (d, J = 7.7 Hz, 1H), 6.73 (d, J = 8.1 Hz, 1H), 5.61 (d, J = 3.1 Hz, 2H), 4.78 (d, J = 13.2 Hz, 1H), 4.46 (d, J = 1.0 Hz, 1H), 4.00-3.82 (m, 2H), 3.67 (t, J = 6.3 Hz, 2H), 3.61-3.45 (m, 3H), 2.84 (t, J = 11.9 Hz, 1H), 2.56-2.20 (m, 3H), 2.14-2.00 (m, 2H), 1.96-1.72 (m, 6H) | 9.3 min, 94.3% 8.7 min, 95.1% |
| 740 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluoro-N-(2-hydroxyethyl)benzamide | | 655.4 | 8.00 (s, 1H), 7.86 (s, 2H), 7.69 (dd, J = 9.9, 1.5 Hz, 1H), 7.62 (dd, J = 6.5, 3.0 Hz, 1H), 7.20-7.10 (m, 2H), 7.03-6.94 (m, 1H), 6.83 (d, J = 7.5 Hz, 1H), 6.73 (d, J = 8.1 Hz, 1H), 5.61 (dd, J = 4.4, 1.3 Hz, 2H), 4.82-4.72 (m, 1H), 4.44 (d, J = 11.9 Hz, 1H), 3.99-3.83 (m, 2H), 3.73 (t, J = 5.7 Hz, 2H), 3.62-3.47 (m, 3H), 2.84 (t, J = 11.3 Hz, 1H), 2.57-2.20 (m, 3H), 2.14-1.99 (m, 2H), 1.92 (s, 3H), 1.79 (d, J = 14.7 Hz, 1H) | 9.2 min, 96.9% 8.6 min, 97.0% |
| 741 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluoro-N-(3-methylsulfonyl)propyl)benzamide | | 733.4 | 7.98 (s, 1H), 7.85-7.81 (m, 2H), 7.65 (dd, J = 9.9, 1.5 Hz, 1H), 7.60 (dd, J = 6.4, 3.1 Hz, 1H), 7.18-7.07 (m, 2H), 7.00-6.91 (m, 1H), 6.81 (d, J = 7.7 Hz, 1H), 6.71 (d, J = 8.1 Hz, 1H), 5.59 (d, J = 2.9 Hz, 2H), 4.75 (d, J = 13.6 Hz, 1H), 4.42 (d, J = 11.7 Hz, 1H), 3.96-3.80 (m, 2H), 3.60-3.45 (m, 3H), 3.26-3.16 (m, 2H), 2.98 (s, 3H), 2.81 (t, J = 11.6 Hz, 1H), 2.53-1.96 (m, 7H), 1.89 (s, 3H), 1.76 (d, J = 14.7 Hz, 1H) | 9.6 min, 95.8% 9.0 min, 96.4% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 742 | (S)-2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)succinic acid | | 727.3 | 7.97 (s, 1H), 7.84 (s, 2H), 7.66 (dd, J = 9.8, 1.4 Hz, 1H), 7.60 (dd, J = 6.5, 3.0 Hz, 1H), 7.17-7.07 (m, 2H), 7.00-6.92 (m, 1H), 6.81 (d, J = 7.9 Hz, 1H), 6.71 (d, J = 8.1 Hz, 1H), 5.58 (d, J = 2.9 Hz, 2H), 5.00-4.90 (m, 1H), 4.75 (d, J = 13.6 Hz, 1H), 4.41 (d, J = 12.1 Hz, 1H), 3.96-3.80 (m, 2H), 3.58-3.49 (m, 1H), 3.07-2.74 (m, 3H), 2.53-2.17 (m, 3H), 2.12-1.96 (m, 2H), 1.90 (s, 3H), 1.76 (d, J = 15.0 Hz, 1H) | 8.8 min, 99.8% 8.4 min, 99.7% |
| 743 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-N-(2,3-dihydroxypropyl)-5-fluorobenzamide | | 685.5 | 8.00 (s, 1H), 7.86 (s, 2H), 7.69 (dd, J = 9.9, 1.5 Hz, 1H), 7.62 (dd, J = 6.5, 3.0 Hz, 1H), 7.21-7.10 (m, 2H), 7.03-6.94 (m, 1H), 6.84 (d, J = 7.7 Hz, 1H), 6.74 (d, J = 8.4 Hz, 1H), 5.64-5.58 (m, 2H), 4.78 (d, J = 12.5 Hz, 1H), 4.45 (d, J = 11.4 Hz, 1H), 3.98-3.81 (m, 3H), 3.64-3.49 (m, 4H), 3.42 (dt, J = 13.6, 6.6 Hz, 1H), 2.89-2.79 (m, 1H), 2.55-2.20 (m, 3H), 2.06 (dd, J = 13.4, 6.6 Hz, 2H), 1.92 (s, 3H), 1.79 (d, J = 14.5 Hz, 1H) | N/A |
| 744 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluoro-N-(2-hydroxy-2-methylpropyl)benzamide | | 683.5 | 8.00 (s, 1H), 7.91-7.82 (m, 2H), 7.70 (dd, J = 9.9, 1.5 Hz, 1H), 7.62 (dd, J = 6.4, 3.1 Hz, 1H), 7.21-7.09 (m, 2H), 7.03-6.94 (m, 1H), 6.83 (d, J = 7.7 Hz, 1H), 6.73 (d, J = 8.1 Hz, 1H), 5.61 (dd, J = 4.3, 1.2 Hz, 2H), 4.78 (d, J = 13.2 Hz, 1H), 4.45 (d, J = 11.9 Hz, 1H), 3.98-3.82 (m, 2H), 3.61-3.52 (m, 1H), 3.43 (d, J = 6.2 Hz, 2H), 2.88-2.78 (m, 1H), 2.56-2.20 (m, 3H), 2.13-1.98 (m, 2H), 1.79 (d, J = 14.7 Hz, 1H), 1.25 (s, 6H) | 9.8 min, 98.6% 9.0 min, 98.6% |
| 745 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluoro-N-(2-methylsulfonyl)ethyl)benzamide | | 717.5 | 7.97 (s, 1H), 7.87-7.77 (m, 2H), 7.69-7.55 (m, 2H), 7.18-7.08 (m, 2H), 7.00-6.92 (m, 1H), 6.81 (d, J = 7.9 Hz, 1H), 6.71 (d, J = 7.9 Hz, 1H), 5.58 (d, J = 3.1 Hz, 2H), 4.75 (d, J = 13.6 Hz, 1H), 4.42 (d, J = 12.1 Hz, 1H), 3.96-3.79 (m, 4H), 3.53 (t, J = 10.7 Hz, 1H), 3.43 (t, J = 6.7 Hz, 2H), 3.03 (s, 2H), 2.81 (t, J = 11.6 Hz, 1H), 2.53-2.15 (m, 3H), 2.11-1.96 (m, 2H), 1.90 (s, 3H), 1.76 (d, J = 14.5 Hz, 1H) | 9.6 min, 99.7% 9.0 min, 100% |

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 746 | (R)-2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)succinic acid | | 727.5 | 7.97 (s, 1H), 7.84 (s, 2H), 7.66 (dd, J = 9.9, 1.5 Hz, 1H), 7.60 (dd, J = 6.5, 3.0 Hz, 1H), 7.18-7.08 (m, 2H), 7.01-6.92 (m, 1H), 6.81 (d, J = 7.7 Hz, 1H), 6.71 (d, J = 8.1 Hz, 1H), 5.59 (d, J = 2.9 Hz, 2H), 4.99-4.91 (m, 1H), 4.75 (d, J = 12.5 Hz, 1H), 4.41 (d, J = 11.2 Hz, 1H), 3.97-3.79 (m, 2H), 3.53 (t, J = 10.9 Hz, 1H), 3.07-3.72 (m, 3H), 2.54-2.16 (m, 3H), 2.12-1.96 (m, 2H), 1.90 (s, 3H), 1.76 (d, J = 14.5 Hz, 1H) | 8.8 min, 100% 8.4 min, 99.8% |
| 747 | (S)-6-Amino-2-(4-((4-(5-(4-(2,3-dimethylphenoxy)butanoyl)-2,3,4,5-tetrahydrobenzo[b][1,4]oxazepin-9-yl)-1H-pyrazol-1-yl)methyl)benzamido)hexanoic acid, TFA salt | | 668.6 | 8.05 (s, 1H), 7.95 (s, 1H), 7.89 (d, J = 8.4 Hz, 2H), 7.66 (dd, J = 5.5, 4.2 Hz, 1H), 7.39 (d, J = 8.4 Hz, 2H), 7.20-7.10 (m, 2H), 6.92 (t, J = 7.9 Hz, 1H), 6.64 (t, J = 7.2 Hz, 2H), 5.47 (d, J = 1.5 Hz, 2H), 4.78 (d, J = 13.4 Hz, 1H), 4.70-4.62 (m, 1H), 4.48 (d, J = 11.7 Hz, 1H), 3.95-3.78 (m, 2H), 3.67-3.54 (m, 1H), 3.03-2.78 (m, 3H), 2.51-2.18 (m, 3H), 2.15-1.98 (m, 6H), 1.97-1.68 (m, 7H), 1.63-1.49 (m, 2H) | 6.2 min, 99.6% 7.2 min, 99.5% |
| 748 | 2-(3-((4-(5-(4-(3-Chloro-2-methylphenoxy)butanoyl)-2,3,4,5-tetrahydrobenzo[b][1,4]thiazepin-9-yl)-1H-pyrazol-1-yl)methyl)benzamido)ethanesulfonic acid | | 683.4 | 8.03 (s, 1H), 7.88-7.73 (m, 3H), 7.54 (dd, J = 7.8, 1.4 Hz, 1H), 7.51-7.43 (m, 2H), 7.38 (t, J = 7.8 Hz, 1H), 7.25 (dd, J = 7.8, 1.4 Hz, 1H), 7.10-6.99 (m, 1H), 6.88 (d, J = 7.9 Hz, 1H), 6.77 (d, J = 8.4 Hz, 1H), 5.49 (s, 2H), 4.66 (d, J = 12.8 Hz, 1H), 4.01-3.88 (m, 2H), 3.86-3.73 (m, 2H), 3.09 (t, J = 6.6 Hz, 2H), 2.95-2.74 (m, 2H), 2.71-2.57 (m, 1H), 2.34-2.18 (m, 3H), 2.17-1.90 (m, 6H) | 10.1 min, 97.6% 7.1 min, 97.0% |
| 749 | 3-((4-(5-(4-(3-Chloro-2-methylphenoxy)butanoyl)-2,3,4,5-tetrahydrobenzo[b][1,4]thiazepin-9-yl)-1H-pyrazol-1-yl)methyl)-N-(2-hydroxyethyl)benazamide | | 619.0 | 7.85-7.69 (m, 3H), 7.59 (s, 1H), 7.50-7.42 (m, 2H), 7.43-7.38 (m, 1H), 7.33 (t, J = 7.7 Hz, 1H), 7.16 (dd, J = 7.9, 1.5 Hz, 1H), 7.06-6.97 (m, 1H), 6.88 (d, J = 7.4 Hz, 1H), 6.70 (d, J = 7.9 Hz, 1H), 5.40 (s, 2H), 4.33-4.27 (m, 1H), 3.97-3.89 (m, 2H), 3.78-3.70 (m, 2H), 3.57-3.49 (m, 2H), 2.88-2.72 (m, 2H), 2.62 (td, J = 13.4, 2.5 Hz, 1H), 2.35-2.02 (m, 5H), 2.02-1.93 (m, 4H) | 100%* |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 750 | 3-((4-(5-(4-(3-Chloro-2-methylphenoxy)butanoyl)-2,3,4,5-tetrahydrobenzo[b][1,4]thiazepan-9-yl)-1H-pyrazol-1-yl)methyl)-N-(2-hydroxy-2-methylpropyl)benzamide | | 647.3 | 7.85-7.75 (m, 3H), 7.72 (s, 1H), 7.51-7.38 (m, 3H), 7.33 (t, J = 7.7 Hz, 1H), 7.17 (dd, J = 7.4, 1.5 Hz, 1H), 7.06-6.98 (m, 1H), 6.88 (d, J = 7.9 Hz, 1H), 6.70 (d, J = 8.4 Hz, 1H), 5.41 (s, 2H), 4.33 (br. s., 1H), 3.98-3.87 (m, 2H), 3.42 (s, 2H), 2.87-2.72 (m, 2H), 2.68-2.57 (m, 1H), 2.37-2.02 (m, 5H), 2.02-1.93 (m, 4H), 1.25 (s, 6H) | 100%* |
| 751 | 3-((4-(5-(4-(3-Chloro-2-methylphenoxy)butanoyl)-2,3,4,5-tetrahydrobenzo[b][1,4]thiazepan-9-yl)-1H-pyrazol-1-yl)methyl)-N-(2,3-dihydroxypropyl)benzamide | | 649.3 | 7.86-7.69 (m, 4H), 7.50-7.39 (m, 3H), 7.33 (t, J = 7.9 Hz, 1H), 7.16 (dd, J = 7.9, 1.5 Hz, 1H), 7.06-6.98 (m, 1H), 6.88 (d, J = 7.9 Hz, 1H), 6.70 (d, J = 7.9 Hz, 1H), 5.41 (s, 2H), 4.33 (br. s., 1H), 3.98-3.90 (m, 2H), 3.84 (dd, J = 6.2, 5.2 Hz, 1H), 3.62-3.54 (m, 3H), 3.50-3.41 (m, 1H), 2.88-2.72 (m, 2H), 2.67-2.58 (m, 1H), 2.35-1.94 (m, 9H) | 100%* |
| 752 | 3-((4-(5-(4-(3-Chloro-2-methylphenoxy)butanoyl)-2,3,4,5-tetrahydrobenzo[b][1,4]thiazepan-9-yl)-1H-pyrazol-1-yl)methyl)-N-(2-(methylsulfonyl)ethyl)benzamide | | 681.3 | 7.83-7.70 (m, 4H), 7.50-7.39 (m, 3H), 7.33 (t, J = 7.7 Hz, 1H), 7.17 (dd, J = 7.7, 1.2 Hz, 1H), 7.06-6.98 (m, 1H), 6.88 (d, J = 7.9 Hz, 1H), 6.70 (d, J = 8.4 Hz, 1H), 5.41 (s, 2H), 4.33 (s, 1H), 3.98-3.90 (m, 2H), 3.86 (t, J = 6.7 Hz, 2H), 3.42 (t, J = 6.4 Hz, 2H), 3.02 (s, 3H), 2.88-2.72 (m, 2H), 2.68-2.57 (m, 1H), 2.35-1.93 (m, 9H) | 100%* |

TABLE 21-continued

| Example | Name | Formula I | LCMS, [M + H]+ | $^1$H NMR (400 MHz, MeOD) δ | HPLC-1: Rt min, purity; HPLC-2: Rt min, purity |
|---|---|---|---|---|---|
| 753 | 3-(3-((4-(5-(4-(3-Chloro-2-methylphenoxy)butanoyl)-2,3,4,5-tetrahydrobenzo[b][1,4]thiazepan-9-yl)-1H-pyrazol-1-yl)methyl)benzamido)propanoic acid | | 647.3 | 7.80-7.68 (m, 4H), 7.49-7.37 (m, 3H), 7.33 (t, J = 7.9 Hz, 1H), 7.16 (dd, J = 7.7, 1.2 Hz, 1H), 7.07-6.98 (m, 1H), 6.88 (d, J = 7.9 Hz, 1H), 6.70 (d, J = 7.9 Hz, 1H), 5.40 (s, 2H), 3.97-3.88 (m, 2H), 3.65 (t, J = 6.7 Hz, 2H), 2.88-2.71 (m, 2H), 2.69-2.58 (m, 3H), 2.35-1.92 (m, 10H) | 98%* |
| 754 | (S)-2-(3-((4-(5-(4-(3-Chloro-2-methylphenoxy)butanoyl)-2,3,4,5-tetrahydrobenzo[b][1,4]thiazepan-9-yl)-1H-pyrazol-1-yl)methyl)benzamido)succinic acid | | 691.3 | 7.89-7.68 (m, 4H), 7.50-7.38 (m, 3H), 7.33 (t, J = 7.7 Hz, 1H), 7.15 (dd, J = 7.9, 1.5 Hz, 1H), 7.06-6.98 (m, 1H), 6.88 (d, J = 7.9 Hz, 1H), 6.70 (d, J = 8.4 Hz, 1H), 5.41 (s, 2H), 4.84 (s, 1H), 3.93 (t, J = 5.7 Hz, 2H), 2.95 (t, J = 5.2 Hz, 2H), 2.88-2.71 (m, 2H), 2.67-2.58 (m, 1H), 2.35-1.91 (m, 10H) | 100%* |
| 755 | (S)-2-Amino-6-(4-((4-(5-(4-(2,3-dimethylphenoxy)butanoyl)-2,3,4,5-tetrahydrobenzo[b][1,4]oxazepan-9-yl)-1H-pyrazol-1-yl)methyl)benzamido)hexanoic acid, TFA salt | | 668.5 | 8.02 (s, 1H), 7.92 (s, 1H), 7.81 (d, J = 8.1 Hz, 2H), 7.63 (dd, J = 5.6, 3.9 Hz, 1H), 7.35 (d, J = 8.1 Hz, 2H), 7.19-7.08 (m, 2H), 6.90 (t, J = 7.9 Hz, 1H), 6.62 (t, J = 6.9 Hz, 2H), 5.43 (s, 2H), 4.76 (d, J = 13.6 Hz, 1H), 4.45 (d, J = 11.7 Hz, 1H), 3.96 (t, J = 6.3 Hz, 1H), 3.91-3.77 (m, 2H), 3.56 (t, J = 10.8 Hz, 1H), 3.40 (t, J = 6.6 Hz, 2H), 2.83 (t, J = 11.4 Hz, 1H), 2.49-2.35 (m, 2H), 2.33-2.18 (m, 1H), 2.13-1.86 (m, 7H), 1.84-1.43 (m, 8H) | 6.4 min, 99.7% 7.3 min, 98.8% |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 756 | 2-(3,5-Dichloro-4-((4-(5-(4-(3-chloro-2-methylphenoxy)butanoyl)-2,3,4,5-tetrahydrobenzo[b][1,4]oxazepan-9-yl)-1H-pyrazol-1-yl)methyl)benzamido)ethanesulfonic acid | | 737.4 | 7.95 (s, 2H), 7.92 (s, 1H), 7.85 (s, 1H), 7.59 (dd, J = 6.7, 3.0 Hz, 1H), 7.18-7.08 (m, 2H), 7.00-6.91 (m, 1H), 6.81 (d, J = 7.7 Hz, 1H), 6.71 (d, J = 8.4 Hz, 1H), 5.71 (d, J = 3.7 Hz, 2H), 4.75 (d, J = 13.0 Hz, 1H), 4.40 (d, J = 11.4 Hz, 1H), 3.96-3.75 (m, 4H), 3.59-3.49 (m, 1H), 3.09 (t, J = 6.7 Hz, 1H), 2.86-2.75 (m, 1H), 2.53-2.17 (m, 3H), 2.09-1.98 (m, 2H), 1.90 (s, 3H), 1.76 (d, J = 15.0 Hz, 1H) | N/A 7.6 min, 99.7% |
| 757 | 3-(3,5-Dichloro-4-((4-(5-(4-(3-chloro-2-methylphenoxy)butanoyl)-2,3,4,5-tetrahydrobenzo[b][1,4]oxazepan-9-yl)-1H-pyrazol-1-yl)methyl)benzamido)propanoic acid | | 699.4 | 7.95 (s, 3H), 7.87 (s, 1H), 7.62 (dd, J = 6.6, 3.1 Hz, 1H), 7.18-7.11 (m, 2H), 7.01-6.93 (m, 1H), 6.83 (d, J = 7.5 Hz, 1H), 6.73 (d, J = 8.1 Hz, 1H), 5.73 (d, J = 4.0 Hz, 2H), 4.81-4.73 (m, 1H), 4.43 (d, J = 11.9 Hz, 1H), 3.98-3.82 (m, 2H), 3.71-3.62 (m, 2H), 3.60-3.52 (m, 1H), 2.90-2.78 (m, 1H), 2.71-2.62 (m, 2H), 2.55-2.19 (m, 3H), 2.13-1.98 (m, 2H), 1.92 (s, 3H), 1.78 (d, J = 14.7 Hz, 1H) | 9.6 min, 95.0% 9.0 min, 99.5% |
| 758 | 2-(3-((4-(5-(4-(3-Chloro-2-methylphenoxy)butanoyl)-2,3,4,5-tetrahydrobenzo[b][1,4]thiazepan-9-yl)-1H-pyrazol-1-yl)methyl)benzamido)-N,N,N-trimethylethanaminium | | 660.4 | 7.85 (s, 1H), 7.82-7.78 (m, 2H), 7.73 (s, 1H), 7.53-7.41 (m, 3H), 7.34 (t, J = 7.7 Hz, 1H), 7.18 (dd, J = 7.7, 1.2 Hz, 1H), 7.06-6.99 (m, 1H), 6.87 (d, J = 7.9 Hz, 1H), 6.71 (d, J = 7.9 Hz, 1H), 5.42 (s, 2H), 4.71-4.64 (m, 1H), 3.99-3.89 (m, 2H), 3.85 (t, J = 6.4 Hz, 2H), 3.58 (t, J = 6.4 Hz, 2H), 3.23 (s, 9H), 2.90-2.72 (m, 2H), 2.68-2.58 (m, 1H), 2.36-1.90 (m, 9H) | 100%* |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 759 | (S)-2-(3,5-Dichloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido)succinic acid | | 743.4 | 7.99 (s, 2H), 7.95 (s, 1H), 7.87 (s, 1H), 7.62 (dd, J = 6.6, 3.1 Hz, 1H), 7.20, 7.10 (m, 2H), 7.03-6.94 (m, 1H), 6.84 (d, J = 7.9 Hz, 1H), 6.73 (d, J = 8.4 Hz, 1H), 5.74 (d, J = 3.7 Hz, 2H), 4.77 (d, J = 13.2 Hz, 1H), 4.42 (d, J = 11.9 Hz, 1H), 3.99-3.83 (m, 2H), 3.61-3.51 (m, 1H), 3.08-2.99 (m, 1H), 2.97-2.77 (m, 2H), 2.56-2.18 (m, 3H), 2.05 (dq, J = 12.2, 6.2 Hz, 2H), 1.93 (s, 3H), 1.78 (d, J = 15.0 Hz, 1H) | 9.1 min, 100% 8.6 min, 100% |
| 760 | 3,5-Dichloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-N-(2-hydroxyethyl)benzamide | | 673.4 | 7.96 (s, 2H), 7.95-7.92 (m, 1H), 7.84 (s, 1H), 7.59 (dd, J = 6.5, 3.0 Hz, 1H), 7.17-7.08 (m, 2H), 7.00-6.90 (m, 1H), 6.81 (d, J = 7.9 Hz, 1H), 6.70 (d, J = 8.1 Hz, 1H), 5.71 (d, J = 4.2 Hz, 2H), 4.75 (d, J = 13.0 Hz, 1H), 4.40 (d, J = 12.3 Hz, 1H), 3.95-3.82 (m, 2H), 3.71 (t, J = 5.6 Hz, 2H), 3.59-3.44 (m, 3H), 2.81 (t, J = 11.6 Hz, 1H), 2.52-2.18 (m, 3H), 2.09-1.96 (m, 2H), 1.90 (s, 3H), 1.76 (d, J = 15.2 Hz, 1H) | 9.5 min, 97.8% 8.8 min, 97.6% |
| 761 | 3,5-Dichloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-N-(2-hydroxy-2-methylpropyl)benzamide | | 701.4 | 7.98 (s, 2H), 7.94 (s, 1H), 7.85 (s, 1H), 7.59 (dd, J = 6.6, 3.1 Hz, 1H), 7.17-7.07 (m, 2H), 7.00-6.90 (m, 1H), 6.81 (d, J = 7.9 Hz, 1H), 6.70 (d, J = 8.1 Hz, 1H), 5.71 (d, J = 4.2 Hz, 2H), 4.75 (d, J = 14.1 Hz, 1H), 4.41 (d, J = 11.9 Hz, 1H), 3.97-3.79 (m, 2H), 3.60-3.49 (m, 1H), 3.40 (d, J = 6.2 Hz, 2H), 2.81 (t, J = 11.4 Hz, 1H), 2.53-2.17 (m, 3H), 2.10-1.96 (m, 2H), 1.90 (s, 3H), 1.76 (d, J = 14.7 Hz, 1H), 1.23 (s, 6H) | 10.2 min, 99.3% 9.2 min, 98.6% |
| 762 | 3,5-Dichloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-N-(2,3-dihydroxypropyl)benzamide | | 703.4 | 7.99 (s, 2H), 7.96 (s, 2H), 7.87 (s, 1H), 7.62 (dd, J = 6.4, 3.1 Hz, 1H), 7.19-7.10 (m, 2H), 7.02-6.93 (m, 1H), 6.84 (d, J = 7.7 Hz, 1H), 6.73 (d, J = 8.4 Hz, 1H), 5.74 (d, J = 4.4 Hz, 2H), 4.81-4.72 (m, 1H), 4.43 (d, J = 11.7 Hz, 1H), 4.00-3.81 (m, 3H), 3.64-3.50 (m, 4H), 3.48-3.38 (m, 1H), 2.83 (t, J = 11.8 Hz, 1H), 2.56-2.16 (m, 3H), 2.12-1.98 (m, 2H), 1.93 (s, 3H), 1.78 (d, J = 15.0 Hz, 1H) | 8.9 min, 100% 8.4 min, 100% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 763 | 3,5-Dichloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-N-(2-(methylsulfonyl)ethyl)benzamide | | 735.4 | 8.00-7.92 (m, 3H), 7.87 (s, 1H), 7.67-7.59 (m, 1H), 7.20-7.10 (m, 2H), 7.02-6.93 (m, 1H), 6.84 (d, J = 7.5 Hz, 1H), 6.73 (d, J = 8.8 Hz, 1H), 5.74 (d, J = 4.2 Hz, 2H), 4.78 (d, J = 10.3 Hz, 1H), 4.43 (d, J = 11.7 Hz, 1H), 3.98-3.82 (m, 3H), 3.51 (dt, J = 3.2, 1.7 Hz, 1H), 3.46 (t, J = 6.8 Hz, 1H), 2.83 (t, J = 11.4 Hz, 1H), 2.69 (s, 3H), 2.55-2.18 (m, 4H), 2.05 (d, J = 6.8 Hz, 3H), 1.92 (s, 3H), 1.79 (d, J = 15.4 Hz, 1H) | 9.9 min, 99.8% 9.3 min, 99.4% |
| 764 | 2-(3,5-Dichloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido)-N,N,N-trimethylethanaminium, TFA salt | | 714.4 | 8.03-7.92 (m, 3H), 7.60 (dd, J = 5.9, 3.5 Hz, 1H), 7.17-7.07 (m, 2H), 7.00-6.91 (m, 1H), 6.81 (d, J = 7.9 Hz, 1H), 6.71 (d, J = 8.4 Hz, 1H), 5.72 (d, J = 5.3 Hz, 2H), 4.75 (d, J = 12.5 Hz, 1H), 4.41 (d, J = 12.3 Hz, 1H), 3.96-3.81 (m, 4H), 3.64-3.47 (m, 3H), 3.23 (s, 9H), 2.81 (t, J = 11.7 Hz, 1H), 2.52-2.17 (m, 3H), 2.09-1.98 (m, 2H), 1.90 (s, 3H), 1.76 (d, J = 14.3 Hz, 1H) | 6.9 min, 99.8% 8.2 min, 99.8% |
| 765 | 2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)-3-methylbenzamido)ethanesulfonic acid | | 681.3 | 7.98 (d, J = 3.3 Hz, 2H), 7.70 (s, 1H), 7.68-7.60 (m, 2H), 7.18-7.12 (m, 2H), 7.07 (d, J = 7.9 Hz, 1H), 7.02-6.94 (m, 1H), 6.83 (d, J = 8.4 Hz, 1H), 6.72 (d, J = 8.4 Hz, 1H), 5.49 (s, 2H), 4.75 (d, J = 13.9 Hz, 1H), 4.40 (d, J = 12.1 Hz, 1H), 3.96-3.75 (m, 4H), 3.61-3.51 (m, 1H), 3.08 (t, J = 6.6 Hz, 2H), 2.82 (t, J = 11.7 Hz, 1H), 2.53-2.16 (m, 6H), 2.12-1.98 (m, 2H), 1.91 (s, 3H), 1.77 (d, J = 14.3 Hz, 1H) | 9.5 min, 99.8% 7.2 min, 99.0% |
| 766 | 2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)ethanesulfonic acid | | 667.3 | 8.14 (s, 1H), 8.02 (s, 1H), 7.84 (d, J = 8.4 Hz, 2H), 7.65 (t, J = 4.7 Hz, 1H), 7.37 (d, J = 8.1 Hz, 2H), 7.16 (d, J = 4.4 Hz, 2H), 7.01-6.94 (m, 1H), 6.81 (d, J = 7.9 Hz, 1H), 6.72 (d, J = 8.4 Hz, 1H), 5.50 (s, 2H), 4.76 (d, J = 13.0 Hz, 1H), 4.46 (d, J = 11.9 Hz, 1H), 3.96-3.76 (m, 4H), 3.57 (t, J = 10.8 Hz, 1H), 3.08 (t, J = 6.6 Hz, 2H), 2.83 (t, J = 11.6 Hz, 1H), 2.55-2.18 (m, 3H), 2.11-1.96 (m, 2H), 1.90 (s, 3H), 1.78 (d, J = 14.7 Hz, 1H) | 9.3 min, 100% 7.1 min, 100% |

TABLE 21-continued

| Example | Name | Formula I | LCMS, [M + H]$^+$ | $^1$H NMR (400 MHz, MeOD) δ | HPLC-1: Rt min, purity; HPLC-2: Rt min, purity |
|---|---|---|---|---|---|
| 767 | (S)-2-(4-((4-(5-(4-(3-Chloro-2-methylphenoxy)butanoyl)-2,3,4,5-tetrahydrobenzo[b][1,4]oxazepin-9-yl)-1H-pyrazol-1-yl)methyl)benzamido)succinic acid | | 675.3 | 8.02 (s, 1H), 7.91 (s, 1H), 7.84 (d, J = 8.4 Hz, 2H), 7.63 (dd, J = 6.5, 3.0 Hz, 1H), 7.36 (d, J = 8.1 Hz, 2H), 7.20-7.07 (m, 2H), 7.02-6.92 (m, 1H), 6.82 (d, J = 8.1 Hz, 1H), 6.72 (d, J = 8.1 Hz, 1H), 5.45 (s, 2H), 4.95 (dd, J = 7.0, 5.5 Hz, 1H), 4.75 (d, J = 13.6 Hz, 1H), 4.45 (d, J = 11.9 Hz, 1H), 3.96-3.81 (m, 2H), 3.56 (t, J = 10.9 Hz, 1H), 3.05-2.85 (m, 2H), 2.53-2.17 (m, 4H), 2.11-1.97 (m, 2H), 1.93 (s, 3H), 1.77 (d, J = 15.0 Hz, 1H) | 8.2 min, 99.6% 7.9 min, 99.3% |
| 768 | 2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido) ethanesulfonic acid | | 701.2 | 8.04 (s, 1H), 7.98-7.91 (m, 2H), 7.73 (dd, J = 8.0, 1.7 Hz, 1H), 7.64 (dd, J = 6.3, 3.2 Hz, 1H), 7.18-7.08 (m, 3H), 7.03-6.95 (m, 1H), 6.83 (d, J = 7.9 Hz, 1H), 6.73 (d, J = 8.1 Hz, 1H), 5.56 (s, 2H), 4.76 (d, J = 13.6 Hz, 1H), 4.44 (d, J = 11.9 Hz, 1H), 3.95-3.75 (m, 4H), 3.56 (t, J = 10.9 Hz, 1H), 3.08 (t, J = 6.7 Hz, 2H), 2.83 (t, J = 11.7 Hz, 1H), 2.54-2.18 (m, 3H), 2.12-1.99 (m, 2H), 1.92 (s, 3H), 1.77 (d, J = 14.1 Hz, 1H) | 11.0 min, 99.2% 7.4 min, 98.7% |
| 769 | 3-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido) propanoic acid | | 665.3 | 8.03 (s, 1H), 7.95-7.89 (m, 2H), 7.72 (dd, J = 8.0, 1.7 Hz, 1H), 7.64 (dd, J = 6.4, 3.1 Hz, 1H), 7.19-7.08 (m, 3H), 7.03-6.94 (m, 1H), 6.83 (d, J = 7.9 Hz, 1H), 6.73 (d, J = 8.1 Hz, 1H), 5.55 (s, 2H), 4.76 (d, J = 13.0 Hz, 1H), 4.44 (d, J = 12.1 Hz, 1H), 3.97-3.80 (m, 2H), 3.66-3.51 (m, 3H), 2.82 (t, J = 11.6 Hz, 1H), 2.63 (t, J = 6.8 Hz, 2H), 2.54-2.17 (m, 3H), 2.03 (dq, J = 13.1, 6.4 Hz, 2H), 1.92 (s, 3H), 1.77 (d, J = 15.0 Hz, 1H) | 9.2 min, 99.3% 8.6 min, 99.2% |
| 770 | (S)-2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido) succinic acid | | 709.3 | 8.06 (s, 1H), 7.97 (dd, J = 5.3, 1.1 Hz, 2H), 7.78 (dd, J = 7.9, 1.8 Hz, 1H), 7.67 (dd, J = 6.4, 3.3 Hz, 1H), 7.23-7.09 (m, 3H), 7.05-6.97 (m, 1H), 6.86 (d, J = 7.7 Hz, 1H), 6.75 (d, J = 8.1 Hz, 1H), 5.58 (s, 2H), 4.97 (dd, J = 7.7, 5.3 Hz, 1H), 4.78 (d, J = 13.0 Hz, 1H), 4.46 (d, J = 11.7 Hz, 1H), 4.00-3.83 (m, 2H), 3.65-3.54 (m, 1H), 3.08-2.98 (m, 1H), 2.96-2.79 (m, 2H), 2.58-2.20 (m, 3H), 2.15-2.00 (m, 2H), 1.94 (s, 3H), 1.79 (d, J = 14.5 Hz, 1H) | 8.7 min, 99.2% 8.3 min, 99.0% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 771 | 2-(2-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido)ethanesulfonic acid | (structure) | 701.3 | 8.03 (s, 1H), 7.89 (s, 1H), 7.62 (dd, J = 6.6, 2.9 Hz, 1H), 7.51-7.40 (m, 2H), 7.32 (dd, J = 8.3, 2.1 Hz, 1H), 7.16-7.08 (m, 2H), 7.03-6.94 (m, 1H), 6.83 (d, J = 7.9 Hz, 1H), 6.72 (d, J = 8.1 Hz, 1H), 5.38 (s, 2H), 4.75 (d, J = 13.2 Hz, 1H), 4.47 (d, J = 12.1 Hz, 1H), 3.96-3.73 (m, 4H), 3.62-3.51 (m, 1H), 3.08 (t, J = 7.0 Hz, 2H), 2.87-2.77 (m, 1H), 2.53-2.17 (m, 3H), 2.10-1.97 (m, 2H), 1.93 (s, 3H), 1.78 (d, J = 14.5 Hz, 1H) | 10.2 min, 96.3% 7.2 min, 96.7% |
| 772 | 3-(2-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido)propanoic acid | (structure) | 665.2 | 8.05 (s, 1H), 7.92 (d, J = 0.4 Hz, 1H), 7.70-7.59 (m, 1H), 7.47 (d, J = 8.1 Hz, 1H), 7.41 (d, J = 2.0 Hz, 1H), 7.39-7.30 (m, 1H), 7.19-7.12 (m, 2H), 7.04-6.97 (m, 1H), 6.86 (d, J = 7.5 Hz, 1H), 6.75 (d, J = 8.1 Hz, 1H), 5.41 (s, 2H), 4.82-4.74 (m, 1H), 4.49 (d, J = 11.9 Hz, 1H), 3.99-3.82 (m, 2H), 3.67-3.54 (m, 3H), 2.89-2.79 (m, 1H), 2.65 (t, J = 6.7 Hz, 2H), 2.55-2.20 (m, 3H), 2.14-1.99 (m, 2H), 1.95 (s, 3H), 1.80 (d, J = 14.7 Hz, 1H) | 8.8 min, 99.1% 8.5 min, 99.2% |
| 773 | (S)-2-(2-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)benzamido)succinic acid | (structure) | 709.3 | 8.04 (s, 1H), 7.92 (s, 1H), 7.64 (dd, J = 6.3, 3.2 Hz, 1H), 7.54-7.45 (m, 2H), 7.36 (dd, J = 8.3, 2.1 Hz, 1H), 7.20-7.11 (m, 2H), 7.06-6.96 (m, 1H), 6.86 (d, J = 7.9 Hz, 1H), 6.75 (d, J = 8.1 Hz, 1H), 5.41 (s, 2H), 4.96 (dd, J = 6.8, 5.5 Hz, 1H), 4.78 (d, J = 13.6 Hz, 1H), 4.48 (d, J = 11.7 Hz, 1H), 3.98-3.84 (m, 2H), 3.58 (t, J = 11.2 Hz, 1H), 3.06-2.78 (m, 3H), 2.56-2.20 (m, 3H), 2.13-1.99 (m, 2H), 1.95 (s, 3H), 1.79 (d, J = 14.7 Hz, 1H) | 8.5 min, 98.8% 8.2 min, 99.2% |
| 774 | 3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-N-(2,3-dihydroxypropyl)benzamide | (structure) | 667.3 | 8.03 (s, 1H), 7.98-7.91 (m, 2H), 7.75 (dd, J = 8.1, 1.8 Hz, 1H), 7.64 (dd, J = 6.4, 3.1 Hz, 1H), 7.20-7.07 (m, 3H), 7.03-6.93 (m, 1H), 6.83 (d, J = 7.9 Hz, 1H), 6.72 (d, J = 8.4 Hz, 1H), 5.55 (s, 2H), 4.76 (d, J = 13.4 Hz, 1H), 4.44 (d, J = 11.9 Hz, 1H), 3.97-3.77 (m, 3H), 3.61-3.49 (m, 4H), 3.45-3.35 (m, 1H), 2.90-2.76 (m, 1H), 2.52-2.16 (m, 3H), 2.13-1.97 (m, 2H), 1.92 (s, 3H), 1.77 (d, J = 14.7 Hz, 1H) | 8.4 min, 100% 8.1 min, 100% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 775 | 2-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-N-(2,3-dihydroxypropyl)benzamide | | 667.3 | 8.05 (s, 1H), 7.92 (d, J = 0.4 Hz, 1H), 7.64 (dd, J = 6.2, 3.3 Hz, 1H), 7.52-7.44 (m, 2H), 7.36 (dd, J = 8.4, 2.2 Hz, 1H), 7.19-7.13 (m, 2H), 7.05-6.97 (m, 1H), 6.86 (d, J = 7.5, Hz, 1H), 6.75 (d, J = 8.1 Hz, 1H), 5.41 (s, 2H), 4.81-4.73 (m, 1H), 4.54-4.45 (m, 1H), 4.00-3.78 (m, 3H), 3.68-3.49 (m, 4H), 3.46-3.38 (m, 1H), 2.90-2.78 (m, 1H), 2.54-2.19 (m, 3H), 2.13-1.99 (m, 2H), 1.95 (s, 3H), 1.80 (d, J = 14.7 Hz, 1H) | 8.3 min, 98.1% N/A |
| 776 | (R)-Diethyl-2-(3-chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)succinate | | 783.3 | 7.97 (s, 1H), 7.87-7.79 (m, 2H), 7.70-7.56 (m, 2H), 7.16-7.09 (m, 2H), 7.00-6.92 (m, 1H), 6.81 (d, J = 7.9 Hz, 1H), 6.71 (d, J = 8.4 Hz, 1H), 5.59 (d, J = 2.9 Hz, 2H), 5.00-4.91 (m, 1H), 4.78-4.70 (m, 1H), 4.42 (d, J = 12.5 Hz, 1H), 4.27-4.11 (m, 4H), 3.96-3.80 (m, 2H), 3.58-3.50 (m, 1H), 3.07-2.74 (m, 3H), 2.53-2.17 (m, 3H), 2.10-1.96 (m, 2H), 1.89 (s, 3H), 1.77 (d, J = 15.2 Hz, 1H), 1.25 (q, J = 7.0 Hz, 6H) | 11.2 min, 94.9% 10.2 min, 98.3% |
| 777 | (R)-Diethyl-2-(4-((4-(5-(4-(2,3-dimethylphenoxy)butanoyl)-2,3,4,5-tetrahydrobenzo[b][1,4]oxazepin-9-yl)-1H-pyrazol-1-yl)methyl)benzamido)succinate | | 711.5 | 7.87 (d, J = 9.4 Hz, 2H), 7.79 (d, J = 8.4 Hz, 2H), 7.54-7.50 (m, 1H), 7.30 (d, J = 8.4 Hz, 2H), 7.14-7.01 (m, 2H), 6.91 (t, J = 7.9 Hz, 1H), 6.64 (d, J = 7.4 Hz, 1H), 6.58 (d, J = 7.9 Hz, 1H), 5.39 (d, J = 2.5 Hz, 2H), 4.96 (t, J = 5.7 Hz, 1H), 4.79-4.71 (m, 1H), 4.48-4.39 (m, 1H), 4.27-4.08 (m, 4H), 3.90-3.75 (m, 2H), 3.62-3.53 (m, 1H), 2.96 (d, J = 5.9 Hz, 2H), 2.84-2.75 (m, 1H), 2.47-2.22 (m, 3H), 2.11 (s, 3H), 2.07-1.95 (m, 2H), 1.84 (s, 3H), 1.76 (d, J = 14.9 Hz, 1H), 1.30-1.17 (m, 6H) | 100%* |
| 778 | (S)-2-(3-Chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzamido)succinic acid | | 729.2 | 8.07-7.94 (m, 2H), 7.83-7.65 (m, 2H), 7.52 (d, J = 8.8 Hz, 1H), 7.37 (d, J = 7.7 Hz, 1H), 7.20-6.85 (m, 3H), 6.64 (d, J = 7.7 Hz, 1H), 5.61 (br. s., 2H), 5.02 (br. s., 1H), 4.59 (br. s., 1H), 4.46 (br. s., 2H), 4.27 (br. s., 1H), 4.09 (br. s., 3H), 3.75 (br. s., 1H), 3.21-2.91 (m, 2H), 2.33 (br. s., 1H), 2.24-2.00 (m, 4H) | 9.2 min, 98.8% 8.8 min, 98.9% |

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 779 | (S)-2-(4-Chloro-3-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)benzamido)succinic acid | | 711.2 | 8.24 (br. s., 3H), 7.92-7.73 (m, 2H), 7.58-7.47 (m, 1H), 7.45-7.22 (m, 1H), 7.20-6.92 (m, 3H), 6.85-6.58 (m, 1H), 5.61 (br. s., 2H), 5.04 (br. s., 1H), 4.68-4.43 (m, 2H), 4.35-3.99 (m, 4H), 3.81 (d, J = 9.5 Hz, 1H), 3.19-2.87 (m, 2H), 2.34 (br. s., 1H), 2.23-2.05 (m, 4H) | 9.2 min, 99.4% 8.8 min, 99.1% |
| 780 | 3-(3-Chloro-4-((4-(5-(4-(3-chloro-2-methylphenoxy)butanoyl)-4,5-dihydro-2H-spiro[benzo[b][1,4]oxazepine-3,1'-cyclopropane]-9-yl)-1H-pyrazol-1-yl)methyl)-5-fluorobenzamido)propanoic acid | | 709.2 | 7.85 (s, 1H), 7.82-7.75 (m, 2H), 7.61 (d, J = 1.5 Hz, 1H), 7.54 (dd, J = 7.9, 1.5 Hz, 1H), 7.15-7.08 (m, 2H), 7.03 (dd, J = 7.9, 1.5 Hz, 1H), 7.00-6.93 (m, 1H), 6.84 (d, J = 7.9 Hz, 1H), 6.67 (d, J = 8.4 Hz, 1H), 5.60-5.45 (m, 2H), 4.36 (br. s., 1H), 3.97-3.84 (m, 2H), 3.67 (br. s., 2H), 3.62 (t, J = 6.7 Hz, 2H), 3.07-2.97 (m, 1H), 2.59 (t, J = 6.4 Hz, 2H), 2.51-2.35 (m, 2H), 2.13-2.02 (m, 2H), 1.95 (s, 3H), 0.98 (d, J = 4.5 Hz, 1H), 0.72-0.62 (m, 1H), 0.54-0.44 (m, 1H), 0.40-0.32 (m, 1H) | 100%* |
| 781 | (S)-2-(3-Chloro-4-((4-(5-(4-(3-chloro-2-methylphenoxy)butanoyl)-4,5-dihydro-2H-spiro[benzo[b][1,4]oxazepine-3,1'-cyclopropane]-9-yl)-1H-pyrazol-1-yl)methyl)-5-fluorobenzamido)succinic acid | | 753.3 | 7.85 (s, 1H), 7.83-7.78 (m, 2H), 7.63 (dd, J = 9.7, 1.2 Hz, 1H), 7.54 (dd, J = 7.9, 1.5 Hz, 1H), 7.15-7.08 (m, 1H), 7.02 (dd, J = 7.9, 1.5 Hz, 1H), 7.00-6.94 (m, 1H), 6.85 (d, J = 7.9 Hz, 1H), 6.67 (d, J = 8.4 Hz, 1H), 5.62-5.47 (m, 2H), 4.91 (t, J = 5.7 Hz, 1H), 4.35 (d, J = 13.4 Hz, 1H), 3.97-3.85 (m, 2H), 3.74-3.64 (m, 2H), 3.01 (d, J = 13.9 Hz, 1H), 2.97 (d, J = 5.9 Hz, 2H), 2.51-2.34 (m, 2H), 2.12-2.00 (m, 2H), 1.95 (s, 3H), 0.98 (d, J = 4.5 Hz, 1H), 0.71-0.61 (m, 1H), 0.53-0.44 (m, 1H), 0.41-0.32 (m, 1H) | 100%* |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 782 | 2-(3-Chloro-4-((4-(5-(4-(3-chloro-2-methylphenoxy)butanoyl)-4,5-dihydro-2H-spiro[benzo[b][1,4]oxazepine-3,1'-cyclopropane]-9-yl)-1H-pyrazol-1-yl)methyl)-5-fluorobenzamido)ethanesulfonic acid | | 745.2 | 7.83 (s, 1H), 7.81-7.76 (m, 2H), 7.65-7.59 (m, 1H), 7.53 (dd, J = 7.7, 1.2 Hz, 1H), 7.11 (t, J = 7.9 Hz, 1H), 7.02 (dd, J = 7.7, 1.2 Hz, 1H), 7.00-6.94 (m, 1H), 6.84 (d, J = 7.9 Hz, 1H), 6.67 (d, J = 8.4 Hz, 1H), 5.60-5.47 (m, 2H), 4.39-4.31 (m, 1H), 3.96-3.85 (m, 2H), 3.81 (s, 2H), 3.77-3.65 (m, 2H), 3.08 (t, J = 6.2 Hz, 2H), 3.04-2.98 (m, 1H), 2.51-2.34 (m, 2H), 2.11-2.02 (m, 2H), 1.95 (s, 3H), 0.98 (d, J = 4.0 Hz, 1H), 0.72-0.62 (m, 1H), 0.53-0.44 (m, 1H), 0.42-0.32 (m, 1H) | 100%* |
| 783 | 2-(3-Chloro-4-((4-(5-(4-(3-chloro-2-methylphenoxy)butanoyl)-4,5-dihydro-2H-spiro[benzo[b][1,4]oxazepine-3,1'-cyclopropane]-9-yl)-1H-pyrazol-1-yl)methyl)-5-fluorobenzamido)-N,N,N-trimethylethanaminium | | 722.3 | 7.89 (s, 1H), 7.86-7.78 (m, 2H), 7.60 (dd, J = 9.7, 1.2 Hz, 1H), 7.54 (dd, J = 7.9, 1.5 Hz, 1H), 7.12 (t, J = 7.7 Hz, 1H), 7.03 (dd, J = 7.9, 1.5 Hz, 1H), 7.00-6.93 (m, 1H), 6.83 (d, J = 7.9 Hz, 1H), 6.68 (d, J = 8.4 Hz, 1H), 5.62-5.49 (m, 2H), 4.35 (d, J = 13.4 Hz, 1H), 3.96-3.86 (m, 2H), 3.83 (t, J = 6.4 Hz, 2H), 3.77-3.66 (m, 2H), 3.57 (t, J = 6.4 Hz, 2H), 3.21 (s, 9H), 3.05-2.98 (m, 1H), 2.51-2.36 (m, 2H), 2.07 (t, J = 6.4 Hz, 2H), 1.93 (s, 3H), 0.99 (br. s., 1H), 0.70-0.62 (m, 1H), 0.54-0.46 (m, 1H), 0.40-0.32 (m, 1H) | N/A |
| 784 | 3-(3-Chloro-4-((4-(10-(4-(3-chloro-2-methylphenoxy)butanoyl)-10,11-dihydrodibenzo[b,f][1,4]oxazepine-6-yl)-1H-pyrazol-1-yl)methyl)-5-fluorobenzamido)propanoic acid | | 731.9 | 7.97 (s, 1H), 7.82 (s, 1H), 7.73 (s, 1H), 7.58-7.48 (m, 2H), 7.27-7.10 (m, 3H), 7.09-6.97 (m, 3H), 6.92 (d, J = 7.5 Hz, 1H), 6.75 (d, J = 8.1 Hz, 1H), 6.61 (d, J = 8.1 Hz, 1H), 5.84-5.65 (m, 3H), 4.26 (d, J = 16.9 Hz, 1H), 3.95-3.72 (m, 4H), 2.77 (t, J = 5.7 Hz, 2H), 2.59 (d, J = 8.1 Hz, 2H), 2.11 (quin, J = 6.3 Hz, 2H), 1.96 (s, 3H) | 10.2 min, 100% 9.4 min, 100% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 785 | 2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)ethyl dihydrogen phosphate | 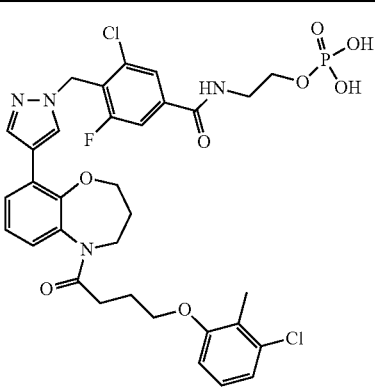 | 735.2 | 8.00 (s, 1H), 7.90-7.82 (m, 2H), 7.70 (dd, J = 9.9, 1.5 Hz, 1H), 7.62 (dd, J = 6.6, 3.1 Hz, 1H), 7.20-7.09 (m, 2H), 7.02-6.96 (m, 1H), 6.84 (d, J = 7.7 Hz, 1H), 6.74 (d, J = 8.1 Hz, 1H), 5.68-5.54 (m, 2H), 4.78 (d, J = 11.0 Hz, 1H), 4.44 (d, J = 11.7 Hz, 1H), 4.19-4.09 (m, 2H), 3.98-3.83 (m, 2H), 3.66 (t, J = 5.3 Hz, 2H), 3.61-3.52 (m, 1H), 2.84 (t, J = 11.8 Hz, 1H), 2.57-2.21 (m, 3H), 2.13-2.00 (m, 2H), 1.93 (s, 3H), 1.79 (d, J = 14.3 Hz, 1H) | 8.5 min, 99.8% 7.8 min, 99.6% |
| 786 | 2-(3-Chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)acetic acid | 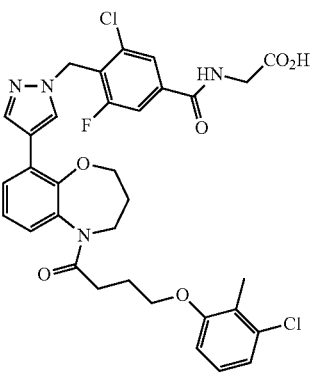 [SMILES: Cc1c(Cl)cccc1OCCCC(=O)N1CCCOc2c(-c3cnn(Cc4c(F)cc(C(=O)NCC(=O)O)cc4Cl)c3)cccc21] | 669.2 | 7.92 (s, 1H), 7.89-7.80 (m, 2H), 7.68 (dd, J = 9.8, 1.7 Hz, 1H), 7.56 (dd, J = 7.6, 1.9 Hz, 1H), 7.17-7.05 (m, 2H), 7.00-6.92 (m, 1H), 6.83 (d, J = 7.5 Hz, 1H), 6.68 (d, J = 8.1 Hz, 1H), 5.58 (dd, J = 5.1, 1.3 Hz, 2H), 4.79 (br. s., 1H), 4.43 (d, J = 11.9 Hz, 1H), 4.15-4.08 (m, 2H), 3.98-3.81 (m, 2H), 3.64-3.53 (m, 1H), 2.88-2.75 (m, 1H), 2.50-2.23 (m, 3H), 2.13-2.00 (m, 2H), 1.79 (d, J = 14.7 Hz, 1H) | 9.3 min, 99.6% 8.7 min, 99.6% |
| 787 | 3-(3-Chloro-4-((4-(5-(4-(3-chloro-2-methylphenoxy)butanoyl)-4,5-dihydro-2H-spiro[benzo[b][1,4]oxazepine-3,1'-cyclobutane]-9-yl)-1H-pyrazol-1-yl)methyl)-5-fluorobenzamido)propanoic acid | 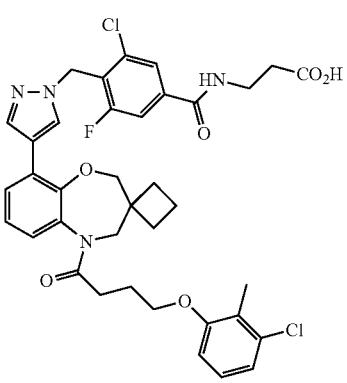 [SMILES: Cc1c(Cl)cccc1OCCCC(=O)N1CC2(CCC2)COc2c(-c3cnn(Cc4c(F)cc(C(=O)NCCS(=O)(=O)O)cc4Cl)c3)cccc21] | 723.2 | 7.90 (s, 1H), 7.84-7.78 (m, 2H), 7.62 (d, J = 1.5 Hz, 1H), 7.50 (dd, J = 7.9, 1.5 Hz, 1H), 7.11-7.05 (m, 1H), 7.03-6.93 (m, 2H), 6.83 (d, J = 7.4 Hz, 1H), 6.65 (d, J = 7.9 Hz, 1H), 5.65-5.50 (m, 2H), 5.08 (d, J = 13.4 Hz, 1H), 4.29 (d, J = 11.4 Hz, 1H), 3.95-3.79 (m, 2H), 3.63 (t, J = 6.7 Hz, 2H), 3.40-3.35 (m, 1H), 2.69-2.56 (m, 3H), 2.55-2.46 (m, 1H), 2.44-2.35 (m, 1H), 2.30 (d, J = 6.4 Hz, 1H), 2.13-1.95 (m, 5H), 1.91 (s, 3H), 1.81-1.67 (m, 1H), 1.63-1.51 (m, 1H) | 91%* |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 788 | (S)-2-(3-Chloro-4-((4-(5-(4-(3-chloro-2-methylphenoxy)butanoyl)-4,5-dihydro-2H-spiro[benzo[b][1,4]oxazepine-3,1'-cyclobutane]-9-yl)-1H-pyrazol-1-yl)methyl)-5-fluorobenzamido)succinic acid | | 767.1 | 7.90 (s, 1H), 7.86-7.79 (m, 2H), 7.66 (dd, J = 9.4, 1.5 Hz, 1H), 7.50 (dd, J = 7.9, 1.5 Hz, 1H), 7.12-7.05 (m, 1H), 7.03-6.94 (m, 2H), 6.83 (d, J = 7.9 Hz, 1H), 6.65 (d, J = 7.9 Hz, 1H), 5.64-5.51 (m, 2H), 5.08 (d, J = 13.4 Hz, 1H), 4.91 (t, J = 5.7 Hz, 1H), 4.30 (d, J = 10.9 Hz, 1H), 3.96-3.80 (m, 2H), 3.37 (d, J = 4.0 Hz, 1H), 2.99-2.94 (m, 2H), 2.63 (d, J = 13.4 Hz, 1H), 2.56-2.46 (m, 1H), 2.44-2.35 (m, 1H), 2.30 (d, J = 6.9 Hz, 1H), 2.14-1.94 (m, 5H), 1.91 (s, 3H), 1.75 (d, J = 4.5 Hz, 1H), 1.58 (dd, J = 8.7, 2.3 Hz, 1H) | 91%* |
| 789 | 2-(3-Chloro-4-((4-(5-(4-(3-chloro-2-methylphenoxy)butanoyl)-4,5-dihydro-2H-spiro[benzo[b][1,4]oxazepine-3,1'-cyclobutane]-9-yl)-1H-pyrazol-1-yl)methyl)-5-fluorobenzamido)ethanesulfonic acid | | 759.1 | 7.88 (s, 2H), 7.84-7.78 (m, 2H), 7.64 (d, J = 1.5 Hz, 1H), 7.50 (dd, J = 7.9, 1.5 Hz, 1H), 7.11-7.05 (m, 1H), 7.02-6.93 (m, 2H), 6.83 (d, J = 7.9 Hz, 1H), 6.65 (d, J = 8.4 Hz, 1H), 5.65-5.50 (m, 2H), 5.08 (d, J = 13.4 Hz, 1H), 4.33-4.25 (m, 1H), 3.95-3.77 (m, 4H), 3.37 (d, J = 5.4 Hz, 1H), 3.09 (t, J = 6.4 Hz, 2H), 2.68-2.59 (m, 1H), 2.56-2.46 (m, 1H), 2.44-2.35 (m, 1H), 2.29 (d, J = 6.9 Hz, 1H), 2.13-1.94 (m, 5H), 1.91 (s, 3H), 1.81-1.70 (m, 1H), 1.58 (dd, J = 8.7, 3.2 Hz, 1H) | 91%* |
| 790 | 2-(3-Chloro-4-((4-(5-(4-(3-chloro-2-methylphenoxy)butanoyl)-4,5-dihydro-2H-spiro[benzo[b][1,4]oxazepine-3,1'-cyclobutane]-9-yl)-1H-pyrazol-1-yl)methyl)-5-fluorobenzamido)-N,N,N,-trimethylethanaminium | | 736.2 | 7.94 (s, 1H), 7.89-7.79 (m, 2H), 7.68 (dd, J = 9.9, 1.5 Hz, 1H), 7.51 (dd, J = 7.7, 1.7 Hz, 1H), 7.09 (t, J = 7.9 Hz, 1H), 7.04-6.93 (m, 2H), 6.82 (d, J = 7.9 Hz, 1H), 6.65 (d, J = 8.4 Hz, 1H), 5.64-5.51 (m, 2H), 5.09 (d, J = 13.4 Hz, 1H), 4.31 (d, J = 10.9 Hz, 1H), 3.94-3.79 (m, 4H), 3.63-3.52 (m, 2H), 3.42-3.35 (m, 1H), 3.26-3.17 (m, 9H), 2.63 (d, J = 13.4 Hz, 1H), 2.56-2.46 (m, 1H), 2.43-2.35 (m, 1H), 2.33-2.25 (m, 1H), 2.12-1.95 (m, 5H), 1.90 (s, 3H), 1.83-1.71 (m, 1H), 1.64-1.53 (m, 1H) | 91%* |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 791 | (S)-6-Amino-2-(3-chloro-4-((4-(5-(4-(3-chloro-2-methylphenoxy)butanoyl)-4,5-dihydro-2H-spiro[benzo[b][1,4]oxazepine-3,1'-cyclobutane]-9-yl)-1H-pyrazol-1-yl)methyl)-5-fluorobenzamido)hexanoic acid | | 780.2 | 7.91 (s, 1H), 7.88-7.79 (m, 2H), 7.68 (dd, J = 9.9, 1.5 Hz, 1H), 7.50 (dd, J = 7.9, 1.5 Hz, 1H), 7.12-7.04 (m, 1H), 7.03-6.92 (m, 2H), 6.83 (d, J = 7.9 Hz, 1H), 6.65 (d, J = 8.4 Hz, 1H), 5.63-5.51 (m, 2H), 5.08 (d, J = 13.4 Hz, 1H), 4.45 (t, J = 5.9 Hz, 1H), 4.30 (d, J = 11.4 Hz, 1H), 3.95-3.78 (m, 2H), 3.40-3.35 (m, 1H), 2.95-2.84 (m, 3H), 2.63 (d, J = 12.9 Hz, 1H), 2.55-2.45 (m, 1H), 2.42-2.34 (m, 1H), 2.30 (d, J = 6.9 Hz, 1H), 2.13-1.93 (m, 8H), 1.91 (s, 3H), 1.89-1.80 (m, 1H), 1.79-1.63 (m, 3H), 1.58 (dd, J = 8.7, 3.2 Hz, 1H), 1.54-1.39 (m, 2H) | 91%* |
| 792 | (S)-6-Amino-2-(3-chloro-4-((4-(5-(4-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)hexanoic acid | | 740.2 | 7.89 (s, 1H), 7.86-7.79 (m, 2H), 7.67 (dd, J = 9.9, 1.5 Hz, 1H), 7.53 (dd, J = 7.7, 1.7 Hz, 1H), 7.14-7.03 (m, 2H), 6.99-6.92 (m, 1H), 6.83 (d, J = 7.9 Hz, 1H), 6.65 (d, J = 8.4 Hz, 1H), 5.63-5.49 (m, 2H), 4.51-4.34 (m, 3H), 3.95-3.80 (m, 2H), 3.56 (t, J = 11.6 Hz, 1H), 2.96-2.74 (m, 3H), 2.45-2.35 (m, 2H), 2.29 (dd, J = 10.9, 4.0 Hz, 1H), 2.05 (quin, J = 6.4 Hz, 2H), 1.99-1.89 (m, 4H), 1.89-1.61 (m, 4H), 1.54-1.36 (m, 2H) | 91%* |
| 793 | 3-(4-Chloro-3-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)benzamido)propanoic acid | | 667.2 | 8.08-7.97 (m, 1H), 7.90 (s, 1H), 7.74 (dd, J = 8.4, 2.0 Hz, 1H), 7.70 (d, J = 2.0 Hz, 1H), 7.54-7.41 (m, 2H), 7.22-6.80 (m, 4H), 6.68 (d, J = 8.4 Hz, 1H), 5.50 (s, 2H), 4.56 (br. s., 1H), 4.42 (br. s., 2H), 4.28 (br. s., 1H), 4.15-4.02 (m, 3H), 3.75 (s, 1H), 3.61 (t, J = 6.7 Hz, 2H), 2.59 (t, J = 6.7 Hz, 2H), 2.31 (s, 1H), 2.20-1.98 (m, 4H) | 95%* |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 794 | 3-(3-Chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzamido)propanoic acid | | 685.2 | 8.03-7.95 (m, 1H), 7.84 (s, 1H), 7.78 (s, 1H), 7.59 (d, J = 1.0 Hz, 1H), 7.41 (d, J = 7.9 Hz, 1H), 7.23-6.79 (m, 4H), 6.67 (d, J = 7.9 Hz, 1H), 5.56 (s, 2H), 4.56 (br. s., 1H), 4.42 (br. s., 2H), 4.28 (br. s., 1H), 4.09 (br. s., 3H), 3.75 (s, 1H), 3.63 (t, J = 6.7 Hz, 2H), 2.61 (t, J = 6.4 Hz, 2H), 2.31 (br. s., 1H), 2.17-1.99 (m, 4H) | 95%* |
| 795 | 2-(3-Chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzamido)acetic acid | | 671.1 | 8.04-7.94 (m, 1H), 7.88-7.81 (m, 2H), 7.66 (dd, J = 9.4, 1.5 Hz, 1H), 7.41 (d, J = 7.9 Hz, 1H), 7.21-6.79 (m, 4H), 6.67 (d, J = 7.9 Hz, 1H), 5.56 (s, 2H), 4.56 (br. s., 1H), 4.42 (br. s., 2H), 4.28 (br. s., 1H), 4.14-3.99 (m, 5H), 3.75 (s, 1H), 2.31 (s, 1H), 2.18-1.96 (m, 4H) | 96%* |
| 796 | (S)-3-(3-Chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzamido)-4-ethoxy-4-oxobutanoic acid | | 757.4 | 8.13 (br. s., 1H), 7.94-7.80 (m, 2H), 7.67 (dd, J = 9.7, 1.5 Hz, 1H), 7.50 (d, J = 7.0 Hz, 1H), 7.21-6.89 (m, 4H), 6.77 (d, J = 7.0 Hz, 1H), 5.63 (d, J = 1.1 Hz, 2H), 5.00-4.91 (m, 1H), 4.59 (br. s., 1H), 4.43 (br. s., 2H), 4.34 (br. s., 1H), 4.29-4.19 (m, 2H), 4.16-4.00 (m, 4H), 3.07-2.85 (m, 2H), 2.34 (br. s., 1H), 2.17-1.98 (m, 4H), 1.29 (t, J = 7.0 Hz, 3H) | 10.2 min, 99.8% 9.6 min, 99.8% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 797 | (S)-Bis(2-morpholinoethyl)2-(3-chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzamido)succinate | | 955.5 | 7.96 (s, 1H), 7.88 (s, 1H), 7.72 (s, 1H), 7.61-7.51 (m, 1H), 7.44-7.33 (m, 2H), 7.16-6.93 (m, 3H), 6.87-6.62 (m, 1H), 5.57 (s, 2H), 5.11-5.01 (m, 1H), 4.65-4.19 (m, 7H), 4.11 (br. s., 2H), 3.82-3.59 (m, 8H), 3.17 (dd, J = 17.3, 4.3 Hz, 1H), 3.07-2.95 (m, 1H), 2.73-2.58 (m, 4H), 2.56-2.43 (m, 7H), 2.36 (br. s., 1H), 2.28-2.02 (m, 4H), 1.74 (br. s., 4H) | 6.2 min, 98.9% 7.7 min, 99.0% |
| 798 | 2-(3-Chloro-2-methylphenoxy)ethyl 9-(1-(2-chloro-6-fluoro-4-(methylsulfonylcarbamoyl)benzyl)-1H-pyrazol-4-yl)-3,4-dihydrobenzo[b][1,4]oxazepine-5(2H)-carboxylate | | 693.3 | 8.16 (br. s., 1H), 7.96-7.85 (m, 2H), 7.74 (dd, J = 9.7, 1.8 Hz, 1H), 7.50 (d, J = 7.0 Hz, 1H), 7.22-6.90 (m, 4H), 6.77 (d, J = 7.9 Hz, 1H), 5.64 (d, J = 1.3 Hz, 2H), 4.59 (br. s., 1H), 4.43 (br. s., 2H), 4.34 (br. s., 1H), 4.18-3.99 (m, 4H), 3.39 (s, 3H), 2.34 (br. s., 1H), 2.17-1.99 (m, 4H) | 10.4 min, 98.4% 9.9 min, 99.9% |
| 799 | 2-(3-Chloro-2-methylphenoxy)ethyl 9-(1-(2-chloro-6-fluoro-4-(methylsulfonamido)-2-oxoethylcarbamoyl)benzyl)-1H-pyrazol-4-yl)-3,4-dihydrobenzo[b][1,4]oxazepine-5(2H)-carboxylate | | 748.3 | 8.14 (br. s., 1H), 7.94-7.85 (m, 2H), 7.70 (dd, J = 9.8, 1.7 Hz, 1H), 7.50 (d, J = 7.9 Hz, 1H), 7.21-6.91 (m, 4H), 6.77 (d, J = 7.3 Hz, 1H), 5.63 (d, J = 1.1 Hz, 2H), 4.59 (br. s., 1H), 4.43 (br. s., 2H), 4.34 (br. s., 1H), 4.19-4.00 (m, 5H), 3.75 (br. s., 1H), 3.29 (s, 3H), 2.34 (br. s., 1H), 2.17-1.99 (m, 4H) | 9.7 min, 98.2% 9.3 min, 98.5% |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 800 | (2S)-Bis(2,3-dihydroxypropyl)2-(3-chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzamido)succinate | | 877.4 | 8.13 (br. s., 1H), 7.88 (d, J = 12.8 Hz, 2H), 7.69 (d, J = 9.5 Hz, 1H), 7.50 (d, J = 6.6 Hz, 1H), 7.22-6.89 (m, 4H), 6.77 (d, J = 7.9 Hz, 1H), 5.63 (s, 2H), 5.06 (ddd, J = 7.7, 5.3, 2.6 Hz, 1H), 4.59 (br. s., 1H), 4.43 (br. s., 2H), 4.39-3.99 (m, 6H), 3.92-3.80 (m, 2H), 3.78-3.66 (m, 1H), 3.58 (dd, J = 5.5, 2.4 Hz, 4H), 3.19-2.95 (m, 4H), 2.34 (br. s., 1H), 2.19-1.98 (m, 4H) | 8.2 min, 90.7% 8.1 min, 91.7% |
| 801 | 2-(3-Chloro-2-methylphenoxy)ethyl 9-(1-(4-((2H-tetrazol-5-yl)methylcarbamoyl)-2-chloro-6-fluorobenzyl)-1H-pyrazol-4-yl)-3,4-dihydrobenzo[b][1,4]oxazepine-5(2H)-carboxylate | | 695.2 | 8.05-7.98 (m, 1H), 7.85 (d, J = 10.9 Hz, 2H), 7.67 (dd, J = 9.4, 1.5 Hz, 1H), 7.46-7.37 (m, 1H), 7.21-6.78 (m, 4H), 6.67 (d, J = 7.9 Hz, 1H), 5.56 (s, 2H), 4.84 (s, 2H), 4.56 (br. s., 1H), 4.42 (br. s., 2H), 4.28 (br. s., 1H), 4.14-3.98 (m, 3H), 3.79-3.67 (m, 1H), 2.31 (s, 1H), 2.19-1.99 (m, 4H) | 99%* |
| 802 | 3-(4-Chloro-3-((4-(5-((2-(3-chloro-2-methylphenoxy)ethoxy)carbonyl)-7-fluoro-2,3,4,5-tetrahydrobenzo[b][1,4]oxazepin-9-yl)-1H-pyrazol-1-yl)methyl)benzamido)propanoic acid | | 685.2 | 8.04-7.87 (m, 2H), 7.79 (d, J = 8.8 Hz, 1H), 7.57-7.43 (m, 2H), 7.18-6.57 (m, 5H), 5.50 (br. s., 2H), 4.62-4.41 (m, 2H), 4.31-4.02 (m, 4H), 3.87-3.52 (m, 4H), 2.75-2.43 (m, 2H), 2.40-2.03 (m, 3H) | 9.8 min, 97.9% 9.2 min, 98.0% |
| 803 | 3-(3-Chloro-4-((4-(5-((2-(3-chloro-2-methylphenoxy)ethoxy)carbonyl)-3-hydroxy-2,3,4,5-tetrahydrobenzo[b][1,4]oxazepin-9-yl)-1H-pyrazol-1-yl)methyl)-5-fluorobenzamido)propanoic acid | | 703.2 | 8.15 (s, 1H), 7.90 (s, 1H), 7.82 (t, J = 1.2 Hz, 1H), 7.65 (dd, J = 9.9, 1.8 Hz, 1H), 7.51 (d, J = 7.7 Hz, 1H), 7.25-6.89 (m, 4H), 6.79 (br. s., 1H), 5.62 (d, J = 1.3 Hz, 2H), 4.69-4.02 (m, 8H), 3.87-3.73 (m, 1H), 3.72-3.57 (m, 2H), 2.66 (t, J = 6.8 Hz, 2H), 2.42-2.04 (m, 3H) | 8.6 min, 99.7% 8.3 min, 99.6% |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 804 | 3-(3-Chloro-4-((4-(5-((2-(3-chloro-2-methylphenoxy)ethoxy)carbonyl)-3,3-difluoro-2,3,4,5-tetrahydrobenzo[b][1,4]oxazepin-9-yl)-1H-pyrazol-1-yl)methyl)-5-fluorobenzamido)propanoic acid | | 721.1 | 8.02 (s, 1H), 7.84 (s, 1H), 7.80 (s, 1H), 7.60 (d, J = 1.5 Hz, 1H), 7.48 (d, J = 7.4 Hz, 2H), 7.26-6.82 (m, 4H), 6.70 (br. s., 1H), 5.58 (s, 2H), 4.65-4.21 (m, 4H), 4.12 (br. s., 4H), 3.63 (t, J = 6.7 Hz, 2H), 2.59 (t, J = 6.7 Hz, 2H), 2.40-2.08 (m, 3H) | 100%* |
| 805 | 3-(3-Chloro-4-((4-(5-(4-(3-chloro-2-fluorophenoxy)butanoyl)-2,3,4,5-tetrahydrobenzo[b][1,4]oxazepin-9-yl)-1H-pyrazol-1-yl)methyl)-5-fluorobenzamido)propanoic acid | | 687.1 | 7.94 (s, 1H), 7.88-7.74 (m, 2H), 7.62 (d, J = 1.5 Hz, 1H), 7.52 (dd, J = 7.7, 1.7 Hz, 1H), 7.18-7.05 (m, 2H), 6.92-6.76 (m, 3H), 5.61-5.50 (m, 3H), 4.81-4.74 (m, 1H), 4.45 (d, J = 11.9 Hz, 1H), 4.03-3.87 (m, 2H), 3.67-3.53 (m, 3H), 2.85-2.75 (m, 1H), 2.61 (t, J = 6.7 Hz, 2H), 2.48-2.38 (m, 1H), 2.36-2.24 (m, 2H), 2.10-1.97 (m, 2H), 1.78 (d, J = 14.4 Hz, 1H) | 100%* |
| 806 | 2-(3-Chloro-4-((4-(5-(4-(3-chloro-2-fluorophenoxy)butanoyl)-2,3,4,5-tetrahydrobenzo[b][1,4]oxazepin-9-yl)-1H-pyrazol-1-yl)methyl)-5-fluorobenzamido)ethanesulfonic acid | | 723.0 | 7.92 (s, 2H), 7.87-7.76 (m, 3H), 7.63 (d, J = 1.5 Hz, 1H), 7.52 (dd, J = 7.7, 1.7 Hz, 1H), 7.18-7.04 (m, 4H), 6.92-6.75 (m, 6H), 5.62-5.48 (m, 2H), 4.82-4.73 (m, 1H), 4.44 (d, J = 11.9 Hz, 2H), 4.04-3.88 (m, 4H), 3.81 (t, J = 6.4 Hz, 4H), 3.64-3.52 (m, 2H), 3.08 (t, J = 6.2 Hz, 4H), 2.85-2.76 (m, 2H), 2.49-2.39 (m, 2H), 2.37-2.24 (m, 4H), 2.09-1.98 (m, 4H), 1.78 (d, J = 14.9 Hz, 2H) | 100%* |
| 807 | 2-(3-Chloro-4-((4-(5-((2-(3-chloro-2-methylphenoxy)-2-methylpropoxy)carbonyl)-2,3,4,5-tetrahydrobenzo[b][1,4]oxazepin-9-yl)-1H-pyrazol-1-yl)methyl)-5-fluorobenzamido)ethanesulfonic acid | | 749.2 | 8.03-7.95 (m, 2H), 7.89-7.84 (m, 1H), 7.79 (s, 1H), 7.64-7.60 (m, 1H), 7.44 (d, J = 7.4 Hz, 1H), 7.19-6.94 (m, 2H), 6.88 (t, J = 8.2 Hz, 1H), 6.73 (d, J = 7.9 Hz, 1H), 5.56 (s, 2H), 4.15 (s, 3H), 3.81 (t, J = 6.2 Hz, 2H), 3.08 (t, J = 6.2 Hz, 2H), 3.04-2.86 (m, 2H), 1.97 (s, 6H), 1.49-1.11 (m, 6H) | 100%* |

TABLE 21-continued

| Example | Name | Formula I | LCMS, [M + H]+ | ¹H NMR (400 MHz, MeOD) δ | HPLC-1: Rt min, purity; HPLC-2: Rt min, purity |
|---|---|---|---|---|---|
| 808 | 3-(3-Chloro-4-((4-(5-((2-(3-chloro-2-methylphenoxy)-2-methylpropoxy)carbonyl)-2,3,4,5-tetrahydrobenzo[b][1,4]oxazepin-9-yl)-1H-pyrazol-1-yl)methyl)-5-fluorobenzamido)propanoic acid | | 715.2 | 8.04-7.95 (m, 1H), 7.90-7.83 (m, 1H), 7.79 (s, 1H), 7.61 (s, 1H), 7.44 (d, J = 7.4 Hz, 1H), 7.22-6.94 (m, 3H), 6.87 (s, 1H), 6.72 (d, J = 8.4 Hz, 1H), 5.56 (s, 2H), 4.35-3.98 (m, 4H), 3.80-3.56 (m, 4H), 2.59 (t, J = 6.4 Hz, 2H), 2.39-1.95 (m, 5H), 1.51-1.10 (m, 6H) | 100%* |
| 809 | 3-(3-Chloro-4-((4-(5-(4-(3-chloro-2,6-difluorophenoxy)butanoyl)-2,3,4,5-tetrahydrobenzo[b][1,4]oxazepin-9-yl)-1H-pyrazol-1-yl)methyl)-5-fluorobenzamido)propanoic acid | | 705.0 | 8.02 (s, 1H), 7.87 (s, 1H), 7.79 (s, 1H), 7.63-7.58 (m, 1H), 7.54 (dd, J = 7.4, 2.0 Hz, 1H), 7.18-7.09 (m, 2H), 7.01 (ddd, J = 9.2, 7.7, 5.4 Hz, 1H), 6.86-6.77 (m, 1H), 5.57 (s, 1H), 4.81-4.74 (m, 1H), 4.47 (d, J = 12.4 Hz, 2H), 4.18-4.01 (m, 2H), 3.68-3.59 (m, 2H), 2.85-2.77 (m, 1H), 2.62 (t, J = 6.7 Hz, 2H), 2.56-2.45 (m, 1H), 2.40-2.11 (m, 2H), 2.09-1.88 (m, 2H), 1.79 (d, J = 14.4 Hz, 1H) | 100% |
| 810 | 3-(3-Chloro-4-((4-(5-(4-(2-chloro-6-fluoro-3-methylphenoxy)butanoyl)-2,3,4,5-tetrahydrobenzo[b][1,4]oxazepin-9-yl)-1H-pyrazol-1-yl)methyl)-5-fluorobenzamido)propanoic acid | | 701.1 | 8.04 (s, 1H), 7.88 (s, 1H), 7.79 (s, 1H), 7.61 (dd, J = 9.4, 1.5 Hz, 1H), 7.59-7.49 (m, 1H), 7.18-7.11 (m, 2H), 6.91-6.83 (m, 2H), 5.57 (s, 2H), 4.52-4.27 (m, 2H), 4.09-3.93 (m, 2H), 3.63 (t, J = 6.7 Hz, 2H), 2.86-2.78 (m, 1H), 2.65-2.52 (m, 3H), 2.40-2.21 (m, 5H), 2.12-1.91 (m, 2H), 1.79 (d, J = 14.9 Hz, 1H) | 99%* |
| 811 | 2-(3-Chloro-4-((4-(5-(4-(2-chloro-3-(trifluoromethyl)phenoxy)butanoyl)-2,3,4,5-tetrahydrobenzo[b][1,4]oxazepin-9-yl)-1H-pyrazol-1-yl)methyl)-5-fluorobenzamido)ethanesulfonic acid | | 773.0 | 7.90 (s, 1H), 7.85-7.75 (m, 2H), 7.66-7.60 (m, 1H), 7.50 (dd, J = 7.4, 2.0 Hz, 1H), 7.25-7.01 (m, 5H), 5.54 (s, 2H), 4.77 (d, J = 12.9 Hz, 1H), 4.45 (d, J = 11.9 Hz, 1H), 4.08-3.92 (m, 2H), 3.81 (t, J = 6.2 Hz, 2H), 3.63-3.52 (m, 1H), 3.08 (t, J = 6.2 Hz, 2H), 2.86-2.75 (m, 1H), 2.55-2.23 (m, 3H), 2.18-2.01 (m, 2H), 1.79 (d, J = 14.9 Hz, 1H) | 100%* |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 812 | 3-(3-Chloro-4-((4-(5-(4-(2-chloro-3-(trifluoromethyl)phenoxy)butanoyl)-2,3,4,5-tetrahydrobenzo[b][1,4]oxazepin-9-yl)-1H-pyrazol-1-yl)methyl)-5-fluorobenzamido)propanoic acid | | 737.0 | 7.92 (s, 1H), 7.83-7.75 (m, 2H), 7.62 (d, J = 1.5 Hz, 1H), 7.50 (dd, J = 7.4, 2.0 Hz, 1H), 7.26-7.02 (m, 5H), 5.63-5.43 (m, 2H), 4.80-4.74 (m, 1H), 4.45 (d, J = 11.9 Hz, 1H), 4.07-3.92 (m, 2H), 3.68-3.53 (m, 3H), 2.85-2.76 (m, 1H), 2.62 (t, J = 6.4 Hz, 2H), 2.55-2.23 (m, 3H), 2.18-2.03 (m, 2H), 1.78 (d, J = 14.9 Hz, 1H) | 100%* |
| 813 | 2-(3-Chloro-4-((4-(5-((2-(3-chloro-2-methylphenoxy)-1,1,2,2-tetradeuteroethoxy)carbonyl)-2,3,4,5-tetrahydrobenzo[b][1,4]oxazepin-9-yl)-1H-pyrazol-1-yl)methyl)-5-fluorobenzamido)ethanesulfonic acid | | 777.2 | 8.02-7.92 (m, 1H), 7.87-7.75 (m, 2H), 7.61 (d, J = 2.0 Hz, 1H), 7.47-7.34 (m, 1H), 7.21-6.88 (m, 4H), 6.68 (s, 1H), 5.55 (s, 2H), 4.71 (br. s, 1H), 4.40-3.55 (m, 5H), 3.08 (t, J = 6.4 Hz, 2H), 2.40-1.98 (m, 5H) | 100%* |
| 814 | 2-(3-Chloro-4-((4-(1-(4-(3-chloro-2-methylphenoxy)butanoyl)-1,2,3,5-tetrahydrobenzo[e][1,4]oxazepin-6-yl)-1H-pyrazol-1-yl)methyl)-5-fluorobenzamido)ethanesulfonic acid | | 719.0 | 7.80 (s, 1H), 7.66-7.60 (m, 2H), 7.52 (s, 1H), 7.36-7.26 (m, 2H), 7.18 (dd, J = 7.4, 1.5 Hz, 1H), 7.07-6.98 (m, 1H), 6.88 (d, J = 7.9 Hz, 1H), 6.69 (d, J = 7.9 Hz, 1H), 5.57 (s, 2H), 4.81-4.70 (m, 2H), 4.16 (d, J = 13.9 Hz, 1H), 4.04-3.87 (m, 3H), 3.85-3.78 (m, 3H), 3.08 (t, J = 6.2 Hz, 2H), 3.01-2.95 (m, 1H), 2.64-2.53 (m, 1H), 2.46 (dt, J = 15.6, 7.6 Hz, 1H), 2.18-2.06 (m, 2H), 1.96 (s, 3H) | 100%* |
| 815 | 3-(3-Chloro-4-((4-(5-(3-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)propanoic acid | | 717.1 | 8.03-7.93 (m, 1H), 7.91-7.79 (m, 2H), 7.64 (dd, J = 9.9, 1.5 Hz, 1H), 7.39 (dd, J = 7.7, 1.2 Hz, 1H), 7.29-7.19 (m, 1H), 7.11 (d, J = 7.4 Hz, 1H), 6.94-6.76 (m, 4H), 6.54 (dd, J = 7.7, 1.2 Hz, 1H), 6.48-6.38 (m, 2H), 5.61 (s, 2H), 4.96 (d, J = 11.9 Hz, 1H), 4.51 (d, J = 9.4 Hz, 1H), 3.71-3.59 (m, 3H), 2.99-2.90 (m, 1H), 2.63 (t, J = 6.7 Hz, 2H), 2.31 (d, J = 9.9 Hz, 1H), 2.02 (s, 3H), 1.91 (d, J = 13.9 Hz, 1H) | 98%* |

TABLE 21-continued

| Example | Name | Formula I | LCMS, [M + H]+ | 1H NMR (400 MHz, MeOD) δ | HPLC-1: Rt min, purity; HPLC-2: Rt min, purity |
|---|---|---|---|---|---|
| 816 | 2-(3-Chloro-4-((4-(5-(3-(3-chloro-2-methylphenoxy)butanoyl)-2,3,4,5-tetrahydrobenzo[b][1,4]oxazepin-9-yl)-1H-pyrazol-1-yl)methyl)-5-fluorobenzamido)ethanesulfonic acid | | 753.1 | 7.97 (s, 1H), 7.89-7.81 (m, 2H), 7.65 (dd, J = 9.7, 1.2 Hz, 1H), 7.39 (dd, J = 7.9, 1.0 Hz, 1H), 7.28-7.19 (m, 1H), 7.10 (d, J = 7.4 Hz, 1H), 6.93-6.77 (m, 4H), 6.54 (dd, J = 7.7, 1.2 Hz, 1H), 6.50-6.40 (m, 2H), 5.60 (s, 2H), 4.96 (d, J = 12.4 Hz, 1H), 4.51 (d, J = 8.9 Hz, 1H), 3.83 (t, J = 6.4 Hz, 2H), 3.65 (t, J = 10.2 Hz, 1H), 3.09 (t, J = 6.2 Hz, 2H), 2.94 (t, J = 11.9 Hz, 1H), 2.31 (d, J = 8.4 Hz, 1H), 2.03 (s, 3H), 1.92 (d, J = 12.9 Hz, 1H) | 100%* |
| 817 | 3-(3-Chloro-4-((4-(1-(4-(3-chloro-2-methylphenoxy)butanoyl)-1,2,3,5-tetrahydrobenzo[e][1,4]oxazepin-6-yl)-1H-pyrazol-1-yl)methyl)-5-fluorobenzamido)propanoic acid | | 683.0 | 7.79 (s, 1H), 7.60 (d, J = 1.5 Hz, 2H), 7.53 (s, 1H), 7.38-7.27 (m, 2H), 7.19 (dd, J = 7.7, 1.2 Hz, 1H), 7.06-6.98 (m, 1H), 6.88 (d, J = 7.9 Hz, 1H), 6.70 (d, J = 8.4 Hz, 1H), 5.58 (s, 1H), 4.79-4.72 (m, 2H), 4.15 (d, J = 13.4 Hz, 1H), 4.02-3.87 (m, 3H), 3.85-3.76 (m, 1H), 3.63 (t, J = 6.7 Hz, 2H), 3.00-2.94 (m, 1H), 2.65-2.54 (m, 3H), 2.47 (dt, J = 15.6, 7.6 Hz, 1H), 2.18-2.07 (m, 2H), 1.95 (s, 3H) | 100%* |
| 818 | 3-(3-Chloro-4-((4-(5-((2-(3-chloro-2-methylphenoxy)-1,1,2,2-tetradeuteroethoxy)carbonyl)-2,3,4,5-tetrahydrobenzo[b][1,4]oxazepin-9-yl)-1H-pyrazol-1-yl)methyl)-5-fluorobenzamido)propanoic acid | | 689.0 | 8.05-7.92 (m, 1H), 7.87-7.73 (m, 2H), 7.66-7.54 (m, 1H), 7.46-7.36 (m, 1H), 7.22-6.89 (m, 4H), 6.87-6.61 (m, 1H), 5.62-5.48 (m, 2H), 4.78-4.71 (m, 1H), 4.34-3.86 (m, 3H), 3.63 (t, J = 6.7 Hz, 2H), 2.61 (t, J = 6.7 Hz, 2H), 2.42-1.96 (m, 5H) | 100%* |
| 819 | (S)-6-Amino-2-(3-chloro-4-((4-(5-((2-(3-chloro-2-methylphenoxy)ethoxy)carbonyl)-2,3,4,5-tetrahydrobenzo[b][1,4]oxazepin-9-yl)-1H-pyrazol-1-yl)methyl)-5-fluorobenzamido)hexanoic acid | | 742.2 | 8.12 (br. s., 1H), 7.86 (d, J = 5.3 Hz, 2H), 7.68 (dd, J = 9.8, 1.4 Hz, 1H), 7.47 (d, J = 6.8 Hz, 1H), 7.22-6.68 (m, 5H), 5.61 (s, 2H), 4.69-4.49 (m, 2H), 4.47-4.25 (m, 2H), 4.21-3.93 (m, 3H), 3.73 (br. s., 1H), 2.94 (t, J = 6.5 Hz, 2H), 2.37-1.81 (m, 7H), 1.79-1.44 (m, 4H) | 7.9 min, 97.2% 9.4 min, 99.5% |

*Injection 1 conditions: Column: Waters Acquity UPLC BEH C18, 2.1 × 50 mm, 1.7-μm particles; Mobile Phase A: 5:95 acetonitrile:water with 10 mM ammonium acetate; Mobile Phase B: 95:5 acetonitrile:water 10 mM ammonium acetate; Temperature: 50° C.; Gradient : 0-100% B over 3 minutes, then a 0.75-minute hold at 100% B; Flow: 1.11 mL/min.
Injection 2 conditions: Column: Waters Acquity UPLC BEH C18, 2.1 × 50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Compounds exemplified in Table 22 were prepared using parallel assay synthesis following the general protocol set forth below.

Amine was treated with a premixed solution of 3-((4-(1-(4-(2,3-dimethylphenoxy)butanoyl)-1,2,3,4-tetrahydroquinolin-5-yl)-1H-pyrazol-1-yl)methyl)benzoic acid, HATU, and DIEA in DMF, at room temperature overnight. The reaction was quenched with methanol and purified by preparative HPLC to give the corresponding amide product.

TABLE 22

| Example | Name | R | LCMS, [M + H]⁺ | HPLC-3: Rt (min) | Purity (%) |
|---------|------|---|----------------|------------------|------------|
| 820 | (S)-4-Amino-2-(3-((4-(1-(4-(2,3-dimethylphenoxy)butanoyl)-1,2,3,4-tetrahydroquinolin-5-yl)-1H-pyrazol-1-yl)methyl)benzamido)-4-oxobutanoic acid | | 638.1 | 1.72 | 100 |
| 821 | 3-(3-((4-(1-(4-(2,3-Dimethylphenoxy)butanoyl)-1,2,3,4-tetrahydroquinolin-5-yl)-1H-pyrazol-1-yl)methyl)benzamido)propanoic acid | | 595.3 | 2.07 | 100 |
| 822 | 3-(3-Chlorophenyl)-3-(3-((4-(1-(4-(2,3-dimethylphenoxy)butanoyl)-1,2,3,4-tetrahydroquinolin-5-yl)-1H-pyrazol-1-yl)methyl)benzamido)propanoic acid | | 705.1 | 1.73 | 99.0 |
| 823 | N-((1H-Tetrazol-5-yl)methyl)-3-((4-(1-(4-(2,3-dimethylphenoxy)butanoyl)-1,2,3,4-tetrahydroquinolin-5-yl)-1H-pyrazol-1-yl)methyl)benzamide | | 605.1 | 1.76 | 98.7 |
| 824 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)pentanedioic acid | | 6531 | 1.72 | 100 |

TABLE 22-continued

| Example | Name | R | LCMS, [M + H]⁺ | HPLC-3: Rt (min) | Purity (%) |
|---|---|---|---|---|---|
| 825 | 2-(N-Cyclohexyl-3-((4-(1-(4-(2,3-dimethylphenoxy)butanoyl)-1,2,3,4-tetrahydroquinolin-5-yl)-1H-pyrazol-1-yl)methyl)benzamido)ethanesulfonic acid | | 713.3 | 2.12 | 99.5 |
| 826 | 3-((4-(1-(4-(2,3-Dimethylphenoxy)butanoyl)-1,2,3,4-tetrahydroquinolin-5-yl)-1H-pyrazol-1-yl)methyl)-N-(4-sulfamoylphenethyl)benzamide | | 706.3 | 2.28 | 97.2 |
| 827 | 1-(3-((4-(1-(4-(2,3-Dimethylphenoxy)butanoyl)-1,2,3,4-tetrahydroquinolin-5-yl)-1H-pyrazol-1-yl)methyl)benzoyl)piperidine-3-carboxylic acid | | 635.3 | 2.32 | 99.5 |
| 828 | 1-(3-((4-(1-(4-(2,3-Dimethylphenoxy)butanoyl)-1,2,3,4-tetrahydroquinolin-5-yl)-1H-pyrazol-1-yl)methyl)benzoyl)piperidine-4-carboxamide | | 634.3 | 2.17 | 99.7 |
| 829 | 2-(3-((4-(1-(4-(2,3-Dimethylphenoxy)butanoyl)-1,2,3,4-tetrahydroquinolin-5-yl)-1H-pyrazol-1-yl)methyl)-N-methylbenzamido)ethanesulfonic acid | | 645.1 | 1.55 | 99.3 |
| 830 | 4-(2,3-Dimethylphenoxy)-1-(5-(1-(3-(3-(hydroxymethyl)piperidine-1-carbonyl)benzyl)-1H-pyrazol-4-yl)-3,4-dihydroquinolin-1(2H)-yl)butan-1-one | | 621.1 | 1.94 | 99.0 |

TABLE 22-continued

| Example | Name | R | LCMS, [M + H]⁺ | HPLC-3: Rt (min) | Purity (%) |
|---|---|---|---|---|---|
| 831 | 4-(2,3-Dimethylphenoxy)-1-(5-(1-(3-(4-hydroxy-4-phenylpiperidine-1-carbonyl)benzyl)-1H-pyrazol-4-yl)-3,4-dihydroquinolin-1(2H)-yl)butan-1-one | | 683.2 | 2.14 | 99.3 |
| 832 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)-3,3-dimethylbutanoic acid | | 637.1 | 2.10 | 99.5 |
| 833 | 3-(3-((4-(1-(4-(2,3-Dimethylphenoxy)butanoyl)-1,2,3,4-tetrahydroquinolin-5-yl)-1H-pyrazol-1-yl)methyl)benzamido)-2-fluoropropanoic acid | | 613.3 | 2.04 | 99.6 |
| 834 | 3-(3-((4-(1-(4-(2,3-Dimethylphenoxy)butanoyl)-1,2,3,4-tetrahydroquinolin-5-yl)-1H-pyrazol-1-yl)methyl)benzamido)-4-ethylhexanoic acid | | 665.4 | 2.27 | 100 |
| 835 | 3-((4-(1-(4-(2,3-Dimethylphenoxy)butanoyl)-1,2,3,4-tetrahydroquinolin-5-yl)-1H-pyrazol-1-yl)methyl)-N-(3-methylisoxazol-5-yl)benzamide | | 604.3 | 2.46 | 98.4 |
| 836 | 4-(2,3-Dimethylphenoxy)-1-(5-(1-(3-(4-(hydroxymethyl)piperidine-1-carbonyl)benzyl)-1H-pyrazol-4-yl)-3,4-dihydroquinolin-1(2H)-yl)butan-1-one | | 621.3 | 2.35 | 100 |

TABLE 22-continued

| Example | Name | R | LCMS, [M + H]+ | HPLC-3: Rt (min) | Purity (%) |
|---|---|---|---|---|---|
| 837 | 1-(3-((4-(1-(4-(2,3-Dimethylphenoxy)butanoyl)-1,2,3,4-tetrahydroquinolin-5-yl)-1H-pyrazol-1-yl)methyl)benzoyl)azetidine-3-carboxylic acid | | 607.2 | 2.11 | 96.9 |
| 838 | 3-((4-(1-(4-(2,3-Dimethylphenoxy)butanoyl)-1,2,3,4-tetrahydroquinolin-5-yl)-1H-pyrazol-1-yl)methyl)-N-(2-hydroxybenzyl)benzamide | | 629.3 | 2.49 | 98.9 |
| 839 | 4-(3-((4-(1-(4-(2,3-Dimethylphenoxy)butanoyl)-1,2,3,4-tetrahydroquinolin-5-yl)-1H-pyrazol-1-yl)methyl)benzamido)cyclopent-2-enecarboxylic acid | | 633.3 | 2.32 | 98.7 |
| 840 | (R)-4-(3-((4-(1-(4-(2,3-Dimethylphenoxy)butanoyl)-1,2,3,4-tetrahydroquinolin-5-yl)-1H-pyrazol-1-yl)methyl)benzamido)-3-hydroxybutanoic acid | | 625.3 | 2.06 | 96.3 |
| 841 | 4-((3-((4-(1-(4-(2,3-Dimethylphenoxy)butanoyl)-1,2,3,4-tetrahydroquinolin-5-yl)-1H-pyrazol-1-yl)methyl)benzamido)methyl)-2,5-dimethylfuran-3-carboxylic acid | | 675.2 | 2.29 | 100 |
| 842 | 3-(3-((4-(1-(4-(2,3-Dimethylphenoxy)butanoyl)-1,2,3,4-tetrahydroquinolin-5-yl)-1H-pyrazol-1-yl)methyl)-N-methylbenzamido)propanoic acid | | 609.3 | 2.11 | 100 |

TABLE 22-continued

| Example | Name | R | LCMS, [M + H]⁺ | HPLC-3: Rt (min) | Purity (%) |
|---|---|---|---|---|---|
| 843 | 3-(3-((4-(1-(4-(2,3-Dimethylphenoxy)butanoyl)-1,2,3,4-tetrahydroquinolin-5-yl)-1H-pyrazol-1-yl)methyl)benzamido)-4,4,4-trifluorobutanoic acid | | 663.2 | 2.18 | 100 |
| 844 | 3-(3-((4-(1-(4-(2,3-Dimethylphenoxy)butanoyl)-1,2,3,4-tetrahydroquinolin-5-yl)-1H-pyrazol-1-yl)methyl)benzamido)-4-phenylbutanoic acid | | 685.3 | 2.25 | 100 |
| 845 | 3-((4-(1-(4-(2,3-Dimethylphenoxy)butanoyl)-1,2,3,4-tetrahydroquinolin-5-yl)-1H-pyrazol-1-yl)methyl)-N-(2-(N-phenylsulfamoyl)ethyl)benzamide | | 706.3 | 2.46 | 100 |
| 846 | 3-((4-(1-(4-(2,3-Dimethylphenoxy)butanoyl)-1,2,3,4-tetrahydroquinolin-5-yl)-1H-pyrazol-1-yl)methyl)-N-(3-hydroxybenzyl)benzamide | | 629.1 | 1.92 | 95.1 |
| 847 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)-3-methylbutanoic acid | | 623.2 | 2.03 | 100 |

TABLE 22-continued

| Example | Name | R | LCMS, [M + H]+ | HPLC-3: Rt (min) | Purity (%) |
|---|---|---|---|---|---|
| 848 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)-3-phenylpropanoic acid | | 671.2 | 2.10 | 99.3 |
| 849 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)-4-(methylthio)butanoic acid | | 655.1 | 2.01 | 100 |
| 850 | (S)-6-Amino-2-(3-((4-(1-(4-(2,3-dimethylphenoxy)butanoyl)-1,2,3,4-tetrahydroquinolin-5-yl)-1H-pyrazol-1-yl)methyl)benzamido)hexanoic acid | | 652.2 | 1.64 | 99.4 |
| 851 | (2S,3S)-2-(3-((4-(1-(4-(2,3-Dimethylphenoxy)butanoyl)-1,2,3,4-tetrahydroquinolin-5-yl)-1H-pyrazol-1-yl)methyl)benzamido)-3-methylpentanoic acid | | 637.2 | 2.11 | 100 |
| 852 | (R)-2-(3-((4-(1-(4-(2,3-Dimethylphenoxy)butanoyl)-1,2,3,4-tetrahydroquinolin-5-yl)-1H-pyrazol-1-yl)methyl)benzamido)-4-methylpentanoic acid | | 637.2 | 2.11 | 100 |
| 853 | (R)-1-(3-((4-(1-(4-(2,3-Dimethylphenoxy)butanoyl)-1,2,3,4-tetrahydroquinolin-5-yl)-1H-pyrazol-1-yl)methyl)benzoyl)pyrrolidine-2-carboxylic acid | | 621.1 | 1.92 | 98.9 |

TABLE 22-continued

| Example | Name | R | LCMS, [M + H]+ | HPLC-3: Rt (min) | Purity (%) |
|---|---|---|---|---|---|
| 854 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)pentanoic acid | NH-CH(CO₂H)-propyl | 623.1 | 2.04 | 100 |
| 855 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)butanoic acid | NH-CH(Et)-CO₂H | 609.1 | 1.96 | 99.3 |
| 856 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)-3-(1H-indol-3-yl)propanoic acid | NH-CH(CO₂H)-CH₂-indole | 710.2 | 1.71 | 100 |
| 857 | (S)-2-Cyclohexyl-2-(3-((4-(1-(4-(2,3-dimethylphenoxy)butanoyl)-1,2,3,4-tetrahydroquinolin-5-yl)-1H-pyrazol-1-yl)methyl)benzamido)acetic acid | NH-CH(CO₂H)-cyclohexyl | 663.2 | 2.21 | 99.5 |
| 858 | (R)-3-(3-((4-(1-(4-(2,3-Dimethylphenoxy)butanoyl)-1,2,3,4-tetrahydroquinolin-5-yl)-1H-pyrazol-1-yl)methyl)benzamido)butanoic acid | NH-CH(Me)-CH₂-CO₂H | 609.1 | 1.89 | 96.9 |
| 859 | 1-(3-((4-(1-(4-(2,3-Dimethylphenoxy)butanoyl)-1,2,3,4-tetrahydroquinolin-5-yl)-1H-pyrazol-1-yl)methyl)benzoyl)pyrrolidine-3-carboxylic acid | pyrrolidin-1-yl-3-CO₂H | 621.1 | 1.85 | 98.4 |

TABLE 22-continued

| Example | Name | R | LCMS, [M + H]+ | HPLC-3: Rt (min) | Purity (%) |
|---|---|---|---|---|---|
| 860 | (S)-3-(3-((4-(1-(4-(2,3-Dimethylphenoxy)butanoyl)-1,2,3,4-tetrahydroquinolin-5-yl)-1H-pyrazol-1-yl)methyl)benzamido)-5-methylhexanoic acid | | 651.2 | 2.11 | 98.9 |
| 861 | 1-(3-((4-(1-(4-(2,3-Dimethylphenoxy)butanoyl)-1,2,3,4-tetrahydroquinolin-5-yl)-1H-pyrazol-1-yl)methyl)benzoyl)piperidine-4-carboxylic acid | | 935.2 | 1.88 | 96.7 |
| 862 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)-2-phenylacetic acid | | 657.2 | 2.07 | 100 |
| 863 | (R)-2-(3-((4-(1-(4-(2,3-Dimethylphenoxy)butanoyl)-1,2,3,4-tetrahydroquinolin-5-yl)-1H-pyrazol-1-yl)methyl)benzamido)-3-phenylpropanoic acid | | 971.1 | 2.10 | 100 |
| 864 | (S)-2-(3-((4-(1-(4-(2,3-Dimethylphenoxy)butanoyl)-1,2,3,4-tetrahydroquinolin-5-yl)-1H-pyrazol-1-yl)methyl)benzamido)propanoic acid | | 595.1 | 1.89 | 98.8 |
| 865 | (S)-3-(3-((4-(1-(4-(2,3-Dimethylphenoxy)butanoyl)-1,2,3,4-tetrahydroquinolin-5-yl)-1H-pyrazol-1-yl)methyl)benzamido)butanoic acid | | 609.1 | 1.89 | 97.7 |
| 866 | (S)-1-(3-((4-(1-(4-(2,3-Dimethylphenoxy)butanoyl)-1,2,3,4-tetrahydroquinolin-5-yl)-1H-pyrazol-1-yl)methyl)benzoyl)pyrrolidine-2-carboxylic acid | | 621.2 | 1.92 | 98.4 |

TABLE 22-continued

| Example | Name | R | LCMS, [M + H]⁺ | HPLC-3: Rt (min) | Purity (%) |
|---|---|---|---|---|---|
| 867 | (S)-5-Amino-2-(3-((4-(1-(4-(2,3-dimethylphenoxy)butanoyl)-1,2,3,4-tetrahydroquinolin-5-yl)-1H-pyrazol-1-yl)methyl)benzamido)-5-oxopentanoic acid | | 652.1 | 1.72 | 95.9 |
| 868 | 3-(3-((4-(1-(4-(2,3-Dimethylphenoxy)butanoyl)-1,2,3,4-tetrahydroquinolin-5-yl)-1H-pyrazol-1-yl)methyl)benzamido)-3-phenylpropanoic acid | | 671.2 | 1.69 | 100 |
| 869 | (S)-4-(2,3-dimethylphenoxy)-1-(5-(1-(3-(3-hydroxypyrrolidine-1-carbonyl)benzyl)-1H-pyrazol-4-yl)-3,4-dihydroquinolin-1(2H)-yl)butan-1-one | | 593.2 | 1.81 | 100 |
| 870 | (1S,2R)-2-(3-((4-(1-(4-(2,3-Dimethylphenoxy)butanoyl)-1,2,3,4-tetrahydroquinolin-5-yl)-1H-pyrazol-1-yl)methyl)benzamido)cyclopentanecarboxylic acid | | 635.2 | 1.62 | 100 |
| 871 | 2-((3-((4-(1-(4-(2,3-Dimethylphenoxy)butanoyl)-1,2,3,4-tetrahydroquinolin-5-yl)-1H-pyrazol-1-yl)methyl)benzamido)methyl)-2-ethylbutanoic acid | | 651.2 | 2.10 | 100 |
| 872 | N-(1-(1H-Tetrazol-5-yl)ethyl)-3-((4-(1-(4-(2,3-dimethylphenoxy)butanoyl)-1,2,3,4-tetrahydroquinolin-5-yl)-1H-pyrazol-1-yl)methyl)benzamide | | 619.2 | 1.59 | 93.2 |

TABLE 22-continued

| Example | Name | R | LCMS, [M + H]⁺ | HPLC-3: Rt (min) | Purity (%) |
|---|---|---|---|---|---|
| 873 | 1-(3-((4-(1-(4-(2,3-Dimethylphenoxy)butanoyl)-1,2,3,4-tetrahydroquinolin-5-yl)-1H-pyrazol-1-yl)methyl)benzoyl)-1,2,5,6-tetrahydropyridine-3-carboxylic acid | | 633.2 | 1.57 | 93.2 |
| 874 | 3-(3-((4-(1-(4-(2,3-Dimethylphenoxy)butanoyl)-1,2,3,4-tetrahydroquinolin-5-yl)-1H-pyrazol-1-yl)methyl)benzamido)cyclohexanecarboxylic acid | | 649.3 | 2.06 | 100 |
| 875 | 4-(2-(3-((4-(1-(4-(2,3-Dimethylphenoxy)butanoyl)-1,2,3,4-tetrahydroquinolin-5-yl)-1H-pyrazol-1-yl)methyl)benzamido)ethyl)benzoic acid | | 671.3 | 1.65 | 100 |
| 876 | 3-(3-((4-(1-(4-(2,3-Dimethylphenoxy)butanoyl)-1,2,3,4-tetrahydroquinolin-5-yl)-1H-pyrazol-1-yl)methyl)benzamido)-5-methylhexanoic acid | | 651.3 | 1.74 | 100 |
| 877 | (R)-2-(3-((4-(1-(4-(2,3-Dimethylphenoxy)butanoyl)-1,2,3,4-tetrahydroquinolin-5-yl)-1H-pyrazol-1-yl)methyl)benzamido)-3,3-dimethylbutanoic acid | | 637.2 | 2.19 | 100 |

The compounds exemplified in Table 23 were prepared in a manner analogous to Example 326.

TABLE 23

| Example | Name | —X—Y | R | LCMS, [M + H]+ | 1H NMR (400 MHz, CDCl3) δ | HPLC-1: Rt min, purity; HPLC-2: Rt min, purity |
|---|---|---|---|---|---|---|
| 878 | 2-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)acetic acid | | Me | 593.1 | 7.87 (d, J = 7.7 Hz, 1H), 7.84 (s, 1H), 7.74 (s, 1H), 7.61 (s, 1H), 7.51-7.38 (m, 2H), 7.21-7.08 (m, 2H), 7.02-6.94 (m, 2H), 6.73 (d, J = 7.4 Hz, 1H), 6.63 (d, J = 7.4 Hz, 1H), 5.51-5.39 (m, 2H), 5.24-4.77 (m, 1H), 4.24 (d, J = 5.2 Hz, 2H), 3.96 (br. s., 1H), 3.88 (br. s., 1H), 2.85-2.69 (m, 2H), 2.61 (br. s., 1H), 2.30-1.97 (m, 8H), 1.90 (br. s., 3H), 1.81-1.61 (m, 1H), 0.95 (d, J = 5.5 Hz, 1H), 0.58 (br. s., 1H) | 10.5 min, 98.6% 10.0 min, 99.1% |
| 879 | (R)-2-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)succinic acid | | Me | 651.4 | 7.80 (t, J = 8.0 Hz, 2H), 7.72 (s, 1H), 7.63 (s, 1H), 7.39 (t, J = 7.7 Hz, 1H), 7.28 (d, J = 8.0 Hz, 1H), 7.16 (br. s., 1H), 7.14-7.08 (m, 1H), 6.98 (t, J = 7.3 Hz, 2H), 6.72 (d, J = 7.2 Hz, 1H), 6.61 (d, J = 6.9 Hz, 1H), 5.57-5.36 (m, 2H), 5.08-5.01 (m, 1H), 3.95 (br. s., 1H), 3.86 (br. s., 1H), 3.16-3.05 (m, 1H), 3.04-2.94 (m, 1H), 2.84-2.68 (m, 2H), 2.62 (br. s., 1H), 2.24-2.06 (m, 6H), 2.01 (br. s., 1H), 1.89 (br. s., 3H), 1.70 (br. s., 1H), 0.95 (br. s., 1H), 0.56 (br. s., 1H) | 7.5 min, 95.9% 7.5 min, 99.8% |
| 880 | (S)-2-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)succinic acid | | Me | 651.4 | 7.81 (t, J = 6.9 Hz, 3H), 7.73 (s, 1H), 7.63 (s, 1H), 7.43-7.37 (m, 1H), 7.31-7.26 (m, 1H), 7.16 (br. s., 1H), 7.14-7.08 (m, 1H), 7.03-6.94 (m, 1H), 6.72 (d, J = 6.9 Hz, 1H), 6.61 (d, J = 6.9 Hz, 1H), 5.55-5.39 (m, 2H), 5.08-5.01 (m, 1H), 3.95 (br. s., 1H), 3.86 (br. s., 1H), 3.14-3.05 (m, 1H), 3.04-2.94 (m, 1H), 2.81-2.70 (m, 2H), 2.61 (br. s., 1H), 2.17-2.04 (m, 6H), 2.01 (s, 1H), 1.89 (br. s., 3H), 1.71 (br. s., 1H), 0.94 (br. s., 1H), 0.56 (br. s., 1H) | 7.4 min, 95.5% 7.4 min, 100% |

TABLE 23-continued

| Example | Name | —X—Y | R | LCMS, [M + H]+ | ¹H NMR (400 MHz, CDCl₃) δ | HPLC-1: Rt min, purity; HPLC-2: Rt min, purity |
|---|---|---|---|---|---|---|
| 881 | Diethyl 2,2'-(3-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)benzoylazanediyl)diacetate | benzamide with N(CH₂CO₂Et)₂ | Me | 707.4 | 7.72-7.67 (m, 1H), 7.55-7.50 (m, 1H), 7.43-7.37 (m, 3H), 7.36-7.30 (m, 1H), 7.17 (d, J = 7.4 Hz, 1H), 7.10 (t, J = 7.8 Hz, 1H), 7.00 (t, J = 7.8 Hz, 1H), 6.95 (br. s., 1H), 6.73 (d, J = 7.4 Hz, 1H), 6.64 (d, J = 7.7 Hz, 1H), 5.36 (s, 2H), 4.30 (s, 2H), 4.23 (q, J = 7.2 Hz, 2H), 4.18 (q, J = 7.2 Hz, 2H), 4.09 (s, 2H), 3.98 (d, J = 4.1 Hz, 1H), 3.89 (br. s., 1H), 2.88-2.68 (m, 2H), 2.58 (br. s., 1H), 2.28-2.06 (m, 7H), 2.01-1.88 (m, 3H), 1.71 (d, J = 5.0 Hz, 1H), 1.30 (t, J = 7.2 Hz, 3H), 1.24 (t, J = 7.2 Hz, 3H), 1.02-0.90 (m, 1H), 0.68-0.37 (m, 1H) | 13.7 min, 98.1% 12.7 min, 99.2% |
| 882 | 2,2'-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzoylazanediyl) diacetic acid | benzamide with N(CH₂CO₂H)₂ | Me | 651.4 | 7.78 (s, 1H), 7.62 (br. s., 1H), 7.44-7.38 (m, 2H), 7.36 (br. s., 1H), 7.30 (br. s., 1H), 7.17 (br. s., 1H), 7.14-7.09 (m, 1H), 6.99 (br. s., 2H), 6.72 (d, J = 6.3 Hz, 1H), 6.62 (br. s., 1H), 5.44 (s, 2H), 4.29 (br. s., 2H), 4.08 (br. s., 2H), 3.95 (br. s., 1H), 3.86 (br. s., 1H), 2.77 (d, J = 5.2 Hz, 2H), 2.62 (br. s., 1H), 2.29-1.97 (m, 7H), 1.90 (br. s., 3H), 1.72 (br. s., 1H), 0.97 (br. s., 1H), 0.57 (br. s., 1H) | 10.6 min, 99.1% 10.2 min, 100% |
| 883 | (S)-3-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)-4-methoxy-4-oxobutanoic acid | benzamide with NH-CH(CO₂Me)-CH₂CO₂H | Me | 665.4 | 7.83-7.71 (m, 3H), 7.58 (br. s., 1H), 7.49-7.40 (m, 2H), 7.38-7.30 (m, 1H), 7.21-7.16 (m, 1H), 7.15-7.08 (m, 1H), 7.04-6.94 (m, 2H), 6.73 (d, J = 7.2 Hz, 1H), 6.62 (d, J = 7.7 Hz, 1H), 5.45 (d, J = 3.3 Hz, 2H), 5.05 (d, J = 7.7 Hz, 1H), 3.96 (br. s., 1H), 3.87 (br. s., 1H), 3.79 (s, 3H), 3.22-3.12 (m, 1H), 3.04 (d, J = 16.2 Hz, 1H), 2.84-2.69 (m, 2H), 2.64 (br. s., 1H), 2.25-2.07 (m, 6H), 2.07-1.98 (m, 1H), 1.89 (br. s., 3H), 1.73 (br. s., 1H), 0.96 (br. s., 1H), 0.58 (br. s., 1H) | 11.4 min, 99.2% 10.9 min, 98.4% |

TABLE 23-continued

| Example | Name | —X—Y | R | LCMS, [M + H]+ | 1H NMR (400 MHz, CDCl3) δ | HPLC-1: Rt min, purity; HPLC-2: Rt min, purity |
|---|---|---|---|---|---|---|
| 884 | 1-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzoyl)-4-hydroxypiperidine-4-carboxylic acid | [3-substituted benzoyl linked to 4-hydroxypiperidine-4-carboxylic acid] | Me | 663.5 | 8.39 (t, J = 5.5 Hz, 1H), 8.03 (s, 1H), 7.75 (s, 1H), 7.69 (d, J = 7.2 Hz, 1H), 7.60 (s, 1H), 7.40-7.30 (m, 2H), 7.15 (br. s., 1H), 7.10-6.99 (m, 2H), 6.90 (t, J = 7.8 Hz, 1H), 6.62 (d, J = 7.4 Hz, 2H), 5.36 (d, J = 1.4 Hz, 2H), 3.85 (br. s., 1H), 3.78-3.66 (m, 2H), 3.62 (tt, J = 8.1, 4.0 Hz, 1H), 2.64 (br. s., 2H), 2.11-1.98 (m, 5H), 1.97-1.82 (m, 4H), 1.79-1.62 (m, 6H), 1.61-1.52 (m, 1H), 1.48-1.34 (m, 3H), 1.30-1.23 (m, 1H), 0.90-0.76 (m, 1H), 0.33 (br. s., 1H) | 7.5 min, 97.3% 7.3 min, 99.4% |
| 885 | (3R,5R)-7-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)-3,5-dihydroxyheptanoic acid | [3-substituted benzamide linked to 3,5-dihydroxyheptanoic acid] | Me | 695.5 | 8.10-8.02 (m, 3H), 7.64 (s, 1H), 7.59 (d, J = 7.7 Hz, 1H), 7.54-7.45 (m, 3H), 7.35-7.29 (m, 1H), 7.16 (td, J = 7.6, 1.1 Hz, 1H), 7.12-7.09 (m, 1H), 7.08-7.04 (m, 2H), 7.02 (d, J = 2.5 Hz, 1H), 6.43 (d, J = 2.8 Hz, 1H), 5.42 (s, 2H), 4.20 (br. s., 2H), 3.78-3.66 (m, 2H), 2.63 (t, J = 6.5 Hz, 2H), 2.45-2.39 (m, 2H), 2.26-2.15 (m, 2H), 1.89-1.80 (m, 2H) | 8.9 min, 98.9% 8.7 min, 100% |
| 886 | 2-Amino-3-(3-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)benzamido)propanoic acid | [3-substituted benzamide linked to 2-amino-propanoic acid] | Me | 622.3 | 8.35 (br. s., 1H), 7.98 (s, 1H), 7.85 (s, 1H), 7.82-7.78 (m, 1H), 7.69 (d, J = 0.6 Hz, 1H), 7.50-7.48 (m, 1H), 7.24-7.19 (m, 1H), 7.18-7.09 (m, 3H), 6.98 (t, J = 7.8 Hz, 1H), 6.73 (dd, J = 7.8, 2.9 Hz, 1H), 5.45 (s, 2H), 4.59 (d, J = 11.6 Hz, 1H), 4.07 (dd, J = 6.6, 5.0 Hz, 1H), 4.02-3.91 (m, 3H), 3.85-3.70 (m, 2H), 3.05-2.94 (m, 1H), 2.76-2.67 (m, 2H), 2.19 (s, 3H), 2.17-2.09 (m, 2H), 2.08-2.00 (m, 2H), 1.99 (s, 3H), 1.86-1.75 (m, 1H), 1.01 (td, J = 8.3, 5.0 Hz, 1H), 0.54 (q, J = 4.8 Hz, 1H) | 7.9 min, 98.1% 9.1 min, 98.1% |
| 887 | (R)-2-Amino-3-(3-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)benzamido)propanoic acid | [3-substituted benzamide linked to (R)-2-amino-propanoic acid] | Me | 622.3 | 8.35 (br. s., 1H), 7.98 (s, 1H), 7.85 (s, 1H), 7.82-7.78 (m, 1H), 7.69 (d, J = 0.6 Hz, 1H), 7.50-7.48 (m, 1H), 7.24-7.19 (m, 1H), 7.18-7.09 (m, 3H), 6.98 (t, J = 7.8 Hz, 1H), 6.73 (dd, J = 7.8, 2.9 Hz, 1H), 5.45 (s, 2H), 4.59 (d, J = 11.6 Hz, 1H), 4.07 (dd, J = 6.6, 5.0 Hz, 1H), 4.02-3.91 (m, 3H), 3.85-3.70 (m, 2H), 3.05-2.94 (m, 1H), 2.76-2.67 (m, 2H), 2.19 (s, 3H), 2.17-2.09 (m, 2H), 2.08-2.00 (m, 2H), 1.99 (s, 3H), 1.86-1.75 (m, 1H), 1.01 (td, J = 8.3, 5.0 Hz, 1H), 0.54 (q, J = 4.8 Hz, 1H) | 7.9 min, 96.8% 9.1 min, 97.6% |

TABLE 23-continued

| Example | Name | —X—Y | R | LCMS, [M + H]+ | 1H NMR (400 MHz, CDCl3) δ | HPLC-1: Rt min, purity; HPLC-2: Rt min, purity |
|---|---|---|---|---|---|---|
| 888 | (S)-2-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)-3-(methylsulfonamido)propanoic acid | | Me | 700.3 | 8.09 (s, 1H), 7.97-7.90 (m, 1H), 7.85 (d, J = 6.9 Hz, 1H), 7.72 (s, 1H), 7.60 (s, 1H), 7.45-7.42 (m, 2H), 7.12 (dt, J = 15.5, 7.5 Hz, 2H), 7.02-6.93 (m, 2H), 6.73 (d, J = 7.4 Hz, 1H), 6.63 (d, J = 7.2 Hz, 1H), 6.11 (t, J = 6.6 Hz, 1H), 5.49-5.39 (m, 2H), 5.08-5.01 (m, 1H), 3.97 (br. s., 1H), 3.92-3.79 (m, 2H), 3.74-3.61 (m, 1H), 2.88 (s, 3H), 2.82-2.68 (m, 2H), 2.58 (br. s., 1H), 2.25-2.08 (m, 5H), 2.06-1.98 (m, 3H), 1.91 (br. s., 2H), 1.76-1.64 (m, 1H), 0.98-0.90 (m, 1H), 0.57 (br. s., 1H) | 11.0 min, 98.4% 10.1 min, 98.4% |
| 889 | (S)-3-(Cyclopropanesulfonamido)-2-(3-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)benzamido)propanoic acid | | Me | 726.3 | 8.09 (s, 1H), 7.93-7.88 (m, 2H), 7.72 (s, 1H), 7.57 (s, 1H), 7.44-7.38 (m, 2H), 7.20-7.06 (m, 2H), 7.04-6.86 (m, 2H), 6.73 (d, J = 7.4 Hz, 1H), 6.63 (d, J = 7.2 Hz, 1H), 6.10 (t, J = 6.9 Hz, 1H), 5.49-5.34 (m, 2H), 5.06-5.00 (m, 1H), 3.97 (d, J = 4.7 Hz, 2H), 3.92-3.78 (m, 2H), 3.66 (ddd, J = 13.8, 6.6, 3.3 Hz, 1H), 2.83-2.68 (m, 2H), 2.57 (br. s., 1H), 2.34 (tt, J = 8.0, 4.8 Hz, 1H), 2.26-2.08 (m, 5H), 2.04-1.96 (m, 1H), 1.92 (br. s., 3H), 1.75-1.62 (m, 1H), 1.05-0.79 (m, 6H), 0.56 (br. s., 1H) | 11.5 min, 98.5% 10.5 min, 98.8% |
| 890 | (S)-3-Amino-2-(3-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)benzamido)propanoic acid | | Me | 622.3 | 8.38 (br. s., 1H), 8.10 (br. s., 2H), 7.83 (br. s., 1H), 7.74-7.57 (m, 3H), 7.25-7.14 (m, 2H), 7.14-7.01 (m, 2H), 6.95 (d, J = 6.9 Hz, 2H), 6.69 (br. s., 1H), 6.59 (br. s., 1H), 5.29 (br. s., 2H), 4.85 (br. s., 1H), 3.91 (br. s., 1H), 3.83 (br. s., 1H), 3.48 (br. s., 1H), 3.36 (br. s., 1H), 2.72 (br. s., 2H), 2.54 (br. s., 1H), 2.26-2.03 (m, 6H), 2.02-1.80 (m, 4H), 1.63 (br. s., 1H), 0.96-0.80 (m, 2H), 0.51 (br. s., 1H) | 7.7 min, 98.3% 9.1 min, 99.2% |

TABLE 23-continued

| Example | Name | —X—Y | R | LCMS, [M + H]+ | 1H NMR (400 MHz, CDCl3) δ | HPLC-1: Rt min, purity; HPLC-2: Rt min, purity |
|---|---|---|---|---|---|---|
| 891 | 3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)-N-((S)-2-oxotetrahydrofuran-3-yl)benzamide | | Me | 619.2 | 7.77 (s, 1H), 7.76-7.72 (m, 1H), 7.72-7.69 (m, 1H), 7.57-7.53 (m, 1H), 7.47-7.42 (m, 2H), 7.20-7.14 (m, 1H), 7.13-7.08 (m, 1H), 7.03-6.97 (m, 1H), 6.96 (br. s., 1H), 6.76-6.67 (m, 2H), 6.63 (d, J = 7.7 Hz, 1H), 5.40 (s, 2H), 5.00 (br. s., 1H), 4.74-4.67 (m, 1H), 4.56-4.50 (m, 1H), 4.38-4.31 (m, 1H), 3.97 (d, J = 4.1 Hz, 1H), 3.89 (br. s., 1H), 3.02-2.92 (m, 1H), 2.82-2.70 (m, 2H), 2.58 (br. s., 1H), 2.31-2.22 (m, 1H), 2.21-2.06 (m, 6H), 1.92 (br. s., 3H), 1.71 (d, J = 5.5 Hz, 1H), 0.97-0.89 (m, 1H), 0.58 (br. s., 1H) | 12.1 min, 95.0% 10.9 min, 95.0% |
| 892 | (S)-2-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzamido)-4-(methylthio)butanoic acid | | Me | 667.3 | 7.89 (s, 1H), 7.83 (d, J = 7.7 Hz, 1H), 7.72 (s, 1H), 7.58 (s, 1H), 7.47-7.37 (m, 3H), 7.18-7.08 (m, 2H), 7.04-6.91 (m, 2H), 6.73 (d, J = 7.4 Hz, 1H), 6.63 (d, J = 8.0 Hz, 1H), 5.50-5.34 (m, 2H), 4.89 (td, J = 7.4, 5.1 Hz, 1H), 3.97 (br. s., 1H), 3.88 (br. s., 1H), 2.83-2.69 (m, 2H), 2.68-2.50 (m, 3H), 2.33-2.24 (m, 1H), 2.23-2.10 (m, 6H), 2.07 (s, 3H), 1.91 (br. s., 3H), 1.71 (d, J = 5.0 Hz, 1H), 1.44-1.36 (m, 1H), 0.99-0.89 (m, 1H), 0.57 (br. s., 1H) | 12.4 min, 98.2% 11.1 min, 98.3% |
| 893 | (2S,4R)-1-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)benzoyl)-4-hydroxypyrrolidine-2-carboxylic acid | | Me | 649.3 | 7.71 (s, 1H), 7.58 (s, 1H), 7.51-7.47 (m, 2H), 7.42 (t, J = 7.8 Hz, 1H), 7.37-7.32 (m, 1H), 7.16 (d, J = 7.7 Hz, 1H), 7.13-7.07 (m, 1H), 7.03-6.92 (m, 2H), 6.73 (d, J = 7.4 Hz, 1H), 6.63 (d, J = 7.4 Hz, 1H), 5.40 (s, 2H), 4.88 (t, J = 8.3 Hz, 1H), 4.45 (br. s., 1H), 3.96 (br. s., 1H), 3.88 (br. s., 1H), 3.68-3.62 (m, 1H), 3.61-3.52 (m, 1H), 2.81-2.68 (m, 2H), 2.57 (br. s., 1H), 2.45 (ddd, J = 13.5, 8.6, 4.5 Hz, 1H), 2.33-2.25 (m, 1H), 2.24-2.05 (m, 8H), 1.92 (br. s., 3H), 1.70 (br. s., 1H), 0.98-0.90 (m, 1H), 0.57 (br. s., 1H) | 10.3 min, 99.5% 9.7 min, 99.1% |

TABLE 23-continued

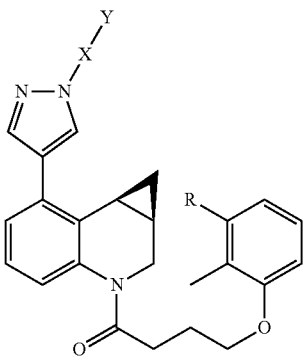

| Example | Name | —X—Y | R | LCMS, [M + H]+ | 1H NMR (400 MHz, CDCl3) δ | HPLC-1: Rt min, purity; HPLC-2: Rt min, purity |
|---|---|---|---|---|---|---|
| 894 | (S)-2-(3-((4-((1aR,7bS)-3-(4-(2,3-Dimethylphenoxy) butanoyl)-1a,2,3,7b-tetrahydro-1H-cyclopropa[c] quinolin-7-yl)-1H-pyrazol-1-yl)methyl)benzamido)-4-hydroxybutanoic acid | | Me | 637.2 | 8.03 (s, 1H), 7.99 (d, J = 5.0 Hz, 1H), 7.69 (s, 1H), 7.64 (d, J = 7.4 Hz, 1H), 7.60 (s, 1H), 7.42-7.33 (m, 2H), 7.15 (br. s., 1H), 7.10-7.00 (m, 2H), 6.90 (t, J = 7.8 Hz, 1H), 6.62 (d, J = 7.4 Hz, 2H), 5.38 (s, 2H), 4.76 (br. s., 1H), 3.85 (br. s., 2H), 3.73 (br. s., 1H), 3.50-3.44 (m, 1H), 3.44-3.37 (m, 1H), 2.65 (d, J = 14.3 Hz, 2H), 2.10-1.97 (m, 5H), 1.96-1.83 (m, 3H), 1.82-1.60 (m, 6H), 0.92-0.74 (m, 1H), 0.32 (br. s., 1H) | 10.5 min, 99.6% 9.8 min, 99.8% |
| 895 | (S)-2-(3-((4-((1aR,7bS)-3-(4-(2,3-Dimethylphenoxy) butanoyl)-1a,2,3,7b-tetrahydro-1H-cyclopropa[c] quinolin-7-yl)-1H-pyrazol-1-yl)methyl)benzamido)-4-(methylsulfonyl)butanoic acid | | Me | 699.2 | 7.96 (s, 1H), 7.85 (d, J = 8.0 Hz, 1H), 7.74 (s, 1H), 7.64 (s, 1H), 7.59 (d, J = 7.7 Hz, 1H), 7.48-7.43 (m, 1H), 7.37 (d, J = 7.7 Hz, 1H), 7.20-7.09 (m, 2H), 7.03-6.95 (m, 2H), 6.73 (d, J = 7.4 Hz, 1H), 6.64 (d, J = 7.7 Hz, 1H), 5.54-5.35 (m, 2H), 5.18-4.92 (m, 1H), 4.86 (td, J = 7.9, 5.1 Hz, 1H), 3.97 (br. s., 1H), 3.93-3.82 (m, 1H), 3.29-3.19 (m, 1H), 3.18-3.09 (m, 1H), 2.90 (s, 3H), 2.83-2.70 (m, 2H), 2.58 (br. s., 1H), 2.51-2.39 (m, 1H), 2.33-2.24 (m, 1H), 2.24-2.08 (m, 5H), 2.08-1.98 (m, 2H), 1.92 (br. s., 3H), 1.73 (br. s., 1H), 0.96 (d, J = 6.1 Hz, 1H), 0.59 (br. s., 1H) | 11.0 min, 99.6% 10.2 min, 99.5% |
| 896 | Diethyl 2,2'-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl) benzoylazanediyl)diacetate | | Cl | 727.5 | 7.71 (s, 1H), 7.54 (s, 1H), 7.44-7.37 (m, 3H), 7.36-7.31 (m, 1H), 7.22-7.17 (m, 1H), 7.12 (t, J = 7.7 Hz, 1H), 7.06-7.00 (m, 1H), 6.97-6.90 (m, 2H), 6.68 (d, J = 8.2 Hz, 1H), 5.38 (s, 2H), 4.30 (s, 2H), 4.28-4.21 (m, 2H), 4.21-4.14 (m, 2H), 4.10 (s, 2H), 4.01 (dt, J = 9.1, 4.8 Hz, 1H), 3.92-3.82 (m, 1H), 2.79-2.70 (m, 2H), 2.66-2.56 (m, 1H), 2.21-2.08 (m, 3H), 2.01 (br. s., 3H), 1.73-1.61 (m, 3H), 1.31 (t, J = 7.1 Hz, 3H), 1.27-1.21 (m, 3H), 0.87 (br. s., 1H), 0.47 (br. s., 1H) | 12.3 min, 98.8% 11.2 min, 98.7% |

TABLE 23-continued

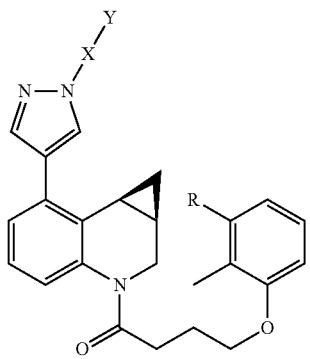

| Example | Name | —X—Y | R | LCMS, [M + H]+ | ¹H NMR (400 MHz, CDCl₃) δ | HPLC-1: Rt min, purity; HPLC-2: Rt min, purity |
|---|---|---|---|---|---|---|
| 897 | (R)-Dimethyl 2-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)benzamido)succinate | 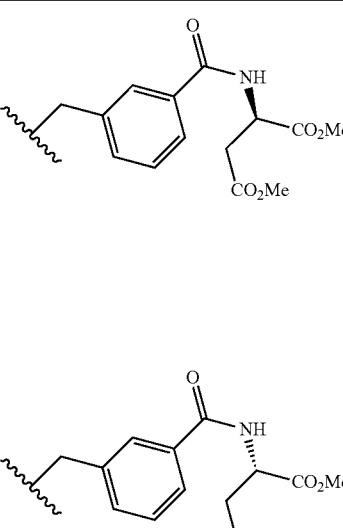 | Cl | 699.5 | 7.79 (s, 1H), 7.74 (dt, J = 7.0, 1.7 Hz, 1H), 7.72 (s, 1H), 7.56 (s, 1H), 7.49-7.41 (m, 2H), 7.25 (d, J = 8.2 Hz, 1H), 7.20 (d, J = 7.7 Hz, 1H), 7.15-7.09 (m, 1H), 7.06-6.99 (m, 1H), 6.98-6.90 (m, 2H), 6.67 (d, J = 8.2 Hz, 1H), 5.42 (s, 2H), 5.09-5.01 (m, 1H), 4.01 (dt, J = 9.2, 4.5 Hz, 1H), 3.93-3.84 (m, 1H), 3.80 (s, 3H), 3.70 (s, 3H), 3.15 (dd, J = 17.3, 4.1 Hz, 1H), 3.01-2.94 (m, 1H), 2.79-2.69 (m, 1H), 2.68-2.55 (m, 1H), 2.23-2.07 (m, 3H), 2.01 (br. s., 3H), 1.70 (br. s., 1H), 0.86 (br. s., 1H), 0.47 (br. s., 1H) | 11.4 min, 99.1% 10.5 min, 99.4% |
| 898 | (S)-Dimethyl 2-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)benzamido)succinate | 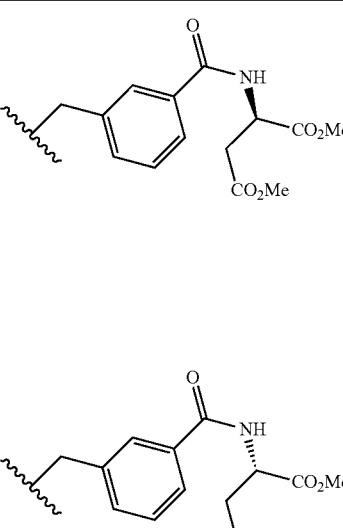 | Cl | 699.5 | 7.80 (s, 1H), 7.74 (dt, J = 7.0, 1.7 Hz, 1H), 7.72 (s, 1H), 7.56 (s, 1H), 7.50-7.41 (m, 2H), 7.25 (d, J = 8.2 Hz, 1H), 7.20 (d, J = 7.1 Hz, 1H), 7.16-7.09 (m, 1H), 7.06-6.99 (m, 1H), 6.97-6.90 (m, 2H), 6.67 (d, J = 8.2 Hz, 1H), 5.42 (s, 2H), 5.09-5.02 (m, 1H), 4.04-3.96 (m, 1H), 3.93-3.85 (m, 1H), 3.80 (s, 3H), 3.70 (s, 3H), 3.19-3.11 (m, 1H), 3.02-2.94 (m, 1H), 2.79-2.69 (m, 1H), 2.62 (d, J = 7.1 Hz, 1H), 2.09 (br. s., 3H), 2.01 (br. s., 3H), 1.70 (br. s., 1H), 0.86 (br. s., 1H), 0.46 (br. s., 1H) | 11.4 min, 99.4% 10.5 min, 99.7% |
| 899 | (S)-Dimethyl 2-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)benzamido)pentanedioate | 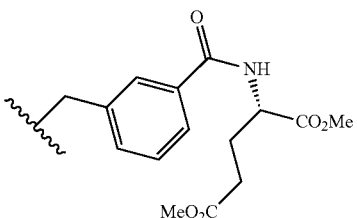 | Cl | 713.5 | 7.82 (s, 1H), 7.76 (dt, J = 7.1, 1.6 Hz, 1H), 7.72 (s, 1H), 7.56 (s, 1H), 7.50-7.41 (m, 2H), 7.22-7.16 (m, 1H), 7.15-7.07 (m, 2H), 7.06-6.99 (m, 1H), 6.93 (d, J = 7.7 Hz, 2H), 6.67 (d, J = 8.2 Hz, 1H), 5.41 (s, 2H), 4.81 (td, J = 7.7, 4.9 Hz, 1H), 4.04-3.96 (m, 1H), 3.92-3.84 (m, 1H), 3.79 (s, 3H), 3.65 (s, 3H), 2.80-2.68 (m, 2H), 2.62 (dd, J = 15.1, 8.0 Hz, 1H), 2.58-2.38 (m, 3H), 2.33 (dtd, J = 14.3, 7.1, 4.9 Hz, 1H), 2.20-2.06 (m, 4H), 2.03-1.96 (m, 3H), 1.69 (br. s., 1H), 0.90-0.80 (m, 1H), 0.47 (br. s., 1H) | 11.4 min, 99.7% 10.6 min, 99.7% |

TABLE 23-continued

| Example | Name | —X—Y | R | LCMS, [M + H]+ | $^1$H NMR (400 MHz, CDCl$_3$) δ | HPLC-1: Rt min, purity; HPLC-2: Rt min, purity |
|---|---|---|---|---|---|---|
| 900 | 2,2'-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzoylazanediyl)diacetic acid | 3-substituted benzoyl group with N(CH$_2$CO$_2$H)$_2$ | Cl | 671.3 | 7.76 (br. s., 1H), 7.66 (br. s., 1H), 7.48-7.31 (m, 3H), 7.23 (d, J = 1.6 Hz, 1H), 7.16 (br. s., 1H), 7.13-7.06 (m, 1H), 7.04-6.92 (m, 2H), 6.88 (d, J = 8.2 Hz, 1H), 6.63 (d, J = 7.7 Hz, 1H), 5.41 (br. s., 2H), 5.06-4.88 (m, 1H), 4.24 (br. s., 2H), 4.07 (br. s., 2H), 3.95 (br. s., 1H), 3.84 (br. s., 1H), 2.83-2.57 (m, 3H), 2.13 (br. s., 3H), 1.93 (br. s., 3H), 1.65 (br. s., 1H), 0.84 (br. s., 1H), 0.41 (br. s., 1H) | 9.5 min, 96.8% 9.0 min, 96.7% |
| 901 | (R)-2-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)succinic acid | 3-substituted benzamide with NH-CH(CO$_2$H)-CH$_2$CO$_2$H | Cl | 671.3 | 7.88 (br. s., 1H), 7.84-7.68 (m, 3H), 7.64 (br. s., 1H), 7.39-7.29 (m, 2H), 7.19-7.07 (m, 2H), 7.04-6.93 (m, 2H), 6.89 (d, J = 7.7 Hz, 1H), 6.64 (d, J = 7.7 Hz, 1H), 5.42 (br. s., 3H), 5.00 (br. s., 2H), 3.96 (br. s., 1H), 3.84 (br. s., 1H), 3.10-2.87 (m, 2H), 2.80-2.58 (m, 3H), 2.14 (br. s., 2H), 1.93 (br. s., 3H), 1.65 (br. s., 1H), 0.82 (br. s., 1H), 0.41 (br. s., 1H) | 9.6 min, 99.5% 9.0 min, 98.8% |
| 902 | (S)-2-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)succinic acid | 3-substituted benzamide with NH-CH(CO$_2$H)-CH$_2$CO$_2$H | Cl | 671.3 | 7.88 (br. s., 1H), 7.82-7.69 (m, 3H), 7.65 (br. s., 1H), 7.41-7.28 (m, 2H), 7.20-7.08 (m, 2H), 7.04-6.93 (m, 2H), 6.89 (d, J = 7.7 Hz, 1H), 6.63 (d, J = 7.7 Hz, 1H), 5.43 (br. s., 3H), 5.00 (br. s., 2H), 3.96 (br. s., 1H), 3.84 (br. s., 1H), 3.09-2.89 (m, 2H), 2.80-2.60 (m, 3H), 2.13 (br. s., 2H), 1.93 (br. s., 3H), 1.66 (br. s., 1H), 0.83 (br. s., 1H), 0.41 (br. s., 1H) | 9.6 min, 99.1% 9.0 min, 98.6% |
| 903 | (S)-2-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)pentanedioic acid | 3-substituted benzamide with NH-CH(CO$_2$H)-CH$_2$CH$_2$CO$_2$H | Cl | 685.3 | 7.93-7.59 (m, 4H), 7.44-7.30 (m, 2H), 7.19-7.06 (m, 2H), 7.05-6.81 (m, 3H), 6.64 (d, J = 7.7 Hz, 1H), 5.40 (br. s., 2H), 4.70 (br. s., 1H), 3.98 (d, J = 8.8 Hz, 2H), 3.85 (br. s., 1H), 2.68 (d, J = 18.7 Hz, 3H), 2.45 (br. s., 2H), 2.33-2.05 (m, 4H), 1.94 (br. s., 3H), 1.65 (br. s., 1H), 0.82 (br. s., 1H), 0.41 (br. s., 1H) | 9.6 min, 99.7% 9.1 min, 98.6% |

The compounds exemplified in Table 24 were prepared in a manner analogous to Example 80.

TABLE 24

| Example | Name | —Y | R | LCMS, [M + H]⁺ | $^1$H NMR (400 MHz, CDCl$_3$) δ | HPLC-1: Rt min, purity; HPLC-2: Rt min, purity |
|---|---|---|---|---|---|---|
| 904 | (3R,5S)-6-(3-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)-3,5-dihydroxyhexanoic acid, Na salt | | Me | 696.4 | 8.60 (s, 1H), 7.96 (s, 1H), 7.58 (s, 1H), 7.26 (s, 1H), 7.22 (d, J = 8.3 Hz, 1H), 7.18-6.98 (m, 5H), 6.90 (t, J = 7.8 Hz, 1H), 6.73 (d, J = 7.7 Hz, 1H), 6.63 (d, J = 7.7 Hz, 2H), 6.11 (t, J = 5.5 Hz, 1H), 5.24 (s, 2H), 3.91-3.80 (m, 2H), 3.73 (br. s., 1H), 3.64-3.53 (m, 1H), 3.16-3.07 (m, 1H), 2.93-2.84 (m, 1H), 2.74-2.50 (br. s., 2H), 2.17 (dd, J = 14.9, 4.4 Hz, 1H), 2.10-1.97 (m, 5H), 1.90 (d, J = 6.1 Hz, 2H), 1.81-1.61 (m, 5H), 1.48-1.33 (m, 2H), 0.92-0.77 (m, 1H), 0.33 (br. s., 1H) | 10.1 min, 93.2% 9.4 min, 94.6% |
| 905 | (3R,5R)-7-(3-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)-3,5-dihydroxyheptanoic acid, Na salt | | Me | 732.1 [M + Na]⁺ | 8.69 (s, 1H), 7.95 (s, 1H), 7.58 (s, 1H), 7.30 (s, 1H), 7.23 (d, J = 8.0 Hz, 1H), 7.18-7.00 (m, 3H), 6.90 (t, J = 7.8 Hz, 1H), 6.77-6.69 (m, 1H), 6.63 (d, J = 7.4 Hz, 2H), 6.28 (br. s., 1H), 5.23 (s, 2H), 3.94-3.79 (m, 2H), 3.73 (br. s., 1H), 3.64-3.53 (m, 1H), 3.14-2.96 (m, 3H), 2.65 (d, J = 15.1 Hz, 1H), 2.60-2.52 (m, 1H), 2.14 (dd, J = 14.9, 4.4 Hz, 1H), 2.09-1.95 (m, 5H), 1.90 (d, J = 6.1 Hz, 3H), 1.81-1.57 (m, 5H), 1.53-1.44 (m, 1H), 1.44-1.37 (m, 1H), 1.37-1.28 (m, 2H), 0.91-0.78 (m, 1H), 0.33 (br. s., 1H) | 10.2 min, 95.0% 9.4 min, 95.0% |
| 906 | 1-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)-3-((S)-2-oxotetrahydrofuran-3-yl)urea | | Me | 634.3 | 7.69 (s, 1H), 7.54 (s, 1H), 7.48-7.44 (m, 1H), 7.42-7.37 (m, 2H), 7.20-7.14 (m, 1H), 7.10 (t, J = 7.8 Hz, 1H), 6.99 (t, J = 7.8 Hz, 1H), 6.95 (br. s., 1H), 6.73 (d, J = 7.7 Hz, 1H), 6.63 (d, J = 8.0 Hz, 1H), 6.07 (s, 1H), 5.39 (s, 2H), 4.28 (dd, J = 8.8, 3.9 Hz, 1H), 4.02-3.95 (m, 2H), 3.94-3.84 (m, 2H), 2.83-2.67 (m, 2H), 2.63-2.46 (m, 1H), 2.27-2.15 (m, 5H), 2.11 (br. s., 2H), 2.07-1.97 (m, 3H), 1.93 (br. s., 3H), 1.88 (br. s., 1H), 1.70 (d, J = 5.2 Hz, 1H), 0.98-0.88 (m, 1H), 0.57 (br. s., 1H) | 11.0 min, 96.2% 10.2 min, 94.3% |

TABLE 24-continued

| Example | Name | —Y | R | LCMS, [M + H]+ | ¹H NMR (400 MHz, CDCl₃) δ | HPLC-1: Rt min, purity; HPLC-2: Rt min, purity |
|---|---|---|---|---|---|---|
| 907 | (S)-2-(3-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenyl)ureido)-4-hydroxybutanoic acid, Na salt | | Me | 652.3 | 8.96 (br. s., 1H), 7.95 (s, 1H), 7.57 (s, 1H), 7.35 (d, J = 1.4 Hz, 1H), 7.23-7.13 (m, 2H), 7.12-6.99 (m, 3H), 6.90 (t, J = 7.7 Hz, 1H), 6.69 (d, J = 7.4 Hz, 1H), 6.63 (d, J = 7.7 Hz, 2H), 6.44 (d, J = 5.0 Hz, 1H), 6.38 (d, J = 5.5 Hz, 1H), 5.22 (s, 2H), 3.85 (br. s., 1H), 3.73 (br. s., 1H), 3.54 (dt, J = 8.0, 4.1 Hz, 1H), 3.49-3.42 (m, 1H), 3.41-3.34 (m, 1H), 2.64 (br. s., 2H), 2.11-1.99 (m, 4H), 1.90 (d, J = 5.8 Hz, 3H), 1.74 (br. s., 3H), 1.70-1.63 (m, 3H), 1.62-1.53 (m, 1H), 0.91-0.77 (m, 1H), 0.33 (br. s., 1H)* | 10.6 min, 98.6% 10.0 min, 98.6% |
| 908 | (4R)-1-(3-((4-((1aR,7bS)-3-(4-(2,3-Dimethylphenoxy)butanoyl)-1a,2,3,7b-tetrahydro-1H-cyclopropa[c]quinolin-7-yl)-1H-pyrazol-1-yl)methyl)phenylcarbamoyl)-4-hydroxypyrrolidine-2-carboxylic acid | | Me | 664.3 | 7.89 (d, J = 4.7 Hz, 2H), 7.65 (d, J = 1.7 Hz, 2H), 7.43 (d, J = 1.7 Hz, 2H), 7.38-7.32 (m, 2H), 7.23-7.06 (m, 10H), 6.98 (t, J = 8.0 Hz, 2H), 6.83 (d, J = 7.4 Hz, 1H), 6.78 (d, J = 7.4 Hz, 1H), 6.75-6.69 (m, 4H), 5.31 (s, 2H), 5.30 (s, 2H), 4.59 (d, J = 12.9 Hz, 2H), 4.27-4.19 (m, 1H), 4.12 (t, J = 4.4 Hz, 1H), 4.05-3.89 (m, 6H), 3.49 (dd, J = 10.6, 3.4 Hz, 1H), 3.41 (dd, J = 11.3, 4.1 Hz, 1H), 3.27-3.18 (m, 2H), 2.98 (d, J = 12.1 Hz, 2H), 2.86 (br. s., 5H), 2.71 (dt, J = 15.8, 6.9 Hz, 2H), 2.24-2.12 (m, 11H), 2.07-2.01 (m, 3H), 2.00-1.96 (m, 6H), 1.86-1.75 (m, 2H), 1.03 (tt, J = 8.3, 4.0 Hz, 2H), 0.52 (q, J = 4.7 Hz, 2H)* | 10.4 min, 10.6 min, 98.6% 9.8 min, 9.9 min, 98.4% |
| 909 | (R)-2-Amino-3-(3-(3-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)phenyl)ureido)propanoic acid, TFA salt | | Me | 637.3 | 8.18 (br. s., 3H), 7.72 (br. s., 1H), 7.61 (br. s., 1H), 7.16-7.03 (m, 3H), 6.97 (br. s., 3H), 6.80-6.65 (m, 3H), 6.60 (br. s., 2H), 5.26 (br. s., 2H), 3.93 (br. s., 2H), 3.85 (br. s., 2H), 3.70 (br. s., 1H), 3.52 (br. s., 1H), 2.90 (br. s., 1H), 2.75 (br. s., 2H), 2.64-2.49 (m, 1H), 2.26-2.03 (m, 5H), 1.97 (br. s., 1H), 1.89 (br. s., 3H), 1.73-1.57 (m, 1H), 1.00-0.84 (m, 1H), 0.54 (br. s., 1H) | 8.0 min, 97.0% 9.3 min, 98.1% |

TABLE 24-continued

| Example | Name | —Y | R | LCMS, [M + H]+ | 1H NMR (400 MHz, CDCl3) δ | HPLC-1: Rt min, purity; HPLC-2: Rt min, purity |
|---|---|---|---|---|---|---|
| 910 | (S)-3-Amino-2-(3-(3-((4-((1aR,7bS)-3-(4-(2,3-dimethylphenoxy)butanoyl)-1a,2,3,7b-tetrahydro-1H-cyclopropa[c]quinolin-7-yl)-1H-pyrazol-1-yl)methyl)phenyl)ureido)propanoic acid, TFA salt | HN-C(=O)-NH-CH(CO2H)-CH2-NH2 | Me | 637.3 | | 7.8 min, 98.3% 9.2 min, 96.3% |
| 911 | (3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)ureido)methanesulfonic acid, Na salt | HN-C(=O)-NH-CH2-SO3H | Cl | 664.2 | 8.78 (br. s., 1H), 8.02 (s, 1H), 7.66 (s, 1H), 7.32 (s, 1H), 7.29 (d, J = 8.1 Hz, 1H), 7.24-7.07 (m, 5H), 6.96 (d, J = 7.8 Hz, 1H), 6.88 (d, J = 8.1 Hz, 1H), 6.80 (d, J = 7.3 Hz, 1H), 6.37 (br. s., 1H), 5.32 (s, 2H), 4.07-3.96 (m, 2H), 3.84 (s., 3H), 2.79-2.65 (m, 2H), 2.10 (br. s., 1H), 2.05-1.89 (m, 4H), 1.75 (br. s., 1H), 0.89 (br. s., 1H), 0.36 (br. s., 1H)* | N/A 8.9 min, 97.8% |
| 912 | 2-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)ureido)ethanesulfonic acid, Na salt | HN-C(=O)-NH-CH2CH2-SO3H | Cl | 678.3 | 7.81 (s, 1H), 7.67 (s, 1H), 7.34-7.14 (m, 5H), 7.10-7.02 (m, 2H), 6.90 (t, J = 6.6 Hz, 2H), 6.76 (d, J = 8.2 Hz, 1H), 5.36 (s, 2H), 4.03-3.96 (m, 1H), 3.88-3.79 (m, 1H), 3.66-3.57 (m, 2H), 3.01-2.95 (m, 2H), 2.78-2.69 (m, 2H), 2.16-2.05 (m, 2H), 1.87 (s, 3H), 1.72 (br. s., 1H), 0.80 (br. s., 1H), 0.38-0.28 (m, 1H)** | 11.2 min, 96.6% 8.8 min, 94.8% |
| 913 | Ethyl 3-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)phenyl)ureido)propanoate | HN-C(=O)-NH-CH2CH2-CO2Et | Cl | 670.4 | 7.70 (s, 1H), 7.56 (s, 1H), 7.34 (br. s., 1H), 7.31-7.24 (m, 2H), 7.24-7.16 (m, 2H), 7.14-7.09 (m, 1H), 7.07-7.00 (m, 1H), 6.97-6.89 (m, 2H), 6.67 (d, J = 8.2 Hz, 1H), 6.61 (br. s., 1H), 5.39 (t, J = 6.0 Hz, 1H), 5.33 (s, 2H), 4.14 (q, J = 7.1 Hz, 2H), 4.06-3.96 (m, 1H), 3.90 (br. s., 1H), 3.52 (q, J = 5.9 Hz, 2H), 2.81-2.66 (m, 2H), 2.64-2.53 (m, 2H), 2.22-2.12 (m, 2H), 2.01 (br. s., 3H), 1.72-1.65 (m, 1H), 1.26 (t, J = 7.1 Hz, 3H), 0.87 (br. s., 1H), 0.47 (br. s., 1H) | 11.6 min, 98.0% 10.7 min, 98.0% |

TABLE 24-continued

| Example | Name | —Y | R | LCMS, [M + H]+ | 1H NMR (400 MHz, CDCl3) δ | HPLC-1: Rt min, purity; HPLC-2: Rt min, purity |
|---|---|---|---|---|---|---|
| 914 | Ethyl 2-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)phenyl)ureido)acetate | HN–C(O)–NH–CH2–CO2Et | Cl | 656.4 | 7.70 (s, 1H), 7.57 (s, 1H), 7.36 (br. s., 1H), 7.26-7.16 (m, 3H), 7.14-7.09 (m, 1H), 7.08-6.99 (m, 2H), 6.96-6.89 (m, 2H), 6.67 (d, J = 8.2 Hz, 1H), 5.55 (t, J = 5.2 Hz, 1H), 5.34-5.27 (m, 2H), 5.21 (t, J = 4.9 Hz, 2H), 4.25-4.17 (m, 2H), 4.03 (d, J = 5.5 Hz, 2H), 2.78-2.70 (m, 2H), 2.61 (dd, J = 15.1, 8.0 Hz, 1H), 2.21-2.13 (m, 2H), 2.01 (br. s., 3H), 1.31-1.25 (m, 3H), 0.87 (br. s., 1H), 0.47 (br. s., 1H) | 11.5 min, 98.8% 10.6 min, 96.8% |
| 915 | Ethyl 4-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)phenyl)ureido)butanoate | HN–C(O)–NH–(CH2)3–CO2Et | Cl | 684.5 | 7.70 (s, 1H), 7.55 (s, 1H), 7.39 (br. s., 1H), 7.26-7.16 (m, 2H), 7.15-6.98 (m, 2H), 6.96-6.83 (m, 3H), 6.67 (d, J = 7.7 Hz, 1H), 5.31 (s, 2H), 5.16 (br. s., 1H), 4.70 (br. s., 1H), 4.12 (m, 4H), 4.04-3.78 (m, 2H), 3.36-3.06 (m, 4H), 2.85-2.53 (m, 2H), 2.37 (td, J = 7.0, 4.7 Hz, 3H), 2.24-2.08 (m, 1H), 2.00 (br. s., 1H), 1.91-1.77 (m, 2H), 1.34-1.17 (m, 5H), 0.86 (br. s., 1H), 0.46 (br. s., 1H) | 11.8 min, 95.0% 10.7 min, 95.3% |
| 916 | 2-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)ureido)acetic acid | HN–C(O)–NH–CH2–CO2H | Cl | 628.3 | 8.11-7.99 (m, 1H), 7.68 (s, 1H), 7.60 (s, 1H), 7.38-7.29 (m, 2H), 7.20-7.05 (m, 3H), 7.04-6.96 (m, 2H), 6.95-6.85 (m, 2H), 6.79 (br. s., 1H), 6.64 (d, J = 7.7 Hz, 1H), 5.24 (br. s., 2H), 4.08-3.54 (m, 4H), 2.84-2.65 (m, 4H), 2.14 (br. s., 2H), 2.05-1.87 (m, 3H), 1.63 (br. s., 1H), 0.81 (br. s., 1H), 0.41 (br. s., 1H) | N/A N/A |
| 917 | 3-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)ureido)propanoic acid | HN–C(O)–NH–(CH2)2–CO2H | Cl | 642.4 | 7.92 (br. s., 1H), 7.75 (s, 1H), 7.64 (s, 1H), 7.30 (d, J = 7.7 Hz, 1H), 7.24-7.07 (m, 2H), 7.06-6.84 (m, 3H), 6.66 (d, J = 7.7 Hz, 1H), 5.34 (s, 2H), 5.01 (br. s., 1H), 4.09-3.77 (m, 2H), 3.76-3.05 (m, 6H), 2.92-2.40 (m, 4H), 2.30-1.85 (m, 4H), 1.69 (br. s., 1H), 0.98-0.76 (m, 1H), 0.57-0.30 (m, 1H) | N/A N/A |

TABLE 24-continued

| Example | Name | —Y | R | LCMS, [M + H]+ | $^1$H NMR (400 MHz, CDCl$_3$) δ | HPLC-1: Rt min, purity; HPLC-2: Rt min, purity |
|---|---|---|---|---|---|---|
| 918 | 4-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)ureido)butanoic acid | | Cl | 656.4 | 8.36 (br. s., 1H), 7.74 (s, 1H), 7.68 (s, 1H), 7.45-7.30 (m, 2H), 7.24-7.11 (m, 4H), 7.10-6.88 (m, 3H), 6.67 (d, J = 8.2 Hz, 1H), 5.50-5.39 (s, 2H), 4.05-3.77 (m, 2H), 3.77-3.27 (m, 5H), 2.84-2.57 (m, 3H), 2.52-2.40 (m, 2H), 2.26-2.11 (m, 2H), 2.07-1.84 (m, 4H), 1.70 (br. s., 1H), 0.84 (br. s., 1H), 0.44 (br. s., 1H) | 9.3 min, 91.6% 9.2 min, 90.8% |
| 919 | 1-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenylcarbamoyl)-4-hydroxypiperidine-4-carboxylic acid | | Cl | 698.4 | 7.71-7.60 (br., s, 1H), 7.59-7.46 (br., s, 1H), 7.43-7.20 (m, 1H), 7.17-6.96 (m, 4H), 6.97-6.69 (m, 4H), 6.57 (d, J = 7.1 Hz, 1H), 5.24 (br. s., 2H), 5.05-4.10 (m, 4H), 3.98-3.70 (m, 3H), 3.19 (br. s., 2H), 2.78-2.42 (m, 2H), 2.22-1.78 (m, 7H), 1.58 (br. s., 2H), 1.19 (d, J = 3.3 Hz, 1H), 0.76 (br. s., 1H), 0.35 (br. s., 1H) | 9.9 min, 100% 9.0 min, 98.6% |
| 920 | Methyl 1-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)phenylcarbamoyl)-4-hydroxypiperidine-4-carboxylate | | Cl | 712.5 | 7.78 (s, 1H), 7.66-7.54 (m, 1H), 7.43-7.28 (m, 2H), 7.24-7.09 (m, 2H), 7.08-6.85 (m, 4H), 6.75-6.52 (m, 2H), 5.38 (s, 2H), 4.10-3.83 (m, 4H), 3.83-3.77 (s, 3H), 3.34 (td, J = 12.9, 2.7 Hz, 2H), 2.87-2.53 (m, 4H), 2.24-2.11 (m, 2H), 2.11-1.88 (m, 6H), 1.69 (d, J = 12.6 Hz, 3H), 0.88 (d, J = 4.4 Hz, 1H), 0.46 (br. s., 1H) | 10.7 min, 98.2% 9.7 min, 98.4% |
| 921 | 2,2'-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenylcarbamoylazanediyl)diacetic acid | | Cl | 668.3 [M − H$_2$O + H]+ | 7.70-7.64 (m, 1H), 7.53 (s, 1H), 7.44-7.28 (m, 3H), 7.18-7.00 (m, 3H), 6.99-6.78 (m, 3H), 6.59 (d, J = 8.2 Hz, 2H), 5.38 (s, 2H), 4.18 (s, 2H), 4.12 (s, 2H), 3.97-3.74 (m, 3H), 2.72-2.50 (m, 3H), 2.16-2.03 (m, 2H), 2.01-1.86 (m, 3H), 1.70-1.53 (m, 1H), 1.33-1.16 (m, 1H), 0.90-0.69 (m, 1H), 0.37 (br. s., 1H) | 10.5 min, 98.2% 9.5 min, 96.5% |

TABLE 24-continued

| Example | Name | —Y | R | LCMS, [M + H]+ | 1H NMR (400 MHz, CDCl3) δ | HPLC-1: Rt min, purity; HPLC-2: Rt min, purity |
|---|---|---|---|---|---|---|
| 922 | (S)-4-Carboxy-4-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)phenyl)ureido)-N,N,N-trimethylbutan-1-aminium | HN-C(O)-NH-CH(CO2H)-...-N+(CH3)3 | Cl | 727.3 | 7.75 (d, J = 4.4 Hz, 1H), 7.62 (s, 2H), 7.51 (dd, J = 13.7, 8.8 Hz, 1H), 7.25-6.96 (m, 5H), 6.93 (d, J = 7.7 Hz, 1H), 6.84-6.67 (m, 2H), 5.20 (br. s., 2H), 4.29 (br. s., 2H), 3.96 (br. s., 2H), 3.83 (br. s., 2H), 3.24 (br. s., 2H), 3.09 (br. s., 2H), 2.78 (br. s., 9H), 2.72-2.59 (m, 2H), 2.54 (br. s., 2H), 2.15-2.08 (m, 2H), 2.08-1.98 (m, 2H), 1.83-1.59 (m, 4H), 0.88 (br. s., 1H), 0.36 (br. s., 1H) | 7.6 min, 99.8% 8.4 min, 99.2% |
| 923 | (3R,5S)-6-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)ureido)-3,5-dihydroxyhexanoic acid, Na salt | HN-C(O)-NH-CH2-CH(OH)-CH2-CH(OH)-CH2-CO2H | Cl | 716.4 | 7.59 (br. s., 1H), 7.55-7.38 (m, 2H), 7.23-7.11 (m, 1H), 7.11-6.90 (m, 3H), 6.85 (br. s., 2H), 6.75-6.47 (m, 3H), 5.51-5.05 (m, 4H), 4.30-3.55 (m, 9H), 2.47-1.29 (m, 11H), 0.76 (br. s., 1H), 0.36 (br. s., 1H) | 9.6 min, 100% 9.0 min, 95.7% |
| 924 | (3R,5R)-7-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)phenyl)ureido)-3,5-dihydroxyheptanoic acid, Na salt | HN-C(O)-NH-CH2-CH2-CH(OH)-CH2-CH(OH)-CH2-CO2H | Cl | 752.3 [M + Na]+ | 7.54 (br. s., Hz, 1H), 7.44 (br. s., 1H), 7.39-7.29 (m, 1H), 7.15-6.86 (m, 4H), 6.80 (br. s., 2H), 6.54 (br. s., 3H), 5.61-4.81 (m, 4H), 4.29-3.21 (m, 9H), 2.80-0.98 (m, 13H), 0.70 (s, 1H), 0.31 (s, 1H) | 9.7 min, 95.4% 9.0 min, 97.5% |
| 924A | 1-((1aR,7bS)-7-(1-(3-Aminobenzyl)-1H-pyrazol-4-yl)-1a,2-dihydro-1H-cyclopropa[c]quinolin-3(7bH)-yl)-4-(3-chloro-2-methylphenoxy)butan-1-one, TFA salt | NH2 | Cl | 527.1 | 7.69 (s, 1H), 7.52 (s, 1H), 7.23-7.07 (m, 3H), 7.05-6.85 (m, 3H), 6.77-6.55 (m, 4H), 5.26 (s, 2H), 4.12-3.77 (m, 2H), 3.23 (br. s., 3H), 2.89-2.47 (m, 3H), 2.28-1.85 (m, 6H), 1.77-1.60 (m, 1H), 0.84 (d, J = 4.8 Hz, 1H), 0.47 (br. s., 1H) | 3.3 min, 93.7%*** |
| 924B | Ethyl 2-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)benzamido)acetate | C(O)-NH-CH2-C(O)-O-Et | Cl | 641.2 | 7.82-7.67 (m, 2H), 7.54 (s, 1H), 7.50-7.38 (m, 2H), 7.22-7.07 (m, 2H), 7.06-6.86 (m, 3H), 6.67 (d, J = 7.8 Hz, 2H), 5.44-5.36 (m, 2H), 4.33-4.17 (m, 4H), 4.05-3.95 (m, 1H), 3.89 (br. s., 1H), 2.88-2.49 (m, 3H), 2.24-1.92 (m, 5H), 1.78-1.49 (m, 3H), 1.39-1.28 (m, 3H), 0.84 (br. s., 1H), 0.46 (br. s., 1H) | 11.6 min, 99.5% 10.1 min, 99.5% |

TABLE 24-continued

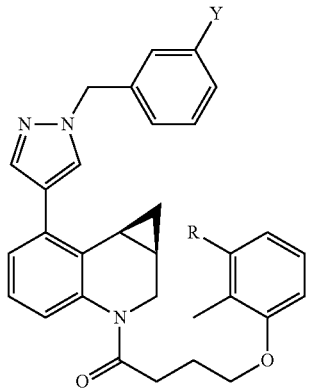

| Example | Name | —Y | R | LCMS, [M + H]+ | $^1$H NMR (400 MHz, CDCl$_3$) δ | HPLC-1: Rt min, purity; HPLC-2: Rt min, purity |
|---|---|---|---|---|---|---|
| 924C | Ethyl 2-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)benzamido)oxetan-3-yl)acetate | | Cl | 697.2 | 7.79-7.64 (m, 3H), 7.56 (s, 1H), 7.50-7.40 (m, 2H), 7.23-7.07 (m, 2H), 7.07-6.85 (m, 4H), 6.67 (d, J = 7.8 Hz, 1H), 5.41 (s, 2H), 4.86 (d, J = 7.1 Hz, 2H), 4.63 (d, J = 7.3 Hz, 2H), 4.11 (q, J = 7.2 Hz, 2H), 4.05-3.95 (m, 1H), 3.90 (d, J = 9.6 Hz, 1H), 3.29 (s, 2H), 2.88-2.50 (m, 3H), 2.28-1.89 (m, 7H), 1.69 (br. s., 1H), 1.23 (t, J = 7.1 Hz, 4H), 0.95-0.75 (m, 1H), 0.46 (br. s., 1H) | 11.6 min, 96.0% 10.0 min, 95.0% |
| 924D | 1-((3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)methyl)cyclopropanecarboxylic acid | | Cl | 653.2 | 7.99-7.88 (m, 1H), 7.77-7.55 (m, 2H), 7.53-7.27 (m, 3H), 7.16-7.00 (m, 2H), 6.98-6.76 (m, 3H), 6.59 (d, J = 7.8 Hz, 1H), 5.43-5.22 (m, 2H), 4.08-3.70 (m, 3H), 3.54 (br. s., 1H), 2.86-2.36 (m, 3H), 2.20-1.76 (m, 8H), 1.60 (br. s., 1H), 1.40-1.14 (m, 3H), 1.05 (br. s., 1H), 0.79 (d, J = 14.1 Hz, 2H), 0.39 (br. s., 1H) | 12.0 min, 92.0% 11.2 min, 92.0% |
| 924E | (S)-2-(3-(3-((4-((1aR,7bS)-3-(4-(3-chloro-2-methylphenoxy)butanoyl)-1a,2,3,7b-tetrahydro-1H-cyclopropa[c]quinolin-7-yl)-1H-pyrazol-1-yl)methyl)benzamido)-4-hydroxybutanoic acid | | Cl | 657.1 | 7.99-7.60 (m, 2H), 7.59-7.32 (m, 3H), 7.09-6.67 (m, 6H), 6.65-6.46 (m, 1H), 5.41-5.18 (m, 2H), 5.10 (br. s., 1H), 4.70-4.20 (m, 1H), 4.04-3.66 (m, 2H), 3.52 (br. s., 1H), 2.78-2.34 (m, 3H), 2.12-1.73 (m, 10H), 1.65-1.12 (m, 2H), 0.89-0.57 (m, 1H), 0.31 (br. s., 1H) | 9.5 min, 100% 8.5 min, 95.2% |
| 924F | 2-(3-(3-((4-((1aR,7bS)-3-(4-(3-Chloro-2-methylphenoxy)butanoyl)-1a,2,3,7b-tetrahydro-1H-cyclopropa[c]quinolin-7-yl)-1H-pyrazol-1-yl)methyl)benzamido)oxetan-3-yl)acetic acid | | Cl | 669.2 | 7.78 (d, J = 4.3 Hz, 3H), 7.68-7.42 (m, 3H), 7.23-7.10 (m, 2H), 7.10-6.81 (m, 3H), 6.76-6.54 (m, 1H), 5.44 (s, 2H), 4.70-4.37 (m, 2H), 4.09-3.73 (m, 4H), 3.22-3.10 (m, 1H), 3.02-2.36 (m, 8H), 2.25-1.91 (m, 5H), 1.71 (br. s., 1H), 0.84 (br. s., 1H), 0.43 (br. s., 1H) | 6.0 min, 94% 5.5 min, 95% |

*$^1$H NMR (400 MHz, DMSO-d$_6$) δ.

**$^1$H NMR (400 MHz, MeOD) δ.

Example 925

3-((4-((1aR,7bS)-3-(2-((2,3-Dimethylphenoxy)methyl)cyclopropanecarbonyl)-1a,2,3,7b-tetrahydro-1H-cyclopropa[c]quinolin-7-yl)-1H-pyrazol-1-yl)methyl)benzoic acid

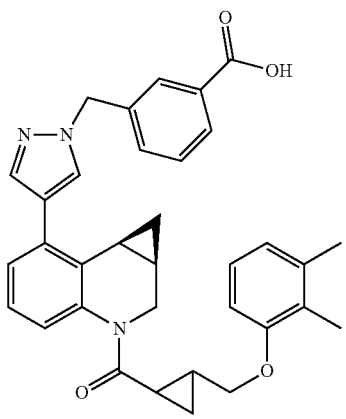 [SMILES: Cc1cccc(OCC2CC2C(=O)N2C[C@@H]3C[C@@H]3c3c(-c4cnn(Cc5cccc(C(=O)O)c5)c4)cccc32)c1C]

Step A. ((1aR,7bS)-7-Bromo-1a,2-dihydro-1H-cyclopropa[c]quinolin-3(7bH)-yl)(2-((2,3-dimethylphenoxy)methyl)cyclopropyl)methanone

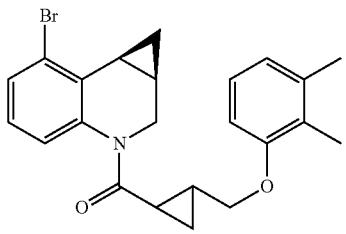 [SMILES: Cc1cccc(OCC2CC2C(=O)N2C[C@@H]3C[C@@H]3c3c(Br)cccc32)c1C]

The title compound was prepared using a procedure analogous to step G, Example 9 except that 4-(2,3-dimethylphenoxy)butanoic acid was replaced with trans-2-((2,3-dimethylphenoxy)methyl)cyclopropanecarboxylic acid. LCMS, [M+H]$^+$=427.9.

Step B. ((1aR,7bS)-7-Bromo-1a,2-dihydro-1H-cyclopropa[c]quinolin-3(7bH)-yl)(2-((2,3-dimethylphenoxy)methyl)cyclopropyl)methanone

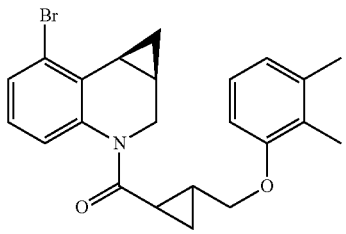 [SMILES: Cc1cccc(OCC2CC2C(=O)N2C[C@@H]3C[C@@H]3c3c(Br)cccc32)c1C]

((1aR,7bS)-7-Bromo-1a,2-dihydro-1H-cyclopropa[c]quinolin-3(7bH)-yl)(2-((2,3-dimethylphenoxy)methyl)cyclopropyl)methanone was purified by flash chromatography (0-50% ethyl acetate:hexanes) to afford ((1aR,7bS)-7-bromo-1a,2-dihydro-1H-cyclopropa[c]quinolin-3(7bH)-yl)(2-((2,3-dimethylphenoxy)methyl)cyclopropyl)methanone (enantiomer 1) as the faster moving diastereomer on column and ((1aR,7bS)-7-bromo-1a,2-dihydro-1H-cyclopropa[c]quinolin-3(7bH)-yl)(2-((2,3-dimethylphenoxy)methyl)cyclopropyl)methanone (enantiomer 2) as the slower moving diastereomer on column. LCMS, [M+H]$^+$=427.9.

Example 925

Example 925 was prepared using a procedure analogous to Example 9 except that 1-(7-bromo-1a,2-dihydro-1H-cyclopropa[c]quinolin-3(7bH)-yl)-4-(2,3-dimethylphenoxy)butan-1-one (enantiomer 1) was replaced with to afford example 925: 3-((4-((1aR,7bS)-3-(2-((2,3-dimethylphenoxy)methyl)cyclopropanecarbonyl)-1a,2,3,7b-tetrahydro-1H-cyclopropa[c]quinolin-7-yl)-1H-pyrazol-1-yl)methyl)benzoic acid LCMS, [M+H]$^+$=548.1. $^1$H NMR (400 MHz, CDCl$_3$) δ 8.13-8.08 (m, 1H), 8.03 (s, 1H), 7.86 (s, 1H), 7.64 (s, 1H), 7.56-7.50 (m, 2H), 7.42-7.37 (m, 1H), 7.12 (d, J=7.7 Hz, 1H), 7.08-6.97 (m, 2H), 6.81 (d, J=7.7 Hz, 1H), 6.66 (d, J=7.7 Hz, 1H), 5.58-5.45 (m, 2H), 5.04 (br. s., 1H), 4.23 (d, J=6.6 Hz, 1H), 3.63-3.55 (m, 1H), 2.82 (br. s., 1H), 2.29 (s, 3H), 2.20 (s, 3H), 2.17-2.11 (m, 1H), 2.06-1.95 (m, 2H), 1.85-1.76 (m, 1H), 1.55 (dt, J=8.8, 4.4 Hz, 1H), 1.14-1.06 (m, 1H), 0.90-0.78 (m, 2H). HPLC-1: Rt=12.6 min, purity=96.8%; HPLC-2: Rt=11.4 min, purity=98.6%.

Example 926

3-((4-((1aR,7bS)-3-(2-((2,3-Dimethylphenoxy)methyl)cyclopropanecarbonyl)-1a,2,3,7b-tetrahydro-1H-cyclopropa[c]quinolin-7-yl)-1H-pyrazol-1-yl)methyl)benzoic acid

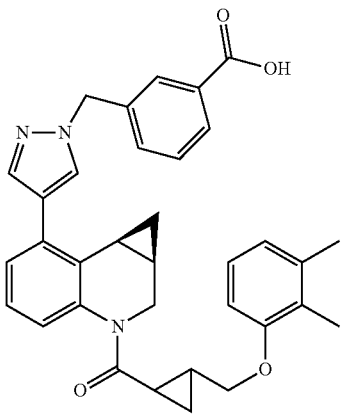 [SMILES: Cc1cccc(OCC2CC2C(=O)N2C[C@@H]3C[C@@H]3c3c(-c4cnn(Cc5cccc(C(=O)O)c5)c4)cccc32)c1C]

Example 926 was prepared using a procedure analogous to Example 9 except that 1-(7-bromo-1a,2-dihydro-1H-cyclopropa[c]quinolin-3(7bH)-yl)-4-(2,3-dimethylphenoxy)butan-1-one was replaced with ((1aR,7bS)-7-bromo-1a,2-dihydro-1H-cyclopropa[c]quinolin-3(7bH)-yl)(2-((2,3-dimethylphenoxy)methyl)cyclopropyl)methanone (enantiomer 2) was replaced with to afford example 926: 3-((4-((1aR,7bS)-3-(2-((2,3-dimethylphenoxy)methyl)cyclopropanecarbonyl)-1a,2,3,7b-tetrahydro-1H-cyclopropa[c]quinolin-7-yl)-1H-pyrazol-1-yl)methyl)benzoic acid. LCMS, [M+H]$^+$=548.1. $^1$H NMR (400 MHz, CDCl$_3$) δ 8.11-8.07 (m, 1H), 8.06 (s, 1H), 7.84 (s, 1H), 7.64 (s, 1H), 7.57-7.47 (m, 2H), 7.22-7.12 (m, 3H), 6.96 (t, J=8.0 Hz, 1H), 6.72 (d, J=7.7 Hz, 1H), 6.54 (d, J=8.2 Hz, 1H), 5.56-5.43 (m, 2H), 5.12-4.90 (m, 1H), 4.03 (d, J=4.9 Hz, 1H), 3.64-3.55 (m, 1H), 2.80 (br. s., 1H), 2.21 (s, 3H), 2.15 (d, J=6.0 Hz, 2H), 2.07-1.96 (m, 4H), 1.83-1.73 (m, 1H), 1.39 (dt, J=8.8, 4.4 Hz, 1H), 1.06 (td, J=8.2, 4.9 Hz, 2H), 0.84 (br. s., 1H). HPLC-1: Rt=12.1 min, purity=98.5%; HPLC-2: Rt=11.0 min, purity=99.4%.

Example 927

3-((4-((1aR,7bS)-3-(2-((3-Chloro-2-methylphenoxy)methyl)cyclopropanecarbonyl)-1a,2,3,7b-tetrahydro-1H-cyclopropa[c]quinolin-7-yl)-1H-pyrazol-1-yl)methyl)benzoic acid

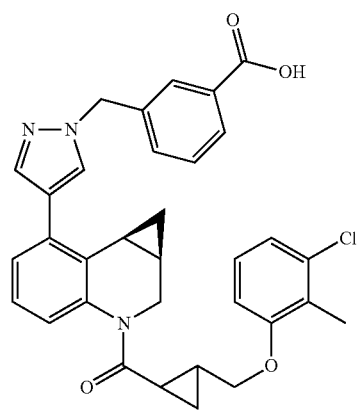 [SMILES: Cc1c(Cl)cccc1OCC1CC1C(=O)N1C[C@@H]2C[C@@H]2c2c(-c3cnn(Cc4cccc(C(=O)O)c4)c3)cccc21]

Example 927 was prepared using a procedure analogous to Example 925 except that 2,3-dimethylphenol was replaced with 3-chloro-2-methylphenol. LCMS, [M+H]$^+$=568.0. $^1$H NMR (400 MHz, CDCl$_3$) δ 8.12-8.07 (m, 1H), 8.03 (s, 1H), 7.84 (s, 1H), 7.64 (s, 1H), 7.58-7.48 (m, 2H), 7.34 (d, J=7.7 Hz, 1H), 7.13 (d, J=7.7 Hz, 1H), 7.10-7.04 (m, 1H), 7.03-6.96 (m, 2H), 6.69 (d, J=8.2 Hz, 1H), 5.56-5.45 (m, 2H), 5.04 (br. s., 1H), 4.24 (d, J=6.0 Hz, 1H), 3.65-3.56 (m, 1H), 2.83 (br. s., 1H), 2.33 (s, 3H), 2.21-2.12 (m, 1H), 2.06-1.93 (m, 2H), 1.85-1.76 (m, 1H), 1.59-1.51 (m, 1H), 1.15-1.05 (m, 1H), 0.89-0.76 (m, 2H). HPLC-1: Rt=13.1 min, purity=98.9%; HPLC-2: Rt=11.7 min, purity=100%.

Example 928

3-((4-((1aR,7bS)-3-(2-((3-Chloro-2-methylphenoxy)methyl)cyclopropanecarbonyl)-1a,2,3,7b-tetrahydro-1H-cyclopropa[c]quinolin-7-yl)-1H-pyrazol-1-yl)methyl)benzoic acid

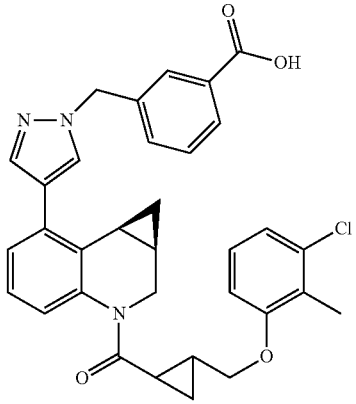 [SMILES: Cc1c(Cl)cccc1OCC1CC1C(=O)N1C[C@@H]2C[C@@H]2c2c(-c3cnn(Cc4cccc(C(=O)O)c4)c3)cccc21]

Example 928 was prepared using a procedure analogous to Example 926 except that 2,3-dimethylphenol was replaced with 3-chloro-2-methylphenol. LCMS, [M+H]$^+$=568.0. $^1$H NMR (400 MHz, CDCl$_3$) δ 8.11-8.07 (m, 1H), 8.06 (s, 1H), 7.85 (s, 1H), 7.66 (s, 1H), 7.57-7.47 (m, 2H), 7.23-7.11 (m, 3H), 7.01-6.87 (m, 2H), 6.58 (d, J=7.7 Hz, 1H), 5.56-5.43 (m, 2H), 5.01 (br. s., 1H), 4.08 (dd, J=9.6, 4.7 Hz, 1H), 3.63-3.52 (m, 1H), 2.79 (br. s., 1H), 2.22-2.06 (m, 5H), 2.06-1.97 (m, 1H), 1.83-1.73 (m, 1H), 1.41 (dt, J=8.7, 4.2 Hz, 1H), 1.05 (td, J=8.2, 5.5 Hz, 2H), 0.75 (d, J=4.4 Hz, 1H). HPLC-1: Rt=12.4 min, purity=99.3%; HPLC-2: Rt=11.3 min, purity=99.9%.

The compounds exemplified in Table 25 were prepared in a manner analogous to Example 327.

TABLE 25

[Structure: core scaffold with Y-substituted benzyl pyrazole, cyclopropa[c]quinoline, and R-substituted phenoxymethyl cyclopropanecarbonyl group]

| Example | Name | —Y | R | LCMS, [M + H]+ | 1H NMR (400 MHz, CDCl3) δ | HPLC-1: Rt min, purity; HPLC-2: Rt min, purity |
|---|---|---|---|---|---|---|
| 929 | (3-((4-((1aR,7bS)-3-(2-((2,3-Dimethylphenoxy)methyl)cyclopropanecarbonyl)-1a,2,3,7b-tetrahydro-1H-cyclopropa[c]quinolin-7-yl)-1H-pyrazol-1-yl)methyl)benzamido)methanesulfonic acid | —C(O)NHCH2SO3H | Me | 641.0 | 8.14 (br. s., 1H), 7.98-7.82 (m, 3H), 7.52-7.46 (m, 2H), 7.34-7.16 (m, 3H), 6.88 (t, J = 7.4 Hz, 1H), 6.66 (d, J = 7.7 Hz, 1H), 6.57 (d, J = 8.2 Hz, 1H), 5.60-5.51 (m, 2H), 4.53 (s, 2H), 4.10 (dd, J = 10.4, 4.9 Hz, 1H), 3.60-3.45 (m, 1H), 2.75 (br. s., 1H), 2.28-2.12 (m, 3H), 2.06 (dd, J = 8.2, 4.4 Hz, 1H), 1.94 (br. s., 3H), 1.84 (d, J = 5.5 Hz, 1H), 1.34-1.23 (m, 1H), 1.15-1.03 (m, 2H), 0.68 (d, J = 4.4 Hz, 1H) | N/A 8.9 min, 99.1% |
| 930 | 2-(3-((4-((1aR,7bS)-3-(2-((2,3-Dimethylphenoxy)methyl)cyclopropanecarbonyl)-1a,2,3,7b-tetrahydro-1H-cyclopropa[c]quinolin-7-yl)-1H-pyrazol-1-yl)methyl)benzamido)ethanesulfonic acid | —C(O)NHCH2CH2SO3H | Me | 655.1 | 8.18 (br. s., 1H), 7.98 (s, 1H), 7.80 (br. s., 2H), 7.49 (d, J = 3.3 Hz, 2H), 7.37-7.16 (m, 3H), 6.87 (d, J = 7.1 Hz, 1H), 6.65 (d, J = 7.1 Hz, 1H), 6.58 (br. s., 1H), 5.56 (s, 2H), 4.10 (dd, J = 10.4, 4.4 Hz, 1H), 3.79 (br. s., 2H), 3.50 (br. s., 1H), 3.08 (br. s., 2H), 2.74 (br. s., 1H), 2.27-2.03 (m, 5H), 2.01-1.78 (m, 5H), 1.29 (br. s., 1H), 1.08 (br. s., 2H), 0.69 (br. s., 1H) | 10.4 min, 95.7% 8.9 min, 98.7% |
| 931 | (3-((4-((1aR,7bS)-3-(2-((3-Chloro-2-methylphenoxy)methyl)cyclopropanecarbonyl)-1a,2,3,7b-tetrahydro-1H-cyclopropa[c]quinolin-7-yl)-1H-pyrazol-1-yl)methyl)benzamido)methanesulfonic acid | —C(O)NHCH2SO3H | Cl | 661.0 | 6.79 (s, 1H), 6.65-6.55 (m, 2H), 6.30-6.17 (m, 2H), 6.06-5.87 (m, 3H), 5.77-5.66 (m, 1H), 5.59 (d, J = 7.7 Hz, 1H), 5.43 (d, J = 7.7 Hz, 1H), 4.28-4.18 (m, 2H), 3.31-3.21 (m, 2H), 2.97-2.84 (m, 2H), 2.32-2.20 (m, 2H), 1.43 (br. s., 2H), 0.93 (br. s., 2H), 0.86-0.74 (m, 5H), 0.69 (d, J = 4.4 Hz, 2H), 0.54 (d, J = 5.5 Hz, 2H), 0.09--0.01 (m, 2H), -0.14--0.29 (m, 2H), -0.68 (d, J = 4.4 Hz, 2H) | 9.9 min, 90.8% 9.1 min, 90.9% |
| 932 | 2-(3-((4-((1aR,7bS)-3-(2-((3-Chloro-2-methylphenoxy)methyl)cyclopropanecarbonyl)-1a,2,3,7b-tetrahydro-1H-cyclopropa[c]quinolin-7-yl)-1H-pyrazol-1-yl)methyl)benzamido)ethanesulfonic acid | —C(O)NHCH2CH2SO3H | Cl | 675.0 | 8.19 (s, 1H), 8.00 (s, 1H), 7.80 (br. s., 2H), 7.54-7.46 (m, 2H), 7.35-7.17 (m, 3H), 7.03-6.93 (m, 1H), 6.86 (d, J = 8.2 Hz, 1H), 6.70 (d, J = 8.2 Hz, 1H), 5.64-5.50 (m, 2H), 4.18 (dd, J = 10.7, 5.2 Hz, 1H), 3.80 (br. s., 2H), 3.54 (br. s., 1H), 3.18-2.99 (m, 2H), 2.74 (br. s., 1H), 2.19 (br. s., 1H), 2.13-1.90 (m, 4H), 1.84 (d, J = 6.0 Hz, 1H), 1.30 (dd, J = 8.8, 4.4 Hz, 1H), 1.14-1.01 (m, 2H), 0.61 (d, J = 4.4 Hz, 1H) | 11.6 min, 98.5% 9.0 min, 100% |

Example 933

3-((4-(1-(4-(tert-Butoxycarbonyl(2,3-dimethylphenyl)amino)butanoyl)-1,2,3,4-tetrahydroquinolin-5-yl)-1H-pyrazol-1-yl)methyl)benzoic acid

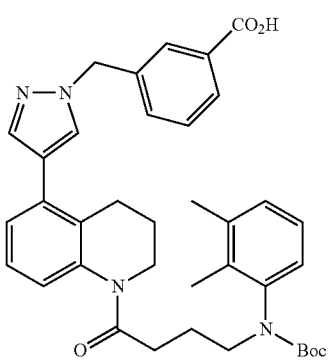 [SMILES: Cc1cccc(N(CCCC(=O)N2CCCc3c(-c4cnn(Cc5cccc(C(=O)O)c5)c4)cccc32)C(=O)OC(C)(C)C)c1C]

Step A.
4((2,3-Dimethylphenyl)amino)-4-oxobutanoic acid

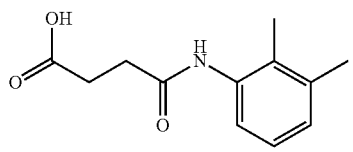 [SMILES: Cc1cccc(NC(=O)CCC(=O)O)c1C]

To a partial suspension of dihydrofuran-2,5-dione (1.0 g, 10.0 mmol) in DCM (40 mL) was added a solution 2,3-dimethylaniline (1.21 g, 10.0 mmol) in DCM (40 mL). The reaction was stirred at room temperature for 3 h and filtered. The solid was washed with CH$_2$Cl$_2$ to afford the title compound (1.89 g, 85% yield). LCMS, [M+H]$^+$=222.4.

Step B. Methyl 4-(2,3-dimethylphenylamino)-4-oxobutanoate

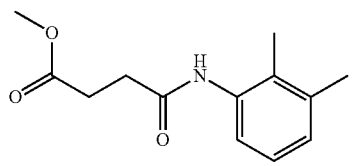 [SMILES: COC(=O)CCC(=O)Nc1cccc(C)c1C]

To a solution of 4-((2,3-dimethylphenyl)amino)-4-oxobutanoic acid (0.5 g, 2.26 mmol) in DCM (9 mL) and MeOH (2 mL) at room temperature was added 2.0 M diazomethyl)trimethylsilane (1.36 mL, 2.71 mmol) dropwise. The reaction was stirred at room temperature for 30 min and quenched with a solution of 20% AcOH in DCM). The mixture was concentrated and purified by flash chromatography (0-100% ethyl acetate:hexanes) to afford the title compound as a white solid (0.52 g, 98% yield). LCMS, [M+H]$^+$=236.4.

Step C. Methyl 4-((2,3-dimethylphenyl)amino)butanoate

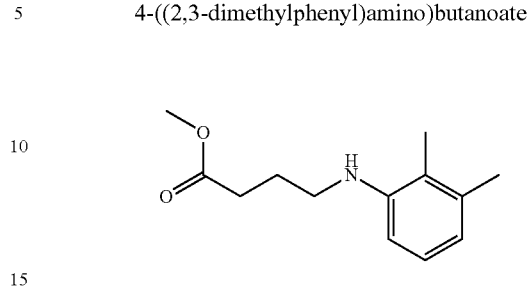

To a partial suspension of methyl 4-(2,3-dimethylphenylamino)-4-oxobutanoate (0.20 g, 0.85 mmol) in THF (8.5 mL) at 0° C. was added 1 M borane tetrahydrofuran complex (2.55 mL, 2.55 mmol) over 2 min. The reaction was allowed to warm to room temperature and stirred overnight. The reaction was cautiously quenched with 50% saturated ammonium chloride, and then excess 50% saturated ammonium chloride and DCM were added. The resulting mixture was stirred vigorously for 15 min. The organic layer was separated, dried over sodium sulfate, filtered, and concentrated. The residue was purified by preparative HPLC (PHENOMENEX® Axia Luna column, 5µ, C18, 30×75 mm; 15 min gradient from 100% A: 0% B to 0% A:100% B and 3 min 100% B (A=90% H$_2$O/10% MeCN+0.1% TFA); (B=90% MeCN/10% H$_2$O+0.1% TFA); detection at 220 nm) to afford the title compound (85 mg, 45% yield). LCMS, [M+H]$^+$=222.1.

Step D. Methyl 4-((tert-butoxycarbonyl)(2,3-dimethylphenyl)amino)butanoate

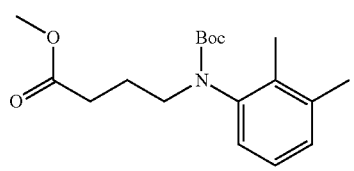 [SMILES: COC(=O)CCCN(C(=O)OC(C)(C)C)c1cccc(C)c1C]

To a solution of methyl 4-((2,3-dimethylphenyl)amino)butanoate (84 mg, 0.38 mmol) in THF (1.9 mL) was added 50% aq. sodium bicarbonate, followed by a 1 M solution of di-tert-butyl dicarbonate (0.60 mL, 0.6 mmol) in THF. The reaction mixture was partitioned between DCM and water. The organic layer was separated, dried over sodium sulfate, filtered, and concentrated. The residue was purified by flash chromatography (0-100% ethyl acetate:hexanes) to afford the title compound as colorless viscous oil (112 mg, 91%). LCMS, [M+Na]$^+$=344.0.

Example 933

Example 933 was prepared using a procedure analogous to Example 95 except that ethyl 4-(2,3-dimethylphenoxy)butanoate was replaced with methyl 4-((tert-butoxycarbonyl)(2,3-dimethylphenyl)amino)butanoate. LCMS, [M+H]$^+$=623.2. $^1$H NMR (500 MHz, CDCl$_3$) δ 8.04 (br. s., 1H), 7.61 (br. s., 1H), 7.51-7.30 (m, 3H), 7.18-7.05 (m, 3H), 7.00 (br. s., 3H), 6.83 (br. s., 1H), 5.35 (br. s., 2H), 3.72-3.59 (m, 2H), 3.31 (br. s., 1H), 2.71-2.57 (m, 2H), 2.47 (d, J=7.4 Hz, 2H), 2.27-2.17 (m, 3H), 2.02 (s, 3H), 1.94-1.73 (m, 4H), 1.51-1.38 (m, 2H), 1.25 (br. s., 9H). HPLC-1: Rt=12.1 min, purity=98.6%; HPLC-2: Rt=11.0 min, purity=98.7%.

Example 934

3-((4-(1-(4-(2,3-Dimethylphenylamino)butanoyl)-1,2,3,4-tetrahydroquinolin-5-yl)-1H-pyrazol-1-yl)methyl)benzoic acid, TFA salt

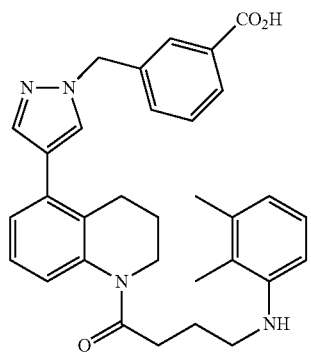

To a solution of Example 933 (0.02 g, 0.032 mmol) in DCM (0.32 mL) was added TFA (0.32 mL). The reaction was stirred at room temperature for 30 min and concentrated. The residue was purified by preparative HPLC (PHENOMENEX® Axia Luna column, 5μ, C18, 30×75 mm; 15 min gradient from 100% A: 0% B to 0% A:100% B and 3 min 100% B (A=90% H$_2$O/10% MeCN+0.1% TFA); (B=90% MeCN/10% H$_2$O+0.1% TFA); detection at 220 nm) to afford Example 934 as a white solid (15 mg, 70% yield). LCMS, [M+H]$^+$=523.1. $^1$H NMR (500 MHz, CDCl$_3$) δ 8.05 (d, J=7.7 Hz, 1H), 8.00 (s, 1H), 7.68 (s, 1H), 7.58-7.50 (m, 2H), 7.51-7.42 (m, 2H), 7.34 (d, J=7.4 Hz, 1H), 7.24-7.13 (m, 170H), 7.05 (br. s., 112H), 5.44 (s, 2H), 3.80 (br. s., 2H), 3.46 (br. s., 2H), 2.81 (br. s., 2H), 2.72 (t, J=6.5 Hz, 2H), 2.34 (s, 3H), 2.31 (s, 3H), 2.21-2.05 (m, 2H), 1.99-1.82 (m, 2H). HPLC-1: Rt=6.8 min, purity=99.7%; HPLC-2: Rt=8.3 min, purity=100%.

Example 935

3-((4-(1-(4-((2,3-Dimethylphenyl)(methyl)amino)butanoyl)-1,2,3,4-tetrahydroquinolin-5-yl)-1H-pyrazol-1-yl)methyl)benzoic acid, TFA salt

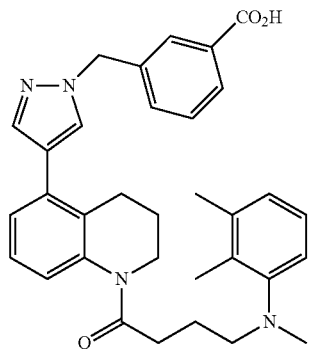 [SMILES: Cc1cccc(N(C)CCCC(=O)N2CCCc3c(-c4cnn(Cc5cccc(C(=O)O)c5)c4)cccc32)c1C]

Example 935 was prepared using a procedure analogous to Example 933 except that 2,3-dimethylaniline was replaced with N,2,3-trimethylaniline. LCMS, [M+H]$^+$=537.2. $^1$H NMR (500 MHz, CDCl$_3$) δ 8.12-8.01 (m, 2H), 7.70-7.62 (m, 1H), 7.56-7.42 (m, 3H), 7.14 (br. s., 2H), 7.07-6.96 (m, 1H), 6.89 (d, J=7.4 Hz, 1H), 6.84 (d, J=5.8 Hz, 1H), 5.43 (s, 2H), 3.75 (t, J=6.3 Hz, 2H), 2.86 (br. s., 2H), 2.67 (t, J=6.5 Hz, 2H), 2.61-2.48 (m, 6H), 2.20 (br. s., 3H), 2.14-2.01 (m, 3H), 1.94-1.81 (m, 5H). HPLC-1: Rt=6.6 min, purity=99.1%; HPLC-2: Rt=8.6 min, purity=99.3%.

Example 938

4-Chloro-3-((4-((1aR,7bS)-3-(((2-trans-(3-chloro-2-methylphenyl)cyclopropyl)methoxy)carbonyl)-1a,2,3,7b-tetrahydro-1H-cyclopropa[c]quinolin-7-yl)-1H-pyrazol-1-yl)methyl)benzoic acid

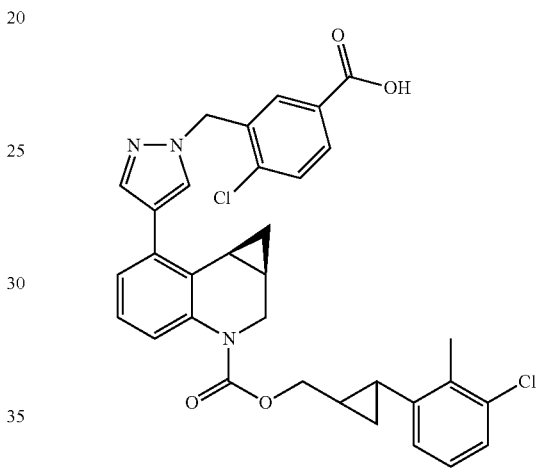

Step A. (E)-Methyl 3-(3-chloro-2-methylphenyl)acrylate

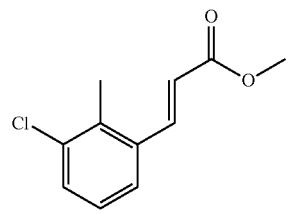

A mixture of (2-methoxy-2-oxoethyl)triphenylphosphonium bromide (10.0 g, 24.08 mmol) in 100 mL DCM, 50 mL water and NaOH (10 N) (4.82 ml, 48.2 mmol) was vigorously shaken in a separatory funnel. The organic layer was separated and the aqueous phase was extracted with DCM. The combined organic layers were dried (MgSO$_4$) and concentrated to give methyl 2-(triphenylphosphoranylidene)acetate (7.5 g, 93% yield) as a white solid. A solution of 3-chloro-2-methylbenzaldehyde (0.7 g, 4.53 mmol) and 2-(triphenylphosphoranylidene)acetate (1.817 g, 5.43 mmol) in MeOH (22.6 ml) was stirred at room temperature for 2 h. The mixture was concentrated and purified by flash chromatography (0-30% ethyl acetate:hexanes) to afford the title compound (0.23 g, 24% yield) as a clear colorless oil. $^1$H NMR (400 MHz, CDCl$_3$) δ 7.99 (d, J=15.9 Hz, 1H), 7.47-7.40 (m, 2H), 7.17-7.15 (m, 1H), 6.33 (d, J=15.9 Hz, 1H), 3.83 (s, 3H), 2.48 (s, 3H).

Step B. trans-Methyl 2-(3-chloro-2-methylphenyl)cyclopropanecarboxylate

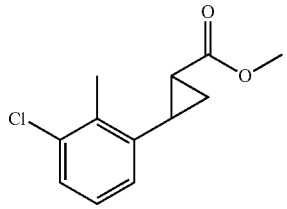

To a solution of trimethylsulfoxonium iodide (0.157 g, 0.712 mmol) in 1 mL DMSO was added NaH (60% in mineral oil) (0.032 g, 0.807 mmol) portion-wise. The mixture was stirred at room temperature for 30 min, and then a solution (E)-methyl 3-(3-chloro-2-methylphenyl)acrylate (0.1 g, 0.475 mmol) in 1 mL DMSO was added in one portion. The reaction was stirred at room temperature for 16 h. The mixture was partitioned between EtOAc and water. The organic layer was washed with water and brine, dried (MgSO$_4$) and concentrated. The crude material was purified by flash chromatography (0-50% ethyl acetate:hexanes) to afford the title compound (0.042 g, 39% yield) as a clear colorless oil. $^1$H NMR (500 MHz, CDCl$_3$) δ 7.29-7.24 (d, J=7.8 Hz, 1H), 7.06 (t, J=7.8 Hz, 1H), 6.95 (d, J=7.7 Hz, 1H), 3.79-3.75 (m, 3H), 2.55 (ddd, J=9.1, 6.7, 4.5 Hz, 1H), 2.45 (s, 3H), 1.81 (dt, J=8.4, 4.9 Hz, 1H), 1.64-1.57 (m, 1H), 1.30 (ddd, J=8.4, 6.7, 4.4 Hz, 1H).

Step C. trans-(2-(3-Chloro-2-methylphenyl)cyclopropyl)methanol

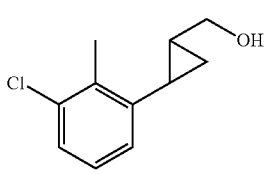

To a solution of trans-methyl 2-(3-chloro-2-methylphenyl) cyclopropanecarboxylate (0.042, 0.187 mmol) in THF (2.0 mL) was added 2.0 M lithium borohydride (0.467 ml, 0.935 mmol) dropwise at room temperature. The reaction was stirred at room temperature for 3 d. The mixture was partitioned between EtOAc and 1 N HCl. The organic layer separated, and the aqueous phase was extracted with EtOAc. The combined organic layer was dried (MgSO$_4$) and concentrated to afford the title compound (23 mg, 63% yield) as pale-yellow oil. $^1$H NMR (500 MHz, CDCl$_3$) δ 7.23 (d, J=8.0 Hz, 1H), 7.04 (t, J=7.7 Hz, 1H), 6.96 (d, J=8.0 Hz, 1H), 3.86-3.65 (m, 2H), 2.53-2.45 (m, 3H), 1.90-1.82 (m, 1H), 1.39 (d, J=5.2 Hz, 1H), 0.97-0.90 (m, 2H).

Step D. (1aR,7bS)-(2-trans-(3-Chloro-2-methylphenyl)cyclopropyl)methyl 7-bromo-1a,2-dihydro-1H-cyclopropa[c]quinoline-3(7bH)-carboxylate

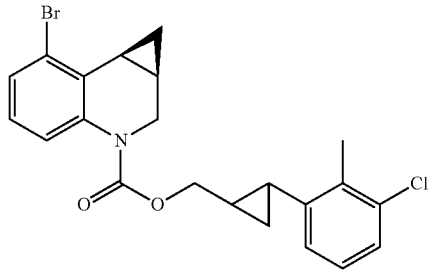 [SMILES: Cc1c(Cl)cccc1C1CC1COC(=O)N1C[C@@H]2C[C@@H]2c2c(Br)cccc21]

To a solution of trans-(2-(3-chloro-2-methylphenyl)cyclopropyl)methanol (0.023 g, 0.117 mmol) in 0.5 mL THF was added NaH (0.012 g, 0.292 mmol) in one portion. The reaction was stirred at room temperature for 30 min and then a solution of (1aR,7bS)-4-nitrophenyl 7-bromo-1a,2-dihydro-1H-cyclopropa[c]quinoline-3(7bH)-carboxylate (0.046 g, 0.117 mmol) in 0.5 mL THF was added and the reaction was stirred at room temperature for 16 h. The mixture was partitioned between EtOAc and saturated NaHCO$_3$. The organic layer was washed with water and brine, dried (MgSO$_4$) and concentrated. The crude material was purified by flash chromatography (0-30% ethyl acetate:hexanes) to afford the title compound (41 mg, 78% yield) as pale-yellow oil. LCMS, [M+Na]$^+$=469.8.

Example 938

Example 938 was prepared using a procedure analogous to Example 368 except that 2-(3-chloro-2-methylphenoxy) ethyl 8-bromo-2H-benzo[b][1,4]thiazine-4(3H)-carboxylate was replaced with (1 aR,7b5)-(2-trans-(3-chloro-2-methylphenyl)-cyclopropyl)methyl 7-bromo-1a,2-dihydro-1H-cyclopropa[c]quinoline-3(7bH)-carboxylate. LCMS, [M+H]$^+$=602.1. $^1$H NMR (500 MHz, CDCl$_3$) δ 8.13 (s, 1H), 8.03 (dd, J=8.3, 2.2 Hz, 1H), 7.85 (dd, J=3.0, 0.6 Hz, 1H), 7.76 (d, J=5.0 Hz, 1H), 7.53 (d, J=8.3 Hz, 1H), 7.33-7.28 (m, 1H), 7.23-7.20 (m, 1H), 7.12 (d, J=3.9 Hz, 2H), 7.02 (td, J=8.0, 3.3 Hz, 1H), 6.92 (t, J=8.0 Hz, 1H), 5.55 (s, 2H), 4.56 (d, J=13.8 Hz, 1H), 4.42-4.32 (m, 1H), 4.15-4.04 (m, 1H), 3.09 (br. s., 1H), 2.41 (br. s., 3H), 2.18-2.12 (m, 1H), 1.92 (br. s., 1H), 1.78 (d, J=6.6 Hz, 1H), 1.49-1.40 (m, 1H), 1.08-1.02 (m, 1H), 1.00-0.95 (m, 2H), 0.81 (d, J=5.0 Hz, 1H). HPLC-1: Rt=11.1 min, purity=91.7%; HPLC-2: Rt=11.1 min, purity=95.6%.

It is noted that the proceeding Examples, while illustrative of the present invention, may not be in sequential order and some example numbers may be missing.

Assay(s) for TGR5 G Protein-Coupled Receptor MODULATION

The in vitro modulation of recombinant human TGR5 was determined as follows.

cAMP Assay

A human TGR5 expression construct of human TGR5 was integrated into the genome of a CHOK1 cell line (Invitrogen). Once a stable CHOK1 cell line was generated, the cells were incubated for 5-10 minutes in culture medium consisting of F-12 (Invitrogen#11765-047) supplemented with 10% fetal bovine serum.

On the day of the cAMP accumulation assay, cells stably expressing the chimeric human/mouse TGR5 construct were centrifuged at 1000 rpm for 5 minutes. The medium was aspirated and the cells were resuspended in 5 mL of assay buffer (phosphate-buffered saline with $Ca^{2+}$ and $Mg^{2+}$, Invitrogen#14040). The cells were counted using 1:2 dilution and then adjusted to $0.4$-$0.5 \times 10^6$ cells/mL in assay buffer, if necessary. Isobutylmethylxanthine (IBMX, Sigma#I5879) was added via a 1:5000 dilution to make a 0.1 mM final concentration and then 10 μL of the media were transferred to each well of a 384 well poly-D-lysine coated solid white plate (BD #35-6661) pre-dotted with 100 nL of with the desired concentration of compound added from a concentrated stock dissolved in dimethyl sulfoxide (DMSO) to give a final concentration of 1% DMSO in the assay. The plates were covered and incubated for 30 minutes at RT. cAMP accumulation was measured using the CisBio homogeneous time resolved fluorescence (HTRF) assay kit (#62AM2PEC) following the manufacturer's protocol. Briefly, 5 μl each of the cAMP-HTRF fluorescence detection reagents were added to each well, and the samples were incubated for at least one hour at room temperature. Fluorescence was excited at 320 nm and measured at 665 and 620 nm using the Envision instrument (Perkin Elmer), the fluorescence ratio of 665/620 was calculated and converted to nanomolar concentrations of cAMP in each well by interpolation from a cAMP standard curve. The concentration-response curves and $EC_{50}$ values were calculated with a four parameter logistic curve fit equation utilizing Excel/XLfit software (Microsoft and IDBS). The $EC_{50}$ value was calculated as the concentration of agonist which increased the cAMP concentration to a value halfway between the baseline and the maximum.

Compounds of the present invention were tested in the cAMP assay described immediately above and the results shown in Table 26 below were obtained. The data is believed to be representative of the ability of the compounds of the present invention to modulate recombinant human TGR5.

TABLE 26

| Example | TGR5 $EC_{50}$ (nM) |
|---|---|
| 1 | 3538 |
| 15 | 5905 |
| 28 | 2859 |
| 29 | 596 |
| 32 | 586 |
| 32A | 3396 |
| 32G | 636 |
| 36 | 2913 |
| 43 | 611 |
| 46 | 1916 |
| 69B | 50 |
| 69C | 58 |
| 69E | 45 |
| 69F | 54 |
| 69G | 51 |
| 69H | 52 |
| 69J | 5000 |
| 81 | 670 |
| 82 | 646 |
| 83 | 107 |
| 110G | 3140 |
| 110H | 6555 |
| 110J | 3305 |
| 110K | 5000 |
| 110T | 609 |
| 112 | 145 |
| 123 | 1266 |
| 124 | 5000 |
| 138 | 3458 |
| 138A | 24 |
| 142 | 647 |
| 146R | 49 |
| 146Y | 2859 |
| 148 | 3306 |
| 168F | 590 |
| 168J | 643 |
| 168N | 4375 |
| 171 | 56 |
| 176 | 47 |
| 177 | 48 |
| 179 | 45 |
| 182 | 589 |
| 197 | 2155 |
| 222 | 55 |
| 231 | 47 |
| 238 | 59 |
| 240 | 49 |
| 242 | 49 |
| 244 | 46 |
| 248 | 56 |
| 249 | 660 |
| 250 | 29 |
| 251 | 644 |
| 257 | 682 |
| 268 | 5019 |
| 270 | 608 |
| 273 | 646 |
| 275 | 608 |
| 282 | 664 |
| 283 | 3185 |
| 288 | 3953 |
| 289 | 2808 |
| 297 | 687 |
| 302 | 593 |
| 316 | 638 |
| 319 | 3817 |
| 324 | 3394 |
| 334 | 1265 |
| 336 | 173 |
| 339 | 2576 |
| 350 | 31 |
| 352 | 196 |
| 354 | 40 |
| 358 | 43 |
| 359 | 1653 |
| 367 | 186 |
| 375 | 188 |
| 392 | 189 |
| 418 | 185 |
| 430 | 197 |
| 434 | 183 |
| 436 | 171 |
| 447 | 1588 |
| 448 | 183 |
| 466 | 3926 |
| 467 | 2964 |
| 471 | 2169 |
| 472 | 1843 |
| 475 | 2595 |
| 481 | 1534 |
| 493 | 4152 |
| 500 | 195 |
| 505 | 1730 |

TABLE 26-continued

| Example | TGR5 EC$_{50}$ (nM) |
|---|---|
| 506 | 1605 |
| 507 | 2106 |
| 521 | 176 |
| 526 | 1501 |
| 527 | 184 |
| 534 | 192 |
| 552 | 2377 |
| 564 | 49 |
| 565 | 48 |
| 566 | 35 |
| 574 | 23 |
| 575 | 49 |
| 576 | 48 |
| 577 | 31 |
| 578 | 45 |
| 581 | 38 |
| 583 | 43 |
| 592 | 30 |
| 593 | 42 |
| 597 | 173 |
| 600 | 42 |
| 614 | 46 |
| 617 | 175 |
| 624 | 1384 |
| 626 | 188 |
| 628 | 195 |
| 635 | 177 |
| 662 | 36 |
| 669 | 1342 |
| 672 | 43 |
| 685 | 49 |
| 690 | 45 |
| 693 | 188 |
| 698 | 28 |
| 699 | 41 |
| 702 | 46 |
| 703 | 46 |
| 719 | 188 |
| 724 | 1304 |
| 730 | 188 |
| 767 | 1520 |
| 784 | 200 |
| 786 | 173 |
| 792 | 185 |
| 807 | 1329 |
| 808 | 1343 |
| 815 | 2001 |
| 829 | 1354 |
| 830 | 176 |
| 836 | 173 |
| 848 | 196 |
| 859 | 1357 |
| 864 | 193 |
| 878 | 42 |
| 882 | 1337 |
| 887 | 184 |
| 891 | 26 |
| 896 | 198 |
| 914 | 32 |
| 916 | 37 |
| 924A | 38 |
| 924B | 27 |
| 933 | 1612 |
| 934 | 191 |

In addition, compounds of the present invention, particularly Examples 1, 69A, 69M, 86, 138A, 168A, 170, 177N, 177P, 215, 231 and 237, were evaluated for their effectiveness as inhibitors of diacylglycerol acyltransferase (DGAT) receptor activity. The compounds were tested in the assay set forth below for inhibition of DGAT1 activity. With one exception (Example 170), the tested compounds exhibited no or minimal activity (IC$_{50}$>10 µM) against the DGAT1 enzyme. Based on these results, it is believed that the compounds of the present invention, particularly Examples 1, 69A, 69M, 86, 138A, 168A, 177N, 177P, 215, 231 and 237, are not effective in inhibiting DGAT receptor activity and therefore would not be effective as inhibitors or modulators of DGAT receptor activity.

Diacylglycerol Acyltransferase (DGAT) Assay

DGAT1 enzyme was assayed using membranes isolated from Sf9 cells expressing the recombinant human DGAT1 cDNA with 2-monooleoylglycerol and [$^3$H]-oleoyl-CoA as substrates as described by Seethala et al. (*Anal Biochem.*, 383(2):144-150 (Dec. 15, 2008)). Briefly, the assays were conducted in 384-well plates in a total volume of 30 µl at 25° C. In each assay, 200 ng of recombinant human DGAT1 membrane was incubated with 10 µM of 2-monooleoylglycerol and 15 µM of [$^3$H]-oleoyl-CoA in 100 mM potassium phosphate (pH 7.4) for 20 min with various concentrations of compounds delivered in DMSO. The assay was terminated by the addition of 20 µl of Stopping Solution (7.5 mg/ml Yittrium Oxide Polylysine beads, 3.3 mg/ml Fraction V BSA and 200 µM Mercuric chloride in 50 mM HEPES, pH 7.4). The signal was measured 1 h after quenching the reaction using LEAD-SEEKER$^{SM}$ for 5 minutes. To calculate the degree of inhibition, the zero level of enzyme activity (blank) was defined by the above assay procedure using membrane form Sf9 cell uninfected with baculovirus (Naive) and the 100% level of DGAT1 enzyme activity was defined by human mutant DGAT1 assay with the vehicle DMSO. The IC$_{50}$s of inhibitors were determined by logistic 4 parameter equation in XL-fit.

UTILITIES AND COMBINATIONS

A. Utilities

The compounds of the present invention possess activity as modulators of the TGR5 receptor, and, therefore, may be used in the treatment of diseases associated with TGR5 receptor activity. Via the modulation of TGR5 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.*-Imm., *Endoc. & Metab. Agents*, 1:1-24 (2001).

B. Combinations

The present invention includes within its scope pharmaceutical compositions comprising, as an active ingredient, a therapeutically effective amount of at least one of the compounds of Formula I, Ia, Ib, Ic, Id, Ie, If, Ig, Ih or Ij, preferably, a compound selected from one of the examples, preferably, Examples 29, 32, 32G, 43, 69B, 69C, 69E, 69F, 69G, 69H, 81, 82, 83, 110T, 112, 138A, 142, 146R, 168F, 168J, 171, 176, 177, 179, 182, 222, 231, 238, 240, 242, 244, 248, 249, 250, 251, 257, 270, 273, 275, 282, 297, 302, 316, 336, 350, 352, 354, 358, 367, 375, 392, 418, 430, 434, 436, 448, 500, 521, 527, 534, 564, 565, 566, 574, 575, 576, 577, 578, 581, 583, 592, 593, 597, 600, 614, 617, 626, 628, 635, 662, 672, 685, 690, 693, 698, 699, 702, 703, 719, 730, 784, 786, 792, 830, 836, 848, 864, 878, 887, 891, 896, 914, 916, 924A, 924B and 934, more preferably, Examples 69B, 69C, 69E, 69G, 69H, 69F, 83, 138A, 146R, 171, 176, 177, 179, 222, 231, 238, 240, 242, 244, 248, 250, 350, 354, 358, 564, 565, 566, 574, 575, 576, 577, 578, 581, 583, 592, 593, 600, 614, 662, 672, 685, 690, 698, 699, 702, 703, 878, 891, 914, 916, 924A and 924B, most preferably, Examples 83, 138A, 250, 350, 566, 574, 577, 581, 592, 662, 698, 891, 914, 916, 924A and 924B, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glipizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar, aleglitazar); SGLT2 inhibitors (e.g., 3-(benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis)), canagliflozin; 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, alogliptin and denagliptin); glucagon-like peptide-1 (GLP-1) receptor agonists (e.g., Exenatide (Byetta), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DACTM); aldose reductase inhibitors (e.g., those disclosed in WO 99/26659); RXR agonists (e.g., reglitazar (JTT-501), 5-[[6-[(2-fluorophenyl)methoxy]-2-naphthalenyl]methyl]-2,4-thiazolidinedione (MCC-555), 5-[[3-(5,6,7,8-tetrahydro-3,5,5,8,8-pentamethyl-2-naphthalenyl)-4-(trifluoromethoxy)-phenyl]methylene]-2,4-thiazolidinedione (MX-6054), DRF2593, farglitazar, (±)-5-[(2,4-dioxothiazolidin-5-yl)methyl]-2-methoxy-N-[[(4-trifluoromethyl)phenyl]-methyl]benzamide (KRP-297), 6-[1-(5,6,7,8-tetrahydro-3,5,5,8,8-pentamethyl-2-naphthalenyl)cyclopropyl]-3-pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., methyl ester[4-[(2R)-2-[[(2R)-2-(3-chlorophenyl)-2-hydroxyethyl]amino]propyl]phenoxy]-acetic acid (BRL 35135), 2-[4-[(2S)-2-[[(2S)-2-(3-chlorophenyl)-2-hydroxyethyl]amino]propyl]phenoxy]-acetic acid (BRL 37344), 4-[(3R)-3-[bis[(2R)-2-hydroxy-2-phenylethyl]amino]butyl]-benzamide (Ro 16-8714), 2-[4-[2-[[(2S)-2-hydroxy-3-phenoxypropyl]amino]ethoxy]phenoxy]-N-(2-methoxyethyl)-acetamide (ICI D7114), 5-[(2R)-2-[[(2R)-2-(3-chlorophenyl)-2-hydroxyethyl]amino]propyl]-3-benzodioxole-2,2-dicarboxylic acid, disodium salt (CL 316,243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386, 398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-cyclohexadiene-1,4-dione (L-783281), TER17411, TER17529); gluconeogenesis inhibitors (e.g., GP3034); somatostatin analogs and antagonists; antilipolytic agents (e.g., nicotinic acid, acipimox, N-cyclohexyl-2'-O-methyl-adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (KaroBio)); glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-pyridinecarboxylic acid (GKA-50 AstraZeneca)); GPR 40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy)phenyl)-1H-benzo[d]imidazole, TAK-875, CNX011, and P1736) and GPR-119 modulators (e.g., PSN821 (OSI Pharmaceuticals)).

Examples of suitable lipid lowering agents and anti-atherosclerotic agents for use in combination with the compounds of the present invention include one or more MTP/ApoB secretion inhibitors (e.g., dirlopatide, N-(2,2,2-trifluoroethyl)-9-[4-[4-[[[4'-(trifluoromethyl)[1,1'- biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid co-transporter inhibitors (e.g., compounds as disclosed in *Drugs of the Future*, 24:425-430 (1999); upregulators of LDL receptor activity (e.g., (3R)-3-[(13R)-13-hydroxy-10-oxotetradecyl]-5,7-dimethoxy-1(3H)-isobenzofuranone (Taisho Pharmaceutical Co. Ltd.) and (3α,4α,5α)-4-(2-propenyl)-cholestan-3-ol (Eli Lilly); bile acid sequestrants (e.g., WELCHOL®, COLESTID®, LoCholest and QUESTRAN®; and fibric acid derivatives, such as Atromid, LOPID® and Tricot); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl) sulfonyl]-4,5-dihydro-N'-methyl-4-phenyl-1H-pyrazole-1-carboximidamide (SLV 319), CP-945598 (Pfizer), Surinabant (SR-147778, Sanofi-Aventis), N-[(1S,2S)-3-(4-chlorophenyl)-2-(3-cyanophenyl)-1-methylpropyl]-2-methyl-2-{[5-(trifluoromethyl)pyridin-2-yl]oxy}propanamide (Merck) and those discussed in Hertzog, D. L., *Expert Opin. Ther. Patents*, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-benzenesulfonamide (L750355, Merck), or CP331648 (Pfizer), or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buproprion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b][1,4]diazepino[6,7,1hi]indole], with lorcaserin hydrochloride being preferred); 5-HT6 receptor antagonists (Suven, Biovitrum, Epix), anti-epileptics topiramate (Johnson & Johnson) and zonisamide, a ciliary neurotrophic factor agonist (e.g., AXOKINE® (Regeneron); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer), PF-04620110, and LCQ908); acetyl-CoA carboxylase (ACC) inhibitors (e.g., N-(4-(4-(4-isopropoxyphenoxy)phenyl)but-3-yn-2-yl)acetamide (A-80040, Abbott), (R)-anthracen-9-yl(3-(morpholine-4-carbonyl)-1,4'-bipiperidin-1'-yl) methanone (CP-640186, Pfizer)), SCD-1 inhibitors as described by Jiang et al., *Diabetes*, 53 (2004), (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH2 (Unigene)), NPY-Y4 agonists (7TM Pharma WO 2005/089786(A2,A3)-1), NPY-5 antagonists (e.g., NPYSRA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to ARICEPT®, razadyne, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

What is claimed is:
1. A compound of formula I

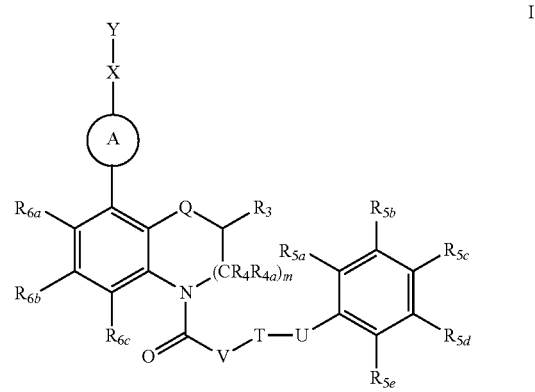

enantiomer, diastereomer, tautomer, prodrug or salt thereof wherein:
m is 1;
Q is $CR_{2a}R_2$;
T is $(C_1-C_5)$-alkyl, $(C_2-C_6)$-alkenyl, $(C_{5-10})$-aryl or $(C_{5-10})$-heteroaryl, all of which may be optionally substituted with one or more substituents selected from hydrogen, $^2H$, halogen, $C_1$-$C_6$ alkyl, $C_1$-$C_6$ alkoxy, CN, $(C_3$-$C_{12})$-cycloalkyl or halo($C_1$-$C_6$)-alkyl and wherein a carbon atom of the alkyl chain may be replaced with a heteroatom selected from N, O, and S;

U is a bond, S, $NR_{7a}$, O or a $(C_3-C_6)$-cycloalkyl;

V is a bond, —$CH_2$—, O or a $(C_3-C_6)$-cycloalkyl;

Ring A is a 5- to 6-membered aryl or heteroaryl, wherein the aryl and heteroaryl may be optionally substituted with one or more substituents selected from hydrogen, halogen, oxo, $C_1-C_6$ alkyl, $C_1-C_6$ alkoxy, CN, $(C_3-C_{12})$-cycloalkyl and halo$(C_1-C_6)$-alkyl and the heteroaryl contains 1-4 heteroatoms selected from N, O, and S;

X is a bond, $(C_1-C_6)$-alkyloxy, $(C_3-C_6)$-cycloalkyl, $(C_3-C_6)$-cycloalkyl-$(C_1-C_6)$-alkyl, $(C_{5-10})$-aryl, $(C_{5-10})$-aryloxy, $(C_{5-10})$-aryl-$(C_1-C_6)$-alkyl, $(C_{5-10})$-aryl-oxy-$(C_1-C_6)$-alkyl, $(C_{5-10})$-aryl-$(C_1-C_6)$-alkyloxy or heteroaryl-$(C_1-C_6)$-alkyl, wherein the heteroaryl contains 4- to 10-members and 1-4 heteroatoms selected from N, O, and S and any alkyl, aryl and heteroaryl may be optionally substituted with one or more substituents selected from hydrogen, halogen, $C_1-C_6$ alkyl, $C_1-C_6$ alkoxy, CN, —COOH, —$NR_{28}R_{29}$, —OH, $(C_3-C_{12})$-cycloalkyl, $(C_3-C_{12})$-cycloalkyloxy and halo$(C_1-C_6)$-alkyl;

Y is —$(CR_{22}R_{22a})_n$—W;

W is hydrogen, —OH, cyano, heteroaryl, which may be optionally substituted with one or more $R_{20}$'s, heterocycle, which may be optionally substituted with one or more $R_{20}$'s, —$N(R_{18})R_{19}$,

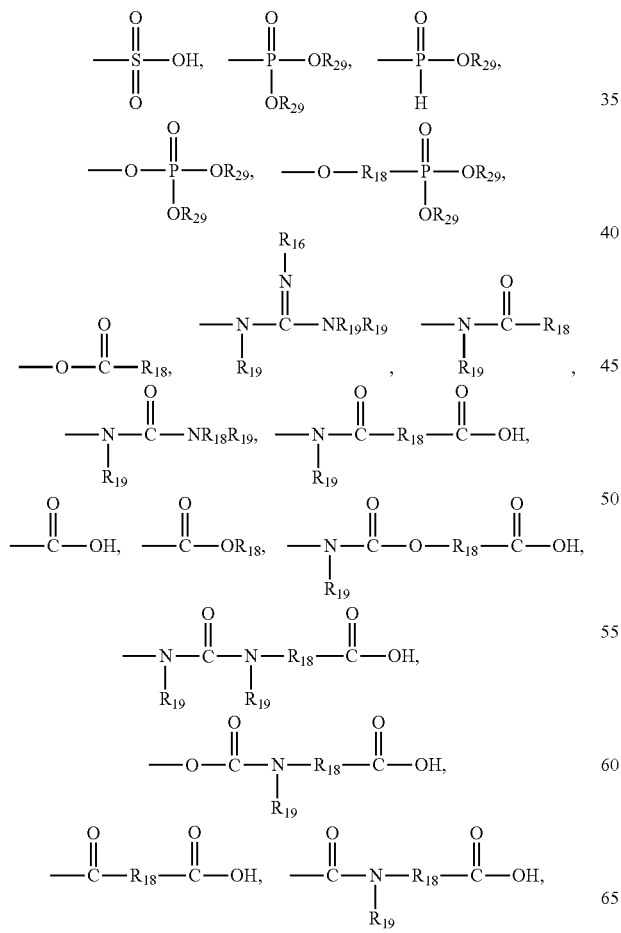

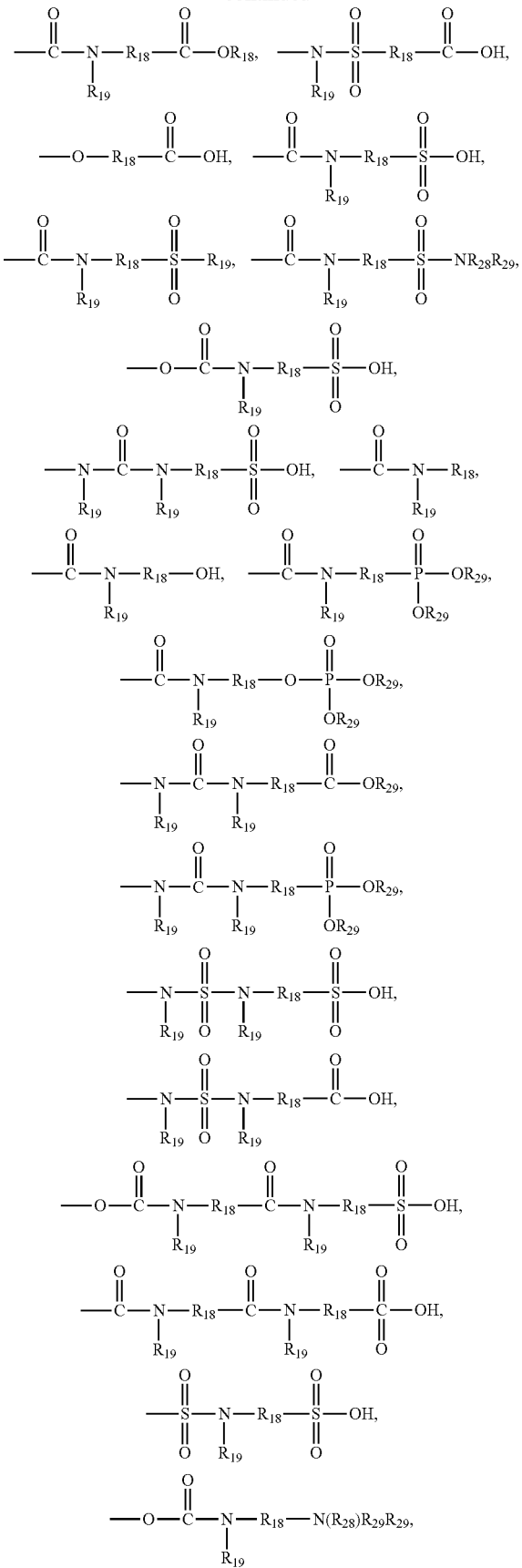

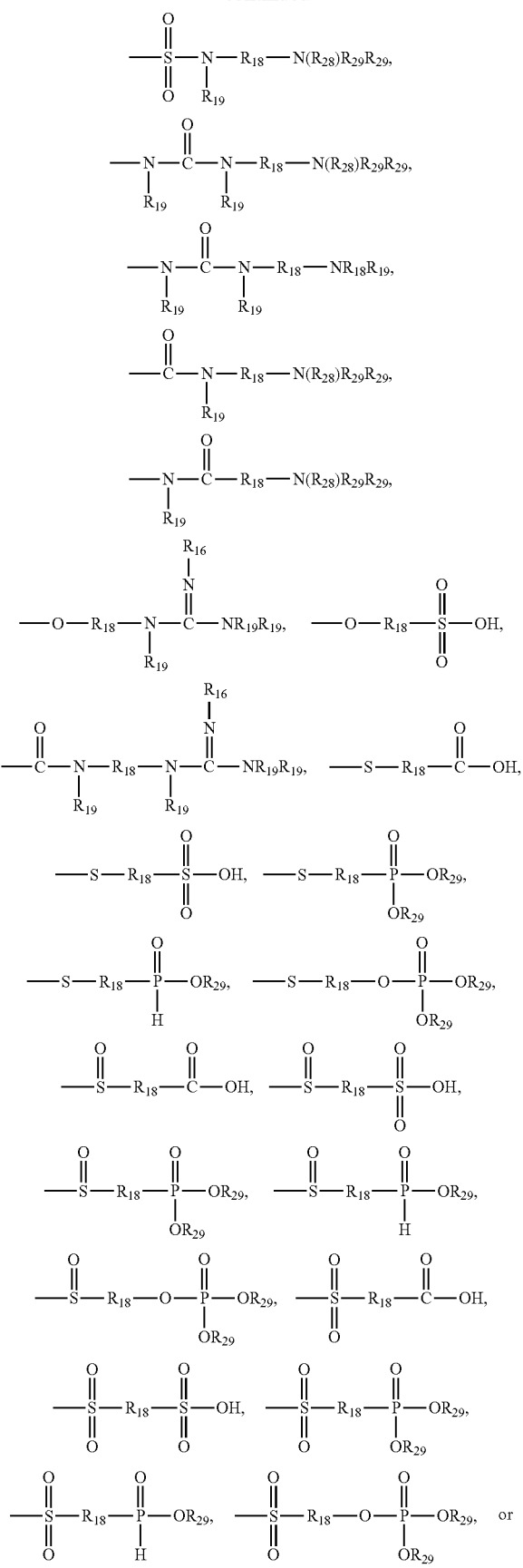

wherein the amino, hydroxy or acidic moiety may attach at any position of $R_{18}$;

$R_2$ is hydrogen, —OH, oxo, $(C_1-C_6)$-alkyl, $(C_3-C_{12})$-cycloalkyl or halo$(C_1-C_6)$-alkyl;

$R_{2a}$ is hydrogen, —OH, oxo, $(C_1-C_6)$-alkyl, $(C_3-C_{12})$-cycloalkyl or halo$(C_1-C_6)$-alkyl;

or $R_2$ and $R_{2a}$ can optionally be linked to form a linking group containing 1-2 carbon atoms;

$R_3$ is hydrogen, $(C_1-C_6)$-alkyl, $(C_3-C_{12})$-cycloalkyl or halo$(C_1-C_6)$-alkyl;

or $R_2$ and $R_3$ can optionally be linked to form a linking group containing 1-5 carbon atoms to form a $(C_3-C_7)$-cycloalkyl ring, a halo$(C_3-C_7)$-cycloalkyl ring or an aryl ring;

$R_4$, at each occurrence, is independently hydrogen, —OH, halogen, halo$(C_1-C_6)$-alkyl or $(C_1-C_8)$alkyl;

$R_{4a}$, at each occurrence, is independently is hydrogen, —OH, halogen, halo$(C_1-C_6)$-alkyl or $(C_1-C_8)$alkyl;

or $R_3$ and $R_4$ can optionally be linked with the carbons to which they are attached to form a linking group containing 1-5 carbon atoms to form a $(C_3-C_7)$-cycloalkyl ring, a halo$(C_3-C_7)$-cycloalkyl ring or an aryl ring;

or $R_4$ and $R_{4a}$ can optionally be linked to form a linking group containing 1-4 carbon atoms;

$R_{5a}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5b}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5c}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5d}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5e}$ is hydrogen, halogen, $C_1-C_6$ alkyl, $C_1-C_6$ alkoxy, CN, $(C_3-C_6)$-cycloalkyl or halo$(C_1-C_6)$-alkyl;

or two of $R_{5a}$, $R_{5b}$, $R_{5c}$, $R_{5d}$ or $R_{5e}$ may be taken together with the atoms to which both are attached form a 3- to 8-membered ring, which may optionally contain 1-4 heteroatoms selected from N, O, and S;

$R_{6a}$ is hydrogen, halogen or $C_1-C_6$ alkyl;
$R_{6b}$ is hydrogen, halogen or $C_1-C_6$ alkyl;
$R_{6c}$ is hydrogen, halogen or $C_1-C_6$ alkyl;
$R_{7a}$ is hydrogen, $C_1-C_6$ alkyl or —CO$_2$$(C_1-C_6)$-alkyl;
n is 0-6;
$R_{16}$ is H or —CN;

$R_{18}$, at each occurrence, is independently $(C_1-C_8)$alkyl, $(C_3-C_{12})$-cycloalkyl, a fused $(C_3-C_{18})$-cycloalkyl, $(C_1-C_8)$alkyl-$(C_3-C_{12})$-cycloalkyl-$(C_1-C_8)$alkyl, $(C_1-C_8)$alkyl-$(C_3-C_{12})$-cycloalkyl, $(C_{5-10})$-aryl, $(C_{5}-C_{10})$-aryl$(C_1-C_8)$alkyl, a heteroaryl, a heteroaryl$(C_1-C_8)$alkyl, a heterocyclo$(C_1-C_8)$alkyl or a heterocyclo, all of which may be optionally substituted with one or more $R_{20}$'s and wherein the heteroaryl and heterocyclo contain 4- to 10-members and contain 1-4 heteroatoms selected from N, O, and S;

$R_{19}$, at each occurrence, is independently hydrogen, $(C_1-C_6)$-alkyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is selected from halo, —OH, ($C_1$-$C_6$)-alkyl, ($C_2$-$C_6$)-alkenyl, ($C_2$-$C_6$)-alkynyl, —($C_3$-$C_{12}$)-cycloalkyl, ($C_1$-$C_6$)-alkyloxy, cyano, oxo, nitro, —COOH, —$SO_3H$, —CO($C_1$-$C_6$)-alkyl, —CO($C_6$-$C_{12}$)-aryl, —$CO_2$($C_1$-$C_6$)-alkyl, —$CONR_{28}R_{29}$, —$NR_{28}R_{29}$, —$NR_{28}C(=O)NR_{28}R_{29}$, —$NR_{28}C(=NR_{29})NR_{28}R_{29}$, —$SR_{28}$, —$S(=O)(=NR_{28})R_{29}$, —S(—OH)$R_{29}$, —$S(=O)R_{29}$, —$S(=O)_2R_{29}$, —$NR_{29}CO_2$($C_1$-$C_6$)-alkyl, —$NR_{28}SO_2R_{19}$, —O(C=O)—($C_1$-$C_6$)-alkyl, —O(C=O)$NR_{28}R_{29}$; —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{28}R_{29}$, —($C_1$-$C_6$)-alkyl-$CO_2$($C_1$-$C_6$)-alkyl, —O—P(=O)(OH)($OR_{29}$), —O—$CR_{28}R_{29}$—P(=O)(OH)($OR_{29}$), —P(=O)(OH)($OR_{29}$), ($C_{6-10}$)aryl, ($C_{6-10}$)aryl($C_1$-$C_6$)-alkyl, ($C_{6-10}$)aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_{28}R_{29}$, —$NR_{28}R_{29}$, —N($R_{28}$)$R_{29}R_{29}$, —O(C=O)—($C_1$-$C_6$)-alkyl, —O(C=O)$NR_{28}R_{29}$; —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{28}R_{29}$, —($C_1$-$C_6$)-alkyl-$CO_2$($C_1$-$C_6$)-alkyl, —O—P(=O)(OH)($OR_{29}$), —O—$CR_{28}R_{29}$—P(=O)(OH)($OR_{29}$), —P(=O)(OH)($OR_{29}$), —$S(=O)_2$OH, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

$R_{22}$, at each occurrence, is independently hydrogen, —OH, ($C_1$-$C_6$)-alkyl, ($C_3$-$C_{12}$)-cycloalkyl, ($C_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, —OH, halogen, $C_1$-$C_6$ alkyl, $C_1$-$C_6$ alkoxy, CN, ($C_3$-$C_{12}$)-cycloalkyl and halo($C_1$-$C_6$)-alkyl;

$R_{22a}$, at each occurrence, is independently hydrogen, —OH, ($C_1$-$C_6$)-alkyl, ($C_3$-$C_{12}$)-cycloalkyl, ($C_{6-10}$)aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, —OH, halogen, $C_1$-$C_6$ alkyl, $C_1$-$C_6$ alkoxy, CN, ($C_3$-$C_{12}$)-cycloalkyl and halo($C_1$-$C_6$)-alkyl;

$R_{28}$ and $R_{29}$, at each occurrence, are independently hydrogen, ($C_3$-$C_{12}$)-cycloalkyl, or ($C_1$-$C_8$)alkyl, wherein the cycloalkyl and alkyl may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_{38}R_{39}$, —$NR_{38}R_{39}$, —O(C=O)—($C_1$-$C_6$)-alkyl, —O(C=O)$NR_{38}R_{39}$; —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{38}R_{39}$, —($C_1$-$C_6$)-alkyl-$CO_2$($C_1$-$C_6$)-alkyl, —O—P(=O)(OH)($OR_{39}$), —O—$CR_{38}R_{39}$—P(=O)(OH)($OR_{39}$), —P(=O)(OH)($OR_{39}$), —$S(=O)_2$OH, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

or $R_{28}$ and $R_{29}$ are taken together with the nitrogen to which both are attached to form a 3- to 8-membered ring, which may optionally contain 1-4 heteroatoms selected from N, O, and S;

$R_{38}$ and $R_{39}$, at each occurrence, are independently hydrogen or ($C_1$-$C_8$)alkyl;

or $R_{38}$ and $R_{39}$ are taken together with the nitrogen to which both are attached to form a 3- to 8-membered ring, which may optionally contain 1-4 heteroatoms selected from N, O, and S.

2. The compound, enantiomer, diastereomer, tautomer, prodrug or salt thereof, of claim 1, wherein:

W is heteroaryl, which may be optionally substituted with one or more $R_{20}$'s,

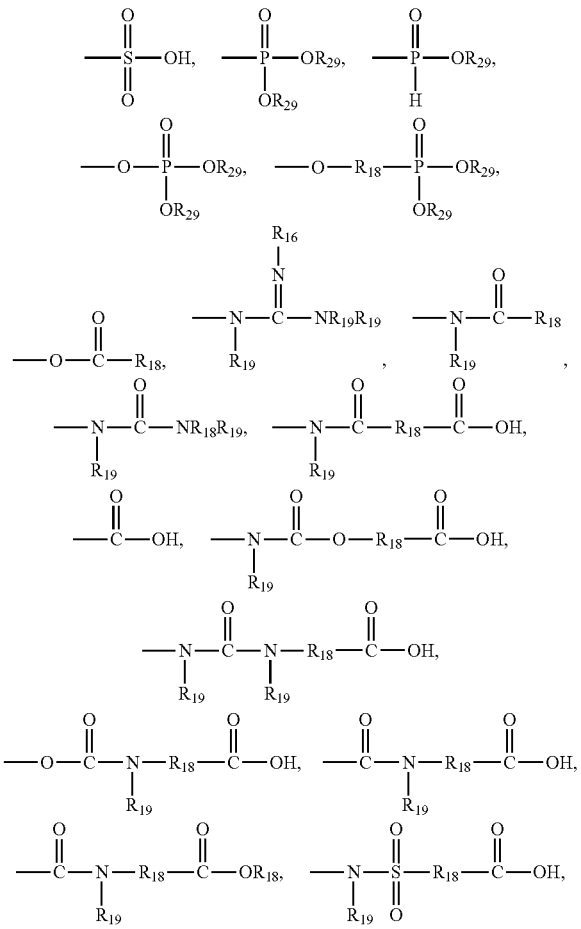

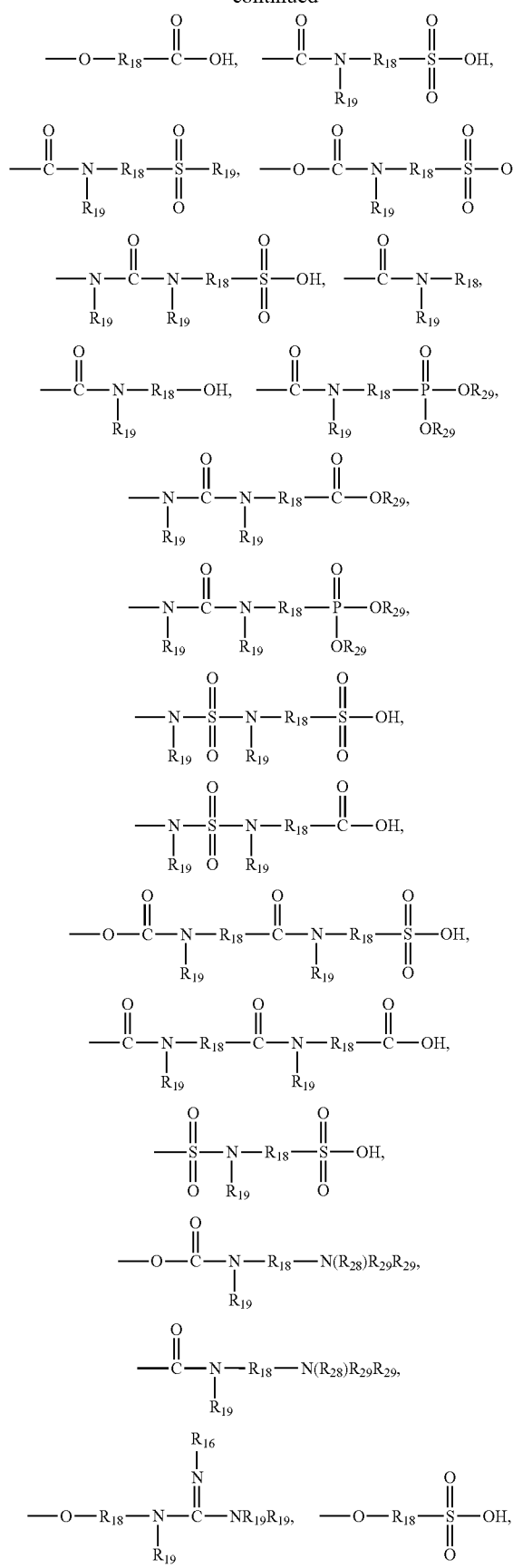
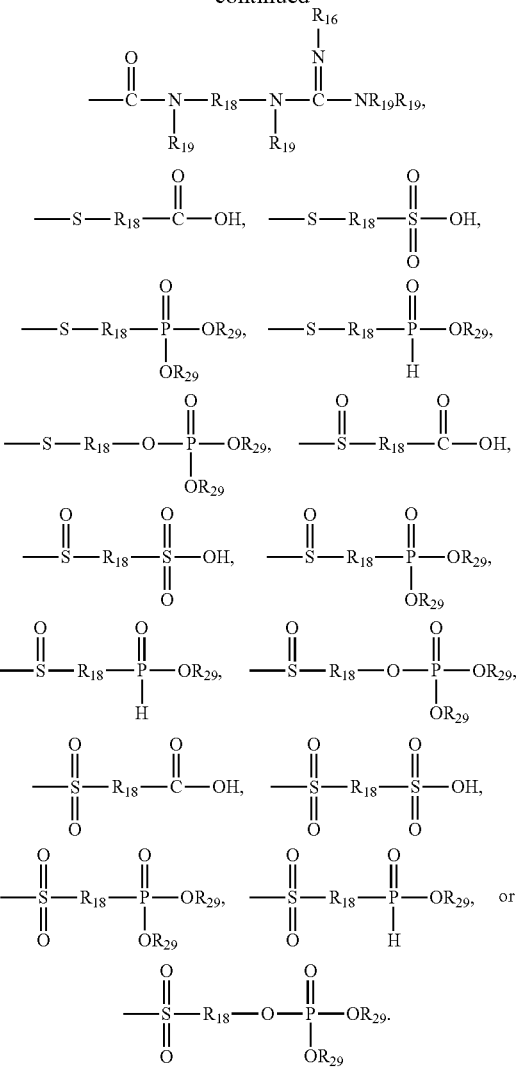
3. The compound, enantiomer, diastereomer, tautomer, prodrug or salt thereof, of claim 1, wherein:
W is heteroaryl, which may be optionally substituted with one or more $R_{20}$'s,
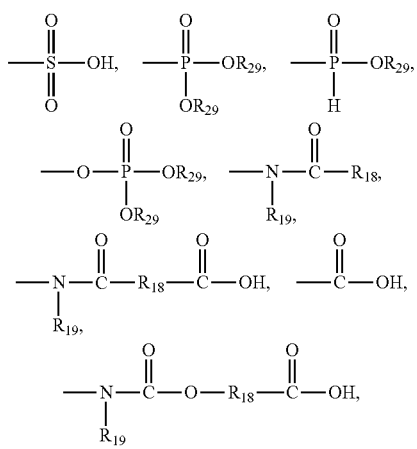

-continued

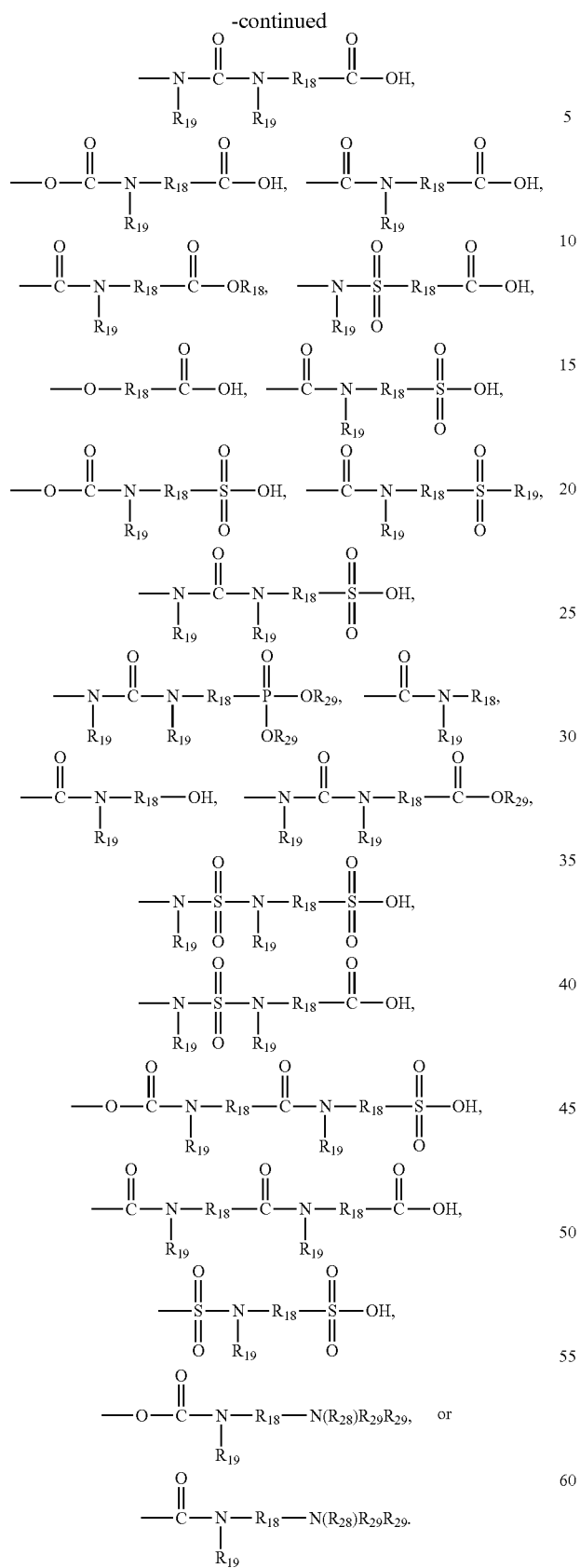

4. The compound, enantiomer, diastereomer, tautomer, prodrug or salt thereof, of claim 1, wherein:

W is

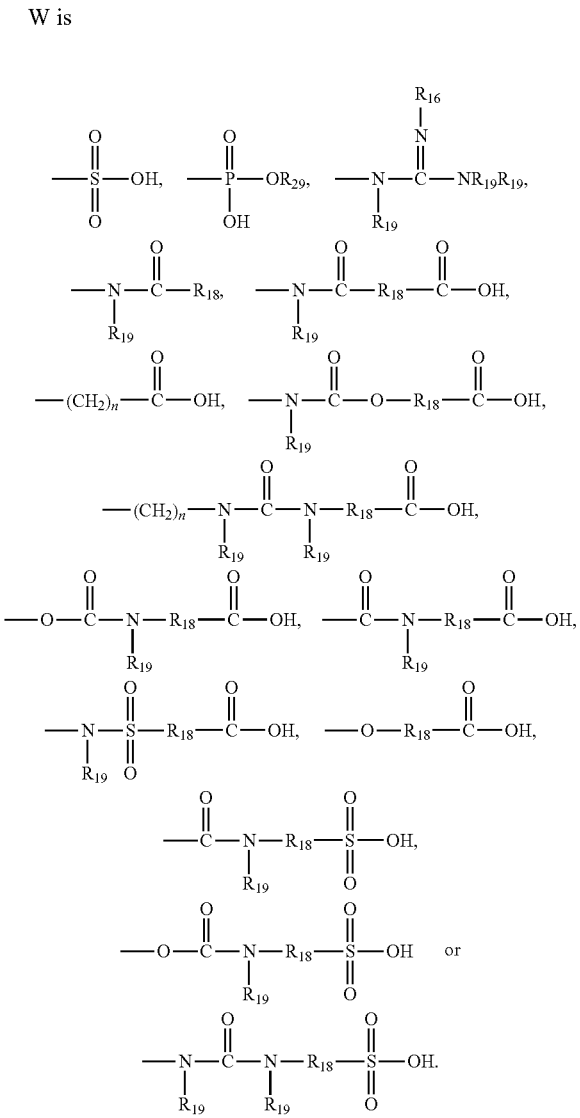

5. The compound, enantiomer, diastereomer, tautomer, prodrug or salt thereof, of claim 1, wherein A is a 5- to 6-membered aryl.

6. The compound, enantiomer, diastereomer, tautomer, prodrug or salt thereof, of claim 1, wherein A is a 5- to 6-membered heteroaryl, wherein the heteroaryl contains 1-4 heteroatoms selected from N, O, and S.

7. The compound, enantiomer, diastereomer, tautomer, prodrug or salt thereof, of claim 1, wherein:

m is 1;

Q is $CR_{2a}R_2$;

T is a $(C_1-C_5)$-alkyl, which may be optionally substituted with one or more substituents selected from hydrogen, halogen, $C_1-C_6$ alkyl, $C_1-C_6$ alkoxy, CN, $(C_3-C_{12})$-cycloalkyl or halo$(C_1-C_6)$-alkyl and wherein a carbon atom of the alkyl chain may be replaced with a heteroatom selected from N, O, and S;

U is a bond or O;

V is a bond, —$CH_2$—, O, or a $(C_3-C_6)$-cycloalkyl;

Ring A is a 5- to 6-membered aryl or heteroaryl, wherein the aryl and heteroaryl may be optionally substituted with one or more substituents selected from hydrogen, halogen, oxo, $C_1-C_6$ alkyl, $C_1-C_6$ alkoxy, CN, $(C_3-C_{12})$- cycloalkyl and halo($C_1$-$C_6$)-alkyl and the heteroaryl contains 1-4 heteroatoms selected from N, O, and S;

X is a bond, ($C_1$-$C_6$)-alkyloxy, ($C_3$-$C_6$)-cycloalkyl, ($C_3$-$C_6$)-cycloalkyl-($C_1$-$C_6$)-alkyl, ($C_{5-10}$)-aryl, ($C_{5-10}$)-aryloxy, ($C_{5-10}$)-aryl-($C_1$-$C_6$)-alkyl, ($C_{5-10}$)-aryl-oxy-($C_1$-$C_6$)-alkyl, ($C_{5-10}$)-aryl-($C_1$-$C_6$)-alkyloxy or heteroaryl-($C_1$-$C_6$)-alkyl, wherein the heteroaryl contains 4- to 10-members and 1-4 heteroatoms selected from N, O, and S and any alkyl, aryl and heteroaryl may be optionally substituted with one or more substituents selected from hydrogen, halogen, $C_1$-$C_6$ alkyl, $C_1$-$C_6$ alkoxy, CN, ($C_3$-$C_{12}$)-cycloalkyl, ($C_3$-$C_{12}$)-cycloalkyloxy and halo($C_1$-$C_6$)-alkyl;

Y is —($CR_{22}R_{22a}$)$_n$—W;

W is heteroaryl, which may be optionally substituted with one or more $R_{20}$'s, heterocyclo, which may be optionally substituted with one or more $R_{20}$'s, —N($R_{18}$)$R_{19}$,

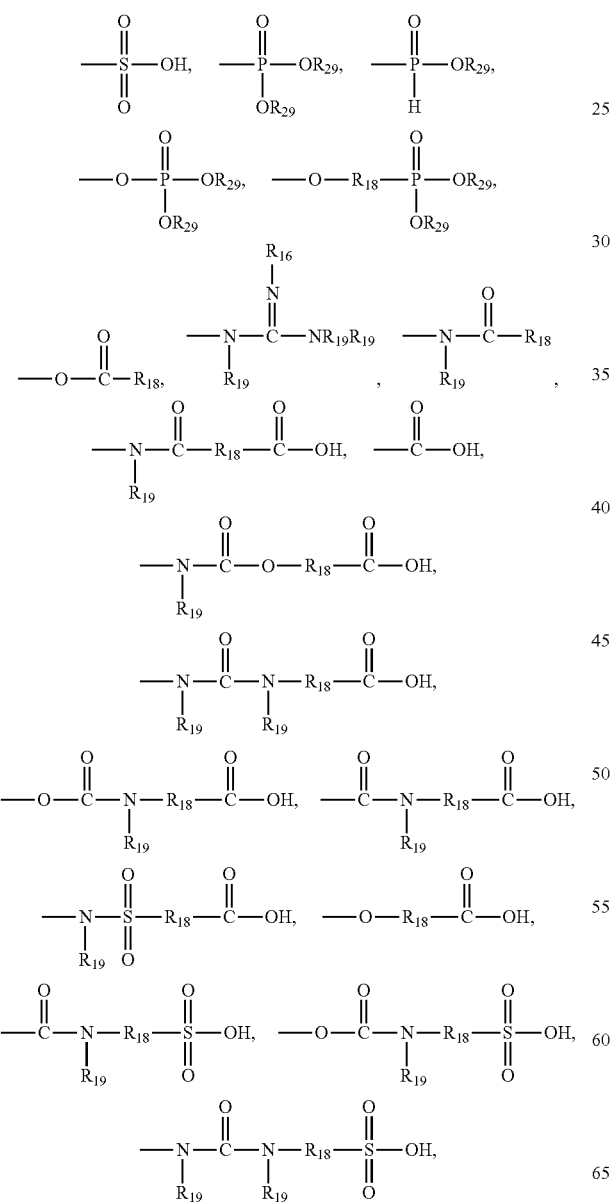

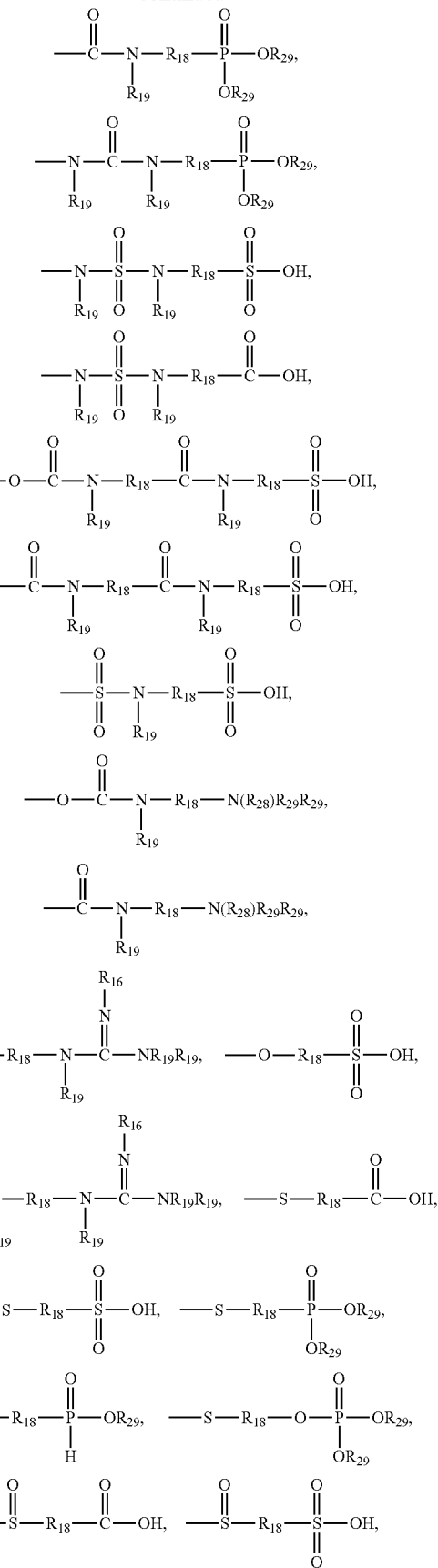

-continued

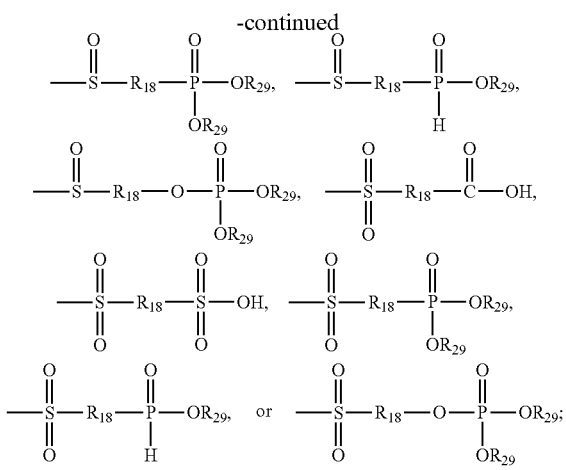

$R_2$ is hydrogen, $(C_1-C_6)$-alkyl, $(C_3-C_{12})$-cycloalkyl or halo$(C_1-C_6)$-alkyl;

$R_{2a}$ is hydrogen, $(C_1-C_6)$-alkyl, $(C_3-C_{12})$-cycloalkyl or halo$(C_1-C_6)$-alkyl;

or $R_2$ and $R_{2a}$ can optionally be linked to form a linking group containing 1-2 carbon atoms;

$R_3$ is hydrogen, $(C_1-C_6)$-alkyl, $(C_3-C_{12})$-cycloalkyl or halo$(C_1-C_6)$-alkyl;

or $R_2$ and $R_3$ can optionally be linked to form a linking group containing 1-2 carbon atoms to form a $(C_3-C_4)$-cycloalkyl ring, a halo$(C_3-C_4)$-cycloalkyl ring or an aryl ring;

$R_4$, at each occurrence, is independently hydrogen or $(C_1-C_8)$alkyl;

$R_{4a}$, at each occurrence, is independently is hydrogen or $(C_1-C_8)$alkyl;

or $R_4$ and $R_{4a}$ can optionally be linked to form a linking group containing 1-2 carbon atoms;

$R_{5a}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5b}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5c}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5d}$ is hydrogen, halogen, $C_1-C_6$ alkyl, $C_1-C_6$ alkoxy, CN, $(C_3-C_6)$-cycloalkyl or halo$(C_1-C_6)$-alkyl;

$R_{5e}$ is hydrogen, halogen, $C_1-C_6$ alkyl, $C_1-C_6$ alkoxy, CN, $(C_3-C_6)$-cycloalkyl or halo$(C_1-C_6)$-alkyl;

or two of $R_{5a}$, $R_{5b}$, $R_{5c}$, $R_{5d}$ or $R_{5e}$ may be taken together with the atoms to which both are attached form a 3- to 8-membered ring, which may optionally contain 1-4 heteroatoms selected from N, O, and S;

$R_{6a}$ is hydrogen, halogen or $C_1-C_6$ alkyl;

$R_{6b}$ is hydrogen, halogen or $C_1-C_6$ alkyl;

$R_{6c}$ is hydrogen, halogen or $C_1-C_6$ alkyl;

n is 0-4;

$R_{16}$ is H or —CN;

$R_{18}$, at each occurrence, is independently $(C_1-C_8)$alkyl, $(C_3-C_{12})$-cycloalkyl, $(C_1-C_8)$alkyl-$(C_3-C_{12})$-cycloalkyl-$(C_1-C_8)$alkyl, $(C_{5-10})$-aryl, $(C_5-C_{10})$-aryl$(C_1-C_8)$alkyl, a heteroaryl, a heteroaryl$(C_1-C_8)$alkyl or a heterocyclo, all of which may be optionally substituted with one or more $R_{20}$'s and wherein the heteroaryl and heterocyclo contain 4- to 10-members and contain 1-4 heteroatoms selected from N, O, and S;

$R_{19}$, at each occurrence, is independently hydrogen, $(C_1-C_6)$-alkyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is selected from halo, —OH, $(C_1-C_6)$-alkyl, $(C_2-C_6)$-alkenyl, $(C_2-C_6)$-alkynyl, —$(C_3-C_{12})$-cycloalkyl, $(C_1-C_6)$-alkyloxy, cyano, oxo, nitro, —COOH, —$SO_3H$, —$CO(C_1-C_6)$-alkyl, —$CO(C_6-C_{12})$-aryl, —$CO_2(C_1-C_6)$-alkyl, —$CONR_{28}R_{29}$, —$NR_{28}R_{29}$, —$NR_{28}C(=O)NR_{28}R_{29}$, —$NR_{28}C(=NR_{29})NR_{28}R_{29}$, —$SR_{28}$, —$S(=O)(=NR_{28})R_{29}$, —$S(—OH)R_{29}$, —$S(=O)R_{29}$, —$NR_{29}CO_2(C_1-C_6)$-alkyl, —$O(C=O)$—$(C_1-C_6)$-alkyl, —$O(C=O)NR_{28}R_{29}$, —$(C_1-C_6)$-alkylCOOH, —$(C_1-C_6)$-alkylOH, —$(C_1-C_6)$-alkyl$(NH_2)$COOH, —$(C_1-C_6)$-alkylCONR$_{28}$R$_{29}$, —$(C_1-C_6)$-alkyl-$CO_2(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), $(C_{6-10})$aryl, $(C_{6-10})$aryl$(C_1-C_6)$-alkyl, $(C_{6-10})$aryloxy, a 4- to 10-membered heteroaryl, which contains 1-4 heteroatoms selected from N, O, and 5; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —$CO(C_1-C_6)$-alkyl, —$CO_2(C_1-C_6)$-alkyl, —$CONR_{28}R_{29}$, —$NR_{28}R_{29}$, —O(C=O)—$(C_1-C_6)$-alkyl, —O(C=O)NR$_{28}$R$_{29}$, —$(C_1-C_6)$-alkyl-COOH, —$(C_1-C_6)$-alkylOH, —$(C_1-C_6)$-alkyl$(NH_2)$COOH, —$(C_1-C_6)$-alkylCONR$_{28}$R$_{29}$, —$(C_1-C_6)$-alkyl-$CO_2(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), —$S(=O)_2OH$, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_{22}$, at each occurrence, is independently hydrogen, $(C_1-C_6)$-alkyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, $C_1-C_6$ alkyl, $C_1-C_6$ alkoxy, CN, $(C_3-C_{12})$-cycloalkyl and halo$(C_1-C_6)$-alkyl;

$R_{22a}$, at each occurrence, is independently hydrogen, $(C_1-C_6)$-alkyl, $(C_3-C_{12})$-cycloalkyl, $(C_{6-10})$aryl, a 4- to 10-membered heteroaryl, which contains 1-4 heteroatoms selected from N, O, and S; or a 4- to 10-membered heterocyclo, which contains 1-4 heteroatoms selected from N, O, and S, wherein the alkyl, cycloalkyl, aryl, heteroaryl and heterocyclo may be optionally substituted with one or more substituents selected from hydrogen, halogen, $C_1-C_6$ alkyl, $C_1-C_6$ alkoxy, CN, $(C_3-C_{12})$-cycloalkyl and halo$(C_1-C_6)$-alkyl;

$R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{38}$R$_{39}$, —NR$_{38}$R$_{39}$, —O(C=O)—$(C_1-C_6)$-alkyl, —O(C=O)NR$_{38}$R$_{39}$, —$(C_1-C_6)$-alkyl-COOH, —$(C_1-C_6)$-alkylOH, —$(C_1-C_6)$-alkyl(NH$_2$)COOH, —$(C_1-C_6)$-alkylCONR$_{38}$R$_{39}$, —$(C_1-C_6)$-alkyl-CO$_2(C_1-C_6)$-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

or $R_{28}$ and $R_{29}$ are taken together with the nitrogen to which both are attached to form a 3- to 8-membered ring, which may optionally contain 1-4 heteroatoms selected from N, O, and S;

$R_{38}$ and $R_{39}$, at each occurrence, are independently hydrogen or $(C_1-C_8)$alkyl;

or $R_{38}$ and $R_{39}$ are taken together with the nitrogen to which both are attached to form a 3- to 8-membered ring, which may optionally contain 1-4 heteroatoms selected from N, O, and S.

8. The compound, enantiomer, diastereomer, tautomer, prodrug or salt thereof, of claim 1, wherein:

m is 1;

Q is CR$_{2a}$R$_2$;

T is $(C_1-C_4)$-alkyl, which may be optionally substituted with one or more substituents selected from hydrogen, $^2$H, halogen, $C_1-C_6$ alkyl, $C_1-C_6$ alkoxy, CN, $(C_3-C_{12})$-cycloalkyl or halo$(C_1-C_6)$-alkyl;

U is a bond or O;

V is a bond or O;

Ring A is a 5- to 6-membered aryl or heteroaryl, wherein the aryl and heteroaryl may be optionally substituted with one or more substituents selected from hydrogen, halogen, oxo, $C_1-C_6$ alkyl, $C_1-C_6$ alkoxy, CN, and halo$(C_1-C_6)$-alkyl and the heteroaryl contains 1-4 heteroatoms selected from N, O, and S;

X is a bond, $(C_1-C_6)$-alkyloxy, $(C_3-C_6)$-cycloalkyl, $(C_3-C_6)$-cycloalkyl-$(C_1-C_6)$-alkyl, $(C_{5-10})$-aryl, $(C_{5-10}$-aryloxy or $(C_{5-10})$-aryl-$(C_1-C_6)$-alkyl, wherein any alkyl and aryl may be optionally substituted with one or more substituents selected from hydrogen, halogen, $C_1-C_6$ alkyl, $C_1-C_6$ alkoxy, CN, $(C_3-C_{12})$-cycloalkyl, $(C_3-C_{12})$-cycloalkyloxy and halo$(C_1-C_6)$-alkyl;

Y is —(CR$_{22}$R$_{22a}$)$_n$—W;

W is heteroaryl, which may be optionally substituted with one or more R$_{20}$'s,

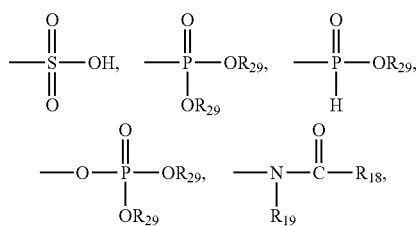

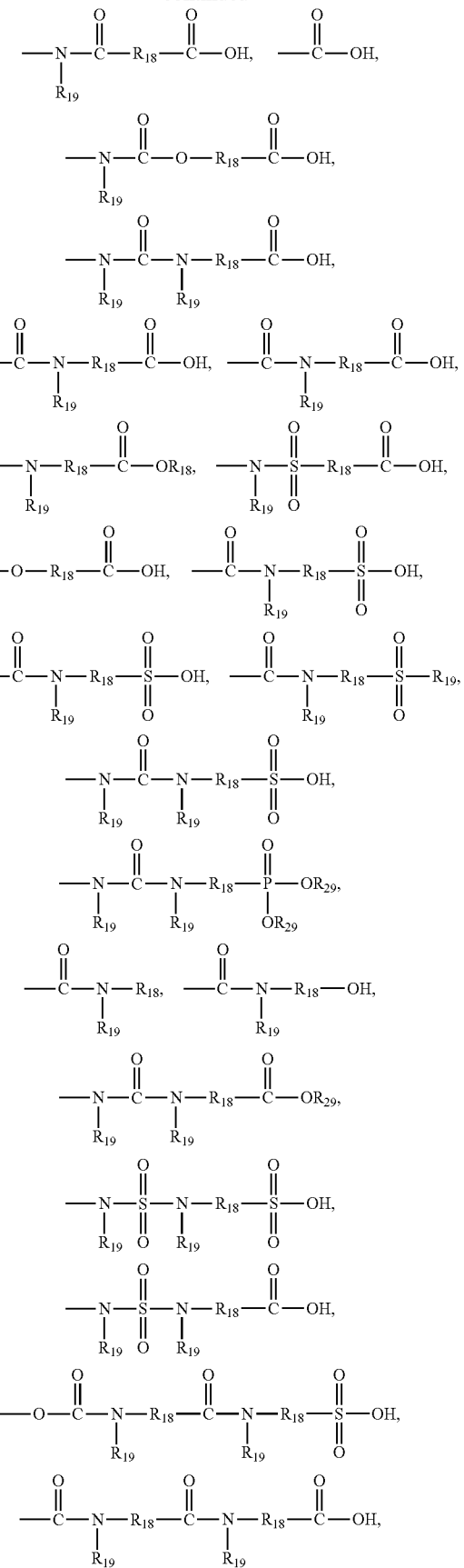

-continued

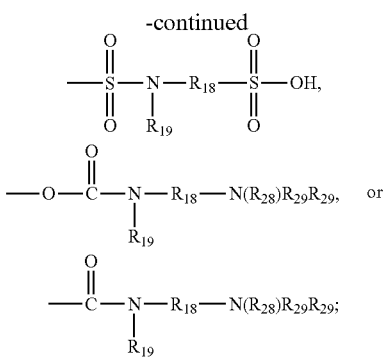

$R_2$ is hydrogen, $(C_1-C_6)$-alkyl, $(C_3-C_{12})$-cycloalkyl or halo$(C_1-C_6)$-alkyl;

$R_{2a}$ is hydrogen, $(C_1-C_6)$-alkyl, $(C_3-C_{12})$-cycloalkyl or halo$(C_1-C_6)$-alkyl;

$R_3$ is hydrogen or $(C_1-C_6)$-alkyl;

or $R_2$ and $R_3$ can optionally be linked to form a linking group containing 1-5 carbon atoms to form a $(C_3-C_7)$-cycloalkyl ring, a halo$(C_3-C_7)$-cycloalkyl ring or an aryl ring;

$R_4$, at each occurrence, is independently hydrogen or $(C_1-C_8)$alkyl;

$R_{4a}$, at each occurrence, is independently is hydrogen or $(C_1-C_8)$alkyl;

or $R_4$ and $R_{4a}$ can optionally be linked to form a linking group containing 1-2 carbon atoms;

$R_{5a}$ is hydrogen, halogen, $C_1-C_6$ alkyl or halo$(C_1-C_6)$-alkyl;

$R_{5b}$ is hydrogen, halogen, $C_1-C_6$ alkyl or halo$(C_1-C_6)$-alkyl;

$R_{5c}$ is hydrogen, halogen, $C_1-C_6$ alkyl or halo$(C_1-C_6)$-alkyl;

$R_{5d}$ is hydrogen, halogen, $C_1-C_6$ alkyl or halo$(C_1-C_6)$-alkyl;

$R_{5e}$ is hydrogen, halogen, $C_1-C_6$ alkyl or halo$(C_1-C_6)$-alkyl;

or two of $R_{5a}$, $R_{5b}$, $R_{5c}$, $R_{5d}$ or $R_{5e}$ may be taken together with the atoms to which both are attached form a 3- to 8-membered ring, which may optionally contain 1-4 heteroatoms selected from N, O, and S;

$R_{6a}$ is hydrogen or $C_1-C_6$ alkyl;

$R_{6b}$ is hydrogen or $C_1-C_6$ alkyl;

$R_{6c}$ is hydrogen or $C_1-C_6$ alkyl;

n is 0-2;

$R_{18}$, at each occurrence, is independently $(C_1-C_8)$alkyl, $(C_3-C_{12})$-cycloalkyl, $(C_{5-10})$-aryl, a heteroaryl or a heteroaryl$(C_1-C_8)$alkyl, all of which may be optionally substituted with one or more $R_{20}$'s and wherein the heteroaryl contains 4- to 10-members and contains 1-4 heteroatoms selected from N, O, and S;

$R_{19}$, at each occurrence, is independently hydrogen, $(C_1-C_6)$-alkyl, $(C_3-C_{12})$-cycloalkyl, $(C_{6-10})$aryl or a 4- to 10-membered heteroaryl, which contains 1-4 heteroatoms selected from N, O, and S;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$, at each occurrence, is selected from halo, —OH, $(C_1-C_6)$-alkyl, $(C_2-C_6)$-alkenyl, $(C_2-C_6)$-alkynyl, —$(C_3-C_{12})$-cycloalkyl, $(C_1-C_6)$-alkyloxy, cyano, oxo, nitro, —COOH, —SO$_3$H, —CO$(C_1-C_6)$-alkyl, —CO$(C_6-C_{12})$-aryl, —CO$_2(C_1-C_6)$-alkyl, —CONR$_{28}$R$_{29}$, —NR$_{28}$R$_{29}$, —NR$_{28}$C(=O)NR$_{28}$R$_{29}$, —NR$_{28}$C(NR$_{29}$)NR$_{28}$R$_{29}$, —SR$_{28}$, —S(=O)(=NR$_{28}$)R$_{29}$, —S(=OH)R$_{29}$, —S(=O)R$_{29}$, —NR$_{29}$CO$_2(C_1-C_6)$-alkyl, —NR$_{28}$SO$_2$R$_{19}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), $(C_{6-10})$aryl, $(C_{6-10})$aryl$(C_1-C_6)$-alkyl, $(C_{6-10})$aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

$R_{22}$, at each occurrence, is independently hydrogen, $(C_1-C_6)$-alkyl, $(C_3-C_{12})$-cycloalkyl, $(C_{6-10})$aryl, or a 4- to 10-membered heteroaryl, which contains 14 heteroatoms selected from N, O, and S; wherein the alkyl, cycloalkyl, aryl and heteroaryl may be optionally substituted with one or more substituents selected from hydrogen, halogen, $C_1-C_6$ alkyl, $C_1-C_6$ alkoxy, CN, $(C_3-C_{12})$-cycloalkyl and halo$(C_1-C_6)$-alkyl;

$R_{22a}$, at each occurrence, is independently hydrogen, $(C_1-C_6)$-alkyl, $(C_3-C_{12})$-cycloalkyl, $(C_{6-10})$aryl, or a 4- to 10-membered heteroaryl, which contains 1-4 heteroatoms selected from N, O, and S; wherein the alkyl, cycloalkyl, aryl and heteroaryl may be optionally substituted with one or more substituents selected from hydrogen, halogen, $C_1-C_6$ alkyl, $C_1-C_6$ alkoxy, CN, $(C_3-C_{12})$-cycloalkyl and halo$(C_1-C_6)$-alkyl;

$R_{28}$ and $R_{29}$, at each occurrence, are independently hydrogen or $(C_1-C_8)$alkyl, wherein the alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{38}$R$_{39}$, —NR$_{38}$R$_{39}$, —O(C=O)—$(C_1-C_6)$-alkyl, —O(C=O)NR$_{38}$R$_{39}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{38}$R$_{39}$, —$(C_1-C_6)$-alkyl-CO$_2(C_1-C_6)$-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, $(C_{6-10})$aryl, a 4- to 10-membered heteroaryl, which contains 1-4 heteroatoms selected from N, O, and S, a 4- to 10-membered heterocyclo, which contains 1-4 heteroatoms selected from N, O, and S; halo$(C_1-C_6)$alkyl, and halo$(C_1-C_6)$alkyloxy;

or $R_{28}$ and $R_{29}$ are taken together with the nitrogen to which both are attached to form a 3- to 8-membered ring, which may optionally contain 1-4 heteroatoms selected from N, O, and S;

$R_{38}$ and $R_{39}$, at each occurrence, are independently hydrogen or $(C_1-C_8)$alkyl;

or $R_{38}$ and $R_{39}$ are taken together with the nitrogen to which both are attached to form a 3- to 8-membered ring, which may optionally contain 1-4 heteroatoms selected from N, O, and S.

9. The compound, enantiomer, diastereomer, tautomer, prodrug or salt thereof, of claim 1, wherein:

m is 1;

Q is $CHR_2$;

T is a $(C_1-C_4)$-alkyl;

U is O;

V is a bond;

A is a 5- to 6-membered aryl or heteroaryl, wherein the heteroaryl contains 1-4 heteroatoms selected from N, O, and S;

X is a bond, $(C_{5-10})$-aryl, or $(C_{5-10})$-aryl-$(C_1-C_6)$-alkyl, wherein any aryl may be optionally substituted with one or more substituents selected from hydrogen, halogen, $C_1-C_6$ alkyl, $C_1-C_6$ alkoxy, CN, $(C_3-C_{12})$-cycloalkyl, $(C_3-C_{12})$-cycloalkyloxy and halo$(C_1-C_6)$-alkyl;

Y is $-(CR_{22}R_{22a})_n-W$;

W is

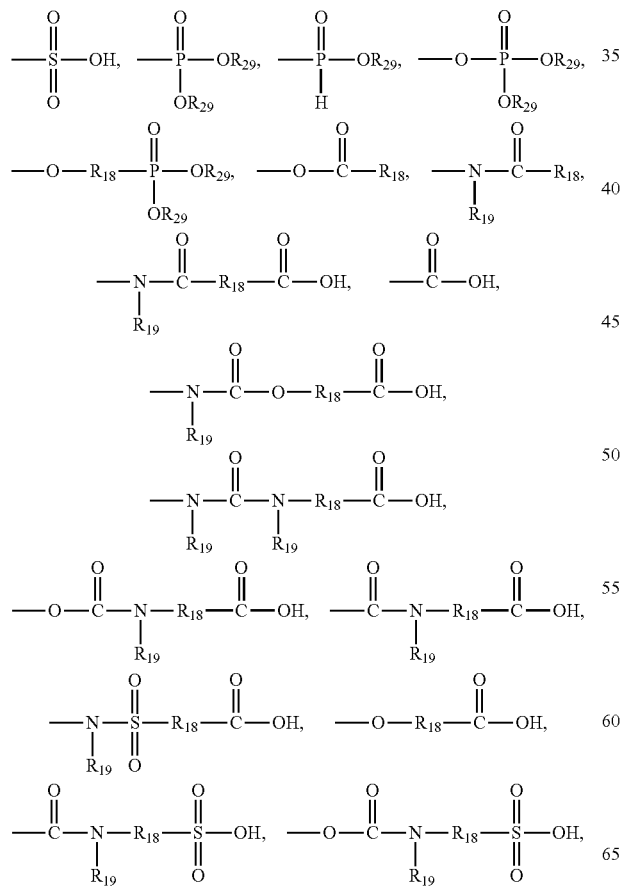

$R_2$ and $R_3$ are hydrogen;

or $R_2$ and $R_3$ can optionally be linked to form a linking group containing 1-3 carbon atoms to form a $(C_3-C_5)$-cycloalkyl ring, a halo$(C_3-C_5)$-cycloalkyl ring or an aryl ring;

$R_4$ and $R_{4a}$ are hydrogen;

$R_{5a}$ is hydrogen, halogen or $C_1-C_6$ alkyl;

$R_{5b}$ is hydrogen, halogen or $C_1-C_6$ alkyl;

$R_{5c}$ is hydrogen, halogen or $C_1-C_6$ alkyl;

$R_{5d}$ is hydrogen, halogen or $C_1-C_6$ alkyl;

$R_{5e}$ is hydrogen, halogen or $C_1-C_6$ alkyl;

$R_{6a}$, $R_{6b}$ and $R_{6c}$ are hydrogen;

n is 0-2;

$R_{18}$, at each occurrence, is independently $(C_1-C_8)$alkyl or $(C_3-C_{12})$-cycloalkyl, both of which may be optionally substituted with one or more $R_{20}$'s;

$R_{19}$, at each occurrence, is independently hydrogen or $(C_1-C_6)$-alkyl;

$R_{20}$, at each occurrence, is selected from halo, —OH, $(C_1-C_6)$-alkyl, $(C_2-C_6)$-alkenyl, $(C_2-C_6)$-alkynyl, —$(C_3-C_{12})$-cycloalkyl, $(C_1-C_6)$-alkyloxy, cyano, oxo, nitro, —COOH, —SO$_3$H, —CO$(C_1-C_6)$-alkyl, —CO$(C_6-C_{12})$-aryl, —CO$_2(C_1-C_6)$-alkyl, —CONR$_{28}$R$_{29}$, —NR$_{28}$R$_{29}$, —NR$_{28}$C(=O)NR$_{28}$R$_{29}$, —NR$_{28}$C(NR$_{29}$)NR$_{28}$R$_{29}$, —SR$_{28}$, —S(=O)(=NR$_{28}$)R$_{29}$, —S(—OH)R$_{29}$, —S(=O)R$_{29}$, —NR$_{29}$CO$_2(C_1-C_6)$-alkyl, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2(C_1-C_6)$-alkyl, —O—P(=O)(OH)(OR$_{29}$), —O—CR$_{28}$R$_{29}$—P(=O)(OH)(OR$_{29}$), —P(=O)(OH)(OR$_{29}$), $(C_{6-10})$aryl, $(C_{6-10})$aryl$(C_1-C_6)$-alkyl, $(C_{6-10})$aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$;

—(C₁-C₆)-alkylCOOH, —(C₁-C₆)-alkylOH, —(C₁-C₆)-alkyl(NH₂)COOH, —(C₁-C₆)-alkylCONR₂₈R₂₉, —(C₁-C₆)-alkyl-CO₂(C₁-C₆)-alkyl, —O—P(=O)(OH)(OR₂₉), —O—CR₂₈R₂₉—P(=O)(OH)(OR₂₉), —P(=O)(OH)(OR₂₉), —S(=O)₂OH, (C₆₋₁₀)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C₁-C₆)alkyl, and halo(C₁-C₆)alkyloxy;

R₂₂, at each occurrence, is independently hydrogen, (C₁-C₆)-alkyl or (C₆₋₁₀)aryl;

R₂₂ₐ, at each occurrence, is independently hydrogen, (C₁-C₆)-alkyl or (C₆₋₁₀)aryl;

R₂₈ and R₂₉, at each occurrence, are independently hydrogen or (C₁-C₈)alkyl, wherein the alkyl may be optionally substituted with one or more substituents selected from the group consisting of: halo, —OH, (C₁-C₆)-alkyl, (C₂-C₆)-alkenyl, (C₂-C₆)-alkynyl, (C₁-C₆)-alkyloxy, cyano, nitro, —COOH, —CO(C₁-C₆)-alkyl, —CO₂(C₁-C₆)-alkyl, —CONR₃₈R₃₉, —NR₃₈R₃₉, —O(C=O)—(C₁-C₆)-alkyl, —O(C=O)NR₃₈R₃₉; —(C₁-C₆)-alkyl-COOH, —(C₁-C₆)-alkylOH, —(C₁-C₆)-alkyl(NH₂)COOH, —(C₁-C₆)-alkylCONR₃₈R₃₉, —(C₁-C₆)-alkyl-CO₂(C₁-C₆)-alkyl, —O—P(=O)(OH)(OR₃₉), —O—CR₃₈R₃₉—P(=O)(OH)(OR₃₉), —P(=O)(OH)(OR₃₉), —S(=O)₂OH, (C₆₋₁₀)aryl, a 4- to 10-membered heteroaryl, which contains 1-4 heteroatoms selected from N, O, and S, a 4- to 10-membered heterocyclo, which contains 1-4 heteroatoms selected from N, O, and S; halo(C₁-C₆)alkyl, and halo(C₁-C₆)alkyloxy; and R₃₈ and R₃₉, at each occurrence, are independently hydrogen or (C₁-C₈)alkyl.

10. The compound, enantiomer, diastereomer, tautomer, prodrug or salt thereof, of claim 1, wherein:

m is 1;
Q is CHR₂;
T is a (C₁-C₄)-alkyl;
U is O;
V is a bond;
Ring A is phenyl, pyrazolyl, tetrazolyl, thiophenyl or pyridinyl;
X is a bond or (C₅₋₁₀)-aryl-(C₁-C₆)-alkyl, wherein the aryl may be optionally substituted with one or more substituents selected from hydrogen, halogen, C₁-C₆ alkyl, C₁-C₆ alkoxy, CN, (C₃-C₁₂)-cycloalkyl, (C₃-C₁₂)-cycloalkyloxy and halo(C₁-C₆)-alkyl;
Y is —(CR₂₂R₂₂ₐ)ₙ—W;
W is

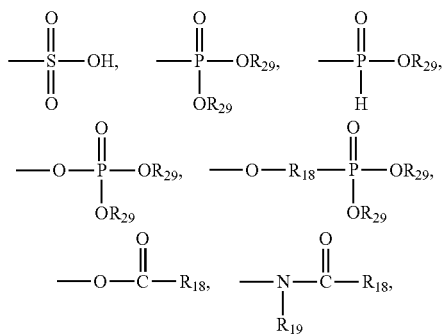

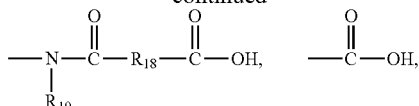
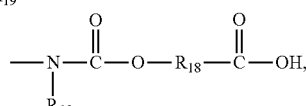
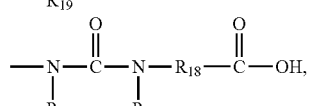
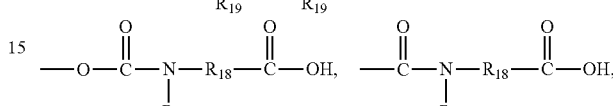
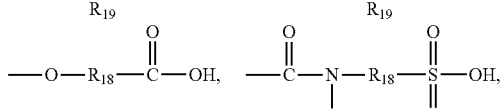
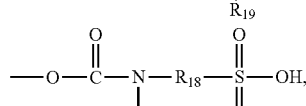
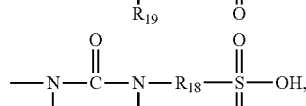
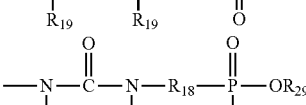
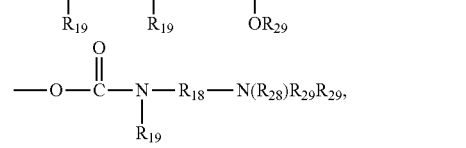
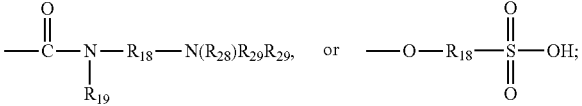

R₂, R₃, R₄ and R₄ₐ are hydrogen;
R₅ₐ is hydrogen, Cl, F or methyl;
R₅ᵦ is hydrogen, Cl, F or methyl;
R₅꜀ is hydrogen, Cl, F or methyl;
R₅d is hydrogen, Cl, F or methyl;
R₅ₑ is hydrogen, Cl, F or methyl;
R₆ₐ, R₆ᵦ and R₆꜀ are hydrogen;
n is 0-2;
R₁₈, at each occurrence, is independently (C₁-C₈)alkyl, which may be optionally substituted with one or more R₂₀'s;
R₁₉, at each occurrence, is independently hydrogen or (C₁-C₆)-alkyl;
R₂₀, at each occurrence, is selected from halo, —OH, (C₁-C₆)-alkyl, (C₂-C₆)-alkenyl, (C₂-C₆)-alkynyl, (C₃-C₁₂)-cycloalkyl, (C₁-C₆)-alkyloxy, cyano, oxo, nitro, —COOH, —SO₃H, —CO(C₁-C₆)-alkyl, —CO(C₆-C₁₂)-aryl, —CO₂(C₁-C₆)-alkyl, —CONR₂₈R₂₉, —NR₂₈R₂₉, —NR₂₈C(=O)NR₂₈R₂₉, —NR₂₈C(=NR₂₉)NR₂₈R₂₉, —SR₂₈, —S(=O)(=NR₂₈)R₂₉, —S(—OH)R₂₉, —S(=O)R₂₉, —NR₂₉CO₂(C₁-C₆)-alkyl, —O(C=O)—(C₁-C₆)-alkyl, —O(C=O)NR₂₈R₂₉; —(C₁-C₆)-alkylCOOH, —(C₁-C₆)-alkylOH, —($C_1$-$C_6$)-alkyl($NH_2$)COOH, —($C_1$-$C_6$)-alkylCONR$_{28}$R$_{29}$, —($C_1$-$C_6$)-alkyl-CO$_2$($C_1$-$C_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), ($C_{6-10}$)aryl, ($C_{6-10}$)aryl($C_1$-$C_6$)-alkyl, ($C_{6-10}$)aryloxy, a 4- to 10-membered heteroaryl, which contains 1-4 heteroatoms selected from N, O, and S; or a 4- to 10-membered heterocyclo, which contains 1-4 heteroatoms selected from N, O, and S; wherein any alkyl, cycloalkyl, aryl, heteroaryl, and heterocyclo may be optionally substituted with one or more substituents selected from the group consisting of halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —O(C=O)—($C_1$-$C_6$)-alkyl, —O(C=O)NR$_{28}$R$_{29}$; —($C_1$-$C_6$)-alkyl-COOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, —O—P(=O)(OH)(OR$_{29}$), —O—CR$_{28}$R$_{29}$—P(=O)(OH)(OR$_{29}$), —P(=O)(OH)(OR$_{29}$), —S(=O)$_2$OH, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy;

R$_{22}$, at each occurrence, is independently hydrogen or ($C_1$-$C_6$)-alkyl;

R$_{22a}$, at each occurrence, is independently hydrogen or ($C_1$-$C_6$)-alkyl;

R$_{28}$ and R$_{29}$, at each occurrence, are independently hydrogen or ($C_1$-$C_8$)alkyl, wherein the alkyl may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{38}$R$_{39}$, —NR$_{38}$R$_{39}$, —O(C=O)—($C_1$-$C_6$)-alkyl, —O(C=O)NR$_{38}$R$_{39}$; —($C_1$-$C_6$)-alkyl-COOH, —($C_1$-$C_6$)-alkylOH, —($C_1$-$C_6$)-alkyl(NH$_2$)COOH, —($C_1$-$C_6$)-alkylCONR$_{38}$R$_{39}$, —($C_1$-$C_6$)-alkyl-CO$_2$($C_1$-$C_6$)-alkyl, —O—P(=O)(OH)(OR$_{39}$), —O—CR$_{38}$R$_{39}$—P(=O)(OH)(OR$_{39}$), —P(=O)(OH)(OR$_{39}$), —S(=O)$_2$OH, ($C_{6-10}$)aryl, a 4- to 10-membered heteroaryl, which contains 1-4 heteroatoms selected from N, O, and S, a 4- to 10-membered heterocyclo, which contains 1-4 heteroatoms selected from N, O, and S; halo($C_1$-$C_6$)alkyl, and halo($C_1$-$C_6$)alkyloxy; and R$_{38}$ and R$_{39}$, at each occurrence, are independently hydrogen or ($C_1$-$C_8$)alkyl.

11. The compound, enantiomer, diastereomer, tautomer, prodrug or salt thereof, of claim 1, wherein the compound is selected from one of the examples.

12. A pharmaceutical composition comprised of a therapeutically effective amount of at least one compound, enantiomer, diastereomer, tautomer, prodrug or salt thereof, of claim 1, and a pharmaceutically acceptable carrier.

13. The pharmaceutical composition of claim 12, further comprising a therapeutically effective amount of one or more other therapeutically active agents.

14. A method for treating the progression or onset of diseases or disorders associated with the activity of the TGR5 receptor comprising administering to a mammalian patient in need of prevention, inhibition, or treatment a therapeutically effective amount of at least one compound, enantiomer, diastereomer, tautomer, prodrug or salt thereof, of claim 1, and optionally an additional therapeutic agent wherein:

(a) the diseases or disorders are selected from the group consisting of diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, vascular restenosis and pancreatitis; and (b) the additional therapeutic agent is selected from the group consisting of anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, and treatments for peripheral arterial disease and anti-inflammatory agents.

\* \* \* \* \*